(12) United States Patent
Zhang et al.

(10) Patent No.: US 11,851,718 B2
(45) Date of Patent: Dec. 26, 2023

(54) **INDEL MARKER GENOTYPE DATABASE OF *MALUS* AND USE IN IDENTITY FINGERPRINTING OF GERMPLASM RESOURCES**

(71) Applicant: China Agricultural University, Beijing (CN)

(72) Inventors: Xinzhong Zhang, Beijing (CN); Xuan Wang, Beijing (CN); Fei Shen, Beijing (CN); Ruiting Chen, Beijing (CN); Zhenhai Han, Beijing (CN); Yi Wang, Beijing (CN); Ting Wu, Beijing (CN); Xuefeng Xu, Beijing (CN); Wei Li, Beijing (CN); Changpeng Qiu, Beijing (CN); Xi Zhang, Beijing (CN)

(73) Assignee: CHINA AGRICULTURAL UNIVERSITY, Beijing (CN)

( * ) Notice: Subject to any disclaimer, the term of this patent is extended or adjusted under 35 U.S.C. 154(b) by 202 days.

(21) Appl. No.: 17/136,209

(22) Filed: Dec. 29, 2020

(65) Prior Publication Data

US 2022/0090213 A1   Mar. 24, 2022

(30) Foreign Application Priority Data

Sep. 15, 2020 (CN) .......................... 202010966745.9

(51) Int. Cl.
  *C12Q 1/6895* (2018.01)
  *C12Q 1/686* (2018.01)
  *C12Q 1/6888* (2018.01)

(52) U.S. Cl.
  CPC .......... *C12Q 1/6895* (2013.01); *C12Q 1/686* (2013.01); *C12Q 1/6888* (2013.01); *C12Q 2600/13* (2013.01); *C12Q 2600/156* (2013.01)

(58) Field of Classification Search
  None
  See application file for complete search history.

(56) References Cited

PUBLICATIONS

Bianco et al. Development and Validation of a 20K Single Nucleotide Polymorphism (SNP) Whole Genome Genotyping Array for Apple (*Malus x domestica* Borkh). PLOS ONE 9(10):e110377. (Year: 2014).*

Wang et al. Application of genome-wide insertion/ deletion markers on genetic structure analysis and identity signature of Malus accessions. BMC Plant Biology 20:540. (Year: 2020).*

Vanderzande et al. High-quality, genome-wide SNP genotypic data for pedigreed germplasm of the diploid outbreeding species apple, peach, and sweet cherry through a common workflow. PLOS ONE 14(6):e0210928. (Year: 2019).*

Wang Supplementary File S1 [online] Nov. 30, 2020 [retrieved on Apr. 5, 2023] retrieved from https://bmcplantbiol.biomedcentral.com/articles/10.1186/s12870-020-02744-2#Sec21 (Year: 2020).*

Wang Supplementary Table S1 [online] Nov. 30, 2020 [retrieved on Apr. 5, 2023] retrieved from https://bmcplantbiol.biomedcentral.com/articles/10.1186/s12870-020-02744-2#Sec21 (Year: 2020).*

Wang Supplementary Table S2 [online] Nov. 30, 2020 [retrieved on Apr. 5, 2023] retrieved from https://bmcplantbiol.biomedcentral.com/articles/10.1186/s12870-020-02744-2#Sec21 (Year: 2020).*

* cited by examiner

*Primary Examiner* — Samuel C Woolwine
(74) *Attorney, Agent, or Firm* — Tutunjian & Bitetto, P.C.

(57) ABSTRACT

The disclosure provides an InDel marker genotype database of whole genome of *Malus* and use in specific identification of germplasm resources thereof, belonging to the technical field of molecular biology. The constructing method of the genotype database comprises: genotyping InDel markers of genomic DNA samples of *Malus* germplasm resources by using primer pairs and multiplex PCR; recording one line data for each *Malus* germplasm resource according to the genotype of InDel marker; collecting all germplasm resources records to obtain an InDel marker genotype database of the whole genome of *Malus*. The whole genome InDel marker genotype database of *Malus* provided by the disclosure can identify the specificity of apple germplasm simply, efficiently and stably, thus overcoming the limitation that DUS test is easily influenced by environment, and providing a powerful tool for the protection of new apple varieties and the management of germplasm resources.

7 Claims, 6 Drawing Sheets

Specification includes a Sequence Listing.

| | |
|---|---|
| C07043-short fragment sequence | TGCAGCTCCAGGGGCCACAAGGTGGTGAAAAGAAACGAAGGAAAAGCAGTTTAACGGATCTACTTGTACTACACAGAACCCCATAACA 90 |
| C07043-long fragment sequence | CGCAGCTCAAGGGGCCACAAGG.TG.TG.AAAAGAAACG.AGGAAAGCAGTTTAACGGATCTACTTGTACTACACAGAACCCCATAACA 94 |
| C07043-predicting InDel segment sequence | ................................................................................. 0 |
| C07043-short fragment sequence | ......AAAGGTCGTACCCGTGCACAAGGCTCCGCTTTATTCAGGGTCTGCAGAGGTGAATGTCGGCTAGCCTTACCCCATTTTATGGAGA 90 |
| C07043-long fragment sequence | .AAAGGTCGTACCCAGTGCACAAGGCTCCGCTTTACGCAGGGTCTGGAGAGGAGGTGAATGTCGGCTAGCCTTACCCCATTTTATGGAGA 184 |
| C07043-predicting InDel segment sequence | .AAAGGTCGTACCCAGTGCACAAGGCTCCGCTTTACGCAGGGTCTGGAGAGGAGGTGAATGTCGGCTAGCCTTACCCCATTTTATGGAGA 89 |
| C07043-short fragment sequence | ......GGCTGCTCCAAGTCTCGAACCCGAGACCTACCGCTCATGGGTGAAGACACTTGCCATCGCTTAGAACCACGAGCAATACCAATAAATT 104 |
| C07043-long fragment sequence | GGCTGCTCCAAGTCTCGAACCCGAGACCTACCGCTCATGGGTGAAGACACTTGCCATCGCTTAGAACCACGAGCAATACCAATAAATT 274 |
| C07043-predicting InDel segment sequence | GGCTGCTCCAAGTCTCCGAACCCGAGACCTACCGCTCATGGGTGAAGACACTTGCCATCGC.....AC............ 152 |
| C07043-short fragment sequence | CAGCATCAAACATGATTTCGGCTTAAAGGCTCAAATTAAGAGGTCCAGACTCGAGCTAAGTAGTTGTACAATACCGACCTCTCCCTCCA 194 |
| C07043-long fragment sequence | CAGCATCAAACATGATTTCGGCTTAAAGGCTCAAATTAAGAGGTCCAGACTCGAGCTAAGTAGTTGTACAATACCGACCTCTCCCTCCA 364 |
| C07043-predicting InDel segment sequence | ................................................................................. 152 |
| C07043-short fragment sequence | TGAATTGGAAAGGAACAGGAAGAAGAACAAAGGATAACGAAAAGTCTCTTAGAACCAGCGAAGCACAAAGA 265 |
| C07043-long fragment sequence | TGAATTGGAAAGGAACAGGAAGAAGAACAAAAGGATAACGAAAAGTCTCTTAGAACCAGACGAACCAGACAGCCACAAGA 435 |
| C07043-predicting InDel segment sequence | ................................................................................. 152 |

FIG.1

```
                        SEQUENCE LISTING

<160> NUMBER OF SEQ ID NOS: 306

<210> SEQ ID NO 1
<211> LENGTH: 178
<212> TYPE: DNA
<213> ORGANISM: Artificial sequence
<220> FEATURE:
<223> OTHER INFORMATION: InDel marker C01001

<400> SEQUENCE: 1
atattaggag gtcgcacttg gtgcgatggc aagtgccttc gcccatgagt ggcaggtctc     60
gggttcgaga cttgggagca gcctctccat aaatgggggt aaggctagcc gacattcacc    120
tttcccagac cctgcgtaaa gcgggagcct tgtgcactgg gtacgacctt ttttattc     178

<210> SEQ ID NO 2
<211> LENGTH: 162
<212> TYPE: DNA
<213> ORGANISM: Artificial sequence
<220> FEATURE:
<223> OTHER INFORMATION: InDel marker C01002

<400> SEQUENCE: 2
aggtcgtacc cagtgcacaa ggctcccgct ttacgcaggg tctgggagag gtgaatgtcg     60
gctagcctta cccccattta tggagaggct gctcccaagt ctcgaacccg agacctactg    120
ctcatgggcg aaggcacttg ccatcgcacc aagtgcgacc tc                       162

<210> SEQ ID NO 3
<211> LENGTH: 165
<212> TYPE: DNA
<213> ORGANISM: Artificial sequence
<220> FEATURE:
<223> OTHER INFORMATION: InDel marker C01003

<400> SEQUENCE: 3
tagaggtcgc acttggtgcg atggcaagtg ccttcgccca tgagcggtag gtctcgggtt     60
cgagacttgg gagcagcctc tccataaatg ggggtaaggc tagccgacat tcacctctcc    120
cagaccctgc gtaaagcggg agccttgtgc actgggtacg acctt                    165

<210> SEQ ID NO 4
<211> LENGTH: 203
<212> TYPE: DNA
```

<213> ORGANISM: Artificial sequence
<220> FEATURE:
<223> OTHER INFORMATION: InDel marker C01004

<400> SEQUENCE: 4

| | | | | | |
|---|---|---|---|---|---|
| gtagggaact | ttaacgaaaa | gcacccggta | ctgttcactt | taacgaaaaa | ccatattttt | 60 |
| atactaaaaa | gtcaatcatg | gtactattca | ctttacccct | tattttgtcc | ttatcattaa | 120 |
| aactcaaagt | tttcaagcca | ttttcatttg | ttttcctttt | aatgtaaata | tgttagatgg | 180 |
| tgttctaaaa | gttactaaag | gtg | | | | 203 |

<210> SEQ ID NO 5
<211> LENGTH: 189
<212> TYPE: DNA
<213> ORGANISM: Artificial sequence
<220> FEATURE:
<223> OTHER INFORMATION: InDel marker C01005

<400> SEQUENCE: 5

| | | | | | |
|---|---|---|---|---|---|
| gtcttctctt | tgcaatccca | ttccaaattt | ggataggaat | tatgaaggaa | aatttataac | 60 |
| tgaagtcagt | agcccatgc | caacaatttc | attaacttct | cttcatctgt | tttagcagga | 120 |
| gtytactttg | gctttctctt | ggtatttggt | gcaacggaat | tgaatgtccc | cttccttcat | 180 |
| agttggtga | | | | | | 189 |

<210> SEQ ID NO 6
<211> LENGTH: 328
<212> TYPE: DNA
<213> ORGANISM: Artificial sequence
<220> FEATURE:
<223> OTHER INFORMATION: InDel marker C02006

<400> SEQUENCE: 6

| | | | | | |
|---|---|---|---|---|---|
| atgaattgag | gttccatcat | aaaatcaatt | ggtaatatgg | ggagtagccc | aagaccatat | 60 |
| aagcacatag | caaaccttgt | ccctcaccaa | tgtgtgacaa | ctctcaacac | gccgccgcac | 120 |
| gtgtagtaaa | ttttcaagcc | tacacgtgga | caacaactgg | gtgacgtgga | gcacgtgtgg | 180 |
| ccatttggct | tcacacgagg | acaacccgct | ctgatactat | gatgaattga | ggttccacca | 240 |
| taaaaccaat | tggtaatatg | gggagtagcc | caagatcata | taagcacata | gcaaaccttg | 300 |
| tccctcacca | atgtgtgaca | actctcaa | | | | 328 |

<210> SEQ ID NO 7
<211> LENGTH: 166
<212> TYPE: DNA
<213> ORGANISM: Artificial sequence
<220> FEATURE:
<223> OTHER INFORMATION: InDel marker C02008

<400> SEQUENCE: 7

| | | | | | |
|---|---|---|---|---|---|
| aaaggtcgta | cccagtgcac | aaggctcccg | ctttacgcag | ggtctgggag | aggtgaatgt | 60 |
| cggctagcct | taccccatt | tatggagagg | ctgctcccaa | gtctcgaacc | cgagacctac | 120 |
| cgctcatggg | cgaaggcact | tgctatcgca | ccaagtgcga | cctctc | | 166 |

<210> SEQ ID NO 8
<211> LENGTH: 151
<212> TYPE: DNA
<213> ORGANISM: Artificial sequence
<220> FEATURE:
<223> OTHER INFORMATION: InDel marker C02009

<400> SEQUENCE: 8

```
gaaaactaat gaaaagggct tgaaaacttt gagttttaat gataaggaca aaataaaggg      60
taaagtgaat agtaccagga ttgactttt agtgtaaaaa tgtggttttt cgttaaagtg      120
aacagtacca agtgcttttc gttaaagttc c                                    151

<210> SEQ ID NO 9
<211> LENGTH: 136
<212> TYPE: DNA
<213> ORGANISM: Artificial sequence
<220> FEATURE:
<223> OTHER INFORMATION: InDel marker C03011

<400> SEQUENCE: 9
aggaaaacta atgaaaaaag tttgaacact ttgaatttca acgataaata caaaataaag      60
ggtaaagtga atagtaccag gattgactt ttagtgtaaa aatgtgattt ttcgttaaag      120
taaataatac catgag                                                     136

<210> SEQ ID NO 10
<211> LENGTH: 84
<212> TYPE: DNA
<213> ORGANISM: Artificial sequence
<220> FEATURE:
<223> OTHER INFORMATION: InDel marker C03012

<400> SEQUENCE: 10
ccaacttccc ccacttgcaa cattgcctat ttgggaagac atcccacccc ggaggattta      60
acctcctcat ctacccaccc acaa                                            84

<210> SEQ ID NO 11
<211> LENGTH: 167
<212> TYPE: DNA
<213> ORGANISM: Artificial sequence
<220> FEATURE:
<223> OTHER INFORMATION: InDel marker C03014

<400> SEQUENCE: 11
aaaaaargkt cgtacccagt gcacaaggct cccgcttaac gcagggtctg ggagaggtga      60
atgtcggcta gccttacccc catttatggg gaggctgctc ccaagtctcg aacccgagac      120
ctaccgctca tgggcgaagg cacttgccat cgcaccaagt gcgacct                   167

<210> SEQ ID NO 12
<211> LENGTH: 151
<212> TYPE: DNA
<213> ORGANISM: Artificial sequence
<220> FEATURE:
<223> OTHER INFORMATION: InDel marker C03017

<400> SEQUENCE: 12
taaaggtcgt acccagtgca caaggctccc gctttaagca gagtctggga gaggtgaatg      60
tcggctagcc ttaccccat ttatggagag gctgctccca agtctcgaac ccgagaccta      120
ccgctcatgg gcgaaggcac ttgccatcgc a                                    151

<210> SEQ ID NO 13
<211> LENGTH: 173
<212> TYPE: DNA
<213> ORGANISM: Artificial sequence
<220> FEATURE:
<223> OTHER INFORMATION: InDel marker C03018

<400> SEQUENCE: 13
```

```
tggaattgta agaggtcgca cttggtgcga tggcaagtgc cttcgcccat gagcagtagg    60
tctcaggttc gagacttggg agcagcctct ccataaatgg ggtaaggcta gccgacattc   120
acctctccca gaccctgcgt aaagcgggag ccttgtgcaa tgggtacgac att          173

<210> SEQ ID NO 14
<211> LENGTH: 167
<212> TYPE: DNA
<213> ORGANISM: Artificial sequence
<220> FEATURE:
<223> OTHER INFORMATION: InDel marker C04019

<400> SEQUENCE: 14
agaggtcgca cttggtgcga tggcaagtgc cttcgcctat gaacggtagg tctcgggttc    60
gagacttggg agcagcctct ccataaaatg ggggtaagac tagccgacat tcacctctcc   120
cagaccctgc gtaaagcggg agccttgtgc actgggtacg actttttt                167

<210> SEQ ID NO 15
<211> LENGTH: 153
<212> TYPE: DNA
<213> ORGANISM: Artificial sequence
<220> FEATURE:
<223> OTHER INFORMATION: InDel marker C04020

<400> SEQUENCE: 15
gggaatttta acgaaaagca cccggtattg ttcattttaa cgaaaaacca cattttttaca    60 ctaaaaagtc aatcatggta ctattcactt tacccttttat tttgtactta tcattaaaac   120
tcaaagtttt caagcccttt tcattagttt tcc                                153

<210> SEQ ID NO 16
<211> LENGTH: 363
<212> TYPE: DNA
<213> ORGANISM: Artificial sequence
<220> FEATURE:
<223> OTHER INFORMATION: InDel marker C04021

<400> SEQUENCE: 16
gccccgtttg ggattgaggt gattttaaaa aaagctactg tgaaaaaaag ctagggtca    60 tttttgtgtt tggtaaactg aaaaaaaaag gcttattttg gaagctgctg tgagaataag   120
ctgaaaatca aggaaaagc tgaagctgct atttgctgct ttgaaaaaaa gccagttttt    180
tcaaagcaca cggatccttt aatgaaaaga cacactatca tcctgctttt ttttccaaaa   240
gcactttcac aaaaaagttt accatacact ctactggctt tatttcacag ccacttattc   300
tcacagcaca gccgcttatt ctcacagcag cttttttttca aagcacagca ataccaaacc   360
agc                                                                 363

<210> SEQ ID NO 17
<211> LENGTH: 153
<212> TYPE: DNA
<213> ORGANISM: Artificial sequence
<220> FEATURE:
<223> OTHER INFORMATION: InDel marker C04022

<400> SEQUENCE: 17
gggaacttta acgaaaagca cccggtactg ttcacttttaa cgaaaaacca cattttttaca    60 ctaaaaagtc aatcctggta ctattcactt tacccttttat tttgttctta tcattaaaac   120
tcaaagtttt caagcccttt tcattagttt tcc                                153
```

-continued

```
<210> SEQ ID NO 18
<211> LENGTH: 172
<212> TYPE: DNA
<213> ORGANISM: Artificial sequence
<220> FEATURE:
<223> OTHER INFORMATION: InDel marker C04023

<400> SEQUENCE: 18
aaaaaaaaaa aggtcgtacc cagtgcacaa ggctcccgct ttacgcaggg tctgggagag      60
gtgaatgtcg gctagcctta cccccattta tggagaggct gctcccaagt ctcgaacccg     120
agacctaccg ctcatgggcg aaggcacttg ccatcgcacc aagtgcgacc tc             172

<210> SEQ ID NO 19
<211> LENGTH: 168
<212> TYPE: DNA
<213> ORGANISM: Artificial sequence
<220> FEATURE:
<223> OTHER INFORMATION: InDel marker C04024

<400> SEQUENCE: 19
ctgagaggtc gcacttggtg cgatggcaag tgccttcgcc catgagcggt aggtctcggg      60
ttcgagactt gggagcagcc tctccataaa tgggggtaag gctagccgac attcacctct     120
cctagaccct gcgtaaagcg ggagccttgt gcactgggta cgaccttt                  168

<210> SEQ ID NO 20
<211> LENGTH: 164
<212> TYPE: DNA
<213> ORGANISM: Artificial sequence
<220> FEATURE:
<223> OTHER INFORMATION: InDel marker C04133

<400> SEQUENCE: 20
taaaaggtcg tacccagtgc acaaggctcc cgctttacgc agggtctggg agaggtgaat      60
gtcggctagc cttacccccca tttatggaga ggctgctccc aagtctcgaa cccgagacct    120
accgctcatg ggcgaaggca cttgccatcg caccaagtgc gacc                      164

<210> SEQ ID NO 21
<211> LENGTH: 352
<212> TYPE: DNA
<213> ORGANISM: Artificial sequence
<220> FEATURE:
<223> OTHER INFORMATION: InDel marker C04134

<400> SEQUENCE: 21
gggctggttt ggtattgctg tgctttgaaa aaaagttgct gtgagaataa gcagctgtga      60
aataaattag tagagtgttt ggtaaacttt tttgtaaaag tgcttctgaa aaaaaaaac     120 agtctgatag tgggtctttt cattaaagga gcactgtaac tccgtgtgct ttgaaaaaaa    180
agccagtttt ccaagctaca aatagcagct tcagttttt cctttgattt cagcttattc    240
tcacagcagc ttccaaaata agccatttt tttcagttta acaaacatct aaaactctca    300 cagcttttt tyatgggtgy ttttttttta agcacctcat tcccaaacca cc             352

<210> SEQ ID NO 22
<211> LENGTH: 108
<212> TYPE: DNA
<213> ORGANISM: Artificial sequence
<220> FEATURE:
<223> OTHER INFORMATION: InDel marker C05026

<400> SEQUENCE: 22
```

```
ttttttttcaa ttgatcgagc ccagtgcaca aggctcccgc tttacgcagg gtctgggaga    60
ggtgaatgtc ggctagcctt accccattt atggagaggc tgctccca                  108

<210> SEQ ID NO 23
<211> LENGTH: 169
<212> TYPE: DNA
<213> ORGANISM: Artificial sequence
<220> FEATURE:
<223> OTHER INFORMATION: InDel marker C05028

<400> SEQUENCE: 23
atattcaata tttcaaatgc ttagtcaaaa agcgattcta ggaacaagaa tttcttccaa    60
actttgttgc aacacagaca catacgcttt tgaatgtata atacattttt tttggtgaga    120
ttgaccttcg caggtgtact gtggtcaata ggggaaggta ctgggtact                169

<210> SEQ ID NO 24
<211> LENGTH: 226
<212> TYPE: DNA
<213> ORGANISM: Artificial sequence
<220> FEATURE:
<223> OTHER INFORMATION: InDel marker C05029

<400> SEQUENCE: 24
gggcttcagt agcaaatgat tttaataatt actctctttc tcaattactg tgggatttgt    60
tagcagcagt aaagtgagtt aggtctagct attgttcctg tagccaaatc ctattgagag    120
tttttcttgt ttcttgtaaa tggtggattt cttatccact tcagtatatt tctcttttct    180
tttataaaat gtttgtttct tctcaaaaaa aaaaaaaaa aaaaaa                    226

<210> SEQ ID NO 25
<211> LENGTH: 150
<212> TYPE: DNA
<213> ORGANISM: Artificial sequence
<220> FEATURE:
<223> OTHER INFORMATION: InDel marker C05030

<400> SEQUENCE: 25
gggaacttta acgaaaagca cccggtactg ttcactttaa cgaaaaacca tattttaca    60 ctaaaaagtc aattctggta ctattcactt tacccttat tttgtccttt tcattaaaac    120
tcaaagtttt caagcccttt tcattagttt                                     150

<210> SEQ ID NO 26
<211> LENGTH: 228
<212> TYPE: DNA
<213> ORGANISM: Artificial sequence
<220> FEATURE:
<223> OTHER INFORMATION: InDel marker C05031

<400> SEQUENCE: 26
gcatggccat ctactacctt tgcaccggag aacaggaagg ggttcttggt ggaatcaact    60
tcaacatggt cactctctcc cgtcatgctt gactcgtcca cttgtaagga atacccatcc    120
aggaacaatc catctgcagg tatttgatct cccatgttca gaaccacaac atctccaact    180
acaatatcga agatggagat ttcttgtctc tgtttgtctc taaatacc                 228

<210> SEQ ID NO 27
<211> LENGTH: 154
<212> TYPE: DNA
<213> ORGANISM: Artificial sequence
<220> FEATURE:
<223> OTHER INFORMATION: InDel marker C05032
```

-continued

```
<400> SEQUENCE: 27
agggaacttt aacgaaaagc acccggtact gttcactttta acgaaaaacc acattttac      60 actaaaaagt caatcctggt actattcact ttacccttta ttttgttctt atcattaaaa     120
ctcaaagttt tcaagccctt ttcattagtt ttcc                                 154

<210> SEQ ID NO 28
<211> LENGTH: 167
<212> TYPE: DNA
<213> ORGANISM: Artificial sequence
<220> FEATURE:
<223> OTHER INFORMATION: InDel marker C05135

<400> SEQUENCE: 28
ttcctgctcg taatgtgttt atgggatgtt ccatcaaata acagcagtga tcrttataac      60
acagcataag ttaccgatac gagcacagat gcattttgca gaaatacacc ataattagat    120
rgataagatt cgaatgtgta cgtacgatca atgttgacaa tgcaaag                  167

<210> SEQ ID NO 29
<211> LENGTH: 119
<212> TYPE: DNA
<213> ORGANISM: Artificial sequence
<220> FEATURE:
<223> OTHER INFORMATION: InDel marker C06037

<400> SEQUENCE: 29
cgtacccagt gcacaaggct cccgctttaa gcatggtctg agagaggtga atgtcggcta      60
gccttacctc catttatgga gaggctgctc ccaaatctcg aacccgagac ctaccgctc     119

<210> SEQ ID NO 30
<211> LENGTH: 158
<212> TYPE: DNA
<213> ORGANISM: Artificial sequence
<220> FEATURE:
<223> OTHER INFORMATION: InDel marker C06038

<400> SEQUENCE: 30
cactacaaat ataggatttc gctgagagag agagtgacaa tgaaaactct ctgaagttcc      60
tctgaacata gtgcaccagt tagggtataa acaaaacttg gcctctacca ttgaaggacc    120
acagaagtat tcacccttca acaagcaaca atccaagc                            158

<210> SEQ ID NO 31
<211> LENGTH: 53
<212> TYPE: DNA
<213> ORGANISM: Artificial sequence
<220> FEATURE:
<223> OTHER INFORMATION: InDel marker C06039

<400> SEQUENCE: 31
gaccagcgga tctggtggtc gacaatcgtt cggacttggt aaaggttgtc gcg            53

<210> SEQ ID NO 32
<211> LENGTH: 74
<212> TYPE: DNA
<213> ORGANISM: Artificial sequence
<220> FEATURE:
<223> OTHER INFORMATION: InDel marker C06040

<400> SEQUENCE: 32
gtgtttcctt ttttatttcg ttgttatgac tattgcttga gatttagcaa caatatgtcc      60
```
attattaata tatt 74

<210> SEQ ID NO 33
<211> LENGTH: 337
<212> TYPE: DNA
<213> ORGANISM: Artificial sequence
<220> FEATURE:
<223> OTHER INFORMATION: InDel marker C06041

<400> SEQUENCE: 33

```
cctcagtaca tataggctat atgatatagc cccgtttaga attgcttttt tagtgcaatg    60
aagtatgcat atcaggagtt tcgtatgcag agaaagaaat tgcgttaggt tatattaaga   120
atttctatcc agggttactg tttaactttta cgaattaact agttgatgat ttaatattga  180
tagaaaagta gatttcaatc cagttccatt agaatatttt agaaaaatgg aaacttcctt   240
tgactattgt cttatattaa agacttatca taaggagatg ataacgtcaa ttaataacta   300
gatgggtcga ctgagtccaa ttcaaaggac ccatttc                            337
```

<210> SEQ ID NO 34
<211> LENGTH: 255
<212> TYPE: DNA
<213> ORGANISM: Artificial sequence
<220> FEATURE:
<223> OTHER INFORMATION: InDel marker C06137

<400> SEQUENCE: 34

```
gcaaatgtca ctcctagata atacggagat gaatgaaaga tgacatgcat gacatcaatc    60
ttgggtccat gtaagccaaa aaacaacgg ttaacttgac ggttcgactg attaagacgg    120
taaatgttga acgaactagt aacttcaagg gttgtaagtt tttgtatgcc atggaccaaa   180
tgttacatgc tcttaacctt gagaaagact tctcatggca cggaacgcca tggttcttgt   240
gtacccgtgc catgg                                                    255
```

<210> SEQ ID NO 35
<211> LENGTH: 152
<212> TYPE: DNA
<213> ORGANISM: Artificial sequence
<220> FEATURE:
<223> OTHER INFORMATION: InDel marker C07043

<400> SEQUENCE: 35

```
aaaggtcgta cccagtgcac aaggctcccg ctttacgcag ggtctgggag aggtgaatgt    60
cggctagcct taccccatt ttatggagag gctgctccca gtctcgaac ccgagaccta    120
ccgctcatgg gtgaagacac ttgccatcgc ac                                 152
```

<210> SEQ ID NO 36
<211> LENGTH: 139
<212> TYPE: DNA
<213> ORGANISM: Artificial sequence
<220> FEATURE:
<223> OTHER INFORMATION: InDel marker C07044

<400> SEQUENCE: 36

```
ggtcttcgcc catgagctgt aggtctcggg ttcgagactt gggagcagcc tctccataaa    60
tgggggtaag gctagccgac attcacctct cccagaccct gcgtaaagcg ggagccttgt   120
gcactgggta cgaccttt                                                 139
```

<210> SEQ ID NO 37
<211> LENGTH: 154

```
<212> TYPE: DNA
<213> ORGANISM: Artificial sequence
<220> FEATURE:
<223> OTHER INFORMATION: InDel marker C07045

<400> SEQUENCE: 37
cagtgtgatg gcaagtgtct tcgcccatga gcagtaggtc tcgggttcga gacttgggag      60
cagcctctcc ataaaatggg ggtaaggctr gccgacattc acctctccca gaccctgcgt     120
aaagcgggag ccttgtgcac tgggtacgac ctca                                 154

<210> SEQ ID NO 38
<211> LENGTH: 195
<212> TYPE: DNA
<213> ORGANISM: Artificial sequence
<220> FEATURE:
<223> OTHER INFORMATION: InDel marker C07047

<400> SEQUENCE: 38
cgttaatttc ataagctgta aggaacacaa gcagaccaat gcttacataa tttcataagc      60
tgtaagcatt ggcctattta catacataat ttcgagactt gggagcagcc tctccataaa     120
tgggggtaag gctagccgac attcacctct cccagaccct gcttaaagcg ggagccttgt     180
gcactgggta cgacc                                                      195

<210> SEQ ID NO 39
<211> LENGTH: 373
<212> TYPE: DNA
<213> ORGANISM: Artificial sequence
<220> FEATURE:
<223> OTHER INFORMATION: InDel marker C07048

<400> SEQUENCE: 39
ggtggtttgg gagtgaggtg cttaaaaaaa aagcacccat gaaaaaaagc tgtgagggtt      60
ttaggtgttt ggtaaactaa aaaaaagggg cttattttgg aagctgctgt gagaataagc     120
tgaaatcaaa ggaaaaagct gaagctgcta tttgcagctt tggaaaactg ccttttttctc    180 aaagcacacg gaactacaat gctcctttaa tggaaagacc cactatcaga ctgctttttt     240
ttttccaaaa gcacttttac aaaaaaattt accaaacact ctgctgattt atttcacatc     300
cgcttattct cacagtacag cygcttattc tcacagcagc tttttttcaa agcacagcaa     360
taccaaacta gcc                                                        373

<210> SEQ ID NO 40
<211> LENGTH: 164
<212> TYPE: DNA
<213> ORGANISM: Artificial sequence
<220> FEATURE:
<223> OTHER INFORMATION: InDel marker C07049

<400> SEQUENCE: 40
agaggtcgca cttggtgcga tggcaagtgc cttcgcccat gagcgtagg tctcgggttc       60 gagacttggg agcagcctct ccataaatgg gggtaaggct agccgacatt cacctctccc     120
agaccctgcg taaagcggga gccttgtgca ctgggtacga cctt                      164

<210> SEQ ID NO 41
<211> LENGTH: 232
<212> TYPE: DNA
<213> ORGANISM: Artificial sequence
<220> FEATURE:
<223> OTHER INFORMATION: InDel marker C07050
```

<400> SEQUENCE: 41

```
tgggagagct ttctgggcag tgccgcctgc ttcggtcatt tgaccaacac tccttcaaaa    60
catataactt gttcttcact ctccatggca agaaaggaaa ggagagacaa ttacaaatct   120
caattacact tgacccgtgg gattacaaat ctcaaatcag aggaattcgc attgacagtc   180
aagggagtta ccatcttcac aattacagac gacccacgga tcaaaccctc ct           232
```

<210> SEQ ID NO 42
<211> LENGTH: 349
<212> TYPE: DNA
<213> ORGANISM: Artificial sequence
<220> FEATURE:
<223> OTHER INFORMATION: InDel marker C07138

<400> SEQUENCE: 42

```
aattgtttat accatattta ggacctctta tttagatctc gtacaaatac tcagggaact    60
taaatgtaat tatgtgataa aggaatgggc aaatatgtaa taagtgagga gttcttattc   120
tataaaatga cccctcaccc tcacaattgg aggaggtcaa ttcctaggcc ctctcacccc   180
ctctcaaagc tctaactctc agagctctct ccctcaaata aatacataat cagtgtggac   240
gtagcccaaa tttagggtg aaccacgatg catcttgtgt tatttacatt tcttgcagat   300
tcacggtcgg atttacgttg ttccaaaacc tccggttttg tgcatcaac                349
```

<210> SEQ ID NO 43
<211> LENGTH: 260
<212> TYPE: DNA
<213> ORGANISM: Artificial sequence
<220> FEATURE:
<223> OTHER INFORMATION: InDel marker C07138

<400> SEQUENCE: 43

```
tgacgctatt ggagctggaa ttaccgcggc tgctggcacc agacttgccc tccaatggat    60
cctcgttaag ggatttagat tgtactcatt ccaattacca gactcataga gcccggtatt   120
gttatttatt gtcactacct ccccgtgtca ggattgggta atttgcgcgc ctgctgcctt   180
ccttggatgt ggtagccgtt tctcaggctc cctctccgga atcgaaccct aattctccgt   240
cacccgtcac caccatggta                                                260
```

<210> SEQ ID NO 44
<211> LENGTH: 207
<212> TYPE: DNA
<213> ORGANISM: Artificial sequence
<220> FEATURE:
<223> OTHER INFORMATION: InDel marker C08052

<400> SEQUENCE: 44

```
gaccwgawts ywcttctaag mtwwggwtgw ktmtycwcct cwtyrmtkwr tmkrsgccgt    60
tkgwtgwraa tmmaayggct ayaatcaggg tccctttaaa gttataataa ttgtaacctt   120
taaagttata ataattgtaa ccgttgaatg aaatcacttg atgaggagaa tcctcatcct   180
tagctcagga gaggatcctg gtccatg                                        207
```

<210> SEQ ID NO 45
<211> LENGTH: 133
<212> TYPE: DNA
<213> ORGANISM: Artificial sequence
<220> FEATURE:
<223> OTHER INFORMATION: InDel marker C08054

<400> SEQUENCE: 45

```
aaaaaggtcg tacccagtgc acaaggctcc cgctttacgc agggtctggg agaggtgaat    60
gtcggctagc cttacccca tttatggaga ggctgctccc aagtctcgaa cccgagacct    120
accgctcatg ggc                                                      133
```

<210> SEQ ID NO 46
<211> LENGTH: 62
<212> TYPE: DNA
<213> ORGANISM: Artificial sequence
<220> FEATURE:
<223> OTHER INFORMATION: InDel marker C08055

<400> SEQUENCE: 46

```
agaggggtcg tacccagtgc acaaggctcc cgctttacgc agggtctggg agaggtgaat    60
gt                                                                  62
```

<210> SEQ ID NO 47
<211> LENGTH: 147
<212> TYPE: DNA
<213> ORGANISM: Artificial sequence
<220> FEATURE:
<223> OTHER INFORMATION: InDel marker C08056

<400> SEQUENCE: 47

```
ggggtgtgct atccacacac cttttttac ttctcacaca ccctttgtta atttctgtcc    60
gttgattttc tttaattcat tcgatccgac ggccgaaaac caaaaaggtg tgagagaagt   120
aaaaaaggat gtgtggatat cacacct                                       147
```

<210> SEQ ID NO 48
<211> LENGTH: 311
<212> TYPE: DNA
<213> ORGANISM: Artificial sequence
<220> FEATURE:
<223> OTHER INFORMATION: InDel marker C08057

<400> SEQUENCE: 48

```
accacaacac aatgttcgat taaccacaat gccatctcaa ggacagtttg ggactgcttc    60
tgctgaagct aaaaccgctc tctggcaatc ataagcccct atgactacgt tttgcataaa   120
aactataata gttcttctat ccctaaacct acttcctttt caggaaacac ttccaagtgc   180
ttttccagga cgcaattggg ttttcaataa aatcttgacg agtttctaat taaagcactt   240
gcattgaaac gaaacatggt tatgccatta catctatgat gaaaaatggg acaggggttt   300
cgattaaatg m                                                        311
```

<210> SEQ ID NO 49
<211> LENGTH: 280
<212> TYPE: DNA
<213> ORGANISM: Artificial sequence
<220> FEATURE:
<223> OTHER INFORMATION: InDel marker C08058

<400> SEQUENCE: 49

```
aaaaaaraaa aagacgtaat catcttmtat gattgaattt ttctctaaaa aagtaaaaat    60
tgggaaatga ttttttcaca cccatttgag tctttgacct gcactctgct aaattstgtc   120
ccctgattct cttgatttat ccaatccaga aagaggacga ggtgtagaaa tcagtcccca   180
aaaaatcrgg ggttgaaaag gggagtgcag aaaccccaaa attgggttca accccctaaaa  240 ttcgggttgc tttagttaac ccaaggcttc ttaacattgc                         280
```

<210> SEQ ID NO 50
<211> LENGTH: 163
<212> TYPE: DNA
<213> ORGANISM: Artificial sequence
<220> FEATURE:
<223> OTHER INFORMATION: InDel marker C08059

<400> SEQUENCE: 50

```
rgctcctgat cccagtgcac aaggctcctg ctttacgcag ggtytgggag aggtgaatgt      60
cggctagcct kaccccccatt tatggagagg ctgctcccaa gtctcgaacc ygagacctac    120
cgctcatggg cgwaggcact tgccatcgca ccaagtgcga tct                       163
```

<210> SEQ ID NO 51
<211> LENGTH: 377
<212> TYPE: DNA
<213> ORGANISM: Artificial sequence
<220> FEATURE:
<223> OTHER INFORMATION: InDel marker C08060

<400> SEQUENCE: 51

```
gatctgtaac gggttggatt tattggatttt ggattggatt caacccgacc cgttaagtta    60
acaggtcacc cgaactcaac ccgttaagtt aacgggtcat ccgaacccga cccgttaagc    120
taacggatca tccattttac ctattaacaa ttattattat tattttttg cataaagttt     180
attttttgtt attaaaactt tactaaaatt attaaaatat ccttaactaa cgggttaacc    240
caaagtgatc cgttatttaa caggttgtta acgggttcat ccgttaacga cccgaccccgt    300
taagtatcca cccaaataca aatattaacg ggttgggtcg gatcgagtta acgggttggg    360
tccaaaatgc cagacct                                                   377
```

<210> SEQ ID NO 52
<211> LENGTH: 281
<212> TYPE: DNA
<213> ORGANISM: Artificial sequence
<220> FEATURE:
<223> OTHER INFORMATION: InDel marker C09062

<400> SEQUENCE: 52

```
agattaccat gcaaaaatgc attgcttaca tccagttgat tgagaaacca atcatattgt     60
gccgccaaca tgaggagaat tcgaatagtg acaagtttag caacttgact aaatgtctta   120
atgtaatcta aaccttcttg ctggttaaaa cctttggcaa ctaggcgtgc cttgtacttc   180
tcaatagtgc catcaggttt cctcttgatc ctgaaaaccc acttacaacc tactatattg   240
gtagaatgag atttgggaac taaagaccac attctagttt g                        281
```

<210> SEQ ID NO 53
<211> LENGTH: 202
<212> TYPE: DNA
<213> ORGANISM: Artificial sequence
<220> FEATURE:
<223> OTHER INFORMATION: InDel marker C09063

<400> SEQUENCE: 53

```
taagatcata aacttataaa tactgcgtac tcatgcttat cccttatcct aaaattcaat     60
actgcatgca gtgtagttgt tatttattca aatgaataac ttagttttt tgttaactat   120
cttttaacct tgttctatcc ttatttccta gttatgtctg gtctggtgtg gctactgact   180
ggttgctgac atgggaattt ca                                              202
```

```
<210> SEQ ID NO 54
<211> LENGTH: 157
<212> TYPE: DNA
<213> ORGANISM: Artificial sequence
<220> FEATURE:
<223> OTHER INFORMATION: InDel marker C09064

<400> SEQUENCE: 54
ggtcgtaccc agtgcacaag gctcccgctt tacgtagggt ctgggagagg tgaatgtcgg      60
ctagccttac ctccatttat ggagaggctg ctcccaagtc ttgaacccga gacctaccgc     120
ttatgggcga aggcacttgc tatcgcacca artgcra                              157

<210> SEQ ID NO 55
<211> LENGTH: 84
<212> TYPE: DNA
<213> ORGANISM: Artificial sequence
<220> FEATURE:
<223> OTHER INFORMATION: InDel marker  C09067

<400> SEQUENCE: 55
aaaaaaaaaa aggtcgtacc cagtgcacaa ggctcccgtt ttacgcaagg tctgggagag      60
gtgaatgtcg gctagcctta cccc                                            84

<210> SEQ ID NO 56
<211> LENGTH: 147
<212> TYPE: DNA
<213> ORGANISM: Artificial sequence
<220> FEATURE:
<223> OTHER INFORMATION: InDel marker C09068

<400> SEQUENCE: 56
tacagctgtc tgacgtgaga attccgttaa tctttgtaag tcctttctct tttcttttg      60 gaaaatattt atctgattgt tggagaaatt taatgatata cattgcccac tcttttgat     120 aattttactg ctcatcatgg taatctc                                        147

<210> SEQ ID NO 57
<211> LENGTH: 66
<212> TYPE: DNA
<213> ORGANISM: Artificial sequence
<220> FEATURE:
<223> OTHER INFORMATION: InDel marker C10070

<400> SEQUENCE: 57
aaggccttac ggaattttct tttagtgatt atgttgtaaa tagtcatgtg ctcttgtgtt      60
cttggg                                                                66

<210> SEQ ID NO 58
<211> LENGTH: 159
<212> TYPE: DNA
<213> ORGANISM: Artificial sequence
<220> FEATURE:
<223> OTHER INFORMATION: InDel marker C10071

<400> SEQUENCE: 58
gtcgtaccca gtgcacaagg ctcccgcttt acgcagggtc tgggagaggt gaatgtcggc      60
tagccttacc cccatttatg gagaggctgc tcccaagtct cgaacccgag acctaccgct     120
catgggcgaa ggcacttgtc atcgcaccaa atgcgacct                            159

<210> SEQ ID NO 59
<211> LENGTH: 56
<212> TYPE: DNA
```

```
<213> ORGANISM: Artificial sequence
<220> FEATURE:
<223> OTHER INFORMATION: InDel marker C10072

<400> SEQUENCE: 59
gtcgtaccca gtgcacaagg ctcccgcttt aggcagggtt tgggagaggt aaatgt       56

<210> SEQ ID NO 60
<211> LENGTH: 108
<212> TYPE: DNA
<213> ORGANISM: Artificial sequence
<220> FEATURE:
<223> OTHER INFORMATION: InDel marker C10073

<400> SEQUENCE: 60
tgyagaatgm cacagawtcc atcwtccttt gacggcattg cagaatttaa ccaacaaata    60
acaaaaaaat aacacaaaga tataagtcca attctttcta caaaacca               108

<210> SEQ ID NO 61
<211> LENGTH: 373
<212> TYPE: DNA
<213> ORGANISM: Artificial sequence
<220> FEATURE:
<223> OTHER INFORMATION: InDel marker C10136

<400> SEQUENCE: 61
gccccgtttg ggattgaggt gattttaaaa aaagcaactg tgaaaaaaag ctgagggtca    60
tttttgtgtt tggtaaactg aaaaaaaggg cttattttgg aagctgctgt gagaataagc   120
tgaaaatcaa aggaaaagct gaagctgcta tttgctgctt tgaaaaaaag ccagtttttt   180
caaagcacac ggagctacag tgctccttta atgaaaagac acactatcat cctgcttttt   240
tttccaaaag cactttcaca aaaaagttta ccaaacactc tactggcttt atttcacagc   300
cgcttattct cacagcacag ccgcttattc tcacagcagc ttttttttcaa agcacagcaa   360 taccaaacca gcc                                                     373

<210> SEQ ID NO 62
<211> LENGTH: 372
<212> TYPE: DNA
<213> ORGANISM: Artificial sequence
<220> FEATURE:
<223> OTHER INFORMATION: InDel marker C11077

<400> SEQUENCE: 62
gacctagttt gggagtgagg tgcttaaaaa aaaagcacat atgaaaaaaa gctgtgaggg    60
ttttaggtgt ttggtaaact gaaaaaaaat ggcttatttt ggaagctgct gtgagaataa   120
gctgaaatca aggaaaaag ctgaagctgc tatttgtagc tttggaaaac tggtttttt    180 tcaaagcaca tggagctaca gtgctccttt aatgaaagga cccactatca grctamyttt   240
ttttccaaaa gctttttgc aaaaaagttt accaaacgct ctgctgattt atttcacagc   300
cgyttattct cacagcacag ccgcttattc tcacagcagc ttttttttcaa agcacagcaa   360 taccaaacca gc                                                      372

<210> SEQ ID NO 63
<211> LENGTH: 159
<212> TYPE: DNA
<213> ORGANISM: Artificial sequence
<220> FEATURE:
<223> OTHER INFORMATION: InDel marker C11078

<400> SEQUENCE: 63
```
aggtcgtacc cagtgcacaa ggctcccgct ttacgcaggg tctgggagag gtgaatgtcg    60
gctagcctta cccccattta tggagaggct gctcccaagt ctcgaacccg agacctaccg   120
ctcatgggcg aaggcacttg ccatcgcacc aagtgcgac                          159

<210> SEQ ID NO 64
<211> LENGTH: 374
<212> TYPE: DNA
<213> ORGANISM: Artificial sequence
<220> FEATURE:
<223> OTHER INFORMATION: InDel marker C11079

<400> SEQUENCE: 64
gggctggttt ggtattgctg tgctttgaaa aaaagctgct gtgagaataa gcggctgtgc    60
tgtgagaata agcggctgtg aaataaagcc agtagagtgt ttggtaaatt tttttgtgaa   120 agtgctttg gaaaaaaaag caggatgata gtgtgtcttt tcattaaagg agcactgtag    180
ctccgtgtgc tttgaaaaaa ctgactttt ttcaaagcag caaatagcag cttcagcttt   240
tcctttgatt ttcagcttat tctcacagca gcttccaaaa taagccctt tttttcagtt   300 taccaaacac aaaaataacc ctcagctttt tttcacagtg gcttttttta aaatcacctc   360
aatcccaaac ggag                                                     374

<210> SEQ ID NO 65
<211> LENGTH: 152
<212> TYPE: DNA
<213> ORGANISM: Artificial sequence
<220> FEATURE:
<223> OTHER INFORMATION: InDel marker C11080

<400> SEQUENCE: 65
gggarcttta asgmmaaaca mcygttactg ttcactttaa cgaaaaacca catttttaca    60
ctaaaaagtc aatcttggta ctattcactt tacccttat tttgtcctta tcattaaaaa   120
tcaaagtttt caagctcttt tcattagttt tc                                 152

<210> SEQ ID NO 66
<211> LENGTH: 170
<212> TYPE: DNA
<213> ORGANISM: Artificial sequence
<220> FEATURE:
<223> OTHER INFORMATION: InDel marker C11081

<400> SEQUENCE: 66
aaaaaaggtc gtacgcagtg cacaaggctt ccgctttacg cagggtctga gagaggtgaa    60
tgtctgctag ccttaccccca tttatggaga ggctgcttcc aagtctcgaa cccgagacct   120
accactcatg gacgaaggca cttgccatcg caccaagtgc gacctcttca                170

<210> SEQ ID NO 67
<211> LENGTH: 157
<212> TYPE: DNA
<213> ORGANISM: Artificial sequence
<220> FEATURE:
<223> OTHER INFORMATION: InDel marker C11082

<400> SEQUENCE: 67
gggaatttta acgaaaagca cccggtactg ttcactttaa cgaaaaacca tatttttaca    60
ctaaaaagtc aatcctggta ctattcactt tacccttat tttgtcctta tcattaaaac   120
tcaaagtttt caagccattt tcattagttt tcctaaa                            157

<210> SEQ ID NO 68
<211> LENGTH: 105
<212> TYPE: DNA
<213> ORGANISM: Artificial sequence
<220> FEATURE:
<223> OTHER INFORMATION: InDel marker C12086

<400> SEQUENCE: 68

```
aaaaaaaagg tcgtacccag tgcacaagac ttccgcttta cacagggtck gggagaggtg    60
aatgtcggct aaccttaccc ccatttatgg agaggctgct cccaa                   105
```

<210> SEQ ID NO 69
<211> LENGTH: 374
<212> TYPE: DNA
<213> ORGANISM: Artificial sequence
<220> FEATURE:
<223> OTHER INFORMATION: InDel marker C12087

<400> SEQUENCE: 69

```
ggctggtttg gtattgctgt gctttgaaaa aaagctgctg tgaaaataag cggytgtrct    60
gtgagaataa gcggctgtga aataaatcag cagagtgttt ggtaaacttt tttgtaaaag   120 tgcttttttgg aaaaaaaaag cagtcaaata gtgggtattt tcattaaaga agyactgtag   180
ctccgtgtgc tttgaaaaaa agccattttt ccaaagctgc aaatagcagc ttcagctttt   240
tcctttgatt ttcagcttat tctcacaaca gcttccaaaa taagcccttt ttttcagtt    300 taccaaacac ataaaaccct cacagctttt tttcatgggt gcttttttt aagcacctca    360 ctcccaaact aggt                                                     374
```

<210> SEQ ID NO 70
<211> LENGTH: 153
<212> TYPE: DNA
<213> ORGANISM: Artificial sequence
<220> FEATURE:
<223> OTHER INFORMATION: InDel marker C12088

<400> SEQUENCE: 70

```
aggaaaacta atgaaaaggg cttgaaaact ttgagtttta atgataagga caaaataaag    60
ggtaaagtga atagtaccag gattgacttt ttagtgtaaa aatgtggttt tttgttaaag   120
taaacagtac cgggtgcttt tcgttaaagt tcc                                153
```

<210> SEQ ID NO 71
<211> LENGTH: 191
<212> TYPE: DNA
<213> ORGANISM: Artificial sequence
<220> FEATURE:
<223> OTHER INFORMATION: InDel marker C12089

<400> SEQUENCE: 71

```
ctaagtcaac gattgataag tgataaaatc taattttgtc aaaatttaat tttgttttag    60
attgaagtgt taaacaaaat ttaagataac acacctaaaa ttaacttaag aaaagttaac   120
aaagaaacca ttattttgta ctacagaaat aaatacccac ataaataaat atatagcctc   180
atatagagct a                                                        191
```

<210> SEQ ID NO 72
<211> LENGTH: 84
<212> TYPE: DNA
<213> ORGANISM: Artificial sequence
<220> FEATURE:
<223> OTHER INFORMATION: InDel marker C12090

<400> SEQUENCE: 72
tataaaccgc atcttgtgtc taagatagtc ttctatttgc ccatatgatt cttagcgatg    60
acccgctttt catccttgaa tttc    84

<210> SEQ ID NO 73
<211> LENGTH: 189
<212> TYPE: DNA
<213> ORGANISM: Artificial sequence
<220> FEATURE:
<223> OTHER INFORMATION: InDel marker C12091

<400> SEQUENCE: 73
agtgcatttt tgctcactac catttagtgt ggtgtatgct catcaccta tttatcacta    60 ttagattagt ttgaattttg agatttgtgc ttattcacta cacgaatctc gaaatycraa    120
ctcatstaac ggtkwtaamt argkyrgtsm aswcwmrtsa mrctwaatrr tggkgakmaa    180 aaatgcwyy    189

<210> SEQ ID NO 74
<211> LENGTH: 318
<212> TYPE: DNA
<213> ORGANISM: Artificial sequence
<220> FEATURE:
<223> OTHER INFORMATION: InDel marker C12092

<400> SEQUENCE: 74
agaatcaaaa tattaattam cmaaaaaaca acaaaaggtc aaaaaacctt ggtaagagat    60
gttttagaac acatagtgca ccaaacgtca agggttcttc cttcaatctg catttctagt    120
agcaaaaaat aaaaaagaaa agagactatt atatttgaa aactaataca taaaatcaaa    180
accagcttca catttactat agataaacac ttagtagtaa gaagaaacat tatggaaagg    240
atacatacat ttataaggaa gacaaataaa tcctcagggt ataccaagcc aattgtcagg    300
aagcaacgct gaacttcg    318

<210> SEQ ID NO 75
<211> LENGTH: 157
<212> TYPE: DNA
<213> ORGANISM: Artificial sequence
<220> FEATURE:
<223> OTHER INFORMATION: InDel marker C13093

<400> SEQUENCE: 75
cgtacccagt gcacaaggct cccgctttac gcagggtctg ggagaggtga atgtcggcta    60
gctttacccc catttatgga gaggctgctc ccaagtctcg aacccgagac ctaccgctca    120
tggacgaagg cacttgccat cgcaccaagt gcgacct    157

<210> SEQ ID NO 76
<211> LENGTH: 172
<212> TYPE: DNA
<213> ORGANISM: Artificial sequence
<220> FEATURE:
<223> OTHER INFORMATION: InDel marker C12132

<400> SEQUENCE: 76
agtattagct tgcatccaca actacaaaaa tcatagtctg ctccgaagta tcatatacac    60
catgmgtttg ggcctaaaga tcatggtcat tggatatttg accagaatc taacagccga    120 aaaccctcgt atagaagata ccacgagtga tactagaaat atccccagaa ca    172

<210> SEQ ID NO 77
<211> LENGTH: 183
<212> TYPE: DNA
<213> ORGANISM: Artificial sequence
<220> FEATURE:
<223> OTHER INFORMATION: InDel marker C13094

<400> SEQUENCE: 77

```
ggatttggat catctcctga gctaatggag agtatcctct tgaccaagtg ttatgggtcg      60
ttggattttt atccaacagc tacaaacagt tgggtccttt taaagttata ataatttcat     120
ccaacggcac ataatactta gtcagaagga tctctccatt agctcaggag aggatccaaa     180
tcc                                                                   183
```

<210> SEQ ID NO 78
<211> LENGTH: 149
<212> TYPE: DNA
<213> ORGANISM: Artificial sequence
<220> FEATURE:
<223> OTHER INFORMATION: InDel marker C13096

<400> SEQUENCE: 78

```
aaggtcgtac ccagtgcaca aggctcccgc tttacgcagg gtctgggaga ggtgaatgtc      60
ggctagcctt accccatt atggagaggc tgctcccaag tctcgaaccc gagacctacc      120
gctcatgggc gaaggtactt gccatcgca                                       149
```

<210> SEQ ID NO 79
<211> LENGTH: 161
<212> TYPE: DNA
<213> ORGANISM: Artificial sequence
<220> FEATURE:
<223> OTHER INFORMATION: InDel marker C13097

<400> SEQUENCE: 79

```
agaggtcgca cttggtgcga tgacaagtgc cttcgcccat gagcggtagg tctcgggttc      60
gagacttggg agcagcctct ccataaatgg gggtaaggct agccgacatt cacctctctc     120
agaccctgcg taaagcggga gccttgtgca ctggatacga c                         161
```

<210> SEQ ID NO 80
<211> LENGTH: 163
<212> TYPE: DNA
<213> ORGANISM: Artificial sequence
<220> FEATURE:
<223> OTHER INFORMATION: InDel marker C13098

<400> SEQUENCE: 80

```
aaaggtcgta cccagtgcac aaggctcccg ctttacgcag ggtctgggag aggtgaatgt      60
cggctagcca taccccatt tatggagagg ctgctcccaa gtctcgaacc cgagacctac     120
cgctcatggg cgaaggcact tgccatcgca ccaagtgcga cct                       163
```

<210> SEQ ID NO 81
<211> LENGTH: 172
<212> TYPE: DNA
<213> ORGANISM: Artificial sequence
<220> FEATURE:
<223> OTHER INFORMATION: InDel marker C13100

<400> SEQUENCE: 81

```
atgctgccga acttcacaaa tgtcacacga caccattctt tccccatcgt cttcctttgc      60
tccacaggga cagtgcacga catagttgat tgctccacat tcatacatct cactaactcc     120
```

```
acccgtctct tgctactcc taccctcaag cacaatattt tgacccacct ca          172
```

<210> SEQ ID NO 82
<211> LENGTH: 204
<212> TYPE: DNA
<213> ORGANISM: Artificial sequence
<220> FEATURE:
<223> OTHER INFORMATION: InDel marker C13101

<400> SEQUENCE: 82

```
gatggcaatt ttggaaaatt caacttctct tgctttccaa acattgttcg tcttcggctt   60
cgtgcaagcg gactcaaggg cagcattcca tctgaaatag gtactctttc caagctcaag  120
caccttgacc tttcttacaa tcaaattact ggttatatcc cttcaagtct tggaacttg   180
aaaaacttgg tcayccttca acta                                         204
```

<210> SEQ ID NO 83
<211> LENGTH: 342
<212> TYPE: DNA
<213> ORGANISM: Artificial sequence
<220> FEATURE:
<223> OTHER INFORMATION: InDel marker C13102

<400> SEQUENCE: 83

```
gcggctgatt ttatagctca tgtgtgggag aaaaagtgct cgtatgatgg ccagctgaag   60
gtctaatggg gcaatacaca gttaacggag aagagattgt tactgggcat gtttggtcaa  120
tgccgaaata caacagcagg aaccaagggg agctgaagga gcttgaagca ttcttacaac  180
gctcttagga aagaattcag gctagttttc aagaagttgg actcgaataa tgaacgactt  240
agtgatgatg ggaagagtat gatgtacgag ctgaaatggg ttgaaaagtc aatgcatttg  300
caagagcccg atgttcctgg ggatgcggcg atgctgagcc tt                     342
```

<210> SEQ ID NO 84
<211> LENGTH: 170
<212> TYPE: DNA
<213> ORGANISM: Artificial sequence
<220> FEATURE:
<223> OTHER INFORMATION: InDel marker C14104

<400> SEQUENCE: 84

```
aaaaaaaggt cgtacccagt gcacaaggct tccgctttac gcagggtctg ggagaggtga   60
atgtcggcta gccttacccc catttatgga gaggctgctc ccaagtctcg aacccgagac  120
ctaccgctca tgggcgaagg cacttgccat cgcaccaagt gcgacctctt              170
```

<210> SEQ ID NO 85
<211> LENGTH: 364
<212> TYPE: DNA
<213> ORGANISM: Artificial sequence
<220> FEATURE:
<223> OTHER INFORMATION: InDel marker C14105

<400> SEQUENCE: 85

```
aacgtttttt gtttcttcaa gagaagtttg ggtaaagctt taaagagtac ttgttctttt   60
wgtaatcctg ttttgacaat cctctggttg catgaattgt tacccttttc caatttgtgc  120
tcgctttgga ttgttgtttt cgcaaataat wtactcaaat tttccatggg atggtactcg  180
ttgtatttgg aatcaatata ttaggtgcag tggttatttt atttgatcaa taatctgta   240
gaattcgtat gttttttgtaa cgttttttgt ttcttcaaga gaagtttggg taaagcttta  300
```

```
aagagtactt gttcttttg taatcctgtt ttgacaatcc tctggttgca tgaattgtta    360
ccct                                                                364

<210> SEQ ID NO 86
<211> LENGTH: 372
<212> TYPE: DNA
<213> ORGANISM: Artificial sequence
<220> FEATURE:
<223> OTHER INFORMATION: InDel marker C14108

<400> SEQUENCE: 86
ggctggtttg rtattgctgt gctttgaaaa aaagctgctg tgagaataag cggctgtgct    60
gtgagaataa gcggctgtga aataaatcag tagagtgttt ggtaaacttt tttgtaaaag   120
tgcttttgga aaaaaagca gtctgatagt gggtcttttc attaaaggag cactgtagtt    180
ctgtgtgctt tgaaaaaaag ccagttttcc aaagctacaa attgcagctt cagctttttc    240
ctttgatttc agcttattct cacatcagct tccaaaataa gccatttttt ttaagtttac    300
caaacaccaa aaacactccc agcttttttt cataggagct ttttttcaaaa tcacctcaat   360 cccaaactgg gg                                                        372

<210> SEQ ID NO 87
<211> LENGTH: 130
<212> TYPE: DNA
<213> ORGANISM: Artificial sequence
<220> FEATURE:
<223> OTHER INFORMATION: InDel marker C15109

<400> SEQUENCE: 87 ttttttttt ttttttaaa acaagatatg caatatcgga cagagatgcc aaaaggttac    60
aagaaagcct accaaagagg caaacaaact gcagcaaata ctaaagaaaa gtagtacaag   120
aaggtacaag                                                         130

<210> SEQ ID NO 88
<211> LENGTH: 162
<212> TYPE: DNA
<213> ORGANISM: Artificial sequence
<220> FEATURE:
<223> OTHER INFORMATION: InDel marker C15110

<400> SEQUENCE: 88
gagaggtcgc acttggtgcg atgacaagtg tcttcgccca tgagcggtag gtctcaggtt    60
cgagacttgg gagcagcctc tccataaatg ggggtaaggc tagccgacat tcacctctcc   120
cagaccctgc gtaaagcgga agccttgtgc actgggtacg ac                      162

<210> SEQ ID NO 89
<211> LENGTH: 159
<212> TYPE: DNA
<213> ORGANISM: Artificial sequence
<220> FEATURE:
<223> OTHER INFORMATION: InDel marker C15111

<400> SEQUENCE: 89
cgaggtcgca cttggtgcga tgcaagtgc cttcgcccat gagcggtagg tctcggttc     60 gagacttggg agcagcctct ccataaatgg gggtaaggct agccgacatt tacctctccc   120
agaccctgcg taaagcggga gccttgtgca ctgggtacg                          159

<210> SEQ ID NO 90
<211> LENGTH: 83
```

```
<212> TYPE: DNA
<213> ORGANISM: Artificial sequence
<220> FEATURE:
<223> OTHER INFORMATION: InDel marker C15114

<400> SEQUENCE: 90
aagtgtgctc tactatgctt gcaaatattt cagtcaagtt attcttgttt atgttcccac    60
aactcattca acaattgttt tgc                                            83

<210> SEQ ID NO 91
<211> LENGTH: 163
<212> TYPE: DNA
<213> ORGANISM: Artificial sequence
<220> FEATURE:
<223> OTHER INFORMATION: InDel marker C15115

<400> SEQUENCE: 91
aaggtcgtac ccagtgcaca aggctcccgc tttaagcagg gtctgggaga ggtgaatgtc    60
ggctagcctt acccccattt atggagaggc tgctcccaag tctcgaaccc gagacctacc   120
gctcatgggc gaaggcactt gccatcgcac caagtgcgac ctc                     163

<210> SEQ ID NO 92
<211> LENGTH: 147
<212> TYPE: DNA
<213> ORGANISM: Artificial sequence
<220> FEATURE:
<223> OTHER INFORMATION: InDel marker C15116

<400> SEQUENCE: 92
gggatgtgct atccacacac ccctttttac ttctcacaca ccccttgtta atttctgtcc    60
gttgatctta ttcaatttat ccgatccaac ggtcgaaaac caaaaaggtg tgggagaagt   120 aaaaagggt gtgtggatat cacaccg                                        147

<210> SEQ ID NO 93
<211> LENGTH: 191
<212> TYPE: DNA
<213> ORGANISM: Artificial sequence
<220> FEATURE:
<223> OTHER INFORMATION: InDel marker C15119

<400> SEQUENCE: 93
cctaagagtg tttagtctaa tggtcaggcc cttggtttgt taccaagagg tctggggttc    60
gacacctctc aaggtaccca cctagcaatt gctagagttt cttgcctacc aaatgttgtg   120
gggtcaggcg ggtggcctag tgagtagtcg ggtcaaagac ccggagacac tagattcaaa   180
aaaaaaaaaa a                                                        191

<210> SEQ ID NO 94
<211> LENGTH: 150
<212> TYPE: DNA
<213> ORGANISM: Artificial sequence
<220> FEATURE:
<223> OTHER INFORMATION: InDel marker C16120

<400> SEQUENCE: 94
aaaactaatg aaaagagctt gaaaacttta agttttaatg ataaggacaa aataaagggt    60
aaagtgaata gtaccaggat tgacttttta gtgtaaaaat gtggttttc gttaaagtga    120 acagtaccgg gtgcttttcg ttaaagttcc                                    150

<210> SEQ ID NO 95
```

-continued

```
<211> LENGTH: 280
<212> TYPE: DNA
<213> ORGANISM: Artificial sequence
<220> FEATURE:
<223> OTHER INFORMATION: InDel marker C16122

<400> SEQUENCE: 95
tggtaatcaa gttcaaarta ctccgcacaa gatactctgg cacttaaaaa aattacaaga      60
agtaaagccc gaaggaacca attcagtcag agtcttgtat ttttcagcac tcaagtccaa     120
gtgtaagttt gccaggaaac cacccaatga aagtactgca agaccagtgc taaggagtaa     180
aacttcgcag taactgtgct cagttccttt cttgatgcca aatataaagg catagttgac     240
acgataacgc ctccagaagt atatgtctgc agcttacatg                            280

<210> SEQ ID NO 96
<211> LENGTH: 143
<212> TYPE: DNA
<213> ORGANISM: Artificial sequence
<220> FEATURE:
<223> OTHER INFORMATION: InDel marker C16123

<400> SEQUENCE: 96
gtcgtaccca gtgcacaagg ctcccgcttt acgcagggtc tgggagaggt gaatgtcggc      60
tagccttacc cccatttatg gagaggccca tttatggaga ggctgctccc atttatggag     120
gtgaatgtcg gctagcctta ccc                                              143

<210> SEQ ID NO 97
<211> LENGTH: 152
<212> TYPE: DNA
<213> ORGANISM: Artificial sequence
<220> FEATURE:
<223> OTHER INFORMATION: InDel marker C16124

<400> SEQUENCE: 97
ggaaaactaa tgaaagggc ttgaaaactt tgaattttaa tgataaggac aaaataaagg       60
gtaaagtgaa tagtaccaga attgacttt tagtgtaaaa atgtggtttt tcgttaaagt      120
gaacagtacc aggtgctttt cgttaaagtt cc                                   152

<210> SEQ ID NO 98
<211> LENGTH: 153
<212> TYPE: DNA
<213> ORGANISM: Artificial sequence
<220> FEATURE:
<223> OTHER INFORMATION: InDel marker C16125

<400> SEQUENCE: 98
aaaggtcgta cccagtgcat aaggctctcg ctttacgcag ggtctgggag aggtgaatgt      60
cggctagcct taccccccatt tatggagagg ctgctcccaa gtctcgaacc cgagacctac    120
cgcttatggg cgaaggcact tgccatcgca cca                                  153

<210> SEQ ID NO 99
<211> LENGTH: 154
<212> TYPE: DNA
<213> ORGANISM: Artificial sequence
<220> FEATURE:
<223> OTHER INFORMATION: InDel marker C17126

<400> SEQUENCE: 99
aggaaaacta atgaaaagga tttgaaaact ttgagtttta atgataagga caaaawaaaa      60
gggtaaagtg aatagtacca ggattgactt tttagtgtaa aatgtggtt tttcgttaaa     120
```
gtgaacagta ccgggtgctt ttcgttaaag ttcc                                154

<210> SEQ ID NO 100
<211> LENGTH: 158
<212> TYPE: DNA
<213> ORGANISM: Artificial sequence
<220> FEATURE:
<223> OTHER INFORMATION: InDel marker C17127

<400> SEQUENCE: 100
ctaagaggtc gcacttggtg cgatgacaag taccttcgcc catgaacggt aggtctcggt    60
tcgagacttg ggagcagcct ctccataaat gggggtaagg ctagccgaca ttcacctctc   120
ccagaccttg cgtaaagcgg gtctgggtac gaccttt                            158

<210> SEQ ID NO 101
<211> LENGTH: 162
<212> TYPE: DNA
<213> ORGANISM: Artificial sequence
<220> FEATURE:
<223> OTHER INFORMATION: InDel marker C17128

<400> SEQUENCE: 101
agaggtcgca cttggtgcga tggcaagtgc tttcgtccat gaacggtagg tctcgggttc    60
gagacttggg agcagcctct ccataaatgg ggtaaggct aaccgacatt cacctctccc   120
agaccctgcg taaagcggga gccttgtgca ctgggtacga cc                      162

<210> SEQ ID NO 102
<211> LENGTH: 198
<212> TYPE: DNA
<213> ORGANISM: Artificial sequence
<220> FEATURE:
<223> OTHER INFORMATION: InDel marker C17129

<400> SEQUENCE: 102
gcgaagagat cccctccgga tctctcccac taaagctcac taatcaatta atccgggtcc    60
ttaaaatttg ataaaacggc tacaaatagg aagctcctta aaaaatcatc ataattttag   120
ccgttggaac aaaatttaaa ggcttgaatt aattgattgg tgagatatgg tgggagagat   180
ccggatggga tctcttcc                                                 198

<210> SEQ ID NO 103
<211> LENGTH: 22
<212> TYPE: DNA
<213> ORGANISM: Artificial sequence
<220> FEATURE:
<223> OTHER INFORMATION: InDel marker(upstream) C01001

<400> SEQUENCE: 103
ctctcttccc ttacagcagc ac                                             22

<210> SEQ ID NO 104
<211> LENGTH: 22
<212> TYPE: DNA
<213> ORGANISM: Artificial sequence
<220> FEATURE:
<223> OTHER INFORMATION: InDel marker(upstream) C01002

<400> SEQUENCE: 104
taatactttt acttcagcac gg                                             22

<210> SEQ ID NO 105

```
<211> LENGTH: 18
<212> TYPE: DNA
<213> ORGANISM: Artificial sequence
<220> FEATURE:
<223> OTHER INFORMATION: InDel marker(upstream) C01003

<400> SEQUENCE: 105
ggcactgcta aggttcta                                                    18

<210> SEQ ID NO 106
<211> LENGTH: 22
<212> TYPE: DNA
<213> ORGANISM: Artificial sequence
<220> FEATURE:
<223> OTHER INFORMATION: InDel marker(upstream) C01004

<400> SEQUENCE: 106
gtgtggtatg ttcctgcctt ga                                               22

<210> SEQ ID NO 107
<211> LENGTH: 18
<212> TYPE: DNA
<213> ORGANISM: Artificial sequence
<220> FEATURE:
<223> OTHER INFORMATION: InDel marker(upstream) C01005

<400> SEQUENCE: 107
tgcatgtggc gaactctt                                                    18

<210> SEQ ID NO 108
<211> LENGTH: 22
<212> TYPE: DNA
<213> ORGANISM: Artificial sequence
<220> FEATURE:
<223> OTHER INFORMATION: InDel marker(upstream) C02006

<400> SEQUENCE: 108
ttggctttgg atttttctt tt                                                22

<210> SEQ ID NO 109
<211> LENGTH: 22
<212> TYPE: DNA
<213> ORGANISM: Artificial sequence
<220> FEATURE:
<223> OTHER INFORMATION: InDel marker(upstream) C02008

<400> SEQUENCE: 109
aaaagagggg aaaaggaaag aa                                               22

<210> SEQ ID NO 110
<211> LENGTH: 22
<212> TYPE: DNA
<213> ORGANISM: Artificial sequence
<220> FEATURE:
<223> OTHER INFORMATION: InDel marker(upstream) C02009

<400> SEQUENCE: 110
gagtttgtgt gaggtaatgg aa                                               22

<210> SEQ ID NO 111
<211> LENGTH: 22
<212> TYPE: DNA
<213> ORGANISM: Artificial sequence
<220> FEATURE:
<223> OTHER INFORMATION: InDel marker(upstream) C03011

<400> SEQUENCE: 111
```
aggttttctc ctgctgctct at					22

<210> SEQ ID NO 112
<211> LENGTH: 22
<212> TYPE: DNA
<213> ORGANISM: Artificial sequence
<220> FEATURE:
<223> OTHER INFORMATION: InDel marker(upstream) C03012

<400> SEQUENCE: 112
ccagtccaaa tcaaaccaca ac					22

<210> SEQ ID NO 113
<211> LENGTH: 22
<212> TYPE: DNA
<213> ORGANISM: Artificial sequence
<220> FEATURE:
<223> OTHER INFORMATION: InDel marker(upstream) C03014

<400> SEQUENCE: 113
ttcattattg ggcgatgtgc tc					22

<210> SEQ ID NO 114
<211> LENGTH: 22
<212> TYPE: DNA
<213> ORGANISM: Artificial sequence
<220> FEATURE:
<223> OTHER INFORMATION: InDel marker(upstream) C03017

<400> SEQUENCE: 114
tgggtcaaaa atcctcatct ac					22

<210> SEQ ID NO 115
<211> LENGTH: 22
<212> TYPE: DNA
<213> ORGANISM: Artificial sequence
<220> FEATURE:
<223> OTHER INFORMATION: InDel marker(upstream) C03018

<400> SEQUENCE: 115
ggcggcagca ggaacaggtg gt					22

<210> SEQ ID NO 116
<211> LENGTH: 18
<212> TYPE: DNA
<213> ORGANISM: Artificial sequence
<220> FEATURE:
<223> OTHER INFORMATION: InDel marker(upstream) C04019

<400> SEQUENCE: 116
ctggcacagg atacaagc					18

<210> SEQ ID NO 117
<211> LENGTH: 22
<212> TYPE: DNA
<213> ORGANISM: Artificial sequence
<220> FEATURE:
<223> OTHER INFORMATION: InDel marker(upstream) C04020

<400> SEQUENCE: 117
cacacaaaca gaagggcacg ga					22

<210> SEQ ID NO 118
<211> LENGTH: 22
<212> TYPE: DNA

-continued

<213> ORGANISM: Artificial sequence
<220> FEATURE:
<223> OTHER INFORMATION: InDel marker(upstream) C04021

<400> SEQUENCE: 118
acttgttttc ttccatttgt gc                                    22

<210> SEQ ID NO 119
<211> LENGTH: 22
<212> TYPE: DNA
<213> ORGANISM: Artificial sequence
<220> FEATURE:
<223> OTHER INFORMATION: InDel marker(upstream) C04022

<400> SEQUENCE: 119
attgtttgcg aatagaatga gt                                    22

<210> SEQ ID NO 120
<211> LENGTH: 22
<212> TYPE: DNA
<213> ORGANISM: Artificial sequence
<220> FEATURE:
<223> OTHER INFORMATION: InDel marker(upstream) C04023

<400> SEQUENCE: 120
cgaaagaacc atcctaacta at                                    22

<210> SEQ ID NO 121
<211> LENGTH: 22
<212> TYPE: DNA
<213> ORGANISM: Artificial sequence
<220> FEATURE:
<223> OTHER INFORMATION: InDel marker(upstream) C04024

<400> SEQUENCE: 121
tcctaccctg ccttggagtt tg                                    22

<210> SEQ ID NO 122
<211> LENGTH: 18
<212> TYPE: DNA
<213> ORGANISM: Artificial sequence
<220> FEATURE:
<223> OTHER INFORMATION: InDel marker(upstream) C04133

<400> SEQUENCE: 122
aggaagtgga ggcaaggt                                         18

<210> SEQ ID NO 123
<211> LENGTH: 22
<212> TYPE: DNA
<213> ORGANISM: Artificial sequence
<220> FEATURE:
<223> OTHER INFORMATION: InDel marker(upstream) C04134

<400> SEQUENCE: 123
agaaaattaa gaacgcaaac aa                                    22

<210> SEQ ID NO 124
<211> LENGTH: 22
<212> TYPE: DNA
<213> ORGANISM: Artificial sequence
<220> FEATURE:
<223> OTHER INFORMATION: InDel marker(upstream) C05026

<400> SEQUENCE: 124
cacacgataa atgctacttc ac                                    22

<210> SEQ ID NO 125
<211> LENGTH: 18
<212> TYPE: DNA
<213> ORGANISM: Artificial sequence
<220> FEATURE:
<223> OTHER INFORMATION: InDel marker(upstream) C05028

<400> SEQUENCE: 125
agggaccgca actaaact                                                18

<210> SEQ ID NO 126
<211> LENGTH: 22
<212> TYPE: DNA
<213> ORGANISM: Artificial sequence
<220> FEATURE:
<223> OTHER INFORMATION: InDel marker(upstream) C05029

<400> SEQUENCE: 126
gtttgctgct ggagtagaat cg                                            22

<210> SEQ ID NO 127
<211> LENGTH: 22
<212> TYPE: DNA
<213> ORGANISM: Artificial sequence
<220> FEATURE:
<223> OTHER INFORMATION: InDel marker(upstream) C05030

<400> SEQUENCE: 127
cctacataac attagtgaga aa                                            22

<210> SEQ ID NO 128
<211> LENGTH: 22
<212> TYPE: DNA
<213> ORGANISM: Artificial sequence
<220> FEATURE:
<223> OTHER INFORMATION: InDel marker(upstream) C05031

<400> SEQUENCE: 128
tacggagcca caacccacca ac                                            22

<210> SEQ ID NO 129
<211> LENGTH: 22
<212> TYPE: DNA
<213> ORGANISM: Artificial sequence
<220> FEATURE:
<223> OTHER INFORMATION: InDel marker(upstream) C05032

<400> SEQUENCE: 129
ttggttttca cttagtttgt tt                                            22

<210> SEQ ID NO 130
<211> LENGTH: 22
<212> TYPE: DNA
<213> ORGANISM: Artificial sequence
<220> FEATURE:
<223> OTHER INFORMATION: InDel marker(upstream) C05135

<400> SEQUENCE: 130
tctttgtaac ttcttcctcc ac                                            22

<210> SEQ ID NO 131
<211> LENGTH: 22
<212> TYPE: DNA
<213> ORGANISM: Artificial sequence
<220> FEATURE:

```
<223> OTHER INFORMATION: InDel marker(upstream) C06037

<400> SEQUENCE: 131
aactagatca atcaagccac at                                              22

<210> SEQ ID NO 132
<211> LENGTH: 22
<212> TYPE: DNA
<213> ORGANISM: Artificial sequence
<220> FEATURE:
<223> OTHER INFORMATION: InDel marker(upstream) C06038

<400> SEQUENCE: 132
acccaaaaga aacctaagcc aa                                              22

<210> SEQ ID NO 133
<211> LENGTH: 22
<212> TYPE: DNA
<213> ORGANISM: Artificial sequence
<220> FEATURE:
<223> OTHER INFORMATION: InDel marker(upstream) C06039

<400> SEQUENCE: 133
aaaactccac ctcactaact tg                                              22

<210> SEQ ID NO 134
<211> LENGTH: 22
<212> TYPE: DNA
<213> ORGANISM: Artificial sequence
<220> FEATURE:
<223> OTHER INFORMATION: InDel marker(upstream) C06040

<400> SEQUENCE: 134
ttgacgaagg gcaagagaac at                                              22

<210> SEQ ID NO 135
<211> LENGTH: 22
<212> TYPE: DNA
<213> ORGANISM: Artificial sequence
<220> FEATURE:
<223> OTHER INFORMATION: InDel marker(upstream) C06041

<400> SEQUENCE: 135
ttctctgtat ttggtaggat tt                                              22

<210> SEQ ID NO 136
<211> LENGTH: 22
<212> TYPE: DNA
<213> ORGANISM: Artificial sequence
<220> FEATURE:
<223> OTHER INFORMATION: InDel marker(upstream) C06137

<400> SEQUENCE: 136
cggttgaaac gaggtgtgta ga                                              22

<210> SEQ ID NO 137
<211> LENGTH: 18
<212> TYPE: DNA
<213> ORGANISM: Artificial sequence
<220> FEATURE:
<223> OTHER INFORMATION: InDel marker(upstream) C07043

<400> SEQUENCE: 137
tggcaaactt accgtgtc                                                   18
```

-continued

```
<210> SEQ ID NO 138
<211> LENGTH: 18
<212> TYPE: DNA
<213> ORGANISM: Artificial sequence
<220> FEATURE:
<223> OTHER INFORMATION: InDel marker(upstream) C07044

<400> SEQUENCE: 138
tggtggaggt ggcgagaa                                                 18

<210> SEQ ID NO 139
<211> LENGTH: 18
<212> TYPE: DNA
<213> ORGANISM: Artificial sequence
<220> FEATURE:
<223> OTHER INFORMATION: InDel marker(upstream) C07045

<400> SEQUENCE: 139
ctgcaaacac cgactcac                                                 18

<210> SEQ ID NO 140
<211> LENGTH: 22
<212> TYPE: DNA
<213> ORGANISM: Artificial sequence
<220> FEATURE:
<223> OTHER INFORMATION: InDel marker(upstream) C07047

<400> SEQUENCE: 140
gtttcttatc ccttactcat ca                                            22

<210> SEQ ID NO 141
<211> LENGTH: 22
<212> TYPE: DNA
<213> ORGANISM: Artificial sequence
<220> FEATURE:
<223> OTHER INFORMATION: InDel marker(upstream) C07048

<400> SEQUENCE: 141
ttgttcagtg gtctgttgct ct                                            22

<210> SEQ ID NO 142
<211> LENGTH: 22
<212> TYPE: DNA
<213> ORGANISM: Artificial sequence
<220> FEATURE:
<223> OTHER INFORMATION: InDel marker(upstream) C07049

<400> SEQUENCE: 142
gttgttttac tgatttttac tc                                            22

<210> SEQ ID NO 143
<211> LENGTH: 22
<212> TYPE: DNA
<213> ORGANISM: Artificial sequence
<220> FEATURE:
<223> OTHER INFORMATION: InDel marker(upstream) C07050

<400> SEQUENCE: 143
atcacaccga ctctcaaaat gg                                            22

<210> SEQ ID NO 144
<211> LENGTH: 22
<212> TYPE: DNA
<213> ORGANISM: Artificial sequence
<220> FEATURE:
<223> OTHER INFORMATION: InDel marker(upstream) C07138
```

<400> SEQUENCE: 144
agaaaggttt tttacgagaa tc                                      22

<210> SEQ ID NO 145
<211> LENGTH: 22
<212> TYPE: DNA
<213> ORGANISM: Artificial sequence
<220> FEATURE:
<223> OTHER INFORMATION: InDel marker(upstream) C08051

<400> SEQUENCE: 145
cttttccact ctctcacact cc                                      22

<210> SEQ ID NO 146
<211> LENGTH: 18
<212> TYPE: DNA
<213> ORGANISM: Artificial sequence
<220> FEATURE:
<223> OTHER INFORMATION: InDel marker(upstream) C08052

<400> SEQUENCE: 146
cggtttgact gttgttcg                                           18

<210> SEQ ID NO 147
<211> LENGTH: 22
<212> TYPE: DNA
<213> ORGANISM: Artificial sequence
<220> FEATURE:
<223> OTHER INFORMATION: InDel marker(upstream) C08054

<400> SEQUENCE: 147
aatcaggtaa ataaaaggaa tc                                      22

<210> SEQ ID NO 148
<211> LENGTH: 22
<212> TYPE: DNA
<213> ORGANISM: Artificial sequence
<220> FEATURE:
<223> OTHER INFORMATION: InDel marker(upstream) C08055

<400> SEQUENCE: 148
tcacaaagca aaaacaacca ag                                      22

<210> SEQ ID NO 149
<211> LENGTH: 22
<212> TYPE: DNA
<213> ORGANISM: Artificial sequence
<220> FEATURE:
<223> OTHER INFORMATION: InDel marker(upstream) C08056

<400> SEQUENCE: 149
ttgagtttat ttcttggttg ta                                      22

<210> SEQ ID NO 150
<211> LENGTH: 22
<212> TYPE: DNA
<213> ORGANISM: Artificial sequence
<220> FEATURE:
<223> OTHER INFORMATION: InDel marker(upstream) C08057

<400> SEQUENCE: 150
gcctccttca aatccttatc ac                                      22

<210> SEQ ID NO 151
<211> LENGTH: 22

```
<212> TYPE: DNA
<213> ORGANISM: Artificial sequence
<220> FEATURE:
<223> OTHER INFORMATION: InDel marker(upstream) C08058

<400> SEQUENCE: 151
tctctgatgc ttgtgaccgt ta                                              22

<210> SEQ ID NO 152
<211> LENGTH: 22
<212> TYPE: DNA
<213> ORGANISM: Artificial sequence
<220> FEATURE:
<223> OTHER INFORMATION: InDel marker(upstream) C08059

<400> SEQUENCE: 152
aatacaacga acaaccaca cc                                               22

<210> SEQ ID NO 153
<211> LENGTH: 22
<212> TYPE: DNA
<213> ORGANISM: Artificial sequence
<220> FEATURE:
<223> OTHER INFORMATION: InDel marker(upstream) C08060

<400> SEQUENCE: 153
gcctttagag aactcggcac ct                                              22

<210> SEQ ID NO 154
<211> LENGTH: 22
<212> TYPE: DNA
<213> ORGANISM: Artificial sequence
<220> FEATURE:
<223> OTHER INFORMATION: InDel marker(upstream) C09062

<400> SEQUENCE: 154
tgagaaccaa tgaatcccag ag                                              22

<210> SEQ ID NO 155
<211> LENGTH: 22
<212> TYPE: DNA
<213> ORGANISM: Artificial sequence
<220> FEATURE:
<223> OTHER INFORMATION: InDel marker(upstream) C09063

<400> SEQUENCE: 155
agtgcgggca gagattggag aa                                              22

<210> SEQ ID NO 156
<211> LENGTH: 22
<212> TYPE: DNA
<213> ORGANISM: Artificial sequence
<220> FEATURE:
<223> OTHER INFORMATION: InDel marker(upstream) C09064

<400> SEQUENCE: 156
gagggttaca aagtctcaca aa                                              22

<210> SEQ ID NO 157
<211> LENGTH: 22
<212> TYPE: DNA
<213> ORGANISM: Artificial sequence
<220> FEATURE:
<223> OTHER INFORMATION: InDel marker(upstream) C09067

<400> SEQUENCE: 157
```
atttgtttct tttatgagtg tt 22

<210> SEQ ID NO 158
<211> LENGTH: 22
<212> TYPE: DNA
<213> ORGANISM: Artificial sequence
<220> FEATURE:
<223> OTHER INFORMATION: InDel marker(upstream) C09068

<400> SEQUENCE: 158
ctgttttcta cggtgctctg gc 22

<210> SEQ ID NO 159
<211> LENGTH: 21
<212> TYPE: DNA
<213> ORGANISM: Artificial sequence
<220> FEATURE:
<223> OTHER INFORMATION: InDel marker(upstream) C10070

<400> SEQUENCE: 159
cactctgact cgtaggaccc c 21

<210> SEQ ID NO 160
<211> LENGTH: 21
<212> TYPE: DNA
<213> ORGANISM: Artificial sequence
<220> FEATURE:
<223> OTHER INFORMATION: InDel marker(upstream) C10071

<400> SEQUENCE: 160
ttcccaactt cggttccttt c 21

<210> SEQ ID NO 161
<211> LENGTH: 18
<212> TYPE: DNA
<213> ORGANISM: Artificial sequence
<220> FEATURE:
<223> OTHER INFORMATION: InDel marker(upstream) C10072

<400> SEQUENCE: 161
acatagaggg tgggacaa 18

<210> SEQ ID NO 162
<211> LENGTH: 18
<212> TYPE: DNA
<213> ORGANISM: Artificial sequence
<220> FEATURE:
<223> OTHER INFORMATION: InDel marker(upstream) C10073

<400> SEQUENCE: 162
aaaatgggcc acttcctt 18

<210> SEQ ID NO 163
<211> LENGTH: 22
<212> TYPE: DNA
<213> ORGANISM: Artificial sequence
<220> FEATURE:
<223> OTHER INFORMATION: InDel marker(upstream) C10136

<400> SEQUENCE: 163 aatctttgggt ttttcgtggt tc 22

<210> SEQ ID NO 164
<211> LENGTH: 21
<212> TYPE: DNA
<213> ORGANISM: Artificial sequence

```
<220> FEATURE:
<223> OTHER INFORMATION: InDel marker(upstream) C11077

<400> SEQUENCE: 164
gccgatttgt tttgatacta a                                              21

<210> SEQ ID NO 165
<211> LENGTH: 22
<212> TYPE: DNA
<213> ORGANISM: Artificial sequence
<220> FEATURE:
<223> OTHER INFORMATION: InDel marker(upstream) C11078

<400> SEQUENCE: 165
tggcagggga agaagagaaa aa                                             22

<210> SEQ ID NO 166
<211> LENGTH: 22
<212> TYPE: DNA
<213> ORGANISM: Artificial sequence
<220> FEATURE:
<223> OTHER INFORMATION: InDel marker(upstream) C11079

<400> SEQUENCE: 166
atgaagtgat gaagtatgtg gg                                             22

<210> SEQ ID NO 167
<211> LENGTH: 22
<212> TYPE: DNA
<213> ORGANISM: Artificial sequence
<220> FEATURE:
<223> OTHER INFORMATION: InDel marker(upstream) C11080

<400> SEQUENCE: 167
tttggtggat tccttagagt gg                                             22

<210> SEQ ID NO 168
<211> LENGTH: 22
<212> TYPE: DNA
<213> ORGANISM: Artificial sequence
<220> FEATURE:
<223> OTHER INFORMATION: InDel marker(upstream) C11081

<400> SEQUENCE: 168
taccttcttt gccttctctt at                                             22

<210> SEQ ID NO 169
<211> LENGTH: 21
<212> TYPE: DNA
<213> ORGANISM: Artificial sequence
<220> FEATURE:
<223> OTHER INFORMATION: InDel marker(upstream) C11082

<400> SEQUENCE: 169
caataaactg cgaagtggac c                                              21

<210> SEQ ID NO 170
<211> LENGTH: 22
<212> TYPE: DNA
<213> ORGANISM: Artificial sequence
<220> FEATURE:
<223> OTHER INFORMATION: InDel marker(upstream) C12086

<400> SEQUENCE: 170
attattggct tactatctat gg                                             22
```

<210> SEQ ID NO 171
<211> LENGTH: 21
<212> TYPE: DNA
<213> ORGANISM: Artificial sequence
<220> FEATURE:
<223> OTHER INFORMATION: InDel marker(upstream) C12087

<400> SEQUENCE: 171
atcagataga ctacccagac a                                      21

<210> SEQ ID NO 172
<211> LENGTH: 22
<212> TYPE: DNA
<213> ORGANISM: Artificial sequence
<220> FEATURE:
<223> OTHER INFORMATION: InDel marker(upstream) C12088

<400> SEQUENCE: 172
ccctctggag acttagcaat ca                                     22

<210> SEQ ID NO 173
<211> LENGTH: 22
<212> TYPE: DNA
<213> ORGANISM: Artificial sequence
<220> FEATURE:
<223> OTHER INFORMATION: InDel marker(upstream) C12089

<400> SEQUENCE: 173
caagaagaat gggaaagatg tt                                     22

<210> SEQ ID NO 174
<211> LENGTH: 23
<212> TYPE: DNA
<213> ORGANISM: Artificial sequence
<220> FEATURE:
<223> OTHER INFORMATION: InDel marker(upstream) C12090

<400> SEQUENCE: 174
tgtttgtgag agagttggtg atg                                    23

<210> SEQ ID NO 175
<211> LENGTH: 21
<212> TYPE: DNA
<213> ORGANISM: Artificial sequence
<220> FEATURE:
<223> OTHER INFORMATION: InDel marker(upstream) C12091

<400> SEQUENCE: 175
cgagagcgat ttagtctcat t                                      21

<210> SEQ ID NO 176
<211> LENGTH: 22
<212> TYPE: DNA
<213> ORGANISM: Artificial sequence
<220> FEATURE:
<223> OTHER INFORMATION: InDel marker(upstream) C12092

<400> SEQUENCE: 176
cgacatacct ctgaaagtgc ct                                     22

<210> SEQ ID NO 177
<211> LENGTH: 21
<212> TYPE: DNA
<213> ORGANISM: Artificial sequence
<220> FEATURE:
<223> OTHER INFORMATION: InDel marker(upstream) C13093

```
<400> SEQUENCE: 177
aacagccctc tcgccctaaa t                                          21

<210> SEQ ID NO 178
<211> LENGTH: 22
<212> TYPE: DNA
<213> ORGANISM: Artificial sequence
<220> FEATURE:
<223> OTHER INFORMATION: InDel marker(upstream) C12132

<400> SEQUENCE: 178
catttattgg aaggtaggga gt                                         22

<210> SEQ ID NO 179
<211> LENGTH: 23
<212> TYPE: DNA
<213> ORGANISM: Artificial sequence
<220> FEATURE:
<223> OTHER INFORMATION: InDel marker(upstream) C13094

<400> SEQUENCE: 179
ttagaaagaa actactgctg ctc                                        23

<210> SEQ ID NO 180
<211> LENGTH: 22
<212> TYPE: DNA
<213> ORGANISM: Artificial sequence
<220> FEATURE:
<223> OTHER INFORMATION: InDel marker(upstream) C13096

<400> SEQUENCE: 180
cgaacctgta ttatcagaag cc                                         22

<210> SEQ ID NO 181
<211> LENGTH: 22
<212> TYPE: DNA
<213> ORGANISM: Artificial sequence
<220> FEATURE:
<223> OTHER INFORMATION: InDel marker(upstream) C13097

<400> SEQUENCE: 181
cgtcccatta tcgcatcttc ta                                         22

<210> SEQ ID NO 182
<211> LENGTH: 22
<212> TYPE: DNA
<213> ORGANISM: Artificial sequence
<220> FEATURE:
<223> OTHER INFORMATION: InDel marker(upstream) C13098

<400> SEQUENCE: 182
taacccaaga aaataggtga ct                                         22

<210> SEQ ID NO 183
<211> LENGTH: 20
<212> TYPE: DNA
<213> ORGANISM: Artificial sequence
<220> FEATURE:
<223> OTHER INFORMATION: InDel marker(upstream) C13100

<400> SEQUENCE: 183
gaagatgaca ctacggagaa                                            20

<210> SEQ ID NO 184
```

-continued

```
<211> LENGTH: 18
<212> TYPE: DNA
<213> ORGANISM: Artificial sequence
<220> FEATURE:
<223> OTHER INFORMATION: InDel marker(upstream) C13101

<400> SEQUENCE: 184
atttcgctgc cacctgat                                              18

<210> SEQ ID NO 185
<211> LENGTH: 22
<212> TYPE: DNA
<213> ORGANISM: Artificial sequence
<220> FEATURE:
<223> OTHER INFORMATION: InDel marker(upstream) C13102

<400> SEQUENCE: 185
tgtgatgaag aagtggcaac ct                                         22

<210> SEQ ID NO 186
<211> LENGTH: 18
<212> TYPE: DNA
<213> ORGANISM: Artificial sequence
<220> FEATURE:
<223> OTHER INFORMATION: InDel marker(upstream) C14104

<400> SEQUENCE: 186
ttgaggtaaa ggcgaaga                                              18

<210> SEQ ID NO 187
<211> LENGTH: 21
<212> TYPE: DNA
<213> ORGANISM: Artificial sequence
<220> FEATURE:
<223> OTHER INFORMATION: InDel marker(upstream) C14105

<400> SEQUENCE: 187
ggcattccac gattattagt t                                          21

<210> SEQ ID NO 188
<211> LENGTH: 22
<212> TYPE: DNA
<213> ORGANISM: Artificial sequence
<220> FEATURE:
<223> OTHER INFORMATION: InDel marker(upstream) C14108

<400> SEQUENCE: 188
catttgtttt cacgcattct tt                                         22

<210> SEQ ID NO 189
<211> LENGTH: 20
<212> TYPE: DNA
<213> ORGANISM: Artificial sequence
<220> FEATURE:
<223> OTHER INFORMATION: InDel marker(upstream) C15109

<400> SEQUENCE: 189
catagaaaag agtcgcacat                                            20

<210> SEQ ID NO 190
<211> LENGTH: 22
<212> TYPE: DNA
<213> ORGANISM: Artificial sequence
<220> FEATURE:
<223> OTHER INFORMATION: InDel marker(upstream) C15110

<400> SEQUENCE: 190
```

-continued attagatttc tcgccgtagt gt                                          22

<210> SEQ ID NO 191
<211> LENGTH: 22
<212> TYPE: DNA
<213> ORGANISM: Artificial sequence
<220> FEATURE:
<223> OTHER INFORMATION: InDel marker(upstream) C15111

<400> SEQUENCE: 191
ttcttcgaca ataaaggcat ag                                          22

<210> SEQ ID NO 192
<211> LENGTH: 22
<212> TYPE: DNA
<213> ORGANISM: Artificial sequence
<220> FEATURE:
<223> OTHER INFORMATION: InDel marker(upstream) C15114

<400> SEQUENCE: 192
gctgagggtg agaaagataa at                                          22

<210> SEQ ID NO 193
<211> LENGTH: 22
<212> TYPE: DNA
<213> ORGANISM: Artificial sequence
<220> FEATURE:
<223> OTHER INFORMATION: InDel marker(upstream) C15115

<400> SEQUENCE: 193
atggtaggaa aggtgctgga gt                                          22

<210> SEQ ID NO 194
<211> LENGTH: 22
<212> TYPE: DNA
<213> ORGANISM: Artificial sequence
<220> FEATURE:
<223> OTHER INFORMATION: InDel marker(upstream) C15116

<400> SEQUENCE: 194
atctcaaaga cgcctcatac at                                          22

<210> SEQ ID NO 195
<211> LENGTH: 22
<212> TYPE: DNA
<213> ORGANISM: Artificial sequence
<220> FEATURE:
<223> OTHER INFORMATION: InDel marker(upstream) C15119

<400> SEQUENCE: 195
cgaatggaag aataatgatg ag                                          22

<210> SEQ ID NO 196
<211> LENGTH: 22
<212> TYPE: DNA
<213> ORGANISM: Artificial sequence
<220> FEATURE:
<223> OTHER INFORMATION: InDel marker(upstream) C16120

<400> SEQUENCE: 196
agtagattga gaagggttgt gt                                          22

<210> SEQ ID NO 197
<211> LENGTH: 22
<212> TYPE: DNA

<213> ORGANISM: Artificial sequence
<220> FEATURE:
<223> OTHER INFORMATION: InDel marker(upstream) C16122

<400> SEQUENCE: 197
attttgaaag ggtagaaggt ga                                              22

<210> SEQ ID NO 198
<211> LENGTH: 22
<212> TYPE: DNA
<213> ORGANISM: Artificial sequence
<220> FEATURE:
<223> OTHER INFORMATION: InDel marker(upstream) C16123

<400> SEQUENCE: 198
aaaaaatgtg ataaaccaac ga                                              22

<210> SEQ ID NO 199
<211> LENGTH: 22
<212> TYPE: DNA
<213> ORGANISM: Artificial sequence
<220> FEATURE:
<223> OTHER INFORMATION: InDel marker(upstream) C16124

<400> SEQUENCE: 199
ctgtaggatg tcattttcac ga                                              22

<210> SEQ ID NO 200
<211> LENGTH: 22
<212> TYPE: DNA
<213> ORGANISM: Artificial sequence
<220> FEATURE:
<223> OTHER INFORMATION: InDel marker(upstream) C16125

<400> SEQUENCE: 200
tttcctaaga atctctcacc tg                                              22

<210> SEQ ID NO 201
<211> LENGTH: 22
<212> TYPE: DNA
<213> ORGANISM: Artificial sequence
<220> FEATURE:
<223> OTHER INFORMATION: InDel marker(upstream) C17126

<400> SEQUENCE: 201
gtgacaaaaa gggataggag ag                                              22

<210> SEQ ID NO 202
<211> LENGTH: 22
<212> TYPE: DNA
<213> ORGANISM: Artificial sequence
<220> FEATURE:
<223> OTHER INFORMATION: InDel marker(upstream) C17127

<400> SEQUENCE: 202
aaaggcactc accacaatcc aa                                              22

<210> SEQ ID NO 203
<211> LENGTH: 22
<212> TYPE: DNA
<213> ORGANISM: Artificial sequence
<220> FEATURE:
<223> OTHER INFORMATION: InDel marker(upstream) C17128

<400> SEQUENCE: 203
aacggctcat tctttctact tc                                              22

```
<210> SEQ ID NO 204
<211> LENGTH: 22
<212> TYPE: DNA
<213> ORGANISM: Artificial sequence
<220> FEATURE:
<223> OTHER INFORMATION: InDel marker(upstream) C17129

<400> SEQUENCE: 204
gaccaccttt ggagcactaa ta                                        22

<210> SEQ ID NO 205
<211> LENGTH: 22
<212> TYPE: DNA
<213> ORGANISM: Artificial sequence
<220> FEATURE:
<223> OTHER INFORMATION: InDel marker(downstream) C01001

<400> SEQUENCE: 205
tagcacatct tatcacatcc at                                        22

<210> SEQ ID NO 206
<211> LENGTH: 22
<212> TYPE: DNA
<213> ORGANISM: Artificial sequence
<220> FEATURE:
<223> OTHER INFORMATION: InDel marker(downstream) C01002

<400> SEQUENCE: 206
atagaatctt cagggatac tc                                         22

<210> SEQ ID NO 207
<211> LENGTH: 18
<212> TYPE: DNA
<213> ORGANISM: Artificial sequence
<220> FEATURE:
<223> OTHER INFORMATION: InDel marker(downstream) C01003

<400> SEQUENCE: 207
gtacacgtcg catttctc                                             18

<210> SEQ ID NO 208
<211> LENGTH: 22
<212> TYPE: DNA
<213> ORGANISM: Artificial sequence
<220> FEATURE:
<223> OTHER INFORMATION: InDel marker(downstream) C01004

<400> SEQUENCE: 208
gctcctttca gcagtctcta tt                                        22

<210> SEQ ID NO 209
<211> LENGTH: 18
<212> TYPE: DNA
<213> ORGANISM: Artificial sequence
<220> FEATURE:
<223> OTHER INFORMATION: InDel marker(downstream) C01005

<400> SEQUENCE: 209
tcaaccaggg agcgatgt                                             18

<210> SEQ ID NO 210
<211> LENGTH: 22
<212> TYPE: DNA
<213> ORGANISM: Artificial sequence
<220> FEATURE:
```

<223> OTHER INFORMATION: InDel marker(downstream) C02006

<400> SEQUENCE: 210
attctttctc tctttccttg tt                           22

<210> SEQ ID NO 211
<211> LENGTH: 22
<212> TYPE: DNA
<213> ORGANISM: Artificial sequence
<220> FEATURE:
<223> OTHER INFORMATION: InDel marker(downstream) C02008

<400> SEQUENCE: 211
caatcggaaa gcgagttgaa gt                           22

<210> SEQ ID NO 212
<211> LENGTH: 22
<212> TYPE: DNA
<213> ORGANISM: Artificial sequence
<220> FEATURE:
<223> OTHER INFORMATION: InDel marker(downstream) C02009

<400> SEQUENCE: 212
agattggaag tttggagttt ga                           22

<210> SEQ ID NO 213
<211> LENGTH: 22
<212> TYPE: DNA
<213> ORGANISM: Artificial sequence
<220> FEATURE:
<223> OTHER INFORMATION: InDel marker(downstream) C03011

<400> SEQUENCE: 213
ttttcctcct cccttacttc tt                           22

<210> SEQ ID NO 214
<211> LENGTH: 22
<212> TYPE: DNA
<213> ORGANISM: Artificial sequence
<220> FEATURE:
<223> OTHER INFORMATION: InDel marker(downstream) C03012

<400> SEQUENCE: 214
tccaaagcga gtaaaagcaa gc                           22

<210> SEQ ID NO 215
<211> LENGTH: 22
<212> TYPE: DNA
<213> ORGANISM: Artificial sequence
<220> FEATURE:
<223> OTHER INFORMATION: InDel marker(downstream) C03014

<400> SEQUENCE: 215 ccctttccc taccttgtgt gc                            22

<210> SEQ ID NO 216
<211> LENGTH: 22
<212> TYPE: DNA
<213> ORGANISM: Artificial sequence
<220> FEATURE:
<223> OTHER INFORMATION: InDel marker(downstream) C03017

<400> SEQUENCE: 216
tcatctaact acaacggcta ca                           22

-continued

```
<210> SEQ ID NO 217
<211> LENGTH: 22
<212> TYPE: DNA
<213> ORGANISM: Artificial sequence
<220> FEATURE:
<223> OTHER INFORMATION: InDel marker(downstream) C03018

<400> SEQUENCE: 217
ttcagttatc gtgtcaaatg ga                                            22

<210> SEQ ID NO 218
<211> LENGTH: 18
<212> TYPE: DNA
<213> ORGANISM: Artificial sequence
<220> FEATURE:
<223> OTHER INFORMATION: InDel marker(downstream) C04019

<400> SEQUENCE: 218
gaggatgcga tgaacaag                                                 18

<210> SEQ ID NO 219
<211> LENGTH: 22
<212> TYPE: DNA
<213> ORGANISM: Artificial sequence
<220> FEATURE:
<223> OTHER INFORMATION: InDel marker(downstream) C04020

<400> SEQUENCE: 219
ggaagagact gaaccccaac ca                                            22

<210> SEQ ID NO 220
<211> LENGTH: 22
<212> TYPE: DNA
<213> ORGANISM: Artificial sequence
<220> FEATURE:
<223> OTHER INFORMATION: InDel marker(downstream) C04021

<400> SEQUENCE: 220
atctccttac tgtcttcaac tt                                            22

<210> SEQ ID NO 221
<211> LENGTH: 22
<212> TYPE: DNA
<213> ORGANISM: Artificial sequence
<220> FEATURE:
<223> OTHER INFORMATION: InDel marker(downstream) C04022

<400> SEQUENCE: 221
gtctgtgacc ttcttgctct ga                                            22

<210> SEQ ID NO 222
<211> LENGTH: 22
<212> TYPE: DNA
<213> ORGANISM: Artificial sequence
<220> FEATURE:
<223> OTHER INFORMATION: InDel marker(downstream) C04023

<400> SEQUENCE: 222
ggtgttatgt tcatccattt ta                                            22

<210> SEQ ID NO 223
<211> LENGTH: 22
<212> TYPE: DNA
<213> ORGANISM: Artificial sequence
<220> FEATURE:
<223> OTHER INFORMATION: InDel marker(downstream) C04024
```

```
<400> SEQUENCE: 223
cattattctt gagcattaca ca                                              22

<210> SEQ ID NO 224
<211> LENGTH: 20
<212> TYPE: DNA
<213> ORGANISM: Artificial sequence
<220> FEATURE:
<223> OTHER INFORMATION: InDel marker(downstream) C04133

<400> SEQUENCE: 224
caaggcaaca tcaagaaata                                                 20

<210> SEQ ID NO 225
<211> LENGTH: 22
<212> TYPE: DNA
<213> ORGANISM: Artificial sequence
<220> FEATURE:
<223> OTHER INFORMATION: InDel marker(downstream) C04134

<400> SEQUENCE: 225
tctcactaac taaggtggga ta                                              22

<210> SEQ ID NO 226
<211> LENGTH: 22
<212> TYPE: DNA
<213> ORGANISM: Artificial sequence
<220> FEATURE:
<223> OTHER INFORMATION: InDel marker(downstream) C05026

<400> SEQUENCE: 226
tttcttagtc tattcactgg ta                                              22

<210> SEQ ID NO 227
<211> LENGTH: 22
<212> TYPE: DNA
<213> ORGANISM: Artificial sequence
<220> FEATURE:
<223> OTHER INFORMATION: InDel marker(downstream) C05028

<400> SEQUENCE: 227
gaggcatctt caacatactt tt                                              22

<210> SEQ ID NO 228
<211> LENGTH: 22
<212> TYPE: DNA
<213> ORGANISM: Artificial sequence
<220> FEATURE:
<223> OTHER INFORMATION: InDel marker(downstream) C05029

<400> SEQUENCE: 228
ttgaaacaac gacaaagaac cc                                              22

<210> SEQ ID NO 229
<211> LENGTH: 22
<212> TYPE: DNA
<213> ORGANISM: Artificial sequence
<220> FEATURE:
<223> OTHER INFORMATION: InDel marker(downstream) C05030

<400> SEQUENCE: 229
tcttccattg aaactttacg ag                                              22

<210> SEQ ID NO 230
<211> LENGTH: 22
```

-continued

<212> TYPE: DNA
<213> ORGANISM: Artificial sequence
<220> FEATURE:
<223> OTHER INFORMATION: InDel marker(downstream) C05031

<400> SEQUENCE: 230
aaaccaatca acaaccgaaa gc                                              22

<210> SEQ ID NO 231
<211> LENGTH: 22
<212> TYPE: DNA
<213> ORGANISM: Artificial sequence
<220> FEATURE:
<223> OTHER INFORMATION: InDel marker(downstream) C05032

<400> SEQUENCE: 231
tttttcttgt catttggctg ct                                              22

<210> SEQ ID NO 232
<211> LENGTH: 22
<212> TYPE: DNA
<213> ORGANISM: Artificial sequence
<220> FEATURE:
<223> OTHER INFORMATION: InDel marker(downstream) C05135

<400> SEQUENCE: 232
gaaacttctc ttatcaatgc ct                                              22

<210> SEQ ID NO 233
<211> LENGTH: 22
<212> TYPE: DNA
<213> ORGANISM: Artificial sequence
<220> FEATURE:
<223> OTHER INFORMATION: InDel marker(downstream) C06037

<400> SEQUENCE: 233
ttagagtaaa cgccttagca ac                                              22

<210> SEQ ID NO 234
<211> LENGTH: 22
<212> TYPE: DNA
<213> ORGANISM: Artificial sequence
<220> FEATURE:
<223> OTHER INFORMATION: InDel marker(downstream) C06038

<400> SEQUENCE: 234
ctccaactca cagagggaaa ga                                              22

<210> SEQ ID NO 235
<211> LENGTH: 22
<212> TYPE: DNA
<213> ORGANISM: Artificial sequence
<220> FEATURE:
<223> OTHER INFORMATION: InDel marker(downstream) C06039

<400> SEQUENCE: 235
tccgtctctc tgtctctatc ct                                              22

<210> SEQ ID NO 236
<211> LENGTH: 22
<212> TYPE: DNA
<213> ORGANISM: Artificial sequence
<220> FEATURE:
<223> OTHER INFORMATION: InDel marker(downstream) C06040

<400> SEQUENCE: 236

-continued

```
ggacgcagaa aagagaaaaa ac                                            22

<210> SEQ ID NO 237
<211> LENGTH: 22
<212> TYPE: DNA
<213> ORGANISM: Artificial sequence
<220> FEATURE:
<223> OTHER INFORMATION: InDel marker(downstream) C06041

<400> SEQUENCE: 237
gattttgctc gctctttggt ct                                            22

<210> SEQ ID NO 238
<211> LENGTH: 22
<212> TYPE: DNA
<213> ORGANISM: Artificial sequence
<220> FEATURE:
<223> OTHER INFORMATION: InDel marker(downstream) C06137

<400> SEQUENCE: 238
aggaacctgg actaatggag aa                                            22

<210> SEQ ID NO 239
<211> LENGTH: 18
<212> TYPE: DNA
<213> ORGANISM: Artificial sequence
<220> FEATURE:
<223> OTHER INFORMATION: InDel marker(downstream) C07043

<400> SEQUENCE: 239
ctttgtgctc gtctggtt                                                 18

<210> SEQ ID NO 240
<211> LENGTH: 18
<212> TYPE: DNA
<213> ORGANISM: Artificial sequence
<220> FEATURE:
<223> OTHER INFORMATION: InDel marker(downstream) C07044

<400> SEQUENCE: 240
gcgaagtgcc ttgcctga                                                 18

<210> SEQ ID NO 241
<211> LENGTH: 18
<212> TYPE: DNA
<213> ORGANISM: Artificial sequence
<220> FEATURE:
<223> OTHER INFORMATION: InDel marker(downstream) C07045

<400> SEQUENCE: 241
tggcattaca gcaccatc                                                 18

<210> SEQ ID NO 242
<211> LENGTH: 22
<212> TYPE: DNA
<213> ORGANISM: Artificial sequence
<220> FEATURE:
<223> OTHER INFORMATION: InDel marker(downstream) C07047

<400> SEQUENCE: 242
gtaaataata gttctttcgg ac                                            22

<210> SEQ ID NO 243
<211> LENGTH: 22
<212> TYPE: DNA
<213> ORGANISM: Artificial sequence
```

```
<220> FEATURE:
<223> OTHER INFORMATION: InDel marker(downstream) C07048

<400> SEQUENCE: 243
ttctccgatt ccttcattct tc                                              22

<210> SEQ ID NO 244
<211> LENGTH: 22
<212> TYPE: DNA
<213> ORGANISM: Artificial sequence
<220> FEATURE:
<223> OTHER INFORMATION: InDel marker(downstream) C07049

<400> SEQUENCE: 244
tttgagatgt atggataggt ag                                              22

<210> SEQ ID NO 245
<211> LENGTH: 22
<212> TYPE: DNA
<213> ORGANISM: Artificial sequence
<220> FEATURE:
<223> OTHER INFORMATION: InDel marker(downstream) C07050

<400> SEQUENCE: 245
gaggaaggta aaaatcgca cg                                               22

<210> SEQ ID NO 246
<211> LENGTH: 22
<212> TYPE: DNA
<213> ORGANISM: Artificial sequence
<220> FEATURE:
<223> OTHER INFORMATION: InDel marker(downstream) C07138

<400> SEQUENCE: 246
ttactatttc ctactcgggt cg                                              22

<210> SEQ ID NO 247
<211> LENGTH: 22
<212> TYPE: DNA
<213> ORGANISM: Artificial sequence
<220> FEATURE:
<223> OTHER INFORMATION: InDel marker(downstream) C08051

<400> SEQUENCE: 247 gcatccctt acaccccctc aa                                               22

<210> SEQ ID NO 248
<211> LENGTH: 18
<212> TYPE: DNA
<213> ORGANISM: Artificial sequence
<220> FEATURE:
<223> OTHER INFORMATION: InDel marker(downstream) C08052

<400> SEQUENCE: 248
taagcagatt gtcccatt                                                   18

<210> SEQ ID NO 249
<211> LENGTH: 22
<212> TYPE: DNA
<213> ORGANISM: Artificial sequence
<220> FEATURE:
<223> OTHER INFORMATION: InDel marker(downstream) C08054

<400> SEQUENCE: 249
ttgctttgag gtaagactgg ag                                              22
```

<210> SEQ ID NO 250
<211> LENGTH: 22
<212> TYPE: DNA
<213> ORGANISM: Artificial sequence
<220> FEATURE:
<223> OTHER INFORMATION: InDel marker(downstream) C08055

<400> SEQUENCE: 250
tcatacaaaa aatacataaa ta                                              22

<210> SEQ ID NO 251
<211> LENGTH: 22
<212> TYPE: DNA
<213> ORGANISM: Artificial sequence
<220> FEATURE:
<223> OTHER INFORMATION: InDel marker(downstream) C08056

<400> SEQUENCE: 251
ctgaaggaat cttttaggtt gg                                              22

<210> SEQ ID NO 252
<211> LENGTH: 22
<212> TYPE: DNA
<213> ORGANISM: Artificial sequence
<220> FEATURE:
<223> OTHER INFORMATION: InDel marker(downstream) C08057

<400> SEQUENCE: 252
aaatagcaag cagcaggtgg tg                                              22

<210> SEQ ID NO 253
<211> LENGTH: 22
<212> TYPE: DNA
<213> ORGANISM: Artificial sequence
<220> FEATURE:
<223> OTHER INFORMATION: InDel marker(downstream) C08058

<400> SEQUENCE: 253
cacctcattc ctttgtttcc tt                                              22

<210> SEQ ID NO 254
<211> LENGTH: 22
<212> TYPE: DNA
<213> ORGANISM: Artificial sequence
<220> FEATURE:
<223> OTHER INFORMATION: InDel marker(downstream) C08059

<400> SEQUENCE: 254
gaacatcaat ctaatgctac ca                                              22

<210> SEQ ID NO 255
<211> LENGTH: 22
<212> TYPE: DNA
<213> ORGANISM: Artificial sequence
<220> FEATURE:
<223> OTHER INFORMATION: InDel marker(downstream) C08060

<400> SEQUENCE: 255
gataagattt gtggctttgc gt                                              22

<210> SEQ ID NO 256
<211> LENGTH: 22
<212> TYPE: DNA
<213> ORGANISM: Artificial sequence
<220> FEATURE:
<223> OTHER INFORMATION: InDel marker(downstream) C09062

```
<400> SEQUENCE: 256
gcaacaaagc attatttacc tc                                              22

<210> SEQ ID NO 257
<211> LENGTH: 22
<212> TYPE: DNA
<213> ORGANISM: Artificial sequence
<220> FEATURE:
<223> OTHER INFORMATION: InDel marker(downstream) C09063

<400> SEQUENCE: 257
ggtaggtcag agagaagagg tt                                              22

<210> SEQ ID NO 258
<211> LENGTH: 22
<212> TYPE: DNA
<213> ORGANISM: Artificial sequence
<220> FEATURE:
<223> OTHER INFORMATION: InDel marker(downstream) C09064

<400> SEQUENCE: 258
tggtttaccg aactgaaatc ta                                              22

<210> SEQ ID NO 259
<211> LENGTH: 22
<212> TYPE: DNA
<213> ORGANISM: Artificial sequence
<220> FEATURE:
<223> OTHER INFORMATION: InDel marker(downstream) C09067

<400> SEQUENCE: 259
atttggtatc ttcttcgttt tc                                              22

<210> SEQ ID NO 260
<211> LENGTH: 22
<212> TYPE: DNA
<213> ORGANISM: Artificial sequence
<220> FEATURE:
<223> OTHER INFORMATION: InDel marker(downstream) C09068

<400> SEQUENCE: 260
tactcgcaaa gtttcccgtt cc                                              22

<210> SEQ ID NO 261
<211> LENGTH: 21
<212> TYPE: DNA
<213> ORGANISM: Artificial sequence
<220> FEATURE:
<223> OTHER INFORMATION: InDel marker(downstream) C10070

<400> SEQUENCE: 261
tcatcttgtc cagcaggttt g                                               21

<210> SEQ ID NO 262
<211> LENGTH: 21
<212> TYPE: DNA
<213> ORGANISM: Artificial sequence
<220> FEATURE:
<223> OTHER INFORMATION: InDel marker(downstream) C10071

<400> SEQUENCE: 262
ggggcacata ctcatccatc t                                               21

<210> SEQ ID NO 263
```

```
<211> LENGTH: 18
<212> TYPE: DNA
<213> ORGANISM: Artificial sequence
<220> FEATURE:
<223> OTHER INFORMATION: InDel marker(downstream) C10072

<400> SEQUENCE: 263
gcaagggaaa gaggagtt                                                     18

<210> SEQ ID NO 264
<211> LENGTH: 18
<212> TYPE: DNA
<213> ORGANISM: Artificial sequence
<220> FEATURE:
<223> OTHER INFORMATION: InDel marker(downstream) C10073

<400> SEQUENCE: 264
ctgctttccg cttcttct                                                     18

<210> SEQ ID NO 265
<211> LENGTH: 22
<212> TYPE: DNA
<213> ORGANISM: Artificial sequence
<220> FEATURE:
<223> OTHER INFORMATION: InDel marker(downstream) C10136

<400> SEQUENCE: 265
ggatgggctt ggctaatgtt gc                                                22

<210> SEQ ID NO 266
<211> LENGTH: 21
<212> TYPE: DNA
<213> ORGANISM: Artificial sequence
<220> FEATURE:
<223> OTHER INFORMATION: InDel marker(downstream) C11077

<400> SEQUENCE: 266
ccaaagtgta aggacaagta a                                                 21

<210> SEQ ID NO 267
<211> LENGTH: 22
<212> TYPE: DNA
<213> ORGANISM: Artificial sequence
<220> FEATURE:
<223> OTHER INFORMATION: InDel marker(downstream) C11078

<400> SEQUENCE: 267
ctgaagcaat cggtaggggt tt                                                22

<210> SEQ ID NO 268
<211> LENGTH: 22
<212> TYPE: DNA
<213> ORGANISM: Artificial sequence
<220> FEATURE:
<223> OTHER INFORMATION: InDel marker(downstream) C11079

<400> SEQUENCE: 268
agatgatttg gtgatagagt ag                                                22

<210> SEQ ID NO 269
<211> LENGTH: 22
<212> TYPE: DNA
<213> ORGANISM: Artificial sequence
<220> FEATURE:
<223> OTHER INFORMATION: InDel marker(downstream) C11080

<400> SEQUENCE: 269
```
ttagttgctt tgttgattgg tt                                              22

<210> SEQ ID NO 270
<211> LENGTH: 22
<212> TYPE: DNA
<213> ORGANISM: Artificial sequence
<220> FEATURE:
<223> OTHER INFORMATION: InDel marker(downstream) C11081

<400> SEQUENCE: 270
agttgtcttt ttccacatct tc                                              22

<210> SEQ ID NO 271
<211> LENGTH: 21
<212> TYPE: DNA
<213> ORGANISM: Artificial sequence
<220> FEATURE:
<223> OTHER INFORMATION: InDel marker(downstream) C11082

<400> SEQUENCE: 271
agcgagcaac tattaggagc a                                               21

<210> SEQ ID NO 272
<211> LENGTH: 21
<212> TYPE: DNA
<213> ORGANISM: Artificial sequence
<220> FEATURE:
<223> OTHER INFORMATION: InDel marker(downstream) C12086

<400> SEQUENCE: 272
cattcaagtc caatcatctg t                                               21

<210> SEQ ID NO 273
<211> LENGTH: 21
<212> TYPE: DNA
<213> ORGANISM: Artificial sequence
<220> FEATURE:
<223> OTHER INFORMATION: InDel marker(downstream) C12087

<400> SEQUENCE: 273
aagggcaaga cagtgaaatc c                                               21

<210> SEQ ID NO 274
<211> LENGTH: 22
<212> TYPE: DNA
<213> ORGANISM: Artificial sequence
<220> FEATURE:
<223> OTHER INFORMATION: InDel marker(downstream) C12088

<400> SEQUENCE: 274
aacacaacaa cgactcccat ct                                              22

<210> SEQ ID NO 275
<211> LENGTH: 22
<212> TYPE: DNA
<213> ORGANISM: Artificial sequence
<220> FEATURE:
<223> OTHER INFORMATION: InDel marker(downstream) C12089

<400> SEQUENCE: 275
aagggttcta caagaggcta ca                                              22

<210> SEQ ID NO 276
<211> LENGTH: 18
<212> TYPE: DNA

```
<213> ORGANISM: Artificial sequence
<220> FEATURE:
<223> OTHER INFORMATION: InDel marker(downstream) C12090

<400> SEQUENCE: 276
ggccttggtg tcgattgt                                                  18

<210> SEQ ID NO 277
<211> LENGTH: 20
<212> TYPE: DNA
<213> ORGANISM: Artificial sequence
<220> FEATURE:
<223> OTHER INFORMATION: InDel marker(downstream) C12091

<400> SEQUENCE: 277
ctttggacat gatggtttgt                                                20

<210> SEQ ID NO 278
<211> LENGTH: 22
<212> TYPE: DNA
<213> ORGANISM: Artificial sequence
<220> FEATURE:
<223> OTHER INFORMATION: InDel marker(downstream) C12092

<400> SEQUENCE: 278
tcaaataaca caagttcctg cc                                             22

<210> SEQ ID NO 279
<211> LENGTH: 21
<212> TYPE: DNA
<213> ORGANISM: Artificial sequence
<220> FEATURE:
<223> OTHER INFORMATION: InDel marker(downstream) C13093

<400> SEQUENCE: 279
aatacgacga catcaggaac a                                              21

<210> SEQ ID NO 280
<211> LENGTH: 22
<212> TYPE: DNA
<213> ORGANISM: Artificial sequence
<220> FEATURE:
<223> OTHER INFORMATION: InDel marker(downstream) C12132

<400> SEQUENCE: 280
tagatgctaa gtgattggga ga                                             22

<210> SEQ ID NO 281
<211> LENGTH: 21
<212> TYPE: DNA
<213> ORGANISM: Artificial sequence
<220> FEATURE:
<223> OTHER INFORMATION: InDel marker(downstream) C13094

<400> SEQUENCE: 281
tctggaatgt ttagttggac g                                              21

<210> SEQ ID NO 282
<211> LENGTH: 22
<212> TYPE: DNA
<213> ORGANISM: Artificial sequence
<220> FEATURE:
<223> OTHER INFORMATION: InDel marker(downstream) C13096

<400> SEQUENCE: 282
cagcacctat gagacctgta ag                                             22
```

<210> SEQ ID NO 283
<211> LENGTH: 22
<212> TYPE: DNA
<213> ORGANISM: Artificial sequence
<220> FEATURE:
<223> OTHER INFORMATION: InDel marker(downstream) C13097

<400> SEQUENCE: 283
atccacattt gttttcttc tt                                    22

<210> SEQ ID NO 284
<211> LENGTH: 22
<212> TYPE: DNA
<213> ORGANISM: Artificial sequence
<220> FEATURE:
<223> OTHER INFORMATION: InDel marker(downstream) C13098

<400> SEQUENCE: 284
catactggat tacaggaaga ag                                   22

<210> SEQ ID NO 285
<211> LENGTH: 20
<212> TYPE: DNA
<213> ORGANISM: Artificial sequence
<220> FEATURE:
<223> OTHER INFORMATION: InDel marker(downstream) C13100

<400> SEQUENCE: 285
gacgacgata accataagaa                                      20

<210> SEQ ID NO 286
<211> LENGTH: 18
<212> TYPE: DNA
<213> ORGANISM: Artificial sequence
<220> FEATURE:
<223> OTHER INFORMATION: InDel marker(downstream) C13101

<400> SEQUENCE: 286
ccaagttgtt caaatccc                                        18

<210> SEQ ID NO 287
<211> LENGTH: 22
<212> TYPE: DNA
<213> ORGANISM: Artificial sequence
<220> FEATURE:
<223> OTHER INFORMATION: InDel marker(downstream) C13102

<400> SEQUENCE: 287
agaccgacaa ctctcaaggg ct                                   22

<210> SEQ ID NO 288
<211> LENGTH: 19
<212> TYPE: DNA
<213> ORGANISM: Artificial sequence
<220> FEATURE:
<223> OTHER INFORMATION: InDel marker(downstream) C14104

<400> SEQUENCE: 288
gaagtcacgg ttgtagttt                                       19

<210> SEQ ID NO 289
<211> LENGTH: 21
<212> TYPE: DNA
<213> ORGANISM: Artificial sequence
<220> FEATURE:

<223> OTHER INFORMATION: InDel marker(downstream) C14105

<400> SEQUENCE: 289
aataccaggg agaacaccac c                                          21

<210> SEQ ID NO 290
<211> LENGTH: 22
<212> TYPE: DNA
<213> ORGANISM: Artificial sequence
<220> FEATURE:
<223> OTHER INFORMATION: InDel marker(downstream) C14108

<400> SEQUENCE: 290
cacatctctc ttccctcttt cc                                         22

<210> SEQ ID NO 291
<211> LENGTH: 18
<212> TYPE: DNA
<213> ORGANISM: Artificial sequence
<220> FEATURE:
<223> OTHER INFORMATION: InDel marker(downstream) C15109

<400> SEQUENCE: 291
gccgatggat aagatgag                                              18

<210> SEQ ID NO 292
<211> LENGTH: 21
<212> TYPE: DNA
<213> ORGANISM: Artificial sequence
<220> FEATURE:
<223> OTHER INFORMATION: InDel marker(downstream) C15110

<400> SEQUENCE: 292
atagggcaga tgagatggat g                                          21

<210> SEQ ID NO 293
<211> LENGTH: 18
<212> TYPE: DNA
<213> ORGANISM: Artificial sequence
<220> FEATURE:
<223> OTHER INFORMATION: InDel marker(downstream) C15111

<400> SEQUENCE: 293
tttgtggtgg ttggttgc                                              18

<210> SEQ ID NO 294
<211> LENGTH: 22
<212> TYPE: DNA
<213> ORGANISM: Artificial sequence
<220> FEATURE:
<223> OTHER INFORMATION: InDel marker(downstream) C15114

<400> SEQUENCE: 294
gatggtgcca atgttgtagt ta                                         22

<210> SEQ ID NO 295
<211> LENGTH: 22
<212> TYPE: DNA
<213> ORGANISM: Artificial sequence
<220> FEATURE:
<223> OTHER INFORMATION: InDel marker(downstream) C15115

<400> SEQUENCE: 295
caatgagtcg cttctaaaat ga                                         22

```
<210> SEQ ID NO 296
<211> LENGTH: 22
<212> TYPE: DNA
<213> ORGANISM: Artificial sequence
<220> FEATURE:
<223> OTHER INFORMATION: InDel marker(downstream) C15116

<400> SEQUENCE: 296
cgggaagaca caacacaaaa ca                                              22

<210> SEQ ID NO 297
<211> LENGTH: 22
<212> TYPE: DNA
<213> ORGANISM: Artificial sequence
<220> FEATURE:
<223> OTHER INFORMATION: InDel marker(downstream) C15119

<400> SEQUENCE: 297
taaaagagag ggcttggtgg ta                                              22

<210> SEQ ID NO 298
<211> LENGTH: 22
<212> TYPE: DNA
<213> ORGANISM: Artificial sequence
<220> FEATURE:
<223> OTHER INFORMATION: InDel marker(downstream) C16120

<400> SEQUENCE: 298
gtgtagttta tccagggaag tt                                              22

<210> SEQ ID NO 299
<211> LENGTH: 22
<212> TYPE: DNA
<213> ORGANISM: Artificial sequence
<220> FEATURE:
<223> OTHER INFORMATION: InDel marker(downstream) C16122

<400> SEQUENCE: 299
tactggatag ggaggagggt gc                                              22

<210> SEQ ID NO 300
<211> LENGTH: 22
<212> TYPE: DNA
<213> ORGANISM: Artificial sequence
<220> FEATURE:
<223> OTHER INFORMATION: InDel marker(downstream) C16123

<400> SEQUENCE: 300
gaaacaagca acaactgaag ag                                              22

<210> SEQ ID NO 301
<211> LENGTH: 22
<212> TYPE: DNA
<213> ORGANISM: Artificial sequence
<220> FEATURE:
<223> OTHER INFORMATION: InDel marker(downstream) C16124

<400> SEQUENCE: 301
ttccaggaga tgtatgggtt ca                                              22

<210> SEQ ID NO 302
<211> LENGTH: 22
<212> TYPE: DNA
<213> ORGANISM: Artificial sequence
<220> FEATURE:
<223> OTHER INFORMATION: InDel marker(downstream) C16125
```

-continued

```
<400> SEQUENCE: 302
ttgtcaaatc taaaaatgtt cc                                        22

<210> SEQ ID NO 303
<211> LENGTH: 22
<212> TYPE: DNA
<213> ORGANISM: Artificial sequence
<220> FEATURE:
<223> OTHER INFORMATION: InDel marker(downstream) C17126

<400> SEQUENCE: 303
ttgaggcttg aatacagaga ta                                        22

<210> SEQ ID NO 304
<211> LENGTH: 22
<212> TYPE: DNA
<213> ORGANISM: Artificial sequence
<220> FEATURE:
<223> OTHER INFORMATION: InDel marker(downstream) C17127

<400> SEQUENCE: 304
atagcccagc ccgcactaaa cc                                        22

<210> SEQ ID NO 305
<211> LENGTH: 22
<212> TYPE: DNA
<213> ORGANISM: Artificial sequence
<220> FEATURE:
<223> OTHER INFORMATION: InDel marker(downstream) C17128

<400> SEQUENCE: 305
atggcttttg cgtctctctc tg                                        22

<210> SEQ ID NO 306
<211> LENGTH: 22
<212> TYPE: DNA
<213> ORGANISM: Artificial sequence
<220> FEATURE:
<223> OTHER INFORMATION: InDel marker(downstream) C17129

<400> SEQUENCE: 306
atgtcattgt ctcaaaagcc ac                                        22
```

INDEL MARKER GENOTYPE DATABASE OF *MALUS* AND USE IN IDENTITY FINGERPRINTING OF GERMPLASM RESOURCES

TECHNICAL FIELD

The disclosure belongs to the technical field of molecular biology, especially relating to an InDel marker genotype database of *Malus* and use in identity fingerprinting of germplasm resources.

Further, this patent application incorporates by reference the Sequence Listing file enclosed herewith having the file name "SEQ.LISTING.txt" which is comprised of 8,080 bytes and has a date of creation of Dec. 1, 2020.

BACKGROUND ART

Apple is one of the five most widely planted fruit trees in the world and has a long history of cultivation. China is a big apple production country, which has the largest cultivation area, output and consumption in the world, and the apple industry occupies an important position in China's agricultural production. Since the founding of New China, apple breeding researchers in China have cultivated hundreds of new varieties through unremitting efforts. However, 'Red Delicious', 'Ralls Janet', 'Golden Delicious', 'Fuji' and 'Jonathan' are the most commonly used breeding parents in cross breeding. Because of the repeated use of backbone parents, the genetic differences between varieties become smaller and the genetic background is narrower, which puts forward higher requirements for accurate identification of apple varieties.

According to the International Convention for the Protection of New Varieties of Plants signed in Paris in 1961, when examining a new plant variety, it is necessary to test its Distinctness, Uniformity and Stability, namely DUS test. Because the traditional field test method is time-consuming and laborious, and is greatly affected by the environment, people gradually focus the new technology of new varieties testing on the fingerprinting technology constructed by DNA molecular markers and the corresponding database, and use it to assist the examination and identification of new varieties.

DNA molecular markers are genetic markers based on DNA polymorphism. Molecular marker technology has gradually developed from RFLP marker, RAPD marker and AFLP marker to SSR marker, and has been widely used. With the popularization of high-throughput sequencing technology in recent years, SNP and InDel as new generation markers have been developed. SNP markers are suitable for a large-scale detection and analysis because of their large number and wide distribution in the genome, and the fact that a large-scale high-throughput automation can be realized without separating DNA according to the fragment size in the process of gene analysis, and therefore they have been widely used in many fields, such as medicine, biology, agronomy and so on. InDel marker, called the most promising molecular marker, is a special type of biallelic genetic marker. The advantages of InDel marker are suitable for constructing multiple electrophoresis, and the whole reaction process can be carried out in a single tube. Compared with other methods, biallelic marker typing can minimize laboratory procedures, thus reducing the risk of pollution, positioning errors or other possible failing reasons. Therefore, InDel marker is a more suitable molecular marker for fingerprinting construction.

At present, InDel markers have been used in mulberry, mustard, sorghum and other crops to identify the specificity of germplasm resources, and achieved ideal results, but there is still no application in apples reported.

SUMMARY OF THE INVENTION

In view of the above, the purpose of the present disclosure is to provide an InDel marker genotype database of whole genome of *Malus* and use in specific identification of germplasm resources thereof.

In order to achieve the purpose of the disclosure, the following technical schemes are provided:

The disclosure provides an InDel marker genotype database of whole genome of *Malus*, the constructing method of the genotype database comprises the following steps: genotyping InDel markers of genomic DNA samples of *Malus* germplasm resources by using primer pairs and multiplex PCR; recording one line data for each *Malus* accession according to the genotypes of InDel markers; collecting all germplasm resources records to obtain an InDel marker genotype database of the whole genome of *Malus*;

the nucleotide sequence of the InDel is set forth in SEQ ID Nos. 1-102;

the nucleotide sequence of the upstream primer of the primer pair is set forth in SEQ ID Nos. 103-204, and the nucleotide sequence of the downstream primer of the primer pair is set forth in SEQ ID Nos. 205-306.

SEQ ID Nos. 103-204 are upstream primers for amplifying SEQ ID Nos. 1-102 in sequence;

SEQ ID Nos. 205-306 are downstream primers for amplifying SEQ ID Nos. 1-102 in sequence;

the condition of each group of the multiplex PCR is shown in the following table:

| Group number | Marker number | Fluorescent label | Marker combination |
|---|---|---|---|
| G1 | 24 | HEX | C06039, C08054, C11078, C15109, C15115, C16124 |
| | | PET | C03012, C04022, C04024, C07044, C09064, C13096 |
| | | NED | C03011, C05028, C08056, C08059, C10073 |
| | | FAM | C02009, C05026, C06037, C13101, C14104, C15110, C15114 |
| G2 | 15 | HEX | C01001, C04019, C09068, C15116, C16120 |
| | | PET | C01002, C03017, C07043, C17127 |
| | | NED | C01003, C06040, C11081, C17126 |
| | | FAM | C05030, C09063 |
| G3 | 9 | HEX | C05032, C07049, C12089 |
| | | PET | C17128 |
| | | NED | C13094 |
| | | FAM | C03018, C08052, C12086, C13093 |

-continued

| Group number | Marker number | Fluorescent label | Marker combination |
|---|---|---|---|
| G4 | 11 | HEX | C01004, C07047, C10070, C12090, C13097 |
| | | NED | C04020, C06038, C08058, C16122 |
| | | FAM | C05029, C15111 |
| G5 | 10 | HEX | C02008, C05031, C12092 |
| | | NED | C11082, C12088 |
| | | FAM | C06041, C07050, C12087, C13100, C13102 |
| G6 | 13 | HEX | C08051, C08057, C14108 |
| | | NED | C01005, C02006, C03014, C04023 |
| | | FAM | C09062, C11077, C11080, C13098, C15119, C16123 |
| G7 | 9 | HEX | C07045, C11079, C17129 |
| | | NED | C07048 |
| | | FAM | C04021, C08060, C12091, C14105, C16125 |
| G8 | 8 | HEX | C05135, C10136 |
| | | NED | C12132, C04133, C06137 |
| | | FAM | C09067, C04134, C07138 |
| G9 | 3 | HEX | C08055 |
| | | NED | C10071 |
| | | FAM | C10072 |

In some embodiments, the reaction procedure of the multiplex PCR is: pre-denaturation at 95° C. for 5 min; denaturation at 95° C. for 30 s, annealing at 55° C. for 90 s, extension at 72° C. for 90 s, 35 cycles; extension at 60° C. for 30 min.

In some embodiments, every 10 µL of the multiplex PCR system includes: 1 µL of 200 ng/µL genomic DNA, 4 µL 2.5× Master Mix I, 1 µL Primer mix and 4 µL ddH$_2$O; the concentration of each pair of primers in the Primer mix is 0.2 µM.

In some embodiments, the genotype combination of all InDel markers of any *Malus* accession in the whole genome InDel marker genotype database of *Malus* is used as molecular identity information for identifying the specificity of the accession.

In some embodiments, the molecular identity information is presented, stored, identified and used in a two-dimensional code.

The disclosure also provides the use of the whole genome InDel marker genotype database of *Malus* in the identification of *Malus* germplasm resources, which comprises the following steps:
  extracting genomic DNA of a sample to be tested, genotyping the genomic DNA by using primer pairs, obtaining InDel marker genotype data of the sample to be tested, and comparing the InDel marker genotype data of the sample to be tested with the data in the whole genome InDel marker genotype database of *Malus* in the above technical scheme;
  when the InDel marker genotype combination of the sample to be tested is the same as the molecular identity information of any germplasm resource in the InDel marker genotype database of the whole genome of *Malus*, it is judged that the sample to be tested has no specificity;
  when the InDel marker genotype combination of the sample to be tested is different from the molecular identity information of all germplasm resources in the InDel marker genotype database of the whole genome of *Malus*, and is different from the molecular identity information of other samples to be tested with known InDel marker genotype combinations, it is judged that the sample to be tested has specificity.

The disclosure also provides the use of the whole genome InDel marker genotype database of *Malus* in paternity testing of *Malus* germplasm resources, which comprises the following steps:
  searching the parents and parents pair of the sample to be tested by using the whole genome InDel marker genotype database of *Malus* described above technical scheme, the search criteria are as follows:
  when the marker genotype of the sample to be tested is D, the genotype of parents is D or DI, and the genotype combination of parents pair is D×D, D×DI, DI×D or DI×DI;
  when the marker genotype of the sample to be tested is I, the genotype of the parent is I or DI, and the genotype combination of the parents pair can be I×I, I×DI, DI×I or DI×DI;
  when the marker genotype of the sample to be tested is DI, the genotype of parents is D, I or DI, and the genotype combination of parents pair is D×I, I×D, D×DI, I×DI, DI×D, DI×I or DI×DI;
  wherein D is deletion homozygous genotype, I is insertion homozygous genotype and DI is insertion deletion heterozygous genotype.

The whole genome InDel marker genotype database of *Malus* provided by the disclosure contains an InDel marker genotype database of 1251 *Malus* germplasm resources, which can be used for specific identification of apple germplasm and parent search. Experiments have proved that the whole genome InDel marker genotype database of *Malus* provided by the disclosure can identify the specificity of apple germplasm simply, efficiently and stably, thus overcoming the limitation that DUS test is easily influenced by environment, and providing a powerful tool for the protection of new apple varieties and the management of germplasm resources.

BRIEF DESCRIPTION OF THE DRAWINGS

FIG. 1 is the first generation sequencing result of the marker set forth in SEQ ID No. 35.

DETAILED DESCRIPTION OF THE EMBODIMENTS

Figure 2:
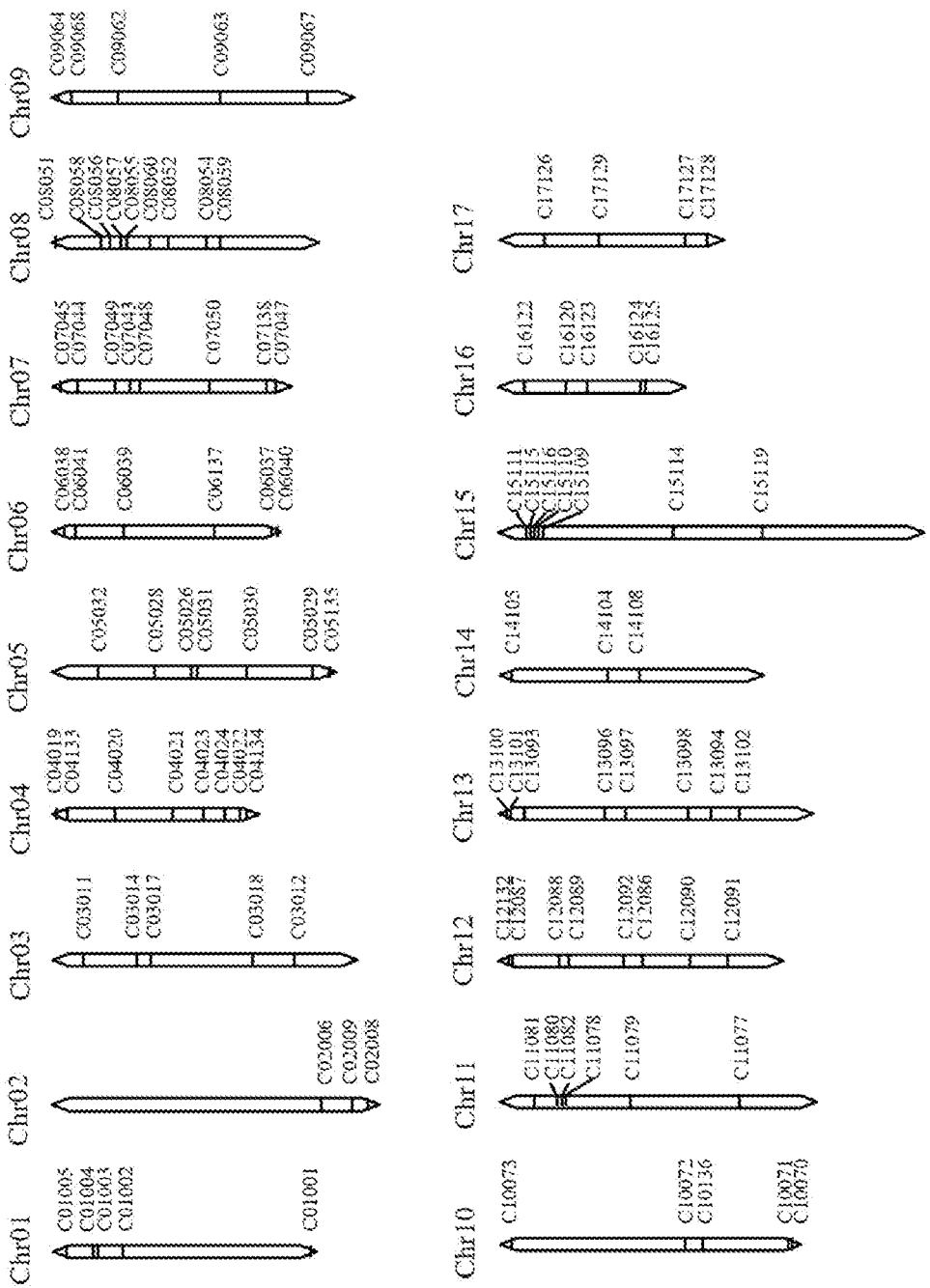
FIG. 2 shows the distribution of 102 InDel markers on the apple genome.

The disclosure provides an InDel marker genotype database of whole genome of *Malus*, the constructing method of the genotype database comprises the following steps: genotyping InDel markers of genomic DNA samples of *Malus* germplasm resources by using primer pairs and multiplex PCR; recording one line data for each *Malus* germplasm resource according to the genotype of InDel marker; collecting all germplasm resources records to obtain an InDel marker genotype database of the whole genome of *Malus*.

The nucleotide sequence of the InDel is set forth in SEQ ID Nos. 1-102.

The nucleotide sequence of the upstream primer of the primer pair is set forth in SEQ ID Nos. 103-204, and the nucleotide sequence of the downstream primer of the primer pair is set forth in SEQ ID Nos. 205-306.

SEQ ID Nos. 103-204 are upstream primers for amplifying SEQ ID Nos. 1-102 in sequence;

SEQ ID Nos. 205-306 are downstream primers for amplifying SEQ ID Nos. 1-102 in sequence;

The condition of each group of the multiplex PCR is shown in the following Table 1:

TABLE 1

| Group number | Marker number | Fluorescent label | Marker combination |
|---|---|---|---|
| G1 | 24 | HEX | C06039, C08054, C11078, C15109, C15115, C16124 |
|  |  | PET | C03012, C04022, C04024, C07044, C09064, C13096 |
|  |  | NED | C03011, C05028, C08056, C08059, C10073 |
|  |  | FAM | C02009, C05026, C06037, C13101, C14104, C15110, C15114 |
| G2 | 15 | HEX | C01001, C04019, C09068, C15116, C16120 |
|  |  | PET | C01002, C03017, C07043, C17127 |
|  |  | NED | C01003, C06040, C11081, C17126 |
|  |  | FAM | C05030, C09063 |
| G3 | 9 | HEX | C05032, C07049, C12089 |
|  |  | PET | C17128 |
|  |  | NED | C13094 |
|  |  | FAM | C03018, C08052, C12086, C13093 |
| G4 | 11 | HEX | C01004, C07047, C10070, C12090, C13097 |
|  |  | NED | C04020, C06038, C08058, C16122 |
|  |  | FAM | C05029, C15111 |
| G5 | 10 | HEX | C02008, C05031, C12092 |
|  |  | NED | C11082, C12088 |
|  |  | FAM | C06041, C07050, C12087, C13100, C13102 |
| G6 | 13 | HEX | C08051, C08057, C14108 |
|  |  | NED | C01005, C02006, C03014, C04023 |
|  |  | FAM | C09062, C11077, C11080, C13098, C15119, C16123 |
| G7 | 9 | HEX | C07045, C11079, C17129 |
|  |  | NED | C07048 |
|  |  | FAM | C04021, C08060, C12091, C14105, C16125 |
| G8 | 8 | HEX | C05135, C10136 |
|  |  | NED | C12132, C04133, C06137 |
|  |  | FAM | C09067, C04134, C07138 |
| G9 | 3 | HEX | C08055 |
|  |  | NED | C10071 |
|  |  | FAM | C10072 |

In some embodiments, the nucleotide sequence of the InDel is set forth in SEQ ID Nos. 1-102. In some embodiments, the InDel: 1) is uniformly distributed on 17 chromosomes of apple genome; 2) is genotypically stable and widely segregated in *Malus* germplasm resources; 3) the variant fragment length of which is between 50 bp and 500 bp.

In some embodiments, the nucleotide sequence of the InDel corresponding to the markers in Table 1 is shown as follows:

There are six degenerate bases in InDel nucleotide sequence, which are R(A/G), Y(C/T), M(A/C), K(G/T), S(G/C) and W(A/T).

Sequence of marker C01001: SEQ ID No. 1:
atattaggaggtcgcacttggtgcgatggcaagtgccttcgcccatgagtggcaggtctcgggttcgagacttgggagcagc ctctccataaatgggggtaaggctagccgacattcaccttcccagaccctgcgtaaagegggagccttgtgcactgggtacgacctt tttattc.

Sequence of marker C01002: SEQ ID No. 2:
aggtcgtacccagtgcacaaggctcccgctttacgcagggtctgggagaggtgaatgtcggctagccttaccccatttatgg agaggctgctcccaagtctcgaacccgagacctactgctcatgggcgaaggcacttgccatcgcaccaagtgcgacctc.

Sequence of marker C01003: SEQ ID No. 3:
tagaggtcgcacttggtgcgatggcaagtgccttcgcccatgagcggtaggtctcgggttcgagacttgggagcagcctctc cataaatgggggtaaggctagccgacattcacctctcccagaccctgcgtaaagcgggagccttgtgcactgggtacgacctt.

Sequence of marker C01004: SEQ ID No. 4:
gtagggaactttaacgaaaagcacccggtactgttcactttaacgaaaaaccatattttatactaaaaagtcaatcatggtacta ttcactttacccttatttttgtccttatcattaaaactcaaagttttcaagccattttcatttgttttccttttaatgtaaatatgttagatggtgttcta aaagttactaaaggtg.

Sequence of marker C01005: SEQ ID No. 5:
gtcttctctttgcaatcccattccaaatttggataggaattatgaaggaaaatttataactgaagtcagtagccccatgccaacaat ttcattaacttctcttcatctgttttagcaggagtytactttggctttctcttggtatttggtgcaacggaattgaatgtccccttccttcatagtt ggtga.

Sequence of marker CO2006: SEQ ID No. 6:
atgaattgaggttccatcataaaatcaattggtaatatggggagtagcccaagaccatataagcacatagcaaaccttgtccct caccaatgtgtgacaactctcaacacgccgccgcacgtgtagtaaattttcaagcctacacgtggacaacaactgggtgacgtggagc acgtgtggccatttggcttcacacgaggacaaaccgctctgatactatgatgaattgaggttccaccataaaaccaattggtaatatggg gagtagcccaagatcatataagcacatagcaaaccttgtccctcaccaatgtgtgacaactctcaa.

Sequence of marker CO2008: SEQ ID No. 7:
aaaggtcgtacccagtgcacaaggctcccgctttacgc agggtctgggagaggtgaatgtcggctagccttaccccatttat ggagaggctgctcccaagtctcgaacccgagacctaccgctcatgggcgaaggcacttgctatcgcaccaagtgcgacctctc.

Sequence of marker CO2009: SEQ ID No. 8:
gaaaactaatgaaaagggcttgaaaactttgagttttaatgataaggacaaaataaagggtaaagtgaatagtaccaggattga attttagtgtaaaaatgtggtattcgttaaagtgaacagtaccaagtgatttcgttaaagttcc.

Sequence of marker C03011: SEQ ID No. 9:
aggaaaactaatgaaaaaagtttgaacactttgaatttcaacgataaatacaaaataaagggtaaagtgaatagtaccaggatt gacttttagtgtaaaaatgtgattttttcgttaaagtaaataataccatgag.

Sequence of marker C03012: SEQ ID No. 10:
ccaacttcccccacttgcaacattgcctatttgggaagacatcccaccccggaggatttaacctcctcatctacccacccacaa Sequence of marker C03014: SEQ ID No. 11:
aaaaaargktcgtacccagtgcacaaggctcccgcttaacgcagggtctgggagaggtgaatgtcggctagccttacccc atttatggggaggctgctcccaagtctcgaacccgagacctaccgctcatgggcgaaggcacttgccatcgcaccaagtgcgacct.

Sequence of marker C03017: SEQ ID No. 12:
Taaaggtcgtacccagtgcacaaggctcccgctttaagcagagtctgggagaggtgaatgtcggctagccttaccccattt atggagaggctgctcccaagtctcgaacccgagacctaccgctcatgggcgaaggcacttgccatcgca.

Sequence of marker C03018: SEQ ID No. 13:
tggaattgtaagaggtcgcacttggtgcgatggcaagtgccttcgcccatgagcagtaggtctcaggttcgagacttgggag cagcctctccataaatgggtaaggctagccgacattcacctctcccagaccctgcgtaaagcgggagccttgtgcaatgggtacga catt.

Sequence of marker C04019: SEQ ID No. 14:
agaggtcgcacttggtgcgatggcaagtgccttcgcctatgaacggtaggtctcgggttcgagacttgggagcagcctctcc ataaaatgggggtaagactagccgacattcacctctcccagaccctgcgtaaagegggagccttgtgcactgggtacgacttttt.

-continued

Sequence of marker C04020: SEQ ID No. 15:
gggaattttaacgaaaagcacccggtattgttcattttaacgaaaaaccacattttttacactaaaaagtcaatcatggtactattca ctttaccetttattttgtacttatcattaaaactcaaagttttcaagcccttttcattagtttttcc.

Sequence of marker C04021: SEQ ID No. 16:
gccccgtttgggattgaggtgattttaaaaaaaagctactgtgaaaaaaagctgagggtcattttttgtgtttggtaaactgaaaaaa aaaggcttattttggaagctgctgtgagaataagctgaaaatcaaaggaaaagctgaagctgctatttgctgctttgaaaaaaagccagt tttttcaaagcacacggatcctttaatgaaaagacacactatcatcctgcttttttttccaaaagcactttcacaaaaaagtttaccatacact ctactggctttatttcacagccacttattctcacagcacagccgcttattctcacagcagctttttttcaaagcacagcaataccaaaccag c.

Sequence of marker C04022: SEQ ID No. 17:
gggaactttaacgaaaagcacccggtactgttcactttaacgaaaaaccacattttttacactaaaaagtcaatcctggtactattc acttttaccctttattttgttcttatcattaaaaactcaaagttttcaagcccttttcattagtttttcc.

Sequence of marker C04023: SEQ ID No. 18:
aaaaaaaaaaaggtcgtacccagtgcacaaggctcccgctttacgcagggtctgggagaggtgaatgtcggctagccttac ccccatttatggagaggctgctcccaagtctcgaacccgagacctaccgctcatgggcgaaggcacttgccatcgcaccaagtgcga cctc.

Sequence of marker C04024: SEQ ID No. 19:
ctgagaggtcgcacttggtgcgatggcaagtgccttcgcccatgagcggtaggtctcgggttcgagacttgggagcagcctc tccataaatggggtaaggctagccgacattcacctctectagaccctgcgtaaagegggagccttgtgcactgggtacgacctttt.

Sequence of marker C04133: SEQ ID No. 20:
taaaaggtcgtacccagtgcacaaggctcccgctttacgcagggtctgggagaggtgaatgtcggctagccttaccccattt atggagaggctgctcccaagtctcgaacccgagacctaccgctcatgggcgaaggcacttgccatcgcaccaagtgcgacc.

Sequence of marker C04134: SEQ ID No. 21:
gggctggtttggtattgctgtgctttgaaaaaaagttgctgtgagaataagcagctgtgaaataaattagtagagtgtttggtaaa ctttttttgtaaaagtgcttctgaaaaaaaaaaacagtctgatagtgggtcttttcattaaaggagcactgtaactccgtgtgctttgaaaaaa aagccagttttccaagctacaaatagcagcttcagttttttcctttgatttcagcttattctcacagcagcttccaaaataagccatttttttca gtttaacaaacatctaaaactctcacagattattyatgggtgyttattttttaagcacctcattcccaaaccacc.

Sequence of marker C05026: SEQ ID No. 22:
ttatttcaattgatcgagcccagtgcacaaggctcccgctttacgcagggtctgggagaggtgaatgtcggctagccttaccc ccatttatggagaggctgctccca.

Sequence of marker C05028: SEQ ID No. 23:
atattcaatatttcaaatgcttagtcaaaaagcgattctaggaacaagaatttcttccaaactttgttgcaacacagacacatacgc ttttgaatgtataatacattattttggtgagattgaccttcgcaggtgtactgtggtcaataggggaaggtactgggtact.

Sequence of marker C05029: SEQ ID No. 24:
gggcttcagtagcaaatgatttaataattactctctttctcaattactgtgggatttgttagcagcagtaaagtgagttaggtctag ctattgttectgtagccaaatcctattgagagttttcttgatcttgtaaatggtggatttcttatccacttcagtatatttctcttttcttttataaa tgtttgtttcttctcaaaaaaaaaaaaaaaaaaaaaaa.

Sequence of marker C05030: SEQ ID No. 25:
gggaactttaacgaaaagcacccggtactgttcactttaacgaaaaaccatattttttacactaaaaagtcaattctggtactattc actttaccctttattttgtccttttcattaaaactcaaagttttcaagcccttttcattagttt.

Sequence of marker C05031: SEQ ID No. 26:
gcatggccatctactacctttgcaccggagaacaggaaggggttatggtggaatcaacttcaacatggtcactctctcccgtc atgcttgactcgtccacttgtaaggaatacccatccaggaacaatccatctgcaggtatttgatctcccatgttcagaaccacaacatctc caactacaatatcgaagatggagatttcttgtctctgtttgtctctaaatacc.

Sequence of marker C05032: SEQ ID No. 27:
agggaactttaacgaaaagcacccggtactgttcactttaacgaaaaaccacattttttacactaaaaagtcaatcctggtactatt cactttaccattattttgacttatcattaaaactcaaagttttcaagccatttcattagtttttcc.

-continued

Sequence of marker C05135: SEQ ID No. 28:
ttcctgctcgtaatgtgtttatgggatgttccatcaaataacagcagtgatcrttataacacagcataagttaccgatacgagcac agatgcattttgcagaaatacaccataattagatrgataagattcgaatgtgtacgtacgatcaatgttgacaatgcaaag.

Sequence of marker C06037: SEQ ID No. 29:
Cgtacccagtgcacaaggctcccgctttaagcatggtctgagagaggtgaatgtcggctagccttacctccatttatggagag gctgctcccaaatctcgaacccgagacctaccgctc.

Sequence of marker C06038: SEQ ID No. 30:
cactacaaatataggatttcgctgagagagagagtgacaatgaaaactctctgaagttcctctgaacatagtgcaccagttagg gtataaacaaaacttggcctctaccattgaaggaccacagaagtattcaccatcaacaagcaacaatccaagc.

Sequence of marker C06039: SEQ ID No. 31:
gaccagcggatctggtggtcgacaatcgttcggacttggtaaaggttgtcgcg.

Sequence of marker C06040: SEQ ID No. 32:
gtgtttccttattatttcgttgttatgactattgcttgagatttagcaacaatatgtccattattaatatatt.

Sequence of marker C06041: SEQ ID No. 33:
cctcagtacatataggctatatgatatagccccgtttagaattgattttagtgcaatgaagtatgcatatcaggagtttcgtatgc agagaaagaaattgcgttaggttatattaagaatttctatccaggggttactgtttaacttacgaattaactagttgatgatttaatattgatag aaaagtagatttcaatccagttccattagaatattttagaaaaatggaaacttcctttgactattgtcttatattaaagacttatcataaggaga tgataacgtcaattaataactagatgggtcgactgagtccaattcaaaggacccatttc.

Sequence of marker C06137: SEQ ID No. 34:
gcaaatgtcactctagataatacggagatgaatgaaagatgacatgcatgacatcaatcttgggtccatgtaagccaaaaaa acaacggttaacttgacggttcgactgattaagacggtaaatgttgaacgaactagtaacttcaagggttgtaagttttttgtatgccatgga ccaaatgttacatgctcttaaccttgagaaagacttctcatggcacggaacgccatggttcttgtgtacccgtgccatgg.

Sequence of marker C07043: SEQ ID No. 35:
Aaaggtcgtacccagtgcacaaggctcccgctttacgcagggtctgggagaggtgaatgtcggctagccttacccccatttt atggagaggctgctcccaagtctcgaacccgagacctaccgctcatgggtgaagacacttgccatcgcac.

Sequence of marker C07044: SEQ ID No. 36:
ggtatcgcccatgagctgtaggtctcggggttcgagacttgggagcagcctctccataaatgggggtaaggctagccgacatt cacctctcccagaccctgcgtaaagcgggagccttgtgcactgggtacgaccttt.

Sequence of marker C07045: SEQ ID No. 37:
cagtgtgatggcaagtgtcttcgcccatgagcagtaggtctcggggttcgagacttgggagcagcctctccataaatgggggt aaggctrgccgacattcacctctcccagaccctgcgtaaagcgggagccttgtgcactgggtacgaccctca.

Sequence of marker C07047: SEQ ID No. 38:
cgttaatttcataagctgtaaggaacacaagcagaccaatgcttacataatttcataagctgtaagcattggcctatttacatacat aatttcgagacttgggagcagcctctccataaatgggggtaaggctagccgacattcacctctcccagaccctgcttaaagcgggagc cttgtgcactgggtacgacc.

Sequence of marker C07048: SEQ ID No. 39:
ggtggtttgggagtgaggtgataaaaaaaaagcacccatgaaaaaaaagctgtgagggattaggtgtttggtaaactaaaaa aaaggggcttatttttggaagctgctgtgagaataagctgaaatcaaaggaaaaagctgaagctgctatttgcagctttggaaaactgcct ttactcaaagcacacggaactacaatgctcctttaatggaaagacccactatcagactgctttttttttttccaaaagcacttttacaaaaaaa tttaccaaacactctgctgatttatttcacatccgcttattctcacagtacagcygcttattctcacagcagattattcaaagcacagcaata ccaaactagcc.

Sequence of marker C07049: SEQ ID No. 40:
agaggtcgcacttggtgcgatggcaagtgccttcgcccatgagcggtaggtctcggggttcgagacttgggagcagcctctcc ataaatgggggtaaggctagccgacattcacctctcccagaccctgcgtaaagcgggagccttgtgcactgggtacgacctt.

Sequence of marker C07050: SEQ ID No. 41:
tgggagagattctgggcagtgccgcctgatcggtcatttgaccaacactccttcaaaacatataacttgttcttcactctccatg gcaagaaaggaaaggagagacaattacaaatctcaattcacttgacccgtgggattacaaatctcaaatcagaggaattcgcattga cagtcaagggagttaccatcttcacaattacagacgacccacggatcaaaccctcct.

Sequence of marker C07138: SEQ ID No. 42:
aattgtttataccatatttaggacctcttatttagatctcgtacaaatactcagggaacttaaatgtaattatgtgataaaggaatgg gcaaatatgtaataagtgaggagttatattctataaaatgacccctcaccctcacaattggaggaggtcaattcctaggccctctcaccc cctctcaaagctctaactctcagagctctctccctcaaataaatacataatcagtgtggacgtagcccaaattttagggtgaaccacgatg catcttgtgttatttacatttcttgcagattcacggtcggatttacgttgttccaaaacctccggttttgtgcatcaac.

Sequence of marker C08051: SEQ ID No. 43:
tgacgctattggagctggaattaccgcggctgctggcaccagacttgccctccaatggatcctcgttaagggatttagattgta ctcattccaattaccagactcatagagcccggtattgttatttattgtcactacctccccgtgtcaggattgggtaatttgcgcgcctgctgc cttccttggatgtggtagccgtttctcaggctccctctccggaatcgaaccctaattctccgtcacccgtcaccaccatggta.

Sequence of marker C08052: SEQ ID No. 44:
gaccwgawtsywcttctaagmtwwggwtgwktmtycwcctcwtyrmtkwrtmkrsgccgttkgwtgwraatm maayggctayaatcagggtccattaaagttataataattgtaacctttaaagttataataattgtaaccgttgaatgaaatcacttgatga ggagaatcctcatccttagctcaggagaggatcctggtccatg.

Sequence of marker C08054: SEQ ID No. 45:
Aaaaaggtcgtacccagtgcacaaggctcccgctttacgcagggtctgggagaggtgaatgtcggctagccttacccccat ttatggagaggctgctcccaagtctcgaacccgagacctaccgctcatgggc.

Sequence of marker C08055: SEQ ID No. 46:
agaggggtcgtacccagtgcacaaggctcccgctttacgcagggtctgggagaggtgaatgt.

Sequence of marker C08056: SEQ ID No. 47:
ggggtgtgctatccacacacctttttttacttctcacacacccctttgttaatttctgtccgttgattttctttaattcattcgatccgacg gccgaaaaccaaaaggtgtgagagaagtaaaaaaggatgtgtggatatcacacct.

Sequence of marker C08057: SEQ ID No. 48:
accacaacacaatgttcgattaaccacaatgccatctcaaggacagtttgggactgatctgctgaagctaaaaccgctctctg gcaatcataagcccctatgactacgttttgcataaaaactataatagttcttctatccctaaacctacttccttttcaggaaacacttccaagt gcttttccaggacgcaattgggttttcaataaaatcttgacgagtttctaattaaagcacttgcattgaaacgaaacatggttatgccattac atctatgatgaaaaatgggacaggggtttcgattaaatgm.

Sequence of marker C08058: SEQ ID No. 49:
aaaaaaraaaaagacgtaatcatcttmtatgattgaattttctctaaaaaagtaaaaattgggaaatgatttttttcacacccatttg agtctttgacctgcactctgctaaattstgtcccctgattctcttgatttatccaatccagaaagaggacgaggtgtagaaatcagtcccca aaaaatcrggggttgaaaaggggagtgcagaaaccccaaaattgggttcaacccctaaaattcgggttgctttagttaacccaaggctt cttaacattgc.

Sequence of marker C08059: SEQ ID No. 50:
rgctectgatcccagtgcacaaggctcctgctttacgcagggtytgggagaggtgaatgteggctagcctkaccccccatttat ggagaggctgctcccaagtctcgaaccygagacctaccgctcatgggcgwaggcacttgccatcgcaccaagtgcgatct.

Sequence of marker C08060: SEQ ID No. 51:
gatctgtaacgggttggatttattggatttggattggattcaacccgacccgttaagttaacaggtcacccgaactcaacccgtt aagttaacgggtcatccgaacccgacccgttaagctaacggatcatccatttttacctattaacaattattattattatttgcataaagttta ttattgttattaaaactttactaaaattattaaaatatccttaactaacgggttaacccaaagtgatccgttatttaacaggttgttaacgggttc atccgttaacgacccgacccgttaagtatccacccaaatacaaatattaacgggttgggtcggatcgagttaacgggttgggtccaaaa tgccagacct.

Sequence of marker C09062: SEQ ID No. 52:
agattaccatgcaaaaatgcattgcttacatccagttgattgagaaaccaatcatattgtgccgccaacatgaggagaattcga atagtgacaagtttagcaacttgactaaatgtataatgtaatctaaaccttatgctggttaaaaacctttggcaactaggcgtgccttgtact tctcaatagtgccatcaggtttcctcttgatcctgaaaacccacttacaacctactatattggtagaatgagatttgggaactaaagaccac attctagtttg.

Sequence of marker C09063: SEQ ID No. 53:
taagatcataaacttataaatactgcgtactcatgatatccatatcctaaaattcaatactgcatgcagtgtagttgttatttattca aatgaataacttagttatttgttaactatatttaaccttgttctatccttatttectagttatgtctggtctggtgtggctactgactggttgctga catgggaatttca.

Sequence of marker C09064: SEQ ID No. 54:
ggtcgtacccagtgcacaaggctcccgctttacgctagggtctgggagaggtgaatgtcggctagccttacctccatttatgga gaggctgctcccaagtcttgaacccgagacctaccgcttatgggcgaaggcacttgctatcgcaccaartgcra.

Sequence of marker C09067: SEQ ID No. 55:
aaaaaaaaaaaggtcgtacccagtgcacaaggctcccgtttacgcaaggtctgggagaggtgaatgtcggctagccttacc cc.

Sequence of marker C09068: SEQ ID No. 56:
tacagctgtctgacgtgagaattccgttaatctttgtaagtcctttctatttattttggaaaatatttatctgattgttggagaaattta atgatatacattgcccactctattgataattttactgctcatcatggtaatctc.

Sequence of marker C10070: SEQ ID No. 57:
aaggccttacggaattttcttttagtgattatgttgtaaatagtcatgtgctcttgtgttcttggg.

Sequence of marker C10071: SEQ ID No. 58:
gtcgtacccagtgcacaaggctcccgctttacgcagggtctgggagaggtgaatgtcggctagccttaccccatttatggag aggctgctcccaagtctcgaacccgagacctaccgctcatgggcgaaggcacttgtcatcgcaccaaatgcgacct.

Sequence of marker C10072: SEQ ID No. 59:
gtcgtacccagtgcacaaggctcccgctttaggcagggtttgggagaggtaaatgt.

Sequence of marker C10073: SEQ ID No. 60:
tgyagaatgmcacagawtccatcwtcctttgacggcattgcagaatttaaccaacaaataacaaaaaaataacacaaagat ataagtccaattctttctacaaaacca.

Sequence of marker C10136: SEQ ID No. 61:
gccccgtttgggattgaggtgattttaaaaaaagcaactgtgaaaaaaagctgagggtcattttttgtgtttggtaaactgaaaaa aagggcttattttggaagctgctgtgagaataagctgaaaatcaaaggaaaagctgaagctgctatttgctgctttgaaaaaagccagt tattcaaagcacacggagctacagtgctcctttaatgaaaagacacactatcatcctgcttattttccaaaagcactttcacaaaaaagttt accaaacactctactggattatttcacagccgcttattctcacagcacagccgcttattctcacagcagattattcaaagcacagcaata ccaaaccagcc.

Sequence of marker C11077: SEQ ID No. 62:
gacctagtttgggagtgaggtgataaaaaaaaagcacatatgaaaaaaagctgtgagggattaggtgtttggtaaactgaaa aaaaatggettattttggaagctgctgtgagaataagctgaaatcaaaggaaaaagctgaagctgctatttgtagctttggaaaactggtt ttattcaaagcacatggagctacagtgctcctttaatgaaaggacccactatcagrctamyttatttccaaaagattttttgcaaaaaagtt taccaaacgctctgctgatttattttcacagccgyttattctcacagcacagccgcttattctcacagcagattattcaaagcacagcaata ccaaaccagc.

Sequence of marker C11078: SEQ ID No. 63:
aggtcgtacccagtgcacaaggctcccgctttacgcagggtctgggagaggtgaatgtcggctagccttaccccatttatgg agaggctgctcccaagtctcgaacccgagacctaccgctcatgggcgaaggcacttgccatcgcaccaagtgcgac.

Sequence of marker C11079: SEQ ID No. 64:
gggctggtttggtattgctgtgctttgaaaaaagctgctgtgagaataagcggctgtgctgtgagaataagcggctgtgaaat aaagccagtagagtgtttggtaaattatttgtgaaagtgatttggaaaaaaaagcaggatgatagtgtgtatttcattaaaggagcactg tagctccgtgtgattgaaaaaactgactttttttcaaagcagcaaatagcagcttcagcttttcctttgattttcagcttattctcacagcagc ttccaaaataagccatttttttcagtttaccaaacacaaaaataaccctcagattattcacagtggcttttittaaaatcacctcaatcccaa acggag.

Sequence of marker C11080: SEQ ID No. 65:
gggarctttaasgmmaaacamcygttactgttcactttaacgaaaaaccacattttacactaaaaagtcaatcttggtactatt cactttacccttttattttgtccttatcattaaaaatcaaagttttcaagctcttttcattagttttc.

Sequence of marker C11081: SEQ ID No. 66:
aaaaaaggtcgtacgcagtgcacaaggcttccgctttacgcagggtctgagagaggtgaatgtctgctagccttaccccattt atggagaggctgcttccaagtctcgaacccgagacctaccactcatggacgaaggcacttgccatcgccaagtgcgacctcttca.

Sequence of marker C11082: SEQ ID No. 67:
gggaattttaacgaaaagcacccggtactgttcactttaacgaaaaaccatattttacactaaaaagtcaatcctggtactattc actttaccattattttgtccttatcattaaaactcaaagttttcaagccattttcattagttttcctaaa.

Sequence of marker C12086: SEQ ID No. 68:
aaaaaaaaggtcgtacccagtgcacaagacttccgctttacacagggtckgggagaggtgaatgtcggctaaccttacccccc atttatggagaggctgctcccaa.

Sequence of marker C12087: SEQ ID No. 69:
ggctggtttggtattgctgtgctttgaaaaaaagctgctgtgaaaataagcggytgtrctgtgagaataagcggctgtgaaata aatcagcagagtgtttggtaaacttattgtaaaagtgattttggaaaaaaaaagcagtcaaatagtgggtattttcattaaagaagyactg tagctccgtgtgattgaaaaaaagccattttttccaaagctgcaaatagcagcttcagcttttttcctttgattttcagcttattctcacaacagc ttccaaaataagccatttttttcagtttaccaaacacataaaaccctcacagattattcatgggtgattatttaagcacctcactcccaaa ctaggt.

Sequence of marker C12088: SEQ ID No. 70:
aggaaaactaatgaaaagggettgaaaactttgagttttaatgataaggacaaaataaagggtaaagtgaatagtaccaggatt gactattagtgtaaaaatgtggtatttgttaaagtaaacagtaccgggtgcttttcgttaaagttcc.

Sequence of marker C12089: SEQ ID No. 71:
ctaagtcaacgattgataagtgataaaaatctaattttgtcaaaatttaattttgattagattgaagtgttaaacaaaatttaagataac acacctaaaattaacttaagaaaagttaacaaagaaaccattattttgtactacagaaataaatacccacataaataaatatatagcctcat atagagcta.

Sequence of marker C12090: SEQ ID No. 72:
tataaaccgcatcttgtgtctaagatagtcttctatttgcccatatgattcttagcgatgacccgcttttcatccttgaatttc.

Sequence of marker C12091: SEQ ID No. 73:
agtgcatttttgctcactaccattagtgtggtgtatgctcatcccctatttatcactattagattagtttgaattttgagatttgtgctt attcactacacgaatctcgaaatycraactcatstaacggtkwtaamtargkyrgtsmaswcwmrtsamrctwaatrrtggkgak maaaaatgcwyy.

Sequence of marker C12092: SEQ ID No. 74:
agaatcaaaatattaattamcmaaaaaacaacaaaaggtcaaaaaaccttggtaagagatgattagaacacatagtgcacc aaacgtcaagggttcttccttcaatctgcatttctagtagcaaaaaataaaaaagaaaagagactattatattttgaaaactaatacataaa atcaaaaccagcttcacatttactatagataaacacttagtagtaagaagaaacattatggaaaggatacatacatttataaggaagacaa ataaatcctcagggtataccaagccaattgtcaggaagcaacgctgaacttcg.

Sequence of marker C13093: SEQ ID No. 75:
cgtacccagtgcacaaggctcccgctttacgcagggtctgggagaggtgaatgtcggctagctttaccccccatttatggagag gctgctcccaagtctcgaacccgagacctaccgctcatggacgaaggcacttgccatcgccaagtgcgacct.

Sequence of marker C12132: SEQ ID No. 76:
agtattagcttgcatccacaactacaaaaatcatagtctgctccgaagtatcatatacaccatgmgtttgggcctaaagatcatg gtcattggatatttgaccaagaatctaacagccgaaaaccctcgtatagaagataccacgagtgatactagaaatatccccagaaca.

Sequence of marker C13094: SEQ ID No. 77:
ggatttggatcatctcctgagctaatggagagtatcctcttgaccaagtgttatgggtcgttggatttttatccaacagctacaaac agttgggtccttttaaagttataataatttcatccaacggcacataatacttagtcagaaggatctctccattagctcaggagaggatccaa atcc.

Sequence of marker C13096: SEQ ID No. 78:
aaggtcgtacccagtgcacaaggctcccgctttacgcagggtctgggagaggtgaatgtcggctagccttaccccccatttatg gagaggctgctcccaagtctcgaacccgagacctaccgctcatgggcgaaggtacttgccatcgca.

Sequence of marker C13097: SEQ ID No. 79:
agaggtcgcacttggtgcgatgacaagtgccttcgcccatgagcggtaggtctcgggttcgagacttgggagcagcctctcc ataaatgggggtaaggctagccgacattcacctctctcagaccctgcgtaaagcgggagccttgtgcactggatacgac.

Sequence of marker C13098: SEQ ID No. 80:
aaaggtcgtacccagtgcacaaggctcccgctttacgcagggtctgggagaggtgaatgtcggctagccatacccccattta tggagaggctgctcccaagtctcgaacccgagacctaccgctcatgggcgaaggcacttgccatcgcaccaagtgcgacct.

Sequence of marker C13100: SEQ ID No. 81:
atgctgccgaacttcacaaatgtcacacgacaccattctttccccatcgtcttcctttgctccacagggacagtgcacgacatag ttgattgctccacattcatacatctcactaactccacccgtctctttgctactcctaccctcaagcacaatattttgacccacctca.

Sequence of marker C13101: SEQ ID No. 82:
gatggcaattttggaaaattcaacttctcttgctttccaaacattgttcgtcttcggcttcgtgcaagcggactcaagggcagcatt ccatctgaaataggtactattccaagctcaagcaccttgacctttatacaatcaaattactggttatatccatcaagtctttggaacttga aaaacttggtcayccttcaacta.

Sequence of marker C13102: SEQ ID No. 83:
gcggctgattttatagctcatgtgtgggagaaaaagtgctcgtatgatggccagctgaaggtctaatgggcaatacacagtta acggagaagagattgttactgggcatgtttggtcaatgccgaaatacaacagcaggaaccaaggggagctgaaggagcttgaagca ttatacaacgctataggaaagaattcaggctagttttcaagaagttggactcgaataatgaacgacttagtgatgatgggaagagtatg atgtacgagctgaaatgggttgaaaagtcaatgcatttgcaagagcccgatgttctggggatcggcgatgctgagcctt.

Sequence of marker C14104: SEQ ID No. 84:
aaaaaaaggtcgtacccagtgcacaaggcttccgctttacgcagggtctgggagaggtgaatgtcggctagccttaccccca tttatggagaggctgctcccaagtctcgaacccgagacctaccgctcatgggcgaaggcacttgccatcgcaccaagtgcgacctctt Sequence of marker C14105: SEQ ID No. 85:
aacgttttttgtttcttcaagagaagtttgggtaaagctttaaagagtacttgttcttttwgtaatcctgttttgacaatcctctggttg catgaattgttaccatttccaatttgtgctcgctttggattgttgttttcgcaaataatwtactcaaattttccatgggatggtactcgttgtatt tggaatcaatatattaggtgcagtggttattttatttgatcaataaatctgtagaattcgtatgttttgtaacgttttttgtttcttcaagagaagt ttgggtaaagctttaaagagtacttgttcttttgtaatcctgttttgacaatcctctggttgcatgaattgttaccct.

Sequence of marker C14108: SEQ ID No. 86:
ggctggtttgrtattgctgtgattgaaaaaaagctgctgtgagaataagcggctgtgctgtgagaataagcggctgtgaaata aatcagtagagtgtttggtaaactttttgtaaaagtgcttttggaaaaaaaagcagtctgatagtgggtcttttcattaaaggagcactgta gttctgtgtgattgaaaaaaagccagttttccaaagctacaaattgcagatcagatttcctttgatttcagatattctcacatcagatcc aaaataagccattttttttaagtttaccaaacaccaaaaacactcccagettttttttcataggagcttttttcaaaatcacctcaatcccaaact gggg Sequence of marker C15109: SEQ ID No. 87:
ttattttttttttttaaaacaagatatgcaatatcggacagagatgccaaaaggttacaagaaagcctaccaaagaggcaaaca aactgcagcaaatactaaagaaaagtagtacaagaaggtacaag.

Sequence of marker C15110: SEQ ID No. 88:
gagaggtcgcacttggtgcgatgacaagtgtcttcgcccatgagcggtaggtctcaggttcgagacttgggagcagcctctc cataaatgggggtaaggctagccgacattcacctctcccagaccctgcgtaaagcggaagccttgtgcactgggtacgac.

Sequence of marker C15111: SEQ ID No. 89:
cgaggtcgcacttggtgcgatggcaagtgccttcgcccatgagcggtaggtctcgggttcgagacttgggagcagcctctcc ataaatgggggtaaggctagccgacatttacctctcccagaccctgcgtaaagcgggagccttgtgcactgggtacg.

Sequence of marker C15114: SEQ ID No. 90:
aagtgtgctctactatgatgcaaatatttcagtcaagttattcttgtttatgttcccacaactcattcaacaattgtttgc.

Sequence of marker C15115: SEQ ID No. 91:
aaggtcgtacccagtgcacaaggctcccgctttaagcagggtctgggagaggtgaatgtcggctagccttaccccattatg gagaggctgctcccaagtctcgaacccgagacctaccgctcatgggcgaaggcacttgccatcgcaccaagtgcgacctc.

-continued

Sequence of marker C15116: SEQ ID No. 92:
gggatgtgctatccacacacccattttacttctcacacacccatgttaatttctgtccgttgatcttattcaatttatccgatccaac ggtcgaaaaccaaaaggtgtgggagaagtaaaaaagggtgtgtggatatcacaccg.

Sequence of marker C15119: SEQ ID No. 93:
cctaagagtgtttagtctaatggtcaggcccttggtttgttaccaagaggtctggggttcgacacctctcaaggtacccacctag caattgctagagtttcttgcctaccaaatgttgtggggtcaggcgggtggcctagtgagtagtcgggtcaaagacccggagacactag attcaaaaaaaaaaaaaa.

Sequence of marker C16120: SEQ ID No. 94:
aaaactaatgaaaagagcttgaaaactttaagttttaatgataaggacaaaataaagggtaaagtgaatagtaccaggattgac tattagtgtaaaaatgtggtattcgttaaagtgaacagtaccgggtgcttttcgttaaagttcc.

Sequence of marker C16122: SEQ ID No. 95:
tggtaatcaagttcaaartactccgcacaagatactctggcacttaaaaaaattacaagaagtaaagcccgaaggaaccaattc agtcagagtcttgtattttcagcactcaagtccaagtgtaagtttgccaggaaaccacccaatgaaagtactgcaagaccagtgctaag gagtaaaacttcgcagtaactgtgctcagttcctttcttgatgccaaatataaaggcatagttgacacgataacgcctccagaagtatatg tctgcagcttacatg.

Sequence of marker C16123: SEQ ID No. 96:
gtcgtacccagtgcacaaggctcccgctttacgcagggtctgggagaggtgaatgtcggctagccttaccccatttatggag aggcccatttatggagaggctgctcccatttatggaggtgaatgtcggctagccttaccc.

Sequence of marker C16124: SEQ ID No. 97:
ggaaaactaatgaaaagggcttgaaaactttgaattttaatgataaggacaaaataaagggtaaagtgaatagtaccagaattg actattagtgtaaaaatgtggtattcgttaaagtgaacagtaccaggtgatttcgttaaagttcc.

Sequence of marker C16125: SEQ ID No. 98:
aaaggtcgtacccagtgcataaggctctcgctttacgcagggtctgggagaggtgaatgtcggctagccttaccccatttat ggagaggctgctcccaagtctcgaacccgagacctaccgcttatgggcgaaggcacttgccatcgcacca.

Sequence of marker C17126: SEQ ID No. 99:
aggaaaactaatgaaaaggatttgaaaactttgagttttaatgataaggacaaaawaaaagggtaaagtgaatagtaccagg attgactattagtgtaaaaatgtggtattcgttaaagtgaacagtaccgggtgcttttcgttaaagttcc.

Sequence of marker C17127: SEQ ID No. 100:
ctaagaggtcgcacttggtgcgatgacaagtaccttcgcccatgaacggtaggtctcggttcgagacttgggagcagcctctc cataaatgggggtaaggctagccgacattcacctctcccagaccttgcgtaaagcgggtctgggtacgacctttt.

Sequence of marker C17128: SEQ ID No. 101:
agaggtcgcacttggtgcgatggcaagtgattcgtccatgaacggtaggtctcgggttcgagacttgggagcagcctacca taaatgggggtaaggctaaccgacattcacctctcccagaccctgcgtaaagcgggagccttgtgcactgggtacgacc.

Sequence of marker C17129: SEQ ID No. 102:
gcgaagagatcccaccggatactcccactaaagctcactaatcaattaatccgggtccttaaaatttgataaaacggctacaa ataggaagctccttaaaaaatcatcataattttagccgttggaacaaaatttaaaggcttgaattaattgattggtgagatatggtgggaga gatccggatgggatctcttcc.

In some embodiments, the nucleotide sequence of the upstream primer of the primer pair is set forth in SEQ ID Nos. 103-204, and the nucleotide sequence of the downstream primer of the primer pair is set forth in SEQ ID Nos. 205-306; the SEQ ID Nos. 103-204 are upstream primers for sequentially amplifying SEQ ID Nos. 1-102 described in the above technical schemes; the SEQ ID Nos. 205-306 are downstream primers for sequentially amplifying SEQ ID Nos. 1-102 described in the above technical schemes. In the disclosure, the primer pairs: 1) have strong specificity in amplification products and no non-specific amplification products; 2) have similar amplification efficiency of Insertion and Deletion for allelic locus.

In some embodiments, the corresponding relationship of InDel marker primer pair is shown in Table 2.

TABLE 2 corresponding relationship between InDel marker and primer pair

| InDel marker | sequence number | Upstream primer sequence | sequence number | Downstream primer sequence |
|---|---|---|---|---|
| C01001 | SEQ ID No. 103 | CTCTCTTCCCTTACAGCAGCAC | SEQ ID No. 205 | TAGCACATCTTATCACATCCAT |
| C01002 | SEQ ID No. 104 | TAATACTTTTACTTCAGCACGG | SEQ ID No. 206 | ATAGAATCTTCAGGGGATACTC |
| C01003 | SEQ ID No. 105 | GGCACTGCTAAGGTTCTA | SEQ ID No. 207 | GTACACGTCGCATTTCTC |
| C01004 | SEQ ID No. 106 | GTGTGGTATGTTCCTGCCTTGA | SEQ ID No. 208 | GCTCCTTTCAGCAGTCTCTATT |
| C01005 | SEQ ID No. 107 | TGCATGTGGCGAACTCTT | SEQ ID No. 209 | TCAACCAGGGAGCGATGT |
| C02006 | SEQ ID No. 108 | TTGGCTTTGGATTTTTCTTTT | SEQ ID No. 210 | ATTCTTTCTCTCTTTCCTTGTT |
| C02008 | SEQ ID No. 109 | AAAAGAGGGGAAAAGGAAAGAA | SEQ ID No. 211 | CAATCGGAAAGCGAGTTGAAGT |
| C02009 | SEQ ID No. 110 | GAGTTTGTGTGAGGTAATGAA | SEQ ID No. 212 | AGATTGGAAGTTTGGAGTTTGA |
| C03011 | SEQ ID No. 111 | AGGTTTTCTCCTGCTGCTCTAT | SEQ ID No. 213 | TTTTCCTCCTCCCTTACTTCTT |
| C03012 | SEQ ID No. 112 | CCAGTCCAAATCAAACCACAAC | SEQ ID No. 214 | TCCAAAGCGAGTAAAAGCAAGC |
| C03014 | SEQ ID No. 113 | TTCATTATTGGGCGATGTGCTC | SEQ ID No. 215 | CCCTTTTCCCTACCTTGTGTGC |
| C03017 | SEQ ID No. 114 | TGGGTCAAAAATCCTCATCTAC | SEQ ID No. 216 | TCATCTAACTACAACGGCTACA |
| C03018 | SEQ ID No. 115 | GGCGGCAGCAGGAACAGGTGGT | SEQ ID No. 217 | TTCAGTTATCGTGTCAAATGGA |
| C04019 | SEQ ID No. 116 | CTGGCACAGGATACAAGC | SEQ ID No. 218 | GAGGATGCGATGAACAAG |
| C04020 | SEQ ID No. 117 | CACACAAACAGAAGGGCACGGA | SEQ ID No. 219 | GGAAGAGACTGAACCCCAACCA |
| C04021 | SEQ ID No. 118 | ACTTGTTTTCTTCCATTTGTGC | SEQ ID No. 220 | ATCTCCTTACTGTCTTCAACTT |
| C04022 | SEQ ID No. 119 | ATTGTTTGCGAATAGAATGAGT | SEQ ID No. 221 | GTCTGTGACCTTCTTGCTCTGA |
| C04023 | SEQ ID No. 120 | CGAAAGAACCATCCTAACTAAT | SEQ ID No. 222 | GGTGTTATGTTCATCCATTTTA |
| C04024 | SEQ ID No. 121 | TCCTACCCTGCCTTGGAGTTTG | SEQ ID No. 223 | CATTATTCTTGAGCATTACACA |
| C04133 | SEQ ID No. 122 | AGGAAGTGGAGGCAAGGT | SEQ ID No. 224 | CAAGGCAACATCAAGAAATA |
| C04134 | SEQ ID No. 123 | AGAAAATTAAGAACGCAAACAA | SEQ ID No. 225 | TCTCACTAACTAAGGTGGGATA |
| C05026 | SEQ ID No. 124 | CACACGATAAATGCTACTTCAC | SEQ ID No. 226 | TTTCTTAGTCTATTCACTGGTA |
| C05028 | SEQ ID No. 125 | AGGGACCGCAACTAAACT | SEQ ID No. 227 | GAGGCATCTTCAACATACTTTT |
| C05029 | SEQ ID No. 126 | GTTTGCTGCTGGAGTAGAATCG | SEQ ID No. 228 | TTGAAACAACGACAAAGAACCC |
| C05030 | SEQ ID No. 127 | CCTACATAACATTAGTGAGAAA | SEQ ID No. 229 | TCTTCCATTGAAACTTTACGAG |
| C05031 | SEQ ID No. 128 | TACGGAGCCACAACCCACCAAC | SEQ ID No. 230 | AAACCAATCAACAACCGAAAGC |
| C05032 | SEQ ID No. 129 | TTGGTTTTCACTTAGTTTGTTT | SEQ ID No. 231 | TTTTTCTTGTCATTTGGCTGCT |
| C05135 | SEQ ID No. 130 | TCTTTGTAACTTCTTCCTCCAC | SEQ ID No. 232 | GAAACTTCTCTTATCAATGCCT |
| C06037 | SEQ ID No. 131 | AACTAGATCAATCAAGCCACAT | SEQ ID No. 233 | TTAGAGTAAACGCCTTAGCAAC |
| C06038 | SEQ ID No. 132 | ACCCAAAAGAAACCTAAGCCAA | SEQ ID No. 234 | CTCCAACTCACAGAGGGAAAGA |
| C06039 | SEQ ID No. 133 | AAAACTCCACCTCACTAACTTG | SEQ ID No. 235 | TCCGTCTCTCTGTCTCTATCCT |
| C06040 | SEQ ID No. 134 | TTGACGAAGGGCAAGAGAACAT | SEQ ID No. 236 | GGACGCAGAAAAGAGAAAAAAC |
| C06041 | SEQ ID No. 135 | TTCTCTGTATTTGGTAGGATTT | SEQ ID No. 237 | GATTTTGCTCGCTCTTTGGTCT |
| C06137 | SEQ ID No. 136 | CGGTTGAAACGAGGTGTGTAGA | SEQ ID No. 238 | AGGAACCTGGACTAATGGAGAA |
| C07043 | SEQ ID No. 137 | TGGCAAACTTACCGTGTC | SEQ ID No. 239 | CTTTGTGCTCGTCTGGTT |
| C07044 | SEQ ID No. 138 | TGGTGGAGGTGGCGAGAA | SEQ ID No. 240 | GCGAAGTGCCTTGCCTGA |

TABLE 2-continued corresponding relationship between InDel marker and primer pair

| Indel marker | sequence number | Upstream primer sequence | sequence number | Downstream primer sequence |
|---|---|---|---|---|
| C07045 | SEQ ID No. 139 | CTGCAAACACCGACTCAC | SEQ ID No. 241 | TGGCATTACAGCACCATC |
| C07047 | SEQ ID No. 140 | GTTTCTTATCCCTTACTCATCA | SEQ ID No. 242 | GTAAATAATAGTTCTTTCGGAC |
| C07048 | SEQ ID No. 141 | TTGTTCAGTGGTCTGTTGCTCT | SEQ ID No. 243 | TTCTCCGATTCCTTCATTCTTC |
| C07049 | SEQ ID No. 142 | GTTGTTTTACTGATTTTTACTC | SEQ ID No. 244 | TTTGAGATGTATGGATAGGTAG |
| C07050 | SEQ ID No. 143 | ATCACACCGACTCTCAAAATGG | SEQ ID No. 245 | GAGGAAGGTAAAAAATCGCACG |
| C07138 | SEQ ID No. 144 | AGAAAGGTTTTTTACGAGAATC | SEQ ID No. 246 | TTACTATTTCCTACTCGGGTCG |
| C08051 | SEQ ID No. 145 | CTTTTCCACTCTCTCACACTCC | SEQ ID No. 247 | GCATCCCTTTACACCCCCTCAA |
| C08052 | SEQ ID No. 146 | CGGTTTGACTGTTGTTCG | SEQ ID No. 248 | TAAGCAGATTGTCCCATT |
| C08054 | SEQ ID No. 147 | AATCAGGTAAATAAAAGGAATC | SEQ ID No. 249 | TTGCTTTGAGGTAAGACTGGAG |
| C08055 | SEQ ID No. 148 | TCACAAAGCAAAAACAACCAAG | SEQ ID No. 250 | TCATACAAAAAATACATAAATA |
| C08056 | SEQ ID No. 149 | TTGAGTTTATTTCTTGGTTGTA | SEQ ID No. 251 | CTGAAGGAATCTTTTAGGTTGG |
| C08057 | SEQ ID No. 150 | GCCTCCTTCAAATCCTTATCAC | SEQ ID No. 252 | AAATAGCAAGCAGCAGGTGGTG |
| C08058 | SEQ ID No. 151 | TCTCTGATGCTTGTGACCGTTA | SEQ ID No. 253 | CACCTCATTCCTTTGTTTCCTT |
| C08059 | SEQ ID No. 152 | AATACAACGAAACAACCACACC | SEQ ID No. 254 | GAACATCAATCTAATGCTACCA |
| C08060 | SEQ ID No. 153 | GCCTTTAGAGAACTCGGCACCT | SEQ ID No. 255 | GATAAGATTTGTGGCTTTGCGT |
| C09062 | SEQ ID No. 154 | TGAGAACCAATGAATCCCAGAG | SEQ ID No. 256 | GCAACAAAGCATTATTTACCTC |
| C09063 | SEQ ID No. 155 | AGTGCGGGCAGAGATTGGAGAA | SEQ ID No. 257 | GGTAGGTCAGAGAGAAGAGGTT |
| C09064 | SEQ ID No. 156 | GAGGGTTACAAAGTCTCACAAA | SEQ ID No. 258 | TGGTTTACCGAACTGAAATCTA |
| C09067 | SEQ ID No. 157 | ATTTGTTTCTTTTATGAGTGTT | SEQ ID No. 259 | ATTTGGTATCTTCTTCGTTTTC |
| C09068 | SEQ ID No. 158 | CTGTTTTCTACGGTGCTCTGGC | SEQ ID No. 260 | TACTCGCAAAGTTTCCCGTTCC |
| C10070 | SEQ ID No. 159 | CACTCTGACTCGTAGGACCCC | SEQ ID No. 261 | TCATCTTGTCCAGCAGGTTTG |
| C10071 | SEQ ID No. 160 | TTCCCAACTTCGGTTCCTTTC | SEQ ID No. 262 | GGGGCACATACTCATCCATCT |
| C10072 | SEQ ID No. 161 | ACATAGAGGGTGGGACAA | SEQ ID No. 263 | GCAAGGGAAAGAGGAGTT |
| C10073 | SEQ ID No. 162 | AAAATGGGCCACTTCCTT | SEQ ID No. 264 | CTGCTTTCCGCTTCTTCT |
| C10136 | SEQ ID No. 163 | AATCTTGGGTTTTTCGTGGTTC | SEQ ID No. 265 | GGATGGGCTTGGCTAATGTTGC |
| C11077 | SEQ ID No. 164 | GCCGATTTGTTTTGATACTAA | SEQ ID No. 266 | CCAAAGTGTAAGGACAAGTAA |
| C11078 | SEQ ID No. 165 | TGGCAGGGAAGAAGAGAAAA | SEQ ID No. 267 | CTGAAGCAATCGGTAGGGTTT |
| C11079 | SEQ ID No. 166 | ATGAAGTGATGAAGTATGTGGG | SEQ ID No. 268 | AGATGATTTGGTGATAGAGTAG |
| C11080 | SEQ ID No. 167 | TTTGGTGGATTCCTTAGAGTGG | SEQ ID No. 269 | TTAGTTGCTTTGTTGATTGGTT |
| C11081 | SEQ ID No. 168 | TACCTTCTTTGCCTTCTCTTAT | SEQ ID No. 270 | AGTTGTCTTTTTCCACATCTTC |
| C11082 | SEQ ID No. 169 | CAATAAACTGCGAAGTGGACC | SEQ ID No. 271 | AGCGAGCAACTATTAGGAGCA |
| C12086 | SEQ ID No. 170 | ATTATTGGCTTACTATCTATGG | SEQ ID No. 272 | CATTCAAGTCCAATCATCTGT |
| C12087 | SEQ ID No. 171 | ATCAGATAGACTACCCAGACA | SEQ ID No. 273 | AAGGGCAAGACAGTGAAATCC |
| C12088 | SEQ ID No. 172 | CCCTCTGGAGACTTAGCAATCA | SEQ ID No. 274 | AACACAACAACGACTCCCATCT |
| C12089 | SEQ ID No. 173 | CAAGAAGAATGGGAAAGATGTT | SEQ ID No. 275 | AAGGGTTCTACAAGAGGCTACA |
| C12090 | SEQ ID No. 174 | TGTTTGTGAGAGAGTTGGTGATG | SEQ ID No. 276 | GGCCTTGGTGTCGATTGT |
| C12091 | SEQ ID No. 175 | CGAGAGCGATTTAGTCTCATT | SEQ ID No. 277 | CTTTGGACATGATGGTTTGT |
| C12092 | SEQ ID No. 176 | CGACATACCTCTGAAAGTGCCT | SEQ ID No. 278 | TCAAATAACACAAGTTCCTGCC |

TABLE 2-continued corresponding relationship between InDel marker and primer pair

| Indel marker | sequence number | Upstream primer sequence | sequence number | Downstream primer sequence |
|---|---|---|---|---|
| C13093 | SEQ ID No. 177 | AACAGCCCTATCGCCCTAAAT | SEQ ID No. 279 | AATACGACGACATCAGGAACA |
| C12132 | SEQ ID No. 178 | CATTTATTGGAAGGTAGGGAGT | SEQ ID No. 280 | TAGATGCTAAGTGATTGGGAGA |
| C13094 | SEQ ID No. 179 | TTAGAAAGAAACTACTGCTGCTC | SEQ ID No. 281 | TCTGGAATGTTTAGTTGGACG |
| C13096 | SEQ ID No. 180 | CGAACCTGTATTATCAGAAGCC | SEQ ID No. 282 | CAGCACCTATGAGACCTGTAAG |
| C13097 | SEQ ID No. 181 | CGTCCCATTATCGCATCTTCTA | SEQ ID No. 283 | ATCCACATTTGTTTTTCTTCTT |
| C13098 | SEQ ID No. 182 | TAACCCAAGAAAATAGGTGACT | SEQ ID No. 284 | CATACTGGATTACAGGAAGAAG |
| C13100 | SEQ ID No. 183 | GAAGATGACACTACGGAGAA | SEQ ID No. 285 | GACGACGATAACCATAAGAA |
| C13101 | SEQ ID No. 184 | ATTTCGCTGCCACCTGAT | SEQ ID No. 286 | CCAAGTTGTTCAAATCCC |
| C13102 | SEQ ID No. 185 | TGTGATGAAGAAGTGGCAACCT | SEQ ID No. 287 | AGACCGACAACTCTCAAGGGCT |
| C14104 | SEQ ID No. 186 | TTGAGGTAAAGGCGAAGA | SEQ ID No. 288 | GAAGTCACGGTTGTAGTTT |
| C14105 | SEQ ID No. 187 | GGCATTCCACGATTATTAGTT | SEQ ID No. 289 | AATACCAGGGAGAACACCACC |
| C14108 | SEQ ID No. 188 | CATTTGTTTTCACGCATTCTTT | SEQ ID No. 290 | CACATCTCTCTTCCCTCTTTCC |
| C15109 | SEQ ID No. 189 | CATAGAAAAGAGTCGCACAT | SEQ ID No. 291 | GCCGATGGATAAGATGAG |
| C15110 | SEQ ID No. 190 | ATTAGATTTCTCGCCGTAGTGT | SEQ ID No. 292 | ATAGGGCAGATGAGATGGATG |
| C15111 | SEQ ID No. 191 | TTCTTCGACAATAAAGGCATAG | SEQ ID No. 293 | TTTGTGGTGGTTGGTTGC |
| C15114 | SEQ ID No. 192 | GCTGAGGGTGAGAAAGATAAAT | SEQ ID No. 294 | GATGGTGCCAATGTTGTAGTTA |
| C15115 | SEQ ID No. 193 | ATGGTAGGAAAGGTGCTGGAGT | SEQ ID No. 295 | CAATGAGTCGCTTCTAAAATGA |
| C15116 | SEQ ID No. 194 | ATCTCAAAGACGCCTCATACAT | SEQ ID No. 296 | CGGGAAGACACAACACAAAACA |
| C15119 | SEQ ID No. 195 | CGAATGGAAGAATAATGATGAG | SEQ ID No. 297 | TAAAAGAGAGGGCTTGGTGGTA |
| C16120 | SEQ ID No. 196 | AGTAGATTGAGAAGGGTTGTGT | SEQ ID No. 298 | GTGTAGTTTATCCAGGGAAGTT |
| C16122 | SEQ ID No. 197 | ATTTTGAAAGGGTAGAAGGTGA | SEQ ID No. 299 | TACTGGATAGGGAGGAGGGTGC |
| C16123 | SEQ ID No. 198 | AAAAAATGTGATAAACCAACGA | SEQ ID No. 300 | GAAACAAGCAACAACTGAAGAG |
| C16124 | SEQ ID No. 199 | CTGTAGGATGTCATTTTCACGA | SEQ ID No. 301 | TTCCAGGAGATGTATGGGTTCA |
| C16125 | SEQ ID No. 200 | TTTCCTAAGAATCTCTCACCTG | SEQ ID No. 302 | TTGTCAAATCTAAAAATGTTCC |
| C17126 | SEQ ID No. 201 | GTGACAAAAAGGGATAGGAGAG | SEQ ID No. 303 | TTGAGGCTTGAATACAGAGATA |
| C17127 | SEQ ID No. 202 | AAAGGCACTCACCACAATCCAA | SEQ ID No. 304 | ATAGCCCAGCCCGCACTAAACC |
| C17128 | SEQ ID No. 203 | AACGGCTCATTCTTTCTACTTC | SEQ ID No. 305 | ATGGCTTTTGCGTCTCTCTCTG |
| C17129 | SEQ ID No. 204 | GACCACCTTTGGAGCACTAATA | SEQ ID No. 306 | ATGTCATTGTCTCAAAAGCCAC |

In some embodiments, the reaction procedure of the multiplex PCR is: pre-denaturation at 95° C. for 5 min; denaturation at 95° C. for 30 s, annealing at 55° C. for 90 s, extension at 72° C. for 90 s, 35 cycles; extension at 60° C. for 30 min; every 10 μL of the multiplex PCR system includes: 1 μL of 200 ng/μL genomic DNA, 4 μL 2.5× Master Mix I, 1 μL Primer mix and 4 μL ddH$_2$O; the concentration of each pair of primers in the Primer mix is 0.2 μM.

In some embodiments, the genotype combination of all InDel markers of any *Malus* accession in the whole genome InDel marker genotype database of *Malus* is used as molecular identity information for identifying the specificity of the accession. In some embodiments, the molecular identity information is presented, stored, identified and used in a two-dimensional code.

In some embodiments, the method for extracting genomic DNA of *Malus* germplasm resources is not particularly limited, the method is preferably CTAB, and the extracted tissues are preferably tender leaves of apple.

In some embodiments, when the primer pair is used, a fluorescent label is preferably added to the 5' end of the upstream primer, and the fluorescent label preferably includes HEX, PET, NED or FAM. The fluorescent multiplex PCR system is constructed with more primers to be mixed in the same reaction system, which has the advantages that: 1) different primers in the same system do not affect the amplification efficiency mutually; 2) the amplification efficiency of different primers in the same system is similar; 3) the fragments of primer amplification products labeled with the same fluorescent label in the same system are obviously different in size, which is easy to distinguish and detect.

The disclosure also provides the use of the whole genome InDel marker genotype database of *Malus* in the identification of *Malus* germplasm resources, which comprises the following steps:

extracting genomic DNA of a sample to be tested, genotyping the genomic DNA by using primer pairs, obtaining InDel marker genotype data of the sample to be tested, and comparing the InDel marker genotype data of the sample to be tested with the data in the whole genome InDel marker genotype database of *Malus* in the above technical scheme;

when the InDel marker genotype combination of the sample to be tested is the same as the molecular identity information of any germplasm resource in the InDel marker genotype database of the whole genome of *Malus*, it is judged that the sample to be tested has no specificity;

when the InDel marker genotype combination of the sample to be tested is different from the molecular identity information of all germplasm resources in the InDel marker genotype database of the whole genome of *Malus*, and is different from the molecular identity information of other samples to be tested with known InDel marker genotype combinations, it is judged that the sample to be tested has specificity.

In some embodiments, the AppleParentage1.0 software (https://github.com/wangx321/AppleParentage1.0) is preferably used for comparison.

In some embodiments, the online two-dimensional code generation software (https://cli.im/) is preferably used to generate two-dimensional codes from InDel marker gene data to construct molecular identity information of germplasm resources.

The disclosure also provides the use of the whole genome InDel marker genotype database of *Malus* in paternity testing of *Malus* germplasm resources, which comprises the following steps:

searching the parents and parents pair of the sample to be tested by using the whole genome InDel marker genotype database of *Malus* described above technical scheme, the search criteria are as follows:

when the marker genotype of the sample to be tested is D, the genotype of parents is D or DI, and the genotype combination of parents pair is D×D, D×DI, DI×D or DI×DI;

when the marker genotype of the sample to be tested is I, the genotype of the parent is I or DI, and the genotype combination of the parents pair can be I×I, I×DI, DI×I or DI×DI;

when the marker genotype of the sample to be tested is DI, the genotype of parents is D, I or DI, and the genotype combination of parents pair is D×I, I×D, D×DI, I×DI, DI×D, DI×I or DI×DI;

wherein D is deletion homozygous genotype, I is insertion homozygous genotype and DI is insertion deletion heterozygous genotype.

The technical scheme of the application will be described clearly and completely in combination with the examples in the application, but they should not be understood as limiting the scope of the present application.

Example 1

InDel Marker Development

Two apple varieties, 'Jonathan' and 'Golden Delicious', were sequenced by Illumina HiSeq2500 sequencer. The sequencing data were analyzed by Delly software, and 66,841 structural variations were obtained, including 16,130 deletions (DEL), 9,794 insertion (INS), 430 inversions (INV), 1132 intrachromosomal translocations (ITX) and 39355 interchromosomal translocations (CTX). In order to conveniently detect the mutation by PCR, the insertion/deletion with the variation sequence length of 50-500 bp was selected as the marker.

Among the 25,924 InDel variants mentioned above, the InDel mutation site which was evenly distributed on 17 chromosomes of apple genome and was genotypically stable and widely separated in *Malus* resources was selected to design primers. The accuracy of predicted InDel variant sequences was verified by PCR and Sanger sequencing. Taking InDel marker C07043 (i.e., SEQ ID No. 35) as an example (FIG. 1), the sequence with the difference between the long segment and the short segment of PCR product was the predicted InDel sequence. A total of 102 InDel markers with high quality were obtained, and their distribution on 17 chromosomes was shown in FIG. 2, and the primer sequence was shown in sequence Table 1.

Construction of Multiplex PCR System

Figure 3A:
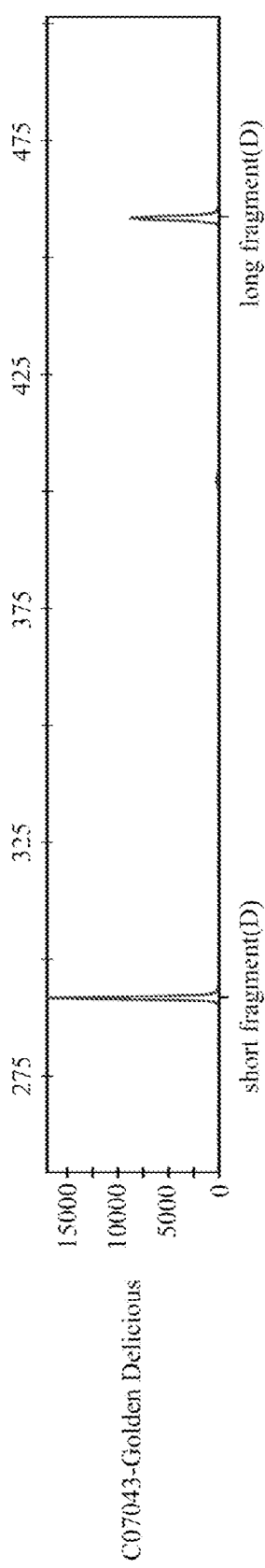
FIGS. 3A and 3B show the preliminary experiment result of capillary electrophoresis of the marker set forth in SEQ ID No. 35.
Figure 3B:
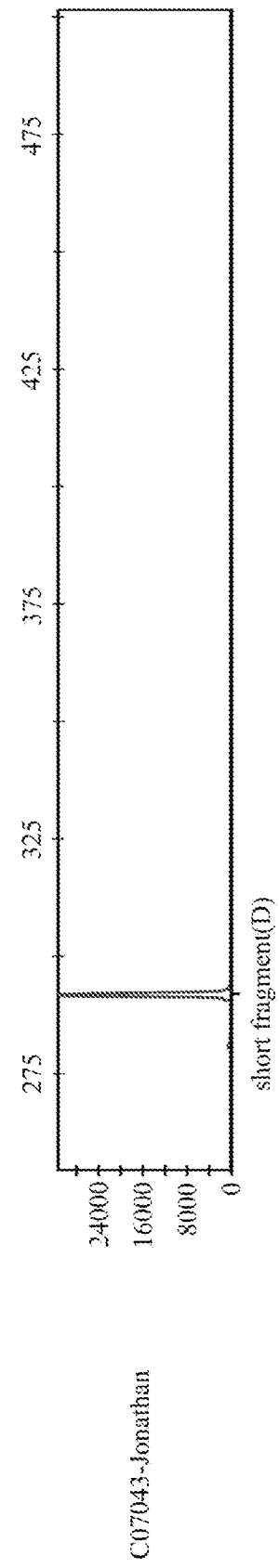
Figure 4A:
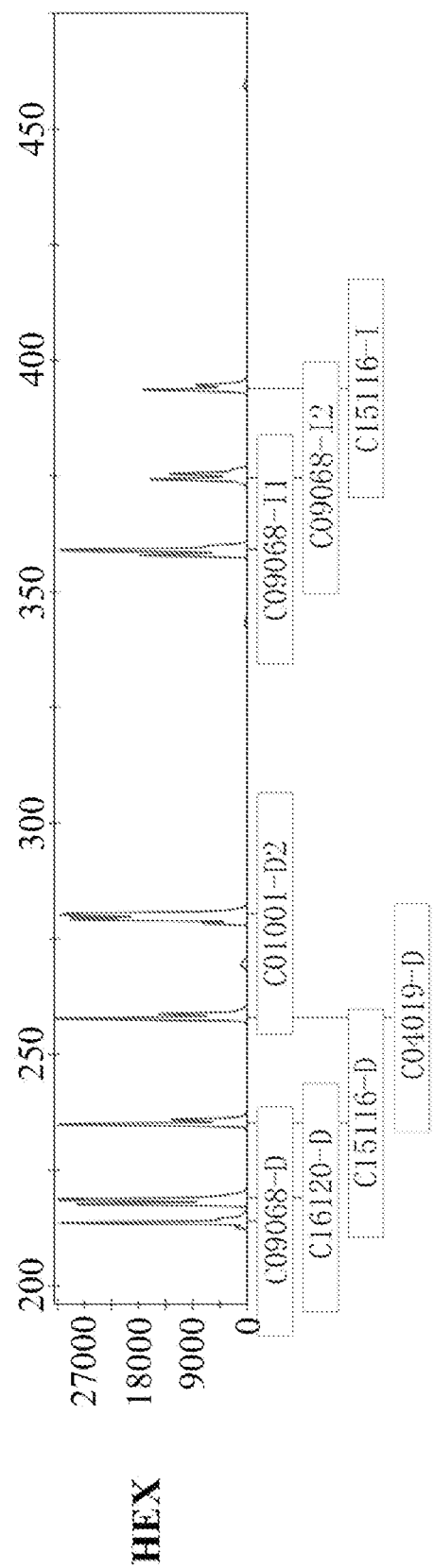
FIG. 4A is the capillary electrophoresis genotyping result (HEX) of SEQ ID No. 35 marker obtained by the multiplex PCR system (G2) for B-10 accession.
Figure 4B:
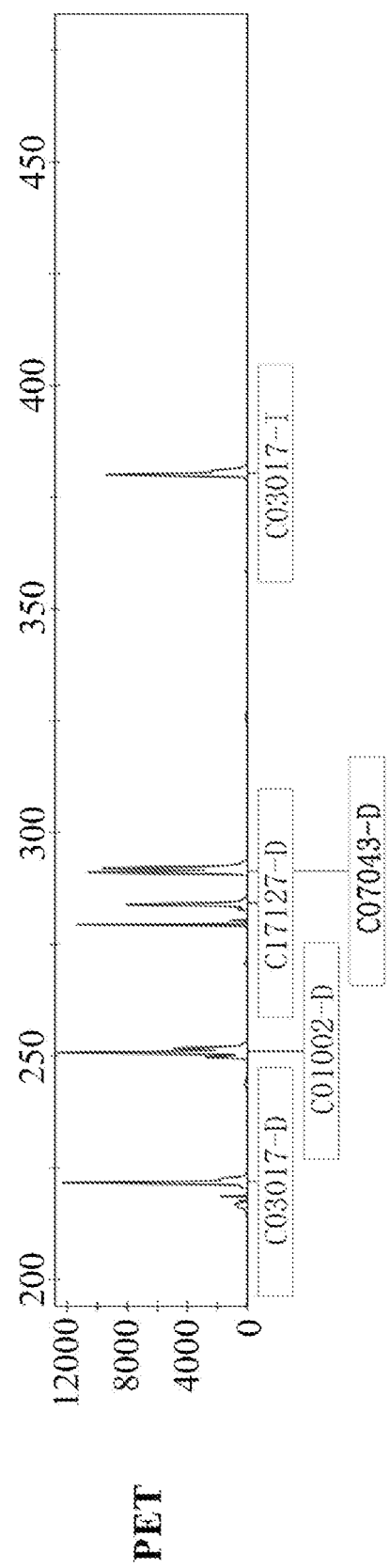
FIG. 4B is the capillary electrophoresis genotyping result (PET) of SEQ ID No. 35 marker obtained by the multiplex PCR system (G2) for B-10 accession.
Figure 4C:
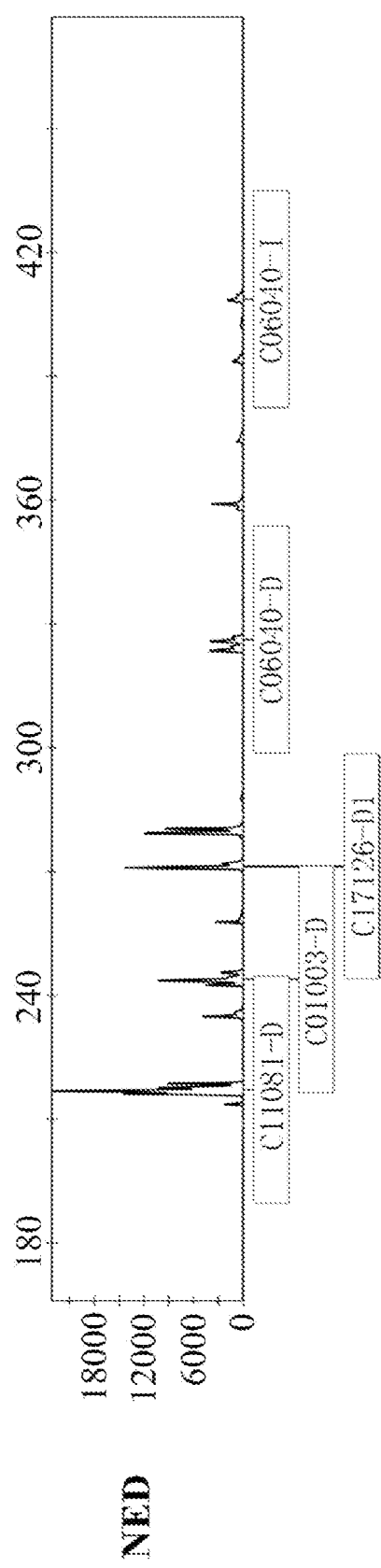
FIG. 4C is the capillary electrophoresis genotyping result (NED) of SEQ ID No. 35 marker obtained by the multiplex PCR system (G2) for B-10 accession.
Figure 4D:
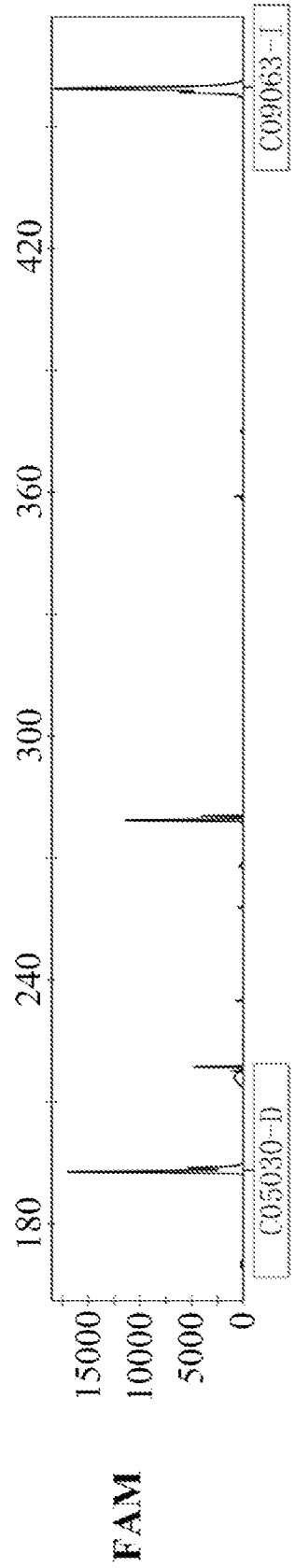
FIG. 4D is the capillary electrophoresis genotyping result (FAM) of SEQ ID No. 35 marker obtained by the multiplex PCR system (G2) for B-10 accession.

A fluorescent label (FAM, HEX, NED or PET) was added to the 5' end of the forward primer of the above 102 pairs of primers, and the genomic DNA of 'Jonathan' and 'Golden Delicious' was used as templates for PCR amplification, and the capillary electrophoresis was used for experimental detection. Taking the InDel marker set forth in SEQ ID No. 35 as an example, the long fragment length detected by capillary electrophoresis shown in FIG. 3 was 458 bp, while the short fragment was 293 bp, and the difference between the two fragments was the InDel marker with a length of 165 bp, which was consistent with the Sanger sequencing results in FIG. 1, indicating that the fluorescent capillary electrophoresis can accurately detect the genotype of InDel markers in germplasm.

The above 102 pairs of InDel primers were matched by multiplex PCR to construct a fluorescent multiplex PCR system. The matching principles were as follows: 1) different primers in the same system did not affect the amplification efficiency mutually; 2) the amplification efficiency of different primers in the same system was similar; 3) the fragments of primer amplification products labeled with the same fluorescent label in the same system were obviously different in size, which was easy to distinguish and detect. Taking the multiplex PCR system G2 where the SEQ ID No. 35 marker located as an example, the results of capillary electrophoresis after typing the B-10 germplasm by the system were shown in FIGS. 4A-D, which showed that the system could meet the above matching principle. Finally, 102 markers were divided into 9 multiplex PCR systems, and each system could carry out 3-24 multiplex amplifications. See Table 1 for the allocation information.

10 µL PCR system was used in each group: 1 µL DNA (concentration: 200 ng/ml), 4 µL 2.5× Master Mix I (from Beijing Yuewei Gene Technology Co., Ltd.), 1 µL Primer Mix (concentration of each primer was 0.2 µM), 4 µL ddH$_2$O.

The PCR reaction procedure was: pre-denaturation at 95° C. for 5 min; denaturation at 95° C. for 30 s, annealing at 55° C. for 90 s, extension at 72° C. for 90 s, 35 cycles; extension at 60° C. for 30 min and stored at 12° C.

Example 2

Construction of InDel Marker Genotype Database of *Malus* Germplasm Resources

A total of 1251 *Malus* germplasm resources were collected in the present example, including 35 species, 981 varieties of cultivated apples, and 322 bud mutation varieties in cultivated species (Table 2).

The application adopted CTAB method to extract genomic DNA of *Malus* germplasm resources, and finally adjusted the concentration of the extracted DNA solution to 200 ng/µL for detection.

The fluorescence multiplex PCR system constructed in Example 1 was used for testing the InDel marker genotype of 1251 *Malus* germplasm resources. The sorting format of the detection results was: the typing results was sorted out according to the format that one germplasm resource corresponding to one all marker genotypes as one line, and a genotype database containing 1251 *Malus* germplasm resources corresponding to 102 InDel markers was constructed, of which the results were shown in Table 3.

TABLE 3

Partial germplasm resources of *Malus* in the present application

| Species | Number | Partial Germplasm (Germplasm Number) | Mutants (Number) |
|---|---|---|---|
| *Malus domestica* Borkh. | 981 | Nagafu 1 (10--12), N2 (13--22), Shengfang 1 (14--14), Yujing II (14--16), Nagafu 7 (14--20), Qunfu 1 (14--23), Saito II (16--23), Lele Fuji (19--11), Red Fuji TAO (19--14), Qian 1 Ace (21--0), Dabinette (22--15), Hirosaki Fuji (23--1), Miya Fuji (23--10), Aomori Spur Fuji (23--4), Akifu 39 (23--9), Fengcun Fuji (24--22), Korin (25--15), Shichinohe 1 (25--9), Yanfu 1 (26--22), Nagafu 2 (27--16), etc | 'Fuji' mutants (160) |
| | | Silver Spur Red Delicious (11--4), Skyline Spureme (11--8), Jie 15 (12--8), Norsan (13--5), StarkSpur Ultra Red Delicious (15--3), Sharp Red Delicious (15--4), Zhanxuan 18 (15--7), Xishan 1 (15--8), Xinhong (16--1), Hardi Brite (16--16), Zhuoai 1 (16--2), Red Delicious (25--2), Ace (28-4), Xinyuanshuai (29--3), Tianwang 1(31--18), Ruby (3--16), Fushan 5 (5--14), Houjiadian Spur (5--18), etc | Red Delicious' mutants (60) |
| | | Hongjin Gala (22--4), Enqi (27--13), Zaohongda Gala(27--6), Fuga (29--17), Gala(BK-gala), Italy Early Red(BK-YDLZH), Mitchgla (HS-3), Buckeye Gala (HS-5), Mitchgala (SX-10), Liga (SX-20), Ennike Gala (SX-28), Qinyang(SX-6), Gala 4x (TA-1), Italy Gala(WH-9), etc | 'Gala' mutants (60) |
| | | Hebei Kangbing Golden Delicious (13--6), Smoothee (21--17), Golden Spur (26--14), Qihe Golden Sper (4--22), Stark Spur Golden (5--5), Enweier Golden (5--6), Spur Golden Delicious (BK-DJG), Golden Delicious (BK-GD), Italy Smothe (WH-10), Golden Spur (YT-24), Jinshuai mutant (YT-95), etc | 'Golden Delicious' mutants (14) |
| | | Sakatakei Tsugaru (10--5), Chu Tsugaru (22--11), Tsugaru (28--5), Meilingxi Tsugaru (8--13), Todoroki Tsugaru (9--12), Tsugaru (YT-94), Fangming (BK-FM), etc | 'Tsugaru' mutants (10) |
| | | Jie 1 (11--0), Jonathan (BK-Jonathan), Jonathan-M41 (YN-17), Jonathan-csan (YT-35), Jonathan-early (YT-73), etc | 'Jonathan' mutants (10) |
| | | Pingzhi Ralls Janet (15--15), Ralls Janet (19--2), Chimeric Ralls Janet (19--4), etc | 'Ralls Janet' mutants (6) |
| | | Longwei (YN-7), Longwei Early Mutant (YN-8) | 'Longwei' mutants (2) |
| | | Early Harvest (1--13), Dongxiangjiao (11--5), Guoling (1--15), Chantecler (11--9), Close (1--19), Aizaohui (1--2), Wuyue (12--1), Bukowka (12--11), Calville Rouge (12--14), Doyle (12--15), Melrose (12--16), Menage (12--17), Bo 26 (12--18), Duoyilu (12--19), De 6 (12--20), Red June (12--21), Helasang (12--23), Hesetiaowen (12--3), Janies Grieve (1--23), Bailuosi Malin (12--4), etc | |
| *Malus sieversii* (Ledeb.) Roem. | 49 | Xinjiang 26 (BK-XJ26), Xinjiang 28 (BK-XJ28), Xinjiang 29 (BK-XJ29), Xinjiang 31 (BK-XJ31), Xinjiang 3 (BK-XJ3H), Xinjiang 6 (BK-XJ6H), Xinjiang 7 (BK-XJ7), Xinjiang 8 (BK-XJ8), Xinjiang 9 (BK-XJ9), Xinjiang Wild Apple (XC-XJYHT), Xinjiang 10 (XN-XJ10), Xinjiang 11 (XN-XJ11), Xinjiang 12 (XN-XJ12), Xinjiang 13 (XN-XJ13), Xinjiang 14 (XN-XJ14), Xinjiang 15 (XN-XJ15), Xinjiang 16 (XN-XJ16), Xinjiang 17 (XN-XJ17), etc | |
| *Malus pumila* Mill. | 31 | Mianpingguo (12--9), Xiangguo(4--12), 147 (B-38), 77-34 (BK-77-34), CG24 (BK-CG24), CG3 (BK-CG3), GM256 (BK-GM256), GM310 (BK-GM310), Liaozhen 1 (BK-LZ1H), M7 (BK-M7), MM106 (BK-MM106), P16 (BK-P16), P22 (BK-P22), T337 (BK-T337), E Zhen 1 (QD-13), E Zhen 2 (QD-14), BP (TA-3), BP-176 (TA-4), G41 (TA-5), G935 (TA-6), P60 (TA-7), NAKT M9 clone (Z-13), NAKB clone (Z-5), M9 pajam2 (Z-6), etc | |
| *Malus asiatica* × *domestica* | 25 | 07-115 (BK-1), 03-010 (YX-03-010), 03-111 (YX-03-111), 04-033 (YX-04-033), 04-087 (YX-04-087), 10-010 (YX-10-010), 21-005 (YX-21-005), 21-018 (YX-21-018), 27-003 (YX-27-003), 30-001 (YX-30-001), 33-018 (YX-33-018), 33-101 (YX-33-101), 33-151 (YX-33-151), etc | |
| *Malus prunifolia* (Willd.) Borkh. | 25 | Luanzhuang Crab (B1-11), Mudanjiang Crab (B1-9), Hong Crab (B3-6), Banbishan Crab (BK-BBSHT), Big Crab (BK-DGHT), Daye Crab (BK-DYHT), Haitangguo (BK-HTG), Lenghaitang (BK-LHT), Laoshan 4(BK-LS4H), Qiuxiang Crab (BK-QXHT), Regunzi (BK-RGZ), Weiai 3 (BK-WA3), Xiaomian Crab (BK-XMHT), Yuanye Crab (BK-YYHT), Xiaofanshan Crab (BK-ZFSHT), Haihong(QD-19), Donghongguo (XC-DHG), Jilin Huang Crab (XC-JLHHT), Qiuzi (XC-QZ), etc | |
| *Malus robusta* Rehder | 21 | Sankuaishi Crab (B1-12), DaBaleng (B-12), Changguo Crab (B-14), Daguo (B-17), Watermelon Crab (B-18), Baleng Crab (B2-3), Xiaofanshan Baleng (B3-11), B68 (B-7), Huaida (B-8), Batougou Aizhen (BK-BTGAZ), Dolgo (BK-DDG), Pingdinghaitang (BK-PDHT), Sdw1 (BK-Sdw1), Fufeng Baleng(GY-2), Qianxian Crab (QX-1), etc | |

TABLE 3-continued

Partial germplasm resources of *Malus* in the present application

| Species | Number | Partial Germplasm (Germplasm Number) | Mutants (Number) |
|---|---|---|---|
| *Malus asiatica* Nakai | 20 | Miguo (28--3), (B2-11), Xiaofan Crab (B2-13), Aihonghua (B2-8), Zaobai Crab (B3-1), White Crab (BK-BHT), Binzi (BK-BZ), Chuangling Crab (BK-CLHT), Wanbai Crab (BK-WBHT), Xiaofanshan Binzi (BK-XFSBZ), Xiaogoumen Naizi (BK-XGMNZ), XGM Suan Binzi (BK-XGMSBZ), XGM Tian Binzi (BK-XGMTBZ), Zisai Pearl (BK-Zisai), Linqin Crab (LQ), Taigu Shaguo Late (SX-17), Taiguo Shaguo Early (SX-7), Huahong (SY-19), Qiufengmi (SY-20), Bai Crab (WH-2) | |
| *Malus baccata* (L.) Borkh. | 13 | Jingbohu Shandingzi (B3-2), Eluosi Daguo Shandingzi (B3-3), KLGDG Shandingzi (BK-KLGDGSDZ), Shandingzi 2 (BK-SDZ2H), Su E Shandingzi (BK-SESDZ), Zhuifeng 1 (BK-ZF1H), Zhuifeng 2 (BK-ZF2H), Y-1 (SX-21), B009 (SX-22), Y-2 (SX-25), Y-3 SX-26), Shandingzi (XC-SDZ), Zhaai (XC-ZA) | |
| *Malus niedzwetzkyana* Dieck. | 12 | Hongrou Pingguo (15--9), Hongxun 1 (QD-22), another Hongrou (SX-18), Hongrou 1 (XN-HR1), Hongrou 2 (XN-HR2), Hongrou 3 (XN-HR3), Hongrou 4 (XN-HR4), Hongrou 5 (XN-HR5), Hongrou 6 (XN-HR6), Hongrou 7 (XN-HR7), Yun Hongrou (YN-12), Xinjiang Hongrou Crab (YT-12) | |
| *Malus domestica* × *asiatica* | 6 | 12-206 (YX-12-206), 13-025 (YX-13-025), 16-155 (YX-16-155), 16-157 (YX-16-157), 17-023 (YX-17-023), 17-199 (YX-17-199) | |
| *Malus zumi* Mats. | 6 | Zumi Crab 3x (B-15), Zumi Crab 4x (B-21), Zumi Crab 3x 2 (B-22), Zumi Crab W1 (B-29), Zumi Crab (B-30), Zumi Crab (XC-ZMHT) | |
| *Malus* hybrid | 5 | Wufengshan 1 (BK-WFS1H), Wufengshan 4 (BK-WFS4H), Wufengshan Crab (BK-WFSHT), Wufengshan Crab 2 (BK-WFSHT2H), Wufengshan Crab 6 (BK-WFSHT6H) | |
| *Malus honanensis* Rehder | 4 | Late Crab (B-1), SH6 (BK-SH6), SH40-2 seedling (QD-4), Chaguo (XC-CG) | |
| *Malus hupehensis* (Pamp.) Rehd. | 4 | Pingyitiancha (BK-PYTC), Lushi Crab (XC-LSHT), Pingyitiancha (XC-PYTC), Taishan Crab (YT-96) | |
| *Malus sieboldii* (Regel.) Rehder | 4 | Lushan Sanye (LSSY), Fuxian Sanye (XC-FXXY), Hongsanye (XC-HSY), Weixi Sanye (XC-WXSY) | |
| *Malus toringoides* (Rehd.) Hughes | 4 | Wushan Bianye (WSBY), Sichuan Bianye (XC-SCBY), Xiaojin Bianye (XC-XJBY), Yajiang Bianye (XC-YJBY) | |
| *Malus sargentii* Rehd. | 3 | Shanjin Crab N1 (QD-11), Shanjin Crab N2 (QD-12), Shajin Crab (XC-JSHT) | |
| *Malus sikkimensis* (Wengzig) Koehne | 3 | Xijin Crab (BK-XJHT), Deqin Crab (DQ), Linzhi (XC-LZ) | |
| *Malus ioensis* (Wood) Britton | 2 | Caoyuan Crab (B2-1), Caoyuan Crab (QD-7) | |
| *Malus micromalus* Makino | 2 | Laiwunanyan (XC-LWNY), Xifu Crab (XC-XFHT) | |
| *Malus spectabilis* (Ait) Borkh. | 2 | Daxiangguo (BK-DXG), Haitanghua (BK-HTH) | |
| *Malus cerasifolia* Spach. | 1 | Yingye Crab (XC-YYHT) | |
| *Malus coronaria* (L.) Mill. | 1 | Huaguan Crab (BK-HGHT) | |
| *Malus domestica* × *robusta* | 1 | Olga (SY-9) | |
| *Malus domestica* ssp. *chinensis* var. *binzi* Li. Y. N. | 1 | Binzi (SW) (BK-BZXN) | |
| Malus kansuensis (Batal.) Schneid. | 1 | Longdong Crab (XC-LDHT) | |
| *Malus manshurica* (Maxim) Komarov | 1 | Mao Shandingzi (XC-MSDZ) | |
| *Malus ombrophila* Hand-Mazz. | 1 | Cangjiang Crab (BK-CJHT) | |
| *Malus orientalis* Uglitzk. | 1 | Oriental Apple(BK-DFPG) | |
| *Malus orientalis.* subsp. *turkmerum* Langenf. | 1 | Turkmen Apple (BK-TKMPG) | |
| *Malus platycarpa* Rehd. | 1 | Biaoguo Crab (BK-PGHT) | |
| *Malus robusta* × *domestica* | 1 | Mrxl(*robusta* × Liberte) (YT-54) | |
| *Malus rockii* Rehd. | 1 | Lijiang Shandingzi (BK-LJSDZ) | |
| *Malus sylvestris* (L.) Mill. | 1 | Forest Apple (BK-SLPG) | |
| *Malus xiaojinensis* Cheng et Jiang | 1 | Xiaojin Crab (QD-8) | |
| others | 15 | Banxiu Crab (BJ-4), 28-253 (BK-28-253), Baotou Linqin (QD-31), 78-M18 (SY-1), Binlang (SY-2), 03-06-04 (SY-8), Cherry Crab (XY-6), Chongban Crab (XY-9), Xichang Yuanzhuiguo (XYZ-2), Ziye zixiaoguo (XYZ-3), Ziye zidaguo (XYZ-4), Shoufenshu 6 (XYZ-5), Lixing Crab (YN-13), Xianhong (YT-28), Yangbai Crab (YT-6), etc | |

| Construction results of InDel marker genotype database of *Malus* germplasm resources | | | | | | | | | | | | | |
|---|---|---|---|---|---|---|---|---|---|---|---|---|---|
| Accession name (Accession ID) | C01002 | C01003 | C01004 | C01005 | C02006 | C02008 | C02009 | C03011 | C03014 | C03017 | C03018 | C04019 | C04020 |
| Black Ben Davis (10--1) | DI | D | D | D | D | D | D | DI | D | D | I | D | DI |
| Lysgolden (10--10) | DI | DI | D | DI | D | DI | DI | DI | D | DI | DI | I | D |
| Dongchengguan 13 (10--11) | DI | DI | DI | DI | D | DI | DI | DI | D | DI | DI | I | D |
| Nagafu 1 (10--12) | DI | DI | DI | DI | D | DI | DI | DI | D | DI | DI | I | D |
| Shengli Hongguan (10--14) | I | D | DI | DI | DI | D | D | D | D | DI | DI | D | DI |
| Shizishan 1 (10--15) | I | D | DI | DI | DI | DI | D | D | D | DI | DI | D | DI |
| Baoman (10--2) | D | D | DI | D | I | DI | DI | D | D | D | I | D | D |
| Melba (10--20) | DI | D | DI | D | DI | DI | D | DI | D | DI | DI | DI | D |
| Kuliesa (10--21) | D | D | D | DI | D | DI | D | DI | D | DI | DI | D | D |
| De 8 (10--22) | D | D | D | DI | DI | DI | D | D | DI | D | DI | DI | DI |
| Bo 5 (10--23) | D | DI | DI | DI | D | D | DI | D | D | D | I | DI | DI |
| Iran Pippin (10--4) | D | D | D | DI | I | DI | D | D | DI | DI | DI | D | DI |
| Sakatakei Tsugaru (10--5) | D | DI | DI | DI | D | D | DI | D | DI | DI | I | DI | DI |
| Khrushchev (10--6) | DI | D | DI | DI | DI | DI | D | DI | D | DI | I | DI | DI |
| Batul (10--7) | DI | D | D | D | DI | DI | DI | D | DI | D | DI | DI | DI |
| Prime Gold (10--9) | DI | D | D | D | DI | D | DI | D | DI | D | DI | DI | DI |
| Jie 1 (11--0) | D | DI | DI | D | D | D | D | D | DI | DI | DI | D | D |
| Guldborg (1--11) | DI | DI | DI | DI | D | DI | DI | DI | D | DI | DI | I | D |
| Shajin Yilamu (11--10) | D | D | D | D | I | DI | I | DI | D | DI | I | D | D |
| Soviet (11--11) | D | D | D | DI | DI | DI | D | DI | D | DI | DI | DI | DI |
| Lobo (11--13) | DI | D | DI | D | DI | DI | D | D | D | DI | DI | I | D |
| Allington Pippin (11--14) | D | D | DI | DI | D | DI | DI | DI | D | D | I | D | D |
| Malinova (11--15) | D | D | D | D | DI | DI | DI | D | D | DI | I | I | D |
| Sweet McIntosh (11--16) | D | D | D | D | DI | DI | DI | D | D | DI | I | I | D |
| McIntosh (11--18) | D | D | D | I | D | DI | I | DI | D | DI | D | I | D |
| Spartan (11--2) | DI | D | D | DI | D | DI | DI | DI | D | D | DI | I | D |
| Fushuai (1--12) | DI | DI | DI | DI | DI | DI | DI | DI | D | DI | D | I | DI |
| Summer Pearmain (11--20) | D | D | DI | DI | I | DI | DI | D | D | D | I | D | D |
| Helm (11--21) | DI | D | D | DI | DI | DI | D | DI | DI | DI | DI | DI | D |
| Domenesti (11--3) | D | D | D | D | D | I | D | DI | D | D | DI | D | D |
| Early Harvest (1--13) | DI | DI | DI | DI | DI | DI | DI | DI | D | DI | D | I | DI |
| Silver Spur Red Delicious (11--4) | D | D | D | DI | D | D | DI | DI | D | DI | DI | I | D |
| Dongxiangjiao (11--5) | DI | D | DI | D | D | I | D | D | DI | DI | DI | D | D |
| Guoling (1--15) | D | DI | DI | DI | DI | D | D | D | D | DI | I | D | DI |
| Skyline Spureme (11--8) | D | D | D | D | D | D | DI | DI | D | DI | DI | I | D |
| Chantecler (11--9) | DI | D | D | DI | DI | DI | D | DI | D | DI | I | I | D |
| Close (1--19) | D | D | DI | DI | I | D | DI | DI | DI | DI | I | D | D |

-continued

| Construction results of InDel marker genotype database of *Malus* germplasm resources |||||||||||||||
|---|---|---|---|---|---|---|---|---|---|---|---|---|---|
| Aizaohui (1--2) | D | DI | DI | DI | DI | DI | D | DI | DI | DI | DI | D | D |
| Wuyue (12--1) | D | D | DI | DI | D | DI | D | DI | DI | DI | DI | DI | D |
| Bukowka (12--11) | I | D | D | D | DI | DI | DI | DI | D | DI | DI | D | D |
| Jinyu (12--12) | D | DI | DI | D | DI | D | D | D | DI | DI | DI | D | D |
| Calville Rouge (12--14) | DI | D | D | D | DI | DI | D | DI | D | DI | I | DI | DI |
| Doyle (12--15) | D | DI | DI | DI | DI | DI | D | DI | I | DI | DI | D | D |
| Melrose (12--16) | D | DI | DI | D | D | D | DI | DI | DI | DI | DI | D | D |
| Menage (12--17) | D | D | DI | DI | DI | DI | D | DI | DI | DI | I | D | D |
| Bo 26 (12--18) | D | D | D | I | DI | DI | D | DI | I | D | DI | D | DI |
| Duoyilu (12--19) | D | D | DI | D | DI | DI | DI | D | D | DI | I | D | DI |
| De 6 (12--20) | D | D | D | DI | DI | DI | D | D | D | D | I | D | D |
| Red June (12--21) | D | D | DI | D | DI | D | DI | D | DI | DI | DI | D | DI |
| Helasang (12--23) | DI | D | DI | DI | DI | I | D | D | D | DI | DI | DI | D |
| Hesetiaowen (12--3) | DI | D | DI | D | D | DI | D | DI | DI | DI | I | D | D |
| James Grieve (1--23) | D | D | D | DI | I | DI | DI | DI | DI | D | D | D | D |
| Bailuosi Malin (12--4) | DI | D | D | DI | DI | DI | DI | DI | D | DI | DI | D | I |
| Jinnhong (12--5) | D | DI | DI | DI | DI | D | DI | DI | DI | DI | DI | DI | DI |
| Kay Sai William (12--6) | DI | D | D | DI | D | DI | DI | DI | D | DI | DI | I | D |
| Xingjiang Pingguo (12--7) | D | D | D | D | DI | DI | I | DI | D | DI | I | D | DI |
| Jie 15 (12--8) | D | D | D | DI | D | D | DI | DI | D | DI | DI | I | D |
| Mianpingguo (12--9) | D | D | D | D | DI | DI | I | DI | D | DI | DI | D | I |
| Lowver (1--3) | D | D | D | D | DI | D | DI | D | DI | D | DI | D | D |
| Benoni (13--1) | D | D | D | DI | DI | DI | D | DI | DI | DI | DI | DI | DI |
| Fa 5 (13--11) | DI | D | D | DI | DI | DI | D | DI | D | DI | DI | DI | DI |
| Babskino (13--12) | D | D | D | DI | DI | I | D | DI | D | DI | DI | D | D |
| Kuluona (13--13) | D | DI | DI | D | DI | D | D | D | D | DI | D | D | D |
| Shidonghaoji (13--16) | I | D | DI | DI | DI | DI | D | DI | D | DI | DI | D | DI |
| Oberkika (13--17) | D | D | DI | D | D | DI | DI | D | D | DI | DI | DI | D |
| Budayi (13--19) | DI | DI | DI | DI | D | DI | DI | D | DI | D | DI | I | D |
| Red Canada (13--2) | DI | D | D | DI | DI | DI | D | DI | D | DI | DI | DI | DI |
| Laidi (13--20) | D | D | D | D | I | DI | DI | D | DI | DI | I | DI | I |
| N2 (13--22) | DI | D | D | DI | D | DI | DI | DI | D | D | DI | DI | DI |
| Norsan (13--5) | D | D | D | DI | D | D | DI | DI | D | DI | DI | I | D |
| Hebei Kangbing Golden Delicious (13--6) | DI | DI | DI | I | D | DI | I | DI | DI | DI | D | I | DI |
| Zhanxuan 14 (13--9) | DI | DI | DI | DI | D | DI | DI | DI | D | DI | DI | I | D |
| Xiangguoguang (14--11) | D | D | D | D | DI | D | DI | DI | DI | DI | DI | I | D |
| Shengfang 1 (14--14) | DI | D | D | DI | DI | DI | DI | DI | D | D | DI | DI | DI |
| Yujing II (14--16) | DI | D | D | DI | DI | DI | DI | DI | D | D | DI | DI | DI |

| Construction results of InDel marker genotype database of *Malus* germplasm resources | | | | | | | | | | | | | |
|---|---|---|---|---|---|---|---|---|---|---|---|---|---|
| Cox's Orange Pippin (14--2) | DI | DI | DI | DI | I | DI | D | DI | D | D | I | D | D |
| Nagafu 7 (14--20) | DI | DI | D | DI | DI | DI | DI | DI | D | D | DI | DI | DI |
| Boiken (14--21) | DI | D | D | D | I | D | D | D | DI | DI | DI | I | D |
| Qunfu 1 (14--23) | DI | D | D | DI | DI | DI | DI | DI | D | D | DI | DI | DI |
| Calville Blanche (14--3) | DI | D | D | D | I | D | D | D | DI | DI | DI | I | D |
| Freybreg (14--4) | DI | DI | DI | DI | DI | I | DI | DI | D | DI | DI | I | DI |
| Husveti Rosmaring (14--5) | DI | D | D | DI | DI | DI | D | D | D | D | I | D | DI |
| Sweet Jonathan (14--7) | D | DI | DI | D | DI | D | D | D | DI | DI | DI | D | D |
| King of Pippin (14--8) | DI | DI | DI | DI | I | DI | D | DI | D | D | I | D | D |
| Duchess of Oldenburg (1--5) | DI | DI | DI | D | D | DI | D | DI | D | D | DI | D | D |
| Kangbing Golden 5 (15--11) | DI | DI | DI | I | DI | DI | I | DI | DI | DI | DI | I | DI |
| Pingzhi Ralls Janet (15--15) | DI | DI | DI | D | DI | DI | D | D | D | DI | I | DI | DI |
| Wase16 (15--16) | DI | D | D | DI | I | D | DI | DI | DI | D | D | DI | DI |
| Kogetsu (15--17) | DI | DI | DI | DI | I | D | DI | DI | D | D | DI | DI | DI |
| Jonared (15--18) | D | DI | DI | D | DI | D | D | D | DI | DI | DI | D | D |
| Zhanxuan 4 (15--21) | DI | DI | DI | DI | D | DI | DI | DI | D | DI | DI | I | DI |
| Strawberry (15--23) | D | DI | DI | DI | D | DI | D | DI | DI | D | DI | D | DI |
| StarkSpur Ultra Red Delicious (15--3) | D | D | D | DI | D | D | DI | DI | D | DI | DI | I | D |
| Sharp Red Delicious (15--4) | D | D | D | DI | D | D | DI | DI | D | DI | DI | I | D |
| Mensi (15--5) | D | D | D | DI | DI | DI | D | D | DI | DI | DI | D | DI |
| Norand (15--6) | D | D | D | DI | D | DI | DI | DI | D | DI | DI | DI | D |
| Zhanxuan 18 (15--7) | D | D | D | DI | D | D | DI | DI | D | DI | DI | I | D |
| Xishan 1 (15--8) | D | D | D | DI | D | D | DI | D | DI | DI | DI | I | D |
| Hongrou Pingguo (15--9) | D | D | D | D | DI | DI | DI | DI | D | DI | DI | D | DI |
| Gravenstein (1--6) | D | D | D | DI | DI | DI | D | DI | DI | DI | DI | D | D |
| Xinhong (16-1) | D | D | D | DI | DI | DI | DI | D | DI | DI | DI | D | D |
| Zhanxuan 6 (16--10) | DI | D | D | D | I | DI | DI | DI | D | DI | DI | I | D | D |
| Behene (16--11) | D | D | DI | DI | DI | DI | D | D | DI | DI | I | D | DI |
| Xindong (16--14) | D | D | D | D | I | DI | D | DI | D | DI | DI | D | D |
| Hardi Brite (16--16) | D | D | D | DI | D | D | DI | DI | D | DI | DI | I | D |
| Charden (16--17) | DI | DI | DI | DI | DI | DI | DI | DI | DI | DI | DI | I | DI |
| Zhuoai 1 (16--2) | DI | DI | DI | DI | D | DI | DI | DI | D | DI | DI | I | DI |
| Jinse Luosuoshan (16--22) | DI | DI | D | D | I | DI | D | DI | D | D | I | D | D |
| Zhaiteng II (16--23) | DI | D | D | DI | DI | DI | DI | D | D | D | DI | DI | DI |
| Zhanxuan 16 (16--6) | DI | DI | DI | DI | D | DI | DI | D | DI | DI | DI | I | D |
| Fa 3 (16--8) | D | D | D | D | D | I | D | D | D | DI | D | DI |
| Jerseymac (1--7) | D | D | DI | DI | I | D | D | DI | DI | D | D | DI | D |

| Construction results of InDel marker genotype database of *Malus* germplasm resources | | | | | | | | | | | | | |
|---|---|---|---|---|---|---|---|---|---|---|---|---|---|
| Mother (17--1) | DI | DI | DI | D | DI | DI | DI | DI | D | DI | DI | I | DI |
| Northern Spy (17--10) | D | D | D | I | DI | DI | DI | DI | DI | D | D | DI | D |
| Rome Beauty (17--11) | D | DI | DI | DI | DI | DI | D | DI | I | DI | DI | D | D |
| Black Ben David (17--12) | D | D | D | D | D | DI | DI | DI | DI | DI | DI | D | I |
| Atlas (17--13) | DI | DI | DI | D | DI | DI | DI | DI | D | D | D | I | DI |
| Roxbury (17--14) | DI | DI | DI | DI | D | DI | DI | DI | D | D | DI | DI | D |
| Laxtons Superb (17--15) | D | D | D | D | D | DI | D | D | D | D | I | D | D |
| Changhong (17--16) | D | DI | DI | DI | DI | D | D | DI | DI | DI | I | DI | DI |
| Cogswell Pearmain (17--17) | D | D | D | D | DI | DI | D | DI | D | D | DI | D | I |
| Twenty Ounce (17--18) | D | DI | DI | DI | D | DI | DI | DI | DI | DI | I | D | DI |
| Lowtosh (17--19) | D | D | DI | I | D | D | D | D | D | DI | I | DI | D |
| Iwaki (17--21) | D | DI | DI | D | I | DI | D | D | D | DI | DI | I |  |
| Qin'guan (17--22) | D | D | D | I | D | I | DI | DI | D | DI | I | I | D |
| Bancroft (17--23) | D | D | D | D | D | DI | D | DI | D | DI | D | I | DI |
| Chenango Strawberry (17--4) | D | D | DI | I | DI | DI | D | D | D | D | I | DI | DI |
| Newfane (17--7) | DI | DI | DI | D | DI | D | DI | DI | D | D | DI | D | D |
| Lord Lambourne (17--9) | D | D | D | I | DI | DI | D | DI | D | D | DI | D |  |
| Rizhiwan (18--0) | D | DI | DI | I | I | DI | DI | DI | D | D | DI | DI | I |
| Campbell (18--11) | DI | DI | DI | DI | D | DI | DI | DI | D | D | DI | DI | D |
| Pigeon (18--13) | DI | D | D | DI | I | DI | DI | DI | D | DI | DI | DI | D |
| Summer Champion (18--14) | D | D | D | D | D | DI | DI | D | D | D | DI | DI | DI |
| Nanpu 3 (18--15) | D | D | D | D | DI | D | D | D | DI | DI | DI | DI | DI |
| Qiulimeng (18--16) | D | D | D | D | D | DI | DI | DI | DI | DI | I | D | D |
| Rutosh (18--17) | DI | D | DI | DI | I | DI | D | DI | D | D | DI | DI | D |
| Xinlimei (18--19) | D | D | D | D | I | DI | DI | D | DI | DI | I | DI | I |
| Huanong 1 (18--2) | I | D | DI | D | I | DI | D | DI | DI | DI | DI | D | DI |
| Lawfam (18--20) | D | D | D | D | DI | DI | DI | D | D | DI | DI | I | DI |
| Akin's Red (18--21) | D | DI | DI | D | DI | DI | DI | DI | DI | DI | DI | D | D |
| Meltosh (18--22) | D | D | DI | DI | DI | DI | D | DI | DI | D | I | DI | DI |
| Hubbardston (18--23) | DI | DI | DI | DI | DI | I | DI | DI | D | DI | DI | I | DI |
| Fenghuangluan Crab (18--3) | I | D | DI | D | I | DI | D | DI | DI | DI | DI | D | DI |
| Jie 9 (18--4) | D | D | D | DI | DI | DI | DI | DI | DI | DI | DI | D | D |
| Bramley's Seedling (18--5) | DI | D | DI | DI | D | DI | DI | DI | DI | DI | DI | DI | DI |
| Shuangyang 1 (18--7) | DI | DI | DI | DI | DI | I | DI | DI | D | DI | DI | I | DI |
| Shengli (18--8) | DI | DI | DI | DI | DI | I | DI | DI | D | DI | DI | I | DI |
| Qingguan (18--9) | DI | D | D | D | I | D | DI | DI | D | D | DI | DI | I |
| Weeping Ralls (19--0) | DI | DI | DI | D | DI | D | D | D | D | DI | I | DI | DI |
| Giant Jeniton (19--1) | D | D | DI | DI | DI | DI | D | DI | DI | DI | I | D | D |

-continued

| Construction results of InDel marker genotype database of *Malus* germplasm resources | | | | | | | | | | | | | |
|---|---|---|---|---|---|---|---|---|---|---|---|---|
| Baldwin (19--10) | D | D | D | DI | DI | DI | DI | DI | DI | DI | DI | D | DI |
| Lele Fuji (19--11) | DI | D | D | DI | DI | DI | DI | DI | D | D | DI | DI | DI |
| Shuahong (19--12) | D | D | DI | DI | DI | D | D | DI | D | D | D | DI | D |
| Red Fuji TAO (19--14) | DI | D | D | DI | DI | DI | DI | DI | D | D | DI | DI | DI |
| Jizaohong (19--17) | DI | DI | DI | DI | DI | I | DI | DI | D | DI | DI | I | DI |
| Karas Tor (19--19) | D | D | D | DI | DI | DI | DI | DI | DI | DI | DI | DI | DI |
| Ralls Janet (19--2) | DI | DI | DI | D | DI | DI | D | D | D | DI | I | DI | DI |
| Stonetosh (19--22) | D | D | D | DI | DI | DI | DI | DI | D | D | DI | DI | D |
| White Pearmain (19--23) | D | D | D | DI | DI | D | I | DI | D | D | DI | I | DI |
| Xiushui Guoguang (19--3) | DI | DI | DI | DI | DI | D | D | DI | D | D | DI | D | DI |
| Chimeric Ralls Janet (19--4) | DI | DI | DI | D | DI | DI | D | D | D | D | I | DI | DI |
| Mutsu (19--7) | DI | DI | DI | I | DI | DI | DI | DI | DI | DI | DI | DI | DI |
| Ben David (19--8) | D | D | D | DI | D | DI | DI | DI | DI | DI | DI | D | I |
| Saint Lawrence (19--9) | D | D | D | DI | I | D | DI | D | D | D | I | D | DI |
| Newtosh (20--0) | D | D | D | D | DI | DI | I | D | D | DI | DI | D | D |
| Geliekekukui (20--1) | D | D | D | DI | DI | DI | DI | D | D | D | D | D | I |
| Sweet Jonathan (20--10) | D | DI | DI | D | DI | D | D | D | DI | DI | DI | D | D |
| Apple of Commerce (20--11) | D | D | D | I | D | DI | D | DI | D | DI | DI | D | DI |
| 600 g Andong (20--12) | D | D | DI | DI | DI | DI | DI | D | D | DI | I | D | DI |
| Winter Banana (20--14) | D | D | D | DI | DI | D | D | DI | D | DI | DI | DI | I |
| Rainier (20--15) | D | D | D | DI | D | DI | D | DI | D | DI | I | DI | DI |
| Winesap (20--16) | D | D | DI | I | DI | DI | DI | DI | DI | DI | DI | D | D |
| Drumbo (20--17) | D | D | DI | DI | DI | DI | D | DI | D | DI | I | DI | DI |
| Blengstid Gaurd (20--2) | D | D | D | D | D | I | D | D | D | D | DI | D | D |
| Jierjisi (20--21) | DI | D | D | DI | DI | DI | I | DI | D | DI | I | D | D |
| Radiant (20--23) | D | D | D | D | DI | DI | I | D | D | DI | DI | D | D |
| King David (20--5) | D | DI | DI | DI | I | DI | D | DI | D | DI | DI | D | D |
| Clapp's Seedling (20--6) | DI | D | D | D | I | D | I | DI | D | D | DI | DI | I |
| Ingram (20--7) | DI | D | D | D | I | D | D | D | D | I | I | D | |
| Qiujin (20--8) | DI | DI | DI | DI | D | DI | DI | DI | D | DI | DI | I | D |
| Sujsleppskoe (2--1) | D | D | D | D | DI | I | D | DI | D | DI | I | D | D |
| Qian 1 Ace (21--0) | DI | D | D | DI | DI | DI | DI | DI | D | D | DI | DI | DI |
| Toko (2--10) | DI | DI | DI | DI | I | D | DI | D | D | D | DI | DI | I |
| Antalue (21--1) | I | DI | DI | DI | D | DI | DI | DI | D | D | D | DI | I |
| Boskoopske Cervene (2--11) | D | D | D | D | D | I | D | D | D | D | DI | D | D |
| Heoersitai (21--10) | DI | D | DI | D | D | I | D | D | D | DI | I | D | DI |
| Lanfengwang (21--11) | D | D | D | D | D | I | D | D | DI | D | I | D | D |
| Aohong (21--14) | D | DI | DI | DI | DI | DI | DI | DI | DI | DI | DI | DI | DI |
| Weiqinni (21--15) | D | D | D | DI | DI | D | DI | DI | DI | D | DI | DI | D |

-continued

| Construction results of InDel marker genotype database of *Malus* germplasm resources | | | | | | | | | | | | | |
|---|---|---|---|---|---|---|---|---|---|---|---|---|---|
| Smoothee (21--17) | h | DI | DI | I | DI | DI | I | DI | DI | DI | DI | I | DI |
| Hongzhiwu (21--18) | D | D | DI | D | D | D | D | D | DI | DI | DI | DI | DI |
| Jieba (21--2) | DI | D | D | DI | DI | I | D | D | D | DI | DI | DI | D |
| Kizashi (21--20) | DI | DI | DI | DI | D | DI | DI | DI | D | DI | D | I | DI |
| Aifeng (21--21) | DI | DI | DI | DI | D | DI | DI | DI | D | DI | D | I | DI |
| Xingping (21--4) | DI | DI | DI | D | DI | DI | D | D | DI | DI | I | DI | DI |
| Esopus Spitzenburg (2--14) | DI | DI | DI | D | I | DI | D | D | D | DI | DI | D | DI |
| Lvguang (21--6) | D | D | D | D | I | DI | I | DI | D | DI | I | D | D |
| Nvyoujidui (2--16) | I | D | DI | D | DI | DI | D | DI | D | DI | DI | D | I |
| Bell Poos (21--7) | DI | D | D | DI | DI | DI | DI | D | DI | DI | DI | D | DI |
| Tian Andongnuo (2--17) | DI | D | DI | D | I | DI | D | DI | D | DI | DI | D | D |
| Pacific Rose (21--8) | D | DI | D | DI | DI | DI | DI | DI | DI | DI | DI | DI | DI |
| 500 g (21--9) | D | D | D | D | D | DI | D | DI | D | D | D | I | DI |
| Nvyoujidui 2 (2--19) | D | D | D | D | DI | I | D | DI | D | DI | I | D | D |
| Tian Andongnuo 2 (2--2) | DI | DI | DI | D | DI | DI | D | DI | D | DI | I | DI | DI |
| Spur Mutsu (22--1) | DI | DI | DI | I | DI | DI | DI | DI | D | DI | DI | DI | DI |
| Red June Sweet (2--21) | I | D | D | D | DI | DI | DI | D | DI | DI | DI | D | D |
| Chu Tsugaru (22--11) | D | DI | DI | DI | D | D | DI | D | DI | DI | I | DI | DI |
| Kermemen (22--13) | DI | D | D | DI | D | D | D | D | D | DI | DI | D | I |
| Bedan (22--14) | D | DI | DI | D | DI | I | D | DI | DI | D | DI | D | DI |
| Dabinette (22--15) | DI | D | D | DI | DI | DI | DI | DI | D | D | DI | DI | DI |
| Zaocuilv (22--16) | DI | DI | DI | DI | DI | I | DI | DI | D | DI | DI | I | DI |
| Chanteline (22--17) | D | D | D | D | D | DI | D | D | D | D | DI | DI | DI |
| Red Baron (22--2) | DI | DI | DI | DI | I | DI | D | DI | D | DI | DI | D | D |
| Hongjin Gala (22--4) | D | DI | DI | DI | DI | DI | DI | DI | D | D | I | D | I |
| Generos (22--7) | D | DI | DI | D | DI | D | D | D | DI | DI | DI | D | D |
| Alberta (2--3) | D | D | D | DI | D | I | DI | DI | D | DI | DI | D | D |
| Hirosaki Fuji (23--1) | D | DI | DI | D | D | D | D | DI | DI | I | DI | DI | DI |
| Miya Fuji (23--10) | DI | D | D | DI | DI | DI | DI | DI | D | D | DI | DI | DI |
| Yanshanhong (23--13) | DI | DI | DI | D | DI | DI | D | DI | D | DI | DI | D | DI |
| Dailv (23--14) | DI | D | DI | DI | D | DI | DI | D | D | D | D | DI | D |
| Frequin Rouge (23--15) | I | DI | D | DI | DI | DI | D | D | D | DI | D | DI | DI |
| Jinguang (23--16) | D | D | DI | DI | DI | DI | DI | DI | DI | DI | I | D | DI |
| Avrolles (23--17) | D | DI | D | DI | DI | D | D | D | DI | D | DI | D | DI |
| Marie Menard (23--18) | DI | D | D | DI | DI | D | DI | D | DI | DI | DI | DI | DI |
| Golden B (23--2) | DI | DI | DI | I | DI | DI | I | DI | DI | DI | DI | I | DI |
| Jurella (23--20) | D | DI | D | D | DI | D | D | D | DI | DI | DI | D | DI |
| GS58 (23--21) | D | DI | DI | DI | D | DI | DI | DI | D | DI | D | I | DI |

-continued

Construction results of InDel marker genotype database of *Malus* germplasm resources

| | | | | | | | | | | | | | |
|---|---|---|---|---|---|---|---|---|---|---|---|---|---|
| Lianji (23--22) | DI | DI | DI | I | DI | DI | DI | D | D | DI | DI | DI | DI |
| Aomori Spur Fuji (23--4) | DI | D | D | DI | DI | DI | DI | DI | D | D | DI | DI | DI |
| Akifu 39 (23--9) | DI | D | D | DI | DI | DI | DI | DI | D | D | DI | DI | DI |
| Shalatuoni (2--4) | D | DI | DI | DI | DI | DI | DI | D | D | DI | I | D | D |
| Guoqing (24--13) | D | D | DI | DI | D | D | DI | DI | D | D | DI | D | DI |
| Ningguang (24--15) | D | D | D | I | D | DI | DI | DI | DI | DI | DI | DI | I |
| Hongqiaowang (24--17) | DI | DI | DI | DI | DI | DI | DI | DI | DI | DI | DI | DI | DI |
| Wemhong (24--18) | D | D | D | DI | D | DI | DI | DI | D | DI | I | I | DI |
| Wijcik McIntosh (24--19) | DI | DI | D | D | DI | DI | D | DI | D | DI | D | I | DI |
| Xinguoguang (24--21) | DI | DI | DI | D | DI | DI | D | D | DI | DI | I | DI | DI |
| Fengcun Fuji (24--22) | DI | D | D | DI | DI | DI | DI | DI | D | D | DI | DI | DI |
| America 8 (24--23) | D | D | DI | DI | D | D | DI | DI | D | D | DI | D | DI |
| GS48 (24--3) | D | D | D | I | D | DI | DI | DI | D | DI | DI | D | D |
| Granny Smith (24--4) | D | DI | DI | D | D | DI | D | D | D | DI | DI | D | I |
| Stark Spur (24--7) | DI | DI | DI | I | DI | DI | I | DI | DI | DI | DI | I | DI |
| Huangguniang (2--5) | D | D | DI | I | I | DI | DI | DI | D | DI | I | D | D |
| Judaine (25--11) | D | DI | DI | DI | DI | DI | DI | D | DI | D | DI | D | I |
| Judeline (25--12) | DI | DI | DI | DI | DI | DI | DI | DI | I | DI | DI | DI | I |
| HoneyCrisp (25--14) | D | DI | DI | D | D | DI | D | D | D | DI | DI | D | D |
| Korin (25--15) | DI | D | D | DI | DI | D | DI | DI | D | D | DI | DI | DI |
| Hongao (25--18) | DI | D | D | DI | D | DI | DI | DI | DI | DI | DI | I | DI |
| Ningguang (25--19) | DI | D | D | DI | D | DI | DI | DI | DI | DI | DI | I | DI |
| Red Delicious (25--2) | D | D | D | D | D | D | DI | DI | D | DI | DI | I | D |
| Youlixiang (25--21) | DI | DI | DI | DI | DI | DI | DI | DI | DI | DI | DI | DI | DI |
| Fuqiu (25--3) | DI | D | D | DI | DI | DI | I | DI | DI | D | D | DI | I |
| Chunxiang (25--4) | D | D | D | DI | DI | D | D | DI | D | D | D | DI | D |
| Fu Hong (25--5) | I | D | D | I | D | D | DI | DI | DI | D | D | I | DI |
| Qingxiang (25--6) | D | DI | DI | DI | DI | D | I | DI | D | DI | DI | I | D |
| Zhongxing (25--7) | D | D | D | D | DI | DI | DI | DI | D | DI | I | I | DI |
| Weixishengming (25--8) | D | D | D | D | DI | DI | DI | DI | DI | DI | I | DI | I |
| Shichinohe 1 (25--9) | DI | D | D | DI | DI | DI | DI | DI | DI | D | D | DI | DI |
| Arkansas Black (2--6) | D | D | D | D | I | I | DI | DI | DI | DI | DI | D | DI |
| Douce Coetligne (26--10) | D | D | D | DI | D | D | D | D | D | DI | DI | D | D |
| Golden Spur (26--14) | DI | DI | DI | I | DI | DI | I | DI | DI | DI | DI | I | DI |
| Orei (26--15) | DI | DI | DI | DI | I | DI | D | DI | D | D | I | D | D |
| Sekaiichii (26--18) | D | DI | DI | DI | DI | DI | DI | DI | D | D | I | DI | I |
| Kokyu (26--19) | D | D | D | DI | DI | D | DI | D | D | DI | D | I | DI |
| Douce Moen (26--2) | D | D | D | D | D | I | D | D | DI | DI | DI | D | DI |
| Yanfu 1 (26--22) | DI | D | D | DI | DI | DI | DI | DI | D | D | DI | DI | DI |

| Construction results of InDel marker genotype database of *Malus* germplasm resources | | | | | | | | | | | | | |
|---|---|---|---|---|---|---|---|---|---|---|---|---|---|
| Ningfeng (26--23) | D | D | DI | DI | D | D | DI | DI | D | D | DI | D | DI |
| Juliana (26--5) | D | D | D | D | D | DI | I | DI | D | DI | DI | D | D |
| Judestar (26--9) | D | D | D | D | D | DI | DI | D | DI | DI | DI | DI | DI |
| Liaofu (2--7) | D | D | D | I | I | D | DI | D | D | D | I | D | DI |
| Sinano Red (27--10) | D | DI | DI | D | D | DI | D | DI | D | DI | DI | D | D |
| Jinyang (27--12) | D | D | D | I | D | D | DI | DI | D | D | DI | I | DI |
| Enqi (27--13) | DI | DI | DI | I | D | DI | I | DI | DI | DI | D | I | DI |
| Miki (27--14) | D | D | D | D | DI | DI | D | DI | DI | DI | I | DI | I |
| Hongbaoshi (27--15) | D | DI | DI | DI | D | D | DI | DI | D | DI | D | I | DI |
| Nagafu 2 (27--16) | DI | D | D | DI | DI | DI | DI | DI | D | D | DI | DI | DI |
| Longguan (27--4) | DI | DI | DI | D | DI | DI | D | D | D | DI | I | DI | DI |
| K9 (27--5) | D | D | D | I | D | D | DI | DI | D | D | DI | I | DI |
| Zaohongda Gala (27--6) | D | D | D | I | D | D | DI | DI | D | D | DI | I | DI |
| Lvshuai (27--7) | D | DI | DI | DI | I | D | DI | D | D | DI | I | DI | DI |
| Hongxia (27--8) | DI | DI | DI | DI | D | DI | DI | DI | D | DI | D | I | DI |
| Zaohongxia (27--9) | DI | D | D | DI | DI | DI | D | DI | D | D | DI | DI | DI |
| Early Golden (2--8) | D | D | D | DI | DI | DI | I | D | D | DI | DI | I | DI |
| Indo (28--0) | D | D | D | DI | I | D | D | DI | D | D | DI | DI | I |
| Jie 1 (28--11) | D | DI | DI | D | DI | D | D | D | DI | DI | DI | D | D |
| Beauty of Bath (28--13) | D | D | DI | D | DI | DI | D | D | D | DI | DI | D | D |
| K10 (28--14) | D | DI | DI | DI | DI | DI | D | DI | DI | DI | DI | DI | D |
| Beifang Xina (28--16) | D | D | DI | D | I | DI | D | D | D | DI | I | D | D |
| Yellow Fuji (28--18) | DI | D | D | I | DI | D | I | DI | D | DI | D | DI | I |
| Sinano Sweet (28--2) | D | DI | DI | DI | DI | DI | DI | DI | D | D | I | DI | DI |
| Miguo (28--3) | DI | DI | DI | DI | D | DI | D | DI | D | DI | DI | I | D |
| Ace (28--4) | DI | D | D | DI | DI | DI | D | DI | D | D | DI | DI | DI |
| Tsugaru (28--5) | D | DI | DI | DI | D | D | D | DI | DI | DI | I | DI | DI |
| K12 (28--8) | D | DI | DI | DI | DI | DI | D | DI | DI | DI | I | DI | DI |
| Jieernianke (28--9) | D | DI | DI | DI | I | DI | D | DI | D | DI | I | DI | D |
| Macoun (2--9) | I | DI | DI | D | I | DI | DI | D | DI | DI | DI | DI | I |
| Qingping (29--1) | DI | D | D | DI | D | I | D | D | DI | D | I | D | D |
| Polka (29--11) | DI | DI | DI | DI | D | I | DI | DI | DI | DI | D | I | DI |
| Longfeng (29--13) | DI | DI | DI | D | D | D | D | D | DI | DI | DI | I | D |
| Very Early Fuji (29--14) | DI | D | D | DI | DI | DI | DI | DI | D | D | DI | DI | DI |
| Longhong (29--15) | DI | DI | DI | DI | DI | D | DI | D | D | DI | I | DI | D |
| Pinova (29--16) | I | DI | DI | DI | I | I | DI | DI | D | DI | DI | DI | D |
| Fuga (29--17) | DI | DI | DI | DI | D | DI | DI | DI | D | DI | D | I | DI |
| Qing n3 (29--2) | D | D | D | DI | D | D | D | DI | D | DI | DI | I | D |

| Construction results of InDel marker genotype database of *Malus* germplasm resources | | | | | | | | | | | | | |
|---|---|---|---|---|---|---|---|---|---|---|---|---|---|
| Xinyuanshuai (29--3) | D | D | D | DI | D | D | D | DI | D | DI | DI | I | D |
| Xinhua (29--5) | DI | D | D | D | I | DI | D | D | D | DI | I | DI | DI |
| Nanpu 2 (29--6) | D | DI | DI | DI | I | D | D | DI | DI | DI | DI | D | DI |
| Liuyu mutant (29--7) | DI | DI | DI | DI | I | DI | D | DI | D | DI | I | D | D |
| Shandao Fuji (30--1) | DI | D | D | DI | DI | DI | DI | DI | D | D | DI | DI | DI |
| Sinano Gold (30--2) | DI | D | D | DI | I | D | I | DI | D | D | DI | D | I |
| Whitney (3--1) | D | D | D | D | DI | DI | D | D | D | DI | DI | D | DI |
| Feixia (31--1) | I | DI | DI | DI | D | DI | DI | D | D | D | DI | I | |
| Willams Faborite (3--11) | DI | D | D | D | DI | D | D | D | DI | D | I | D | DI |
| Zhangye 2 (31--12) | D | D | D | DI | D | D | DI | D | D | D | DI | I | D |
| Youfangcun Ralls Janet (31--14) | D | D | D | DI | D | DI | DI | DI | DI | DI | DI | D | I |
| Yueyanghong (31--15) | D | D | DI | D | DI | D | DI | D | D | DI | DI | DI | |
| Shuohong (31--17) | DI | DI | DI | DI | D | D | DI | DI | D | D | I | I | DI |
| Tianwang 1 (31--18) | D | D | D | DI | D | D | DI | D | D | D | DI | I | D |
| Huadan (31--2) | D | D | D | I | D | DI | DI | DI | D | DI | D | DI | DI |
| Dalu 52 (3--12) | DI | D | D | D | I | DI | D | DI | D | DI | DI | DI | DI |
| Cameo (31--3) | DI | DI | DI | DI | D | DI | I | DI | DI | DI | DI | I | DI |
| Tianhuangkui (3--13) | D | D | D | DI | I | D | D | D | D | DI | I | D | D |
| Qiulu (31--4) | D | DI | DI | D | D | D | D | DI | DI | DI | D | D | D |
| Liehuangjiatena (3--15) | DI | D | D | DI | I | D | I | DI | D | D | DI | DI | DI |
| Lubi (3--16) | D | D | D | DI | D | DI | DI | DI | D | DI | DI | I | DI |
| Huayu (31--8) | DI | DI | DI | DI | D | DI | DI | D | DI | DI | DI | DI | DI |
| Fameuse (3--18) | D | D | D | DI | I | D | D | D | DI | D | I | D | DI |
| Zhanhanxiang (3--19) | D | DI | DI | DI | DI | DI | DI | DI | D | I | I | D | |
| Siberian White Spot (3--2) | DI | D | D | DI | DI | D | D | DI | DI | D | D | D | |
| Zhengding 2 (3--21) | DI | D | D | D | DI | DI | D | DI | D | DI | DI | D | D |
| Kuihua (3--22) | DI | D | D | DI | I | DI | D | DI | DI | D | DI | D | I |
| Early Worcester (3--23) | DI | D | D | D | DI | D | D | DI | D | DI | D | DI | D |
| Lowland Raspderry (3--3) | DI | D | D | DI | I | DI | D | DI | DI | D | DI | DI | DI |
| Miqiulin Jinian (3--4) | D | D | D | D | I | DI | D | D | DI | DI | DI | D | DI |
| Huangtianguo (3--5) | D | D | D | D | D | DI | I | DI | D | DI | DI | D | DI |
| Huadao (3--7) | D | D | D | DI | DI | DI | D | DI | DI | DI | D | DI | |
| Red Astrachan (3--9) | DI | DI | DI | D | D | D | D | D | D | DI | D | D | D |
| Black Gilliflower (4--1) | D | D | DI | D | DI | D | DI | D | D | DI | D | D | DI |
| Nimaiyisuo (4--10) | D | D | D | DI | DI | D | D | D | D | DI | DI | DI | DI |
| Zaohong (4--11) | DI | DI | DI | DI | DI | D | D | DI | D | DI | I | DI | DI |
| Xiangguo (4--12) | DI | D | D | D | D | DI | I | DI | D | DI | DI | D | DI |
| Vista Bella (4--16) | D | D | D | DI | I | DI | DI | DI | DI | D | D | D | D |

-continued

| Construction results of InDel marker genotype database of *Malus* germplasm resources | | | | | | | | | | | | | |
|---|---|---|---|---|---|---|---|---|---|---|---|---|---|
| Saiwen (4--17) | D | D | D | D | I | I | DI | DI | DI | DI | DI | D | DI |
| Summerland (4--20) | DI | DI | DI | I | DI | DI | I | DI | DI | DI | DI | I | DI |
| Qihe Golden Spur (4--22) | DI | DI | DI | I | DI | DI | I | DI | DI | DI | DI | I | DI |
| Yellow Risharde (4--3) | DI | DI | DI | D | DI | D | DI | DI | D | D | DI | D | D |
| Patten (4--5) | D | D | DI | D | D | DI | D | DI | D | DI | DI | DI | DI |
| Early Red Bird (4--6) | DI | DI | DI | DI | I | DI | D | DI | D | DI | I | D | D |
| Fuhong (4--7) | D | DI | DI | D | D | DI | D | DI | D | D | DI | D | D |
| Bisimake (4--8) | D | D | DI | DI | DI | DI | D | D | D | D | DI | D | D |
| York Imperial (4--9) | DI | D | D | I | D | DI | D | DI | DI | DI | DI | DI | D |
| Jonagold (5--1) | DI | DI | DI | DI | DI | DI | DI | DI | DI | DI | DI | DI | DI |
| Ayiwaniya (5--10) | D | D | D | D | I | DI | I | DI | D | DI | DI | D | DI |
| Fushan 5 (5--14) | D | D | D | DI | D | D | DI | DI | D | DI | DI | I | D |
| Houjiadian Spur (5--18) | D | D | D | DI | D | D | DI | DI | D | DI | DI | I | D |
| Guoshuai (5--19) | D | D | D | DI | DI | DI | D | DI | D | DI | I | D | DI |
| Huashuai 1 (5--21) | DI | DI | DI | D | D | DI | DI | DI | D | D | DI | I | D |
| Xiongyue 2 (5--22) | D | D | D | DI | D | D | DI | DI | D | DI | DI | I | D |
| Honeygod (5--3) | DI | DI | DI | I | DI | D | DI | DI | D | DI | DI | I | D |
| Joyal (5--4) | DI | D | DI | DI | I | DI | D | DI | D | D | DI | DI | D |
| Stark Spur Golden (5--5) | DI | DI | DI | I | DI | DI | I | DI | DI | DI | DI | I | DI |
| Enweier Golden (5--6) | DI | DI | DI | I | DI | DI | I | DI | DI | DI | DI | I | DI |
| Stark Gold (5--8) | DI | DI | DI | D | DI | DI | D | D | D | DI | I | DI | DI |
| Sishui Spur (6--10) | D | D | D | DI | D | D | DI | DI | D | DI | DI | I | D |
| Red Spur Delicious (6--12) | D | D | D | DI | D | D | DI | DI | D | DI | DI | I | D |
| Qingdao 1 (6--13) | D | D | D | DI | D | D | DI | DI | D | DI | DI | I | D |
| Bianqiangzi 1 (6--14) | D | D | D | DI | D | D | DI | DI | D | DI | DI | I | D |
| Zhangjiakou Spur (6--16) | D | D | D | DI | D | D | DI | DI | D | DI | DI | I | D |
| Richard Red Delicious (6--18) | D | D | D | DI | D | D | DI | DI | D | DI | DI | I | D |
| Well Spur Delicious (6--19) | D | D | D | DI | D | D | DI | DI | D | DI | DI | I | D |
| Bianqiangzi 2 (6--20) | D | D | D | DI | D | D | DI | DI | D | DI | DI | I | D |
| Hardi Spur Delicious (6--21) | D | D | D | DI | D | D | DI | DI | D | DI | DI | I | D |
| Fushan 1 (6--3) | D | D | D | DI | D | D | DI | DI | D | DI | DI | I | D |
| Pinyin Spur (6--4) | D | D | D | DI | D | D | DI | DI | D | DI | DI | I | D |
| Nanshan 2 (6--8) | D | D | D | DI | D | D | DI | DI | D | DI | DI | I | D |
| Meiduan 1 (7--10) | D | D | D | DI | D | D | D | DI | D | DI | I | DI | DI |
| Shisanling Spur (7--11) | D | D | D | DI | D | D | DI | DI | D | DI | DI | I | D |
| Kelisike (7--13) | D | D | D | D | I | DI | DI | D | D | D | D | DI | DI |
| Jie 18 (7--16) | D | D | D | DI | D | DI | D | DI | D | DI | DI | D | D |

-continued

| | | | | | | | | | | | | | |
|---|---|---|---|---|---|---|---|---|---|---|---|---|---|
| Bo 25 (7--17) | D | D | D | I | I | DI | D | DI | DI | DI | DI | DI | DI |
| Ruixiang (7--18) | D | DI | DI | D | D | D | D | D | DI | DI | DI | D | D |
| Wealthy (7--19) | D | DI | DI | DI | D | DI | D | DI | D | DI | I | D | D |
| Nanshan 4 (7--2) | DI | D | D | D | D | D | D | D | D | D | I | D | DI |
| De 14 (7--20) | D | D | D | DI | D | DI | D | DI | D | DI | DI | D | D |
| Napoleon (7--22) | DI | DI | DI | DI | D | DI | DI | D | DI | DI | DI | I | D |
| Youyi (7--23) | D | D | D | DI | DI | D | DI | D | DI | D | I | D | D |
| Oregon Spur (7--3) | DI | D | D | D | D | D | D | DI | D | D | I | D | DI |
| Kangtun Spur (7--6) | D | D | D | DI | D | D | DI | DI | D | DI | DI | I | D |
| White Pippin (7--9) | D | D | D | DI | I | D | D | D | DI | D | I | D | DI |
| Zach Lebel (8--1) | DI | D | D | D | D | DI | DI | DI | DI | D | DI | D | D |
| Cortland (8--10) | D | DI | DI | DI | D | DI | D | D | D | DI | I | D | D |
| Raritan (8--12) | DI | D | D | DI | DI | DI | DI | DI | D | D | DI | DI | DI |
| Meilingxi Tsugaru (8--13) | DI | D | D | DI | D | D | I | DI | D | DI | D | I | D |
| Moscow Transparent (8--14) | DI | DI | DI | DI | I | DI | D | DI | D | D | I | D | DI |
| Cooper's Market (8--15) | D | D | D | DI | I | DI | D | DI | D | DI | DI | DI | I |
| Xite Shisheng (8--16) | DI | D | D | D | DI | DI | D | DI | DI | DI | DI | D | I |
| Tian Yisaye (8--17) | D | D | D | DI | D | DI | D | DI | DI | DI | I | D | D |
| Shennong 2 (8--19) | DI | DI | DI | DI | DI | DI | I | D | DI | DI | DI | DI | DI |
| Maigold (8--20) | I | D | DI | DI | DI | D | DI | D | DI | DI | I | DI | D |
| Magu (8--21) | D | DI | D | D | D | DI | DI | DI | D | DI | D | D | DI |
| Cellini (8--23) | D | D | DI | DI | DI | D | D | D | D | DI | D | D | |
| Simonffy Piros (8--3) | D | D | D | D | DI | DI | D | D | D | DI | D | D | |
| Luxiang (8--5) | D | DI | DI | D | D | D | DI | DI | DI | DI | DI | D | D |
| Zhongqiu (8--6) | D | D | D | DI | I | D | DI | DI | D | DI | I | D | D |
| De 2 (8--7) | D | DI | DI | DI | I | DI | D | D | D | DI | D | DI | |
| Grimes Golden (8--8) | DI | DI | DI | DI | DI | DI | I | DI | DI | D | DI | I | DI |
| Early Straw Berry (8--9) | D | D | D | D | DI | D | DI | D | D | DI | I | D | DI |
| Kelia (9--10) | DI | D | DI | DI | DI | DI | D | DI | D | DI | I | DI | DI |
| French Apple (9--11) | D | D | D | D | D | DI | D | D | DI | DI | DI | D | |
| Todoroki Tsugaru (9--12) | D | DI | DI | DI | D | D | DI | D | DI | DI | I | DI | DI |
| Cuihong (9--13) | D | D | D | DI | DI | DI | D | D | DI | DI | I | D | D |
| De 4 (9--14) | D | D | D | D | D | I | D | D | D | D | DI | D | D |
| Early McIntosh (9--18) | DI | D | D | D | I | D | D | DI | D | D | D | DI | D |
| Adam Mickewier (9--19) | D | DI | DI | D | DI | D | I | D | D | DI | DI | D | D |
| Norda (9--2) | DI | D | D | D | DI | DI | D | DI | D | DI | DI | D | D |
| Cardinal (9--20) | DI | DI | DI | DI | DI | I | DI | DI | D | DI | DI | I | DI |
| Evelyn (9--21) | DI | D | DI | DI | D | DI | D | D | DI | DI | I | D | D |

-continued

| Construction results of InDel marker genotype database of *Malus* germplasm resources |||||||||||||
|---|---|---|---|---|---|---|---|---|---|---|---|---|
| Situonuowei (9--22) | D | D | D | D | DI | I | D | DI | D | DI | I | D | D |
| Yingqiu (9--23) | D | D | D | D | I | DI | D | D | DI | D | DI | D | D |
| Kelongxieer (9--3) | DI | DI | DI | DI | I | DI | D | DI | D | D | I | D | DI |
| Cloden (9--5) | DI | DI | DI | DI | DI | DI | D | DI | DI | DI | DI | DI | DI |
| Qiutianhong (9--6) | D | D | D | D | DI | I | D | DI | D | DI | I | D | DI |
| Gaidebao (9--7) | DI | DI | DI | D | DI | D | D | D | DI | DI | DI | DI | D |
| Starkjam (9--9) | DI | DI | DI | DI | D | DI | DI | DI | D | DI | DI | I | D |
| Wan Crab (B-1) | DI | DI | DI | DI | DI | D | D | D | D | DI | DI | D | D |
| Minjiandaguo Crab (B-10) | D | D | D | DI | DI | DI | DI | DI | D | DI | I | D | I |
| Luanzhuang Crab (B1-11) | DI | DI | DI | D | DI | DI | DI | D | DI | DI | I | D |
| Sankuaishi Crab (B1-12) | D | D | D | D | D | DI | I | DI | D | DI | DI | D | I |
| Xiongyue Crab 1 (B1-13) | D | DI | DI | DI | DI | DI | I | DI | D | DI | D | I | D |
| Sankuaishi Crab 2 (B1-14) | DI | DI | DI | DI | D | DI | I | DI | D | DI | D | DI | D |
| Dabaleng (B-12) | DI | DI | DI | D | DI | DI | DI | D | D | DI | DI | D | I |
| Sankuaishi Crab 2 (B-13) | DI | D | D | DI | DI | DI | DI | DI | D | D | DI | DI | DI |
| Changguo Crab (B-14) | DI | DI | DI | DI | DI | DI | I | DI | DI | DI | D | I | I |
| Dagucheng Baleng (B1-5) | D | D | D | D | I | DI | I | D | D | DI | D | D | D |
| Zumi Crab 3x (B-15) | DI | DI | DI | DI | DI | DI | I | DI | DI | DI | DI | I | DI |
| 26105 (B-16) | D | DI | DI | D | I | D | D | DI | DI | DI | I | D | D |
| Daguo Crab (B-17) | D | D | D | DI | DI | DI | DI | DI | D | DI | I | D | I |
| Xiongyue Crab 2 (B1-8) | D | D | D | D | D | DI | D | D | D | D | D | D | D |
| Watermelon Crab (B-18) | DI | DI | DI | DI | D | DI | I | DI | DI | DI | DI | DI | DI |
| Mudanjiang Crab (B1-9) | D | D | D | D | D | D | D | DI | DI | DI | DI | DI | DI |
| Tianhong 1 (B-19) | DI | D | D | DI | DI | DI | DI | DI | D | D | DI | DI | DI |
| Jiping 1 (B-2) | DI | D | DI | DI | D | DI | DI | DI | DI | DI | DI | DI | D |
| Caoyuan Crab (B2-1) | D | D | D | D | D | D | D | D | D | D | D | D | DI |
| Zumi Crab 4x (B-21) | DI | DI | DI | DI | DI | DI | I | DI | DI | DI | DI | I | DI |
| Luanzhuang Shaguo (B2-11) | D | D | D | D | DI | DI | I | DI | D | DI | D | D | D |
| Xiaofan Crab (B2-13) | DI | D | D | D | D | DI | I | DI | DI | DI | DI | D | DI |
| Hebing Pingding Crab (B2-14) | D | D | D | D | D | DI | I | D | D | DI | D | D | DI |
| Zumi Crab 3x 2 (B-22) | DI | DI | DI | DI | DI | DI | I | DI | DI | DI | DI | I | DI |
| Baleng Crab (B2-3) | D | D | D | D | D | DI | I | DI | D | DI | D | D | I |
| Baleng seedling 14 (B-25) | D | D | D | D | D | DI | I | DI | DI | D | D | I | I |
| Russian White apple (B2-6) | D | D | D | DI | I | D | D | DI | D | DI | I | D | D |
| Nagafu 2 (B-26) | DI | D | D | DI | DI | DI | DI | DI | D | D | DI | DI | DI |
| Ambrosia (B-27) | DI | DI | D | DI | DI | D | DI | DI | DI | DI | D | I | DI |
| Aihonghua (B2-8) | D | DI | DI | D | DI | DI | I | D | D | D | D | DI | D |
| Nanshennan (B-28) | DI | D | D | DI | DI | DI | DI | DI | D | D | DI | DI | DI |

-continued

| Construction results of InDel marker genotype database of *Malus* germplasm resources | | | | | | | | | | | | |
|---|---|---|---|---|---|---|---|---|---|---|---|---|
| Zumi Crab W1 (B-29) | DI | DI | DI | DI | DI | DI | I | DI | DI | DI | I | DI |
| Hong 4G (B-3) | D | DI | DI | D | I | DI | D | DI | D | DI | DI | D |
| Zumi Crab (B-30) | DI | DI | DI | DI | DI | DI | I | DI | DI | DI | I | DI |
| Zaobai Crab (B3-1) | D | D | D | D | DI | DI | I | DI | D | DI | D | DI |
| Mollie's Delicious (B-31) | DI | DI | DI | DI | D | I | DI | D | DI | DI | I | DI | D |
| Regunzi Spur (B3-10) | D | D | D | D | DI | DI | I | DI | D | DI | DI | D | I |
| Xiaofanshan Baleng (B3-11) | D | DI | DI | DI | I | DI | DI | DI | D | DI | DI | D | D |
| Huamei (B3-12) | DI | DI | DI | DI | D | DI | I | DI | DI | DI | D | I | DI |
| Huashuo (B3-13) | D | DI | DI | D | D | DI | DI | DI | DI | D | DI | D | DI |
| Yuhong (B3-14) | D | D | D | D | D | D | DI | DI | D | DI | DI | I | D |
| Huayue (B3-15) | DI | D | D | DI | DI | DI | D | DI | D | DI | DI | DI | DI |
| Jingbohu Shandingzi (B3-2) | D | D | D | D | D | D | D | D | D | D | D | D |
| Eluosi Daguo Shandingzi (B3-3) | D | D | D | D | D | D | D | DI | DI | DI | DI | D | D |
| HY (B-33) | DI | D | D | D | DI | D | I | DI | D | D | DI | D | D |
| Hong Crab (B3-6) | D | D | D | D | DI | DI | I | DI | D | DI | D | D | DI |
| 23# (B-37) | DI | DI | DI | DI | D | DI | DI | DI | DI | DI | DI | DI | DI |
| Russian apple (B3-8) | DI | D | D | D | D | D | D | DI | DI | DI | DI | D | D |
| 147 (B-38) | DI | D | D | DI | DI | DI | DI | DI | DI | DI | D | DI | DI |
| Xiaofanshan Baleng 1 (B3-9) | D | D | D | D | D | DI | I | DI | D | DI | D | D | I |
| Lvshuai (B-4) | D | DI | DI | DI | I | D | DI | D | D | DI | I | DI | DI |
| Dounan (B-40) | DI | DI | DI | DI | DI | DI | DI | DI | DI | DI | DI | DI | DI |
| 11906 (B-41) | D | D | DI | D | DI | DI | D | D | DI | DI | I | D | D |
| Luli (B-5) | DI | I | DI | DI | D | DI | D | D | DI | DI | DI | D | D |
| Jinxiuhong (B-6) | I | DI | DI | DI | D | DI | DI | DI | D | D | D | DI | I |
| B68 (B-7) | D | D | D | D | D | DI | D | DI | DI | DI | D | D |
| Huaida (B-8) | DI | DI | DI | DI | DI | DI | DI | D | D | DI | DI | I | D |
| Nanshennan mutant (B-9) | DI | D | D | DI | DI | DI | DI | DI | D | D | DI | DI | DI |
| Xiahong (BH-1) | DI | DI | D | I | DI | DI | DI | D | D | DI | DI | DI | DI |
| Wuming1 (BJ-1) | DI | DI | DI | DI | D | I | D | D | I | DI | DI | DI | D |
| Canzy ? (BJ-10) | I | D | D | DI | DI | D | DI | DI | I | DI | DI | I | DI |
| Xiangfu (BJ-11) | DI | DI | DI | DI | DI | DI | DI | DI | D | D | DI | DI | D |
| Envy (BJ-12) | DI | D | D | DI | D | D | DI | D | I | DI | D | I | D |
| Fuji_KiKu (BJ-2) | DI | DI | DI | DI | DI | DI | DI | DI | D | D | DI | DI | D |
| Banxiu Crab (BJ-4) | D | D | D | DI | D | D | DI | D | D | DI | DI | D | DI |
| Jazz (BJ-5) | I | DI | DI | DI | DI | DI | DI | DI | I | DI | DI | I | D |
| Early Red Bird 2 (BJ-7) | D | DI | DI | D | D | D | D | DI | DI | DI | DI | D | DI |

-continued

Construction results of InDel marker genotype database of *Malus* germplasm resources

| | | | | | | | | | | | | | |
|---|---|---|---|---|---|---|---|---|---|---|---|---|---|
| Qiuhong Gala (BJ-8) | DI | D | DI | DI | DI | DI | DI | DI | D | D | DI | DI | DI |
| Hongxiangcui (BJ-9) | DI | I | D | DI | D | D | DI | DI | D | DI | D | I | DI |
| 07-115 (BK-1) | DI | D | D | D | D | D | I | DI | D | D | D | D | I |
| Nagafu 3 (BK-2) | DI | D | D | DI | DI | DI | DI | DI | DI | D | DI | DI | DI |
| 28-253 (BK-28-253) | DI | D | D | DI | DI | DI | DI | D | DI | D | DI | D | DI |
| Nagafu 3-R (BK-3) | DI | D | D | DI | DI | DI | DI | DI | DI | D | DI | DI | DI |
| 4354 (BK-4) | D | I | DI | D | D | D | DI | DI | D | DI | DI | DI | DI |
| 4-23 (BK-4-23) | I | D | D | DI | D | DI | DI | DI | DI | D | D | I | D |
| 4354-R ? (BK-5) | D | D | D | I | DI | DI | DI | DI | DI | D | D | DI | D |
| 77-34 (BK-77-34) | D | D | D | D | I | DI | DI | D | D | D | DI | D | D |
| Red Spur Delicious (BK-AH) | D | D | D | DI | D | D | DI | DI | D | DI | DI | I | D |
| Ozark Gold (BK-AJ) | DI | D | D | DI | DI | D | I | DI | D | D | D | DI | I |
| Michinoku (BK-AZ) | D | DI | DI | D | D | DI | D | DI | D | DI | DI | D | D |
| Azwell (BK-Azwell) | D | D | D | DI | D | D | DI | DI | D | D | DI | I | D |
| Banbishan Crab (BK-BBSHT) | D | D | D | D | D | DI | I | DI | D | DI | DI | D | I |
| Hokudo (BK-BD) | DI | D | D | DI | DI | DI | DI | DI | DI | D | DI | DI | DI |
| Baifugao (BK-BFG) | D | D | D | DI | DI | DI | D | DI | D | D | DI | D | D |
| White Crab (BK-BHT) | D | DI | DI | DI | I | DI | DI | DI | D | DI | DI | D | D |
| Buming Kangbing (BK-BMKB) | D | D | D | DI | DI | D | D | D | DI | D | I | D | DI |
| Batougou 1 (BK-BTG1H) | D | D | D | D | D | DI | I | D | D | D | D | D | D |
| Batougou 2 (BK-BTG2H) | D | D | D | D | D | DI | I | DI | D | DI | D | D | DI |
| Batougou Aizhen (BK-BTGAZ) | D | D | D | D | DI | D | D | D | DI | D | D | D | D |
| Binzi (BK-BZ) | DI | D | D | D | D | DI | I | DI | D | DI | DI | D | DI |
| Kitanosach (BK-BZX) | D | D | DI | DI | DI | D | DI | D | D | DI | I | DI | DI |
| Binzi (SW) (BK-BZXN) | DI | D | D | D | D | DI | I | DI | D | DI | DI | D | DI |
| Nagafu 2 (BK-CF2H) | DI | D | D | DI | DI | DI | DI | DI | D | D | DI | DI | DI |
| Nagafu 36 (BK-CF36) | DI | D | D | DI | DI | DI | DI | DI | D | DI | DI | DI | DI |
| Nagafu 6 (BK-CF6H) | DI | D | D | DI | DI | DI | DI | DI | D | DI | DI | DI | DI |
| CG24 (BK-CG24) | D | D | D | DI | D | D | DI | DI | D | DI | DI | I | D |
| CG3 (BK-CG3) | DI | D | D | DI | DI | DI | D | DI | DI | DI | D | D | DI |
| CG80 (BK-CG80) | D | D | D | DI | I | I | DI | DI | D | D | I | D | D |
| Changhong (BK-CH) | DI | D | D | DI | DI | DI | DI | DI | D | DI | DI | DI | DI |
| Chieftan (BK-chieftan) | DI | DI | DI | D | DI | DI | I | D | DI | DI | I | DI | DI |
| Cangjiang Crab (BK-CJHT) | D | D | D | D | D | D | I | D | D | DI | DI | D | D |
| Chuanling Crab (BK-CLHT) | DI | D | D | D | DI | DI | D | DI | D | DI | I | D | I |
| Hatsuaki (BK-CQ) | DI | D | D | DI | D | I | DI | DI | D | DI | DI | I | DI |
| Crispin (BK-crispin) | DI | DI | DI | DI | DI | DI | DI | DI | DI | DI | DI | DI | DI |

| Construction results of InDel marker genotype database of *Malus* germplasm resources | | | | | | | | | | | | | |
|---|---|---|---|---|---|---|---|---|---|---|---|---|---|
| Caozigang Yuanshuai (BK-CZGYS) | D | D | D | DI | D | D | DI | DI | D | DI | DI | I | D |
| Danxia (BK-DANXIA) | D | DI | DI | I | D | DI | I | DI | D | DI | DI | I | DI |
| Dolgo (BK-DDG) | D | D | D | D | DI | D | D | DI | DI | DI | DI | D | D |
| Darwin (BK-DEW) | DI | D | D | D | D | DI | I | DI | D | DI | DI | D | D |
| Oriental Apple (BK-DFPG) | D | DI | DI | D | DI | DI | DI | D | D | DI | I | D | I |
| Big Crab (BK-DGHT) | D | D | D | DI | D | DI | I | DI | D | D | DI | I | D |
| Daguo Jinhong (BK-DGJH) | DI | DI | DI | DI | DI | DI | DI | D | D | DI | DI | I | D |
| Daihong (BK-DH) | D | D | D | D | D | D | DI | DI | D | D | DI | I | D |
| Daihao 261 (BK-DH261) | D | DI | DI | D | DI | D | D | DI | I | DI | DI | D | D |
| Spur Golden Delicious (BK-DJG) | DI | DI | DI | I | DI | DI | I | DI | DI | DI | DI | I | DI |
| Daxianguo (BK-DXG) | D | D | D | D | DI | DI | I | DI | D | DI | D | D | DI |
| Daye Crab (BK-DYHT) | D | D | D | D | D | DI | I | D | D | D | D | D | I |
| Spur Fuji (BK-DZFS) | DI | D | D | DI | DI | DI | DI | DI | D | D | DI | DI | DI |
| Huaguan Spur (BK-DZHG) | I | DI | DI | DI | D | DI | DI | DI | D | D | D | DI | I |
| Elite (BK-Elite) | D | D | D | DI | D | D | DI | DI | D | DI | DI | I | D |
| Fa 8 (BK-F8) | DI | D | D | DI | DI | DI | D | DI | D | DI | DI | DI | DI |
| Fukushima Spur Fuji (BK-FDDZ) | DI | D | D | DI | DI | DI | DI | DI | D | D | DI | DI | DI |
| Fujin (BK-FJ) | D | D | D | DI | DI | D | DI | DI | D | D | D | DI | D |
| Florina (BK-Florina) | D | D | D | D | DI | D | DI | DI | DI | D | DI | D | DI |
| Fangming (BK-FM) | D | DI | DI | DI | D | D | DI | D | DI | DI | I | DI | DI |
| Fuji (BK-Fuji) | DI | D | D | DI | DI | DI | DI | DI | D | D | DI | DI | DI |
| Fengyan (BK-FY) | D | D | D | DI | DI | D | D | D | DI | D | I | DI | D |
| Yanfu 1 (BK-FY1) | DI | D | D | DI | DI | DI | DI | DI | D | D | DI | DI | DI |
| King of Tompkins County (BK-FZY) | DI | DI | DI | DI | I | DI | D | D | D | DI | DI | D | DI |
| G30 (BK-G30) | D | D | D | D | D | DI | D | D | D | D | DI | DI | D |
| Gao #5 (BK-G-5) | D | D | DI | DI | DI | DI | D | DI | D | DI | I | DI | DI |
| Gala (BK-gala) | DI | DI | DI | I | D | DI | I | DI | DI | DI | D | DI | DI |
| Golden Delicious (BK-GD) | DI | DI | DI | I | DI | DI | DI | DI | DI | DI | DI | I | DI |
| Gloster69 (BK-Gloster69) | D | D | D | DI | D | D | DI | DI | DI | DI | D | I | D |
| GM256 (BK-GM256) | D | D | D | D | DI | D | D | D | D | D | DI | D | D |
| GM310 (BK-GM310) | D | D | D | D | D | DI | DI | D | D | DI | DI | D | D |
| Gaoqiu (BK-GQ) | D | DI | DI | DI | D | DI | DI | D | D | D | D | I | DI |
| Miyazaki Spur Fuji (BK-GQDZ) | DI | D | D | DI | DI | DI | DI | DI | D | D | D | DI | DI |
| HAC-9 (BK-HAC-9) | DI | D | D | DI | DI | DI | DI | DI | DI | DI | DI | DI | DI |
| Huifeng Orin (BK-HFWL) | D | DI | DI | D | D | D | D | D | D | D | DI | I | DI | D |
| Red Ralls Janet (BK-HGG) | DI | DI | DI | D | DI | DI | D | D | D | D | I | DI | DI |
| Huaguan Crab (BK-HGHT) | D | D | D | D | D | DI | I | DI | D | DI | DI | D | D |

-continued

Construction results of InDel marker genotype database of *Malus* germplasm resources

| | | | | | | | | | | | | | |
|---|---|---|---|---|---|---|---|---|---|---|---|---|---|
| Harrold Red Delicious (BK-HH) | D | D | D | DI | D | D | DI | DI | D | DI | DI | I | D |
| Hong Crab 2 (BK-HHT2H) | D | D | D | D | DI | DI | I | DI | D | DI | DI | D | I |
| Stark Redgold (BK-HJ) | DI | D | D | DI | D | DI | I | DI | DI | DI | DI | I | D |
| HLWQ (BK-HLWQ) | I | DI | DI | D | I | D | DI | DI | DI | DI | D | DI | DI |
| Holly (BK-Holly) | D | D | D | D | DI | D | DI | DI | DI | DI | DI | DI | D |
| Red Jonagold (BK-HQNJ) | DI | DI | DI | DI | DI | DI | DI | D | DI | DI | DI | DI | D |
| Red Sekaiichii (BK-HSJY) | D | D | D | DI | DI | D | DI | DI | D | DI | D | I | DI |
| Hongte (BK-HT) | DI | D | D | D | DI | D | D | DI | DI | D | DI | DI | DI |
| Haitangguo (BK-HTG) | DI | D | D | D | D | DI | DI | DI | D | DI | DI | DI | D |
| Haitanghua (BK-HTH) | D | D | D | D | D | DI | DI | DI | D | D | D | D | D |
| Huangtaiping (BK-HTP) | D | DI | DI | DI | I | DI | DI | DI | D | DI | DI | D | D |
| Hongxue (BK-HX) | D | D | D | DI | I | D | D | DI | D | I | D | DI |
| Jincui (BK-JC) | DI | D | D | DI | DI | D | I | DI | DI | DI | DI | I | DI |
| Juda Fuji (BK-JDFS) | DI | D | D | DI | DI | DI | DI | DI | D | DI | DI | DI | D |
| Jiguan (BK-JG) | D | D | D | I | D | D | DI | DI | D | D | DI | I | DI |
| Jinhong (BK-JH) | DI | DI | DI | I | DI | DI | DI | DI | D | D | DI | I | D |
| Jonagored (BK-Jonagored) | DI | DI | DI | DI | DI | DI | DI | DI | DI | DI | DI | DI | DI |
| Jonathan (BK-Jonathan) | D | DI | DI | D | DI | D | DI | D | DI | DI | DI | D | D |
| Himekami (BK-JS) | DI | DI | DI | D | DI | D | D | DI | D | DI | DI | D | DI |
| Stark Blushing Golden (BK-JY) | D | DI | DI | DI | DI | D | DI | DI | D | DI | D | I | D |
| Classic Red Delicious (BK-KAHONG) | D | D | D | DI | D | D | DI | DI | D | DI | DI | I | D |
| KLGDG Shandingzi (BK-KLGDGSDZ) | D | D | D | D | D | DI | D | DI | D | DI | DI | D | D |
| KOSZTELQ (BK-KOSZTELQ) | D | D | D | I | DI | DI | D | DI | I | D | DI | D | DI |
| Sunflower (BK-KUIHUA) | D | DI | DI | I | D | DI | DI | DI | DI | D | DI | I | D |
| Lenghaitang (BK-LHT) | D | D | D | D | D | DI | I | DI | D | DI | DI | D | I |
| Liberty (BK-liberty) | DI | DI | DI | D | DI | DI | I | D | DI | D | I | DI | DI |
| Lijiang Shandingzi (BK-LJSDZ) | DI | D | D | D | D | DI | I | DI | D | DI | I | D | D |
| Laoshan 4 (BK-LS4H) | D | D | D | D | DI | DI | I | DI | D | DI | D | D | DI |
| Ryoka no Kisetsu (BK-LX) | DI | D | D | DI | DI | DI | DI | DI | D | D | DI | DI | DI |
| Lvxiangjiao (BK-LXJ) | DI | DI | DI | DI | DI | DI | DI | D | DI | I | I | D |
| Liaozhen 1 (BK-LZ1H) | D | D | D | D | I | DI | D | D | D | D | DI | D | D |
| M7 (BK-M7) | D | D | D | I | DI | DI | DI | DI | D | D | D | DI | DI |
| Meiguihong (BK-MGH) | D | D | D | DI | D | D | DI | DI | D | DI | DI | I | D |
| Meile (BK-ML) | DI | DI | DI | I | DI | DI | I | DI | D | D | DI | I | D |
| MM106 (BK-MM106) | D | D | D | DI | I | I | DI | DI | D | D | I | D | D |
| Mengpaisi (BK-MPS) | D | D | D | D | D | I | D | D | D | D | DI | D | D |

-continued

| Construction results of InDel marker genotype database of *Malus* germplasm resources | | | | | | | | | | | | | |
|---|---|---|---|---|---|---|---|---|---|---|---|---|---|
| Meixiang (BK-MX) | DI | D | D | DI | DI | DI | DI | DI | D | D | DI | DI | DI |
| Ningqiu (BK-NQ) | D | D | D | DI | I | DI | D | D | D | DI | I | DI | D |
| P16 (BK-P16) | D | D | D | DI | D | D | D | DI | D | D | DI | DI | I |
| P22 (BK-P22) | D | D | D | D | I | DI | D | D | D | D | D | D | I |
| Pingdinghaitang (BK-PDHT) | D | D | D | D | DI | DI | I | DI | D | DI | D | D | DI |
| Bianguo Crab (BK-PGHT) | D | D | D | DI | D | D | DI | DI | DI | D | DI | DI | D |
| Pionier (BK-Pionier) | D | D | D | D | D | DI | D | D | D | D | DI | I | I |
| Prima (BK-Prima) | D | DI | DI | D | D | D | DI | D | D | D | D | DI | DI |
| Pingyitiancha (BK-PYTC) | D | D | D | D | D | D | D | D | D | D | D | D | D |
| Qianxue (BK-QAINXUE) | I | I | D | I | I | D | DI | DI | D | D | DI | DI | D |
| Akifu 1 (BK-QF1) | DI | D | D | DI | DI | DI | DI | DI | D | D | DI | DI | DI |
| Qingfu 13 (BK-QF13) | DI | D | D | DI | DI | DI | DI | DI | D | DI | DI | DI | DI |
| Seimei (BK-QM) | D | DI | DI | DI | DI | DI | DI | DI | D | D | I | DI | I |
| Senshu (BK-QQ) | D | D | D | DI | I | DI | DI | DI | D | D | DI | DI | I |
| Aomori Early (BK-QSZS) | DI | DI | DI | I | DI | DI | I | DI | DI | DI | DI | I | DI |
| Qiuxiang (BK-QX) | D | DI | DI | DI | D | D | DI | D | DI | DI | I | DI | DI |
| Qiuxing Crab (BK-QXHT) | D | D | D | DI | D | DI | D | DI | D | D | DI | D | DI |
| Yanqing (BK-QY) | D | D | D | DI | DI | D | I | DI | D | D | DI | I | DI |
| Regunzi (BK-RGZ) | D | D | D | D | DI | DI | I | DI | D | DI | DI | D | I |
| Ruby (BK-Ruby) | DI | D | D | D | D | D | D | DI | D | D | I | D | DI |
| Scarlet (BK-scarlet) | D | D | D | DI | D | D | DI | DI | D | DI | DI | I | D |
| Sdw1 (BK-Sdw1) | D | D | D | D | D | DI | I | DI | D | DI | D | D | D |
| Shandingzi 2 (BK-SDZ2H) | D | D | D | D | D | D | I | D | D | D | DI | D | DI |
| Su E Shandingzi (BK-SESDZ) | D | D | D | D | D | DI | DI | D | D | DI | DI | D | I |
| Shengfang 2 (BK-SF2) | DI | D | D | DI | DI | DI | DI | DI | D | D | DI | DI | DI |
| SH6 (BK-SH6) | D | D | D | DI | DI | DI | D | D | D | D | DI | D | I |
| Sankuaishi Crab 1 (BK-SKSHT1H) | D | D | D | D | D | DI | I | DI | D | DI | D | D | I |
| Forest Apple (BK-SLPG) | D | D | D | I | D | DI | DI | DI | D | DI | I | I | D |
| Sieversii (BK-SWS) | DI | D | D | D | DI | DI | I | DI | D | DI | I | D | D |
| Sansa (BK-SX) | DI | DI | DI | DI | DI | DI | DI | D | I | DI | DI | D | D |
| Szampion (BK-Szampion) | DI | DI | DI | DI | DI | DI | DI | DI | I | D | DI | DI | DI |
| T337 (BK-T337) | D | D | D | D | DI | DI | DI | D | D | I | D | D | D |
| Turkmen Apple (BK-TKMPG) | DI | D | D | D | DI | DI | I | DI | D | DI | I | D | D |
| Mato 1 (BK-TMYH) | D | DI | DI | D | D | D | D | D | DI | D | DI | D | D |
| Trajian (BK-Trajian) | I | DI | D | D | I | DI | DI | DI | D | DI | DI | DI | I |
| Weiai 3 (BK-WA3) | D | D | D | D | D | DI | I | DI | D | D | D | D | I |
| Wanbai Crab (BK-WBHT) | DI | D | D | DI | D | D | I | DI | DI | DI | D | I | I |
| Wufengshan 1 (BK-WFS1H) | D | D | D | D | D | DI | I | DI | D | DI | D | D | DI |

Construction results of InDel marker genotype database of *Malus* germplasm resources

| Name | | | | | | | | | | | | |
|---|---|---|---|---|---|---|---|---|---|---|---|---|
| Wufengshan 4 (BK-WFS4H) | D | D | D | D | DI | DI | D | D | D | DI | DI | DI | DI |
| Wufengshan Crab (BK-WFSHT) | D | D | D | D | D | DI | I | DI | D | DI | D | D | I |
| Wufengshan Crab 2 (BK-WFSHT2H) | D | D | D | DI | D | D | I | DI | D | DI | D | I | D |
| Wufengshan Crab 6 (BK-WFSHT6H) | D | D | D | D | DI | DI | D | DI | D | DI | D | DI | DI |
| Wifos (BK-wifos) | DI | DI | D | D | DI | DI | D | DI | D | DI | DI | DI | DI |
| Orei (BK-WL) | D | DI | DI | DI | D | D | DI | DI | D | DI | D | I | D |
| Maypole (BK-WM) | D | D | D | D | DI | DI | DI | DI | D | D | D | I | D |
| Waltz (BK-WZ) | DI | DI | D | DI | D | I | DI | DI | DI | DI | D | I | DI |
| Kotoku (BK-XD) | D | DI | DI | I | I | DI | DI | DI | D | D | DI | DI | I |
| Xiaofanshan Binzi (BK-XFSBZ) | DI | D | D | D | D | DI | I | DI | D | DI | DI | D | D |
| Xiaofanshan Crab 4 (BK-XFSHT4H) | DI | D | D | D | D | DI | I | DI | D | DI | DI | D | DI |
| Xiaogoumen Naizi (BK-XGMNZ) | D | D | D | D | D | DI | I | DI | D | DI | DI | D | I |
| XGM Suan Binzi (BK-XGMSBZ) | DI | D | D | D | D | DI | I | DI | D | DI | DI | D | DI |
| XGM Tian Binzi (BK-XGMTBZ) | D | D | D | D | DI | DI | I | DI | D | DI | D | D | I |
| Starkrimson (BK-XHX) | D | D | D | DI | D | D | DI | DI | D | DI | DI | I | D |
| Xinjiang 1 (BK-XJ1) | D | D | D | D | DI | DI | I | DI | D | DI | I | D | DI |
| Xinjiang 11 (BK-XJ11) | D | D | D | DI | DI | DI | D | DI | DI | DI | DI | D | D |
| Xinjiang 14 (BK-XJ14) | D | D | D | DI | DI | DI | D | DI | DI | DI | DI | D | D |
| Xinjiang 15 (BK-XJ15) | D | D | D | DI | DI | DI | D | DI | D | D | DI | DI | D |
| Xinjiang 16 (BK-XJ16) | D | D | D | DI | I | DI | D | DI | D | DI | D | D | D |
| Xinjiang 17 (BK-XJ17) | D | D | D | D | DI | DI | D | DI | DI | DI | DI | D | DI |
| Xinjiang 18 (BK-XJ18) | D | D | D | D | DI | DI | D | DI | DI | DI | DI | D | DI |
| Xinjiang 19 (BK-XJ19) | D | D | D | DI | D | DI | D | DI | D | DI | I | DI | DI |
| Xinjiang 21 (BK-XJ21) | D | D | D | D | I | DI | D | DI | D | DI | DI | D | D |
| Xinjiang 22 (BK-XJ22) | DI | D | D | D | DI | DI | I | DI | D | DI | I | D | D |
| Xinjiang 24 (BK-XJ24) | DI | D | D | D | I | DI | I | DI | D | DI | I | D | D |
| Xinjiang 26 (BK-XJ26) | D | D | D | DI | DI | DI | D | DI | DI | DI | DI | D | D |
| Xinjiang 28 (BK-XJ28) | D | D | D | D | D | DI | D | DI | D | DI | I | DI | DI |
| Xinjiang 29 (BK-XJ29) | D | D | D | DI | DI | I | DI | DI | DI | DI | D | I | DI |
| Xinjiang 31 (BK-XJ31) | DI | D | D | D | DI | DI | D | DI | D | DI | DI | D | D |
| Xinjiang 3 (BK-XJ3H) | DI | D | D | DI | DI | DI | D | DI | D | DI | DI | DI | D |
| Xinjiang 6 (BK-XJ6H) | DI | D | D | DI | D | DI | D | D | D | DI | DI | D | DI |
| Xinjiang 7 (BK-XJ7) | D | D | D | D | DI | DI | D | DI | DI | DI | DI | D | D |
| Xinjiang 8 (BK-XJ8) | D | D | DI | D | DI | DI | D | DI | D | DI | I | D | DI |
| Xinjiang 9 (BK-XJ9) | D | D | D | DI | DI | I | DI | DI | DI | DI | D | I | DI |
| Xijin Crab (BK-XJHT) | D | DI | DI | D | D | D | D | DI | D | D | DI | D | D |
| Xiaomian Crab (BK-XMHT) | D | D | DI | D | D | DI | I | DI | D | DI | D | D | I |
| New Jonagold (BK-XQNJ) | DI | DI | DI | DI | DI | DI | DI | DI | DI | DI | DI | DI | DI |

-continued

Construction results of InDel marker genotype database of *Malus* germplasm resources

| | | | | | | | | | | | | | |
|---|---|---|---|---|---|---|---|---|---|---|---|---|---|
| Xiaoshuai (BK-XS) | D | D | D | DI | DI | D | DI | DI | DI | DI | I | DI | D |
| Shinsekai (BK-XSJ) | DI | D | D | DI | DI | D | DI | D | DI | D | DI | D | DI |
| Xiangyanghong (BK-XYH) | DI | D | D | D | DI | DI | DI | DI | D | DI | DI | D | DI |
| Italy Early Red (BK-YDLZH) | DI | DI | D | I | D | DI | I | DI | DI | DI | D | I | DI |
| Yanfu 10 (BK-YF10) | DI | D | D | DI | DI | DI | DI | DI | D | D | DI | DI | DI |
| Yoko (BK-YG) | DI | D | D | DI | D | DI | DI | DI | I | DI | DI | DI | D |
| Yuanhong (BK-YH) | D | D | D | D | DI | DI | DI | DI | D | DI | DI | D | D |
| Tehong 2 (BK-YH2) | DI | D | D | DI | DI | DI | DI | DI | D | D | DI | DI | D |
| Yanhongmi (BK-YHM) | D | D | D | D | D | DI | D | D | DI | DI | DI | D | D |
| Youliang Spur (BK-YLDZ) | DI | D | D | DI | DI | DI | DI | DI | D | D | DI | DI | DI |
| Yuanye Crab (BK-YYHT) | D | D | D | D | DI | DI | I | DI | D | DI | DI | D | I |
| Stark Jumbo (BK-ZB) | DI | D | D | D | DI | D | I | DI | D | D | DI | D | D |
| Jumbo Orin (BK-ZBWL) | DI | DI | DI | I | DI | DI | I | DI | DI | DI | DI | I | DI |
| Zhuifeng 1 (BK-ZF1H) | D | D | D | D | DI | D | D | D | D | DI | DI | DI | D |
| Zhuifeng 2 (BK-ZF2H) | D | D | D | D | D | D | I | D | D | DI | DI | D | DI |
| Early Fuji (BK-ZFS) | DI | D | D | DI | DI | DI | DI | DI | D | D | DI | DI | DI |
| Xiaofanshan Crab (BK-ZFSHT) | DI | D | D | D | D | DI | I | DI | D | DI | DI | D | DI |
| Zisai Pearl (BK-Zisai) | D | D | D | DI | DI | D | DI | DI | D | D | D | D | I |
| Geneva Early (BK-ZJ) | D | D | D | D | I | DI | DI | DI | D | DI | I | D | D |
| 13-26W (CL-1) | D | DI | DI | D | DI | D | I | DI | D | D | I | D | I |
| 23-127 (CL-2) | DI | DI | DI | DI | D | DI | DI | DI | DI | DI | DI | DI | DI |
| 50-30 (CL-3) | DI | D | D | D | D | D | DI | DI | D | D | DI | DI | DI |
| 50-32 (CL-4) | DI | DI | DI | DI | DI | D | I | D | DI | D | D | D | DI |
| H5-101 (CL-5) | DI | DI | DI | DI | DI | DI | DI | DI | DI | D | D | I | D |
| Pingyan (CL-6) | D | D | D | I | DI | DI | DI | DI | D | DI | DI | D | DI |
| Deqin Crab (DQ) | D | D | D | D | D | D | D | D | D | D | D | D | DI |
| Jin 18 (GY-1) | DI | D | DI | DI | DI | DI | DI | DI | D | D | DI | DI | DI |
| Fengfeng Baleng (GY-2) | D | D | DI | D | D | D | D | DI | D | D | DI | D | D |
| Hanfu 6 (GY-3) | DI | D | D | DI | DI | DI | DI | DI | D | D | DI | DI | D |
| Hanfu 3 (GY-4) | D | D | D | D | DI | D | D | DI | DI | DI | DI | I | I |
| 95/06 (GZ-1) | D | D | D | D | DI | DI | D | DI | D | DI | I | D | D |
| 107/06 (GZ-2) | D | D | D | D | DI | I | D | D | DI | DI | I | D | D |
| 117/06 (GZ-3) | D | DI | DI | D | D | D | DI | D | DI | D | I | D | D |
| 119/06 (GZ-4) | D | D | DI | D | DI | D | D | DI | DI | DI | I | D | D |
| Jinxiu Crab (GZ-5) | D | D | D | D | D | D | DI | D | DI | DI | DI | DI | D |
| Zhizun Fuji (HS-1) | DI | D | D | DI | DI | DI | DI | D | D | D | DI | DI | DI |
| Fuji No. 1 (HS-10) | DI | D | D | DI | D | DI | DI | DI | D | D | DI | DI | DI |
| Red Jonaprince (HS-12) | DI | DI | DI | DI | DI | DI | DI | DI | DI | DI | DI | DI | DI |

| Construction results of InDel marker genotype database of *Malus* germplasm resources | | | | | | | | | | | | | |
|---|---|---|---|---|---|---|---|---|---|---|---|---|
| Nic29 (HS-13) | D | D | D | D | DI | DI | DI | DI | D | D | I | D | D |
| Azhen Fuji (HS-14) | DI | D | D | DI | DI | DI | DI | DI | D | D | DI | DI | DI |
| Envy (HS-15) | DI | D | D | DI | D | D | DI | D | I | DI | D | I | D |
| Rosegrow (HS-16) | D | DI | DI | DI | DI | DI | DI | DI | DI | DI | DI | DI | DI |
| Canzy (HS-17) | I | D | D | DI | DI | D | DI | DI | I | DI | DI | I | DI |
| Fubrax (HS-2) | DI | D | D | DI | DI | DI | DI | DI | D | D | DI | DI | DI |
| Mitchgla (HS-3) | DI | DI | DI | I | D | DI | I | DI | DI | DI | D | I | DI |
| Fujiko (HS-4) | DI | D | D | DI | DI | DI | DI | DI | D | D | DI | DI | DI |
| Buckeye Gala (HS-5) | DI | DI | DI | I | D | DI | I | DI | DI | DI | D | I | DI |
| Fujion (HS-6) | DI | D | D | D | D | D | D | DI | D | D | DI | DI | DI |
| Modi (HS-7) | DI | DI | DI | DI | DI | DI | I | DI | D | DI | DI | DI | DI |
| Jiangxue (HS-8) | D | DI | DI | D | D | D | DI | DI | D | DI | DI | I | DI |
| September Wonder Fuji (HS-9) | DI | D | D | DI | DI | DI | DI | DI | D | D | DI | DI | DI |
| Linqin Crab (LQ) | D | D | D | D | D | DI | DI | DI | D | DI | D | D | I |
| Lushan Sanye (LSSY) | D | D | D | D | D | D | D | D | D | D | D | D | D |
| 83-2 (MDJ-1) | DI | DI | DI | DI | DI | DI | DI | D | D | DI | DI | I | D |
| Tianfeng (MDJ-9) | DI | D | DI | D | DI | DI | D | DI | DI | DI | DI | D | D |
| Oregon Spur II-red (OR-1) | D | D | DI | DI | D | D | DI | DI | D | DI | DI | I | D |
| Oregon Spur II-green (OR-2) | D | D | DI | DI | D | D | DI | DI | D | DI | DI | I | DI |
| E3N2 (OR-3) | D | D | D | DI | D | D | DI | DI | D | DI | DI | I | I |
| E4N1 (OR-4) | D | D | DI | DI | D | D | DI | DI | D | DI | DI | I | D |
| E4N2 (OR-5) | D | D | DI | DI | D | D | DI | DI | D | DI | DI | I | D |
| W6N1 (OR-6) | D | D | DI | DI | D | D | DI | DI | D | DI | DI | I | DI |
| W6S5 (OR-7) | D | D | DI | DI | D | D | DI | DI | D | DI | DI | I | D |
| W8S3 (OR-8) | D | D | D | DI | D | D | DI | DI | D | DI | DI | I | D |
| Daihong (QD-1) | D | D | DI | DI | DI | DI | DI | D | DI | DI | D | I | DI |
| Tangmutian (QD-10) | DI | D | D | DI | DI | DI | DI | DI | D | D | DI | DI | DI |
| Shanjin Crab N1 (QD-11) | D | D | D | D | D | D | D | D | D | D | D | D | D |
| Shanjin Crab N2 (QD-12) | D | D | D | D | D | D | D | D | D | D | D | D | D |
| E zhen 1 (QD-13) | D | D | D | DI | I | DI | I | D | D | DI | D | I |
| E zhen 2 (QD-14) | D | D | D | DI | I | DI | I | D | D | DI | DI | D | I |
| E zhen 3 (QD-15) | D | D | DI | D | I | DI | I | D | DI | I | D | I |
| E zhen 4 (QD-16) | D | D | D | D | DI | DI | I | DI | D | DI | DI | D | I |
| E zhen 5 (QD-17) | D | D | D | D | DI | I | DI | D | DI | DI | D | I |
| Haihong (QD-19) | D | D | D | D | DI | I | DI | D | D | D | D | DI |
| Qingfu 2 (QD-2) | DI | D | D | DI | DI | DI | DI | D | D | DI | DI | DI |
| Telamon (QD-20) | DI | DI | DI | DI | D | I | DI | DI | DI | DI | D | I | DI |

-continued

Construction results of InDel marker genotype database of *Malus* germplasm resources

| | | | | | | | | | | | | | |
|---|---|---|---|---|---|---|---|---|---|---|---|---|---|
| Fuyan (QD-21) | D | DI | DI | D | D | DI | DI | DI | D | DI | D | I | DI |
| Hongxun 1 (QD-22) | DI | D | D | DI | D | DI | D | DI | DI | DI | DI | DI | D |
| Rushan Fuji (QD-23) | DI | D | D | DI | DI | DI | DI | DI | D | DI | DI | DI | DI |
| Jiudian Spur (QD-24) | DI | D | D | DI | DI | DI | DI | DI | D | D | DI | DI | DI |
| Ruihong (QD-25) | DI | DI | DI | I | DI | DI | I | DI | DI | DI | D | I | DI |
| Zhongnvshi (QD-26) | D | D | D | D | DI | D | D | DI | DI | DI | DI | D | D |
| 2001 Spur (QD-27) | DI | D | D | DI | DI | DI | DI | DI | D | D | DI | DI | DI |
| Fuli (QD-28) | DI | D | D | DI | D | DI | I | DI | DI | DI | DI | DI | D |
| Tuanwang semi-Spur (QD-29) | DI | D | D | DI | DI | DI | DI | DI | D | D | DI | DI | DI |
| Qingfu 3 (QD-3) | DI | D | D | DI | DI | DI | DI | DI | D | D | DI | DI | DI |
| Longfu (QD-30) | DI | D | D | DI | DI | DI | DI | DI | D | D | DI | DI | DI |
| Baotou Linqin (QD-31) | D | D | D | D | D | DI | D | DI | D | DI | D | D | D |
| Yanfu 6 (QD-32) | DI | D | D | DI | DI | DI | DI | DI | D | D | DI | DI | DI |
| SH40-2 seedling (QD-4) | D | D | D | D | DI | D | D | D | D | DI | D | D | D |
| Saijin (QD-5) | DI | DI | DI | I | D | DI | I | DI | DI | DI | D | I | DI |
| Nagafu 12 (QD-6) | DI | D | D | DI | DI | DI | DI | DI | D | DI | DI | DI | DI |
| Caoyuan Crab (QD-7) | D | D | D | D | D | D | D | D | D | D | D | D | DI |
| Xiaojin Crab (QD-8) | D | DI | DI | DI | DI | DI | I | D | D | D | D | DI | D |
| Shuangyanghong (QD-9) | DI | DI | DI | DI | D | DI | I | DI | DI | DI | D | I | DI |
| Qianxian Crab (QX-1) | D | D | D | DI | D | D | D | DI | D | D | I | D | D |
| Ruixue (ruixue) | D | DI | DI | DI | DI | D | DI | D | DI | DI | DI | DI | DI |
| Ruiyang (RY) | D | D | D | DI | D | D | DI | D | D | DI | DI | DI | DI |
| Yanyuan 1 (SC-1) | DI | DI | DI | I | DI | DI | I | DI | DI | DI | DI | I | DI |
| Yanyuan 2 (SC-2) | D | DI | DI | DI | D | D | DI | D | DI | DI | I | DI | DI |
| Yanyuan 3 (SC-3) | DI | D | D | DI | DI | DI | DI | DI | D | D | DI | DI | DI |
| Yanyuan 4 (SC-4) | D | DI | DI | DI | D | D | DI | D | DI | DI | I | DI | DI |
| Yanyuan 5 (SC-5) | D | DI | DI | D | D | DI | DI | D | D | DI | I | D | D |
| Yanyuan 6 (SC-6) | D | DI | DI | D | D | D | DI | D | DI | DI | DI | DI | DI |
| Yanyuan 7 (SC-7) | DI | DI | DI | DI | DI | DI | DI | DI | DI | DI | DI | DI | DI |
| Mitchgala (SX-10) | DI | DI | D | I | D | DI | I | DI | DI | DI | D | I | D |
| Zhongqiuwang Linyi (SX-11) | DI | DI | DI | DI | DI | D | DI | DI | D | DI | D | I | D |
| Linyi Meiguo 5 (SX-12) | D | D | D | D | D | DI | I | D | D | D | DI | D | DI |
| Liquan Spur Fuji (SX-13) | DI | D | D | DI | DI | DI | DI | DI | D | D | DI | DI | DI |
| Qiulimu (SX-14) | D | D | D | D | D | DI | DI | DI | DI | DI | I | D | D |
| Qincui (SX-15) | DI | D | D | D | DI | DI | D | DI | D | D | DI | D | D |
| Taigu Shaguo Late (SX-17) | DI | D | D | D | D | DI | I | DI | D | DI | DI | D | DI |
| Lingyige Hongrou (SX-18) | D | D | D | D | DI | I | D | D | DI | DI | I | D | D |

-continued

Construction results of InDel marker genotype database of *Malus* germplasm resources

| | | | | | | | | | | | | | |
|---|---|---|---|---|---|---|---|---|---|---|---|---|---|
| Shenai LS (SX-19) | D | D | D | DI | DI | DI | DI | DI | D | D | DI | DI | D |
| Linyi Meiguo 8 (SX-2) | D | DI | DI | DI | DI | DI | DI | DI | D | D | I | DI | I |
| Liga (SX-20) | DI | DI | DI | I | D | DI | I | DI | DI | DI | D | I | DI |
| Y-1 (SX-21) | D | D | D | D | D | D | D | D | D | D | D | D | DI |
| B009 (SX-22) | D | D | D | D | DI | DI | D | D | D | D | D | D | DI |
| Jinfu 1 (SX-23) | DI | D | D | DI | DI | DI | DI | DI | D | D | DI | DI | DI |
| Hongmantang (SX-24) | D | D | D | D | DI | DI | DI | D | D | D | D | DI | D |
| Y-2 (SX-25) | D | D | D | D | D | D | D | D | D | D | D | D | D |
| Y-3 (SX-26) | D | D | D | D | D | D | D | D | D | D | D | D | D |
| Xinliangxiang (SX-27) | DI | D | D | DI | DI | DI | DI | DI | D | D | DI | DI | DI |
| Ennike Gala (SX-28) | DI | DI | DI | I | D | DI | I | DI | DI | DI | D | I | DI |
| Linyi Meiguo 6 (SX-3) | D | DI | DI | DI | DI | DI | DI | DI | D | DI | DI | DI | DI |
| Linyi Meiguo 2 (SX-30) | DI | D | D | DI | DI | DI | DI | DI | D | D | DI | DI | DI |
| Donglimu (SX-33) | D | D | D | D | D | DI | DI | DI | DI | DI | I | D | D |
| Linyi Meiguo 1 (SX-34) | D | DI | DI | DI | DI | DI | DI | DI | D | D | I | DI | I |
| Linyi Meiguo 4 (SX-4) | DI | D | D | DI | I | D | I | DI | D | D | DI | D | I |
| Qinyang (SX-6) | DI | D | D | DI | D | DI | DI | DI | D | DI | DI | DI | I |
| Taiguo Shaguo Early (SX-7) | DI | D | D | D | D | DI | I | DI | D | DI | DI | D | DI |
| Yuhua Zaofu (SX-8) | DI | D | D | DI | DI | DI | DI | DI | D | D | DI | DI | DI |
| 78-M18 (SY-1) | D | DI | DI | DI | DI | D | D | D | D | DI | DI | I | D |
| Jinping (SY-10) | D | D | DI | D | D | D | DI | D | D | DI | DI | D | D |
| Longqiu (SY-11) | D | D | DI | DI | I | DI | D | DI | D | DI | DI | I | I |
| Longfeng (SY-12) | D | D | D | D | D | D | D | DI | D | D | DI | D | D |
| Xiangjiaoguo (SY-14) | DI | DI | DI | DI | DI | DI | I | D | DI | DI | DI | DI | DI |
| Longguan (SY-15) | DI | DI | DI | DI | DI | D | DI | DI | D | DI | I | DI | D |
| Longshuai (SY-16) | D | D | DI | DI | D | DI | D | D | D | DI | D | D | D |
| Zixiang (SY-17) | D | D | D | D | DI | D | D | I | D | D | DI | DI | DI |
| Huahong (SY-19) | DI | D | D | D | D | DI | I | DI | D | D | DI | D | D |
| Binlang (SY-2) | DI | DI | DI | DI | DI | DI | I | D | DI | DI | DI | DI | DI |
| Qiufengmi (SY-20) | D | D | D | D | D | DI | I | DI | D | DI | DI | D | I |
| Honglingdang (SY-21) | D | D | D | D | I | D | D | DI | DI | D | I | D | D |
| Qiulu (SY-22) | D | D | DI | D | D | DI | D | DI | D | DI | D | D | D |
| Longhong (SY-23) | DI | DI | DI | DI | DI | D | DI | DI | DI | DI | I | DI | D |
| Milk (SY-3) | D | D | D | DI | D | D | DI | DI | D | D | I | D | D |
| Hanfu (SY-4) | DI | D | DI | DI | DI | D | DI | D | DI | DI | DI | DI | D |
| Toko (SY-5) | DI | D | D | I | D | D | D | D | D | D | DI | D | DI |
| Jinhong (SY-6) | DI | DI | DI | DI | DI | DI | D | D | DI | DI | I | DI | D |
| K9 (SY-7) | D | D | D | D | DI | D | D | DI | DI | D | I | D | D |

| Construction results of InDel marker genotype database of *Malus* germplasm resources | | | | | | | | | | | | |
|---|---|---|---|---|---|---|---|---|---|---|---|---|
| 03-06-04 (SY-8) | D | D | D | D | DI | DI | D | DI | D | D | D | I |
| Olga (SY-9) | D | D | DI | D | I | DI | D | DI | DI | DI | D | D |
| Gala 4x (TA-1) | DI | DI | DI | I | D | DI | I | DI | DI | DI | D | I | DI |
| Juda Fuji (TA-11) | DI | D | D | DI | DI | DI | DI | DI | D | D | DI | DI |
| Luli (TA-12) | DI | I | DI | DI | D | DI | DI | D | DI | DI | D | D |
| Luping 1 (TA-13) | DI | DI | DI | DI | DI | DI | DI | D | DI | D | DI | DI |
| Luping 2 (TA-14) | DI | DI | DI | I | D | DI | DI | DI | DI | D | DI | DI |
| Luping 5 (TA-15) | I | DI | DI | I | D | DI | DI | DI | DI | D | D | DI |
| Luyan (TA-16) | D | DI | DI | DI | D | DI | DI | DI | D | DI | DI | DI |
| Meinong (TA-17) | I | D | D | D | DI | D | DI | DI | D | D | I | I | D |
| Akifu 19 (TA-18) | DI | D | D | DI | DI | DI | DI | DI | D | D | DI | DI | DI |
| Akifu 39 (TA-19) | DI | D | D | DI | DI | DI | DI | DI | D | D | DI | DI | DI |
| Hanfu 4x (TA-2) | D | DI | DI | DI | I | DI | D | DI | D | DI | I | DI | DI |
| Qiufuhong (TA-20) | DI | D | D | DI | DI | DI | DI | DI | D | D | DI | DI | DI |
| Qunfu 1 (TA-21) | DI | D | D | DI | DI | DI | DI | DI | D | D | DI | DI | DI |
| Shengfang (TA-22) | DI | D | D | DI | DI | DI | DI | DI | D | D | DI | DI | DI |
| Alps Otome (TA-27) | D | DI | DI | D | D | D | D | D | D | DI | DI | D | D |
| Early Fuji (TA-28) | DI | D | D | DI | DI | DI | DI | DI | D | D | DI | DI | DI |
| BP (TA-3) | D | D | D | D | I | DI | I | D | D | DI | I | D | I |
| Yishuihong (TA-32) | DI | D | D | DI | DI | DI | DI | DI | D | D | DI | DI | DI |
| BP-176 (TA-4) | D | D | D | DI | I | DI | I | D | D | DI | I | D | I |
| G41 (TA-5) | D | D | D | D | D | DI | D | D | D | D | DI | D | DI |
| G935 (TA-6) | D | DI | D | D | DI | DI | D | DI | D | D | DI | DI | D |
| P60 (TA-7) | D | D | D | DI | I | DI | I | DI | D | DI | I | D | DI |
| Fuji (TA-9) | DI | D | D | DI | DI | DI | DI | DI | D | D | DI | DI | DI |
| Tianfu 1 (TS-1) | DI | D | D | DI | DI | DI | DI | DI | D | D | DI | DI | DI |
| &28 (TS-13) | DI | D | D | DI | DI | DI | DI | DI | D | D | DI | DI | DI |
| Red Chief (TS-14) | D | D | D | DI | D | D | DI | DI | D | DI | DI | I | D |
| New Redchief (TS-2) | D | D | D | DI | D | D | DI | DI | D | DI | DI | I | D |
| Chaohongxing (TS-3) | D | D | D | DI | D | D | DI | DI | D | DI | DI | I | D |
| Aozhou 1 (TS-5) | D | DI | DI | DI | I | DI | D | D | D | D | DI | DI | DI |
| Tianfu 2 (TS-6) | DI | D | D | DI | DI | DI | DI | DI | D | D | DI | DI | DI |
| Judeline (TS-7) | DI | DI | DI | DI | DI | DI | DI | DI | I | DI | DI | DI | I |
| Judestar (TS-8) | D | I | DI | DI | D | DI | DI | DI | D | DI | D | I | I |
| Judaine (TS-9) | DI | DI | DI | DI | DI | DI | DI | DI | I | DI | DI | DI | I |
| WH-5 (WH-1) | DI | D | D | DI | DI | DI | DI | DI | D | D | DI | DI | DI |
| Italy Smothe (WH-10) | DI | DI | DI | I | DI | DI | I | DI | DI | DI | DI | I | DI |
| Bai Crab (WH-2) | D | D | DI | D | DI | DI | I | DI | D | DI | D | D | DI |

| | | | | | | | | | | | | | |
|---|---|---|---|---|---|---|---|---|---|---|---|---|---|
| Construction results of InDel marker genotype database of *Malus* germplasm resources | | | | | | | | | | | | | |
| Hongguang (WH-4) | DI | D | D | D | I | D | DI | DI | D | D | DI | DI | I |
| Huangcui (WH-5) | DI | DI | DI | I | DI | D | DI | DI | DI | DI | DI | DI | DI |
| Qinglin (WH-6) | DI | DI | DI | DI | DI | DI | DI | DI | DI | DI | I | DI | I |
| Harlikar (WH-8) | DI | DI | DI | I | D | DI | I | DI | DI | DI | DI | I | DI |
| Italy Gala (WH-9) | DI | DI | DI | I | D | DI | I | DI | DI | DI | D | I | DI |
| Wushan Bianye (WSBY) | D | D | D | DI | D | D | D | D | D | D | D | D | D |
| Xin 1 (XC-1) | I | I | DI | I | D | I | I | DI | I | DI | D | I | I |
| Xin 5 (XC-2) | I | D | D | I | D | I | I | DI | DI | D | DI | D |
| Hanfu 3x (XC-3) | D | D | D | I | I | D | D | D | D | D | D | D |
| Gala 4x (XC-4) | DI | DI | DI | I | DI | DI | I | DI | DI | DI | D | I | DI |
| Weizhimuben (XC-5) | D | DI | DI | DI | D | DI | DI | DI | D | DI | DI | D | D |
| Chaguo (XC-CG) | D | D | D | D | D | DI | I | DI | D | DI | D | D | I |
| Donghongguo (XC-DHG) | D | D | D | D | D | DI | I | DI | D | DI | DI | D | DI |
| Fuxian Sanye (XC-FXXY) | D | D | D | D | D | D | D | D | D | D | D | D | D |
| Hongsanye (XC-HSY) | D | D | D | D | D | D | D | D | D | D | D | D | D |
| Jilin Xiaohong Crab (XC-JILINXIAOHONG-HAITANG) | D | D | D | D | I | DI | D | D | D | DI | D | D | D |
| Jilin Xiaohuang Crab (XC-JILINXIAOHUANG-HAITANG) | D | D | D | DI | I | DI | D | DI | D | DI | D | D | D |
| Jilin Huang Crab (XC-JLHHT) | D | D | D | DI | I | DI | D | DI | D | DI | D | D | D |
| Shajin Crab (XC-JSHT) | D | D | D | DI | D | D | D | D | D | D | D | D | D |
| Longdong Crab (XC-LDHT) | D | D | D | D | D | D | D | D | D | D | D | D | D |
| Lushi Crab (XC-LSHT) | D | D | D | D | D | D | D | D | D | D | D | D | D |
| Laiwunanyan (XC-LWNY) | D | D | D | D | D | DI | I | DI | D | DI | D | D | I |
| Linzhi (XC-LZ) | D | D | D | DI | D | D | D | D | D | D | D | D | D |
| Mao Shandingzi (XC-MSDZ) | D | D | DI | D | D | D | D | D | D | D | D | D | DI |
| Pingyitiancha (XC-PYTC) | D | D | D | D | D | D | D | D | D | D | D | D | D |
| Qiuzi (XC-QZ) | D | D | D | D | DI | DI | I | DI | D | DI | DI | D | I |
| Sichuan Bianye (XC-SCBY) | D | D | D | I | D | D | D | D | D | D | D | D | D |
| Shandingzi (XC-SDZ) | D | D | D | D | D | D | D | D | DI | D | D | D | D |
| Weixi Sanye (XC-WXSY) | D | D | D | D | D | D | DI | D | DI | D | DI | DI | D |
| Xifu Crb (XC-XFHT) | DI | D | D | D | D | D | DI | D | D | D | D | D | D |
| Xiaojin Bianye (XC-XJBY) | D | D | D | DI | D | D | D | D | D | D | D | D | D |
| Xinjiang Yepingguo (XC-XJYHT) | DI | D | D | D | DI | DI | I | DI | D | DI | I | D | D |
| Yajiang Bianye (XC-YJBY) | D | D | D | DI | D | D | D | D | D | D | D | D | D |
| Yingye Crab (XC-YYHT) | D | D | D | DI | DI | DI | D | D | D | D | DI | D | D |
| Zhaai (XC-ZA) | D | D | D | D | D | D | D | D | D | D | D | D | D |
| Zumi Crab (XC-ZMHT) | D | D | D | D | D | D | DI | D | DI | D | DI | D | D |
| Pink Lady (XN-FHNS) | D | DI | DI | DI | DI | DI | DI | DI | DI | DI | DI | DI | DI |

| Construction results of InDel marker genotype database of *Malus* germplasm resources |
|---|

| | | | | | | | | | | | | |
|---|---|---|---|---|---|---|---|---|---|---|---|---|
| Hongrou 1 (XN-HR1) | D | D | D | D | DI | DI | I | DI | D | DI | I | D | DI |
| Hongrou 2 (XN-HR2) | D | D | D | D | DI | DI | I | DI | D | DI | I | D | D |
| Hongrou 3 (XN-HR3) | DI | D | D | D | DI | DI | I | DI | D | DI | I | D | D |
| Hongrou 4 (XN-HR4) | D | D | D | D | DI | DI | I | DI | D | DI | I | D | D |
| Hongrou 5 (XN-HR5) | D | D | D | D | DI | DI | DI | DI | D | DI | I | D | D |
| Hongrou 6 (XN-HR6) | DI | DI | DI | DI | DI | DI | DI | DI | DI | DI | I | D | D |
| Hongrou 7 (XN-HR7) | D | D | DI | D | DI | D | DI | DI | D | DI | I | D | DI |
| Ambrosia (XN-MW) | DI | DI | D | DI | DI | D | DI | DI | DI | DI | D | I | DI |
| Xinjiang 10 (XN-XJ10) | DI | D | D | D | D | DI | I | DI | D | DI | I | D | D |
| Xinjiang 11 (XN-XJ11) | D | D | D | D | I | DI | I | DI | D | DI | D | D | D |
| Xinjiang 12 (XN-XJ12) | DI | D | D | D | D | DI | I | DI | D | DI | I | D | D |
| Xinjiang 13 (XN-XJ13) | D | D | D | DI | D | DI | DI | DI | D | DI | DI | D | D |
| Xinjiang 14 (XN-XJ14) | D | D | D | D | D | DI | DI | DI | D | DI | I | D | DI |
| Xinjiang 15 (XN-XJ15) | D | D | DI | DI | DI | DI | D | D | D | DI | DI | D | DI |
| Xinjiang 16 (XN-XJ16) | D | D | D | D | D | DI | DI | DI | DI | DI | I | D | D |
| Xinjiang 17 (XN-XJ17) | D | D | D | D | DI | DI | I | DI | D | DI | I | D | D |
| Xinjiang 18 (XN-XJ18) | D | D | DI | DI | DI | DI | D | DI | D | DI | I | D | D |
| Xinjiang 19 (XN-XJ19) | DI | D | D | D | DI | DI | I | DI | D | DI | I | D | D |
| Xinjiang 2 (XN-XJ2) | D | D | D | D | I | DI | I | DI | D | DI | DI | D | D |
| Xinjiang 20 (XN-XJ20) | D | D | DI | D | DI | DI | DI | DI | DI | DI | DI | D | DI |
| Xinjiang 21 (XN-XJ21) | D | D | D | D | D | DI | DI | DI | DI | DI | I | D | D |
| Xinjiang 23 (XN-XJ23) | D | D | D | DI | I | D | DI | DI | D | DI | I | D | D |
| Xinjiang 24 (XN-XJ24) | DI | D | D | D | DI | DI | DI | DI | D | DI | DI | D | I |
| Xinjiang 25 (XN-XJ25) | D | D | D | D | D | DI | I | DI | D | DI | I | D | DI |
| Xinjiang 27 (XN-XJ27) | D | D | DI | DI | DI | DI | D | D | D | DI | DI | D | DI |
| Xinjiang 3 (XN-XJ3) | DI | D | D | D | DI | DI | I | DI | D | DI | I | D | D |
| Xinjiang 4 (XN-XJ4) | D | D | DI | D | DI | DI | DI | DI | DI | DI | DI | D | D |
| Xinjiang 5 (XN-XJ5) | D | D | D | D | I | D | DI | D | D | D | D | D | D |
| Xinjiang 7 (XN-XJ7) | DI | D | D | D | I | D | DI | DI | D | DI | DI | D | D |
| Xinjiang 8 (XN-XJ8) | DI | D | D | DI | DI | DI | I | DI | D | DI | I | D | DI |
| Xinjiang 9 (XN-XJ9) | D | D | D | DI | DI | DI | DI | DI | DI | DI | I | D | DI |
| Yueguan (XY-10) | DI | DI | DI | I | DI | DI | DI | D | D | DI | DI | I | D |
| Yuehua (XY-11) | D | DI | DI | DI | I | DI | D | DI | D | DI | DI | I | I |
| Yueyan (XY-12) | DI | D | DI | DI | I | DI | D | D | DI | DI | I | DI | D |
| Bud Sport 5 (XY-13) | DI | D | D | DI | DI | DI | DI | DI | D | D | DI | DI | DI |
| Bud Sport 3 (XY-14) | DI | D | D | DI | DI | DI | DI | DI | D | D | DI | DI | DI |
| Longfu (XY-15) | DI | D | D | DI | DI | DI | DI | DI | D | D | DI | DI | DI |
| Yuemei (XY-18) | D | DI | DI | DI | D | DI | DI | D | DI | DI | DI | D | D |

| Construction results of InDel marker genotype database of *Malus* germplasm resources | | | | | | | | | | | | | |
|---|---|---|---|---|---|---|---|---|---|---|---|---|---|
| Hanfu (XY-2) | DI | D | DI | DI | DI | DI | D | DI | D | DI | DI | DI | D |
| Linyi Fuji (XY-20) | DI | DI | DI | DI | DI | D | D | DI | D | D | DI | D | DI |
| Yishui Fuji (XY-22) | DI | D | D | DI | DI | DI | DI | DI | D | D | DI | DI | DI |
| Hongjinfu (XY-25) | DI | D | D | DI | DI | DI | DI | DI | D | D | DI | DI | DI |
| Beni Oshu (XY-26) | DI | D | D | DI | DI | DI | DI | DI | D | D | DI | DI | DI |
| Chuizhi Fuji (XY-27) | DI | D | D | DI | DI | DI | DI | DI | D | D | DI | DI | DI |
| Yueshuai (XY-28) | D | DI | DI | DI | DI | D | I | DI | DI | DI | DI | DI | D |
| Shichinohe 2 (XY-29) | DI | D | D | DI | DI | DI | DI | DI | D | D | DI | DI | DI |
| 74-178 (XY-3) | DI | D | D | I | DI | DI | DI | D | D | DI | DI | DI | DI |
| KAKUFUJI (XY-30) | DI | D | D | DI | DI | DI | DI | DI | D | D | DI | DI | DI |
| Royal Fuji 21 (XY-35) | DI | D | D | DI | DI | DI | DI | DI | D | D | DI | DI | DI |
| Qiquan Spur (XY-36) | DI | D | D | DI | DI | DI | DI | DI | D | D | DI | DI | DI |
| Juda Fuji (XY-37) | DI | D | D | D | I | D | DI | DI | D | D | DI | DI | I |
| 7-211 (XY-4) | D | D | DI | DI | D | DI | DI | D | D | DI | I | D | D |
| Yanfu 0 (XY-41) | DI | D | D | DI | DI | DI | DI | DI | D | D | DI | DI | DI |
| Spur Fuji (XY-42) | DI | D | D | DI | DI | DI | DI | DI | D | D | DI | DI | DI |
| Bayue fushiwang (XY-43) | DI | D | D | DI | DI | DI | DI | DI | D | D | DI | DI | DI |
| Huangfu 7 (XY-44) | DI | D | D | DI | DI | DI | DI | DI | D | D | DI | DI | DI |
| Aomori Spur Fuji (XY-46) | DI | D | D | DI | DI | DI | DI | DI | D | D | DI | DI | DI |
| Qiu Fuji (XY-47) | DI | D | D | DI | DI | DI | DI | DI | D | D | DI | DI | DI |
| Fuji Champion (XY-48) | DI | D | D | DI | DI | DI | DI | DI | D | D | DI | DI | DI |
| 26-34 (XY-5) | D | D | D | DI | D | D | D | DI | D | DI | DI | DI | DI |
| Akifu 19 (XY-50) | DI | D | D | DI | DI | DI | DI | DI | D | D | DI | DI | DI |
| Fuji (XY-54) | DI | D | D | DI | DI | DI | DI | DI | D | D | DI | DI | DI |
| Qinfu 1 (XY-55) | DI | D | D | DI | DI | DI | DI | DI | D | D | DI | DI | DI |
| Feng Fuji (XY-56) | DI | D | D | DI | DI | DI | DI | DI | D | D | DI | DI | DI |
| Tianxing (XY-57) | DI | D | D | DI | DI | DI | DI | DI | D | D | DI | DI | DI |
| Taiyang Fuji (XY-58) | DI | D | D | DI | DI | DI | DI | DI | D | D | DI | DI | DI |
| Cherry Crab (XY-6) | D | D | D | D | D | D | D | DI | D | DI | D | D | D |
| Yueping (XY-60) | DI | DI | DI | DI | DI | DI | DI | DI | D | D | DI | DI | D |
| 23-63 (XY-61) | DI | D | D | DI | DI | DI | DI | DI | D | D | DI | I | DI |
| 23-42 (XY-62) | D | D | DI | I | DI | DI | D | DI | D | D | DI | DI | D |
| 7-171 (XY-63) | D | DI | DI | D | D | D | D | D | DI | DI | DI | DI | D |
| Shengfang 3A (XY-65) | DI | D | D | DI | DI | DI | DI | DI | D | D | DI | DI | DI |
| Meinong Fuji (XY-67) | DI | D | D | DI | DI | DI | DI | DI | D | D | DI | DI | DI |
| 62-45 (XY-68) | D | DI | DI | DI | DI | DI | DI | D | DI | D | I | D |  |
| Fengfeng Fuji (XY-70) | DI | D | D | DI | DI | DI | DI | DI | D | D | DI | DI | DI |
| GM256 (XY-71) | DI | D | D | DI | DI | DI | DI | DI | D | D | DI | DI | DI |
| Jinfu 2 (XY-73) | DI | D | D | DI | DI | DI | DI | DI | D | D | DI | DI | DI |

| Construction results of InDel marker genotype database of *Malus* germplasm resources | | | | | | | | | | | | | |
|---|---|---|---|---|---|---|---|---|---|---|---|---|---|
| Qiufu (XY-75) | DI | D | D | DI | DI | DI | DI | DI | D | D | DI | DI | DI |
| Shanfu 6 (XY-76) | DI | D | D | DI | DI | DI | DI | DI | D | D | DI | DI | DI |
| Nagafu 8 (XY-77) | DI | D | D | DI | DI | DI | DI | DI | D | D | DI | DI | DI |
| 58-34 (XY-78) | D | DI | DI | DI | I | DI | DI | DI | D | DI | DI | D | D |
| 2001 Fuji (XY-79) | DI | D | D | DI | DI | DI | DI | DI | D | D | DI | DI | DI |
| 15-26 (XY-8) | DI | DI | DI | I | DI | DI | DI | D | DI | D | I | D | D |
| Wangshanhong (XY-80) | DI | D | D | DI | DI | DI | DI | DI | D | D | DI | DI | DI |
| Jinfu 1 (XY-81) | DI | D | D | DI | DI | DI | DI | DI | D | D | D | DI | DI |
| Qingfu 1 (XY-84) | DI | D | D | DI | DI | DI | DI | DI | D | D | DI | DI | DI |
| Qiufu 39 (XY-85) | DI | D | D | DI | D | DI | DI | DI | D | D | DI | DI | DI |
| Nagafu 1 (XY-86) | DI | D | D | DI | DI | DI | DI | DI | D | D | DI | DI | DI |
| Shou Fuji (XY-87) | DI | D | D | DI | DI | DI | DI | DI | D | D | DI | DI | DI |
| Yueli (XY-88) | DI | D | DI | D | D | DI | DI | D | DI | DI | DI | DI | D |
| Shanfu 2 (XY-89) | DI | D | D | DI | DI | DI | DI | DI | D | D | DI | DI | DI |
| Chongban Crab (XY-9) | D | D | D | D | D | DI | I | DI | D | DI | D | D | I |
| Harica (XY-90) | DI | DI | DI | DI | DI | DI | DI | DI | DI | DI | I | DI | I |
| Akifu 1 (XY-91) | DI | D | D | DI | DI | DI | DI | DI | D | D | DI | DI | DI |
| Wangfu (XY-92) | DI | D | D | DI | DI | DI | DI | DI | D | D | DI | DI | DI |
| Hong Manao (XYZ-1) | D | D | DI | DI | D | D | D | DI | D | D | DI | D | DI |
| Modi (XYZ-10) | DI | DI | D | DI | DI | DI | I | DI | D | DI | DI | DI | DI |
| C37 (XYZ-11) | DI | DI | D | DI | DI | D | DI | DI | DI | D | D | D | D |
| Envy ? (XYZ-12) | DI | D | D | DI | D | D | DI | D | I | DI | D | I | D |
| Xichang Yuanzhuiguo (XYZ-2) | DI | D | D | D | DI | DI | DI | D | D | DI | DI | I | D |
| Ziye Zixiaoguo (XYZ-3) | D | D | DI | D | I | DI | I | D | D | D | D | D | D |
| Ziye Zidaguo (XYZ-4) | D | DI | D | D | DI | DI | D | D | D | D | DI | DI | D |
| Shoufenshu 6 (XYZ-5) | DI | D | DI | D | DI | D | D | D | D | DI | DI | D | D |
| Changhua (XYZ-6) | DI | DI | D | I | D | DI | I | DI | DI | DI | D | I | DI |
| Jinshiji (XYZ-7) | DI | DI | DI | I | D | DI | I | DI | DI | DI | D | I | D |
| 19-147 (XYZ-9) | D | D | DI | DI | D | I | D | DI | D | DI | I | DI | DI |
| Malong Gala 1 (YN-1) | DI | DI | DI | I | D | DI | I | DI | DI | DI | D | I | DI |
| Shouer hong (YN-11) | DI | D | D | DI | DI | DI | DI | DI | D | D | DI | DI | DI |
| Yun Hongrou (YN-12) | D | DI | DI | D | DI | D | D | D | D | D | DI | DI | D |
| Lixing Crab (YN-13) | D | D | D | D | D | DI | I | DI | D | DI | DI | D | D |
| Siana (YN-15) | D | D | D | DI | I | I | DI | DI | D | D | I | D | D |
| Jonathan-M41 (YN-17) | D | DI | DI | D | DI | D | D | D | DI | DI | DI | D | D |
| Morlie's Delicious (YN-18) | DI | DI | DI | D | D | I | D | DI | DI | DI | I | DI | D |
| Britegold (YN-19) | DI | D | D | DI | DI | DI | DI | DI | D | D | DI | DI | DI |
| Malong Gala 1 blush (YN-2) | DI | DI | DI | I | D | DI | I | DI | DI | DI | D | I | DI |

| | | | | | | | | | | | | | |
|---|---|---|---|---|---|---|---|---|---|---|---|---|---|
| Line 5 (YN-22) | D | D | D | DI | I | I | DI | DI | D | D | I | D | D |
| Line 6 (YN-23) | D | DI | DI | D | D | I | D | D | D | D | DI | DI | D |
| Line 13 (YN-24) | DI | DI | DI | DI | DI | DI | DI | DI | DI | DI | I | DI | DI |
| row 3 (YN-25) | DI | I | DI | DI | D | DI | DI | D | DI | DI | DI | D | D |
| row 4 (YN-26) | DI | I | DI | DI | D | DI | DI | D | DI | DI | DI | D | D |
| row 5 (YN-27) | DI | I | DI | DI | D | DI | DI | D | DI | DI | DI | D | D |
| row 6 (YN-28) | DI | I | DI | DI | D | DI | DI | D | DI | DI | DI | D | D |
| row 9 (YN-29) | I | DI | DI | DI | DI | DI | DI | DI | I | DI | DI | I | DI |
| Malong xin Gala 1 (YN-3) | DI | DI | DI | I | D | DI | I | DI | DI | DI | D | I | DI |
| row 10 (YN-30) | D | DI | DI | DI | DI | DI | DI | DI | DI | DI | DI | DI | DI |
| row 11 (YN-31) | I | DI | DI | DI | DI | DI | DI | DI | I | DI | DI | I | DI |
| row 12 (YN-32) | DI | DI | DI | I | D | DI | I | DI | DI | DI | D | I | DI |
| row 13 (YN-33) | D | DI | DI | DI | D | DI | DI | DI | D | DI | DI | DI | DI |
| row 14 (YN-34) | DI | I | DI | DI | D | DI | DI | D | DI | DI | DI | D | D |
| row 15 (YN-35) | DI | DI | DI | DI | DI | DI | DI | DI | D | DI | D | DI | DI |
| row 16 (YN-36) | DI | DI | DI | DI | DI | DI | DI | DI | DI | DI | DI | DI | DI |
| row 17 (YN-37) | D | D | DI | D | D | DI | DI | D | D | DI | I | D | D |
| row 18 (YN-38) | D | D | DI | D | D | D | DI | D | DI | DI | DI | DI | DI |
| row 19 (YN-39) | D | D | D | D | I | D | DI | DI | D | D | DI | D | DI |
| Malong xin Gala 1 strip (YN-4) | DI | DI | DI | I | D | DI | I | DI | DI | DI | D | I | DI |
| row 20 (YN-40) | D | DI | DI | DI | D | D | DI | D | DI | DI | I | DI | DI |
| row 21 (YN-41) | DI | D | D | DI | DI | DI | DI | DI | D | D | DI | DI | DI |
| row 22 (YN-42) | D | DI | DI | DI | D | D | DI | D | DI | DI | I | DI | DI |
| row 23 (YN-43) | D | DI | DI | DI | D | D | DI | D | DI | DI | I | DI | DI |
| row 24 (YN-44) | DI | D | D | DI | DI | DI | DI | DI | DI | D | DI | DI | DI |
| row 25 (YN-45) | DI | D | D | DI | DI | DI | DI | DI | D | D | DI | DI | DI |
| Malong Gala2 (YN-5) | DI | DI | DI | I | D | DI | I | DI | DI | DI | D | I | DI |
| Malong Gala 2 blush (YN-6) | DI | DI | DI | I | D | DI | I | DI | DI | DI | D | I | DI |
| Longwei (YN-7) | D | DI | DI | DI | D | D | DI | D | DI | D | DI | I | DI |
| Longwei Early Mutant (YN-8) | D | DI | DI | DI | D | D | DI | DI | D | DI | DI | I | DI |
| Cherry Gala (YN-9) | DI | DI | DI | I | D | DI | I | DI | DI | DI | D | I | DI |
| Siyana (YT-1) | DI | DI | DI | DI | D | DI | DI | DI | D | D | DI | DI | D |
| Yanfu 10 (YT-100) | I | D | D | DI | DI | DI | DI | DI | D | D | DI | DI | DI |
| Chadel (YT-102) | I | DI | DI | DI | D | I | DI | DI | DI | DI | DI | DI | I |
| Charden (YT-103) | DI | DI | D | DI | DI | DI | DI | DI | DI | DI | D | I | DI |
| Tuskan (YT-104) | DI | D | D | DI | DI | DI | D | DI | D | DI | DI | I | DI |
| Prima × Sekaiichii (YT-105) | DI | D | DI | DI | DI | D | DI | D | DI | D | DI | D | D |
| Toppax_apple (YT-11) | D | DI | DI | D | D | I | I | DI | I | D | DI | DI | D |
| Xinjiang Hongrou Crab (YT-12) | D | D | D | D | D | DI | I | DI | DI | D | DI | D | D |

-continued

Construction results of InDel marker genotype database of *Malus* germplasm resources

| | | | | | | | | | | | | | |
|---|---|---|---|---|---|---|---|---|---|---|---|---|---|
| Melfree (YT-13) | DI | DI | DI | DI | DI | DI | DI | DI | DI | D | DI | D | DI |
| Yanfu 3 (YT-14) | D | DI | DI | D | DI | D | D | D | DI | DI | DI | D | D |
| Gold milecnirum (YT-15) | DI | D | D | I | D | D | D | DI | DI | DI | DI | I | D |
| Ganhong (YT-16) | D | DI | DI | DI | D | DI | D | D | DI | DI | DI | DI | D |
| Cornoet (YT-17) | DI | D | D | D | D | DI | DI | D | D | D | DI | D | DI |
| Priw (YT-18) | DI | DI | DI | D | D | D | DI | D | D | I | D | D | |
| Aichi (YT-19) | D | DI | DI | DI | DI | DI | D | DI | D | DI | DI | I | DI |
| Auraria (YT-2) | DI | DI | DI | DI | D | DI | D | DI | DI | D | I | D | D |
| Meile (YT-20) | DI | D | D | DI | DI | DI | DI | DI | D | D | DI | DI | DI |
| Qiulimeng (YT-21) | D | D | D | D | D | DI | DI | DI | DI | I | D | D | |
| Aliusitan (YT-22) | DI | D | D | D | DI | DI | DI | DI | DI | DI | I | D | D |
| Geaooza (YT-23) | D | D | D | D | DI | DI | D | DI | DI | DI | I | D | DI |
| Golden Spur (YT-24) | DI | DI | DI | I | DI | DI | I | DI | DI | DI | DI | I | DI |
| Starking (YT-25) | D | D | D | DI | D | D | DI | DI | D | DI | DI | I | D |
| Indo (YT-26) | D | DI | D | DI | I | D | DI | DI | D | D | DI | DI | I |
| Teser (YT-27) | D | D | D | D | D | DI | DI | DI | DI | DI | DI | I | DI |
| Xianhong (YT-28) | D | DI | DI | DI | DI | DI | DI | DI | DI | DI | DI | DI | D |
| Gala × Mato 8 (YT-29) | D | DI | DI | DI | D | DI | DI | D | DI | D | DI | DI | DI |
| Very Early Fuji (YT-3) | DI | D | D | DI | DI | DI | DI | D | D | DI | DI | DI | DI |
| Qiuhuapi (YT-30) | D | D | D | DI | D | DI | DI | DI | DI | DI | DI | D | I |
| Piga 70 (YT-31) | DI | D | DI | I | DI | DI | I | D | DI | DI | D | I | D |
| Yanzhen 1 (YT-32) | D | DI | DI | DI | D | D | D | DI | D | DI | DI | DI | D |
| Matail (YT-34) | DI | DI | DI | I | D | DI | I | DI | DI | DI | D | I | DI |
| Jonathan-csan (YT-35) | D | DI | DI | D | DI | D | D | D | DI | DI | DI | D | D |
| Huashuai (YT-36) | D | D | D | DI | D | D | D | DI | D | DI | I | DI | DI |
| Wengao 1 (YT-38) | DI | D | DI | DI | DI | DI | DI | D | D | DI | DI | D | |
| Wengao 2 (YT-39) | DI | D | D | DI | DI | DI | DI | DI | D | D | DI | DI | DI |
| Elegia (YT-4) | D | DI | DI | DI | D | D | DI | DI | DI | DI | DI | DI | D |
| Wengao 3 (YT-40) | DI | D | D | DI | DI | DI | DI | DI | D | D | DI | DI | D |
| Hong Anka (YT-41) | D | DI | DI | DI | DI | DI | DI | DI | D | DI | I | D | D |
| Yanfu 2 (YT-42) | DI | D | D | DI | DI | DI | DI | DI | D | D | DI | DI | I |
| Belgolden (YT-43) | DI | DI | DI | I | DI | DI | I | DI | DI | DI | DI | I | D |
| Rubinola (YT-44) | D | D | DI | I | D | D | D | D | DI | DI | DI | I | I |
| Wangqiuhong (YT-45) | D | DI | DI | D | DI | D | DI | D | DI | DI | DI | I | D |
| Pulanhong (YT-46) | DI | D | D | D | DI | D | D | D | D | D | DI | DI | DI |
| Bosh (YT-47) | DI | D | D | DI | DI | D | DI | D | D | I | D | DI | |
| Chengji 1 (YT-48) | DI | D | D | DI | DI | DI | DI | D | D | DI | DI | DI | |
| Hongli (YT-49) | D | D | DI | DI | DI | D | D | DI | D | D | D | DI | D |

-continued

| Construction results of InDel marker genotype database of *Malus* germplasm resources | | | | | | | | | | | | | |
|---|---|---|---|---|---|---|---|---|---|---|---|---|---|
| Guoqinghong (YT-5) | DI | DI | DI | DI | DI | DI | DI | DI | DI | DI | DI | DI | DI |
| Reandra (YT-50) | D | DI | DI | DI | D | I | DI | DI | DI | DI | D | I | DI |
| Revbihola (YT-51) | DI | DI | D | DI | DI | I | DI | DI | DI | D | DI | DI | DI |
| Melrose (YT-52) | D | DI | D | D | D | D | DI | DI | DI | DI | D | DI |
| Rewena (YT-53) | DI | D | D | D | D | DI | D | D | D | DI | I | D | DI |
| Mrxl(robusta × Liberte) (YT-54) | D | D | D | DI | D | D | DI | DI | D | DI | DI | I | DI |
| Mollies_Del_open (YT-55) | DI | DI | DI | I | D | DI | DI | DI | I | D | DI | DI | D |
| Renora (YT-56) | DI | DI | D | DI | D | I | DI | DI | DI | D | DI | DI | DI |
| Rosmadzin (YT-57) | DI | D | D | DI | DI | D | DI | DI | D | D | I | D | DI |
| Remo (YT-58) | DI | DI | D | DI | DI | DI | DI | D | I | DI | DI | D | DI |
| Pilot (YT-59) | DI | DI | D | DI | DI | D | D | DI | D | D | I | DI | DI |
| Yangbai Crab (YT-6) | D | D | DI | D | DI | DI | I | DI | D | DI | D | D | DI |
| Free Red Star (YT-60) | D | DI | D | D | I | D | D | D | D | D | D | I | I |
| Idared (YT-61) | D | D | D | D | D | DI | D | D | DI | DI | DI | D | DI |
| Mingyue (YT-62) | DI | DI | D | I | DI | D | DI | D | DI | D | DI | I | DI |
| Piga 101 (YT-63) | DI | D | D | DI | DI | DI | DI | DI | DI | D | D | I | DI |
| Yanfu 5 (YT-64) | DI | D | D | DI | DI | DI | DI | D | D | DI | DI | DI |
| Early Jonagold (YT-65) | DI | DI | D | DI | DI | DI | DI | DI | DI | DI | DI | DI | DI |
| Wengao 2 mutant (YT-66) | DI | D | D | DI | DI | DI | DI | D | D | DI | DI | DI |
| Fenhong Gala 44 (YT-67) | DI | DI | D | DI | DI | DI | DI | DI | DI | D | I | DI |
| Yiyuanhong (YT-68) | DI | D | D | DI | DI | DI | DI | D | D | DI | DI | DI |
| Yanfu 4 (YT-69) | DI | D | D | DI | DI | DI | D | D | D | DI | DI | DI |
| White Pearmain (YT-70) | D | D | D | DI | DI | D | I | DI | D | D | DI | I | DI |
| Jonathan-early (YT-73) | D | DI | D | D | DI | D | D | D | DI | DI | DI | D | DI |
| Jonathan-midle (YT-74) | D | DI | D | D | DI | D | D | D | DI | DI | DI | D | DI |
| Gornan (YT-75) | D | D | D | D | D | D | D | D | DI | DI | I | DI | DI |
| Regilndel (YT-76) | DI | DI | DI | DI | DI | I | DI | DI | DI | D | DI | DI | D |
| Golden Bell (YT-77) | DI | DI | D | DI | I | D | DI | DI | DI | DI | I | DI | DI |
| Arkcharm (YT-78) | D | DI | D | D | D | DI | DI | DI | DI | D | I | DI | D |
| Redchif (YT-79) | DI | D | DI | DI | DI | DI | D | DI | D | DI | I | D | D |
| Mouping Guanghua Fuji (YT-8) | DI | D | D | DI | DI | DI | DI | D | D | DI | DI | DI |
| Freedom (YT-80) | DI | DI | D | DI | DI | D | D | DI | D | D | I | DI | DI |
| Martinike (YT-81) | DI | DI | D | D | DI | D | D | DI | D | D | I | DI | DI |
| Sweetle (YT-82) | D | DI | DI | DI | D | D | DI | DI | D | DI | DI | I | D |
| Aleksanader (YT-83) | D | DI | D | D | I | DI | D | D | D | DI | I | D | DI |
| Yan 6 Fenhong 143 (YT-84) | DI | DI | D | I | DI | D | I | DI | I | DI | D | I | DI |
| Ruitina (YT-85) | D | D | D | DI | I | I | DI | DI | D | D | I | DI | DI |
| Wengao 1 mutant (YT-86) | DI | D | D | DI | DI | DI | DI | D | D | DI | DI | DI |
| Wengao 3 mutant (YT-87) | DI | D | D | DI | DI | DI | DI | DI | D | D | DI | DI | DI |

-continued

| Construction results of InDel marker genotype database of *Malus* germplasm resources |||||||||||||||
| --- | --- | --- | --- | --- | --- | --- | --- | --- | --- | --- | --- | --- | --- |
| Shajinyilamu (YT-88) | D | D | D | D | I | DI | I | DI | D | DI | DI | D | DI |
| Qiuhong (YT-89) | D | D | DI | D | D | D | D | DI | D | DI | DI | I | D |
| Changyanghong (YT-9) | DI | D | D | DI | DI | DI | DI | DI | D | D | DI | DI | DI |
| Yanfu 8 (YT-90) | DI | D | D | DI | DI | DI | DI | DI | D | D | DI | DI | DI |
| Jinduhong Gala (YT-91) | DI | DI | D | I | D | DI | I | DI | DI | DI | D | I | DI |
| Nagafu 2 (YT-92) | DI | D | D | DI | DI | DI | DI | DI | D | D | DI | DI | DI |
| Honglu seedling 65 (YT-93) | DI | DI | D | I | I | DI | D | DI | DI | DI | DI | I | DI |
| Tsugaru (YT-94) | D | DI | D | DI | D | D | DI | D | DI | DI | I | DI | DI |
| Jinshuai mutant (YT-95) | DI | DI | D | I | DI | DI | I | DI | DI | DI | DI | DI | DI |
| Taishan Crab (YT-96) | D | DI | D | D | I | D | D | DI | D | DI | DI | D | DI |
| Luli (YT-98) | DI | I | DI | DI | D | DI | DI | D | DI | DI | DI | D | D |
| 10-182 (YX-10-182) | D | D | D | DI | D | D | DI | D | D | D | D | D | I |
| 01-001 (YX-01-001) | D | D | D | I | D | DI | I | D | D | D | DI | D | I |
| 01-121 (YX-01-121) | DI | D | D | DI | I | DI | I | D | D | D | DI | D | I |
| 02-009 (YX-02-009) | D | D | D | I | D | DI | I | DI | D | D | DI | DI | DI |
| 03-010 (YX-03-010) | D | D | D | DI | D | D | I | DI | D | D | D | D | DI |
| 03-111 (YX-03-111) | DI | D | D | I | I | D | I | D | D | D | DI | D | I |
| 04-033 (YX-04-033) | D | D | D | D | I | D | I | DI | D | D | D | DI | DI |
| 04-087 (YX-04-087) | D | D | D | D | I | DI | DI | D | D | D | DI | D | I |
| 06-056 (YX-06-056) | D | D | D | D | DI | DI | I | D | D | D | DI | DI | DI |
| 08-034 (YX-08-034) | DI | D | D | DI | D | DI | DI | DI | D | D | DI | DI | DI |
| 09-037 (YX-09-037) | DI | D | D | DI | I | D | D | D | D | D | D | D | I |
| 09-079 (YX-09-079) | D | D | D | DI | I | DI | I | D | D | D | D | D | DI |
| 10-010 (YX-10-010) | D | D | D | DI | DI | D | I | DI | D | D | D | DI | DI |
| 11-037 (YX-11-037) | D | D | D | I | D | D | D | DI | D | D | D | DI | DI |
| 11-206 (YX-11-206) | DI | D | D | DI | I | DI | DI | DI | D | D | D | DI | DI |
| 12-206 (YX-12-206) | D | D | D | D | D | D | I | DI | D | D | DI | DI | DI |
| 13-025 (YX-13-025) | DI | D | D | DI | DI | DI | I | D | D | D | DI | D | DI |
| 16-155 (YX-16-155) | D | D | D | DI | DI | D | D | DI | D | D | DI | D | I |
| 16-157 (YX-16-157) | DI | D | D | I | I | D | DI | DI | D | D | DI | D | I |
| 17-023 (YX-17-023) | D | D | D | I | DI | D | D | DI | D | D | D | DI | DI |
| 17-199 (YX-17-199) | DI | D | D | DI | I | D | D | D | D | D | DI | D | I |
| 21-005 (YX-21-005) | D | D | D | DI | D | D | I | DI | DI | D | D | DI | I |
| 21-018 (YX-21-018) | D | DI | DI | DI | D | DI | DI | DI | D | D | DI | DI | DI |
| 22-186 (YX-22-186) | D | DI | DI | I | DI | D | I | DI | D | DI | DI | DI | DI |
| 27-003 (YX-27-003) | DI | DI | DI | DI | D | DI | I | DI | DI | DI | DI | DI | I |
| 29-176 (YX-29-176) | DI | D | D | DI | I | D | I | DI | DI | DI | DI | DI | DI |
| 30-001 (YX-30-001) | D | D | D | I | D | DI | I | DI | D | DI | DI | DI | DI |

-continued

| Construction results of InDel marker genotype database of *Malus* germplasm resources | | | | | | | | | | | | | |
|---|---|---|---|---|---|---|---|---|---|---|---|---|---|
| 33-018 (YX-33-018) | D | D | D | I | I | DI | DI | D | D | D | DI | DI | DI |
| 33-101 (YX-33-101) | D | D | D | DI | I | D | D | DI | DI | D | DI | D | I |
| 33-151 (YX-33-151) | DI | D | D | I | I | DI | I | DI | DI | DI | DI | DI | I |
| 51-007 (YX-51-007) | D | I | DI | DI | I | D | DI | DI | D | D | DI | DI | D |
| 51-031 (YX-51-031) | DI | DI | DI | DI | D | DI | DI | DI | D | D | DI | DI | D |
| 51-077 (YX-51-077) | D | D | D | DI | DI | DI | DI | D | DI | DI | I | DI | D |
| 51-102 (YX-51-102) | DI | DI | DI | DI | D | D | DI | D | DI | DI | DI | DI | D |
| 51-139 (YX-51-139) | DI | D | D | DI | DI | DI | DI | DI | D | DI | D | DI | D |
| 51-165 (YX-51-165) | DI | DI | DI | DI | DI | DI | DI | DI | I | DI | DI | DI | D |
| 51-166 (YX-51-166) | DI | DI | D | DI | I | DI | DI | DI | DI | D | DI | DI | DI |
| 51-209 (YX-51-209) | D | I | DI | DI | I | D | D | D | D | DI | DI | DI | DI |
| 52-049 (YX-52-049) | D | DI | DI | DI | D | DI | DI | D | DI | DI | I | DI | D |
| 52-151 (YX-52-151) | D | DI | DI | DI | D | D | DI | DI | I | D | DI | DI | D |
| 52-160 (YX-52-160) | DI | DI | DI | DI | DI | DI | DI | D | DI | DI | I | DI | DI |
| 53-040 (YX-53-040) | DI | DI | DI | DI | DI | DI | DI | D | I | DI | DI | DI | DI |
| 53-205 (YX-53-205) | D | D | D | D | I | DI | DI | DI | D | DI | DI | D | D |
| 54-001 (YX-54-001) | DI | DI | DI | DI | DI | D | DI | D | DI | DI | DI | DI | D |
| 54-188 (YX-54-188) | D | DI | DI | DI | DI | DI | DI | DI | DI | D | DI | DI | D |
| 55-006 (YX-55-006) | D | DI | DI | DI | DI | DI | DI | D | DI | D | DI | DI | D |
| 55-023 (YX-55-023) | DI | DI | DI | DI | DI | DI | DI | DI | DI | DI | DI | DI | D |
| 55-042 (YX-55-042) | DI | DI | DI | DI | DI | D | DI | D | DI | DI | I | DI | D |
| 56-081 (YX-56-081) | D | I | DI | DI | DI | D | DI | DI | DI | DI | DI | DI | DI |
| 57-128 (YX-57-128) | DI | D | D | DI | DI | DI | DI | D | DI | D | DI | DI | D |
| 58-036 (YX-58-036) | D | DI | DI | DI | D | DI | DI | D | I | DI | DI | DI | DI |
| 58-089 (YX-58-089) | DI | DI | DI | DI | D | DI | DI | DI | DI | DI | DI | DI | DI |
| 58-144 (YX-58-144) | D | DI | DI | DI | DI | DI | DI | D | DI | D | DI | DI | D |
| 58-177 (YX-58-177) | D | I | DI | DI | DI | DI | DI | DI | DI | DI | I | DI | DI |
| 58-211 (YX-58-211) | DI | DI | DI | DI | DI | DI | DI | D | DI | DI | DI | DI | D |
| 59-086 (YX-59-086) | DI | DI | DI | DI | D | DI | DI | D | D | DI | DI | DI | D |
| 59-130 (YX-59-130) | D | DI | DI | DI | DI | DI | DI | D | I | DI | DI | DI | D |
| Jersey Mac (Z-1) | D | D | DI | DI | I | D | D | DI | DI | D | D | DI | D |
| Gale Gala (Z-10) | DI | DI | DI | I | D | DI | I | DI | DI | DI | D | I | DI |
| Li Gala (Z-11) | DI | DI | DI | I | D | DI | I | DI | DI | DI | D | I | DI |
| Yanga 1 (Z-12) | DI | DI | DI | I | D | DI | I | DI | DI | DI | D | I | DI |
| NAKT M9 clone (Z-13) | D | D | D | D | DI | DI | DI | NAKT | D | D | I | D | D |
| Royal Gala (Z-14) | DI | DI | DI | I | D | DI | I | DI | DI | DI | D | I | DI |
| Huajia (Z-15) | D | D | D | DI | DI | DI | DI | D | DI | DI | I | D | DI |
| Dorsett Golden (Z-16) | D | D | D | D | DI | DI | I | DI | D | DI | DI | DI | D |
| 99-2-58 (Z-17) | D | DI | DI | I | DI | DI | DI | DI | D | D | I | DI | DI |

-continued

| Construction results of InDel marker genotype database of *Malus* germplasm resources | | | | | | | | | | | | | |
|---|---|---|---|---|---|---|---|---|---|---|---|---|
| Galaxy (Z-18) | DI | DI | DI | I | D | DI | I | DI | DI | DI | D | I | DI |
| Royal New Gala (Z-19) | DI | DI | DI | I | D | DI | I | DI | DI | DI | D | I | DI |
| 99-1-29 (Z-22) | D | D | D | D | I | D | DI | DI | D | D | DI | D | DI |
| Seokwang (Z-23) | D | DI | DI | DI | DI | DI | DI | D | DI | DI | I | DI | DI |
| Fuhong Zaoga (Z-24) | DI | DI | DI | I | D | DI | I | DI | DI | DI | D | I | DI |
| Maiyan (Z-25) | D | D | D | DI | DI | DI | D | DI | D | DI | DI | D | D |
| Shandong 1 (Z-26) | DI | DI | DI | I | D | DI | I | DI | DI | DI | D | I | DI |
| Gala Queen (Z-27) | DI | DI | DI | I | D | DI | I | DI | DI | DI | D | I | DI |
| 99-2-39 (Z-29) | D | DI | DI | DI | DI | DI | DI | DI | DI | D | I | DI | DI |
| Sweetle (Z-3) | D | DI | DI | DI | D | D | DI | D | DI | DI | I | DI |
| Dalian Da Gala (Z-30) | DI | DI | DI | I | D | DI | I | DI | DI | DI | D | I | DI |
| Huaxing (Z-31) | DI | DI | DI | DI | D | DI | DI | D | D | DI | DI | D | D |
| Li Gala (Z-32) | DI | DI | DI | I | D | DI | I | DI | DI | DI | D | I | DI |
| Fuhong Zaoga (Z-33) | DI | DI | DI | DI | D | DI | DI | D | DI | DI | DI | DI | DI |
| Yanga (Z-34) | DI | DI | DI | DI | D | DI | DI | D | DI | DI | DI | DI | DI |
| Royal Gala (Z-35) | DI | DI | DI | I | D | DI | I | DI | DI | DI | D | I | DI |
| Shijiazhuang Gala (Z-37) | DI | DI | DI | I | D | DI | I | DI | DI | DI | D | I | DI |
| Taihong Gala (Z-38) | DI | DI | DI | I | D | DI | I | DI | DI | DI | D | I | DI |
| Anna (Z-39) | D | D | D | D | DI | DI | DI | DI | D | DI | DI | DI | D |
| Hong Zhenzhu (Z-4) | D | I | DI | DI | D | DI | DI | DI | D | DI | DI | DI | DI |
| Qiuhong Gala (Z-40) | D | DI | DI | DI | D | D | DI | DI | DI | DI | I | DI | DI |
| Shandong 2 (Z-41) | DI | DI | DI | I | D | DI | I | DI | DI | DI | D | I | DI |
| Shandong 6 (Z-42) | DI | DI | DI | I | D | DI | I | DI | DI | DI | D | I | DI |
| Chenyang (Z-43) | DI | DI | DI | DI | D | I | D | D | I | DI | DI | DI | DI |
| Dongqie Gala (Z-44) | DI | DI | DI | DI | DI | DI | DI | D | I | DI | DI | D | D |
| Royal Gala (Z-45) | DI | DI | DI | I | D | DI | I | DI | DI | DI | D | I | DI |
| Taishan Gala (Z-47) | I | DI | DI | I | D | DI | I | DI | DI | DI | D | I | DI |
| Shandong 7 (Z-48) | DI | DI | DI | I | D | DI | I | DI | DI | DI | D | I | DI |
| Regal gala (Z-49) | DI | DI | DI | I | D | DI | I | DI | DI | DI | D | I | DI |
| NAKB clone (Z-5) | D | D | D | D | DI | DI | DI | DI | D | D | I | D | D |
| Royal gala (Z-50) | DI | DI | DI | I | D | DI | I | DI | DI | DI | D | I | DI |
| Znoga (Z-51) | DI | DI | DI | D | DI | DI | DI | DI | DI | DI | I | D | D |
| Shandong 5 (Z-52) | DI | DI | DI | I | D | DI | I | DI | DI | DI | D | I | DI |
| Rockit (Z-53) | I | D | D | DI | D | D | I | DI | I | DI | D | I | DI |
| Shandong 3 (Z-54) | DI | DI | DI | I | D | DI | I | DI | DI | DI | D | I | DI |
| Mondel Gala (Z-55) | DI | DI | DI | I | D | DI | I | DI | DI | DI | D | I | DI |
| Alvinagala (Z-56) | DI | DI | DI | I | D | DI | I | DI | DI | DI | D | I | DI |
| M9 pajam2 (Z-6) | D | D | D | D | DI | DI | DI | DI | D | D | I | D | D |

| Construction results of InDel marker genotype database of *Malus* germplasm resources | | | | | | | | | | | | | |
|---|---|---|---|---|---|---|---|---|---|---|---|---|---|
| Jinshiji (Z-7) | DI | DI | DI | DI | D | DI | I | DI | DI | DI | D | I | DI |
| Huarui (Z-8) | D | DI | DI | D | D | D | D | DI | DI | DI | DI | D | DI |
| Hongcuibao (Z-9) | DI | DI | DI | DI | D | DI | DI | DI | DI | DI | DI | DI | DI |

| Accession name (Accession ID) | C04022 | C04023 | C04024 | C05028 | C05029 | C05030 | C05031 | C06037 | C06038 | C06039 | C06040 | C06041 | C07043 |
|---|---|---|---|---|---|---|---|---|---|---|---|---|---|
| Black Ben Davis (10--1) | D | D | D | I | DI | DI | DI | D | D | D | DI | I | D |
| Lysgolden (10--10) | D | D | D | D | D | DI | D | DI | D | D | DI | I | D |
| Dongchengguan 13 (10--11) | D | D | D | D | D | DI | D | DI | D | D | DI | I | D |
| Nagafu 1 (10--12) | D | D | D | D | D | DI | D | DI | DI | D | DI | I | D |
| Shengli Hongguan (10--14) | D | D | D | D | D | D | D | D | I | D | DI | DI | D |
| Shizishan 1 (10--15) | D | D | D | D | D | D | D | D | I | D | DI | DI | D |
| Baoman (10--2) | DI | D | D | DI | D | D | DI | D | I | DI | DI | DI | D |
| Melba (10--20) | D | D | D | I | D | D | D | D | DI | DI | DI | DI | D |
| Kuliesa (10--21) | D | DI | D | DI | DI | DI | DI | DI | DI | D | DI | DI | D |
| De 8 (10--22) | D | D | D | I | DI | DI | D | DI | I | D | D | I | I |
| Bo 5 (10--23) | D | DI | D | D | D | D | DI | D | I | DI | DI | DI | D |
| Iran Pippin (10--4) | DI | D | DI | DI | DI | I | DI | D | DI | DI | DI | I | DI |
| Sakatakei Tsugaru (10--5) | D | D | D | DI | DI | DI | D | DI | D | DI | DI | DI | DI |
| Khrushchev (10--6) | D | DI | D | DI | DI | D | D | D | DI | D | DI | I | DI |
| Batul (10--7) | D | D | DI | I | D | D | D | DI | D | DI | DI | DI | D |
| Prime Gold (10--9) | D | D | DI | I | D | D | D | DI | DI | D | DI | DI | D |
| Jie 1 (11--0) | D | DI | D | DI | D | DI | D | D | DI | D | DI | DI | D |
| Guldborg (1--11) | D | D | D | D | D | DI | D | DI | D | D | DI | I | D |
| Shajin Yilamu (11--10) | D | D | DI | D | D | D | D | D | I | D | DI | DI | DI |
| Soviet (11--11) | DI | D | DI | DI | D | D | D | D | DI | DI | D | DI | D |
| Lobo (11--13) | DI | D | D | D | D | D | DI | D | D | I | DI | I | D |
| Allington Pippin (11--14) | D | DI | D | I | DI | D | D | D | DI | D | DI | DI | D |
| Malinova (11--15) | D | DI | D | I | DI | D | D | D | I | DI | DI | DI | D |
| Sweet McIntosh (11--16) | D | DI | D | I | D | D | D | D | I | DI | DI | DI | D |
| McIntosh (11--18) | DI | I | DI | DI | DI | D | DI | DI | D | D | DI | DI | D |
| Spartan (11--2) | D | DI | D | DI | DI | DI | D | D | D | DI | DI | I | D |
| Fushuai (1--12) | DI | D | DI | DI | DI | D | D | D | DI | DI | DI | DI | D |
| Summer Pearmain (11--20) | D | D | D | DI | DI | DI | DI | D | D | D | DI | I | D |
| Helm (11--21) | D | D | D | DI | DI | DI | D | D | D | D | DI | I | DI |
| Domenesti (11--3) | DI | DI | D | I | D | DI | DI | D | I | D | DI | DI | D |
| Early Harvest (1--13) | DI | D | DI | DI | DI | D | DI | D | DI | DI | DI | DI | D |
| Silver Spur Red Delicious (11--4) | D | DI | D | DI | DI | DI | DI | DI | D | D | DI | I | D |
| Dongxiangjiao (11--5) | D | D | D | DI | DI | DI | DI | DI | D | D | DI | DI | DI |

| Construction results of InDel marker genotype database of *Malus* germplasm resources | | | | | | | | | | | | | |
|---|---|---|---|---|---|---|---|---|---|---|---|---|---|
| Guoling (1--15) | D | D | DI | DI | DI | I | D | D | D | D | DI | I | D |
| Skyline Spureme (11--8) | D | DI | D | DI | DI | DI | DI | DI | D | D | DI | I | D |
| Chantecler (11--9) | D | DI | DI | D | DI | D | D | DI | D | DI | DI | DI | D |
| Close (1--19) | DI | DI | DI | DI | DI | DI | D | DI | D | D | DI | I | DI |
| Aizaohui (1--2) | DI | DI | DI | D | DI | D | DI | D | DI | D | DI | DI | D |
| Wuyue (12--1) | DI | D | DI | D | D | D | D | DI | I | D | DI | DI | D |
| Bukowka (12--11) | DI | D | DI | DI | D | D | D | DI | DI | D | DI | DI | D |
| Jinyu (12--12) | D | DI | D | DI | D | DI | DI | D | DI | D | DI | DI | D |
| Calville Rouge (12--14) | D | D | D | DI | D | DI | I | DI | DI | D | DI | DI | D |
| Doyle (12--15) | D | D | DI | DI | D | DI | D | D | DI | D | DI | DI | D |
| Melrose (12--16) | D | I | D | DI | DI | DI | DI | DI | D | D | DI | DI | D |
| Menage (12--17) | D | D | D | DI | D | D | D | D | I | I | D | I | D |
| Bo 26 (12--18) | DI | D | DI | D | D | D | D | DI | D | DI | DI | I | D |
| Duoyilu (12--19) | DI | D | DI | DI | DI | DI | DI | DI | D | D | DI | DI | DI |
| De 6 (12--20) | DI | D | DI | DI | D | D | DI | DI | DI | DI | DI | I | D |
| Red June (12--21) | DI | D | I | I | DI | DI | DI | DI | D | D | DI | DI | DI |
| Helasang (12--23) | D | D | D | D | D | D | D | DI | D | DI | DI | D |
| Hesetiaowen (12--3) | D | D | D | D | D | DI | D | D | D | DI | DI | DI | D |
| James Grieve (1--23) | D | D | D | I | D | DI | DI | D | I | DI | DI | I | D |
| Bailuosi Malin (12--4) | DI | D | DI | DI | D | DI | D | D | DI | D | DI | DI | D |
| Jinnhong (12--5) | DI | D | DI | DI | D | I | D | D | D | D | DI | DI | D |
| Kay Sai William (12--6) | D | DI | D | DI | DI | DI | D | D | D | DI | DI | I | D |
| Xingjiang Pingguo (12--7) | D | D | DI | D | D | D | D | D | DI | D | DI | DI | DI |
| Jie 15 (12--8) | D | DI | D | DI | DI | DI | DI | DI | D | D | DI | I | D |
| Mianpingguo (12--9) | D | D | D | D | D | D | D | D | DI | D | DI | DI | D |
| Lowver (1--3) | D | D | D | D | D | D | D | DI | I | D | DI | DI | D |
| Benoni (13--1) | DI | DI | DI | DI | D | DI | D | D | D | DI | DI | I | D |
| Fa 5 (13--11) | D | DI | DI | DI | DI | D | DI | DI | DI | D | DI | DI | D |
| Babskino (13--12) | DI | D | D | D | D | D | D | DI | I | I | DI | DI | D |
| Kuluona (13--13) | D | DI | D | I | D | D | DI | D | DI | D | DI | I | D |
| Shidonghaoji (13--16) | D | D | D | D | D | D | D | D | I | D | DI | DI | D |
| Oberkika (13--17) | D | D | I | D | D | D | D | DI | D | DI | DI | D |
| Budayi (13--19) | D | D | D | D | D | DI | D | DI | D | D | DI | I | D |
| Red Canada (13--2) | D | DI | DI | DI | DI | D | DI | DI | DI | D | DI | DI | D |
| Laidi (13--20) | DI | D | D | DI | D | D | D | DI | I | D | DI | DI | D |
| N2 (13--22) | D | DI | D | I | DI | DI | DI | D | D | D | DI | I | D |
| Norsan (13--5) | D | DI | D | DI | DI | DI | DI | DI | D | D | DI | I | D |
| Hebei Kangbing Golden Delicious (13--6) | DI | I | DI | D | DI | DI | D | D | DI | DI | DI | DI | D |

| Construction results of InDel marker genotype database of *Malus* germplasm resources | | | | | | | | | | | | | |
|---|---|---|---|---|---|---|---|---|---|---|---|---|---|
| Zhanxuan 14 (13--9) | D | D | D | D | D | DI | D | DI | D | D | DI | I | D |
| Xiangguoguang (14--11) | D | DI | D | D | I | I | D | D | D | DI | DI | DI | D |
| Shengfang 1 (14--14) | D | DI | D | I | DI | DI | DI | D | D | D | DI | I | D |
| Yujing II (14--16) | D | DI | D | I | DI | DI | DI | D | D | D | DI | I | D |
| Cox's Orange Pippin (14--2) | D | D | D | DI | D | DI | D | D | DI | D | DI | DI | D |
| Nagafu 7 (14--20) | D | DI | D | I | DI | DI | DI | D | D | D | DI | I | D |
| Boiken (14--21) | D | DI | D | DI | D | D | D | D | DI | D | DI | DI | D |
| Qunfu 1 (14--23) | D | D | D | I | DI | DI | DI | D | D | D | DI | I | D |
| Calville Blanche (14--3) | D | DI | D | DI | D | D | D | D | DI | D | DI | DI | D |
| Freybreg (14--4) | DI | DI | DI | DI | DI | I | D | DI | D | I | DI | DI | DI |
| Husveti Rosmaring (14--5) | DI | D | D | I | DI | DI | DI | DI | DI | D | DI | DI | DI |
| Sweet Jonathan (14--7) | D | DI | D | DI | D | DI | DI | D | DI | D | DI | DI | D |
| King of Pippin (14--8) | D | D | D | DI | D | DI | D | D | DI | D | DI | DI | D |
| Duchess of Oldenburg (1--5) | I | D | DI | I | D | D | D | D | DI | DI | DI | DI | D |
| Kangbing Golden 5 (15--11) | DI | DI | DI | DI | I | DI | DI | DI | DI | DI | DI | DI | DI |
| Pingzhi Ralls Janet (15--15) | D | D | DI | DI | DI | DI | D | D | D | D | DI | I | D |
| Wase16 (15--16) | D | D | D | I | DI | DI | DI | DI | DI | DI | DI | DI | D |
| Kogetsu (15--17) | D | D | D | I | DI | DI | DI | D | DI | D | DI | DI | D |
| Jonared (15--18) | D | DI | D | DI | D | DI | DI | D | DI | D | DI | DI | D |
| Zhanxuan 4 (15--21) | D | D | D | D | D | DI | D | DI | D | D | DI | I | D |
| Strawberry (15--23) | D | D | DI | I | D | D | DI | D | DI | D | D | DI | D |
| StarkSpur Ultra Red Delicious (15--3) | D | DI | D | DI | DI | DI | DI | DI | D | D | DI | I | D |
| Sharp Red Delicious (15--4) | D | DI | D | DI | DI | DI | DI | DI | D | D | DI | I | D |
| Mensi (15--5) | D | D | D | DI | DI | D | DI | D | DI | D | DI | I | D |
| Norand (15--6) | D | D | DI | D | D | DI | D | D | D | D | DI | I | D |
| Zhanxuan 18 (15--7) | D | DI | D | DI | DI | DI | DI | D | D | DI | DI | I | D |
| Xishan 1 (15--8) | D | DI | D | DI | DI | DI | DI | D | D | D | DI | I | D |
| Hongrou Pingguo (15--9) | D | D | D | DI | D | DI | D | DI | DI | D | DI | I | D |
| Gravenstein (1--6) | D | D | DI | D | D | DI | D | DI | DI | DI | DI | I | D |
| Xinhong (16--1) | DI | D | D | DI | I | DI | D | DI | DI | D | DI | DI | D |
| Zhanxuan 6 (16--10) | D | DI | DI | D | D | D | D | D | I | D | D | DI | D |
| Behene (16--11) | D | I | D | DI | DI | DI | D | D | D | D | DI | I | DI |
| Xindong (16--14) | DI | D | DI | D | D | D | DI | I | D | DI | DI | DI | D |
| Hardi Brite (16--16) | D | DI | D | DI | DI | DI | DI | DI | D | D | DI | I | D |
| Charden (16--17) | DI | DI | DI | DI | DI | DI | DI | DI | DI | DI | DI | DI | DI |
| Zhuoai 1 (16--2) | D | D | D | D | D | DI | D | DI | D | D | DI | I | D |
| Jinse Luosuoshan (16--22) | DI | D | D | D | D | D | D | D | I | D | DI | DI | D |

-continued

| Construction results of InDel marker genotype database of *Malus* germplasm resources | | | | | | | | | | | | | |
|---|---|---|---|---|---|---|---|---|---|---|---|---|
| Zhaiteng II (16--23) | D | DI | D | I | DI | DI | DI | D | D | D | DI | I | D |
| Zhanxuan 16 (16--6) | D | D | D | D | D | DI | D | DI | D | D | DI | I | D |
| Fa 3 (16--8) | DI | DI | D | I | D | D | DI | D | I | D | DI | DI | D |
| Jerseymac (1--7) | D | D | D | I | D | D | I | D | DI | DI | DI | I | D |
| Mother (17--1) | D | D | D | DI | DI | D | D | DI | DI | D | DI | I | D |
| Northern Spy (17--10) | DI | DI | DI | I | DI | D | D | DI | D | I | DI | DI | DI |
| Rome Beauty (17--11) | D | D | DI | DI | D | DI | D | D | DI | D | DI | DI | D |
| Black Ben David (17--12) | DI | D | DI | DI | DI | D | I | D | DI | D | D | DI | D |
| Atlas (17--13) | D | D | D | I | D | DI | D | D | DI | DI | DI | I | D |
| Roxbury (17--14) | DI | D | DI | I | D | I | DI | D | DI | D | DI | I | D |
| Laxtons Superb (17--15) | DI | D | DI | I | I | DI | DI | DI | DI | D | DI | DI | D |
| Changhong (17--16) | D | D | D | DI | D | I | D | D | D | D | DI | DI | D |
| Cogswell Pearmain (17--17) | D | D | D | DI | I | DI | D | D | DI | D | DI | I | D |
| Twenty Ounce (17--18) | DI | DI | DI | DI | DI | DI | I | D | I | D | DI | DI | D |
| Lowtosh (17--19) | DI | D | D | DI | D | D | D | D | DI | D | DI | DI | D |
| Iwaki (17--21) | DI | D | DI | I | DI | DI | DI | D | DI | D | DI | I | D |
| Qin'guan (17--22) | DI | D | DI | DI | DI | D | DI | DI | D | D | DI | DI | DI |
| Bancroft (17--23) | D | D | D | D | DI | D | D | DI | D | D | D | I | D |
| Chenango Strawberry (17--4) | D | D | D | I | D | DI | D | D | DI | DI | DI | DI | D |
| Newfane (17--7) | DI | DI | DI | I | D | D | D | D | D | D | DI | I | D |
| Lord Lambourne (17--9) | DI | DI | DI | I | DI | D | D | DI | D | I | DI | DI | DI |
| Rizhiwan (18--0) | D | D | D | I | DI | I | D | D | D | DI | DI | DI | D |
| Campbell (18--11) | DI | D | DI | I | D | I | DI | D | DI | D | DI | I | D |
| Pigeon (18--13) | DI | D | D | I | D | DI | D | D | D | DI | DI | I | D |
| Summer Champion (18--14) | DI | D | DI | I | DI | DI | DI | D | I | DI | DI | DI | D |
| Nanpu 3 (18--15) | D | D | DI | DI | D | DI | DI | D | D | D | D | DI | D |
| Qiulimeng (18--16) | D | DI | DI | D | D | D | D | D | DI | DI | DI | DI | D |
| Rutosh (18--17) | D | D | D | DI | D | DI | DI | D | DI | DI | DI | DI | D |
| Xinlimei (18--19) | DI | D | D | DI | DI | D | DI | D | I | D | DI | DI | D |
| Huanong 1 (18--2) | D | DI | D | D | DI | D | D | D | DI | I | DI | DI | D |
| Lawfam (18--20) | D | D | D | D | D | DI | D | D | DI | DI | DI | DI | D |
| Akin's Red (18--21) | DI | DI | DI | I | D | D | DI | D | DI | D | DI | DI | D |
| Meltosh (18--22) | D | D | D | D | D | DI | D | DI | I | D | DI | DI | D |
| Hubbardston (18--23) | DI | DI | DI | DI | DI | I | D | DI | D | I | DI | DI | DI |
| Fenghuangluan Crab (18--3) | D | DI | D | D | DI | D | D | D | DI | I | DI | DI | D |
| Jie 9 (18--4) | D | DI | D | DI | D | D | D | D | DI | D | DI | DI | D |
| Bramley's Seedling (18--5) | DI | DI | DI | DI | D | DI | DI | D | DI | D | DI | I | D |
| Shuangyang 1 (18--7) | DI | DI | DI | DI | I | D | DI | D | I | DI | DI | DI | DI |
| Shengli (18--8) | DI | DI | DI | DI | DI | I | D | DI | D | I | DI | DI | DI |

-continued

| Construction results of InDel marker genotype database of *Malus* germplasm resources | | | | | | | | | | | | | |
|---|---|---|---|---|---|---|---|---|---|---|---|---|---|
| Qingguan (18--9) | DI | D | D | I | DI | DI | D | DI | DI | D | DI | DI | D |
| Weeping Ralls (19--0) | D | D | DI | DI | DI | DI | D | D | D | D | DI | I | D |
| Giant Jeniton (19--1) | D | D | D | DI | D | D | D | D | I | I | D | I | D |
| Baldwin (19--10) | D | DI | D | DI | DI | D | DI | DI | DI | D | DI | DI | DI |
| Lele Fuji (19--11) | D | DI | D | I | DI | DI | DI | D | D | D | DI | I | D |
| Shuahong (19--12) | D | D | D | I | D | DI | DI | D | DI | I | DI | I | D |
| Red Fuji TAO (19--14) | D | DI | D | I | DI | DI | DI | D | D | D | DI | I | D |
| Jizaohong (19--17) | DI | DI | DI | DI | DI | I | D | DI | D | I | DI | DI | DI |
| Karas Tor (19--19) | D | D | D | DI | I | D | DI | D | DI | D | DI | DI | D |
| Ralls Janet (19--2) | D | D | DI | DI | DI | DI | D | D | D | D | DI | I | D |
| Stonetosh (19--22) | D | D | D | DI | D | D | D | D | DI | DI | DI | DI | D |
| White Pearmain (19--23) | D | DI | D | I | D | DI | DI | D | D | D | DI | DI | D |
| Xiushui Guoguang (19--3) | D | DI | D | I | DI | I | D | DI | D | D | DI | I | D |
| Chimeric Ralls Janet (19--4) | D | D | DI | DI | DI | DI | D | D | D | D | DI | I | D |
| Mutsu (19--7) | DI | DI | DI | DI | DI | DI | DI | DI | DI | DI | DI | DI | DI |
| Ben David (19--8) | DI | D | DI | DI | DI | D | I | D | DI | D | D | DI | D |
| Saint Lawrence (19--9) | DI | D | D | I | D | DI | DI | D | D | DI | DI | DI | D |
| Newtosh (20--0) | D | D | D | I | D | D | D | D | D | D | DI | DI | D |
| Geliekekukui (20--1) | D | D | D | I | D | D | D | I | D | DI | DI | DI | D |
| Sweet Jonathan (20--10) | D | DI | D | DI | D | DI | DI | D | DI | D | DI | DI | D |
| Apple of Commerce (20--11) | I | D | DI | DI | DI | D | I | D | I | D | D | DI | D |
| 600 g Andong (20--12) | D | I | D | DI | DI | DI | D | D | D | D | DI | I | DI |
| Winter Banana (20--14) | D | DI | D | DI | I | DI | D | DI | D | DI | DI | I | D |
| Rainier (20--15) | D | D | D | D | DI | D | D | DI | DI | D | DI | I | D |
| Winesap (20--16) | DI | D | DI | D | D | DI | D | D | DI | DI | DI | DI | D |
| Drumbo (20--17) | D | D | DI | D | D | DI | D | DI | I | D | DI | DI | D |
| Blengstid Gaurd (20--2) | DI | DI | D | I | D | D | DI | D | I | D | DI | DI | D |
| Jierjisi (20--21) | D | D | D | DI | D | D | D | D | I | D | DI | DI | D |
| Radiant (20--23) | D | D | D | I | D | D | D | D | D | D | DI | DI | D |
| King David (20--5) | D | I | D | D | DI | DI | I | D | D | D | DI | DI | D |
| Clapp's Seedling (20--6) | DI | D | D | I | DI | DI | D | DI | DI | D | DI | DI | D |
| Ingram (20--7) | D | DI | D | DI | I | D | D | D | D | D | D | DI | D |
| Qiujin (20--8) | D | D | D | D | D | DI | D | DI | D | D | DI | I | D |
| Sujsleppskoe (2--1) | DI | D | D | DI | D | D | D | D | DI | DI | DI | I | D |
| Qian 1 Ace (21--0) | D | DI | D | I | DI | DI | D | D | D | D | DI | I | D |
| Toko (2--10) | D | DI | D | I | DI | I | DI | D | D | DI | DI | DI | DI |
| Antalue (21--1) | D | D | D | DI | DI | D | D | D | D | D | DI | DI | DI |
| Boskoopske Cervene (2--11) | DI | DI | D | I | D | D | DI | D | I | D | DI | DI | D |

-continued

| Construction results of InDel marker genotype database of *Malus* germplasm resources | | | | | | | | | | | | | |
|---|---|---|---|---|---|---|---|---|---|---|---|---|---|
| Heoersitai (21--10) | D | D | D | DI | DI | DI | D | DI | D | D | D | DI | D |
| Lanfengwang (21--11) | DI | D | DI | I | DI | D | DI | D | DI | DI | DI | I | D |
| Aohong (21--14) | DI | I | DI | DI | DI | D | DI | D | DI | DI | DI | DI | D |
| Weiqinni (21--15) | D | D | D | I | D | DI | D | D | D | DI | D | DI | DI |
| Smoothee (21--17) | DI | DI | DI | DI | I | DI | D | DI | DI | DI | DI | DI | DI |
| Hongzhiwu (21--18) | D | D | D | DI | D | DI | D | D | DI | DI | DI | DI | DI |
| Jieba (21--2) | D | D | D | DI | D | D | DI | D | DI | D | DI | DI | D |
| Kizashi (21--20) | I | I | I | DI | D | DI | D | D | D | D | DI | I | D |
| Aifeng (21--21) | I | I | I | DI | D | DI | D | D | D | D | DI | I | D |
| Xingping (21--4) | D | D | DI | DI | DI | DI | D | D | D | D | DI | I | D |
| Esopus Spitzenburg (2--14) | D | D | D | D | D | D | D | DI | D | DI | DI | D |
| Lvguang (21--6) | D | D | DI | D | D | D | D | DI | D | DI | DI | D |
| Nvyoujidui (2--16) | D | DI | D | D | DI | D | D | D | DI | DI | DI | I | D |
| Bell Poos (21--7) | D | D | DI | DI | D | DI | D | D | D | D | DI | DI | D |
| Tian Andongnuo (2--17) | D | D | D | D | D | D | D | D | I | DI | DI | DI | D |
| Pacific Rose (21--8) | DI | I | DI | DI | DI | D | DI | DI | DI | DI | DI | DI | D |
| 500 g (21--9) | D | D | DI | D | D | D | D | D | D | D | DI | DI | D |
| Nvyoujidui 2 (2--19) | DI | D | D | DI | D | D | D | D | DI | DI | DI | I | D |
| Tian Andongnuo 2 (2--2) | DI | D | DI | D | DI | D | DI | D | D | D | DI | I | D |
| Spur Mutsu (22--1) | DI | DI | DI | DI | DI | DI | DI | DI | DI | DI | DI | DI | DI |
| Red June Sweet (2--21) | DI | D | DI | D | D | D | D | DI | DI | D | DI | DI | D |
| Chu Tsugaru (22--11) | D | D | D | DI | DI | D | DI | D | DI | DI | DI | DI | DI |
| Kermemen (22--13) | D | DI | D | DI | D | DI | D | D | DI | DI | DI | DI | D |
| Bedan (22--14) | D | DI | D | I | DI | D | D | D | DI | D | D | DI | D |
| Dabinette (22--15) | D | DI | D | I | DI | DI | D | D | D | D | DI | I | D |
| Zaocuilv (22--16) | DI | DI | DI | DI | DI | I | D | DI | D | I | DI | DI | DI |
| Chanteline (22--17) | D | DI | D | I | DI | D | DI | D | I | D | DI | DI | D |
| Red Baron (22--2) | D | D | D | DI | D | DI | D | D | DI | DI | DI | I | D |
| Hongjin Gala (22--4) | D | D | D | I | D | D | D | DI | D | DI | DI | DI | DI |
| Generos (22--7) | D | DI | D | I | D | DI | DI | D | DI | D | DI | DI | D |
| Alberta (2--3) | DI | D | DI | D | D | D | D | I | I | I | DI | DI | D |
| Hirosaki Fuji (23--1) | D | D | D | DI | DI | DI | D | DI | D | I | DI | DI | DI |
| Miya Fuji (23--10) | D | DI | D | I | DI | DI | DI | D | D | D | DI | I | D |
| Yanshanhong (23--13) | D | D | D | D | DI | DI | D | D | D | DI | I | D |
| Dailv (23--14) | D | D | D | DI | D | D | D | D | D | D | DI | DI | D |
| Frequin Rouge (23--15) | DI | D | DI | D | DI | D | D | D | DI | DI | DI | DI | D |
| Jinguang (23--16) | D | I | D | DI | DI | DI | D | D | D | D | DI | I | DI |
| Avrolles (23--17) | DI | D | D | I | D | D | D | DI | D | DI | DI | DI | D |
| Marie Menard (23--18) | I | D | DI | I | DI | DI | DI | D | DI | DI | DI | DI | DI |

| Construction results of InDel marker genotype database of *Malus* germplasm resources | | | | | | | | | | | | | |
|---|---|---|---|---|---|---|---|---|---|---|---|---|---|
| Golden B (23--2) | DI | DI | DI | DI | I | DI | DI | DI | DI | DI | DI | DI | DI |
| Jurella (23--20) | DI | D | D | DI | D | D | DI | D | DI | D | DI | DI | DI |
| GS58 (23--21) | D | DI | DI | DI | I | DI | DI | DI | DI | DI | DI | DI | D |
| Lianji (23--22) | D | D | D | D | D | D | D | D | DI | DI | DI | DI | DI |
| Aomori Spur Fuji (23--4) | D | DI | D | I | DI | DI | DI | D | D | D | DI | I | D |
| Akifu 39 (23--9) | D | DI | D | I | DI | DI | DI | D | DI | DI | I | I | D |
| Shalatuoni (2--4) | D | DI | D | D | DI | I | I | D | D | D | DI | DI | D |
| Guoqing (24--13) | DI | D | D | I | DI | D | D | DI | D | D | DI | I | D |
| Ningguang (24--15) | D | D | D | DI | I | DI | DI | D | DI | D | DI | DI | D |
| Hongqiaowang (24--17) | DI | DI | DI | DI | DI | DI | DI | DI | DI | DI | DI | DI | DI |
| Wemhong (24--18) | D | D | D | DI | D | I | DI | D | DI | D | DI | I | DI |
| Wijcik McIntosh (24--19) | D | D | D | DI | D | D | D | D | D | DI | D | DI | D |
| Xinguoguang (24--21) | D | D | DI | DI | DI | DI | D | D | D | D | DI | I | D |
| Fengcun Fuji (24--22) | D | DI | D | I | DI | DI | DI | D | D | D | DI | I | D |
| America 8 (24--23) | DI | D | D | I | DI | D | D | D | DI | D | DI | I | D |
| GS48 (24--3) | D | D | DI | DI | D | D | D | D | DI | DI | DI | DI | D |
| Granny Smith (24--4) | D | DI | D | DI | DI | D | D | D | DI | D | D | DI | D |
| Stark Spur (24--7) | DI | DI | DI | DI | I | DI | DI | DI | DI | DI | DI | DI | DI |
| Huangguniang (2--5) | DI | D | DI | I | DI | DI | D | D | DI | D | DI | I | DI |
| Judaine (25--11) | D | D | D | I | I | D | DI | D | D | D | DI | DI | D |
| Judeline (25--12) | DI | DI | DI | I | I | D | D | DI | DI | DI | DI | DI | DI |
| HoneyCrisp (25--14) | DI | D | D | DI | I | I | D | D | DI | D | DI | I | D |
| Korin (25--15) | D | DI | D | I | DI | DI | DI | D | D | D | DI | I | D |
| Hongao (25--18) | DI | D | DI | DI | DI | D | DI | D | DI | DI | DI | DI | DI |
| Ningguang (25--19) | DI | D | DI | DI | DI | D | DI | D | DI | DI | DI | DI | DI |
| Red Delicious (25--2) | D | DI | D | DI | DI | DI | DI | DI | D | D | DI | I | D |
| Youlixiang (25--21) | D | D | D | DI | DI | I | DI | D | D | DI | DI | DI | DI |
| Fuqiu (25--3) | D | D | D | I | DI | D | DI | D | D | D | DI | I | D |
| Chunxiang (25--4) | D | D | D | I | D | DI | DI | D | DI | I | DI | I | D |
| Fu Hong (25--5) | D | DI | D | I | DI | D | D | D | D | D | DI | I | D |
| Qingxiang (25--6) | D | DI | DI | DI | DI | DI | DI | DI | DI | DI | DI | DI | DI |
| Zhongxing (25--7) | D | DI | D | DI | D | DI | DI | DI | D | DI | DI | DI | DI |
| Weixishengming (25--8) | D | D | D | I | D | DI | DI | D | D | I | DI | DI | DI |
| Shichinohe 1 (25--9) | D | DI | D | I | DI | DI | DI | D | D | D | DI | I | D |
| Arkansas Black (2--6) | D | DI | D | DI | DI | DI | DI | D | D | D | D | I | DI |
| Douce Coetligne (26--10) | D | DI | DI | D | D | D | D | D | DI | D | D | DI | DI |
| Golden Spur (26--14) | DI | DI | DI | DI | I | DI | DI | DI | DI | DI | DI | DI | DI |
| Orei (26--15) | D | D | D | DI | D | DI | D | D | DI | DI | DI | DI | D |

Construction results of InDel marker genotype database of *Malus* germplasm resources

| | | | | | | | | | | | | | |
|---|---|---|---|---|---|---|---|---|---|---|---|---|---|
| Sekaiichii (26--18) | D | D | D | I | D | DI | D | DI | D | DI | DI | DI | DI |
| Kokyu (26--19) | D | DI | D | DI | DI | D | DI | DI | D | DI | DI | DI | DI |
| Douce Moen (26--2) | D | DI | D | I | DI | DI | DI | D | DI | D | DI | DI | D |
| Yanfu 1 (26--22) | D | DI | D | I | DI | DI | DI | D | D | D | DI | I | D |
| Ningfeng (26--23) | DI | D | D | I | DI | D | D | D | DI | D | DI | DI | D |
| Juliana (26--5) | D | D | D | D | DI | DI | D | D | D | D | DI | DI | D |
| Judestar (26--9) | D | D | D | DI | I | D | D | D | D | DI | DI | DI | D |
| Liaofu (2--7) | D | DI | D | I | DI | I | D | DI | D | DI | I | D |   |
| Sinano Red (27--10) | D | D | D | DI | D | DI | D | D | DI | D | DI | DI | D |
| Jinyang (27--12) | DI | D | DI | I | D | DI | D | D | D | D | DI | DI | D |
| Enqi (27--13) | DI | I | DI | D | DI | DI | D | D | DI | DI | DI | DI | D |
| Miki (27--14) | D | D | D | I | D | DI | DI | D | D | I | DI | DI | DI |
| Hongbaoshi (27--15) | D | D | D | DI | I | DI | I | DI | DI | D | DI | DI | D |
| Nagafu 2 (27--16) | D | DI | D | I | DI | DI | DI | D | D | D | DI | I | D |
| Longguan (27--4) | D | D | DI | DI | DI | DI | D | D | D | D | DI | I | D |
| K9 (27--5) | DI | D | DI | I | D | D | D | D | D | D | DI | DI | D |
| Zaohongda Gala (27--6) | DI | D | DI | I | D | DI | D | D | D | D | DI | DI | D |
| Lvshuai (27--7) | DI | D | D | DI | I | DI | D | DI | D | DI | DI | DI | DI |
| Hongxia (27--8) | I | I | I | DI | D | DI | D | D | D | D | DI | DI | D |
| Zaohongxia (27--9) | D | DI | D | I | DI | DI | DI | D | D | D | DI | I | D |
| Early Golden (2--8) | DI | D | D | D | I | DI | DI | D | DI | DI | DI | DI | DI |
| Indo (28--0) | D | DI | D | I | DI | DI | I | D | D | D | DI | DI | D |
| Jie 1 (28--11) | D | DI | D | D | D | DI | D | D | DI | D | DI | DI | D |
| Beauty of Bath (28--13) | D | D | D | DI | I | I | DI | D | DI | D | DI | I | DI |
| K10 (28--14) | D | DI | DI | I | DI | I | DI | DI | DI | D | DI | I | D |
| Beifang Xina (28--16) | DI | D | D | D | D | D | D | D | DI | DI | DI | DI | D |
| Yellow Fuji (28--18) | DI | I | DI | DI | DI | DI | D | DI | DI | DI | DI | DI | DI |
| Sinano Sweet (28--2) | D | D | D | I | DI | DI | DI | DI | DI | DI | DI | DI | D |
| Miguo (28--3) | D | D | D | D | D | D | D | D | D | D | DI | I | D |
| Ace (28--4) | D | DI | D | I | DI | DI | DI | D | D | D | DI | I | D |
| Tsugaru (28--5) | D | D | D | DI | DI | DI | D | D | DI | D | DI | DI | DI |
| K12 (28--8) | D | D | D | DI | D | DI | D | DI | DI | I | DI | DI | DI |
| Jieernianke (28--9) | DI | D | DI | I | DI | D | DI | D | DI | D | D | DI | D |
| Macoun (2--9) | D | D | D | DI | D | DI | D | D | DI | DI | DI | DI | D |
| Qingping (29--1) | DI | DI | D | I | DI | DI | DI | DI | DI | D | DI | DI | D |
| Polka (29--11) | D | DI | DI | DI | DI | D | D | DI | DI | DI | D | DI | DI |
| Longfeng (29--13) | DI | DI | DI | D | D | D | DI | I | D | DI | DI | DI |   |
| Very Early Fuji (29--14) | D | DI | D | I | DI | DI | D | D | D | DI | I | D |   |
| Longhong (29--15) | DI | DI | DI | D | I | D | DI | D | D | I | DI | DI | DI |

-continued

| Construction results of InDel marker genotype database of *Malus* germplasm resources |||||||||||||||
|---|---|---|---|---|---|---|---|---|---|---|---|---|---|
| Pinova (29--16) | D | DI | D | DI | DI | D | DI | D | DI | DI | DI | DI | DI |
| Fuga (29--17) | I | I | DI | D | DI | D | D | D | D | DI | DI | D |  |
| Qing n3 (29--2) | D | DI | D | DI | DI | DI | DI | DI | D | D | DI | I | D |
| Xinyuanshuai (29--3) | D | DI | D | DI | DI | DI | DI | DI | D | D | DI | I | D |
| Xinhua (29--5) | DI | D | D | D | I | DI | D | D | DI | D | DI | I | D |
| Nanpu 2 (29--6) | D | D | D | DI | D | D | DI | DI | D | D | DI | DI | D |
| Liuyu mutant (29--7) | D | D | DI | D | D | DI | D | D | DI | DI | DI | DI | D |
| Shandao Fuji (30--1) | D | DI | D | I | DI | DI | DI | D | D | D | DI | I | D |
| Sinano Gold (30--2) | DI | DI | DI | I | DI | DI | I | DI | D | D | DI | DI | D |
| Whitney (3--1) | D | D | DI | DI | D | DI | D | D | DI | D | DI | I | DI |
| Feixia (31--1) | D | D | D | DI | DI | D | D | D | D | D | DI | DI | DI |
| Willams Faborite (3--11) | D | D | D | DI | I | DI | D | D | DI | DI | DI | DI | D |
| Zhangye 2 (31--12) | DI | I | DI | I | DI | D | I | DI | D | DI | DI | DI | DI |
| Youfangcun Ralls Janet (31--14) | DI | D | DI | DI | DI | D | I | D | DI | D | D | DI | D |
| Yueyanghong (31--15) | DI | DI | D | DI | D | DI | D | D | D | D | DI | DI | D |
| Shuohong (31--17) | D | D | D | I | D | DI | D | DI | D | D | DI | I | D |
| Tianwang 1 (31--18) | D | DI | D | DI | DI | DI | DI | DI | D | D | DI | I | D |
| Huadan (31--2) | D | DI | D | D | DI | D | D | D | DI | D | D | I | D |
| Dalu 52 (3--12) | D | D | DI | I | D | D | D | D | DI | I | DI | DI | D |
| Cameo (31--3) | D | D | D | DI | DI | DI | DI | D | D | DI | DI | DI | D |
| Tianhuangkui (3--13) | D | D | D | D | DI | DI | D | D | DI | DI | DI | I | D |
| Qiulu (31--4) | D | D | D | DI | D | D | DI | D | DI | D | DI | DI | D |
| Liehuangjiatena (3--15) | D | DI | D | I | I | DI | D | DI | D | DI | DI | DI | DI |
| Lubi (3--16) | D | DI | D | DI | DI | I | DI | DI | D | D | DI | I | D |
| Huayu (31--8) | DI | DI | DI | DI | D | D | D | D | DI | D | DI | DI | D |
| Fameuse (3--18) | D | D | D | I | D | DI | DI | DI | DI | DI | DI | DI | D |
| Zhanhanxiang (3--19) | DI | I | DI | I | DI | DI | DI | DI | DI | I | DI | DI | D |
| Siberian White Spot (3--2) | D | D | D | D | D | D | D | DI | DI | I | DI | I | D |
| Zhengding 2 (3--21) | DI | D | DI | I | D | DI | D | D | DI | D | D | DI | D |
| Kuihua (3--22) | D | DI | DI | I | D | DI | I | DI | DI | D | DI | DI | D |
| Early Worcester (3--23) | D | D | DI | I | D | D | D | D | D | DI | DI | DI | D |
| Lowland Raspderry (3--3) | DI | DI | DI | DI | DI | D | D | D | DI | DI | DI | DI | D |
| Miqiulin Jinian (3--4) | D | D | D | D | D | D | D | DI | I | D | D | DI | D |
| Huangtianguo (3--5) | D | D | D | DI | D | D | D | D | DI | D | DI | DI | D |
| Huadao (3--7) | D | D | DI | D | DI | D | D | D | D | D | DI | DI | D |
| Red Astrachan (3--9) | I | D | DI | I | D | D | D | D | DI | DI | DI | DI | D |
| Black Gilliflower (4--1) | DI | D | DI | I | DI | D | DI | DI | D | DI | DI | DI | DI |
| Nimaiyisuo (4--10) | D | D | D | I | D | DI | DI | D | D | DI | DI | DI | D |

-continued

Construction results of InDel marker genotype database of *Malus* germplasm resources

| | | | | | | | | | | | | | |
|---|---|---|---|---|---|---|---|---|---|---|---|---|---|
| Zaohong (4--11) | D | D | DI | DI | DI | DI | D | D | D | D | DI | I | D |
| Xiangguo (4--12) | D | DI | DI | DI | D | D | D | D | DI | D | DI | DI | D |
| Vista Bella (4--16) | D | D | D | I | D | D | DI | D | I | DI | DI | I | D |
| Saiwen (4--17) | D | D | D | DI | DI | DI | DI | D | D | D | D | I | DI |
| Summerland (4--20) | DI | DI | DI | DI | I | DI | DI | DI | DI | DI | DI | DI | DI |
| Qihe Golden Spur (4--22) | DI | DI | DI | DI | I | DI | DI | DI | DI | DI | DI | DI | DI |
| Yellow Risharde (4--3) | DI | DI | DI | I | D | D | D | D | D | D | DI | I | D |
| Patten (4--5) | DI | D | DI | D | D | D | D | D | D | DI | DI | DI | D |
| Early Red Bird (4--6) | D | D | DI | D | D | DI | D | D | DI | DI | DI | DI | D |
| Fuhong (4--7) | DI | I | DI | I | D | D | DI | D | DI | D | DI | DI | D |
| Bisimake (4--8) | I | D | DI | DI | DI | DI | D | D | DI | DI | DI | I | D |
| York Imperial (4--9) | DI | D | D | DI | D | D | DI | D | DI | D | DI | DI | DI |
| Jonagold (5--1) | DI | DI | DI | DI | DI | DI | DI | DI | DI | DI | DI | DI | DI |
| Ayiwaniya (5--10) | D | DI | D | DI | D | D | D | DI | DI | D | DI | I | D |
| Fushan 5 (5--14) | D | DI | D | DI | DI | DI | DI | DI | D | D | DI | I | D |
| Houjiadian Spur (5--18) | D | DI | D | DI | DI | DI | DI | DI | D | D | DI | I | D |
| Guoshuai (5--19) | D | DI | D | I | DI | DI | D | DI | D | D | DI | I | D |
| Huashuai 1 (5--21) | DI | DI | DI | I | D | I | D | DI | D | D | DI | I | DI |
| Xiongyue 2 (5--22) | D | DI | D | DI | DI | DI | DI | DI | D | D | DI | I | D |
| Honeygod (5--3) | DI | DI | DI | DI | DI | D | DI | DI | D | D | DI | DI | DI |
| Joyal (5--4) | D | D | D | DI | D | DI | DI | D | DI | DI | DI | DI | D |
| Stark Spur Golden (5--5) | DI | DI | DI | DI | I | DI | DI | DI | DI | DI | DI | DI | DI |
| Enweier Golden (5--6) | DI | DI | DI | DI | I | DI | DI | DI | DI | DI | DI | DI | DI |
| Stark Gold (5--8) | D | D | DI | DI | DI | DI | D | D | D | D | DI | I | D |
| Sishui Spur (6--10) | D | DI | D | DI | DI | DI | DI | DI | D | D | DI | I | D |
| Red Spur Delicious (6--12) | D | DI | D | DI | DI | DI | DI | DI | D | D | DI | I | D |
| Qingdao 1 (6--13) | D | DI | D | DI | DI | DI | DI | DI | D | D | DI | I | D |
| Bianqiangzi 1 (6--14) | D | DI | D | DI | DI | DI | DI | DI | D | D | DI | I | D |
| Zhangjiakou Spur (6--16) | D | DI | D | DI | DI | DI | DI | DI | D | D | DI | I | D |
| Richard Red Delicious (6--18) | D | DI | D | DI | DI | DI | DI | DI | D | D | DI | I | D |
| Well Spur Delicious (6--19) | D | DI | D | DI | DI | DI | DI | DI | D | D | DI | I | D |
| Bianqiangzi 2 (6--20) | D | DI | D | DI | DI | DI | DI | DI | D | D | DI | I | D |
| Hardi Spur Delicious (6--21) | D | DI | D | DI | DI | DI | DI | DI | D | D | DI | I | D |
| Fushan 1 (6--3) | D | DI | D | DI | DI | DI | DI | DI | D | D | DI | I | D |
| Pinyin Spur (6--4) | D | DI | D | DI | DI | DI | DI | DI | D | D | DI | I | D |
| Nanshan 2 (6--8) | D | DI | D | DI | DI | DI | DI | DI | D | D | DI | I | D |

-continued

| Construction results of InDel marker genotype database of *Malus* germplasm resources | | | | | | | | | | | | | |
|---|---|---|---|---|---|---|---|---|---|---|---|---|---|
| Meiduan 1 (7--10) | D | D | D | DI | DI | DI | D | I | D | D | DI | I | D |
| Shisanling Spur (7--11) | D | DI | D | DI | DI | DI | DI | DI | D | D | DI | I | D |
| Kelisike (7--13) | D | D | DI | D | D | D | D | I | DI | D | DI | DI | D |
| Jie 18 (7--16) | D | DI | DI | DI | D | D | D | D | D | DI | DI | DI | D |
| Bo 25 (7--17) | DI | D | D | D | D | D | D | DI | D | DI | DI | I | D |
| Ruixiang (7--18) | DI | D | DI | DI | D | D | D | D | D | D | DI | DI | D |
| Wealthy (7--19) | DI | DI | D | D | D | D | I | D | DI | DI | DI | D | D |
| Nanshan 4 (7--2) | D | D | D | I | DI | DI | DI | D | D | D | DI | I | D |
| De 14 (7--20) | D | DI | DI | DI | D | D | D | D | D | DI | DI | DI | D |
| Napoleon (7--22) | D | D | D | D | D | DI | D | DI | D | D | DI | I | D |
| Youyi (7--23) | D | D | D | I | D | DI | DI | D | D | D | DI | DI | D |
| Oregon Spur (7--3) | D | D | D | I | DI | DI | DI | D | D | D | DI | I | D |
| Kangtun Spur (7--6) | D | DI | D | DI | DI | DI | DI | DI | D | D | DI | I | D |
| White Pippin (7--9) | D | D | D | I | D | DI | DI | DI | DI | DI | DI | DI | D |
| Zach Lebel (8--1) | DI | D | D | I | D | D | D | D | I | D | DI | DI | DI |
| Cortland (8--10) | DI | DI | DI | D | D | D | I | D | DI | DI | DI | DI | D |
| Raritan (8--12) | D | DI | D | I | DI | DI | D | D | D | D | DI | I | D |
| Meilingxi Tsugaru (8--13) | D | DI | D | D | D | D | DI | DI | D | D | DI | DI | D |
| Moscow Transparent (8--14) | D | DI | D | DI | DI | D | D | D | I | D | DI | DI | D |
| Cooper's Market (8--15) | D | I | DI | DI | I | DI | DI | D | D | D | DI | DI | D |
| Xite Shisheng (8--16) | D | D | DI | D | D | D | D | D | DI | D | DI | DI | D |
| Tian Yisaye (8--17) | D | D | D | D | D | D | D | D | DI | DI | DI | DI | D |
| Shennong 2 (8--19) | D | D | D | D | DI | DI | DI | DI | DI | I | DI | DI | D |
| Maigold (8--20) | DI | DI | DI | DI | DI | DI | D | I | DI | D | DI | DI | DI |
| Magu (8--21) | D | DI | DI | I | DI | DI | DI | D | D | DI | DI | DI | D |
| Cellini (8--23) | I | D | DI | DI | DI | DI | DI | D | DI | DI | DI | DI | D |
| Simonffy Piros (8--3) | DI | DI | D | DI | D | D | D | D | DI | DI | DI | DI | D |
| Luxiang (8--5) | D | DI | D | DI | D | DI | D | D | D | D | DI | DI | D |
| Zhongqiu (8--6) | D | DI | DI | DI | D | D | D | D | DI | I | DI | DI | D |
| De 2 (8--7) | DI | D | D | DI | D | D | D | D | DI | D | DI | I | DI |
| Grimes Golden (8--8) | DI | DI | DI | I | DI | DI | D | D | DI | D | DI | DI | I |
| Early Straw Berry (8--9) | DI | DI | D | I | D | DI | DI | D | DI | D | DI | DI | D |
| Kelia (9--10) | D | DI | D | DI | D | D | D | DI | D | DI | DI | I | DI |
| French Apple (9--11) | DI | DI | D | DI | DI | D | D | D | DI | D | DI | DI | D |
| Todoroki Tsugaru (9--12) | D | D | D | DI | DI | DI | D | DI | D | DI | DI | DI | DI |
| Cuihong (9--13) | D | D | D | DI | DI | DI | D | D | DI | D | DI | DI | D |
| De 4 (9--14) | DI | DI | D | I | D | D | DI | D | I | D | DI | DI | D |
| Early McIntosh (9--18) | D | D | D | I | D | D | D | D | D | I | DI | DI | D |
| Adam Mickewier (9--19) | DI | DI | D | DI | D | D | D | D | D | D | D | DI | D |

-continued

Construction results of InDel marker genotype database of *Malus* germplasm resources

| | | | | | | | | | | | | | |
|---|---|---|---|---|---|---|---|---|---|---|---|---|---|
| Norda (9--2) | DI | D | DI | D | D | DI | D | D | DI | D | DI | DI | D |
| Cardinal (9--20) | DI | DI | DI | DI | DI | I | D | DI | D | I | DI | DI | DI |
| Evelyn (9--21) | D | I | D | I | D | D | D | D | DI | D | DI | DI | D |
| Situonuowei (9--22) | DI | D | DI | DI | D | D | D | D | DI | DI | DI | DI | DI |
| Yingqiu (9--23) | D | DI | D | I | D | D | DI | D | D | D | DI | DI | D |
| Kelongxieer (9--3) | D | DI | D | DI | DI | D | D | D | I | D | DI | DI | D |
| Cloden (9--5) | I | DI | DI | DI | DI | D | D | DI | D | DI | DI | DI | DI |
| Qiutianhong (9--6) | DI | D | D | DI | D | D | D | D | DI | DI | DI | DI | D |
| Gaidebao (9--7) | D | D | DI | DI | DI | D | DI | D | D | D | DI | DI | D |
| Starkjam (9--9) | D | D | D | D | D | DI | D | DI | D | D | DI | I | D |
| Wan Crab (B-1) | DI | D | D | DI | D | D | D | D | DI | DI | DI | I | DI |
| Minjiandaguo Crab (B-10) | D | D | D | D | I | D | DI | D | DI | D | D | DI | D |
| Luanzhuang Crab (B1-11) | D | D | DI | D | D | DI | D | D | D | D | DI | I | D |
| Sankuaishi Crab (B1-12) | D | D | D | D | D | D | D | D | D | D | DI | D | D |
| Xiongyue Crab 1 (B1-13) | DI | D | D | D | D | D | D | D | D | I | DI | DI | DI |
| Sankuaishi Crab 2 (B1-14) | DI | DI | DI | D | DI | DI | D | DI | I | D | DI | DI | DI |
| Dabaleng (B-12) | D | D | D | DI | D | DI | D | D | DI | D | DI | DI | D |
| Sankuaishi Crab 2 (B-13) | D | DI | D | I | DI | DI | DI | D | D | D | DI | I | D |
| Changguo Crab (B-14) | D | D | D | DI | I | DI | DI | DI | DI | D | DI | DI | DI |
| Dagucheng Baleng (B1-5) | D | D | D | D | D | D | D | D | I | D | DI | DI | D |
| Zumi Crab 3x (B-15) | D | D | D | DI | I | DI | D | DI | I | D | DI | DI | D |
| 26105 (B-16) | DI | DI | D | D | D | D | D | DI | D | D | DI | DI | D |
| Daguo Crab (B-17) | D | D | D | D | I | D | DI | D | DI | D | DI | DI | D |
| Xiongyue Crab 2 (B1-8) | D | D | DI | I | D | D | D | D | I | D | DI | I | D |
| Watermelon Crab (B-18) | DI | DI | DI | D | DI | D | D | D | DI | DI | DI | DI | DI |
| Mudanjiang Crab (B1-9) | DI | D | DI | D | D | DI | D | D | DI | DI | DI | I | D |
| Tianhong 1 (B-19) | D | DI | D | I | DI | DI | DI | D | D | D | DI | I | D |
| Jiping 1 (B-2) | D | DI | D | D | D | I | D | D | D | D | DI | I | D |
| Caoyuan Crab (B2-1) | D | D | D | I | D | D | D | DI | I | DI | DI | D | D |
| Zumi Crab 4x (B-21) | D | D | D | DI | I | DI | D | DI | I | D | DI | DI | D |
| Luanzhuang Shaguo (B2-11) | D | D | D | DI | D | D | D | D | DI | D | DI | DI | D |
| Xiaofan Crab (B2-13) | D | DI | DI | DI | D | D | D | D | DI | D | DI | DI | D |
| Hebing Pingding Crab (B2-14) | D | D | D | D | D | D | D | D | I | D | DI | DI | D |
| Zumi Crab 3x 2 (B-22) | D | D | D | DI | I | DI | D | DI | I | D | DI | DI | D |
| Baleng Crab (B2-3) | D | D | D | DI | D | D | D | D | I | D | DI | DI | D |
| Baleng seedling 14 (B-25) | D | D | D | I | I | D | D | DI | DI | I | DI | DI | D |
| Russian White apple (B2-6) | D | D | DI | DI | D | D | D | D | DI | I | DI | DI | D |

| Construction results of InDel marker genotype database of *Malus* germplasm resources | | | | | | | | | | | | | |
|---|---|---|---|---|---|---|---|---|---|---|---|---|---|
| Nagafu 2 (B-26) | D | DI | D | I | DI | DI | DI | D | D | D | DI | I | D |
| Ambrosia (B-27) | DI | I | DI | DI | DI | D | DI | DI | D | D | DI | DI | D |
| Aihonghua (B2-8) | DI | DI | DI | I | DI | DI | DI | DI | DI | DI | DI | DI | D |
| Nanshennan (B-28) | D | DI | D | I | DI | DI | D | D | D | D | DI | I | D |
| Zumi Crab W1 (B-29) | D | D | D | DI | I | DI | D | DI | I | D | DI | DI | D |
| Hong 4G (B-3) | D | D | D | DI | D | DI | D | D | D | DI | DI | DI | D |
| Zumi Crab (B-30) | D | D | D | DI | I | DI | D | DI | I | D | DI | DI | D |
| Zaobai Crab (B3-1) | D | D | D | D | D | D | D | D | I | D | DI | DI | D |
| Mollie's Delicious (B-31) | DI | I | DI | D | I | I | D | DI | DI | I | DI | DI | I |
| Regunzi Spur (B3-10) | D | D | D | DI | D | D | D | D | D | D | DI | DI | D |
| Xiaofanshan Baleng (B3-11) | DI | D | D | DI | D | DI | D | D | I | D | DI | DI | D |
| Huamei (B3-12) | DI | I | DI | D | DI | DI | D | D | DI | DI | DI | DI | D |
| Huashuo (B3-13) | D | D | D | I | DI | D | D | D | DI | D | DI | DI | D |
| Yuhong (B3-14) | D | DI | D | DI | DI | DI | DI | DI | D | D | DI | I | D |
| Huayue (B3-15) | D | DI | D | DI | DI | D | DI | DI | DI | D | DI | DI | D |
| Jingbohu Shandingzi (B3-2) | D | D | D | I | D | D | D | D | D | D | D | D | D |
| Eluosi Daguo Shandingzi (B3-3) | D | D | DI | D | D | D | D | D | I | I | DI | DI | D |
| HY (B-33) | D | DI | D | DI | DI | D | D | D | DI | D | DI | DI | D |
| Hong Crab (B3-6) | D | D | D | D | D | D | D | D | D | D | D | DI | D |
| 23# (B-37) | DI | DI | DI | DI | D | I | D | D | I | D | DI | DI | D |
| Russian apple (B3-8) | D | D | D | D | D | D | D | D | I | I | DI | DI | D |
| 147 (B-38) | DI | I | DI | D | I | D | D | D | DI | DI | DI | DI | D |
| Xiaofanshan Baleng 1 (B3-9) | D | D | D | DI | D | D | D | D | I | D | DI | DI | D |
| Lvshuai (B-4) | DI | D | D | DI | I | DI | D | DI | D | DI | DI | DI | DI |
| Dounan (B-40) | DI | DI | DI | DI | DI | I | DI | DI | D | DI | DI | DI | D |
| 11906 (B-41) | DI | D | D | DI | D | D | D | DI | DI | D | DI | DI | DI |
| Luli (B-5) | D | DI | D | D | D | D | D | D | D | D | D | DI | D |
| Jinxiuhong (B-6) | D | D | D | DI | DI | D | D | D | D | D | DI | DI | DI |
| B68 (B-7) | D | DI | D | DI | D | D | D | D | DI | D | DI | DI | D |
| Huaida (B-8) | I | DI | DI | D | I | DI | D | DI | DI | I | DI | DI | DI |
| Nanshennan mutant (B-9) | D | DI | D | I | DI | DI | D | D | D | D | DI | I | D |
| Xiahong (BH-1) | D | D | D | DI | D | D | D | D | D | DI | DI | DI | DI |
| Wuming1 (BJ-1) | DI | DI | D | DI | D | DI | DI | D | D | DI | DI | DI | I |
| Canzy ? (BJ-10) | DI | I | DI | DI | D | I | D | D | D | DI | DI | DI | D |
| Xiangfu (BJ-11) | D | DI | D | I | DI | DI | DI | D | D | D | DI | I | D |
| Envy (BJ-12) | D | DI | D | DI | DI | D | D | D | I | DI | DI | DI | D |

-continued

| Construction results of InDel marker genotype database of *Malus* germplasm resources |
|---|

| | | | | | | | | | | | | | |
|---|---|---|---|---|---|---|---|---|---|---|---|---|---|
| Fuji_KiKu (BJ-2) | D | DI | D | I | DI | DI | DI | D | DI | D | DI | I | D |
| Banxiu Crab (BJ-4) | D | DI | DI | I | D | D | D | D | D | DI | DI | D |
| Jazz (BJ-5) | DI | DI | D | DI | DI | D | D | D | DI | DI | DI | I | D |
| Early Red Bird 2 (BJ-7) | D | D | D | DI | DI | D | D | D | D | D | DI | DI | D |
| Qiuhong Gala (BJ-8) | D | DI | D | DI | DI | DI | DI | D | I | D | DI | I | D |
| Hongxiangcui (BJ-9) | D | DI | DI | D | DI | DI | DI | DI | D | DI | DI | I | D |
| 07-115 (BK-1) | D | DI | D | I | DI | DI | I | D | DI | D | DI | DI | D |
| Nagafu 3 (BK-2) | D | DI | D | I | DI | DI | DI | D | D | D | DI | I | D |
| 28-253 (BK-28-253) | D | DI | D | I | I | DI | D | D | D | DI | DI | DI | DI |
| Nagafu 3-R (BK-3) | D | DI | D | I | DI | DI | DI | D | D | D | DI | I | D |
| 4354 (BK-4) | D | D | D | DI | I | D | I | D | DI | D | DI | DI | D |
| 4-23 (BK-4-23) | DI | I | DI | I | DI | I | I | DI | D | D | DI | I | D |
| 4354-R ? (BK-5) | DI | DI | DI | I | DI | D | D | DI | D | I | DI | DI | DI |
| 77-34 (BK-77-34) | D | D | D | D | D | D | D | D | D | D | DI | DI | D |
| Red Spur Delicious (BK-AH) | D | DI | D | DI | DI | DI | DI | DI | D | D | DI | I | D |
| Ozark Gold (BK-AJ) | DI | I | DI | DI | DI | D | D | DI | D | DI | DI | DI | DI |
| Michinoku (BK-AZ) | D | D | D | DI | D | DI | D | D | DI | D | DI | DI | D |
| Azwell (BK-Azwell) | D | DI | D | DI | DI | DI | DI | DI | D | D | DI | I | D |
| Banbishan Crab (BK-BBSHT) | D | D | D | D | D | D | D | D | D | D | DI | DI | D |
| Hokudo (BK-BD) | D | DI | D | DI | DI | DI | DI | D | D | DI | DI | I | DI |
| Baifugao (BK-BFG) | DI | D | DI | D | D | D | D | D | I | DI | DI | DI | D |
| White Crab (BK-BHT) | DI | D | D | DI | D | DI | DI | D | I | D | DI | DI | D |
| Buming Kangbing (BK-BMKB) | D | D | D | I | D | DI | DI | DI | DI | DI | DI | DI | D |
| Batougou 1 (BK-BTG1H) | D | D | D | I | D | D | D | D | I | DI | DI | D | D |
| Batougou 2 (BK-BTG2H) | D | D | D | DI | D | D | D | D | I | D | DI | DI | D |
| Batougou Aizhen (BK-BTGAZ) | D | D | D | D | D | D | D | D | I | D | DI | DI | D |
| Binzi (BK-BZ) | D | DI | DI | DI | D | D | D | DI | D | DI | DI | D |
| Kitanosach (BK-BZX) | D | D | D | DI | DI | D | DI | D | DI | DI | DI | D |
| Binzi (SW) (BK-BZXN) | D | DI | DI | DI | D | D | D | DI | D | D | DI | D |
| Nagafu 2 (BK-CF2H) | D | DI | D | I | DI | DI | DI | D | D | D | DI | I | D |
| Nagafu 36 (BK-CF36) | D | DI | D | I | DI | DI | DI | D | D | D | DI | I | D |
| Nagafu 6 (BK-CF6H) | D | DI | D | I | DI | DI | DI | D | D | D | DI | I | D |
| CG24 (BK-CG24) | D | DI | D | DI | DI | DI | DI | D | D | DI | DI | I | D |
| CG3 (BK-CG3) | D | DI | D | I | I | DI | D | D | D | DI | DI | DI | DI |
| CG80 (BK-CG80) | D | D | D | DI | DI | D | D | D | DI | D | DI | DI | D |
| Changhong (BK-CH) | D | DI | D | I | DI | DI | DI | D | D | D | DI | I | D |
| Chieftan (BK-chieftan) | D | D | D | DI | D | D | D | D | DI | DI | I | DI |
| Cangjiang Crab (BK-CJHT) | D | D | D | DI | D | D | D | D | D | DI | DI | D |

-continued

| Construction results of InDel marker genotype database of *Malus* germplasm resources | | | | | | | | | | | | | |
|---|---|---|---|---|---|---|---|---|---|---|---|---|
| Chuanling Crab (BK-CLHT) | D | D | DI | D | DI | D | D | D | DI | DI | DI | I | D |
| Hatsuaki (BK-CQ) | D | D | D | D | DI | D | D | D | DI | DI | DI | DI | DI |
| Crispin (BK-crispin) | DI | DI | DI | DI | DI | DI | DI | DI | DI | DI | DI | DI | DI |
| Caozigang Yuanshuai (BK-CZGYS) | D | D | D | DI | DI | DI | DI | DI | D | D | DI | I | D |
| Danxia (BK-DANXIA) | D | DI | D | DI | I | I | DI | I | DI | D | DI | DI | D |
| Dolgo (BK-DDG) | D | D | DI | D | D | D | D | D | I | I | DI | DI | D |
| Darwin (BK-DEW) | D | DI | DI | DI | D | D | D | D | DI | D | DI | DI | D |
| Oriental Apple (BK-DFPG) | D | D | DI | D | D | I | D | DI | DI | I | D | D | D |
| Big Crab (BK-DGHT) | D | D | D | DI | D | D | D | D | DI | D | DI | DI | D |
| Daguo Jinhong (BK-DGJH) | I | DI | DI | D | I | DI | D | DI | DI | I | DI | DI | DI |
| Daihong (BK-DH) | D | DI | D | DI | DI | DI | DI | DI | D | D | DI | I | D |
| Daihao 261 (BK-DH261) | D | DI | D | D | D | D | D | D | I | DI | DI | DI | D |
| Spur Golden Delicious (BK-DJG) | DI | DI | DI | DI | I | DI | DI | DI | DI | DI | DI | DI | DI |
| Daxianguo (BK-DXG) | DI | D | D | D | D | D | D | D | I | D | DI | DI | D |
| Daye Crab (BK-DYHT) | D | D | D | I | D | D | D | D | D | D | DI | DI | D |
| Spur Fuji (BK-DZFS) | D | DI | D | I | DI | DI | D | D | D | DI | I | D |  |
| Huaguan Spur (BK-DZHG) | D | D | D | DI | DI | D | D | D | D | D | DI | DI | DI |
| Elite (BK-Elite) | DI | DI | D | DI | DI | DI | DI | DI | D | D | DI | I | D |
| Fa 8 (BK-F8) | D | DI | DI | DI | DI | D | DI | DI | DI | D | DI | DI | D |
| Fukushima Spur Fuji (BK-FDDZ) | D | DI | D | I | DI | DI | D | D | D | D | DI | I | D |
| Fujin (BK-FJ) | D | I | DI | DI | DI | D | DI | DI | DI | DI | DI | I | D |
| Florina (BK-Florina) | D | DI | D | I | DI | DI | D | D | D | DI | DI | DI | D |
| Fangming (BK-FM) | D | D | D | DI | DI | D | DI | D | DI | D | DI | DI | DI |
| Fuji (BK-Fuji) | D | DI | D | I | DI | DI | DI | D | D | D | DI | DI | D |
| Fengyan (BK-FY) | D | D | D | DI | D | DI | I | D | D | DI | DI | I | D |
| Yanfu 1 (BK-FY1) | D | DI | D | I | DI | DI | D | D | D | D | DI | I | D |
| King of Tompkins County (BK-FZY) | D | D | D | DI | D | D | D | DI | D | DI | DI | DI |  |
| G30 (BK-G30) | D | D | D | D | D | DI | D | D | DI | D | DI | DI | D |
| Gao #5 (BK-G-5) | D | D | DI | D | D | DI | D | DI | I | D | DI | DI | D |
| Gala (BK-gala) | DI | I | DI | D | DI | D | D | DI | DI | DI | DI | D |  |
| Golden Delicious (BK-GD) | DI | DI | DI | DI | I | DI | DI | DI | DI | DI | DI | DI | DI |
| Gloster69 (BK-Gloster69) | D | D | D | DI | DI | D | DI | DI | D | D | DI | I | D |
| GM256 (BK-GM256) | D | DI | D | D | D | D | D | DI | D | D | DI | D |  |
| GM310 (BK-GM310) | DI | I | DI | D | D | D | D | DI | DI | DI | DI | DI |  |
| Gaoqiu (BK-GQ) | D | D | D | I | DI | D | DI | D | DI | DI | DI | D |  |
| Miyazaki Spur Fuji (BK-GQDZ) | D | DI | D | I | DI | DI | D | D | D | DI | I | D |  |

-continued

| Construction results of InDel marker genotype database of *Malus* germplasm resources | | | | | | | | | | | | | |
|---|---|---|---|---|---|---|---|---|---|---|---|---|---|
| HAC-9 (BK-HAC-9) | D | DI | D | DI | DI | DI | DI | DI | D | DI | DI | I | D |
| Huifeng Orin (BK-HFWL) | D | D | D | DI | D | DI | D | D | D | D | DI | DI | D |
| Red Ralls Janet (BK-HGG) | D | D | DI | DI | DI | DI | D | D | D | D | DI | I | D |
| Huaguan Crab (BK-HGHT) | D | DI | DI | DI | D | D | D | D | I | D | DI | DI | D |
| Harrold Red Delicious (BK-HH) | D | DI | D | DI | DI | DI | DI | DI | D | D | DI | I | D |
| Hong Crab 2 (BK-HHT2H) | D | D | D | DI | D | D | D | D | D | D | DI | DI | D |
| Stark Redgold (BK-HJ) | DI | I | DI | DI | DI | DI | DI | I | D | DI | DI | DI | D |
| HLWQ (BK-HLWQ) | D | DI | D | DI | D | DI | D | D | I | D | DI | DI | D |
| Holly (BK-Holly) | D | D | D | DI | D | D | D | D | D | D | DI | DI | D |
| Red Jonagold (BK-HQNJ) | DI | DI | DI | D | DI | DI | D | D | D | D | DI | DI | D |
| Red Sekaiichii (BK-HSJY) | D | DI | D | DI | DI | D | DI | DI | D | DI | DI | DI | DI |
| Hongte (BK-HT) | D | DI | D | I | DI | D | DI | D | D | D | DI | DI | D |
| Haitangguo (BK-HTG) | I | DI | DI | D | I | D | D | D | D | I | DI | DI | DI |
| Haitanghua (BK-HTH) | D | D | D | DI | D | D | D | D | D | D | DI | DI | D |
| Huangtaiping (BK-HTP) | DI | D | D | DI | D | DI | DI | D | I | D | DI | DI | D |
| Hongxue (BK-HX) | D | D | D | I | D | DI | DI | DI | DI | DI | DI | DI | D |
| Jincui (BK-JC) | D | D | D | DI | I | DI | DI | D | DI | DI | DI | D |
| Juda Fuji (BK-JDFS) | D | DI | D | I | DI | DI | DI | D | D | D | DI | I | D |
| Jiguan (BK-JG) | DI | D | DI | I | D | DI | D | D | D | D | DI | DI | D |
| Jinhong (BK-JH) | I | DI | DI | D | I | D | DI | DI | I | DI | DI | DI |
| Jonagored (BK-Jonagored) | DI | DI | DI | DI | DI | DI | DI | DI | DI | DI | DI | DI | DI |
| Jonathan (BK-Jonathan) | D | DI | D | DI | D | DI | DI | DI | D | D | DI | DI | D |
| Himekami (BK-JS) | D | DI | D | DI | DI | DI | DI | D | DI | D | DI | DI | D |
| Stark Blushing Golden (BK-JY) | DI | I | DI | DI | I | DI | D | DI | DI | D | DI | DI | D |
| Classic Red Delicious (BK-KAHONG) | D | DI | D | DI | DI | DI | DI | DI | D | D | DI | I | D |
| KLGDG Shandingzi (BK-KLGDGSDZ) | D | D | D | DI | D | D | D | D | D | DI | DI | D | D |
| KOSZTELQ (BK-KOSZTELQ) | DI | D | DI | D | D | D | D | DI | D | DI | DI | DI | D |
| Sunflower (BK-KUIHUA) | D | DI | D | I | DI | D | I | DI | D | DI | DI | DI | DI |
| Lenghaitang (BK-LHT) | D | D | D | D | D | D | D | D | D | D | DI | DI | D |
| Liberty (BK-liberty) | D | D | D | DI | D | D | D | D | D | DI | DI | I | DI |
| Lijiang Shandingzi (BK-LJSDZ) | D | D | D | DI | D | D | D | D | I | D | DI | DI | D |
| Laoshan 4 (BK-LS4H) | D | D | D | D | D | D | D | D | I | D | DI | DI | D |
| Ryoka no Kisetsu (BK-LX) | D | DI | D | I | DI | DI | DI | D | D | D | DI | I | D |
| Lvxiangjiao (BK-LXJ) | DI | D | DI | DI | DI | I | D | D | DI | DI | DI | DI | D |
| Liaozhen 1 (BK-LZ1H) | DI | D | D | DI | D | D | D | D | DI | D | DI | DI | D |
| M7 (BK-M7) | D | I | D | DI | D | D | D | DI | I | DI | DI | I | D |
| Meiguihong (BK-MGH) | D | DI | D | DI | DI | DI | DI | DI | D | D | DI | I | D |

Construction results of InDel marker genotype database of *Malus* germplasm resources

| | | | | | | | | | | | | | |
|---|---|---|---|---|---|---|---|---|---|---|---|---|---|
| Meile (BK-ML) | DI | DI | DI | I | I | D | DI | DI | D | DI | DI | DI | DI |
| MM106 (BK-MM106) | D | D | D | DI | DI | D | D | D | DI | D | DI | DI | D |
| Mengpaisi (BK-MPS) | DI | DI | D | I | D | D | DI | D | I | D | DI | DI | D |
| Meixiang (BK-MX) | D | DI | D | I | DI | DI | DI | D | D | D | DI | I | D |
| Ningqiu (BK-NQ) | D | D | DI | D | DI | DI | D | D | DI | DI | DI | I | D |
| P16 (BK-P16) | D | D | D | I | D | D | D | D | D | D | DI | I | D |
| P22 (BK-P22) | D | D | D | I | D | D | D | D | D | D | DI | D | D |
| Pingdinghaitang (BK-PDHT) | D | D | D | D | D | D | D | D | I | D | DI | DI | D |
| Bianguo Crab (BK-PGHT) | D | D | D | I | D | DI | D | D | DI | D | DI | DI | DI |
| Pionier (BK-Pionier) | D | D | D | I | D | I | D | D | DI | D | DI | DI | D |
| Prima (BK-Prima) | DI | D | D | I | D | D | I | D | D | D | DI | I | D |
| Pingyitiancha (BK-PYTC) | D | D | D | I | D | D | D | D | DI | I | D | D | D |
| Qianxue (BK-QAINXUE) | DI | I | DI | I | DI | I | I | D | D | D | DI | DI | DI |
| Akifu 1 (BK-QF1) | D | DI | D | I | DI | DI | DI | D | D | D | DI | I | D |
| Qingfu 13 (BK-QF13) | D | DI | D | I | DI | DI | D | D | D | D | DI | I | D |
| Seimei (BK-QM) | D | D | D | I | D | DI | D | DI | D | DI | DI | DI | DI |
| Senshu (BK-QQ) | D | D | D | I | D | I | DI | D | DI | DI | DI | DI | D |
| Aomori Early (BK-QSZS) | DI | DI | DI | DI | I | DI | DI | DI | DI | DI | DI | DI | DI |
| Qiuxiang (BK-QX) | D | D | D | DI | DI | DI | D | DI | D | D | DI | DI | DI |
| Qiuxing Crab (BK-QXHT) | DI | D | DI | D | D | D | DI | D | D | D | DI | DI | D |
| Yanqing (BK-QY) | D | DI | D | I | D | DI | D | D | D | D | DI | DI | D |
| Regunzi (BK-RGZ) | D | D | D | DI | D | D | D | D | D | D | DI | DI | D |
| Ruby (BK-Ruby) | D | D | D | I | DI | DI | D | D | D | D | DI | I | D |
| Scarlet (BK-scarlet) | D | DI | D | DI | DI | DI | DI | DI | D | D | DI | I | D |
| Sdw1 (BK-Sdw1) | D | D | D | DI | D | D | D | D | D | DI | DI | D | D |
| Shandingzi 2 (BK-SDZ2H) | D | D | D | D | D | D | D | D | D | D | DI | DI | D |
| Su E Shandingzi (BK-SESDZ) | D | D | D | DI | D | D | D | D | D | D | DI | D | D |
| Shengfang 2 (BK-SF2) | D | DI | D | I | DI | DI | D | D | D | D | DI | I | D |
| SH6 (BK-SH6) | D | D | D | I | DI | D | D | D | DI | D | DI | DI | D |
| Sankuaishi Crab 1 (BK-SKSHT1H) | D | D | D | DI | D | D | D | D | I | D | D | DI | D |
| Forest Apple (BK-SLPG) | DI | D | DI | DI | DI | D | DI | DI | D | D | DI | DI | DI |
| Sieversii (BK-SWS) | D | D | D | DI | D | D | D | D | I | D | D | DI | D |
| Sansa (BK-SX) | D | I | D | D | D | I | D | D | DI | DI | DI | DI | D |
| Szampion (BK-Szampion) | D | D | DI | I | I | DI | D | DI | DI | I | DI | DI | D |
| T337 (BK-T337) | D | DI | D | D | D | D | D | D | D | D | D | DI | D |
| Turkmen Apple (BK-TKMPG) | D | D | D | DI | D | D | D | D | I | D | DI | DI | D |
| Mato 1 (BK-TMYH) | D | D | D | DI | D | DI | D | D | DI | D | DI | DI | D |
| Trajian (BK-Trajian) | D | D | D | DI | D | DI | D | D | DI | DI | DI | DI | D |

-continued

| Construction results of InDel marker genotype database of *Malus* germplasm resources | | | | | | | | | | | | | |
|---|---|---|---|---|---|---|---|---|---|---|---|---|---|
| Weiai 3 (BK-WA3) | D | D | D | DI | D | D | D | D | I | D | DI | DI | D |
| Wanbai Crab (BK-WBHT) | D | D | D | D | I | DI | D | D | DI | DI | DI | DI | DI |
| Wufengshan 1 (BK-WFS1H) | D | D | DI | DI | D | D | D | D | D | D | DI | DI | D |
| Wufengshan 4 (BK-WFS4H) | D | D | D | DI | I | D | D | D | D | D | DI | I | D |
| Wufengshan Crab (BK-WFSHT) | D | D | D | DI | D | D | DI | D | I | D | DI | DI | D |
| Wufengshan Crab 2 (BK-WFSHT2H) | D | DI | D | DI | D | D | D | D | D | D | DI | I | D |
| Wufengshan Crab 6 (BK-WFSHT6H) | I | D | DI | D | D | D | D | D | I | DI | DI | DI | D |
| Wifos (BK-wifos) | D | D | DI | I | DI | D | D | DI | DI | DI | I | D |
| Orei (BK-WL) | DI | I | DI | DI | I | DI | D | DI | DI | D | DI | DI | D |
| Maypole (BK-WM) | D | DI | D | I | D | D | D | D | DI | DI | DI | D |
| Waltz (BK-WZ) | D | DI | DI | DI | DI | D | D | D | DI | DI | DI | DI | D |
| Kotoku (BK-XD) | D | D | D | I | DI | I | D | D | D | DI | DI | DI | D |
| Xiaofanshan Binzi (BK-XFSBZ) | D | DI | DI | DI | D | D | D | D | DI | D | DI | DI | D |
| Xiaofanshan Crab 4 (BK-XFSHT4H) | D | DI | DI | DI | D | D | D | D | DI | D | DI | DI | D |
| Xiaogoumen Naizi (BK-XGMNZ) | D | DI | DI | DI | D | D | D | D | DI | D | DI | DI | D |
| XGM Suan Binzi (BK-XGMSBZ) | D | DI | DI | DI | D | D | D | D | DI | D | DI | DI | D |
| XGM Tian Binzi (BK-XGMTBZ) | D | D | D | D | D | D | D | D | DI | D | DI | DI | D |
| Starkrimson (BK-XHX) | D | DI | D | DI | DI | DI | DI | DI | D | D | DI | I | D |
| Xinjiang 1 (BK-XJ1) | D | D | D | D | D | D | D | DI | I | D | D | I | D |
| Xinjiang 11 (BK-XJ11) | D | D | DI | D | D | DI | D | DI | DI | DI | DI | DI | D |
| Xinjiang 14 (BK-XJ14) | D | D | DI | D | D | DI | D | DI | DI | DI | DI | DI | D |
| Xinjiang 15 (BK-XJ15) | D | D | D | D | D | D | D | D | DI | I | DI | DI | D |
| Xinjiang 16 (BK-XJ16) | D | D | DI | DI | DI | D | D | DI | DI | I | DI | DI | D |
| Xinjiang 17 (BK-XJ17) | D | D | D | D | D | I | D | D | I | DI | DI | DI | D |
| Xinjiang 18 (BK-XJ18) | D | D | D | D | D | I | D | D | I | DI | DI | DI | D |
| Xinjiang 19 (BK-XJ19) | D | D | D | D | DI | D | D | DI | DI | D | DI | I | D |
| Xinjiang 21 (BK-XJ21) | DI | D | DI | D | D | D | D | D | I | DI | DI | DI | D |
| Xinjiang 22 (BK-XJ22) | D | D | DI | D | D | D | D | D | DI | D | DI | D | D |
| Xinjiang 24 (BK-XJ24) | D | DI | D | DI | D | D | D | D | DI | D | DI | I | D |
| Xinjiang 26 (BK-XJ26) | D | D | DI | D | D | DI | D | DI | DI | DI | DI | DI | D |
| Xinjiang 28 (BK-XJ28) | D | D | D | D | DI | D | D | DI | DI | D | DI | I | D |
| Xinjiang 29 (BK-XJ29) | DI | D | D | D | DI | DI | DI | D | DI | I | DI | DI | DI |
| Xinjiang 31 (BK-XJ31) | I | D | D | D | D | D | D | D | D | D | DI | DI | D |
| Xinjiang 3 (BK-XJ3H) | D | DI | D | DI | DI | DI | DI | D | D | D | DI | DI | D |
| Xinjiang 6 (BK-XJ6H) | D | D | DI | D | D | DI | D | D | I | D | DI | I | D |
| Xinjiang 7 (BK-XJ7) | D | D | DI | D | D | DI | D | DI | DI | DI | DI | I | D |
| Xinjiang 8 (BK-XJ8) | DI | D | DI | D | D | D | D | D | D | I | DI | DI | D |
| Xinjiang 9 (BK-XJ9) | DI | D | D | D | DI | DI | D | DI | I | DI | DI | DI | DI |
| Xijin Crab (BK-XJHT) | DI | D | DI | I | D | D | D | D | D | DI | DI | D |

-continued

Construction results of InDel marker genotype database of *Malus* germplasm resources

| | | | | | | | | | | | | | |
|---|---|---|---|---|---|---|---|---|---|---|---|---|---|
| Xiaomian Crab (BK-XMHT) | D | D | DI | DI | D | D | D | D | I | D | DI | DI | D |
| New Jonagold (BK-XQNJ) | DI | DI | DI | DI | DI | DI | DI | DI | DI | DI | DI | DI | DI |
| Xiaoshuai (BK-XS) | D | D | D | DI | D | D | D | D | DI | DI | DI | I | D |
| Shinsekai (BK-XSJ) | D | DI | D | I | I | D | D | D | DI | DI | DI | DI | DI |
| Xiangyanghong (BK-XYH) | D | D | DI | DI | D | DI | DI | D | D | D | DI | I | D |
| Italy Early Red (BK-YDLZH) | DI | I | DI | D | DI | D | D | DI | DI | D | DI | DI | D |
| Yanfu 10 (BK-YF10) | D | DI | D | I | DI | DI | DI | D | D | D | DI | I | D |
| Yoko (BK-YG) | D | DI | D | DI | D | DI | D | D | D | DI | D | DI | D |
| Yuanhong (BK-YH) | DI | D | D | DI | D | D | D | DI | DI | D | DI | DI | D |
| Tehong 2 (BK-YH2) | D | DI | D | I | DI | DI | DI | D | D | D | D | I | D |
| Yanhongmi (BK-YHM) | D | D | D | D | DI | D | DI | D | D | D | D | DI | D |
| Youliang Spur (BK-YLDZ) | D | DI | D | I | DI | DI | DI | D | D | D | D | I | D |
| Yuanye Crab (BK-YYHT) | D | D | D | DI | D | D | D | D | D | D | DI | DI | D |
| Stark Jumbo (BK-ZB) | D | DI | D | DI | DI | D | D | D | DI | D | DI | DI | D |
| Jumbo Orin (BK-ZBWL) | D | DI | D | DI | I | DI | DI | DI | DI | DI | DI | DI | DI |
| Zhuifeng 1 (BK-ZF1H) | DI | DI | DI | D | D | D | D | D | I | I | DI | DI | DI |
| Zhuifeng 2 (BK-ZF2H) | D | D | D | D | D | D | D | D | D | D | DI | DI | D |
| Early Fuji (BK-ZFS) | D | DI | D | I | DI | DI | DI | D | D | D | D | I | D |
| Xiaofanshan Crab (BK-ZFSHT) | D | DI | DI | DI | D | D | D | D | DI | D | DI | DI | D |
| Zisai Pearl (BK-Zisai) | D | D | D | I | DI | D | DI | D | DI | DI | DI | DI | D |
| Geneva Early (BK-ZJ) | D | D | D | DI | D | I | D | D | I | DI | DI | DI | D |
| 13-26W (CL-1) | D | DI | D | I | I | I | D | DI | D | D | DI | D | DI |
| 23-127 (CL-2) | D | DI | D | DI | DI | D | D | D | D | D | DI | DI | DI |
| 50-30 (CL-3) | D | D | D | I | DI | DI | DI | D | D | D | DI | I | D |
| 50-32 (CL-4) | DI | D | D | DI | I | DI | D | DI | DI | D | DI | DI | DI |
| H5-101 (CL-5) | D | DI | D | I | DI | I | DI | D | DI | D | DI | DI | D |
| Pingyan (CL-6) | D | D | D | I | D | DI | D | D | D | D | DI | DI | D |
| Deqin Crab (DQ) | D | D | D | I | D | D | D | D | I | D | DI | D | D |
| Jin 18 (GY-1) | D | DI | D | I | DI | DI | DI | D | DI | D | DI | I | D |
| Fengfeng Baleng (GY-2) | D | DI | DI | I | D | D | D | D | DI | D | DI | DI | D |
| Hanfu 6 (GY-3) | D | DI | D | I | DI | DI | DI | D | D | D | DI | I | D |
| Hanfu 3 (GY-4) | DI | DI | D | I | D | DI | DI | D | D | D | DI | I | D |
| 95/06 (GZ-1) | D | D | D | D | D | D | D | DI | D | D | DI | I | DI |
| 107/06 (GZ-2) | DI | D | D | DI | D | D | D | D | D | DI | DI | DI | D |
| 117/06 (GZ-3) | D | D | D | D | D | D | D | D | DI | D | DI | DI | DI |
| 119/06 (GZ-4) | DI | D | D | DI | D | D | D | DI | DI | DI | DI | DI | DI |
| Jinxiu Crab (GZ-5) | D | D | DI | D | I | DI | D | D | DI | DI | DI | I | D |
| Zhizun Fuji (HS-1) | D | DI | D | I | DI | DI | DI | D | D | D | DI | I | D |

| | | | | | | | | | | | | | |
|---|---|---|---|---|---|---|---|---|---|---|---|---|---|
| Construction results of InDel marker genotype database of *Malus* germplasm resources | | | | | | | | | | | | | |
| Fuji No. 1 (HS-10) | D | DI | D | I | DI | DI | DI | D | D | D | DI | I | D |
| Red Jonaprince (HS-12) | DI | DI | DI | DI | DI | DI | DI | DI | DI | DI | DI | DI | DI |
| Nic29 (HS-13) | D | DI | D | D | D | D | D | D | D | D | DI | DI | D |
| Azhen Fuji (HS-14) | D | DI | D | I | DI | DI | DI | D | D | D | DI | I | D |
| Envy (HS-15) | D | D | D | DI | DI | D | D | D | DI | DI | DI | DI | D |
| Rosegrow (HS-16) | DI | I | DI | DI | DI | DI | DI | DI | DI | DI | DI | DI | D |
| Canzy (HS-17) | DI | I | DI | DI | D | DI | D | D | I | DI | DI | DI | D |
| Fubrax (HS-2) | D | DI | D | I | DI | DI | DI | D | D | D | DI | I | D |
| Mitchgla (HS-3) | DI | I | DI | D | DI | DI | D | D | DI | DI | DI | DI | D |
| Fujiko (HS-4) | D | DI | D | I | DI | DI | DI | D | D | D | DI | I | D |
| Buckeye Gala (HS-5) | DI | I | DI | D | DI | DI | D | D | DI | DI | DI | DI | D |
| Fujion (HS-6) | D | DI | D | I | D | D | DI | D | D | DI | DI | DI | D |
| Modi (HS-7) | DI | DI | DI | DI | DI | D | D | D | DI | I | DI | I | D |
| Jiangxue (HS-8) | D | DI | D | D | DI | I | D | D | DI | D | DI | I | D |
| September Wonder Fuji (HS-9) | D | DI | D | I | DI | DI | DI | D | D | D | DI | I | D |
| Linqin Crab (LQ) | D | D | D | D | D | D | D | D | D | DI | D | D | D |
| Lushan Sanye (LSSY) | D | D | D | DI | D | D | D | D | I | I | DI | D | D |
| 83-2 (MDJ-1) | DI | DI | DI | D | DI | D | D | D | DI | D | DI | DI | DI |
| Tianfeng (MDJ-9) | D | D | D | D | DI | D | D | D | I | I | DI | DI | D |
| Oregon Spur II-red (OR-1) | D | DI | D | DI | DI | DI | DI | DI | DI | D | DI | I | D |
| Oregon Spur II-green (OR-2) | D | DI | D | DI | DI | DI | DI | DI | DI | D | DI | I | D |
| E3N2 (OR-3) | D | DI | D | DI | DI | DI | DI | DI | DI | D | DI | I | D |
| E4N1 (OR-4) | D | DI | D | DI | DI | DI | DI | DI | DI | D | DI | I | D |
| E4N2 (OR-5) | D | DI | D | DI | DI | DI | DI | DI | DI | D | DI | I | D |
| W6N1 (OR-6) | D | DI | D | DI | DI | DI | DI | DI | DI | D | DI | I | D |
| W6S5 (OR-7) | D | DI | D | DI | DI | DI | DI | DI | DI | D | DI | I | D |
| W8S3 (OR-8) | D | DI | D | DI | DI | DI | DI | DI | D | D | DI | I | D |
| Daihong (QD-1) | I | D | D | DI | DI | D | D | DI | DI | D | DI | DI | DI |
| Tangmutian (QD-10) | D | DI | D | I | DI | DI | DI | D | D | D | DI | I | D |
| Shanjin Crab N1 (QD-11) | D | D | D | I | D | D | D | D | I | DI | DI | D | D |
| Shanjin Crab N2 (QD-12) | D | D | D | I | D | D | D | D | I | D | DI | D | D |
| E zhen 1 (QD-13) | D | DI | D | D | D | D | D | D | D | DI | D | DI | D |
| E zhen 2 (QD-14) | D | DI | D | D | D | DI | D | DI | D | D | DI | DI | D |
| E zhen 3 (QD-15) | D | DI | D | D | D | D | D | D | I | D | DI | DI | D |
| E zhen 4 (QD-16) | D | DI | D | D | D | DI | D | DI | DI | D | DI | DI | D |
| E zhen 5 (QD-17) | D | DI | D | D | D | DI | D | DI | DI | D | DI | DI | D |
| Haihong (QD-19) | D | DI | DI | DI | D | D | D | D | DI | D | DI | I | D |

| Construction results of InDel marker genotype database of *Malus* germplasm resources | | | | | | | | | | | | | |
|---|---|---|---|---|---|---|---|---|---|---|---|---|---|
| Qingfu 2 (QD-2) | D | DI | D | I | DI | DI | DI | D | D | D | DI | I | D |
| Telamon (QD-20) | D | DI | DI | DI | DI | D | D | D | DI | DI | DI | DI | D |
| Fuyan (QD-21) | D | DI | DI | D | D | D | D | DI | DI | DI | DI | DI | D |
| Hongxun 1 (QD-22) | D | D | D | D | D | DI | D | D | D | D | DI | D | D |
| Rushan Fuji (QD-23) | D | DI | D | I | DI | DI | DI | D | D | D | DI | I | D |
| Jiudian Spur (QD-24) | D | DI | D | I | DI | DI | DI | D | D | D | DI | I | D |
| Ruihong (QD-25) | DI | I | DI | D | DI | DI | D | D | DI | DI | DI | DI | D |
| Zhongnvshi (QD-26) | D | D | DI | D | D | D | D | D | I | I | DI | DI | D |
| 2001 Spur (QD-27) | D | DI | D | I | DI | DI | DI | D | D | D | DI | I | D |
| Fuli (QD-28) | D | DI | D | DI | DI | D | DI | D | DI | D | DI | DI | D |
| Tuanwang semi-Spur (QD-29) | D | DI | D | I | DI | DI | DI | D | D | D | DI | I | D |
| Qingfu 3 (QD-3) | D | DI | D | I | DI | DI | DI | D | D | D | DI | I | D |
| Longfu (QD-30) | D | DI | D | I | DI | DI | DI | D | D | D | DI | I | D |
| Baotou Linqin (QD-31) | I | D | D | D | D | D | D | D | I | D | DI | DI | D |
| Yanfu 6 (QD-32) | D | DI | D | I | DI | DI | DI | D | D | D | DI | I | D |
| SH40-2 seedling (QD-4) | DI | D | D | I | DI | DI | D | D | DI | DI | DI | DI | D |
| Saijin (QD-5) | D | DI | D | D | I | DI | D | D | D | D | DI | I | D |
| Nagafu 12 (QD-6) | D | DI | D | I | DI | DI | DI | D | D | D | DI | I | D |
| Caoyuan Crab (QD-7) | D | D | D | DI | D | D | D | DI | I | DI | I | DI | D |
| Xiaojin Crab (QD-8) | D | D | DI | I | DI | DI | DI | DI | DI | DI | DI | DI | D |
| Shuangyanghong (QD-9) | DI | I | DI | DI | DI | DI | D | D | DI | DI | DI | DI | D |
| Qianxian Crab (QX-1) | D | DI | DI | I | D | D | D | D | I | D | DI | DI | D |
| Ruixue (ruixue) | D | D | D | DI | D | I | DI | DI | D | D | DI | DI | D |
| Ruiyang (RY) | D | D | D | DI | I | D | D | DI | D | D | DI | I | DI |
| Yanyuan 1 (SC-1) | DI | DI | DI | DI | I | DI | DI | DI | DI | DI | DI | DI | D |
| Yanyuan 2 (SC-2) | D | D | D | DI | DI | DI | D | DI | D | DI | DI | DI | DI |
| Yanyuan 3 (SC-3) | D | DI | D | I | DI | DI | DI | D | D | D | DI | I | D |
| Yanyuan 4 (SC-4) | D | D | D | DI | DI | DI | D | D | D | DI | D | DI | DI |
| Yanyuan 5 (SC-5) | D | D | D | DI | DI | DI | D | DI | DI | DI | DI | DI | D |
| Yanyuan 6 (SC-6) | D | D | D | DI | D | DI | D | D | DI | DI | DI | DI | DI |
| Yanyuan 7 (SC-7) | DI | DI | DI | DI | DI | DI | DI | DI | DI | DI | DI | DI | DI |
| Mitchgala (SX-10) | DI | I | DI | D | DI | DI | D | D | D | DI | DI | DI | D |
| Zhongqiuwang Linyi (SX-11) | DI | I | DI | DI | DI | DI | D | DI | DI | D | DI | DI | DI |
| Linyi Meiguo 5 (SX-12) | D | D | D | DI | D | D | DI | DI | D | DI | D | DI | D |
| Liquan Spur Fuji (SX-13) | D | DI | D | I | DI | DI | DI | D | D | D | DI | I | D |
| Qiulimu (SX-14) | D | DI | DI | D | D | DI | D | D | D | DI | DI | DI | D |
| Qincui (SX-15) | D | DI | D | I | DI | I | DI | D | D | D | DI | I | D |
| Taigu Shaguo Late (SX-17) | D | DI | DI | DI | D | D | D | D | DI | D | DI | DI | D |

| Construction results of InDel marker genotype database of *Malus* germplasm resources | | | | | | | | | | | | | |
|---|---|---|---|---|---|---|---|---|---|---|---|---|---|
| Lingyige Hongrou (SX-18) | DI | D | D | DI | D | D | D | D | D | D | DI | DI | D |
| Shenai LS (SX-19) | D | DI | D | DI | D | DI | DI | D | D | D | DI | DI | D |
| Linyi Meiguo 8 (SX-2) | D | D | D | I | D | DI | D | DI | D | DI | DI | DI | DI |
| Liga (SX-20) | DI | I | DI | D | DI | D | D | D | DI | DI | DI | DI | D |
| Y-1 (SX-21) | D | D | DI | I | D | D | D | D | I | D | I | D | D |
| B009 (SX-22) | D | DI | DI | DI | D | D | D | D | DI | D | DI | D | D |
| Jinfu 1 (SX-23) | D | DI | D | I | DI | DI | DI | D | D | D | DI | I | D |
| Hongmantang (SX-24) | D | D | D | DI | D | DI | D | D | DI | D | DI | I | D |
| Y-2 (SX-25) | D | D | DI | I | D | D | D | D | I | D | DI | D | D |
| Y-3 (SX-26) | D | D | DI | I | D | D | D | D | I | D | DI | D | D |
| Xinliangxiang (SX-27) | D | DI | D | I | DI | I | DI | D | D | D | DI | I | D |
| Ennike Gala (SX-28) | DI | I | DI | D | DI | DI | D | D | DI | DI | DI | DI | D |
| Linyi Meiguo 6 (SX-3) | DI | DI | DI | DI | DI | DI | I | DI | D | DI | DI | DI | D |
| Linyi Meiguo 2 (SX-30) | D | DI | D | I | DI | DI | DI | D | D | D | DI | I | D |
| Donglimu (SX-33) | D | DI | DI | D | D | DI | D | D | DI | DI | DI | DI | D |
| Linyi Meiguo 1 (SX-34) | D | D | D | I | D | DI | D | D | DI | DI | DI | DI | DI |
| Linyi Meiguo 4 (SX-4) | DI | DI | DI | I | DI | DI | I | DI | D | D | DI | DI | D |
| Qinyang (SX-6) | DI | DI | DI | DI | D | DI | D | D | D | D | DI | I | D |
| Taiguo Shaguo Early (SX-7) | D | DI | DI | DI | D | D | D | DI | D | DI | DI | DI | D |
| Yuhua Zaofu (SX-8) | D | DI | D | I | DI | DI | DI | D | D | D | DI | I | D |
| 78-M18 (SY-1) | DI | D | D | D | I | DI | DI | D | D | I | DI | I | I |
| Jinping (SY-10) | DI | DI | DI | DI | D | D | D | D | DI | D | DI | DI | D |
| Longqiu (SY-11) | DI | D | D | DI | D | D | D | D | D | D | DI | DI | D |
| Longfeng (SY-12) | D | D | D | D | D | D | D | D | D | D | D | DI | D |
| Xiangjiaoguo (SY-14) | D | D | D | D | DI | DI | DI | DI | DI | I | DI | DI | D |
| Longguan (SY-15) | DI | DI | DI | D | I | D | DI | D | D | I | DI | DI | DI |
| Longshuai (SY-16) | D | D | D | D | D | D | D | DI | D | DI | DI | DI | D |
| Zixiang (SY-17) | D | D | DI | D | D | D | D | D | DI | I | DI | I | D |
| Huahong (SY-19) | D | DI | DI | DI | D | D | D | D | DI | D | DI | DI | D |
| Binlang (SY-2) | D | D | D | D | DI | DI | DI | DI | DI | I | DI | DI | D |
| Qiufengmi (SY-20) | D | D | D | D | D | D | D | D | I | D | D | DI | D |
| Honglingdang (SY-21) | D | D | DI | I | D | D | D | D | DI | I | DI | I | D |
| Qiulu (SY-22) | DI | DI | DI | I | D | D | D | I | D | DI | D | DI | D |
| Longhong (SY-23) | DI | DI | DI | D | I | D | DI | D | D | I | DI | DI | DI |
| Milk (SY-3) | D | D | D | DI | D | D | D | D | DI | DI | D | I | D |
| Hanfu (SY-4) | D | DI | D | DI | DI | D | D | D | DI | D | DI | DI | D |
| Toko (SY-5) | D | D | D | I | D | DI | D | D | D | D | DI | D | D |
| Jinhong (SY-6) | I | DI | DI | D | I | DI | D | DI | DI | I | DI | DI | DI |

-continued

Construction results of InDel marker genotype database of *Malus* germplasm resources

| | | | | | | | | | | | | | |
|---|---|---|---|---|---|---|---|---|---|---|---|---|---|
| K9 (SY-7) | D | D | DI | I | D | D | D | D | DI | I | DI | I | D |
| 03-06-04 (SY-8) | D | D | D | DI | I | D | D | D | DI | D | D | D | D |
| Olga (SY-9) | DI | D | DI | D | D | D | D | D | I | D | DI | DI | D |
| Gala 4x (TA-1) | DI | I | DI | DI | DI | D | Gala | D | DI | DI | DI | DI | D |
| Juda Fuji (TA-11) | D | DI | D | I | DI | DI | DI | D | D | D | DI | I | D |
| Luli (TA-12) | D | DI | D | D | DI | D | D | D | D | D | DI | DI | D |
| Luping 1 (TA-13) | DI | I | DI | DI | DI | DI | D | D | DI | DI | DI | I | D |
| Luping 2 (TA-14) | DI | DI | DI | DI | D | DI | D | D | DI | DI | DI | DI | D |
| Luping 5 (TA-15) | DI | DI | DI | DI | DI | DI | D | D | DI | DI | DI | DI | D |
| Luyan (TA-16) | D | DI | D | D | D | I | D | D | D | D | DI | DI | D |
| Meinong (TA-17) | D | DI | D | I | D | DI | DI | D | D | D | DI | I | D |
| Akifu 19 (TA-18) | D | DI | D | I | DI | DI | DI | D | D | D | DI | I | D |
| Akifu 39 (TA-19) | D | DI | D | DI | DI | DI | DI | D | D | D | DI | I | D |
| Hanfu 4x (TA-2) | D | D | D | D | DI | D | DI | D | I | I | D | DI | DI |
| Qiufuhong (TA-20) | D | DI | D | I | DI | DI | DI | D | D | D | DI | I | D |
| Qunfu 1 (TA-21) | D | DI | D | I | DI | DI | DI | D | D | D | DI | I | D |
| Shengfang (TA-22) | D | DI | D | I | DI | DI | DI | D | D | D | DI | I | D |
| Alps Otome (TA-27) | D | DI | D | DI | DI | D | DI | D | D | D | DI | DI | D |
| Early Fuji (TA-28) | D | DI | D | I | DI | DI | DI | D | D | D | DI | I | D |
| BP (TA-3) | D | D | D | D | D | DI | D | D | DI | D | DI | DI | D |
| Yishuihong (TA-32) | D | DI | D | I | DI | DI | DI | D | D | D | DI | I | D |
| BP-176 (TA-4) | D | DI | D | D | D | DI | D | D | DI | D | DI | DI | D |
| G41 (TA-5) | I | D | DI | I | D | DI | D | D | DI | D | DI | DI | D |
| G935 (TA-6) | I | D | D | D | D | DI | DI | D | DI | D | DI | DI | D |
| P60 (TA-7) | DI | D | D | D | D | I | DI | D | D | DI | DI | DI | D |
| Fuji (TA-9) | D | DI | D | I | DI | DI | DI | D | D | D | DI | I | D |
| Tianfu 1 (TS-1) | D | DI | D | I | DI | DI | DI | D | D | D | DI | I | D |
| &28 (TS-13) | D | DI | D | I | DI | DI | DI | D | D | D | DI | I | D |
| Red Chief (TS-14) | D | DI | D | DI | DI | DI | DI | DI | D | D | DI | I | D |
| New Redchief (TS-2) | D | DI | D | DI | DI | DI | DI | DI | D | D | DI | I | D |
| Chaohongxing (TS-3) | D | DI | D | DI | DI | DI | DI | D | D | DI | DI | I | D |
| Aozhou 1 (TS-5) | DI | D | D | D | D | I | DI | D | I | D | DI | I | D |
| Tianfu 2 (TS-6) | D | DI | D | I | DI | DI | DI | D | D | D | DI | I | D |
| Judeline (TS-7) | DI | DI | DI | I | I | D | D | DI | DI | DI | DI | DI | DI |
| Judestar (TS-8) | D | D | DI | DI | DI | D | D | DI | I | DI | DI | DI | DI |
| Judaine (TS-9) | DI | DI | DI | I | I | D | D | DI | DI | DI | DI | DI | DI |
| WH-5 (WH-1) | D | DI | D | I | DI | DI | DI | D | D | D | DI | I | D |
| Italy Smothe (WH-10) | DI | DI | DI | DI | I | DI | DI | DI | DI | DI | DI | DI | DI |
| Bai Crab (WH-2) | D | DI | D | D | D | D | D | D | I | D | DI | DI | D |

-continued

| Construction results of InDel marker genotype database of *Malus* germplasm resources |||||||||||||||
|---|---|---|---|---|---|---|---|---|---|---|---|---|---|
| Hongguang (WH-4) | D | DI | D | I | DI | DI | D | D | DI | D | DI | DI | D |
| Huangcui (WH-5) | D | D | D | DI | DI | DI | D | D | DI | D | DI | DI | D |
| Qinglin (WH-6) | DI | D | DI | DI | DI | DI | DI | D | D | I | DI | DI | DI |
| Harlikar (WH-8) | DI | DI | DI | DI | DI | DI | D | DI | DI | D | DI | DI | D |
| Italy Gala (WH-9) | DI | I | DI | D | DI | DI | D | D | DI | DI | DI | DI | D |
| Wushan Bianye (WSBY) | D | D | D | I | D | D | D | D | D | D | DI | D | D |
| Xin 1 (XC-1) | D | I | D | D | D | D | D | D | D | D | DI | DI | D |
| Xin 5 (XC-2) | D | I | D | D | D | I | D | D | D | D | DI | DI | D |
| Hanfu 3x (XC-3) | D | D | D | I | I | D | D | D | D | D | DI | DI | D |
| Gala 4x (XC-4) | DI | I | DI | D | DI | DI | D | D | DI | DI | DI | DI | D |
| Weizhimuben (XC-5) | DI | D | D | DI | D | DI | DI | D | I | D | DI | DI | D |
| Chaguo (XC-CG) | D | D | D | D | D | D | D | D | DI | D | DI | DI | D |
| Donghongguo (XC-DHG) | D | D | D | D | D | D | DI | D | I | D | DI | DI | D |
| Fuxian Sanye (XC-FXXY) | D | D | D | I | D | D | D | D | I | D | DI | D | D |
| Hongsanye (XC-HSY) | D | D | D | I | D | D | D | D | I | D | DI | D | D |
| Jilin Xiaohong Crab (XC-JILINXIAOHONG-HAITANG) | D | D | D | D | D | D | D | D | I | I | DI | DI | D |
| Jilin Xiaohuang Crab (XC-JILINXIAOHUANG-HAITANG) | DI | D | D | D | D | D | D | D | I | D | DI | DI | D |
| Jilin Huang Crab (XC-JLHHT) | DI | D | D | D | D | D | D | D | I | D | DI | DI | D |
| Shajin Crab (XC-JSHT) | DI | D | D | I | D | D | D | D | I | D | DI | D | D |
| Longdong Crab (XC-LDHT) | D | D | D | I | D | D | D | D | I | D | DI | DI | D |
| Lushi Crab (XC-LSHT) | D | D | D | I | D | D | D | D | D | D | I | D | D |
| Laiwunanyan (XC-LWNY) | D | D | D | D | D | D | D | D | DI | D | DI | DI | D |
| Linzhi (XC-LZ) | D | D | D | I | D | D | D | D | I | D | DI | DI | D |
| Mao Shandingzi (XC-MSDZ) | D | D | D | I | D | D | D | D | D | DI | DI | D | D |
| Pingyitiancha (XC-PYTC) | D | D | D | I | D | D | D | D | D | D | I | D | D |
| Qiuzi (XC-QZ) | D | D | D | D | D | D | D | D | D | D | DI | DI | D |
| Sichuan Bianye (XC-SCBY) | D | D | D | I | D | D | D | D | I | D | DI | D | D |
| Shandingzi (XC-SDZ) | D | D | D | I | D | D | D | D | I | D | DI | D | D |
| Weixi Sanye (XC-WXSY) | D | D | D | I | D | D | D | D | D | D | DI | DI | D |
| Xifu Crb (XC-XFHT) | D | DI | D | I | D | D | D | D | I | D | DI | D | D |
| Xiaojin Bianye (XC-XJBY) | D | D | D | DI | D | D | D | D | I | D | DI | D | D |
| Xinjiang Yepingguo (XC-XJYHT) | D | D | D | DI | D | D | D | D | I | D | DI | DI | D |
| Yajiang Bianye (XC-YJBY) | D | D | D | D | D | D | D | D | I | D | DI | D | D |
| Yingye Crab (XC-YYHT) | D | D | D | I | D | D | D | D | D | DI | DI | D | D |
| Zhaai (XC-ZA) | D | D | D | I | D | D | D | D | I | D | DI | D | D |
| Zumi Crab (XC-ZMHT) | D | D | D | DI | D | D | D | D | I | D | DI | DI | D |

-continued

| Construction results of InDel marker genotype database of *Malus* germplasm resources | | | | | | | | | | | | | |
|---|---|---|---|---|---|---|---|---|---|---|---|---|---|
| Pink Lady (XN-FHNS) | DI | I | DI | DI | DI | DI | DI | DI | DI | DI | DI | DI | D |
| Hongrou 1 (XN-HR1) | D | I | D | D | D | D | D | D | DI | DI | DI | DI | D |
| Hongrou 2 (XN-HR2) | D | D | DI | D | D | D | D | D | DI | D | DI | DI | D |
| Hongrou 3 (XN-HR3) | D | D | D | D | D | D | D | D | DI | D | DI | DI | D |
| Hongrou 4 (XN-HR4) | D | D | D | D | D | D | D | D | I | DI | DI | DI | D |
| Hongrou 5 (XN-HR5) | I | D | D | D | D | D | D | D | DI | D | DI | DI | D |
| Hongrou 6 (XN-HR6) | DI | D | DI | I | D | D | DI | D | DI | D | DI | DI | D |
| Hongrou 7 (XN-HR7) | D | DI | DI | D | D | D | D | D | I | DI | DI | I | D |
| Ambrosia (XN-MW) | DI | I | DI | DI | DI | D | DI | DI | D | D | DI | DI | D |
| Xinjiang 10 (XN-XJ10) | D | D | D | D | D | D | D | DI | I | D | DI | DI | D |
| Xinjiang 11 (XN-XJ11) | D | DI | DI | D | D | D | D | D | I | D | D | I | D |
| Xinjiang 12 (XN-XJ12) | D | D | D | D | D | D | D | DI | I | D | DI | DI | D |
| Xinjiang 13 (XN-XJ13) | D | D | D | D | D | DI | D | D | I | I | DI | DI | D |
| Xinjiang 14 (XN-XJ14) | D | DI | DI | D | D | DI | D | DI | DI | D | DI | I | D |
| Xinjiang 15 (XN-XJ15) | D | DI | D | D | DI | D | D | DI | DI | D | DI | DI | D |
| Xinjiang 16 (XN-XJ16) | D | DI | DI | D | D | DI | D | D | DI | DI | DI | DI | D |
| Xinjiang 17 (XN-XJ17) | D | D | D | DI | D | D | D | D | D | D | D | I | D |
| Xinjiang 18 (XN-XJ18) | DI | D | D | DI | D | D | D | D | DI | D | DI | DI | D |
| Xinjiang 19 (XN-XJ19) | D | D | D | D | D | D | DI | I | D | DI | DI | D |  |
| Xinjiang 2 (XN-XJ2) | D | DI | D | D | D | D | D | D | DI | D | DI | DI | D |
| Xinjiang 20 (XN-XJ20) | DI | D | D | D | D | D | D | DI | DI | DI | DI | D |  |
| Xinjiang 21 (XN-XJ21) | D | D | D | D | D | DI | D | DI | I | DI | DI | DI | D |
| Xinjiang 23 (XN-XJ23) | D | DI | D | D | D | D | DI | I | DI | DI | DI | D |  |
| Xinjiang 24 (XN-XJ24) | DI | D | D | DI | D | DI | D | D | DI | D | DI | DI | D |
| Xinjiang 25 (XN-XJ25) | I | DI | D | I | D | D | D | DI | D | D | DI | DI | D |
| Xinjiang 27 (XN-XJ27) | D | DI | D | D | DI | D | D | DI | DI | D | DI | DI | D |
| Xinjiang 3 (XN-XJ3) | D | D | D | D | D | D | D | D | DI | DI | DI | DI | D |
| Xinjiang 4 (XN-XJ4) | DI | D | D | D | DI | D | D | DI | I | D | DI | DI | D |
| Xinjiang 5 (XN-XJ5) | D | D | D | D | D | D | D | I | D | D | DI | D | D |
| Xinjiang 7 (XN-XJ7) | D | D | D | D | D | D | D | D | DI | D | DI | DI | D |
| Xinjiang 8 (XN-XJ8) | D | D | DI | D | D | DI | D | D | I | D | D | DI | D |
| Xinjiang 9 (XN-XJ9) | D | DI | D | D | D | D | D | DI | DI | D | DI | D | D |
| Yueguan (XY-10) | D | DI | D | DI | DI | D | DI | DI | D | D | DI | DI | D |
| Yuehua (XY-11) | DI | D | D | DI | D | D | D | D | D | D | DI | DI | D |
| Yueyan (XY-12) | D | DI | D | DI | D | DI | D | D | DI | D | DI | DI | D |
| Bud Sport 5 (XY-13) | D | DI | D | I | DI | DI | DI | D | D | D | DI | I | D |
| Bud Sport 3 (XY-14) | D | DI | D | I | DI | DI | DI | D | D | D | DI | I | D |
| Longfu (XY-15) | D | DI | D | I | DI | DI | D | D | D | DI | I | D |  |
| Yuemei (XY-18) | D | DI | D | D | DI | I | D | DI | DI | DI | DI | DI | DI |

-continued

| Construction results of InDel marker genotype database of Malus germplasm resources | | | | | | | | | | | | | | |
|---|---|---|---|---|---|---|---|---|---|---|---|---|---|---|
| Hanfu (XY-2) | D | DI | D | DI | D | D | D | D | DI | D | DI | DI | D |
| Linyi Fuji (XY-20) | D | DI | D | I | DI | I | D | DI | D | D | DI | I | D |
| Yishui Fuji (XY-22) | D | DI | D | I | DI | DI | DI | D | D | D | DI | I | D |
| Hongjinfu (XY-25) | D | DI | D | I | DI | DI | DI | D | D | D | DI | I | D |
| Beni Oshu (XY-26) | D | DI | D | I | DI | DI | DI | D | D | D | DI | I | D |
| Chuizhi Fuji (XY-27) | D | DI | D | I | DI | DI | D | D | D | D | DI | I | D |
| Yueshuai (XY-28) | DI | DI | DI | DI | DI | D | I | DI | DI | D | DI | DI | D |
| Shichinohe 2 (XY-29) | D | DI | D | DI | DI | DI | DI | D | D | D | DI | I | D |
| 74-178 (XY-3) | D | DI | D | D | DI | D | D | D | DI | D | DI | DI | DI |
| KAKUFUJI (XY-30) | D | DI | D | I | DI | DI | DI | D | D | D | DI | I | D |
| Royal Fuji 21 (XY-35) | D | DI | D | I | DI | DI | DI | D | D | D | DI | I | D |
| Qiquan Spur (XY-36) | D | DI | D | I | DI | DI | DI | D | D | D | DI | I | D |
| Juda Fuji (XY-37) | D | DI | D | I | DI | DI | D | D | DI | D | DI | DI | D |
| 7-211 (XY-4) | D | DI | D | D | DI | DI | D | DI | DI | DI | DI | DI | DI |
| Yanfu 0 (XY-41) | D | DI | D | I | DI | DI | DI | D | D | D | DI | I | D |
| Spur Fuji (XY-42) | D | DI | D | I | DI | DI | DI | D | D | D | DI | I | D |
| Bayue fushiwang (XY-43) | D | DI | D | I | DI | DI | DI | D | D | D | DI | I | D |
| Huangfu 7 (XY-44) | D | DI | D | DI | DI | DI | DI | D | D | D | DI | I | D |
| Aomori Spur Fuji (XY-46) | D | DI | D | I | DI | DI | DI | D | D | D | DI | I | D |
| Qiu Fuji (XY-47) | D | DI | D | I | DI | DI | DI | D | D | D | DI | I | D |
| Fuji Champion (XY-48) | D | DI | D | I | DI | DI | DI | D | D | D | DI | I | D |
| 26-34 (XY-5) | D | D | D | DI | DI | D | DI | DI | DI | D | DI | I | D |
| Akifu 19 (XY-50) | D | DI | D | I | DI | DI | DI | D | D | D | DI | I | D |
| Fuji (XY-54) | D | DI | D | I | DI | DI | DI | D | D | D | DI | I | D |
| Qinfu 1 (XY-55) | D | DI | D | I | DI | DI | DI | D | D | D | DI | I | D |
| Feng Fuji (XY-56) | D | DI | D | I | DI | DI | DI | D | D | D | DI | I | D |
| Tianxing (XY-57) | D | DI | D | I | DI | DI | DI | D | D | D | DI | I | D |
| Taiyang Fuji (XY-58) | D | DI | D | I | DI | DI | DI | D | D | D | DI | I | D |
| Cherry Crab (XY-6) | D | DI | D | DI | D | D | DI | D | DI | D | DI | DI | D |
| Yueping (XY-60) | D | D | D | I | DI | D | DI | D | DI | D | DI | I | D |
| 23-63 (XY-61) | D | D | D | I | D | DI | D | D | DI | D | DI | I | D |
| 23-42 (XY-62) | D | DI | D | I | DI | DI | D | D | DI | D | DI | DI | D |
| 7-171 (XY-63) | D | DI | D | D | DI | DI | D | D | I | DI | DI | DI | DI |
| Shengfang 3A (XY-65) | D | DI | D | I | DI | DI | DI | D | D | D | DI | I | D |
| Meinong Fuji (XY-67) | D | DI | D | I | DI | DI | DI | D | D | D | DI | I | D |
| 62-45 (XY-68) | D | I | D | DI | DI | D | DI | D | DI | D | DI | DI | D |
| Fengfeng Fuji (XY-70) | D | DI | D | I | DI | DI | DI | D | D | D | DI | I | D |
| GM256 (XY-71) | D | DI | D | I | DI | DI | DI | D | D | D | DI | I | D |

| Construction results of InDel marker genotype database of *Malus* germplasm resources | | | | | | | | | | | | | |
|---|---|---|---|---|---|---|---|---|---|---|---|---|---|
| Jinfu 2 (XY-73) | D | DI | D | I | DI | DI | DI | D | D | D | DI | I | D |
| Qiufu (XY-75) | D | DI | D | I | DI | DI | DI | D | D | D | DI | I | D |
| Shanfu 6 (XY-76) | D | DI | D | I | DI | DI | DI | D | D | D | DI | I | D |
| Nagafu 8 (XY-77) | D | DI | D | I | DI | DI | DI | D | D | D | DI | I | D |
| 58-34 (XY-78) | D | D | D | D | D | D | DI | DI | DI | D | DI | DI | D |
| 2001 Fuji (XY-79) | D | DI | D | I | DI | DI | D | D | D | D | DI | I | D |
| 15-26 (XY-8) | D | DI | DI | DI | DI | I | D | D | DI | DI | DI | I | DI |
| Wangshanhong (XY-80) | D | DI | D | I | DI | I | DI | D | D | D | DI | I | D |
| Jinfu 1 (XY-81) | D | DI | D | DI | DI | DI | DI | D | D | D | DI | I | D |
| Qingfu 1 (XY-84) | D | DI | D | I | DI | DI | DI | D | D | D | DI | I | D |
| Qiufu 39 (XY-85) | D | DI | D | I | DI | DI | DI | D | D | D | DI | I | D |
| Nagafu 1 (XY-86) | D | DI | D | I | DI | DI | DI | D | D | D | DI | I | D |
| Shou Fuji (XY-87) | D | DI | D | I | D | DI | DI | D | D | D | DI | I | D |
| Yueli (XY-88) | DI | DI | DI | D | DI | I | D | D | DI | DI | DI | I | DI |
| Shanfu 2 (XY-89) | D | DI | D | I | DI | DI | DI | D | D | D | DI | I | D |
| Chongban Crab (XY-9) | D | D | D | D | D | D | D | D | I | D | DI | DI | D |
| Harica (XY-90) | DI | D | DI | DI | DI | DI | DI | D | D | I | DI | DI | DI |
| Akifu 1 (XY-91) | D | DI | D | I | DI | DI | DI | D | D | D | DI | I | D |
| Wangfu (XY-92) | D | DI | D | I | DI | DI | DI | D | D | D | DI | I | D |
| Hong Manao (XYZ-1) | D | DI | DI | I | D | D | D | D | DI | D | DI | DI | D |
| Modi (XYZ-10) | DI | DI | DI | DI | DI | D | D | D | I | DI | DI | DI | D |
| C37 (XYZ-11) | D | DI | D | DI | DI | I | DI | DI | DI | D | DI | DI | D |
| Envy ? (XYZ-12) | D | DI | D | DI | DI | D | D | D | I | DI | DI | DI | D |
| Xichang Yuanzhuiguo (XYZ-2) | D | D | DI | DI | D | DI | D | D | D | D | DI | DI | D |
| Ziye Zixiaoguo (XYZ-3) | D | D | D | I | D | D | D | D | DI | D | DI | DI | D |
| Ziye Zidaguo (XYZ-4) | D | D | DI | I | D | DI | D | D | DI | D | DI | DI | D |
| Shoufenshu 6 (XYZ-5) | D | D | D | D | D | D | D | D | D | D | DI | DI | D |
| Changhua (XYZ-6) | DI | I | DI | D | DI | DI | D | D | D | DI | DI | DI | D |
| Jinshiji (XYZ-7) | DI | I | DI | D | DI | DI | D | D | DI | DI | DI | DI | D |
| 19-147 (XYZ-9) | I | D | DI | DI | I | DI | D | DI | DI | D | D | I | D |
| Malong Gala 1 (YN-1) | DI | I | DI | D | DI | DI | D | D | DI | DI | DI | DI | D |
| Shouer hong (YN-11) | D | DI | D | I | DI | DI | DI | D | D | D | DI | I | D |
| Yun Hongrou (YN-12) | D | DI | D | I | D | D | D | D | D | D | DI | DI | DI |
| Lixing Crab (YN-13) | D | DI | DI | DI | D | D | D | D | I | D | DI | DI | D |
| Siana (YN-15) | D | D | D | DI | DI | D | D | D | DI | D | DI | DI | D |
| Jonathan-M41 (YN-17) | D | DI | D | DI | D | DI | D | D | DI | D | DI | DI | D |
| Morlie's Delicious (YN-18) | DI | I | DI | D | I | I | D | DI | DI | I | DI | DI | I |
| Britegold (YN-19) | D | DI | D | I | DI | I | DI | D | D | D | DI | I | D |

-continued

| Construction results of InDel marker genotype database of *Malus* germplasm resources | | | | | | | | | | | | | |
|---|---|---|---|---|---|---|---|---|---|---|---|---|---|
| Malong Gala 1 blush (YN-2) | DI | I | DI | D | DI | DI | D | D | DI | DI | DI | DI | D |
| Line 5 (YN-22) | D | D | D | DI | DI | D | D | D | DI | D | DI | DI | D |
| Line 6 (YN-23) | DI | D | D | DI | I | DI | DI | D | D | D | DI | I | D |
| Line 13 (YN-24) | I | DI | I | DI | DI | D | DI | DI | I | D | DI | DI | DI |
| row 3 (YN-25) | D | DI | D | D | DI | DI | D | D | D | D | DI | DI | D |
| row 4 (YN-26) | D | DI | D | D | D | D | D | D | D | D | D | DI | D |
| row 5 (YN-27) | D | DI | D | D | DI | DI | D | D | D | D | DI | DI | D |
| row 6 (YN-28) | D | DI | D | D | DI | DI | D | D | D | D | DI | DI | D |
| row 9 (YN-29) | DI | DI | D | DI | DI | D | D | D | D | DI | DI | I | D |
| Malong xin Gala 1 (YN-3) | DI | I | DI | D | DI | DI | D | D | DI | DI | DI | DI | D |
| row 10 (YN-30) | DI | I | DI | DI | DI | DI | DI | DI | DI | DI | DI | DI | D |
| row 11 (YN-31) | DI | DI | D | DI | D | D | D | D | D | DI | DI | I | D |
| row 12 (YN-32) | DI | I | DI | D | DI | DI | D | D | DI | DI | DI | DI | D |
| row 13 (YN-33) | D | DI | D | D | D | I | D | D | D | D | DI | DI | D |
| row 14 (YN-34) | D | DI | D | D | DI | DI | D | D | D | D | DI | DI | D |
| row 15 (YN-35) | DI | I | DI | DI | DI | DI | D | D | DI | DI | DI | I | D |
| row 16 (YN-36) | DI | DI | DI | DI | DI | DI | DI | DI | DI | DI | DI | DI | D |
| row 17 (YN-37) | D | D | D | DI | DI | DI | D | DI | DI | DI | DI | DI | D |
| row 18 (YN-38) | D | D | D | DI | D | DI | D | D | DI | DI | DI | DI | DI |
| row 19 (YN-39) | D | D | D | I | D | DI | D | D | DI | DI | DI | DI | D |
| Malong xin Gala 1 strip (YN-4) | DI | I | DI | D | DI | DI | D | D | DI | DI | DI | DI | D |
| row 20 (YN-40) | D | D | D | DI | DI | DI | D | DI | D | DI | DI | DI | DI |
| row 21 (YN-41) | D | DI | D | I | DI | DI | DI | D | D | D | DI | I | D |
| row 22 (YN-42) | D | D | D | DI | DI | DI | D | DI | D | DI | DI | DI | DI |
| row 23 (YN-43) | D | D | D | DI | DI | DI | D | D | D | DI | DI | DI | DI |
| row 24 (YN-44) | D | DI | D | I | DI | DI | D | D | D | DI | DI | I | D |
| row 25 (YN-45) | D | DI | D | I | DI | DI | DI | D | D | D | DI | I | D |
| Malong Gala2 (YN-5) | DI | I | DI | D | DI | DI | D | D | DI | DI | DI | DI | D |
| Malong Gala 2 blush (YN-6) | DI | I | DI | D | DI | DI | D | D | DI | DI | DI | DI | D |
| Longwei (YN-7) | D | I | D | DI | D | DI | DI | D | D | D | D | DI | D |
| Longwei Early Mutant (YN-8) | D | I | D | DI | D | DI | DI | D | D | D | D | DI | D |
| Cherry Gala (YN-9) | DI | I | DI | D | DI | DI | D | D | DI | DI | DI | DI | D |
| Siyana (YT-1) | DI | DI | D | I | D | D | D | D | D | I | DI | I | D |
| Yanfu 10 (YT-100) | D | DI | D | I | DI | I | DI | D | D | D | DI | I | D |
| Chadel (YT-102) | DI | D | D | DI | D | DI | D | DI | D | DI | DI | DI | D |
| Charden (YT-103) | DI | D | DI | DI | DI | DI | D | DI | D | DI | DI | DI | D |
| Tuskan (YT-104) | DI | DI | DI | DI | DI | D | DI | D | D | DI | DI | DI | DI |
| Prima × Sekaiichii (YT-105) | D | DI | D | I | I | DI | D | D | DI | D | DI | I | D |

-continued

Construction results of InDel marker genotype database of *Malus* germplasm resources

| | | | | | | | | | | | | | |
|---|---|---|---|---|---|---|---|---|---|---|---|---|---|
| Toppax_apple (YT-11) | DI | DI | D | I | I | DI | DI | D | D | I | DI | DI | D |
| Xinjiang Hongrou Crab (YT-12) | D | D | D | DI | D | D | D | D | I | DI | DI | D | D |
| Melfree (YT-13) | DI | DI | DI | I | DI | D | DI | D | DI | DI | DI | DI | D |
| Yanfu 3 (YT-14) | D | DI | D | DI | D | DI | DI | DI | D | DI | DI | DI | D |
| Gold milecnirum (YT-15) | D | DI | DI | DI | DI | DI | D | D | DI | DI | DI | I | D |
| Ganhong (YT-16) | D | I | D | D | DI | D | I | DI | D | DI | DI | DI | DI |
| Cornoet (YT-17) | D | DI | DI | I | D | DI | DI | D | D | DI | D | DI | D |
| Priw (YT-18) | DI | DI | D | DI | D | D | DI | DI | D | DI | D | DI | D |
| Aichi (YT-19) | D | DI | DI | DI | DI | D | D | D | DI | DI | DI | DI | D |
| Auraria (YT-2) | DI | D | D | I | DI | D | D | DI | DI | D | DI | I | D |
| Meile (YT-20) | D | DI | D | I | DI | DI | DI | D | D | D | DI | I | D |
| Qiulimeng (YT-21) | D | DI | DI | D | D | DI | D | D | DI | DI | D | DI | D |
| Aliusitan (YT-22) | D | D | D | D | D | DI | D | D | I | DI | DI | DI | D |
| Geaooza (YT-23) | D | D | DI | D | DI | D | D | D | DI | D | DI | DI | D |
| Golden Spur (YT-24) | DI | DI | DI | DI | I | DI | DI | DI | DI | DI | DI | DI | DI |
| Starking (YT-25) | D | DI | D | DI | DI | DI | DI | DI | D | D | DI | I | D |
| Indo (YT-26) | D | DI | D | I | DI | DI | I | D | D | DI | DI | DI | D |
| Teser (YT-27) | D | DI | D | DI | I | I | DI | DI | D | D | D | DI | D |
| Xianhong (YT-28) | D | DI | DI | I | DI | I | DI | DI | DI | D | DI | I | D |
| Gala × Mato 8 (YT-29) | D | DI | D | D | D | I | D | D | DI | D | DI | DI | D |
| Very Early Fuji (YT-3) | D | DI | D | I | DI | DI | DI | D | D | D | DI | I | D |
| Qiuhuapi (YT-30) | DI | D | DI | DI | DI | D | I | D | DI | D | D | DI | D |
| Piga 70 (YT-31) | D | I | D | DI | I | DI | D | D | DI | D | DI | DI | DI |
| Yanzhen 1 (YT-32) | DI | DI | I | DI | D | DI | D | D | DI | D | DI | I | D |
| Matail (YT-34) | DI | I | DI | D | DI | DI | D | D | DI | DI | DI | DI | D |
| Jonathan-csan (YT-35) | D | DI | D | DI | D | DI | D | DI | D | DI | DI | DI | D |
| Huashuai (YT-36) | D | D | D | DI | D | D | DI | DI | DI | D | DI | I | D |
| Wengao 1 (YT-38) | D | DI | D | I | DI | DI | D | D | DI | D | DI | I | D |
| Wengao 2 (YT-39) | D | DI | D | I | DI | DI | D | DI | D | DI | D | I | D |
| Elegia (YT-4) | D | I | D | D | DI | D | D | DI | DI | D | D | I | D |
| Wengao 3 (YT-40) | D | DI | D | I | D | DI | D | DI | D | DI | D | I | D |
| Hong Anka (YT-41) | D | DI | D | DI | DI | DI | D | DI | DI | D | DI | DI | D |
| Yanfu 2 (YT-42) | D | DI | D | I | DI | DI | DI | D | I | D | DI | I | D |
| Belgolden (YT-43) | DI | DI | DI | DI | I | DI | DI | DI | D | DI | DI | DI | DI |
| Rubinola (YT-44) | D | D | D | DI | DI | D | DI | D | D | D | DI | I | D |
| Wangqiuhong (YT-45) | DI | DI | DI | D | I | I | DI | D | DI | D | DI | I | DI |
| Pulanhong (YT-46) | D | D | D | DI | D | D | D | D | D | DI | DI | I | D |
| Bosh (YT-47) | DI | D | DI | DI | DI | D | I | D | D | D | DI | DI | D |

-continued

Construction results of InDel marker genotype database of *Malus* germplasm resources

| | | | | | | | | | | | | | |
|---|---|---|---|---|---|---|---|---|---|---|---|---|---|
| Chengji 1 (YT-48) | D | DI | D | I | DI | DI | DI | D | D | D | DI | I | D |
| Hongli (YT-49) | D | D | D | I | D | DI | D | D | DI | I | DI | I | D |
| Guoqinghong (YT-5) | DI | DI | DI | DI | DI | I | DI | DI | D | D | DI | DI | D |
| Reandra (YT-50) | DI | I | DI | DI | I | D | D | DI | D | D | DI | DI | DI |
| Revbihola (YT-51) | D | D | D | DI | I | DI | DI | DI | D | D | DI | I | D |
| Melrose (YT-52) | D | I | D | DI | DI | DI | DI | DI | D | D | DI | DI | D |
| Rewena (YT-53) | D | D | D | D | D | D | D | D | D | D | DI | I | DI |
| Mrxl(robusta × Liberte) (YT-54) | D | DI | D | DI | DI | I | DI | DI | D | D | D | I | D |
| Mollies_Del_open (YT-55) | D | D | D | I | DI | D | DI | DI | DI | DI | DI | DI | DI |
| Renora (YT-56) | I | DI | DI | I | I | DI | DI | D | D | I | DI | DI | D |
| Rosmadzin (YT-57) | DI | D | DI | DI | DI | D | I | D | D | D | DI | DI | D |
| Remo (YT-58) | D | I | D | DI | D | I | D | D | D | DI | DI | DI | D |
| Pilot (YT-59) | D | D | D | I | DI | DI | DI | DI | D | I | DI | DI | D |
| Yangbai Crab (YT-6) | D | D | D | D | D | D | D | D | I | D | DI | DI | D |
| Free Red Star (YT-60) | DI | D | D | I | D | DI | DI | D | DI | D | DI | I | D |
| Idared (YT-61) | D | D | D | D | DI | D | DI | D | D | D | DI | DI | D |
| Mingyue (YT-62) | D | DI | D | I | DI | DI | D | DI | D | DI | DI | DI | D |
| Piga 101 (YT-63) | D | DI | D | I | D | DI | D | DI | D | DI | DI | DI | D |
| Yanfu 5 (YT-64) | D | DI | D | I | DI | DI | D | D | D | D | DI | I | D |
| Early Jonagold (YT-65) | DI | DI | DI | DI | DI | DI | DI | DI | D | DI | DI | DI | DI |
| Wengao 2 mutant (YT-66) | D | DI | D | I | DI | DI | D | D | D | D | DI | I | D |
| Fenhong Gala 44 (YT-67) | D | I | DI | DI | D | I | D | DI | D | I | DI | DI | D |
| Yiyuanhong (YT-68) | D | DI | D | I | DI | DI | DI | D | D | D | DI | I | D |
| Yanfu 4 (YT-69) | D | DI | D | I | DI | DI | DI | D | D | D | DI | I | D |
| White Pearmain (YT-70) | D | DI | D | I | D | DI | DI | D | D | D | D | DI | D |
| Jonathan-early (YT-73) | D | DI | D | DI | D | DI | DI | D | D | D | DI | DI | D |
| Jonathan-midle (YT-74) | D | DI | D | DI | D | DI | DI | D | D | D | DI | DI | D |
| Gornan (YT-75) | D | D | D | D | DI | D | DI | D | D | D | DI | DI | D |
| RegiIndel (YT-76) | D | D | D | DI | I | DI | DI | DI | DI | D | DI | I | D |
| Golden Bell (YT-77) | DI | I | DI | DI | DI | DI | D | DI | DI | I | DI | DI | DI |
| Arkcharm (YT-78) | DI | DI | DI | DI | DI | DI | D | D | DI | D | DI | DI | D |
| Redchif (YT-79) | D | D | DI | DI | I | D | D | DI | I | D | DI | I | D |
| Mouping Guanghua Fuji (YT-8) | D | DI | D | I | DI | DI | DI | D | D | D | DI | I | D |
| Freedom (YT-80) | D | D | D | I | DI | DI | DI | D | I | DI | DI | DI | D |
| Martinike (YT-81) | DI | DI | D | I | D | D | DI | D | D | D | D | DI | D |
| Sweetle (YT-82) | D | I | D | DI | D | DI | D | DI | D | DI | DI | DI | D |
| Aleksanader (YT-83) | D | DI | D | DI | D | D | D | D | D | DI | DI | I | D |
| Yan 6 Fenhong 143 (YT-84) | D | I | DI | DI | DI | I | DI | DI | D | DI | DI | DI | D |

-continued

| Construction results of InDel marker genotype database of *Malus* germplasm resources | | | | | | | | | | | | | |
|---|---|---|---|---|---|---|---|---|---|---|---|---|---|
| Ruitina (YT-85) | D | D | D | DI | DI | D | D | DI | D | DI | DI | I | DI |
| Wengao 1 mutant (YT-86) | D | DI | D | I | DI | DI | DI | D | D | D | DI | I | D |
| Wengao 3 mutant (YT-87) | D | DI | D | I | DI | DI | DI | D | D | D | DI | I | D |
| Shajinyilamu (YT-88) | D | DI | D | D | D | D | D | D | D | D | D | DI | D |
| Qiuhong (YT-89) | D | DI | DI | I | D | D | I | D | DI | D | DI | I | D |
| Changyanghong (YT-9) | D | DI | D | I | DI | DI | D | D | D | D | DI | I | D |
| Yanfu 8 (YT-90) | D | DI | D | I | DI | DI | DI | D | D | D | DI | I | D |
| Jinduhong Gala (YT-91) | DI | I | DI | D | DI | DI | D | D | D | DI | DI | DI | D |
| Nagafu 2 (YT-92) | D | DI | D | I | DI | DI | DI | D | D | D | DI | I | D |
| Honglu seedling 65 (YT-93) | D | I | DI | I | DI | D | DI | D | D | D | DI | I | D |
| Tsugaru (YT-94) | D | D | D | DI | DI | DI | D | DI | DI | DI | DI | DI | DI |
| Jinshuai mutant (YT-95) | DI | DI | DI | DI | I | DI | DI | D | DI | DI | DI | DI | DI |
| Taishan Crab (YT-96) | D | D | D | DI | D | I | D | D | D | D | DI | DI | D |
| Luli (YT-98) | D | DI | D | D | DI | DI | D | D | DI | D | DI | DI | D |
| 10-182 (YX-10-182) | D | D | D | I | DI | DI | D | D | D | D | DI | DI | D |
| 01-001 (YX-01-001) | D | DI | D | I | D | DI | DI | D | DI | D | DI | DI | D |
| 01-121 (YX-01-121) | D | DI | D | I | I | D | D | D | D | D | DI | DI | D |
| 02-009 (YX-02-009) | D | DI | D | I | D | DI | D | D | D | D | DI | DI | D |
| 03-010 (YX-03-010) | D | DI | D | I | DI | DI | D | D | D | DI | DI | DI | D |
| 03-111 (YX-03-111) | D | D | D | I | I | D | I | D | DI | DI | DI | DI | D |
| 04-033 (YX-04-033) | D | D | D | I | D | DI | D | D | DI | DI | DI | DI | D |
| 04-087 (YX-04-087) | D | D | D | I | DI | D | I | D | D | D | DI | DI | D |
| 06-056 (YX-06-056) | D | DI | D | I | DI | D | DI | D | D | D | DI | DI | D |
| 08-034 (YX-08-034) | D | DI | D | I | D | D | DI | D | D | D | DI | DI | D |
| 09-037 (YX-09-037) | D | D | D | I | DI | D | DI | D | DI | DI | DI | DI | D |
| 09-079 (YX-09-079) | D | DI | D | I | D | DI | DI | D | D | D | DI | DI | D |
| 10-010 (YX-10-010) | D | DI | D | I | I | D | D | D | DI | D | DI | DI | D |
| 11-037 (YX-11-037) | D | D | D | I | D | DI | D | D | D | D | DI | DI | D |
| 11-206 (YX-11-206) | D | DI | D | I | D | DI | DI | D | DI | D | DI | DI | D |
| 12-206 (YX-12-206) | D | DI | D | I | I | D | D | D | DI | DI | DI | DI | D |
| 13-025 (YX-13-025) | D | DI | D | I | D | D | I | D | DI | D | DI | DI | D |
| 16-155 (YX-16-155) | D | D | D | I | D | DI | DI | D | D | D | DI | DI | D |
| 16-157 (YX-16-157) | D | D | D | I | DI | DI | DI | D | DI | D | DI | DI | D |
| 17-023 (YX-17-023) | D | D | D | I | I | D | D | D | D | D | DI | DI | D |
| 17-199 (YX-17-199) | D | D | D | I | I | DI | DI | D | D | D | DI | DI | D |
| 21-005 (YX-21-005) | D | D | D | I | I | D | D | D | DI | DI | DI | DI | D |
| 21-018 (YX-21-018) | D | DI | DI | DI | I | DI | D | D | DI | DI | DI | DI | D |
| 22-186 (YX-22-186) | DI | DI | DI | I | I | DI | DI | D | DI | DI | DI | DI | D |

-continued

| Construction results of InDel marker genotype database of *Malus* germplasm resources | | | | | | | | | | | | | |
|---|---|---|---|---|---|---|---|---|---|---|---|---|---|
| 27-003 (YX-27-003) | D | D | D | DI | DI | DI | DI | DI | DI | DI | DI | DI | DI |
| 29-176 (YX-29-176) | DI | DI | DI | DI | DI | D | DI | DI | I | DI | DI | DI | D |
| 30-001 (YX-30-001) | D | DI | DI | DI | I | DI | D | D | D | DI | DI | DI | D |
| 33-018 (YX-33-018) | D | DI | D | I | I | DI | I | D | D | D | D | DI | D |
| 33-101 (YX-33-101) | D | D | D | I | D | D | D | D | D | D | D | DI | DI | D |
| 33-151 (YX-33-151) | D | D | D | DI | I | DI | DI | DI | I | D | DI | DI | D |
| 51-007 (YX-51-007) | D | I | DI | DI | DI | I | DI | D | I | D | DI | DI | D |
| 51-031 (YX-51-031) | DI | I | DI | I | DI | DI | DI | D | DI | D | DI | DI | D |
| 51-077 (YX-51-077) | DI | DI | DI | DI | DI | D | I | DI | D | DI | DI | DI | D |
| 51-102 (YX-51-102) | D | I | D | DI | DI | DI | DI | D | DI | DI | DI | DI | D |
| 51-139 (YX-51-139) | D | DI | D | DI | DI | DI | I | DI | DI | D | DI | DI | DI |
| 51-165 (YX-51-165) | D | I | D | DI | DI | DI | DI | DI | D | DI | DI | DI | DI |
| 51-166 (YX-51-166) | DI | I | DI | I | DI | DI | D | DI | I | DI | DI | DI | D |
| 51-209 (YX-51-209) | DI | DI | DI | D | DI | DI | D | DI | D | DI | DI | DI | D |
| 52-049 (YX-52-049) | DI | DI | DI | D | DI | D | D | DI | D | DI | DI | DI | D |
| 52-151 (YX-52-151) | D | I | D | I | DI | I | DI | DI | I | D | DI | DI | DI |
| 52-160 (YX-52-160) | D | D | D | DI | DI | D | I | D | I | D | DI | DI | DI |
| 53-040 (YX-53-040) | DI | DI | DI | D | DI | DI | DI | D | I | D | DI | DI | DI |
| 53-205 (YX-53-205) | D | I | D | DI | D | DI | DI | D | DI | D | DI | DI | D |
| 54-001 (YX-54-001) | D | DI | D | DI | DI | I | D | D | DI | DI | DI | DI | D |
| 54-188 (YX-54-188) | DI | DI | DI | DI | DI | DI | DI | D | D | DI | DI | DI | D |
| 55-006 (YX-55-006) | D | DI | D | I | DI | D | DI | DI | DI | DI | DI | DI | DI |
| 55-023 (YX-55-023) | DI | I | DI | DI | DI | DI | I | DI | I | D | DI | DI | D |
| 55-042 (YX-55-042) | DI | I | DI | D | DI | DI | I | D | I | D | DI | DI | D |
| 56-081 (YX-56-081) | DI | DI | DI | DI | DI | D | D | D | DI | DI | DI | DI | DI |
| 57-128 (YX-57-128) | D | DI | D | DI | DI | DI | I | DI | DI | D | DI | DI | DI |
| 58-036 (YX-58-036) | D | D | D | D | DI | DI | I | D | I | DI | DI | DI | DI |
| 58-089 (YX-58-089) | DI | DI | D | DI | DI | DI | D | D | DI | DI | DI | DI | DI |
| 58-144 (YX-58-144) | DI | DI | DI | I | DI | DI | DI | D | D | DI | DI | DI | D |
| 58-177 (YX-58-177) | D | DI | D | D | DI | DI | DI | D | DI | DI | DI | DI | D |
| 58-211 (YX-58-211) | DI | I | DI | D | DI | I | DI | DI | DI | DI | DI | DI | DI |
| 59-086 (YX-59-086) | D | DI | DI | DI | DI | I | D | D | DI | DI | DI | DI | DI |
| 59-130 (YX-59-130) | DI | I | DI | D | DI | DI | DI | DI | DI | D | DI | DI | DI |
| Jersey Mac (Z-1) | D | D | D | I | D | D | I | D | DI | DI | DI | I | D |
| Gale Gala (Z-10) | DI | I | DI | D | DI | DI | DI | D | DI | DI | DI | DI | D |
| Li Gala (Z-11) | DI | I | DI | D | DI | DI | DI | D | DI | DI | DI | DI | D |
| Yanga 1 (Z-12) | DI | I | DI | D | DI | DI | D | D | DI | DI | DI | DI | D |
| NAKT M9 clone (Z-13) | D | DI | D | D | D | D | D | D | D | D | DI | DI | D |

-continued

| Construction results of InDel marker genotype database of *Malus* germplasm resources | | | | | | | | | | | | | |
|---|---|---|---|---|---|---|---|---|---|---|---|---|---|
| Royal Gala (Z-14) | DI | I | DI | D | DI | DI | D | D | DI | DI | DI | DI | D |
| Huajia (Z-15) | D | DI | DI | I | D | D | D | D | I | D | DI | I | D |
| Dorsett Golden (Z-16) | D | D | D | D | D | I | D | DI | D | DI | DI | I | DI |
| 99-2-58 (Z-17) | D | DI | D | I | D | D | D | D | DI | D | DI | I | D |
| Galaxy (Z-18) | DI | I | DI | D | DI | DI | D | D | DI | DI | DI | DI | D |
| Royal New Gala (Z-19) | DI | I | DI | D | DI | DI | D | D | DI | DI | DI | DI | D |
| 99-1-29 (Z-22) | D | D | D | DI | D | DI | D | D | DI | DI | DI | DI | D |
| Seokwang (Z-23) | D | D | D | DI | D | DI | D | DI | DI | I | DI | DI | DI |
| Fuhong Zaoga (Z-24) | DI | I | DI | D | DI | DI | D | D | DI | DI | DI | DI | D |
| Maiyan (Z-25) | DI | D | D | DI | D | D | D | D | DI | DI | DI | I | D |
| Shandong 1 (Z-26) | DI | I | DI | D | DI | DI | D | D | DI | DI | DI | DI | D |
| Gala Queen (Z-27) | DI | I | DI | D | DI | DI | D | D | DI | DI | DI | DI | D |
| 99-2-39 (Z-29) | D | D | D | I | D | D | D | D | I | DI | DI | I | D |
| Sweetle (Z-3) | D | I | D | DI | D | I | DI | D | D | D | DI | DI | D |
| Dalian Da Gala (Z-30) | DI | I | DI | D | DI | DI | D | D | DI | DI | DI | DI | D |
| Huaxing (Z-31) | D | DI | D | D | DI | DI | D | D | DI | DI | DI | DI | D |
| Li Gala (Z-32) | DI | I | DI | D | DI | DI | D | D | DI | DI | DI | DI | D |
| Fuhong Zaoga (Z-33) | DI | DI | DI | DI | D | D | D | D | DI | D | DI | DI | D |
| Yanga (Z-34) | DI | DI | DI | DI | D | D | D | D | DI | D | DI | DI | D |
| Royal Gala (Z-35) | DI | I | DI | D | DI | DI | D | D | DI | DI | DI | DI | D |
| Shijiazhuang Gala (Z-37) | DI | I | DI | D | DI | DI | D | D | DI | DI | DI | DI | D |
| Taihong Gala (Z-38) | DI | I | DI | D | DI | DI | D | D | DI | DI | DI | DI | D |
| Anna (Z-39) | DI | D | DI | DI | D | DI | D | D | DI | D | DI | DI | DI |
| Hong Zhenzhu (Z-4) | DI | DI | DI | D | DI | D | D | D | DI | D | DI | I | D |
| Qiuhong Gala (Z-40) | D | D | D | DI | DI | DI | D | DI | D | DI | DI | DI | DI |
| Shandong 2 (Z-41) | DI | I | DI | D | DI | DI | D | D | DI | DI | DI | DI | D |
| Shandong 6 (Z-42) | DI | I | DI | D | DI | DI | D | D | DI | DI | DI | DI | D |
| Chenyang (Z-43) | DI | DI | D | DI | D | DI | DI | D | DI | DI | DI | DI | I |
| Dongqie Gala (Z-44) | D | I | D | DI | D | I | D | D | DI | DI | DI | DI | D |
| Royal Gala (Z-45) | DI | I | DI | D | DI | DI | D | D | DI | DI | DI | DI | D |
| Taishan Gala (Z-47) | DI | I | DI | D | DI | DI | D | D | DI | DI | DI | DI | D |
| Shandong 7 (Z-48) | DI | I | DI | D | DI | DI | D | D | DI | DI | DI | DI | D |
| Regal gala (Z-49) | DI | I | DI | D | DI | DI | D | D | DI | DI | DI | DI | D |
| NAKB clone (Z-5) | D | DI | D | D | D | D | D | D | D | D | DI | DI | D |
| Royal gala (Z-50) | DI | I | DI | D | DI | DI | D | D | DI | DI | DI | DI | D |
| Znoga (Z-51) | DI | DI | D | D | DI | DI | D | DI | DI | DI | DI | DI | D |
| Shandong 5 (Z-52) | DI | I | DI | D | DI | DI | D | D | DI | DI | DI | DI | D |
| Rockit (Z-53) | DI | I | DI | D | DI | DI | DI | DI | DI | DI | DI | DI | D |

-continued

Construction results of InDel marker genotype database of *Malus* germplasm resources

| | | | | | | | | | | | | | |
|---|---|---|---|---|---|---|---|---|---|---|---|---|---|
| Shandong 3 (Z-54) | DI | I | DI | D | DI | DI | D | D | DI | DI | DI | DI | D |
| Mondel Gala (Z-55) | DI | I | DI | D | DI | DI | D | D | DI | DI | DI | DI | D |
| Alvinagala (Z-56) | DI | I | DI | D | DI | DI | D | D | DI | DI | DI | DI | D |
| M9 pajam2 (Z-6) | D | DI | D | D | D | D | D | D | D | D | DI | DI | D |
| Jinshiji (Z-7) | DI | I | DI | D | DI | DI | D | D | DI | DI | DI | DI | D |
| Huarui (Z-8) | D | D | D | DI | DI | D | D | D | DI | D | DI | DI | D |
| Hongcuibao (Z-9) | DI | DI | DI | DI | D | I | D | D | I | D | DI | DI | D |

| Accession name (Accession ID) | C07047 | C07050 | C08051 | C08054 | C08059 | C08060 | C09062 | C09063 | C09064 | C09067 | C10070 | C10071 | C10072 |
|---|---|---|---|---|---|---|---|---|---|---|---|---|---|
| Black Ben Davis (10--1) | DI | DI | D | DI | DI | DI | DI | I | D | DI | D | D | I |
| Lysgolden (10--10) | D | DI | DI | DI | DI | DI | DI | I | D | D | D | D | DI |
| Dongchengguan 13 (10--11) | D | DI | DI | DI | DI | DI | DI | I | D | D | D | D | DI |
| Nagafu 1 (10--12) | D | DI | DI | DI | DI | DI | DI | I | D | D | D | D | DI |
| Shengli Hongguan (10--14) | DI | D | D | D | I | D | D | DI | DI | D | D | D | D |
| Shizishan 1 (10--15) | DI | D | D | D | I | D | D | DI | DI | D | D | D | D |
| Baoman (10--2) | D | DI | D | D | I | DI | DI | I | D | D | DI | D | I |
| Melba (10--20) | D | DI | D | D | I | D | D | DI | DI | D | DI | I | D |
| Kuliesa (10--21) | DI | DI | D | D | DI | DI | DI | DI | DI | D | D | DI | |
| De 8 (10--22) | D | DI | DI | DI | I | I | DI | DI | D | D | DI | DI | DI |
| Bo 5 (10--23) | D | DI | DI | D | DI | D | DI | DI | D | D | D | D | D |
| Iran Pippin (10--4) | D | D | D | D | I | D | I | DI | I | D | D | D | I |
| Sakatakei Tsugaru (10--5) | DI | DI | DI | D | DI | D | DI | DI | D | D | DI | D | I |
| Khrushchev (10--6) | D | D | DI | D | I | DI | I | DI | D | D | D | DI | I |
| Batul (10--7) | D | D | D | D | D | DI | DI | I | D | DI | DI | I | I |
| Prime Gold (10--9) | D | D | D | D | D | DI | DI | I | D | DI | DI | DI | I |
| Jie 1 (11--0) | DI | DI | D | D | D | D | D | DI | D | D | D | D | DI |
| Guldborg (1--11) | D | DI | DI | DI | DI | DI | DI | I | D | D | D | D | DI |
| Shajin Yilamu (11--10) | D | D | D | D | D | D | DI | I | I | I | DI | I | I |
| Soviet (11--11) | D | I | D | D | D | D | DI | I | D | DI | D | DI | DI |
| Lobo (11--13) | D | DI | D | D | DI | D | DI | DI | DI | D | D | DI | DI |
| Allington Pippin (11--14) | D | I | D | D | DI | DI | DI | DI | I | D | D | D | I |
| Malinova (11--15) | D | D | D | D | DI | D | DI | I | D | D | DI | I | D |
| Sweet McIntosh (11--16) | D | D | D | D | DI | D | DI | I | D | D | DI | I | D |
| McIntosh (11--18) | DI | DI | DI | I | I | DI | DI | DI | D | DI | D | D | I |
| Spartan (11--2) | D | DI | DI | D | I | D | DI | DI | I | DI | D | DI | DI |
| Fushuai (1--12) | DI | I | DI | D | I | DI | DI | DI | I | I | DI | DI | I |
| Summer Pearmain (11--20) | D | D | D | I | I | D | DI | DI | DI | D | D | I | I |
| Helm (11--21) | D | D | D | DI | I | DI | D | DI | DI | D | DI | DI | DI |
| Domenesti (11--3) | DI | D | DI | D | DI | DI | DI | DI | DI | D | D | DI | DI |

| Construction results of InDel marker genotype database of *Malus* germplasm resources | | | | | | | | | | | | | |
|---|---|---|---|---|---|---|---|---|---|---|---|---|---|
| Early Harvest (1--13) | DI | I | DI | D | I | DI | DI | DI | I | I | DI | DI | I |
| Silver Spur Red Delicious (11--4) | D | D | DI | I | I | D | I | I | DI | DI | D | D | DI |
| Dongxiangjiao (11--5) | D | DI | DI | D | I | DI | DI | DI | DI | D | D | D | DI |
| Guoling (1--15) | DI | DI | D | D | I | D | D | I | D | D | DI | DI | DI |
| Skyline Spureme (11--8) | D | D | DI | I | I | D | I | I | DI | DI | D | D | DI |
| Chantecler (11--9) | DI | D | DI | DI | I | D | I | I | D | D | D | D | DI |
| Close (1--19) | DI | DI | D | D | D | DI | DI | DI | I | DI | D | D | DI |
| Aizaohui (1--2) | DI | DI | D | D | DI | D | DI | DI | D | D | DI | DI | DI |
| Wuyue (12--1) | D | DI | D | D | D | D | I | I | D | D | I | DI | DI |
| Bukowka (12--11) | DI | D | D | D | I | DI | DI | I | DI | I | D | D | D |
| Jinyu (12--12) | DI | DI | D | D | D | D | DI | D | D | D | D | D | DI |
| Calville Rouge (12--14) | DI | D | DI | D | DI | DI | D | DI | D | D | D | D | I |
| Doyle (12--15) | D | I | D | D | DI | D | D | D | D | D | DI | DI | DI |
| Melrose (12--16) | DI | DI | DI | DI | DI | D | DI | DI | DI | DI | D | D | DI |
| Menage (12--17) | D | DI | D | D | I | D | I | I | D | D | DI | D | DI |
| Bo 26 (12--18) | D | D | D | DI | I | DI | DI | DI | I | D | D | DI | I |
| Duoyilu (12--19) | D | DI | D | DI | DI | D | DI | DI | DI | DI | D | D | DI |
| De 6 (12--20) | D | D | D | DI | I | DI | I | DI | I | DI | DI | D | I |
| Red June (12--21) | D | DI | D | D | D | DI | DI | DI | DI | DI | D | D | DI |
| Helasang (12--23) | D | DI | D | DI | I | D | DI | DI | I | DI | D | DI | D |
| Hesetiaowen (12--3) | D | D | D | D | I | D | I | I | D | D | DI | D | I |
| James Grieve (1--23) | D | I | DI | D | I | D | DI | DI | DI | D | I | I | I |
| Bailuosi Malin (12--4) | D | D | D | D | I | D | D | I | I | I | DI | I | DI |
| Jinnhong (12--5) | I | I | D | D | DI | D | DI | I | D | D | D | D | D |
| Kay Sai William (12--6) | D | DI | DI | D | I | D | DI | DI | I | DI | D | DI | DI |
| Xingjiang Pingguo (12--7) | D | D | D | D | D | D | D | I | I | I | DI | I | I |
| Jie 15 (12--8) | D | D | DI | DI | I | D | I | I | DI | DI | D | D | DI |
| Mianpingguo (12--9) | D | D | D | D | DI | D | DI | DI | I | I | D | I | I |
| Lowver (1--3) | D | D | D | D | D | D | I | DI | DI | DI | I | DI | DI |
| Benoni (13--1) | DI | DI | DI | D | I | D | DI | DI | DI | D | D | D | I |
| Fa 5 (13--11) | DI | DI | DI | D | DI | DI | DI | DI | D | D | D | D | DI |
| Babskino (13--12) | D | D | D | D | I | D | I | I | DI | I | DI | DI | DI |
| Kuluona (13--13) | DI | D | DI | D | DI | DI | DI | DI | I | D | D | D | DI |
| Shidonghaoji (13--16) | DI | D | D | D | I | D | D | DI | DI | D | D | D | DI |
| Oberkika (13--17) | DI | D | D | DI | I | D | DI | DI | D | D | DI | DI | DI |
| Budayi (13--19) | D | DI | DI | DI | DI | DI | DI | I | D | D | D | D | DI |
| Red Canada (13--2) | DI | DI | DI | D | DI | DI | DI | DI | D | D | D | D | DI |
| Laidi (13--20) | DI | DI | D | DI | I | D | D | I | DI | D | DI | I | DI |

| Construction results of InDel marker genotype database of *Malus* germplasm resources | | | | | | | | | | | | | |
|---|---|---|---|---|---|---|---|---|---|---|---|---|---|
| N2 (13--22) | DI | DI | D | D | DI | DI | DI | I | DI | DI | D | D | D |
| Norsan (13--5) | D | D | DI | DI | I | D | I | I | DI | DI | D | D | DI |
| Hebei Kangbing Golden Delicious (13--6) | DI | I | DI | D | I | D | DI | DI | D | D | D | D | DI |
| Zhanxuan 14 (13--9) | D | DI | DI | DI | DI | DI | DI | I | D | D | D | D | DI |
| Xiangguoguang (14--11) | DI | D | DI | D | I | D | DI | I | D | D | DI | DI | DI |
| Shengfang 1 (14--14) | DI | DI | D | D | DI | DI | DI | I | DI | DI | D | D | D |
| Yujing II (14--16) | DI | DI | D | D | DI | DI | DI | I | DI | DI | D | D | D |
| Cox's Orange Pippin (14--2) | D | I | D | DI | I | DI | DI | I | D | D | D | D | I |
| Nagafu 7 (14--20) | DI | DI | D | D | DI | DI | DI | I | DI | DI | D | D | D |
| Boiken (14--21) | D | DI | D | DI | I | DI | I | DI | DI | D | DI | DI | DI |
| Qunfu 1 (14--23) | DI | DI | D | D | DI | DI | DI | I | DI | DI | D | D | D |
| Calville Blanche (14--3) | D | DI | D | D | I | DI | I | DI | DI | D | DI | DI | DI |
| Freybreg (14--4) | DI | I | DI | DI | I | DI | I | DI | DI | DI | DI | DI | DI |
| Husveti Rosmaring (14--5) | DI | D | D | DI | I | I | D | I | DI | D | DI | DI | DI |
| Sweet Jonathan (14--7) | DI | DI | D | D | D | D | D | DI | D | D | D | D | DI |
| King of Pippin (14--8) | D | I | D | DI | I | DI | DI | I | D | D | D | D | I |
| Duchess of Oldenburg (1--5) | D | DI | DI | D | D | I | I | I | D | DI | D | DI | D |
| Kangbing Golden 5 (15--11) | I | DI | DI | DI | I | DI | DI | DI | DI | DI | DI | DI | I |
| Pingzhi Ralls Janet (15--15) | DI | I | DI | D | DI | DI | D | I | D | D | D | D | DI |
| Wase16 (15--16) | DI | DI | DI | DI | I | DI | DI | DI | I | DI | DI | DI | I |
| Kogetsu (15--17) | DI | DI | DI | DI | DI | DI | DI | I | DI | DI | DI | DI | I |
| Jonared (15--18) | DI | DI | D | D | DI | D | D | DI | D | D | D | D | DI |
| Zhanxuan 4 (15--21) | D | DI | DI | DI | DI | DI | DI | I | D | D | D | D | DI |
| Strawberry (15--23) | DI | D | D | D | D | I | I | I | DI | D | D | D | DI |
| StarkSpur Ultra Red Delicious (15--3) | D | D | DI | DI | I | D | I | I | DI | DI | D | D | DI |
| Sharp Red Delicious (15--4) | D | D | DI | DI | I | D | I | I | DI | DI | D | D | DI |
| Mensi (15--5) | DI | D | DI | D | DI | D | I | DI | D | DI | D | D | DI |
| Norand (15--6) | D | I | DI | D | I | D | D | DI | DI | D | I | D | D |
| Zhanxuan 18 (15--7) | D | D | DI | DI | I | D | I | I | DI | DI | D | D | DI |
| Xishan 1 (15--8) | D | D | DI | DI | I | D | I | I | DI | DI | D | D | DI |
| Hongrou Pingguo (15--9) | D | D | DI | DI | DI | D | D | DI | I | I | I | DI | I |
| Gravenstein (1--6) | D | D | DI | DI | I | D | I | DI | DI | D | DI | DI | DI |
| Xinhong (16--1) | D | D | DI | DI | DI | D | DI | I | DI | D | DI | D | DI |
| Zhanxuan 6 (16--10) | D | D | D | D | I | D | I | I | D | I | I | I | I |
| Behene (16--11) | D | D | D | D | I | D | I | DI | DI | D | D | DI | DI |
| Xindong (16--14) | D | DI | D | D | I | D | DI | I | DI | D | DI | DI | DI |

-continued

| Construction results of InDel marker genotype database of *Malus* germplasm resources | | | | | | | | | | | | | |
|---|---|---|---|---|---|---|---|---|---|---|---|---|---|
| Hardi Brite (16--16) | D | D | DI | DI | I | D | I | I | DI | DI | D | D | DI |
| Charden (16--17) | DI | DI | DI | DI | I | DI | DI | DI | DI | DI | DI | D | DI |
| Zhuoai 1 (16--2) | D | DI | DI | DI | DI | DI | DI | I | D | D | D | D | DI |
| Jinse Luosuoshan (16--22) | D | I | D | D | I | D | DI | DI | D | DI | DI | DI | DI |
| Zhaiteng II (16--23) | DI | DI | D | D | D | DI | DI | I | DI | DI | D | D | D |
| Zhanxuan 16 (16--6) | D | DI | DI | DI | DI | DI | DI | I | D | D | D | D | DI |
| Fa 3 (16--8) | DI | D | DI | D | DI | DI | DI | DI | DI | D | D | DI | DI |
| Jerseymac (1--7) | D | DI | D | D | I | D | DI | I | I | D | DI | DI | DI |
| Mother (17--1) | DI | D | DI | D | I | DI | I | DI | D | D | D | DI | I |
| Northern Spy (17--10) | I | DI | DI | DI | DI | I | DI | DI | I | I | DI | DI | I |
| Rome Beauty (17--11) | D | I | D | D | DI | DI | D | DI | D | D | DI | DI | DI |
| Black Ben David (17--12) | D | DI | D | DI | DI | DI | I | DI | D | DI | D | D | DI |
| Atlas (17--13) | D | I | D | D | I | DI | D | DI | DI | D | D | DI | D |
| Roxbury (17--14) | DI | DI | DI | D | I | DI | D | DI | I | D | D | D | I |
| Laxtons Superb (17--15) | D | D | DI | D | I | DI | I | DI | DI | D | D | DI | DI |
| Changhong (17--16) | DI | I | D | D | DI | DI | D | DI | D | D | D | D | DI |
| Cogswell Pearmain (17--17) | DI | DI | DI | D | DI | DI | I | I | DI | D | DI | I | I |
| Twenty Ounce (17--18) | D | DI | D | DI | DI | DI | DI | DI | D | DI | D | D | DI |
| Lowtosh (17--19) | DI | DI | D | D | I | DI | DI | DI | DI | DI | D | D | D |
| Iwaki (17--21) | DI | DI | D | D | I | I | DI | I | D | D | DI | DI | DI |
| Qin'guan (17--22) | DI | DI | DI | DI | DI | DI | DI | DI | D | DI | DI | DI | I |
| Bancroft (17--23) | D | I | DI | DI | I | D | I | DI | DI | DI | D | DI | DI |
| Chenango Strawberry (17--4) | D | D | D | D | I | DI | DI | DI | DI | I | DI | DI | DI |
| Newfane (17--7) | DI | DI | DI | D | I | DI | DI | I | D | D | D | D | D |
| Lord Lambourne (17--9) | I | DI | DI | DI | DI | I | DI | DI | I | I | DI | DI | I |
| Rizhiwan (18--0) | D | D | D | D | DI | DI | I | DI | I | D | DI | DI | D |
| Campbell (18--11) | DI | DI | DI | D | I | DI | D | DI | I | D | D | D | I |
| Pigeon (18--13) | D | D | DI | D | I | D | DI | I | D | D | D | D | DI |
| Summer Champion (18--14) | D | DI | D | DI | I | I | DI | DI | D | D | D | D | I |
| Nanpu 3 (18--15) | D | I | DI | D | DI | DI | DI | I | D | D | D | D | DI |
| Qiulimeng (18--16) | D | D | D | D | D | D | DI | I | DI | D | DI | DI | I |
| Rutosh (18--17) | D | DI | D | D | I | D | DI | DI | I | DI | D | DI | D |
| Xinlimei (18--19) | DI | DI | D | DI | I | D | D | I | DI | D | DI | I | DI |
| Huanong 1 (18--2) | D | D | D | D | DI | D | D | DI | DI | D | DI | D | D |
| Lawfam (18--20) | D | DI | D | D | I | D | DI | DI | DI | D | D | DI | DI |
| Akin's Red (18--21) | DI | DI | D | D | D | D | DI | DI | D | D | D | D | D |
| Meltosh (18--22) | D | DI | D | D | I | D | DI | DI | I | D | D | DI | DI |
| Hubbardston (18--23) | DI | I | DI | DI | I | DI | I | DI | DI | DI | DI | DI | DI |
| Fenghuangluan Crab (18--3) | D | D | D | D | DI | D | D | DI | DI | D | DI | D | D |

-continued

| Construction results of InDel marker genotype database of *Malus* germplasm resources | | | | | | | | | | | | | |
|---|---|---|---|---|---|---|---|---|---|---|---|---|---|
| Jie 9 (18--4) | D | D | D | D | DI | DI | DI | DI | DI | DI | DI | D | DI |
| Bramley's Seedling (18--5) | D | DI | D | DI | I | DI | DI | DI | DI | D | DI | DI | I |
| Shuangyang 1 (18--7) | DI | I | DI | DI | I | DI | I | DI | DI | DI | DI | DI | DI |
| Shengli (18--8) | DI | I | DI | DI | I | DI | I | DI | DI | DI | DI | DI | DI |
| Qingguan (18--9) | DI | DI | DI | D | I | I | D | I | DI | D | D | D | DI |
| Weeping Ralls (19--0) | DI | I | DI | D | DI | D | I | D | D | D | D | D | DI |
| Giant Jeniton (19--1) | D | DI | D | D | I | D | I | I | D | D | DI | D | DI |
| Baldwin (19--10) | D | DI | D | DI | I | DI | I | DI | DI | D | D | D | DI |
| Lele Fuji (19--11) | DI | DI | D | D | DI | DI | DI | I | DI | DI | D | D | D |
| Shuahong (19--12) | D | DI | D | D | I | DI | DI | DI | DI | D | DI | D | DI |
| Red Fuji TAO (19--14) | DI | DI | D | D | DI | DI | DI | I | DI | DI | D | D | D |
| Jizaohong (19--17) | DI | I | DI | DI | I | DI | I | DI | DI | DI | DI | D | DI |
| Karas Tor (19--19) | DI | D | D | D | I | D | DI | DI | D | DI | D | D | I |
| Ralls Janet (19--2) | DI | I | DI | D | DI | DI | D | I | D | D | D | D | DI |
| Stonetosh (19--22) | D | DI | DI | DI | I | D | D | DI | I | D | D | I | D |
| White Pearmain (19--23) | DI | DI | DI | D | I | DI | DI | I | D | DI | D | D | I |
| Xiushui Guoguang (19--3) | D | DI | DI | D | I | DI | DI | I | D | D | D | D | DI |
| Chimeric Ralls Janet (19--4) | DI | I | DI | D | DI | DI | D | I | D | D | D | D | I |
| Mutsu (19--7) | I | DI | DI | DI | I | DI | DI | DI | DI | DI | DI | DI | DI |
| Ben David (19--8) | D | DI | D | DI | DI | DI | I | DI | D | DI | D | D | DI |
| Saint Lawrence (19--9) | D | D | D | DI | I | DI | DI | DI | D | D | DI | I | DI |
| Newtosh (20--0) | D | I | D | D | D | D | DI | I | I | I | I | D | D |
| Geliekekukui (20--1) | DI | D | D | D | I | I | DI | DI | I | D | I | I | DI |
| Sweet Jonathan (20--10) | DI | DI | D | D | D | D | D | DI | D | D | D | D | DI |
| Apple of Commerce (20--11) | D | I | D | DI | I | D | I | I | D | D | D | D | D |
| 600 g Andong (20--12) | D | D | D | D | I | D | I | DI | DI | D | D | D | DI |
| Winter Banana (20--14) | DI | DI | DI | D | I | DI | I | DI | DI | D | D | D | D |
| Rainier (20--15) | D | DI | DI | I | I | D | DI | D | D | DI | DI | DI | I |
| Winesap (20--16) | D | DI | DI | D | I | D | I | DI | D | D | DI | D | DI |
| Drumbo (20--17) | D | DI | D | D | I | D | DI | DI | I | D | D | D | DI |
| Blengstid Gaurd (20--2) | DI | D | DI | D | DI | DI | DI | DI | DI | D | D | D | DI |
| Jierjisi (20--21) | D | D | D | D | DI | D | DI | DI | I | DI | DI | D | I |
| Radiant (20--23) | D | I | D | D | D | D | DI | I | I | I | I | D | D |
| King David (20--5) | DI | I | D | D | DI | D | DI | I | D | D | D | D | DI |
| Clapp's Seedling (20--6) | DI | DI | DI | D | I | I | D | I | DI | D | D | D | DI |
| Ingram (20--7) | D | DI | DI | D | D | DI | D | I | D | D | DI | DI | I |
| Qiujin (20--8) | D | DI | DI | DI | DI | DI | DI | I | D | D | D | D | DI |
| Sujsleppskoe (2--1) | D | D | DI | DI | DI | DI | I | I | I | I | D | D | DI |

| Construction results of InDel marker genotype database of *Malus* germplasm resources | | | | | | | | | | | | | |
|---|---|---|---|---|---|---|---|---|---|---|---|---|---|
| Qian 1 Ace (21--0) | DI | DI | D | D | DI | DI | DI | I | DI | DI | D | D | D |
| Toko (2--10) | I | DI | DI | DI | I | DI | DI | I | D | I | DI | DI | DI |
| Antalue (21--1) | DI | I | DI | D | I | DI | DI | DI | I | DI | D | I | DI |
| Boskoopske Cervene (2--11) | DI | D | DI | D | DI | DI | DI | DI | DI | D | D | DI | DI |
| Heoersitai (21--10) | D | DI | D | D | I | DI | I | DI | DI | D | D | DI | I |
| Lanfengwang (21--11) | D | DI | D | DI | I | D | I | DI | I | D | D | D | DI |
| Aohong (21--14) | I | DI | DI | DI | I | DI | DI | DI | D | DI | I | I | DI |
| Weiqinni (21--15) | D | DI | D | D | DI | DI | I | DI | D | D | D | D | DI |
| Smoothee (21--17) | DI | DI | DI | DI | I | DI | DI | DI | DI | DI | DI | DI | I |
| Hongzhiwu (21--18) | DI | D | D | D | DI | D | DI | DI | D | D | DI | DI | I |
| Jieba (21--2) | D | I | D | D | I | D | DI | DI | I | D | DI | DI | I |
| Kizashi (21--20) | DI | DI | DI | D | I | D | I | DI | D | D | D | D | DI |
| Aifeng (21--21) | DI | DI | DI | D | I | D | I | DI | D | D | D | D | DI |
| Xingping (21--4) | DI | I | DI | D | DI | DI | D | I | D | D | D | D | DI |
| Esopus Spitzenburg (2--14) | DI | DI | D | D | DI | D | DI | I | D | D | D | D | DI |
| Lvguang (21--6) | D | D | D | D | I | D | DI | DI | I | I | D | DI | I |
| Nvyoujidui (2--16) | DI | D | D | D | I | D | D | DI | D | D | D | D | D |
| Bell Poos (21--7) | D | D | DI | D | I | DI | DI | DI | D | D | I | DI | DI |
| Tian Andongnuo (2--17) | D | D | D | D | I | D | DI | DI | I | D | I | D | I |
| Pacific Rose (21--8) | I | DI | DI | DI | I | DI | DI | DI | D | DI | I | I | DI |
| 500 g (21--9) | D | DI | D | D | DI | D | DI | DI | D | D | DI | DI | I |
| Nvyoujidui 2 (2--19) | D | D | DI | DI | DI | DI | I | I | I | I | D | D | DI |
| Tian Andongnuo 2 (2--2) | D | I | D | D | I | D | DI | DI | D | D | D | D | DI |
| Spur Mutsu (22--1) | I | DI | DI | DI | I | DI | DI | DI | DI | D | DI | DI | DI |
| Red June Sweet (2--21) | DI | D | D | D | I | DI | DI | I | DI | I | D | D | DI |
| Chu Tsugaru (22--11) | DI | DI | DI | DI | DI | D | DI | DI | D | D | D | D | I |
| Kermemen (22--13) | D | DI | D | D | I | DI | DI | DI | D | DI | DI | D | DI |
| Bedan (22--14) | D | DI | D | D | I | DI | D | DI | D | D | D | DI | DI |
| Dabinette (22--15) | DI | DI | D | D | DI | DI | DI | I | DI | DI | D | D | D |
| Zaocuilv (22--16) | DI | I | DI | DI | I | DI | I | DI | DI | DI | DI | D | DI |
| Chanteline (22--17) | D | D | DI | D | I | DI | I | DI | DI | D | DI | DI | D |
| Red Baron (22--2) | D | I | D | D | I | D | DI | DI | D | D | D | D | I |
| Hongjin Gala (22--4) | DI | DI | DI | DI | I | D | DI | D | D | D | DI | DI | DI |
| Generos (22--7) | DI | DI | D | D | D | D | D | DI | D | D | D | D | DI |
| Alberta (2--3) | D | D | D | DI | I | D | DI | D | D | DI | DI | D | D |
| Hirosaki Fuji (23--1) | DI | DI | DI | D | DI | D | DI | DI | D | D | D | D | I |
| Miya Fuji (23--10) | DI | D | D | D | DI | D | DI | I | DI | DI | D | D | D |
| Yanshanhong (23--13) | DI | DI | D | D | DI | D | DI | I | DI | D | D | D | D |

| Construction results of InDel marker genotype database of *Malus* germplasm resources |||||||||||||
|---|---|---|---|---|---|---|---|---|---|---|---|---|
| Dailv (23--14) | DI | D | DI | D | I | I | DI | DI | D | D | I | I | DI |
| Frequin Rouge (23--15) | DI | DI | D | D | I | D | D | DI | D | D | D | D | DI |
| Jinguang (23--16) | D | D | D | D | I | D | I | DI | DI | D | D | DI | DI |
| Avrolles (23--17) | D | I | D | D | I | I | DI | I | D | D | DI | I | D |
| Marie Menard (23--18) | DI | I | D | D | I | DI | DI | I | D | I | D | DI | I |
| Golden B (23--2) | I | DI | DI | DI | I | DI | DI | DI | DI | DI | DI | DI | I |
| Jurella (23--20) | DI | DI | DI | D | I | D | DI | I | D | D | DI | D | I |
| GS58 (23--21) | I | I | DI | DI | I | DI | DI | DI | DI | D | D | D | I |
| Lianji (23--22) | DI | DI | DI | D | I | D | DI | DI | I | D | DI | DI | DI |
| Aomori Spur Fuji (23--4) | DI | DI | D | D | DI | DI | DI | I | DI | DI | D | D | D |
| Akifu 39 (23--9) | DI | DI | D | D | DI | DI | DI | I | DI | DI | D | D | D |
| Shalatuoni (2--4) | DI | DI | D | D | D | DI | DI | DI | D | DI | D | DI | DI |
| Guoqing (24--13) | D | D | D | D | DI | DI | I | I | D | DI | D | D | D |
| Ningguang (24--15) | DI | DI | DI | DI | I | DI | DI | DI | DI | DI | D | D | I |
| Hongqiaowang (24--17) | I | DI | DI | DI | DI | DI | DI | DI | DI | DI | DI | DI | I |
| Wemhong (24--18) | DI | DI | D | D | I | I | D | DI | D | DI | D | D | DI |
| Wijcik McIntosh (24--19) | D | I | D | D | I | D | DI | DI | I | D | DI | I | D |
| Xinguoguang (24--21) | DI | I | DI | D | DI | DI | D | I | D | D | D | D | DI |
| Fengcun Fuji (24--22) | DI | DI | D | D | DI | DI | DI | I | DI | DI | D | D | D |
| America 8 (24--23) | D | D | D | D | DI | DI | I | I | D | DI | D | D | D |
| GS48 (24--3) | D | DI | D | D | DI | D | I | I | DI | I | DI | D | DI |
| Granny Smith (24--4) | D | DI | D | D | I | DI | DI | D | D | D | I | DI | D |
| Stark Spur (24--7) | I | DI | DI | DI | I | DI | DI | DI | DI | DI | DI | DI | I |
| Huangguniang (2--5) | D | D | D | D | D | D | DI | DI | I | D | DI | DI | DI |
| Judaine (25--11) | DI | DI | DI | D | I | DI | DI | DI | DI | D | D | D | I |
| Judeline (25--12) | DI | DI | DI | DI | I | DI | DI | DI | DI | DI | DI | DI | I |
| HoneyCrisp (25--14) | D | DI | DI | D | I | DI | DI | DI | DI | DI | DI | DI | D |
| Korin (25--15) | DI | DI | D | D | DI | DI | DI | I | DI | DI | D | D | D |
| Hongao (25--18) | DI | D | DI | DI | DI | I | DI | DI | D | D | D | DI | DI |
| Ningguang (25--19) | DI | D | DI | DI | DI | I | DI | DI | D | D | D | DI | DI |
| Red Delicious (25--2) | D | D | DI | DI | I | D | I | I | DI | DI | D | D | DI |
| Youlixiang (25--21) | DI | DI | DI | D | DI | DI | D | DI | DI | D | DI | DI | I |
| Fuqiu (25--3) | I | D | DI | D | DI | DI | DI | I | D | D | DI | DI | DI |
| Chunxiang (25--4) | D | DI | D | D | I | DI | DI | DI | DI | D | DI | D | DI |
| Fu Hong (25--5) | D | DI | D | D | I | D | D | DI | D | D | D | DI | DI |
| Qingxiang (25--6) | I | I | DI | DI | I | D | D | I | DI | DI | DI | DI | I |
| Zhongxing (25--7) | DI | DI | D | DI | D | D | I | DI | DI | D | D | DI | DI |
| Weixishengming (25--8) | DI | DI | DI | DI | DI | D | DI | DI | DI | D | D | D | DI |
| Shichinohe 1 (25--9) | DI | DI | D | D | DI | DI | DI | I | DI | DI | D | D | D |

-continued

| Construction results of InDel marker genotype database of *Malus* germplasm resources | | | | | | | | | | | | | |
|---|---|---|---|---|---|---|---|---|---|---|---|---|---|
| Arkansas Black (2--6) | D | DI | DI | D | I | DI | I | I | DI | D | D | D | DI |
| Douce Coetligne (26--10) | DI | DI | D | D | I | D | I | I | D | D | D | DI | DI |
| Golden Spur (26--14) | I | DI | DI | DI | I | DI | DI | DI | DI | DI | DI | DI | I |
| Orei (26--15) | D | I | D | DI | I | DI | DI | I | D | D | D | D | I |
| Sekaiichii (26--18) | DI | DI | DI | DI | I | D | DI | DI | D | D | DI | DI | DI |
| Kokyu (26--19) | DI | D | DI | DI | I | DI | I | I | DI | DI | DI | DI | DI |
| Douce Moen (26--2) | D | DI | D | D | I | D | D | DI | D | D | DI | I | DI |
| Yanfu 1 (26--22) | DI | DI | D | D | DI | DI | DI | I | DI | DI | D | D | D |
| Ningfeng (26--23) | D | D | D | D | DI | DI | I | I | D | DI | D | D | D |
| Juliana (26--5) | DI | DI | D | D | I | D | DI | DI | D | D | DI | D | DI |
| Judestar (26--9) | DI | I | D | D | DI | D | DI | DI | D | D | D | D | DI |
| Liaofu (2--7) | D | D | D | DI | DI | DI | D | DI | DI | DI | D | DI | I |
| Sinano Red (27--10) | D | DI | D | D | DI | D | DI | D | D | DI | D | DI |
| Jinyang (27--12) | DI | DI | D | D | DI | I | DI | DI | D | D | DI | DI | DI |
| Enqi (27--13) | DI | I | DI | D | I | D | DI | DI | D | D | D | D | I |
| Miki (27--14) | DI | DI | DI | D | DI | D | DI | DI | DI | D | D | D | DI |
| Hongbaoshi (27--15) | DI | DI | DI | DI | I | DI | DI | DI | I | D | DI | DI | DI |
| Nagafu 2 (27--16) | DI | DI | D | D | DI | DI | DI | I | DI | DI | D | D | D |
| Longguan (27--4) | DI | I | DI | D | DI | DI | D | I | D | D | D | D | DI |
| K9 (27--5) | DI | DI | D | D | DI | I | DI | DI | D | D | DI | DI | DI |
| Zaohongda Gala (27--6) | DI | DI | D | D | DI | I | DI | DI | D | D | DI | DI | DI |
| Lvshuai (27--7) | DI | DI | DI | DI | I | DI | DI | I | I | DI | D | D | I |
| Hongxia (27--8) | DI | DI | DI | D | I | D | I | DI | D | D | D | D | DI |
| Zaohongxia (27--9) | DI | DI | D | D | DI | DI | DI | I | DI | DI | D | D | D |
| Early Golden (2--8) | DI | D | DI | D | I | D | I | DI | D | D | DI | DI | DI |
| Indo (28--0) | I | D | D | D | I | DI | DI | I | D | D | DI | DI | DI |
| Jie 1 (28--11) | DI | DI | D | D | D | D | D | DI | D | D | D | D | DI |
| Beauty of Bath (28--13) | D | D | D | DI | I | DI | DI | DI | DI | D | D | D | I |
| K10 (28--14) | D | DI | DI | DI | DI | DI | DI | DI | DI | DI | D | D | DI |
| Beifang Xina (28--16) | D | D | D | D | I | D | DI | I | DI | D | DI | D | I |
| Yellow Fuji (28--18) | DI | D | DI | D | I | DI | DI | DI | DI | D | D | DI |
| Sinano Sweet (28--2) | D | I | DI | DI | I | D | I | DI | DI | D | DI | DI | DI |
| Miguo (28--3) | D | DI | DI | DI | DI | DI | DI | I | D | D | D | D | DI |
| Ace (28--4) | DI | DI | D | D | DI | DI | DI | I | DI | DI | D | D | D |
| Tsugaru (28--5) | I | DI | DI | DI | DI | D | DI | DI | D | D | D | D | I |
| K12 (28--8) | DI | I | DI | DI | I | D | DI | DI | D | DI | DI | DI | DI |
| Jieernianke (28--9) | DI | DI | D | D | DI | DI | I | DI | D | D | D | D | D |
| Macoun (2--9) | D | I | DI | D | I | DI | D | I | I | D | D | I | DI |

-continued

| | | | | | | | | | | | | | |
|---|---|---|---|---|---|---|---|---|---|---|---|---|---|
| Qingping (29--1) | D | DI | D | D | I | D | DI | I | D | D | DI | DI | DI |
| Polka (29--11) | DI | I | DI | D | I | DI | D | DI | I | D | D | DI | DI |
| Longfeng (29--13) | D | D | DI | DI | I | D | D | DI | DI | D | I | I | DI |
| Very Early Fuji (29--14) | DI | DI | D | D | DI | DI | DI | I | DI | D | D | D | D |
| Longhong (29--15) | DI | DI | DI | D | DI | D | I | I | D | D | D | D | DI |
| Pinova (29--16) | DI | I | DI | I | I | DI | DI | DI | DI | D | D | DI | DI |
| Fuga (29--17) | DI | DI | DI | D | I | D | I | DI | D | D | D | D | DI |
| Qing n3 (29--2) | D | D | DI | DI | I | D | I | I | DI | DI | D | D | DI |
| Xinyuanshuai (29--3) | D | D | DI | DI | I | D | I | I | DI | DI | D | D | DI |
| Xinhua (29--5) | D | D | D | D | D | D | D | I | D | D | DI | D | DI |
| Nanpu 2 (29--6) | DI | DI | D | D | DI | DI | D | I | D | D | DI | DI | I |
| Liuyu mutant (29--7) | D | DI | D | D | D | D | I | DI | D | DI | D | DI | DI |
| Shandao Fuji (30--1) | DI | DI | D | D | DI | DI | DI | I | DI | DI | D | D | D |
| Sinano Gold (30--2) | I | DI | DI | DI | I | D | D | I | D | D | D | D | D |
| Whitney (3--1) | DI | DI | D | D | DI | D | DI | DI | DI | D | I | DI | D |
| Feixia (31--1) | DI | I | DI | D | I | DI | DI | DI | I | DI | D | D | DI |
| Willams Faborite (3--11) | D | DI | D | D | DI | DI | DI | I | DI | D | DI | D | DI |
| Zhangye 2 (31--12) | DI | DI | DI | DI | I | DI | I | I | DI | DI | DI | DI | DI |
| Youfangcun Ralls Janet (31--14) | D | DI | D | DI | DI | DI | I | DI | D | DI | D | D | DI |
| Yueyanghong (31--15) | D | D | D | D | D | D | I | I | DI | D | D | D | D |
| Shuohong (31--17) | DI | DI | DI | DI | DI | DI | DI | I | DI | D | D | D | DI |
| Tianwang 1 (31--18) | D | D | DI | DI | I | D | I | I | DI | DI | D | D | DI |
| Huadan (31--2) | DI | DI | DI | D | I | D | I | DI | DI | D | DI | DI | I |
| Dalu 52 (3--12) | D | I | D | D | DI | D | DI | DI | DI | D | DI | DI | D |
| Cameo (31--3) | DI | DI | DI | D | I | D | I | DI | DI | D | D | DI |
| Tianhuangkui (3--13) | D | DI | D | DI | DI | D | DI | DI | I | DI | D | DI | DI |
| Qiulu (31--4) | DI | I | D | D | I | D | DI | I | D | D | DI | DI | D |
| Liehuangjiatena (3--15) | I | D | DI | DI | DI | DI | I | I | DI | DI | D | D | DI |
| Lubi (3--16) | DI | D | DI | DI | I | DI | DI | DI | DI | D | D | D | DI |
| Huayu (31--8) | DI | DI | DI | D | I | D | DI | D | D | D | D | D | DI |
| Fameuse (3--18) | D | DI | D | I | I | D | D | DI | DI | D | D | DI | DI |
| Zhanhanxiang (3--19) | DI | I | DI | DI | I | I | I | DI | DI | I | D | D | DI |
| Siberian White Spot (3--2) | D | D | D | D | I | DI | I | DI | D | DI | D | D | I |
| Zhengding 2 (3--21) | DI | DI | D | D | I | DI | I | I | D | D | DI | D | I |
| Kuihua (3--22) | DI | I | DI | DI | I | D | I | I | DI | D | DI | D | I |
| Early Worcester (3--23) | D | DI | D | DI | I | D | DI | DI | DI | D | I | DI | DI |
| Lowland Raspderry (3--3) | DI | D | DI | D | I | DI | DI | I | I | D | DI | DI | DI |
| Miqiulin Jinian (3--4) | I | D | D | D | I | D | DI | I | DI | D | DI | D | DI |

| Construction results of InDel marker genotype database of *Malus* germplasm resources | | | | | | | | | | | | | |
|---|---|---|---|---|---|---|---|---|---|---|---|---|---|
| Huangtianguo (3--5) | D | DI | D | D | DI | D | DI | DI | DI | D | DI | DI | DI |
| Huadao (3--7) | D | D | DI | D | I | DI | DI | DI | D | D | I | DI | DI |
| Red Astrachan (3--9) | D | DI | DI | D | D | DI | I | I | D | DI | D | DI | D |
| Black Gilliflower (4--1) | D | DI | D | D | D | DI | DI | DI | DI | D | D | DI | |
| Nimaiyisuo (4--10) | D | DI | D | D | I | DI | DI | I | D | D | D | I | DI |
| Zaohong (4--11) | DI | I | DI | D | DI | D | I | D | D | D | D | DI | |
| Xiangguo (4--12) | D | DI | D | D | DI | D | DI | DI | DI | D | DI | DI | DI |
| Vista Bella (4--16) | D | I | D | D | I | D | DI | DI | D | I | I | D | |
| Saiwen (4--17) | D | DI | DI | D | I | DI | I | I | DI | D | D | D | DI |
| Summerland (4--20) | DI | DI | DI | DI | I | DI | DI | DI | DI | DI | DI | I | I |
| Qihe Golden Spur (4--22) | I | DI | DI | D | I | DI | DI | DI | DI | DI | DI | DI | I |
| Yellow Risharde (4--3) | DI | DI | DI | D | I | DI | DI | I | D | D | D | D | D |
| Patten (4--5) | D | DI | D | D | I | D | DI | DI | DI | D | DI | DI | D |
| Early Red Bird (4--6) | D | DI | D | D | I | D | I | DI | DI | D | DI | DI | DI |
| Fuhong (4--7) | DI | DI | DI | D | D | DI | DI | DI | D | D | D | D | D |
| Bisimake (4--8) | D | D | D | DI | I | D | I | DI | DI | DI | DI | I | |
| York Imperial (4--9) | DI | I | D | D | I | DI | DI | DI | DI | D | D | D | DI |
| Jonagold (5--1) | I | DI | DI | DI | DI | DI | DI | DI | D | DI | DI | DI | I |
| Ayiwaniya (5--10) | D | D | DI | DI | DI | D | I | I | I | D | DI | I | I |
| Fushan 5 (5--14) | D | D | DI | DI | I | D | I | I | DI | DI | D | D | DI |
| Houjiadian Spur (5--18) | D | D | DI | DI | I | D | I | I | DI | DI | D | D | DI |
| Guoshuai (5--19) | DI | DI | DI | DI | DI | D | DI | I | DI | DI | D | D | D |
| Huashuai 1 (5--21) | DI | DI | DI | DI | I | DI | DI | I | D | D | D | D | DI |
| Xiongyue 2 (5--22) | D | D | DI | DI | I | D | I | I | DI | DI | D | D | DI |
| Honeygod (5--3) | DI | DI | DI | DI | I | DI | D | I | I | I | DI | DI | DI |
| Joyal (5--4) | DI | DI | D | D | I | D | DI | DI | I | DI | D | DI | D |
| Stark Spur Golden (5--5) | I | DI | DI | DI | I | DI | DI | DI | DI | DI | DI | DI | I |
| Enweier Golden (5--6) | I | DI | DI | DI | I | DI | DI | DI | DI | DI | DI | DI | I |
| Stark Gold (5--8) | DI | I | DI | D | DI | D | I | D | D | D | D | DI | |
| Sishui Spur (6--10) | D | D | DI | DI | I | D | I | I | DI | DI | D | D | DI |
| Red Spur Delicious (6--12) | D | D | DI | DI | I | D | I | I | DI | DI | D | D | DI |
| Qingdao 1 (6--13) | D | D | DI | DI | I | D | I | I | DI | DI | D | D | DI |
| Bianqiangzi 1 (6--14) | D | D | DI | DI | I | D | I | I | DI | DI | D | D | DI |
| Zhangjiakou Spur (6--16) | D | D | DI | DI | I | D | I | I | DI | DI | D | D | DI |
| Richard Red Delicious (6--18) | D | D | DI | DI | I | D | I | I | DI | DI | D | D | DI |
| Well Spur Delicious (6--19) | D | D | DI | DI | I | D | I | I | DI | DI | D | D | DI |
| Bianqiangzi 2 (6--20) | D | D | DI | DI | I | D | I | I | DI | DI | D | D | DI |

-continued

Construction results of InDel marker genotype database of *Malus* germplasm resources

| | | | | | | | | | | | | |
|---|---|---|---|---|---|---|---|---|---|---|---|---|
| Hardi Spur Delicious (6--21) | D | D | DI | DI | I | D | I | I | DI | DI | D | D | DI |
| Fushan 1 (6--3) | D | D | DI | DI | I | D | I | I | DI | DI | D | D | DI |
| Pinyin Spur (6--4) | D | D | DI | DI | I | D | I | I | DI | DI | D | D | DI |
| Nanshan 2 (6--8) | D | D | DI | DI | I | D | I | I | DI | DI | D | D | DI |
| Meiduan 1 (7--10) | D | DI | DI | I | I | D | I | DI | DI | D | D | D | DI |
| Shisanling Spur (7--11) | D | D | DI | DI | I | D | I | I | DI | DI | D | D | DI |
| Kelisike (7--13) | D | D | D | D | I | D | DI | DI | I | D | I | DI | DI |
| Jie 18 (7--16) | DI | DI | D | D | I | DI | DI | I | DI | DI | D | D | D |
| Bo 25 (7--17) | D | D | D | D | I | DI | D | DI | DI | D | D | DI | DI |
| Ruixiang (7--18) | DI | DI | DI | D | D | D | DI | DI | D | D | D | D | D |
| Wealthy (7--19) | D | DI | D | D | DI | D | DI | DI | D | D | DI | DI | D |
| Nanshan 4 (7--2) | DI | DI | D | D | DI | DI | DI | I | D | DI | D | D | I |
| De 14 (7--20) | DI | DI | D | D | I | DI | DI | I | DI | DI | D | D | D |
| Napoleon (7--22) | D | DI | DI | DI | DI | DI | DI | I | D | D | D | D | DI |
| Youyi (7--23) | D | D | D | D | DI | D | D | DI | D | D | D | DI | DI |
| Oregon Spur (7--3) | DI | DI | D | DI | DI | DI | DI | I | D | DI | D | D | I |
| Kangtun Spur (7--6) | D | D | DI | DI | I | D | I | I | DI | DI | D | D | DI |
| White Pippin (7--9) | D | DI | D | I | I | D | D | DI | DI | D | D | DI | DI |
| Zach Lebel (8--1) | DI | DI | D | DI | DI | DI | DI | D | DI | D | D | DI | DI |
| Cortland (8--10) | D | DI | D | D | D | D | DI | D | D | D | DI | DI | D |
| Raritan (8--12) | DI | DI | D | D | DI | DI | DI | I | DI | DI | D | D | D |
| Meilingxi Tsugaru (8--13) | DI | D | DI | DI | I | DI | DI | DI | D | D | DI | DI | DI |
| Moscow Transparent (8--14) | D | DI | DI | D | DI | DI | D | DI | D | D | I | I | D |
| Cooper's Market (8--15) | DI | D | DI | D | DI | D | D | DI | D | D | D | D | DI |
| Xite Shisheng (8--16) | D | D | D | D | I | D | D | DI | D | D | D | D | DI |
| Tian Yisaye (8--17) | D | D | D | D | D | D | DI | DI | D | D | D | D | DI |
| Shennong 2 (8--19) | DI | I | DI | DI | DI | D | DI | D | DI | DI | I | DI | DI |
| Maigold (8--20) | DI | DI | DI | I | I | DI | I | DI | DI | DI | D | D | I |
| Magu (8--21) | D | DI | D | DI | DI | DI | DI | DI | D | D | D | D | DI |
| Cellini (8--23) | D | D | D | I | I | D | I | DI | DI | DI | DI | DI | I |
| Simonffy Piros (8--3) | D | DI | D | D | DI | DI | DI | I | DI | D | D | DI | I |
| Luxiang (8--5) | DI | DI | DI | D | DI | D | DI | DI | DI | D | D | D | D |
| Zhongqiu (8--6) | D | DI | D | D | DI | DI | DI | DI | I | DI | D | D | DI |
| De 2 (8--7) | D | I | DI | DI | I | D | D | DI | D | D | D | DI | D |
| Grimes Golden (8--8) | DI | DI | DI | D | I | DI | DI | DI | D | D | D | DI | DI |
| Early Straw Berry (8--9) | D | D | D | DI | I | DI | I | I | DI | D | D | D | DI |
| Kelia (9--10) | D | D | DI | D | I | D | I | DI | D | D | D | DI | I |
| French Apple (9--11) | D | DI | DI | D | I | DI | D | DI | DI | DI | DI | D | I |

-continued

Construction results of InDel marker genotype database of *Malus* germplasm resources

| | | | | | | | | | | | | |
|---|---|---|---|---|---|---|---|---|---|---|---|---|
| Todoroki Tsugaru (9--12) | DI | DI | DI | DI | DI | D | DI | D | D | D | D | D | I |
| Cuihong (9--13) | D | D | D | DI | DI | D | D | DI | DI | D | D | DI | I |
| De 4 (9--14) | DI | D | DI | D | DI | DI | DI | DI | DI | D | D | DI | DI |
| Early McIntosh (9--18) | D | I | D | D | I | DI | I | DI | I | DI | DI | DI | DI |
| Adam Mickewier (9--19) | DI | D | DI | D | I | D | DI | DI | I | D | D | DI | I |
| Norda (9--2) | D | D | DI | DI | I | D | DI | I | DI | D | DI | D | I |
| Cardinal (9--20) | DI | I | DI | DI | I | DI | I | DI | DI | DI | DI | DI | DI |
| Evelyn (9--21) | D | D | D | DI | DI | DI | DI | D | DI | D | DI | DI | DI |
| Situonuowei (9--22) | D | D | DI | DI | DI | DI | I | I | I | I | D | D | DI |
| Yingqiu (9--23) | DI | D | D | D | DI | D | DI | I | D | D | D | DI | DI |
| Kelongxieer (9--3) | D | DI | DI | D | DI | DI | D | DI | D | D | I | I | D |
| Cloden (9--5) | DI | DI | DI | DI | I | DI | I | I | DI | DI | I | I | DI |
| Qiutianhong (9--6) | D | D | DI | DI | DI | DI | I | I | I | I | D | D | DI |
| Gaidebao (9--7) | DI | I | DI | D | DI | D | D | DI | D | D | D | D | DI |
| Starkjam (9--9) | D | DI | DI | DI | DI | DI | DI | I | D | D | D | D | DI |
| Wan Crab (B-1) | DI | I | D | D | DI | D | DI | DI | DI | D | DI | DI | I |
| Minjiandaguo Crab (B-10) | D | I | D | D | D | D | DI | I | DI | DI | D | D | DI |
| Luanzhuang Crab (B1-11) | DI | DI | D | D | D | D | DI | I | D | DI | D | D | DI |
| Sankuaishi Crab (B1-12) | D | I | D | D | D | D | DI | I | I | DI | D | D | DI |
| Xiongyue Crab 1 (B1-13) | D | I | D | D | D | D | DI | I | D | DI | DI | D | DI |
| Sankuaishi Crab 2 (B1-14) | D | DI | D | D | D | D | DI | DI | D | DI | DI | D | DI |
| Dabaleng (B-12) | DI | I | D | D | D | D | DI | DI | D | D | D | D | DI |
| Sankuaishi Crab 2 (B-13) | DI | DI | D | D | DI | DI | DI | I | DI | DI | D | D | D |
| Changguo Crab (B-14) | DI | DI | DI | DI | I | DI | I | DI | D | I | D | D | DI |
| Dagucheng Baleng (B1-5) | D | D | D | D | DI | D | I | I | DI | DI | D | DI | D |
| Zumi Crab 3x (B-15) | DI | I | DI | DI | I | D | DI | DI | DI | D | D | D | DI |
| 26105 (B-16) | D | I | D | D | I | D | D | I | DI | DI | DI | D | DI |
| Daguo Crab (B-17) | D | I | D | D | D | D | DI | I | DI | DI | D | D | DI |
| Xiongyue Crab 2 (B1-8) | D | I | D | D | D | D | I | DI | D | D | I | DI | DI |
| Watermelon Crab (B-18) | DI | I | DI | D | I | D | I | D | DI | D | D | D | DI |
| Mudanjiang Crab (B1-9) | DI | I | D | D | I | D | D | I | DI | D | DI | DI | DI |
| Tianhong 1 (B-19) | DI | DI | D | D | DI | DI | DI | I | DI | DI | D | D | D |
| Jiping 1 (B-2) | D | DI | DI | D | DI | D | DI | DI | D | D | DI | D | I |
| Caoyuan Crab (B2-1) | D | DI | D | D | D | D | I | I | D | D | I | D | I |
| Zumi Crab 4x (B-21) | DI | I | DI | DI | I | D | DI | DI | DI | D | D | D | DI |
| Luanzhuang Shaguo (B2-11) | D | DI | D | D | I | D | DI | DI | I | DI | D | DI | D |
| Xiaofan Crab (B2-13) | D | DI | D | D | D | DI | DI | DI | D | DI | DI | DI | DI |
| Hebing Pingding Crab (B2-14) | D | DI | D | D | I | D | I | I | DI | D | D | DI | I |

-continued

Construction results of InDel marker genotype database of *Malus* germplasm resources

| | | | | | | | | | | | | |
|---|---|---|---|---|---|---|---|---|---|---|---|---|
| Zumi Crab 3x 2 (B-22) | DI | I | DI | DI | I | D | DI | DI | DI | D | D | D | DI |
| Baleng Crab (B2-3) | D | DI | D | D | DI | D | I | DI | DI | D | D | I | DI |
| Baleng seedling 14 (B-25) | DI | DI | DI | DI | I | DI | DI | DI | DI | D | DI | DI | DI |
| Russian White apple (B2-6) | DI | DI | D | D | D | DI | I | I | I | I | D | DI | DI |
| Nagafu 2 (B-26) | DI | DI | D | D | DI | DI | DI | I | DI | DI | D | D | D |
| Ambrosia (B-27) | DI | DI | DI | DI | I | D | DI | I | DI | D | D | D | I |
| Aihonghua (B2-8) | DI | I | DI | DI | DI | DI | I | DI | D | DI | DI | DI | DI |
| Nanshennan (B-28) | DI | DI | D | D | DI | DI | DI | I | DI | D | D | D | D |
| Zumi Crab W1 (B-29) | DI | I | DI | DI | I | D | DI | DI | DI | D | D | D | DI |
| Hong 4G (B-3) | D | I | D | D | DI | D | D | I | D | DI | DI | DI | DI |
| Zumi Crab (B-30) | DI | I | DI | DI | I | D | DI | DI | DI | D | D | D | DI |
| Zaobai Crab (B3-1) | D | D | D | D | DI | D | DI | I | I | D | DI | I | DI |
| Mollie's Delicious (B-31) | I | DI | DI | I | I | D | D | DI | DI | D | DI | DI | DI |
| Regunzi Spur (B3-10) | D | DI | D | D | D | D | DI | I | DI | DI | D | DI | DI |
| Xiaofanshan Baleng (B3-11) | DI | I | D | DI | DI | DI | DI | DI | DI | D | DI | DI | DI |
| Huamei (B3-12) | DI | I | DI | D | DI | D | DI | DI | D | D | D | D | I |
| Huashuo (B3-13) | D | I | D | D | I | DI | DI | I | D | D | D | D | DI |
| Yuhong (B3-14) | D | D | DI | DI | I | D | I | I | DI | DI | D | D | DI |
| Huayue (B3-15) | DI | DI | DI | D | DI | DI | DI | DI | D | D | D | D | DI |
| Jingbohu Shandingzi (B3-2) | D | I | D | D | D | D | I | I | D | D | D | D | D |
| Eluosi Daguo Shandingzi (B3-3) | D | I | D | D | DI | D | DI | DI | D | D | D | D | D |
| HY (B-33) | DI | D | DI | D | I | DI | DI | DI | DI | D | D | D | I |
| Hong Crab (B3-6) | D | DI | D | D | DI | D | DI | I | DI | DI | D | D | DI |
| 23# (B-37) | DI | DI | DI | D | I | D | I | DI | D | D | D | D | DI |
| Russian apple (B3-8) | D | D | D | D | DI | D | DI | DI | I | D | D | D | DI |
| 147 (B-38) | DI | I | DI | D | DI | D | I | DI | DI | D | D | D | DI |
| Xiaofanshan Baleng 1 (B3-9) | D | DI | D | D | DI | D | I | DI | DI | D | D | DI | DI |
| Lvshuai (B-4) | DI | DI | DI | DI | I | DI | DI | I | DI | D | D | D | I |
| Dounan (B-40) | I | DI | DI | DI | DI | DI | DI | I | D | DI | DI | DI | DI |
| 11906 (B-41) | D | DI | D | D | I | D | DI | DI | D | DI | D | DI | DI |
| Luli (B-5) | D | I | DI | D | DI | D | DI | DI | D | D | D | D | DI |
| Jinxiuhong (B-6) | DI | I | DI | D | I | DI | DI | DI | I | DI | D | D | DI |
| B68 (B-7) | D | DI | D | D | D | D | DI | I | DI | I | DI | DI | DI |
| Huaida (B-8) | DI | DI | DI | DI | DI | D | D | DI | DI | D | I | DI | I |
| Nanshennan mutant (B-9) | DI | DI | D | D | DI | DI | DI | I | DI | DI | D | D | D |

-continued

| Construction results of InDel marker genotype database of *Malus* germplasm resources |
|---|

| | | | | | | | | | | | | | |
|---|---|---|---|---|---|---|---|---|---|---|---|---|---|
| Xiahong (BH-1) | DI | DI | DI | D | I | D | DI | DI | I | D | DI | D | I |
| Wuming1 (BJ-1) | I | DI | DI | DI | I | DI | DI | DI | D | D | D | I | I |
| Canzy ? (BJ-10) | DI | DI | DI | I | I | D | DI | DI | DI | D | D | DI | I |
| Xiangfu (BJ-11) | DI | DI | D | D | DI | DI | DI | I | DI | DI | D | D | D |
| Envy (BJ-12) | I | DI | DI | D | I | D | I | DI | DI | D | D | DI | I |
| Fuji_KiKu (BJ-2) | DI | DI | D | D | DI | DI | DI | I | DI | DI | DI | D | D |
| Banxiu Crab (BJ-4) | D | I | D | D | D | DI | I | DI | D | D | D | DI | DI |
| Jazz (BJ-5) | DI | DI | DI | DI | I | D | DI | DI | DI | D | D | D | DI |
| Early Red Bird 2 (BJ-7) | D | I | DI | D | I | DI | DI | DI | D | D | DI | D | DI |
| Qiuhong Gala (BJ-8) | DI | DI | D | D | DI | D | DI | I | DI | DI | DI | D | D |
| Hongxiangcui (BJ-9) | I | I | DI | DI | I | D | I | DI | DI | D | D | D | DI |
| 07-115 (BK-1) | D | DI | D | D | D | D | I | DI | I | D | D | DI | DI |
| Nagafu 3 (BK-2) | DI | DI | D | D | DI | DI | DI | I | DI | DI | D | D | D |
| 28-253 (BK-28-253) | DI | DI | DI | D | DI | DI | DI | I | DI | D | D | D | DI |
| Nagafu 3-R (BK-3) | DI | DI | D | D | DI | DI | DI | I | DI | DI | D | D | D |
| 4354 (BK-4) | D | I | DI | D | I | DI | I | I | DI | D | DI | I | I |
| 4-23 (BK-4-23) | I | DI | DI | DI | I | DI | DI | I | D | D | D | D | DI |
| 4354-R ? (BK-5) | I | DI | DI | DI | DI | I | DI | DI | I | I | DI | DI | I |
| 77-34 (BK-77-34) | D | DI | D | D | D | D | D | DI | I | DI | DI | DI | DI |
| Red Spur Delicious (BK-AH) | D | D | DI | DI | I | D | I | I | DI | DI | D | D | DI |
| Ozark Gold (BK-AJ) | DI | D | DI | D | I | DI | DI | DI | DI | DI | D | D | DI |
| Michinoku (BK-AZ) | D | DI | D | D | D | D | DI | DI | D | D | DI | D | DI |
| Azwell (BK-Azwell) | D | D | DI | I | I | D | I | I | DI | DI | D | D | DI |
| Banbishan Crab (BK-BBSHT) | D | D | D | D | DI | D | DI | DI | I | DI | D | DI | DI |
| Hokudo (BK-BD) | DI | DI | DI | DI | DI | DI | DI | I | DI | DI | D | D | DI |
| Baifugao (BK-BFG) | D | DI | D | D | I | D | DI | I | DI | DI | DI | DI | DI |
| White Crab (BK-BHT) | D | I | D | DI | DI | DI | DI | DI | D | DI | DI | DI | DI |
| Buming Kangbing (BK-BMKB) | D | DI | D | I | I | D | D | DI | DI | D | D | DI | DI |
| Batougou 1 (BK-BTG1H) | D | DI | D | D | DI | D | I | I | D | DI | D | DI | I |
| Batougou 2 (BK-BTG2H) | D | DI | D | D | DI | D | I | DI | DI | D | D | D | D |
| Batougou Aizhen (BK-BTGAZ) | D | D | D | D | D | D | I | I | D | D | D | D | D |
| Binzi (BK-BZ) | D | D | D | D | D | DI | DI | I | D | DI | I | I | |
| Kitanosach (BK-BZX) | D | D | DI | I | I | D | D | DI | D | D | D | DI | I |
| Binzi (SW) (BK-BZXN) | D | D | D | D | D | DI | DI | I | D | DI | I | I | |
| Nagafu 2 (BK-CF2H) | DI | DI | D | D | DI | DI | DI | I | DI | DI | D | D | D |
| Nagafu 36 (BK-CF36) | DI | DI | D | D | DI | DI | DI | I | DI | DI | D | D | D |
| Nagafu 6 (BK-CF6H) | DI | DI | D | D | DI | DI | DI | I | DI | DI | D | D | D |

| | | | | | | | | | | | | | |
|---|---|---|---|---|---|---|---|---|---|---|---|---|---|
| Construction results of InDel marker genotype database of *Malus* germplasm resources | | | | | | | | | | | | | |
| CG24 (BK-CG24) | D | D | DI | I | I | D | I | I | DI | DI | D | DI | DI |
| CG3 (BK-CG3) | I | DI | DI | D | DI | DI | DI | I | DI | D | D | D | DI |
| CG80 (BK-CG80) | DI | D | DI | D | DI | D | DI | DI | DI | I | D | DI | I |
| Changhong (BK-CH) | DI | DI | D | D | DI | DI | DI | I | DI | DI | D | D | D |
| Chieftan (BK-chieftan) | D | DI | DI | D | DI | DI | DI | DI | DI | D | D | DI | DI |
| Cangjiang Crab (BK-CJHT) | D | DI | D | D | D | D | I | I | D | D | I | DI | DI |
| Chuanling Crab (BK-CLHT) | D | I | D | D | D | DI | DI | I | D | D | D | DI | DI |
| Hatsuaki (BK-CQ) | DI | DI | DI | D | I | D | DI | DI | DI | D | DI | DI | DI |
| Crispin (BK-crispin) | I | DI | DI | DI | DI | DI | DI | DI | DI | DI | DI | DI | I |
| Caozigang Yuanshuai (BK-CZGYS) | DI | D | DI | DI | I | D | I | I | DI | DI | D | D | DI |
| Danxia (BK-DANXIA) | DI | DI | DI | I | I | DI | I | DI | I | DI | D | D | I |
| Dolgo (BK-DDG) | D | I | D | D | DI | D | D | D | D | D | D | D | D |
| Darwin (BK-DEW) | D | D | D | D | D | D | DI | DI | I | D | DI | I | I |
| Oriental Apple (BK-DFPG) | DI | I | D | D | DI | DI | DI | DI | DI | DI | DI | DI | D |
| Big Crab (BK-DGHT) | D | D | D | D | D | D | DI | DI | D | D | DI | I | I |
| Daguo Jinhong (BK-DGJH) | DI | DI | DI | DI | DI | D | D | DI | D | I | DI | I |  |
| Daihong (BK-DH) | D | D | DI | DI | I | D | I | I | DI | DI | D | D | DI |
| Daihao 261 (BK-DH261) | DI | DI | D | D | D | D | DI | D | D | D | D | DI | DI |
| Spur Golden Delicious (BK-DJG) | I | DI | DI | DI | I | DI | DI | DI | DI | DI | DI | DI | I |
| Daxianguo (BK-DXG) | D | DI | D | D | D | D | DI | I | DI | DI | D | DI | DI |
| Daye Crab (BK-DYHT) | D | DI | D | D | D | D | DI | I | DI | DI | D | DI | DI |
| Spur Fuji (BK-DZFS) | DI | DI | D | D | DI | DI | DI | I | DI | DI | D | D | D |
| Huaguan Spur (BK-DZHG) | DI | I | DI | D | I | DI | DI | DI | I | DI | D | D | DI |
| Elite (BK-Elite) | D | D | DI | DI | I | D | I | I | DI | DI | D | D | DI |
| Fa 8 (BK-F8) | DI | DI | DI | D | DI | DI | DI | DI | D | D | D | D | DI |
| Fukushima Spur Fuji (BK-FDDZ) | DI | DI | D | D | DI | DI | DI | I | DI | DI | D | D | D |
| Fujin (BK-FJ) | DI | DI | D | DI | DI | DI | I | I | DI | DI | D | D | DI |
| Florina (BK-Florina) | D | D | DI | D | D | D | DI | I | DI | DI | DI | DI | DI |
| Fangming (BK-FM) | DI | DI | DI | DI | DI | D | DI | DI | D | D | D | D | I |
| Fuji (BK-Fuji) | DI | DI | D | D | DI | DI | I | I | DI | DI | D | DI | DI |
| Fengyan (BK-FY) | D | I | D | D | I | D | D | DI | DI | D | DI | D | DI |
| Yanfu 1 (BK-FY1) | DI | DI | D | D | DI | DI | DI | I | DI | DI | D | D | D |
| King of Tompkins County (BK-FZY) | DI | DI | DI | D | DI | DI | DI | DI | DI | D | D | D | DI |
| G30 (BK-G30) | D | I | D | D | D | D | D | I | I | DI | D | DI | DI |
| Gao #5 (BK-G-5) | D | DI | D | D | I | D | DI | DI | I | D | D | DI | DI |
| Gala (BK-gala) | DI | I | DI | D | I | D | DI | DI | D | D | D | D | I |
| Golden Delicious (BK-GD) | I | DI | DI | DI | I | DI | DI | DI | DI | DI | DI | DI | I |

| Construction results of InDel marker genotype database of *Malus* germplasm resources | | | | | | | | | | | | | |
|---|---|---|---|---|---|---|---|---|---|---|---|---|
| Gloster69 (BK-Gloster69) | DI | DI | DI | I | I | DI | DI | I | DI | D | DI | DI | DI |
| GM256 (BK-GM256) | D | I | D | D | D | D | DI | DI | I | DI | DI | D | DI |
| GM310 (BK-GM310) | D | D | D | D | D | D | D | DI | DI | DI | DI | D | I |
| Gaoqiu (BK-GQ) | I | I | DI | DI | I | DI | DI | DI | DI | DI | DI | DI | DI |
| Miyazaki Spur Fuji (BK-GQDZ) | DI | DI | D | D | DI | DI | DI | I | DI | DI | D | D | D |
| HAC-9 (BK-HAC-9) | DI | DI | D | DI | DI | DI | DI | DI | DI | DI | D | DI | DI |
| Huifeng Orin (BK-HFWL) | I | DI | D | D | D | D | D | DI | D | D | D | D | DI |
| Red Ralls Janet (BK-HGG) | DI | I | DI | D | DI | DI | D | I | D | D | D | D | DI |
| Huaguan Crab (BK-HGHT) | D | DI | D | D | D | D | DI | DI | I | D | DI | DI | DI |
| Harrold Red Delicious (BK-HH) | D | D | DI | DI | I | D | I | I | DI | DI | D | D | DI |
| Hong Crab 2 (BK-HHT2H) | D | DI | D | D | D | D | DI | I | DI | DI | D | DI | DI |
| Stark Redgold (BK-HJ) | DI | D | DI | I | I | D | DI | DI | DI | DI | DI | DI | DI |
| HLWQ (BK-HLWQ) | D | DI | DI | DI | I | DI | DI | I | I | D | DI | DI | DI |
| Holly (BK-Holly) | DI | D | DI | D | DI | D | DI | I | DI | D | D | D | D |
| Red Jonagold (BK-HQNJ) | DI | I | DI | DI | DI | D | I | DI | D | D | DI | I | I |
| Red Sekaiichii (BK-HSJY) | DI | D | DI | DI | I | DI | I | I | DI | DI | DI | DI | DI |
| Hongte (BK-HT) | DI | D | DI | D | DI | D | DI | I | DI | DI | D | D | D |
| Haitangguo (BK-HTG) | DI | DI | D | D | DI | D | DI | DI | D | DI | DI | DI | I |
| Haitanghua (BK-HTH) | D | DI | D | D | D | D | I | DI | DI | DI | D | DI | DI |
| Huangtaiping (BK-HTP) | D | I | D | DI | DI | DI | DI | DI | DI | D | DI | DI | DI |
| Hongxue (BK-HX) | D | DI | D | I | I | D | D | DI | DI | D | D | DI | DI |
| Jincui (BK-JC) | DI | D | DI | I | I | D | I | I | D | DI | DI | DI | DI |
| Juda Fuji (BK-JDFS) | DI | DI | D | D | DI | DI | DI | I | DI | DI | D | D | D |
| Jiguan (BK-JG) | DI | DI | D | D | DI | I | DI | DI | D | D | DI | DI | DI |
| Jinhong (BK-JH) | DI | DI | DI | DI | DI | D | D | I | DI | D | I | DI | DI |
| Jonagored (BK-Jonagored) | I | DI | DI | DI | DI | DI | DI | DI | DI | DI | DI | DI | DI |
| Jonathan (BK-Jonathan) | DI | DI | D | D | D | D | D | DI | D | D | D | D | DI |
| Himekami (BK-JS) | DI | I | D | D | DI | DI | D | I | D | D | D | D | D |
| Stark Blushing Golden (BK-JY) | DI | I | DI | DI | I | DI | DI | I | DI | D | D | D | I |
| Classic Red Delicious (BK-KAHONG) | D | D | DI | DI | I | D | I | I | DI | DI | D | D | DI |
| KLGDG Shandingzi (BK-KLGDGSDZ) | D | DI | D | D | D | D | I | I | D | D | D | DI | DI |
| KOSZTELQ (BK-KOSZTELQ) | D | D | D | DI | I | DI | DI | DI | I | D | D | DI | I |
| Sunflower (BK-KUIHUA) | DI | DI | DI | DI | I | D | I | DI | I | D | D | D | DI |
| Lenghaitang (BK-LHT) | D | DI | D | D | DI | D | D | DI | I | DI | D | DI | DI |
| Liberty (BK-liberty) | D | DI | DI | D | DI | DI | DI | DI | DI | D | D | DI | DI |
| Lijiang Shandingzi (BK-LJSDZ) | D | D | D | D | DI | D | DI | DI | I | DI | DI | DI | I |

| Construction results of InDel marker genotype database of *Malus* germplasm resources | | | | | | | | | | | | | |
|---|---|---|---|---|---|---|---|---|---|---|---|---|---|
| Laoshan 4 (BK-LS4H) | D | DI | D | D | D | D | DI | I | DI | DI | D | DI | DI |
| Ryoka no Kisetsu (BK-LX) | DI | DI | D | D | DI | DI | DI | I | DI | DI | D | D | D |
| Lvxiangjiao (BK-LXJ) | DI | DI | DI | D | D | D | D | I | D | DI | DI | DI | DI |
| Liaozhen 1 (BK-LZ1H) | D | I | D | D | D | D | DI | DI | I | DI | DI | DI | I |
| M7 (BK-M7) | D | I | D | D | I | D | DI | DI | DI | DI | I | I | DI |
| Meiguihong (BK-MGH) | D | D | DI | DI | I | D | I | I | DI | DI | D | D | DI |
| Meile (BK-ML) | I | DI | DI | DI | I | I | D | DI | DI | D | D | D | I |
| MM106 (BK-MM106) | DI | D | DI | D | DI | D | DI | DI | DI | I | D | DI | I |
| Mengpaisi (BK-MPS) | DI | D | DI | D | DI | DI | DI | DI | DI | D | D | DI | I |
| Meixiang (BK-MX) | DI | DI | D | D | DI | DI | DI | I | DI | DI | D | D | D |
| Ningqiu (BK-NQ) | I | I | D | D | I | DI | DI | I | DI | DI | D | D | DI |
| P16 (BK-P16) | D | D | D | D | I | DI | DI | DI | DI | D | DI | DI | DI |
| P22 (BK-P22) | D | DI | D | D | DI | D | DI | I | I | I | D | I | DI |
| Pingdinghaitang (BK-PDHT) | D | DI | D | D | D | D | DI | I | DI | DI | D | DI | DI |
| Bianguo Crab (BK-PGHT) | D | DI | D | D | DI | DI | I | DI | D | D | D | DI | DI |
| Pionier (BK-Pionier) | I | DI | DI | D | I | D | DI | DI | D | D | D | D | DI |
| Prima (BK-Prima) | DI | I | DI | D | DI | DI | DI | DI | D | D | D | D | D |
| Pingyitiancha (BK-PYTC) | D | I | D | D | D | D | I | DI | D | D | D | D | DI |
| Qianxue (BK-QAINXUE) | I | DI | DI | DI | I | I | I | I | D | DI | DI | DI | DI |
| Akifu 1 (BK-QF1) | DI | DI | D | D | DI | DI | DI | I | DI | DI | D | D | D |
| Qingfu 13 (BK-QF13) | DI | DI | D | D | DI | DI | DI | I | DI | DI | D | D | D |
| Seimei (BK-QM) | DI | DI | DI | DI | I | D | DI | DI | D | D | DI | DI | DI |
| Senshu (BK-QQ) | DI | DI | DI | D | I | D | I | I | DI | DI | DI | DI | D |
| Aomori Early (BK-QSZS) | I | DI | DI | DI | I | DI | DI | DI | D | DI | DI | DI | DI |
| Qiuxiang (BK-QX) | DI | DI | DI | DI | DI | D | DI | DI | D | D | D | D | I |
| Qiuxing Crab (BK-QXHT) | D | D | D | DI | I | D | I | DI | DI | DI | D | DI | I |
| Yanqing (BK-QY) | DI | DI | DI | D | I | DI | DI | I | D | DI | D | D | I |
| Regunzi (BK-RGZ) | D | DI | D | D | D | D | DI | I | DI | DI | D | DI | DI |
| Ruby (BK-Ruby) | DI | DI | D | D | DI | DI | DI | I | D | DI | D | D | I |
| Scarlet (BK-scarlet) | D | D | DI | DI | I | D | I | I | DI | DI | D | D | DI |
| Sdw1 (BK-Sdw1) | D | D | D | D | D | D | DI | DI | DI | I | D | D | D |
| Shandingzi 2 (BK-SDZ2H) | D | DI | D | D | D | D | I | I | D | D | D | DI | DI |
| Su E Shandingzi (BK-SESDZ) | D | I | D | D | D | D | I | I | DI | D | D | DI | DI |
| Shengfang 2 (BK-SF2) | DI | DI | D | D | D | DI | DI | I | DI | D | D | D | D |
| SH6 (BK-SH6) | D | I | D | D | DI | D | DI | I | D | D | DI | D | D |
| Sankuaishi Crab 1 (BK-SKSHT1H) | D | DI | D | D | DI | D | I | DI | DI | D | D | I | DI |
| Forest Apple (BK-SLPG) | DI | DI | DI | DI | DI | DI | DI | DI | D | DI | DI | DI | I |
| Sieversii (BK-SWS) | D | D | D | D | DI | D | DI | DI | I | DI | DI | DI | I |
| Sansa (BK-SX) | I | I | DI | D | DI | D | DI | DI | DI | D | D | DI | I |

-continued

| Construction results of InDel marker genotype database of *Malus* germplasm resources |||||||||||||
|---|---|---|---|---|---|---|---|---|---|---|---|---|
| Szampion (BK-Szampion) | DI | DI | DI | DI | I | DI | DI | DI | DI | D | DI | DI | I |
| T337 (BK-T337) | D | DI | D | D | D | D | D | DI | I | I | DI | DI | DI |
| Turkmen Apple (BK-TKMPG) | D | D | D | D | DI | D | DI | DI | I | DI | DI | DI | I |
| Mato 1 (BK-TMYH) | D | DI | D | D | DI | D | DI | DI | D | D | DI | D | DI |
| Trajian (BK-Trajian) | D | I | DI | D | I | DI | D | I | I | D | D | I | DI |
| Weiai 3 (BK-WA3) | D | DI | D | D | DI | D | I | DI | DI | D | D | DI | DI |
| Wanbai Crab (BK-WBHT) | DI | DI | DI | DI | DI | DI | I | DI | DI | I | D | DI | I |
| Wufengshan 1 (BK-WFS1H) | D | DI | D | D | D | D | DI | DI | DI | D | DI | DI | DI |
| Wufengshan 4 (BK-WFS4H) | D | DI | DI | D | DI | D | DI | DI | DI | D | D | D | DI |
| Wufengshan Crab (BK-WFSHT) | D | D | D | DI | DI | DI | I | DI | D | DI | D | DI | I |
| Wufengshan Crab 2 (BK-WFSHT2H) | D | D | D | D | I | D | I | I | I | D | D | DI | I |
| Wufengshan Crab 6 (BK-WFSHT6H) | D | D | D | D | D | DI | I | DI | DI | D | DI | DI | DI |
| Wifos (BK-wifos) | D | I | D | D | I | D | DI | DI | DI | D | DI | DI | D |
| Orei (BK-WL) | DI | I | DI | DI | I | DI | DI | I | DI | D | D | D | I |
| Maypole (BK-WM) | D | DI | D | D | DI | D | DI | I | DI | DI | DI | I | DI |
| Waltz (BK-WZ) | DI | I | DI | D | I | DI | D | D | I | DI | D | DI | DI |
| Kotoku (BK-XD) | D | D | D | D | DI | DI | I | DI | I | D | DI | DI | D |
| Xiaofanshan Binzi (BK-XFSBZ) | DI | D | D | D | D | D | DI | DI | I | D | DI | I | I |
| Xiaofanshan Crab 4 (BK-XFSHT4H) | D | DI | D | D | D | D | DI | DI | DI | D | DI | DI | DI |
| Xiaogoumen Naizi (BK-XGMNZ) | D | D | D | D | I | D | DI | DI | DI | DI | DI | I | I |
| XGM Suan Binzi (BK-XGMSBZ) | D | D | D | D | D | D | DI | DI | I | D | DI | I | I |
| XGM Tian Binzi (BK-XGMTBZ) | D | DI | D | D | D | D | DI | DI | DI | DI | DI | I | I |
| Starkrimson (BK-XHX) | D | D | DI | DI | I | D | I | I | DI | DI | D | D | DI |
| Xinjiang 1 (BK-XJ1) | DI | D | D | D | D | D | D | DI | DI | D | D | I | D |
| Xinjiang 11 (BK-XJ11) | D | D | DI | DI | I | D | I | DI | DI | D | DI | DI | DI |
| Xinjiang 14 (BK-XJ14) | D | D | DI | DI | I | D | I | DI | DI | D | DI | DI | DI |
| Xinjiang 15 (BK-XJ15) | DI | DI | DI | DI | D | D | I | I | D | D | DI | I | D |
| Xinjiang 16 (BK-XJ16) | D | DI | D | D | D | DI | I | DI | DI | DI | D | D | I |
| Xinjiang 17 (BK-XJ17) | D | D | DI | DI | D | D | DI | DI | D | D | DI | DI | I |
| Xinjiang 18 (BK-XJ18) | D | D | DI | DI | D | D | DI | DI | D | D | DI | DI | I |
| Xinjiang 19 (BK-XJ19) | D | DI | DI | I | I | D | DI | DI | D | DI | DI | DI | I |
| Xinjiang 21 (BK-XJ21) | D | DI | D | D | I | D | DI | I | DI | D | DI | DI | DI |
| Xinjiang 22 (BK-XJ22) | D | D | D | D | D | D | D | DI | I | D | I | I | D |
| Xinjiang 24 (BK-XJ24) | D | D | D | D | D | D | DI | I | D | D | I | DI |
| Xinjiang 26 (BK-XJ26) | D | D | DI | DI | I | D | I | DI | D | D | DI | DI |
| Xinjiang 28 (BK-XJ28) | D | DI | DI | I | I | D | DI | DI | D | DI | DI | DI | I |
| Xinjiang 29 (BK-XJ29) | DI | D | DI | D | DI | DI | D | DI | I | D | D | DI | DI |
| Xinjiang 31 (BK-XJ31) | D | I | D | D | DI | D | I | I | DI | D | I | D | DI |

-continued

Construction results of InDel marker genotype database of *Malus* germplasm resources

| Name | | | | | | | | | | | | | |
|---|---|---|---|---|---|---|---|---|---|---|---|---|---|
| Xinjiang 3 (BK-XJ3H) | DI | DI | D | D | DI | DI | DI | I | DI | DI | D | DI | DI |
| Xinjiang 6 (BK-XJ6H) | D | D | DI | DI | I | D | D | I | DI | D | I | I | DI |
| Xinjiang 7 (BK-XJ7) | D | D | DI | DI | I | D | I | DI | DI | D | DI | DI | DI |
| Xinjiang 8 (BK-XJ8) | D | D | D | D | D | D | D | DI | I | D | DI | DI | DI |
| Xinjiang 9 (BK-XJ9) | DI | D | DI | D | DI | DI | D | DI | I | D | D | DI | I |
| Xijin Crab (BK-XJHT) | D | DI | D | D | D | DI | I | DI | D | D | D | D | I |
| Xiaomian Crab (BK-XMHT) | D | DI | D | D | D | D | DI | DI | I | D | D | DI | DI |
| New Jonagold (BK-XQNJ) | I | DI | DI | DI | DI | DI | DI | DI | DI | DI | DI | DI | I |
| Xiaoshuai (BK-XS) | D | DI | DI | D | I | D | I | DI | D | DI | D | D | D |
| Shinsekai (BK-XSJ) | DI | DI | DI | D | DI | DI | DI | I | DI | D | D | D | DI |
| Xiangyanghong (BK-XYH) | D | DI | DI | D | DI | DI | DI | I | DI | D | D | D | D |
| Italy Early Red (BK-YDLZH) | DI | I | DI | D | I | D | DI | DI | D | D | D | D | I |
| Yanfu 10 (BK-YF10) | DI | DI | D | D | DI | DI | DI | I | DI | DI | D | D | D |
| Yoko (BK-YG) | I | DI | DI | D | DI | DI | DI | DI | DI | DI | D | D | I |
| Yuanhong (BK-YH) | D | D | DI | DI | DI | D | I | I | DI | DI | DI | D | D |
| Tehong 2 (BK-YH2) | DI | DI | D | D | DI | DI | DI | I | DI | DI | D | D | D |
| Yanhongmi (BK-YHM) | DI | DI | D | D | DI | D | DI | DI | D | D | DI | DI | I |
| Youliang Spur (BK-YLDZ) | DI | DI | D | D | DI | D | DI | I | DI | DI | D | D | D |
| Yuanye Crab (BK-YYHT) | D | DI | D | D | D | D | DI | I | DI | DI | D | DI | DI |
| Stark Jumbo (BK-ZB) | DI | D | DI | D | I | DI | DI | DI | DI | D | D | D | I |
| Jumbo Orin (BK-ZBWL) | I | DI | DI | DI | I | DI | DI | DI | D | DI | DI | DI | I |
| Zhuifeng 1 (BK-ZF1H) | DI | DI | D | D | D | D | DI | I | D | D | DI | D | DI |
| Zhuifeng 2 (BK-ZF2H) | D | DI | D | D | D | D | I | I | D | D | D | DI | DI |
| Early Fuji (BK-ZFS) | DI | DI | D | D | DI | DI | DI | I | DI | DI | D | D | D |
| Xiaofanshan Crab (BK-ZFSHT) | D | DI | D | D | D | D | D | DI | DI | D | DI | DI | DI |
| Zisai Pearl (BK-Zisai) | D | I | D | DI | DI | DI | DI | DI | DI | D | D | DI | I |
| Geneva Early (BK-ZJ) | D | I | D | D | I | D | DI | DI | DI | D | DI | DI | DI |
| 13-26W (CL-1) | DI | D | DI | I | I | DI | DI | DI | D | D | D | D | DI |
| 23-127 (CL-2) | DI | I | DI | DI | D | DI | DI | DI | D | DI | DI | DI | I |
| 50-30 (CL-3) | DI | DI | DI | D | DI | D | I | I | I | DI | D | D | DI |
| 50-32 (CL-4) | DI | DI | D | D | DI | D | I | I | D | D | D | D | DI |
| H5-101 (CL-5) | I | DI | DI | D | I | I | DI | DI | DI | DI | D | D | DI |
| Pingyan (CL-6) | DI | DI | D | D | DI | D | I | DI | DI | D | D | D | DI |
| Deqin Crab (DQ) | D | I | D | D | D | D | I | I | D | D | DI | D | D |
| Jin 18 (GY-1) | DI | DI | D | D | DI | DI | DI | I | DI | DI | D | D | DI |
| Fengfeng Baleng (GY-2) | D | I | D | D | D | DI | I | DI | D | D | DI | DI | I |
| Hanfu 6 (GY-3) | DI | DI | D | D | DI | DI | DI | I | DI | DI | D | D | D |
| Hanfu 3 (GY-4) | DI | D | DI | I | I | D | I | DI | I | D | DI | DI | D |
| 95/06 (GZ-1) | D | D | D | D | I | D | DI | DI | DI | DI | D | DI | I |

-continued

Construction results of InDel marker genotype database of *Malus* germplasm resources

| | | | | | | | | | | | | | |
|---|---|---|---|---|---|---|---|---|---|---|---|---|---|
| 107/06 (GZ-2) | D | DI | D | D | DI | D | DI | DI | DI | DI | D | I | I |
| 117/06 (GZ-3) | D | I | D | D | DI | D | DI | DI | DI | DI | D | I | I |
| 119/06 (GZ-4) | D | DI | D | D | I | D | DI | DI | D | DI | D | DI | DI |
| Jinxiu Crab (GZ-5) | D | DI | DI | D | I | D | DI | I | DI | D | D | D | D |
| Zhizun Fuji (HS-1) | DI | DI | D | D | DI | DI | DI | I | DI | DI | D | D | D |
| Fuji No. 1 (HS-10) | DI | DI | D | D | DI | DI | DI | I | DI | DI | D | D | D |
| Red Jonaprince (HS-12) | I | DI | DI | DI | DI | DI | DI | DI | DI | DI | DI | D | I |
| Nic29 (HS-13) | D | DI | D | D | D | D | D | DI | DI | I | DI | I | DI |
| Azhen Fuji (HS-14) | DI | DI | D | D | DI | DI | DI | I | DI | DI | D | D | D |
| Envy (HS-15) | I | DI | DI | D | I | D | I | DI | DI | D | D | DI | DI |
| Rosegrow (HS-16) | I | DI | DI | I | I | DI | DI | DI | D | DI | I | I | I |
| Canzy (HS-17) | DI | DI | DI | DI | I | D | DI | DI | DI | D | D | DI | DI |
| Fubrax (HS-2) | DI | DI | D | D | DI | DI | DI | I | DI | DI | D | D | D |
| Mitchgla (HS-3) | DI | I | DI | D | I | D | DI | DI | D | D | D | D | I |
| Fujiko (HS-4) | DI | DI | D | D | DI | D | DI | I | DI | DI | D | D | D |
| Buckeye Gala (HS-5) | DI | I | DI | D | I | D | DI | DI | D | D | D | D | I |
| Fujion (HS-6) | D | DI | D | D | D | D | I | I | I | DI | DI | D | D |
| Modi (HS-7) | DI | DI | DI | D | DI | D | DI | DI | D | D | D | D | DI |
| Jiangxue (HS-8) | D | DI | DI | D | I | D | I | DI | D | D | DI | DI | D |
| September Wonder Fuji (HS-9) | DI | DI | D | D | DI | DI | DI | I | DI | DI | D | D | D |
| Linqin Crab (LQ) | D | DI | D | D | DI | D | I | DI | I | D | D | DI | DI |
| Lushan Sanye (LSSY) | D | I | D | D | D | D | I | DI | D | D | D | D | D |
| 83-2 (MDJ-1) | DI | DI | DI | DI | DI | DI | D | DI | D | D | DI | D | DI |
| Tianfeng (MDJ-9) | DI | D | D | D | DI | D | DI | DI | I | D | D | D | DI |
| Oregon Spur II-red (OR-1) | D | D | DI | I | I | D | I | I | DI | DI | D | D | DI |
| Oregon Spur II-green (OR-2) | D | D | DI | I | I | D | I | I | DI | DI | D | D | DI |
| E3N2 (OR-3) | D | D | DI | I | I | D | I | I | DI | DI | D | D | DI |
| E4N1 (OR-4) | D | D | DI | I | I | D | I | I | DI | DI | D | D | DI |
| E4N2 (OR-5) | D | D | DI | I | I | D | I | I | DI | DI | DI | D | DI |
| W6N1 (OR-6) | D | D | DI | I | I | D | I | I | DI | DI | D | D | DI |
| W6S5 (OR-7) | D | D | DI | I | I | D | I | I | DI | DI | D | D | I |
| W8S3 (OR-8) | D | D | DI | DI | I | D | I | I | DI | DI | D | D | DI |
| Daihong (QD-1) | DI | DI | DI | DI | I | D | D | DI | I | I | D | D | DI |
| Tangmutian (QD-10) | DI | DI | D | D | DI | D | DI | I | DI | DI | D | D | D |
| Shanjin Crab N1 (QD-11) | D | I | D | D | D | DI | I | DI | D | D | DI | D | D |
| Shanjin Crab N2 (QD-12) | D | DI | D | D | D | D | I | DI | D | D | DI | DI | DI |
| E zhen 1 (QD-13) | D | D | D | D | D | D | DI | I | I | DI | DI | D | DI |

-continued

| Construction results of InDel marker genotype database of *Malus* germplasm resources | | | | | | | | | | | | | |
|---|---|---|---|---|---|---|---|---|---|---|---|---|
| E zhen 2 (QD-14) | D | D | D | DI | DI | D | D | I | DI | I | I | DI | D |
| E zhen 3 (QD-15) | D | D | D | D | D | D | D | I | I | DI | DI | D | D |
| E zhen 4 (QD-16) | D | D | D | DI | DI | D | DI | I | DI | DI | DI | DI | D |
| E zhen 5 (QD-17) | D | D | D | DI | DI | D | DI | I | DI | DI | DI | DI | D |
| Haihong (QD-19) | D | DI | D | D | D | D | DI | DI | I | D | DI | DI | DI |
| Qingfu 2 (QD-2) | DI | DI | D | D | DI | DI | DI | I | DI | DI | D | D | DI |
| Telamon (QD-20) | DI | I | DI | D | DI | D | D | DI | I | DI | DI | D | DI |
| Fuyan (QD-21) | DI | DI | D | DI | I | D | DI | DI | I | DI | D | D | I |
| Hongxun 1 (QD-22) | D | DI | D | D | DI | D | DI | I | D | DI | I | DI | I |
| Rushan Fuji (QD-23) | DI | DI | D | D | DI | D | DI | I | DI | DI | D | D | D |
| Jiudian Spur (QD-24) | DI | DI | D | D | DI | DI | DI | I | DI | DI | D | D | D |
| Ruihong (QD-25) | DI | I | DI | D | I | D | DI | DI | D | D | D | D | I |
| Zhongnvshi (QD-26) | D | I | D | D | DI | D | DI | DI | D | D | D | D | D |
| 2001 Spur (QD-27) | DI | DI | D | D | DI | D | DI | I | DI | DI | D | D | D |
| Fuli (QD-28) | I | I | D | D | I | DI | D | DI | DI | DI | D | D | DI |
| Tuanwang semi-Spur (QD-29) | DI | DI | D | D | DI | D | DI | I | DI | DI | D | D | D |
| Qingfu 3 (QD-3) | DI | DI | D | D | DI | D | DI | I | DI | DI | D | D | D |
| Longfu (QD-30) | DI | DI | D | D | DI | D | DI | I | DI | DI | D | D | D |
| Baotou Linqin (QD-31) | D | I | D | D | D | D | DI | I | D | D | I | DI | D |
| Yanfu 6 (QD-32) | DI | DI | D | D | DI | DI | DI | I | DI | DI | D | D | D |
| SH40-2 seedling (QD-4) | D | I | D | D | DI | D | DI | I | D | D | DI | D | D |
| Saijin (QD-5) | DI | I | DI | D | I | D | DI | DI | DI | DI | D | D | I |
| Nagafu 12 (QD-6) | DI | DI | D | D | DI | DI | DI | I | DI | DI | D | D | D |
| Caoyuan Crab (QD-7) | D | DI | D | D | DI | D | I | I | D | D | I | D | DI |
| Xiaojin Crab (QD-8) | DI | I | DI | DI | DI | D | DI | DI | D | DI | DI | D | DI |
| Shuangyanghong (QD-9) | DI | I | DI | D | I | D | DI | DI | D | D | D | D | I |
| Qianxian Crab (QX-1) | D | I | D | D | D | DI | I | D | DI | DI | I | DI | DI |
| Ruixue (ruixue) | DI | DI | DI | DI | I | DI | D | DI | D | I | DI | DI | I |
| Ruiyang (RY) | DI | I | D | DI | I | D | D | I | DI | D | DI | DI | DI |
| Yanyuan 1 (SC-1) | I | DI | DI | DI | I | DI | DI | DI | DI | DI | DI | DI | DI |
| Yanyuan 2 (SC-2) | DI | DI | DI | DI | DI | D | DI | DI | D | D | D | D | I |
| Yanyuan 3 (SC-3) | DI | DI | D | D | DI | DI | DI | I | DI | DI | D | D | D |
| Yanyuan 4 (SC-4) | DI | DI | DI | DI | DI | D | DI | DI | D | D | D | D | DI |
| Yanyuan 5 (SC-5) | D | D | DI | DI | I | D | DI | DI | D | D | DI | D | I |
| Yanyuan 6 (SC-6) | DI | D | D | D | DI | D | DI | D | D | D | DI | DI | I |
| Yanyuan 7 (SC-7) | I | DI | DI | DI | DI | DI | DI | DI | DI | DI | DI | D | I |
| Mitchgala (SX-10) | DI | I | DI | D | I | D | DI | DI | D | D | D | D | I |

Construction results of InDel marker genotype database of *Malus* germplasm resources

| | | | | | | | | | | | | | |
|---|---|---|---|---|---|---|---|---|---|---|---|---|---|
| Zhongqiuwang Linyi (SX-11) | DI | DI | DI | DI | I | DI | DI | I | I | D | D | D | I |
| Linyi Meiguo 5 (SX-12) | DI | D | D | DI | DI | D | DI | DI | D | DI | D | D | DI |
| Liquan Spur Fuji (SX-13) | DI | DI | D | D | DI | DI | DI | I | DI | DI | D | D | D |
| Qiulimu (SX-14) | D | D | D | D | D | D | DI | I | DI | D | DI | DI | I |
| Qincui (SX-15) | DI | DI | DI | D | I | D | I | DI | DI | D | DI | DI | D |
| Taigu Shaguo Late (SX-17) | D | DI | D | D | I | D | DI | DI | DI | D | DI | DI | DI |
| Lingyige Hongrou (SX-18) | D | DI | D | D | DI | D | DI | DI | DI | DI | D | I | DI |
| Shenai LS (SX-19) | DI | DI | DI | D | DI | D | D | I | DI | DI | D | D | I |
| Linyi Meiguo 8 (SX-2) | DI | DI | DI | I | I | D | DI | DI | D | D | DI | DI | DI |
| Liga (SX-20) | DI | I | DI | D | I | D | DI | DI | D | D | D | D | I |
| Y-1 (SX-21) | D | I | D | D | D | D | D | I | D | DI | D | D | D |
| B009 (SX-22) | D | DI | D | D | D | D | DI | I | D | D | D | D | D |
| Jinfu 1 (SX-23) | DI | DI | D | D | DI | DI | DI | I | DI | DI | D | D | D |
| Hongmantang (SX-24) | D | I | D | D | D | DI | D | I | D | DI | D | D | I |
| Y-2 (SX-25) | D | I | D | D | D | D | I | I | D | D | D | D | D |
| Y-3 (SX-26) | D | I | D | D | D | D | I | I | D | D | D | D | D |
| Xinliangxiang (SX-27) | DI | DI | D | D | DI | DI | DI | I | DI | DI | D | D | D |
| Ennike Gala (SX-28) | DI | I | DI | D | I | D | DI | DI | D | D | D | D | I |
| Linyi Meiguo 6 (SX-3) | DI | D | DI | DI | DI | D | DI | DI | D | D | D | D | I |
| Linyi Meiguo 2 (SX-30) | DI | DI | D | D | DI | DI | DI | I | DI | DI | D | D | D |
| Donglimu (SX-33) | D | D | D | D | D | D | DI | I | DI | D | DI | DI | I |
| Linyi Meiguo 1 (SX-34) | DI | DI | DI | DI | I | D | DI | DI | D | D | DI | DI | DI |
| Linyi Meiguo 4 (SX-4) | I | DI | DI | I | I | D | D | I | D | D | D | D | D |
| Qinyang (SX-6) | DI | I | DI | D | I | DI | DI | DI | D | D | D | D | I |
| Taiguo Shaguo Early (SX-7) | D | DI | D | D | DI | D | DI | DI | DI | D | DI | DI | I |
| Yuhua Zaofu (SX-8) | DI | DI | D | D | DI | DI | DI | I | DI | DI | D | D | D |
| 78-M18 (SY-1) | DI | DI | DI | D | DI | D | DI | I | D | D | DI | DI | DI |
| Jinping (SY-10) | D | DI | DI | D | DI | DI | DI | DI | DI | DI | DI | I | DI |
| Longqiu (SY-11) | D | D | D | D | DI | D | I | I | DI | D | D | DI | I |
| Longfeng (SY-12) | D | D | DI | D | I | D | D | D | D | D | I | D | D |
| Xiangjiaoguo (SY-14) | DI | I | DI | DI | DI | D | DI | DI | DI | DI | I | DI | DI |
| Longguan (SY-15) | DI | DI | DI | D | I | D | I | I | D | D | D | D | DI |
| Longshuai (SY-16) | DI | DI | DI | D | DI | D | D | D | D | D | DI | DI | D |
| Zixiang (SY-17) | D | I | D | D | DI | D | DI | DI | D | DI | DI | DI | D |
| Huahong (SY-19) | D | DI | D | D | DI | D | DI | DI | DI | DI | DI | DI | DI |
| Binlang (SY-2) | DI | I | DI | DI | DI | D | DI | DI | DI | I | D | DI | DI |
| Qiufengmi (SY-20) | D | DI | D | D | D | D | DI | DI | D | DI | I | I | |
| Honglingdang (SY-21) | D | DI | D | D | D | DI | I | I | DI | D | D | D | DI |

-continued

| Construction results of InDel marker genotype database of *Malus* germplasm resources | | | | | | | | | | | | | |
|---|---|---|---|---|---|---|---|---|---|---|---|---|
| Qiulu (SY-22) | D | D | DI | D | I | D | I | I | DI | D | DI | DI | D |
| Longhong (SY-23) | DI | DI | DI | D | DI | D | I | I | D | D | D | D | DI |
| Milk (SY-3) | D | DI | DI | D | I | D | I | DI | D | DI | D | DI | D |
| Hanfu (SY-4) | DI | D | D | D | I | DI | DI | DI | D | D | D | D | D |
| Toko (SY-5) | I | DI | D | D | I | I | DI | DI | D | D | D | D | DI |
| Jinhong (SY-6) | DI | DI | DI | DI | DI | D | D | DI | D | D | I | DI | I |
| K9 (SY-7) | D | DI | D | D | D | DI | I | I | DI | DI | D | DI | DI |
| 03-06-04 (SY-8) | D | I | DI | D | DI | D | D | I | D | D | D | D | DI |
| Olga (SY-9) | D | D | D | D | I | D | DI | DI | D | D | DI | D | DI |
| Gala 4x (TA-1) | DI | I | DI | D | I | D | DI | DI | D | D | D | D | I |
| Juda Fuji (TA-11) | DI | DI | D | D | DI | D | DI | I | DI | DI | D | D | D |
| Luli (TA-12) | D | I | DI | D | DI | D | DI | DI | D | D | D | D | DI |
| Luping 1 (TA-13) | DI | DI | DI | D | I | D | DI | D | D | D | D | D | DI |
| Luping 2 (TA-14) | DI | DI | DI | D | I | DI | DI | DI | D | D | D | D | I |
| Luping 5 (TA-15) | DI | DI | DI | D | I | DI | DI | DI | D | D | D | D | I |
| Luyan (TA-16) | D | I | DI | D | DI | D | D | DI | D | D | DI | D | DI |
| Meinong (TA-17) | D | DI | D | D | DI | DI | D | I | D | DI | D | D | DI |
| Akifu 19 (TA-18) | DI | DI | D | D | DI | DI | DI | I | DI | DI | D | D | D |
| Akifu 39 (TA-19) | DI | DI | D | D | DI | DI | DI | I | DI | DI | D | D | D |
| Hanfu 4x (TA-2) | DI | I | DI | D | I | D | I | I | I | D | D | DI | I |
| Qiufuhong (TA-20) | DI | DI | D | D | DI | DI | DI | I | DI | DI | D | D | D |
| Qunfu 1 (TA-21) | DI | DI | D | D | DI | DI | DI | I | DI | DI | D | D | D |
| Shengfang (TA-22) | DI | DI | D | D | DI | DI | DI | I | DI | DI | D | D | DI |
| Alps Otome (TA-27) | DI | DI | D | D | DI | D | DI | DI | D | D | D | DI | I |
| Early Fuji (TA-28) | DI | DI | D | D | DI | DI | DI | I | DI | DI | D | D | D |
| BP (TA-3) | D | D | D | DI | DI | D | D | I | I | I | I | DI | DI |
| Yishuihong (TA-32) | DI | DI | D | D | DI | DI | DI | I | DI | DI | D | D | D |
| BP-176 (TA-4) | D | D | D | DI | DI | D | D | I | I | I | I | DI | DI |
| G41 (TA-5) | D | DI | D | D | DI | DI | D | DI | I | I | I | DI | DI |
| G935 (TA-6) | D | I | D | D | D | D | DI | I | I | DI | I | DI | D |
| P60 (TA-7) | D | D | D | D | D | D | D | I | I | I | DI | D | D |
| Fuji (TA-9) | DI | DI | D | D | DI | DI | DI | I | DI | DI | D | D | D |
| Tianfu 1 (TS-1) | DI | DI | D | D | DI | DI | DI | I | DI | DI | D | D | D |
| &28 (TS-13) | DI | DI | D | D | DI | DI | DI | I | DI | DI | D | D | D |
| Red Chief (TS-14) | D | D | DI | DI | I | D | I | I | DI | DI | D | D | DI |
| New Redchief (TS-2) | D | D | DI | DI | I | D | I | I | DI | DI | D | D | DI |
| Chaohongxing (TS-3) | D | D | DI | DI | I | D | I | I | DI | DI | D | D | DI |
| Aozhou 1 (TS-5) | DI | DI | DI | D | I | D | I | I | DI | DI | I | I | I |

-continued

| Construction results of InDel marker genotype database of *Malus* germplasm resources |||||||||||||
|---|---|---|---|---|---|---|---|---|---|---|---|---|
| Tianfu 2 (TS-6) | DI | DI | D | D | DI | DI | DI | I | DI | DI | D | D | D |
| Judeline (TS-7) | DI | DI | DI | DI | I | DI | DI | DI | DI | DI | DI | DI | I |
| Judestar (TS-8) | DI | I | DI | DI | I | D | DI | DI | DI | DI | D | D | I |
| Judaine (TS-9) | DI | DI | DI | DI | I | DI | DI | DI | DI | DI | DI | DI | DI |
| WH-5 (WH-1) | DI | DI | D | D | DI | DI | DI | I | DI | DI | D | D | D |
| Italy Smothe (WH-10) | I | DI | DI | DI | I | DI | DI | DI | DI | DI | DI | DI | I |
| Bai Crab (WH-2) | D | D | D | D | DI | D | DI | I | I | D | DI | I | DI |
| Hongguang (WH-4) | D | D | DI | D | I | D | I | I | DI | DI | D | D | D |
| Huangcui (WH-5) | DI | DI | DI | D | I | DI | DI | I | DI | D | D | D | DI |
| Qinglin (WH-6) | I | DI | DI | DI | I | D | DI | DI | D | D | DI | DI | DI |
| Harlikar (WH-8) | DI | DI | DI | I | DI | D | DI | DI | I | DI | D | D | DI |
| Italy Gala (WH-9) | DI | I | DI | D | I | D | DI | DI | D | D | D | D | I |
| Wushan Bianye (WSBY) | D | I | D | D | D | D | I | I | D | D | DI | D | D |
| Xin 1 (XC-1) | I | I | DI | D | I | D | D | DI | D | D | D | D | I |
| Xin 5 (XC-2) | I | I | DI | D | I | D | I | DI | D | D | D | D | I |
| Hanfu 3x (XC-3) | I | D | D | D | I | D | D | I | D | D | D | D | D |
| Gala 4x (XC-4) | DI | I | DI | D | I | D | DI | DI | D | D | D | D | I |
| Weizhimuben (XC-5) | D | I | D | DI | DI | DI | DI | DI | DI | D | DI | DI | I |
| Chaguo (XC-CG) | D | DI | D | D | DI | D | I | DI | I | DI | D | DI | DI |
| Donghongguo (XC-DHG) | D | D | D | D | D | D | DI | DI | DI | D | DI | DI | DI |
| Fuxian Sanye (XC-FXXY) | D | I | D | D | D | D | I | I | D | D | D | D | D |
| Hongsanye (XC-HSY) | D | I | D | D | D | DI | I | DI | D | D | DI | D | D |
| Jilin Xiaohong Crab (XC-JILINXIAOHONG-HAITANG) | D | D | D | D | DI | D | DI | I | DI | D | I | D | DI |
| Jilin Xiaohuang Crab (XC-JILINXIAOHUANG-HAITANG) | D | I | D | D | D | D | DI | DI | DI | D | I | DI | D |
| Jilin Huang Crab (XC-JLHHT) | D | I | D | D | D | D | DI | DI | DI | D | I | DI | D |
| Shajin Crab (XC-JSHT) | D | I | D | D | D | D | I | I | D | D | D | D | D |
| Longdong Crab (XC-LDHT) | D | I | D | D | D | D | I | I | D | D | DI | D | D |
| Lushi Crab (XC-LSHT) | D | I | D | D | D | D | I | I | D | D | D | D | D |
| Laiwunanyan (XC-LWNY) | D | DI | D | D | DI | D | I | DI | I | DI | D | DI | DI |
| Linzhi (XC-LZ) | D | I | D | D | D | D | I | I | D | D | DI | D | D |
| Mao Shandingzi (XC-MSDZ) | D | DI | D | D | D | D | I | I | D | D | D | DI | DI |
| Pingyitiancha (XC-PYTC) | D | I | D | D | D | D | I | DI | D | D | D | D | D |
| Qiuzi (XC-QZ) | D | DI | D | D | DI | D | D | I | I | I | DI | I | DI |
| Sichuan Bianye (XC-SCBY) | D | I | D | D | D | D | I | I | D | D | DI | D | D |
| Shandingzi (XC-SDZ) | D | I | D | D | D | D | I | I | D | D | D | D | D |
| Weixi Sanye (XC-WXSY) | DI | DI | D | D | D | D | I | DI | DI | DI | D | D | DI |

-continued

Construction results of InDel marker genotype database of *Malus* germplasm resources

| | | | | | | | | | | | | | |
|---|---|---|---|---|---|---|---|---|---|---|---|---|---|
| Xifu Crb (XC-XFHT) | D | DI | D | D | D | D | DI | DI | DI | D | I | D | DI |
| Xiaojin Bianye (XC-XJBY) | D | I | D | D | D | D | I | I | D | D | I | D | D |
| Xinjiang Yepingguo (XC-XJYHT) | D | D | D | D | DI | D | DI | DI | I | DI | DI | DI | I |
| Yajiang Bianye (XC-YJBY) | D | I | D | D | D | D | I | I | D | D | DI | D | D |
| Yingye Crab (XC-YYHT) | D | I | D | D | DI | D | I | DI | D | D | D | DI | D |
| Zhaai (XC-ZA) | D | I | D | D | D | D | I | I | D | D | D | D | D |
| Zumi Crab (XC-ZMHT) | D | I | D | D | D | D | DI | I | D | D | D | D | D |
| Pink Lady (XN-FHNS) | I | DI | DI | DI | I | DI | DI | DI | D | DI | I | I | DI |
| Hongrou 1 (XN-HR1) | D | D | D | D | D | D | D | I | I | I | DI | DI | DI |
| Hongrou 2 (XN-HR2) | D | D | D | D | D | D | DI | I | I | I | DI | DI | I |
| Hongrou 3 (XN-HR3) | D | D | D | D | D | D | D | I | I | I | I | I | DI |
| Hongrou 4 (XN-HR4) | D | D | D | D | D | D | D | I | I | I | DI | I | I |
| Hongrou 5 (XN-HR5) | D | D | D | D | DI | D | I | I | I | I | DI | DI | DI |
| Hongrou 6 (XN-HR6) | D | DI | D | D | I | DI | DI | I | I | DI | I | I | I |
| Hongrou 7 (XN-HR7) | D | D | D | D | D | D | DI | DI | I | DI | I | DI | I |
| Ambrosia (XN-MW) | DI | DI | DI | DI | I | D | DI | I | DI | D | D | D | I |
| Xinjiang 10 (XN-XJ10) | D | D | D | D | DI | D | D | DI | I | DI | I | I | DI |
| Xinjiang 11 (XN-XJ11) | D | D | D | D | D | D | D | I | I | DI | DI | I | I |
| Xinjiang 12 (XN-XJ12) | D | D | D | D | DI | D | D | DI | I | DI | I | I | DI |
| Xinjiang 13 (XN-XJ13) | D | DI | D | D | DI | D | DI | I | I | D | I | DI | I |
| Xinjiang 14 (XN-XJ14) | D | D | D | D | D | D | D | DI | I | D | DI | D | DI |
| Xinjiang 15 (XN-XJ15) | D | D | D | D | I | D | DI | DI | I | D | DI | I | DI |
| Xinjiang 16 (XN-XJ16) | D | D | D | D | D | D | DI | I | DI | D | DI | DI | I |
| Xinjiang 17 (XN-XJ17) | D | D | D | D | DI | D | D | DI | I | D | DI | DI | I |
| Xinjiang 18 (XN-XJ18) | D | DI | D | D | D | DI | DI | I | I | DI | DI | DI | DI |
| Xinjiang 19 (XN-XJ19) | D | D | D | D | I | D | DI | DI | I | I | I | I | DI |
| Xinjiang 2 (XN-XJ2) | D | D | D | D | D | D | D | I | I | DI | I | I | I |
| Xinjiang 20 (XN-XJ20) | D | DI | D | D | D | D | DI | I | DI | DI | DI | DI | I |
| Xinjiang 21 (XN-XJ21) | D | D | DI | DI | D | D | DI | DI | DI | D | DI | I | I |
| Xinjiang 23 (XN-XJ23) | D | DI | D | D | I | D | DI | I | DI | D | I | DI | I |
| Xinjiang 24 (XN-XJ24) | D | D | D | D | I | D | D | I | I | I | DI | I | DI |
| Xinjiang 25 (XN-XJ25) | D | D | D | D | D | D | DI | DI | I | D | I | I | DI |
| Xinjiang 27 (XN-XJ27) | D | D | D | D | I | D | DI | DI | I | D | DI | I | DI |
| Xinjiang 3 (XN-XJ3) | D | D | D | D | I | D | DI | DI | I | I | I | I | DI |
| Xinjiang 4 (XN-XJ4) | D | D | D | D | D | D | DI | I | I | DI | I | DI | I |
| Xinjiang 5 (XN-XJ5) | D | D | D | D | DI | D | D | I | D | D | DI | D | DI |
| Xinjiang 7 (XN-XJ7) | D | D | D | D | D | D | DI | I | D | D | I | DI | DI |
| Xinjiang 8 (XN-XJ8) | D | D | D | DI | DI | D | D | DI | I | I | DI | I | I |

-continued

Construction results of InDel marker genotype database of *Malus* germplasm resources

| | | | | | | | | | | | | | |
|---|---|---|---|---|---|---|---|---|---|---|---|---|---|
| Xinjiang 9 (XN-XJ9) | D | D | D | D | I | D | DI | I | DI | DI | D | D | DI |
| Yueguan (XY-10) | I | DI | DI | DI | I | D | I | DI | DI | D | D | D | D |
| Yuehua (XY-11) | D | D | D | D | DI | D | I | I | DI | D | D | DI | I |
| Yueyan (XY-12) | I | DI | DI | D | I | D | DI | D | D | D | D | D | DI |
| Bud Sport 5 (XY-13) | DI | DI | D | D | DI | DI | DI | I | DI | DI | D | D | D |
| Bud Sport 3 (XY-14) | DI | DI | D | D | DI | DI | DI | I | DI | DI | D | D | D |
| Longfu (XY-15) | DI | DI | D | D | DI | DI | DI | I | DI | DI | D | D | D |
| Yuemei (XY-18) | DI | DI | DI | DI | I | D | D | DI | DI | D | I | DI | DI |
| Hanfu (XY-2) | DI | D | D | D | I | DI | DI | DI | D | D | D | D | D |
| Linyi Fuji (XY-20) | D | DI | DI | D | I | DI | DI | I | D | D | D | D | DI |
| Yishui Fuji (XY-22) | DI | DI | D | D | DI | DI | DI | I | DI | DI | D | D | D |
| Hongjinfu (XY-25) | DI | DI | D | D | DI | DI | DI | I | DI | DI | D | D | D |
| Beni Oshu (XY-26) | DI | DI | D | D | DI | DI | DI | I | DI | DI | D | D | D |
| Chuizhi Fuji (XY-27) | DI | DI | D | D | DI | DI | DI | I | DI | DI | D | D | D |
| Yueshuai (XY-28) | DI | DI | DI | DI | I | DI | DI | DI | I | D | DI | DI | DI |
| Shichinohe 2 (XY-29) | DI | DI | D | D | DI | DI | DI | I | DI | DI | D | D | DI |
| 74-178 (XY-3) | DI | DI | D | D | I | DI | I | DI | DI | D | D | D | D |
| KAKUFUJI (XY-30) | DI | DI | D | D | DI | DI | DI | I | DI | DI | D | D | D |
| Royal Fuji 21 (XY-35) | DI | DI | D | D | DI | DI | DI | I | DI | DI | D | D | D |
| Qiquan Spur (XY-36) | DI | DI | D | D | DI | DI | DI | I | DI | DI | D | D | D |
| Juda Fuji (XY-37) | D | D | D | DI | D | I | D | I | I | DI | DI | D | D | D |
| 7-211 (XY-4) | DI | D | DI | DI | DI | D | D | DI | D | D | DI | D | I |
| Yanfu 0 (XY-41) | DI | DI | D | D | DI | DI | DI | I | DI | DI | D | D | D |
| Spur Fuji (XY-42) | DI | DI | D | D | DI | DI | DI | I | DI | DI | D | D | D |
| Bayue fushiwang (XY-43) | DI | DI | D | D | DI | DI | DI | I | DI | DI | D | D | D |
| Huangfu 7 (XY-44) | DI | DI | D | D | DI | DI | DI | I | DI | DI | D | D | DI |
| Aomori Spur Fuji (XY-46) | DI | DI | D | D | DI | DI | DI | I | DI | DI | D | D | D |
| Qiu Fuji (XY-47) | DI | DI | D | D | DI | DI | DI | I | DI | DI | D | D | D |
| Fuji Champion (XY-48) | DI | DI | D | D | DI | DI | DI | I | DI | DI | D | D | D |
| 26-34 (XY-5) | D | DI | DI | DI | I | D | DI | DI | D | D | D | D | D |
| Akifu 19 (XY-50) | DI | DI | D | D | DI | DI | DI | I | DI | DI | D | D | D |
| Fuji (XY-54) | DI | DI | D | D | DI | DI | DI | I | DI | DI | D | D | D |
| Qinfu 1 (XY-55) | DI | DI | D | D | DI | DI | DI | DI | DI | DI | D | D | D |
| Feng Fuji (XY-56) | DI | DI | D | D | DI | DI | DI | I | DI | DI | D | D | D |
| Tianxing (XY-57) | DI | DI | D | D | D | DI | DI | I | DI | DI | D | D | D |
| Taiyang Fuji (XY-58) | DI | DI | D | D | DI | DI | DI | I | DI | DI | D | D | DI |
| Cherry Crab (XY-6) | D | I | DI | D | DI | D | I | I | D | DI | DI | D | DI |
| Yueping (XY-60) | DI | DI | D | D | DI | DI | I | DI | DI | D | D | D | DI |

-continued

Construction results of InDel marker genotype database of *Malus* germplasm resources

| | | | | | | | | | | | | |
|---|---|---|---|---|---|---|---|---|---|---|---|---|
| 23-63 (XY-61) | I | I | D | D | I | DI | I | DI | DI | D | D | D | D |
| 23-42 (XY-62) | DI | DI | D | D | I | DI | DI | DI | D | D | D | D | D |
| 7-171 (XY-63) | DI | I | DI | DI | I | D | D | DI | DI | D | DI | DI | I |
| Shengfang 3A (XY-65) | DI | DI | D | D | DI | DI | DI | I | DI | DI | D | D | D |
| Meinong Fuji (XY-67) | DI | DI | D | D | DI | DI | DI | I | DI | DI | D | D | D |
| 62-45 (XY-68) | DI | DI | D | D | I | DI | DI | DI | D | D | D | D | D |
| Fengfeng Fuji (XY-70) | DI | DI | D | D | DI | DI | DI | I | DI | DI | D | D | D |
| GM256 (XY-71) | DI | DI | D | D | DI | DI | DI | I | DI | D | D | D | DI |
| Jinfu 2 (XY-73) | DI | DI | D | D | DI | DI | DI | I | DI | DI | D | D | D |
| Qiufu (XY-75) | DI | DI | D | D | DI | DI | DI | I | DI | DI | D | D | D |
| Shanfu 6 (XY-76) | DI | DI | D | D | DI | DI | DI | I | DI | DI | D | D | D |
| Nagafu 8 (XY-77) | DI | DI | D | D | DI | DI | DI | I | DI | DI | D | D | D |
| 58-34 (XY-78) | DI | D | DI | DI | I | D | I | DI | DI | D | D | D | DI |
| 2001 Fuji (XY-79) | DI | DI | D | D | DI | DI | DI | I | DI | DI | D | D | D |
| 15-26 (XY-8) | DI | DI | DI | DI | DI | DI | D | DI | DI | D | D | DI | I |
| Wangshanhong (XY-80) | DI | DI | D | D | D | DI | DI | I | DI | DI | D | D | D |
| Jinfu 1 (XY-81) | DI | DI | D | D | DI | DI | DI | I | DI | DI | D | D | D |
| Qingfu 1 (XY-84) | DI | DI | D | D | DI | DI | DI | I | DI | DI | D | D | D |
| Qiufu 39 (XY-85) | DI | DI | D | D | DI | DI | DI | I | DI | DI | D | D | D |
| Nagafu 1 (XY-86) | DI | DI | D | D | DI | DI | DI | I | DI | DI | D | D | D |
| Shou Fuji (XY-87) | DI | DI | D | D | DI | DI | DI | I | DI | DI | D | D | D |
| Yueli (XY-88) | DI | DI | DI | DI | DI | D | D | DI | DI | D | D | D | D |
| Shanfu 2 (XY-89) | DI | DI | D | D | DI | DI | DI | I | DI | DI | D | D | D |
| Chongban Crab (XY-9) | D | DI | D | D | I | D | DI | DI | DI | I | D | DI | DI |
| Harica (XY-90) | I | DI | DI | DI | I | D | DI | DI | D | DI | DI | DI | I |
| Akifu 1 (XY-91) | DI | DI | D | D | DI | DI | DI | I | DI | DI | D | D | D |
| Wangfu (XY-92) | DI | DI | D | D | DI | D | DI | I | DI | DI | D | D | D |
| Hong Manao (XYZ-1) | D | I | D | D | D | DI | I | D | DI | D | D | DI | I |
| Modi (XYZ-10) | DI | DI | DI | D | DI | DI | DI | DI | D | D | D | D | I |
| C37 (XYZ-11) | I | D | DI | I | I | DI | DI | DI | DI | I | DI | DI | I |
| Envy ? (XYZ-12) | I | DI | DI | D | I | D | I | DI | DI | D | DI | D | I |
| Xichang Yuanzhuiguo (XYZ-2) | D | I | D | D | DI | D | D | I | DI | D | DI | D | DI |
| Ziye Zixiaoguo (XYZ-3) | D | I | D | D | D | D | I | I | D | DI | D | D | D |
| Ziye Zidaguo (XYZ-4) | DI | I | D | D | D | D | I | DI | DI | DI | D | D | D |
| Shoufenshu 6 (XYZ-5) | D | I | DI | D | I | D | DI | I | DI | D | DI | D | I |
| Changhua (XYZ-6) | DI | I | DI | D | I | D | DI | DI | D | D | D | D | I |
| Jinshiji (XYZ-7) | DI | I | DI | D | I | D | DI | DI | D | D | D | D | I |
| 19-147 (XYZ-9) | D | D | DI | I | I | DI | DI | DI | D | D | D | DI | I |

| Construction results of InDel marker genotype database of *Malus* germplasm resources | | | | | | | | | | | | | |
|---|---|---|---|---|---|---|---|---|---|---|---|---|---|
| Malong Gala 1 (YN-1) | DI | I | DI | D | I | D | DI | DI | D | D | D | D | I |
| Shouer hong (YN-11) | DI | DI | D | D | DI | DI | DI | I | DI | DI | D | D | D |
| Yun Hongrou (YN-12) | DI | DI | D | D | DI | DI | DI | I | DI | I | DI | D | DI |
| Lixing Crab (YN-13) | D | DI | D | D | D | D | DI | DI | I | D | DI | D | DI |
| Siana (YN-15) | DI | D | DI | D | DI | D | DI | DI | DI | I | D | D | I |
| Jonathan-M41 (YN-17) | DI | DI | D | D | D | D | D | DI | D | D | D | D | I |
| Morlie's Delicious (YN-18) | I | DI | DI | I | I | D | D | DI | DI | D | DI | DI | I |
| Britegold (YN-19) | DI | DI | D | D | D | D | DI | I | DI | DI | D | D | D |
| Malong Gala 1 blush (YN-2) | DI | I | DI | D | I | D | DI | DI | D | D | D | D | I |
| Line 5 (YN-22) | DI | D | DI | D | DI | D | DI | DI | DI | I | D | D | I |
| Line 6 (YN-23) | D | DI | D | D | DI | DI | DI | DI | D | D | DI | DI | DI |
| Line 13 (YN-24) | DI | DI | DI | DI | DI | D | DI | DI | D | I | D | D | I |
| row 3 (YN-25) | D | I | DI | D | DI | D | DI | DI | D | D | D | D | I |
| row 4 (YN-26) | D | I | DI | D | DI | D | DI | DI | D | D | D | D | I |
| row 5 (YN-27) | D | I | DI | D | DI | D | DI | DI | D | D | D | D | I |
| row 6 (YN-28) | D | I | DI | D | DI | D | DI | DI | D | D | D | D | I |
| row 9 (YN-29) | DI | DI | DI | DI | I | D | DI | DI | DI | D | D | D | I |
| Malong xin Gala 1 (YN-3) | DI | I | DI | D | I | D | DI | DI | D | D | D | D | I |
| row 10 (YN-30) | I | DI | DI | I | I | D | DI | DI | D | DI | I | I | I |
| row 11 (YN-31) | DI | DI | DI | I | I | D | DI | DI | DI | D | D | D | I |
| row 12 (YN-32) | DI | I | DI | D | I | D | DI | DI | D | D | D | D | I |
| row 13 (YN-33) | D | I | DI | D | DI | D | D | DI | D | D | DI | D | I |
| row 14 (YN-34) | D | I | DI | D | DI | D | DI | DI | D | D | D | D | I |
| row 15 (YN-35) | DI | DI | DI | D | I | D | DI | DI | D | D | D | D | I |
| row 16 (YN-36) | I | DI | DI | DI | DI | DI | DI | DI | DI | DI | DI | D | I |
| row 17 (YN-37) | D | D | DI | DI | I | D | DI | DI | D | D | DI | DI | I |
| row 18 (YN-38) | DI | D | D | D | DI | D | DI | DI | D | D | DI | DI | I |
| row 19 (YN-39) | DI | I | D | D | I | DI | I | DI | D | D | DI | DI | D |
| Malong xin Gala 1 strip (YN-4) | DI | I | DI | D | I | D | DI | DI | D | D | D | D | I |
| row 20 (YN-40) | DI | DI | DI | DI | DI | D | DI | DI | D | D | D | D | I |
| row 21 (YN-41) | DI | DI | D | D | DI | DI | DI | I | DI | DI | D | D | DI |
| row 22 (YN-42) | DI | DI | DI | DI | DI | D | DI | DI | D | D | D | D | I |
| row 23 (YN-43) | DI | DI | DI | DI | DI | DI | DI | DI | D | D | D | D | I |
| row 24 (YN-44) | DI | DI | D | D | DI | DI | DI | I | DI | DI | D | D | DI |
| row 25 (YN-45) | DI | DI | D | D | DI | DI | DI | I | DI | DI | D | D | D |
| Malong Gala2 (YN-5) | DI | I | DI | D | I | D | DI | DI | D | D | D | D | I |
| Malong Gala 2 blush (YN-6) | DI | I | DI | D | I | D | DI | DI | D | D | D | D | I |
| Longwei (YN-7) | DI | DI | DI | D | I | D | I | DI | DI | D | D | D | DI |

-continued

Construction results of InDel marker genotype database of *Malus* germplasm resources

| | | | | | | | | | | | | |
|---|---|---|---|---|---|---|---|---|---|---|---|---|
| Longwei Early Mutant (YN-8) | DI | DI | DI | D | I | D | I | DI | DI | D | D | D | DI |
| Cherry Gala (YN-9) | DI | I | DI | D | I | D | DI | DI | D | D | D | D | I |
| Siyana (YT-1) | DI | I | DI | D | I | DI | I | DI | DI | D | D | DI | DI |
| Yanfu 10 (YT-100) | DI | DI | D | D | DI | DI | DI | I | DI | DI | D | D | D |
| Chadel (YT-102) | DI | I | DI | DI | DI | DI | DI | DI | D | DI | DI | I | I |
| Charden (YT-103) | DI | DI | DI | DI | I | DI | DI | DI | DI | D | DI | DI | DI |
| Tuskan (YT-104) | D | I | D | D | I | D | DI | DI | I | D | D | I | DI |
| Prima × Sekaiichii (YT-105) | D | D | DI | D | I | DI | DI | DI | D | DI | D | DI | DI |
| Toppax_apple (YT-11) | DI | DI | D | D | DI | DI | I | DI | DI | D | D | DI | DI |
| Xinjiang Hongrou Crab (YT-12) | D | I | D | D | DI | D | I | I | DI | D | D | D | DI |
| Melfree (YT-13) | D | DI | DI | D | DI | DI | I | DI | D | D | D | I |
| Yanfu 3 (YT-14) | DI | DI | D | D | D | D | D | DI | D | D | D | D | DI |
| Gold milecnirum (YT-15) | DI | DI | DI | D | DI | DI | DI | I | DI | DI | DI | DI | DI |
| Ganhong (YT-16) | I | DI | DI | DI | DI | D | DI | I | DI | D | DI | DI | I |
| Cornoet (YT-17) | DI | D | DI | D | DI | DI | DI | I | D | D | D | DI | I |
| Priw (YT-18) | DI | I | D | DI | I | D | DI | DI | DI | D | D | DI | DI |
| Aichi (YT-19) | D | DI | D | DI | I | DI | DI | I | D | D | D | D | DI |
| Auraria (YT-2) | D | DI | DI | D | I | I | DI | DI | D | D | DI | DI | DI |
| Meile (YT-20) | DI | DI | D | D | DI | DI | DI | I | DI | DI | D | D | D |
| Qiulimeng (YT-21) | D | D | D | D | D | D | DI | I | DI | D | DI | DI | I |
| Aliusitan (YT-22) | D | D | DI | DI | D | D | I | I | DI | I | DI | DI | I |
| Geaooza (YT-23) | D | D | D | I | I | D | I | DI | DI | D | D | DI | I |
| Golden Spur (YT-24) | I | DI | DI | DI | I | DI | DI | DI | DI | DI | DI | DI | I |
| Starking (YT-25) | D | D | DI | DI | I | D | I | I | DI | DI | D | D | DI |
| Indo (YT-26) | I | D | D | D | I | DI | DI | I | D | D | DI | DI | DI |
| Teser (YT-27) | D | DI | DI | I | I | DI | I | DI | DI | D | DI | DI | D |
| Xianhong (YT-28) | D | DI | DI | DI | DI | DI | DI | DI | DI | DI | D | D | DI |
| Gala × Mato 8 (YT-29) | DI | I | DI | D | DI | D | D | I | D | D | D | D | DI |
| Very Early Fuji (YT-3) | DI | DI | D | D | DI | DI | DI | I | DI | DI | D | D | DI |
| Qiuhuapi (YT-30) | D | DI | D | DI | DI | DI | I | DI | D | DI | D | D | DI |
| Piga 70 (YT-31) | D | I | DI | I | I | DI | DI | DI | D | D | D | D | I |
| Yanzhen 1 (YT-32) | D | DI | D | D | DI | D | I | DI | DI | D | DI | DI | I |
| Matail (YT-34) | DI | I | DI | D | I | D | DI | DI | D | D | D | D | I |
| Jonathan-csan (YT-35) | DI | DI | D | D | D | D | D | DI | D | D | D | D | DI |
| Huashuai (YT-36) | D | DI | DI | I | I | D | DI | DI | D | DI | D | D | DI |
| Wengao 1 (YT-38) | DI | DI | D | D | DI | DI | DI | I | DI | DI | DI | D | D |
| Wengao 2 (YT-39) | DI | DI | D | D | DI | DI | DI | I | DI | DI | D | D | D |
| Elegia (YT-4) | D | DI | D | I | I | D | I | DI | I | D | D | D | DI |

-continued

Construction results of InDel marker genotype database of *Malus* germplasm resources

| | | | | | | | | | | | | | |
|---|---|---|---|---|---|---|---|---|---|---|---|---|---|
| Wengao 3 (YT-40) | DI | DI | D | D | DI | DI | DI | I | DI | DI | DI | D | D |
| Hong Anka (YT-41) | I | I | DI | I | I | DI | DI | DI | D | D | D | D | DI |
| Yanfu 2 (YT-42) | DI | DI | D | D | DI | DI | DI | I | DI | DI | D | D | D |
| Belgolden (YT-43) | I | DI | DI | DI | I | DI | DI | DI | DI | D | DI | D | I |
| Rubinola (YT-44) | D | DI | D | D | I | DI | I | DI | DI | DI | D | D | D |
| Wangqiuhong (YT-45) | D | DI | DI | DI | DI | D | DI | I | DI | D | D | DI | DI |
| Pulanhong (YT-46) | D | DI | D | D | I | D | D | DI | I | D | D | I | D |
| Bosh (YT-47) | D | DI | DI | D | DI | DI | DI | DI | DI | D | D | DI | DI |
| Chengji 1 (YT-48) | DI | DI | D | D | DI | DI | DI | I | DI | DI | D | D | D |
| Hongli (YT-49) | D | DI | D | D | I | DI | DI | DI | DI | D | I | D | DI |
| Guoqinghong (YT-5) | I | DI | DI | DI | DI | DI | DI | I | D | DI | DI | DI | I |
| Reandra (YT-50) | I | I | DI | I | I | D | DI | DI | D | DI | D | D | DI |
| Revbihola (YT-51) | D | DI | D | D | DI | DI | DI | I | D | D | D | D | DI |
| Melrose (YT-52) | DI | DI | DI | DI | DI | D | DI | DI | DI | DI | D | DI | DI |
| Rewena (YT-53) | D | DI | D | D | DI | D | DI | DI | DI | D | D | DI | DI |
| Mrxl(robusta × Liberte) (YT-54) | D | D | DI | I | I | D | I | I | DI | DI | D | D | DI |
| Mollies_Del_open (YT-55) | DI | I | DI | DI | I | I | DI | DI | DI | DI | DI | I | DI |
| Renora (YT-56) | DI | DI | DI | D | DI | DI | I | DI | DI | D | D | DI | I |
| Rosmadzin (YT-57) | D | DI | DI | D | DI | DI | DI | DI | DI | D | D | DI | DI |
| Remo (YT-58) | I | I | DI | D | DI | D | DI | DI | DI | D | D | D | I |
| Pilot (YT-59) | D | I | DI | DI | I | I | DI | I | DI | D | D | DI | DI |
| Yangbai Crab (YT-6) | D | D | D | D | DI | D | DI | I | I | D | DI | I | DI |
| Free Red Star (YT-60) | D | I | DI | D | DI | D | DI | I | DI | D | D | DI | DI |
| Idared (YT-61) | DI | DI | D | D | DI | D | DI | DI | D | D | D | DI | I |
| Mingyue (YT-62) | D | DI | D | DI | DI | D | DI | I | I | I | D | D | DI |
| Piga 101 (YT-63) | DI | I | DI | I | I | DI | DI | DI | D | DI | D | DI | I |
| Yanfu 5 (YT-64) | DI | DI | D | D | DI | D | DI | I | DI | DI | D | D | D |
| Early Jonagold (YT-65) | I | DI | DI | D | DI | DI | DI | DI | DI | D | D | DI | I |
| Wengao 2 mutant (YT-66) | DI | DI | D | D | DI | DI | DI | I | DI | DI | D | D | D |
| Fenhong Gala 44 (YT-67) | I | I | DI | I | I | DI | DI | DI | D | D | D | DI | DI |
| Yiyuanhong (YT-68) | DI | DI | D | D | DI | DI | DI | I | DI | DI | D | D | D |
| Yanfu 4 (YT-69) | DI | DI | D | D | DI | DI | DI | I | DI | DI | D | D | D |
| White Pearmain (YT-70) | DI | DI | DI | D | I | DI | DI | I | D | DI | D | D | I |
| Jonathan-early (YT-73) | DI | DI | D | D | D | D | D | DI | D | D | D | D | DI |
| Jonathan-midle (YT-74) | DI | DI | D | D | D | D | D | DI | D | D | D | D | DI |
| Gornan (YT-75) | DI | I | DI | D | DI | D | DI | DI | D | DI | D | DI | I |
| Regilndel (YT-76) | D | DI | D | D | DI | DI | DI | I | D | D | D | D | DI |
| Golden Bell (YT-77) | DI | DI | DI | DI | I | DI | D | I | D | DI | D | DI | DI |

| | | | | | | | | | | | | | |
|---|---|---|---|---|---|---|---|---|---|---|---|---|---|
| Construction results of InDel marker genotype database of *Malus* germplasm resources | | | | | | | | | | | | | |
| Arkcharm (YT-78) | DI | I | DI | D | I | DI | D | DI | DI | D | D | DI | I |
| Redchif (YT-79) | D | DI | D | DI | I | DI | DI | DI | DI | D | DI | DI | I |
| Mouping Guanghua Fuji (YT-8) | DI | DI | D | D | DI | DI | DI | I | DI | DI | D | D | D |
| Freedom (YT-80) | D | I | DI | DI | I | I | DI | I | D | D | D | DI | DI |
| Martinike (YT-81) | DI | DI | D | I | I | DI | I | DI | DI | D | D | DI | DI |
| Sweetle (YT-82) | DI | DI | DI | D | I | D | I | DI | DI | D | D | DI | DI |
| Aleksanader (YT-83) | D | DI | D | D | I | D | I | DI | DI | D | D | DI | DI |
| Yan 6 Fenhong 143 (YT-84) | I | I | DI | DI | I | DI | I | DI | D | D | D | DI | DI |
| Ruitina (YT-85) | D | D | DI | D | DI | DI | DI | DI | D | D | D | D | DI |
| Wengao 1 mutant (YT-86) | DI | DI | D | D | DI | DI | DI | I | DI | DI | D | D | D |
| Wengao 3 mutant (YT-87) | DI | DI | D | D | DI | DI | DI | I | DI | DI | D | D | DI |
| Shajinyilamu (YT-88) | D | D | D | D | D | D | D | I | I | DI | D | I | I |
| Qiuhong (YT-89) | D | D | D | D | I | D | DI | I | DI | DI | D | DI | D |
| Changyanghong (YT-9) | DI | DI | D | D | DI | DI | DI | I | DI | DI | D | D | D |
| Yanfu 8 (YT-90) | DI | DI | D | D | DI | DI | DI | I | DI | DI | D | D | D |
| Jinduhong Gala (YT-91) | DI | I | DI | D | I | D | DI | DI | D | D | D | D | I |
| Nagafu 2 (YT-92) | DI | DI | D | D | DI | DI | DI | I | DI | DI | D | D | D |
| Honglu seedling 65 (YT-93) | DI | I | DI | D | DI | D | DI | I | DI | I | D | D | D |
| Tsugaru (YT-94) | DI | DI | DI | DI | DI | D | DI | DI | D | D | D | D | I |
| Jinshuai mutant (YT-95) | I | DI | DI | DI | DI | DI | DI | DI | DI | DI | D | I | I |
| Taishan Crab (YT-96) | D | I | D | D | D | D | D | I | DI | D | D | D | D |
| Luli (YT-98) | D | I | DI | D | DI | D | DI | DI | D | D | D | D | DI |
| 10-182 (YX-10-182) | DI | DI | D | D | I | DI | DI | I | DI | D | D | D | I |
| 01-001 (YX-01-001) | D | DI | D | DI | I | DI | DI | DI | D | DI | D | D | DI |
| 01-121 (YX-01-121) | D | I | D | DI | I | I | I | I | DI | DI | D | D | DI |
| 02-009 (YX-02-009) | D | I | D | D | D | DI | I | DI | I | D | D | D | DI |
| 03-010 (YX-03-010) | D | I | D | D | DI | DI | DI | I | DI | D | D | DI | DI |
| 03-111 (YX-03-111) | D | DI | D | DI | DI | DI | DI | I | DI | DI | D | DI | DI |
| 04-033 (YX-04-033) | DI | DI | D | D | DI | I | I | I | DI | D | D | DI | DI |
| 04-087 (YX-04-087) | DI | DI | D | DI | I | I | DI | I | DI | D | D | D | DI |
| 06-056 (YX-06-056) | D | I | D | D | DI | DI | DI | DI | I | D | D | D | DI |
| 08-034 (YX-08-034) | DI | DI | D | D | DI | I | I | I | I | D | D | D | DI |
| 09-037 (YX-09-037) | DI | DI | DI | DI | I | D | I | I | I | D | D | DI | DI |
| 09-079 (YX-09-079) | DI | I | D | D | DI | DI | I | I | DI | DI | D | D | DI |
| 10-010 (YX-10-010) | DI | DI | D | D | D | DI | DI | I | DI | D | D | D | DI |
| 11-037 (YX-11-037) | DI | DI | D | D | DI | I | I | DI | DI | D | D | DI | DI |
| 11-206 (YX-11-206) | DI | DI | D | D | DI | D | I | I | DI | DI | D | DI | DI |
| 12-206 (YX-12-206) | DI | I | D | DI | I | DI | I | DI | D | DI | D | DI | DI |

-continued

| Construction results of InDel marker genotype database of *Malus* germplasm resources | | | | | | | | | | | | | |
|---|---|---|---|---|---|---|---|---|---|---|---|---|---|
| 13-025 (YX-13-025) | DI | I | D | D | DI | DI | DI | I | D | D | D | DI | DI |
| 16-155 (YX-16-155) | D | I | D | D | DI | DI | I | DI | I | DI | D | DI | DI |
| 16-157 (YX-16-157) | DI | DI | D | DI | DI | DI | DI | I | DI | D | D | DI | DI |
| 17-023 (YX-17-023) | DI | DI | D | DI | I | D | DI | DI | DI | D | D | D | DI |
| 17-199 (YX-17-199) | DI | I | D | DI | I | DI | DI | I | DI | DI | D | DI | DI |
| 21-005 (YX-21-005) | DI | DI | DI | DI | DI | DI | DI | DI | DI | D | DI | DI | I |
| 21-018 (YX-21-018) | DI | I | DI | DI | I | DI | I | DI | D | D | D | D | I |
| 22-186 (YX-22-186) | DI | I | DI | DI | I | D | I | DI | DI | DI | D | D | I |
| 27-003 (YX-27-003) | DI | I | DI | DI | DI | D | DI | DI | I | DI | D | D | I |
| 29-176 (YX-29-176) | DI | DI | DI | I | DI | DI | I | I | D | DI | D | DI | I |
| 30-001 (YX-30-001) | DI | DI | DI | D | DI | DI | DI | DI | I | DI | DI | I | I |
| 33-018 (YX-33-018) | D | DI | D | DI | DI | DI | DI | I | DI | D | D | D | DI |
| 33-101 (YX-33-101) | D | I | D | DI | DI | DI | I | I | DI | D | D | D | I |
| 33-151 (YX-33-151) | DI | DI | DI | DI | DI | DI | I | I | DI | DI | D | DI | I |
| 51-007 (YX-51-007) | DI | I | DI | D | DI | DI | DI | I | D | DI | DI | DI | DI |
| 51-031 (YX-51-031) | I | DI | DI | DI | DI | D | D | DI | DI | DI | D | D | DI |
| 51-077 (YX-51-077) | DI | DI | DI | DI | DI | D | DI | DI | D | DI | DI | DI | DI |
| 51-102 (YX-51-102) | DI | DI | DI | DI | DI | D | DI | DI | DI | D | DI | DI | DI |
| 51-139 (YX-51-139) | DI | DI | DI | DI | DI | DI | DI | DI | D | DI | DI | DI | DI |
| 51-165 (YX-51-165) | I | DI | DI | DI | DI | DI | D | DI | DI | DI | D | D | I |
| 51-166 (YX-51-166) | I | DI | DI | DI | DI | DI | D | I | DI | DI | DI | DI | I |
| 51-209 (YX-51-209) | DI | DI | DI | DI | DI | D | DI | I | D | D | DI | DI | I |
| 52-049 (YX-52-049) | DI | DI | DI | D | DI | D | DI | DI | D | DI | D | D | DI |
| 52-151 (YX-52-151) | I | DI | DI | DI | DI | DI | DI | DI | D | DI | DI | DI | DI |
| 52-160 (YX-52-160) | I | DI | DI | DI | DI | D | DI | DI | D | D | DI | DI | DI |
| 53-040 (YX-53-040) | DI | DI | DI | DI | DI | DI | DI | DI | D | D | D | D | I |
| 53-205 (YX-53-205) | DI | D | D | D | DI | DI | DI | I | DI | DI | D | D | D |
| 54-001 (YX-54-001) | I | DI | DI | D | DI | D | DI | DI | D | DI | DI | DI | DI |
| 54-188 (YX-54-188) | I | DI | D | D | DI | DI | D | DI | DI | D | D | D | DI |
| 55-006 (YX-55-006) | I | DI | DI | DI | DI | DI | D | DI | DI | DI | D | D | I |
| 55-023 (YX-55-023) | I | DI | DI | DI | DI | DI | D | DI | DI | D | D | D | DI |
| 55-042 (YX-55-042) | DI | DI | DI | D | DI | D | DI | DI | DI | DI | D | D | I |
| 56-081 (YX-56-081) | I | DI | DI | D | DI | DI | D | DI | DI | DI | D | D | I |
| 57-128 (YX-57-128) | DI | DI | DI | DI | DI | DI | DI | DI | D | DI | DI | DI | DI |
| 58-036 (YX-58-036) | I | DI | DI | D | DI | D | DI | DI | D | DI | DI | DI | DI |
| 58-089 (YX-58-089) | I | D | DI | DI | D | D | DI | DI | D | D | D | D | I |
| 58-144 (YX-58-144) | I | DI | DI | D | DI | D | DI | DI | D | D | D | D | DI |
| 58-177 (YX-58-177) | I | I | DI | D | DI | D | DI | DI | D | D | D | D | DI |

-continued

| Construction results of InDel marker genotype database of *Malus* germplasm resources | | | | | | | | | | | | | |
|---|---|---|---|---|---|---|---|---|---|---|---|---|
| 58-211 (YX-58-211) | DI | D | DI | DI | DI | DI | DI | DI | D | DI | D | D | DI |
| 59-086 (YX-59-086) | I | DI | DI | DI | DI | D | D | DI | DI | D | D | D | DI |
| 59-130 (YX-59-130) | I | DI | DI | DI | DI | D | DI | DI | D | DI | DI | DI | DI |
| Jersey Mac (Z-1) | D | DI | D | D | I | D | DI | I | I | D | DI | D | DI |
| Gale Gala (Z-10) | DI | I | DI | D | I | D | DI | DI | D | D | D | D | I |
| Li Gala (Z-11) | DI | I | DI | D | I | D | DI | DI | D | D | D | D | I |
| Yanga 1 (Z-12) | DI | I | DI | D | I | D | DI | DI | D | D | D | D | I |
| NAKT M9 clone (Z-13) | D | DI | D | D | D | D | D | DI | I | I | DI | DI | DI |
| Royal Gala (Z-14) | DI | I | DI | D | I | D | DI | DI | D | D | D | D | I |
| Huajia (Z-15) | DI | I | DI | D | I | DI | DI | I | DI | D | DI | DI | I |
| Dorsett Golden (Z-16) | I | DI | D | DI | I | D | D | DI | I | D | D | DI | DI |
| 99-2-58 (Z-17) | D | DI | DI | D | I | DI | DI | DI | D | D | I | I | DI |
| Galaxy (Z-18) | DI | I | DI | D | I | D | DI | DI | D | D | D | D | I |
| Royal New Gala (Z-19) | DI | I | DI | D | I | D | DI | DI | D | D | D | D | I |
| 99-1-29 (Z-22) | DI | I | D | D | I | DI | DI | DI | D | D | DI | DI | DI |
| Seokwang (Z-23) | DI | I | DI | DI | I | D | DI | DI | DI | D | DI | DI | DI |
| Fuhong Zaoga (Z-24) | DI | I | DI | D | I | D | DI | DI | D | D | D | D | I |
| Maiyan (Z-25) | D | DI | D | D | I | D | I | I | DI | D | I | I | I |
| Shandong 1 (Z-26) | DI | I | DI | D | I | D | DI | DI | D | D | D | D | I |
| Gala Queen (Z-27) | DI | I | DI | D | I | D | DI | DI | D | D | D | D | I |
| 99-2-39 (Z-29) | DI | I | DI | D | I | DI | DI | I | D | D | DI | DI | DI |
| Sweetle (Z-3) | DI | DI | DI | D | I | D | I | DI | DI | D | D | DI | DI |
| Dalian Da Gala (Z-30) | DI | I | DI | D | I | D | DI | DI | D | D | D | D | I |
| Huaxing (Z-31) | DI | I | DI | D | I | D | D | DI | D | D | DI | D | I |
| Li Gala (Z-32) | DI | I | DI | D | I | D | DI | DI | D | D | D | D | I |
| Fuhong Zaoga (Z-33) | DI | DI | DI | D | I | D | DI | DI | D | D | D | D | DI |
| Yanga (Z-34) | DI | DI | DI | D | I | D | DI | DI | D | D | D | D | DI |
| Royal Gala (Z-35) | DI | I | DI | D | I | D | DI | DI | D | D | D | D | I |
| Shijiazhuang Gala (Z-37) | DI | I | DI | D | I | D | DI | DI | D | D | D | D | I |
| Taihong Gala (Z-38) | DI | I | DI | D | I | D | DI | DI | D | D | D | D | I |
| Anna (Z-39) | DI | DI | DI | DI | I | D | D | I | DI | D | D | DI | DI |
| Hong Zhenzhu (Z-4) | D | I | DI | D | I | D | D | DI | D | D | D | D | DI |
| Qiuhong Gala (Z-40) | DI | DI | DI | DI | DI | D | DI | DI | D | D | D | D | I |
| Shandong 2 (Z-41) | DI | I | DI | D | I | D | DI | DI | D | D | D | D | I |
| Shandong 6 (Z-42) | DI | I | DI | D | I | D | DI | D | D | D | D | D | I |
| Chenyang (Z-43) | I | DI | DI | DI | I | DI | DI | DI | D | D | DI | I | I |
| Dongqie Gala (Z-44) | I | I | DI | D | DI | D | DI | DI | DI | D | D | D | I |
| Royal Gala (Z-45) | DI | I | DI | D | I | D | DI | DI | D | D | D | D | I |

| Construction results of InDel marker genotype database of *Malus* germplasm resources | | | | | | | | | | | | | |
|---|---|---|---|---|---|---|---|---|---|---|---|---|---|
| Taishan Gala (Z-47) | DI | I | DI | D | I | D | DI | DI | D | D | D | D | I |
| Shandong 7 (Z-48) | DI | I | DI | D | I | D | DI | DI | D | D | D | D | I |
| Regal gala (Z-49) | DI | I | DI | D | I | D | DI | DI | D | D | D | D | I |
| NAKB clone (Z-5) | D | DI | D | D | D | D | D | DI | I | I | DI | DI | DI |
| Royal gala (Z-50) | DI | I | DI | D | I | D | DI | DI | D | D | D | D | I |
| Znoga (Z-51) | DI | DI | DI | DI | I | D | I | DI | DI | D | D | I | I |
| Shandong 5 (Z-52) | DI | I | DI | D | I | D | DI | DI | D | D | D | D | I |
| Rockit (Z-53) | I | I | DI | D | I | D | D | DI | DI | D | D | D | I |
| Shandong 3 (Z-54) | DI | I | DI | D | I | D | DI | DI | D | D | D | D | I |
| Mondel Gala (Z-55) | DI | I | DI | D | I | D | DI | DI | D | D | D | D | I |
| Alvinagala (Z-56) | DI | I | DI | D | I | D | DI | DI | D | D | D | D | I |
| M9 pajam2 (Z-6) | D | DI | D | D | D | D | D | DI | I | I | DI | DI | DI |
| Jinshiji (Z-7) | DI | I | DI | D | I | D | DI | DI | D | D | D | D | I |
| Huarui (Z-8) | D | I | DI | D | I | DI | DI | DI | D | D | D | D | DI |
| Hongcuibao (Z-9) | DI | DI | DI | D | I | D | I | DI | D | D | D | D | DI |

| Accession name (Accession ID) | C10073 | C11077 | C11079 | C11080 | C11081 | C12087 | C12088 | C12089 | C12091 | C12092 | C13093 | C13094 | C13097 |
|---|---|---|---|---|---|---|---|---|---|---|---|---|---|
| Black Ben Davis (10--1) | D | D | I | D | D | DI | D | DI | D | DI | DI | D | I |
| Lysgolden (10--10) | D | DI | I | D | D | DI | D | DI | D | DI | DI | D | D |
| Dongchengguan 13 (10--11) | D | DI | I | D | D | DI | D | DI | D | DI | DI | D | D |
| Nagafu 1 (10--12) | D | DI | I | D | D | DI | D | DI | D | DI | DI | D | D |
| Shengli Hongguan (10--14) | D | D | DI | DI | D | I | D | DI | D | DI | D | DI | DI |
| Shizishan 1 (10--15) | D | D | DI | DI | D | I | D | DI | D | DI | D | DI | DI |
| Baoman (10--2) | DI | DI | DI | DI | DI | DI | D | I | DI | DI | DI | D | DI |
| Melba (10--20) | I | DI | D | D | D | DI | D | D | D | DI | DI | D | DI |
| Kuliesa (10--21) | I | DI | DI | DI | D | DI | D | DI | D | DI | DI | D | DI |
| De 8 (10--22) | I | DI | DI | D | DI | DI | D | D | D | DI | I | DI | DI |
| Bo 5 (10--23) | DI | D | D | D | D | D | DI | D | D | D | DI | DI | DI |
| Iran Pippin (10--4) | I | DI | D | D | DI | D | D | I | DI | DI | DI | DI | DI |
| Sakatakei Tsugaru (10--5) | I | DI | DI | I | D | DI | DI | D | D | DI | I | DI | DI |
| Khrushchev (10--6) | DI | DI | I | D | DI | DI | DI | D | D | DI | DI | DI | DI |
| Batul (10--7) | D | DI | DI | DI | DI | I | D | I | DI | I | I | DI | DI |
| Prime Gold (10--9) | D | DI | DI | DI | DI | I | D | I | DI | I | I | DI | DI |
| Jie 1 (11--0) | DI | D | D | DI | DI | D | DI | D | DI | D | I | D | DI |
| Guldborg (1--11) | D | DI | I | D | D | DI | D | DI | D | DI | DI | D | D |
| Shajin Yilamu (11--10) | D | DI | D | DI | D | D | D | DI | DI | I | I | D | DI |
| Soviet (11--11) | D | D | DI | D | DI | DI | D | D | D | DI | DI | D | DI |
| Lobo (11--13) | DI | D | D | DI | DI | I | D | DI | DI | DI | DI | D | DI |

-continued

Construction results of InDel marker genotype database of *Malus* germplasm resources

| | | | | | | | | | | | | | |
|---|---|---|---|---|---|---|---|---|---|---|---|---|---|
| Allington Pippin (11--14) | D | D | DI | DI | D | D | D | DI | D | DI | I | D | D |
| Malinova (11--15) | DI | D | DI | D | D | DI | D | DI | D | DI | I | D | D |
| Sweet McIntosh (11--16) | DI | D | DI | D | D | DI | D | DI | D | DI | I | D | D |
| McIntosh (11--18) | I | DI | DI | DI | DI | DI | D | D | DI | I | DI | DI | |
| Spartan (11--2) | DI | D | D | DI | D | DI | D | D | DI | DI | I | DI | DI |
| Fushuai (1--12) | DI | I | DI | D | DI | DI | D | I | D | DI | D | DI | D |
| Summer Pearmain (11--20) | D | D | DI | DI | D | D | D | I | DI | DI | DI | DI | DI |
| Helm (11--21) | D | DI | DI | DI | DI | I | DI | D | DI | DI | I | DI | DI |
| Domenesti (11--3) | D | D | D | DI | DI | DI | DI | DI | D | DI | DI | D | DI |
| Early Harvest (1--13) | DI | DI | DI | D | DI | DI | D | I | D | DI | D | DI | D |
| Silver Spur Red Delicious (11--4) | DI | DI | DI | DI | D | D | D | D | D | DI | I | DI | DI |
| Dongxiangjiao (11--5) | DI | DI | DI | DI | DI | DI | DI | DI | DI | DI | I | D | DI |
| Guoling (1--15) | DI | D | DI | D | DI | D | D | I | D | DI | DI | D | I |
| Skyline Spureme (11--8) | DI | DI | DI | DI | D | D | D | D | D | DI | I | DI | DI |
| Chantecler (11--9) | D | DI | I | D | DI | DI | D | I | I | DI | DI | I | D |
| Close (1--19) | DI | DI | DI | DI | DI | DI | D | DI | DI | DI | I | DI | DI |
| Aizaohui (1--2) | DI | D | D | D | DI | D | D | D | D | DI | DI | D | D |
| Wuyue (12--1) | D | D | DI | D | D | D | D | I | D | DI | DI | D | I |
| Bukowka (12--11) | D | DI | DI | D | DI | DI | D | I | D | DI | DI | DI | D |
| Jinyu (12--12) | DI | D | D | DI | D | D | DI | DI | D | DI | I | D | DI |
| Calville Rouge (12--14) | D | DI | D | D | DI | DI | DI | D | D | DI | DI | D | D |
| Doyle (12--15) | DI | D | DI | D | DI | D | D | I | D | DI | I | D | DI |
| Melrose (12--16) | D | DI | D | DI | DI | D | DI | DI | D | DI | I | D | D |
| Menage (12--17) | I | DI | DI | DI | DI | D | D | I | DI | DI | DI | DI | DI |
| Bo 26 (12--18) | DI | DI | I | D | DI | I | D | DI | DI | DI | I | DI | D |
| Duoyilu (12--19) | DI | DI | I | DI | D | D | D | DI | D | DI | I | DI | DI |
| De 6 (12--20) | I | DI | DI | DI | DI | D | DI | D | D | DI | D | D | D |
| Red June (12--21) | DI | DI | I | DI | D | I | D | DI | D | DI | I | D | D |
| Helasang (12--23) | D | D | DI | D | DI | DI | D | D | DI | DI | DI | D | D |
| Hesetiaowen (12--3) | D | DI | DI | DI | D | D | D | DI | I | DI | D | D | DI |
| James Grieve (1--23) | DI | D | DI | D | D | D | D | D | DI | D | D | D | D |
| Bailuosi Malin (12--4) | D | DI | DI | D | D | I | DI | DI | D | DI | DI | D | DI |
| Jinnhong (12--5) | DI | D | D | D | DI | D | DI | DI | DI | DI | I | DI | DI |
| Kay Sai William (12--6) | DI | D | D | D | DI | D | D | DI | DI | DI | I | DI | DI |
| Xingjiang Pingguo (12--7) | D | D | D | D | DI | D | DI | DI | D | I | I | D | DI |
| Jie 15 (12--8) | DI | DI | DI | D | D | D | D | D | DI | DI | I | DI | DI |
| Mianpingguo (12--9) | D | DI | DI | D | D | D | DI | D | I | I | D | D | |
| Lowver (1--3) | DI | DI | D | D | DI | DI | D | I | DI | DI | D | D | D |

| Construction results of InDel marker genotype database of *Malus* germplasm resources |||||||||||||||
| --- | --- | --- | --- | --- | --- | --- | --- | --- | --- | --- | --- | --- |
| Benoni (13--1) | D | D | DI | D | DI | DI | D | DI | DI | DI | I | D | DI |
| Fa 5 (13--11) | DI | D | D | D | DI | DI | DI | DI | DI | DI | DI | DI | D |
| Babskino (13--12) | DI | DI | D | DI | D | D | D | I | DI | DI | I | D | D |
| Kuluona (13--13) | D | D | D | D | DI | DI | DI | D | DI | DI | D | DI |
| Shidonghaoji (13--16) | D | D | DI | DI | D | I | D | DI | D | DI | D | DI | DI |
| Oberkika (13--17) | D | DI | D | D | D | D | D | DI | D | DI | D | D |
| Budayi (13--19) | D | DI | I | D | D | DI | D | DI | D | DI | DI | D | D |
| Red Canada (13--2) | DI | D | D | D | DI | DI | DI | DI | DI | DI | DI | DI | D |
| Laidi (13--20) | D | DI | D | D | DI | I | D | D | DI | DI | DI | D | D |
| N2 (13--22) | DI | D | D | DI | D | DI | D | DI | D | DI | DI | DI | DI |
| Norsan (13--5) | DI | DI | DI | DI | D | D | D | D | D | DI | I | DI | DI |
| Hebei Kangbing Golden Delicious (13--6) | D | DI | I | I | D | DI | D | I | DI | DI | D | DI | D |
| Zhanxuan 14 (13--9) | D | DI | I | D | D | DI | D | DI | D | DI | DI | D | D |
| Xiangguoguang (14--11) | D | DI | I | D | D | DI | D | DI | DI | D | I | DI | D |
| Shengfang 1 (14--14) | DI | D | D | DI | D | DI | D | DI | D | DI | DI | DI | DI |
| Yujing II (14--16) | DI | D | D | DI | D | DI | D | DI | D | DI | DI | DI | DI |
| Cox's Orange Pippin (14--2) | I | D | D | DI | D | DI | D | I | DI | DI | I | DI | DI |
| Nagafu 7 (14--20) | DI | D | D | DI | D | DI | D | DI | D | DI | DI | DI | DI |
| Boiken (14--21) | D | DI | DI | D | D | DI | DI | D | DI | DI | I | DI | DI |
| Qunfu 1 (14--23) | DI | D | D | DI | D | DI | D | DI | D | DI | DI | DI | DI |
| Calville Blanche (14--3) | D | DI | DI | D | D | DI | DI | D | DI | DI | I | DI | DI |
| Freybreg (14--4) | DI | DI | DI | DI | DI | I | D | DI | DI | DI | I | DI | DI |
| Husveti Rosmaring (14--5) | I | DI | DI | DI | DI | DI | D | I | D | DI | DI | DI | DI |
| Sweet Jonathan (14--7) | DI | D | D | DI | DI | D | DI | DI | D | DI | I | D | DI |
| King of Pippin (14--8) | I | D | D | DI | D | DI | D | I | DI | DI | I | DI | DI |
| Duchess of Oldenburg (1--5) | D | D | DI | DI | DI | DI | D | DI | D | DI | DI | DI | DI |
| Kangbing Golden 5 (15--11) | DI | DI | I | DI | DI | I | DI | DI | DI | DI | I | DI |
| Pingzhi Ralls Janet (15--15) | D | D | I | D | D | DI | D | I | D | DI | D | D | DI |
| Wase16 (15--16) | D | D | DI | D | DI | I | D | I | DI | DI | DI | DI | DI |
| Kogetsu (15--17) | I | DI | I | DI | DI | DI | DI | D | D | DI | I | DI | I |
| Jonared (15--18) | DI | D | D | DI | DI | D | DI | D | DI | D | I | D | DI |
| Zhanxuan 4 (15--21) | D | DI | I | D | D | DI | D | DI | D | DI | DI | D | D |
| Strawberry (15--23) | D | D | DI | D | DI | I | D | DI | D | DI | I | DI | DI |
| StarkSpur Ultra Red Delicious (15--3) | DI | DI | DI | DI | D | D | D | D | D | D | I | DI | DI |
| Sharp Red Delicious (15--4) | DI | DI | DI | DI | D | D | D | D | D | DI | I | DI | DI |
| Mensi (15--5) | D | D | DI | D | DI | D | D | D | DI | D | DI | D |
| Norand (15--6) | DI | D | DI | D | D | DI | D | DI | D | DI | I | D | DI |

-continued

| Construction results of InDel marker genotype database of *Malus* germplasm resources |||||||||||||| 
|---|---|---|---|---|---|---|---|---|---|---|---|---|
| Zhanxuan 18 (15--7) | DI | DI | DI | DI | D | D | D | D | D | DI | I | DI | DI |
| Xishan 1 (15--8) | DI | DI | DI | DI | D | D | D | D | D | DI | I | DI | DI |
| Hongrou Pingguo (15--9) | D | DI | D | I | D | DI | D | I | DI | DI | DI | I | D |
| Gravenstein (1--6) | D | D | D | DI | D | DI | D | D | D | DI | DI | D | DI |
| Xinhong (16--1) | DI | DI | DI | D | DI | D | D | D | D | DI | DI | D | D |
| Zhanxuan 6 (16--10) | D | DI | D | I | D | D | D | I | D | DI | I | D | D |
| Behene (16--11) | DI | D | D | D | DI | D | D | D | D | DI | I | D | DI |
| Xindong (16--14) | DI | DI | DI | DI | D | D | D | DI | DI | DI | DI | D | D |
| Hardi Brite (16--16) | DI | DI | DI | DI | D | D | D | D | D | DI | I | DI | DI |
| Charden (16--17) | DI | DI | I | DI | DI | DI | DI | DI | DI | DI | DI | I | DI |
| Zhuoai 1 (16--2) | D | DI | I | D | D | DI | D | DI | D | DI | DI | D | D |
| Jinse Luosuoshan (16--22) | DI | D | DI | D | DI | DI | DI | DI | D | DI | I | D | D |
| Zhaiteng II (16--23) | DI | D | D | DI | D | DI | D | DI | D | DI | DI | DI | DI |
| Zhanxuan 16 (16--6) | D | DI | I | D | D | DI | D | DI | D | DI | DI | D | D |
| Fa 3 (16--8) | D | D | D | DI | DI | DI | DI | DI | D | DI | DI | D | DI |
| Jerseymac (1--7) | D | D | I | D | D | DI | D | D | DI | DI | D | D | D |
| Mother (17--1) | D | DI | D | D | D | I | D | DI | DI | DI | I | D | D |
| Northern Spy (17--10) | D | DI | DI | DI | D | DI | DI | D | DI | DI | DI | DI | D |
| Rome Beauty (17--11) | DI | D | DI | D | DI | D | D | I | D | DI | I | D | DI |
| Black Ben David (17--12) | D | D | I | D | D | DI | D | DI | DI | DI | I | D | DI |
| Atlas (17--13) | DI | D | D | D | DI | I | D | DI | D | DI | I | DI | D |
| Roxbury (17--14) | D | DI | I | D | DI | DI | DI | D | D | DI | DI | D | DI |
| Laxtons Superb (17--15) | D | DI | I | DI | DI | D | D | I | D | D | D | D | DI |
| Changhong (17--16) | D | D | DI | DI | DI | DI | D | I | D | DI | I | D | D |
| Cogswell Pearmain (17--17) | DI | D | D | D | DI | I | DI | DI | D | DI | D | D | D |
| Twenty Ounce (17--18) | DI | D | DI | DI | D | DI | DI | DI | D | DI | I | D | D |
| Lowtosh (17--19) | D | D | D | DI | DI | D | DI | D | D | I | D | D | D |
| Iwaki (17--21) | D | D | D | D | DI | DI | D | DI | D | D | DI | D | D |
| Qin'guan (17--22) | D | DI | I | DI | DI | I | DI | DI | D | DI | DI | DI | DI |
| Bancroft (17--23) | D | DI | D | D | DI | DI | D | DI | D | DI | I | D | DI |
| Chenango Strawberry (17--4) | I | DI | I | DI | DI | D | D | DI | D | DI | I | DI | I |
| Newfane (17--7) | DI | D | D | DI | D | D | DI | D | D | DI | I | DI | DI |
| Lord Lambourne (17--9) | D | DI | DI | DI | D | DI | DI | D | DI | DI | DI | DI | D |
| Rizhiwan (18--0) | D | D | DI | D | D | D | D | D | D | DI | DI | I | DI |
| Campbell (18--11) | D | DI | I | D | DI | DI | DI | D | D | DI | D | D | DI |
| Pigeon (18--13) | DI | D | D | DI | DI | DI | DI | DI | D | DI | I | D | DI |
| Summer Champion (18--14) | DI | D | I | DI | D | DI | D | I | D | DI | I | DI | I |
| Nanpu 3 (18--15) | D | D | I | D | D | D | D | I | D | DI | DI | D | I |

-continued

| Construction results of InDel marker genotype database of *Malus* germplasm resources | | | | | | | | | | | | | |
|---|---|---|---|---|---|---|---|---|---|---|---|---|
| Qiulimeng (18--16) | D | D | DI | DI | D | DI | D | DI | DI | I | DI | D | D |
| Rutosh (18--17) | DI | D | D | D | DI | D | D | D | D | DI | D | D | DI |
| Xinlimei (18--19) | D | DI | D | D | DI | I | D | D | DI | DI | DI | D | D |
| Huanong 1 (18--2) | DI | D | DI | DI | D | DI | D | DI | DI | I | DI | DI | DI |
| Lawfam (18--20) | I | DI | D | D | DI | DI | D | DI | DI | DI | I | D | DI |
| Akin's Red (18--21) | DI | D | D | DI | D | D | D | DI | D | DI | DI | D | D |
| Meltosh (18--22) | D | DI | D | DI | DI | DI | D | D | D | DI | I | D | D |
| Hubbardston (18--23) | DI | DI | DI | DI | DI | I | D | DI | DI | DI | I | DI | DI |
| Fenghuangluan Crab (18--3) | DI | D | DI | DI | DI | DI | D | DI | DI | DI | I | DI | DI |
| Jie 9 (18--4) | D | DI | DI | DI | D | DI | D | DI | D | DI | I | D | DI |
| Bramley's Seedling (18--5) | DI | DI | DI | DI | DI | DI | DI | D | DI | DI | I | DI | DI |
| Shuangyang 1 (18--7) | DI | DI | DI | DI | DI | I | D | DI | DI | DI | I | DI | DI |
| Shengli (18--8) | DI | DI | DI | DI | DI | I | D | DI | DI | DI | I | DI | DI |
| Qingguan (18--9) | DI | DI | DI | D | DI | DI | D | I | D | DI | DI | D | DI |
| Weeping Ralls (19--0) | D | D | DI | D | D | DI | D | I | D | DI | D | D | DI |
| Giant Jeniton (19--1) | I | DI | DI | DI | DI | D | D | I | DI | DI | DI | DI | DI |
| Baldwin (19--10) | I | DI | I | D | D | D | D | D | DI | DI | I | D | DI |
| Lele Fuji (19--11) | DI | D | D | DI | D | DI | D | DI | D | DI | DI | DI | DI |
| Shuahong (19--12) | D | D | DI | DI | D | D | D | D | D | DI | DI | D | D |
| Red Fuji TAO (19--14) | DI | D | D | DI | D | DI | D | DI | D | DI | DI | DI | DI |
| Jizaohong (19--17) | DI | DI | DI | DI | DI | I | D | DI | DI | DI | I | DI | DI |
| Karas Tor (19--19) | D | DI | DI | D | DI | D | DI | D | D | DI | I | DI | D |
| Ralls Janet (19--2) | D | D | DI | D | D | DI | D | I | D | DI | D | D | DI |
| Stonetosh (19--22) | DI | DI | D | D | DI | DI | D | D | DI | DI | DI | D | DI |
| White Pearmain (19--23) | DI | DI | DI | DI | DI | D | DI | DI | D | DI | I | I | D |
| Xiushui Guoguang (19--3) | DI | DI | D | DI | D | DI | D | DI | D | DI | DI | D | DI |
| Chimeric Ralls Janet (19--4) | D | D | DI | D | DI | D | D | I | D | DI | D | D | DI |
| Mutsu (19--7) | DI | DI | DI | DI | DI | DI | DI | DI | DI | DI | DI | I | DI |
| Ben David (19--8) | D | D | I | D | D | DI | D | DI | DI | DI | I | D | DI |
| Saint Lawrence (19--9) | D | D | D | DI | D | D | D | I | DI | D | DI | I | I |
| Newtosh (20--0) | I | DI | D | I | D | D | DI | I | D | I | DI | D | DI |
| Geliekekukui (20--1) | D | D | D | DI | DI | D | D | DI | D | I | DI | DI | DI |
| Sweet Jonathan (20--10) | DI | D | D | DI | D | DI | D | DI | DI | DI | I | D | DI |
| Apple of Commerce (20--11) | DI | D | I | D | DI | I | D | DI | DI | DI | I | D | D |
| 600 g Andong (20--12) | DI | D | D | D | D | D | D | D | D | DI | I | D | DI |
| Winter Banana (20--14) | D | DI | I | D | DI | DI | DI | DI | D | DI | DI | DI | D |
| Rainier (20--15) | D | DI | DI | D | D | I | DI | DI | D | DI | DI | D | D |
| Winesap (20--16) | DI | DI | DI | D | DI | DI | D | DI | D | DI | D | D | DI |
| Drumbo (20--17) | D | DI | D | DI | DI | DI | D | D | D | DI | I | D | D |

-continued

| Construction results of InDel marker genotype database of *Malus* germplasm resources | | | | | | | | | | | | | |
|---|---|---|---|---|---|---|---|---|---|---|---|---|
| Blengstid Gaurd (20--2) | D | D | D | DI | DI | DI | DI | DI | D | DI | DI | D | DI |
| Jierjisi (20--21) | DI | DI | D | D | D | DI | D | I | D | DI | DI | D | I |
| Radiant (20--23) | I | DI | D | I | D | D | DI | I | D | I | DI | D | DI |
| King David (20--5) | I | D | I | D | D | D | D | DI | D | DI | I | D | DI |
| Clapp's Seedling (20--6) | DI | DI | DI | D | DI | DI | D | I | D | DI | DI | D | DI |
| Ingram (20--7) | DI | D | I | D | DI | D | D | DI | D | DI | DI | D | DI |
| Qiujin (20--8) | D | DI | I | D | D | DI | D | DI | D | DI | DI | D | D |
| Sujsleppskoe (2--1) | D | D | DI | DI | D | I | D | DI | D | DI | DI | DI | DI |
| Qian 1 Ace (21--0) | DI | D | D | DI | D | DI | D | DI | D | DI | DI | DI | DI |
| Toko (2--10) | DI | DI | DI | DI | DI | DI | I | DI | D | DI | DI | DI | D |
| Antalue (21--1) | DI | DI | I | D | DI | I | D | DI | D | D | DI | I | DI |
| Boskoopske Cervene (2--11) | D | D | D | DI | DI | DI | DI | DI | D | DI | DI | D | DI |
| Heoersitai (21--10) | DI | DI | DI | DI | DI | D | D | I | D | DI | DI | D | D |
| Lanfengwang (21--11) | D | D | D | I | D | D | DI | DI | DI | DI | DI | D | DI |
| Aohong (21--14) | DI | DI | I | DI | DI | I | DI | DI | DI | DI | I | I | I |
| Weiqinni (21--15) | DI | DI | D | DI | DI | DI | D | I | DI | DI | DI | DI | DI |
| Smoothee (21--17) | DI | DI | I | DI | DI | I | DI | DI | DI | DI | DI | I | DI |
| Hongzhiwu (21--18) | DI | D | DI | DI | DI | DI | DI | D | DI | DI | I | D | DI |
| Jieba (21--2) | D | D | DI | D | DI | D | D | DI | DI | DI | D | D | D |
| Kizashi (21--20) | D | DI | DI | I | D | DI | D | DI | DI | DI | DI | I | D |
| Aifeng (21--21) | D | DI | DI | I | D | DI | D | DI | DI | DI | DI | I | D |
| Xingping (21--4) | D | D | I | D | D | DI | D | I | D | DI | D | D | DI |
| Esopus Spitzenburg (2--14) | DI | DI | D | DI | DI | D | I | D | D | DI | I | DI | DI |
| Lvguang (21--6) | D | DI | D | DI | D | DI | D | I | D | DI | I | D | DI |
| Nvyoujidui (2--16) | D | D | D | DI | D | I | D | DI | D | DI | DI | DI | DI |
| Bell Poos (21--7) | D | D | D | D | D | I | D | DI | D | DI | DI | D | DI |
| Tian Andongnuo (2--17) | DI | DI | D | D | DI | D | D | DI | DI | DI | DI | D | DI |
| Pacific Rose (21--8) | DI | DI | I | DI | DI | I | DI | DI | DI | DI | I | I | I |
| 500 g (21--9) | DI | D | D | DI | DI | D | DI | DI | DI | D | DI | I | DI |
| Nvyoujidui 2 (2--19) | D | D | DI | DI | D | I | D | DI | D | DI | DI | DI | DI |
| Tian Andongnuo 2 (2--2) | DI | D | D | DI | D | I | D | I | D | DI | D | D | DI |
| Spur Mutsu (22--1) | DI | DI | I | DI | DI | DI | DI | I | DI | DI | DI | I | DI |
| Red June Sweet (2--21) | D | DI | DI | D | DI | D | DI | I | D | DI | DI | I | D |
| Chu Tsugaru (22--11) | DI | DI | DI | I | D | DI | DI | DI | D | DI | DI | I | DI | DI |
| Kermemen (22--13) | I | D | D | D | DI | D | D | I | D | DI | DI | DI | DI |
| Bedan (22--14) | DI | DI | D | I | DI | DI | D | I | DI | DI | DI | D | DI |
| Dabinette (22--15) | DI | D | D | DI | D | DI | D | DI | D | DI | DI | DI | DI |
| Zaocuilv (22--16) | DI | DI | DI | DI | DI | I | D | DI | DI | DI | I | DI | DI |

-continued

| Construction results of InDel marker genotype database of *Malus* germplasm resources | | | | | | | | | | | | | |
|---|---|---|---|---|---|---|---|---|---|---|---|---|---|
| Chanteline (22--17) | D | D | D | DI | DI | D | DI | D | DI | DI | DI | DI | D |
| Red Baron (22--2) | D | D | DI | DI | D | DI | D | DI | DI | DI | D | D | D |
| Hongjin Gala (22--4) | DI | DI | I | DI | D | D | DI | I | D | DI | I | DI | I |
| Generos (22--7) | DI | D | D | DI | DI | D | DI | D | DI | I | D | DI |
| Alberta (2--3) | DI | DI | D | DI | D | DI | D | DI | DI | DI | I | DI | DI |
| Hirosaki Fuji (23--1) | I | DI | DI | I | D | DI | DI | D | DI | I | DI | DI |
| Miya Fuji (23--10) | DI | D | D | DI | D | DI | D | DI | D | DI | DI | DI | DI |
| Yanshanhong (23--13) | D | DI | DI | D | D | DI | D | DI | D | DI | DI | DI | DI |
| Dailv (23--14) | D | D | DI | I | D | DI | DI | D | D | DI | I | D | D |
| Frequin Rouge (23--15) | DI | D | D | D | DI | DI | D | I | D | DI | DI | D | D |
| Jinguang (23--16) | DI | D | D | D | DI | D | D | D | D | DI | I | D | DI |
| Avrolles (23--17) | I | D | D | D | DI | DI | D | D | I | DI | DI | DI | DI |
| Marie Menard (23--18) | I | D | D | DI | DI | DI | D | DI | DI | D | DI | D | DI |
| Golden B (23--2) | DI | DI | I | DI | DI | I | DI | DI | DI | DI | DI | I | DI |
| Jurella (23--20) | DI | DI | D | D | DI | DI | D | DI | D | DI | DI | DI | D |
| GS58 (23--21) | DI | DI | I | DI | D | DI | D | DI | D | DI | DI | I | D |
| Lianji (23--22) | DI | DI | DI | DI | DI | DI | D | D | D | DI | DI | DI | DI |
| Aomori Spur Fuji (23--4) | DI | D | D | DI | D | DI | D | DI | D | DI | DI | DI | DI |
| Akifu 39 (23--9) | DI | D | D | D | D | DI | D | DI | D | DI | DI | DI | D |
| Shalatuoni (2--4) | DI | D | D | D | DI | D | DI | DI | DI | DI | D | D |
| Guoqing (24--13) | DI | D | D | DI | D | DI | D | D | D | D | D | D | DI |
| Ningguang (24--15) | DI | DI | I | DI | D | DI | DI | DI | D | DI | DI | DI | DI |
| Hongqiaowang (24--17) | DI | DI | I | DI | DI | DI | DI | DI | DI | DI | DI | DI | DI |
| Wemhong (24--18) | D | D | D | DI | D | I | D | I | D | DI | I | D | DI |
| Wijcik McIntosh (24--19) | DI | D | D | D | DI | DI | D | D | DI | DI | DI | D | DI |
| Xinguoguang (24--21) | D | D | I | D | D | DI | D | I | D | D | D | D | DI |
| Fengcun Fuji (24--22) | DI | D | D | DI | D | DI | D | DI | D | DI | DI | DI | DI |
| America 8 (24--23) | DI | D | D | DI | D | D | D | D | D | DI | D | D | D |
| GS48 (24--3) | DI | D | D | DI | D | DI | D | I | DI | DI | DI | D | D |
| Granny Smith (24--4) | D | D | I | DI | D | DI | D | DI | D | DI | D | DI | DI |
| Stark Spur (24--7) | DI | DI | I | DI | DI | I | DI | DI | DI | DI | DI | I | DI |
| Huangguniang (2--5) | I | D | I | D | DI | D | D | D | D | DI | DI | DI | I |
| Judaine (25--11) | DI | DI | DI | DI | DI | DI | DI | D | DI | DI | DI | DI | D |
| Judeline (25--12) | DI | I | I | I | D | DI | D | I | DI | DI | DI | DI | DI |
| HoneyCrisp (25--14) | D | D | D | D | DI | D | DI | DI | D | DI | DI | DI | DI |
| Korin (25--15) | DI | D | D | DI | D | DI | D | D | D | DI | DI | DI | DI |
| Hongao (25--18) | DI | DI | DI | D | DI | I | D | I | DI | DI | DI | DI | DI |
| Ningguang (25--19) | DI | DI | DI | D | DI | I | D | I | DI | DI | DI | DI | DI |

-continued

Construction results of InDel marker genotype database of *Malus* germplasm resources

| | | | | | | | | | | | | | |
|---|---|---|---|---|---|---|---|---|---|---|---|---|---|
| Red Delicious (25--2) | DI | DI | DI | DI | D | D | D | D | D | DI | I | DI | DI |
| Youlixiang (25--21) | DI | DI | DI | D | DI | DI | DI | D | D | DI | I | DI | I |
| Fuqiu (25--3) | D | D | D | DI | D | DI | DI | DI | DI | DI | DI | DI | DI |
| Chunxiang (25--4) | D | D | DI | DI | D | D | D | D | DI | DI | D | D |
| Fu Hong (25--5) | DI | DI | DI | I | D | I | D | I | DI | DI | I | DI | I |
| Qingxiang (25--6) | DI | DI | I | DI | DI | DI | DI | D | D | DI | I | I | DI |
| Zhongxing (25--7) | DI | D | DI | DI | D | D | DI | I | D | DI | D | D | D |
| Weixishengming (25--8) | I | D | D | DI | D | D | DI | I | D | DI | DI | DI | D |
| Shichinohe 1 (25--9) | DI | D | D | DI | D | DI | D | DI | D | DI | DI | DI | DI |
| Arkansas Black (2--6) | I | D | I | D | D | D | DI | D | DI | DI | I | D | DI |
| Douce Coetligne (26--10) | I | D | DI | DI | DI | D | D | DI | DI | DI | D | D | I |
| Golden Spur (26--14) | DI | DI | I | DI | DI | I | DI | DI | DI | DI | DI | I | DI |
| Orei (26--15) | I | D | D | DI | D | DI | D | I | DI | DI | I | DI | DI |
| Sekaiichii (26--18) | DI | DI | DI | DI | D | D | DI | I | D | DI | I | DI | I |
| Kokyu (26--19) | I | DI | I | D | DI | DI | DI | D | D | DI | I | I | D |
| Douce Moen (26--2) | DI | DI | D | DI | D | D | D | DI | DI | DI | I | D | DI |
| Yanfu 1 (26--22) | DI | D | D | DI | D | DI | D | DI | D | DI | DI | DI | DI |
| Ningfeng (26--23) | DI | D | D | DI | DI | D | D | D | D | DI | D | D | DI |
| Juliana (26--5) | DI | D | DI | D | DI | D | D | D | D | DI | I | DI | D |
| Judestar (26--9) | D | D | DI | D | D | I | DI | D | D | DI | DI | DI | DI |
| Liaofu (2--7) | D | DI | I | DI | DI | DI | D | I | D | DI | D | I | D |
| Sinano Red (27--10) | D | D | D | I | D | D | D | DI | D | DI | DI | D | DI |
| Jinyang (27--12) | DI | D | DI | D | DI | DI | DI | DI | D | DI | I | D | DI |
| Enqi (27--13) | D | DI | I | I | D | DI | D | I | DI | DI | D | DI | D |
| Miki (27--14) | I | D | D | DI | D | D | D | I | D | DI | DI | DI | D |
| Hongbaoshi (27--15) | DI | DI | I | DI | D | DI | DI | D | D | DI | DI | I | D |
| Nagafu 2 (27--16) | DI | D | D | DI | D | DI | D | D | D | DI | DI | DI | DI |
| Longguan (27--4) | D | D | DI | D | D | DI | D | I | D | DI | D | D | DI |
| K9 (27--5) | DI | D | DI | D | D | DI | DI | DI | DI | DI | I | D | DI |
| Zaohongda Gala (27--6) | DI | D | DI | D | DI | DI | DI | DI | D | DI | I | D | DI |
| Lvshuai (27--7) | DI | DI | I | DI | D | I | DI | DI | D | DI | DI | DI | DI |
| Hongxia (27--8) | D | D | DI | I | D | DI | D | DI | DI | DI | DI | I | D |
| Zaohongxia (27--9) | DI | D | D | DI | D | DI | DI | DI | DI | DI | DI | DI | DI |
| Early Golden (2--8) | D | DI | I | DI | DI | I | DI | D | D | D | DI | D |
| Indo (28--0) | D | DI | D | DI | D | D | DI | I | D | DI | DI | DI | D |
| Jie 1 (28--11) | DI | D | D | DI | DI | D | DI | D | DI | D | I | D | DI |
| Beauty of Bath (28--13) | DI | DI | DI | DI | DI | DI | DI | D | D | DI | I | D | DI |
| K10 (28--14) | DI | DI | DI | D | DI | DI | D | DI | D | DI | I | D | D |
| Beifang Xina (28--16) | DI | DI | I | DI | D | DI | D | I | DI | DI | D | D | D |

| Construction results of InDel marker genotype database of *Malus* germplasm resources | | | | | | | | | | | | | |
|---|---|---|---|---|---|---|---|---|---|---|---|---|---|
| Yellow Fuji (28--18) | DI | DI | I | DI | DI | DI | D | DI | D | DI | DI | DI | D |
| Sinano Sweet (28--2) | DI | DI | D | DI | D | D | DI | D | D | DI | DI | DI | DI |
| Miguo (28--3) | D | DI | I | D | D | DI | D | DI | D | DI | DI | D | D |
| Ace (28--4) | DI | D | D | DI | D | D | D | D | D | DI | DI | DI | DI |
| Tsugaru (28--5) | I | DI | DI | I | D | DI | DI | DI | D | DI | I | DI | DI |
| K12 (28--8) | DI | D | I | DI | D | DI | DI | DI | D | DI | DI | DI | DI |
| Jieernianke (28--9) | D | D | DI | DI | D | DI | D | DI | D | DI | I | DI | D |
| Macoun (2--9) | D | D | D | D | D | I | D | DI | DI | DI | I | D | DI |
| Qingping (29--1) | I | D | DI | D | D | DI | D | I | I | I | I | DI | DI |
| Polka (29--11) | I | DI | DI | D | DI | D | D | DI | DI | DI | DI | DI | DI |
| Longfeng (29--13) | I | DI | DI | DI | D | DI | D | D | D | DI | D | DI | I |
| Very Early Fuji (29--14) | DI | D | D | DI | D | D | D | DI | D | DI | DI | DI | DI |
| Longhong (29--15) | D | DI | DI | D | DI | DI | D | DI | D | DI | I | DI | DI |
| Pinova (29--16) | DI | DI | I | D | DI | DI | D | I | DI | DI | DI | DI | DI |
| Fuga (29--17) | D | DI | DI | I | D | DI | D | DI | DI | DI | DI | I | D |
| Qing n3 (29--2) | DI | DI | DI | DI | D | D | D | D | D | DI | I | DI | DI |
| Xinyuanshuai (29--3) | DI | DI | DI | DI | D | D | D | D | D | DI | I | DI | DI |
| Xinhua (29--5) | DI | D | D | D | DI | DI | D | I | D | DI | D | D | D |
| Nanpu 2 (29--6) | DI | D | D | D | DI | D | D | I | D | DI | I | DI | D |
| Liuyu mutant (29--7) | DI | D | I | DI | D | DI | D | D | D | DI | DI | D | DI |
| Shandao Fuji (30--1) | DI | D | D | D | D | DI | D | DI | D | DI | DI | DI | DI |
| Sinano Gold (30--2) | DI | DI | D | DI | DI | I | DI | DI | D | DI | DI | DI | D |
| Whitney (3--1) | DI | D | DI | D | DI | I | D | D | D | DI | DI | D | DI |
| Feixia (31--1) | DI | DI | DI | D | DI | I | D | DI | D | DI | DI | I | DI |
| Willams Faborite (3--11) | D | D | DI | DI | DI | DI | DI | DI | D | DI | I | D | D |
| Zhangye 2 (31--12) | I | DI | I | DI | D | DI | DI | D | D | DI | I | I | DI |
| Youfangcun Ralls Janet (31--14) | D | D | I | D | DI | D | DI | DI | DI | DI | I | D | DI |
| Yueyanghong (31--15) | DI | D | D | I | DI | D | DI | D | D | DI | D | D | DI |
| Shuohong (31--17) | DI | DI | DI | DI | D | DI | D | DI | D | DI | DI | D | D |
| Tianwang 1 (31--18) | DI | DI | DI | DI | D | D | D | D | D | DI | I | DI | DI |
| Huadan (31--2) | D | DI | DI | DI | D | D | D | D | D | DI | DI | D | DI |
| Dalu 52 (3--12) | D | D | D | D | DI | DI | D | DI | D | DI | DI | D | D |
| Cameo (31--3) | DI | DI | DI | I | DI | DI | D | DI | DI | DI | I | DI | DI |
| Tianhuangkui (3--13) | D | D | D | D | DI | D | DI | D | D | DI | DI | D | D |
| Qiulu (31--4) | I | D | DI | D | D | D | D | D | D | DI | D | D | I |
| Liehuangjiatena (3--15) | DI | DI | I | DI | D | I | DI | DI | DI | DI | DI | DI | I |
| Lubi (3--16) | D | DI | I | D | D | D | DI | D | D | DI | I | D | DI |
| Huayu (31--8) | D | D | DI | I | D | DI | D | I | DI | DI | DI | D | DI |

-continued

| Construction results of InDel marker genotype database of *Malus* germplasm resources |||||||||||||
|---|---|---|---|---|---|---|---|---|---|---|---|---|
| Fameuse (3--18) | DI | DI | D | DI | D | DI | D | DI | I | DI | DI | DI | DI |
| Zhanhanxiang (3--19) | DI | DI | DI | DI | DI | I | DI | DI | DI | DI | I | DI | DI |
| Siberian White Spot (3--2) | DI | DI | D | I | DI | DI | D | I | I | DI | I | D | D |
| Zhengding 2 (3--21) | DI | D | D | DI | DI | D | D | I | D | DI | D | D | D |
| Kuihua (3--22) | D | D | I | DI | D | DI | DI | DI | DI | I | I | DI | D |
| Early Worcester (3--23) | D | D | D | DI | D | DI | DI | D | I | DI | D | D | DI |
| Lowland Raspderry (3--3) | DI | DI | I | DI | D | DI | D | I | DI | DI | I | DI | DI |
| Miqiulin Jinian (3--4) | DI | DI | D | DI | DI | DI | D | I | D | D | DI | D | DI |
| Huangtianguo (3--5) | DI | DI | D | I | D | DI | D | I | D | DI | I | D | DI |
| Huadao (3--7) | D | D | D | D | D | I | D | DI | D | DI | DI | D | DI |
| Red Astrachan (3--9) | D | D | DI | DI | DI | DI | D | DI | D | DI | DI | DI | DI |
| Black Gilliflower (4-1) | DI | DI | I | DI | D | I | D | DI | D | DI | I | D | D |
| Nimaiyisuo (4--10) | DI | D | DI | D | DI | DI | D | D | D | DI | D | D | DI |
| Zaohong (4--11) | D | D | I | D | D | DI | D | I | D | DI | D | D | DI |
| Xiangguo (4--12) | DI | DI | DI | I | D | DI | D | I | D | I | DI | D | DI |
| Vista Bella (4--16) | D | D | DI | D | D | D | D | D | DI | DI | D | D | D |
| Saiwen (4--17) | I | D | I | D | D | D | DI | D | DI | DI | I | D | DI |
| Summerland (4--20) | DI | DI | I | DI | DI | I | DI | DI | DI | DI | DI | I | DI |
| Qihe Golden Spur (4--22) | DI | DI | I | DI | DI | I | DI | DI | DI | DI | DI | I | DI |
| Yellow Risharde (4--3) | DI | D | D | DI | D | D | DI | D | D | DI | I | DI | DI |
| Patten (4--5) | D | D | D | D | DI | D | D | D | DI | DI | DI | D | D |
| Early Red Bird (4--6) | DI | D | I | DI | D | DI | D | D | D | DI | DI | D | DI |
| Fuhong (4--7) | D | D | D | D | DI | D | DI | D | D | DI | I | DI | D |
| Bisimake (4--8) | DI | DI | I | DI | D | I | D | DI | DI | DI | DI | D | D |
| York Imperial (4--9) | DI | DI | I | DI | D | I | DI | DI | D | DI | D | D | D |
| Jonagold (5--1) | DI | DI | I | DI | DI | DI | DI | DI | DI | DI | DI | DI | DI |
| Ayiwaniya (5--10) | D | DI | DI | DI | D | D | D | D | DI | I | I | D | DI |
| Fushan 5 (5--14) | DI | DI | DI | DI | D | DI | D | D | D | DI | I | DI | DI |
| Houjiadian Spur (5--18) | DI | DI | DI | DI | D | D | D | D | D | DI | I | DI | DI |
| Guoshuai (5--19) | DI | DI | I | D | D | D | D | DI | D | DI | DI | D | DI |
| Huashuai 1 (5--21) | D | DI | D | DI | D | D | DI | D | D | DI | I | DI | DI |
| Xiongyue 2 (5--22) | DI | DI | DI | DI | D | D | D | D | DI | DI | I | DI | DI |
| Honeygod (5--3) | D | DI | DI | DI | DI | DI | DI | DI | DI | D | D | DI | D |
| Joyal (5--4) | DI | DI | D | D | DI | DI | D | DI | D | DI | D | D | DI |
| Stark Spur Golden (5--5) | DI | DI | I | DI | DI | I | DI | DI | DI | DI | DI | I | DI |
| Enweier Golden (5--6) | DI | DI | I | DI | DI | I | DI | DI | DI | DI | DI | I | DI |
| Stark Gold (5--8) | D | D | I | D | D | DI | D | I | D | DI | D | D | DI |
| Sishui Spur (6--10) | DI | DI | DI | DI | D | D | D | D | D | DI | I | DI | DI |

-continued

Construction results of InDel marker genotype database of *Malus* germplasm resources

| | | | | | | | | | | | | | |
|---|---|---|---|---|---|---|---|---|---|---|---|---|---|
| Red Spur Delicious (6--12) | DI | DI | DI | DI | D | D | D | D | D | DI | I | DI | DI |
| Qingdao 1 (6--13) | DI | DI | DI | DI | D | D | D | D | D | DI | I | DI | DI |
| Bianqiangzi 1 (6--14) | DI | DI | DI | DI | D | D | D | D | D | DI | I | DI | DI |
| Zhangjiakou Spur (6--16) | DI | DI | DI | DI | D | D | D | D | D | DI | I | DI | DI |
| Richard Red Delicious (6--18) | DI | DI | DI | DI | D | D | D | D | D | DI | I | DI | DI |
| Well Spur Delicious (6--19) | DI | DI | DI | DI | D | D | D | D | D | DI | I | DI | DI |
| Bianqiangzi 2 (6--20) | DI | DI | DI | DI | D | D | D | D | D | DI | I | DI | DI |
| Hardi Spur Delicious (6--21) | DI | DI | DI | DI | D | D | D | D | D | DI | I | DI | DI |
| Fushan 1 (6--3) | DI | DI | DI | DI | D | D | D | D | D | DI | I | DI | DI |
| Pinyin Spur (6--4) | DI | DI | DI | DI | D | D | D | D | D | DI | I | DI | DI |
| Nanshan 2 (6--8) | DI | DI | DI | DI | D | D | D | D | D | DI | I | DI | DI |
| Meiduan 1 (7--10) | D | DI | DI | D | DI | DI | D | DI | D | DI | DI | DI | D |
| Shisanling Spur (7--11) | DI | DI | DI | DI | D | D | D | D | D | DI | I | DI | DI |
| Kelisike (7--13) | D | DI | D | D | D | D | D | D | D | I | I | D | DI |
| Jie 18 (7--16) | I | D | DI | D | DI | DI | D | D | D | DI | DI | DI | D |
| Bo 25 (7--17) | D | DI | DI | DI | DI | I | D | D | DI | DI | I | D | D |
| Ruixiang (7--18) | DI | D | I | DI | DI | D | D | DI | D | DI | DI | DI | DI |
| Wealthy (7--19) | D | D | D | DI | D | D | DI | D | D | DI | DI | D | D |
| Nanshan 4 (7--2) | D | D | I | D | DI | D | DI | D | DI | DI | D | I |  |
| De 14 (7--20) | I | D | DI | D | DI | DI | D | D | D | DI | DI | DI | D |
| Napoleon (7--22) | D | DI | I | D | DI | D | DI | D | DI | DI | D | D |  |
| Youyi (7--23) | DI | D | D | D | DI | D | DI | DI | DI | DI | DI | D | DI |
| Oregon Spur (7--3) | D | D | I | D | DI | D | DI | D | DI | DI | D | I |  |
| Kangtun Spur (7--6) | DI | DI | DI | DI | D | D | D | D | D | DI | I | DI | DI |
| White Pippin (7--9) | DI | DI | D | DI | DI | D | DI | D | DI | I | DI | DI | DI |
| Zach Lebel (8--1) | D | DI | DI | DI | D | DI | DI | DI | D | I | DI | DI | D |
| Cortland (8--10) | D | D | D | DI | D | D | D | D | D | DI | DI | D | D |
| Raritan (8--12) | DI | D | D | DI | D | DI | D | DI | D | DI | DI | DI | DI |
| Meilingxi Tsugaru (8--13) | DI | DI | I | DI | D | DI | D | D | DI | DI | D | D |  |
| Moscow Transparent (8--14) | DI | D | DI | D | DI | DI | D | DI | D | DI | DI | D | DI |
| Cooper's Market (8--15) | DI | D | I | DI | DI | D | D | DI | DI | DI | D | DI |  |
| Xite Shisheng (8--16) | D | DI | DI | DI | DI | DI | DI | DI | D | DI | D | D | DI |
| Tian Yisaye (8--17) | D | DI | DI | I | D | D | D | D | DI | DI | D | D | DI |
| Shennong 2 (8--19) | I | DI | I | I | D | I | DI | D | DI | DI | DI | DI | D |
| Maigold (8--20) | DI | DI | DI | D | DI | DI | D | I | DI | DI | D | DI | D |
| Magu (8--21) | D | D | DI | D | DI | D | D | D | DI | DI | I | D | DI |
| Cellini (8--23) | DI | DI | I | DI | D | I | D | DI | DI | DI | DI | D | D |

-continued

| Construction results of InDel marker genotype database of *Malus* germplasm resources ||||||||||||||
|---|---|---|---|---|---|---|---|---|---|---|---|---|---|
| Simonffy Piros (8--3) | D | D | DI | D | DI | I | D | DI | D | DI | D | D | DI |
| Luxiang (8--5) | DI | D | DI | DI | D | D | D | DI | D | DI | I | D | DI |
| Zhongqiu (8--6) | DI | DI | DI | DI | DI | DI | DI | DI | D | DI | I | DI | D |
| De 2 (8--7) | DI | D | D | D | DI | D | DI | DI | DI | DI | DI | DI | DI |
| Grimes Golden (8--8) | DI | DI | DI | DI | D | DI | DI | DI | DI | DI | I | DI | DI |
| Early Straw Berry (8--9) | DI | I | DI | D | DI | D | D | D | D | DI | DI | DI | DI |
| Kelia (9--10) | DI | DI | I | D | DI | DI | DI | DI | D | DI | DI | DI | DI |
| French Apple (9--11) | I | DI | DI | D | DI | DI | D | DI | DI | DI | DI | DI | DI |
| Todoroki Tsugaru (9--12) | I | DI | DI | I | D | DI | DI | DI | D | DI | I | DI | DI |
| Cuihong (9--13) | D | D | DI | DI | DI | D | D | I | D | DI | DI | D | DI |
| De 4 (9--14) | D | D | D | DI | DI | DI | DI | DI | D | DI | DI | D | DI |
| Early McIntosh (9--18) | DI | DI | D | D | D | DI | D | DI | DI | DI | D | D | D |
| Adam Mickewier (9--19) | DI | DI | D | D | D | DI | D | I | D | DI | DI | D | DI |
| Norda (9--2) | DI | DI | D | D | DI | DI | D | DI | DI | DI | I | D | D |
| Cardinal (9--20) | DI | DI | DI | DI | DI | I | D | DI | DI | DI | I | DI | DI |
| Evelyn (9--21) | D | DI | DI | DI | D | D | D | DI | DI | I | I | DI | D |
| Situonuowei (9--22) | D | D | DI | DI | D | I | D | DI | D | DI | DI | DI | DI |
| Yingqiu (9--23) | DI | D | DI | DI | D | D | D | I | DI | DI | DI | D | DI |
| Kelongxieer (9--3) | DI | D | DI | D | DI | D | D | DI | D | DI | DI | D | DI |
| Cloden (9--5) | D | DI | DI | D | DI | DI | D | DI | I | DI | I | I | D |
| Qiutianhong (9--6) | D | D | DI | D | D | I | D | DI | D | DI | DI | DI | DI |
| Gaidebao (9--7) | DI | D | DI | D | DI | DI | D | I | D | DI | DI | D | DI |
| Starkjam (9--9) | D | DI | I | D | D | DI | D | DI | D | DI | DI | D | D |
| Wan Crab (B-1) | DI | D | D | D | DI | DI | DI | D | D | DI | D | DI | D |
| Minjiandaguo Crab (B-10) | DI | DI | I | DI | D | DI | D | DI | D | DI | DI | D | D |
| Luanzhuang Crab (B1-11) | D | DI | I | D | D | DI | D | I | D | DI | DI | D | I |
| Sankuaishi Crab (B1-12) | DI | D | D | D | D | D | D | I | D | I | DI | D | DI |
| Xiongyue Crab 1 (B1-13) | D | DI | D | D | DI | D | D | DI | DI | DI | DI | DI | DI |
| Sankuaishi Crab 2 (B1-14) | DI | DI | DI | D | DI | DI | I | D | D | DI | D | DI | D |
| Dabaleng (B-12) | D | D | I | D | D | I | D | I | D | DI | DI | D | DI |
| Sankuaishi Crab 2 (B-13) | DI | D | D | DI | D | DI | D | DI | D | DI | DI | DI | DI |
| Changguo Crab (B-14) | I | DI | I | I | DI | DI | D | DI | I | DI | DI | DI | D |
| Dagucheng Baleng (B1-5) | I | DI | D | D | DI | D | D | D | D | I | I | D | D |
| Zumi Crab 3x (B-15) | DI | DI | DI | DI | DI | DI | D | I | DI | DI | DI | I | DI |
| 26105 (B-16) | DI | DI | I | DI | DI | DI | D | I | I | DI | I | D | D |
| Daguo Crab (B-17) | DI | DI | I | DI | D | DI | D | DI | D | DI | DI | D | D |
| Xiongyue Crab 2 (B1-8) | DI | DI | D | D | DI | DI | I | DI | D | DI | DI | D | D |
| Watermelon Crab (B-18) | I | DI | DI | D | DI | I | D | I | I | DI | I | DI | DI |

-continued

| Construction results of InDel marker genotype database of *Malus* germplasm resources |||||||||||||
| --- | --- | --- | --- | --- | --- | --- | --- | --- | --- | --- | --- | --- |
| Mudanjiang Crab (B1-9) | I | DI | D | D | DI | D | DI | DI | D | I | I | D | D |
| Tianhong 1 (B-19) | DI | D | D | DI | D | DI | D | DI | D | DI | DI | DI | DI |
| Jiping 1 (B-2) | D | DI | DI | I | D | DI | D | I | DI | DI | DI | D | D |
| Caoyuan Crab (B2-1) | I | D | D | D | D | D | D | D | D | I | D | D | I |
| Zumi Crab 4x (B-21) | DI | DI | DI | DI | DI | DI | D | I | DI | DI | DI | I | DI |
| Luanzhuang Shaguo (B2-11) | DI | DI | DI | I | DI | D | D | I | D | I | DI | D | DI |
| Xiaofan Crab (B2-13) | DI | DI | DI | I | DI | D | D | I | D | I | DI | D | DI |
| Hebing Pingding Crab (B2-14) | DI | D | D | D | D | D | D | D | D | I | DI | D | D |
| Zumi Crab 3x 2 (B-22) | DI | DI | DI | DI | DI | DI | D | I | DI | DI | DI | DI | DI |
| Baleng Crab (B2-3) | DI | D | D | D | DI | D | D | D | D | I | DI | D | D |
| Baleng seedling 14 (B-25) | DI | DI | I | D | DI | I | D | I | I | DI | D | DI | I |
| Russian White apple (B2-6) | D | DI | D | D | DI | D | DI | D | DI | D | DI | DI | D |
| Nagafu 2 (B-26) | DI | D | D | DI | D | DI | D | D | D | DI | DI | DI | DI |
| Ambrosia (B-27) | D | DI | DI | DI | D | DI | D | DI | DI | DI | I | DI | DI |
| Aihonghua (B2-8) | I | DI | DI | D | DI | DI | I | D | D | DI | DI | DI | D |
| Nanshennan (B-28) | DI | D | D | D | D | DI | D | DI | D | DI | DI | DI | DI |
| Zumi Crab W1 (B-29) | DI | DI | DI | DI | DI | DI | D | I | DI | DI | DI | I | DI |
| Hong 4G (B-3) | DI | D | D | I | D | D | D | I | D | DI | DI | D | DI |
| Zumi Crab (B-30) | DI | DI | DI | DI | DI | DI | D | I | DI | DI | DI | I | DI |
| Zaobai Crab (B3-1) | D | DI | DI | I | D | DI | D | D | D | I | DI | D | D |
| Mollie's Delicious (B-31) | D | DI | I | DI | D | I | D | DI | DI | DI | DI | DI | DI |
| Regunzi Spur (B3-10) | DI | DI | DI | I | D | D | D | D | D | I | DI | D | D |
| Xiaofanshan Baleng (B3-11) | DI | DI | DI | DI | DI | D | D | I | D | DI | DI | D | DI |
| Huamei (B3-12) | D | DI | I | I | D | DI | D | I | DI | DI | D | DI | D |
| Huashuo (B3-13) | D | D | D | DI | DI | D | D | I | DI | DI | I | D | D |
| Yuhong (B3-14) | DI | DI | DI | D | D | D | D | D | DI | I | DI | DI | DI |
| Huayue (B3-15) | DI | D | D | D | DI | DI | DI | DI | DI | DI | DI | DI | D |
| Jingbohu Shandingzi (B3-2) | I | D | D | D | DI | D | DI | DI | D | I | D | D | D |
| Eluosi Daguo Shandingzi (B3-3) | DI | DI | D | D | DI | D | D | I | D | I | DI | DI | D |
| HY (B-33) | D | DI | D | D | DI | DI | D | DI | D | DI | DI | D | D |
| Hong Crab (B3-6) | DI | DI | DI | I | D | D | D | D | D | I | DI | D | D |
| 23# (B-37) | D | DI | DI | I | D | DI | D | DI | DI | DI | D | D | D |
| Russian apple (B3-8) | DI | D | D | D | DI | D | D | DI | D | DI | DI | D | I |
| 147 (B-38) | D | D | DI | DI | DI | I | D | I | DI | DI | D | D | D |
| Xiaofanshan Baleng 1 (B3-9) | DI | D | D | D | DI | D | D | D | D | I | DI | D | D |
| Lvshuai (B-4) | DI | DI | I | DI | D | I | DI | DI | D | DI | DI | DI | DI |

-continued

Construction results of InDel marker genotype database of *Malus* germplasm resources

| | | | | | | | | | | | | |
|---|---|---|---|---|---|---|---|---|---|---|---|---|
| Dounan (B-40) | DI | DI | I | DI | DI | DI | DI | DI | DI | DI | DI | DI |
| 11906 (B-41) | DI | DI | I | DI | D | I | D | DI | DI | DI | DI | D | D |
| Luli (B-5) | D | D | DI | I | D | DI | D | DI | DI | DI | D | DI | D |
| Jinxiuhong (B-6) | DI | DI | I | D | DI | I | D | DI | D | DI | DI | I | DI |
| B68 (B-7) | DI | D | D | D | DI | I | DI | D | D | DI | DI | D | D |
| Huaida (B-8) | DI | DI | DI | DI | DI | DI | DI | DI | DI | D | DI | D |
| Nanshennan mutant (B-9) | DI | D | D | DI | D | DI | D | DI | D | DI | DI | DI | DI |
| Xiahong (BH-1) | DI | DI | I | DI | DI | DI | D | D | D | DI | DI | DI |
| Wuming1 (BJ-1) | D | DI | DI | I | D | DI | D | I | I | DI | I | DI | DI |
| Canzy ? (BJ-10) | D | D | DI | DI | D | I | DI | DI | DI | DI | D | D | DI |
| Xiangfu (BJ-11) | DI | D | D | DI | D | DI | D | DI | D | DI | DI | DI | DI |
| Envy (BJ-12) | D | DI | I | DI | D | DI | DI | DI | DI | DI | DI | DI | D |
| Fuji_KiKu (BJ-2) | DI | D | D | DI | D | DI | D | DI | D | DI | DI | DI | D |
| Banxiu Crab (BJ-4) | DI | D | D | D | DI | DI | I | D | D | DI | DI | D | DI |
| Jazz (BJ-5) | D | DI | I | DI | D | I | DI | DI | DI | DI | D | DI | DI |
| Early Red Bird 2 (BJ-7) | D | DI | D | DI | DI | D | D | DI | DI | DI | I | D | DI |
| Qiuhong Gala (BJ-8) | DI | D | D | DI | D | DI | D | DI | DI | D | DI | DI | D |
| Hongxiangcui (BJ-9) | DI | DI | I | I | D | I | D | DI | DI | D | DI | D | DI |
| 07-115 (BK-1) | DI | D | DI | DI | D | DI | D | I | D | DI | DI | DI | I |
| Nagafu 3 (BK-2) | DI | D | D | DI | D | DI | D | DI | D | DI | DI | DI | DI |
| 28-253 (BK-28-253) | DI | D | DI | I | D | I | D | DI | DI | DI | DI | DI | I |
| Nagafu 3-R (BK-3) | DI | D | D | DI | D | DI | D | DI | DI | DI | DI | DI | DI |
| 4354 (BK-4) | DI | D | I | DI | D | I | DI | DI | D | DI | DI | DI | DI |
| 4-23 (BK-4-23) | D | DI | I | D | DI | I | D | I | DI | DI | I | DI | DI |
| 4354-R ? (BK-5) | D | DI | DI | DI | D | DI | DI | D | DI | DI | DI | DI | D |
| 77-34 (BK-77-34) | I | DI | D | D | DI | D | D | I | D | DI | DI | D | I |
| Red Spur Delicious (BK-AH) | DI | DI | DI | DI | D | D | D | D | D | DI | I | DI | DI |
| Ozark Gold (BK-AJ) | DI | DI | I | DI | DI | DI | D | DI | D | DI | DI | DI | D |
| Michinoku (BK-AZ) | D | D | D | I | D | D | D | DI | D | DI | DI | D | DI |
| Azwell (BK-Azwell) | DI | DI | DI | DI | D | D | D | D | D | DI | I | DI | DI |
| Banbishan Crab (BK-BBSHT) | DI | D | D | D | DI | D | D | D | D | I | DI | D | D |
| Hokudo (BK-BD) | DI | D | D | DI | D | DI | DI | I | D | DI | DI | DI | DI |
| Baifugao (BK-BFG) | DI | DI | D | I | DI | DI | D | I | DI | DI | D | DI | DI |
| White Crab (BK-BHT) | DI | DI | DI | DI | D | D | I | D | DI | DI | D | DI |
| Buming Kangbing (BK-BMKB) | DI | DI | D | DI | D | DI | D | DI | I | DI | DI | DI | DI |
| Batougou 1 (BK-BTG1H) | DI | D | D | D | DI | D | DI | DI | D | I | D | D | D |
| Batougou 2 (BK-BTG2H) | I | D | D | D | DI | D | D | I | D | I | DI | D | D |

-continued

| Construction results of InDel marker genotype database of *Malus* germplasm resources | | | | | | | | | | | | | |
|---|---|---|---|---|---|---|---|---|---|---|---|---|
| Batougou Aizhen (BK-BTGAZ) | DI | D | D | D | DI | D | D | I | I | DI | D | D | D |
| Binzi (BK-BZ) | D | DI | DI | I | DI | D | D | I | D | I | I | D | DI |
| Kitanosach (BK-BZX) | DI | DI | D | I | D | DI | DI | DI | DI | DI | I | D | I |
| Binzi (SW) (BK-BZXN) | D | DI | DI | I | D | D | D | I | D | I | I | D | DI |
| Nagafu 2 (BK-CF2H) | DI | D | D | DI | D | DI | D | DI | D | DI | DI | DI | DI |
| Nagafu 36 (BK-CF36) | DI | D | D | DI | D | DI | D | DI | D | DI | DI | DI | DI |
| Nagafu 6 (BK-CF6H) | DI | D | D | DI | D | DI | D | DI | D | DI | DI | DI | DI |
| CG24 (BK-CG24) | DI | DI | DI | DI | D | D | D | D | D | DI | I | DI | DI |
| CG3 (BK-CG3) | DI | D | DI | I | D | I | D | DI | DI | DI | DI | DI | I |
| CG80 (BK-CG80) | DI | DI | D | D | DI | DI | D | D | D | I | D | DI |
| Changhong (BK-CH) | DI | D | D | DI | D | DI | D | DI | D | DI | DI | DI | DI |
| Chieftan (BK-chieftan) | D | D | D | D | D | I | D | DI | I | DI | DI | D | D |
| Cangjiang Crab (BK-CJHT) | DI | D | D | D | DI | D | DI | I | D | I | D | D | D |
| Chuanling Crab (BK-CLHT) | DI | D | D | D | D | DI | D | I | D | DI | D | DI | D |
| Hatsuaki (BK-CQ) | D | DI | I | DI | DI | I | DI | D | DI | DI | D | DI | DI |
| Crispin (BK-crispin) | DI | DI | I | DI | DI | DI | DI | DI | DI | DI | DI | DI | DI |
| Caozigang Yuanshuai (BK-CZGYS) | DI | DI | DI | DI | D | D | D | D | D | DI | I | DI | DI |
| Danxia (BK-DANXIA) | DI | DI | I | I | D | DI | DI | D | D | DI | I | DI | DI |
| Dolgo (BK-DDG) | DI | DI | D | D | DI | D | D | I | D | I | DI | DI | D |
| Darwin (BK-DEW) | D | DI | DI | I | DI | D | D | I | D | I | I | D | DI |
| Oriental Apple (BK-DFPG) | I | DI | D | DI | DI | D | D | D | D | DI | I | DI | D |
| Big Crab (BK-DGHT) | I | D | D | D | DI | DI | D | I | D | DI | DI | D | DI |
| Daguo Jinhong (BK-DGJH) | DI | DI | DI | DI | DI | DI | DI | DI | DI | DI | D | DI | D |
| Daihong (BK-DH) | DI | DI | DI | DI | D | D | D | D | D | D | I | DI | DI |
| Daihao 261 (BK-DH261) | DI | DI | D | D | DI | D | D | I | D | DI | DI | D | D |
| Spur Golden Delicious (BK-DJG) | DI | DI | I | DI | DI | I | DI | DI | DI | DI | DI | I | DI |
| Daxianguo (BK-DXG) | DI | DI | D | D | DI | D | D | I | D | I | DI | D | D |
| Daye Crab (BK-DYHT) | D | D | DI | DI | D | D | D | D | D | I | DI | D | D |
| Spur Fuji (BK-DZFS) | DI | D | D | DI | D | DI | D | DI | D | DI | DI | DI | DI |
| Huaguan Spur (BK-DZHG) | DI | DI | I | D | DI | I | D | DI | D | DI | DI | I | DI |
| Elite (BK-Elite) | DI | DI | DI | DI | D | D | D | D | D | DI | I | DI | DI |
| Fa 8 (BK-F8) | DI | D | D | D | DI | DI | DI | DI | DI | DI | DI | DI | D |
| Fukushima Spur Fuji (BK-FDDZ) | DI | D | D | DI | D | DI | D | DI | D | DI | DI | DI | DI |
| Fujin (BK-FJ) | DI | DI | DI | D | D | D | D | D | D | DI | DI | DI | DI |
| Florina (BK-Florina) | D | D | D | DI | D | DI | D | D | D | DI | I | DI | DI |
| Fangming (BK-FM) | I | DI | DI | I | D | DI | DI | DI | D | DI | I | DI | DI |
| Fuji (BK-Fuji) | DI | D | D | DI | D | DI | D | DI | D | DI | DI | DI | DI |

-continued

Construction results of InDel marker genotype database of *Malus* germplasm resources

| | | | | | | | | | | | | |
|---|---|---|---|---|---|---|---|---|---|---|---|---|
| Fengyan (BK-FY) | D | D | I | D | D | I | D | DI | DI | DI | DI | D | D |
| Yanfu 1 (BK-FY1) | DI | D | D | DI | D | DI | D | DI | DI | DI | DI | DI | DI |
| King of Tompkins County (BK-FZY) | DI | DI | DI | DI | DI | DI | DI | D | D | DI | DI | DI | DI |
| G30 (BK-G30) | DI | D | DI | D | DI | D | I | D | D | I | I | D | D |
| Gao #5 (BK-G-5) | D | DI | D | DI | DI | DI | D | D | D | DI | I | D | D |
| Gala (BK-gala) | D | DI | I | I | D | DI | D | I | DI | DI | D | DI | D |
| Golden Delicious (BK-GD) | DI | DI | I | DI | DI | I | DI | DI | DI | DI | DI | I | DI |
| Gloster69 (BK-Gloster69) | D | DI | I | D | D | DI | D | D | D | D | I | DI | DI |
| GM256 (BK-GM256) | DI | D | D | D | DI | DI | D | I | D | DI | DI | D | DI |
| GM310 (BK-GM310) | DI | D | DI | D | DI | D | D | I | DI | DI | DI | DI | D |
| Gaoqiu (BK-GQ) | I | DI | DI | DI | DI | DI | DI | D | D | DI | DI | I | D |
| Miyazaki Spur Fuji (BK-GQDZ) | DI | D | D | D | DI | D | DI | D | DI | DI | DI | DI | DI |
| HAC-9 (BK-HAC-9) | DI | DI | D | DI | D | DI | D | DI | DI | DI | DI | DI | DI |
| Huifeng Orin (BK-HFWL) | DI | D | DI | DI | D | D | DI | DI | D | DI | DI | D | D |
| Red Ralls Janet (BK-HGG) | D | D | I | D | D | DI | D | I | D | DI | D | D | DI |
| Huaguan Crab (BK-HGHT) | DI | DI | DI | I | D | DI | D | I | D | I | DI | D | DI |
| Harrold Red Delicious (BK-HH) | DI | DI | DI | DI | D | D | D | D | D | DI | I | DI | DI |
| Hong Crab 2 (BK-HHT2H) | DI | DI | DI | I | D | D | D | D | D | I | DI | D | D |
| Stark Redgold (BK-HJ) | DI | DI | DI | I | D | DI | D | DI | DI | DI | I | I | I |
| HLWQ (BK-HLWQ) | D | DI | DI | D | D | I | DI | DI | I | DI | I | D | DI |
| Holly (BK-Holly) | DI | D | DI | DI | D | D | D | D | D | DI | I | D | DI |
| Red Jonagold (BK-HQNJ) | I | DI | I | DI | DI | DI | D | I | DI | DI | D | DI | DI |
| Red Sekaiichii (BK-HSJY) | I | DI | I | D | DI | DI | DI | D | D | DI | I | I | D |
| Hongte (BK-HT) | D | D | D | DI | DI | DI | D | I | D | DI | DI | DI | DI |
| Haitangguo (BK-HTG) | I | D | DI | I | DI | DI | I | D | D | DI | D | DI | D |
| Haitanghua (BK-HTH) | D | DI | DI | DI | DI | D | DI | D | I | I | D | DI | |
| Huangtaiping (BK-HTP) | DI | DI | DI | DI | D | D | I | D | DI | DI | D | DI | |
| Hongxue (BK-HX) | DI | DI | D | DI | D | DI | D | DI | I | DI | DI | I | DI |
| Jincui (BK-JC) | DI | DI | DI | D | DI | DI | D | DI | DI | DI | I | DI | DI |
| Juda Fuji (BK-JDFS) | DI | D | D | DI | D | DI | D | DI | D | DI | DI | DI | DI |
| Jiguan (BK-JG) | DI | D | DI | D | DI | DI | DI | D | DI | I | D | DI | |
| Jinhong (BK-JH) | DI | DI | DI | DI | D | DI | DI | DI | DI | D | DI | D | |
| Jonagored (BK-Jonagored) | DI | DI | DI | DI | DI | DI | DI | DI | DI | DI | DI | DI | |
| Jonathan (BK-Jonathan) | DI | D | D | DI | D | D | DI | D | D | I | D | DI | |
| Himekami (BK-JS) | DI | D | D | D | DI | DI | D | D | D | DI | DI | DI | |
| Stark Blushing Golden (BK-JY) | I | DI | I | D | DI | DI | DI | D | D | DI | DI | DI | D |

Construction results of InDel marker genotype database of *Malus* germplasm resources

| | | | | | | | | | | | | | |
|---|---|---|---|---|---|---|---|---|---|---|---|---|---|
| Classic Red Delicious (BK-KAHONG) | DI | DI | DI | DI | D | D | D | D | D | DI | I | DI | DI |
| KLGDG Shandingzi (BK-KLGDGSDZ) | DI | D | D | D | DI | D | D | D | D | I | DI | D | D |
| KOSZTELQ (BK-KOSZTELQ) | DI | DI | I | D | DI | I | D | DI | DI | DI | I | DI | D |
| Sunflower (BK-KUIHUA) | DI | DI | DI | I | D | DI | D | DI | DI | DI | I | I | DI |
| Lenghaitang (BK-LHT) | DI | D | D | D | D | D | D | D | D | I | DI | D | D |
| Liberty (BK-liberty) | D | D | D | DI | D | I | D | DI | I | DI | DI | D | D |
| Lijiang Shandingzi (BK-LJSDZ) | DI | DI | D | D | D | DI | D | I | D | DI | DI | D | I |
| Laoshan 4 (BK-LS4H) | DI | DI | D | D | DI | D | D | I | D | I | DI | D | D |
| Ryoka no Kisetsu (BK-LX) | DI | D | D | DI | D | DI | D | DI | D | DI | DI | DI | DI |
| Lvxiangjiao (BK-LXJ) | DI | D | I | I | D | DI | D | I | DI | DI | D | D | D |
| Liaozhen 1 (BK-LZ1H) | I | D | D | D | DI | D | D | I | D | DI | DI | D | D |
| M7 (BK-M7) | DI | DI | I | D | DI | DI | D | DI | D | DI | I | D | DI |
| Meiguihong (BK-MGH) | DI | DI | DI | DI | D | D | D | D | D | DI | I | DI | DI |
| Meile (BK-ML) | I | DI | I | DI | DI | I | D | DI | DI | DI | I | I | D |
| MM106 (BK-MM106) | DI | DI | D | D | DI | DI | D | D | D | DI | I | D | DI |
| Mengpaisi (BK-MPS) | D | D | D | DI | DI | DI | D | DI | D | DI | DI | D | D |
| Meixiang (BK-MX) | DI | D | D | DI | D | DI | D | DI | D | DI | DI | DI | DI |
| Ningqiu (BK-NQ) | D | DI | D | D | D | D | D | I | D | DI | DI | D | D |
| P16 (BK-P16) | DI | D | DI | D | DI | DI | D | DI | D | DI | DI | D | I |
| P22 (BK-P22) | DI | DI | D | DI | D | DI | D | D | D | I | DI | D | D |
| Pingdinghaitang (BK-PDHT) | DI | DI | D | D | D | D | D | I | D | I | DI | D | D |
| Bianguo Crab (BK-PGHT) | DI | DI | D | DI | DI | DI | D | I | DI | DI | DI | DI | I |
| Pionier (BK-Pionier) | DI | D | D | D | DI | I | DI | D | D | DI | DI | DI | D |
| Prima (BK-Prima) | D | D | DI | D | DI | I | DI | DI | D | DI | I | I | DI |
| Pingyitiancha (BK-PYTC) | I | D | D | D | DI | D | DI | D | D | I | D | D | D |
| Qianxue (BK-QAINXUE) | DI | DI | D | DI | DI | I | DI | DI | D | DI | DI | DI | D |
| Akifu 1 (BK-QF1) | DI | D | D | D | D | DI | D | DI | D | DI | DI | DI | DI |
| Qingfu 13 (BK-QF13) | DI | D | D | DI | D | DI | D | DI | D | DI | DI | DI | DI |
| Seimei (BK-QM) | DI | DI | I | DI | D | D | DI | I | D | DI | I | DI | I |
| Senshu (BK-QQ) | DI | D | DI | DI | D | D | DI | D | D | DI | DI | D | DI |
| Aomori Early (BK-QSZS) | DI | DI | DI | DI | DI | DI | DI | DI | DI | DI | DI | I | DI |
| Qiuxiang (BK-QX) | I | DI | DI | I | D | DI | DI | DI | DI | DI | I | DI | DI |
| Qiuxing Crab (BK-QXHT) | D | D | I | DI | D | D | D | D | D | DI | DI | D | D |
| Yanqing (BK-QY) | DI | DI | DI | DI | D | DI | D | DI | D | DI | I | I | D |
| Regunzi (BK-RGZ) | DI | DI | DI | I | D | D | D | D | D | I | DI | D | D |
| Ruby (BK-Ruby) | D | D | I | D | D | DI | D | DI | D | DI | DI | D | I |
| Scarlet (BK-scarlet) | DI | DI | DI | DI | D | D | D | D | D | DI | I | DI | D |

-continued

| Construction results of InDel marker genotype database of *Malus* germplasm resources | | | | | | | | | | | | | |
|---|---|---|---|---|---|---|---|---|---|---|---|---|---|
| Sdw1 (BK-Sdw1) | DI | D | D | D | DI | D | DI | DI | D | I | DI | D | D |
| Shandingzi 2 (BK-SDZ2H) | DI | D | D | D | DI | D | D | D | D | I | DI | D | D |
| Su E Shandingzi (BK-SESDZ) | D | D | I | I | DI | D | D | D | D | I | D | D | D |
| Shengfang 2 (BK-SF2) | DI | D | D | DI | D | DI | D | DI | D | DI | DI | DI | DI |
| SH6 (BK-SH6) | DI | D | D | D | D | D | D | I | D | DI | D | D | I |
| Sankuaishi Crab 1 (BK-SKSHT1H) | DI | D | D | D | D | D | D | D | D | I | DI | D | D |
| Forest Apple (BK-SLPG) | D | DI | I | DI | DI | I | DI | DI | D | DI | DI | DI | DI |
| Sieversii (BK-SWS) | DI | DI | D | D | D | DI | D | I | D | DI | DI | D | I |
| Sansa (BK-SX) | D | DI | DI | I | D | D | D | I | I | DI | DI | D | D |
| Szampion (BK-Szampion) | D | DI | DI | I | D | DI | DI | DI | I | DI | DI | DI | D |
| T337 (BK-T337) | DI | D | DI | D | DI | DI | DI | DI | D | DI | I | D | DI |
| Turkmen Apple (BK-TKMPG) | DI | DI | D | D | D | DI | D | I | D | DI | DI | D | I |
| Mato 1 (BK-TMYH) | D | D | D | I | D | D | D | DI | D | DI | DI | D | DI |
| Trajian (BK-Trajian) | D | D | D | D | D | I | D | DI | DI | DI | I | D | DI |
| Weiai 3 (BK-WA3) | DI | D | D | D | DI | D | D | D | D | I | DI | D | D |
| Wanbai Crab (BK-WBHT) | DI | DI | DI | DI | D | DI | D | DI | DI | DI | D | DI | D |
| Wufengshan 1 (BK-WFS1H) | DI | DI | DI | DI | DI | DI | D | I | D | I | DI | D | DI |
| Wufengshan 4 (BK-WFS4H) | DI | D | D | D | D | D | D | I | D | DI | DI | D | D |
| Wufengshan Crab (BK-WFSHT) | D | D | DI | D | D | DI | D | I | D | DI | I | D | DI |
| Wufengshan Crab 2 (BK-WFSHT2H) | DI | D | D | I | DI | D | D | D | D | DI | I | D | D |
| Wufengshan Crab 6 (BK-WFSHT6H) | D | DI | D | D | DI | D | D | I | D | I | D | D | D |
| Wifos (BK-wifos) | D | D | D | DI | DI | D | D | D | DI | DI | DI | D | D |
| Orei (BK-WL) | I | DI | I | D | DI | DI | DI | D | D | DI | DI | DI | D |
| Maypole (BK-WM) | DI | D | D | DI | DI | D | D | DI | DI | DI | D | D | DI |
| Waltz (BK-WZ) | I | DI | DI | D | DI | DI | D | DI | DI | DI | DI | DI | DI |
| Kotoku (BK-XD) | D | D | DI | D | DI | DI | D | D | D | DI | DI | I | DI |
| Xiaofanshan Binzi (BK-XFSBZ) | D | DI | DI | I | DI | D | D | I | D | I | I | D | DI |
| Xiaofanshan Crab 4 (BK-XFSHT4H) | DI | DI | DI | I | DI | D | D | I | D | I | DI | D | DI |
| Xiaogoumen Naizi (BK-XGMNZ) | DI | DI | D | DI | D | D | D | I | D | I | I | D | DI |
| XGM Suan Binzi (BK-XGMSBZ) | D | DI | DI | I | DI | D | D | I | D | I | I | D | DI |
| XGM Tian Binzi (BK-XGMTBZ) | DI | DI | DI | I | D | DI | D | DI | D | I | I | D | DI |
| Starkrimson (BK-XHX) | DI | DI | DI | DI | D | D | D | D | D | DI | I | DI | DI |
| Xinjiang 1 (BK-XJ1) | D | DI | D | I | D | I | D | I | D | DI | I | D | I |
| Xinjiang 11 (BK-XJ11) | D | DI | D | DI | D | DI | D | D | D | DI | DI | D | DI |
| Xinjiang 14 (BK-XJ14) | D | DI | D | DI | D | DI | D | D | D | DI | D | D | DI |
| Xinjiang 15 (BK-XJ15) | D | DI | D | I | DI | DI | D | DI | DI | DI | DI | D | DI |
| Xinjiang 16 (BK-XJ16) | DI | DI | DI | DI | D | DI | D | I | D | D | I | DI | D |
| Xinjiang 17 (BK-XJ17) | D | DI | DI | D | D | I | D | DI | DI | DI | DI | D | DI |

| Construction results of InDel marker genotype database of *Malus* germplasm resources | | | | | | | | | | | | | |
|---|---|---|---|---|---|---|---|---|---|---|---|---|---|
| Xinjiang 18 (BK-XJ18) | D | DI | DI | D | D | I | D | DI | DI | DI | DI | D | DI |
| Xinjiang 19 (BK-XJ19) | D | DI | DI | D | DI | I | D | DI | DI | DI | DI | D | D |
| Xinjiang 21 (BK-XJ21) | DI | DI | DI | DI | DI | D | D | DI | DI | DI | DI | D | D |
| Xinjiang 22 (BK-XJ22) | D | DI | D | I | D | I | D | I | D | DI | I | D | I |
| Xinjiang 24 (BK-XJ24) | D | DI | D | I | D | I | D | I | D | DI | I | D | I |
| Xinjiang 26 (BK-XJ26) | D | DI | D | DI | D | DI | D | D | D | DI | D | D | DI |
| Xinjiang 28 (BK-XJ28) | D | DI | DI | D | DI | I | DI | DI | D | DI | DI | D | D |
| Xinjiang 29 (BK-XJ29) | DI | DI | DI | D | DI | DI | DI | DI | I | DI | DI | DI | D |
| Xinjiang 31 (BK-XJ31) | DI | D | D | D | DI | DI | D | I | D | DI | D | DI | I |
| Xinjiang 3 (BK-XJ3H) | DI | DI | D | DI | D | DI | D | DI | D | DI | DI | DI | DI |
| Xinjiang 6 (BK-XJ6H) | DI | DI | D | D | D | I | D | DI | DI | DI | D | D | D |
| Xinjiang 7 (BK-XJ7) | D | DI | D | DI | D | DI | D | D | D | DI | DI | D | DI |
| Xinjiang 8 (BK-XJ8) | I | DI | DI | I | DI | I | D | DI | D | DI | DI | D | DI |
| Xinjiang 9 (BK-XJ9) | DI | DI | DI | D | DI | DI | DI | DI | I | DI | DI | DI | D |
| Xijin Crab (BK-XJHT) | I | D | DI | D | DI | DI | D | D | D | DI | DI | D | I |
| Xiaomian Crab (BK-XMHT) | DI | D | D | D | DI | D | D | I | D | I | DI | D | D |
| New Jonagold (BK-XQNJ) | DI | DI | I | DI | DI | DI | D | DI | DI | DI | DI | DI | DI |
| Xiaoshuai (BK-XS) | I | D | D | DI | D | D | D | DI | D | DI | DI | DI | D |
| Shinsekai (BK-XSJ) | DI | D | DI | I | D | I | D | DI | DI | DI | DI | DI | I |
| Xiangyanghong (BK-XYH) | DI | D | D | D | D | DI | D | DI | D | DI | DI | DI | I |
| Italy Early Red (BK-YDLZH) | D | DI | I | I | D | DI | D | I | DI | DI | D | DI | D |
| Yanfu 10 (BK-YF10) | DI | D | D | DI | D | D | D | DI | D | DI | DI | DI | DI |
| Yoko (BK-YG) | I | DI | DI | DI | DI | DI | D | I | DI | DI | I | DI | DI |
| Yuanhong (BK-YH) | I | DI | D | DI | DI | D | D | DI | DI | DI | DI | DI | DI |
| Tehong 2 (BK-YH2) | DI | D | D | DI | D | DI | D | D | D | DI | DI | DI | DI |
| Yanhongmi (BK-YHM) | DI | D | DI | D | D | DI | D | DI | D | DI | DI | D | DI |
| Youliang Spur (BK-YLDZ) | DI | D | D | DI | D | DI | D | D | D | DI | DI | DI | DI |
| Yuanye Crab (BK-YYHT) | DI | DI | DI | I | D | D | D | D | D | I | DI | D | D |
| Stark Jumbo (BK-ZB) | D | DI | D | D | DI | DI | D | DI | D | DI | DI | D | D |
| Jumbo Orin (BK-ZBWL) | DI | DI | I | DI | DI | I | DI | DI | DI | DI | DI | I | DI |
| Zhuifeng 1 (BK-ZF1H) | DI | D | I | I | D | D | D | I | DI | DI | D | DI | D |
| Zhuifeng 2 (BK-ZF2H) | DI | D | D | D | DI | D | D | D | I | DI | DI | D | D |
| Early Fuji (BK-ZFS) | DI | D | D | DI | D | DI | D | DI | D | DI | DI | DI | DI |
| Xiaofanshan Crab (BK-ZFSHT) | DI | DI | DI | I | DI | D | D | I | D | I | DI | D | DI |
| Zisai Pearl (BK-Zisai) | D | DI | I | DI | D | DI | D | D | DI | D | DI | D | DI |
| Geneva Early (BK-ZJ) | D | D | I | DI | D | D | D | D | I | DI | DI | D | DI |
| 13-26W (CL-1) | I | DI | DI | DI | D | D | D | D | D | DI | I | DI | DI |
| 23-127 (CL-2) | DI | DI | DI | D | DI | DI | DI | DI | DI | DI | DI | DI | D |

| \multicolumn{13}{c}{Construction results of InDel marker genotype database of *Malus* germplasm resources} |
|---|---|---|---|---|---|---|---|---|---|---|---|---|
| 50-30 (CL-3) | D | D | DI | DI | D | DI | D | DI | D | DI | DI | D | DI |
| 50-32 (CL-4) | I | DI | D | D | DI | DI | D | DI | DI | DI | D | DI | D |
| H5-101 (CL-5) | D | DI | DI | DI | DI | DI | D | DI | DI | DI | DI | DI | I |
| Pingyan (CL-6) | DI | D | D | I | D | D | D | DI | D | DI | I | DI | I |
| Deqin Crab (DQ) | I | D | D | D | DI | D | D | D | D | I | D | D | D |
| Jin 18 (GY-1) | DI | D | D | DI | D | DI | D | I | D | DI | DI | DI | D |
| Fengfeng Baleng (GY-2) | DI | D | D | D | DI | DI | I | D | D | DI | DI | D | DI |
| Hanfu 6 (GY-3) | DI | D | D | DI | D | DI | D | DI | D | DI | DI | DI | DI |
| Hanfu 3 (GY-4) | D | DI | DI | D | D | DI | DI | D | D | DI | DI | DI | D |
| 95/06 (GZ-1) | DI | DI | I | DI | DI | D | D | I | D | DI | I | D | D |
| 107/06 (GZ-2) | DI | D | I | DI | DI | D | D | I | I | DI | DI | D | D |
| 117/06 (GZ-3) | DI | D | I | DI | DI | DI | D | I | D | DI | DI | D | D |
| 119/06 (GZ-4) | DI | DI | I | DI | D | I | D | I | DI | DI | DI | D | D |
| Jinxiu Crab (GZ-5) | DI | DI | D | I | DI | D | D | D | D | DI | I | DI | D |
| Zhizun Fuji (HS-1) | DI | D | D | DI | D | DI | D | DI | D | DI | DI | DI | DI |
| Fuji No. 1 (HS-10) | DI | D | D | DI | D | DI | D | DI | D | DI | DI | DI | DI |
| Red Jonaprince (HS-12) | DI | DI | I | DI | DI | DI | DI | DI | DI | DI | DI | DI | DI |
| Nic29 (HS-13) | DI | D | DI | D | DI | DI | DI | DI | D | DI | I | D | DI |
| Azhen Fuji (HS-14) | DI | D | D | DI | D | DI | D | I | D | DI | DI | DI | DI |
| Envy (HS-15) | D | DI | I | DI | D | DI | DI | DI | DI | DI | DI | DI | D |
| Rosegrow (HS-16) | DI | DI | I | DI | DI | I | DI | DI | DI | DI | I | I | I |
| Canzy (HS-17) | D | D | DI | DI | D | I | DI | DI | DI | DI | D | D | D |
| Fubrax (HS-2) | DI | D | D | DI | D | DI | D | I | D | DI | DI | DI | DI |
| Mitchgla (HS-3) | D | DI | I | I | D | DI | D | I | DI | DI | D | DI | D |
| Fujiko (HS-4) | DI | D | D | DI | D | DI | D | I | D | DI | DI | DI | DI |
| Buckeye Gala (HS-5) | D | DI | I | I | D | D | D | I | DI | DI | D | DI | D |
| Fujion (HS-6) | DI | D | D | D | DI | DI | D | DI | D | DI | I | DI | D |
| Modi (HS-7) | D | DI | I | I | D | DI | D | I | DI | DI | DI | D | D |
| Jiangxue (HS-8) | DI | D | DI | I | D | D | D | DI | D | DI | I | D | DI |
| September Wonder Fuji (HS-9) | D | D | D | DI | D | DI | D | DI | D | DI | DI | DI | DI |
| Linqin Crab (LQ) | DI | D | DI | I | DI | D | D | I | D | I | DI | D | D |
| Lushan Sanye (LSSY) | DI | D | D | D | DI | D | D | DI | D | I | D | D | D |
| 83-2 (MDJ-1) | DI | DI | DI | DI | DI | DI | D | I | D | DI | D | DI | D |
| Tianfeng (MDJ-9) | DI | D | D | D | DI | D | D | DI | D | DI | DI | D | I |
| Oregon Spur II-red (OR-1) | DI | DI | DI | DI | D | D | D | D | D | DI | I | DI | D |
| Oregon Spur II-green (OR-2) | DI | DI | DI | D | D | D | D | D | D | DI | I | DI | D |
| E3N2 (OR-3) | DI | DI | DI | DI | D | D | D | D | D | DI | I | DI | DI |

-continued

Construction results of InDel marker genotype database of *Malus* germplasm resources

| | | | | | | | | | | | | | |
|---|---|---|---|---|---|---|---|---|---|---|---|---|---|
| E4N1 (OR-4) | DI | DI | DI | DI | D | D | D | D | D | DI | I | DI | DI |
| E4N2 (OR-5) | DI | DI | DI | DI | D | D | D | D | D | DI | I | DI | DI |
| W6N1 (OR-6) | DI | DI | DI | DI | D | D | D | D | D | DI | I | DI | D |
| W6S5 (OR-7) | DI | DI | DI | DI | D | D | D | D | D | DI | I | DI | DI |
| W8S3 (OR-8) | DI | DI | DI | DI | D | D | D | D | D | DI | I | DI | DI |
| Daihong (QD-1) | D | DI | D | D | DI | D | DI | DI | DI | DI | DI | D | D |
| Tangmutian (QD-10) | DI | D | D | DI | D | DI | D | DI | D | DI | DI | DI | DI |
| Shanjin Crab N1 (QD-11) | I | D | D | D | DI | D | D | D | I | D | D | D | D |
| Shanjin Crab N2 (QD-12) | I | D | D | D | DI | DI | DI | D | D | I | D | D | D |
| E zhen 1 (QD-13) | D | D | D | I | DI | D | D | DI | D | DI | DI | DI | D |
| E zhen 2 (QD-14) | DI | DI | D | DI | DI | D | D | I | D | DI | DI | DI | DI |
| E zhen 3 (QD-15) | DI | D | D | I | DI | DI | D | I | D | DI | DI | DI | D |
| E zhen 4 (QD-16) | DI | DI | D | DI | DI | DI | D | DI | D | DI | I | DI | DI |
| E zhen 5 (QD-17) | DI | DI | D | DI | DI | DI | D | DI | D | DI | I | DI | DI |
| Haihong (QD-19) | DI | DI | D | I | D | D | D | I | D | I | DI | D | D |
| Qingfu 2 (QD-2) | DI | D | D | DI | D | D | D | DI | D | DI | DI | DI | DI |
| Telamon (QD-20) | DI | DI | I | D | DI | DI | D | DI | DI | DI | DI | DI | DI |
| Fuyan (QD-21) | DI | I | DI | DI | DI | D | D | D | D | DI | DI | D | D |
| Hongxun 1 (QD-22) | DI | D | D | I | DI | D | D | I | D | I | I | D | D |
| Rushan Fuji (QD-23) | DI | D | D | DI | D | DI | D | DI | D | DI | DI | DI | DI |
| Jiudian Spur (QD-24) | DI | D | D | DI | D | DI | D | DI | D | DI | DI | DI | DI |
| Ruihong (QD-25) | D | DI | I | I | D | DI | D | I | DI | DI | D | DI | D |
| Zhongnvshi (QD-26) | DI | DI | D | D | DI | D | D | I | D | I | DI | DI | D |
| 2001 Spur (QD-27) | DI | D | D | DI | D | DI | D | DI | D | DI | DI | DI | DI |
| Fuli (QD-28) | DI | DI | D | DI | D | D | D | DI | DI | DI | DI | DI | DI |
| Tuanwang semi-Spur (QD-29) | DI | D | D | DI | D | DI | D | DI | D | DI | DI | DI | DI |
| Qingfu 3 (QD-3) | DI | D | D | DI | D | DI | D | DI | D | DI | DI | DI | DI |
| Longfu (QD-30) | DI | D | D | DI | D | DI | D | DI | D | DI | DI | DI | DI |
| Baotou Linqin (QD-31) | DI | DI | D | D | DI | D | DI | D | D | I | D | D | D |
| Yanfu 6 (QD-32) | DI | D | D | DI | D | DI | D | I | D | DI | DI | DI | DI |
| SH40-2 seedling (QD-4) | I | D | D | D | DI | D | D | I | D | DI | D | D | D |
| Saijin (QD-5) | DI | DI | I | DI | DI | DI | D | DI | I | DI | DI | DI | DI |
| Nagafu 12 (QD-6) | DI | D | D | DI | D | DI | D | DI | D | DI | DI | DI | DI |
| Caoyuan Crab (QD-7) | I | D | D | D | D | D | D | DI | D | I | D | D | D |
| Xiaojin Crab (QD-8) | I | DI | DI | D | DI | DI | D | D | D | DI | DI | DI | D |
| Shuangyanghong (QD-9) | D | DI | I | I | D | DI | D | I | DI | DI | D | DI | D |
| Qianxian Crab (QX-1) | DI | D | D | D | DI | DI | I | D | D | DI | DI | D | I |
| Ruixue (ruixue) | DI | DI | DI | DI | DI | DI | D | DI | D | DI | DI | DI | I |

-continued

| Construction results of InDel marker genotype database of *Malus* germplasm resources |||||||||||||
|---|---|---|---|---|---|---|---|---|---|---|---|---|
| Ruiyang (RY) | D | DI | DI | D | DI | DI | DI | D | D | DI | I | I | I |
| Yanyuan 1 (SC-1) | DI | DI | DI | DI | DI | DI | DI | DI | DI | DI | DI | I | DI |
| Yanyuan 2 (SC-2) | I | DI | DI | I | D | DI | DI | DI | D | DI | I | DI | DI |
| Yanyuan 3 (SC-3) | DI | D | D | DI | D | DI | D | DI | D | DI | DI | DI | DI |
| Yanyuan 4 (SC-4) | I | DI | DI | I | D | DI | DI | DI | D | DI | I | DI | DI |
| Yanyuan 5 (SC-5) | DI | DI | D | DI | DI | DI | DI | D | D | DI | I | D | DI |
| Yanyuan 6 (SC-6) | DI | D | DI | DI | DI | DI | DI | D | DI | DI | I | D | DI |
| Yanyuan 7 (SC-7) | DI | DI | I | DI | DI | DI | DI | DI | DI | DI | DI | DI | DI |
| Mitchgala (SX-10) | D | DI | I | I | D | DI | D | I | DI | DI | D | DI | D |
| Zhongqiuwang Linyi (SX-11) | DI | DI | DI | DI | DI | DI | DI | D | D | DI | I | I | DI |
| Linyi Meiguo 5 (SX-12) | DI | DI | DI | DI | D | D | DI | D | D | DI | I | I | D |
| Liquan Spur Fuji (SX-13) | DI | D | D | D | DI | D | DI | D | D | DI | DI | DI | DI |
| Qiulimu (SX-14) | D | D | DI | DI | D | DI | D | DI | DI | I | DI | D | D |
| Qincui (SX-15) | DI | D | D | D | DI | DI | D | I | D | DI | DI | D | D |
| Taigu Shaguo Late (SX-17) | DI | D | DI | I | DI | DI | D | I | D | I | DI | D | DI |
| Lingyige Hongrou (SX-18) | DI | D | I | DI | D | DI | D | I | I | DI | DI | D | D |
| Shenai LS (SX-19) | D | D | D | DI | DI | DI | I | DI | D | I | I | DI | DI |
| Linyi Meiguo 8 (SX-2) | DI | DI | I | DI | D | D | DI | I | D | DI | I | DI | I |
| Liga (SX-20) | D | DI | I | I | D | DI | D | I | DI | DI | D | DI | D |
| Y-1 (SX-21) | I | D | D | DI | DI | DI | D | DI | D | I | D | D | DI |
| B009 (SX-22) | DI | D | D | I | DI | D | D | D | D | I | D | D | D |
| Jinfu 1 (SX-23) | DI | D | D | DI | D | DI | D | D | DI | DI | DI | DI | DI |
| Hongmantang (SX-24) | D | D | D | DI | DI | D | D | D | DI | DI | D | D | D |
| Y-2 (SX-25) | I | D | D | DI | DI | D | D | DI | D | I | D | D | DI |
| Y-3 (SX-26) | I | D | D | DI | DI | D | D | DI | D | I | D | D | DI |
| Xinliangxiang (SX-27) | DI | D | D | DI | D | DI | D | DI | D | DI | DI | DI | DI |
| Ennike Gala (SX-28) | D | DI | I | I | D | DI | D | I | DI | DI | D | DI | D |
| Linyi Meiguo 6 (SX-3) | DI | DI | I | DI | DI | DI | DI | DI | D | DI | DI | DI | D |
| Linyi Meiguo 2 (SX-30) | DI | D | D | DI | D | DI | D | I | D | DI | DI | DI | DI |
| Donglimu (SX-33) | D | D | DI | DI | D | DI | D | DI | DI | I | DI | D | D |
| Linyi Meiguo 1 (SX-34) | DI | DI | I | DI | D | D | DI | I | D | DI | I | DI | I |
| Linyi Meiguo 4 (SX-4) | DI | DI | D | DI | DI | I | DI | DI | D | DI | DI | DI | D |
| Qinyang (SX-6) | D | DI | I | DI | D | DI | D | DI | D | DI | DI | DI | D |
| Taiguo Shaguo Early (SX-7) | DI | DI | DI | I | DI | DI | D | I | D | I | DI | D | DI |
| Yuhua Zaofu (SX-8) | DI | D | D | DI | D | DI | D | DI | D | DI | DI | DI | DI |
| 78-M18 (SY-1) | DI | DI | D | D | DI | D | D | I | DI | DI | DI | DI | DI |
| Jinping (SY-10) | D | D | DI | I | D | D | D | DI | DI | DI | D | D | D |
| Longqiu (SY-11) | DI | DI | D | D | DI | D | D | I | DI | DI | I | D | DI |

-continued

| Construction results of InDel marker genotype database of *Malus* germplasm resources | | | | | | | | | | | | | |
|---|---|---|---|---|---|---|---|---|---|---|---|---|---|
| Longfeng (SY-12) | I | DI | DI | DI | D | D | DI | D | D | DI | D | DI | D |
| Xiangjiaoguo (SY-14) | I | DI | I | I | D | I | DI | D | DI | DI | DI | DI | D |
| Longguan (SY-15) | D | DI | DI | D | DI | DI | D | DI | D | DI | I | DI | DI |
| Longshuai (SY-16) | DI | D | DI | DI | D | D | D | I | D | DI | D | DI | D |
| Zixiang (SY-17) | D | D | D | D | D | D | D | D | I | DI | DI | DI | DI |
| Huahong (SY-19) | DI | DI | DI | I | DI | DI | D | I | D | I | DI | D | DI |
| Binlang (SY-2) | I | DI | I | I | D | I | DI | D | DI | DI | DI | DI | D |
| Qiufengmi (SY-20) | DI | I | D | I | D | DI | D | I | D | DI | I | D | DI |
| Honglingdang (SY-21) | D | D | D | D | D | D | D | DI | D | DI | I | D | D |
| Qiulu (SY-22) | I | DI | D | I | D | D | D | D | D | DI | DI | D | DI |
| Longhong (SY-23) | D | I | DI | D | DI | DI | D | DI | D | DI | I | DI | DI |
| Milk (SY-3) | I | D | D | DI | D | D | D | DI | D | DI | DI | DI | D |
| Hanfu (SY-4) | DI | D | D | D | DI | DI | DI | DI | D | DI | DI | D | DI |
| Toko (SY-5) | DI | D | D | D | DI | DI | D | DI | D | DI | DI | D | D |
| Jinhong (SY-6) | DI | DI | DI | DI | DI | DI | DI | DI | DI | DI | D | DI | D |
| K9 (SY-7) | D | D | D | D | D | D | D | DI | D | DI | I | D | D |
| 03-06-04 (SY-8) | D | D | D | D | D | DI | D | I | D | DI | DI | D | I |
| Olga (SY-9) | I | DI | D | D | DI | D | D | D | D | I | D | D | I |
| Gala 4x (TA-1) | D | DI | I | I | D | DI | D | I | DI | DI | D | DI | D |
| Juda Fuji (TA-11) | DI | D | D | DI | D | D | D | DI | D | DI | DI | DI | DI |
| Luli (TA-12) | D | D | DI | I | D | DI | D | DI | DI | D | DI | D |
| Luping 1 (TA-13) | DI | DI | DI | DI | DI | DI | D | I | D | DI | D | D | D |
| Luping 2 (TA-14) | DI | DI | DI | DI | DI | DI | DI | DI | D | DI | DI | D | D |
| Luping 5 (TA-15) | D | DI | I | DI | D | I | D | I | DI | DI | DI | DI | DI |
| Luyan (TA-16) | D | DI | DI | I | D | D | D | DI | D | DI | D | D | D |
| Meinong (TA-17) | D | D | I | D | D | I | D | I | D | DI | DI | D | I |
| Akifu 19 (TA-18) | DI | D | D | DI | D | DI | D | DI | D | DI | DI | DI | DI |
| Akifu 39 (TA-19) | DI | D | D | D | D | DI | D | DI | D | DI | DI | DI | DI |
| Hanfu 4x (TA-2) | DI | DI | I | D | DI | DI | DI | DI | DI | D | DI | D |
| Qiufuhong (TA-20) | DI | D | D | DI | D | DI | D | DI | D | DI | DI | DI | DI |
| Qunfu 1 (TA-21) | DI | D | D | DI | D | DI | D | DI | D | DI | DI | DI | DI |
| Shengfang (TA-22) | DI | D | D | DI | D | D | D | DI | D | DI | DI | DI | DI |
| Alps Otome (TA-27) | DI | D | D | D | DI | D | D | I | DI | DI | D | D |
| Early Fuji (TA-28) | DI | D | D | DI | D | D | D | DI | D | DI | DI | DI | DI |
| BP (TA-3) | D | D | D | DI | D | DI | D | D | D | DI | DI | DI | DI |
| Yishuihong (TA-32) | DI | D | D | DI | D | D | D | DI | D | DI | DI | DI | DI |
| BP-176 (TA-4) | D | D | D | I | DI | DI | D | DI | D | DI | DI | DI | DI |
| G41 (TA-5) | DI | D | DI | D | DI | I | D | I | D | DI | D | D | I |

| Construction results of InDel marker genotype database of *Malus* germplasm resources | | | | | | | | | | | | | |
|---|---|---|---|---|---|---|---|---|---|---|---|---|---|
| G935 (TA-6) | DI | D | D | D | DI | I | D | I | D | DI | I | D | DI |
| P60 (TA-7) | DI | DI | D | DI | D | DI | D | D | D | DI | DI | DI | DI |
| Fuji (TA-9) | DI | D | D | DI | D | DI | D | DI | D | DI | DI | DI | DI |
| Tianfu 1 (TS-1) | DI | D | D | DI | D | DI | D | DI | D | DI | DI | DI | DI |
| &28 (TS-13) | DI | D | D | DI | D | DI | D | I | D | DI | DI | DI | DI |
| Red Chief (TS-14) | DI | DI | DI | DI | D | D | D | D | D | DI | I | DI | DI |
| New Redchief (TS-2) | DI | DI | DI | DI | D | D | D | D | D | DI | I | DI | DI |
| Chaohongxing (TS-3) | DI | DI | DI | DI | D | D | D | D | D | DI | I | DI | DI |
| Aozhou 1 (TS-5) | I | DI | DI | D | DI | DI | D | I | D | I | I | DI | I |
| Tianfu 2 (TS-6) | DI | D | D | DI | D | DI | D | DI | D | DI | DI | DI | DI |
| Judeline (TS-7) | DI | I | I | I | D | DI | D | I | DI | DI | DI | DI | DI |
| Judestar (TS-8) | DI | DI | I | DI | D | DI | DI | D | D | DI | DI | DI | D |
| Judaine (TS-9) | DI | DI | I | I | D | DI | D | I | DI | DI | DI | DI | DI |
| WH-5 (WH-1) | DI | D | D | DI | D | DI | D | DI | D | DI | DI | DI | DI |
| Italy Smothe (WH-10) | DI | DI | I | DI | DI | I | DI | DI | DI | DI | DI | I | DI |
| Bai Crab (WH-2) | D | DI | DI | I | D | DI | D | D | D | I | DI | D | D |
| Hongguang (WH-4) | D | D | D | D | D | I | DI | DI | D | DI | DI | DI | DI |
| Huangcui (WH-5) | DI | DI | I | DI | D | I | D | I | DI | DI | DI | DI | I |
| Qinglin (WH-6) | I | DI | I | DI | D | DI | DI | I | DI | DI | DI | DI | DI |
| Harlikar (WH-8) | DI | DI | I | DI | D | DI | D | DI | DI | DI | I | I | DI |
| Italy Gala (WH-9) | D | DI | I | I | D | DI | D | I | DI | DI | D | DI | D |
| Wushan Bianye (WSBY) | I | D | D | D | DI | D | D | D | D | I | D | D | D |
| Xin 1 (XC-1) | D | D | I | I | D | I | D | I | I | DI | D | D | D |
| Xin 5 (XC-2) | D | DI | I | I | D | I | D | I | I | DI | D | I | D |
| Hanfu 3x (XC-3) | I | DI | D | D | D | D | I | D | D | DI | I | D | I |
| Gala 4x (XC-4) | D | DI | I | I | D | DI | D | I | DI | DI | D | DI | D |
| Weizhimuben (XC-5) | DI | DI | DI | DI | DI | D | D | I | D | DI | DI | D | DI |
| Chaguo (XC-CG) | DI | D | D | I | DI | D | D | I | D | I | DI | D | D |
| Donghongguo (XC-DHG) | DI | D | DI | D | DI | D | D | I | D | DI | I | D | DI |
| Fuxian Sanye (XC-FXXY) | I | D | D | D | DI | D | D | DI | D | I | D | D | D |
| Hongsanye (XC-HSY) | I | D | D | D | DI | D | D | DI | D | I | D | D | D |
| Jilin Xiaohong Crab (XC-JILINXIAOHONG-HAITANG) | I | DI | D | D | DI | DI | D | I | D | I | D | D | DI |
| Jilin Xiaohuang Crab (XC-JILINXIAOHUANG-HAITANG) | DI | DI | D | D | DI | D | D | I | D | DI | D | D | DI |
| Jilin Huang Crab (XC-JLHHT) | DI | DI | D | D | D | D | D | I | D | DI | D | D | DI |
| Shajin Crab (XC-JSHT) | I | D | D | D | DI | DI | D | DI | D | I | D | D | D |
| Longdong Crab (XC-LDHT) | I | D | D | D | D | D | D | D | D | I | D | D | D |
| Lushi Crab (XC-LSHT) | I | D | D | D | DI | D | D | DI | D | I | D | D | D |

| Construction results of InDel marker genotype database of *Malus* germplasm resources |
|---|

| | | | | | | | | | | | | |
|---|---|---|---|---|---|---|---|---|---|---|---|---|
| Laiwunanyan (XC-LWNY) | DI | D | D | I | DI | D | D | I | D | I | DI | D | D |
| Linzhi (XC-LZ) | I | D | D | D | DI | D | D | D | D | I | D | D | D |
| Mao Shandingzi (XC-MSDZ) | DI | D | D | D | DI | D | D | DI | D | I | DI | D | D |
| Pingyitiancha (XC-PYTC) | I | D | D | D | DI | D | D | DI | D | I | D | D | D |
| Qiuzi (XC-QZ) | DI | DI | D | D | D | D | D | D | D | I | I | D | D |
| Sichuan Bianye (XC-SCBY) | I | D | D | D | DI | D | D | D | D | I | D | D | D |
| Shandingzi (XC-SDZ) | I | D | D | DI | DI | D | D | D | D | I | D | D | DI |
| Weixi Sanye (XC-WXSY) | DI | DI | I | D | DI | D | D | D | D | DI | DI | DI | I |
| Xifu Crb (XC-XFHT) | DI | DI | D | D | DI | D | DI | I | D | I | D | D | DI |
| Xiaojin Bianye (XC-XJBY) | I | D | D | D | DI | D | D | DI | D | I | D | D | DI |
| Xinjiang Yepingguo (XC-XJYHT) | DI | DI | D | D | D | DI | D | I | D | DI | DI | D | I |
| Yajiang Bianye (XC-YJBY) | I | D | D | D | DI | D | D | D | D | I | D | D | D |
| Yingye Crab (XC-YYHT) | I | D | D | D | DI | D | D | DI | D | I | D | D | D |
| Zhaai (XC-ZA) | I | D | D | D | DI | D | D | DI | D | I | D | D | DI |
| Zumi Crab (XC-ZMHT) | DI | D | D | D | DI | D | D | I | D | DI | D | DI | D |
| Pink Lady (XN-FHNS) | DI | DI | I | DI | DI | I | DI | DI | DI | DI | I | I | I |
| Hongrou 1 (XN-HR1) | D | DI | D | DI | D | D | D | DI | D | DI | DI | D | DI |
| Hongrou 2 (XN-HR2) | D | DI | D | I | D | D | D | DI | DI | DI | DI | D | D |
| Hongrou 3 (XN-HR3) | D | D | D | DI | D | D | D | DI | DI | I | I | D | I |
| Hongrou 4 (XN-HR4) | D | D | DI | DI | D | DI | D | I | D | I | I | D | D |
| Hongrou 5 (XN-HR5) | D | DI | DI | I | D | DI | D | DI | D | DI | DI | DI | DI |
| Hongrou 6 (XN-HR6) | DI | DI | D | I | D | DI | D | DI | D | DI | I | D | D |
| Hongrou 7 (XN-HR7) | I | DI | I | DI | D | D | D | DI | D | I | D | D | DI |
| Ambrosia (XN-MW) | D | DI | DI | DI | D | DI | D | DI | DI | DI | I | DI | DI |
| Xinjiang 10 (XN-XJ10) | D | DI | D | I | D | I | D | I | DI | I | I | D | I |
| Xinjiang 11 (XN-XJ11) | D | DI | D | DI | D | DI | D | I | D | I | I | D | DI |
| Xinjiang 12 (XN-XJ12) | D | DI | D | I | D | I | D | I | DI | I | I | D | I |
| Xinjiang 13 (XN-XJ13) | DI | D | D | D | DI | D | D | D | D | I | I | DI | D |
| Xinjiang 14 (XN-XJ14) | D | D | D | DI | D | DI | D | DI | D | I | DI | D | DI |
| Xinjiang 15 (XN-XJ15) | D | DI | D | D | DI | D | D | D | D | I | I | D | I |
| Xinjiang 16 (XN-XJ16) | D | D | DI | DI | D | DI | D | DI | DI | I | DI | D | D |
| Xinjiang 17 (XN-XJ17) | D | D | D | DI | D | D | D | I | D | DI | I | D | DI |
| Xinjiang 18 (XN-XJ18) | D | D | D | DI | DI | D | D | D | I | D | DI | DI | D | DI |
| Xinjiang 19 (XN-XJ19) | D | D | D | DI | D | DI | D | DI | DI | I | I | D | D |
| Xinjiang 2 (XN-XJ2) | D | DI | D | I | D | I | D | DI | I | I | I | D | DI |
| Xinjiang 20 (XN-XJ20) | I | DI | DI | D | D | DI | D | DI | DI | DI | DI | D | DI |
| Xinjiang 21 (XN-XJ21) | D | DI | DI | DI | D | D | D | I | D | I | I | D | D |
| Xinjiang 23 (XN-XJ23) | D | DI | D | DI | D | DI | D | DI | DI | DI | I | D | DI |

| Construction results of InDel marker genotype database of *Malus* germplasm resources | | | | | | | | | | | | |
|---|---|---|---|---|---|---|---|---|---|---|---|---|
| Xinjiang 24 (XN-XJ24) | D | DI | DI | D | D | I | DI | DI | D | DI | DI | D | DI |
| Xinjiang 25 (XN-XJ25) | D | DI | D | I | D | I | D | I | D | I | DI | D | DI |
| Xinjiang 27 (XN-XJ27) | D | DI | D | D | DI | D | D | D | D | I | I | D | I |
| Xinjiang 3 (XN-XJ3) | D | D | D | DI | D | DI | D | DI | DI | I | I | D | D |
| Xinjiang 4 (XN-XJ4) | D | DI | DI | D | D | D | D | DI | DI | I | DI | D | D |
| Xinjiang 5 (XN-XJ5) | D | DI | D | D | D | D | D | D | I | I | D | D | D |
| Xinjiang 7 (XN-XJ7) | DI | DI | D | DI | DI | D | D | DI | DI | DI | I | D | DI |
| Xinjiang 8 (XN-XJ8) | D | DI | D | D | D | DI | D | I | D | I | DI | D | D |
| Xinjiang 9 (XN-XJ9) | D | DI | DI | DI | D | DI | D | DI | DI | DI | DI | D | DI |
| Yueguan (XY-10) | D | DI | DI | DI | D | DI | D | I | D | DI | I | DI | I |
| Yuehua (XY-11) | DI | DI | D | D | DI | D | D | I | DI | DI | I | D | DI |
| Yueyan (XY-12) | D | DI | DI | DI | D | D | DI | DI | DI | DI | DI | D | D |
| Bud Sport 5 (XY-13) | DI | D | D | DI | D | DI | D | DI | D | DI | DI | DI | DI |
| Bud Sport 3 (XY-14) | DI | D | D | DI | D | DI | D | DI | D | DI | DI | DI | DI |
| Longfu (XY-15) | DI | D | D | DI | D | DI | D | DI | D | DI | DI | DI | DI |
| Yuemei (XY-18) | D | DI | DI | I | D | DI | D | D | DI | DI | D | DI | D |
| Hanfu (XY-2) | DI | D | D | D | DI | DI | DI | DI | D | DI | DI | D | DI |
| Linyi Fuji (XY-20) | DI | DI | D | DI | D | DI | D | DI | D | DI | DI | D | DI |
| Yishui Fuji (XY-22) | DI | D | D | DI | D | DI | D | DI | D | DI | DI | DI | DI |
| Hongjinfu (XY-25) | DI | D | D | DI | D | DI | D | DI | D | DI | DI | DI | DI |
| Beni Oshu (XY-26) | DI | D | D | DI | D | DI | D | DI | D | DI | DI | DI | DI |
| Chuizhi Fuji (XY-27) | D | D | D | DI | D | DI | D | DI | D | DI | DI | DI | DI |
| Yueshuai (XY-28) | I | DI | DI | I | D | DI | DI | DI | D | DI | I | DI | DI |
| Shichinohe 2 (XY-29) | DI | D | D | DI | D | DI | D | DI | D | DI | DI | DI | DI |
| 74-178 (XY-3) | I | DI | DI | D | DI | DI | DI | DI | D | DI | DI | DI | DI |
| KAKUFUJI (XY-30) | DI | D | D | DI | D | DI | D | DI | D | DI | DI | DI | DI |
| Royal Fuji 21 (XY-35) | DI | D | D | DI | D | DI | D | DI | D | DI | DI | DI | DI |
| Qiquan Spur (XY-36) | DI | D | D | DI | D | DI | D | DI | D | DI | DI | DI | DI |
| Juda Fuji (XY-37) | D | D | D | D | D | I | DI | DI | D | DI | DI | DI | DI |
| 7-211 (XY-4) | D | DI | DI | I | D | DI | D | D | D | DI | I | DI | I |
| Yanfu 0 (XY-41) | DI | D | D | DI | D | DI | D | DI | D | DI | DI | DI | DI |
| Spur Fuji (XY-42) | DI | D | D | DI | D | DI | D | DI | D | DI | DI | DI | DI |
| Bayue fushiwang (XY-43) | DI | D | D | DI | D | DI | D | DI | D | DI | DI | DI | DI |
| Huangfu 7 (XY-44) | DI | D | D | DI | D | DI | D | DI | D | DI | DI | DI | DI |
| Aomori Spur Fuji (XY-46) | DI | D | D | DI | D | DI | D | DI | D | DI | DI | DI | DI |
| Qiu Fuji (XY-47) | DI | D | D | DI | D | DI | D | DI | D | DI | DI | DI | DI |
| Fuji Champion (XY-48) | DI | D | D | DI | D | DI | D | DI | D | DI | DI | DI | DI |
| 26-34 (XY-5) | D | DI | DI | D | D | D | DI | D | D | DI | DI | D | D |
| Akifu 19 (XY-50) | DI | D | D | DI | D | DI | D | DI | D | DI | DI | DI | DI |

| Construction results of InDel marker genotype database of *Malus* germplasm resources | | | | | | | | | | | | | |
|---|---|---|---|---|---|---|---|---|---|---|---|---|---|
| Fuji (XY-54) | DI | D | D | DI | D | DI | D | DI | D | DI | DI | DI | DI |
| Qinfu 1 (XY-55) | DI | D | D | DI | D | D | D | DI | D | DI | DI | DI | DI |
| Feng Fuji (XY-56) | DI | D | D | DI | D | DI | D | DI | D | DI | DI | DI | DI |
| Tianxing (XY-57) | DI | D | D | DI | D | DI | D | DI | D | DI | DI | DI | DI |
| Taiyang Fuji (XY-58) | DI | D | D | DI | D | DI | D | DI | D | DI | DI | DI | DI |
| Cherry Crab (XY-6) | DI | DI | D | I | D | DI | D | I | D | I | DI | D | I |
| Yueping (XY-60) | I | D | D | DI | DI | I | DI | D | D | DI | DI | DI | DI |
| 23-63 (XY-61) | D | D | D | I | D | DI | D | DI | D | DI | D | D | DI |
| 23-42 (XY-62) | D | D | D | I | D | D | D | DI | D | DI | DI | D | DI |
| 7-171 (XY-63) | D | DI | DI | DI | D | DI | D | D | DI | DI | DI | DI | D |
| Shengfang 3A (XY-65) | DI | D | D | DI | D | DI | D | DI | D | DI | DI | DI | DI |
| Meinong Fuji (XY-67) | DI | D | D | DI | D | DI | D | DI | D | DI | DI | DI | DI |
| 62-45 (XY-68) | I | D | DI | DI | D | D | DI | D | D | DI | DI | DI | DI |
| Fengfeng Fuji (XY-70) | DI | D | D | DI | D | DI | D | DI | D | DI | DI | DI | DI |
| GM256 (XY-71) | DI | D | D | DI | D | DI | D | DI | D | DI | DI | DI | DI |
| Jinfu 2 (XY-73) | DI | D | D | DI | D | DI | D | DI | D | DI | DI | DI | DI |
| Qiufu (XY-75) | DI | D | D | DI | D | DI | D | I | D | DI | DI | DI | DI |
| Shanfu 6 (XY-76) | DI | D | D | DI | D | DI | D | DI | D | DI | DI | DI | DI |
| Nagafu 8 (XY-77) | DI | D | D | DI | D | DI | D | DI | D | DI | DI | DI | DI |
| 58-34 (XY-78) | DI | DI | DI | DI | DI | DI | I | D | D | DI | DI | DI | DI |
| 2001 Fuji (XY-79) | DI | D | D | DI | D | DI | D | DI | D | DI | DI | DI | DI |
| 15-26 (XY-8) | D | DI | I | D | DI | DI | D | I | DI | DI | DI | DI | D |
| Wangshanhong (XY-80) | DI | D | D | DI | D | DI | D | DI | D | DI | DI | DI | DI |
| Jinfu 1 (XY-81) | DI | D | D | DI | D | DI | D | DI | D | DI | D | D | DI |
| Qingfu 1 (XY-84) | DI | D | D | DI | D | DI | D | DI | D | DI | DI | DI | DI |
| Qiufu 39 (XY-85) | DI | D | D | DI | D | DI | D | DI | D | DI | DI | DI | DI |
| Nagafu 1 (XY-86) | DI | D | D | DI | D | DI | D | DI | D | DI | DI | DI | DI |
| Shou Fuji (XY-87) | DI | D | D | DI | D | DI | D | DI | D | DI | DI | DI | DI |
| Yueli (XY-88) | D | DI | DI | DI | D | DI | D | DI | DI | DI | I | DI | I |
| Shanfu 2 (XY-89) | DI | D | D | DI | D | DI | D | DI | D | DI | DI | DI | DI |
| Chongban Crab (XY-9) | I | D | D | D | DI | D | D | I | D | I | I | D | D |
| Harica (XY-90) | I | DI | I | DI | D | DI | DI | I | DI | DI | DI | DI | DI |
| Akifu 1 (XY-91) | DI | D | D | DI | D | DI | D | DI | D | DI | DI | DI | DI |
| Wangfu (XY-92) | DI | D | D | DI | D | DI | D | DI | D | DI | DI | DI | DI |
| Hong Manao (XYZ-1) | DI | D | D | D | DI | DI | I | D | D | DI | I | D | I |
| Modi (XYZ-10) | D | DI | I | I | D | DI | D | I | DI | DI | DI | D | DI |
| C37 (XYZ-11) | I | DI | I | D | DI | DI | D | I | DI | DI | D | D | D |
| Envy ? (XYZ-12) | D | DI | I | DI | D | DI | DI | DI | DI | DI | DI | DI | DI |

-continued

| Construction results of InDel marker genotype database of *Malus* germplasm resources | | | | | | | | | | | | | |
|---|---|---|---|---|---|---|---|---|---|---|---|---|---|
| Xichang Yuanzhuiguo (XYZ-2) | DI | D | DI | DI | D | D | D | I | D | DI | DI | D | DI |
| Ziye Zixiaoguo (XYZ-3) | I | D | D | D | D | D | D | I | D | I | D | D | DI |
| Ziye Zidaguo (XYZ-4) | DI | D | I | D | DI | D | D | I | D | DI | D | D | DI |
| Shoufenshu 6 (XYZ-5) | DI | D | DI | D | D | I | D | I | D | DI | D | D | D |
| Changhua (XYZ-6) | D | DI | I | I | D | DI | D | I | DI | DI | D | DI | D |
| Jinshiji (XYZ-7) | D | DI | I | I | D | DI | D | I | DI | DI | D | DI | DI |
| 19-147 (XYZ-9) | D | DI | DI | DI | DI | DI | DI | I | D | DI | D | D | DI |
| Malong Gala 1 (YN-1) | D | DI | I | I | D | DI | D | I | DI | DI | D | DI | D |
| Shouer hong (YN-11) | DI | D | D | DI | D | DI | D | DI | D | DI | DI | DI | DI |
| Yun Hongrou (YN-12) | DI | D | D | I | D | D | D | D | DI | DI | D | D | DI |
| Lixing Crab (YN-13) | DI | DI | DI | I | D | DI | D | I | D | I | DI | D | DI |
| Siana (YN-15) | DI | DI | D | D | DI | D | D | D | DI | I | D | DI |
| Jonathan-M41 (YN-17) | DI | D | D | DI | DI | D | DI | DI | D | DI | I | D | DI |
| Morlie's Delicious (YN-18) | D | DI | I | DI | D | I | D | DI | DI | DI | DI | DI | DI |
| Britegold (YN-19) | DI | D | D | DI | D | DI | D | DI | D | DI | DI | DI | DI |
| Malong Gala 1 blush (YN-2) | D | DI | I | I | D | DI | D | I | DI | DI | D | DI | D |
| Line 5 (YN-22) | DI | DI | D | D | DI | DI | D | D | D | DI | I | D | DI |
| Line 6 (YN-23) | D | D | DI | DI | DI | DI | I | D | D | DI | DI | DI | DI |
| Line 13 (YN-24) | I | DI | I | D | D | DI | D | DI | DI | D | D | DI | D |
| row 3 (YN-25) | D | D | DI | I | D | DI | D | DI | DI | DI | D | DI | D |
| row 4 (YN-26) | D | D | DI | I | D | DI | D | DI | DI | DI | D | DI | D |
| row 5 (YN-27) | D | D | DI | I | D | DI | D | DI | DI | DI | D | DI | D |
| row 6 (YN-28) | D | D | DI | I | D | DI | D | DI | DI | DI | D | DI | D |
| row 9 (YN-29) | D | DI | I | DI | D | I | DI | DI | DI | DI | D | DI | D |
| Malong xin Gala 1 (YN-3) | D | DI | I | I | D | DI | D | I | DI | DI | D | DI | D |
| row 10 (YN-30) | DI | DI | I | DI | DI | I | DI | DI | DI | DI | I | I | DI |
| row 11 (YN-31) | D | DI | I | DI | I | DI | D | I | DI | DI | D | DI | D |
| row 12 (YN-32) | D | DI | I | I | D | DI | D | I | DI | DI | D | DI | D |
| row 13 (YN-33) | D | DI | DI | I | D | D | D | D | DI | D | DI | D | D |
| row 14 (YN-34) | D | D | DI | I | D | DI | D | DI | DI | DI | D | DI | D |
| row 15 (YN-35) | DI | I | DI | DI | DI | DI | D | I | D | DI | D | D | D |
| row 16 (YN-36) | DI | DI | I | DI | DI | DI | DI | DI | DI | DI | DI | DI | DI |
| row 17 (YN-37) | DI | I | D | DI | DI | DI | DI | D | D | DI | I | D | DI |
| row 18 (YN-38) | DI | D | DI | DI | DI | DI | DI | D | DI | DI | I | D | DI |
| row 19 (YN-39) | D | D | I | D | DI | D | D | DI | DI | DI | DI | D | DI |
| Malong xin Gala 1 strip (YN-4) | D | DI | I | I | D | DI | D | I | DI | DI | D | DI | D |
| row 20 (YN-40) | I | DI | DI | I | D | DI | DI | DI | D | DI | I | DI | DI |
| row 21 (YN-41) | DI | D | D | DI | D | DI | D | DI | D | DI | DI | DI | DI |
| row 22 (YN-42) | I | DI | DI | I | D | DI | DI | DI | D | DI | I | DI | DI |

-continued

Construction results of InDel marker genotype database of *Malus* germplasm resources

| | | | | | | | | | | | | | |
|---|---|---|---|---|---|---|---|---|---|---|---|---|---|
| row 23 (YN-43) | I | DI | DI | I | D | DI | DI | DI | D | DI | I | DI | DI |
| row 24 (YN-44) | DI | D | D | DI | D | DI | D | DI | D | DI | DI | DI | DI |
| row 25 (YN-45) | DI | D | D | DI | D | DI | D | DI | D | DI | DI | DI | DI |
| Malong Gala2 (YN-5) | D | DI | I | I | D | DI | D | I | DI | DI | D | DI | D |
| Malong Gala 2 blush (YN-6) | D | DI | I | I | D | DI | D | I | DI | DI | D | DI | D |
| Longwei (YN-7) | D | DI | I | DI | D | D | D | DI | D | DI | DI | D | D |
| Longwei Early Mutant (YN-8) | D | DI | I | DI | D | D | D | DI | D | DI | DI | D | D |
| Cherry Gala (YN-9) | D | DI | I | I | D | DI | D | I | DI | DI | D | DI | D |
| Siyana (YT-1) | DI | D | DI | D | D | I | D | DI | DI | DI | DI | I | DI |
| Yanfu 10 (YT-100) | DI | D | D | DI | D | DI | D | DI | D | DI | DI | DI | DI |
| Chadel (YT-102) | D | DI | I | D | DI | I | D | DI | DI | DI | D | DI | DI |
| Charden (YT-103) | DI | DI | I | DI | DI | DI | DI | DI | DI | DI | DI | I | DI |
| Tuskan (YT-104) | DI | D | I | DI | DI | DI | D | DI | D | DI | DI | D | DI |
| Prima × Sekaiichii (YT-105) | DI | D | DI | DI | D | D | D | DI | D | DI | I | DI | DI |
| Toppax_apple (YT-11) | DI | D | D | I | D | D | DI | DI | I | DI | I | D | DI |
| Xinjiang Hongrou Crab (YT-12) | DI | D | D | D | D | DI | D | D | D | DI | DI | D | D |
| Melfree (YT-13) | D | DI | DI | DI | D | I | D | I | DI | DI | I | I | I |
| Yanfu 3 (YT-14) | DI | D | D | DI | D | D | DI | DI | D | DI | DI | D | DI |
| Gold milecnirum (YT-15) | D | DI | D | D | D | DI | D | I | DI | DI | DI | DI | DI |
| Ganhong (YT-16) | DI | D | I | D | DI | D | D | D | D | DI | I | DI | D |
| Cornoet (YT-17) | D | D | I | D | DI | D | D | I | DI | I | DI | D | D |
| Priw (YT-18) | D | DI | D | DI | DI | D | D | I | D | DI | DI | DI | DI |
| Aichi (YT-19) | DI | D | DI | D | D | D | D | D | DI | DI | DI | DI | DI |
| Auraria (YT-2) | DI | DI | I | DI | D | D | DI | DI | DI | DI | I | D | D |
| Meile (YT-20) | D | D | D | DI | D | DI | D | DI | D | DI | DI | DI | DI |
| Qiulimeng (YT-21) | D | D | DI | DI | D | DI | D | DI | DI | I | DI | D | D |
| Aliusitan (YT-22) | D | DI | DI | DI | D | DI | D | DI | DI | DI | I | D | DI |
| Geaooza (YT-23) | D | DI | DI | DI | DI | D | DI | DI | DI | DI | DI | DI | D |
| Golden Spur (YT-24) | DI | DI | I | DI | DI | I | DI | DI | DI | DI | DI | I | DI |
| Starking (YT-25) | DI | DI | DI | DI | D | D | D | D | D | DI | I | DI | DI |
| Indo (YT-26) | D | DI | D | DI | DI | D | DI | I | D | DI | DI | DI | D |
| Teser (YT-27) | DI | DI | DI | DI | D | D | D | I | D | DI | DI | D | DI |
| Xianhong (YT-28) | DI | DI | DI | D | DI | DI | D | I | D | DI | I | D | D |
| Gala × Mato 8 (YT-29) | D | D | DI | I | D | D | D | DI | D | DI | D | D | D |
| Very Early Fuji (YT-3) | DI | D | D | DI | D | DI | D | D | D | DI | DI | DI | DI |
| Qiuhuapi (YT-30) | D | D | I | D | D | DI | D | DI | DI | DI | I | D | DI |
| Piga 70 (YT-31) | D | DI | I | DI | DI | D | D | I | DI | DI | DI | DI | DI |
| Yanzhen 1 (YT-32) | DI | D | I | D | DI | I | DI | I | D | DI | I | D | DI |

| Construction results of InDel marker genotype database of *Malus* germplasm resources | | | | | | | | | | | | | |
|---|---|---|---|---|---|---|---|---|---|---|---|---|---|
| Matail (YT-34) | D | DI | I | I | D | DI | D | I | DI | DI | D | DI | D |
| Jonathan-csan (YT-35) | DI | D | D | DI | DI | D | DI | DI | D | DI | I | D | DI |
| Huashuai (YT-36) | D | DI | DI | D | DI | DI | DI | D | D | DI | DI | D | DI |
| Wengao 1 (YT-38) | DI | D | D | DI | D | DI | D | DI | D | DI | DI | DI | I |
| Wengao 2 (YT-39) | DI | D | D | DI | D | DI | D | DI | D | DI | DI | DI | D |
| Elegia (YT-4) | D | DI | DI | DI | DI | D | D | DI | D | DI | DI | I | DI |
| Wengao 3 (YT-40) | DI | D | D | DI | D | DI | D | DI | D | DI | DI | DI | I |
| Hong Anka (YT-41) | I | DI | D | DI | D | DI | DI | D | D | DI | I | DI | D |
| Yanfu 2 (YT-42) | DI | D | D | DI | D | DI | D | DI | D | DI | DI | DI | D |
| Belgolden (YT-43) | DI | DI | I | DI | DI | I | DI | DI | DI | DI | DI | I | I |
| Rubinola (YT-44) | D | D | D | DI | DI | D | DI | D | D | DI | DI | D | DI |
| Wangqiuhong (YT-45) | DI | D | D | DI | D | D | D | DI | DI | DI | DI | DI | D |
| Pulanhong (YT-46) | DI | DI | I | D | D | DI | D | D | D | DI | DI | D | DI |
| Bosh (YT-47) | DI | DI | DI | DI | D | DI | D | I | D | DI | DI | D | DI |
| Chengji 1 (YT-48) | DI | D | D | DI | D | DI | D | DI | D | DI | DI | DI | DI |
| Hongli (YT-49) | D | D | DI | DI | D | D | D | D | D | DI | DI | D | D |
| Guoqinghong (YT-5) | DI | DI | I | DI | DI | DI | D | DI | DI | DI | DI | DI | DI |
| Reandra (YT-50) | DI | DI | I | DI | D | DI | DI | D | DI | DI | D | DI | DI |
| Revbihola (YT-51) | D | D | I | D | D | DI | D | DI | I | DI | I | D | DI |
| Melrose (YT-52) | D | D | D | DI | DI | D | DI | DI | D | DI | I | D | DI |
| Rewena (YT-53) | DI | D | DI | D | D | DI | D | DI | D | DI | DI | D | DI |
| Mrxl(robusta × Liberte) (YT-54) | DI | DI | DI | DI | D | D | D | D | D | DI | I | DI | DI |
| Mollies_Del_open (YT-55) | I | DI | I | DI | D | DI | DI | DI | I | DI | DI | DI | DI |
| Renora (YT-56) | DI | DI | DI | DI | DI | DI | D | I | DI | DI | I | DI | DI |
| Rosmadzin (YT-57) | DI | DI | DI | DI | D | DI | D | I | DI | DI | DI | D | DI |
| Remo (YT-58) | D | DI | I | I | D | D | D | I | I | DI | DI | D | DI |
| Pilot (YT-59) | DI | DI | D | D | D | DI | D | DI | D | I | DI | D | DI |
| Yangbai Crab (YT-6) | D | DI | DI | I | D | DI | D | D | D | I | DI | D | D |
| Free Red Star (YT-60) | DI | D | D | D | DI | DI | D | DI | D | DI | I | DI | DI |
| Idared (YT-61) | DI | D | I | D | D | DI | D | I | D | DI | DI | D | DI |
| Mingyue (YT-62) | D | DI | DI | I | D | DI | D | I | D | DI | I | DI | DI |
| Piga 101 (YT-63) | I | DI | DI | DI | DI | DI | D | I | DI | DI | DI | DI | DI |
| Yanfu 5 (YT-64) | DI | D | D | DI | D | DI | D | I | D | DI | DI | DI | DI |
| Early Jonagold (YT-65) | DI | DI | I | DI | DI | DI | DI | DI | DI | DI | DI | DI | DI |
| Wengao 2 mutant (YT-66) | DI | D | D | DI | D | DI | D | DI | D | DI | DI | DI | DI |
| Fenhong Gala 44 (YT-67) | DI | DI | I | DI | DI | I | D | I | I | DI | DI | DI | DI |
| Yiyuanhong (YT-68) | DI | D | D | DI | D | DI | D | DI | D | DI | DI | DI | DI |
| Yanfu 4 (YT-69) | DI | D | D | D | DI | DI | D | DI | D | DI | DI | DI | DI |
| White Pearmain (YT-70) | DI | DI | DI | DI | DI | D | DI | DI | D | DI | I | I | DI |

-continued

| Construction results of InDel marker genotype database of *Malus* germplasm resources |||||||||||||||
|---|---|---|---|---|---|---|---|---|---|---|---|---|---|
| Jonathan-early (YT-73) | DI | D | D | DI | DI | D | DI | DI | D | DI | I | D | DI |
| Jonathan-midle (YT-74) | DI | D | D | DI | DI | D | DI | DI | D | DI | I | D | DI |
| Gornan (YT-75) | D | D | DI | D | DI | DI | D | D | D | DI | DI | D | DI |
| Regilndel (YT-76) | D | D | I | D | D | DI | D | DI | I | DI | I | D | DI |
| Golden Bell (YT-77) | D | DI | I | DI | D | DI | D | DI | DI | DI | DI | DI | DI |
| Arkcharm (YT-78) | D | D | I | D | D | DI | D | DI | DI | DI | DI | D | DI |
| Redchif (YT-79) | DI | DI | DI | I | DI | D | D | I | D | DI | DI | DI | D |
| Mouping Guanghua Fuji (YT-8) | DI | D | D | DI | D | DI | D | DI | D | DI | DI | DI | DI |
| Freedom (YT-80) | DI | DI | D | D | D | DI | D | I | D | DI | I | D | DI |
| Martinike (YT-81) | D | DI | DI | D | D | D | D | DI | D | DI | DI | DI | DI |
| Sweetle (YT-82) | D | DI | I | DI | D | D | D | DI | D | DI | DI | D | DI |
| Aleksanader (YT-83) | D | DI | I | DI | D | D | DI | DI | I | DI | DI | DI | DI |
| Yan 6 Fenhong 143 (YT-84) | DI | DI | I | I | D | I | DI | DI | I | DI | DI | DI | DI |
| Ruitina (YT-85) | D | D | I | D | DI | DI | DI | I | D | DI | I | D | DI |
| Wengao 1 mutant (YT-86) | DI | D | D | DI | D | DI | D | DI | D | DI | DI | DI | DI |
| Wengao 3 mutant (YT-87) | DI | D | D | DI | D | DI | D | DI | D | DI | DI | DI | DI |
| Shajinyilamu (YT-88) | D | DI | D | I | D | I | D | DI | DI | I | I | D | DI |
| Qiuhong (YT-89) | I | DI | D | D | DI | D | D | D | D | DI | DI | D | DI |
| Changyanghong (YT-9) | DI | D | D | DI | D | DI | D | DI | D | DI | DI | DI | DI |
| Yanfu 8 (YT-90) | DI | D | D | DI | D | DI | D | DI | D | DI | DI | DI | DI |
| Jinduhong Gala (YT-91) | D | DI | I | I | D | DI | D | I | DI | DI | D | DI | DI |
| Nagafu 2 (YT-92) | DI | D | D | DI | D | DI | D | DI | D | DI | DI | DI | DI |
| Honglu seedling 65 (YT-93) | DI | D | DI | DI | DI | DI | D | I | D | DI | I | DI | DI |
| Tsugaru (YT-94) | I | DI | DI | I | D | DI | DI | DI | D | DI | I | DI | DI |
| Jinshuai mutant (YT-95) | DI | DI | I | D | DI | I | DI | DI | DI | DI | DI | I | DI |
| Taishan Crab (YT-96) | I | D | D | D | D | D | I | D | D | DI | DI | I | DI |
| Luli (YT-98) | D | D | DI | I | D | DI | D | DI | DI | DI | D | DI | I |
| 10-182 (YX-10-182) | D | DI | DI | D | D | DI | D | I | D | DI | DI | DI | DI |
| 01-001 (YX-01-001) | D | D | DI | DI | D | D | D | DI | D | DI | I | DI | D |
| 01-121 (YX-01-121) | DI | D | DI | DI | D | DI | D | I | D | DI | DI | DI | I |
| 02-009 (YX-02-009) | D | D | DI | DI | D | D | DI | D | DI | D | DI | DI | D |
| 03-010 (YX-03-010) | D | D | DI | DI | D | DI | D | I | D | DI | D | DI | I |
| 03-111 (YX-03-111) | DI | D | DI | DI | D | I | D | I | D | DI | I | DI | D |
| 04-033 (YX-04-033) | D | D | DI | DI | D | DI | D | DI | D | DI | DI | DI | D |
| 04-087 (YX-04-087) | D | D | DI | DI | D | D | D | I | D | DI | I | DI | D |
| 06-056 (YX-06-056) | D | D | DI | D | D | D | D | DI | D | DI | DI | DI | I |
| 08-034 (YX-08-034) | D | D | DI | D | D | DI | D | I | D | DI | DI | DI | I |
| 09-037 (YX-09-037) | D | D | DI | DI | D | DI | D | I | D | DI | D | DI | I |

| Construction results of InDel marker genotype database of *Malus* germplasm resources | | | | | | | | | | | | | |
|---|---|---|---|---|---|---|---|---|---|---|---|---|---|
| 09-079 (YX-09-079) | D | D | DI | DI | D | DI | D | DI | D | DI | I | DI | DI |
| 10-010 (YX-10-010) | D | D | DI | DI | D | D | D | DI | D | DI | DI | DI | I |
| 11-037 (YX-11-037) | D | D | DI | D | D | DI | D | DI | D | DI | D | DI | D |
| 11-206 (YX-11-206) | DI | D | DI | DI | D | DI | D | I | D | DI | DI | DI | I |
| 12-206 (YX-12-206) | D | D | DI | DI | D | D | D | DI | D | DI | DI | D | D |
| 13-025 (YX-13-025) | DI | D | DI | DI | D | DI | D | DI | D | DI | DI | D | D |
| 16-155 (YX-16-155) | DI | D | DI | D | D | D | D | DI | D | DI | I | D | DI |
| 16-157 (YX-16-157) | D | D | DI | DI | D | I | D | I | D | DI | DI | DI | I |
| 17-023 (YX-17-023) | DI | D | DI | DI | D | DI | D | DI | D | DI | I | DI | DI |
| 17-199 (YX-17-199) | D | D | DI | DI | D | I | D | I | D | DI | DI | D | I |
| 21-005 (YX-21-005) | DI | I | I | DI | DI | I | DI | I | DI | DI | DI | DI | I |
| 21-018 (YX-21-018) | D | I | I | DI | DI | I | DI | DI | DI | DI | I | DI | DI |
| 22-186 (YX-22-186) | D | DI | I | D | DI | DI | DI | DI | D | DI | DI | DI | D |
| 27-003 (YX-27-003) | D | DI | I | I | D | I | D | I | DI | DI | DI | DI | I |
| 29-176 (YX-29-176) | D | DI | I | DI | DI | DI | D | I | DI | DI | DI | DI | DI |
| 30-001 (YX-30-001) | D | DI | I | DI | DI | DI | DI | DI | D | DI | D | DI | I |
| 33-018 (YX-33-018) | D | D | DI | I | D | DI | D | DI | D | DI | D | D | I |
| 33-101 (YX-33-101) | DI | D | DI | I | D | D | D | I | D | DI | I | DI | I |
| 33-151 (YX-33-151) | D | DI | I | DI | D | I | D | I | DI | DI | DI | DI | DI |
| 51-007 (YX-51-007) | DI | DI | DI | DI | DI | DI | I | D | D | DI | I | DI | DI |
| 51-031 (YX-51-031) | I | DI | DI | DI | DI | DI | D | I | DI | DI | I | DI | DI |
| 51-077 (YX-51-077) | DI | DI | DI | I | D | DI | I | DI | DI | DI | DI | DI | DI |
| 51-102 (YX-51-102) | DI | DI | DI | I | DI | DI | DI | I | DI | DI | DI | DI | D |
| 51-139 (YX-51-139) | DI | DI | DI | D | DI | DI | D | I | D | DI | DI | DI | DI |
| 51-165 (YX-51-165) | DI | DI | DI | DI | DI | DI | D | I | DI | DI | I | DI | I |
| 51-166 (YX-51-166) | I | DI | DI | I | D | DI | D | I | DI | I | I | DI | D |
| 51-209 (YX-51-209) | I | DI | DI | D | DI | DI | DI | DI | D | DI | DI | DI | D |
| 52-049 (YX-52-049) | I | DI | DI | DI | DI | DI | DI | DI | D | DI | I | DI | I |
| 52-151 (YX-52-151) | D | DI | DI | DI | DI | DI | DI | D | DI | DI | DI | DI | D |
| 52-160 (YX-52-160) | DI | DI | DI | DI | DI | DI | DI | DI | DI | DI | I | DI | DI |
| 53-040 (YX-53-040) | DI | DI | DI | I | D | DI | D | I | DI | DI | DI | DI | D |
| 53-205 (YX-53-205) | DI | D | D | DI | DI | D | DI | D | D | DI | I | D | D |
| 54-001 (YX-54-001) | DI | DI | DI | I | D | DI | D | I | DI | DI | I | DI | I |
| 54-188 (YX-54-188) | D | DI | DI | I | D | DI | DI | DI | D | DI | I | DI | D |
| 55-006 (YX-55-006) | DI | DI | DI | DI | DI | DI | DI | D | D | DI | DI | DI | D |
| 55-023 (YX-55-023) | D | DI | DI | D | DI | DI | D | I | DI | DI | I | DI | DI |
| 55-042 (YX-55-042) | DI | DI | DI | DI | DI | DI | D | I | D | DI | I | DI | DI |
| 56-081 (YX-56-081) | D | DI | DI | D | DI | DI | DI | DI | D | DI | DI | DI | D |
| 57-128 (YX-57-128) | DI | DI | DI | D | DI | DI | D | I | D | DI | DI | DI | DI |

| Construction results of InDel marker genotype database of *Malus* germplasm resources | | | | | | | | | | | | | |
|---|---|---|---|---|---|---|---|---|---|---|---|---|---|
| 58-036 (YX-58-036) | I | DI | DI | D | DI | DI | DI | DI | DI | DI | DI | DI | D |
| 58-089 (YX-58-089) | DI | DI | DI | D | DI | DI | DI | DI | DI | DI | I | DI | DI |
| 58-144 (YX-58-144) | DI | DI | DI | I | D | DI | DI | DI | D | DI | DI | DI | D |
| 58-177 (YX-58-177) | I | DI | DI | I | D | DI | I | D | DI | DI | DI | DI | D |
| 58-211 (YX-58-211) | I | DI | DI | D | DI | DI | D | DI | D | DI | I | DI | I |
| 59-086 (YX-59-086) | I | DI | DI | DI | DI | DI | DI | DI | DI | DI | DI | DI | D |
| 59-130 (YX-59-130) | I | DI | DI | D | DI | DI | DI | DI | D | DI | DI | DI | D |
| Jersey Mac (Z-1) | D | D | I | D | D | DI | D | D | DI | DI | D | D | D |
| Gale Gala (Z-10) | D | DI | I | I | D | DI | D | I | DI | DI | D | DI | D |
| Li Gala (Z-11) | D | DI | I | I | D | DI | D | I | DI | DI | D | DI | D |
| Yanga 1 (Z-12) | D | DI | I | I | D | D | D | I | DI | DI | D | DI | D |
| NAKT M9 clone (Z-13) | DI | D | DI | D | DI | DI | DI | DI | D | DI | I | D | DI |
| Royal Gala (Z-14) | D | DI | I | I | D | DI | D | I | DI | DI | D | DI | D |
| Huajia (Z-15) | D | DI | DI | D | DI | D | D | DI | DI | DI | DI | D | D |
| Dorsett Golden (Z-16) | D | D | DI | DI | DI | DI | DI | D | D | DI | DI | I | D |
| 99-2-58 (Z-17) | D | D | DI | D | DI | D | D | D | D | DI | DI | D | DI |
| Galaxy (Z-18) | D | DI | I | I | D | DI | D | I | DI | DI | D | DI | D |
| Royal New Gala (Z-19) | D | DI | I | I | D | DI | D | I | DI | DI | D | DI | D |
| 99-1-29 (Z-22) | D | D | DI | D | DI | D | D | DI | DI | DI | DI | D | DI |
| Seokwang (Z-23) | DI | D | I | DI | D | DI | DI | DI | D | DI | DI | DI | DI |
| Fuhong Zaoga (Z-24) | D | DI | I | I | D | DI | D | I | DI | DI | D | DI | D |
| Maiyan (Z-25) | D | DI | DI | D | D | D | D | DI | D | DI | DI | D | DI |
| Shandong 1 (Z-26) | D | DI | I | I | D | DI | D | I | DI | DI | D | DI | D |
| Gala Queen (Z-27) | D | DI | I | I | D | DI | D | I | DI | DI | D | DI | D |
| 99-2-39 (Z-29) | D | D | DI | DI | D | D | D | D | D | DI | DI | D | DI |
| Sweetle (Z-3) | D | DI | I | DI | D | D | D | DI | D | DI | DI | D | D |
| Dalian Da Gala (Z-30) | D | DI | I | I | D | DI | D | I | DI | DI | D | DI | D |
| Huaxing (Z-31) | D | DI | DI | I | D | DI | D | I | D | DI | D | D | D |
| Li Gala (Z-32) | D | DI | I | I | D | DI | D | I | DI | DI | D | DI | D |
| Fuhong Zaoga (Z-33) | D | D | DI | I | D | DI | D | I | DI | DI | DI | D | DI |
| Yanga (Z-34) | D | D | DI | I | D | DI | D | I | DI | DI | DI | D | DI |
| Royal Gala (Z-35) | D | DI | I | I | D | DI | D | I | DI | DI | D | DI | D |
| Shijiazhuang Gala (Z-37) | D | DI | I | I | D | DI | D | I | DI | DI | D | DI | D |
| Taihong Gala (Z-38) | D | DI | I | I | D | DI | D | I | DI | DI | D | DI | D |
| Anna (Z-39) | D | D | D | D | DI | D | D | DI | D | DI | DI | DI | D |
| Hong Zhenzhu (Z-4) | D | D | DI | I | D | D | D | I | D | D | D | DI | D |
| Qiuhong Gala (Z-40) | DI | DI | DI | I | D | DI | DI | I | D | DI | DI | DI | DI |
| Shandong 2 (Z-41) | D | DI | I | I | D | DI | D | I | DI | DI | D | DI | D |

-continued

Construction results of InDel marker genotype database of *Malus* germplasm resources

| Accession name (Accession ID) | | | | | | | | | | | | |
|---|---|---|---|---|---|---|---|---|---|---|---|---|
| Shandong 6 (Z-42) | D | DI | I | I | D | DI | D | I | DI | DI | D | DI | D |
| Chenyang (Z-43) | D | DI | DI | I | D | DI | D | I | I | DI | I | DI | D |
| Dongqie Gala (Z-44) | D | DI | I | I | D | D | D | I | I | DI | DI | D | D |
| Royal Gala (Z-45) | D | DI | I | I | D | DI | D | I | DI | DI | D | DI | D |
| Taishan Gala (Z-47) | D | DI | I | I | D | DI | D | I | DI | DI | D | DI | D |
| Shandong 7 (Z-48) | D | DI | I | I | D | DI | D | I | DI | DI | D | DI | D |
| Regal gala (Z-49) | D | DI | I | I | D | DI | D | I | DI | DI | D | DI | D |
| NAKB clone (Z-5) | DI | D | DI | D | DI | DI | DI | DI | D | DI | I | D | DI |
| Royal gala (Z-50) | D | DI | I | I | D | DI | D | I | DI | DI | D | DI | D |
| Znoga (Z-51) | DI | DI | DI | DI | DI | D | D | DI | DI | DI | DI | D | D |
| Shandong 5 (Z-52) | D | DI | I | I | D | DI | D | I | DI | DI | D | DI | D |
| Rockit (Z-53) | D | I | I | I | D | I | D | I | I | DI | D | DI | D |
| Shandong 3 (Z-54) | D | DI | I | I | D | DI | D | I | DI | DI | D | DI | D |
| Mondel Gala (Z-55) | D | DI | I | I | D | DI | D | I | DI | DI | D | DI | D |
| Alvinagala (Z-56) | D | DI | I | I | D | DI | D | I | DI | DI | D | DI | D |
| M9 pajam2 (Z-6) | DI | D | DI | D | DI | DI | DI | DI | D | DI | I | D | DI |
| Jinshiji (Z-7) | D | DI | I | I | D | DI | D | I | DI | DI | D | DI | D |
| Huarui (Z-8) | D | DI | D | DI | DI | D | D | DI | DI | DI | I | D | D |
| Hongcuibao (Z-9) | D | DI | DI | I | D | DI | D | DI | DI | DI | D | D | D |

| Accession name (Accession ID) | C13098 | C13100 | C13101 | C13102 | C14104 | C14105 | C14108 | C15109 | C15110 | C15111 | C15114 | C15115 | C15116 |
|---|---|---|---|---|---|---|---|---|---|---|---|---|---|
| Black Ben Davis (10--1) | I | D | D | DI | DI | DI | D | D | DI | DI | DI | DI | DI |
| Lysgolden (10--10) | I | D | D | DI | D | DI | D | D | D | D | DI | D | DI |
| Dongchengguan 13 (10--11) | I | D | D | DI | D | DI | D | D | D | D | DI | D | DI |
| Nagafu 1 (10--12) | I | D | D | DI | D | DI | D | D | D | D | DI | D | DI |
| Shengli Hongguan (10--14) | DI | D | I | DI | DI | I | DI | D | DI | I | DI | DI | DI |
| Shizishan 1 (10--15) | DI | D | I | DI | DI | I | DI | D | DI | I | DI | DI | DI |
| Baoman (10--2) | I | DI | DI | DI | DI | DI | DI | D | D | D | DI | D | DI |
| Melba (10--20) | I | DI | DI | DI | D | D | D | D | D | D | DI | DI | DI |
| Kuliesa (10--21) | DI | D | DI | I | I | DI | D | DI | DI | D | DI | D | DI |
| De 8 (10--22) | I | I | I | I | D | D | D | D | D | D | DI | DI | DI |
| Bo 5 (10--23) | D | D | D | D | I | D | DI | DI | I | DI | DI | DI | DI |
| Iran Pippin (10--4) | I | DI | DI | I | I | D | DI | D | D | D | DI | D | D |
| Sakatakei Tsugaru (10--5) | DI | I | I | I | D | D | D | DI | D | D | DI | D | DI |
| Khrushchev (10--6) | DI | DI | DI | DI | DI | D | D | D | DI | I | DI | I | D |
| Batul (10--7) | I | I | I | I | I | D | D | DI | DI | DI | DI | DI | DI |
| Prime Gold (10--9) | I | I | I | I | D | D | DI | D | DI | DI | DI | DI | DI |
| Jie 1 (11--0) | DI | DI | DI | DI | D | D | DI | DI | I | DI | DI | DI | DI |
| Guldborg (1--11) | I | D | D | DI | D | DI | D | D | D | DI | D | DI |

| Construction results of InDel marker genotype database of *Malus* germplasm resources | | | | | | | | | | | | | |
|---|---|---|---|---|---|---|---|---|---|---|---|---|---|
| Shajin Yilamu (11--10) | I | I | I | I | D | D | D | D | D | D | DI | D | DI |
| Soviet (11--11) | DI | DI | DI | DI | DI | DI | D | D | D | DI | I | D | DI |
| Lobo (11--13) | I | I | I | I | D | D | D | D | D | D | D | D | DI |
| Allington Pippin (11--14) | I | DI | DI | DI | D | DI | D | D | I | I | DI | I | DI |
| Malinova (11--15) | I | I | I | I | DI | D | DI | D | DI | I | DI | DI | DI |
| Sweet McIntosh (11--16) | I | I | I | I | DI | D | DI | D | DI | I | DI | DI | DI |
| McIntosh (11--18) | DI | DI | DI | I | I | I | DI | D | D | D | DI | D | DI |
| Spartan (11--2) | I | DI | DI | I | I | D | D | D | D | D | D | D | DI |
| Fushuai (1--12) | DI | DI | I | I | I | DI | I | D | DI | DI | DI | DI | DI |
| Summer Pearmain (11--20) | I | I | I | DI | DI | I | DI | D | DI | D | D | D | DI |
| Helm (11--21) | I | DI | I | DI | D | DI | D | D | D | D | DI | DI | DI |
| Domenesti (11--3) | I | DI | I | I | DI | DI | D | D | D | D | D | D | DI |
| Early Harvest (1--13) | DI | DI | I | I | I | DI | I | D | DI | DI | DI | DI | DI |
| Silver Spur Red Delicious (11--4) | I | D | D | I | I | DI | D | DI | D | D | DI | D | DI |
| Dongxiangjiao (11--5) | DI | I | I | DI | D | DI | D | D | DI | DI | DI | DI | DI |
| Guoling (1--15) | DI | DI | DI | D | D | D | D | D | D | D | D | D | D |
| Skyline Spureme (11--8) | I | D | D | I | I | DI | D | DI | D | D | DI | D | DI |
| Chantecler (11--9) | DI | D | DI | DI | D | DI | DI | D | D | I | DI | I | DI |
| Close (1--19) | I | I | I | DI | D | D | D | D | D | DI | DI | DI | DI |
| Aizaohui (1--2) | DI | D | D | DI | D | D | D | D | DI | D | DI | DI | DI |
| Wuyue (12--1) | I | DI | DI | I | D | D | D | D | D | DI | DI | D | D |
| Bukowka (12--11) | I | D | D | DI | D | DI | D | D | D | I | DI | D | DI |
| Jinyu (12--12) | DI | DI | DI | DI | DI | D | D | DI | DI | I | DI | DI | DI |
| Calville Rouge (12--14) | I | DI | DI | I | DI | I | DI | D | DI | I | DI | DI | DI |
| Doyle (12--15) | DI | D | D | DI | D | DI | D | D | D | D | DI | D | DI |
| Melrose (12--16) | I | D | D | I | I | D | D | I | D | D | DI | D | DI |
| Menage (12--17) | DI | DI | DI | DI | D | D | D | D | D | D | DI | D | DI |
| Bo 26 (12--18) | I | DI | DI | DI | D | DI | D | D | DI | DI | DI | D | DI |
| Duoyilu (12--19) | DI | DI | DI | D | D | D | D | D | D | D | DI | D | DI |
| De 6 (12--20) | I | DI | DI | D | D | DI | D | D | I | DI | DI | DI | D |
| Red June (12--21) | DI | DI | DI | DI | DI | I | D | D | D | I | DI | DI | DI |
| Helasang (12--23) | DI | I | I | DI | D | DI | D | D | D | D | DI | D | DI |
| Hesetiaowen (12--3) | I | D | D | I | D | D | D | D | D | I | DI | DI | DI |
| James Grieve (1--23) | I | DI | DI | I | DI | DI | D | D | DI | D | DI | DI | DI |
| Bailuosi Malin (12--4) | DI | D | DI | DI | D | D | D | D | D | D | D | D | DI |
| Jinnhong (12--5) | DI | DI | DI | D | DI | D | D | I | DI | DI | DI | DI | DI |
| Kay Sai William (12--6) | I | DI | DI | I | I | D | D | D | D | D | DI | D | DI |
| Xingjiang Pingguo (12--7) | I | I | I | I | D | D | D | D | D | D | D | D | DI |

| Construction results of InDel marker genotype database of *Malus* germplasm resources | | | | | | | | | | | | | |
|---|---|---|---|---|---|---|---|---|---|---|---|---|---|
| Jie 15 (12--8) | I | D | D | I | I | DI | D | DI | D | D | DI | D | DI |
| Mianpingguo (12--9) | I | I | I | I | D | D | D | D | D | D | D | D | DI |
| Lowver (1--3) | D | DI | D | DI | D | D | D | D | DI | D | DI | D | DI |
| Benoni (13--1) | DI | DI | I | DI | D | DI | D | D | DI | I | DI | I | DI |
| Fa 5 (13--11) | DI | DI | DI | DI | DI | I | DI | D | DI | I | DI | DI | DI |
| Babskino (13--12) | I | DI | I | I | D | D | D | D | DI | D | DI | D | D |
| Kuluona (13--13) | DI | I | I | DI | DI | DI | DI | D | D | D | DI | D | DI |
| Shidonghaoji (13--16) | DI | D | I | DI | DI | I | DI | D | DI | I | DI | DI | DI |
| Oberkika (13--17) | DI | DI | DI | DI | D | DI | D | D | DI | D | DI | D | DI |
| Budayi (13--19) | I | D | D | DI | D | DI | D | D | D | DI | D | D | DI |
| Red Canada (13--2) | DI | DI | DI | DI | DI | I | DI | D | DI | I | DI | DI | DI |
| Laidi (13--20) | I | I | I | I | DI | DI | D | DI | DI | DI | DI | DI | DI |
| N2 (13--22) | I | D | D | DI | DI | DI | D | D | DI | DI | DI | DI | DI |
| Norsan (13--5) | I | D | D | I | I | DI | D | DI | D | D | DI | D | DI |
| Hebei Kangbing Golden Delicious (13--6) | DI | D | DI | DI | I | D | DI | I | D | D | DI | D | DI |
| Zhanxuan 14 (13--9) | I | D | D | DI | D | DI | D | D | D | D | DI | D | DI |
| Xiangguoguang (14--11) | DI | DI | DI | I | I | DI | D | I | D | D | DI | D | DI |
| Shengfang 1 (14--14) | I | D | D | DI | DI | DI | D | D | DI | DI | DI | DI | DI |
| Yujing II (14--16) | I | D | D | DI | DI | DI | D | D | DI | DI | DI | DI | DI |
| Cox's Orange Pippin (14--2) | DI | I | I | DI | D | D | D | D | I | I | DI | I | DI |
| Nagafu 7 (14--20) | I | D | D | DI | DI | DI | D | D | DI | DI | DI | DI | DI |
| Boiken (14--21) | DI | DI | DI | D | D | DI | D | D | DI | I | DI | DI | DI |
| Qunfu 1 (14--23) | I | D | D | DI | DI | DI | D | D | DI | DI | DI | DI | DI |
| Calville Blanche (14--3) | DI | DI | DI | D | D | DI | D | D | DI | I | DI | DI | DI |
| Freybreg (14--4) | DI | DI | I | DI | DI | I | DI | D | DI | I | DI | I | DI |
| Husveti Rosmaring (14--5) | DI | D | DI | DI | D | DI | D | D | D | DI | DI | D | DI |
| Sweet Jonathan (14--7) | DI | DI | DI | DI | DI | D | D | DI | DI | I | DI | DI | DI |
| King of Pippin (14--8) | DI | I | I | DI | DI | D | D | D | I | I | DI | I | DI |
| Duchess of Oldenburg (1--5) | I | DI | DI | I | D | DI | D | D | D | D | DI | D | D |
| Kangbing Golden 5 (15--11) | DI | DI | I | I | I | DI | DI | DI | DI | DI | DI | DI | DI |
| Pingzhi Ralls Janet (15--15) | I | D | D | D | D | DI | D | D | DI | DI | DI | DI | DI |
| Wase16 (15--16) | I | I | I | I | I | D | D | DI | D | D | D | D | DI |
| Kogetsu (15--17) | DI | I | I | DI | DI | D | D | D | D | D | D | D | DI |
| Jonared (15--18) | DI | DI | DI | DI | DI | D | D | DI | DI | I | DI | DI | DI |
| Zhanxuan 4 (15--21) | I | D | D | DI | DI | D | D | D | D | D | D | D | DI |
| Strawberry (15--23) | D | D | D | D | D | DI | D | D | D | D | DI | D | D |
| StarkSpur Ultra Red Delicious (15--3) | I | D | D | I | I | DI | D | DI | D | D | DI | D | DI |

| Construction results of InDel marker genotype database of *Malus* germplasm resources | | | | | | | | | | | | | |
|---|---|---|---|---|---|---|---|---|---|---|---|---|
| Sharp Red Delicious (15--4) | I | D | D | I | I | DI | D | DI | D | D | DI | D | DI |
| Mensi (15--5) | DI | D | D | DI | DI | I | DI | D | D | D | DI | D | DI |
| Norand (15--6) | I | DI | DI | DI | D | DI | D | D | DI | DI | DI | DI | DI |
| Zhanxuan 18 (15--7) | I | D | D | I | I | DI | D | DI | D | D | DI | D | DI |
| Xishan 1 (15--8) | I | D | D | I | I | DI | D | DI | D | D | DI | D | DI |
| Hongrou Pingguo (15--9) | D | DI | DI | I | D | D | D | D | DI | DI | I | D | DI |
| Gravenstein (1--6) | DI | D | D | DI | DI | DI | D | D | D | I | DI | D | DI |
| Xinhong (16--1) | DI | D | D | DI | D | D | D | D | D | D | DI | D | DI |
| Zhanxuan 6 (16--10) | I | I | I | I | D | D | D | D | D | D | I | D | DI |
| Behene (16--11) | DI | DI | DI | D | I | I | DI | D | DI | D | DI | D | D |
| Xindong (16--14) | DI | DI | DI | DI | D | DI | D | D | DI | D | DI | D | DI |
| Hardi Brite (16--16) | I | D | D | I | I | DI | D | DI | D | D | DI | D | DI |
| Charden (16--17) | DI | DI | DI | DI | DI | DI | DI | DI | DI | DI | DI | DI | DI |
| Zhuoai 1 (16--2) | I | D | D | DI | D | DI | D | D | D | D | DI | D | DI |
| Jinse Luosuoshan (16--22) | I | I | I | DI | D | D | D | D | D | D | DI | DI | DI |
| Zhaiteng II (16--23) | I | D | D | DI | DI | DI | D | D | DI | DI | DI | DI | DI |
| Zhanxuan 16 (16--6) | I | D | D | DI | D | DI | D | D | D | D | DI | D | DI |
| Fa 3 (16--8) | I | DI | I | I | DI | DI | DI | D | D | D | D | D | DI |
| Jerseymac (1--7) | I | D | D | I | D | DI | D | D | I | DI | DI | DI | DI |
| Mother (17--1) | I | I | I | DI | D | DI | D | D | DI | DI | DI | DI | DI |
| Northern Spy (17--10) | DI | D | DI | I | I | DI | DI | D | DI | DI | DI | DI | DI |
| Rome Beauty (17--11) | DI | D | D | DI | D | DI | D | D | D | D | DI | D | DI |
| Black Ben David (17--12) | D | D | DI | D | DI | DI | D | D | DI | DI | DI | D | DI |
| Atlas (17--13) | I | DI | DI | I | I | DI | DI | D | DI | D | D | D | DI |
| Roxbury (17--14) | I | I | I | I | I | D | D | I | DI | D | DI | D | DI |
| Laxtons Superb (17--15) | DI | D | D | D | D | D | D | D | DI | I | DI | DI | DI |
| Changhong (17--16) | I | I | I | DI | D | D | D | D | DI | D | DI | D | DI |
| Cogswell Pearmain (17--17) | I | D | D | DI | I | I | DI | D | DI | I | DI | DI | DI |
| Twenty Ounce (17--18) | DI | DI | DI | DI | D | D | D | D | DI | I | DI | DI | DI |
| Lowtosh (17--19) | DI | DI | DI | DI | I | DI | D | I | D | D | DI | D | D |
| Iwaki (17--21) | I | DI | DI | I | DI | I | DI | D | DI | I | DI | DI | DI |
| Qin'guan (17--22) | DI | DI | I | DI | I | D | D | DI | D | D | DI | D | DI |
| Bancroft (17--23) | DI | DI | DI | DI | DI | D | DI | D | D | D | DI | D | DI |
| Chenango Strawberry (17--4) | I | DI | I | DI | DI | DI | DI | D | D | DI | DI | DI | DI |
| Newfane (17--7) | DI | D | D | DI | D | DI | D | D | D | D | DI | D | D |
| Lord Lambourne (17--9) | DI | D | DI | I | I | DI | DI | D | DI | DI | DI | DI | DI |
| Rizhiwan (18--0) | I | D | D | I | DI | DI | D | D | I | DI | D | DI |
| Campbell (18--11) | I | I | I | I | I | D | D | I | DI | D | DI | D | DI |

-continued

| Construction results of InDel marker genotype database of *Malus* germplasm resources |||||||||||||
|---|---|---|---|---|---|---|---|---|---|---|---|---|
| Pigeon (18--13) | DI | D | D | D | DI | DI | D | DI | D | DI | DI | D | DI |
| Summer Champion (18--14) | DI | D | I | DI | I | I | DI | D | DI | D | DI | D | DI |
| Nanpu 3 (18--15) | DI | D | D | D | D | DI | D | D | I | D | DI | DI | DI |
| Qiulimeng (18--16) | I | DI | DI | I | DI | DI | DI | D | D | I | DI | D | DI |
| Rutosh (18--17) | I | I | I | I | D | D | D | D | D | D | DI | D | DI |
| Xinlimei (18--19) | I | I | I | I | DI | DI | D | DI | DI | DI | DI | DI | DI |
| Huanong 1 (18--2) | DI | DI | DI | DI | D | D | D | D | DI | I | DI | D | DI |
| Lawfam (18--20) | DI | DI | I | DI | DI | DI | D | D | D | D | DI | D | DI |
| Akin's Red (18--21) | DI | D | D | DI | DI | D | D | I | DI | I | DI | DI | DI |
| Meltosh (18--22) | I | D | D | I | I | DI | D | DI | DI | DI | DI | DI | DI |
| Hubbardston (18--23) | DI | DI | I | DI | DI | I | DI | D | DI | I | DI | I | DI |
| Fenghuangluan Crab (18--3) | DI | DI | DI | DI | D | D | D | D | DI | I | DI | D | DI |
| Jie 9 (18--4) | DI | DI | DI | D | DI | D | DI | D | D | D | DI | D | DI |
| Bramley's Seedling (18--5) | DI | D | I | DI | DI | DI | DI | D | DI | I | DI | D | DI |
| Shuangyang 1 (18--7) | DI | DI | I | DI | DI | I | DI | D | DI | I | DI | I | DI |
| Shengli (18--8) | DI | DI | I | DI | DI | I | DI | D | DI | I | DI | I | DI |
| Qingguan (18--9) | D | D | D | I | D | DI | D | DI | DI | DI | DI | DI | DI |
| Weeping Ralls (19--0) | I | D | D | D | D | DI | D | D | DI | DI | DI | DI | DI |
| Giant Jeniton (19--1) | DI | DI | DI | DI | D | D | D | D | D | D | DI | D | DI |
| Baldwin (19--10) | DI | DI | DI | DI | DI | I | D | D | DI | D | DI | D | DI |
| Lele Fuji (19--11) | I | D | D | DI | DI | DI | D | D | DI | DI | DI | DI | DI |
| Shuahong (19--12) | I | D | D | I | DI | D | D | D | DI | DI | DI | DI | DI |
| Red Fuji TAO (19--14) | I | D | D | DI | DI | DI | D | D | DI | DI | DI | DI | DI |
| Jizaohong (19--17) | DI | DI | I | DI | DI | I | DI | D | DI | I | DI | I | DI |
| Karas Tor (19--19) | I | I | I | DI | D | DI | D | DI | D | DI | D | DI | DI |
| Ralls Janet (19--2) | I | D | D | D | D | DI | D | D | DI | DI | DI | DI | DI |
| Stonetosh (19--22) | DI | I | I | DI | D | DI | D | D | DI | D | DI | D | DI |
| White Pearmain (19--23) | DI | DI | DI | DI | I | DI | DI | D | D | D | DI | D | DI |
| Xiushui Guoguang (19--3) | I | D | D | DI | DI | DI | D | D | DI | DI | DI | DI | DI |
| Chimeric Ralls Janet (19--4) | I | D | D | D | D | DI | D | D | DI | DI | DI | DI | DI |
| Mutsu (19--7) | DI | DI | DI | I | DI | I | DI | DI | DI | DI | DI | DI | DI |
| Ben David (19--8) | D | D | DI | D | DI | DI | D | D | DI | DI | DI | D | DI |
| Saint Lawrence (19--9) | DI | DI | I | I | D | D | D | DI | DI | I | DI | DI | DI |
| Newtosh (20--0) | D | I | I | I | D | D | D | D | D | D | I | D | DI |
| Geliekekukui (20--1) | DI | I | DI | DI | D | D | D | D | D | D | DI | D | DI |
| Sweet Jonathan (20--10) | DI | DI | DI | DI | DI | D | DI | DI | DI | I | DI | DI | DI |
| Apple of Commerce (20--11) | D | DI | DI | D | DI | DI | D | D | D | D | DI | D | DI |
| 600 g Andong (20--12) | DI | DI | DI | D | I | I | DI | D | DI | D | DI | D | D |

-continued

| Construction results of InDel marker genotype database of *Malus* germplasm resources | | | | | | | | | | | | | |
|---|---|---|---|---|---|---|---|---|---|---|---|---|
| Winter Banana (20--14) | DI | D | D | DI | DI | DI | DI | D | DI | D | DI | D | DI |
| Rainier (20--15) | DI | D | DI | DI | I | DI | DI | DI | DI | D | DI | D | DI |
| Winesap (20--16) | DI | D | D | DI | D | DI | D | D | D | DI | DI | D | DI |
| Drumbo (20--17) | I | D | D | DI | I | DI | D | DI | DI | DI | DI | DI | DI |
| Blengstid Gaurd (20--2) | I | DI | I | I | DI | DI | DI | D | D | D | DI | D | DI |
| Jierjisi (20--21) | DI | DI | I | I | D | D | D | DI | D | D | DI | D | DI |
| Radiant (20--23) | D | I | I | I | D | D | D | D | D | D | I | D | DI |
| King David (20--5) | I | DI | DI | I | DI | DI | D | DI | D | DI | D | DI |
| Clapp's Seedling (20--6) | D | D | D | I | D | DI | D | D | DI | DI | DI | DI | DI |
| Ingram (20--7) | DI | D | D | D | D | DI | D | D | DI | I | DI | I | DI |
| Qiujin (20--8) | I | D | D | DI | D | DI | D | D | D | D | DI | D | DI |
| Sujsleppskoe (2--1) | DI | D | D | DI | D | DI | DI | D | D | D | DI | D | D |
| Qian 1 Ace (21--0) | I | D | D | DI | DI | DI | D | D | DI | DI | DI | DI | DI |
| Toko (2--10) | DI | D | DI | I | I | DI | DI | D | D | D | DI | D | DI |
| Antalue (21--1) | DI | D | DI | DI | I | DI | D | I | D | D | DI | D | DI |
| Boskoopske Cervene (2--11) | I | DI | I | I | DI | DI | DI | D | D | D | DI | D | DI |
| Heoersitai (21--10) | I | DI | DI | D | DI | D | D | D | I | I | DI | I | D |
| Lanfengwang (21--11) | DI | DI | DI | DI | D | D | D | D | DI | DI | DI | DI | D |
| Aohong (21--14) | I | DI | DI | I | DI | DI | D | DI | DI | DI | DI | DI | DI |
| Weiqinni (21--15) | DI | DI | I | DI | DI | D | D | DI | DI | I | DI | D | D |
| Smoothee (21--17) | DI | DI | I | I | I | DI | DI | DI | DI | DI | DI | DI | DI |
| Hongzhiwu (21--18) | DI | DI | DI | I | DI | D | D | D | D | D | DI | D | DI |
| Jieba (21--2) | I | DI | DI | DI | D | DI | D | D | DI | DI | DI | DI | DI |
| Kizashi (21--20) | D | DI | I | DI | I | DI | DI | DI | DI | D | DI | D | D |
| Aifeng (21--21) | D | DI | I | DI | I | DI | DI | DI | DI | D | DI | D | D |
| Xingping (21--4) | I | D | D | D | D | DI | D | D | DI | DI | DI | DI | DI |
| Esopus Spitzenburg (2--14) | DI | I | I | DI | D | DI | D | D | I | I | DI | I | DI |
| Lvguang (21--6) | DI | I | I | I | D | DI | D | D | D | D | I | D | DI |
| Nvyoujidui (2--16) | DI | DI | DI | I | D | DI | D | D | D | I | DI | D | DI |
| Bell Poos (21--7) | DI | DI | DI | D | D | DI | D | D | D | D | DI | D | DI |
| Tian Andongnuo (2--17) | I | DI | DI | I | D | D | D | D | D | D | D | D | DI |
| Pacific Rose (21--8) | I | DI | DI | I | DI | DI | DI | DI | DI | DI | DI | DI | DI |
| 500 g (21--9) | D | DI | I | D | D | D | D | D | D | D | D | D | DI |
| Nvyoujidui 2 (2--19) | DI | D | D | DI | D | DI | D | D | D | D | DI | D | D |
| Tian Andongnuo 2 (2--2) | I | DI | DI | DI | D | DI | D | DI | I | DI | DI | DI |
| Spur Mutsu (22--1) | DI | DI | DI | I | DI | DI | DI | DI | DI | DI | DI | DI | DI |
| Red June Sweet (2--21) | I | D | D | DI | D | D | D | D | I | DI | D | DI |
| Chu Tsugaru (22--11) | DI | I | I | I | DI | D | DI | D | D | DI | D | DI |
| Kermemen (22--13) | D | I | I | D | D | D | D | DI | D | DI | D | DI |

-continued

Construction results of InDel marker genotype database of *Malus* germplasm resources

| | | | | | | | | | | | | | |
|---|---|---|---|---|---|---|---|---|---|---|---|---|---|
| Bedan (22--14) | DI | D | D | DI | D | DI | D | I | D | D | DI | D | DI |
| Dabinette (22--15) | I | D | D | DI | DI | DI | D | D | DI | DI | DI | DI | DI |
| Zaocuilv (22--16) | DI | DI | I | DI | DI | I | DI | D | DI | I | DI | I | DI |
| Chanteline (22--17) | DI | D | D | DI | D | DI | D | D | D | I | DI | DI | DI |
| Red Baron (22--2) | DI | DI | DI | DI | D | DI | D | D | DI | DI | DI | I | DI |
| Hongjin Gala (22--4) | DI | DI | DI | DI | DI | D | D | D | D | D | D | D | DI |
| Generos (22--7) | DI | DI | DI | DI | DI | D | D | DI | DI | I | DI | DI | DI |
| Alberta (2--3) | DI | D | D | DI | D | D | D | D | D | D | D | D | DI |
| Hirosaki Fuji (23--1) | DI | I | I | I | DI | D | D | DI | D | D | DI | D | DI |
| Miya Fuji (23--10) | I | D | D | DI | DI | DI | D | D | DI | DI | DI | DI | DI |
| Yanshanhong (23--13) | I | D | D | DI | DI | DI | D | D | D | D | DI | D | DI |
| Dailv (23--14) | I | D | D | I | D | DI | D | D | DI | DI | DI | DI | DI |
| Frequin Rouge (23--15) | D | DI | DI | DI | D | DI | D | DI | D | D | DI | D | DI |
| Jinguang (23--16) | DI | DI | DI | D | I | I | DI | D | DI | D | D | D | DI |
| Avrolles (23--17) | I | D | D | DI | D | DI | D | D | D | D | DI | D | DI |
| Marie Menard (23--18) | D | DI | DI | DI | D | D | D | D | DI | I | DI | DI | DI |
| Golden B (23--2) | DI | DI | I | I | I | DI | D | DI | DI | DI | DI | DI | DI |
| Jurella (23--20) | DI | DI | D | DI | I | I | D | D | D | D | DI | D | DI |
| GS58 (23--21) | DI | D | DI | I | I | DI | D | DI | D | D | DI | D | DI |
| Lianji (23--22) | D | DI | I | DI | DI | DI | D | D | D | DI | DI | DI | DI |
| Aomori Spur Fuji (23--4) | I | D | D | DI | DI | DI | D | D | DI | DI | DI | DI | DI |
| Akifu 39 (23--9) | I | D | D | DI | DI | DI | D | D | DI | DI | DI | DI | DI |
| Shalatuoni (2--4) | I | DI | DI | I | DI | DI | D | DI | DI | DI | D | DI | DI |
| Guoqing (24--13) | DI | DI | DI | D | DI | DI | D | I | DI | I | DI | DI | D |
| Ningguang (24--15) | D | D | I | DI | DI | DI | DI | D | DI | D | DI | D | DI |
| Hongqiaowang (24--17) | DI | DI | DI | DI | DI | DI | DI | DI | DI | DI | DI | DI | DI |
| Wemhong (24--18) | D | D | D | D | D | I | D | D | I | DI | DI | DI | DI |
| Wijcik McIntosh (24--19) | I | I | I | I | DI | D | D | D | D | D | DI | D | DI |
| Xinguoguang (24--21) | I | D | D | D | D | DI | D | D | DI | DI | DI | DI | DI |
| Fengcun Fuji (24--22) | I | D | D | DI | DI | DI | D | D | DI | DI | DI | DI | DI |
| America 8 (24--23) | DI | DI | DI | D | DI | DI | D | I | DI | DI | DI | DI | D |
| GS48 (24--3) | I | I | I | I | D | DI | D | D | D | D | DI | D | D |
| Granny Smith (24--4) | DI | DI | I | DI | I | DI | DI | D | D | D | D | D | DI |
| Stark Spur (24--7) | DI | DI | I | I | I | DI | DI | DI | DI | DI | DI | DI | DI |
| Huangguniang (2--5) | I | I | I | I | D | D | D | D | D | D | D | D | DI |
| Judaine (25--11) | DI | DI | DI | DI | DI | I | DI | D | DI | DI | DI | DI | DI |
| Judeline (25--12) | DI | DI | I | I | DI | I | I | D | DI | DI | DI | DI | DI |
| HoneyCrisp (25--14) | I | DI | DI | DI | DI | DI | DI | D | D | D | DI | D | DI |

| Construction results of InDel marker genotype database of *Malus* germplasm resources | | | | | | | | | | | | | |
|---|---|---|---|---|---|---|---|---|---|---|---|---|---|
| Korin (25--15) | I | D | D | DI | DI | DI | D | D | DI | DI | DI | DI | DI |
| Hongao (25--18) | DI | DI | I | I | DI | DI | DI | D | DI | I | DI | DI | DI |
| Ningguang (25--19) | DI | DI | I | I | DI | DI | DI | D | DI | I | DI | DI | DI |
| Red Delicious (25--2) | I | D | D | I | I | DI | D | DI | D | D | DI | D | DI |
| Youlixiang (25--21) | DI | I | I | DI | I | D | D | I | D | D | DI | D | DI |
| Fuqiu (25--3) | I | DI | DI | I | DI | D | D | D | DI | DI | D | DI | DI |
| Chunxiang (25--4) | I | D | D | I | DI | D | D | D | DI | DI | DI | DI | DI |
| Fu Hong (25--5) | I | DI | DI | DI | DI | DI | D | D | DI | DI | DI | D | DI |
| Qingxiang (25--6) | I | D | DI | I | I | I | DI | D | DI | I | DI | DI | DI |
| Zhongxing (25--7) | I | DI | I | I | DI | D | D | DI | D | D | DI | D | D |
| Weixishengming (25--8) | I | DI | I | I | DI | D | D | DI | D | D | DI | D | DI |
| Shichinohe 1 (25--9) | I | D | D | DI | DI | DI | D | D | DI | DI | DI | DI | DI |
| Arkansas Black (2--6) | DI | DI | I | DI | I | DI | D | D | DI | DI | DI | DI | DI |
| Douce Coetligne (26--10) | DI | I | I | DI | DI | DI | DI | DI | DI | D | DI | DI | DI |
| Golden Spur (26--14) | DI | DI | I | I | I | DI | DI | DI | DI | DI | DI | DI | DI |
| Orei (26--15) | DI | I | I | DI | D | D | D | D | I | I | DI | I | DI |
| Sekaiichii (26--18) | DI | DI | DI | DI | DI | D | D | D | D | D | DI | D | DI |
| Kokyu (26--19) | DI | DI | DI | I | I | I | DI | D | D | D | DI | D | DI |
| Douce Moen (26--2) | I | DI | DI | I | D | DI | D | I | DI | D | DI | D | DI |
| Yanfu 1 (26--22) | I | D | D | DI | DI | DI | D | D | DI | DI | DI | DI | DI |
| Ningfeng (26--23) | DI | DI | DI | D | DI | DI | D | I | DI | I | DI | DI | D |
| Juliana (26--5) | I | DI | DI | D | D | DI | D | D | I | DI | DI | DI | DI |
| Judestar (26--9) | DI | D | D | D | D | DI | D | D | D | D | DI | DI | DI |
| Liaofu (2--7) | I | DI | DI | DI | DI | DI | DI | D | DI | D | DI | D | DI |
| Sinano Red (27--10) | DI | I | I | I | DI | I | D | I | I | I | DI | I | DI |
| Jinyang (27--12) | DI | I | I | DI | D | DI | D | D | DI | D | DI | D | DI |
| Enqi (27--13) | DI | D | DI | DI | I | D | DI | I | D | DI | D | D | DI |
| Miki (27--14) | I | DI | I | I | D | D | D | DI | D | D | DI | D | DI |
| Hongbaoshi (27--15) | I | D | DI | I | I | D | D | I | D | D | DI | D | DI |
| Nagafu 2 (27--16) | I | D | D | DI | DI | DI | D | D | DI | DI | DI | DI | DI |
| Longguan (27--4) | I | D | D | D | D | DI | D | DI | DI | DI | DI | DI | DI |
| K9 (27--5) | DI | I | I | DI | D | DI | D | D | DI | D | DI | D | DI |
| Zaohongda Gala (27--6) | DI | I | I | DI | D | DI | D | D | DI | D | DI | D | DI |
| Lvshuai (27--7) | I | DI | I | I | DI | D | D | DI | DI | DI | DI | DI | DI |
| Hongxia (27--8) | D | DI | I | DI | I | DI | DI | DI | DI | D | DI | D | D |
| Zaohongxia (27--9) | I | D | D | DI | DI | D | D | D | DI | DI | DI | DI | DI |
| Early Golden (2--8) | DI | I | I | I | DI | D | D | I | DI | DI | DI | DI | DI |
| Indo (28--0) | I | D | D | I | DI | DI | D | D | D | D | DI | D | DI |
| Jie 1 (28--11) | DI | DI | DI | DI | DI | D | D | DI | DI | I | DI | DI | DI |

-continued

| Construction results of InDel marker genotype database of *Malus* germplasm resources | | | | | | | | | | | | | |
|---|---|---|---|---|---|---|---|---|---|---|---|---|
| Beauty of Bath (28--13) | DI | D | I | D | D | D | D | D | D | D | DI | D | DI |
| K10 (28--14) | DI | D | D | I | DI | D | D | DI | I | D | DI | D | DI |
| Beifang Xina (28--16) | I | D | D | DI | D | D | D | D | D | D | DI | D | DI |
| Yellow Fuji (28--18) | DI | DI | I | I | I | D | D | I | D | D | DI | D | DI |
| Sinano Sweet (28--2) | DI | I | I | I | DI | DI | D | I | DI | D | DI | DI | DI |
| Miguo (28--3) | I | D | D | DI | D | D | D | D | D | D | D | D | DI |
| Ace (28--4) | I | D | D | DI | D | DI | D | D | DI | DI | DI | DI | DI |
| Tsugaru (28--5) | DI | I | I | I | DI | D | D | DI | D | D | DI | D | DI |
| K12 (28--8) | DI | DI | DI | I | DI | DI | D | I | DI | DI | DI | DI | DI |
| Jieernianke (28--9) | DI | D | D | DI | D | DI | DI | D | D | D | DI | D | D |
| Macoun (2--9) | I | DI | DI | I | DI | D | D | D | D | D | DI | D | DI |
| Qingping (29--1) | DI | I | I | DI | D | I | D | I | DI | D | DI | D | DI |
| Polka (29--11) | DI | I | I | I | I | DI | DI | D | DI | DI | DI | DI | DI |
| Longfeng (29--13) | DI | D | DI | I | I | DI | DI | DI | D | I | DI | DI | DI |
| Very Early Fuji (29--14) | I | D | D | DI | DI | DI | D | D | DI | DI | DI | DI | DI |
| Longhong (29--15) | DI | I | I | I | DI | D | DI | DI | D | D | DI | D | DI |
| Pinova (29--16) | I | DI | DI | DI | DI | DI | DI | D | DI | I | DI | DI | DI |
| Fuga (29--17) | D | DI | I | DI | I | DI | DI | DI | D | DI | D | D | |
| Qing n3 (29--2) | I | D | D | I | I | DI | D | DI | D | DI | D | D | DI |
| Xinyuanshuai (29--3) | I | D | D | I | I | I | D | DI | D | D | D | D | DI |
| Xinhua (29--5) | DI | D | D | DI | D | D | D | D | D | D | DI | DI | DI |
| Nanpu 2 (29--6) | I | DI | DI | I | DI | DI | D | DI | DI | I | DI | DI | DI |
| Liuyu mutant (29--7) | D | I | I | D | D | D | D | D | DI | D | DI | DI | D |
| Shandao Fuji (30--1) | I | D | D | DI | DI | DI | D | D | DI | DI | DI | DI | DI |
| Sinano Gold (30--2) | DI | D | DI | DI | I | DI | D | I | DI | DI | DI | DI | DI |
| Whitney (3--1) | I | DI | D | I | D | D | D | I | DI | D | I | D | DI |
| Feixia (31--1) | DI | D | DI | DI | I | DI | DI | I | D | DI | DI | D | DI |
| Willams Faborite (3--11) | I | D | D | I | DI | DI | DI | D | DI | D | DI | DI | DI |
| Zhangye 2 (31--12) | I | DI | DI | I | I | I | D | D | D | D | D | D | DI |
| Youfangcun Ralls Janet (31--14) | D | D | DI | D | DI | DI | D | D | DI | DI | DI | D | DI |
| Yueyanghong (31--15) | DI | DI | DI | D | DI | DI | D | DI | D | D | DI | D | DI |
| Shuohong (31--17) | I | D | D | DI | D | D | D | D | DI | I | DI | DI | DI |
| Tianwang 1 (31--18) | I | D | D | I | I | DI | D | DI | D | D | DI | D | DI |
| Huadan (31--2) | I | D | D | DI | DI | DI | DI | D | D | D | DI | D | DI |
| Dalu 52 (3--12) | I | I | I | I | I | D | D | D | D | D | D | D | DI |
| Cameo (31--3) | DI | DI | DI | I | I | D | D | I | D | D | D | D | DI |
| Tianhuangkui (3--13) | I | I | I | I | D | DI | D | D | DI | DI | DI | D | DI |
| Qiulu (31--4) | D | DI | D | DI | D | D | D | D | DI | I | DI | DI | DI |

| Construction results of InDel marker genotype database of *Malus* germplasm resources |||||||||||||
|---|---|---|---|---|---|---|---|---|---|---|---|---|
| Liehuangjiatena (3--15) | I | D | DI | DI | I | DI | D | I | DI | DI | DI | DI | DI |
| Lubi (3--16) | DI | D | D | DI | DI | I | D | D | DI | I | DI | DI | DI |
| Huayu (31--8) | I | DI | DI | DI | DI | DI | DI | I | DI | DI | DI | DI | DI |
| Fameuse (3--18) | I | I | I | DI | D | D | D | D | DI | DI | DI | DI | DI |
| Zhanhanxiang (3--19) | I | I | I | I | I | DI | DI | D | DI | DI | DI | DI | DI |
| Siberian White Spot (3--2) | I | D | I | I | D | D | D | D | D | D | DI | D | D |
| Zhengding 2 (3--21) | D | D | D | D | D | D | D | D | D | D | DI | D | DI |
| Kuihua (3--22) | I | I | I | DI | D | DI | DI | D | DI | I | DI | DI | DI |
| Early Worcester (3--23) | I | DI | DI | DI | DI | D | D | D | DI | DI | DI | DI | DI |
| Lowland Raspderry (3--3) | I | DI | DI | DI | I | DI | DI | D | D | I | DI | D | DI |
| Miqiulin Jinian (3--4) | I | DI | I | DI | D | DI | D | D | D | D | DI | D | DI |
| Huangtianguo (3--5) | DI | I | I | I | D | D | D | D | D | I | D | DI |
| Huadao (3--7) | DI | DI | DI | D | D | DI | D | D | D | D | DI | D | DI |
| Red Astrachan (3--9) | I | DI | DI | I | D | DI | DI | D | D | D | DI | D | D |
| Black Gilliflower (4--1) | DI | DI | DI | DI | DI | DI | D | D | D | I | DI | DI | DI |
| Nimaiyisuo (4--10) | DI | D | D | DI | D | D | D | D | D | DI | DI | D | DI |
| Zaohong (4--11) | I | D | D | DI | D | DI | D | D | DI | DI | DI | DI | DI |
| Xiangguo (4--12) | DI | I | I | I | D | D | D | D | D | D | DI | D | DI |
| Vista Bella (4--16) | DI | DI | DI | DI | DI | DI | D | D | I | DI | DI | I | DI |
| Saiwen (4--17) | DI | DI | I | DI | I | DI | D | D | DI | DI | DI | DI | DI |
| Summerland (4--20) | DI | DI | I | I | I | DI | DI | DI | DI | DI | DI | DI | DI |
| Qihe Golden Spur (4--22) | DI | DI | I | I | I | DI | DI | DI | DI | DI | DI | DI | DI |
| Yellow Risharde (4--3) | DI | D | D | DI | D | DI | D | D | D | D | DI | D | D |
| Patten (4--5) | DI | I | I | DI | D | D | D | D | DI | DI | DI | DI | DI |
| Early Red Bird (4--6) | D | I | I | D | D | D | D | D | DI | D | DI | DI | D |
| Fuhong (4--7) | I | I | I | I | DI | DI | DI | DI | D | D | DI | D | DI |
| Bisimake (4--8) | DI | DI | DI | D | D | DI | D | D | DI | D | DI | D | DI |
| York Imperial (4--9) | DI | DI | DI | DI | I | DI | D | D | D | DI | DI | D | DI |
| Jonagold (5--1) | DI | DI | DI | DI | DI | DI | DI | DI | DI | DI | DI | DI | DI |
| Ayiwaniya (5--10) | DI | I | I | DI | D | DI | D | D | DI | DI | DI | DI | DI |
| Fushan 5 (5--14) | I | D | D | I | I | DI | D | DI | D | D | DI | D | DI |
| Houjiadian Spur (5--18) | I | D | D | I | I | DI | D | DI | D | D | DI | D | DI |
| Guoshuai (5--19) | I | D | D | DI | D | DI | D | D | D | D | DI | D | DI |
| Huashuai 1 (5--21) | I | D | D | I | I | DI | D | D | DI | I | DI | DI | DI |
| Xiongyue 2 (5--22) | I | D | D | I | I | DI | D | DI | D | D | DI | D | DI |
| Honeygod (5--3) | DI | DI | I | DI | I | DI | DI | DI | I | DI | DI | DI |
| Joyal (5--4) | I | I | I | I | D | D | D | D | D | D | DI | D | DI |
| Stark Spur Golden (5--5) | DI | DI | I | I | I | DI | DI | DI | DI | DI | DI | DI | DI |

-continued

| Construction results of InDel marker genotype database of *Malus* germplasm resources | | | | | | | | | | | | | |
|---|---|---|---|---|---|---|---|---|---|---|---|---|
| Enweier Golden (5--6) | DI | DI | I | I | I | DI | DI | DI | DI | DI | DI | DI | DI |
| Stark Gold (5--8) | I | D | D | D | D | DI | D | D | DI | DI | DI | DI | DI |
| Sishui Spur (6--10) | I | D | D | I | I | DI | D | DI | D | D | DI | D | DI |
| Red Spur Delicious (6--12) | I | D | D | I | I | DI | D | DI | D | D | DI | D | DI |
| Qingdao 1 (6--13) | I | D | D | I | I | DI | D | DI | D | D | DI | D | DI |
| Bianqiangzi 1 (6--14) | I | D | D | I | I | DI | D | DI | D | D | DI | D | DI |
| Zhangjiakou Spur (6--16) | I | D | D | I | I | DI | D | DI | D | D | DI | D | DI |
| Richard Red Delicious (6--18) | I | D | D | I | I | DI | D | DI | D | D | DI | D | DI |
| Well Spur Delicious (6--19) | I | D | D | I | I | DI | D | DI | D | D | DI | D | DI |
| Bianqiangzi 2 (6--20) | I | D | D | I | I | DI | D | DI | D | D | DI | D | DI |
| Hardi Spur Delicious (6--21) | I | D | D | I | I | DI | D | DI | D | D | DI | D | DI |
| Fushan 1 (6--3) | I | D | D | I | I | DI | D | DI | D | D | DI | D | DI |
| Pinyin Spur (6--4) | I | D | D | I | I | DI | D | DI | D | D | DI | D | DI |
| Nanshan 2 (6--8) | I | D | D | I | I | DI | D | DI | D | D | DI | D | DI |
| Meiduan 1 (7--10) | I | D | DI | I | I | DI | DI | D | DI | D | DI | D | DI |
| Shisanling Spur (7--11) | I | D | D | I | I | DI | D | DI | D | D | DI | D | DI |
| Kelisike (7--13) | I | I | I | I | DI | DI | D | D | DI | DI | DI | DI | DI |
| Jie 18 (7--16) | DI | DI | DI | DI | D | D | D | D | D | DI | DI | D | DI |
| Bo 25 (7--17) | DI | DI | DI | DI | D | DI | D | D | D | DI | DI | D | DI |
| Ruixiang (7--18) | DI | DI | DI | DI | D | DI | D | D | DI | DI | DI | DI | DI |
| Wealthy (7--19) | D | DI | DI | D | DI | D | D | I | DI | I | DI | DI | DI |
| Nanshan 4 (7--2) | I | D | D | DI | DI | DI | D | D | DI | DI | DI | DI | DI |
| De 14 (7--20) | DI | DI | DI | DI | D | D | D | D | D | D | DI | D | DI |
| Napoleon (7--22) | I | D | D | DI | D | DI | D | D | D | D | DI | D | DI |
| Youyi (7--23) | DI | I | DI | DI | I | DI | DI | DI | DI | DI | DI | DI | DI |
| Oregon Spur (7--3) | I | D | D | DI | DI | DI | D | D | DI | DI | DI | DI | DI |
| Kangtun Spur (7--6) | I | D | D | I | I | DI | D | DI | D | D | DI | D | DI |
| White Pippin (7--9) | I | I | I | DI | D | D | D | D | DI | DI | DI | DI | DI |
| Zach Lebel (8--1) | I | D | D | I | D | D | D | D | D | D | DI | D | DI |
| Cortland (8--10) | D | DI | DI | D | DI | D | D | I | D | D | DI | D | DI |
| Raritan (8--12) | I | D | D | DI | DI | D | D | D | DI | DI | DI | DI | DI |
| Meilingxi Tsugaru (8--13) | DI | D | DI | I | D | D | D | D | D | D | DI | D | DI |
| Moscow Transparent (8--14) | I | DI | DI | I | D | D | D | D | DI | DI | DI | I | DI |
| Cooper's Market (8--15) | DI | D | DI | D | D | I | D | D | DI | I | DI | DI | DI |
| Xite Shisheng (8--16) | DI | DI | I | DI | D | D | D | D | D | I | D | DI |
| Tian Yisaye (8--17) | DI | D | D | DI | D | D | D | DI | I | DI | DI | DI |
| Shennong 2 (8--19) | DI | D | DI | I | DI | D | D | I | DI | DI | DI | DI | DI |

-continued

Construction results of InDel marker genotype database of *Malus* germplasm resources

| | | | | | | | | | | | | | |
|---|---|---|---|---|---|---|---|---|---|---|---|---|---|
| Maigold (8--20) | DI | D | DI | DI | D | DI | DI | D | I | I | DI | I | DI |
| Magu (8--21) | D | DI | DI | D | DI | D | D | DI | I | DI | DI | DI | DI |
| Cellini (8--23) | DI | DI | DI | D | D | I | D | D | DI | D | DI | D | DI |
| Simonffy Piros (8--3) | I | D | DI | I | D | D | D | D | D | D | D | D | DI |
| Luxiang (8--5) | DI | D | D | DI | D | D | D | D | DI | DI | DI | DI | DI |
| Zhongqiu (8--6) | DI | I | I | DI | D | D | D | DI | D | D | D | D | DI |
| De 2 (8--7) | I | DI | DI | DI | D | I | D | D | DI | DI | DI | DI | DI |
| Grimes Golden (8--8) | I | I | I | DI | I | D | D | DI | I | I | DI | DI | DI |
| Early Straw Berry (8--9) | I | D | DI | DI | DI | DI | DI | DI | DI | DI | DI | D | DI |
| Kelia (9--10) | DI | DI | DI | DI | DI | DI | D | D | DI | I | DI | I | D |
| French Apple (9--11) | I | DI | DI | I | D | DI | D | D | D | I | DI | DI | DI |
| Todoroki Tsugaru (9--12) | DI | I | I | I | DI | D | D | DI | D | D | D | D | DI |
| Cuihong (9--13) | DI | I | I | DI | D | DI | D | D | I | DI | DI | DI | DI |
| De 4 (9--14) | I | DI | I | I | D | DI | DI | D | D | D | DI | D | DI |
| Early McIntosh (9--18) | I | DI | DI | I | I | D | D | D | D | D | DI | D | DI |
| Adam Mickewier (9--19) | DI | D | DI | DI | DI | I | DI | D | D | I | DI | DI | DI |
| Norda (9--2) | DI | DI | DI | D | D | DI | D | D | D | I | DI | D | DI |
| Cardinal (9--20) | DI | DI | I | DI | DI | I | DI | D | DI | I | DI | I | DI |
| Evelyn (9--21) | DI | I | I | D | DI | DI | D | DI | D | D | DI | D | DI |
| Situonuowei (9--22) | DI | D | D | DI | D | DI | DI | D | D | D | DI | D | D |
| Yingqiu (9--23) | I | I | I | DI | DI | DI | D | DI | I | DI | DI | DI | DI |
| Kelongxieer (9--3) | I | DI | DI | I | D | D | D | D | DI | DI | DI | I | DI |
| Cloden (9--5) | D | DI | DI | DI | DI | I | DI | D | D | D | DI | D | DI |
| Qiutianhong (9--6) | DI | D | D | DI | D | DI | DI | D | D | D | DI | D | D |
| Gaidebao (9--7) | DI | D | D | D | D | D | D | D | I | DI | DI | DI | DI |
| Starkjam (9--9) | I | D | D | DI | D | DI | D | D | D | DI | D | DI | |
| Wan Crab (B-1) | D | DI | I | I | DI | D | D | I | D | D | DI | D | DI |
| Minjiandaguo Crab (B-10) | D | DI | I | DI | D | D | D | D | DI | DI | D | DI | |
| Luanzhuang Crab (B1-11) | I | D | D | DI | D | DI | D | D | DI | DI | DI | DI | DI |
| Sankuaishi Crab (B1-12) | D | I | I | I | D | D | D | DI | D | D | I | D | DI |
| Xiongyue Crab 1 (B1-13) | DI | D | D | I | D | DI | D | D | DI | DI | DI | DI | DI |
| Sankuaishi Crab 2 (B1-14) | DI | D | DI | I | D | DI | D | D | DI | DI | DI | DI | DI |
| Dabaleng (B-12) | I | DI | DI | DI | D | DI | D | D | DI | DI | DI | DI | DI |
| Sankuaishi Crab 2 (B-13) | I | D | D | DI | DI | DI | D | D | DI | DI | DI | DI | DI |
| Changguo Crab (B-14) | DI | DI | I | I | DI | D | D | DI | I | DI | DI | DI | |
| Dagucheng Baleng (B1-5) | I | I | I | I | D | D | D | D | D | I | D | D | |
| Zumi Crab 3x (B-15) | DI | DI | I | I | DI | DI | D | DI | DI | DI | DI | DI | DI |
| 26105 (B-16) | DI | DI | DI | D | DI | D | D | DI | DI | D | DI | D | DI |

-continued

| Construction results of InDel marker genotype database of *Malus* germplasm resources | | | | | | | | | | | | | |
|---|---|---|---|---|---|---|---|---|---|---|---|---|
| Daguo Crab (B-17) | D | DI | I | DI | D | D | D | D | D | DI | DI | D | DI |
| Xiongyue Crab 2 (B1-8) | D | DI | I | I | D | D | D | D | D | I | D | D | |
| Watermelon Crab (B-18) | I | I | I | I | DI | DI | D | DI | D | D | DI | D | DI |
| Mudanjiang Crab (B1-9) | D | DI | DI | D | I | D | D | D | D | D | DI | D | DI |
| Tianhong 1 (B-19) | I | D | D | DI | DI | DI | D | D | DI | DI | DI | DI | DI |
| Jiping 1 (B-2) | I | DI | DI | DI | DI | DI | DI | I | DI | DI | DI | DI | D |
| Caoyuan Crab (B2-1) | D | I | D | I | D | D | D | D | D | DI | D | D | |
| Zumi Crab 4x (B-21) | DI | DI | I | I | DI | DI | DI | DI | DI | DI | DI | DI | DI |
| Luanzhuang Shaguo (B2-11) | DI | I | I | I | D | D | D | D | D | I | D | DI | |
| Xiaofan Crab (B2-13) | DI | I | I | I | D | D | D | D | D | DI | D | DI | |
| Hebing Pingding Crab (B2-14) | D | I | I | I | D | D | D | D | D | I | D | D | |
| Zumi Crab 3x 2 (B-22) | DI | DI | I | I | DI | DI | DI | DI | DI | DI | DI | DI | |
| Baleng Crab (B2-3) | DI | I | I | I | D | D | D | D | D | I | D | DI | |
| Baleng seedling 14 (B-25) | DI | DI | I | I | DI | DI | D | DI | DI | DI | DI | DI | |
| Russian White apple (B2-6) | I | DI | DI | I | D | D | D | D | D | DI | D | D | |
| Nagafu 2 (B-26) | I | D | D | DI | DI | DI | D | D | DI | DI | DI | DI | DI |
| Ambrosia (B-27) | I | DI | DI | I | I | DI | DI | D | DI | DI | DI | DI | DI |
| Aihonghua (B2-8) | D | I | I | I | DI | DI | D | I | DI | DI | DI | DI | |
| Nanshennan (B-28) | I | D | D | DI | DI | DI | D | D | DI | DI | DI | DI | DI |
| Zumi Crab W1 (B-29) | DI | DI | I | I | DI | DI | DI | DI | DI | DI | DI | DI | DI |
| Hong 4G (B-3) | DI | I | I | I | D | DI | D | D | DI | DI | DI | DI | DI |
| Zumi Crab (B-30) | DI | DI | I | I | DI | DI | DI | DI | DI | DI | DI | DI | DI |
| Zaobai Crab (B3-1) | DI | I | I | I | D | D | D | D | DI | D | DI | D | DI |
| Mollie's Delicious (B-31) | DI | D | DI | I | D | DI | D | DI | I | DI | DI | I | DI |
| Regunzi Spur (B3-10) | DI | I | I | I | D | D | D | D | D | D | DI | D | DI |
| Xiaofanshan Baleng (B3-11) | DI | DI | D | DI | DI | D | DI | D | DI | D | DI | DI | |
| Huamei (B3-12) | DI | D | DI | DI | I | D | DI | I | D | D | D | DI | |
| Huashuo (B3-13) | I | DI | DI | DI | D | DI | D | DI | DI | I | DI | DI | DI |
| Yuhong (B3-14) | I | D | D | I | I | DI | D | DI | D | DI | D | DI | |
| Huayue (B3-15) | DI | DI | DI | DI | D | I | DI | D | DI | I | DI | DI | DI |
| Jingbohu Shandingzi (B3-2) | D | I | D | I | D | D | D | I | D | D | I | DI | D |
| Eluosi Daguo Shandingzi (B3-3) | DI | D | D | I | DI | D | D | DI | D | D | DI | D | DI |
| HY (B-33) | DI | D | DI | DI | DI | D | D | D | DI | DI | DI | DI | |
| Hong Crab (B3-6) | DI | I | I | I | D | D | D | D | D | DI | D | DI | |
| 23# (B-37) | DI | DI | I | DI | DI | DI | D | I | DI | DI | DI | DI | D |
| Russian apple (B3-8) | I | DI | DI | I | D | D | D | DI | D | DI | DI | D | DI |

-continued

Construction results of InDel marker genotype database of *Malus* germplasm resources

| | | | | | | | | | | | | |
|---|---|---|---|---|---|---|---|---|---|---|---|---|
| 147 (B-38) | I | DI | D | DI | DI | D | DI | DI | D | D | DI | D | D |
| Xiaofanshan Baleng 1 (B3-9) | DI | I | I | I | D | D | D | D | D | D | I | D | DI |
| Lvshuai (B-4) | I | DI | I | I | DI | D | DI | D | DI | DI | DI | DI | DI |
| Dounan (B-40) | DI | D | DI | DI | DI | D | D | D | DI | D | DI | D | DI |
| 11906 (B-41) | DI | DI | DI | I | D | DI | D | D | I | I | DI | DI | DI |
| Luli (B-5) | DI | DI | I | I | D | DI | D | I | DI | DI | DI | DI | DI |
| Jinxiuhong (B-6) | DI | D | DI | DI | I | DI | D | I | D | D | DI | D | DI |
| B68 (B-7) | DI | DI | I | I | I | D | D | D | DI | DI | DI | DI | DI |
| Huaida (B-8) | D | D | DI | I | DI | D | D | DI | DI | DI | DI | DI | DI |
| Nanshennan mutant (B-9) | I | D | D | DI | DI | DI | D | D | DI | DI | DI | DI | DI |
| Xiahong (BH-1) | D | DI | I | DI | DI | DI | DI | DI | D | I | DI | DI | DI |
| Wuming1 (BJ-1) | DI | DI | DI | I | DI | DI | D | D | DI | D | DI | DI | DI |
| Canzy ? (BJ-10) | DI | D | DI | DI | I | DI | DI | I | DI | DI | DI | DI | D |
| Xiangfu (BJ-11) | I | D | D | DI | DI | DI | D | D | DI | DI | DI | DI | DI |
| Envy (BJ-12) | I | D | D | DI | I | DI | DI | I | D | D | DI | D | D |
| Fuji_KiKu (BJ-2) | I | D | D | DI | DI | DI | D | D | DI | DI | DI | DI | DI |
| Banxiu Crab (BJ-4) | D | D | I | DI | D | D | D | D | D | DI | DI | D | DI |
| Jazz (BJ-5) | I | D | DI | D | DI | DI | D | D | DI | DI | DI | DI | DI |
| Early Red Bird 2 (BJ-7) | DI | DI | DI | DI | I | D | DI | DI | DI | D | DI | DI | DI |
| Qiuhong Gala (BJ-8) | I | D | D | DI | DI | DI | D | D | DI | D | DI | DI | DI |
| Hongxiangcui (BJ-9) | I | D | DI | DI | I | D | DI | I | D | DI | DI | D | DI |
| 07-115 (BK-1) | DI | D | DI | DI | I | I | D | D | D | D | DI | D | DI |
| Nagafu 3 (BK-2) | I | D | D | DI | DI | DI | D | D | DI | DI | DI | DI | DI |
| 28-253 (BK-28-253) | DI | DI | DI | DI | DI | D | D | D | D | D | DI | D | DI |
| Nagafu 3-R (BK-3) | I | D | D | DI | DI | DI | D | D | DI | DI | DI | DI | DI |
| 4354 (BK-4) | I | D | DI | I | I | I | D | DI | D | DI | DI | D | DI |
| 4-23 (BK-4-23) | DI | D | D | I | I | DI | DI | D | DI | D | DI | D | DI |
| 4354-R ? (BK-5) | DI | D | DI | I | I | DI | DI | D | DI | DI | DI | DI | DI |
| 77-34 (BK-77-34) | DI | I | I | I | D | D | D | DI | D | D | I | DI | DI |
| Red Spur Delicious (BK-AH) | I | D | D | I | I | DI | D | DI | D | D | DI | D | DI |
| Ozark Gold (BK-AJ) | DI | DI | I | I | I | DI | D | I | D | D | DI | D | DI |
| Michinoku (BK-AZ) | DI | I | I | I | DI | DI | D | I | I | I | DI | I | DI |
| Azwell (BK-Azwell) | I | D | D | I | I | DI | D | DI | D | D | DI | D | DI |
| Banbishan Crab (BK-BBSHT) | DI | I | I | I | D | D | D | DI | D | D | I | D | DI |
| Hokudo (BK-BD) | DI | D | D | DI | DI | DI | D | D | DI | DI | DI | DI | DI |
| Baifugao (BK-BFG) | DI | DI | DI | DI | D | D | D | D | D | D | DI | D | DI |
| White Crab (BK-BHT) | DI | DI | D | DI | DI | DI | D | DI | DI | D | DI | DI | DI |

-continued

| Construction results of InDel marker genotype database of *Malus* germplasm resources |||||||||||||
|---|---|---|---|---|---|---|---|---|---|---|---|---|
| Burning Kangbing (BK-BMKB) | I | I | I | DI | D | D | D | D | DI | DI | DI | DI | DI |
| Batougou 1 (BK-BTG1H) | DI | I | D | I | D | D | D | DI | D | D | DI | D | D |
| Batougou 2 (BK-BTG2H) | D | I | I | I | D | D | D | D | D | D | DI | DI | D |
| Batougou Aizhen (BK-BTGAZ) | D | DI | D | I | D | D | D | D | D | D | DI | DI | D |
| Binzi (BK-BZ) | DI | I | I | I | D | D | D | D | D | D | DI | D | DI |
| Kitanosach (BK-BZX) | DI | I | I | I | I | DI | DI | DI | D | D | D | D | DI |
| Binzi (SW) (BK-BZXN) | DI | I | I | I | D | DI | D | D | D | D | DI | D | DI |
| Nagafu 2 (BK-CF2H) | I | D | D | DI | DI | DI | D | D | DI | DI | DI | DI | DI |
| Nagafu 36 (BK-CF36) | I | D | D | DI | DI | DI | D | D | DI | DI | DI | DI | DI |
| Nagafu 6 (BK-CF6H) | I | D | D | DI | DI | DI | D | D | DI | DI | DI | DI | DI |
| CG24 (BK-CG24) | I | D | D | I | I | DI | D | DI | D | D | DI | D | DI |
| CG3 (BK-CG3) | DI | DI | DI | DI | DI | D | D | D | D | D | DI | D | D |
| CG80 (BK-CG80) | I | I | I | DI | DI | I | D | DI | I | D | DI | D | DI |
| Changhong (BK-CH) | I | D | D | DI | DI | DI | D | D | DI | DI | DI | DI | DI |
| Chieftan (BK-chieftan) | DI | DI | DI | DI | DI | D | D | DI | D | D | DI | D | DI |
| Cangjiang Crab (BK-CJHT) | D | I | I | I | D | D | D | I | DI | D | I | D | D |
| Chuanling Crab (BK-CLHT) | DI | D | D | D | D | DI | D | DI | D | D | DI | D | DI |
| Hatsuaki (BK-CQ) | DI | DI | I | I | I | DI | D | D | D | D | DI | D | DI |
| Crispin (BK-crispin) | DI | DI | DI | DI | DI | DI | DI | DI | DI | DI | DI | DI | DI |
| Caozigang Yuanshuai (BK-CZGYS) | I | D | D | I | I | DI | D | DI | D | D | DI | D | DI |
| Danxia (BK-DANXIA) | I | D | DI | I | I | D | DI | D | DI | D | DI | DI | DI |
| Dolgo (BK-DDG) | DI | D | D | I | DI | D | D | DI | D | D | DI | D | D |
| Darwin (BK-DEW) | DI | I | I | I | D | DI | D | D | D | D | DI | D | DI |
| Oriental Apple (BK-DFPG) | DI | I | I | I | D | DI | D | D | D | D | DI | D | D |
| Big Crab (BK-DGHT) | DI | I | I | DI | D | DI | D | D | D | D | I | D | DI |
| Daguo Jinhong (BK-DGJH) | D | D | DI | I | DI | D | D | DI | DI | DI | DI | DI | DI |
| Daihong (BK-DH) | I | D | D | I | I | DI | D | DI | D | D | DI | D | DI |
| Daihao 261 (BK-DH261) | I | D | D | I | D | D | D | D | D | D | DI | D | DI |
| Spur Golden Delicious (BK-DJG) | DI | DI | I | I | I | DI | DI | DI | DI | DI | DI | DI | DI |
| Daxianguo (BK-DXG) | DI | I | I | I | D | D | D | D | D | D | I | D | DI |
| Daye Crab (BK-DYHT) | D | I | I | I | D | D | D | D | D | D | I | D | DI |
| Spur Fuji (BK-DZFS) | I | D | D | DI | DI | DI | D | D | DI | DI | DI | DI | DI |
| Huaguan Spur (BK-DZHG) | DI | D | DI | DI | I | DI | DI | I | D | D | DI | D | DI |
| Elite (BK-Elite) | I | D | D | I | I | DI | D | DI | D | D | DI | D | DI |
| Fa 8 (BK-F8) | DI | DI | DI | DI | D | I | DI | D | DI | I | DI | DI | DI |
| Fukushima Spur Fuji (BK-FDDZ) | I | D | D | DI | DI | DI | D | D | DI | DI | DI | DI | DI |
| Fujin (BK-FJ) | I | D | D | I | I | DI | D | D | D | D | DI | D | DI |

-continued

Construction results of InDel marker genotype database of *Malus* germplasm resources

| | | | | | | | | | | | | | |
|---|---|---|---|---|---|---|---|---|---|---|---|---|---|
| Florina (BK-Florina) | DI | D | D | DI | D | D | D | D | D | D | DI | D | DI |
| Fangming (BK-FM) | DI | I | I | I | DI | D | D | DI | D | D | DI | D | DI |
| Fuji (BK-Fuji) | I | D | D | DI | DI | DI | D | DI | DI | DI | DI | DI | DI |
| Fengyan (BK-FY) | I | D | D | I | D | D | D | I | DI | DI | DI | DI | DI |
| Yanfu 1 (BK-FY1) | I | D | D | DI | DI | DI | D | D | DI | DI | DI | DI | DI |
| King of Tompkins County (BK-FZY) | DI | I | I | DI | DI | DI | D | DI | DI | I | DI | I | DI |
| G30 (BK-G30) | I | D | I | DI | DI | D | D | I | D | DI | DI | DI | DI |
| Gao #5 (BK-G-5) | I | D | D | I | I | DI | D | DI | DI | DI | DI | DI | DI |
| Gala (BK-gala) | DI | D | DI | DI | DI | D | DI | I | D | D | DI | D | DI |
| Golden Delicious (BK-GD) | DI | DI | I | DI | I | DI | D | DI | DI | DI | DI | DI | DI |
| Gloster69 (BK-Gloster69) | I | D | DI | I | I | DI | D | D | D | D | DI | D | DI |
| GM256 (BK-GM256) | I | I | I | I | D | D | D | DI | D | DI | DI | DI | DI |
| GM310 (BK-GM310) | DI | DI | I | I | DI | D | D | DI | D | DI | DI | DI | DI |
| Gaoqiu (BK-GQ) | I | D | DI | I | DI | D | D | DI | I | I | DI | I | DI |
| Miyazaki Spur Fuji (BK-GQDZ) | I | D | D | DI | DI | DI | D | D | DI | DI | DI | DI | DI |
| HAC-9 (BK-HAC-9) | I | DI | DI | DI | DI | DI | DI | D | DI | DI | DI | DI | DI |
| Huifeng Orin (BK-HFWL) | I | DI | DI | DI | D | DI | D | D | DI | I | DI | DI | DI |
| Red Ralls Janet (BK-HGG) | I | D | D | D | D | DI | D | D | DI | DI | DI | DI | DI |
| Huaguan Crab (BK-HGHT) | DI | I | I | I | D | DI | D | D | D | D | DI | D | DI |
| Harrold Red Delicious (BK-HH) | I | D | D | I | I | DI | D | DI | D | D | DI | D | DI |
| Hong Crab 2 (BK-HHT2H) | DI | I | I | I | D | D | D | D | D | D | DI | D | DI |
| Stark Redgold (BK-HJ) | DI | DI | DI | I | I | DI | D | D | DI | DI | DI | DI | DI |
| HLWQ (BK-HLWQ) | I | DI | DI | DI | DI | D | D | D | DI | DI | DI | DI | DI |
| Holly (BK-Holly) | I | DI | DI | I | D | DI | D | D | D | D | DI | D | DI |
| Red Jonagold (BK-HQNJ) | I | D | DI | DI | DI | DI | D | DI | DI | DI | DI | DI | DI |
| Red Sekaiichii (BK-HSJY) | DI | DI | DI | I | I | I | DI | D | D | DI | D | DI | |
| Hongte (BK-HT) | I | D | D | DI | I | D | DI | D | D | DI | D | D | DI |
| Haitangguo (BK-HTG) | D | DI | I | I | D | D | D | D | D | D | DI | D | DI |
| Haitanghua (BK-HTH) | DI | I | I | I | D | D | D | DI | D | I | D | DI | |
| Huangtaiping (BK-HTP) | DI | DI | D | DI | DI | DI | D | DI | DI | D | DI | DI | DI |
| Hongxue (BK-HX) | I | I | I | DI | D | D | D | D | DI | DI | DI | DI | DI |
| Jincui (BK-JC) | DI | DI | DI | I | I | DI | D | I | D | D | DI | D | DI |
| Juda Fuji (BK-JDFS) | I | D | D | DI | DI | DI | D | D | DI | DI | DI | DI | DI |
| Jiguan (BK-JG) | DI | I | I | DI | D | D | D | D | D | D | DI | D | DI |
| Jinhong (BK-JH) | D | D | DI | I | DI | D | D | DI | DI | DI | DI | DI | DI |
| Jonagored (BK-Jonagored) | DI | DI | DI | DI | DI | DI | D | DI | DI | DI | DI | DI | DI |
| Jonathan (BK-Jonathan) | DI | DI | DI | I | DI | D | D | DI | DI | DI | DI | DI | DI |

| | | | | | | | | | | | | |
|---|---|---|---|---|---|---|---|---|---|---|---|---|
| Construction results of InDel marker genotype database of *Malus* germplasm resources ||||||||||||| 
| Himekami (BK-JS) | I | DI | DI | DI | DI | DI | D | D | D | D | DI | D | DI |
| Stark Blushing Golden (BK-JY) | D | D | DI | I | I | DI | D | I | DI | DI | DI | DI | DI |
| Classic Red Delicious (BK-KAHONG) | I | D | D | I | I | DI | D | DI | D | D | DI | D | DI |
| KLGDG Shandingzi (BK-KLGDGSDZ) | D | I | I | I | D | D | D | D | D | D | I | D | D |
| KOSZTELQ (BK-KOSZTELQ) | I | DI | DI | DI | D | DI | D | D | DI | DI | DI | D | DI |
| Sunflower (BK-KUIHUA) | DI | DI | DI | I | I | DI | D | I | DI | DI | DI | DI | DI |
| Lenghaitang (BK-LHT) | DI | I | I | I | D | D | D | DI | D | D | I | D | DI |
| Liberty (BK-liberty) | DI | DI | DI | DI | DI | D | D | DI | D | D | DI | D | DI |
| Lijiang Shandingzi (BK-LJSDZ) | DI | DI | I | I | D | D | D | DI | D | D | DI | D | DI |
| Laoshan 4 (BK-LS4H) | DI | I | I | I | D | D | D | D | D | D | I | D | DI |
| Ryoka no Kisetsu (BK-LX) | I | D | D | DI | DI | D | D | D | DI | DI | DI | DI | DI |
| Lvxiangjiao (BK-LXJ) | DI | D | DI | I | D | D | D | D | I | I | DI | I | DI |
| Liaozhen 1 (BK-LZ1H) | DI | I | I | I | DI | D | D | DI | D | DI | DI | DI | D |
| M7 (BK-M7) | I | DI | I | I | D | D | D | D | D | DI | DI | DI | DI |
| Meiguihong (BK-MGH) | I | D | D | I | I | DI | D | DI | D | D | D | D | DI |
| Meile (BK-ML) | I | DI | DI | I | I | DI | I | D | DI | I | DI | DI | DI |
| MM106 (BK-MM106) | I | I | I | DI | DI | I | D | DI | I | D | D | D | DI |
| Mengpaisi (BK-MPS) | I | DI | I | I | DI | DI | DI | D | D | D | DI | D | DI |
| Meixiang (BK-MX) | I | D | D | DI | DI | DI | D | D | DI | DI | DI | DI | DI |
| Ningqiu (BK-NQ) | I | DI | DI | DI | D | D | D | D | D | D | DI | D | DI |
| P16 (BK-P16) | DI | I | I | I | D | D | D | D | DI | D | DI | D | DI |
| P22 (BK-P22) | I | I | I | I | D | D | D | D | D | D | DI | D | DI |
| Pingdinghaitang (BK-PDHT) | DI | I | I | I | D | D | D | D | D | D | I | D | DI |
| Bianguo Crab (BK-PGHT) | DI | DI | I | DI | DI | D | D | DI | DI | I | DI | D | D |
| Pionier (BK-Pionier) | I | D | D | DI | D | DI | D | D | DI | D | DI | DI | DI |
| Prima (BK-Prima) | I | D | D | DI | D | I | D | D | DI | DI | DI | DI | DI |
| Pingyitiancha (BK-PYTC) | D | I | D | I | D | D | D | I | D | D | DI | DI | D |
| Qianxue (BK-QAINXUE) | D | D | DI | I | I | DI | DI | D | DI | DI | DI | DI | DI |
| Akifu 1 (BK-QF1) | I | D | D | DI | DI | DI | D | D | DI | DI | DI | DI | DI |
| Qingfu 13 (BK-QF13) | I | D | D | DI | DI | DI | D | D | DI | DI | DI | DI | DI |
| Seimei (BK-QM) | DI | DI | DI | DI | D | D | D | D | D | D | D | D | DI |
| Senshu (BK-QQ) | I | D | DI | DI | DI | DI | DI | D | D | D | D | D | DI |
| Aomori Early (BK-QSZS) | DI | DI | DI | I | DI | DI | DI | DI | DI | DI | DI | DI | DI |
| Qiuxiang (BK-QX) | DI | I | I | I | DI | D | D | D | D | D | D | D | DI |
| Qiuxing Crab (BK-QXHT) | DI | DI | D | DI | D | D | DI | DI | D | I | D | D | DI |
| Yanqing (BK-QY) | DI | DI | DI | DI | I | DI | DI | D | D | D | DI | D | DI |
| Regunzi (BK-RGZ) | DI | I | I | I | D | D | D | D | D | D | DI | D | DI |

| | | | | | | | | | | | | | |
|---|---|---|---|---|---|---|---|---|---|---|---|---|---|
| Construction results of InDel marker genotype database of *Malus* germplasm resources |||||||||||||
| Ruby (BK-Ruby) | I | D | D | DI | DI | DI | D | D | DI | DI | DI | DI | DI |
| Scarlet (BK-scarlet) | I | D | D | I | I | DI | D | DI | D | D | DI | D | DI |
| Sdw1 (BK-Sdw1) | DI | I | I | I | D | D | D | D | D | D | I | D | DI |
| Shandingzi 2 (BK-SDZ2H) | D | I | I | I | D | D | D | I | D | D | I | D | D |
| Su E Shandingzi (BK-SESDZ) | D | I | I | I | D | D | D | D | D | D | DI | D | DI |
| Shengfang 2 (BK-SF2) | I | D | D | DI | DI | D | D | D | DI | DI | DI | DI | DI |
| SH6 (BK-SH6) | DI | D | DI | DI | D | DI | D | D | D | DI | DI | DI | DI |
| Sankuaishi Crab 1 (BK-SKSHT1H) | DI | I | I | I | D | D | D | D | D | D | I | D | DI |
| Forest Apple (BK-SLPG) | DI | DI | I | DI | I | D | D | DI | D | D | DI | D | DI |
| Sieversii (BK-SWS) | DI | DI | I | I | D | D | D | DI | D | D | DI | D | DI |
| Sansa (BK-SX) | I | DI | I | DI | DI | D | DI | DI | DI | DI | DI | DI | D |
| Szampion (BK-Szampion) | DI | DI | I | DI | DI | D | D | DI | DI | DI | DI | DI | DI |
| T337 (BK-T337) | DI | DI | I | DI | DI | D | D | DI | D | DI | DI | DI | DI |
| Turkmen Apple (BK-TKMPG) | DI | DI | I | I | D | D | D | DI | D | D | DI | D | DI |
| Mato 1 (BK-TMYH) | DI | I | I | I | DI | DI | D | I | I | I | DI | I | DI |
| Trajian (BK-Trajian) | I | DI | DI | I | DI | D | D | D | D | D | DI | D | DI |
| Weiai 3 (BK-WA3) | DI | I | I | I | D | D | D | D | D | D | I | D | DI |
| Wanbai Crab (BK-WBHT) | D | DI | I | I | DI | DI | DI | D | DI | DI | DI | DI | DI |
| Wufengshan 1 (BK-WFS1H) | DI | I | I | I | D | D | D | D | D | D | I | D | DI |
| Wufengshan 4 (BK-WFS4H) | I | DI | DI | DI | D | DI | D | D | DI | DI | DI | DI | DI |
| Wufengshan Crab (BK-WFSHT) | D | DI | I | D | D | D | D | D | D | D | DI | D | D |
| Wufengshan Crab 2 (BK-WFSHT2H) | I | DI | DI | I | DI | D | D | I | D | D | DI | D | DI |
| Wufengshan Crab 6 (BK-WFSHT6H) | DI | DI | D | DI | D | D | D | D | D | D | DI | D | DI |
| Wifos (BK-wifos) | DI | I | I | DI | DI | D | D | DI | DI | DI | DI | DI | DI |
| Orei (BK-WL) | D | D | DI | I | I | DI | D | I | DI | DI | DI | DI | DI |
| Maypole (BK-WM) | DI | I | I | I | DI | D | D | D | D | D | DI | D | DI |
| Waltz (BK-WZ) | DI | I | I | I | I | DI | DI | DI | DI | DI | DI | DI | DI |
| Kotoku (BK-XD) | I | D | D | I | DI | DI | D | D | D | I | DI | D | DI |
| Xiaofanshan Binzi (BK-XFSBZ) | DI | I | I | I | D | DI | D | D | DI | D | DI | D | DI |
| Xiaofanshan Crab 4 (BK-XFSHT4H) | DI | I | I | I | D | D | D | D | D | D | DI | D | DI |
| Xiaogoumen Naizi (BK-XGMNZ) | DI | I | I | I | D | D | D | D | D | D | DI | D | DI |
| XGM Suan Binzi (BK-XGMSBZ) | DI | I | I | I | D | DI | D | D | DI | D | DI | D | DI |
| XGM Tian Binzi (BK-XGMTBZ) | I | I | I | I | D | D | D | DI | D | D | DI | D | DI |
| Starkrimson (BK-XHX) | I | D | D | I | I | DI | D | DI | D | D | DI | D | DI |
| Xinjiang 1 (BK-XJ1) | I | I | I | I | D | D | D | D | D | D | D | D | DI |
| Xinjiang 11 (BK-XJ11) | DI | D | D | DI | DI | DI | D | D | D | I | DI | D | DI |
| Xinjiang 14 (BK-XJ14) | DI | D | D | DI | DI | DI | D | D | D | I | DI | D | DI |
| Xinjiang 15 (BK-XJ15) | DI | DI | D | I | DI | I | D | D | D | DI | DI | D | D |
| Xinjiang 16 (BK-XJ16) | I | DI | DI | I | D | D | D | D | D | D | DI | D | DI |

| Construction results of InDel marker genotype database of *Malus* germplasm resources | | | | | | | | | | | | | |
|---|---|---|---|---|---|---|---|---|---|---|---|---|---|
| Xinjiang 17 (BK-XJ17) | DI | DI | DI | DI | DI | DI | D | D | DI | I | DI | D | DI |
| Xinjiang 18 (BK-XJ18) | DI | DI | DI | DI | DI | DI | D | D | DI | I | DI | D | DI |
| Xinjiang 19 (BK-XJ19) | DI | D | DI | DI | I | DI | DI | DI | DI | D | DI | D | DI |
| Xinjiang 21 (BK-XJ21) | DI | DI | DI | DI | D | D | D | D | D | D | DI | DI | DI |
| Xinjiang 22 (BK-XJ22) | I | I | I | I | D | D | D | D | I | D | DI | D | DI |
| Xinjiang 24 (BK-XJ24) | DI | I | I | I | D | D | D | D | D | D | DI | D | DI |
| Xinjiang 26 (BK-XJ26) | DI | D | D | DI | DI | DI | D | D | D | I | DI | D | DI |
| Xinjiang 28 (BK-XJ28) | DI | D | DI | DI | I | DI | DI | DI | DI | D | DI | D | DI |
| Xinjiang 29 (BK-XJ29) | D | DI | DI | I | DI | D | D | DI | D | DI | DI | D | DI |
| Xinjiang 31 (BK-XJ31) | I | D | D | DI | D | DI | D | D | D | DI | DI | D | D |
| Xinjiang 3 (BK-XJ3H) | I | DI | DI | DI | DI | DI | D | D | DI | DI | DI | DI | DI |
| Xinjiang 6 (BK-XJ6H) | D | D | D | DI | D | D | D | D | DI | DI | DI | D | DI |
| Xinjiang 7 (BK-XJ7) | DI | D | D | DI | DI | DI | D | D | D | I | DI | D | DI |
| Xinjiang 8 (BK-XJ8) | I | DI | DI | I | D | DI | D | D | DI | D | DI | D | DI |
| Xinjiang 9 (BK-XJ9) | D | DI | DI | I | DI | D | D | DI | D | DI | DI | D | DI |
| Xijin Crab (BK-XJHT) | D | DI | I | DI | D | D | D | D | DI | D | DI | D | DI |
| Xiaomian Crab (BK-XMHT) | D | I | I | I | D | D | D | D | D | I | D | DI |
| New Jonagold (BK-XQNJ) | DI | DI | DI | DI | DI | DI | DI | DI | DI | DI | DI | DI | DI |
| Xiaoshuai (BK-XS) | I | D | D | I | I | DI | D | D | D | DI | D | D |
| Shinsekai (BK-XSJ) | DI | DI | DI | DI | DI | D | D | D | D | DI | D | DI |
| Xiangyanghong (BK-XYH) | I | D | D | DI | DI | I | D | D | DI | DI | DI | DI | DI |
| Italy Early Red (BK-YDLZH) | DI | D | DI | DI | I | D | DI | I | D | D | DI | D | DI |
| Yanfu 10 (BK-YF10) | I | D | D | DI | DI | D | D | D | DI | DI | DI | DI |
| Yoko (BK-YG) | DI | I | I | DI | DI | DI | DI | D | DI | DI | DI | DI | DI |
| Yuanhong (BK-YH) | DI | D | D | DI | D | D | D | D | D | D | DI | DI | D |
| Tehong 2 (BK-YH2) | I | D | D | DI | DI | DI | D | D | DI | DI | DI | DI | DI |
| Yanhongmi (BK-YHM) | D | D | D | D | D | DI | D | D | D | I | DI | DI | DI |
| Youliang Spur (BK-YLDZ) | I | D | D | DI | DI | DI | D | D | DI | DI | DI | DI | DI |
| Yuanye Crab (BK-YYHT) | DI | I | I | I | D | D | D | D | D | D | DI | D | DI |
| Stark Jumbo (BK-ZB) | DI | D | DI | DI | DI | D | D | D | DI | DI | DI | DI | DI |
| Jumbo Orin (BK-ZBWL) | DI | DI | I | I | I | DI | DI | DI | DI | DI | DI | DI | DI |
| Zhuifeng 1 (BK-ZF1H) | D | DI | D | I | DI | D | D | I | D | D | D | D | DI |
| Zhuifeng 2 (BK-ZF2H) | D | I | I | I | D | D | D | I | D | I | D | D |
| Early Fuji (BK-ZFS) | I | D | D | DI | DI | DI | D | D | DI | DI | DI | DI | DI |
| Xiaofanshan Crab (BK-ZFSHT) | DI | I | I | I | D | D | D | D | D | D | DI | D | DI |
| Zisai Pearl (BK-Zisai) | D | DI | DI | DI | DI | DI | D | DI | DI | DI | DI | D | D |
| Geneva Early (BK-ZJ) | I | DI | DI | I | D | I | D | D | D | D | DI | DI | DI |
| 13-26W (CL-1) | DI | DI | DI | DI | DI | D | D | DI | DI | DI | DI | DI | DI |

-continued

Construction results of InDel marker genotype database of *Malus* germplasm resources

| | | | | | | | | | | | | | |
|---|---|---|---|---|---|---|---|---|---|---|---|---|---|
| 23-127 (CL-2) | DI | I | I | I | DI | DI | D | DI | DI | DI | DI | DI | DI |
| 50-30 (CL-3) | I | D | D | DI | DI | DI | D | D | DI | DI | DI | DI | DI |
| 50-32 (CL-4) | I | D | D | I | I | DI | D | D | D | D | DI | D | DI |
| H5-101 (CL-5) | I | DI | DI | DI | I | DI | D | I | DI | DI | DI | DI | DI |
| Pingyan (CL-6) | DI | DI | DI | DI | DI | D | D | DI | DI | DI | DI | DI | DI |
| Deqin Crab (DQ) | D | I | I | I | D | D | D | I | D | D | DI | DI | D |
| Jin 18 (GY-1) | I | D | D | DI | DI | DI | D | D | DI | D | DI | DI | DI |
| Fengfeng Baleng (GY-2) | D | D | I | DI | D | D | D | D | D | DI | DI | D | DI |
| Hanfu 6 (GY-3) | I | D | D | DI | DI | DI | D | D | DI | D | DI | DI | DI |
| Hanfu 3 (GY-4) | I | D | D | DI | I | I | I | D | DI | D | DI | DI | D |
| 95/06 (GZ-1) | D | DI | DI | DI | D | DI | D | D | DI | D | DI | D | DI |
| 107/06 (GZ-2) | I | DI | DI | DI | D | D | D | D | I | I | DI | DI | DI |
| 117/06 (GZ-3) | I | DI | DI | DI | DI | D | D | DI | DI | I | DI | DI | DI |
| 119/06 (GZ-4) | DI | DI | DI | I | D | DI | D | D | I | I | DI | DI | DI |
| Jinxiu Crab (GZ-5) | I | D | D | I | I | DI | D | D | D | D | DI | D | DI |
| Zhizun Fuji (HS-1) | I | D | D | DI | DI | DI | D | D | DI | DI | DI | DI | DI |
| Fuji No. 1 (HS-10) | I | D | D | DI | DI | DI | D | D | DI | DI | DI | DI | DI |
| Red Jonaprince (HS-12) | DI | DI | DI | DI | DI | DI | DI | DI | DI | DI | DI | DI | DI |
| Nic29 (HS-13) | DI | DI | I | DI | DI | D | D | DI | D | DI | DI | DI | DI |
| Azhen Fuji (HS-14) | I | D | D | DI | DI | DI | D | D | DI | DI | DI | DI | DI |
| Envy (HS-15) | I | D | D | DI | I | DI | DI | DI | D | D | DI | D | D |
| Rosegrow (HS-16) | I | DI | DI | I | DI | DI | DI | I | DI | DI | DI | DI | DI |
| Canzy (HS-17) | DI | D | DI | DI | I | DI | DI | I | DI | DI | DI | DI | D |
| Fubrax (HS-2) | I | D | D | DI | DI | DI | D | D | DI | DI | DI | DI | DI |
| Mitchgla (HS-3) | DI | D | DI | DI | I | D | DI | I | D | D | DI | D | DI |
| Fujiko (HS-4) | I | D | D | DI | DI | DI | D | D | DI | DI | DI | DI | DI |
| Buckeye Gala (HS-5) | DI | DI | DI | DI | I | D | I | I | D | D | DI | D | DI |
| Fujion (HS-6) | I | D | D | I | I | DI | D | DI | D | D | DI | D | DI |
| Modi (HS-7) | DI | DI | DI | I | D | D | D | I | D | D | DI | D | DI |
| Jiangxue (HS-8) | DI | D | D | I | DI | DI | D | I | D | D | DI | D | DI |
| September Wonder Fuji (HS-9) | I | D | D | DI | DI | DI | D | D | DI | DI | DI | DI | DI |
| Linqin Crab (LQ) | D | I | I | I | D | D | D | DI | D | D | DI | DI | DI |
| Lushan Sanye (LSSY) | D | DI | I | I | D | D | D | I | D | D | DI | D | D |
| 83-2 (MDJ-1) | DI | DI | DI | I | DI | D | D | DI | DI | DI | DI | DI | DI |
| Tianfeng (MDJ-9) | I | DI | DI | I | D | D | D | D | D | DI | DI | D | DI |
| Oregon Spur II-red (OR-1) | I | D | D | I | I | DI | D | DI | D | DI | D | D | DI |
| Oregon Spur II-green (OR-2) | I | D | D | I | I | DI | D | DI | D | DI | DI | D | DI |

| Construction results of InDel marker genotype database of *Malus* germplasm resources | | | | | | | | | | | | | |
|---|---|---|---|---|---|---|---|---|---|---|---|---|
| E3N2 (OR-3) | I | D | D | I | I | DI | D | DI | D | DI | DI | D | DI |
| E4N1 (OR-4) | I | D | D | I | I | DI | D | DI | D | D | DI | D | DI |
| E4N2 (OR-5) | I | D | D | I | I | DI | D | DI | D | D | DI | D | DI |
| W6N1 (OR-6) | I | D | D | I | I | DI | D | DI | D | D | DI | D | DI |
| W6S5 (OR-7) | I | D | D | I | I | DI | D | DI | D | DI | DI | D | DI |
| W8S3 (OR-8) | I | D | D | I | I | DI | D | D | D | D | DI | D | DI |
| Daihong (QD-1) | I | DI | I | I | I | DI | DI | D | D | D | DI | D | DI |
| Tangmutian (QD-10) | I | D | D | DI | DI | DI | D | D | DI | DI | DI | DI | DI |
| Shanjin Crab N1 (QD-11) | D | I | I | I | D | D | D | I | D | D | I | D | D |
| Shanjin Crab N2 (QD-12) | D | I | I | I | D | DI | D | I | DI | D | I | D | D |
| E zhen 1 (QD-13) | D | I | I | I | D | D | D | D | DI | I | DI | DI | DI |
| E zhen 2 (QD-14) | D | DI | I | DI | D | D | D | D | D | D | DI | D | DI |
| E zhen 3 (QD-15) | D | DI | DI | DI | D | D | D | D | D | I | DI | D | DI |
| E zhen 4 (QD-16) | D | DI | I | DI | D | D | D | D | DI | DI | DI | DI | DI |
| E zhen 5 (QD-17) | D | DI | I | DI | D | D | D | D | DI | DI | DI | DI | DI |
| Haihong (QD-19) | DI | I | I | I | D | D | D | D | D | D | DI | D | DI |
| Qingfu 2 (QD-2) | I | D | D | DI | DI | DI | D | D | DI | DI | DI | DI | DI |
| Telamon (QD-20) | DI | I | I | I | I | DI | D | D | DI | DI | DI | DI | DI |
| Fuyan (QD-21) | DI | DI | DI | I | I | DI | I | D | DI | DI | DI | DI | DI |
| Hongxun 1 (QD-22) | DI | I | D | I | D | DI | D | D | D | D | D | D | D |
| Rushan Fuji (QD-23) | I | D | D | DI | DI | DI | D | D | DI | DI | DI | DI | DI |
| Jiudian Spur (QD-24) | I | D | D | DI | DI | DI | D | D | DI | DI | DI | DI | DI |
| Ruihong (QD-25) | DI | D | DI | DI | I | D | DI | I | D | D | DI | D | DI |
| Zhongnvshi (QD-26) | DI | D | D | I | DI | D | D | DI | D | D | DI | D | DI |
| 2001 Spur (QD-27) | I | D | D | DI | DI | DI | D | D | DI | DI | DI | DI | DI |
| Fuli (QD-28) | I | DI | DI | DI | I | I | D | D | DI | D | DI | D | DI |
| Tuanwang semi-Spur (QD-29) | I | D | D | DI | DI | DI | D | D | DI | DI | DI | DI | DI |
| Qingfu 3 (QD-3) | I | D | D | DI | DI | DI | D | D | DI | DI | DI | DI | DI |
| Longfu (QD-30) | I | D | D | DI | DI | DI | D | D | DI | DI | DI | DI | DI |
| Baotou Linqin (QD-31) | D | DI | D | I | D | DI | D | I | D | D | DI | D | DI |
| Yanfu 6 (QD-32) | I | D | D | DI | DI | DI | D | D | DI | DI | DI | DI | DI |
| SH40-2 seedling (QD-4) | DI | I | I | DI | D | D | D | D | D | D | DI | DI | DI |
| Saijin (QD-5) | D | DI | I | I | I | D | D | D | DI | DI | DI | DI | DI |
| Nagafu 12 (QD-6) | I | D | D | DI | DI | DI | D | D | DI | DI | DI | DI | DI |
| Caoyuan Crab (QD-7) | I | D | I | I | D | D | D | D | D | D | DI | D | D |
| Xiaojin Crab (QD-8) | D | I | DI | I | DI | DI | D | I | DI | DI | DI | DI | DI |
| Shuangyanghong (QD-9) | DI | D | DI | DI | I | D | DI | I | D | D | DI | D | DI |
| Qianxian Crab (QX-1) | D | DI | I | DI | D | D | D | D | D | D | DI | D | DI |

-continued

| Construction results of InDel marker genotype database of *Malus* germplasm resources | | | | | | | | | | | | | |
|---|---|---|---|---|---|---|---|---|---|---|---|---|
| Ruixue (ruixue) | DI | DI | DI | DI | D | DI | D | D | I | I | DI | I | DI |
| Ruiyang (RY) | DI | DI | DI | D | I | DI | D | D | DI | DI | DI | DI | DI |
| Yanyuan 1 (SC-1) | DI | DI | DI | I | DI | DI | D | DI | DI | DI | DI | DI | DI |
| Yanyuan 2 (SC-2) | DI | I | I | I | DI | D | D | DI | D | D | DI | D | DI |
| Yanyuan 3 (SC-3) | I | D | D | DI | DI | DI | D | D | DI | DI | DI | DI | DI |
| Yanyuan 4 (SC-4) | DI | I | I | I | DI | D | D | DI | D | D | DI | D | DI |
| Yanyuan 5 (SC-5) | DI | DI | DI | I | D | DI | D | D | DI | DI | DI | DI | DI |
| Yanyuan 6 (SC-6) | DI | DI | DI | I | DI | D | D | D | D | D | DI | D | DI |
| Yanyuan 7 (SC-7) | DI | DI | DI | DI | DI | DI | D | DI | DI | DI | DI | DI | DI |
| Mitchgala (SX-10) | DI | D | DI | DI | I | D | DI | I | D | D | DI | D | DI |
| Zhongqiuwang Linyi (SX-11) | I | DI | DI | I | I | I | DI | D | D | D | DI | D | DI |
| Linyi Meiguo 5 (SX-12) | DI | DI | DI | I | I | DI | D | I | D | D | DI | D | DI |
| Liquan Spur Fuji (SX-13) | I | D | D | DI | DI | DI | D | D | DI | DI | DI | DI | DI |
| Qiulimu (SX-14) | I | DI | DI | I | DI | DI | D | D | D | I | DI | D | DI |
| Qincui (SX-15) | I | DI | DI | DI | DI | DI | D | D | D | D | DI | D | D |
| Taigu Shaguo Late (SX-17) | DI | I | I | I | D | D | DI | D | D | D | DI | D | DI |
| Lingyige Hongrou (SX-18) | I | DI | DI | DI | D | D | D | D | I | I | DI | DI | DI |
| Shenai LS (SX-19) | D | I | I | D | D | DI | D | D | D | D | DI | D | DI |
| Linyi Meiguo 8 (SX-2) | DI | DI | DI | DI | DI | D | D | D | D | D | DI | D | DI |
| Liga (SX-20) | DI | D | DI | DI | I | D | DI | I | D | D | DI | D | DI |
| Y-1 (SX-21) | D | I | D | I | D | D | D | I | D | DI | DI | DI | D |
| B009 (SX-22) | DI | DI | D | I | D | D | D | I | D | DI | DI | D | D |
| Jinfu 1 (SX-23) | I | D | D | DI | DI | DI | D | D | DI | DI | DI | DI | DI |
| Hongmantang (SX-24) | D | I | I | I | DI | D | D | DI | D | D | DI | D | DI |
| Y-2 (SX-25) | D | I | D | I | D | D | D | I | D | D | DI | D | D |
| Y-3 (SX-26) | D | I | D | I | D | D | D | I | D | D | DI | D | D |
| Xinliangxiang (SX-27) | I | D | D | DI | DI | D | D | DI | DI | DI | DI | DI | DI |
| Ennike Gala (SX-28) | DI | D | DI | DI | I | D | DI | I | D | D | DI | D | DI |
| Linyi Meiguo 6 (SX-3) | DI | DI | DI | DI | I | D | D | I | D | D | DI | D | DI |
| Linyi Meiguo 2 (SX-30) | I | D | D | DI | DI | DI | D | D | DI | DI | DI | DI | DI |
| Donglimu (SX-33) | I | DI | DI | I | DI | DI | D | D | D | I | DI | D | DI |
| Linyi Meiguo 1 (SX-34) | DI | DI | DI | DI | DI | D | D | D | D | D | DI | D | DI |
| Linyi Meiguo 4 (SX-4) | DI | D | DI | DI | I | DI | D | I | DI | DI | DI | DI | DI |
| Qinyang (SX-6) | DI | D | DI | I | I | D | DI | I | D | D | DI | D | D |
| Taiguo Shaguo Early (SX-7) | DI | I | I | I | D | D | D | D | D | D | DI | D | DI |
| Yuhua Zaofu (SX-8) | I | D | D | DI | DI | DI | D | D | DI | DI | DI | DI | DI |
| 78-M18 (SY-1) | D | DI | I | I | I | D | D | DI | D | D | DI | DI | DI |
| Jinping (SY-10) | DI | D | DI | I | I | DI | D | DI | I | I | DI | I | D |

| | | | | | | | | | | | | | |
|---|---|---|---|---|---|---|---|---|---|---|---|---|---|
| Construction results of InDel marker genotype database of *Malus* germplasm resources ||||||||||||||
| Longqiu (SY-11) | I | DI | DI | DI | D | D | D | D | D | D | DI | D | D |
| Longfeng (SY-12) | D | D | D | DI | D | D | D | D | D | I | DI | D | D |
| Xiangjiaoguo (SY-14) | DI | D | DI | I | DI | D | D | I | DI | DI | DI | DI | DI |
| Longguan (SY-15) | DI | I | DI | I | DI | D | D | D | D | D | D | D | DI |
| Longshuai (SY-16) | D | D | D | I | D | D | D | DI | DI | DI | DI | D | DI |
| Zixiang (SY-17) | I | DI | DI | I | D | D | DI | D | D | I | D | DI |
| Huahong (SY-19) | DI | I | DI | I | DI | D | D | D | D | DI | D | DI |
| Binlang (SY-2) | DI | D | DI | I | DI | D | D | I | DI | DI | DI | DI | DI |
| Qiufengmi (SY-20) | I | I | I | I | D | D | D | D | D | I | D | DI |
| Honglingdang (SY-21) | DI | DI | DI | I | D | D | D | D | D | DI | D | D |
| Qiulu (SY-22) | D | D | D | DI | DI | DI | D | D | D | DI | D | DI |
| Longhong (SY-23) | DI | I | I | I | DI | D | D | D | D | DI | D | DI |
| Milk (SY-3) | I | D | D | I | I | DI | D | D | D | DI | D | DI |
| Hanfu (SY-4) | I | DI | DI | DI | DI | D | D | DI | DI | I | DI | DI | DI |
| Toko (SY-5) | DI | DI | DI | D | I | D | D | I | D | D | DI | D | DI |
| Jinhong (SY-6) | D | D | DI | I | DI | D | D | DI | DI | DI | DI | DI | DI |
| K9 (SY-7) | DI | DI | DI | I | D | D | D | D | D | DI | D | D |
| 03-06-04 (SY-8) | D | DI | DI | DI | D | D | D | DI | DI | DI | DI | DI |
| Olga (SY-9) | DI | DI | D | I | DI | DI | DI | D | D | DI | D | DI |
| Gala 4x (TA-1) | DI | D | DI | DI | I | D | DI | I | D | D | DI | D | DI |
| Juda Fuji (TA-11) | I | D | D | DI | DI | DI | D | DI | DI | DI | DI | DI |
| Luli (TA-12) | DI | DI | I | I | D | DI | D | I | DI | DI | DI | DI |
| Luping 1 (TA-13) | DI | DI | DI | DI | DI | D | D | DI | D | D | DI | D | DI |
| Luping 2 (TA-14) | DI | D | DI | DI | DI | D | D | DI | D | D | DI | D | DI |
| Luping 5 (TA-15) | DI | D | D | DI | DI | D | D | DI | DI | DI | DI | DI | DI |
| Luyan (TA-16) | DI | DI | I | I | D | DI | D | DI | DI | DI | DI | DI |
| Meinong (TA-17) | I | D | D | DI | DI | DI | D | D | DI | DI | DI | DI |
| Akifu 19 (TA-18) | I | D | D | DI | DI | DI | D | D | DI | DI | DI | DI |
| Akifu 39 (TA-19) | I | D | D | DI | DI | DI | D | D | DI | DI | DI | DI |
| Hanfu 4x (TA-2) | DI | DI | DI | DI | DI | I | DI | DI | D | D | DI | D | DI |
| Qiufuhong (TA-20) | I | D | D | DI | DI | D | D | DI | DI | DI | DI | DI |
| Qunfu 1 (TA-21) | I | D | D | DI | DI | DI | D | D | DI | DI | DI | DI |
| Shengfang (TA-22) | I | D | D | DI | DI | DI | D | D | DI | DI | DI | DI |
| Alps Otome (TA-27) | DI | I | I | I | DI | D | D | I | DI | DI | DI | DI |
| Early Fuji (TA-28) | I | D | D | DI | DI | DI | D | D | DI | DI | DI | DI |
| BP (TA-3) | DI | DI | I | I | D | D | D | D | DI | I | I | DI | DI |
| Yishuihong (TA-32) | I | D | D | DI | DI | DI | D | D | DI | DI | DI | DI |
| BP-176 (TA-4) | DI | DI | DI | I | D | D | D | DI | I | DI | DI | DI |
| G41 (TA-5) | DI | I | I | D | D | I | D | DI | D | D | DI | D | DI |

-continued

| Construction results of InDel marker genotype database of *Malus* germplasm resources | | | | | | | | | | | | | |
|---|---|---|---|---|---|---|---|---|---|---|---|---|
| G935 (TA-6) | I | I | I | DI | DI | D | D | DI | D | DI | DI | DI | DI |
| P60 (TA-7) | DI | I | I | I | DI | DI | D | D | DI | D | I | D | DI |
| Fuji (TA-9) | I | D | D | DI | DI | DI | D | D | DI | DI | DI | DI | DI |
| Tianfu 1 (TS-1) | I | D | D | DI | DI | DI | D | D | DI | DI | DI | DI | DI |
| &28 (TS-13) | I | D | D | DI | DI | DI | D | D | DI | DI | DI | DI | DI |
| Red Chief (TS-14) | I | D | D | I | I | DI | D | D | D | DI | D | DI |
| New Redchief (TS-2) | I | D | D | I | I | DI | D | D | D | DI | D | DI |
| Chaohongxing (TS-3) | I | D | D | I | I | DI | D | DI | D | D | DI | D | DI |
| Aozhou 1 (TS-5) | DI | DI | DI | I | I | I | D | D | D | DI | D | DI |
| Tianfu 2 (TS-6) | I | D | D | DI | DI | DI | D | D | DI | DI | DI | DI | DI |
| Judeline (TS-7) | DI | DI | I | I | DI | I | I | D | DI | DI | DI | DI | DI |
| Judestar (TS-8) | I | DI | I | I | I | I | D | D | DI | DI | DI | DI | DI |
| Judaine (TS-9) | DI | DI | I | I | DI | I | I | D | DI | DI | DI | DI | DI |
| WH-5 (WH-1) | I | D | D | DI | D | DI | D | D | DI | DI | DI | DI | DI |
| Italy Smothe (WH-10) | DI | DI | I | I | I | DI | DI | DI | DI | DI | DI | DI | DI |
| Bai Crab (WH-2) | DI | I | I | I | D | D | D | D | DI | D | DI | D | DI |
| Hongguang (WH-4) | DI | DI | DI | DI | I | DI | D | I | DI | DI | DI | DI | DI |
| Huangcui (WH-5) | I | DI | DI | DI | I | DI | D | I | DI | DI | DI | DI | DI |
| Qinglin (WH-6) | I | DI | I | I | I | I | DI | D | D | DI | D | DI |
| Harlikar (WH-8) | I | DI | DI | I | I | I | DI | D | DI | I | DI | DI | DI |
| Italy Gala (WH-9) | DI | D | DI | DI | I | D | DI | I | D | D | DI | D | DI |
| Wushan Bianye (WSBY) | D | I | I | I | D | D | D | I | D | D | DI | DI | DI |
| Xin 1 (XC-1) | I | D | D | D | I | D | D | I | D | DI | D | DI |
| Xin 5 (XC-2) | I | D | D | D | I | D | D | D | D | D | DI | D | D |
| Hanfu 3x (XC-3) | I | D | D | D | I | D | D | I | I | I | DI | I | DI |
| Gala 4x (XC-4) | DI | D | DI | DI | I | D | DI | I | D | D | DI | D | DI |
| Weizhimuben (XC-5) | DI | DI | D | DI | DI | DI | D | DI | DI | D | DI | DI | DI |
| Chaguo (XC-CG) | DI | I | I | I | D | D | D | DI | D | D | DI | DI | DI |
| Donghongguo (XC-DHG) | DI | DI | D | DI | D | DI | D | D | D | DI | I | DI | DI |
| Fuxian Sanye (XC-FXXY) | D | I | I | I | D | D | D | I | D | D | I | D | D |
| Hongsanye (XC-HSY) | D | I | D | I | D | I | D | I | D | D | I | DI | D |
| Jilin Xiaohong Crab (XC-JILINXIAOHONG-HAITANG) | DI | DI | D | I | D | D | D | DI | D | D | DI | DI | DI |
| Jilin Xiaohuang Crab (XC-JILINXIAOHUANG-HAITANG) | DI | DI | D | I | D | I | D | I | D | D | DI | DI | DI |
| Jilin Huang Crab (XC-JLHHT) | DI | DI | D | I | D | I | D | I | D | D | DI | DI | DI |
| Shajin Crab (XC-JSHT) | D | I | I | I | D | D | D | I | D | D | I | D | D |
| Longdong Crab (XC-LDHT) | D | I | I | I | D | D | D | I | D | D | I | D | D |

-continued

Construction results of InDel marker genotype database of *Malus* germplasm resources

| | | | | | | | | | | | | | |
|---|---|---|---|---|---|---|---|---|---|---|---|---|---|
| Lushi Crab (XC-LSHT) | D | I | I | I | D | D | D | I | D | D | I | D | D |
| Laiwunanyan (XC-LWNY) | DI | I | I | I | D | D | D | DI | D | D | DI | DI | DI |
| Linzhi (XC-LZ) | D | I | I | I | D | DI | D | I | D | D | DI | DI | DI |
| Mao Shandingzi (XC-MSDZ) | D | I | I | I | D | D | D | I | D | D | I | D | D |
| Pingyitiancha (XC-PYTC) | D | I | D | I | D | D | D | DI | D | D | DI | DI | D |
| Qiuzi (XC-QZ) | I | I | I | I | D | D | D | DI | D | D | D | D | DI |
| Sichuan Bianye (XC-SCBY) | D | I | I | I | D | D | D | I | D | D | DI | DI | DI |
| Shandingzi (XC-SDZ) | D | I | D | I | D | D | D | DI | D | D | I | D | D |
| Weixi Sanye (XC-WXSY) | DI | I | DI | I | D | D | D | I | D | D | DI | D | D |
| Xifu Crb (XC-XFHT) | D | I | I | I | D | D | D | I | D | D | I | DI | DI |
| Xiaojin Bianye (XC-XJBY) | D | I | DI | I | D | D | D | I | D | D | DI | DI | D |
| Xinjiang Yepingguo (XC-XJYHT) | DI | DI | I | I | D | D | D | DI | D | D | DI | D | DI |
| Yajiang Bianye (XC-YJBY) | D | I | I | I | D | D | D | I | D | D | DI | D | D |
| Yingye Crab (XC-YYHT) | D | I | I | I | D | DI | D | I | D | D | I | D | D |
| Zhaai (XC-ZA) | D | I | D | I | D | DI | D | I | D | D | I | D | D |
| Zumi Crab (XC-ZMHT) | D | DI | D | I | D | D | D | I | D | D | DI | D | DI |
| Pink Lady (XN-FHNS) | I | DI | DI | I | DI | D | DI | DI | DI | DI | DI | DI | DI |
| Hongrou 1 (XN-HR1) | DI | DI | DI | I | D | D | D | D | D | I | DI | D | DI |
| Hongrou 2 (XN-HR2) | I | DI | DI | I | DI | DI | D | D | D | DI | DI | D | DI |
| Hongrou 3 (XN-HR3) | I | I | I | I | D | D | D | DI | D | DI | DI | D | DI |
| Hongrou 4 (XN-HR4) | I | I | I | I | DI | DI | D | D | D | DI | DI | D | DI |
| Hongrou 5 (XN-HR5) | DI | DI | DI | I | D | D | D | D | D | D | DI | D | DI |
| Hongrou 6 (XN-HR6) | DI | D | D | I | DI | DI | D | D | D | D | DI | D | DI |
| Hongrou 7 (XN-HR7) | I | D | D | I | D | D | D | D | D | D | DI | D | DI |
| Ambrosia (XN-MW) | I | DI | DI | I | I | DI | DI | D | DI | DI | DI | DI | DI |
| Xinjiang 10 (XN-XJ10) | I | I | I | I | D | D | D | D | D | D | DI | DI | DI |
| Xinjiang 11 (XN-XJ11) | DI | I | I | I | D | D | D | D | D | D | DI | DI | DI |
| Xinjiang 12 (XN-XJ12) | I | I | I | I | D | D | D | D | D | D | DI | DI | DI |
| Xinjiang 13 (XN-XJ13) | DI | I | I | I | DI | DI | D | D | D | I | DI | D | DI |
| Xinjiang 14 (XN-XJ14) | DI | DI | DI | I | D | D | D | D | D | I | D | DI | |
| Xinjiang 15 (XN-XJ15) | I | I | I | DI | I | DI | DI | D | DI | I | DI | DI | DI |
| Xinjiang 16 (XN-XJ16) | I | DI | DI | I | DI | DI | D | D | D | I | DI | D | DI |
| Xinjiang 17 (XN-XJ17) | D | I | I | I | D | D | D | D | D | D | DI | D | DI |
| Xinjiang 18 (XN-XJ18) | DI | D | D | I | D | DI | D | D | D | D | DI | D | DI |
| Xinjiang 19 (XN-XJ19) | DI | I | I | I | D | D | D | D | D | D | DI | D | DI |
| Xinjiang 2 (XN-XJ2) | D | I | I | I | D | D | D | D | D | D | I | D | DI |
| Xinjiang 20 (XN-XJ20) | I | DI | DI | I | D | D | D | D | D | D | DI | DI | DI |
| Xinjiang 21 (XN-XJ21) | D | I | I | DI | D | D | D | D | D | I | DI | D | DI |
| Xinjiang 23 (XN-XJ23) | DI | DI | I | DI | D | D | D | D | D | D | DI | DI | DI |

-continued

| Construction results of InDel marker genotype database of *Malus* germplasm resources | | | | | | | | | | | | | |
|---|---|---|---|---|---|---|---|---|---|---|---|---|---|
| Xinjiang 24 (XN-XJ24) | DI | D | DI | DI | D | D | D | D | D | D | DI | D | DI |
| Xinjiang 25 (XN-XJ25) | I | I | I | I | D | DI | D | D | D | D | DI | D | DI |
| Xinjiang 27 (XN-XJ27) | I | I | I | DI | I | DI | DI | D | DI | I | DI | DI | DI |
| Xinjiang 3 (XN-XJ3) | DI | I | I | I | D | D | D | D | D | D | DI | D | DI |
| Xinjiang 4 (XN-XJ4) | DI | I | I | DI | D | D | D | D | D | D | DI | D | DI |
| Xinjiang 5 (XN-XJ5) | DI | I | I | DI | D | D | D | D | D | D | I | D | D |
| Xinjiang 7 (XN-XJ7) | DI | I | D | I | D | D | D | D | D | D | DI | D | DI |
| Xinjiang 8 (XN-XJ8) | DI | DI | I | DI | D | D | D | D | D | D | DI | D | DI |
| Xinjiang 9 (XN-XJ9) | I | DI | DI | I | D | D | D | D | D | DI | DI | D | DI |
| Yueguan (XY-10) | DI | D | D | D | DI | D | D | D | DI | DI | DI | DI | DI |
| Yuehua (XY-11) | I | DI | DI | DI | DI | D | D | D | D | D | DI | D | D |
| Yueyan (XY-12) | I | I | I | I | D | DI | DI | DI | DI | DI | DI | DI | DI |
| Bud Sport 5 (XY-13) | I | D | D | DI | DI | DI | D | D | DI | DI | DI | DI | DI |
| Bud Sport 3 (XY-14) | I | D | D | DI | DI | DI | D | D | DI | DI | DI | DI | DI |
| Longfu (XY-15) | I | D | D | DI | DI | DI | D | D | DI | DI | DI | DI | DI |
| Yuemei (XY-18) | D | DI | DI | I | DI | I | D | I | I | DI | DI | I | DI |
| Hanfu (XY-2) | I | DI | DI | DI | DI | D | D | DI | DI | I | DI | DI | DI |
| Linyi Fuji (XY-20) | I | D | D | DI | DI | DI | D | D | DI | DI | DI | DI | DI |
| Yishui Fuji (XY-22) | I | D | D | DI | DI | DI | D | D | DI | DI | DI | DI | DI |
| Hongjinfu (XY-25) | I | D | D | DI | DI | DI | D | D | DI | DI | DI | DI | DI |
| Beni Oshu (XY-26) | I | D | D | DI | DI | DI | D | D | DI | DI | DI | DI | DI |
| Chuizhi Fuji (XY-27) | I | D | D | DI | DI | DI | D | D | DI | DI | DI | DI | DI |
| Yueshuai (XY-28) | D | DI | DI | DI | I | DI | DI | D | DI | DI | DI | DI | DI |
| Shichinohe 2 (XY-29) | I | D | D | DI | DI | DI | D | D | DI | DI | DI | DI | DI |
| 74-178 (XY-3) | I | DI | I | DI | I | D | D | I | DI | DI | DI | DI | DI |
| KAKUFUJI (XY-30) | I | D | D | DI | DI | DI | D | D | DI | DI | DI | DI | DI |
| Royal Fuji 21 (XY-35) | I | D | D | DI | DI | DI | D | D | DI | DI | DI | DI | DI |
| Qiquan Spur (XY-36) | I | D | D | DI | DI | DI | D | D | DI | DI | DI | DI | DI |
| Juda Fuji (XY-37) | DI | DI | DI | DI | I | DI | D | I | DI | DI | DI | DI | DI |
| 7-211 (XY-4) | D | DI | DI | I | DI | D | D | I | I | DI | DI | I | DI |
| Yanfu 0 (XY-41) | I | D | D | DI | DI | DI | D | D | DI | DI | DI | DI | DI |
| Spur Fuji (XY-42) | I | D | D | DI | DI | DI | D | D | DI | DI | DI | DI | DI |
| Bayue fushiwang (XY-43) | I | D | D | DI | DI | DI | D | D | DI | DI | DI | DI | DI |
| Huangfu 7 (XY-44) | I | D | D | DI | DI | DI | D | D | DI | DI | DI | DI | DI |
| Aomori Spur Fuji (XY-46) | I | D | D | DI | DI | DI | D | D | DI | DI | DI | DI | DI |
| Qiu Fuji (XY-47) | I | D | D | DI | DI | DI | D | D | DI | DI | DI | DI | DI |
| Fuji Champion (XY-48) | I | D | D | DI | DI | DI | D | D | DI | DI | DI | DI | DI |
| 26-34 (XY-5) | DI | D | DI | DI | I | DI | D | I | I | DI | DI | DI | DI |

-continued

Construction results of InDel marker genotype database of *Malus* germplasm resources

| | | | | | | | | | | | | | |
|---|---|---|---|---|---|---|---|---|---|---|---|---|---|
| Akifu 19 (XY-50) | I | D | D | DI | DI | DI | D | D | DI | DI | DI | DI | DI |
| Fuji (XY-54) | I | D | D | DI | DI | DI | D | D | DI | DI | DI | DI | DI |
| Qinfu 1 (XY-55) | I | D | D | DI | DI | DI | D | D | DI | DI | DI | DI | DI |
| Feng Fuji (XY-56) | I | D | D | DI | DI | DI | D | D | DI | DI | DI | DI | DI |
| Tianxing (XY-57) | I | D | D | DI | DI | DI | D | D | DI | DI | DI | DI | DI |
| Taiyang Fuji (XY-58) | I | D | D | DI | DI | DI | D | D | DI | DI | DI | DI | DI |
| Cherry Crab (XY-6) | D | I | D | DI | D | D | D | D | D | D | I | DI | DI |
| Yueping (XY-60) | DI | I | I | I | DI | D | D | D | DI | DI | DI | DI | DI |
| 23-63 (XY-61) | DI | D | D | DI | DI | DI | D | DI | DI | DI | DI | DI | DI |
| 23-42 (XY-62) | I | D | D | DI | DI | DI | D | DI | DI | DI | DI | DI | DI |
| 7-171 (XY-63) | DI | DI | DI | I | DI | D | D | I | I | DI | DI | I | DI |
| Shengfang 3A (XY-65) | I | D | D | DI | DI | DI | D | D | DI | DI | DI | DI | DI |
| Meinong Fuji (XY-67) | I | D | D | DI | DI | DI | D | D | DI | DI | DI | DI | DI |
| 62-45 (XY-68) | DI | DI | DI | D | DI | D | D | D | D | D | DI | D | DI |
| Fengfeng Fuji (XY-70) | I | D | D | DI | DI | DI | D | D | DI | DI | DI | DI | DI |
| GM256 (XY-71) | I | D | D | DI | DI | DI | D | D | DI | DI | DI | DI | DI |
| Jinfu 2 (XY-73) | I | D | D | DI | DI | DI | D | D | DI | DI | DI | DI | DI |
| Qiufu (XY-75) | I | D | D | DI | DI | DI | D | D | DI | DI | DI | DI | DI |
| Shanfu 6 (XY-76) | I | D | D | DI | DI | DI | D | D | DI | DI | DI | DI | DI |
| Nagafu 8 (XY-77) | I | D | D | DI | DI | DI | D | D | DI | DI | DI | DI | DI |
| 58-34 (XY-78) | DI | DI | DI | DI | DI | D | DI | D | D | D | DI | D | DI |
| 2001 Fuji (XY-79) | I | D | D | DI | DI | DI | D | D | DI | DI | DI | DI | DI |
| 15-26 (XY-8) | DI | DI | DI | I | D | DI | D | D | DI | D | DI | DI | DI |
| Wangshanhong (XY-80) | I | D | D | DI | DI | DI | D | D | DI | DI | DI | DI | DI |
| Jinfu 1 (XY-81) | I | D | D | DI | DI | DI | D | D | DI | DI | DI | DI | DI |
| Qingfu 1 (XY-84) | I | D | D | DI | DI | DI | D | D | DI | DI | DI | DI | DI |
| Qiufu 39 (XY-85) | I | D | D | DI | DI | DI | D | D | DI | DI | DI | DI | DI |
| Nagafu 1 (XY-86) | I | D | D | DI | DI | DI | D | D | DI | DI | DI | DI | DI |
| Shou Fuji (XY-87) | I | D | D | DI | DI | DI | D | D | DI | DI | DI | DI | DI |
| Yueli (XY-88) | DI | DI | I | I | D | DI | D | I | I | DI | DI | I | DI |
| Shanfu 2 (XY-89) | I | D | D | DI | DI | DI | D | D | DI | DI | DI | DI | DI |
| Chongban Crab (XY-9) | DI | I | I | I | D | D | D | D | D | D | I | D | DI |
| Harica (XY-90) | I | DI | I | I | I | I | DI | D | D | DI | D | DI | DI |
| Akifu 1 (XY-91) | I | D | D | DI | DI | DI | D | D | DI | DI | DI | DI | DI |
| Wangfu (XY-92) | I | D | D | DI | DI | DI | D | D | DI | DI | DI | DI | DI |
| Hong Manao (XYZ-1) | D | D | I | DI | D | D | D | D | DI | DI | D | DI | DI |
| Modi (XYZ-10) | DI | DI | DI | I | D | D | D | I | D | DI | D | D | DI |
| C37 (XYZ-11) | I | D | DI | DI | DI | DI | D | DI | I | DI | D | DI | DI |
| Envy ? (XYZ-12) | I | D | D | DI | I | DI | DI | I | D | I | DI | D | D |

-continued

Construction results of InDel marker genotype database of *Malus* germplasm resources

| | | | | | | | | | | | | | |
|---|---|---|---|---|---|---|---|---|---|---|---|---|---|
| Xichang Yuanzhuiguo (XYZ-2) | DI | DI | I | DI | D | DI | D | D | DI | DI | DI | DI | DI |
| Ziye Zixiaoguo (XYZ-3) | D | I | DI | I | D | D | D | D | D | DI | I | DI | D |
| Ziye Zidaguo (XYZ-4) | DI | DI | D | DI | D | D | D | D | DI | DI | DI | DI | DI |
| Shoufenshu 6 (XYZ-5) | DI | D | DI | DI | D | D | D | D | D | DI | D | D | DI |
| Changhua (XYZ-6) | DI | D | DI | DI | I | D | DI | I | D | DI | DI | D | DI |
| Jinshiji (XYZ-7) | DI | D | DI | DI | I | D | DI | I | D | I | DI | D | DI |
| 19-147 (XYZ-9) | I | D | DI | I | DI | D | D | I | D | D | DI | D | DI |
| Malong Gala 1 (YN-1) | DI | D | DI | DI | I | D | DI | I | D | D | DI | D | DI |
| Shouer hong (YN-11) | I | D | D | DI | DI | DI | D | DI | DI | DI | DI | DI | DI |
| Yun Hongrou (YN-12) | I | DI | DI | I | DI | D | D | DI | D | DI | DI | D | DI |
| Lixing Crab (YN-13) | DI | I | I | I | D | D | D | D | D | D | DI | D | DI |
| Siana (YN-15) | I | I | I | DI | DI | I | D | DI | DI | D | D | D | DI |
| Jonathan-M41 (YN-17) | DI | DI | DI | DI | DI | D | D | DI | DI | I | DI | DI | DI |
| Morlie's Delicious (YN-18) | DI | D | DI | I | DI | DI | D | I | I | DI | DI | I | DI |
| Britegold (YN-19) | I | D | D | DI | DI | DI | D | D | DI | DI | DI | DI | DI |
| Malong Gala 1 blush (YN-2) | DI | D | DI | DI | I | D | DI | I | D | D | DI | D | DI |
| Line 5 (YN-22) | I | I | I | DI | DI | I | D | DI | I | D | DI | D | DI |
| Line 6 (YN-23) | DI | DI | I | D | DI | D | D | I | D | D | DI | D | DI |
| Line 13 (YN-24) | DI | D | DI | DI | DI | DI | D | D | I | I | DI | I | DI |
| row 3 (YN-25) | DI | DI | I | I | D | DI | D | DI | DI | DI | DI | DI | DI |
| row 4 (YN-26) | DI | DI | I | I | D | DI | D | DI | DI | DI | DI | DI | DI |
| row 5 (YN-27) | DI | DI | I | I | D | DI | D | DI | DI | DI | DI | DI | DI |
| row 6 (YN-28) | DI | DI | I | I | D | DI | D | D | DI | DI | DI | DI | DI |
| row 9 (YN-29) | I | D | DI | D | DI | DI | DI | D | DI | DI | DI | DI | DI |
| Malong xin Gala 1 (YN-3) | DI | D | DI | DI | I | D | DI | I | D | D | DI | D | DI |
| row 10 (YN-30) | I | DI | DI | I | DI | DI | D | DI | DI | DI | DI | DI | DI |
| row 11 (YN-31) | I | D | DI | D | DI | DI | DI | DI | DI | DI | DI | DI | DI |
| row 12 (YN-32) | DI | D | DI | DI | I | D | DI | I | D | D | DI | D | DI |
| row 13 (YN-33) | DI | DI | I | I | D | DI | D | DI | DI | DI | DI | DI | DI |
| row 14 (YN-34) | DI | DI | I | I | D | DI | D | DI | DI | DI | DI | DI | DI |
| row 15 (YN-35) | DI | DI | DI | DI | D | D | DI | D | D | DI | D | D | DI |
| row 16 (YN-36) | DI | DI | DI | DI | DI | DI | D | DI | DI | DI | DI | DI | DI |
| row 17 (YN-37) | DI | DI | DI | I | D | DI | D | D | DI | DI | DI | DI | DI |
| row 18 (YN-38) | DI | DI | DI | I | DI | D | D | D | D | D | DI | D | DI |
| row 19 (YN-39) | DI | DI | DI | DI | DI | DI | D | D | D | D | D | D | D |
| Malong xin Gala 1 strip (YN-4) | DI | D | DI | DI | I | D | DI | I | D | D | DI | D | DI |
| row 20 (YN-40) | DI | I | I | I | DI | D | D | DI | D | D | DI | D | DI |
| row 21 (YN-41) | I | D | D | DI | DI | DI | D | D | DI | DI | DI | DI | DI |

-continued

| Construction results of InDel marker genotype database of *Malus* germplasm resources | | | | | | | | | | | | | |
|---|---|---|---|---|---|---|---|---|---|---|---|---|
| row 22 (YN-42) | DI | I | I | I | DI | D | D | DI | D | D | DI | D | DI |
| row 23 (YN-43) | DI | I | I | I | DI | D | D | DI | D | D | DI | D | DI |
| row 24 (YN-44) | I | D | D | DI | DI | DI | D | D | DI | DI | DI | DI | DI |
| row 25 (YN-45) | I | D | D | DI | DI | DI | D | D | DI | DI | DI | DI | DI |
| Malong Gala2 (YN-5) | DI | D | DI | DI | I | D | DI | I | D | D | DI | D | DI |
| Malong Gala 2 blush (YN-6) | DI | D | DI | DI | I | D | DI | I | D | D | DI | D | DI |
| Longwei (YN-7) | I | D | DI | D | I | DI | I | I | D | D | DI | D | DI |
| Longwei Early Mutant (YN-8) | I | D | DI | D | I | DI | I | I | D | D | DI | D | DI |
| Cherry Gala (YN-9) | DI | D | DI | DI | I | D | I | I | D | D | DI | D | DI |
| Siyana (YT-1) | I | DI | I | I | I | DI | D | D | D | D | D | D | DI |
| Yanfu 10 (YT-100) | I | D | D | DI | DI | DI | D | D | DI | DI | DI | DI | DI |
| Chadel (YT-102) | D | D | DI | DI | D | D | D | DI | DI | D | DI | DI | DI |
| Charden (YT-103) | DI | DI | DI | DI | DI | DI | D | DI | DI | DI | DI | DI | DI |
| Tuskan (YT-104) | I | I | I | DI | DI | DI | DI | D | DI | DI | DI | DI | DI |
| Prima × Sekaiichii (YT-105) | I | DI | DI | DI | D | D | D | D | DI | I | DI | D | DI |
| Toppax_apple (YT-11) | I | I | I | DI | D | D | D | D | DI | DI | DI | DI | DI |
| Xinjiang Hongrou Crab (YT-12) | D | I | I | I | DI | I | D | D | D | D | DI | D | D |
| Melfree (YT-13) | I | DI | DI | D | D | DI | D | D | D | DI | DI | DI | DI |
| Yanfu 3 (YT-14) | DI | DI | DI | DI | DI | D | D | DI | DI | DI | DI | DI | DI |
| Gold milecnirum (YT-15) | I | D | D | I | I | I | DI | D | D | DI | DI | D | DI |
| Ganhong (YT-16) | I | D | D | I | DI | DI | D | D | D | D | DI | DI | DI |
| Cornoet (YT-17) | DI | DI | DI | D | D | D | D | D | DI | DI | DI | DI | DI |
| Priw (YT-18) | DI | DI | DI | D | D | DI | D | D | D | I | DI | D | DI |
| Aichi (YT-19) | I | DI | D | DI | D | DI | D | D | D | D | DI | DI | DI |
| Auraria (YT-2) | DI | I | I | D | D | D | D | D | DI | I | DI | DI | DI |
| Meile (YT-20) | I | D | D | DI | DI | DI | D | D | DI | DI | DI | DI | DI |
| Qiulimeng (YT-21) | I | DI | DI | I | DI | D | D | D | DI | I | DI | D | DI |
| Aliusitan (YT-22) | I | I | DI | I | DI | DI | D | D | DI | I | DI | DI | DI |
| Geaooza (YT-23) | I | D | D | I | D | D | D | D | D | D | DI | D | DI |
| Golden Spur (YT-24) | DI | DI | I | I | I | DI | D | DI | DI | DI | DI | DI | DI |
| Starking (YT-25) | I | D | D | I | I | DI | D | D | D | D | DI | D | DI |
| Indo (YT-26) | I | D | D | I | D | DI | D | D | D | D | DI | D | DI |
| Teser (YT-27) | DI | DI | DI | I | D | DI | D | D | DI | I | I | I | DI |
| Xianhong (YT-28) | DI | D | D | I | DI | D | D | DI | I | D | DI | D | DI |
| Gala × Mato 8 (YT-29) | I | DI | DI | DI | I | D | D | I | DI | DI | DI | DI | DI |
| Very Early Fuji (YT-3) | I | D | D | DI | DI | DI | D | D | DI | DI | DI | DI | DI |
| Qiuhuapi (YT-30) | D | D | DI | D | DI | D | D | DI | DI | DI | DI | D | DI |
| Piga 70 (YT-31) | I | DI | DI | DI | D | D | D | D | D | DI | D | D | D |
| Yanzhen 1 (YT-32) | D | DI | I | DI | D | D | D | D | DI | D | DI | D | DI |

Construction results of InDel marker genotype database of *Malus* germplasm resources

| | | | | | | | | | | | | | |
|---|---|---|---|---|---|---|---|---|---|---|---|---|---|
| Matail (YT-34) | DI | D | DI | DI | I | D | I | I | D | D | DI | D | DI |
| Jonathan-csan (YT-35) | DI | DI | DI | DI | DI | D | D | DI | DI | DI | DI | DI | DI |
| Huashuai (YT-36) | DI | D | DI | DI | I | I | D | I | DI | DI | DI | D | DI |
| Wengao 1 (YT-38) | I | D | D | DI | DI | DI | D | D | DI | DI | DI | DI | DI |
| Wengao 2 (YT-39) | I | D | D | DI | DI | DI | D | D | DI | DI | DI | DI | DI |
| Elegia (YT-4) | DI | D | D | DI | DI | DI | D | D | D | DI | DI | D | DI |
| Wengao 3 (YT-40) | I | D | D | DI | DI | DI | D | D | DI | D | DI | DI | DI |
| Hong Anka (YT-41) | I | DI | DI | I | DI | D | D | DI | DI | D | DI | DI | DI |
| Yanfu 2 (YT-42) | I | D | D | DI | DI | DI | D | D | DI | D | DI | DI | DI |
| Belgolden (YT-43) | DI | DI | DI | I | I | DI | DI | DI | DI | DI | DI | DI | DI |
| Rubinola (YT-44) | I | DI | DI | I | I | D | D | I | D | D | DI | D | D |
| Wangqiuhong (YT-45) | DI | D | D | I | D | DI | D | D | DI | DI | DI | DI | DI |
| Pulanhong (YT-46) | DI | I | I | DI | DI | D | D | D | D | DI | DI | DI | DI |
| Bosh (YT-47) | DI | DI | I | DI | DI | D | D | D | D | DI | DI | D | DI |
| Chengji 1 (YT-48) | I | D | D | DI | DI | DI | D | D | DI | DI | DI | DI | DI |
| Hongli (YT-49) | I | D | D | I | DI | D | D | D | DI | DI | DI | DI | DI |
| Guoqinghong (YT-5) | DI | D | DI | DI | DI | D | D | D | DI | D | DI | D | DI |
| Reandra (YT-50) | DI | DI | DI | I | DI | I | DI | D | D | DI | DI | D | DI |
| Revbihola (YT-51) | I | DI | I | DI | DI | D | DI | DI | DI | DI | DI | DI | D |
| Melrose (YT-52) | I | D | D | I | I | D | D | I | D | DI | DI | D | DI |
| Rewena (YT-53) | DI | D | D | D | D | DI | D | D | D | DI | DI | D | D |
| Mrxl(robusta × Liberte) (YT-54) | I | D | D | DI | I | DI | D | DI | D | DI | DI | D | DI |
| Mollies_Del_open (YT-55) | DI | DI | I | DI | DI | D | D | D | D | DI | DI | D | DI |
| Renora (YT-56) | I | I | I | DI | DI | DI | D | D | DI | DI | DI | DI | DI |
| Rosmadzin (YT-57) | DI | DI | I | DI | DI | D | DI | D | D | DI | DI | D | DI |
| Remo (YT-58) | I | DI | I | DI | DI | D | DI | DI | DI | DI | DI | DI | D |
| Pilot (YT-59) | DI | DI | DI | DI | D | DI | D | D | D | DI | DI | D | DI |
| Yangbai Crab (YT-6) | DI | I | I | I | D | D | D | D | DI | D | DI | D | DI |
| Free Red Star (YT-60) | I | D | D | DI | I | I | D | D | D | DI | DI | D | DI |
| Idared (YT-61) | D | D | D | D | D | DI | D | D | D | DI | DI | DI | DI |
| Mingyue (YT-62) | I | DI | DI | DI | I | DI | DI | D | DI | DI | DI | DI | DI |
| Piga 101 (YT-63) | I | DI | I | DI | DI | D | D | DI | I | DI | DI | I | DI |
| Yanfu 5 (YT-64) | I | D | D | DI | DI | D | D | D | DI | DI | DI | DI | DI |
| Early Jonagold (YT-65) | DI | DI | DI | DI | DI | DI | D | DI | DI | DI | DI | DI | DI |
| Wengao 2 mutant (YT-66) | I | D | D | DI | DI | DI | D | D | DI | DI | DI | DI | DI |
| Fenhong Gala 44 (YT-67) | DI | DI | I | I | I | DI | I | D | DI | DI | DI | D | DI |
| Yiyuanhong (YT-68) | I | D | D | DI | DI | D | D | D | DI | DI | DI | DI | DI |
| Yanfu 4 (YT-69) | I | D | D | DI | DI | DI | D | D | DI | DI | DI | DI | DI |

-continued

| Construction results of InDel marker genotype database of *Malus* germplasm resources | | | | | | | | | | | | | |
|---|---|---|---|---|---|---|---|---|---|---|---|---|---|
| White Pearmain (YT-70) | DI | DI | DI | DI | I | DI | DI | D | D | DI | DI | D | DI |
| Jonathan-early (YT-73) | DI | DI | DI | DI | DI | D | D | DI | DI | DI | DI | DI | DI |
| Jonathan-midle (YT-74) | DI | DI | DI | DI | DI | D | D | DI | DI | DI | DI | DI | DI |
| Gornan (YT-75) | D | D | D | D | DI | D | DI | D | D | DI | DI | DI | DI |
| Regilndel (YT-76) | I | DI | I | DI | DI | D | DI | DI | DI | DI | DI | DI | D |
| Golden Bell (YT-77) | DI | DI | I | I | DI | DI | DI | D | DI | DI | DI | I | DI |
| Arkcharm (YT-78) | DI | DI | I | I | D | DI | D | D | DI | I | DI | DI | DI |
| Redchif (YT-79) | DI | DI | DI | DI | D | D | D | D | DI | DI | DI | D | DI |
| Mouping Guanghua Fuji (YT-8) | I | D | D | DI | DI | DI | D | D | DI | DI | DI | DI | DI |
| Freedom (YT-80) | DI | DI | DI | DI | D | DI | D | D | D | DI | DI | D | DI |
| Martinike (YT-81) | I | DI | DI | D | DI | D | D | D | D | DI | DI | D | D |
| Sweetle (YT-82) | I | D | DI | D | I | DI | DI | I | D | D | DI | D | DI |
| Aleksanader (YT-83) | I | D | D | DI | D | DI | D | D | DI | DI | DI | DI | DI |
| Yan 6 Fenhong 143 (YT-84) | DI | D | D | I | I | DI | DI | DI | DI | DI | DI | DI | DI |
| Ruitina (YT-85) | I | DI | DI | DI | D | DI | D | D | I | DI | DI | D | D |
| Wengao 1 mutant (YT-86) | I | D | D | DI | DI | DI | D | D | DI | DI | DI | DI | DI |
| Wengao 3 mutant (YT-87) | I | D | D | DI | DI | DI | D | D | DI | DI | DI | DI | DI |
| Shajinyilamu (YT-88) | D | I | I | I | D | D | D | D | D | DI | I | D | DI |
| Qiuhong (YT-89) | I | D | D | I | DI | DI | D | D | D | DI | D | D | DI |
| Changyanghong (YT-9) | I | D | D | DI | DI | DI | D | D | DI | DI | DI | DI | DI |
| Yanfu 8 (YT-90) | I | D | D | DI | DI | DI | D | D | DI | DI | DI | DI | DI |
| Jinduhong Gala (YT-91) | DI | D | DI | DI | I | D | DI | I | D | DI | DI | D | DI |
| Nagafu 2 (YT-92) | I | D | D | DI | DI | DI | D | D | DI | DI | DI | DI | DI |
| Honglu seedling 65 (YT-93) | DI | D | D | DI | DI | D | D | DI | DI | DI | DI | D | DI |
| Tsugaru (YT-94) | DI | I | I | I | DI | D | D | DI | D | DI | DI | D | DI |
| Jinshuai mutant (YT-95) | D | DI | I | I | I | DI | I | DI | DI | DI | DI | DI | DI |
| Taishan Crab (YT-96) | DI | DI | D | DI | D | D | D | D | D | DI | DI | D | DI |
| Luli (YT-98) | DI | DI | I | I | D | DI | D | I | DI | DI | DI | DI | DI |
| 10-182 (YX-10-182) | DI | DI | DI | DI | I | DI | D | D | I | DI | DI | DI | DI |
| 01-001 (YX-01-001) | DI | D | DI | I | D | D | D | DI | D | D | DI | D | D |
| 01-121 (YX-01-121) | DI | D | DI | DI | DI | DI | D | D | I | D | DI | DI | D |
| 02-009 (YX-02-009) | DI | D | DI | I | DI | DI | D | D | I | DI | DI | DI | D |
| 03-010 (YX-03-010) | DI | D | DI | DI | DI | DI | D | D | I | I | DI | DI | DI |
| 03-111 (YX-03-111) | DI | D | DI | DI | DI | DI | D | D | I | D | DI | DI | DI |
| 04-033 (YX-04-033) | DI | DI | DI | I | DI | DI | D | D | I | I | DI | DI | D |
| 04-087 (YX-04-087) | DI | D | DI | I | D | D | D | DI | I | DI | DI | DI | DI |
| 06-056 (YX-06-056) | DI | D | DI | DI | DI | D | D | D | DI | D | D | D | DI |
| 08-034 (YX-08-034) | DI | DI | DI | DI | I | DI | D | D | D | D | DI | D | DI |
| 09-037 (YX-09-037) | DI | DI | DI | DI | DI | DI | D | D | D | D | DI | D | D |

-continued

Construction results of InDel marker genotype database of *Malus* germplasm resources

| | | | | | | | | | | | | | |
|---|---|---|---|---|---|---|---|---|---|---|---|---|---|
| 09-079 (YX-09-079) | DI | DI | DI | D | DI | DI | D | D | DI | DI | DI | DI | D |
| 10-010 (YX-10-010) | DI | D | DI | I | D | DI | D | DI | DI | DI | DI | DI | DI |
| 11-037 (YX-11-037) | DI | DI | DI | I | DI | DI | D | I | D | D | DI | D | D |
| 11-206 (YX-11-206) | DI | DI | DI | D | D | D | D | DI | I | DI | DI | DI | D |
| 12-206 (YX-12-206) | DI | DI | DI | I | DI | I | D | D | I | DI | DI | DI | D |
| 13-025 (YX-13-025) | DI | DI | DI | DI | D | DI | D | DI | I | D | DI | D | DI |
| 16-155 (YX-16-155) | DI | D | DI | DI | DI | DI | D | I | DI | D | DI | D | D |
| 16-157 (YX-16-157) | DI | D | DI | DI | DI | DI | D | D | DI | DI | DI | DI | DI |
| 17-023 (YX-17-023) | DI | D | DI | D | DI | I | D | D | I | DI | DI | DI | DI |
| 17-199 (YX-17-199) | DI | D | DI | DI | DI | I | D | D | D | D | DI | D | DI |
| 21-005 (YX-21-005) | DI | I | I | DI | I | I | D | D | DI | DI | DI | DI | DI |
| 21-018 (YX-21-018) | D | DI | I | DI | I | D | D | DI | DI | DI | DI | DI | DI |
| 22-186 (YX-22-186) | D | D | I | I | I | DI | D | DI | DI | DI | DI | DI | DI |
| 27-003 (YX-27-003) | DI | D | I | I | DI | I | D | D | DI | DI | DI | DI | DI |
| 29-176 (YX-29-176) | D | D | I | DI | I | DI | D | DI | DI | DI | DI | DI | DI |
| 30-001 (YX-30-001) | DI | D | I | I | DI | D | D | I | DI | DI | DI | DI | DI |
| 33-018 (YX-33-018) | DI | D | DI | DI | DI | DI | D | D | I | DI | DI | DI | DI |
| 33-101 (YX-33-101) | D | DI | I | DI | DI | D | D | I | DI | DI | DI | DI | D |
| 33-151 (YX-33-151) | DI | D | I | DI | DI | I | D | DI | DI | DI | DI | DI | DI |
| 51-007 (YX-51-007) | D | DI | DI | DI | DI | D | D | DI | I | I | DI | I | DI |
| 51-031 (YX-51-031) | DI | I | I | DI | I | D | D | I | I | I | DI | I | DI |
| 51-077 (YX-51-077) | DI | DI | I | I | I | D | D | I | DI | I | DI | DI | DI |
| 51-102 (YX-51-102) | I | DI | DI | DI | DI | DI | D | DI | DI | DI | DI | DI | DI |
| 51-139 (YX-51-139) | DI | D | DI | I | I | D | D | I | I | I | DI | I | DI |
| 51-165 (YX-51-165) | DI | DI | DI | DI | DI | D | D | DI | DI | I | DI | DI | DI |
| 51-166 (YX-51-166) | I | I | I | I | I | DI | DI | DI | DI | I | DI | DI | DI |
| 51-209 (YX-51-209) | I | DI | I | I | I | DI | DI | DI | DI | I | DI | DI | DI |
| 52-049 (YX-52-049) | DI | DI | I | DI | DI | D | DI | DI | I | I | DI | I | DI |
| 52-151 (YX-52-151) | DI | I | I | I | I | D | D | I | DI | I | DI | DI | DI |
| 52-160 (YX-52-160) | D | DI | DI | DI | I | DI | DI | DI | I | I | DI | I | DI |
| 53-040 (YX-53-040) | DI | DI | I | I | DI | D | D | DI | DI | I | DI | DI | DI |
| 53-205 (YX-53-205) | I | DI | DI | I | DI | D | D | D | DI | DI | DI | DI | DI |
| 54-001 (YX-54-001) | DI | I | DI | DI | DI | D | D | I | I | I | DI | I | DI |
| 54-188 (YX-54-188) | DI | I | I | I | DI | DI | DI | D | DI | I | DI | DI | DI |
| 55-006 (YX-55-006) | DI | DI | I | I | DI | DI | DI | D | DI | DI | DI | DI | DI |
| 55-023 (YX-55-023) | D | DI | DI | DI | I | D | D | I | DI | I | DI | I | DI |
| 55-042 (YX-55-042) | I | DI | DI | I | DI | DI | DI | D | I | I | DI | I | DI |
| 56-081 (YX-56-081) | DI | I | I | I | I | DI | D | I | I | I | DI | I | DI |

| Construction results of InDel marker genotype database of *Malus* germplasm resources |||||||||||||
|---|---|---|---|---|---|---|---|---|---|---|---|---|
| 57-128 (YX-57-128) | DI | D | DI | I | I | D | D | I | I | I | DI | I | DI |
| 58-036 (YX-58-036) | DI | DI | I | I | I | D | D | I | I | I | DI | I | DI |
| 58-089 (YX-58-089) | DI | I | I | I | DI | D | D | DI | I | I | DI | I | DI |
| 58-144 (YX-58-144) | DI | I | I | I | DI | D | D | DI | I | DI | DI | DI | DI |
| 58-177 (YX-58-177) | D | I | DI | DI | I | D | D | I | D | I | I | I | DI |
| 58-211 (YX-58-211) | DI | D | DI | DI | I | D | D | I | I | I | DI | I | DI |
| 59-086 (YX-59-086) | I | DI | I | I | I | DI | DI | DI | DI | DI | DI | DI | DI |
| 59-130 (YX-59-130) | I | D | DI | I | DI | DI | D | DI | DI | I | DI | DI | DI |
| Jersey Mac (Z-1) | I | D | D | I | D | DI | D | DI | I | DI | DI | DI | DI |
| Gale Gala (Z-10) | DI | D | DI | DI | I | D | DI | I | D | D | DI | D | DI |
| Li Gala (Z-11) | DI | D | DI | DI | I | D | DI | I | D | D | DI | D | DI |
| Yanga 1 (Z-12) | DI | D | DI | DI | I | D | DI | I | D | D | DI | D | DI |
| NAKT M9 clone (Z-13) | DI | DI | I | DI | DI | D | D | DI | D | DI | DI | DI | DI |
| Royal Gala (Z-14) | DI | D | DI | DI | I | D | DI | I | D | D | DI | D | DI |
| Huajia (Z-15) | I | DI | DI | DI | DI | D | D | D | D | D | DI | D | DI |
| Dorsett Golden (Z-16) | DI | D | D | I | I | I | I | D | D | I | DI | D | DI |
| 99-2-58 (Z-17) | I | DI | DI | DI | DI | D | D | D | D | D | DI | D | DI |
| Galaxy (Z-18) | DI | D | DI | DI | I | D | DI | I | D | D | DI | D | DI |
| Royal New Gala (Z-19) | DI | D | DI | DI | I | D | DI | I | D | D | DI | D | DI |
| 99-1-29 (Z-22) | DI | DI | DI | DI | DI | DI | DI | D | D | D | DI | D | D |
| Seokwang (Z-23) | DI | DI | DI | I | DI | DI | D | I | DI | DI | DI | DI | DI |
| Fuhong Zaoga (Z-24) | DI | D | DI | DI | I | D | DI | I | D | D | DI | D | DI |
| Maiyan (Z-25) | I | DI | DI | I | D | DI | D | D | D | D | DI | D | DI |
| Shandong 1 (Z-26) | DI | D | DI | DI | I | D | DI | I | D | D | DI | D | DI |
| Gala Queen (Z-27) | DI | D | DI | DI | I | D | DI | I | D | D | DI | D | DI |
| 99-2-39 (Z-29) | I | D | D | DI | D | DI | D | D | D | D | DI | D | DI |
| Sweetle (Z-3) | I | D | DI | D | I | DI | DI | I | D | D | DI | D | DI |
| Dalian Da Gala (Z-30) | DI | D | DI | DI | I | D | DI | I | D | D | DI | D | DI |
| Huaxing (Z-31) | DI | DI | I | I | D | D | D | DI | DI | DI | DI | DI | DI |
| Li Gala (Z-32) | DI | D | DI | DI | I | D | DI | I | D | D | DI | D | DI |
| Fuhong Zaoga (Z-33) | I | DI | DI | DI | DI | DI | DI | I | DI | DI | DI | DI | DI |
| Yanga (Z-34) | I | DI | DI | DI | DI | DI | DI | I | DI | DI | DI | DI | DI |
| Royal Gala (Z-35) | DI | D | DI | DI | I | D | DI | I | D | D | DI | D | DI |
| Shijiazhuang Gala (Z-37) | DI | D | DI | DI | I | D | DI | I | D | D | DI | D | DI |
| Taihong Gala (Z-38) | DI | D | DI | DI | I | D | DI | I | D | D | DI | D | DI |
| Anna (Z-39) | DI | D | D | I | DI | DI | D | D | DI | I | DI | DI | DI |
| Hong Zhenzhu (Z-4) | I | DI | DI | DI | D | DI | D | DI | DI | DI | DI | DI | DI |
| Qiuhong Gala (Z-40) | DI | I | I | I | DI | D | D | DI | D | DI | DI | D | DI |
| Shandong 2 (Z-41) | DI | D | DI | DI | I | D | DI | I | D | D | DI | D | DI |

-continued

Construction results of InDel marker genotype database of *Malus* germplasm resources

| | | | | | | | | | | | | | |
|---|---|---|---|---|---|---|---|---|---|---|---|---|---|
| Shandong 6 (Z-42) | DI | D | DI | DI | I | D | DI | I | D | D | DI | D | DI |
| Chenyang (Z-43) | DI | DI | DI | I | DI | D | D | DI | D | DI | DI | DI | DI |
| Dongqie Gala (Z-44) | I | DI | I | DI | DI | D | DI | DI | DI | DI | DI | DI | D |
| Royal Gala (Z-45) | DI | D | DI | DI | I | D | DI | I | D | D | DI | D | DI |
| Taishan Gala (Z-47) | DI | D | DI | DI | I | D | DI | I | D | D | DI | D | DI |
| Shandong 7 (Z-48) | DI | D | DI | DI | I | D | DI | I | D | D | DI | D | DI |
| Regal gala (Z-49) | DI | D | DI | DI | I | D | DI | I | D | D | DI | D | DI |
| NAKB clone (Z-5) | DI | DI | I | DI | DI | D | D | DI | D | DI | DI | DI | DI |
| Royal gala (Z-50) | DI | D | DI | DI | I | D | DI | I | D | D | DI | D | DI |
| Znoga (Z-51) | I | DI | I | DI | DI | DI | D | DI | DI | DI | DI | DI | DI |
| Shandong 5 (Z-52) | DI | D | DI | DI | I | D | DI | I | D | D | DI | D | DI |
| Rockit (Z-53) | DI | D | DI | DI | I | D | I | I | D | D | DI | D | DI |
| Shandong 3 (Z-54) | DI | D | DI | DI | I | D | DI | I | D | D | DI | D | DI |
| Mondel Gala (Z-55) | DI | D | DI | DI | I | D | DI | I | D | D | DI | D | DI |
| Alvinagala (Z-56) | DI | D | DI | DI | I | D | DI | I | D | D | DI | D | DI |
| M9 pajam2 (Z-6) | DI | DI | I | DI | DI | D | D | DI | D | DI | DI | DI | DI |
| Jinshiji (Z-7) | DI | D | DI | DI | I | D | DI | I | D | D | DI | D | DI |
| Huarui (Z-8) | DI | DI | DI | DI | I | D | DI | DI | DI | DI | DI | DI | DI |
| Hongcuibao (Z-9) | DI | DI | I | DI | DI | DI | D | I | DI | DI | DI | DI | D |

| Accession name (Accession ID) | C15119 | C16120 | C16122 | C16123 | C16124 | C16125 | C17127 | C17128 | C17129 | C04133 | C04134 | C06137 | C07138 |
|---|---|---|---|---|---|---|---|---|---|---|---|---|---|
| Black Ben Davis (10--1) | D | DI | DI | D | DI | D | D | DI | DI | I | D | DI |
| Lysgolden (10--10) | DI | DI | DI | D | D | DI | I | D | DI | I | DI | DI |
| Dongchengguan 13 (10--11) | DI | DI | DI | D | D | DI | I | D | DI | I | DI | DI |
| Nagafu 1 (10--12) | DI | DI | DI | D | D | DI | I | D | DI | I | DI | DI |
| Shengli Hongguan (10--14) | D | DI | DI | DI | I | D | I | D | DI | D | DI | I | DI |
| Shizishan 1 (10--15) | D | DI | DI | DI | I | D | I | D | DI | D | DI | I | DI |
| Baoman (10--2) | DI | DI | DI | D | I | D | D | DI | DI | D | DI | DI | DI |
| Melba (10--20) | D | D | DI | D | DI | DI | DI | D | DI | DI | DI | DI | DI |
| Kuliesa (10--21) | DI | DI | DI | D | I | D | D | D | DI | DI | I | I | DI |
| De 8 (10--22) | D | D | DI | D | DI | DI | D | DI | DI | D | I | DI | DI |
| Bo 5 (10--23) | DI | I | I | D | D | I | DI | D | DI | D | I | I | DI |
| Iran Pippin (10--4) | D | D | DI | D | I | D | DI | D | DI | D | DI | I | I |
| Sakatakei Tsugaru (10--5) | DI | I | DI | DI | DI | DI | DI | D | DI | DI | I | I | DI |
| Khrushchev (10--6) | D | D | DI | D | DI | DI | I | D | DI | DI | I | I | DI |
| Batul (10--7) | D | D | I | D | DI | D | I | D | DI | DI | I | D | DI |
| Prime Gold (10--9) | D | D | I | D | DI | D | I | D | DI | D | I | D | DI |
| Jie 1 (11--0) | DI | DI | DI | D | DI | DI | D | DI | DI | D | I | DI | DI |

-continued

Construction results of InDel marker genotype database of *Malus* germplasm resources

| | | | | | | | | | | | | | |
|---|---|---|---|---|---|---|---|---|---|---|---|---|---|
| Guldborg (1--11) | DI | DI | DI | D | D | DI | I | D | DI | DI | I | DI | DI |
| Shajin Yilamu (11--10) | D | D | I | D | D | D | D | D | DI | D | I | D | DI |
| Soviet (11--11) | D | D | DI | D | DI | DI | D | D | DI | DI | DI | DI | I |
| Lobo (11--13) | D | D | DI | D | DI | D | D | DI | D | I | DI | DI | DI |
| Allington Pippin (11--14) | DI | D | DI | D | DI | D | DI | D | DI | D | DI | DI | I |
| Malinova (11--15) | D | D | DI | D | D | D | D | D | D | D | D | DI | DI |
| Sweet McIntosh (11--16) | D | D | DI | D | DI | D | D | D | D | D | D | DI | DI |
| McIntosh (11--18) | DI | DI | DI | DI | DI | DI | I | D | DI | DI | DI | DI | DI |
| Spartan (11--2) | D | D | DI | D | D | DI | D | DI | DI | I | I | DI | DI |
| Fushuai (1--12) | I | DI | I | DI | D | DI | DI | D | DI | I | DI | D | DI |
| Summer Pearmain (11--20) | D | DI | DI | D | DI | DI | I | D | DI | D | I | I | DI |
| Helm (11--21) | D | D | DI | D | DI | D | D | DI | D | DI | DI | DI | DI |
| Domenesti (11--3) | D | DI | DI | D | D | DI | DI | D | DI | D | DI | DI | DI |
| Early Harvest (1--13) | I | DI | I | DI | D | DI | DI | D | DI | I | DI | D | DI |
| Silver Spur Red Delicious (11--4) | D | D | DI | D | DI | DI | D | DI | DI | DI | I | DI | DI |
| Dongxiangjiao (11--5) | DI | DI | DI | D | DI | D | DI | DI | DI | D | I | D | DI |
| Guoling (1--15) | DI | DI | DI | D | D | DI | DI | D | DI | D | DI | DI | DI |
| Skyline Spureme (11--8) | D | D | DI | D | DI | DI | D | DI | DI | DI | I | DI | DI |
| Chantecler (11--9) | D | DI | DI | D | D | DI | D | I | DI | D | D | D | I |
| Close (1--19) | DI | DI | I | D | DI | DI | DI | D | DI | DI | DI | DI | DI |
| Aizaohui (1--2) | DI | DI | DI | D | D | DI | D | D | DI | D | DI | DI | DI |
| Wuyue (12--1) | DI | D | I | D | I | D | D | DI | D | DI | I | DI | DI |
| Bukowka (12--11) | D | DI | DI | D | D | DI | D | D | DI | D | DI | DI | DI |
| Jinyu (12--12) | DI | DI | DI | D | DI | DI | D | DI | D | I | DI | DI | DI |
| Calville Rouge (12--14) | D | DI | DI | D | DI | DI | D | D | DI | D | I | D | DI |
| Doyle (12--15) | I | I | I | D | I | D | D | I | DI | DI | DI | I | DI |
| Melrose (12--16) | DI | DI | DI | D | D | DI | D | DI | DI | DI | I | D | I |
| Menage (12--17) | D | D | DI | D | I | D | DI | DI | DI | D | I | I | DI |
| Bo 26 (12--18) | D | D | DI | D | I | D | I | D | DI | D | DI | I | DI |
| Duoyilu (12--19) | D | DI | I | I | I | D | DI | D | D | D | DI | DI | DI |
| De 6 (12--20) | D | D | DI | D | D | DI | D | DI | DI | D | DI | DI | DI |
| Red June (12--21) | D | D | I | I | I | D | D | D | DI | D | DI | DI | I |
| Helasang (12--23) | D | D | I | D | D | DI | D | DI | DI | DI | I | I | |
| Hesetiaowen (12--3) | D | DI | I | D | I | D | D | DI | DI | D | DI | DI | |
| James Grieve (1--23) | DI | DI | DI | D | DI | D | D | DI | D | I | DI | I | |
| Bailuosi Malin (12--4) | D | D | I | D | DI | D | D | D | DI | DI | DI | DI | |
| Jinnhong (12--5) | I | DI | I | D | DI | D | D | D | D | DI | I | DI | |
| Kay Sai William (12--6) | D | D | DI | D | D | DI | D | DI | DI | I | I | DI | DI |

-continued

| Construction results of InDel marker genotype database of *Malus* germplasm resources | | | | | | | | | | | | | |
|---|---|---|---|---|---|---|---|---|---|---|---|---|
| Xingjiang Pingguo (12--7) | D | D | I | D | D | D | D | D | DI | D | I | D | DI |
| Jie 15 (12--8) | D | D | DI | D | DI | DI | D | DI | DI | DI | I | DI | DI |
| Mianpingguo (12--9) | D | D | I | D | D | D | D | D | DI | D | I | DI | DI |
| Lowver (1--3) | D | D | DI | D | DI | D | D | D | DI | D | D | I | DI |
| Benoni (13--1) | DI | DI | I | DI | I | D | D | D | DI | D | DI | D | DI |
| Fa 5 (13--11) | D | D | DI | D | DI | DI | D | DI | DI | DI | I | DI | DI |
| Babskino (13--12) | D | D | I | D | DI | DI | D | D | DI | D | DI | I | DI |
| Kuluona (13--13) | D | DI | DI | D | DI | DI | DI | D | DI | D | I | DI | I |
| Shidonghaoji (13--16) | D | DI | DI | DI | I | D | I | D | DI | D | DI | I | DI |
| Oberkika (13--17) | D | D | DI | D | DI | DI | I | D | DI | D | I | D | DI |
| Budayi (13--19) | DI | DI | DI | D | D | DI | I | D | DI | DI | I | DI | DI |
| Red Canada (13--2) | D | DI | DI | D | DI | DI | DI | D | DI | DI | I | DI | DI |
| Laidi (13--20) | D | DI | I | D | DI | DI | DI | D | DI | D | DI | D | I |
| N2 (13--22) | D | DI | DI | D | D | DI | DI | DI | DI | D | I | DI | I |
| Norsan (13--5) | D | D | DI | D | DI | DI | D | DI | DI | DI | I | DI | DI |
| Hebei Kangbing Golden Delicious (13--6) | I | DI | DI | DI | DI | DI | D | DI | DI | I | DI | DI | DI |
| Zhanxuan 14 (13--9) | DI | DI | DI | D | D | DI | I | D | DI | DI | I | DI | DI |
| Xiangguoguang (14--11) | D | DI | DI | DI | I | D | D | DI | D | D | I | DI | I |
| Shengfang 1 (14--14) | D | DI | DI | D | D | DI | DI | DI | DI | D | I | DI | I |
| Yujing II (14--16) | D | DI | DI | D | D | DI | DI | DI | DI | D | I | DI | I |
| Cox's Orange Pippin (14--2) | DI | I | DI | DI | DI | DI | I | D | DI | D | I | DI | DI |
| Nagafu 7 (14--20) | D | DI | DI | D | D | DI | DI | DI | DI | D | I | DI | I |
| Boiken (14--21) | I | DI | DI | D | DI | DI | DI | D | DI | D | I | DI | DI |
| Qunfu 1 (14--23) | D | DI | DI | D | D | DI | DI | DI | DI | D | I | DI | I |
| Calville Blanche (14--3) | I | DI | DI | D | DI | DI | DI | D | DI | D | I | DI | DI |
| Freybreg (14--4) | DI | DI | DI | DI | I | D | I | D | DI | I | DI | DI | I |
| Husveti Rosmaring (14--5) | D | D | DI | D | I | D | DI | D | DI | D | DI | I | DI |
| Sweet Jonathan (14--7) | DI | DI | DI | D | DI | DI | D | DI | DI | D | I | DI | DI |
| King of Pippin (14--8) | DI | I | DI | DI | DI | DI | I | D | DI | D | I | DI | DI |
| Duchess of Oldenburg (1--5) | DI | D | DI | I | DI | D | I | D | DI | DI | D | DI | DI |
| Kangbing Golden 5 (15--11) | DI | I | DI | DI | DI | DI | DI | DI | DI | DI | DI | DI | I |
| Pingzhi Ralls Janet (15--15) | DI | DI | DI | D | D | DI | DI | D | DI | D | I | D | DI |
| Wase16 (15--16) | D | DI | I | D | D | DI | DI | D | DI | D | I | DI | I |
| Kogetsu (15--17) | DI | DI | DI | DI | DI | DI | DI | D | DI | D | I | DI | DI |
| Jonared (15--18) | DI | DI | DI | D | DI | DI | D | DI | DI | D | I | DI | DI |
| Zhanxuan 4 (15--21) | DI | DI | DI | D | D | DI | I | D | DI | DI | I | DI | DI |
| Strawberry (15--23) | D | D | I | D | DI | D | D | D | DI | D | I | I | I |

-continued

| Construction results of InDel marker genotype database of *Malus* germplasm resources | | | | | | | | | | | | | |
|---|---|---|---|---|---|---|---|---|---|---|---|---|---|
| StarkSpur Ultra Red Delicious (15--3) | D | D | DI | D | DI | DI | D | DI | DI | DI | I | DI | DI |
| Sharp Red Delicious (15--4) | D | D | DI | D | DI | DI | D | DI | DI | DI | I | DI | DI |
| Mensi (15--5) | D | DI | DI | D | D | D | D | D | DI | D | I | I | DI |
| Norand (15--6) | DI | D | I | D | DI | DI | D | D | DI | D | DI | I | D |
| Zhanxuan 18 (15--7) | D | D | DI | D | DI | DI | D | DI | DI | DI | I | DI | DI |
| Xishan 1 (15--8) | D | D | DI | D | DI | DI | D | DI | DI | DI | I | DI | DI |
| Hongrou Pingguo (15--9) | D | D | I | D | D | DI | D | D | DI | D | D | D | I |
| Gravenstein (1--6) | DI | D | I | D | I | D | D | DI | DI | D | DI | I | DI |
| Xinhong (16--1) | D | D | DI | D | DI | DI | DI | DI | DI | DI | DI | I | D |
| Zhanxuan 6 (16--10) | D | D | DI | D | D | DI | D | D | DI | D | I | D | DI |
| Behene (16--11) | D | DI | DI | D | DI | DI | I | D | DI | DI | I | DI | DI |
| Xindong (16--14) | DI | D | I | D | DI | DI | DI | D | DI | D | DI | DI | DI |
| Hardi Brite (16--16) | D | D | DI | D | DI | DI | D | DI | DI | DI | I | DI | DI |
| Charden (16--17) | DI | DI | DI | DI | DI | DI | DI | DI | DI | DI | DI | DI | I |
| Zhuoai 1 (16--2) | DI | DI | DI | D | D | DI | I | D | DI | DI | I | DI | DI |
| Jinse Luosuoshan (16--22) | I | D | I | D | D | DI | D | D | DI | D | DI | D | D |
| Zhaiteng II (16--23) | D | DI | DI | D | D | DI | DI | DI | DI | D | I | DI | I |
| Zhanxuan 16 (16--6) | DI | DI | DI | D | D | DI | I | D | DI | DI | I | DI | DI |
| Fa 3 (16--8) | D | DI | DI | D | D | DI | DI | D | DI | D | DI | DI | DI |
| Jerseymac (1--7) | DI | DI | DI | D | I | D | D | DI | DI | D | I | DI | DI |
| Mother (17--1) | D | DI | DI | DI | DI | DI | DI | DI | DI | I | I | DI | DI |
| Northern Spy (17--10) | DI | DI | DI | D | D | DI | D | DI | DI | D | D | I | DI |
| Rome Beauty (17--11) | I | I | I | D | I | D | D | I | DI | DI | DI | I | DI |
| Black Ben David (17--12) | D | D | DI | DI | I | D | D | D | DI | D | DI | I | DI |
| Atlas (17--13) | DI | DI | DI | D | D | DI | D | D | DI | DI | I | D | I |
| Roxbury (17--14) | DI | D | DI | D | DI | D | D | D | DI | DI | I | DI | I |
| Laxtons Superb (17--15) | D | D | DI | D | DI | D | D | D | DI | D | DI | DI | DI |
| Changhong (17--16) | I | I | I | D | I | D | D | D | DI | D | I | I | DI |
| Cogswell Pearmain (17--17) | DI | D | DI | D | D | DI | I | D | DI | DI | DI | DI | DI |
| Twenty Ounce (17--18) | DI | D | DI | DI | DI | DI | D | D | DI | D | DI | I | DI |
| Lowtosh (17--19) | DI | D | I | DI | DI | DI | D | DI | DI | DI | DI | I | DI |
| Iwaki (17--21) | DI | D | D | D | D | D | D | D | DI | DI | DI | DI | DI |
| Qin'guan (17--22) | DI | DI | DI | D | DI | D | DI | D | DI | D | DI | I | DI |
| Bancroft (17--23) | DI | D | DI | D | DI | D | D | D | DI | DI | I | D | DI |
| Chenango Strawberry (17--4) | D | DI | DI | D | DI | D | D | DI | DI | D | I | I | D |
| Newfane (17--7) | DI | DI | DI | D | DI | D | I | D | DI | DI | DI | DI | DI |
| Lord Lambourne (17--9) | DI | DI | DI | D | D | DI | D | DI | DI | D | D | I | DI |

-continued

| Construction results of InDel marker genotype database of *Malus* germplasm resources | | | | | | | | | | | | | |
|---|---|---|---|---|---|---|---|---|---|---|---|---|
| Rizhiwan (18--0) | D | D | I | D | DI | D | D | DI | DI | DI | I | I | DI |
| Campbell (18--11) | DI | D | DI | D | DI | D | D | D | DI | I | DI | I | |
| Pigeon (18--13) | D | I | DI | DI | DI | DI | D | D | DI | D | DI | DI | DI |
| Summer Champion (18--14) | D | DI | DI | D | I | D | D | DI | D | DI | I | DI | |
| Nanpu 3 (18--15) | D | DI | DI | DI | DI | DI | I | D | DI | D | I | DI | I |
| Qiulimeng (18--16) | D | D | I | D | DI | D | D | I | DI | D | I | I | D |
| Rutosh (18--17) | D | D | DI | D | D | I | D | D | DI | DI | I | DI | DI |
| Xinlimei (18--19) | D | DI | I | D | DI | DI | D | DI | D | DI | D | I | |
| Huanong 1 (18--2) | D | D | DI | DI | DI | DI | DI | DI | DI | D | DI | I | DI |
| Lawfam (18--20) | D | DI | I | D | D | DI | D | D | DI | DI | I | DI | I |
| Akin's Red (18--21) | DI | DI | I | D | I | D | DI | DI | DI | D | DI | I | DI |
| Meltosh (18--22) | D | D | I | D | DI | DI | DI | D | DI | D | I | DI | I |
| Hubbardston (18--23) | DI | DI | DI | DI | I | D | I | D | DI | I | DI | DI | I |
| Fenghuangluan Crab (18--3) | D | D | DI | D | DI | DI | DI | DI | DI | D | DI | I | DI |
| Jie 9 (18--4) | D | DI | I | DI | DI | DI | DI | DI | DI | D | I | DI | DI |
| Bramley's Seedling (18--5) | DI | D | DI | DI | DI | D | DI | D | DI | DI | I | DI | DI |
| Shuangyang 1 (18--7) | DI | DI | DI | DI | I | D | I | D | DI | I | DI | DI | I |
| Shengli (18--8) | DI | DI | DI | DI | I | D | I | D | DI | I | DI | DI | I |
| Qingguan (18--9) | D | D | DI | D | D | DI | DI | D | DI | D | DI | D | DI |
| Weeping Ralls (19--0) | DI | DI | DI | D | D | DI | DI | D | DI | D | I | D | DI |
| Giant Jeniton (19--1) | D | D | DI | D | I | D | DI | DI | DI | D | I | I | DI |
| Baldwin (19--10) | DI | DI | DI | D | DI | D | D | DI | DI | I | DI | DI | |
| Lele Fuji (19--11) | D | DI | DI | D | D | DI | DI | DI | DI | D | I | DI | I |
| Shuahong (19--12) | DI | DI | DI | DI | I | D | DI | D | DI | D | DI | DI | I |
| Red Fuji TAO (19--14) | D | DI | DI | D | D | DI | DI | DI | DI | D | I | DI | I |
| Jizaohong (19--17) | DI | DI | DI | DI | I | D | I | D | DI | I | DI | DI | I |
| Karas Tor (19--19) | D | DI | DI | D | D | DI | I | D | DI | DI | DI | DI | I |
| Ralls Janet (19--2) | DI | DI | DI | D | DI | D | DI | D | DI | D | I | D | DI |
| Stonetosh (19--22) | D | DI | I | D | D | I | D | D | DI | I | I | DI | DI |
| White Pearmain (19--23) | DI | D | DI | D | DI | D | D | I | DI | DI | I | DI | I |
| Xiushui Guoguang (19--3) | DI | DI | DI | D | DI | DI | D | D | DI | DI | I | DI | DI |
| Chimeric Ralls Janet (19--4) | DI | DI | DI | D | D | DI | D | D | DI | D | I | D | DI |
| Mutsu (19--7) | DI | DI | DI | DI | DI | DI | DI | DI | DI | DI | DI | DI | I |
| Ben David (19--8) | D | D | DI | DI | I | D | D | D | D | D | DI | I | DI |
| Saint Lawrence (19--9) | D | I | DI | D | I | D | DI | DI | D | D | DI | DI | I |
| Newtosh (20--0) | D | D | I | D | D | DI | D | D | DI | D | DI | I | I |
| Geliekekukui (20--1) | D | D | I | D | D | D | D | D | D | DI | DI | DI | |
| Sweet Jonathan (20--10) | DI | DI | DI | D | DI | DI | D | DI | DI | D | I | DI | DI |

-continued

| Construction results of InDel marker genotype database of *Malus* germplasm resources | | | | | | | | | | | | | |
|---|---|---|---|---|---|---|---|---|---|---|---|---|---|
| Apple of Commerce (20--11) | D | D | DI | DI | I | D | D | D | DI | D | D | I | I |
| 600 g Andong (20--12) | D | DI | DI | D | DI | DI | I | D | DI | I | DI | DI | |
| Winter Banana (20--14) | D | D | DI | D | D | DI | D | I | DI | DI | I | DI | I |
| Rainier (20--15) | DI | D | DI | D | D | D | D | D | DI | I | DI | DI | |
| Winesap (20--16) | DI | DI | I | D | DI | DI | I | D | DI | DI | D | I | DI |
| Drumbo (20--17) | D | D | I | D | DI | DI | D | D | DI | D | I | DI | I |
| Blengstid Gaurd (20--2) | D | DI | DI | D | D | DI | DI | D | DI | D | DI | DI | DI |
| Jierjisi (20--21) | D | DI | I | D | D | D | D | D | DI | D | I | I | DI |
| Radiant (20--23) | D | D | I | D | D | DI | D | D | DI | D | DI | I | I |
| King David (20--5) | I | D | DI | D | DI | DI | D | DI | DI | D | I | DI | I |
| Clapp's Seedling (20--6) | D | D | DI | D | D | DI | DI | D | DI | D | DI | D | DI |
| Ingram (20--7) | D | DI | DI | D | DI | DI | DI | D | DI | D | I | DI | DI |
| Qiujin (20--8) | DI | DI | DI | D | D | DI | I | D | DI | DI | I | DI | DI |
| Sujsleppskoe (2--1) | D | D | I | D | I | D | D | D | DI | D | DI | DI | DI |
| Qian 1 Ace (21--0) | D | DI | DI | D | D | DI | DI | DI | DI | D | I | DI | I |
| Toko (2--10) | DI | DI | DI | DI | DI | DI | D | DI | DI | DI | I | I | I |
| Antalue (21--1) | DI | DI | DI | DI | DI | DI | D | I | DI | DI | I | D | I |
| Boskoopske Cervene (2--11) | D | DI | DI | D | D | DI | DI | D | DI | D | DI | DI | DI |
| Heoersitai (21--10) | DI | D | DI | D | DI | D | D | DI | DI | D | I | D | DI |
| Lanfengwang (21--11) | D | D | DI | D | DI | DI | DI | DI | DI | D | DI | D | I |
| Aohong (21--14) | DI | DI | DI | I | I | D | DI | DI | DI | D | DI | D | I |
| Weiqinni (21--15) | D | DI | I | DI | DI | D | D | D | DI | D | DI | DI | DI |
| Smoothee (21--17) | DI | I | DI | DI | DI | DI | DI | DI | DI | DI | DI | DI | I |
| Hongzhiwu (21--18) | D | DI | DI | DI | DI | DI | D | D | DI | DI | DI | DI | DI |
| Jieba (21--2) | D | D | I | D | DI | DI | DI | DI | DI | DI | I | DI | I |
| Kizashi (21--20) | DI | D | DI | D | D | DI | DI | DI | DI | I | D | D | I |
| Aifeng (21--21) | DI | D | DI | D | D | DI | DI | DI | DI | I | D | D | I |
| Xingping (21--4) | DI | DI | DI | D | D | DI | DI | D | DI | DI | I | D | DI |
| Esopus Spitzenburg (2--14) | DI | DI | I | D | DI | DI | DI | DI | DI | D | I | D | DI |
| Lvguang (21--6) | D | D | I | D | D | DI | D | D | DI | D | I | D | D |
| Nvyoujidui (2--16) | D | D | DI | D | DI | DI | DI | DI | DI | D | DI | I | DI |
| Bell Poos (21--7) | D | DI | DI | DI | DI | D | D | DI | DI | D | I | DI | DI |
| Tian Andongnuo (2--17) | D | DI | DI | D | I | D | D | DI | DI | DI | D | I | DI |
| Pacific Rose (21--8) | DI | DI | DI | I | I | D | D | DI | DI | D | DI | D | I |
| 500 g (21--9) | DI | D | I | D | D | DI | I | D | D | D | DI | D | D |
| Nvyoujidui 2 (2--19) | D | D | I | D | I | D | D | D | DI | D | DI | DI | DI |
| Tian Andongnuo 2 (2--2) | DI | DI | DI | D | D | D | D | D | DI | DI | DI | DI | DI |
| Spur Mutsu (22--1) | DI | DI | DI | DI | DI | DI | DI | DI | DI | DI | DI | DI | I |

| Construction results of InDel marker genotype database of *Malus* germplasm resources | | | | | | | | | | | | | |
|---|---|---|---|---|---|---|---|---|---|---|---|---|---|
| Red June Sweet (2--21) | D | DI | DI | D | D | DI | D | D | DI | D | DI | DI | DI |
| Chu Tsugaru (22--11) | DI | I | DI | DI | DI | DI | D | DI | DI | I | I | DI | |
| Kermemen (22--13) | DI | D | DI | D | DI | D | D | D | DI | I | I | DI | |
| Bedan (22--14) | DI | D | I | D | D | DI | D | D | DI | I | DI | DI | |
| Dabinette (22--15) | D | DI | DI | D | D | DI | DI | DI | DI | D | DI | DI | I |
| Zaocuilv (22--16) | DI | DI | DI | DI | I | D | I | D | DI | I | DI | DI | I |
| Chanteline (22--17) | D | D | DI | D | DI | D | DI | DI | DI | I | DI | I | |
| Red Baron (22--2) | DI | D | DI | D | DI | DI | D | DI | DI | D | DI | DI | DI |
| Hongjin Gala (22--4) | DI | DI | DI | DI | DI | DI | I | D | DI | I | I | DI | DI |
| Generos (22--7) | DI | DI | DI | D | DI | DI | D | DI | DI | D | I | DI | DI |
| Alberta (2--3) | DI | DI | I | D | DI | D | D | DI | DI | DI | DI | I | DI |
| Hirosaki Fuji (23--1) | DI | I | DI | DI | DI | DI | DI | D | DI | DI | I | I | DI |
| Miya Fuji (23--10) | D | DI | DI | D | D | DI | DI | DI | DI | D | I | DI | I |
| Yanshanhong (23--13) | D | DI | DI | D | DI | DI | D | DI | DI | DI | I | D | I |
| Dailv (23--14) | D | D | DI | D | D | DI | I | D | DI | DI | DI | DI | I |
| Frequin Rouge (23--15) | DI | D | DI | D | DI | D | DI | DI | DI | D | DI | I | I |
| Jinguang (23--16) | D | DI | DI | D | DI | DI | I | D | DI | DI | I | DI | DI |
| Avrolles (23--17) | DI | DI | DI | D | I | D | D | DI | DI | D | I | DI | DI |
| Marie Menard (23--18) | D | DI | DI | DI | DI | D | I | DI | DI | D | DI | I | I |
| Golden B (23--2) | DI | I | DI | DI | DI | DI | DI | DI | DI | DI | DI | DI | I |
| Jurella (23--20) | DI | D | DI | D | D | D | D | D | DI | D | DI | I | DI |
| GS58 (23--21) | I | I | DI | DI | I | D | D | I | DI | DI | I | D | I |
| Lianji (23--22) | DI | DI | DI | DI | DI | DI | D | I | DI | D | DI | I | DI |
| Aomori Spur Fuji (23--4) | D | DI | DI | D | D | DI | DI | DI | DI | D | I | DI | I |
| Akifu 39 (23--9) | D | DI | DI | D | D | DI | DI | DI | DI | D | I | DI | I |
| Shalatuoni (2--4) | DI | DI | DI | D | DI | DI | DI | DI | DI | D | I | DI | DI |
| Guoqing (24--13) | DI | DI | DI | DI | DI | DI | DI | DI | DI | D | DI | DI | DI |
| Ningguang (24--15) | D | DI | DI | DI | I | D | D | DI | DI | D | I | I | I |
| Hongqiaowang (24--17) | DI | DI | DI | DI | DI | DI | DI | DI | DI | DI | DI | DI | I |
| Wemhong (24--18) | DI | DI | I | DI | DI | DI | D | I | DI | DI | I | DI | I |
| Wijcik McIntosh (24--19) | D | D | DI | D | D | DI | D | D | DI | DI | I | DI | I |
| Xinguoguang (24--21) | DI | DI | DI | D | D | DI | D | DI | DI | D | I | D | DI |
| Fengcun Fuji (24--22) | D | DI | DI | D | D | DI | DI | DI | DI | D | I | DI | I |
| America 8 (24--23) | DI | DI | DI | DI | DI | DI | DI | DI | DI | D | DI | DI | DI |
| GS48 (24--3) | D | D | I | D | DI | D | D | DI | DI | D | DI | I | D |
| Granny Smith (24--4) | D | DI | DI | D | I | D | D | D | DI | D | I | DI | I |
| Stark Spur (24--7) | DI | I | DI | DI | DI | DI | DI | DI | DI | DI | DI | DI | I |
| Huangguniang (2--5) | D | DI | I | D | DI | DI | DI | D | DI | D | D | I | DI |

Construction results of InDel marker genotype database of *Malus* germplasm resources

| | | | | | | | | | | | | | |
|---|---|---|---|---|---|---|---|---|---|---|---|---|---|
| Judaine (25--11) | DI | DI | I | DI | DI | DI | D | D | DI | D | I | I | DI |
| Judeline (25--12) | DI | I | DI | DI | DI | DI | DI | D | DI | DI | DI | I | I |
| HoneyCrisp (25--14) | DI | DI | I | D | D | DI | D | DI | DI | D | DI | DI | DI |
| Korin (25--15) | D | DI | DI | D | D | DI | DI | DI | DI | D | I | DI | I |
| Hongao (25--18) | D | DI | DI | D | DI | DI | I | D | DI | DI | DI | I | DI |
| Ningguang (25--19) | D | DI | DI | D | DI | DI | I | D | DI | DI | DI | I | DI |
| Red Delicious (25--2) | D | D | DI | D | DI | DI | D | DI | DI | DI | I | DI | DI |
| Youlixiang (25--21) | DI | DI | DI | DI | DI | DI | D | I | DI | DI | I | DI | DI |
| Fuqiu (25--3) | D | I | DI | D | D | DI | D | DI | DI | D | I | DI | DI |
| Chunxiang (25--4) | DI | DI | DI | DI | I | D | DI | D | D | D | DI | DI | I |
| Fu Hong (25--5) | DI | I | DI | D | D | DI | D | DI | DI | D | I | I | DI |
| Qingxiang (25--6) | I | DI | DI | DI | I | D | D | I | DI | D | I | D | I |
| Zhongxing (25--7) | DI | DI | DI | DI | D | DI | D | DI | DI | DI | I | I | DI |
| Weixishengming (25--8) | DI | DI | DI | DI | DI | DI | I | D | DI | DI | I | DI | DI |
| Shichinohe 1 (25--9) | D | DI | DI | D | D | DI | DI | DI | DI | D | I | DI | I |
| Arkansas Black (2--6) | D | D | DI | D | DI | D | D | D | DI | D | I | I | DI |
| Douce Coetligne (26--10) | DI | D | DI | D | DI | DI | D | D | DI | DI | I | DI | I |
| Golden Spur (26--14) | DI | I | DI | DI | DI | DI | DI | DI | DI | DI | DI | DI | I |
| Orei (26--15) | DI | I | DI | DI | DI | DI | I | D | DI | D | I | DI | DI |
| Sekaiichii (26--18) | DI | DI | DI | DI | DI | DI | I | D | DI | I | I | DI | DI |
| Kokyu (26--19) | D | DI | DI | DI | DI | DI | DI | DI | DI | I | D | I |
| Douce Moen (26--2) | DI | D | DI | D | DI | D | D | DI | DI | D | I | D | DI |
| Yanfu 1 (26--22) | D | DI | DI | D | D | DI | DI | DI | DI | D | I | DI | I |
| Ningfeng (26--23) | DI | DI | DI | DI | DI | DI | DI | DI | DI | D | DI | DI | DI |
| Juliana (26--5) | D | DI | I | D | DI | D | DI | D | DI | D | I | DI | DI |
| Judestar (26--9) | DI | DI | DI | D | DI | DI | D | DI | DI | D | I | DI | I |
| Liaofu (2--7) | D | DI | I | D | D | DI | I | D | DI | D | I | I | DI |
| Sinano Red (27--10) | DI | D | I | DI | I | D | D | DI | DI | D | DI | D | DI |
| Jinyang (27--12) | DI | DI | I | D | DI | D | D | D | DI | D | DI | I | DI |
| Enqi (27--13) | I | DI | DI | DI | DI | DI | D | DI | DI | I | DI | DI | DI |
| Miki (27--14) | DI | DI | DI | DI | DI | DI | I | D | DI | DI | I | DI | DI |
| Hongbaoshi (27--15) | DI | DI | DI | DI | I | D | D | I | DI | DI | I | D | I |
| Nagafu 2 (27--16) | D | DI | DI | D | D | DI | DI | DI | DI | D | I | DI | I |
| Longguan (27--4) | DI | DI | DI | D | D | DI | D | DI | D | D | I | D | DI |
| K9 (27--5) | DI | DI | I | D | DI | D | D | D | D | D | DI | I | DI |
| Zaohongda Gala (27--6) | DI | DI | I | D | DI | D | D | D | DI | D | DI | I | DI |
| Lvshuai (27--7) | DI | DI | I | DI | DI | D | D | DI | DI | DI | DI | DI | DI |
| Hongxia (27--8) | DI | D | DI | D | D | DI | DI | DI | DI | I | D | D | I |

-continued

Construction results of InDel marker genotype database of *Malus* germplasm resources

| | | | | | | | | | | | | | |
|---|---|---|---|---|---|---|---|---|---|---|---|---|---|
| Zaohongxia (27--9) | D | DI | DI | D | D | DI | DI | DI | DI | D | I | DI | I |
| Early Golden (2--8) | D | DI | I | D | DI | DI | DI | D | DI | DI | DI | D | DI |
| Indo (28--0) | D | D | DI | D | DI | DI | D | DI | DI | D | I | I | I |
| Jie 1 (28--11) | DI | DI | DI | D | DI | DI | D | DI | DI | D | I | DI | DI |
| Beauty of Bath (28--13) | D | D | I | DI | I | D | DI | D | DI | DI | D | DI | DI |
| K10 (28--14) | DI | I | I | D | D | D | D | DI | DI | I | DI | DI | |
| Beifang Xina (28--16) | D | D | I | DI | I | D | D | I | DI | D | DI | I | DI |
| Yellow Fuji (28--18) | D | DI | DI | DI | DI | DI | I | D | DI | DI | DI | DI | |
| Sinano Sweet (28--2) | DI | I | DI | DI | I | D | DI | D | DI | I | I | DI | DI |
| Miguo (28--3) | DI | DI | DI | D | D | DI | I | D | DI | DI | I | DI | DI |
| Ace (28--4) | D | DI | DI | D | D | DI | DI | DI | DI | D | I | DI | I |
| Tsugaru (28--5) | DI | I | DI | DI | DI | DI | DI | D | DI | DI | I | I | DI |
| K12 (28--8) | DI | DI | I | D | DI | DI | DI | D | DI | DI | I | I | I |
| Jieernianke (28--9) | DI | D | I | D | I | D | DI | DI | DI | DI | D | I | DI |
| Macoun (2--9) | DI | D | DI | D | D | DI | DI | D | DI | D | I | DI | DI |
| Qingping (29--1) | DI | D | DI | D | D | DI | DI | DI | DI | DI | DI | DI | DI |
| Polka (29--11) | DI | DI | DI | D | DI | DI | DI | D | DI | DI | I | I | I |
| Longfeng (29--13) | D | D | I | D | DI | D | D | DI | D | D | I | DI | |
| Very Early Fuji (29--14) | D | DI | DI | D | D | DI | DI | DI | DI | D | I | DI | I |
| Longhong (29--15) | DI | DI | I | D | D | DI | I | D | DI | DI | DI | DI | |
| Pinova (29--16) | I | DI | I | D | DI | DI | D | I | DI | D | I | DI | I |
| Fuga (29--17) | DI | D | DI | D | D | DI | DI | DI | I | D | D | I | |
| Qing n3 (29--2) | D | D | DI | D | DI | DI | D | DI | DI | DI | I | DI | DI |
| Xinyuanshuai (29--3) | D | D | DI | D | DI | DI | D | DI | DI | DI | I | DI | DI |
| Xinhua (29--5) | D | D | DI | DI | DI | DI | I | D | DI | D | DI | DI | |
| Nanpu 2 (29--6) | DI | DI | I | D | DI | DI | D | I | DI | D | I | DI | DI |
| Liuyu mutant (29--7) | DI | D | DI | D | DI | DI | D | DI | DI | DI | DI | DI | |
| Shandao Fuji (30--1) | D | DI | DI | D | D | DI | DI | DI | DI | D | I | DI | I |
| Sinano Gold (30--2) | D | I | DI | D | D | DI | I | D | DI | D | DI | DI | I |
| Whitney (3--1) | D | D | I | DI | I | D | D | D | DI | DI | DI | DI | DI |
| Feixia (31--1) | DI | DI | DI | DI | DI | DI | D | I | DI | DI | I | D | I |
| Willams Faborite (3--11) | D | DI | DI | D | I | D | D | DI | DI | D | I | D | I |
| Zhangye 2 (31--12) | DI | DI | DI | D | D | DI | D | D | DI | DI | DI | DI | DI |
| Youfangcun Ralls Janet (31--14) | D | D | DI | DI | I | D | D | D | DI | D | DI | I | DI |
| Yueyanghong (31--15) | DI | DI | DI | D | D | DI | DI | D | DI | DI | DI | DI | DI |
| Shuohong (31--17) | DI | D | DI | D | D | I | D | D | DI | D | I | DI | I |
| Tianwang 1 (31--18) | D | D | DI | D | DI | DI | D | DI | DI | DI | I | DI | DI |
| Huadan (31--2) | DI | D | DI | D | DI | DI | D | D | DI | DI | I | I | DI |

-continued

| \multicolumn{13}{c}{Construction results of InDel marker genotype database of *Malus* germplasm resources} |

| Dalu 52 (3--12) | D | D | I | D | D | DI | D | D | DI | D | DI | D | DI |
| Cameo (31--3) | DI | DI | DI | D | D | DI | D | DI | D | I | D | DI |
| Tianhuangkui (3--13) | DI | DI | I | D | D | D | DI | D | DI | D | DI | I | DI |
| Qiulu (31--4) | DI | DI | DI | D | D | DI | I | D | D | DI | DI | DI |
| Liehuangjiatena (3--15) | D | I | DI | D | D | DI | DI | DI | DI | D | I | D | I |
| Lubi (3--16) | D | D | DI | DI | DI | DI | D | DI | D | I | I | DI |
| Huayu (31--8) | DI | DI | DI | DI | I | D | D | D | DI | DI | D | D | DI |
| Fameuse (3--18) | D | DI | DI | D | DI | DI | I | D | D | I | DI | I |
| Zhanhanxiang (3--19) | I | DI | DI | I | DI | D | D | DI | DI | DI | DI | I | DI |
| Siberian White Spot (3--2) | D | D | I | D | D | I | D | D | DI | D | D | I | DI |
| Zhengding 2 (3--21) | D | DI | DI | D | DI | D | I | D | DI | D | DI | DI | I |
| Kuihua (3--22) | I | D | DI | D | D | DI | D | D | DI | D | I | I | I |
| Early Worcester (3--23) | D | D | I | D | DI | DI | D | D | DI | DI | I | DI | I |
| Lowland Raspderry (3--3) | D | DI | DI | D | D | D | DI | DI | DI | D | DI | I | DI |
| Miqiulin Jinian (3--4) | D | D | DI | D | DI | DI | D | D | DI | D | DI | I | DI |
| Huangtianguo (3--5) | D | D | I | D | D | DI | DI | D | DI | D | I | DI | DI |
| Huadao (3--7) | D | DI | DI | DI | DI | D | D | DI | DI | D | DI | DI | DI |
| Red Astrachan (3--9) | DI | D | DI | I | DI | D | I | D | DI | D | DI | DI |
| Black Gilliflower (4--1) | D | D | I | I | I | D | D | D | DI | D | DI | DI | I |
| Nimaiyisuo (4--10) | D | DI | DI | D | D | D | DI | D | DI | D | I | DI | DI |
| Zaohong (4--11) | D | DI | DI | D | D | DI | DI | D | DI | D | I | D | DI |
| Xiangguo (4--12) | D | D | I | D | D | DI | DI | D | DI | D | I | DI | DI |
| Vista Bella (4--16) | DI | DI | DI | D | DI | DI | D | D | DI | DI | I | DI | I |
| Saiwen (4--17) | D | D | DI | D | DI | DI | D | D | DI | D | I | I | DI |
| Summerland (4--20) | DI | I | DI | DI | DI | DI | DI | DI | DI | DI | DI | I |
| Qihe Golden Spur (4--22) | DI | I | DI | DI | DI | DI | DI | DI | DI | DI | DI | I |
| Yellow Risharde (4--3) | DI | DI | DI | D | DI | D | I | D | DI | DI | DI | DI |
| Patten (4--5) | D | D | DI | D | D | I | DI | D | DI | D | DI | DI | DI |
| Early Red Bird (4--6) | DI | D | DI | D | DI | DI | D | DI | D | DI | DI | DI |
| Fuhong (4--7) | DI | D | DI | DI | I | D | DI | DI | DI | DI | D | DI |
| Bisimake (4--8) | D | D | DI | D | D | DI | D | DI | DI | D | D | I | DI |
| York Imperial (4--9) | I | D | DI | DI | DI | DI | D | D | DI | D | DI | DI | I |
| Jonagold (5--1) | DI | DI | DI | DI | DI | DI | DI | DI | DI | DI | DI | I |
| Ayiwaniya (5--10) | D | DI | DI | D | D | DI | D | D | D | I | DI | DI |
| Fushan 5 (5--14) | D | D | DI | D | DI | D | DI | D | DI | DI | I | DI | DI |
| Houjiadian Spur (5--18) | D | D | DI | D | DI | DI | D | DI | DI | I | DI | DI |
| Guoshuai (5--19) | D | D | DI | D | DI | DI | I | DI | DI | DI | I | DI | I |
| Huashuai 1 (5--21) | DI | D | DI | D | DI | D | I | D | DI | D | DI | D | DI |

-continued

Construction results of InDel marker genotype database of *Malus* germplasm resources

| | | | | | | | | | | | | | |
|---|---|---|---|---|---|---|---|---|---|---|---|---|---|
| Xiongyue 2 (5--22) | D | D | DI | D | DI | DI | D | DI | DI | DI | I | DI | DI |
| Honeygod (5--3) | I | DI | I | DI | DI | DI | D | DI | DI | I | D | I | DI |
| Joyal (5--4) | D | D | DI | D | D | I | D | D | DI | DI | I | DI | DI |
| Stark Spur Golden (5--5) | DI | I | DI | DI | DI | DI | DI | DI | DI | DI | DI | DI | I |
| Enweier Golden (5--6) | DI | I | DI | DI | DI | DI | DI | DI | DI | DI | DI | DI | I |
| Stark Gold (5--8) | DI | DI | DI | D | D | DI | DI | D | DI | D | I | D | DI |
| Sishui Spur (6--10) | D | D | DI | D | DI | DI | D | DI | DI | DI | I | DI | DI |
| Red Spur Delicious (6--12) | D | D | DI | D | DI | DI | D | DI | DI | DI | I | DI | DI |
| Qingdao 1 (6--13) | D | D | DI | D | DI | DI | D | DI | DI | DI | I | DI | DI |
| Bianqiangzi 1 (6--14) | D | D | DI | D | DI | DI | D | DI | DI | DI | I | DI | DI |
| Zhangjiakou Spur (6--16) | D | D | DI | D | DI | DI | D | DI | DI | DI | I | DI | DI |
| Richard Red Delicious (6--18) | D | D | DI | D | DI | DI | D | DI | DI | DI | I | DI | DI |
| Well Spur Delicious (6--19) | D | D | DI | D | DI | DI | D | DI | DI | DI | I | DI | DI |
| Bianqiangzi 2 (6--20) | D | D | DI | D | DI | DI | D | DI | DI | DI | I | DI | DI |
| Hardi Spur Delicious (6--21) | D | D | DI | D | DI | DI | D | DI | DI | DI | I | DI | DI |
| Fushan 1 (6--3) | D | D | DI | D | DI | DI | D | DI | DI | DI | I | DI | DI |
| Pinyin Spur (6--4) | D | D | DI | D | DI | DI | D | DI | DI | DI | I | DI | DI |
| Nanshan 2 (6--8) | D | D | DI | D | DI | DI | D | DI | DI | DI | I | DI | DI |
| Meiduan 1 (7--10) | DI | D | DI | D | D | DI | D | DI | DI | D | I | DI | DI |
| Shisanling Spur (7--11) | D | D | DI | D | DI | DI | D | DI | DI | DI | I | DI | DI |
| Kelisike (7--13) | DI | DI | I | D | D | DI | D | D | DI | D | I | D | DI |
| Jie 18 (7--16) | DI | DI | DI | D | I | D | D | D | DI | D | I | I | DI |
| Bo 25 (7--17) | D | D | DI | D | I | D | D | D | DI | D | DI | I | DI |
| Ruixiang (7--18) | DI | DI | DI | DI | I | D | DI | DI | DI | DI | DI | DI | DI |
| Wealthy (7--19) | DI | DI | I | D | DI | DI | DI | DI | D | DI | I | DI |  |
| Nanshan 4 (7--2) | D | DI | DI | D | DI | DI | D | DI | DI | I | D | I |  |
| De 14 (7--20) | DI | DI | DI | DI | I | D | D | D | DI | D | I | I | DI |
| Napoleon (7--22) | DI | DI | DI | D | D | DI | I | D | DI | DI | I | DI | DI |
| Youyi (7--23) | D | DI | DI | D | DI | DI | DI | DI | D | I | I | DI |  |
| Oregon Spur (7--3) | D | DI | DI | D | DI | DI | D | D | DI | DI | I | D | I |
| Kangtun Spur (7--6) | D | D | DI | D | DI | DI | D | DI | DI | DI | I | DI | DI |
| White Pippin (7--9) | D | DI | DI | D | DI | DI | I | D | DI | D | I | DI | I |
| Zach Lebel (8--1) | DI | D | DI | D | DI | DI | DI | DI | D | DI | DI | DI |  |
| Cortland (8--10) | DI | DI | I | D | DI | DI | DI | DI | D | DI | I | DI |  |
| Raritan (8--12) | D | DI | DI | D | D | DI | DI | DI | D | I | DI | I |  |
| Meilingxi Tsugaru (8--13) | D | DI | DI | D | D | DI | D | D | DI | I | I | I | I |

-continued

| Construction results of InDel marker genotype database of *Malus* germplasm resources | | | | | | | | | | | | | |
|---|---|---|---|---|---|---|---|---|---|---|---|---|---|
| Moscow Transparent (8--14) | DI | DI | I | D | DI | DI | DI | D | DI | D | DI | DI | DI |
| Cooper's Market (8--15) | D | D | DI | D | DI | DI | DI | DI | DI | DI | I | I | DI |
| Xite Shisheng (8--16) | DI | D | I | D | D | DI | I | D | DI | D | I | DI | DI |
| Tian Yisaye (8--17) | D | DI | I | DI | I | D | D | DI | D | DI | DI | DI | DI |
| Shennong 2 (8--19) | I | DI | I | D | D | DI | D | DI | DI | I | DI | DI | DI |
| Maigold (8--20) | DI | DI | DI | DI | DI | D | D | I | DI | D | I | DI | DI |
| Magu (8--21) | DI | D | I | DI | I | D | D | DI | DI | D | I | DI | DI |
| Cellini (8--23) | D | D | DI | D | DI | DI | D | DI | DI | D | D | I | DI |
| Simonffy Piros (8--3) | D | D | I | D | D | DI | DI | DI | DI | D | DI | I | DI |
| Luxiang (8--5) | DI | D | DI | D | D | DI | D | DI | DI | DI | I | DI | I |
| Zhongqiu (8--6) | DI | DI | I | I | DI | D | DI | D | DI | DI | DI | I | DI |
| De 2 (8--7) | I | D | DI | D | I | D | DI | DI | D | DI | DI | DI | DI |
| Grimes Golden (8--8) | DI | I | DI | DI | DI | D | I | D | DI | DI | DI | D | DI |
| Early Straw Berry (8--9) | D | DI | DI | D | D | D | DI | DI | DI | D | I | I | DI |
| Kelia (9--10) | D | D | DI | D | DI | DI | I | D | DI | DI | I | I | DI |
| French Apple (9--11) | D | D | DI | D | D | D | DI | DI | DI | D | DI | DI | DI |
| Todoroki Tsugaru (9--12) | DI | I | DI | DI | DI | DI | DI | D | DI | DI | I | I | DI |
| Cuihong (9--13) | D | DI | DI | D | I | D | D | DI | DI | D | I | DI | DI |
| De 4 (9--14) | D | DI | DI | D | D | DI | DI | D | DI | D | DI | DI | DI |
| Early McIntosh (9--18) | DI | D | I | D | D | DI | D | D | DI | DI | DI | DI | DI |
| Adam Mickewier (9--19) | D | DI | DI | D | D | DI | D | DI | DI | D | DI | DI | DI |
| Norda (9--2) | D | D | I | D | I | D | I | D | DI | D | D | I | DI |
| Cardinal (9--20) | DI | DI | DI | DI | I | D | I | D | DI | I | DI | DI | I |
| Evelyn (9--21) | D | DI | DI | D | DI | DI | DI | D | DI | D | I | DI | DI |
| Situonuowei (9--22) | D | D | I | D | I | DI | DI | DI | DI | D | DI | DI | DI |
| Yingqiu (9--23) | D | DI | DI | D | I | D | DI | D | DI | D | I | DI | DI |
| Kelongxieer (9--3) | DI | DI | I | D | DI | DI | DI | D | DI | D | DI | DI | DI |
| Cloden (9--5) | DI | I | DI | DI | DI | D | DI | DI | DI | D | D | DI | I |
| Qiutianhong (9--6) | D | D | I | D | I | D | D | DI | D | DI | DI | DI | DI |
| Gaidebao (9--7) | DI | DI | DI | D | D | DI | DI | DI | DI | D | I | DI | DI |
| Starkjam (9--9) | DI | DI | DI | D | D | DI | I | D | DI | DI | I | DI | DI |
| Wan Crab (B-1) | DI | DI | I | D | DI | D | D | DI | D | DI | D | DI | DI |
| Minjiandaguo Crab (B-10) | D | D | DI | D | DI | D | D | D | DI | D | DI | I | DI |
| Luanzhuang Crab (B1-11) | D | DI | DI | D | D | I | I | D | DI | D | DI | D | DI |
| Sankuaishi Crab (B1-12) | D | D | I | D | D | D | D | D | DI | D | DI | D | D |
| Xiongyue Crab 1 (B1-13) | DI | DI | DI | DI | D | DI | DI | DI | DI | D | DI | I | DI |
| Sankuaishi Crab 2 (B1-14) | DI | D | DI | DI | D | DI | D | DI | D | DI | DI | DI | DI |
| Dabaleng (B-12) | DI | D | DI | D | D | DI | D | D | DI | D | DI | DI | DI |

-continued

Construction results of InDel marker genotype database of *Malus* germplasm resources

| | | | | | | | | | | | | | |
|---|---|---|---|---|---|---|---|---|---|---|---|---|---|
| Sankuaishi Crab 2 (B-13) | D | DI | DI | D | D | DI | DI | DI | DI | D | I | DI | I |
| Changguo Crab (B-14) | DI | DI | I | D | D | DI | D | DI | DI | D | DI | D | DI |
| Dagucheng Baleng (B1-5) | D | D | I | D | D | D | D | D | DI | D | DI | D | DI |
| Zumi Crab 3x (B-15) | DI | DI | I | DI | DI | DI | D | DI | DI | DI | DI | I | I |
| 26105 (B-16) | I | D | DI | D | I | D | D | D | DI | D | DI | I | I |
| Daguo Crab (B-17) | D | D | DI | D | DI | D | D | D | DI | D | DI | I | DI |
| Xiongyue Crab 2 (B1-8) | DI | D | I | D | D | DI | D | D | DI | D | I | I | I |
| Watermelon Crab (B-18) | DI | DI | DI | D | D | DI | DI | D | DI | D | DI | DI | DI |
| Mudanjiang Crab (B1-9) | D | D | I | D | I | D | D | D | DI | DI | DI | I | DI |
| Tianhong 1 (B-19) | D | DI | DI | D | D | DI | DI | DI | DI | D | I | DI | I |
| Jiping 1 (B-2) | DI | D | DI | DI | DI | DI | D | DI | DI | DI | I | D | D |
| Caoyuan Crab (B2-1) | D | D | I | D | D | D | D | D | D | D | D | I | I |
| Zumi Crab 4x (B-21) | DI | DI | I | DI | DI | DI | D | DI | DI | DI | DI | I | I |
| Luanzhuang Shaguo (B2-11) | D | D | I | D | D | DI | DI | D | DI | D | DI | D | D |
| Xiaofan Crab (B2-13) | D | D | I | D | D | DI | D | D | DI | D | I | I | DI |
| Hebing Pingding Crab (B2-14) | D | D | I | D | D | D | D | D | DI | D | D | D | DI |
| Zumi Crab 3x 2 (B-22) | DI | DI | I | DI | DI | DI | D | DI | DI | DI | DI | I | I |
| Baleng Crab (B2-3) | D | D | I | D | D | D | D | D | DI | D | DI | DI | DI |
| Baleng seedling 14 (B-25) | D | DI | I | DI | DI | D | DI | D | DI | DI | I | I | DI |
| Russian White apple (B2-6) | DI | D | I | D | DI | D | DI | D | DI | DI | DI | I | DI |
| Nagafu 2 (B-26) | D | DI | DI | D | D | DI | DI | DI | DI | D | I | DI | I |
| Ambrosia (B-27) | DI | DI | DI | DI | I | D | I | D | DI | DI | DI | D | DI |
| Aihonghua (B2-8) | DI | DI | DI | D | D | DI | DI | D | DI | D | D | I | DI |
| Nanshennan (B-28) | D | DI | DI | D | D | DI | DI | DI | DI | D | I | DI | I |
| Zumi Crab W1 (B-29) | DI | DI | DI | DI | DI | DI | D | DI | DI | DI | DI | I | I |
| Hong 4G (B-3) | DI | D | I | DI | DI | DI | D | DI | DI | DI | DI | D | DI |
| Zumi Crab (B-30) | DI | DI | I | DI | DI | DI | D | DI | DI | DI | DI | I | I |
| Zaobai Crab (B3-1) | D | D | I | D | D | D | D | D | DI | D | DI | D | DI |
| Mollie's Delicious (B-31) | DI | D | DI | D | DI | DI | I | D | DI | D | DI | D | I |
| Regunzi Spur (B3-10) | D | D | I | D | D | D | D | D | DI | D | DI | I | D |
| Xiaofanshan Baleng (B3-11) | DI | D | DI | D | D | DI | DI | D | DI | D | D | DI | D |
| Huamei (B3-12) | I | DI | DI | DI | DI | DI | D | DI | DI | I | DI | DI | DI |
| Huashuo (B3-13) | I | D | DI | D | DI | D | D | D | DI | D | I | D | DI |
| Yuhong (B3-14) | D | D | D | D | DI | DI | DI | DI | DI | DI | I | DI | DI |
| Huayue (B3-15) | D | DI | DI | D | DI | DI | DI | D | DI | DI | I | DI | DI |
| Jingbohu Shandingzi (B3-2) | D | D | I | D | D | D | D | D | DI | D | D | I | D |

-continued

| Construction results of InDel marker genotype database of *Malus* germplasm resources | | | | | | | | | | | | | |
|---|---|---|---|---|---|---|---|---|---|---|---|---|---|
| Eluosi Daguo Shandingzi (B3-3) | DI | D | I | D | DI | DI | D | D | DI | DI | DI | I | DI |
| HY (B-33) | D | DI | DI | D | D | DI | D | D | DI | D | I | DI | DI |
| Hong Crab (B3-6) | D | D | I | D | D | D | D | D | DI | D | DI | I | D |
| 23# (B-37) | DI | DI | DI | DI | I | D | D | D | DI | DI | DI | D | I |
| Russian apple (B3-8) | D | D | DI | D | I | D | D | DI | DI | D | D | DI | DI |
| 147 (B-38) | DI | D | DI | D | DI | DI | D | D | DI | DI | DI | D | DI |
| Xiaofanshan Baleng 1 (B3-9) | D | D | I | D | D | D | D | D | DI | D | DI | I | D |
| Lvshuai (B-4) | DI | DI | I | DI | DI | D | D | DI | DI | DI | DI | DI | DI |
| Dounan (B-40) | DI | DI | DI | D | D | DI | D | DI | DI | D | DI | DI | I |
| 11906 (B-41) | DI | D | DI | D | I | D | D | D | DI | D | I | I | I |
| Luli (B-5) | I | D | DI | I | I | D | D | I | DI | DI | DI | D | DI |
| Jinxiuhong (B-6) | DI | DI | DI | DI | DI | DI | D | I | DI | DI | I | D | I |
| B68 (B-7) | DI | D | I | D | DI | DI | DI | D | DI | DI | I | I | D |
| Huaida (B-8) | DI | DI | DI | I | I | D | D | DI | DI | D | D | I | DI |
| Nanshennan mutant (B-9) | D | DI | DI | D | D | DI | DI | DI | DI | D | I | DI | I |
| Xiahong (BH-1) | DI | DI | DI | DI | DI | D | I | DI | D | DI | I | DI | |
| Wuming1 (BJ-1) | DI | DI | I | D | D | DI | DI | DI | D | DI | D | I | |
| Canzy ? (BJ-10) | DI | I | DI | DI | DI | D | D | D | DI | DI | DI | DI | DI |
| Xiangfu (BJ-11) | D | DI | DI | D | D | DI | DI | DI | DI | D | I | DI | I |
| Envy (BJ-12) | DI | I | DI | DI | DI | D | D | DI | DI | DI | I | DI | I |
| Fuji_KiKu (BJ-2) | D | DI | DI | D | D | DI | DI | DI | DI | D | I | DI | I |
| Banxiu Crab (BJ-4) | DI | D | I | D | D | DI | D | D | DI | DI | I | I | I |
| Jazz (BJ-5) | DI | I | DI | DI | DI | D | D | DI | DI | DI | DI | DI | DI |
| Early Red Bird 2 (BJ-7) | I | D | I | D | DI | DI | D | D | DI | D | DI | D | I |
| Qiuhong Gala (BJ-8) | D | DI | DI | D | D | DI | DI | DI | DI | D | I | DI | I |
| Hongxiangcui (BJ-9) | I | I | DI | D | DI | D | DI | DI | DI | I | D | I | |
| 07-115 (BK-1) | D | DI | DI | DI | DI | DI | D | DI | DI | D | I | DI | DI |
| Nagafu 3 (BK-2) | D | DI | DI | D | D | DI | DI | DI | DI | D | I | DI | I |
| 28-253 (BK-28-253) | DI | DI | DI | DI | DI | DI | I | D | DI | D | I | DI | I |
| Nagafu 3-R (BK-3) | D | DI | DI | D | D | DI | DI | DI | DI | D | I | DI | I |
| 4354 (BK-4) | DI | I | DI | DI | I | D | DI | DI | DI | D | I | DI | I |
| 4-23 (BK-4-23) | D | DI | DI | D | D | DI | DI | DI | DI | D | DI | DI | I |
| 4354-R ? (BK-5) | DI | DI | DI | D | D | D | DI | DI | DI | D | D | I | DI |
| 77-34 (BK-77-34) | D | D | I | D | D | DI | DI | DI | DI | D | DI | D | D |
| Red Spur Delicious (BK-AH) | D | D | DI | D | DI | DI | D | DI | DI | DI | I | DI | DI |
| Ozark Gold (BK-AJ) | D | DI | DI | DI | DI | DI | I | D | DI | DI | DI | DI | DI |

Construction results of InDel marker genotype database of *Malus* germplasm resources

| | | | | | | | | | | | | | |
|---|---|---|---|---|---|---|---|---|---|---|---|---|---|
| Michinoku (BK-AZ) | DI | D | I | DI | I | D | D | DI | DI | D | DI | D | DI |
| Azwell (BK-Azwell) | D | D | DI | D | DI | DI | D | DI | DI | DI | I | DI | DI |
| Banbishan Crab (BK-BBSHT) | D | D | I | D | D | D | D | D | DI | D | DI | D | D |
| Hokudo (BK-BD) | D | DI | DI | D | D | DI | DI | DI | DI | D | I | DI | I |
| Baifugao (BK-BFG) | DI | DI | I | D | I | D | D | D | DI | D | DI | DI | DI |
| White Crab (BK-BHT) | DI | D | DI | D | D | DI | DI | D | DI | D | D | DI | D |
| Buming Kangbing (BK-BMKB) | D | DI | DI | D | DI | DI | I | D | DI | D | I | DI | I |
| Batougou 1 (BK-BTG1H) | D | D | I | D | D | D | D | DI | D | D | I | DI |
| Batougou 2 (BK-BTG2H) | D | D | I | D | D | D | D | DI | D | DI | I | DI |
| Batougou Aizhen (BK-BTGAZ) | D | D | DI | D | D | D | D | D | DI | D | D | I | DI |
| Binzi (BK-BZ) | D | D | I | D | D | DI | DI | D | DI | D | I | DI | DI |
| Kitanosach (BK-BZX) | D | I | I | D | D | DI | D | D | DI | DI | I | I | DI |
| Binzi (SW) (BK-BZXN) | D | D | DI | D | D | DI | DI | D | DI | D | I | DI | DI |
| Nagafu 2 (BK-CF2H) | D | DI | DI | D | D | DI | DI | DI | DI | D | I | DI | I |
| Nagafu 36 (BK-CF36) | D | DI | DI | D | D | DI | DI | DI | DI | D | I | DI | I |
| Nagafu 6 (BK-CF6H) | D | DI | DI | D | D | DI | DI | DI | DI | D | I | DI | I |
| CG24 (BK-CG24) | D | D | DI | D | DI | DI | D | DI | DI | DI | I | DI | DI |
| CG3 (BK-CG3) | DI | DI | DI | DI | DI | DI | I | D | DI | D | I | DI | I |
| CG80 (BK-CG80) | D | DI | I | D | DI | D | DI | D | DI | DI | D | DI | DI |
| Changhong (BK-CH) | D | DI | DI | D | D | DI | DI | DI | DI | D | I | DI | I |
| Chieftan (BK-chieftan) | D | D | DI | D | DI | DI | I | D | DI | D | I | DI | I |
| Cangjiang Crab (BK-CJHT) | D | D | I | D | D | D | D | D | DI | D | D | I | D |
| Chuanling Crab (BK-CLHT) | DI | DI | DI | D | D | DI | DI | D | DI | D | I | DI | DI |
| Hatsuaki (BK-CQ) | D | DI | DI | DI | DI | DI | D | DI | DI | DI | I | I | I |
| Crispin (BK-crispin) | DI | DI | DI | DI | DI | DI | DI | DI | DI | DI | DI | DI | I |
| Caozigang Yuanshuai (BK-CZGYS) | D | D | DI | D | DI | DI | D | DI | DI | DI | I | DI | DI |
| Danxia (BK-DANXIA) | DI | DI | DI | D | D | DI | D | DI | DI | DI | I | I | DI |
| Dolgo (BK-DDG) | DI | D | I | DI | D | D | D | D | DI | DI | DI | I | DI |
| Darwin (BK-DEW) | D | D | I | D | D | DI | DI | D | DI | D | I | DI | DI |
| Oriental Apple (BK-DFPG) | I | DI | I | D | DI | D | D | D | DI | D | I | D | DI |
| Big Crab (BK-DGHT) | D | DI | I | D | D | D | D | D | DI | D | I | DI | DI |
| Daguo Jinhong (BK-DGJH) | DI | DI | DI | I | I | D | DI | DI | DI | D | D | I | DI |
| Daihong (BK-DH) | D | D | DI | D | DI | DI | D | DI | DI | DI | I | DI | DI |
| Daihao 261 (BK-DH261) | DI | DI | I | D | I | D | D | D | DI | D | I | DI | DI |
| Spur Golden Delicious (BK-DJG) | DI | I | DI | DI | DI | DI | DI | DI | DI | DI | DI | DI | I |
| Daxianguo (BK-DXG) | D | D | I | D | D | D | D | DI | D | DI | I | D |
| Daye Crab (BK-DYHT) | D | D | I | D | D | D | D | D | DI | D | DI | I | D |

-continued

Construction results of InDel marker genotype database of *Malus* germplasm resources

| | | | | | | | | | | | | | |
|---|---|---|---|---|---|---|---|---|---|---|---|---|---|
| Spur Fuji (BK-DZFS) | D | DI | DI | D | D | DI | DI | DI | DI | D | I | DI | I |
| Huaguan Spur (BK-DZHG) | DI | DI | DI | DI | D | D | I | DI | DI | I | D | I | |
| Elite (BK-Elite) | D | D | DI | D | DI | DI | D | DI | DI | DI | I | DI | DI |
| Fa 8 (BK-F8) | D | D | DI | D | DI | DI | D | DI | DI | I | DI | DI | |
| Fukushima Spur Fuji (BK-FDDZ) | D | DI | DI | D | D | DI | DI | DI | DI | D | I | DI | I |
| Fujin (BK-FJ) | DI | D | DI | D | D | DI | I | D | DI | D | I | I | DI |
| Florina (BK-Florina) | D | D | DI | D | D | DI | DI | DI | DI | D | I | I | DI |
| Fangming (BK-FM) | DI | I | DI | DI | DI | DI | DI | D | DI | DI | I | I | DI |
| Fuji (BK-Fuji) | DI | DI | DI | D | D | DI | DI | DI | DI | D | I | DI | I |
| Fengyan (BK-FY) | DI | DI | DI | I | I | D | DI | D | DI | DI | I | DI | DI |
| Yanfu 1 (BK-FY1) | D | DI | DI | D | D | DI | DI | DI | DI | D | I | DI | I |
| King of Tompkins County (BK-FZY) | DI | DI | I | DI | DI | DI | DI | DI | DI | D | I | DI | DI |
| G30 (BK-G30) | D | D | I | D | DI | D | DI | D | DI | DI | DI | D | D |
| Gao #5 (BK-G-5) | D | D | I | D | DI | DI | D | DI | D | I | DI | I | |
| Gala (BK-gala) | I | DI | DI | DI | DI | DI | D | DI | DI | I | DI | DI | |
| Golden Delicious (BK-GD) | DI | I | DI | DI | DI | DI | DI | DI | DI | DI | DI | DI | I |
| Gloster69 (BK-Gloster69) | DI | DI | DI | DI | DI | DI | D | D | DI | D | I | I | I |
| GM256 (BK-GM256) | D | D | I | D | I | D | I | D | DI | D | DI | D | DI |
| GM310 (BK-GM310) | D | DI | DI | DI | DI | D | DI | DI | D | DI | DI | DI | |
| Gaoqiu (BK-GQ) | DI | I | DI | D | D | DI | DI | DI | DI | I | DI | I | |
| Miyazaki Spur Fuji (BK-GQDZ) | D | DI | DI | D | D | DI | DI | DI | DI | D | I | DI | I |
| HAC-9 (BK-HAC-9) | D | DI | DI | D | D | DI | DI | DI | DI | D | I | DI | I |
| Huifeng Orin (BK-HFWL) | I | DI | DI | D | DI | DI | D | DI | DI | D | I | D | I |
| Red Ralls Janet (BK-HGG) | DI | DI | DI | D | D | DI | D | DI | D | I | D | DI | |
| Huaguan Crab (BK-HGHT) | D | D | I | D | D | DI | DI | D | DI | D | I | I | D |
| Harrold Red Delicious (BK-HH) | D | D | DI | D | DI | D | D | DI | DI | I | DI | DI | |
| Hong Crab 2 (BK-HHT2H) | D | D | I | D | D | D | D | D | DI | D | DI | I | D |
| Stark Redgold (BK-HJ) | D | DI | DI | D | DI | DI | D | I | DI | DI | DI | D | I |
| HLWQ (BK-HLWQ) | I | DI | DI | D | D | DI | D | D | DI | D | I | D | DI |
| Holly (BK-Holly) | D | DI | DI | D | DI | DI | D | DI | DI | D | I | D | I |
| Red Jonagold (BK-HQNJ) | I | DI | I | I | DI | D | DI | D | D | DI | D | DI | |
| Red Sekaiichii (BK-HSJY) | D | DI | DI | D | DI | DI | DI | DI | DI | I | D | I | |
| Hongte (BK-HT) | D | DI | DI | D | D | DI | D | DI | D | I | DI | I | |
| Haitangguo (BK-HTG) | D | D | I | D | DI | D | D | DI | D | D | DI | DI | |
| Haitanghua (BK-HTH) | D | D | I | D | D | D | D | DI | D | DI | D | D | |
| Huangtaiping (BK-HTP) | DI | D | DI | D | D | DI | DI | D | D | D | DI | D | |
| Hongxue (BK-HX) | D | DI | DI | D | DI | DI | I | D | DI | D | I | DI | I |

-continued

| Construction results of InDel marker genotype database of *Malus* germplasm resources | | | | | | | | | | | | | |
|---|---|---|---|---|---|---|---|---|---|---|---|---|---|
| Jincui (BK-JC) | D | DI | DI | DI | DI | DI | D | DI | DI | DI | I | D | I |
| Juda Fuji (BK-JDFS) | D | DI | DI | D | D | DI | DI | DI | DI | D | I | DI | I |
| Jiguan (BK-JG) | DI | DI | I | D | DI | D | D | D | DI | D | DI | I | DI |
| Jinhong (BK-JH) | DI | DI | DI | I | I | D | D | DI | D | D | I | DI | DI |
| Jonagored (BK-Jonagored) | DI | DI | DI | DI | DI | DI | DI | DI | DI | DI | DI | I | I |
| Jonathan (BK-Jonathan) | DI | DI | DI | D | DI | D | D | DI | D | I | DI | DI |
| Himekami (BK-JS) | DI | DI | DI | D | DI | DI | D | DI | DI | D | I | D | I |
| Stark Blushing Golden (BK-JY) | I | DI | DI | DI | I | D | I | D | DI | I | DI | DI | DI |
| Classic Red Delicious (BK-KAHONG) | D | D | DI | D | DI | D | D | DI | DI | DI | I | DI | DI |
| KLGDG Shandingzi (BK-KLGDGSDZ) | D | D | I | D | D | D | D | D | DI | D | D | DI | D |
| KOSZTELQ (BK-KOSZTELQ) | D | D | DI | D | I | D | I | D | DI | D | DI | I | DI |
| Sunflower (BK-KUIHUA) | DI | DI | DI | D | DI | DI | DI | DI | DI | DI | I | I | DI |
| Lenghaitang (BK-LHT) | D | D | I | D | D | D | D | D | DI | D | DI | D | D |
| Liberty (BK-liberty) | D | D | DI | D | DI | DI | I | D | DI | D | I | DI | I |
| Lijiang Shandingzi (BK-LJSDZ) | D | DI | I | D | D | D | D | D | DI | D | I | I | DI |
| Laoshan 4 (BK-LS4H) | D | D | I | D | D | D | D | D | DI | D | DI | I | D |
| Ryoka no Kisetsu (BK-LX) | D | DI | DI | D | D | DI | DI | DI | DI | D | I | DI | I |
| Lvxiangjiao (BK-LXJ) | DI | D | DI | DI | DI | DI | I | D | DI | D | DI | DI | DI |
| Liaozhen 1 (BK-LZ1H) | DI | D | I | D | DI | D | DI | DI | D | D | DI | D | DI |
| M7 (BK-M7) | DI | DI | I | D | DI | D | D | DI | DI | D | I | I | I |
| Meiguihong (BK-MGH) | D | D | DI | D | DI | D | DI | DI | DI | DI | I | DI | DI |
| Meile (BK-ML) | DI | I | DI | D | D | DI | DI | DI | DI | DI | DI | DI | I |
| MM106 (BK-MM106) | D | DI | I | D | DI | D | DI | D | DI | D | DI | DI |
| Mengpaisi (BK-MPS) | D | DI | DI | D | D | DI | DI | D | DI | D | DI | DI | DI |
| Meixiang (BK-MX) | D | DI | DI | D | D | DI | DI | DI | DI | D | I | DI | I |
| Ningqiu (BK-NQ) | DI | D | DI | D | DI | DI | D | D | DI | D | I | DI | DI |
| P16 (BK-P16) | D | DI | I | D | DI | D | D | D | DI | D | I | DI | DI |
| P22 (BK-P22) | D | D | I | D | D | D | D | DI | D | DI | DI | DI |
| Pingdinghaitang (BK-PDHT) | D | D | I | D | D | D | D | DI | D | DI | I | D |
| Bianguo Crab (BK-PGHT) | D | DI | I | DI | DI | D | DI | DI | D | DI | DI | DI |
| Pionier (BK-Pionier) | D | DI | I | D | DI | DI | D | DI | D | I | I | I |
| Prima (BK-Prima) | DI | DI | I | D | DI | D | D | DI | DI | D | I | DI | I |
| Pingyitiancha (BK-PYTC) | D | D | I | D | D | D | D | DI | D | D | I | D |
| Qianxue (BK-QAINXUE) | DI | D | DI | D | D | D | D | D | DI | D | I | I | I |
| Akifu 1 (BK-QF1) | D | DI | DI | D | D | DI | DI | DI | DI | D | I | DI | I |
| Qingfu 13 (BK-QF13) | D | DI | DI | D | D | D | DI | DI | DI | D | I | DI | I |
| Seimei (BK-QM) | DI | DI | DI | DI | DI | DI | I | D | DI | I | I | DI | DI |

| | | | | | | | | | | | | |
|---|---|---|---|---|---|---|---|---|---|---|---|---|
| Construction results of InDel marker genotype database of *Malus* germplasm resources | | | | | | | | | | | | |
| Senshu (BK-QQ) | DI | D | DI | DI | DI | DI | I | D | DI | DI | I | DI | I |
| Aomori Early (BK-QSZS) | DI | DI | DI | DI | DI | DI | DI | DI | DI | DI | DI | DI | I |
| Qiuxiang (BK-QX) | DI | I | DI | DI | DI | DI | DI | D | DI | DI | I | I | DI |
| Qiuxing Crab (BK-QXHT) | D | D | DI | D | DI | D | D | D | DI | D | D | I | I |
| Yanqing (BK-QY) | DI | D | DI | D | DI | DI | D | I | DI | DI | I | DI | I |
| Regunzi (BK-RGZ) | D | D | I | D | D | D | D | D | D | D | DI | I | D |
| Ruby (BK-Ruby) | D | DI | DI | D | DI | DI | D | D | DI | DI | I | D | I |
| Scarlet (BK-scarlet) | D | D | DI | D | DI | DI | D | DI | DI | DI | I | DI | DI |
| Sdw1 (BK-Sdw1) | D | D | I | D | D | D | D | D | DI | D | D | I | DI |
| Shandingzi 2 (BK-SDZ2H) | D | D | I | D | D | D | D | D | DI | D | D | D | DI |
| Su E Shandingzi (BK-SESDZ) | D | D | I | D | D | D | D | D | DI | D | D | DI | D |
| Shengfang 2 (BK-SF2) | D | DI | DI | D | D | DI | DI | DI | DI | D | I | DI | I |
| SH6 (BK-SH6) | D | DI | DI | D | D | DI | D | D | DI | D | DI | D | DI |
| Sankuaishi Crab 1 (BK-SKSHT1H) | D | D | I | D | D | D | D | D | DI | D | DI | DI | DI |
| Forest Apple (BK-SLPG) | DI | DI | DI | D | DI | DI | D | DI | DI | D | DI | I | DI |
| Sieversii (BK-SWS) | D | DI | I | D | D | D | D | D | DI | D | I | I | DI |
| Sansa (BK-SX) | I | D | DI | D | DI | DI | D | D | DI | DI | I | DI | I |
| Szampion (BK-Szampion) | DI | DI | I | I | I | D | DI | D | DI | DI | I | DI | I |
| T337 (BK-T337) | D | D | I | D | DI | D | I | D | DI | D | I | D | DI |
| Turkmen Apple (BK-TKMPG) | D | DI | I | D | D | D | D | DI | DI | D | I | I | DI |
| Mato 1 (BK-TMYH) | DI | D | I | DI | I | D | D | DI | DI | D | DI | D | DI |
| Trajian (BK-Trajian) | DI | D | DI | D | D | DI | DI | D | DI | D | I | DI | DI |
| Weiai 3 (BK-WA3) | D | D | I | D | D | D | D | D | DI | D | DI | DI | DI |
| Wanbai Crab (BK-WBHT) | D | DI | DI | D | DI | D | DI | D | DI | DI | DI | DI | DI |
| Wufengshan 1 (BK-WFS1H) | D | D | I | D | D | D | D | D | DI | D | DI | DI | DI |
| Wufengshan 4 (BK-WFS4H) | D | DI | DI | D | D | DI | D | D | DI | D | DI | DI | DI |
| Wufengshan Crab (BK-WFSHT) | D | D | I | DI | DI | D | D | D | DI | D | D | I | DI |
| Wufengshan Crab 2 (BK-WFSHT2H) | D | D | DI | D | D | D | D | D | DI | D | DI | I | DI |
| Wufengshan Crab 6 (BK-WFSHT6H) | D | D | I | D | DI | D | D | D | DI | D | D | I | DI |
| Wifos (BK-wifos) | DI | D | DI | DI | DI | DI | D | DI | DI | DI | I | DI | DI |
| Orei (BK-WL) | I | DI | DI | DI | I | D | I | D | DI | I | DI | DI | DI |
| Maypole (BK-WM) | D | D | I | D | D | DI | D | D | DI | DI | I | I | DI |
| Waltz (BK-WZ) | DI | DI | DI | D | DI | DI | D | D | DI | DI | I | I | I |
| Kotoku (BK-XD) | D | D | I | D | DI | D | D | DI | DI | D | I | I | DI |
| Xiaofanshan Binzi (BK-XFSBZ) | D | D | I | D | D | DI | DI | D | DI | D | I | DI | DI |
| Xiaofanshan Crab 4 (BK-XFSHT4H) | D | D | I | D | D | DI | D | D | DI | D | I | I | DI |
| Xiaogoumen Naizi (BK-XGMNZ) | D | D | I | D | D | DI | D | D | DI | D | I | I | DI |
| XGM Suan Binzi (BK-XGMSBZ) | D | D | I | D | D | DI | DI | D | DI | D | I | DI | DI |

-continued

Construction results of InDel marker genotype database of *Malus* germplasm resources

| | | | | | | | | | | | | | |
|---|---|---|---|---|---|---|---|---|---|---|---|---|---|
| XGM Tian Binzi (BK-XGMTBZ) | D | D | I | D | D | DI | DI | D | DI | D | I | I | DI |
| Starkrimson (BK-XHX) | D | D | DI | D | DI | DI | D | DI | D | DI | I | DI | DI |
| Xinjiang 1 (BK-XJ1) | D | D | DI | D | D | DI | D | D | DI | D | I | D | I |
| Xinjiang 11 (BK-XJ11) | DI | D | I | D | I | D | D | DI | D | D | I | DI |
| Xinjiang 14 (BK-XJ14) | DI | D | I | D | I | D | D | DI | D | DI | I | DI |
| Xinjiang 15 (BK-XJ15) | DI | D | I | D | DI | D | D | DI | D | DI | I | I |
| Xinjiang 16 (BK-XJ16) | DI | D | I | D | DI | DI | DI | D | DI | DI | I | DI |
| Xinjiang 17 (BK-XJ17) | D | D | I | D | DI | DI | D | DI | D | DI | I | DI |
| Xinjiang 18 (BK-XJ18) | D | D | I | D | DI | D | D | DI | D | DI | I | DI |
| Xinjiang 19 (BK-XJ19) | DI | D | DI | D | DI | D | D | D | DI | I | DI | DI |
| Xinjiang 21 (BK-XJ21) | DI | D | I | D | DI | DI | DI | D | DI | D | DI | DI | DI |
| Xinjiang 22 (BK-XJ22) | D | D | I | D | D | DI | D | D | DI | D | I | D | DI |
| Xinjiang 24 (BK-XJ24) | D | D | I | D | D | DI | D | D | DI | D | I | D | DI |
| Xinjiang 26 (BK-XJ26) | DI | D | I | D | I | D | D | DI | D | DI | I | DI |
| Xinjiang 28 (BK-XJ28) | DI | D | DI | D | DI | D | D | D | DI | DI | I | DI | DI |
| Xinjiang 29 (BK-XJ29) | D | DI | I | D | D | DI | DI | DI | DI | I | DI | I | DI |
| Xinjiang 31 (BK-XJ31) | DI | DI | I | D | DI | D | DI | DI | D | D | D | DI |
| Xinjiang 3 (BK-XJ3H) | D | DI | DI | D | D | DI | DI | DI | DI | D | I | DI | I |
| Xinjiang 6 (BK-XJ6H) | D | D | I | D | D | D | D | DI | D | I | I | D |
| Xinjiang 7 (BK-XJ7) | DI | D | I | D | I | D | D | DI | D | DI | I | DI |
| Xinjiang 8 (BK-XJ8) | D | D | I | D | D | DI | D | DI | DI | D | D | DI | DI |
| Xinjiang 9 (BK-XJ9) | D | DI | I | D | D | DI | DI | DI | I | DI | I | DI |
| Xijin Crab (BK-XJHT) | D | DI | I | D | D | DI | D | D | DI | D | D | I | DI |
| Xiaomian Crab (BK-XMHT) | D | D | I | D | D | D | D | D | DI | D | I | D | D |
| New Jonagold (BK-XQNJ) | DI | DI | DI | DI | DI | DI | DI | DI | DI | DI | DI | DI | I |
| Xiaoshuai (BK-XS) | DI | D | DI | D | DI | DI | D | DI | DI | DI | DI | I | DI |
| Shinsekai (BK-XSJ) | DI | DI | DI | DI | DI | DI | DI | D | DI | D | I | DI | I |
| Xiangyanghong (BK-XYH) | D | DI | DI | D | D | DI | DI | DI | DI | DI | I | D | DI |
| Italy Early Red (BK-YDLZH) | I | DI | DI | DI | DI | DI | D | DI | DI | I | DI | DI | DI |
| Yanfu 10 (BK-YF10) | D | DI | DI | D | D | DI | DI | DI | DI | D | I | DI | I |
| Yoko (BK-YG) | DI | DI | DI | DI | DI | DI | DI | DI | DI | DI | I | I | I |
| Yuanhong (BK-YH) | D | D | DI | D | DI | DI | DI | DI | DI | DI | DI | D | D |
| Tehong 2 (BK-YH2) | D | D | DI | D | D | D | DI | DI | DI | D | I | DI | I |
| Yanhongmi (BK-YHM) | DI | DI | DI | D | I | D | D | D | DI | D | I | DI | I |
| Youliang Spur (BK-YLDZ) | D | DI | DI | D | D | DI | DI | DI | DI | D | I | DI | I |
| Yuanye Crab (BK-YYHT) | D | D | I | D | D | D | D | D | DI | D | DI | I | D |
| Stark Jumbo (BK-ZB) | D | DI | DI | D | D | D | D | D | DI | D | I | DI | DI |
| Jumbo Orin (BK-ZBWL) | DI | I | DI | DI | DI | DI | DI | DI | DI | DI | DI | DI | I |

-continued

| Construction results of InDel marker genotype database of *Malus* germplasm resources |||||||||||||||
|---|---|---|---|---|---|---|---|---|---|---|---|---|---|
| Zhuifeng 1 (BK-ZF1H) | D | D | I | D | DI | D | D | DI | DI | D | D | I | DI |
| Zhuifeng 2 (BK-ZF2H) | D | D | I | D | D | D | D | D | DI | D | D | D | DI |
| Early Fuji (BK-ZFS) | D | DI | DI | D | D | DI | DI | DI | DI | D | I | DI | I |
| Xiaofanshan Crab (BK-ZFSHT) | D | D | I | D | D | DI | D | DI | D | D | I | I | DI |
| Zisai Pearl (BK-Zisai) | DI | D | D | DI | DI | D | D | D | DI | D | I | I | DI |
| Geneva Early (BK-ZJ) | DI | D | I | D | DI | D | DI | DI | D | D | I | D | DI |
| 13-26W (CL-1) | DI | I | DI | DI | DI | DI | D | DI | DI | D | I | DI | I |
| 23-127 (CL-2) | I | DI | DI | DI | DI | DI | DI | D | DI | DI | I | D | DI |
| 50-30 (CL-3) | D | DI | DI | D | DI | DI | DI | D | DI | D | I | D | I |
| 50-32 (CL-4) | DI | I | DI | D | D | DI | DI | DI | DI | D | DI | I | I |
| H5-101 (CL-5) | DI | DI | DI | D | D | DI | DI | DI | DI | D | I | DI | I |
| Pingyan (CL-6) | DI | I | DI | DI | DI | DI | D | DI | DI | D | I | I | DI |
| Deqin Crab (DQ) | D | D | I | D | D | D | D | D | DI | D | D | I | D |
| Jin 18 (GY-1) | D | DI | DI | D | D | DI | DI | DI | DI | D | I | DI | I |
| Fengfeng Baleng (GY-2) | DI | D | I | D | D | DI | D | D | DI | DI | I | I | I |
| Hanfu 6 (GY-3) | D | DI | DI | D | D | DI | DI | DI | DI | D | I | DI | I |
| Hanfu 3 (GY-4) | D | DI | DI | D | DI | D | D | DI | DI | D | DI | D | DI |
| 95/06 (GZ-1) | D | D | DI | D | DI | D | D | D | DI | D | I | DI | I |
| 107/06 (GZ-2) | DI | D | DI | D | DI | D | D | DI | D | D | DI | I | I |
| 117/06 (GZ-3) | I | D | DI | D | I | D | D | D | DI | D | I | DI | DI |
| 119/06 (GZ-4) | DI | D | DI | D | I | D | D | D | DI | D | I | I | I |
| Jinxiu Crab (GZ-5) | D | D | DI | D | I | D | D | DI | DI | DI | I | DI | DI |
| Zhizun Fuji (HS-1) | D | DI | DI | D | D | DI | DI | DI | DI | D | I | DI | I |
| Fuji No. 1 (HS-10) | D | DI | DI | D | D | DI | DI | DI | DI | D | I | DI | I |
| Red Jonaprince (HS-12) | DI | DI | DI | DI | D | DI | DI | DI | DI | DI | DI | DI | I |
| Nic29 (HS-13) | D | D | I | D | DI | D | I | D | DI | D | I | D | D |
| Azhen Fuji (HS-14) | D | DI | DI | D | D | DI | DI | DI | DI | D | I | DI | I |
| Envy (HS-15) | DI | I | DI | DI | DI | D | D | DI | DI | DI | I | DI | I |
| Rosegrow (HS-16) | DI | DI | DI | I | I | D | D | DI | DI | D | DI | D | I |
| Canzy (HS-17) | DI | I | DI | DI | DI | D | D | D | DI | DI | DI | DI | DI |
| Fubrax (HS-2) | D | DI | DI | D | D | DI | DI | DI | DI | D | I | DI | I |
| Mitchgla (HS-3) | I | DI | DI | DI | DI | DI | D | DI | DI | I | DI | DI | DI |
| Fujiko (HS-4) | D | DI | DI | D | D | DI | DI | DI | DI | D | I | DI | I |
| Buckeye Gala (HS-5) | I | DI | DI | DI | DI | DI | D | DI | DI | I | DI | DI | DI |
| Fujion (HS-6) | D | DI | D | D | D | DI | I | D | DI | D | I | DI | I |
| Modi (HS-7) | DI | DI | DI | DI | DI | DI | DI | D | DI | DI | DI | DI | DI |
| Jiangxue (HS-8) | DI | D | DI | D | DI | DI | D | DI | DI | DI | I | D | I |
| September Wonder Fuji (HS-9) | D | DI | DI | D | D | DI | DI | DI | DI | D | I | DI | D |

| | | | | | | | | | | | | | |
|---|---|---|---|---|---|---|---|---|---|---|---|---|---|
| Linqin Crab (LQ) | D | D | I | D | D | D | D | D | DI | D | D | D | D |
| Lushan Sanye (LSSY) | D | D | I | D | D | D | D | D | DI | DI | DI | I | DI |
| 83-2 (MDJ-1) | DI | D | DI | DI | DI | DI | D | DI | DI | D | DI | I | DI |
| Tianfeng (MDJ-9) | D | D | DI | D | I | D | D | DI | D | D | DI | DI | |
| Oregon Spur II-red (OR-1) | D | D | DI | D | DI | DI | D | DI | DI | DI | I | DI | DI |
| Oregon Spur II-green (OR-2) | D | D | DI | D | DI | DI | D | DI | DI | DI | I | DI | DI |
| E3N2 (OR-3) | D | D | DI | D | DI | DI | D | DI | DI | DI | I | DI | DI |
| E4N1 (OR-4) | D | D | DI | D | DI | DI | D | DI | DI | DI | I | DI | DI |
| E4N2 (OR-5) | D | D | DI | D | DI | DI | D | DI | DI | DI | I | DI | DI |
| W6N1 (OR-6) | D | D | DI | D | DI | DI | D | DI | DI | DI | I | DI | DI |
| W6S5 (OR-7) | D | D | DI | D | DI | DI | D | DI | DI | DI | I | DI | DI |
| W8S3 (OR-8) | D | D | DI | D | DI | DI | D | DI | DI | DI | I | DI | I |
| Daihong (QD-1) | DI | D | DI | DI | DI | D | D | D | DI | I | DI | DI | I |
| Tangmutian (QD-10) | D | DI | DI | D | D | DI | DI | DI | DI | D | I | DI | D |
| Shanjin Crab N1 (QD-11) | D | D | I | D | D | D | D | D | DI | DI | DI | I | D |
| Shanjin Crab N2 (QD-12) | D | D | I | D | D | D | D | D | DI | D | DI | I | D |
| E zhen 1 (QD-13) | D | DI | I | D | DI | D | DI | D | DI | D | DI | I | DI |
| E zhen 2 (QD-14) | D | DI | I | D | D | D | I | D | DI | I | DI | DI | |
| E zhen 3 (QD-15) | D | D | I | D | DI | D | DI | DI | DI | D | I | DI | D |
| E zhen 4 (QD-16) | D | DI | I | D | D | D | I | D | DI | D | I | D | D |
| E zhen 5 (QD-17) | D | DI | I | D | D | D | I | D | DI | D | I | D | D |
| Haihong (QD-19) | D | D | I | D | D | DI | DI | D | DI | D | DI | DI | I |
| Qingfu 2 (QD-2) | D | DI | DI | D | D | DI | DI | DI | DI | D | I | DI | I |
| Telamon (QD-20) | DI | DI | DI | D | DI | DI | DI | D | DI | DI | I | I | DI |
| Fuyan (QD-21) | DI | D | DI | D | D | DI | D | D | DI | DI | I | DI | D |
| Hongxun 1 (QD-22) | D | D | DI | D | D | D | D | DI | D | D | I | I | |
| Rushan Fuji (QD-23) | D | DI | DI | D | D | DI | DI | DI | DI | D | I | DI | I |
| Jiudian Spur (QD-24) | D | DI | DI | D | D | DI | DI | DI | DI | D | I | DI | DI |
| Ruihong (QD-25) | I | DI | DI | DI | DI | DI | D | DI | DI | I | DI | DI | DI |
| Zhongnvshi (QD-26) | DI | D | I | D | DI | DI | D | D | DI | DI | DI | I | I |
| 2001 Spur (QD-27) | D | DI | DI | D | D | DI | DI | DI | DI | D | I | DI | I |
| Fuli (QD-28) | DI | DI | DI | D | DI | DI | I | D | DI | DI | I | DI | I |
| Tuanwang semi-Spur (QD-29) | D | DI | DI | D | D | DI | DI | DI | DI | D | I | DI | I |
| Qingfu 3 (QD-3) | D | DI | DI | D | D | DI | DI | DI | DI | D | I | DI | I |
| Longfu (QD-30) | D | DI | DI | D | D | DI | DI | DI | DI | D | I | DI | I |
| Baotou Linqin (QD-31) | DI | D | I | D | D | D | D | D | DI | D | D | I | I |
| Yanfu 6 (QD-32) | D | DI | DI | D | D | DI | DI | DI | DI | D | I | DI | DI |

-continued

Construction results of InDel marker genotype database of *Malus* germplasm resources

| | | | | | | | | | | | | | |
|---|---|---|---|---|---|---|---|---|---|---|---|---|---|
| SH40-2 seedling (QD-4) | D | D | DI | D | D | DI | D | D | DI | D | D | D | DI |
| Saijin (QD-5) | I | DI | DI | D | DI | DI | D | DI | DI | DI | I | I | I |
| Nagafu 12 (QD-6) | D | DI | DI | D | D | DI | DI | DI | DI | D | I | DI | I |
| Caoyuan Crab (QD-7) | D | D | I | D | D | D | D | D | D | D | D | D | DI |
| Xiaojin Crab (QD-8) | D | DI | DI | D | D | DI | DI | D | DI | D | D | DI | DI |
| Shuangyanghong (QD-9) | I | DI | DI | DI | DI | D | DI | DI | I | DI | DI | I |
| Qianxian Crab (QX-1) | DI | D | I | D | D | DI | D | D | DI | DI | I | I | I |
| Ruixue (ruixue) | DI | DI | DI | DI | D | D | D | D | D | I | DI | I |
| Ruiyang (RY) | DI | I | DI | D | DI | DI | D | I | DI | D | I | DI | DI |
| Yanyuan 1 (SC-1) | DI | DI | DI | DI | D | DI | DI | DI | DI | DI | DI | DI | I |
| Yanyuan 2 (SC-2) | DI | I | DI | DI | DI | DI | DI | D | DI | DI | I | I | DI |
| Yanyuan 3 (SC-3) | D | DI | DI | D | D | DI | DI | DI | DI | D | I | DI | I |
| Yanyuan 4 (SC-4) | DI | I | DI | DI | DI | DI | DI | D | DI | DI | I | I | DI |
| Yanyuan 5 (SC-5) | D | I | DI | DI | DI | DI | D | D | DI | D | DI | DI | DI |
| Yanyuan 6 (SC-6) | D | DI | DI | DI | DI | DI | D | D | DI | DI | DI | DI | DI |
| Yanyuan 7 (SC-7) | DI | DI | DI | DI | DI | DI | DI | DI | DI | DI | DI | DI | I |
| Mitchgala (SX-10) | I | DI | DI | DI | DI | DI | D | DI | DI | I | DI | DI | DI |
| Zhongqiuwang Linyi (SX-11) | DI | DI | DI | DI | DI | DI | DI | DI | DI | DI | D | D | DI |
| Linyi Meiguo 5 (SX-12) | D | I | DI | D | DI | DI | DI | DI | DI | D | I | D | I |
| Liquan Spur Fuji (SX-13) | D | DI | DI | D | D | DI | DI | DI | DI | D | I | DI | I |
| Qiulimu (SX-14) | D | D | I | D | DI | D | D | I | DI | D | I | I | DI |
| Qincui (SX-15) | DI | DI | DI | D | D | DI | DI | D | DI | D | I | D | DI |
| Taigu Shaguo Late (SX-17) | D | D | I | D | D | DI | DI | D | DI | D | I | DI | DI |
| Lingyige Hongrou (SX-18) | DI | D | DI | D | DI | D | D | D | DI | D | DI | I | I |
| Shenai LS (SX-19) | D | D | DI | D | DI | DI | DI | DI | DI | D | I | DI | DI |
| Linyi Meiguo 8 (SX-2) | DI | DI | DI | DI | DI | DI | I | D | DI | I | I | DI | DI |
| Liga (SX-20) | I | DI | DI | DI | DI | DI | D | DI | DI | I | DI | DI | DI |
| Y-1 (SX-21) | D | D | I | D | D | D | D | D | DI | D | D | I | DI |
| B009 (SX-22) | D | D | DI | D | D | D | D | D | DI | D | DI | DI | DI |
| Jinfu 1 (SX-23) | D | DI | DI | D | D | DI | DI | DI | DI | D | I | DI | I |
| Hongmantang (SX-24) | DI | D | I | D | D | DI | D | D | DI | DI | DI | D | D |
| Y-2 (SX-25) | D | D | I | D | D | D | D | D | DI | D | D | I | DI |
| Y-3 (SX-26) | D | D | I | D | D | D | D | D | D | D | D | I | DI |
| Xinliangxiang (SX-27) | D | DI | DI | D | D | DI | DI | DI | DI | D | I | DI | I |
| Ennike Gala (SX-28) | I | DI | DI | DI | DI | DI | D | DI | DI | I | DI | DI | DI |
| Linyi Meiguo 6 (SX-3) | D | DI | DI | D | DI | DI | DI | DI | DI | DI | DI | D | DI |
| Linyi Meiguo 2 (SX-30) | D | DI | DI | D | D | DI | DI | DI | DI | D | I | DI | I |
| Donglimu (SX-33) | D | D | DI | D | DI | D | D | I | DI | D | I | I | DI |

| Construction results of InDel marker genotype database of *Malus* germplasm resources | | | | | | | | | | | | | |
|---|---|---|---|---|---|---|---|---|---|---|---|---|---|
| Linyi Meiguo 1 (SX-34) | DI | DI | DI | DI | DI | DI | I | D | DI | I | I | DI | DI |
| Linyi Meiguo 4 (SX-4) | D | I | DI | D | D | DI | I | D | DI | D | DI | DI | I |
| Qinyang (SX-6) | I | D | DI | D | D | DI | DI | D | DI | DI | DI | D | DI |
| Taiguo Shaguo Early (SX-7) | D | D | I | D | D | DI | D | D | DI | D | I | DI | DI |
| Yuhua Zaofu (SX-8) | D | DI | DI | D | D | DI | DI | DI | DI | D | I | DI | I |
| 78-M18 (SY-1) | DI | I | DI | D | DI | D | I | D | DI | D | DI | DI | DI |
| Jinping (SY-10) | I | D | I | I | I | D | I | D | DI | D | DI | DI | DI |
| Longqiu (SY-11) | D | DI | I | D | DI | D | DI | D | DI | D | DI | DI | DI |
| Longfeng (SY-12) | D | D | DI | D | D | D | D | D | DI | D | D | I | D |
| Xiangjiaoguo (SY-14) | I | DI | I | D | D | DI | D | DI | DI | I | DI | DI | DI |
| Longguan (SY-15) | DI | DI | I | D | D | DI | I | D | DI | DI | DI | DI | DI |
| Longshuai (SY-16) | D | D | DI | D | D | DI | D | DI | DI | D | D | I | DI |
| Zixiang (SY-17) | DI | D | DI | D | DI | DI | D | D | DI | D | I | DI | DI |
| Huahong (SY-19) | D | D | I | D | D | DI | DI | D | DI | D | I | DI | DI |
| Binlang (SY-2) | I | DI | I | D | D | DI | D | DI | DI | I | DI | DI | DI |
| Qiufengmi (SY-20) | D | D | I | D | D | D | I | D | DI | D | I | DI | DI |
| Honglingdang (SY-21) | D | D | I | D | DI | D | DI | D | DI | DI | DI | I | DI |
| Qiulu (SY-22) | D | DI | DI | D | DI | DI | I | D | DI | DI | DI | I | I |
| Longhong (SY-23) | DI | DI | I | D | D | DI | I | D | DI | DI | DI | DI | DI |
| Milk (SY-3) | DI | D | DI | D | DI | D | D | DI | DI | DI | DI | I | DI |
| Hanfu (SY-4) | DI | DI | DI | D | D | DI | DI | DI | DI | D | I | DI | DI |
| Toko (SY-5) | D | DI | D | D | D | DI | DI | DI | DI | D | I | I | DI |
| Jinhong (SY-6) | DI | DI | DI | I | I | D | D | DI | DI | D | D | I | DI |
| K9 (SY-7) | D | D | I | D | DI | D | DI | D | DI | DI | DI | I | DI |
| 03-06-04 (SY-8) | D | DI | DI | D | D | DI | D | D | DI | D | I | D | DI |
| Olga (SY-9) | D | DI | I | D | DI | D | DI | D | DI | D | D | D | DI |
| Gala 4x (TA-1) | I | DI | DI | DI | DI | DI | D | DI | DI | I | DI | DI | DI |
| Juda Fuji (TA-11) | D | DI | DI | D | DI | DI | DI | DI | DI | D | I | DI | I |
| Luli (TA-12) | I | D | DI | I | I | D | D | I | DI | DI | DI | D | DI |
| Luping 1 (TA-13) | I | DI | DI | D | D | DI | D | DI | DI | DI | DI | DI | DI |
| Luping 2 (TA-14) | DI | DI | DI | D | D | DI | D | DI | DI | DI | DI | DI | DI |
| Luping 5 (TA-15) | DI | DI | DI | DI | DI | DI | D | DI | DI | DI | DI | I | DI |
| Luyan (TA-16) | I | DI | DI | DI | DI | DI | D | DI | DI | DI | DI | DI | DI |
| Meinong (TA-17) | D | DI | DI | D | DI | DI | I | D | DI | DI | I | D | DI |
| Akifu 19 (TA-18) | D | DI | DI | D | D | DI | DI | DI | DI | D | I | DI | I |
| Akifu 39 (TA-19) | D | DI | DI | D | D | DI | DI | DI | DI | D | I | DI | I |
| Hanfu 4x (TA-2) | I | DI | I | D | DI | DI | DI | DI | DI | D | I | D | DI |
| Qiufuhong (TA-20) | D | DI | DI | D | D | DI | DI | DI | DI | D | I | DI | I |

-continued

| | | | | | | | | | | | | | |
|---|---|---|---|---|---|---|---|---|---|---|---|---|---|
| Construction results of InDel marker genotype database of *Malus* germplasm resources | | | | | | | | | | | | | |
| Qunfu 1 (TA-21) | D | DI | DI | D | D | DI | DI | DI | DI | D | I | DI | I |
| Shengfang (TA-22) | D | DI | DI | D | D | DI | DI | DI | DI | D | I | DI | I |
| Alps Otome (TA-27) | DI | DI | I | D | I | D | DI | DI | DI | D | I | DI | DI |
| Early Fuji (TA-28) | D | DI | DI | D | D | DI | DI | DI | DI | D | I | DI | I |
| BP (TA-3) | D | DI | I | D | DI | D | I | D | DI | D | I | DI | DI |
| Yishuihong (TA-32) | D | DI | DI | D | D | DI | DI | DI | DI | D | I | DI | I |
| BP-176 (TA-4) | D | DI | I | D | DI | D | I | D | DI | D | I | DI | DI |
| G41 (TA-5) | D | DI | I | D | DI | D | DI | D | DI | D | D | I | D |
| G935 (TA-6) | D | D | I | D | DI | D | DI | D | DI | DI | D | I | D |
| P60 (TA-7) | D | DI | DI | D | DI | D | I | D | DI | D | DI | DI | DI |
| Fuji (TA-9) | D | DI | DI | D | D | DI | DI | DI | DI | D | I | DI | I |
| Tianfu 1 (TS-1) | D | DI | DI | D | D | DI | DI | DI | DI | D | I | DI | I |
| &28 (TS-13) | D | DI | DI | D | D | DI | DI | DI | DI | D | I | DI | DI |
| Red Chief (TS-14) | D | D | DI | D | DI | DI | D | DI | DI | DI | I | DI | DI |
| New Redchief (TS-2) | D | D | D | D | DI | DI | D | DI | DI | DI | I | DI | DI |
| Chaohongxing (TS-3) | D | D | DI | D | DI | DI | D | DI | DI | DI | I | DI | I |
| Aozhou 1 (TS-5) | DI | DI | I | D | I | D | DI | D | DI | I | D | I | I |
| Tianfu 2 (TS-6) | D | DI | DI | D | D | DI | DI | DI | DI | D | I | DI | I |
| Judeline (TS-7) | DI | I | DI | DI | DI | DI | DI | D | DI | DI | DI | I | I |
| Judestar (TS-8) | I | I | DI | DI | DI | DI | D | DI | DI | D | I | DI | I |
| Judaine (TS-9) | DI | I | DI | DI | DI | DI | D | DI | DI | DI | I | DI | I |
| WH-5 (WH-1) | D | DI | DI | D | D | DI | DI | DI | DI | D | I | DI | I |
| Italy Smothe (WH-10) | DI | I | DI | DI | D | DI | DI | DI | DI | DI | DI | DI | I |
| Bai Crab (WH-2) | D | D | DI | D | D | D | D | D | DI | D | DI | D | DI |
| Hongguang (WH-4) | D | I | DI | D | D | DI | DI | DI | DI | DI | I | D | DI |
| Huangcui (WH-5) | DI | I | DI | D | DI | DI | DI | DI | DI | DI | I | I | DI |
| Qinglin (WH-6) | DI | DI | DI | D | D | DI | I | D | DI | DI | DI | D | I |
| Harlikar (WH-8) | DI | DI | DI | DI | DI | D | I | DI | DI | DI | DI | DI | DI |
| Italy Gala (WH-9) | I | DI | DI | DI | DI | DI | D | DI | DI | I | DI | DI | DI |
| Wushan Bianye (WSBY) | D | D | DI | D | D | D | D | D | DI | D | D | I | D |
| Xin 1 (XC-1) | I | I | DI | I | I | D | D | D | DI | I | I | D | I |
| Xin 5 (XC-2) | I | I | DI | I | I | D | D | I | DI | I | I | I | I |
| Hanfu 3x (XC-3) | D | I | I | D | D | DI | D | I | DI | D | I | I | DI |
| Gala 4x (XC-4) | I | DI | DI | DI | DI | DI | D | DI | DI | I | DI | DI | DI |
| Weizhimuben (XC-5) | DI | D | DI | D | DI | DI | D | DI | D | D | D | DI | DI |
| Chaguo (XC-CG) | D | D | I | D | D | D | D | D | DI | D | DI | D | D |
| Donghongguo (XC-DHG) | D | D | I | DI | DI | D | D | D | DI | D | DI | DI | I |
| Fuxian Sanye (XC-FXXY) | D | D | I | D | D | D | D | D | DI | D | D | I | D |

Construction results of InDel marker genotype database of *Malus* germplasm resources

| | | | | | | | | | | | | | |
|---|---|---|---|---|---|---|---|---|---|---|---|---|---|
| Hongsanye (XC-HSY) | D | D | I | D | D | D | D | D | DI | D | D | I | D |
| Jilin Xiaohong Crab (XC-JILINXIAOHONG-HAITANG) | D | D | I | D | DI | D | D | D | DI | DI | D | I | DI |
| Jilin Xiaohuang Crab (XC-JILINXIAOHUANG-HAITANG) | DI | D | DI | D | D | DI | D | D | DI | D | D | I | DI |
| Jilin Huang Crab (XC-JLHHT) | DI | D | DI | D | D | DI | D | D | DI | D | D | I | DI |
| Shajin Crab (XC-JSHT) | D | D | I | D | D | D | D | D | DI | D | D | I | D |
| Longdong Crab (XC-LDHT) | D | D | I | D | D | D | D | D | DI | D | D | I | D |
| Lushi Crab (XC-LSHT) | D | D | I | D | D | D | D | D | DI | D | D | I | D |
| Laiwunanyan (XC-LWNY) | D | D | I | D | D | D | D | D | DI | D | DI | D | D |
| Linzhi (XC-LZ) | D | D | I | D | D | D | D | D | DI | D | D | I | D |
| Mao Shandingzi (XC-MSDZ) | D | D | I | D | D | D | D | D | DI | D | D | I | D |
| Pingyitiancha (XC-PYTC) | D | D | I | D | D | D | D | D | DI | D | D | I | D |
| Qiuzi (XC-QZ) | D | D | I | D | D | DI | D | D | DI | D | I | I | D |
| Sichuan Bianye (XC-SCBY) | D | D | I | D | D | D | D | D | DI | D | D | I | D |
| Shandingzi (XC-SDZ) | D | D | I | D | D | D | D | D | DI | D | D | I | D |
| Weixi Sanye (XC-WXSY) | D | D | DI | D | D | DI | D | DI | DI | D | D | DI | DI |
| Xifu Crb (XC-XFHT) | D | D | I | D | D | D | DI | D | DI | D | I | I | DI |
| Xiaojin Bianye (XC-XJBY) | D | D | I | D | D | D | D | D | DI | D | D | I | D |
| Xinjiang Yepingguo (XC-XJYHT) | D | DI | I | D | D | D | D | D | DI | D | I | I | DI |
| Yajiang Bianye (XC-YJBY) | D | D | I | D | D | D | D | D | DI | D | D | I | D |
| Yingye Crab (XC-YYHT) | D | D | I | D | D | D | D | D | DI | D | DI | I | DI |
| Zhaai (XC-ZA) | D | D | I | D | D | D | D | D | DI | D | D | I | D |
| Zumi Crab (XC-ZMHT) | DI | D | I | D | D | D | D | D | DI | D | DI | I | D |
| Pink Lady (XN-FHNS) | DI | DI | DI | I | I | D | D | DI | D | D | DI | D | I |
| Hongrou 1 (XN-HR1) | D | D | I | D | D | D | D | DI | DI | D | DI | DI | DI |
| Hongrou 2 (XN-HR2) | D | D | I | D | DI | D | D | DI | DI | D | I | DI | DI |
| Hongrou 3 (XN-HR3) | D | D | I | D | D | D | D | D | DI | D | I | D | DI |
| Hongrou 4 (XN-HR4) | D | D | I | D | DI | D | D | DI | DI | D | I | DI | DI |
| Hongrou 5 (XN-HR5) | D | D | I | D | DI | D | D | D | DI | D | DI | DI | DI |
| Hongrou 6 (XN-HR6) | DI | D | DI | D | DI | DI | D | DI | D | D | D | DI | DI |
| Hongrou 7 (XN-HR7) | D | D | I | D | DI | D | D | DI | DI | D | I | DI | DI |
| Ambrosia (XN-MW) | DI | DI | DI | DI | I | D | I | D | DI | DI | DI | D | DI |
| Xinjiang 10 (XN-XJ10) | D | D | I | D | D | DI | D | D | DI | D | I | D | DI |
| Xinjiang 11 (XN-XJ11) | D | D | I | D | D | DI | D | D | DI | D | I | D | DI |
| Xinjiang 12 (XN-XJ12) | D | D | I | D | D | DI | D | D | DI | D | I | D | DI |
| Xinjiang 13 (XN-XJ13) | DI | D | I | D | I | D | D | I | DI | D | DI | I | DI |
| Xinjiang 14 (XN-XJ14) | D | D | I | D | DI | DI | D | DI | DI | D | I | DI | DI |
| Xinjiang 15 (XN-XJ15) | D | DI | I | D | DI | DI | DI | D | DI | D | I | DI | DI |

-continued

Construction results of InDel marker genotype database of *Malus* germplasm resources

| | | | | | | | | | | | | |
|---|---|---|---|---|---|---|---|---|---|---|---|---|
| Xinjiang 16 (XN-XJ16) | D | D | I | D | DI | D | D | I | DI | D | I | I | DI |
| Xinjiang 17 (XN-XJ17) | D | D | I | D | D | D | D | D | DI | D | I | D | DI |
| Xinjiang 18 (XN-XJ18) | DI | D | I | DI | I | D | D | I | DI | D | DI | DI | I |
| Xinjiang 19 (XN-XJ19) | D | D | I | D | D | DI | D | D | DI | D | DI | D | DI |
| Xinjiang 2 (XN-XJ2) | D | D | I | D | D | DI | D | D | DI | D | DI | DI | I |
| Xinjiang 20 (XN-XJ20) | DI | D | I | D | DI | D | D | DI | DI | D | DI | I | DI |
| Xinjiang 21 (XN-XJ21) | D | D | I | D | DI | DI | D | D | DI | D | DI | DI | DI |
| Xinjiang 23 (XN-XJ23) | DI | D | I | D | D | DI | D | D | DI | DI | DI | I | DI |
| Xinjiang 24 (XN-XJ24) | D | D | I | D | D | DI | D | D | DI | D | DI | DI | DI |
| Xinjiang 25 (XN-XJ25) | D | D | I | D | D | D | D | D | DI | D | DI | D | DI |
| Xinjiang 27 (XN-XJ27) | D | DI | I | D | DI | DI | D | D | DI | D | I | DI | DI |
| Xinjiang 3 (XN-XJ3) | D | D | I | D | D | DI | D | D | DI | D | DI | D | DI |
| Xinjiang 4 (XN-XJ4) | D | D | I | D | DI | D | D | DI | DI | D | DI | DI | DI |
| Xinjiang 5 (XN-XJ5) | D | D | DI | D | D | D | D | D | DI | D | I | I | DI |
| Xinjiang 7 (XN-XJ7) | D | D | I | D | D | D | D | I | DI | D | I | DI | DI |
| Xinjiang 8 (XN-XJ8) | D | D | I | D | D | DI | D | DI | DI | D | I | DI | DI |
| Xinjiang 9 (XN-XJ9) | D | D | I | D | D | DI | D | DI | DI | D | DI | DI | I |
| Yueguan (XY-10) | DI | DI | DI | D | D | DI | DI | I | DI | D | I | I | DI |
| Yuehua (XY-11) | D | DI | DI | D | DI | D | D | D | DI | D | DI | DI | I |
| Yueyan (XY-12) | I | DI | DI | D | DI | DI | DI | D | DI | D | I | DI | I |
| Bud Sport 5 (XY-13) | D | DI | DI | D | D | DI | DI | DI | DI | D | I | DI | I |
| Bud Sport 3 (XY-14) | D | DI | DI | D | D | DI | DI | DI | DI | D | I | DI | I |
| Longfu (XY-15) | D | DI | DI | D | D | DI | DI | DI | DI | D | I | DI | I |
| Yuemei (XY-18) | DI | D | DI | DI | I | D | DI | D | DI | D | I | D | I |
| Hanfu (XY-2) | DI | DI | DI | D | D | DI | DI | DI | DI | D | I | DI | DI |
| Linyi Fuji (XY-20) | DI | DI | DI | D | DI | DI | D | D | DI | DI | I | DI | DI |
| Yishui Fuji (XY-22) | D | DI | DI | D | D | DI | DI | DI | DI | D | I | DI | DI |
| Hongjinfu (XY-25) | D | DI | DI | D | D | DI | DI | DI | DI | D | I | DI | I |
| Beni Oshu (XY-26) | D | DI | DI | D | D | DI | DI | DI | DI | D | I | DI | I |
| Chuizhi Fuji (XY-27) | D | DI | DI | D | D | DI | DI | DI | DI | D | I | DI | DI |
| Yueshuai (XY-28) | DI | DI | DI | D | D | DI | DI | DI | DI | D | DI | I | I |
| Shichinohe 2 (XY-29) | D | DI | DI | D | D | DI | DI | DI | DI | D | DI | DI | I |
| 74-178 (XY-3) | D | DI | DI | DI | DI | DI | DI | DI | DI | DI | I | DI | DI |
| KAKUFUJI (XY-30) | D | DI | DI | D | D | DI | DI | DI | DI | D | I | DI | I |
| Royal Fuji 21 (XY-35) | D | DI | DI | D | D | DI | DI | DI | DI | D | I | DI | I |
| Qiquan Spur (XY-36) | D | DI | DI | D | D | DI | DI | DI | DI | D | I | DI | I |
| Juda Fuji (XY-37) | D | I | DI | D | D | DI | DI | DI | DI | D | I | DI | I |
| 7-211 (XY-4) | D | D | DI | D | I | D | DI | D | DI | D | DI | D | I |

| Construction results of InDel marker genotype database of *Malus* germplasm resources | | | | | | | | | | | | | |
|---|---|---|---|---|---|---|---|---|---|---|---|---|---|
| Yanfu 0 (XY-41) | D | DI | DI | D | D | DI | DI | DI | DI | D | I | DI | I |
| Spur Fuji (XY-42) | D | DI | DI | D | D | DI | DI | DI | DI | D | I | DI | I |
| Bayue fushiwang (XY-43) | D | DI | DI | D | D | DI | DI | DI | DI | D | I | DI | I |
| Huangfu 7 (XY-44) | D | DI | DI | D | D | DI | DI | DI | DI | D | DI | DI | I |
| Aomori Spur Fuji (XY-46) | D | DI | DI | D | D | DI | DI | DI | DI | D | I | DI | I |
| Qiu Fuji (XY-47) | D | DI | DI | D | D | DI | DI | DI | DI | D | I | DI | I |
| Fuji Champion (XY-48) | D | DI | DI | D | D | DI | DI | DI | DI | D | I | DI | I |
| 26-34 (XY-5) | I | D | DI | D | DI | DI | D | D | DI | D | I | DI | DI |
| Akifu 19 (XY-50) | D | DI | DI | D | D | DI | DI | DI | DI | D | I | DI | I |
| Fuji (XY-54) | D | DI | DI | D | D | DI | DI | DI | DI | D | I | DI | I |
| Qinfu 1 (XY-55) | D | DI | DI | D | D | DI | DI | DI | DI | D | I | DI | I |
| Feng Fuji (XY-56) | D | DI | DI | D | D | DI | DI | DI | DI | D | I | DI | I |
| Tianxing (XY-57) | D | DI | DI | D | D | DI | DI | DI | DI | D | I | DI | I |
| Taiyang Fuji (XY-58) | D | DI | DI | D | D | DI | DI | DI | DI | D | I | DI | I |
| Cherry Crab (XY-6) | D | D | I | I | DI | D | D | D | DI | DI | I | I | D |
| Yueping (XY-60) | DI | DI | DI | D | D | DI | I | D | DI | D | DI | DI | I |
| 23-63 (XY-61) | D | DI | DI | DI | DI | DI | DI | DI | DI | DI | I | DI | DI |
| 23-42 (XY-62) | DI | DI | DI | DI | DI | DI | DI | DI | DI | DI | I | DI | I |
| 7-171 (XY-63) | I | D | DI | D | DI | DI | DI | DI | DI | D | DI | D | I |
| Shengfang 3A (XY-65) | D | DI | DI | D | D | DI | DI | DI | DI | D | I | DI | I |
| Meinong Fuji (XY-67) | D | DI | DI | D | D | DI | DI | DI | DI | D | I | DI | I |
| 62-45 (XY-68) | I | DI | DI | D | D | I | I | D | DI | D | I | DI | I |
| Fengfeng Fuji (XY-70) | D | DI | DI | D | D | DI | DI | DI | DI | D | I | DI | I |
| GM256 (XY-71) | D | DI | DI | D | D | DI | DI | DI | DI | DI | I | DI | I |
| Jinfu 2 (XY-73) | D | DI | DI | D | D | DI | DI | DI | DI | D | I | DI | I |
| Qiufu (XY-75) | D | DI | DI | D | D | DI | DI | DI | DI | D | I | DI | I |
| Shanfu 6 (XY-76) | D | DI | DI | D | D | DI | DI | DI | DI | D | I | DI | I |
| Nagafu 8 (XY-77) | D | DI | DI | D | D | DI | DI | DI | DI | D | I | DI | I |
| 58-34 (XY-78) | DI | DI | DI | D | D | I | I | D | DI | D | I | DI | DI |
| 2001 Fuji (XY-79) | D | DI | DI | D | D | DI | DI | DI | DI | D | I | DI | I |
| 15-26 (XY-8) | DI | D | DI | D | DI | D | I | D | DI | D | I | DI | DI |
| Wangshanhong (XY-80) | D | DI | DI | D | D | DI | DI | DI | DI | D | I | DI | I |
| Jinfu 1 (XY-81) | D | DI | DI | D | D | DI | DI | D | DI | D | I | DI | I |
| Qingfu 1 (XY-84) | D | DI | DI | D | D | DI | DI | DI | DI | D | I | DI | I |
| Qiufu 39 (XY-85) | D | DI | DI | D | D | DI | DI | DI | DI | D | I | DI | I |
| Nagafu 1 (XY-86) | D | DI | DI | D | D | DI | DI | DI | DI | D | I | DI | I |
| Shou Fuji (XY-87) | D | DI | DI | D | D | DI | DI | DI | DI | D | I | DI | I |
| Yueli (XY-88) | DI | D | DI | DI | I | D | DI | DI | DI | D | D | D | I |
| Shanfu 2 (XY-89) | D | DI | DI | D | D | DI | DI | DI | DI | D | I | DI | I |

-continued

| Construction results of InDel marker genotype database of *Malus* germplasm resources | | | | | | | | | | | | | |
|---|---|---|---|---|---|---|---|---|---|---|---|---|---|
| Chongban Crab (XY-9) | D | D | I | D | D | D | D | D | DI | D | I | D | D |
| Harica (XY-90) | DI | DI | DI | D | D | DI | I | D | DI | DI | DI | D | I |
| Akifu 1 (XY-91) | D | DI | DI | D | D | DI | DI | DI | DI | D | I | DI | I |
| Wangfu (XY-92) | D | DI | DI | D | D | DI | DI | DI | DI | D | I | DI | I |
| Hong Manao (XYZ-1) | DI | D | I | D | D | DI | D | D | DI | DI | I | I | I |
| Modi (XYZ-10) | DI | DI | DI | DI | DI | DI | DI | D | DI | DI | DI | DI | I |
| C37 (XYZ-11) | D | DI | DI | D | D | DI | I | D | DI | D | DI | I | I |
| Envy ? (XYZ-12) | DI | I | DI | DI | D | D | D | DI | DI | DI | I | DI | I |
| Xichang Yuanzhuiguo (XYZ-2) | D | DI | DI | D | D | DI | DI | D | DI | D | I | D | DI |
| Ziye Zixiaoguo (XYZ-3) | D | D | I | D | D | I | D | D | DI | D | D | I | I |
| Ziye Zidaguo (XYZ-4) | D | D | DI | D | D | DI | DI | D | DI | D | DI | D | DI |
| Shoufenshu 6 (XYZ-5) | D | D | DI | D | D | I | DI | D | DI | D | DI | D | I |
| Changhua (XYZ-6) | I | DI | DI | DI | DI | DI | D | DI | DI | I | DI | DI | DI |
| Jinshiji (XYZ-7) | I | DI | DI | DI | DI | DI | D | DI | DI | I | DI | DI | DI |
| 19-147 (XYZ-9) | D | D | I | D | DI | DI | D | D | DI | D | D | DI | DI |
| Malong Gala 1 (YN-1) | I | DI | DI | DI | DI | DI | D | DI | DI | I | DI | I | DI |
| Shouer hong (YN-11) | D | DI | DI | D | D | DI | DI | D | DI | D | I | DI | DI |
| Yun Hongrou (YN-12) | DI | D | DI | D | D | DI | DI | D | DI | DI | I | DI | D |
| Lixing Crab (YN-13) | D | D | I | D | DI | DI | D | DI | D | D | I | DI | DI |
| Siana (YN-15) | D | DI | I | D | DI | D | DI | D | DI | DI | D | DI | DI |
| Jonathan-M41 (YN-17) | DI | DI | DI | D | DI | DI | D | DI | DI | D | I | DI | I |
| Morlie's Delicious (YN-18) | DI | D | DI | D | DI | DI | I | D | DI | D | DI | D | I |
| Britegold (YN-19) | D | DI | DI | D | D | DI | DI | DI | DI | D | I | DI | DI |
| Malong Gala 1 blush (YN-2) | I | DI | DI | DI | DI | DI | D | DI | DI | I | DI | DI | DI |
| Line 5 (YN-22) | D | DI | I | D | DI | D | DI | D | DI | D | DI | DI | DI |
| Line 6 (YN-23) | DI | DI | DI | D | DI | DI | D | DI | DI | D | DI | I | DI |
| Line 13 (YN-24) | DI | DI | DI | D | D | DI | DI | D | DI | D | D | D | I |
| row 3 (YN-25) | I | D | DI | I | I | D | D | I | DI | DI | DI | D | DI |
| row 4 (YN-26) | I | D | DI | I | I | D | D | I | DI | DI | DI | D | DI |
| row 5 (YN-27) | I | D | DI | I | I | D | D | I | DI | DI | DI | D | DI |
| row 6 (YN-28) | I | D | DI | I | I | D | D | I | DI | DI | DI | D | DI |
| row 9 (YN-29) | DI | I | DI | DI | DI | D | D | DI | DI | DI | DI | DI | DI |
| Malong xin Gala 1 (YN-3) | I | DI | DI | DI | DI | DI | D | DI | DI | I | DI | DI | DI |
| row 10 (YN-30) | DI | DI | DI | I | I | D | D | DI | DI | D | DI | D | I |
| row 11 (YN-31) | DI | I | DI | DI | DI | D | D | DI | DI | DI | DI | DI | DI |
| row 12 (YN-32) | I | DI | DI | DI | DI | D | D | DI | DI | I | DI | DI | DI |
| row 13 (YN-33) | I | DI | DI | D | DI | DI | D | D | DI | DI | DI | DI | DI |
| row 14 (YN-34) | I | D | DI | I | I | D | D | I | DI | DI | DI | D | DI |

-continued

| Construction results of InDel marker genotype database of *Malus* germplasm resources | | | | | | | | | | | | | |
|---|---|---|---|---|---|---|---|---|---|---|---|---|---|
| row 15 (YN-35) | I | DI | DI | D | D | DI | D | DI | DI | DI | DI | DI | DI |
| row 16 (YN-36) | DI | DI | DI | D | DI | DI | DI | DI | DI | DI | DI | DI | I |
| row 17 (YN-37) | D | I | DI | DI | DI | DI | D | D | DI | D | DI | DI | DI |
| row 18 (YN-38) | D | DI | DI | DI | DI | DI | D | D | DI | DI | DI | DI | DI |
| row 19 (YN-39) | DI | D | DI | D | D | DI | D | D | DI | D | I | D | DI |
| Malong xin Gala 1 strip (YN-4) | I | DI | DI | DI | DI | DI | D | DI | DI | I | DI | DI | DI |
| row 20 (YN-40) | DI | I | DI | DI | DI | DI | DI | D | DI | DI | I | I | I |
| row 21 (YN-41) | D | DI | DI | D | D | DI | DI | DI | DI | D | I | DI | DI |
| row 22 (YN-42) | DI | I | DI | DI | DI | DI | DI | D | DI | DI | I | I | DI |
| row 23 (YN-43) | DI | I | DI | DI | DI | DI | DI | D | DI | DI | I | I | I |
| row 24 (YN-44) | D | DI | DI | D | D | DI | DI | DI | DI | D | I | DI | I |
| row 25 (YN-45) | D | DI | DI | D | D | DI | DI | DI | DI | D | I | DI | I |
| Malong Gala2 (YN-5) | I | DI | DI | DI | DI | DI | D | DI | DI | I | D | D | DI |
| Malong Gala 2 blush (YN-6) | I | DI | DI | DI | DI | DI | D | DI | DI | I | DI | DI | DI |
| Longwei (YN-7) | DI | D | DI | DI | I | D | D | D | DI | DI | I | D | DI |
| Longwei Early Mutant (YN-8) | DI | D | DI | DI | I | D | D | D | DI | DI | I | D | DI |
| Cherry Gala (YN-9) | I | DI | DI | DI | DI | DI | D | DI | DI | I | DI | DI | DI |
| Siyana (YT-1) | DI | D | I | D | D | DI | D | I | DI | DI | I | DI | DI |
| Yanfu 10 (YT-100) | D | D | DI | D | D | DI | DI | DI | DI | D | I | DI | DI |
| Chadel (YT-102) | I | I | DI | D | DI | D | DI | DI | DI | DI | DI | I | I |
| Charden (YT-103) | DI | DI | DI | DI | DI | DI | DI | DI | DI | DI | DI | DI | I |
| Tuskan (YT-104) | D | DI | DI | D | DI | DI | D | D | DI | D | DI | DI | I |
| Prima × Sekaiichii (YT-105) | D | D | DI | D | DI | D | D | DI | DI | DI | I | DI | I |
| Toppax_apple (YT-11) | DI | D | DI | D | DI | DI | DI | DI | DI | DI | DI | DI | I |
| Xinjiang Hongrou Crab (YT-12) | D | D | I | D | D | D | D | D | DI | D | D | D | DI |
| Melfree (YT-13) | DI | D | DI | D | DI | DI | DI | DI | DI | D | DI | DI | I |
| Yanfu 3 (YT-14) | DI | DI | DI | D | DI | D | DI | DI | DI | DI | I | DI | DI |
| Gold milecnirum (YT-15) | D | I | I | D | I | D | D | DI | DI | DI | I | D | I |
| Ganhong (YT-16) | DI | D | D | D | D | D | D | DI | D | DI | I | DI | I |
| Cornoet (YT-17) | D | D | DI | D | DI | D | D | DI | DI | D | I | I | DI |
| Priw (YT-18) | I | DI | DI | D | DI | D | D | D | D | DI | I | D | I |
| Aichi (YT-19) | DI | D | DI | D | D | DI | D | DI | DI | DI | I | DI | I |
| Auraria (YT-2) | DI | D | DI | D | D | D | D | D | D | DI | DI | DI | I |
| Meile (YT-20) | D | DI | DI | D | D | DI | DI | DI | DI | D | I | DI | I |
| Qiulimeng (YT-21) | D | D | I | D | DI | D | D | I | DI | D | I | I | DI |
| Aliusitan (YT-22) | D | D | I | D | D | D | DI | DI | DI | D | DI | DI | DI |
| Geaooza (YT-23) | D | D | DI | D | D | DI | DI | DI | DI | D | I | DI | DI |
| Golden Spur (YT-24) | DI | I | DI | DI | D | DI | DI | DI | DI | DI | DI | DI | I |
| Starking (YT-25) | D | D | DI | D | DI | DI | D | DI | DI | I | DI | DI | DI |

-continued

| Construction results of InDel marker genotype database of *Malus* germplasm resources | | | | | | | | | | | | | |
|---|---|---|---|---|---|---|---|---|---|---|---|---|---|
| Indo (YT-26) | D | D | DI | D | DI | DI | D | DI | DI | D | I | I | I |
| Teser (YT-27) | DI | DI | DI | D | DI | D | D | D | DI | DI | I | I | I |
| Xianhong (YT-28) | DI | I | I | D | D | DI | D | D | DI | DI | I | DI | DI |
| Gala × Mato 8 (YT-29) | I | D | DI | D | DI | D | DI | DI | DI | DI | DI | DI | I |
| Very Early Fuji (YT-3) | D | DI | DI | D | D | DI | DI | DI | DI | D | I | DI | I |
| Qiuhuapi (YT-30) | D | D | DI | DI | I | D | D | D | D | D | DI | I | DI |
| Piga 70 (YT-31) | I | DI | DI | D | DI | DI | D | DI | DI | DI | I | DI | DI |
| Yanzhen 1 (YT-32) | DI | DI | I | D | DI | DI | D | D | DI | D | DI | I | DI |
| Matail (YT-34) | I | DI | DI | DI | DI | DI | D | DI | DI | I | DI | DI | DI |
| Jonathan-csan (YT-35) | DI | DI | DI | D | DI | DI | D | DI | DI | D | I | DI | DI |
| Huashuai (YT-36) | DI | D | DI | D | I | D | D | D | DI | D | I | DI | DI |
| Wengao 1 (YT-38) | D | DI | DI | D | D | DI | DI | DI | DI | D | I | DI | DI |
| Wengao 2 (YT-39) | D | DI | DI | D | D | DI | DI | DI | DI | D | I | DI | I |
| Elegia (YT-4) | DI | D | DI | D | DI | DI | D | D | DI | D | I | DI | DI |
| Wengao 3 (YT-40) | D | DI | DI | D | D | DI | DI | DI | DI | D | I | DI | I |
| Hong Anka (YT-41) | DI | I | DI | D | D | DI | DI | DI | DI | D | I | DI | I |
| Yanfu 2 (YT-42) | D | DI | DI | D | D | DI | DI | DI | DI | D | I | DI | I |
| Belgolden (YT-43) | DI | I | DI | DI | D | DI | DI | DI | DI | DI | DI | DI | I |
| Rubinola (YT-44) | D | D | DI | DI | I | D | D | D | DI | DI | I | I | I |
| Wangqiuhong (YT-45) | DI | D | DI | D | I | D | D | DI | DI | DI | DI | DI | DI |
| Pulanhong (YT-46) | D | D | DI | D | DI | DI | D | D | DI | DI | DI | DI | DI |
| Bosh (YT-47) | D | D | DI | D | DI | DI | I | D | DI | DI | DI | DI | DI |
| Chengji 1 (YT-48) | D | DI | DI | D | D | DI | DI | DI | DI | D | I | DI | DI |
| Hongli (YT-49) | DI | DI | DI | DI | I | D | DI | D | DI | D | DI | DI | I |
| Guoqinghong (YT-5) | D | DI | DI | D | D | DI | D | DI | DI | D | DI | DI | I |
| Reandra (YT-50) | I | I | DI | DI | DI | DI | D | DI | DI | DI | DI | I | I |
| Revbihola (YT-51) | DI | DI | DI | D | D | DI | DI | DI | DI | DI | I | DI | I |
| Melrose (YT-52) | DI | DI | DI | D | DI | DI | DI | DI | DI | DI | I | D | I |
| Rewena (YT-53) | DI | D | I | D | DI | D | DI | DI | DI | D | I | I | DI |
| Mrxl(robusta × Liberte) (YT-54) | D | D | DI | D | DI | DI | D | DI | DI | DI | I | DI | DI |
| Mollies_Del_open (YT-55) | I | DI | I | D | D | DI | D | DI | DI | D | I | DI | I |
| Renora (YT-56) | DI | DI | DI | D | DI | DI | I | DI | DI | DI | D | D | I |
| Rosmadzin (YT-57) | D | D | D | D | DI | DI | I | DI | DI | DI | DI | DI | DI |
| Remo (YT-58) | I | D | DI | D | DI | DI | D | D | DI | DI | I | DI | I |
| Pilot (YT-59) | I | DI | DI | D | DI | D | I | DI | DI | D | I | I | I |
| Yangbai Crab (YT-6) | D | D | I | D | D | D | D | DI | D | D | DI | D | DI |
| Free Red Star (YT-60) | DI | DI | DI | D | D | DI | D | DI | DI | D | I | I | DI |
| Idared (YT-61) | DI | DI | DI | D | I | D | D | D | DI | D | I | DI | I |

-continued

| Construction results of InDel marker genotype database of *Malus* germplasm resources | | | | | | | | | | | | | |
|---|---|---|---|---|---|---|---|---|---|---|---|---|---|
| Mingyue (YT-62) | DI | I | DI | D | DI | DI | I | D | DI | DI | I | DI | DI |
| Piga 101 (YT-63) | DI | DI | DI | D | DI | DI | DI | DI | DI | DI | I | DI | I |
| Yanfu 5 (YT-64) | D | DI | DI | D | D | DI | DI | DI | DI | D | I | DI | I |
| Early Jonagold (YT-65) | DI | DI | DI | DI | DI | DI | DI | DI | DI | DI | DI | DI | I |
| Wengao 2 mutant (YT-66) | D | DI | DI | D | D | DI | DI | DI | DI | D | I | DI | I |
| Fenhong Gala 44 (YT-67) | I | DI | DI | I | I | D | D | D | DI | DI | I | D | I |
| Yiyuanhong (YT-68) | D | DI | DI | D | D | DI | DI | DI | DI | D | I | DI | I |
| Yanfu 4 (YT-69) | D | DI | DI | D | D | DI | DI | DI | DI | D | I | DI | I |
| White Pearmain (YT-70) | DI | D | DI | D | DI | DI | D | I | DI | DI | I | DI | I |
| Jonathan-early (YT-73) | DI | DI | DI | D | DI | DI | D | DI | DI | D | I | DI | DI |
| Jonathan-midle (YT-74) | DI | DI | DI | D | DI | DI | D | DI | DI | D | I | DI | DI |
| Gornan (YT-75) | DI | D | DI | D | DI | DI | D | D | DI | D | I | D | I |
| RegiIndel (YT-76) | DI | DI | DI | D | D | D | DI | DI | DI | DI | I | DI | I |
| Golden Bell (YT-77) | DI | DI | DI | DI | DI | D | DI | D | DI | D | DI | DI | DI |
| Arkcharm (YT-78) | I | D | DI | D | DI | DI | DI | D | DI | D | D | DI | I |
| Redchif (YT-79) | DI | D | DI | D | DI | D | DI | D | DI | D | I | I | DI |
| Mouping Guanghua Fuji (YT-8) | D | DI | DI | D | D | DI | DI | DI | DI | D | DI | DI | I |
| Freedom (YT-80) | I | DI | DI | D | DI | D | I | DI | DI | D | I | I | I |
| Martinike (YT-81) | DI | DI | DI | D | DI | DI | D | D | DI | D | I | DI | DI |
| Sweetle (YT-82) | DI | D | DI | DI | I | D | D | D | DI | DI | I | D | DI |
| Aleksanader (YT-83) | DI | D | DI | I | I | D | DI | DI | DI | D | I | DI | DI |
| Yan 6 Fenhong 143 (YT-84) | I | DI | DI | DI | DI | DI | D | D | DI | I | I | D | I |
| Ruitina (YT-85) | D | DI | DI | D | D | D | DI | DI | DI | DI | I | DI | I |
| Wengao 1 mutant (YT-86) | D | DI | DI | D | D | DI | DI | DI | DI | D | I | DI | I |
| Wengao 3 mutant (YT-87) | D | DI | DI | D | DI | DI | DI | DI | DI | D | I | DI | I |
| Shajinyilamu (YT-88) | D | D | I | D | D | DI | D | D | DI | D | I | DI | I |
| Qiuhong (YT-89) | D | DI | DI | D | I | D | D | D | DI | DI | DI | D | DI |
| Changyanghong (YT-9) | D | DI | DI | D | D | DI | DI | DI | DI | D | I | DI | I |
| Yanfu 8 (YT-90) | D | DI | DI | D | DI | DI | DI | DI | DI | D | I | DI | I |
| Jinduhong Gala (YT-91) | I | DI | DI | DI | DI | DI | D | DI | DI | I | DI | DI | DI |
| Nagafu 2 (YT-92) | D | DI | DI | D | D | DI | DI | DI | DI | D | I | DI | I |
| Honglu seedling 65 (YT-93) | DI | DI | DI | D | D | DI | D | DI | DI | DI | I | I | DI |
| Tsugaru (YT-94) | DI | I | DI | DI | DI | DI | DI | D | DI | DI | I | I | DI |
| Jinshuai mutant (YT-95) | DI | DI | DI | DI | DI | DI | DI | DI | DI | DI | DI | DI | I |
| Taishan Crab (YT-96) | DI | DI | I | D | DI | D | D | DI | DI | D | DI | D | DI |
| Luli (YT-98) | I | D | DI | I | I | D | D | I | DI | DI | DI | D | DI |
| 10-182 (YX-10-182) | D | DI | DI | DI | D | DI | D | DI | DI | D | I | I | I |
| 01-001 (YX-01-001) | D | DI | DI | D | D | DI | DI | DI | DI | D | I | DI | DI |
| 01-121 (YX-01-121) | D | DI | DI | DI | DI | DI | D | DI | DI | D | I | I | DI |

-continued

| Construction results of InDel marker genotype database of *Malus* germplasm resources | | | | | | | | | | | | | |
|---|---|---|---|---|---|---|---|---|---|---|---|---|---|
| 02-009 (YX-02-009) | D | DI | DI | D | D | DI | D | DI | DI | D | I | I | DI |
| 03-010 (YX-03-010) | D | DI | DI | D | D | DI | D | DI | DI | D | I | DI | DI |
| 03-111 (YX-03-111) | D | DI | DI | DI | DI | DI | D | DI | DI | D | I | I | DI |
| 04-033 (YX-04-033) | D | DI | DI | D | D | DI | D | DI | DI | D | I | DI | DI |
| 04-087 (YX-04-087) | D | DI | DI | DI | DI | DI | D | DI | DI | D | I | DI | DI |
| 06-056 (YX-06-056) | D | DI | DI | D | D | DI | D | DI | DI | D | I | DI | DI |
| 08-034 (YX-08-034) | D | DI | DI | DI | DI | DI | D | DI | DI | D | I | DI | DI |
| 09-037 (YX-09-037) | D | DI | DI | D | D | DI | D | DI | DI | D | I | I | DI |
| 09-079 (YX-09-079) | D | D | DI | DI | DI | DI | D | DI | DI | D | I | DI | DI |
| 10-010 (YX-10-010) | D | DI | DI | D | D | DI | D | DI | DI | D | I | DI | DI |
| 11-037 (YX-11-037) | D | DI | DI | D | D | DI | D | DI | DI | D | I | I | DI |
| 11-206 (YX-11-206) | D | DI | DI | DI | DI | DI | D | DI | DI | D | I | DI | DI |
| 12-206 (YX-12-206) | D | DI | DI | DI | DI | DI | DI | D | DI | D | I | DI | DI |
| 13-025 (YX-13-025) | D | DI | DI | D | D | DI | DI | D | DI | D | I | I | DI |
| 16-155 (YX-16-155) | D | D | DI | D | D | DI | DI | D | DI | D | I | I | DI |
| 16-157 (YX-16-157) | D | DI | DI | DI | DI | DI | D | DI | DI | D | I | I | DI |
| 17-023 (YX-17-023) | D | DI | DI | D | D | DI | D | DI | DI | D | I | I | DI |
| 17-199 (YX-17-199) | D | D | DI | D | D | DI | DI | D | DI | D | I | DI | DI |
| 21-005 (YX-21-005) | D | DI | DI | D | DI | D | D | DI | DI | DI | I | DI | DI |
| 21-018 (YX-21-018) | DI | DI | DI | D | D | DI | D | D | DI | DI | I | I | DI |
| 22-186 (YX-22-186) | DI | DI | DI | D | D | DI | D | DI | DI | D | DI | I | DI |
| 27-003 (YX-27-003) | DI | DI | DI | D | D | DI | D | DI | DI | DI | I | DI | DI |
| 29-176 (YX-29-176) | D | DI | DI | D | D | DI | D | DI | DI | DI | I | DI | DI |
| 30-001 (YX-30-001) | D | DI | DI | D | DI | D | DI | D | DI | D | I | I | DI |
| 33-018 (YX-33-018) | D | D | DI | DI | DI | DI | D | DI | DI | D | I | I | DI |
| 33-101 (YX-33-101) | DI | DI | DI | D | D | DI | D | DI | DI | D | I | I | DI |
| 33-151 (YX-33-151) | D | DI | DI | DI | DI | D | DI | D | DI | D | I | DI | DI |
| 51-007 (YX-51-007) | I | DI | DI | D | DI | DI | D | DI | DI | D | I | I | I |
| 51-031 (YX-51-031) | DI | DI | DI | D | DI | DI | D | DI | DI | D | DI | DI | I |
| 51-077 (YX-51-077) | DI | DI | DI | D | DI | DI | DI | DI | DI | D | DI | I | DI |
| 51-102 (YX-51-102) | DI | DI | DI | DI | DI | D | DI | DI | DI | D | I | DI | DI |
| 51-139 (YX-51-139) | DI | DI | DI | DI | D | DI | D | I | DI | D | I | I | DI |
| 51-165 (YX-51-165) | DI | I | DI | DI | DI | DI | DI | D | DI | D | I | D | I |
| 51-166 (YX-51-166) | D | I | DI | D | D | DI | D | I | DI | DI | DI | I | I |
| 51-209 (YX-51-209) | DI | I | DI | DI | DI | DI | D | DI | DI | DI | DI | DI | DI |
| 52-049 (YX-52-049) | DI | DI | DI | D | D | DI | D | I | DI | D | DI | DI | DI |
| 52-151 (YX-52-151) | DI | DI | I | D | DI | DI | D | DI | D | I | D | I |
| 52-160 (YX-52-160) | DI | DI | DI | DI | DI | DI | DI | DI | DI | DI | I | DI | I |

-continued

Construction results of InDel marker genotype database of *Malus* germplasm resources

| | | | | | | | | | | | | | |
|---|---|---|---|---|---|---|---|---|---|---|---|---|---|
| 53-040 (YX-53-040) | DI | DI | DI | DI | DI | DI | D | DI | DI | DI | DI | DI | I |
| 53-205 (YX-53-205) | D | DI | DI | D | D | DI | DI | DI | DI | D | I | D | I |
| 54-001 (YX-54-001) | D | I | DI | DI | DI | DI | D | DI | DI | D | I | D | I |
| 54-188 (YX-54-188) | DI | DI | DI | DI | DI | DI | DI | DI | DI | D | DI | I | I |
| 55-006 (YX-55-006) | DI | DI | DI | DI | I | D | DI | D | DI | D | I | DI | I |
| 55-023 (YX-55-023) | DI | DI | D | D | DI | DI | D | I | DI | D | DI | DI | I |
| 55-042 (YX-55-042) | DI | DI | DI | DI | I | D | D | I | DI | D | DI | DI | DI |
| 56-081 (YX-56-081) | DI | I | DI | DI | I | D | D | DI | DI | DI | DI | DI | I |
| 57-128 (YX-57-128) | DI | DI | DI | DI | D | DI | D | I | DI | D | I | I | DI |
| 58-036 (YX-58-036) | DI | I | DI | D | D | DI | D | I | DI | DI | I | DI | I |
| 58-089 (YX-58-089) | D | I | DI | D | I | D | DI | D | DI | DI | DI | D | I |
| 58-144 (YX-58-144) | D | DI | DI | DI | DI | DI | DI | DI | DI | D | DI | DI | I |
| 58-177 (YX-58-177) | I | I | I | D | DI | DI | D | DI | DI | D | I | DI | I |
| 58-211 (YX-58-211) | D | DI | DI | D | DI | DI | DI | D | DI | D | DI | D | DI |
| 59-086 (YX-59-086) | DI | I | DI | DI | I | D | D | I | DI | D | I | DI | I |
| 59-130 (YX-59-130) | DI | DI | DI | DI | I | D | D | DI | DI | D | DI | I | I |
| Jersey Mac (Z-1) | DI | DI | DI | D | I | D | D | DI | DI | D | I | DI | DI |
| Gale Gala (Z-10) | I | DI | DI | DI | DI | DI | D | DI | DI | I | DI | DI | DI |
| Li Gala (Z-11) | I | DI | DI | DI | DI | DI | D | DI | DI | I | DI | DI | DI |
| Yanga 1 (Z-12) | I | DI | DI | DI | DI | DI | D | DI | DI | I | DI | DI | DI |
| NAKT M9 clone (Z-13) | D | D | I | D | DI | D | I | D | DI | D | I | D | DI |
| Royal Gala (Z-14) | I | DI | DI | DI | DI | DI | D | DI | DI | I | DI | DI | DI |
| Huajia (Z-15) | I | D | DI | D | D | I | D | D | DI | D | I | DI | DI |
| Dorsett Golden (Z-16) | DI | DI | DI | D | D | D | DI | DI | DI | D | I | D | I |
| 99-2-58 (Z-17) | DI | D | DI | D | DI | DI | D | D | DI | DI | I | I | DI |
| Galaxy (Z-18) | I | DI | DI | DI | DI | DI | D | DI | DI | I | D | D | DI |
| Royal New Gala (Z-19) | I | DI | DI | DI | DI | DI | D | DI | DI | I | DI | DI | DI |
| 99-1-29 (Z-22) | DI | D | DI | D | D | DI | D | D | DI | D | I | D | DI |
| Seokwang (Z-23) | DI | DI | I | D | DI | DI | D | DI | DI | DI | I | I | I |
| Fuhong Zaoga (Z-24) | I | DI | DI | DI | DI | DI | D | DI | DI | I | DI | DI | DI |
| Maiyan (Z-25) | DI | D | DI | D | DI | DI | D | D | DI | DI | DI | DI | DI |
| Shandong 1 (Z-26) | I | DI | DI | DI | DI | DI | D | DI | DI | I | DI | I | DI |
| Gala Queen (Z-27) | I | DI | DI | DI | DI | DI | D | DI | DI | I | DI | DI | DI |
| 99-2-39 (Z-29) | I | D | DI | D | D | I | D | D | DI | DI | I | DI | DI |
| Sweetle (Z-3) | DI | D | DI | DI | I | D | D | D | DI | DI | I | D | DI |
| Dalian Da Gala (Z-30) | I | DI | DI | DI | DI | DI | D | DI | DI | I | DI | DI | DI |
| Huaxing (Z-31) | I | DI | DI | I | I | D | D | DI | DI | DI | DI | DI | DI |
| Li Gala (Z-32) | I | DI | DI | DI | DI | DI | D | DI | DI | I | DI | DI | DI |
| Fuhong Zaoga (Z-33) | DI | DI | DI | DI | I | D | D | D | DI | DI | D | D | DI |

-continued

Construction results of InDel marker genotype database of *Malus* germplasm resources

| | | | | | | | | | | | | | |
|---|---|---|---|---|---|---|---|---|---|---|---|---|---|
| Yanga (Z-34) | DI | DI | DI | DI | I | D | D | D | DI | DI | D | D | DI |
| Royal Gala (Z-35) | I | DI | DI | DI | DI | DI | D | DI | DI | I | DI | DI | DI |
| Shijiazhuang Gala (Z-37) | I | DI | DI | DI | DI | DI | D | DI | DI | I | DI | DI | DI |
| Taihong Gala (Z-38) | I | DI | DI | DI | DI | DI | D | DI | DI | I | DI | DI | DI |
| Anna (Z-39) | DI | D | DI | D | DI | D | DI | D | DI | D | DI | D | I |
| Hong Zhenzhu (Z-4) | I | DI | DI | DI | DI | DI | D | DI | DI | D | DI | DI | D |
| Qiuhong Gala (Z-40) | DI | I | DI | DI | DI | DI | DI | D | DI | DI | I | I | DI |
| Shandong 2 (Z-41) | I | DI | DI | DI | DI | DI | D | DI | DI | I | DI | DI | DI |
| Shandong 6 (Z-42) | I | DI | DI | DI | DI | DI | D | DI | DI | I | DI | DI | DI |
| Chenyang (Z-43) | DI | DI | I | D | D | DI | DI | DI | DI | D | DI | D | I |
| Dongqie Gala (Z-44) | I | D | DI | D | DI | DI | D | D | DI | DI | I | DI | I |
| Royal Gala (Z-45) | I | DI | DI | DI | DI | DI | D | DI | DI | I | DI | DI | DI |
| Taishan Gala (Z-47) | I | DI | DI | DI | DI | DI | D | DI | DI | I | DI | DI | DI |
| Shandong 7 (Z-48) | I | DI | DI | DI | DI | DI | D | DI | DI | I | DI | DI | DI |
| Regal gala (Z-49) | I | DI | DI | DI | DI | DI | D | DI | DI | I | DI | DI | DI |
| NAKB clone (Z-5) | D | D | I | D | DI | D | I | D | DI | D | I | D | DI |
| Royal gala (Z-50) | I | DI | DI | DI | DI | DI | D | DI | DI | I | DI | DI | DI |
| Znoga (Z-51) | DI | DI | DI | DI | DI | D | DI | DI | DI | D | DI | DI | DI |
| Shandong 5 (Z-52) | I | DI | DI | DI | DI | DI | D | DI | DI | I | DI | DI | DI |
| Rockit (Z-53) | I | D | DI | DI | D | I | D | DI | DI | I | DI | D | I |
| Shandong 3 (Z-54) | I | DI | DI | DI | DI | DI | D | DI | DI | I | DI | DI | DI |
| Mondel Gala (Z-55) | I | DI | DI | DI | DI | DI | D | DI | DI | I | DI | DI | DI |
| Alvinagala (Z-56) | I | DI | DI | DI | DI | DI | D | DI | DI | I | DI | DI | DI |
| M9 pajam2 (Z-6) | D | D | I | D | DI | D | I | D | DI | D | I | D | D |
| Jinshiji (Z-7) | I | DI | DI | DI | DI | DI | D | DI | DI | I | DI | DI | DI |
| Huarui (Z-8) | I | D | I | D | DI | DI | D | D | DI | D | DI | D | I |
| Hongcuibao (Z-9) | DI | DI | DI | DI | I | D | D | D | DI | DI | DI | D | I |

| Accession name (Accession ID) | C01001 | C03012 | C05026 | C07044 | C07045 | C07049 | C08052 | C08055 | C11078 | C11082 | C17126 | C12132 | C10136 |
|---|---|---|---|---|---|---|---|---|---|---|---|---|---|
| Black Ben Davis (10--1) | D1D2I | D2I | I | D2I | D1D2 | I | D2I | D2I | D1D2 | D2 | D1 | D1D2I | I |
| Lysgolden (10--10) | D1I | D2I | I | D2 | D1D2 | D1I | D2I | D1I | D1D2 | D2 | D1 | D1I | I |
| Dongchengguan 13 (10--11) | D1I | D2I | I | D2 | D1D2 | D1I | D2I | D1I | D1D2 | D2 | D1 | D1I | I |
| Nagafu 1 (10--12) | D1I | D2I | I | D2 | D1D2 | D1I | D2I | D1I | D1D2 | D2 | D1 | D1I | I |
| Shengli Hongguan (10--14) | D1D2I | D2I | D | D2 | D1 | D1D2 | D2 | D1 | D1D2I | D1D2 | D1D2 | D2I | D1I |
| Shizishan 1 (10--15) | D1D2I | D2I | D | D2 | D1 | D1D2 | D2 | D1 | D1D2I | D1D2 | D1D2 | D2I | D1I |
| Baoman (10--2) | D1D2 | D1D2I | DI | D2I | D1I | D2I | D1I | D1 | D2I | D1D2 | D1 | I | I |
| Melba (10--20) | D1D2I | D2I | D | D2 | D1D2I | I | D2 | D1D2 | D1D2 | D2 | D1 | I | D1I |
| Kuliesa (10--21) | D1I | D2I | D | D1I | D1I | D2I | D1D2 | D1D2I | D1D2 | D1D2 | D2I | D2I | |

-continued

| Construction results of InDel marker genotype database of *Malus* germplasm resources | | | | | | | | | | | | | |
|---|---|---|---|---|---|---|---|---|---|---|---|---|---|
| De 8 (10--22) | D1I | D1D2I | D | D1D2 | D1I | I | D2I | D2I | D1 | D2 | D1 | I | I |
| Bo 5 (10--23) | I | D2I | D | D1I | D1D2 | D1I | D1D2I | D1D2I | D1D2 | D1 | D2I | D1D2 |
| Iran Pippin (10--4) | D1D2 | D2I | D | D1 | D1 | D1I | D1D2 | D1D2 | D1D2 | D2 | D1 | I | D1I |
| Sakatakei Tsugaru (10--5) | D1D2I | D1D2I | D | D1D2I | D1D2I | D1I | D1I | D1I | D2I | D1 | D2I | I | I |
| Khrushchev (10--6) | D1D2 | D1D2I | D | D2I | D1I | D1D2I | D1D2 | D1I | D1D2I | D2 | D1D2 | D2I | I |
| Batul (10--7) | D1D2 | D2I | D | D2I | D1 | D2 | D2 | D2 | D1D2I | D2 | D1 | D1I | D1I |
| Prime Gold (10--9) | D1D2 | D2I | D | D2I | D1 | D2 | D2 | D2 | D1I | D2 | D1 | D1I | D1I |
| Jie 1 (11--0) | D1D2 | D1D2I | D | D1D2 | D1D2 | D1 | D1I | D1D2 | D1D2I | D1D2 | D1D2 | D2I | D1I |
| Guldborg (1--11) | D1I | D2I | I | D2 | D1D2 | D1I | D2I | D1I | D1D2 | D2 | D1 | D1I | I |
| Shajin Yilamu (11--10) | D2 | D2I | D | D2 | D1 | D1 | D2 | D2 | D1D2I | D2 | D2 | I | D1 |
| Soviet (11--11) | D1D2I | D2I | D | D2I | D2I | D1I | D2I | D1D2 | D1D2 | D2 | D1 | I | D1I |
| Lobo (11--13) | D1D2 | D2I | D | D2I | D1I | D1I | D1D2 | D2I | D1D2I | D1D2 | D1 | I | D1I |
| Allington Pippin (11--14) | D1I | D2I | DI | D2I | D1I | D1D2 | D2 | D2I | D1D2I | D1D2 | D1 | D1D2 | I |
| Malinova (11--15) | D1D2I | D2I | D | D2 | D1 | D1 | D2I | D1D2 | D1D2 | D2 | D1 | D2I | D1D2 |
| Sweet McIntosh (11--16) | D1D2I | D2I | D | D2 | D1 | D1 | D2I | D1D2 | D1D2 | D2 | D1 | D2I | D1D2 |
| McIntosh (11--18) | D1D2I | D2I | DI | D2I | D1I | D1I | D1I | D1I | D1D2I | D2I | D1I | D2I | I |
| Spartan (11--2) | D1D2 | D2I | D | D2I | D1I | D1I | D1 | D1I | D1D2I | D2 | D1I | D2I | D1I |
| Fushuai (1--12) | D1D2I | D2I | DI | D2I | D1D2I | I | D2 | D1D2 | D1D2 | I | D1 | I | D2I |
| Summer Pearmain (11--20) | D1D2 | D2I | D | D2 | D1D2 | D1I | D1 | I | D1D2I | D1D2 | D1D2 | D1D2 | I |
| Helm (11--21) | D1D2 | D2I | D | D1D2 | D1I | I | D1D2 | D1 | D1D2I | D1D2 | D1 | D2I | I |
| Domenesti (11--3) | D1I | D2I | NA | D2I | D1D2I | D1D2I | D1I | D1D2I | D1D2 | D1D2 | D2I | D2I |
| Early Harvest (1--13) | D1D2I | D2I | DI | D2I | D1D2I | I | D2 | D1D2 | D1D2 | I | D1 | I | D2I |
| Silver Spur Red Delicious (11--4) | D1D2 | D2I | I | D2I | D1 | D1I | D1I | D1D2 | D1D2I | D2 | D1 | D1D2 | I |
| Dongxiangjiao (11--5) | D1I | D2I | D | D2 | D1I | I | D1D2 | D1D2I | D1D2I | D1D2 | D1D2 | D1D2I | D2I |
| Guoling (1--15) | D1I | D2I | D | D2 | I | D1D2 | D2 | D2I | D1D2 | D2 | D1D2 | I | D1I |
| Skyline Spureme (11--8) | D1D2 | D2I | I | D2I | D1 | D1I | D1I | D1D2 | D1D2I | D2 | D1 | D1D2I | I |
| Chantecler (11--9) | I | D2I | DI | D2I | I | I | D2I | D1I | D1D2 | D2I | D1I | D2I | D1I |
| Close (1--19) | D1D2 | D2I | D | D2I | D1D2 | I | D1D2 | D1I | D1D2I | D1D2 | D1 | D1I | D2I |
| Aizaohui (1--2) | D1I | D1I | D | D1D2 | D1 | D2I | D1 | D1 | D1D2 | D2 | D1 | D2 | D2 |
| Wuyue (12--1) | D1 | D1D2I | DI | D2I | D1D2I | D2I | D2 | D1D2 | D1D2 | D2 | D1 | I | D1D2 |
| Bukowka (12--11) | I | D1D2I | D | D2 | D1 | D2I | D2 | D1D2 | D1D2 | D2 | D1 | I | D1I |
| Jinyu (12--12) | D1D2 | D1D2I | D | D1D2 | D1D2 | D1 | D1I | D1D2 | D1D2I | D1D2 | D1D2 | D2I | D1I |
| Calville Rouge (12--14) | D1 | D2I | D | D2I | D1I | D1I | D1I | D1I | D1D2 | D2 | D1 | D1D2 | D2I |
| Doyle (12--15) | D1D2 | D1D2I | D | D1D2 | D1D2 | D1I | D2I | D1D2 | D1D2 | D2 | D1 | D2I | D2I |
| Melrose (12--16) | D1D2 | D1D2I | D | D2I | D1D2 | D1I | I | D2 | D1D2I | D1D2 | D1D2 | I |
| Menage (12--17) | D1 | D2I | DI | D2 | D2 | D2I | D1I | D1I | D1D2I | D1D2 | D1 | I |
| Bo 26 (12--18) | D1 | D1D2I | D | D2 | D1 | D2I | D2 | D1 | D1D2 | D2 | D1 | I | I |
| Duoyilu (12--19) | D2 | D2I | D | D2 | D1D2I | I | D1D2 | D1I | D1D2I | D1D2 | D1 | D1 | D2I |

-continued

| Construction results of InDel marker genotype database of *Malus* germplasm resources | | | | | | | | | | | | | |
|---|---|---|---|---|---|---|---|---|---|---|---|---|---|
| De 6 (12-20) | D1D2I | D2I | DI | D2 | D1 | D1D2 | D1D2 | D1 | D1D2I | D1D2 | D2 | D2I | I |
| Red June (12-21) | D1D2 | D2I | D | D2 | D1I | I | D1D2 | D1I | D1D2I | D1D2 | D1 | I | D2I |
| Helasang (12-23) | D2 | D2I | D | D2 | D1 | D2I | D2 | D1D2 | D1D2 | D2 | D1I | D2I | D1 |
| Hesetiaowen (12-3) | D1I | D2I | DI | D1D2 | D1 | D1D2 | D2 | D1D2 | D1D2I | D2I | D1I | I | I |
| James Grieve (1-23) | D1D2I | D2I | D | D2 | D1I | D1I | D2 | D1D2 | D1D2 | D2 | D1 | D2I | D1D2 |
| Bailuosi Malin (12-4) | D2 | D2I | D | D1D2 | D1 | D2I | D2 | D2I | D1D2I | D1D2 | D1 | I | D1I |
| Jinnhong (12-5) | D1 | D1D2I | D | D1D2 | D1I | D1D2 | D1D2 | D1I | D1D2 | D2 | D1D2 | D1D2 | D1D2 |
| Kay Sai William (12-6) | D1D2 | D2I | D | D2I | D1I | D1I | D1 | D1I | D1D2I | D2 | D1I | D2I | D1I |
| Xingjiang Pingguo (12-7) | D2 | D1D2I | D | D2 | D1D2 | D1 | D2 | D2 | D1D2I | D2 | D2 | I | D1 |
| Jie 15 (12-8) | D1D2 | D2I | I | D2I | D1 | D1I | D1I | D1D2 | D1D2I | D2 | D1 | D1D2 | I |
| Mianpingguo (12-9) | D2 | I | D | D2 | D1 | D1D2 | D2 | D2 | D1D2I | D2 | D2 | I | D1 |
| Lowver (1-3) | D1I | D2I | D | D1D2I | D1D2I | D2I | D1 | D1I | D1D2 | NA | D1 | I | D1I |
| Benoni (13-1) | D1D2 | D2I | D | D2I | D1I | D1I | D1D2 | D1I | D1D2 | D2 | D1 | D1D2 | D2I |
| Fa 5 (13-11) | D1I | D2I | DI | D2I | D1I | D1I | D2I | D1D2 | D1D2 | D2 | D1D2 | D2I | D1I |
| Babskino (13-12) | D1D2I | D2I | DI | D1D2 | D1 | D2I | D2 | D1D2 | D1D2I | D2 | D1 | D2 | D2I |
| Kuluona (13-13) | D1I | D2I | NA | D2I | D1I | D1I | D1D2I | D1I | D1D2 | D2 | D1D2 | D2I | D2I |
| Shidonghaoji (13-16) | D1D2I | D2I | D | D2 | D1 | D1D2 | D2 | D1 | D1D2I | D1D2 | D2 | D2I | D1I |
| Oberkika (13-17) | D1D2 | D2I | DI | D2I | D1D2 | I | D2 | D1D2 | D1D2I | D2 | D1D2 | D1I | D2I |
| Budayi (13-19) | D1I | D2I | I | D2 | D1D2 | D1I | D2I | D1I | D1D2 | D2 | D1 | D1I | I |
| Red Canada (13-2) | D1I | D2I | DI | D2I | D1I | D1I | D2I | D1D2 | D1D2 | D2 | D1D2 | D2I | D1I |
| Laidi (13-20) | D2 | D2I | D | D2 | D1 | D1 | D1D2 | D1 | D1D2 | D2 | D1D2 | I | D1D2 |
| N2 (13-22) | D1D2I | D2I | I | D2I | D1I | D1I | D1D2 | D1I | D1D2I | D2 | D1 | D2I | I |
| Norsan (13-5) | D1D2 | D2I | I | D2I | D1 | D1I | D1I | D1D2 | D1D2I | D2 | D1 | D1D2 | I |
| Hebei Kangbing Golden Delicious (13-6) | D1I | D2I | DI | D2I | D1I | I | D1I | D1I | D2I | D1 | D2I | D2I | I |
| Zhanxuan 14 (13-9) | D1I | D2I | I | D2 | D1D2 | D1I | D2I | D1I | D1D2 | D2 | D1 | D1I | I |
| Xiangguoguang (14-11) | D1D2I | D2I | D | D2I | D1I | D1I | D1D2 | D1D2 | D1D2 | D2I | D1I | D2I | I |
| Shengfang 1 (14-14) | D1D2I | D2I | I | D2I | D1I | D1I | D1D2 | D1I | D1D2I | D2 | D1 | D2I | I |
| Yujing II (14-16) | D1D2I | D2I | I | D2I | D1I | D1I | D1D2 | D1I | D1D2I | D2 | D1 | D2I | I |
| Cox's Orange Pippin (14-2) | D2 | D2I | D | D1D2 | D1 | D1 | D1D2 | D2 | D1D2I | D2 | D1D2 | I | D2I |
| Nagafu 7 (14-20) | D1D2I | D2I | I | D2I | D1I | D1I | D1D2 | D1I | D1D2I | D2 | D1 | D2I | I |
| Boiken (14-21) | D1D2 | D1D2I | D | D2I | I | D1D2 | D2 | D1 | D1D2 | D2 | D1 | D2I | D1D2 |
| Qunfu 1 (14-23) | D1D2I | D2I | I | D2I | D1I | D1I | D1D2 | D1I | D1D2I | D2 | D1 | D2I | I |
| Calville Blanche (14-3) | D1D2 | D1D2I | D | D2I | I | D1D2 | D2 | D1 | D1D2 | D2 | D1 | D2I | D1D2 |
| Freybreg (14-4) | D1D2I | D2I | DI | I | D1I | D2I | D1I | I | D1D2I | D1D2 | D1I | D1I | D2I |
| Husveti Rosmaring (14-5) | D1D2I | D1D2I | D | D2 | D1 | D1D2I | D1D2 | D2I | D1D2I | D1D2 | D1 | I | D1I |
| Sweet Jonathan (14-7) | D1D2 | D1D2I | D | D1D2 | D1D2 | D1 | D1I | D1D2 | D1D2I | D1D2 | D1D2 | D2I | D1I |
| King of Pippin (14-8) | D2 | D2I | D | D1D2 | D1 | D1 | D1D2 | D2 | D1D2I | D2 | D1D2 | I | D2I |
| Duchess of Oldenburg (1-5) | D1D2 | D2I | D | D2 | D1 | D1I | D2I | D1I | D1D2I | D2 | D1I | I | D2I |

Construction results of InDel marker genotype database of *Malus* germplasm resources

| Name | | | | | | | | | | | | | |
|---|---|---|---|---|---|---|---|---|---|---|---|---|---|
| Kangbing Golden 5 (15-11) | I | D2I | DI | I | I | I | D2I | D2I | D1D2I | D1I | D1I | I | I |
| Pingzhi Ralls Janet (15-15) | I | D2I | I | D2 | D2I | D1I | D2 | D2I | D1D2 | D2 | D1 | I | I |
| Wase16 (15-16) | D1D2I | D2I | D | D2I | D1I | I | D2I | D1I | D1D2 | D2I | D1 | I | D2I |
| Kogetsu (15-17) | D1I | D2I | I | D1I | D1I | D1I | D1I | D1I | D1D2I | D1D2 | D1 | D2I | I |
| Jonared (15-18) | D1D2 | D1D2I | D | D1D2 | D1D2 | D1 | D1I | D1D2 | D1D2I | D1D2 | D1D2 | D2I | D1I |
| Zhanxuan 4 (15-21) | D1I | D2I | I | D2 | D1D2 | D1I | D2I | D1I | D1D2 | D2 | D1 | D1I | I |
| Strawberry (15-23) | D1I | D1D2I | DI | D1D2 | D1D2 | D2I | D1D2 | D1D2I | D1D2 | D2 | D1 | D2I | D2I |
| StarkSpur Ultra Red Delicious (15-3) | D1D2 | D2I | I | D2I | D1 | D1I | D1I | D1D2 | D1D2I | D2 | D1 | D1D2 | I |
| Sharp Red Delicious (15-4) | D1D2 | D2I | I | D2I | D1 | D1I | D1I | D1D2 | D1D2I | D2 | D1 | D1D2 | I |
| Mensi (15-5) | D1I | D2I | D | D2 | D1 | D2I | D2 | D2I | D1D2 | D2I | D1 | D2 | I |
| Norand (15-6) | D1D2 | D2I | DI | D2 | D1D2 | D2I | D2I | D2 | D1D2 | D2 | D1 | I | D1D2I |
| Zhanxuan 18 (15-7) | D1D2 | D2I | I | D2I | D1 | D1I | D1I | D1D2 | D1D2I | D2 | D1 | D1D2 | I |
| Xishan 1 (15-8) | D1D2 | D2I | I | D2I | D1 | D1I | D1I | D1D2 | D1D2I | D2 | D1 | D1D2 | I |
| Hongrou Pingguo (15-9) | D1D2I | D1D2I | D | D2 | D1D2I | D1D2 | D2 | D2 | D1D2I | D2 | D2 | I | D1I |
| Gravenstein (1-6) | D1I | D1D2I | D | D2 | D1D2 | D1 | D1D2 | D2I | D1D2I | D2 | D1D2 | I | D2I |
| Xinhong (16-1) | D1D2 | D2I | D | D2 | D1D2 | D1 | I | D2 | D1D2 | D2 | D1D2 | D1I | D1I |
| Zhanxuan 6 (16-10) | I | D2I | D | D1D2 | D1 | D1D2 | D2 | D2I | D2I | D2 | D2 | I | D1I |
| Behene (16-11) | D1 | D1D2I | D | D2 | D1D2 | D1 | D2 | D1D2 | D2I | D1D2 | D1D2 | D2I | |
| Xindong (16-14) | D1D2I | D1D2I | D | D2I | D1D2I | D1I | D2 | D2I | D1D2I | D1D2 | D1 | D2I | D1I |
| Hardi Brite (16-16) | D1D2 | D2I | I | D2I | D1 | D1I | D1I | D1D2 | D1D2I | D2 | D1 | D1D2 | I |
| Charden (16-17) | D1D2I | D2I | DI | I | I | I | D2I | D2I | D1D2I | D1D2I | D1I | D2I | D1I |
| Zhuoai 1 (16-2) | D1I | D2I | I | D2 | D1D2 | D1I | D2I | D1I | D1D2 | D2 | D1 | D1I | I |
| Jinse Luosuoshan (16-22) | D1 | D2I | DI | D1I | D1D2I | D1D2 | D2 | D1I | D1D2 | D2 | D1 | I | D1I |
| Zhaiteng II (16-23) | D1D2I | D2I | I | D2I | D1I | D1I | D1D2 | D1I | D1D2I | D2 | D1 | D2I | I |
| Zhanxuan 16 (16-6) | D1I | D2I | I | D2 | D1D2 | D1I | D2I | D1I | D1D2 | D2 | D1 | D1I | I |
| Fa 3 (16-8) | D1I | D2I | NA | D2I | D1D2I | D1D2I | D1I | D1D2I | D1D2I | D1D2 | D1 | D2I | D2I |
| Jerseymac (1-7) | D1D2I | D2I | D | D2 | I | I | D2 | D2 | D1D2 | D2 | D1I | D1I | D1D2 |
| Mother (17-1) | I | D2I | D | D2 | D2I | I | D1D2 | D1D2 | D1D2 | D2 | D1D2 | I | D2I |
| Northern Spy (17-10) | I | D2I | DI | I | D1I | I | D2I | D1I | D1D2I | D1D2 | D1I | I | D2I |
| Rome Beauty (17-11) | D1D2 | D1D2I | D | D1D2 | D2 | D1I | D2I | D1I | D1D2 | D2 | D1 | D2I | D2I |
| Black Ben David (17-12) | D1D2I | D2I | D | D2 | I | D1I | D2I | D1 | D1D2 | D2 | D1 | D2I | D2I |
| Atlas (17-13) | D2 | D2I | D | D2I | D2I | D2I | D1D2 | D2I | D2I | D1I | D1I | D1D2 | |
| Roxbury (17-14) | D1 | D2I | D | D2I | D1D2I | D1I | D2I | D2I | D1D2 | D2 | D1 | D1I | D1D2 |
| Laxtons Superb (17-15) | I | D2I | D | D2 | D1 | D1 | D1D2 | D1D2 | D1D2I | D1D2 | D1D2 | D2 | D2I |
| Changhong (17-16) | D1D2 | D1D2I | D | D1D2 | D1I | D1D2 | D1I | D1D2I | D1I | D1D2I | D2 | I | D2I |
| Cogswell Pearmain (17-17) | D1D2 | D1D2I | D | D2I | D1I | D1I | D2 | D1D2 | D1D2 | D2 | D1D2 | I | D2I |
| Twenty Ounce (17-18) | D1D2 | D1D2I | D | D1D2 | D1D2I | D1I | D1I | D1 | D1D2I | D1D2 | D1D2 | D2I | D2I |

| Construction results of InDel marker genotype database of *Malus* germplasm resources | | | | | | | | | | | | | |
|---|---|---|---|---|---|---|---|---|---|---|---|---|---|
| Lowtosh (17-19) | D1D2I | D2I | D | D2I | I | I | D1D2 | D1I | D1D2I | D1D2 | D1 | D2I | D2I |
| Iwaki (17-21) | D1 | D2I | D | D2 | I | D1I | D2 | D1D2 | D1D2I | D2 | D1 | I | D2I |
| Qin'guan (17-22) | D1I | D2I | DI | D2I | I | D2I | I | D1I | D1D2I | D1D2 | D1I | I | I |
| Bancroft (17-23) | D1D2 | D2I | D | D2I | D1D2I | D2I | D1I | D2 | D1D2 | D2 | D1I | D1I | D1I |
| Chenango Strawberry (17-4) | D2 | D2I | D | D2 | D1 | D2 | D2 | D1D2 | D1D2I | D1D2 | D1D2 | D2 | D1I |
| Newfane (17-7) | D1D2 | D2I | DI | I | D1I | D1I | D1D2 | D1D2 | D2I | D2 | D1 | D1D2 | D2I |
| Lord Lambourne (17-9) | I | D2I | DI | I | D1I | I | D2I | D1I | D1D2I | D1D2 | D1I | I | D2I |
| Rizhiwan (18-0) | D2 | D2I | DI | D2 | D1I | D1D2 | D1I | D2I | D1D2 | D2 | D1D2 | D1I | D2 |
| Campbell (18-11) | D1 | D2I | D | D2I | D1D2I | D1I | D1D2 | D2I | D1D2 | D2 | D1 | D1I | D1D2 |
| Pigeon (18-13) | D1D2 | D2I | D | D2 | D1 | I | D2 | D1I | D1D2I | D1 | D1 | D1 | D2I |
| Summer Champion (18-14) | D1D2I | D2I | D | D2 | D1I | I | D2 | D1D2 | D1D2I | D1D2 | D1D2 | D2I | D1I |
| Nanpu 3 (18-15) | D1D2I | D2I | D | D2 | I | D1I | D2I | D1D2 | D1D2 | D2 | D1 | I | I |
| Qiulimeng (18-16) | D1D2 | D2I | D | D2 | D1D2 | D1D2 | D2 | D1D2 | D1D2I | D2 | D1D2 | I | D1I |
| Rutosh (18-17) | D1D2 | D2I | D | D2I | D2I | I | D2 | D1D2 | D1D2 | D2 | D1 | D1I | D1D2 |
| Xinlimei (18-19) | D2 | D2I | D | D2 | D1 | D1 | D1D2 | D1 | D1D2 | D2 | D1D2 | I | D1D2 |
| Huanong 1 (18-2) | D1D2 | D2I | D | D2 | D1D2I | D1I | D2 | D1I | D1D2 | D2 | D1 | I | D1 |
| Lawfam (18-20) | D2 | D2I | D | D2I | D1D2 | D2I | D1D2 | D2I | D1D2 | D2I | D1I | D1I | D1I |
| Akin's Red (18-21) | D1I | D1I | D | D1 | D1I | D1 | D1 | D1 | D1D2I | D1D2 | D1D2 | I | D1D2 |
| Meltosh (18-22) | D1D2 | D2I | D | D2 | D1D2I | D1 | D1D2 | D1 | D1D2I | D2 | D2 | I | D2I |
| Hubbardston (18-23) | D1D2I | D2I | DI | I | D1I | D2I | D1I | I | D1D2I | D1D2 | D1I | D1I | D2I |
| Fenghuangluan Crab (18-3) | D1D2 | D2I | D | D2 | D1D2I | D1I | D2 | D1I | D1D2 | D2 | D1 | I | D1 |
| Jie 9 (18-4) | D1 | D1D2I | D | D2I | D1D2I | D1D2 | D1D2 | D1I | D1D2I | D1D2 | D1I | D1D2I | D2I |
| Bramley's Seedling (18-5) | D1I | D1D2I | D | D1D2I | D1D2I | D1I | D2I | D1D2 | D1D2I | D2 | D1 | D1I | D1I |
| Shuangyang 1 (18-7) | D1D2I | D2I | DI | I | D1I | D2I | D1I | I | D1D2I | D1D2 | D1I | D1I | D2I |
| Shengli (18-8) | D1D2I | D2I | DI | I | D1I | D2I | D1I | I | D1D2I | D1D2 | D1I | D1I | D2I |
| Qingguan (18-9) | D1 | D2I | D | D2 | D1 | D1I | D2 | D1I | D1D2 | D2 | D1D2 | I | D2 |
| Weeping Ralls (19-0) | I | D2I | I | D2 | D2I | D1I | D2 | D2I | D1D2 | D2 | D1 | I | I |
| Giant Jeniton (19-1) | D1 | D2I | DI | D2 | D1D2 | D2I | D1I | D1I | D1D2I | D1D2 | D1D2 | I | I |
| Baldwin (19-10) | D1D2 | D2I | D | D2 | D1I | D1I | D2I | D1I | D1D2 | D1D2 | D1D2 | D2 | D1D2I |
| Lele Fuji (19-11) | D1D2I | D2I | I | D2I | D1I | D1I | D1D2 | D1I | D1D2I | D2 | D1 | D2I | I |
| Shuahong (19-12) | D1D2 | D2I | DI | D2 | I | D1I | D2 | D2 | D1D2I | D2I | D2I | I | D1D2 |
| Red Fuji TAO (19-14) | D1D2I | D2I | I | D2I | D1I | D1I | D1D2 | D1I | D1D2I | D2 | D1 | D2I | I |
| Jizaohong (19-17) | D1D2I | D2I | DI | I | D1I | D2I | D1I | I | D1D2I | D1D2 | D1I | D1I | D2I |
| Karas Tor (19-19) | D1D2I | D1D2I | D | D2I | D1I | D2I | D1D2 | D1I | D1D2 | D2 | D1 | D2 | I |
| Ralls Janet (19-2) | I | D2I | I | D2 | D2I | D1I | D2 | D2I | D1D2 | D2 | D1 | I | I |
| Stonetosh (19-22) | D1D2 | D2I | D | D2 | D1 | I | D1D2 | I | D1D2 | D2 | D1I | D1I | D1I |
| White Pearmain (19-23) | D1D2I | D2I | DI | D1I | D1I | I | D1D2 | D1D2 | D1D2I | D2 | D1 | D1D2 | I |
| Xiushui Guoguang (19-3) | D1D2I | D2I | NA | D2I | D1D2I | D1I | D2I | D2 | D1D2I | D2 | D1 | D2I | I |
| Chimeric Ralls Janet (19-4) | I | D2I | I | D2 | D2I | D1I | D2 | D2I | D1D2 | D2 | D1 | I | I |

-continued

Construction results of InDel marker genotype database of *Malus* germplasm resources

| | | | | | | | | | | | | | |
|---|---|---|---|---|---|---|---|---|---|---|---|---|---|
| Mutsu (19--7) | D1I | D2I | DI | D1I | I | I | D2I | D2I | D1D2I | D1D2I | D1I | D2I | I |
| Ben David (19--8) | D1D2I | D2I | D | D2 | I | D1I | D2I | D1 | D1D2 | D2 | D1 | D2I | D2I |
| Saint Lawrence (19--9) | D1D2 | D1D2I | D | D2 | D1D2 | D1I | D1D2 | D1 | D1D2I | D1D2 | D1 | D2I | I |
| Newtosh (20--0) | D1 | D2I | D | D2 | D1D2 | D2 | D2 | D2 | D1I | D2 | D2 | I | D1 |
| Geliekekukui (20--1) | D1D2 | D2I | D | D2 | D1D2 | D1I | D2 | D1D2 | D1D2I | D1D2 | D1 | I | I |
| Sweet Jonathan (20--10) | D1D2 | D1D2I | D | D1D2 | D1D2 | D1 | D1I | D1D2 | D1D2I | D1D2 | D1D2 | D2I | D1I |
| Apple of Commerce (20--11) | D1I | D2I | D | D2 | D1D2I | D1I | D2 | D1D2 | D1D2I | D2 | D1 | D1I | D2I |
| 600 g Andong (20--12) | D1 | D1D2I | D | D2 | D1D2 | D1 | D2 | D1D2 | D1D2 | D2I | D1D2 | D1D2 | D2I |
| Winter Banana (20--14) | D1D2I | D2I | DI | D1D2 | D1I | D1I | D2I | D1 | D1D2 | D2I | D1I | D1I | D2 |
| Rainier (20--15) | D1I | D1D2I | DI | D2 | D1D2 | D1D2 | D1I | D2 | D1D2 | D2I | D1 | D1I | I |
| Winesap (20--16) | D1I | D1D2I | DI | D1D2 | D1 | D1 | D1D2 | D2I | D1D2 | D2 | D1 | D2I | D1I |
| Drumbo (20--17) | D1D2 | D2I | D | D2 | D1D2I | D1 | D1D2 | D1 | D1D2I | D2 | D2 | I | D2I |
| Blengstid Gaurd (20--2) | D1I | D2I | NA | D2I | D1D2I | D1D2I | D1I | D1D2I | D1D2I | D1D2 | D1D2 | D2I | D2I |
| Jierjisi (20--21) | D1I | D1D2I | D | D2 | D1D2 | D1 | D2 | D1I | D1D2 | D2 | D2 | I | D1D2 |
| Radiant (20--23) | D1 | D2I | D | D2 | D1D2 | D2 | D2 | D2 | D1I | D2 | D2 | I | D1 |
| King David (20--5) | D1 | D1D2I | D | D2 | D1 | D1I | D1D2 | D1 | D1D2 | D2 | D1 | D2I | D1D2 |
| Clapp's Seedling (20--6) | D1 | D2I | D | D2 | D1 | D1I | D2 | D1I | D1D2 | D2 | D1D2 | I | D2 |
| Ingram (20--7) | I | D2I | DI | D2 | D1D2I | D1I | D2 | D2 | D1D2 | D2 | D1 | D2I | I |
| Qiujin (20--8) | D1I | D2I | I | D2 | D1D2 | D1I | D2I | D1I | D1D2 | D2 | D1 | D1I | I |
| Sujsleppskoe (2--1) | D1D2 | D1D2I | DI | D1D2 | D1D2 | D1I | D1I | D1D2 | D1D2I | D1 | D1D2 | I | D2 |
| Qian 1 Ace (21--0) | D1D2I | D2I | I | D2I | D1I | D1I | D1D2 | D1I | D1D2I | D2 | D1 | D2I | I |
| Toko (2--10) | I | D2I | D | D2I | D1I | I | D2I | D2I | D1D2I | D1D2 | D1I | D2I | I |
| Antalue (21--1) | I | D2I | I | I | D1I | I | D1D2 | D2I | D1D2 | I | D1I | I | I |
| Boskoopske Cervene (2--11) | D1I | D2I | NA | D2I | D1D2I | D1D2I | D1I | D1D2I | D1D2I | D1D2 | D1D2 | D2I | D2I |
| Heoersitai (21--10) | D1I | D2I | D | D2 | D1 | D1I | D1D2 | D1I | D1D2I | D1D2 | D1D2 | D1D2 | I |
| Lanfengwang (21--11) | D1D2 | D2I | D | D2 | D1D2 | D1I | D1D2 | I | D2I | D1 | D1 | D1D2 | D2I |
| Aohong (21--14) | D1I | D2I | DI | D2I | D1D2I | D1I | I | D1D2 | D1D2I | D1I | D1I | I | D2I |
| Weiqinni (21--15) | D1D2 | D2I | D | D1D2I | D1D2 | D1D2 | D1D2 | D1D2I | D1D2 | D1D2 | D1D2 | D1I | D1I |
| Smoothee (21--17) | I | D2I | DI | I | I | I | D2I | D2I | D1D2I | D1D2I | D1I | I | D2I |
| Hongzhiwu (21--18) | D1I | D2I | DI | D2I | I | D1I | D1D2 | D2I | D1D2I | D1D2 | D2 | I | D2I |
| Jieba (21--2) | D1 | D2I | D | D2 | D1 | D1I | D1 | D1I | D1D2 | D2 | D1 | D1I | I |
| Kizashi (21--20) | I | D2I | D | D2 | D1 | D1I | I | D1I | D2I | D1D2 | D1D2 | I | D2I |
| Aifeng (21--21) | D1I | D2I | D | D2 | D1 | D1I | I | D1I | D1I | D1D2 | D1D2 | I | D2I |
| Xingping (21--4) | I | D2I | I | D2 | D2I | D1I | D2 | D2I | D1D2 | D2 | D1 | I | I |
| Esopus Spitzenburg (2--14) | D1I | D2I | D | D2 | D1 | D1I | D1I | D1D2 | D1D2I | D2 | D1 | D1D2 | I |
| Lvguang (21--6) | D2 | D1D2I | D | D2 | D1 | D1 | D2 | D2I | D2I | D2 | D2 | I | D1 |
| Nvyoujidui (2--16) | D2 | D2I | D | D2 | D1D2I | D1I | D2 | D1 | D1D2 | D1D2 | D1D2 | D2I | D1I |
| Bell Poos (21--7) | D1D2I | D1D2I | D | D2I | D1D2I | D1D2 | D1D2 | D1D2 | D2I | D1D2 | D2 | D1 | I | D1I |

-continued

| Construction results of InDel marker genotype database of *Malus* germplasm resources | | | | | | | | | | | | | |
|---|---|---|---|---|---|---|---|---|---|---|---|---|---|
| Tian Andongnuo (2--17) | D1D2 | D1D2I | D | D2 | D1 | D1 | D1 | D1 | D1D2 | D2 | D1 | I | I |
| Pacific Rose (21--8) | D1I | D2I | DI | D2I | D1D2I | D1I | I | D1D2 | D1D2I | D1I | D1I | I | D2I |
| 500 g (21--9) | D1I | D2I | D | I | D2I | D1 | D2 | D1I | D1D2I | D1 | D1 | D2I | D1I |
| Nvyoujidui 2 (2--19) | D1D2 | D1D2I | DI | D1D2 | D1D2 | D1I | D1I | D1D2 | D1D2I | D1 | D1D2 | I | D2 |
| Tian Andongnuo 2 (2--2) | D1D2I | D2I | D | D2 | D1I | D1I | D2 | I | D1D2I | D1 | D1 | I | I |
| Spur Mutsu (22--1) | D1I | D2I | DI | D1I | I | I | D2I | D2I | D1D2I | D1D2I | D1I | NA | NA |
| Red June Sweet (2--21) | I | D1D2I | D | D2 | D1 | D2I | D2 | D1D2 | D1D2 | D2 | D1 | I | D1I |
| Chu Tsugaru (22--11) | D1D2I | D1D2I | D | D1I | D1D2I | D1I | D1I | D1I | D2I | D1 | D2I | I | I |
| Kermemen (22--13) | D1D2I | D1I | D | D2I | D1I | D1I | D2 | D1 | D1D2 | D2 | D1D2 | D2I | D2I |
| Bedan (22--14) | D1D2I | D1D2I | I | D2I | D1I | D1 | D2I | D2I | D2I | D1D2 | D1D2 | I | D2I |
| Dabinette (22--15) | D1D2I | D2I | I | D2I | D1I | D1I | D1D2 | D1I | D1D2I | D2 | D1 | D2I | I |
| Zaocuilv (22--16) | D1D2I | D2I | DI | I | D1I | D2I | D1I | I | D1D2I | D1D2 | D1I | D1I | D2I |
| Chanteline (22--17) | D2 | D2I | DI | D2I | I | I | D1D2 | D1D2 | D1D2I | D2 | D1D2 | D2I | D1 |
| Red Baron (22--2) | D1 | D2I | D | D2 | D1 | D1 | D2 | D1D2 | D1D2I | D2 | D1 | D2I | I |
| Hongjin Gala (22--4) | D1D2I | D2I | D | I | D1I | I | I | I | D1D2I | D1 | D1I | D2I | I |
| Generos (22--7) | D1D2 | D1D2I | D | D1D2 | D1D2 | D1 | D1I | D1D2 | D1D2I | D1D2 | D1D2 | D2I | D1I |
| Alberta (2--3) | D1 | D2I | D | D1 | D1 | D1D2 | D1D2 | D2I | D1D2I | D2I | D1 | D2I | D1D2 |
| Hirosaki Fuji (23--1) | D1D2I | D1D2I | D | D1I | D1D2I | D1I | D1I | D1I | D2I | D1 | D2I | I | I |
| Miya Fuji (23--10) | D1D2I | D2I | I | D2I | D1I | D1I | D1D2 | D1I | D1D2I | D2 | D1 | D2I | I |
| Yanshanhong (23--13) | D1I | D2I | I | D2 | D1I | D1 | D1D2 | D1I | D1D2 | D2 | D1 | D2I | I |
| Dailv (23--14) | D1D2 | D2I | DI | D2 | D1 | D1I | D1D2 | D1D2 | D2I | D1 | D1D2 | I | D2I |
| Frequin Rouge (23--15) | D1I | D1I | DI | D2 | D1 | D2I | D2I | D1D2 | D1D2 | D2 | D1D2 | D2I | I |
| Jinguang (23--16) | D1 | D1D2I | D | D2 | D1D2 | D1 | D2 | D1D2 | D1D2I | D1 | D1D2 | D1D2 | D2I |
| Avrolles (23--17) | D1I | D1D2I | DI | D2 | D1D2 | D2I | D2 | D2 | D1D2 | D2 | D1D2 | D1D2I | I |
| Marie Menard (23--18) | D1D2I | D1D2I | I | D2I | D1I | D1 | D2 | D1 | D1D2I | D1D2 | D1D2 | D2I | D2I |
| Golden B (23--2) | I | D2I | DI | I | I | I | D2I | D2I | D1D2I | D1I | D1I | I | I |
| Jurella (23--20) | D2I | D1D2I | D | D2I | D1 | D2I | D1 | D2I | D1D2 | D1D2 | D2 | D1D2 | I |
| GS58 (23--21) | D1D2 | D2I | I | D2I | D1I | I | D1I | D1I | D1D2I | D1D2 | I | D2I | I |
| Lianji (23--22) | D1D2 | D2I | D | D1I | D2 | D1 | D1D2 | D2I | D1D2 | D2 | D1I | D1 | D1I |
| Aomori Spur Fuji (23--4) | D1D2I | D2I | I | D2I | D1I | D1I | D1D2 | D1I | D1D2I | D2 | D1 | D2I | I |
| Akifu 39 (23--9) | D1D2I | D2I | I | D2I | D1I | D1I | D1D2 | D1I | D1D2I | D2 | D1 | D2I | I |
| Shalatuoni (2--4) | D1D2 | D2I | D | D2 | D1D2 | D1I | D1 | D1I | D1D2 | D2 | D2 | D1D2 | D1I |
| Guoqing (24--13) | D1D2I | D2I | DI | D2 | I | D1I | D2 | D1D2 | D1D2 | D2 | D1 | D2I | D2I |
| Ningguang (24--15) | D1D2I | D2I | D | D2I | I | I | D2 | D1D2 | D1D2I | D1D2 | D1I | D2I | I |
| Hongqiaowang (24--17) | D1D2I | D2I | DI | D1I | D1I | D1I | D1D2I | D2I | D1D2I | D1D2I | D1I | I | I |
| Wemhong (24--18) | D1D2 | D2I | D | D2 | D1I | I | D2 | D2I | D1D2I | D1D2 | D2 | D1I | D1D2 |
| Wijcik McIntosh (24--19) | D2 | D2I | D | D2I | D1D2I | I | D1D2 | D1D2 | D1D2 | D1D2 | D2 | D1I | D1I |
| Xinguoguang (24--21) | I | D2I | I | D2 | D2I | D1I | D2 | D2I | D1D2 | D2 | D1 | I | I |
| Fengcun Fuji (24--22) | D1D2I | D2I | I | D2I | D1I | D1I | D1D2 | D1I | D1D2I | D2 | D1 | D2I | I |

-continued

| Construction results of InDel marker genotype database of *Malus* germplasm resources | | | | | | | | | | | | | |
|---|---|---|---|---|---|---|---|---|---|---|---|---|---|
| America 8 (24--23) | D1D2I | D2I | DI | D2 | I | D1I | D1D2 | D1I | D1D2I | D2 | D1 | D2I | D2I |
| GS48 (24--3) | D1 | I | D | D1D2 | D1D2 | D1D2 | D1D2 | D1D2I | D2 | D1D2 | I | D1 | |
| Granny Smith (24--4) | D1D2I | D2I | D | I | D1D2I | I | D2I | D1 | D1D2I | D1D2 | D1 | D2I | D2I |
| Stark Spur (24--7) | I | D2I | DI | I | I | I | D2I | D2I | D1D2I | D1I | D1I | I | I |
| Huangguniang (2--5) | D1D2 | D2I | D | D1D2 | D1D2 | I | D1 | D1I | D1D2 | D2 | D1 | D1D2 | D1I |
| Judaine (25--11) | D1 | D2I | D | D2 | D1 | D1I | D2I | I | D1D2I | D1D2 | D1 | D2I | I |
| Judeline (25--12) | D1I | D1D2I | DI | D2I | D1I | D1I | D2I | D2 | D2I | D1 | D1D2 | I | I |
| HoneyCrisp (25--14) | D1D2I | D2I | D | D2I | D1D2I | I | D2 | D1D2 | D1D2 | D2I | D1I | D2 | D2 |
| Korin (25--15) | D1D2I | D2I | I | D2I | D1I | D1I | D1D2 | D1I | D1D2I | D2 | D1 | D2I | I |
| Hongao (25--18) | D1I | D2I | DI | D2I | D1I | D1I | D2I | I | D1D2 | D2I | D1I | I | I |
| Ningguang (25--19) | D1I | D2I | DI | D2I | D1I | D1I | D2I | I | D1D2 | D2I | D1I | I | I |
| Red Delicious (25--2) | D1D2 | D2I | I | D2I | D1 | D1I | D1I | D1D2 | D1D2I | D2 | D1 | D1D2 | I |
| Youlixiang (25--21) | D1D2I | D1D2I | D | D1I | D1D2I | D1I | D1D2 | D1D2 | D1D2 | D2I | D2I | D2I | I |
| Fuqiu (25--3) | D2 | D2I | DI | D1D2 | D1I | D1D2 | D1D2 | D1I | D1D2I | D2 | D1 | D2I | I |
| Chunxiang (25--4) | D1D2 | D2I | DI | D2 | I | D1I | D2 | D2 | D1D2I | D1D2 | D2I | I | D1D2 |
| Fu Hong (25--5) | I | D2I | DI | D2 | D1I | D1D2 | D1D2 | D1D2 | D2I | D1D2 | D1 | I | I |
| Qingxiang (25--6) | D1D2I | D2I | DI | D1I | I | I | D2I | D2I | D1D2I | D1D2 | D1I | D1I | I |
| Zhongxing (25--7) | D1D2I | D2I | D | D2I | D1I | D1I | D1I | D1D2 | D1D2I | D1 | D1 | D1D2 | D1I |
| Weixishengming (25--8) | D1D2I | D1D2I | D | I | D1D2I | I | D1I | D1I | D1D2I | D1 | D1I | D2I | I |
| Shichinohe 1 (25--9) | D1D2I | D2I | I | D2I | D1I | D1I | D1D2 | D1I | D1D2I | D2 | D1 | D2I | I |
| Arkansas Black (2--6) | D1D2 | D2I | I | D2I | D1I | D1I | D2 | D2 | D1D2 | D2 | D1 | D2 | D1D2 |
| Douce Coetligne (26--10) | D1I | D2I | D | D2 | D1 | D1I | D1I | D1D2 | D1D2I | D1D2 | D1D2 | D2 | D2I |
| Golden Spur (26--14) | I | D2I | DI | I | I | I | D2I | D2I | D1D2I | D1D2I | D1I | I | I |
| Orei (26--15) | D2 | D2I | D | D1D2 | D1 | D1 | D1D2 | D2 | D1D2I | D2 | D1D2 | I | D2I |
| Sekaiichii (26--18) | D1D2I | D2I | D | I | D1I | I | I | I | D1D2I | D1 | D1I | D2I | I |
| Kokyu (26--19) | D1I | D2I | D | I | D1I | I | D1I | D1I | D1D2 | D2I | D1 | D2I | I |
| Douce Moen (26--2) | D1D2 | D2I | D | D2 | D1D2 | D1I | D2I | D1 | D1D2I | D1D2 | D1D2 | D2I | D2I |
| Yanfu 1 (26--22) | D1D2I | D2I | I | D2I | D1I | D1I | D1D2 | D1I | D1D2I | D2 | D1 | D2I | I |
| Ningfeng (26--23) | D1D2I | D2I | DI | D2 | I | D1I | D1D2 | D1I | D1D2I | D2 | D1 | D2I | D2I |
| Juliana (26--5) | D2 | D2I | DI | D1D2 | D2I | D1D2 | I | D1D2 | D1D2 | D2 | D1 | D2I | D1D2I |
| Judestar (26--9) | D1 | D2I | D | D2I | D2I | D1I | I | D1I | D1D2 | D2 | D1 | D1 | D2I |
| Liaofu (2--7) | D1D2 | D1D2I | D | D2 | D1 | D1D2 | D1 | I | D1D2I | D1D2 | D1 | D1D2 | D2I |
| Sinano Red (27--10) | D1D2 | D2I | I | D2I | D1 | D1D2 | D1D2 | D1D2 | D2I | D1 | D1 | I | D2 |
| Jinyang (27--12) | D1D2 | D2I | D | D2 | D1I | D1D2 | D2I | D1I | D1 | D2 | D1D2 | D1I | D2I |
| Enqi (27--13) | D1I | D2I | D | D2I | D1 | I | D1I | D1I | D2I | D1 | D2I | D2I | I |
| Miki (27--14) | D1D2I | D1D2I | D | I | D1D2I | I | D1I | D1I | D1D2I | D1 | D1I | D2I | I |
| Hongbaoshi (27--15) | D1D2I | D2I | NA | D2I | D1I | D1I | D1I | D1I | D1D2I | D1D2 | D1I | D1I | I |
| Nagafu 2 (27--16) | D1D2I | D2I | I | D2I | D1I | D1I | D1D2 | D1I | D1D2I | D2 | D1 | D2I | I |

-continued

| Construction results of InDel marker genotype database of *Malus* germplasm resources | | | | | | | | | | | | |
|---|---|---|---|---|---|---|---|---|---|---|---|---|
| Longguan (27--4) | I | D2I | NA | D2 | D2I | D1I | D2 | D2I | D1D2 | D2 | D1 | I | I |
| K9 (27--5) | D1D2 | D2I | D | D2 | D1I | D1D2 | D2I | D1I | D1 | D2 | D1D2 | D1I | D2I |
| Zaohongda Gala (27--6) | D1D2 | D2I | D | D2 | D1I | D1D2I | D2I | D1I | D1 | D2 | D1D2 | D1I | D2I |
| Lvshuai (27--7) | D1D2I | D2I | I | D2I | D1D2I | D1I | D1I | I | D1D2I | D1I | D1I | D1I | D2I |
| Hongxia (27--8) | D1I | D2I | D | D2 | D1 | D1I | I | D1I | D2I | D1D2 | D1D2 | I | D2I |
| Zaohongxia (27--9) | D1D2I | D2I | NA | D2I | D1I | D1I | D1D2 | D1I | D1D2I | D2 | D1 | D2I | I |
| Early Golden (2--8) | D1I | D1D2I | I | D1I | D2I | I | I | D1I | D1D2I | D1 | D1 | D1I | D1I |
| Indo (28--0) | D1I | D2I | D | D1D2 | D1I | I | D1D2 | D2 | D1D2I | D2 | D1 | D2I | I |
| Jie 1 (28--11) | D1D2 | D1D2I | D | D1D2 | D1D2 | D1 | D1I | D1D2 | D1D2I | D1D2 | D1D2 | D2I | D1I |
| Beauty of Bath (28--13) | D2 | D1D2I | D | D1D2 | D1D2 | I | D1D2 | D2I | D1D2I | D1D2 | D1 | D2 | D2I |
| K10 (28--14) | D1D2I | D1D2I | D | D1D2 | D1I | D2I | D1I | D1I | D1D2 | D2I | D1D2 | D2I | D2I |
| Beifang Xina (28--16) | D1D2 | D2I | DI | D2 | D1 | D1D2 | D2I | D1I | D1D2I | D1 | D1 | I | I |
| Yellow Fuji (28--18) | I | D2I | D | D2I | D1I | D1I | D1D2 | D1D2 | D1D2I | D1I | D1I | I | D1I |
| Sinano Sweet (28--2) | D1I | D2I | D | D1D2 | D1D2 | D1 | D1D2 | D1I | D1D2I | D1D2 | D1I | I | D1I |
| Miguo (28--3) | D1I | D2I | I | D2 | D1D2 | D1I | D2I | D1I | D1D2 | D2 | D1 | D1I | I |
| Ace (28--4) | D1D2I | D2I | NA | D2I | D1I | D1I | D1D2 | D1I | D1D2I | D2 | D1 | D2I | I |
| Tsugaru (28--5) | D1D2I | D1D2I | D | D1D2I | D1D2I | D1I | D1I | D1I | D2I | D1 | D2I | I | I |
| K12 (28--8) | D1I | D1D2I | D | D2I | D1I | D1I | D2I | D1I | D1D2I | D1D2 | D1I | I | D1I |
| Jieernianke (28--9) | D1I | D2I | D | D2I | D1I | D1D2 | D2 | D1D2 | D1D2I | D2 | D1 | I | D2 |
| Macoun (2--9) | D1D2 | D2I | D | D2I | D2I | D1I | D1D2 | I | D1D2 | D2 | D2I | I | D1D2 |
| Qingping (29--1) | D1I | D2I | D | D2 | D1D2 | D1I | D2 | D1 | D1D2 | D2 | D1 | D2I | D2I |
| Polka (29--11) | D1D2I | D2I | DI | I | I | I | D1D2 | D2I | D1D2 | D2I | D1I | I | D1I |
| Longfeng (29--13) | D1I | D2I | D | D2I | D1D2I | D1I | I | D2I | D1D2I | D1D2 | D1D2 | I | D1I |
| Very Early Fuji (29--14) | D1D2I | D2I | I | D2I | D1I | D1I | D1D2 | D1I | D1D2I | D2 | D1 | D2I | I |
| Longhong (29--15) | D1D2I | D2I | I | D1D2I | I | D2 | D1D2 | D1D2 | I | D1 | D1I | I |
| Pinova (29--16) | I | D2I | DI | D2I | D1I | D1I | D2I | D1I | D1D2 | D2I | D2I | D1I | I |
| Fuga (29--17) | D1I | D2I | D | D2 | D1 | D1I | I | D1I | D2I | D1D2 | D1D2 | I | D2I |
| Qing n3 (29--2) | D1D2 | D2I | I | D2I | D1 | D1I | D1I | D1I | D1D2I | D2 | D1 | D1D2 | I |
| Xinyuanshuai (29--3) | D1D2 | D2I | I | D2I | D1 | D1I | D1I | D1I | D1D2I | D2 | D1 | D1D2 | I |
| Xinhua (29--5) | D1I | D2I | NA | D2 | D1D2 | D2I | D2 | D2I | D1D2 | D2 | D1 | I | D1I |
| Nanpu 2 (29--6) | D1D2I | D1D2I | D | D2 | D1 | D1I | D1D2 | D2 | D1D2I | D1D2 | D1 | I | I |
| Liuyu mutant (29--7) | D1I | D2I | D | D1D2 | D1 | D1D2 | D1I | D1I | D1D2I | D2 | D1D2 | D2I | D1I |
| Shandao Fuji (30--1) | D1D2I | D2I | I | D1D2 | D1I | D1I | D1I | D1I | D1D2I | D2 | D1 | D2I | I |
| Sinano Gold (30--2) | D1I | D2I | I | D1I | D1 | D1 | D1I | D1I | D1D2I | D2 | D1I | I | D1I |
| Whitney (3--1) | D1 | D1D2I | D | D1D2 | D1D2I | D2I | I | D1D2 | D1D2 | D2 | D1 | D1I | D1I |
| Feixia (31--1) | I | D2I | I | I | D1I | I | D1D2 | D2I | D1D2 | I | D1I | I | I |
| Willams Faborite (3--11) | D1 | D2I | NA | D2 | I | I | D2I | D1D2 | D1D2I | D2 | D1 | D1I | D2I |
| Zhangye 2 (31--12) | D1D2 | D2I | D | I | D1I | I | I | D2I | D1D2I | D1D2 | D1 | D2I | I |

-continued

| Construction results of InDel marker genotype database of *Malus* germplasm resources | | | | | | | | | | | | |
|---|---|---|---|---|---|---|---|---|---|---|---|---|
| Youfangcun Ralls Janet (31--14) | D1D2I | D2I | D | D2 | I | D1I | D2I | D1 | D1D2 | D2 | D1 | D2I | D2I |
| Yueyanghong (31--15) | D2 | D2I | NA | D2I | I | D1I | D1D2 | I | D2I | D1D2 | D1 | D2 | D2I |
| Shuohong (31--17) | D1I | D2I | I | D2 | D1D2I | D1 | D2I | D2 | D1D2I | D2 | D1 | D1I | I |
| Tianwang 1 (31--18) | D1D2 | D2I | I | D2I | D1 | D1I | D1I | D1D2 | D1D2I | D2 | D1 | D1D2 | I |
| Huadan (31--2) | D1D2I | I | DI | D2I | D1I | I | D1I | I | D1D2I | D1D2 | D1D2 | D2I | I |
| Dalu 52 (3--12) | D1D2 | D2I | D | D2 | D1D2 | D1I | D1I | D1I | D1D2 | D2 | D1I | D2I | D1I |
| Cameo (31--3) | D1D2I | D2I | I | D2I | D1I | D1I | D1D2 | D1I | D2I | D1D2 | D1 | D2I | I |
| Tianhuangkui (3--13) | D2I | D2I | D | D2I | D1D2 | I | D1D2 | D1I | D1D2 | D2 | D1 | D1I | D2I |
| Qiulu (31--4) | D2 | D1D2I | D | D1D2 | D1D2 | D1 | D1 | D1 | D1D2 | D2 | D1 | I | D1 |
| Liehuangjiatena (3--15) | I | D2I | DI | I | D1I | D1I | D2I | I | D1D2I | D1 | D1 | I | I |
| Lubi (3--16) | D1D2 | D2I | D | D2 | D1I | D1I | D2I | D1D2 | D1D2 | D2 | D1D2 | D2I | D1I |
| Huayu (31--8) | NA | D2I | I | D2I | D1I | D1I | D1D2 | D1D2 | D2I | D1 | NA | I | D2I |
| Fameuse (3--18) | D2 | D2I | D | D1D2I | D1D2I | D1I | D1D2 | D1 | D1D2I | D2 | D1D2 | I | D2I |
| Zhanhanxiang (3--19) | D1D2I | D2I | D | I | D1I | I | D1I | I | D1D2I | D1D2 | D1I | I | D2I |
| Siberian White Spot (3--2) | D2 | D2I | D | D1D2 | D1 | D1I | D2 | D1 | D2I | D1D2 | D1D2 | D2I | D1I |
| Zhengding 2 (3--21) | D1D2 | D1D2I | DI | D2 | D1D2I | D1I | D2I | D1I | D1D2I | D2 | D1 | D1I | I |
| Kuihua (3--22) | D1D2 | D2I | D | D2 | D1 | I | D1D2 | D2I | D1D2I | D1D2 | D1D2 | I | D1 |
| Early Worcester (3--23) | D2 | D2I | D | D2I | D2I | D1I | D1 | D1D2 | D1D2I | D2 | D1 | D1I | I |
| Lowland Raspderry (3--3) | D1I | D1D2I | D | D2I | D1D2I | I | D2I | D1D2 | D1D2I | D1D2 | D1 | I | D2I |
| Miqiulin Jinian (3--4) | I | D1D2I | D | D2 | D1 | D1 | D1D2 | D1 | D1D2I | D1D2 | D2 | D2 | I |
| Huangtianguo (3--5) | D1D2 | D2I | D | D2 | D1D2 | D1 | D2 | D2 | D1D2 | D1D2 | D2 | I | D1I |
| Huadao (3--7) | D1D2 | D1D2I | D | D2I | D1D2I | D1D2 | D1D2 | D2I | D1D2 | D2 | D1 | I | D1D2I |
| Red Astrachan (3--9) | D1D2 | D2I | D | D2 | D1 | D1I | D2I | D1I | D1D2I | D2 | D1I | I | D2I |
| Black Gilliflower (4--1) | D1D2 | D2I | D | D2 | D1I | I | D1D2 | D1I | D1D2I | D1D2 | D1 | I | D2I |
| Nimaiyisuo (4--10) | D2 | D2I | D | D2 | D1 | I | D2 | D1 | D1D2 | D2 | D1 | D2I | D1 |
| Zaohong (4--11) | I | D2I | I | D2 | D2I | D1I | D2 | D2I | D1D2 | D2 | D1 | I | I |
| Xiangguo (4--12) | D1D2 | D2I | DI | D2 | D1D2 | D1D2 | D2 | D1D2 | D1D2 | D2 | I | D1I | |
| Vista Bella (4--16) | D1D2 | D2I | D | D2 | D1D2 | D1I | D2 | D1 | D2 | D2 | D1I | D2I | D1 |
| Saiwen (4--17) | D1D2 | D2I | I | D2I | D1I | D1I | D2 | D2 | D1D2 | D2 | D1 | D2 | D1D2 |
| Summerland (4--20) | I | D2I | DI | I | I | I | D2I | D2I | D1D2I | D1I | D1I | I | I |
| Qihe Golden Spur (4--22) | I | D2I | DI | I | I | I | D2I | D2 | D1D2I | D1I | D1I | I | I |
| Yellow Risharde (4--3) | D1D2 | D2I | DI | I | D1I | D1I | D1D2 | D1D2 | D2I | D2 | D1 | D1D2 | D2I |
| Patten (4--5) | D1D2 | D2I | D | D1I | D1I | D1I | D2 | D1D2 | D1D2 | D2 | D1D2 | I | D1I |
| Early Red Bird (4--6) | D1I | D2I | D | D1D2 | D1 | D1D2 | D2I | D1I | D1D2I | D2 | D1D2 | D2I | D1I |
| Fuhong (4--7) | D2 | D2I | D | D1D2 | D1D2 | D1I | D2 | D2I | D1D2I | D1D2 | D1D2 | D2I | D1D2 |
| Bisimake (4--8) | D2 | D2I | I | D2 | D1D2 | D1D2 | D2 | D1I | D1D2I | D1D2 | D2 | I | I |
| York Imperial (4--9) | D1I | D1D2I | D | D2 | I | D2I | D1I | D2I | D1I | D1D2 | D1D2 | I | I |
| Jonagold (5--1) | D1D2I | D2I | DI | D1I | D1I | D1I | D1D2I | D1D2 | D1D2I | D1D2I | D1I | I | I |

-continued

| Construction results of InDel marker genotype database of *Malus* germplasm resources | | | | | | | | | | | | |
|---|---|---|---|---|---|---|---|---|---|---|---|---|
| Ayiwaniya (5--10) | D2 | D1D2I | D | D2 | D1D2 | D2 | D1D2 | D2 | D1D2I | D2 | D1D2 | I | D1 |
| Fushan 5 (5--14) | D1D2 | D2I | I | D2I | D1 | D1I | D1I | D1D2 | D1D2I | D2 | D1 | D1D2 | I |
| Houjiadian Spur (5--18) | D1D2 | D2I | I | D2I | D1 | D1I | D1I | D1D2 | D1D2I | D2 | D1 | D1D2 | I |
| Guoshuai (5--19) | D1D2I | D2I | I | D2 | D1 | D1 | D2I | D1I | D1D2 | D2 | D1 | D2I | I |
| Huashuai 1 (5--21) | D1D2 | D2I | D | D2I | D1 | D1 | D2I | D1I | D2I | D2 | D1 | D1D2 | D2I |
| Xiongyue 2 (5--22) | D1D2 | D2I | I | D2I | D1 | D1I | D1I | D1D2 | D1D2I | D2 | D1 | D1D2 | I |
| Honeygod (5--3) | I | D2I | DI | D2I | I | I | D1I | D1D2 | D1D2I | D1D2 | D1I | D2I | I |
| Joyal (5--4) | D1D2 | D2I | D | D2I | D2I | I | D2 | D1I | D1D2 | D2 | D1 | D1I | D1D2 |
| Stark Spur Golden (5--5) | I | D2I | DI | I | I | I | D2I | D1I | D1D2I | D1I | D1I | I | I |
| Enweier Golden (5--6) | I | D2I | DI | I | I | I | D2I | D1D2 | D1D2I | D1D2I | D1I | I | I |
| Stark Gold (5--8) | I | D2I | I | D2 | D2I | D1I | D2 | D1D2 | D1D2 | D2 | D1 | I | I |
| Sishui Spur (6--10) | D1D2 | D2I | I | D2I | D1 | D1I | D1I | D1D2 | D1D2I | D2 | D1 | D1D2 | I |
| Red Spur Delicious (6--12) | D1D2 | D2I | I | D2I | D1 | D1I | D1I | D1D2 | D1D2I | D2 | D1 | D1D2 | I |
| Qingdao 1 (6--13) | D1D2 | D2I | I | D2I | D1 | D1I | D1I | D1D2 | D1D2I | D2 | D1 | D1D2 | I |
| Bianqiangzi 1 (6--14) | D1D2 | D2I | I | D2I | D1 | D1I | D1I | D1D2 | D1D2I | D2 | D1 | D1D2 | I |
| Zhangjiakou Spur (6--16) | D1D2 | D2I | I | D2I | D1 | D1I | D1I | D1D2 | D1D2I | D2 | D1 | D1D2 | I |
| Richard Red Delicious (6--18) | D1D2 | D2I | I | D2I | D1 | D1I | D1I | D1D2 | D1D2I | D2 | D1 | D1D2 | I |
| Well Spur Delicious (6--19) | D1D2 | D2I | I | D2I | D1 | D1I | D1I | D1D2 | D1D2I | D2 | D1 | D1D2 | I |
| Bianqiangzi 2 (6--20) | D1D2 | D2I | I | D2I | D1 | D1I | D1I | D1D2 | D1D2I | D2 | D1 | D1D2 | I |
| Hardi Spur Delicious (6--21) | D1D2 | D2I | I | D2I | D1 | D1I | D1I | D1D2 | D1D2I | D2 | D1 | D1D2 | I |
| Fushan 1 (6--3) | D1D2 | D2I | I | D2I | D1 | D1I | D1I | D1D2 | D1D2I | D2 | D1 | D1D2 | I |
| Pinyin Spur (6--4) | D1D2 | D2I | I | D2I | D1 | D1I | D1I | D1D2 | D1D2I | D2 | D1 | D1D2 | I |
| Nanshan 2 (6--8) | D1D2 | D2I | I | D2I | D1 | D1I | D1I | D1D2 | D1D2I | D2 | D1 | D1D2 | I |
| Meiduan 1 (7--10) | D1D2 | D1D2I | D | D2I | D1D2 | D1I | D1I | D2 | D1D2 | D2I | D1 | D1D2 | I |
| Shisanling Spur (7--11) | D1D2 | D2I | I | D2I | D1 | D1I | D1I | D1D2 | D1D2I | D2 | D1 | D1D2 | I |
| Kelisike (7--13) | D1 | D2I | D | D1D2 | D1D2 | D2I | D2 | D1D2 | D2 | D1D2 | I | D1I |
| Jie 18 (7--16) | D1D2I | D1D2I | D | D2 | D1D2 | D2I | D2 | I | D1D2 | D2 | D1 | D2I | D2 |
| Bo 25 (7--17) | D1 | D1D2I | D | D2 | D1 | D2I | D2 | D1 | D1D2I | D1D2 | D1D2 | I | D2I |
| Ruixiang (7--18) | D1D2 | D1D2I | D | D1D2 | D1D2 | D1 | D1D2 | D2I | D1D2I | D2 | D1D2 | I | D1D2 |
| Wealthy (7--19) | D1I | D2I | D | D1D2 | D1D2I | D1I | D1D2 | D1 | D1D2I | D1D2 | D1D2 | I | D1D2 |
| Nanshan 4 (7--2) | D1D2I | D2I | I | D2I | D1D2 | I | D2I | D2I | D1D2 | D2 | D1 | D2I | I |
| De 14 (7--20) | D1D2I | D1D2I | D | D2 | D1D2 | D2I | D2 | I | D1D2 | D2 | D1 | D2I | D2 |
| Napoleon (7--22) | D1I | D2I | I | D2 | D1D2 | D1I | D2I | D1I | D1D2 | D2 | D1 | D1I | I |
| Youyi (7--23) | D2 | D1D2I | D | D2 | D1 | D1 | D1I | D1D2 | D2 | D1D2 | D1I |
| Oregon Spur (7--3) | D1D2I | D2I | I | D2I | D1D2 | I | D2I | D2I | D1D2 | D2 | D1 | D2I | I |
| Kangtun Spur (7--6) | D1D2 | D2I | I | D2I | D1 | D1I | D1I | D1D2 | D1D2I | D2 | D1 | D1D2 | I |

-continued

| Construction results of InDel marker genotype database of *Malus* germplasm resources | | | | | | | | | | | | |
|---|---|---|---|---|---|---|---|---|---|---|---|---|
| White Pippin (7--9) | D2 | D2I | D | D1D2I | D1D2I | D1I | D1D2 | D1 | D1D2I | D2 | D1D2 | I | D2I |
| Zach Lebel (8--1) | D1D2I | D1D2I | D | D2 | D1I | D1D2 | D1I | D2I | D1D2I | D1D2 | D1 | D2I | D1D2I |
| Cortland (8--10) | D1I | D2I | D | D1D2 | D1D2I | D1I | D1D2 | D1 | D1D2I | D1D2 | D1D2 | I | D1D2 |
| Raritan (8--12) | D1D2I | D2I | I | D2I | D1I | D1I | D1D2 | D1I | D1D2I | D2 | D1 | D2I | I |
| Meilingxi Tsugaru (8--13) | D1D2I | D2I | DI | D1D2I | D1D2 | D1I | D1I | D1I | D1D2I | D1D2 | D1D2 | D2I | I |
| Moscow Transparent (8--14) | D1D2 | D2I | DI | D1D2 | D1 | D1D2 | D2I | D1D2 | D1D2 | D2 | D1 | I | D1I |
| Cooper's Market (8--15) | D1I | D2I | I | D2I | D1D2I | D1I | D1I | D2I | D1D2I | D1 | D1 | D2I | I |
| Xite Shisheng (8--16) | D1I | D2I | D | D2I | D1I | D1D2 | D2 | D1I | D1D2I | D1D2 | D1 | D2I | D2I |
| Tian Yisaye (8--17) | I | D2I | I | D1D2 | D1 | D1 | D1D2 | D1D2 | D2I | D1D2 | D1I | I | D1I |
| Shennong 2 (8--19) | D1I | D1D2I | D | D2I | D1I | D2I | D2I | D1I | D2I | D1D2 | D1I | I | D1I |
| Maigold (8--20) | I | D2I | D | D2I | D1I | I | D1I | D1D2 | D1D2 | D2I | D1 | D1I | I |
| Magu (8--21) | D1I | D2I | D | D1D2 | D1I | D1I | D2I | D1D2 | D1D2 | D2 | D1 | D2I | D1I |
| Cellini (8--23) | D2 | D2I | I | D2 | D1D2 | D1D2 | D2 | D1I | D1D2I | D1D2 | D1D2 | I | I |
| Simonffy Piros (8--3) | D1I | D2I | D | D2I | D1D2I | D1I | D2 | D2 | D1D2 | D2 | D1I | I | I |
| Luxiang (8--5) | D2 | D1D2I | DI | D1I | D1D2 | D1 | D1 | D1 | D1D2I | D1D2 | D1D2 | D1I | D1I |
| Zhongqiu (8--6) | D1D2I | D2I | D | D1D2I | D1 | D1I | D1D2I | D1I | D1D2I | D1D2 | D1D2 | I | D2I |
| De 2 (8--7) | D1D2I | D1D2I | D | D2 | D1D2I | I | D2 | D1D2 | D1D2 | D2 | D1 | D2I | I |
| Grimes Golden (8--8) | D1I | D2I | D | D1I | D1I | I | D1D2 | D2I | D1D2I | D1D2 | D1 | D2I | I |
| Early Straw Berry (8--9) | I | D2I | D | D2 | D1D2 | D1D2 | D2 | D1I | D1D2 | D2 | D1 | D1D2 | D1I |
| Kelia (9--10) | D1D2 | D1D2I | D | D2I | D1I | D1D2I | D1D2 | D1I | D1D2I | D2 | D1D2 | D2I | I |
| French Apple (9--11) | D1D2I | D2I | D | D2I | D1D2I | D1D2 | D2 | D1I | D1D2 | D2 | D1 | D1D2I | I |
| Todoroki Tsugaru (9--12) | D1D2I | D1D2I | D | D1I | D1D2I | D1I | D1I | D1I | D2I | D1 | D2I | I | I |
| Cuihong (9--13) | D1D2 | D1D2I | NA | D2 | D1D2 | D1 | D1 | D1I | D1D2I | D1D2 | D2 | D1I | I |
| De 4 (9--14) | D1I | D2I | NA | D2I | D1D2I | D1D2I | D1I | D1D2I | D1D2I | D1D2 | D1D2 | D2I | D2I |
| Early McIntosh (9--18) | D2 | D2I | D | D1D2 | I | D1D2 | D1I | D1D2 | D2 | D1 | I | D1D2 |
| Adam Mickewier (9--19) | D1I | D2I | D | D2I | D1I | I | D1I | D1I | D1D2 | D2 | D1 | D2I | I |
| Norda (9--2) | D1D2I | D2I | D | D1D2 | D1 | D1D2 | D1 | D2 | D1D2 | NA | D1 | I | I |
| Cardinal (9--20) | D1D2I | D2I | DI | D2I | D1I | D2I | D1I | I | D1D2I | D1D2 | D1I | D1I | D2I |
| Evelyn (9--21) | I | D2I | D | D2 | D1D2I | D2I | D2 | D1 | D1I | D1D2 | D1 | D2I | D2 |
| Situonuowei (9--22) | D1D2 | D1D2I | DI | D1D2 | D1D2 | D1I | D1I | D1D2 | D1D2I | D1 | NA | I | D2 |
| Yingqiu (9--23) | D1D2 | D1D2I | D | D2 | D1 | D1I | D1I | D2I | D1D2I | D1D2 | D1D2 | D1I | D1I |
| Kelongxieer (9--3) | D1D2 | D2I | DI | D1D2 | D1 | D1D2 | D2I | D1D2 | D1D2 | D2 | D1 | I | D1I |
| Cloden (9--5) | D1D2I | D2I | DI | I | I | D2I | D2I | D2I | D2I | D1 | D2I | D1I |
| Qiutianhong (9--6) | D1D2 | D1D2I | DI | D1D2 | D1D2 | D1I | D1I | D1D2I | D1 | D1D2 | I | D2 |
| Gaidebao (9--7) | D1I | NA | NA | NA | D1D2 | D1 | D1D2 | D1D2 | NA | D2 | D1 | I | I |
| Starkjam (9--9) | D1I | D2I | I | D2 | D1D2 | D1I | D2I | D1I | D1D2 | D2 | D1 | D1I | I |
| Wan Crab (B-1) | D1D2 | D2I | I | D2I | D1D2I | D1I | D2 | D1 | D1D2 | D2 | D2I | I | D1I |
| Minjiandaguo Crab (B-10) | D2 | D2I | D | D1I | D1I | D2I | D1 | D1 | D1D2I | D2 | D1 | I | D1I |

-continued

Construction results of InDel marker genotype database of *Malus* germplasm resources

| | | | | | | | | | | | | |
|---|---|---|---|---|---|---|---|---|---|---|---|---|
| Luanzhuang Crab (B1-11) | D1I | D2I | D | D2 | D1D2I | D1D2 | D2 | D2I | D1D2 | D2 | D1 | I | D1I |
| Sankuaishi Crab (B1-12) | D1 | D2I | D | D2 | D1D2 | D1D2 | D2 | D1 | D1D2 | D2 | D2 | I | D1 |
| Xiongyue Crab 1 (B1-13) | D1 | D2I | I | D1D2I | D1D2I | D1I | D2 | D1D2 | D1D2 | D2 | D2I | D1I | D1I |
| Sankuaishi Crab 2 (B1-14) | D1 | D2I | D | D2I | D1D2I | D1I | D2 | D1D2 | D1 | D2 | D1I | I | D1I |
| Dabaleng (B-12) | D1I | D2I | D | D2 | D1D2 | D1I | D2 | D1I | D1D2 | D2 | D1D2 | D2I | D1I |
| Sankuaishi Crab 2 (B-13) | D1D2I | D2I | I | D2I | D1I | D1I | D1D2 | D1I | D1D2I | D2 | D1 | D2I | I |
| Changguo Crab (B-14) | D1I | D2I | D | D2I | D1I | D1I | D2I | D1I | D1D2I | D1 | D2I | I | D1I |
| Dagucheng Baleng (B1-5) | D1D2 | I | D | D2 | D1D2 | D2 | D2 | D2 | D1D2 | D2 | D2 | D2I | D1 |
| Zumi Crab 3x (B-15) | D1I | D2I | D | D2I | D1D2I | D1I | D2I | D1I | D1D2I | D1 | D2I | I | D1I |
| 26105 (B-16) | D1D2I | D1D2I | D | D2 | D1I | D1I | D1D2 | D1D2 | D1D2I | D1D2 | D1D2 | I | D1D2 |
| Daguo Crab (B-17) | D2 | D2I | D | D2 | D1I | D1I | D2I | D1 | D1D2I | D2 | D1 | I | D1I |
| Xiongyue Crab 2 (B1-8) | D1 | D2I | D | D2 | D1D2 | D2 | D2 | D1D2 | D1D2 | D2 | D1D2 | D1 | I |
| Watermelon Crab (B-18) | D1D2I | D2I | DI | D2I | D1D2I | D2I | D2 | D2 | D1D2 | D2I | D2I | D2I | I |
| Mudanjiang Crab (B1-9) | D1D2I | D2I | D | D2 | D1D2I | D2 | D2 | D2 | D1D2 | D2 | D1 | D1D2 | D1I |
| Tianhong 1 (B-19) | D1D2I | D2I | I | D2I | D1I | D1I | D1D2 | D1I | D1D2I | D2 | D1 | D2I | I |
| Jiping 1 (B-2) | D1D2I | D2I | DI | I | D1I | D2I | D1I | D1I | D2I | D1 | D1D2 | I | D2I |
| Caoyuan Crab (B2-1) | D1 | D2 | NA | D2 | D1 | D1 | D2I | D1 | D1D2 | NA | D1 | D2I | D2 |
| Zumi Crab 4x (B-21) | D1I | D2I | D | D2I | D1D2I | D1I | D2I | D1I | D1D2I | D1 | D2I | I | D1I |
| Luanzhuang Shaguo (B2-11) | D1D2 | D2I | D | D1D2 | D1D2 | D1D2 | D2 | D2 | D1 | D1D2 | D2 | I | D1 |
| Xiaofan Crab (B2-13) | D1D2 | D2I | D | D2 | D1D2 | D1D2 | D2 | D1D2 | D1 | D1D2 | D2 | I | D1 |
| Hebing Pingding Crab (B2-14) | D1D2 | I | D | D2 | D1D2 | D2 | D2 | D1D2 | D1D2 | NA | D2 | I | D1 |
| Zumi Crab 3x 2 (B-22) | D1I | D2I | D | D2I | D1D2I | D1I | D2I | D1I | D1D2I | D1 | D2I | I | D1I |
| Baleng Crab (B-2-3) | D1D2 | I | D | D2 | D1D2 | D1D2 | D2 | D1D2 | D1D2 | D2 | D2 | D2I | D1 |
| Baleng seedling 14 (B-25) | D1I | D2I | I | D2I | D1D2I | D2I | D2 | D2 | D1D2 | I | D1D2 | D2I | D1I |
| Russian White apple (B2-6) | D1D2I | D2I | D | D2I | D1 | I | D1D2 | D1I | D1D2 | D2 | D1 | I | D2 |
| Nagafu 2 (B-26) | D1D2I | D2I | I | D2I | D1I | D1I | D1I | D1I | D1D2I | D2 | D1 | D2I | I |
| Ambrosia (B-27) | D1D2I | D2I | I | D2I | D1I | D1I | D1I | D1I | D1D2I | D1D2 | D1I | D2I | I |
| Aihonghua (B2-8) | D1I | D2I | D | D1D2I | D1D2I | D1D2I | D2I | D1I | D1D2 | I | D2I | D2I | D1I |
| Nanshennan (B-28) | D1D2I | D2I | I | D2I | D1I | D1I | D1D2 | D1I | D1D2I | D2 | D1 | D2I | I |
| Zumi Crab W1 (B-29) | D1I | D2I | D | D2I | D1D2I | D1I | D1I | D1I | D1D2I | D1 | D2I | I | D1I |
| Hong 4G (B-3) | D2 | D2I | DI | I | D1I | D2I | D1 | D1I | D1D2I | D1D2 | D1D2 | D2I | D1D2 |
| Zumi Crab (B-30) | D1I | D2I | D | D2I | D1D2I | D1I | D1I | D1I | D1D2I | D1 | D2I | I | D1I |
| Zaobai Crab (B3-1) | D1D2 | D2I | D | D1D2 | D1D2 | D2 | D2 | D1D2 | D1D2I | D2 | D2 | I | D1 |
| Mollie's Delicious (B-31) | I | D2I | D | D2I | D1I | I | I | D1I | D1D2I | D1D2 | D1 | D2I | D2 |
| Regunzi Spur (B3-10) | D1D2 | I | D | D2 | D1D2 | D1 | D2 | D1D2 | D1D2 | D2 | D2 | I | D1 |
| Xiaofanshan Baleng (B3-11) | D1 | D2I | D | D1D2 | D1D2 | D1D2I | D2I | D1D2I | D1 | D1D2 | I | D1D2I | |
| Huamei (B3-12) | D1I | D2I | DI | D2I | D1I | I | D1I | D1I | D2I | D1 | D2I | D2I | I |

| Construction results of InDel marker genotype database of *Malus* germplasm resources |||||||||||||
|---|---|---|---|---|---|---|---|---|---|---|---|---|
| Huashuo (B3-13) | D1 | D2I | I | D2 | D1 | D1D2 | D1D2 | NA | D1D2I | D1D2 | D1D2 | D2I | D2 |
| Yuhong (B3-14) | D1D2 | D2I | I | D2I | D1 | D1I | D1I | D1D2 | D1D2I | D2 | D1 | D1D2 | I |
| Huayue (B3-15) | D1I | D2I | DI | D2I | D1I | D1I | D2I | D1D2 | D1D2 | D2 | D1D2 | D2I | D1I |
| Jingbohu Shandingzi (B3-2) | D1 | I | NA | D2 | D1D2 | D1 | D2 | D1 | D1 | NA | D2 | D2I | D1 |
| Eluosi Daguo Shandingzi (B3-3) | D1I | D2I | D | D2 | D1D2 | D1D2 | D1D2 | D1I | D1D2 | D2 | D1 | D2I | D1I |
| HY (B-33) | D1D2 | D2I | D | D1I | D1I | D1I | I | D1D2 | D1D2 | D2 | D1 | D2I | I |
| Hong Crab (B3-6) | D1D2 | I | D | D2 | D1D2 | D1 | D2 | D1D2 | D1D2 | D2 | D2 | I | D1 |
| 23# (B-37) | D1D2 | D2I | DI | I | D1I | D2I | D2I | D2I | D2I | D1 | D1I | I | D2I |
| Russian apple (B3-8) | D1D2 | D1D2I | D | D2 | D1D2I | D1 | D2 | D1 | D1D2 | D2I | D1 | I | D1I |
| 147 (B-38) | D1I | D2I | I | D2 | D1 | I | D1D2 | D1 | D1D2I | D1 | D2 | I | D1I |
| Xiaofanshan Baleng 1 (B3-9) | D1D2 | I | D | D2 | D1D2 | D1D2 | D2 | D1D2 | D1D2 | NA | D2 | D2I | D1I |
| Lvshuai (B-4) | D1D2I | D2I | I | D2I | D1D2I | D1I | D1I | I | D1D2I | D1D2I | D1I | D1I | D2I |
| Dounan (B-40) | I | D2I | D | D2I | D1I | D1I | D2I | I | D1D2I | D1D2 | D1I | D2I | I |
| 11906 (B-41) | D1D2I | D2I | D | D2 | D1I | D1I | D1D2 | D1 | D1D2I | D2I | D1 | I | D1D2I |
| Luli (B-5) | D1D2 | D2I | I | I | D1I | D1 | D1 | D2I | D1 | D1D2 | I | D2I |
| Jinxiuhong (B-6) | I | D2I | I | I | D1I | I | D1D2 | D2I | D1D2 | I | D1I | I | I |
| B68 (B-7) | D1 | D2I | D | D2I | D1D2I | D1 | D2 | D1 | D1D2I | D2 | D1D2 | D1I | D2I |
| Huaida (B-8) | D1I | D2I | D | D1D2I | D1D2I | D1I | D2I | D1 | D1D2I | D1D2 | D2I | I | D1I |
| Nanshennan mutant (B-9) | D1D2I | D2I | I | D2I | D1I | D1I | D1D2 | D1I | D1D2I | D2 | D1 | D2I | I |
| Xiahong (BH-1) | D1D2 | D2I | D | D1I | D1I | D2I | D1 | D1D2 | D1D2I | D2 | D1I | D2I | D1I |
| Wuming1 (BJ-1) | D1I | D2I | D | I | D1I | I | D1I | I | D2I | D1 | I | I | I |
| Canzy ? (BJ-10) | D1I | D2I | DI | D1I | D1D2I | D1I | D1D2 | D1 | D1D2I | D1D2 | D2 | I | I |
| Xiangfu (BJ-11) | D1D2I | D2I | I | D2I | D1I | D1I | D1D2 | D1I | D1D2I | D2 | D1 | D2I | I |
| Envy (BJ-12) | D1D2 | D2I | I | D1I | D1I | D1I | D1I | D1I | D1D2I | D1D2 | D2I | D2I | I |
| Fuji_KiKu (BJ-2) | D1D2I | D2I | I | D2I | D1I | D1I | D1D2 | D1I | D1D2I | D2 | D1 | D2I | I |
| Banxiu Crab (BJ-4) | D1 | D2I | D | D2I | D1 | D2 | D2I | D1 | D1D2 | D2 | D1D2 | D1I | D2I |
| Jazz (BJ-5) | D1D2 | D2I | I | D1I | D1D2I | D1I | D1D2 | D1 | D1D2I | D1D2 | D1I | I | I |
| Early Red Bird 2 (BJ-7) | D1D2 | D2I | I | D2I | D1 | D2 | D1D2 | D1D2 | D1D2I | D1D2 | D1D2 | D2I | D2 |
| Qiuhong Gala (BJ-8) | D1D2I | D2I | I | D2I | D1I | D1I | D1D2 | D1I | D1D2I | D2 | D1 | D2I | I |
| Hongxiangcui (BJ-9) | D1D2 | D2I | DI | D2I | D1I | D1I | D1I | D1I | D2I | D1 | D1D2 | I | I |
| 07-115 (BK-1) | D2 | D2I | D | D2I | D1I | D1I | D2 | D2I | D1I | D2 | D2 | D1D2 | I | I |
| Nagafu 3 (BK-2) | D1D2I | D2I | I | D2I | D1I | D1I | D1D2 | D1I | D1D2I | D2 | D1 | D2I | I |
| 28-253 (BK-28-253) | I | D2I | I | D2 | D1D2I | D1I | D1 | D1I | D2I | D1D2 | D1I | I | I |
| Nagafu 3-R (BK-3) | D1D2I | D2I | I | D2I | D1I | D1I | D1D2 | D1D2I | D1D2I | D2 | D1 | D2I | I |
| 4354 (BK-4) | D1D2I | D2I | DI | D2I | D1D2I | D1I | D1I | D1 | D1D2I | D1D2 | D1 | I | I |
| 4-23 (BK-4-23) | I | D2I | D | D2I | D1 | I | D1I | D1I | D1D2 | D2 | D1I | I | I |

-continued

| Construction results of InDel marker genotype database of *Malus* germplasm resources | | | | | | | | | | | | |
|---|---|---|---|---|---|---|---|---|---|---|---|---|
| 4354-R ? (BK-5) | I | D2I | DI | I | D1I | I | D2I | D1I | D1D2I | D1D2 | D1I | I | D2I |
| 77-34 (BK-77-34) | D1D2 | D2I | D | D2 | D1D2 | D1D2 | D1D2 | D2I | D1 | D2 | D1D2 | D2I | D1I |
| Red Spur Delicious (BK-AH) | D1D2 | D2I | I | D2I | D1 | D1I | D1I | D1D2 | D1D2I | D2 | D1 | D1D2 | I |
| Ozark Gold (BK-AJ) | I | D2I | D | D2I | D1I | D1I | D1D2 | D1D2 | D1D2I | D1I | D1I | I | D1I |
| Michinoku (BK-AZ) | D1D2 | D2I | I | D2I | D1 | D1D2 | D1D2 | D1D2 | D2I | D1 | D1 | I | D2 |
| Azwell (BK-Azwell) | D1D2 | D2I | I | D2I | D1 | D1I | D1I | D1D2 | D1D2I | D2 | D1 | D1D2 | I |
| Banbishan Crab (BK-BBSHT) | D1D2 | D2I | D | D2 | D1 | D1D2 | D2 | D1D2 | D1D2 | D2 | D2 | I | D1 |
| Hokudo (BK-BD) | D1D2I | D2I | I | D2I | D1I | D1I | D1D2I | D1I | D1D2I | D2 | D1I | D1D2I | I |
| Baifugao (BK-BFG) | D1I | D1D2I | DI | D2 | D1D2 | D1 | D1 | D1 | D2I | D2 | D1 | D1I | D1I |
| White Crab (BK-BHT) | D1 | D2I | D | D1D2 | D1D2 | D1D2I | D1D2 | D1 | D1D2I | D1 | D1D2 | I | D1D2I |
| Buming Kangbing (BK-BMKB) | D2 | D2I | D | D1D2I | D1D2I | D1I | D1D2 | D1 | D1D2I | D2 | D1D2 | I | D2I |
| Batougou 1 (BK-BTG1H) | D1D2 | NA | D | D2 | D1D2I | D1 | D2 | D1D2 | D1 | NA | D2 | D2I | D1 |
| Batougou 2 (BK-BTG2H) | D1D2 | I | D | D2 | D1D2 | D1D2 | D2 | D1D2 | D1 | NA | D2 | D2I | D1 |
| Batougou Aizhen (BK-BTGAZ) | D1 | I | D | D1D2 | D1 | D1 | D2 | D1 | D1 | D2 | D1D2 | I | D1 |
| Binzi (BK-BZ) | D1D2 | D2I | D | D1D2 | D1D2 | D1D2 | D2 | D2I | D1D2I | D1D2 | D2 | I | D1I |
| Kitanosach (BK-BZX) | D1I | D2I | D | D2I | D1D2I | D1I | D1I | I | D2I | D1 | D2 | D2I | I |
| Binzi (SW) (BK-BZXN) | D1D2 | D2I | D | D1D2 | D1D2 | D1D2 | D2 | D2I | D1D2I | D1D2 | D2 | I | D1I |
| Nagafu 2 (BK-CF2H) | D1D2I | D2I | I | D2I | D1I | D1I | D1D2 | D1I | D1D2I | D2 | D1 | D2I | I |
| Nagafu 36 (BK-CF36) | D1D2I | D2I | I | D2I | D1I | D1I | D1D2 | D1I | D1D2I | D2 | D1 | D2I | I |
| Nagafu 6 (BK-CF6H) | D1D2I | D2I | I | D2I | D1I | D1I | D1D2 | D1I | D1I | D2 | D1 | D2I | I |
| CG24 (BK-CG24) | D1D2 | D2I | I | D2I | D1 | D1I | D1I | D1D2 | D1D2I | D2 | D1 | D1D2 | I |
| CG3 (BK-CG3) | I | D2I | I | D2 | D1D2I | D1I | D1 | D1I | D2I | D1D2 | D1I | I | I |
| CG80 (BK-CG80) | D1D2I | D2I | D | D2 | D1I | D1I | D1D2 | D1I | D1D2 | D2 | D1 | D2I | I |
| Changhong (BK-CH) | D1D2I | D2I | I | D2I | D1I | D1I | D1D2 | D1I | D1D2 | D2 | D1 | D2I | I |
| Chieftan (BK-chieftan) | D1D2I | D2I | D | D2 | I | D1 | D2I | D1I | D1D2I | D1D2 | D1I | I | D1D2 |
| Cangjiang Crab (BK-CJHT) | D1 | D2I | D | D1D2 | D1 | D2I | D2 | D1D2 | D2 | NA | D1 |
| Chuanling Crab (BK-CLHT) | D1I | D2I | D | D2 | D1D2I | D1D2 | D2 | D1I | D1D2 | D2 | D1 | D2I | I |
| Hatsuaki (BK-CQ) | D1D2I | D2I | D | D2 | I | I | D1D2 | D2 | D1D2 | D1I | I | D1I |
| Crispin (BK-crispin) | D1D2I | D2I | DI | D1I | D1I | D1I | D1D2I | D2I | D1D2I | D1D2I | D1I | I | I |
| Caozigang Yuanshuai (BK-CZGYS) | D1D2 | D2I | I | D2I | D1 | D1I | D1I | D1D2 | D1D2I | D2 | D1 | D1D2 | I |
| Danxia (BK-DANXIA) | D1D2I | D2I | D | D2I | D1I | D1I | I | D2I | D2I | D1D2 | D1I | D1I | I |
| Dolgo (BK-DDG) | D1I | D2I | D | D2 | D1D2 | D1D2 | D1 | I | D1D2 | D2 | D1 | D2I | D1I |
| Darwin (BK-DEW) | D1D2 | D2I | D | D1D2 | D1D2 | D1 | D2 | D2I | D1D2I | D1D2 | D2 | I | D1I |
| Oriental Apple (BK-DFPG) | D2 | D1D2I | D | D2 | D1D2 | D1 | D2 | D1I | D1D2 | D1D2 | D2I | D2 |
| Big Crab (BK-DGHT) | D1D2 | D2I | D | D2 | D1D2I | D1D2 | D2I | D1 | D1D2 | D2 | D2 | D2I | D1I |
| Daguo Jinhong (BK-DGJH) | D1I | D2I | D | D1D2I | D1D2I | D1I | D2I | D1I | D1D2I | D1D2 | D2I | I | I |
| Daihong (BK-DH) | D1D2 | D2I | I | D2I | D1 | D1I | D1I | D1D2 | D1D2I | D2 | D1 | D1D2 | I |

-continued

Construction results of InDel marker genotype database of *Malus* germplasm resources

| | | | | | | | | | | | | | |
|---|---|---|---|---|---|---|---|---|---|---|---|---|---|
| Daihao 261 (BK-DH261) | D1I | D1D2I | D | D2 | D1D2 | D1 | D2I | D1D2 | D1D2 | D2 | D1 | D2I | D1I |
| Spur Golden Delicious (BK-DJG) | I | D2I | DI | I | I | I | D2I | D2I | D1D2I | D1I | D1I | I | I |
| Daxianguo (BK-DXG) | D1D2 | I | D | D2 | D1D2 | D1D2 | D2 | D1D2 | D1 | D2 | D2 | I | D1 |
| Daye Crab (BK-DYHT) | D1D2 | I | D | D2 | D1D2 | D1 | D2 | D1 | D1D2I | D2 | D2 | I | D1 |
| Spur Fuji (BK-DZFS) | D1D2I | D2I | I | D2I | D1I | D1I | D1D2 | D1I | D1D2I | D2 | D1 | D2I | I |
| Huaguan Spur (BK-DZHG) | I | D2I | I | I | D1I | I | D1D2 | D2I | D1D2 | I | D1I | I | I |
| Elite (BK-Elite) | D1D2 | D2I | I | D2I | D1 | D1I | D1I | D1D2 | D1D2I | D2 | D1 | D1D2 | I |
| Fa 8 (BK-F8) | D1I | D2I | DI | D2I | D1I | D1I | D2I | D1D2 | D2 | D1D2 | D2I | D1I | |
| Fukushima Spur Fuji (BK-FDDZ) | D1D2I | D2I | I | D2I | D1I | D1I | D1D2 | D1I | D1D2I | D2 | D1 | D1D2I | I |
| Fujin (BK-FJ) | D2 | D2I | D | D2I | D1 | I | D2I | D1D2 | D1D2 | D2 | D1 | D2I | D2I |
| Florina (BK-Florina) | D1D2I | D1D2I | D | D1D2 | D1 | D1 | D1I | D1I | D1D2I | D2 | D1 | D1D2I | I |
| Fangming (BK-FM) | D1D2I | D1D2I | D | D1I | D1D2I | D1I | D1I | D1I | D2I | D1 | D2I | I | I |
| Fuji (BK-Fuji) | D1D2I | D2I | I | D2I | D1I | D1I | D1D2 | D1I | D1D2I | D2 | D1 | D2I | I |
| Fengyan (BK-FY) | D1D2I | D2I | DI | D2 | D1I | D1I | D2 | D2 | D1D2 | D2 | D2I | D1 | D1D2 |
| Yanfu 1 (BK-FY1) | D1D2I | D2I | I | D2I | D1I | D1I | D1D2 | D1I | D1D2I | D2 | D1 | D2I | I |
| King of Tompkins County (BK-FZY) | D1I | D2I | D | D2 | D1 | D1I | D1I | D1D2 | D1D2I | D2 | D1 | D1D2I | I |
| G30 (BK-G30) | D1D2 | I | D | D2 | D1D2I | D1D2 | D1 | D1 | D1D2I | D2 | D1 | D2I | D1I |
| Gao #5 (BK-G-5) | D1D2 | D2I | D | D2 | D1D2I | D1 | D1D2 | D1 | D1D2I | D2 | D2 | I | D2 |
| Gala (BK-gala) | D1I | D2I | DI | D2I | D1I | I | D1I | D1I | D2I | D1 | D2I | D2I | I |
| Golden Delicious (BK-GD) | I | D2I | DI | I | I | I | D2I | D1I | D1D2I | D1I | D1I | I | I |
| Gloster69 (BK-Gloster69) | D2 | D2I | DI | D1D2 | D1 | D1 | D1I | D1 | D1D2 | D2 | D1I | D1I | D2I |
| GM256 (BK-GM256) | D1D2 | D2I | D | D1D2 | D1D2 | D2I | D1D2 | D1 | D1D2 | D2 | D1D2 | I | D1I |
| GM310 (BK-GM310) | D1D2I | D2I | D | D1D2I | D1D2I | I | D1D2 | D1I | D1D2I | D2 | D1I | D2I | D1I |
| Gaoqiu (BK-GQ) | I | D2I | I | D2I | I | D1I | D1I | D1I | D1D2I | D2I | D1I | D2I | I |
| Miyazaki Spur Fuji (BK-GQDZ) | D1D2I | D2I | I | D2I | D1I | D1I | D1D2 | D1I | D1D2I | D2 | D1 | D2I | I |
| HAC-9 (BK-HAC-9) | D1D2I | D2I | I | D2I | D1I | D1I | D1D2 | D1I | D1D2I | D1D2 | D1 | D2I | I |
| Huifeng Orin (BK-HFWL) | D1D2I | D2I | D | D2 | D1D2 | D1I | D1I | D1I | D1D2I | D1D2 | D1 | D2I | D1I |
| Red Ralls Janet (BK-HGG) | I | D2I | I | D2 | D2I | D1I | D2 | D2I | D1D2 | D2 | D1 | I | I |
| Huaguan Crab (BK-HGHT) | D1D2 | D2I | D | D2 | D1 | D1 | D2 | D2 | D1D2 | D1D2 | D2 | I | D1I |
| Harrold Red Delicious (BK-HH) | D1D2 | D2I | I | D2I | D1 | D1I | D1I | D1D2 | D1D2I | D2 | D1 | D1D2 | I |
| Hong Crab 2 (BK-HHT2H) | D1D2 | I | D | D2 | D1D2 | D1 | D2 | D1D2 | D1D2I | D2 | D2 | I | D1 |
| Stark Redgold (BK-HJ) | D1D2I | D2I | DI | I | D1I | I | I | D2I | D2I | D1D2 | D1I | D2I | I |
| HLWQ (BK-HLWQ) | D1 | D2I | D | D2I | D2I | D1 | D1D2 | D1I | D1D2 | D2 | D1I | I | D2 |
| Holly (BK-Holly) | D1D2 | D1D2I | D | D1I | D1 | D1I | D1I | D1I | D1D2I | D1D2 | D1 | D1I | D1I |
| Red Jonagold (BK-HQNJ) | D1I | D2I | D | D2I | D1I | D1I | D2I | D2I | D1D2I | D1I | D1I | I | I |
| Red Sekaiichii (BK-HSJY) | D1I | D2I | D | I | D1I | I | D1I | D1I | D1D2 | D2I | D1 | D2I | I |

-continued

Construction results of InDel marker genotype database of *Malus* germplasm resources

| | | | | | | | | | | | | |
|---|---|---|---|---|---|---|---|---|---|---|---|---|
| Hongte (BK-HT) | D1I | D1D2I | DI | D2 | I | D1I | D1D2 | D1I | D1D2I | D2 | D1 | I | D1I |
| Haitangguo (BK-HTG) | D1 | D2I | D | D2I | D1I | D2I | D2 | D1 | D1D2I | D1 | D2 | I | D1I |
| Haitanghua (BK-HTH) | D1D2 | D2I | D | D1D2 | D1D2 | D1D2 | D2I | D1D2 | D1D2 | D2 | D2 | I | D1I |
| Huangtaiping (BK-HTP) | D1 | D2I | D | D1D2 | D1D2 | D1D2I | D1D2 | D2I | D1D2I | D1 | D1D2 | I | D1D2I |
| Hongxue (BK-HX) | D2 | D2I | D | D1D2I | D1D2I | D1I | D1D2 | D1 | D1D2I | D2 | D1D2 | I | D2I |
| Jincui (BK-JC) | D1D2I | D2I | I | D2I | D1I | D1I | D1I | D1I | D1D2 | D2I | D1I | D1I | I |
| Juda Fuji (BK-JDFS) | D1D2I | D2I | I | D2I | D1I | D1I | D1D2 | D1I | D1D2I | D2 | D1 | D2I | I |
| Jiguan (BK-JG) | D1D2 | D2I | D | D2 | D1I | D1D2 | D2I | D1I | D1 | D2 | D1D2 | D1I | D2I |
| Jinhong (BK-JH) | D1I | NA | D | D2I | D1D2I | D1I | I | D1I | D1D2I | D1D2 | I | I | D1I |
| Jonagored (BK-Jonagored) | D1D2I | D2I | DI | D1I | D1I | D1I | D1D2I | D2I | D1D2I | D1D2I | D1I | I | I |
| Jonathan (BK-Jonathan) | D1D2 | D1D2I | D | D1D2 | D1D2 | D1 | D1I | D1D2 | D1D2I | D1D2 | D1D2 | D2I | D1I |
| Himekami (BK-JS) | D1I | D2I | I | D1I | D1 | D1I | D1D2 | D1I | D1D2 | D2 | D1 | D2I | D1I |
| Stark Blushing Golden (BK-JY) | D1I | D2I | I | D2I | D1I | D1I | D2I | D1I | D1D2 | D2I | D2I | D2I | D2I |
| Classic Red Delicious (BK-KAHONG) | D1D2 | D2I | I | D2I | D1 | D1I | D1I | D1I | D1D2I | D2 | D1 | D1D2 | I |
| KLGDG Shandingzi (BK-KLGDGSDZ) | D1 | I | D | D2 | D1D2 | D1D2 | D2 | D1 | D1D2 | NA | D2 | I | D1 |
| KOSZTELQ (BK-KOSZTELQ) | D1 | D1D2I | D | D2 | D1 | D2I | D2I | D1 | D1D2 | D2 | D1 | I | I |
| Sunflower (BK-KUIHUA) | D1D2I | D2I | I | I | D1I | I | D2I | D2 | D2I | D1D2 | D1I | D1I | I |
| Lenghaitang (BK-LHT) | D1D2 | D2I | D | D2 | D1 | D1D2 | D2 | D1D2 | D1D2 | D2 | D2 | I | D1 |
| Liberty (BK-liberty) | D1D2I | D2I | D | D2 | I | D1 | D2I | D1I | D1D2I | D1D2 | D1I | I | D1D2 |
| Lijiang Shandingzi (BK-LJSDZ) | D1I | D1D2I | D | D2 | D1D2 | D1 | D2 | I | D1D2 | D2 | D2 | I | D1D2 |
| Laoshan 4 (BK-LS4H) | D1D2 | I | D | D1D2 | D1D2 | D2 | D1D2 | D1 | D2 | D2 | I | D1 | |
| Ryoka no Kisetsu (BK-LX) | D1D2I | D2I | I | D2I | D1I | D1I | D1D2 | D1I | D1D2I | D2 | D1 | D2I | I |
| Lvxiangjiao (BK-LXJ) | D1I | D2I | DI | D1D2 | D1D2 | D1I | D2 | D1D2 | D2I | D1D2 | D1D2 | I | I |
| Liaozhen 1 (BK-LZ1H) | D1D2 | I | D | D2 | D1I | D1I | D1 | D1 | D2 | D1 | I | D1 | |
| M7 (BK-M7) | D2 | D2I | D | D2I | D1 | D2 | D2 | D1I | D1D2 | D2 | D1 | D1D2 | D2I |
| Meiguihong (BK-MGH) | D1D2 | D2I | I | D2I | D1 | D1I | D1I | D1D2 | D1D2I | D2 | D1 | D1D2 | I |
| Meile (BK-ML) | I | D2I | D | D1I | I | I | D2I | D2I | D1D2I | D1I | D1I | I | I |
| MM106 (BK-MM106) | D1D2I | D2I | D | D2 | D1I | D1I | D1D2 | D1I | D1D2 | D2 | D1 | D2I | I |
| Mengpaisi (BK-MPS) | D1I | D2I | NA | D2I | D1D2I | D1D2I | D1I | D1D2I | D1D2I | D1D2 | D1D2 | D2I | D2I |
| Meixiang (BK-MX) | D1D2I | D2I | I | D2I | D1I | D1I | D1D2 | D1I | D1D2 | D2 | D1 | D2I | I |
| Ningqiu (BK-NQ) | D1D2I | D2I | D | D2I | D1 | I | D1D2 | I | D1D2 | D2 | D1 | I | D2I |
| P16 (BK-P16) | D2 | D2I | D | D2 | D1 | D2 | D2 | D2 | D2 | D2 | D2 | D2I | D1I |
| P22 (BK-P22) | D1D2 | I | D | D2 | D1D2 | D2 | D2 | D1D2 | D1D2 | D2 | D2 | I | D1 |
| Pingdinghaitang (BK-PDHT) | D1D2 | I | D | D2 | D1D2 | D1D2 | D1D2 | D1D2 | D1 | D2 | D2 | I | D1 |
| Bianguo Crab (BK-PGHT) | D1D2 | D2I | D | D1D2I | D1D2 | D1D2 | D1 | D1D2 | D1D2I | D1D2 | D1D2 | D1I | D1I |
| Pionier (BK-Pionier) | D1D2 | D1D2I | D | D2 | D1D2 | D1 | D2 | D1D2 | D1D2 | D2I | D1 | D1D2 | D2I |
| Prima (BK-Prima) | D1 | D2I | D | D2I | D2I | D1I | I | D1I | D1D2 | D2I | D1I | D1I | D1D2 |

-continued

| \multicolumn{13}{c}{Construction results of InDel marker genotype database of *Malus* germplasm resources} |
|---|---|---|---|---|---|---|---|---|---|---|---|---|
| Pingyitiancha (BK-PYTC) | D1 | D2I | D | D1D2 | D1D2 | D1D2 | D2 | D1 | D1 | D2 | D2 | D2I | D1 |
| Qianxue (BK-QAINXUE) | D1D2I | D2I | D | I | I | I | D1I | D1I | D1D2I | D1D2 | D1I | I | I |
| Akifu 1 (BK-QF1) | D1D2I | D2I | I | D2I | D1I | D1I | D1D2 | D1I | D1D2I | D2 | D1 | D2I | I |
| Qingfu 13 (BK-QF13) | D1D2I | D2I | I | D2I | D1I | D1I | D1D2 | D1I | D1D2I | D2 | D1 | D2I | I |
| Seimei (BK-QM) | D1D2I | D2I | D | I | D1I | I | I | I | D1D2I | D1 | D1I | D2I | I |
| Senshu (BK-QQ) | I | D2I | D | D2I | D1 | D1I | D2I | I | D1D2I | D1 | D1 | D2 | I |
| Aomori Early (BK-QSZS) | D1I | D2I | DI | D2I | D1I | I | D2I | D2I | D1D2I | D1D2I | D1I | I | I |
| Qiuxiang (BK-QX) | D1D2I | D1D2I | D | D1I | D1D2I | D1I | D1I | D1I | D2I | D1 | D2I | I | I |
| Qiuxing Crab (BK-QXHT) | D1D2I | D2I | D | D2 | D1I | D1D2 | D2 | D1D2 | D1D2I | D2 | D1D2 | D2I | D1I |
| Yanqing (BK-QY) | D1D2I | D2I | DI | D1I | D1I | I | D1D2 | D1D2 | D1D2I | D2 | D1 | D1D2 | I |
| Regunzi (BK-RGZ) | D1D2 | I | D | D2 | D1D2 | D1 | D2 | D1D2 | D1D2I | D2 | D2 | I | D1 |
| Ruby (BK-Ruby) | D1D2I | D2I | I | D2I | D1D2 | I | D2I | D2I | D1D2 | D2 | D1 | D2I | I |
| Scarlet (BK-scarlet) | D1D2 | D2I | I | D2I | D1 | D1I | D1I | D1D2 | D1D2I | D2 | D1 | D1D2I | I |
| Sdw1 (BK-Sdw1) | D2 | I | D | D2 | D1D2 | D1D2 | D2 | D1 | D1D2 | D2 | D2 | D2I | D1 |
| Shandingzi 2 (BK-SDZ2H) | D1 | I | D | D2 | NA | D1 | D2 | D1 | D1D2 | D2 | NA | I | D1 |
| Su E Shandingzi (BK-SESDZ) | D1 | NA | D | D2 | D1D2 | D1D2 | D2 | D2 | D1D2I | D2 | D1D2 | I | D1 |
| Shengfang 2 (BK-SF2) | D1D2I | D2I | I | D2I | D1I | D1I | D1D2 | D1I | D1D2I | D2 | D1 | D2I | I |
| SH6 (BK-SH6) | D1I | D2I | DI | D2 | D1I | D1 | D2 | D1D2 | D1D2 | NA | D1 | I | D2I |
| Sankuaishi Crab 1 (BK-SKSHT1H) | D1D2 | I | D | D2 | D1D2 | D1D2 | D2 | D1D2 | D1D2I | D2 | D2 | D2I | D1 |
| Forest Apple (BK-SLPG) | D1I | D2I | DI | D2I | I | D2I | I | D1I | D1D2I | D1D2 | D1I | I | I |
| Sieversii (BK-SWS) | D1I | D1D2I | D | D2 | D1D2 | D1 | D2 | D1I | D1D2 | D2 | D2 | I | D1D2 |
| Sansa (BK-SX) | D1D2I | D2I | D | D2I | D1D2I | D1I | D1 | D1 | D2I | D1 | D1D2 | D2I | I |
| Szampion (BK-Szampion) | D1D2I | D2I | D | D2I | D1D2I | D1I | D1I | I | D2I | D1 | D1I | D2I | I |
| T337 (BK-T337) | D2 | D2I | D | D2 | D1I | D1I | D1 | NA | D1D2I | D2 | D1 | D2I | D1I |
| Turkmen Apple (BK-TKMPG) | D1I | D1D2I | D | D1D2 | D1 | D2 | D1I | D1D2 | D2 | D2 | I | D1D2 |
| Mato 1 (BK-TMYH) | D1D2 | D2I | I | D2I | D1 | D1D2 | D1D2 | D1D2 | D2I | D1 | D1 | I | D2 |
| Trajian (BK-Trajian) | D1D2 | D2I | D | D2I | D2I | D1I | D1D2 | I | D1D2 | D2 | D2I | I | D1D2 |
| Weiai 3 (BK-WA3) | D1D2 | I | D | D2 | D1D2 | D2 | D1D2 | D2 | D1D2 | D2 | D2 | D2I | D1 |
| Wanbai Crab (BK-WBHT) | D1D2I | D2I | D | D2I | D1D2I | D1I | D2I | D1I | D1D2I | D1D2 | D2I | I | D1I |
| Wufengshan 1 (BK-WFS1H) | D2 | D2I | D | D2 | D1D2 | D1D2I | D2 | D2 | D1D2 | D2 | D2 | I | D1I |
| Wufengshan 4 (BK-WFS4H) | D1I | D2I | DI | D2 | D1I | D2I | D2 | D1D2 | D1D2 | NA | D1D2 | D2I | D1I |
| Wufengshan Crab (BK-WFSHT) | D1I | D2I | D | D2 | D1D2I | D1I | D2 | D1 | D1D2 | D2 | D1D2 | I | D1I |
| Wufengshan Crab 2 (BK-WFSHT2H) | D1 | D2I | DI | D2I | D2I | D2I | D2I | D2 | D1D2I | D2 | D1I | D1I |
| Wufengshan Crab 6 (BK-WFSHT6H) | D1I | I | D | D2 | D1 | D1 | D2 | D1D2 | D1D2 | NA | D2 | I | D1 |
| Wifos (BK-wifos) | D1D2 | D2I | D | D2I | D1I | D1I | D2 | D1D2I | D1D2I | D1D2 | D1D2 | I | D1D2 |
| Orei (BK-WL) | D1I | D2I | I | D2I | D1I | D1I | D2I | D1I | D1D2 | D2I | D2I | D2I | D2I |
| Maypole (BK-WM) | D2 | D2I | D | D2I | D1D2 | D2I | D1D2 | D1I | D1D2 | D2 | D2I | D2I | D1 |
| Waltz (BK-WZ) | D1D2I | D2I | DI | I | I | I | D1D2 | D2I | D1D2 | D2I | D1I | I | D1I |

-continued

| Construction results of InDel marker genotype database of *Malus* germplasm resources | | | | | | | | | | | | |
|---|---|---|---|---|---|---|---|---|---|---|---|---|
| Kotoku (BK-XD) | D2 | D2I | DI | D2 | D1I | D1D2 | D1I | D2I | D1D2 | D2 | D1D2 | D1I | D2 |
| Xiaofanshan Binzi (BK-XFSBZ) | D1D2 | D2I | D | D1D2 | D1D2 | D1D2 | D2 | D2I | D1D2I | D1D2 | D2 | I | D1I |
| Xiaofanshan Crab 4 (BK-XFSHT4H) | D1D2 | D2I | D | D2 | D1D2 | D1D2 | D2 | D1D2 | D1D2 | D2 | I | D1 |
| Xiaogoumen Naizi (BK-XGMNZ) | D1D2 | D2I | D | D2 | D1 | D1 | D2 | D2 | D1D2 | D2 | I | D1I |
| XGM Suan Binzi (BK-XGMSBZ) | D1D2 | D2I | D | D1D2 | D1D2 | D1D2 | D2 | D2I | D1D2I | D1D2 | D2 | I | D1I |
| XGM Tian Binzi (BK-XGMTBZ) | D2 | D2I | D | D2 | D1D2 | D1D2 | D2 | D2 | D1D2I | D2 | D2 | I | D1I |
| Starkrimson (BK-XHX) | D1D2 | D2I | I | D2I | D1 | D1I | D1I | D1D2 | D1D2I | D2 | D1 | D1D2 | I |
| Xinjiang 1 (BK-XJ1) | D1D2I | D2I | D | D1D2 | D1D2 | D1D2 | D2 | I | D1D2 | D2 | D1D2 | I | D1 |
| Xinjiang 11 (BK-XJ11) | D1I | D1D2I | D | D2 | D1D2 | D1 | D1D2 | D2I | D1D2I | D2 | D1D2 | I | D2I |
| Xinjiang 14 (BK-XJ14) | D1I | D1D2I | D | D2 | D1D2 | D1 | D1D2 | D2I | D1D2I | D2 | D1D2 | I | D2I |
| Xinjiang 15 (BK-XJ15) | D1 | D2I | D | D1D2 | D1 | D1D2 | D1D2 | D1D2 | D1D2I | D2 | D2 | D2I | D1D2 |
| Xinjiang 16 (BK-XJ16) | D1I | D1D2I | D | D2I | D1 | D1I | D2 | D1 | D1D2I | D1 | D1 | I | D1D2 |
| Xinjiang 17 (BK-XJ17) | D1 | D2I | D | D2 | D1 | D1 | D1D2 | D1D2 | D1D2 | D2 | D1I | I | I |
| Xinjiang 18 (BK-XJ18) | D1 | D2I | D | D2 | D1 | D1 | D1D2 | D1D2 | D1D2 | D2 | D1I | I | I |
| Xinjiang 19 (BK-XJ19) | D1I | D1D2I | DI | D2 | D1D2 | D1D2 | D1I | D2 | D1D2 | D2I | D1 | D1I | I |
| Xinjiang 21 (BK-XJ21) | D1D2I | D1D2I | D | D2I | D1D2I | D1I | D2 | D2I | D1D2I | D1D2 | D1 | D2I | D1I |
| Xinjiang 22 (BK-XJ22) | D1D2I | D2I | D | D1D2 | D1 | D1 | D2 | D2I | D2I | D2 | D2 | I | D1 |
| Xinjiang 24 (BK-XJ24) | D2 | D2I | D | D2 | D1D2 | D1 | D2 | I | D2I | D2 | D2 | I | D1 |
| Xinjiang 26 (BK-XJ26) | D1I | D1D2I | D | D2 | D1D2 | D1 | D1D2 | D2I | D1D2I | D2 | D1D2 | I | D2I |
| Xinjiang 28 (BK-XJ28) | D1I | D1D2I | DI | D2 | D1D2 | D1D2 | D1I | D2 | D1D2 | D2I | D1 | D1I | I |
| Xinjiang 29 (BK-XJ29) | D1I | D2I | D | D2I | D1I | D1I | D2 | D1D2 | D1D2 | I | D1D2I | I | D1I |
| Xinjiang 31 (BK-XJ31) | D1D2 | D2I | I | D2I | D1D2 | D2I | D2I | D2I | D1D2 | NA | D1 | I | D1I |
| Xinjiang 3 (BK-XJ3H) | D1D2I | D2I | DI | D2I | D1D2I | D1I | D1D2 | D1I | D1D2I | D2 | D1D2 | D2I | D1I |
| Xinjiang 6 (BK-XJ6H) | D1D2 | D2I | D | D2 | D1 | D1I | D1D2 | D1D2 | D1D2I | D1 | D2I | I | D1I |
| Xinjiang 7 (BK-XJ7) | D1I | D1D2I | D | D2 | D1D2 | D1 | D1D2 | D2I | D1D2 | D2 | D1D2 | I | D2I |
| Xinjiang 8 (BK-XJ8) | D2 | D2I | D | D1D2 | D1D2 | D1 | D2 | D1I | D1D2I | D1 | D1D2 | I | D1I |
| Xinjiang 9 (BK-XJ9) | D1I | D2I | D | D2I | D1I | D1I | D2 | D1D2 | D1D2 | I | D1I | I | D1I |
| Xijin Crab (BK-XJHT) | D1I | D2I | D | D2 | D1D2 | D1D2 | D2I | D1 | D1D2 | D2 | D2 | D1 | D1I |
| Xiaomian Crab (BK-XMHT) | D2 | I | D | D2 | D1D2 | D1D2 | D2 | D1 | D1D2 | NA | D2 | D2I | D1 |
| New Jonagold (BK-XQNJ) | D1D2I | D2I | DI | D1I | D1I | D1I | D1D2I | D2I | D1D2I | D1D2I | D1I | I | I |
| Xiaoshuai (BK-XS) | D1D2 | D2I | I | D2I | D1D2 | D1 | D1D2 | D1 | D1D2I | D2 | D1 | D2 | D1I |
| Shinsekai (BK-XSJ) | I | D2I | I | D2 | D1D2I | D1I | D1 | D1I | D2I | D1D2 | D1I | I | D1I |
| Xiangyanghong (BK-XYH) | D1D2I | D2I | I | D2 | D1I | D1 | D1D2 | D1I | D1D2 | D2 | D1 | D2I | I |
| Italy Early Red (BK-YDLZH) | D1I | D2I | DI | D2I | D1I | I | D1I | D1I | D2I | D1 | D2I | D2I | I |
| Yanfu 10 (BK-YF10) | D1D2I | D2I | I | D2I | D1I | D1I | D1D2 | D1I | D1D2 | D2 | D1 | D2I | I |
| Yoko (BK-YG) | D1I | D1D2I | DI | D2 | D1D2I | D1I | D1D2 | D1D2 | D1D2I | D1D2 | D2I | I | I |
| Yuanhong (BK-YH) | D1D2 | D2I | I | D1D2 | D1D2 | D1D2 | I | D2 | D1D2I | D1D2 | D1D2 | D1I | D1I |
| Tehong 2 (BK-YH2) | D1D2I | D2I | I | D2I | D1I | D1I | D1D2 | D1 | D1D2I | D2 | D1 | D2I | I |
| Yanhongmi (BK-YHM) | D1I | D1D2I | D | D2I | D1I | D1I | D1I | D2I | D1D2 | D2 | D1 | D1I | I |

-continued

| Construction results of InDel marker genotype database of *Malus* germplasm resources | | | | | | | | | | | | |
|---|---|---|---|---|---|---|---|---|---|---|---|---|
| Youliang Spur (BK-YLDZ) | D1D2I | D2I | I | D2I | D1I | D1I | D1D2 | D1I | D1D2I | D2 | D1 | D2I | I |
| Yuanye Crab (BK-YYHT) | D1D2 | I | D | D2 | D1D2 | D1 | D2 | D1D2 | D1D2I | D2 | D2 | I | D1 |
| Stark Jumbo (BK-ZB) | D1D2 | D2I | D | D1I | D1I | D1I | I | D1D2 | D1D2 | D2 | D1 | D2I | I |
| Jumbo Orin (BK-ZBWL) | I | D2I | DI | D2I | I | I | D2I | D2I | D1D2I | D1I | D1I | I | I |
| Zhuifeng 1 (BK-ZF1H) | D1I | I | D | D1D2I | D1D2I | I | D2 | D1 | D1D2I | D1 | I | I | D1I |
| Zhuifeng 2 (BK-ZF2H) | D1 | I | D | NA | D1 | D1 | D2 | D1 | D1D2 | D2 | NA | I | D1 |
| Early Fuji (BK-ZFS) | D1D2I | D2I | I | D2I | D1I | D1I | D1D2 | D1I | D1D2I | D2 | D1 | D2I | I |
| Xiaofanshan Crab (BK-ZFSHT) | D1D2 | D2I | D | D2 | D1D2 | D1D2 | D2 | D2 | D1D2 | D1D2 | D2 | I | D1 |
| Zisai Pearl (BK-Zisai) | D1D2 | D2I | D | D2 | D1D2 | D1D2 | D2 | D1D2 | D1D2 | D1D2 | D2 | I | D1I |
| Geneva Early (BK-ZJ) | D1D2I | D2I | D | D1D2 | D1I | D1I | D2 | D1D2 | D1D2I | D2 | D1 | D2 | D1I |
| 13-26W (CL-1) | D2 | D1D2I | D | D2 | D1I | D1I | D1I | D1I | D1D2I | NA | D1I | D2I | I |
| 23-127 (CL-2) | D1D2I | D2I | DI | D1I | D1D2I | D1I | D1I | D1I | D1D2 | D2I | D1D2 | D2I | I |
| 50-30 (CL-3) | D2 | D2I | NA | D2I | D1 | D1I | D1 | D1 | D1D2I | D2 | D1 | D2I | I |
| 50-32 (CL-4) | D1D2I | D2I | I | D2I | D1I | D1I | D2 | D2I | D1D2 | I | D1 | D2I | D2I |
| H5-101 (CL-5) | I | D2I | D | I | D1I | I | D1I | D1I | D1D2I | D1D2I | D1 | D2I | I |
| Pingyan (CL-6) | I | D2I | D | D1D2 | D1D2I | D1 | D1D2 | D1I | D2I | D1D2 | D1D2I | D2I | I |
| Deqin Crab (DQ) | D1 | D1D2I | D | D2 | D1D2 | D2 | D2 | D1 | D1D2 | NA | D2 | D2I | D1 |
| Jin 18 (GY-1) | D1D2I | D2I | I | D2I | D1I | D1I | D1D2 | D1I | D1D2I | D2 | D1 | D2I | I |
| Fengfeng Baleng (GY-2) | D1 | D2I | D | D2I | D1 | D2 | D2I | D1 | D2 | D2 | D1D2 | D1I | D2I |
| Hanfu 6 (GY-3) | D1D2I | D2I | I | D2I | D1I | D1I | D1D2 | D1I | D1D2I | D2 | D1 | D2I | I |
| Hanfu 3 (GY-4) | D1D2 | D2I | I | D1I | D1D2 | D1 | D1D2 | D1I | D1D2 | D2 | D1D2 | D2I | I |
| 95/06 (GZ-1) | D1D2I | D2I | D | D2 | D1 | D1I | D1D2 | D1D2 | D1D2I | D1D2 | D1 | D2I | D1D2 |
| 107/06 (GZ-2) | D1D2I | D2I | D | D1D2 | D1 | D1I | D2I | D1 | D1D2I | D1D2 | D1D2 | D2I | I |
| 117/06 (GZ-3) | D1I | D2I | D | D2 | D1 | D1I | D1D2 | D1 | D1D2I | D1D2 | D1D2 | I | D1I |
| 119/06 (GZ-4) | D1D2I | D2I | D | D2 | D1 | D1I | D1D2 | D1 | D1D2I | D1D2 | D1 | I | D1D2I |
| Jinxiu Crab (GZ-5) | D1D2 | D2I | NA | D2 | D1D2 | D1D2 | D1 | D1I | D1D2I | D2 | D1 | D2 | D1I |
| Zhizun Fuji (HS-1) | D1D2I | D2I | I | D2I | D1I | D1I | D1D2 | D1I | D1D2I | D2 | D1 | D2I | I |
| Fuji No. 1 (HS-10) | D1D2I | D2I | I | D2I | D1I | D1I | D1D2 | D1I | D1D2I | D2 | D1 | D2I | I |
| Red Jonaprince (HS-12) | D1D2I | D2I | DI | D1I | D1I | D1I | D1D2I | D2I | D1D2I | D1D2I | D1I | I | I |
| Nic29 (HS-13) | D2 | D2I | D | D2 | D1I | D1I | D1 | D1I | D1D2I | D2 | D1 | D2I | D1I |
| Azhen Fuji (HS-14) | D1D2I | D2I | I | D2I | D1I | D1I | D1D2 | D1I | D1D2 | D2 | D1 | D2I | I |
| Envy (HS-15) | D1D2 | D2I | I | D1I | D1I | D1I | D1I | D1 | D1D2I | D1D2 | D2I | D2I | I |
| Rosegrow (HS-16) | D1I | D2I | DI | D1I | D1D2I | D1I | I | D1D2 | D1D2I | D1D2I | D1I | I | D2I |
| Canzy (HS-17) | D1I | D2I | DI | D1I | D1D2I | D1I | D1D2 | D1 | D1D2I | D2 | D1 | I | I |
| Fubrax (HS-2) | D1D2I | D2I | I | D2I | D1I | D1I | D1D2 | D1I | D1D2I | D2 | D1 | D2I | I |
| Mitchgla (HS-3) | D1I | D2I | DI | D2I | D1I | I | D1I | D1I | D2I | D1 | D2 | D2I | I |
| Fujiko (HS-4) | D1D2I | D2I | I | D2I | D1I | D1I | D1D2 | D1I | D1D2I | D2 | D1 | D2I | I |
| Buckeye Gala (HS-5) | D1I | D2I | DI | D2I | D1I | I | D1I | D1I | D2I | D1 | D2I | D1D2I | I |

| Construction results of InDel marker genotype database of *Malus* germplasm resources | | | | | | | | | | | | |
|---|---|---|---|---|---|---|---|---|---|---|---|---|
| Fujion (HS-6) | I | D2I | DI | D1I | D1 | D1I | D1D2 | D1I | D1D2 | D2 | D1 | D1I | I |
| Modi (HS-7) | I | D2I | DI | D2 | D1I | D1I | I | I | D2I | D1 | D1D2 | D2I | D2I |
| Jiangxue (HS-8) | D1D2 | D2I | D | I | D1D2 | D1I | D1I | D1I | D2I | D1D2 | D1 | D2I | D2I |
| September Wonder Fuji (HS-9) | D1D2I | D2I | I | D2I | D1I | D1I | D1D2 | D1I | D1D2I | D2 | D1 | D2I | I |
| Linqin Crab (LQ) | D1D2 | I | D | D2 | D1D2 | D1D2 | D2 | D1D2 | D1I | D2I | D2 | I | D1 |
| Lushan Sanye (LSSY) | D1 | D2I | D | D1D2 | D1D2 | D1 | D2 | D1 | D1D2 | D2 | D2 | I | D1D2 |
| 83-2 (MDJ-1) | D1D2I | D2I | DI | D1D2I | D1D2I | D1I | D1I | D1I | D1D2I | D1D2 | D1I | I | D1I |
| Tianfeng (MDJ-9) | D1D2 | D1D2I | D | D2 | D1D2I | D1 | D2 | D1 | D1D2 | D2I | D1 | I | D1I |
| Oregon Spur II-red (OR-1) | D1D2 | D2I | I | D2I | D1 | D1I | D1I | D1D2 | D1D2I | D2 | D1 | D1D2 | I |
| Oregon Spur II-green (OR-2) | D1D2 | D2I | I | D2I | D1 | D1I | D1I | D1D2 | D1D2I | D2 | D1 | D1D2 | I |
| E3N2 (OR-3) | D1D2 | D2I | I | D2I | D1 | D1I | D1I | D1D2 | D1D2I | D2 | D1 | D1D2 | I |
| E4N1 (OR-4) | D1D2 | D2I | I | D2I | D1 | D1I | D1I | D1D2 | D1D2I | D2 | D1 | D1D2 | I |
| E4N2 (OR-5) | D1D2 | D2I | I | D2I | D1 | D1I | D1I | D1D2 | D1D2I | D2 | D1 | D1D2 | I |
| W6N1 (OR-6) | D1D2 | D2I | I | D2I | D1 | D1I | D1I | D1D2 | D1D2I | D2 | D1 | D1D2 | I |
| W6S5 (OR-7) | D1D2 | D2I | I | D2I | D1 | D1I | D1I | D1D2 | D1D2I | D2 | D1 | D1D2 | I |
| W8S3 (OR-8) | D1D2 | D2I | I | D2I | D1 | D1I | D1I | D1D2 | D1D2I | D2 | D1 | D1D2 | I |
| Daihong (QD-1) | D1D2I | D2I | DI | D2I | D1I | D1I | D1I | NA | D1D2 | D2 | D1 | D2I | I |
| Tangmutian (QD-10) | D1D2I | D2I | I | D2I | D1I | D1I | D1D2 | D1I | D1D2I | D2 | D1 | D2I | I |
| Shanjin Crab N1 (QD-11) | D1 | D2I | D | D1D2 | D1D2 | D1 | D2 | D1 | D2 | D2 | D2 | I | D1D2 |
| Shanjin Crab N2 (QD-12) | D1 | D2I | D | D2 | D1D2 | D1 | D2 | D1 | D2 | D2 | D2 | I | D1D2 |
| E zhen 1 (QD-13) | D1D2 | D2I | D | D2 | D1I | D1D2 | D1I | I | D1I | D1D2 | D1D2 | D2I | D1I |
| E zhen 2 (QD-14) | D1D2 | D2I | D | D2 | D1D2I | D1 | D1D2 | D2I | D1D2I | D1 | D1 | D2I | D1 |
| E zhen 3 (QD-15) | D1 | D2I | D | D2 | D1D2I | D1D2 | D1 | D1I | D2I | D1 | D1 | D2I | D1 |
| E zhen 4 (QD-16) | D1 | D2I | D | D2 | D1D2I | D1 | D1D2 | D1D2 | D1D2I | D1 | D1 | D2I | D1I |
| E zhen 5 (QD-17) | D1 | D2I | D | D2 | D1D2I | D1I | D1D2 | D1D2I | D1D2I | D1 | D1 | D2I | D1I |
| Haihong (QD-19) | D1D2 | D2I | D | D1D2 | D1D2 | D1I | D2 | D1D2 | D1D2 | D1D2 | D2 | D2I | D1I |
| Qingfu 2 (QD-2) | D1D2I | D2I | I | D2I | D1I | D1I | D1D2 | D1I | D1D2I | D2 | D1 | D2I | I |
| Telamon (QD-20) | D1D2I | D2I | DI | I | I | I | D1D2 | D2I | D1D2 | D2I | D1I | I | D1I |
| Fuyan (QD-21) | D1D2I | D2I | I | D2I | D1I | D1I | D2I | D2I | D1D2I | D2I | D1I | D1I | I |
| Hongxun 1 (QD-22) | D2 | D2 | NA | D2 | D1D2 | D2 | D1 | NA | NA | D2 | D1D2 | I | D1 |
| Rushan Fuji (QD-23) | D1D2I | D2I | I | D2I | D1I | D1I | D1D2 | D1I | D1D2I | D2 | D1 | D2I | I |
| Jiudian Spur (QD-24) | D1D2I | D2I | I | D2I | D1I | D1I | D1D2 | D1I | D1D2I | D2 | D1 | D2I | I |
| Ruihong (QD-25) | D1I | D2I | DI | D2I | D1I | I | D1I | D1I | D2I | D1 | D2I | D2I | I |
| Zhongnvshi (QD-26) | D1I | D2I | D | D2 | D1D2 | D1D2 | D1D2 | D1I | D1D2 | D1D2 | D1 | D2I | D1I |
| 2001 Spur (QD-27) | D1D2I | D2I | I | D2I | D1I | D1I | D1D2 | D1I | D1D2I | D2 | D1 | D2I | I |
| Fuli (QD-28) | D1D2I | D2I | DI | D2I | I | D1I | D1 | D1I | D1D2I | D1I | D2I | I | |
| Tuanwang semi-Spur (QD-29) | D1D2I | D2I | I | D2I | D1I | D1I | D1D2 | D1I | D1D2I | D2 | D1 | D2I | I |

-continued

| Construction results of InDel marker genotype database of *Malus* germplasm resources | | | | | | | | | | | | |
|---|---|---|---|---|---|---|---|---|---|---|---|---|
| Qingfu 3 (QD-3) | D1D2I | D2I | I | D2I | D1I | D1I | D1D2 | D1D2I | D1D2I | D2 | D1 | D2I | I |
| Longfu (QD-30) | D1D2I | D2I | I | D2I | D1I | D1I | D1D2 | D1I | D1D2I | D2 | D1 | D2I | I |
| Baotou Linqin (QD-31) | D1 | I | D | D2 | D1D2 | D1 | D2 | D1D2 | D1D2 | NA | D2 | NA | D1D2 |
| Yanfu 6 (QD-32) | D1D2I | D2I | I | D2I | D1I | D1I | D1D2 | D1I | D1D2I | D2 | D1 | D2I | I |
| SH40-2 seedling (QD-4) | D1D2 | D2I | D | D1D2 | D1D2I | D2I | D1D2 | D1D2I | D1D2 | NA | D2 | I | D1D2 |
| Saijin (QD-5) | D1D2I | D2I | D | D2I | D1I | I | D1 | D1I | D1D2I | D1I | D1I | I | I |
| Nagafu 12 (QD-6) | D1D2I | D2I | I | D2I | D1I | D1I | D1D2 | D1I | D1D2I | D2 | D1 | D2I | I |
| Caoyuan Crab (QD-7) | D1 | D2 | NA | D2 | D1 | D1 | D2 | D1D2I | D1D2 | NA | NA | D2 | D2 |
| Xiaojin Crab (QD-8) | D1I | D2I | D | D1D2I | D1D2I | D1D2I | D2I | D1D2I | D1D2 | D1I | D2I | D2I | D1I |
| Shuangyanghong (QD-9) | D1I | D2I | DI | D2 | D1I | I | D1I | D1I | D2I | D1 | D2I | D2I | I |
| Qianxian Crab (QX-1) | D1 | D2I | D | D2I | D1 | D2 | D2I | D1 | D1D2 | D2 | D1D2 | D1I | D2I |
| Ruixue (ruixue) | D1I | D2I | I | I | D1I | D1I | D1I | D1I | D1D2 | D2 | D1I | D2I | I |
| Ruiyang (RY) | D1I | D2I | I | I | D1I | D1I | D1I | D1I | D1D2 | D2 | D1I | D2I | I |
| Yanyuan 1 (SC-1) | D1I | D2I | DI | D2I | D1I | I | D2I | D2I | D1D2I | D1D2I | D1I | I | I |
| Yanyuan 2 (SC-2) | D1D2I | D1D2I | D | D1I | D1D2I | D1I | D1I | D1I | D2I | D1 | D2I | I | I |
| Yanyuan 3 (SC-3) | D1D2I | D2I | I | D2I | D1I | D1I | D1D2 | D1I | D1D2I | D2 | D1 | D2I | I |
| Yanyuan 4 (SC-4) | D1D2I | D1D2I | D | D1I | D1D2I | D1I | D1I | D1I | D2I | D1 | D2I | I | I |
| Yanyuan 5 (SC-5) | D1I | D2I | D | D1D2 | D1D2 | D1 | D2I | D2I | D1D2I | D1D2 | D1D2 | I | D2I |
| Yanyuan 6 (SC-6) | D1I | D2I | DI | D2I | I | D1I | D1D2 | D1I | D1D2I | D1D2 | D2 | I | D2I |
| Yanyuan 7 (SC-7) | D1D2I | D2I | DI | D1I | D1I | D1I | D1D2I | D2I | D1D2I | D1D2I | D1I | I | I |
| Mitchgala (SX-10) | D1I | D2I | DI | D2I | D1I | I | D1I | D1I | D2I | D1 | D2I | D2I | I |
| Zhongqiuwang Linyi (SX-11) | D1I | D2I | I | D2I | D1I | D1I | D2I | D2 | D1D2I | D1D2I | D1I | D1I | I |
| Linyi Meiguo 5 (SX-12) | D1I | D2I | I | I | D1 | I | D2I | D1I | D1D2I | D1 | D1I | D2 | I |
| Liquan Spur Fuji (SX-13) | D1D2I | D2I | I | D2I | D1I | D1I | D1D2 | D1I | D1D2I | D2 | D1 | D2I | I |
| Qiulimu (SX-14) | D1D2 | D2I | D | D2 | D1D2 | D1D2 | D2 | D1D2 | D1D2I | D2 | D1D2 | I | D1I |
| Qincui (SX-15) | D1D2I | D2I | D | D2I | D2I | D1I | D1D2 | D1D2 | D1D2 | D1I | D1 | D2I | D2I |
| Taigu Shaguo Late (SX-17) | D1D2 | D2I | D | D2 | D1D2 | D1D2 | D2 | D1D2 | D1D2 | D1D2 | D2 | I | D1I |
| Lingyige Hongrou (SX-18) | D1D2I | D2I | D | D1D2 | D1 | D1I | D2I | D1 | D1D2I | D1D2 | D1D2 | D2I | I |
| Shenai LS (SX-19) | D2 | D2I | D | D2I | D1I | D1I | D1 | D1I | D1D2I | D2 | D1 | D2I | I |
| Linyi Meiguo 8 (SX-2) | D1D2I | D2I | D | I | D1I | I | I | I | D1D2I | D1 | D1I | D2I | I |
| Liga (SX-20) | D1I | D2I | DI | D2I | D1I | I | D1I | D1I | D2I | D1 | D2I | D2I | I |
| Y-1 (SX-21) | D1 | D2I | D | D2 | D1D2 | D1D2 | D2 | D1 | D1D2 | D2 | D1D2 | NA | D1 |
| B009 (SX-22) | D1 | D2I | D | D2 | D1D2I | D2 | D2 | D1D2I | D1 | D2 | D2 | D2 | D1I |
| Jinfu 1 (SX-23) | D1D2I | D2I | I | D2I | D1I | D1I | D1D2 | D1I | D1D2I | D2 | D1 | D2I | I |
| Hongmantang (SX-24) | D1D2I | D2I | D | D2 | D1 | D1D2 | D1 | D1I | D1D2 | D2 | D2 | I | D1I |
| Y-2 (SX-25) | D1 | NA | D | D2 | D1D2 | D1D2 | D2 | D1 | D1D2 | D2 | D1D2 | NA | D1 |
| Y-3 (SX-26) | D1 | D2I | D | D2 | D1D2 | D2 | D2 | D1 | D1D2I | D2 | D2 | NA | NA |
| Xinliangxiang (SX-27) | D1D2I | D2I | I | D2I | D1I | D1I | D1D2 | D1I | D1D2I | D2 | D1 | D2I | I |

-continued

| Construction results of InDel marker genotype database of *Malus* germplasm resources | | | | | | | | | | | | |
|---|---|---|---|---|---|---|---|---|---|---|---|---|
| Ennike Gala (SX-28) | D1I | D2I | DI | D2I | D1I | I | D1I | D1I | D2I | D1 | D2I | D2I | I |
| Linyi Meiguo 6 (SX-3) | D1I | D2I | I | D1D2I | D1I | I | D2I | D1D2I | D1D2 | D1I | D1I |
| Linyi Meiguo 2 (SX-30) | D1D2I | D2I | I | D2I | D1I | D1I | D1D2I | D1I | D1D2I | D2 | D1 | D2I | I |
| Donglimu (SX-33) | D1D2 | D2I | D | D2 | D1D2 | D1D2 | D2 | D1D2I | D2 | D1D2 | I | D1I |
| Linyi Meiguo 1 (SX-34) | D1D2I | D2I | D | I | D1I | I | I | I | D1D2I | D1 | D1I | D2I | I |
| Linyi Meiguo 4 (SX-4) | D1I | D2I | I | D1I | D1 | D1 | D1I | D1I | D1D2I | D2 | D1I | I | D1I |
| Qinyang (SX-6) | D1I | D2I | DI | D2I | D1I | I | D1I | I | D1D2I | D1D2 | D2 | I | D2I |
| Taiguo Shaguo Early (SX-7) | D1D2 | D2I | D | D2 | D1D2 | D1D2 | D2 | D2 | D1D2 | D1D2 | D2 | I | D1I |
| Yuhua Zaofu (SX-8) | D1D2I | D2I | I | D2I | D1I | D1I | D1D2 | D1I | D1D2I | D2 | D1 | D2I | I |
| 78-M18 (SY-1) | D1I | D2I | DI | D1D2I | D1D2I | I | D2 | D1D2I | D1D2 | D2 | D1D2 | D2I | I |
| Jinping (SY-10) | NA | D2I | I | D1D2 | D1D2I | D1 | D1 | NA | D2 | D1D2 | D1D2 | I | D1I |
| Longqiu (SY-11) | D1 | D2I | D | D2 | D1 | D1D2 | I | D1D2 | D1D2 | NA | D1D2 | D1I | I |
| Longfeng (SY-12) | D1 | D2I | NA | D2 | D1D2I | D1I | I | NA | D2 | D1D2 | D1D2 | I | D1 |
| Xiangjiaoguo (SY-14) | D1I | D1D2I | D | D2I | D1I | D2I | D2I | D1I | D2I | D1D2 | D1I | I | D1I |
| Longguan (SY-15) | D1D2I | D2I | I | D2I | D1D2I | I | D2 | D2 | D1D2 | I | D1 | D2I | D1I |
| Longshuai (SY-16) | D1D2 | D2I | D | D1D2 | D1D2I | D1I | D1I | NA | D1D2 | D1D2 | D1 | I | D1I |
| Zixiang (SY-17) | D1D2 | D2I | D | D2I | D1D2I | D2I | D1D2 | D2I | D1D2 | D2 | D1I | I | D1I |
| Huahong (SY-19) | D1D2 | D2I | D | D2 | D1 | D1D2 | D2 | D1D2 | D1D2 | D2 | D2 | I | D1I |
| Binlang (SY-2) | D1I | D1D2I | D | D2I | D1I | D2 | D2I | D1I | D2I | D1D2 | D1I | I | D1I |
| Qiufengmi (SY-20) | D1D2 | D2I | D | D2 | D1 | D1D2 | D2 | D1D2 | D1D2I | D1D2 | D2 | I | D1 |
| Honglingdang (SY-21) | D1D2 | D2I | D | D2 | D1D2 | D2I | D2 | D1I | D1D2 | D2 | D1 | D2I | D1D2 |
| Qiulu (SY-22) | D2 | D2I | DI | D1 | D1D2I | D1 | D1I | D1D2 | D1D2I | D1 | D1D2 | D1I | D1 |
| Longhong (SY-23) | D1D2I | D2I | I | D2I | D1D2I | I | D2 | NA | D1D2 | I | D1 | D2I | D1I |
| Milk (SY-3) | NA | D2I | I | D2I | D1D2 | D1 | D1 | D1 | D1D2I | D2 | NA | D2 | D1I |
| Hanfu (SY-4) | D1D2I | D2I | DI | D2I | D1I | I | D1D2 | D1 | D1D2 | D2 | D1 | D2I | D2I |
| Toko (SY-5) | D1D2I | D2I | D | D2 | I | D1 | D1D2 | NA | D1D2 | D2 | D1 | I | I |
| Jinhong (SY-6) | D1I | D2I | D | D1D2I | D1D2I | D1I | I | D1I | D1D2I | D2 | D2I | I | D1I |
| K9 (SY-7) | D1D2 | D2I | D | D2 | D1D2 | D2I | D2 | D1 | D1D2 | D2 | D1 | D2I | D1D2 |
| 03-06-04 (SY-8) | D1 | D2I | I | D2 | D1D2I | D1 | D2 | NA | D1D2 | D2 | D1D2 | I | D1I |
| Olga (SY-9) | D1D2 | D2I | D | D1D2 | D1D2I | D1D2 | I | D1D2 | D1D2 | D2 | D1D2 | D2I | D1I |
| Gala 4x (TA-1) | D1I | D2I | DI | D2I | D1I | I | D1I | D1I | D2I | D1 | D2I | D2I | I |
| Juda Fuji (TA-11) | D1D2I | D2I | I | D2I | D1I | D1I | D1D2 | D1I | D1D2I | D2 | D1 | D2I | I |
| Luli (TA-12) | D1D2 | D2I | I | I | D1I | D2I | D1 | D1 | D2I | D1 | D1D2 | I | D2I |
| Luping 1 (TA-13) | D1D2I | D2I | DI | D2I | D1I | I | D2I | D1I | D1D2I | D1D2 | D1D2 | D2I | D2I |
| Luping 2 (TA-14) | D1D2I | D2I | DI | D2I | D1I | I | D1I | D1I | D1D2I | D1D2 | D1D2 | D2I | I |
| Luping 5 (TA-15) | D1I | D2I | DI | D2I | D1I | I | D1D2I | D1I | D1D2I | D1 | D1D2I | I | D2I |
| Luyan (TA-16) | D1 | D2I | DI | D2I | D1I | D1I | D1I | D1I | D2I | D1 | D1I | D2I | D2I |
| Meinong (TA-17) | I | D2I | I | D2I | D2I | D1I | D1D2 | D1I | D1D2 | D2 | D1 | I | I |

-continued

| Construction results of InDel marker genotype database of *Malus* germplasm resources | | | | | | | | | | | | |
|---|---|---|---|---|---|---|---|---|---|---|---|---|
| Akifu 19 (TA-18) | D1D2I | D2I | I | D2I | D1I | D1I | D1D2 | D1I | D1D2I | D2 | D1 | D2I | I |
| Akifu 39 (TA-19) | D1D2I | D2I | I | D2I | D1I | D1I | D1D2 | D1I | D1D2I | D2 | D1 | D2I | I |
| Hanfu 4x (TA-2) | D1D2I | D2I | DI | D1I | D2I | I | D2 | D2 | D1D2 | D2I | D1I | D2I | D1I |
| Qiufuhong (TA-20) | D1D2I | D2I | I | D2I | D1I | D1I | D1D2 | D1I | D1D2I | D2 | D1 | D2I | I |
| Qunfu 1 (TA-21) | D1D2I | D2I | I | D2I | D1I | D1I | D1D2 | D1I | D1D2I | D2 | D1 | D2I | I |
| Shengfang (TA-22) | D1D2I | D2I | I | D2I | D1I | D1I | D1D2 | D1I | D1D2I | D2 | D1 | D2I | I |
| Alps Otome (TA-27) | D1 | D2I | D | D2 | D1D2 | D1 | D1 | D1I | D1D2 | D2 | D1D2 | I | D1I |
| Early Fuji (TA-28) | D1D2I | D2I | I | D2I | D1I | D1I | D1D2 | D1I | D1D2I | D2 | D1 | D2I | I |
| BP (TA-3) | D1D2 | D2I | D | D2 | D1I | D1 | D1 | D2I | D1D2I | D1D2 | D1 | D2 | D1I |
| Yishuihong (TA-32) | D1D2I | D2I | I | D2I | D1I | D1I | D1D2 | D1I | D1D2 | D2 | D1 | D2I | I |
| BP-176 (TA-4) | D1D2 | D2I | D | D2 | D1I | D1I | D1 | D2I | D1D2I | D2 | D1 | D2 | D1I |
| G41 (TA-5) | D1D2 | D2I | D | D2 | D1D2 | D1I | D2I | D1 | D1D2I | D2 | D2 | D1I | D1I |
| G935 (TA-6) | D1D2 | I | D | D2 | D1D2I | D1I | D2 | D1 | D1D2 | D1D2 | D1D2 | I | D1 |
| P60 (TA-7) | D1D2 | D2I | D | D2 | D1 | D1D2 | D1D2 | I | D1D2 | D2 | D1 | D2 | D1D2 |
| Fuji (TA-9) | D1D2I | D2I | I | D2I | D1I | D1I | D1D2 | D1I | D1D2 | D2 | D1 | D2I | I |
| Tianfu 1 (TS-1) | D1D2I | D2I | I | D2I | D1I | D1I | D1D2 | D1I | D1D2I | D2 | D1 | D2I | I |
| &28 (TS-13) | D1D2I | D2I | I | D2I | D1I | D1I | D1D2 | D1I | D1D2I | D2 | D1 | D2I | I |
| Red Chief (TS-14) | D1D2 | D2I | I | D2I | D1 | D1I | D1I | D1D2 | D1D2I | D2 | D1 | D1D2 | I |
| New Redchief (TS-2) | D1D2 | D2I | I | D2I | D1 | D1I | D1I | D1D2 | D1D2I | D2 | D1 | D1D2 | I |
| Chaohongxing (TS-3) | D1D2 | D2I | I | D2I | D1 | D1I | D1I | NA | D1D2I | D2 | D1 | D1D2 | I |
| Aozhou 1 (TS-5) | D1D2I | D2I | D | D1I | D1D2I | D1I | D2I | D1D2 | D1D2 | D2 | D2I | D2I | I |
| Tianfu 2 (TS-6) | D1D2I | D2I | I | D2I | D1I | D1I | D1D2 | D1I | D1D2I | D2 | D1 | D2I | I |
| Judeline (TS-7) | D1I | D1D2I | DI | D2I | D1I | D1I | D2I | D2 | D2I | D1 | D1D2 | I | I |
| Judestar (TS-8) | D1D2I | D2I | D | I | I | I | D1I | I | D1D2I | D1D2 | D1I | I | I |
| Judaine (TS-9) | D1I | D1D2I | DI | D2I | D1I | D1I | D2I | D2 | D2I | D1 | D1D2 | I | I |
| WH-5 (WH-1) | D1D2I | D2I | I | D2I | D1I | D1I | D1D2 | D1I | D1 | D2 | D1 | D2I | I |
| Italy Smothe (WH-10) | I | D2I | DI | I | I | I | D2I | D2I | D1D2I | D1D2I | D1I | I | I |
| Bai Crab (WH-2) | D1D2 | D2I | D | D1D2 | D1D2 | D2 | D2 | D1D2 | D1D2I | D2 | D2 | I | D1 |
| Hongguang (WH-4) | D1D2I | D2I | I | D2I | D1 | D1I | D1 | D1 | D1D2 | D2 | D1I | I | I |
| Huangcui (WH-5) | I | D2I | DI | D2I | I | I | D1D2 | D1I | D1D2I | D1 | D1I | I | I |
| Qinglin (WH-6) | I | D2I | DI | D2I | I | I | D2I | D2I | D1D2I | D1 | D1D2I | D2I | I |
| Harlikar (WH-8) | D1D2I | D2I | I | D2I | D1I | D1I | D1I | D1I | D1D2I | D1D2 | D1I | D2I | I |
| Italy Gala (WH-9) | D1I | D2I | DI | D2I | D1I | I | D1I | D1I | D2I | D1 | D2I | D2I | I |
| Wushan Bianye (WSBY) | D1 | D2 | D | D1D2 | D1D2 | NA | D2 | D1 | D1D2 | NA | D2 | D2I | D1 |
| Xin 1 (XC-1) | I | D2I | I | D2 | D1 | I | D1 | I | D2I | D1 | D2 | I | I |
| Xin 5 (XC-2) | D1 | D2I | DI | I | I | I | I | I | D2I | D1 | I | I | I |
| Hanfu 3x (XC-3) | I | D2I | I | D2 | I | I | D1 | D1 | D1D2 | D1 | D1 | D2 | I |
| Gala 4x (XC-4) | D1I | D2I | DI | D2I | D1I | I | D1I | D1I | D2I | D1 | D2I | D2I | I |
| Weizhimuben (XC-5) | D1 | D2I | D | D1D2 | D1D2 | D1D2I | D1D2 | NA | D1D2I | D1 | D1D2 | I | D1D2I |

| Construction results of InDel marker genotype database of *Malus* germplasm resources | | | | | | | | | | | | |
|---|---|---|---|---|---|---|---|---|---|---|---|---|
| Chaguo (XC-CG) | D1D2 | I | D | D2 | D1D2 | D1D2 | D2 | D1D2 | D1I | D2 | D2 | I | D1 |
| Donghongguo (XC-DHG) | D1I | D2I | D | D2 | D1D2I | D1I | D2 | D1 | D1D2 | D2 | D1D2 | I | D1D2 |
| Fuxian Sanye (XC-FXXY) | D1 | D2I | D | D2 | D1D2 | D1D2 | D2 | D1 | D1D2 | D2 | D2 | I | D1 |
| Hongsanye (XC-HSY) | D1 | D2 | D | D2 | D1D2 | D1D2 | D2 | D1 | D1D2 | NA | D2 | D2I | D1 |
| Jilin Xiaohong Crab (XC-JILINXIAOHONG-HAITANG) | D1 | D2I | D | D1D2 | D1D2 | D2 | D2I | D1D2 | D1D2 | NA | D1D2 | I | D1I |
| Jilin Xiaohuang Crab (XC-JILINXIAOHUANG-HAITANG) | D1 | D2I | D | D2 | D1D2 | D1D2 | D2 | D1D2 | D1D2 | NA | D1D2 | I | D1D2 |
| Jilin Huang Crab (XC-JLHHT) | D1 | D2I | D | D2 | D1D2 | D1D2 | D2 | D1D2 | D1D2 | NA | D1D2 | I | D1D2 |
| Shajin Crab (XC-JSHT) | D1 | D2I | D | D1D2 | D1D2I | D1D2 | D2 | D1 | D1 | D2 | D2 | I | D1 |
| Longdong Crab (XC-LDHT) | D1 | D2I | D | D2 | D1D2 | D1D2 | D2 | D1 | D1D2 | NA | D2 | I | D1 |
| Lushi Crab (XC-LSHT) | D1 | I | D | D2 | D1D2 | D1D2 | D2 | D1 | D1D2 | D2 | D2 | D2 | D1D2 |
| Laiwunanyan (XC-LWNY) | D1D2 | I | D | D2 | D1D2 | D1D2 | D2 | D1D2 | D1I | D2 | D2 | I | D1 |
| Linzhi (XC-LZ) | D1 | D2 | D | D1D2 | D1D2 | D2 | D2 | D1 | D1D2 | NA | D2 | D2I | D1 |
| Mao Shandingzi (XC-MSDZ) | D1D2 | I | D | D2 | D1D2 | D1D2 | D2 | D1 | D1 | NA | D2 | I | D1 |
| Pingyitiancha (XC-PYTC) | D1 | D2I | D | D1D2 | D1D2 | D1D2 | D2 | D1 | D1 | D2 | D2 | D2I | D1 |
| Qiuzi (XC-QZ) | D1D2 | I | D | D2 | D1D2 | D1 | D2I | D2 | D1D2 | D2 | D2 | I | D1 |
| Sichuan Bianye (XC-SCBY) | D1 | D2 | D | D1D2 | D1D2 | D2 | D2 | D1 | D1D2 | NA | D2 | D2I | D1 |
| Shandingzi (XC-SDZ) | D1 | NA | D | D2 | D1D2 | D1 | D2 | D1 | D1 | NA | D2 | I | D1 |
| Weixi Sanye (XC-WXSY) | D1D2 | D2I | D | D1D2 | D1D2 | D1I | D1D2 | D1I | D1D2 | D2 | D1D2 | D2I | D1D2 |
| Xifu Crb (XC-XFHT) | D1D2 | I | D | D2 | D1D2 | D1D2 | D2 | D1 | D1 | NA | D2 | I | D1 |
| Xiaojin Bianye (XC-XJBY) | D1 | D2 | D | D1D2 | D1D2 | D2 | D2 | D1 | D1 | D2 | D2 | I | D1 |
| Xinjiang Yepingguo (XC-XJYHT) | D1I | D1D2I | D | D2 | D1D2 | D1 | D2 | I | D1D2 | D2 | D2 | I | D1 |
| Yajiang Bianye (XC-YJBY) | D1 | D2 | D | D2 | D1D2 | D2 | D2 | D1 | D1D2 | NA | D2 | D2I | D1 |
| Yingye Crab (XC-YYHT) | D1 | D2I | D | D1D2 | D1D2 | D1 | D1D2 | D1 | D1D2 | NA | D2 | I | D1 |
| Zhaai (XC-ZA) | D1 | NA | D | NA | D1D2 | D1 | D2 | D1 | D1D2 | D2 | D2 | D2 | D1 |
| Zumi Crab (XC-ZMHT) | D1 | D2I | D | D2 | D1D2 | D2 | D2 | D1D2 | D1D2 | NA | D1 | I | D1 |
| Pink Lady (XN-FHNS) | D1I | D2I | DI | D2I | D1D2I | D1I | I | D1D2 | D1D2I | D1I | D1I | I | D2I |
| Hongrou 1 (XN-HR1) | D2 | D2I | D | D1D2 | D1 | D1 | D2 | D1D2 | D1D2 | D2 | D2 | I | D1I |
| Hongrou 2 (XN-HR2) | D1D2 | D1D2I | D | D2 | D1 | D1D2 | D2 | D2 | D2I | D2 | D2 | I | D1I |
| Hongrou 3 (XN-HR3) | D2 | D2I | D | D2 | D1 | D1 | D2 | D2I | D1D2 | D1D2 | D2 | I | D1 |
| Hongrou 4 (XN-HR4) | D1D2 | D2I | D | D2 | D1D2 | D1D2 | D2 | D1D2 | D1D2I | D2 | D1D2 | I | D1 |
| Hongrou 5 (XN-HR5) | D1D2 | D1D2I | D | D1D2 | D1D2 | D1 | D2I | D2I | D1D2I | D1D2 | D1D2 | I | D1D2 |
| Hongrou 6 (XN-HR6) | D1D2I | D2I | DI | D2 | D1 | D2 | D2 | D1D2 | D1D2I | D1 | D1 | I | D1I |
| Hongrou 7 (XN-HR7) | D1D2 | D2I | D | D2 | D1 | D1 | D2 | I | D1D2I | D1D2 | D1D2 | D2I | D1I |
| Ambrosia (XN-MW) | D1D2I | D2I | I | D2I | D1I | D1I | D1I | D1I | D1D2I | D1D2 | D1I | D2I | I |
| Xinjiang 10 (XN-XJ10) | D2 | D1D2I | D | D2 | D1 | D1 | D2 | D2 | D1D2 | D2 | D2 | I | D1I |
| Xinjiang 11 (XN-XJ11) | I | D2I | D | D2 | D1 | D1 | D2 | D2I | D1D2I | D2 | D2 | I | D1 |

-continued

| Construction results of InDel marker genotype database of *Malus* germplasm resources | | | | | | | | | | | | | |
|---|---|---|---|---|---|---|---|---|---|---|---|---|---|
| Xinjiang 12 (XN-XJ12) | D2 | D1D2I | D | D2 | D1 | D1 | D2 | D2 | D1D2 | D2 | D2 | I | D1I |
| Xinjiang 13 (XN-XJ13) | D1 | D2I | D | D2 | D1D2 | D1D2 | D2 | D1 | D1D2 | D2 | D2 | I | D1I |
| Xinjiang 14 (XN-XJ14) | D1I | D2I | D | D2 | D1D2 | D1D2 | D2 | D2 | D2I | D2 | D1D2 | I | D1I |
| Xinjiang 15 (XN-XJ15) | D1 | D1D2I | D | D2 | D1D2 | D1I | D2 | D2 | D1D2 | D2 | D1 | D2I | I |
| Xinjiang 16 (XN-XJ16) | D1D2 | D2I | D | D2 | D1D2 | D1D2 | D2 | D1D2 | D1D2I | D2 | D1D2 | I | D1I |
| Xinjiang 17 (XN-XJ17) | D2 | D2I | D | D1D2 | D1D2 | D1D2 | D2 | D1D2 | D1D2I | D2 | D2 | I | D1I |
| Xinjiang 18 (XN-XJ18) | D1D2 | D2I | DI | D2I | D1D2 | D1D2 | D1D2 | D2I | D1D2 | D1 | D1 | D2I | D1I |
| Xinjiang 19 (XN-XJ19) | D1D2I | D1D2I | D | D2 | D1 | D1 | D2 | D2 | D1D2 | D2 | D2 | I | D1I |
| Xinjiang 2 (XN-XJ2) | D2 | D1D2I | D | D2 | D1 | D1D2 | D2 | D2 | D1D2I | D2 | D2 | I | D1 |
| Xinjiang 20 (XN-XJ20) | D1D2 | D1D2I | DI | D2I | D1 | D1 | D2 | D2I | D1D2 | NA | D1 | I | D1I |
| Xinjiang 21 (XN-XJ21) | D1I | D2I | D | D2 | D1 | D1 | D1D2 | D2I | D1D2I | D2 | D2I | I | D1I |
| Xinjiang 23 (XN-XJ23) | D1D2 | D1D2I | DI | D2 | D1 | D1D2 | D2 | D1 | D1D2 | D2 | D1D2 | I | I |
| Xinjiang 24 (XN-XJ24) | D2 | D2I | D | D1D2 | D1 | D2I | D2 | D2I | D1D2I | D1D2 | D1 | I | D1I |
| Xinjiang 25 (XN-XJ25) | D1D2I | D2I | D | D1D2 | D1 | D1 | D2 | D2 | D1I | D1D2 | D2 | I | D1 |
| Xinjiang 27 (XN-XJ27) | D1 | D1D2I | D | D2 | D1D2 | D1I | D2 | D2 | D1D2 | D2 | D1 | D2I | I |
| Xinjiang 3 (XN-XJ3) | D1D2I | D1D2I | D | D2 | D1 | D1 | D2 | D2 | D1D2 | D2 | D2 | I | D1I |
| Xinjiang 4 (XN-XJ4) | D1D2I | D2I | D | D2 | D1 | D1D2 | D2 | D1D2 | D1D2 | D2 | D1D2 | I | D1I |
| Xinjiang 5 (XN-XJ5) | D2 | D1D2 | NA | D2 | D1 | D2 | D2 | D2 | D1D2 | NA | D2 | NA | NA |
| Xinjiang 7 (XN-XJ7) | D1D2I | NA | NA | NA | D1 | D1 | D2 | D2I | NA | D2 | D1D2 | I | D1I |
| Xinjiang 8 (XN-XJ8) | D2 | D2I | DI | D1D2 | D1 | D1I | D2 | D2 | D1D2 | D2 | D1 | I | D1I |
| Xinjiang 9 (XN-XJ9) | D1D2 | D1D2I | D | D1D2 | D1D2I | D1D2 | D2 | I | D1D2 | D2 | D1D2 | I | D1I |
| Yueguan (XY-10) | I | D2I | D | D1I | D1I | I | D2I | D1I | D1D2I | D1 | D1 | I | D2I |
| Yuehua (XY-11) | D1 | D2I | D | D2 | D1 | D1D2 | I | D1D2 | D1 | D1D2 | D1I | I | |
| Yueyan (XY-12) | D1D2I | D2I | D | D2I | D1D2I | D1I | D1D2 | D1 | D1D2I | D1 | D1D2 | D2I | D2I |
| Bud Sport 5 (XY-13) | D1D2I | D2I | I | D2I | D1I | D1I | D1D2 | D1I | D1D2I | D2 | D1 | D2I | I |
| Bud Sport 3 (XY-14) | D1D2I | D2I | I | D2I | D1I | D1I | D1D2 | D1I | D1D2I | D2 | D1 | D2I | I |
| Longfu (XY-15) | D1D2I | D2I | I | D2I | D1I | D1I | D1D2 | D1I | D1D2I | D2 | D1 | D2I | I |
| Yuemei (XY-18) | D1D2I | D2I | I | D2I | D1 | D2 | D2I | D1 | D2I | D1 | D1 | D2I | D2 |
| Hanfu (XY-2) | D1D2I | D2I | DI | D2I | D1I | I | D1D2 | D1 | D1D2 | D1 | D1 | D2I | D2I |
| Linyi Fuji (XY-20) | D1D2I | D2I | I | D2I | D1D2I | D1I | D2I | D2 | D1D2I | D2 | D1 | D2I | I |
| Yishui Fuji (XY-22) | D1D2I | D2I | I | D2I | D1I | D1I | D1D2 | D1I | D1D2I | D2 | D1 | D2I | I |
| Hongjinfu (XY-25) | D1D2I | D2I | I | D2I | D1I | D1I | D1D2 | D1I | D1D2I | D2 | D1 | D2I | I |
| Beni Oshu (XY-26) | D1D2I | D2I | I | D2I | D1I | D1I | D1D2 | D1I | D1D2I | D2 | D1 | D2I | I |
| Chuizhi Fuji (XY-27) | D1D2I | D2I | I | D2I | D1I | D1I | D1D2 | D1I | D1D2I | D2 | D1 | D2I | I |
| Yueshuai (XY-28) | D1D2I | D1D2I | D | D1I | D1D2I | D1I | D1I | D1I | D2I | D1 | D1D2 | NA | NA |
| Shichinohe 2 (XY-29) | D1D2I | D2I | I | D2I | D1I | D1I | D1D2 | D1I | D1D2I | D2 | D1 | D2I | D1D2I |
| 74-178 (XY-3) | I | D2I | DI | D2I | I | I | D1D2 | D1I | D1D2 | D2I | D1I | D2I | D2I |
| KAKUFUJI (XY-30) | D1D2I | D2I | I | D2I | D1I | D1I | D1D2 | D1I | D1D2I | D2 | D1 | NA | I |
| Royal Fuji 21 (XY-35) | D1D2I | D2I | I | D2I | D1I | D1I | D1D2 | D1I | D1D2I | D2 | D1 | D2I | I |

-continued

| Construction results of InDel marker genotype database of *Malus* germplasm resources |||||||||||||
|---|---|---|---|---|---|---|---|---|---|---|---|---|
| Qiquan Spur (XY-36) | D1D2I | D2I | I | D2I | D1I | D1I | D1D2 | D1I | D1D2I | D2 | D1 | D1D2I | I |
| Juda Fuji (XY-37) | D1D2I | D2I | I | D2I | D1 | D1I | D1 | D1 | D1D2 | D2 | D1I | NA | I |
| 7-211 (XY-4) | D1D2I | D2I | I | D2I | D1 | D1 | D1I | D1 | D2I | D1 | D1 | D2I | D2 |
| Yanfu 0 (XY-41) | D1D2I | D2I | I | D2I | D1I | D1I | D1D2 | D1I | D1D2I | D2 | D1 | D2I | I |
| Spur Fuji (XY-42) | D1D2I | D2I | I | D2I | D1I | D1I | D1D2 | D1I | D1D2I | D2 | D1 | D2I | I |
| Bayue fushiwang (XY-43) | D1D2I | D2I | I | D2I | D1I | D1I | D1D2 | D1I | D1D2I | D2 | D1 | D2I | I |
| Huangfu 7 (XY-44) | D1D2I | D2I | I | D2I | D1I | D1I | D1D2 | D1I | D1D2 | D2 | D1 | D2I | I |
| Aomori Spur Fuji (XY-46) | D1D2I | D2I | I | D2I | D1I | D1I | D1D2 | D1I | D1D2I | D2 | NA | D2I | I |
| Qiu Fuji (XY-47) | D1D2I | D2I | I | D2I | D1I | D1I | D1D2 | D1I | D1D2I | D2 | D1 | D2I | I |
| Fuji Champion (XY-48) | D1D2I | D2I | I | D2I | D1I | D1I | D1D2 | D1I | D1D2I | D2 | D1 | D2I | I |
| 26-34 (XY-5) | D2 | D2I | DI | D2 | D1D2I | D1I | D2I | D1D2 | D1D2 | D2 | D1 | D2 | D2I |
| Akifu 19 (XY-50) | D1D2I | D2I | I | D2I | D1I | D1I | D1D2 | D1I | D1D2I | D2 | D1 | NA | I |
| Fuji (XY-54) | D1D2I | D2I | I | D2I | D1I | D1I | D1D2 | D1I | D1D2I | D2 | D1 | NA | I |
| Qinfu 1 (XY-55) | D1D2I | D2I | I | D2I | D1I | D1I | D1D2 | D1I | D1D2I | D2 | D1 | D2I | I |
| Feng Fuji (XY-56) | D1D2I | D2I | I | D2I | D1I | D1I | D1D2 | D1I | D1D2I | D2 | D1 | NA | I |
| Tianxing (XY-57) | D1D2I | D2I | I | D2I | D1I | D1I | D1D2 | D1I | D1D2I | D2 | D1 | D2I | I |
| Taiyang Fuji (XY-58) | D1D2I | D2I | I | D2I | D1I | D1I | D1D2 | D1I | D1D2I | D2 | D1 | D2I | I |
| Cherry Crab (XY-6) | D2 | D2I | DI | D2 | D1D2 | D1 | D1D2 | D2I | D1D2 | D2 | NA | D2I | D1 |
| Yueping (XY-60) | D1D2I | D2I | DI | I | D1D2I | I | D1 | D1 | D1D2I | D1D2 | D1 | NA | NA |
| 23-63 (XY-61) | I | D2I | D | D2 | I | D1I | D1D2 | D1 | D2I | D1D2 | D1 | I | D2I |
| 23-42 (XY-62) | I | D2I | DI | D2 | I | D1I | D1 | D1I | D2I | D1D2 | D1 | NA | NA |
| 7-171 (XY-63) | D1I | D2I | DI | D2I | D1 | D2 | D2I | D2I | D1D2I | D1D2 | D1 | D2I | D1D2 |
| Shengfang 3A (XY-65) | D1D2I | D2I | I | D2I | D1I | D1I | D1D2 | D1I | D1D2I | D1D2 | D1 | D2I | I |
| Meinong Fuji (XY-67) | D1D2I | D2I | I | D2I | D1I | D1I | D1D2 | D1I | D1D2I | D2 | D1 | D2I | I |
| 62-45 (XY-68) | D1D2I | D2I | D | D1D2 | D1D2I | D1I | D1D2 | D1 | D1D2I | D1 | D1 | D2I | D1D2I |
| Fengfeng Fuji (XY-70) | D1D2I | D2I | I | D2I | D1I | D1I | D1D2 | D1I | D1D2I | D2 | D1 | D2I | I |
| GM256 (XY-71) | D1D2I | D2I | I | D2I | D1I | D1I | D1D2 | D1I | D1D2I | D2 | D1 | NA | NA |
| Jinfu 2 (XY-73) | D1D2I | D2I | I | D2I | D1I | D1I | D1D2 | D1I | D1D2I | D2 | D1 | D2I | I |
| Qiufu (XY-75) | D1D2I | D2I | I | D2I | D1I | D1I | D1D2 | D1I | D1D2I | D2 | D1 | D2I | I |
| Shanfu 6 (XY-76) | D1D2I | D2I | I | D2I | D1I | D1I | D1D2 | D1I | D1D2I | D2 | D1 | D2I | I |
| Nagafu 8 (XY-77) | D1D2I | D2I | I | D2I | D1I | D1I | D1D2 | D1I | D1D2I | D2 | D1 | D2I | I |
| 58-34 (XY-78) | I | D2I | D | D2I | D1I | I | D2I | D1I | D1D2I | D1D2 | D1 | D2I | D2I |
| 2001 Fuji (XY-79) | D1D2I | D2I | I | D2I | D1I | D1I | D1D2 | D1I | D1D2I | D2 | D1 | D2I | I |
| 15-26 (XY-8) | D1I | D2I | D | D2 | D1I | D2 | D1I | D1I | D1D2 | D2 | NA | D2I | D2I |
| Wangshanhong (XY-80) | D1D2I | D2I | I | D2I | D1I | D1I | D1D2 | D1I | D1D2I | D2 | D1 | D2I | I |
| Jinfu 1 (XY-81) | D1D2I | D2I | I | D2I | D1I | D1 | D1D2 | D1I | D1D2I | D2 | D1 | D2I | I |
| Qingfu 1 (XY-84) | D1D2I | D2I | I | D2I | D1I | D1I | D1D2 | D1I | D1D2I | D2 | D1 | D2I | I |
| Qiufu 39 (XY-85) | D1D2I | D2I | I | D2I | D1I | D1I | D1D2 | D1I | D1D2I | D2 | D1 | D2I | I |

-continued

| Construction results of InDel marker genotype database of *Malus* germplasm resources | | | | | | | | | | | | | |
|---|---|---|---|---|---|---|---|---|---|---|---|---|---|
| Nagafu 1 (XY-86) | D1D2I | D2I | I | D2I | D1I | D1I | D1D2 | D1I | D1D2I | D2 | D1 | D2I | I |
| Shou Fuji (XY-87) | D1D2I | D2I | I | D2I | D1I | D1I | D1D2 | D1I | D1D2I | D2 | D1 | D2I | I |
| Yueli (XY-88) | D1I | D2I | DI | D2I | D1I | D2 | D2I | D2I | D1D2I | D1D2 | D1 | I | D2 |
| Shanfu 2 (XY-89) | D2I | D2I | I | D2I | D1I | D1I | D1D2 | D1I | D1D2I | D2 | D1 | D2I | I |
| Chongban Crab (XY-9) | D1D2 | I | D | D2 | D1D2I | D1 | D2 | D1 | D1D2 | D2 | D2 | D2I | D1 |
| Harica (XY-90) | I | D2I | DI | D2I | D1I | I | D2I | D2I | D1D2I | D1 | D1I | D2I | I |
| Akifu 1 (XY-91) | D1D2I | D2I | I | D2I | D1I | D1I | D1D2 | D1I | D1D2I | D2 | D1 | D2I | I |
| Wangfu (XY-92) | D1D2I | D2I | I | D2I | D1I | D1I | D1D2 | D1I | D1D2I | D2 | D1 | D2I | I |
| Hong Manao (XYZ-1) | D1 | D2I | D | D2I | D1 | D2 | I | D1 | D1D2 | D2 | D1D2 | D1I | D2I |
| Modi (XYZ-10) | I | D2I | DI | D2 | D1I | D1I | I | I | D2I | D1 | D1D2 | D1D2I | D2I |
| C37 (XYZ-11) | I | D2I | D | D2I | D1 | I | I | I | D1D2 | I | D1 | D2I | I |
| Envy ? (XYZ-12) | D1D2 | D2I | I | D1I | D1I | D1I | D1I | D1I | D1D2I | D1D2 | D2I | D2I | I |
| Xichang Yuanzhuiguo (XYZ-2) | D1I | D2I | D | D2 | D1 | D2I | D2 | I | D1I | D2 | D1D2 | I | D1I |
| Ziye Zixiaoguo (XYZ-3) | D1 | D2 | D | D2 | D1D2 | D1D2 | D2 | D1D2 | D1 | D2 | D2 | I | D1 |
| Ziye Zidaguo (XYZ-4) | D1I | D2I | D | D2 | D1I | D1D2 | D2 | D1I | D1D2 | D2 | D1D2 | I | D1I |
| Shoufenshu 6 (XYZ-5) | D1I | D2I | I | D2 | D1I | D1 | D2 | D1D2 | D1D2 | D2 | D1D2 | I | D1I |
| Changhua (XYZ-6) | D1I | D2I | DI | D2I | D1I | I | D1I | D1I | D2I | D1 | D2I | D2I | I |
| Jinshiji (XYZ-7) | D1I | D2I | DI | D2I | D1I | I | D1I | D1I | D2I | D1 | D2I | D2I | I |
| 19-147 (XYZ-9) | D1D2I | D2I | DI | D2I | D2I | D2I | D2I | D2I | D1D2I | D1D2I | D1I | D2I | D2I |
| Malong Gala 1 (YN-1) | D1I | D2I | DI | D2I | D1I | I | D1I | D1I | D2I | D1 | D2I | D2I | I |
| Shouer hong (YN-11) | D1D2I | D2I | I | D2I | D1I | D1I | D1D2 | D1I | D1D2I | D2 | D1 | D2I | I |
| Yun Hongrou (YN-12) | D1D2I | D2I | D | D2I | D1D2I | I | D1 | D1I | D1D2I | D2 | D1I | D2I | D1 |
| Lixing Crab (YN-13) | D1D2 | D2I | D | D1D2 | D1 | D1 | D2 | D2 | D1D2 | D1D2 | D2 | I | D1I |
| Siana (YN-15) | D1D2I | D2I | D | D2 | D1I | D1I | D1D2 | D1I | D1D2 | D2 | D1 | D2I | I |
| Jonathan-M41 (YN-17) | D1D2 | D1D2I | D | D1D2 | D1D2 | D1 | D1I | D1D2 | D1D2I | D1D2 | D1D2 | D1D2 | D1I |
| Morlie's Delicious (YN-18) | I | D2I | D | D2I | D1I | I | I | D1I | D1D2I | D1D2 | D1 | D2I | D2 |
| Britegold (YN-19) | D1D2I | D2I | I | D2I | D1I | D1I | D1D2 | D1I | D1D2I | D2 | D1 | D2I | I |
| Malong Gala 1 blush (YN-2) | D1I | D2I | DI | D2I | D1I | I | D1I | D1I | D2I | D1 | D2I | D2I | I |
| Line 5 (YN-22) | D1D2I | D2I | D | D2 | D1I | D1I | D1D2 | D1I | D1D2 | D2 | D1 | D2I | I |
| Line 6 (YN-23) | D1D2 | D2I | DI | I | D2I | I | D2I | D1 | D1D2I | D1I | D1 | D2I | D2I |
| Line 13 (YN-24) | I | D2I | DI | D2I | I | D1I | I | D1I | D1D2I | D2I | D1D2 | I | I |
| row 3 (YN-25) | D1D2 | D2I | I | I | D1I | D2I | D1 | D1 | D2I | D1 | D1D2 | I | D2I |
| row 4 (YN-26) | D1D2 | D2I | I | I | D1I | D2I | D1 | D1 | D2I | D1 | D1D2 | I | D2I |
| row 5 (YN-27) | D1D2 | D2I | I | I | D1I | D2I | D1 | D1 | D2I | D1 | D1D2 | I | D2I |
| row 6 (YN-28) | D1D2 | D2I | I | I | D1I | D2I | D1 | D1 | D2I | D1 | D1D2 | I | D2I |
| row 9 (YN-29) | D1D2 | D2I | I | D1I | D1D2I | D1I | D1D2 | D1 | D1D2I | D1D2 | D1I | I | I |
| Malong xin Gala 1 (YN-3) | D1I | D2I | DI | D2I | D1I | I | D1I | D1I | D2I | D1 | D2I | D2I | I |
| row 10 (YN-30) | D1I | D2I | DI | D2I | D1D2I | D1I | I | D1D2 | D1D2I | D1D2I | D1I | I | D2I |
| row 11 (YN-31) | D1D2 | D2I | I | D1I | D1D2I | D1I | D1D2 | D1 | D1D2I | D1D2 | D1I | I | I |

-continued

| Construction results of InDel marker genotype database of *Malus* germplasm resources | | | | | | | | | | | | |
|---|---|---|---|---|---|---|---|---|---|---|---|---|
| row 12 (YN-32) | D1I | D2I | DI | D2I | D1I | I | D1I | D1I | D2I | D1 | D2I | D2I | I |
| row 13 (YN-33) | D1 | D2I | DI | D2I | D1I | D1I | D1I | D1I | D2I | D1 | D1I | D2I | D2I |
| row 14 (YN-34) | D1D2 | D2I | I | I | D1I | D2I | D1 | D1 | D2I | D1 | D1D2 | I | D2I |
| row 15 (YN-35) | D1D2I | D2I | DI | D2I | D1I | I | D2I | D1I | D1D2I | D1D2 | D1D2 | D2I | D2I |
| row 16 (YN-36) | D1D2I | D2I | DI | D1I | D1I | D1I | D1D2I | D2I | D1D2I | D1D2I | D1I | I | I |
| row 17 (YN-37) | D1I | D2I | D | D1D2 | D1D2I | D1 | D2I | D1I | D1D2I | D1D2 | D1D2 | I | D2I |
| row 18 (YN-38) | D1I | D2I | DI | D2I | I | D1I | D1D2 | D1D2 | D1D2I | D1D2 | D2 | I | D2I |
| row 19 (YN-39) | D1D2I | D2I | DI | D1I | D1I | D2I | D1D2 | D2I | D1D2 | D2 | D1D2 | D2 | D1D2 |
| Malong xin Gala 1 strip (YN-4) | D1I | D2I | DI | D2I | D1I | I | D1I | D1I | D2I | D1 | D2I | D2I | I |
| row 20 (YN-40) | D1D2I | D1D2I | D | D1I | D1D2I | D1I | D1I | D1I | D2I | D1 | D2I | I | I |
| row 21 (YN-41) | D1D2I | D2I | I | D2I | D1I | D1I | D1D2 | D1I | D1D2I | D2 | D1 | D2I | I |
| row 22 (YN-42) | D1D2I | D1D2I | D | D1I | D1D2I | D1I | D1I | D1I | D2I | D1 | D2I | I | I |
| row 23 (YN-43) | D1D2I | D1D2I | D | D1I | D1D2I | D1I | D1I | D1I | D2I | D1 | D2I | I | I |
| row 24 (YN-44) | D1D2I | D2I | I | D2I | D1I | D1I | D1D2 | D1I | D1D2I | D2 | D1 | D2I | I |
| row 25 (YN-45) | D1D2I | D2I | I | D2I | D1I | D1I | D1D2 | D1I | D1D2I | D2 | D1 | D2I | I |
| Malong Gala2 (YN-5) | D1I | D2I | DI | D2I | D1I | I | D1I | D1I | D2I | D1 | D2I | D2I | I |
| Malong Gala 2 blush (YN-6) | D1I | D2I | DI | D2I | D1I | I | D1I | D1I | D2 | D1 | D2I | D2I | I |
| Longwei (YN-7) | D1I | D2I | I | D1I | D1I | D1I | D1I | D1I | D1D2I | D1D2 | D1D2 | D2 | I |
| Longwei Early Mutant (YN-8) | D1I | D2I | I | D1I | D1I | D1I | D1I | D1I | D1D2I | D1D2 | D1D2 | D2 | I |
| Cherry Gala (YN-9) | D1I | D2I | DI | D2I | D1I | I | D1I | D1I | D2I | D1 | D2I | D2I | I |
| Siyana (YT-1) | D1 | D2I | D | D2I | D1D2I | D1I | D1 | D1 | D1D2 | D2 | D1I | D1I | D1I |
| Yanfu 10 (YT-100) | D1D2I | D2I | I | D2I | D1I | D1I | D1D2 | D1I | D1D2I | D2 | D1 | D2I | I |
| Chadel (YT-102) | D1I | D2I | DI | D2I | I | D1I | I | D2I | D1D2 | D2I | D1I | D1I | I |
| Charden (YT-103) | D1D2I | D2I | DI | I | I | I | D2I | D2I | D1D2I | D1D2I | D1I | D2I | D1I |
| Tuskan (YT-104) | D1D2 | D2I | DI | D2I | D1D2 | I | D2I | D2I | D1D2I | D1D2 | D1I | D2I | D1I |
| Prima × Sekaiichii (YT-105) | D1D2 | D2I | D | D2 | D1 | D1 | D1D2 | D1I | D1D2I | D1D2 | D1D2 | D1I | D2I |
| Toppax_apple (YT-11) | D1D2 | D2I | D | D2 | D1 | D1I | D1 | D1I | D2I | D1 | D1I | D1D2 | D1I |
| Xinjiang Hongrou Crab (YT-12) | D1 | D2I | D | D2 | D1D2 | D1D2 | D2 | D1 | D1D2I | D2 | NA | D2I | D1I |
| Melfree (YT-13) | D1I | D2I | D | D2I | I | D1I | D2I | D2I | D1D2I | D1D2 | D1I | D1I | D1I |
| Yanfu 3 (YT-14) | D1D2 | D1D2I | D | D1D2 | D1D2 | D1 | D1I | D1D2 | D1D2I | D1D2 | D2I | D1I | D1I |
| Gold milecnirum (YT-15) | D1 | D1D2I | DI | D2I | D1I | D1I | D2I | D1D2 | D1D2I | D1D2 | D1I | D2I | D1I |
| Ganhong (YT-16) | D1 | D1D2I | D | D2I | D1I | I | I | D1I | D1D2 | D2I | D1 | D2 | D2I |
| Cornoet (YT-17) | I | D2I | D | D2 | D1D2 | I | D2 | D1D2 | D1D2 | D2 | D1 | D2I | I |
| Priw (YT-18) | D1D2 | D2I | D | D2 | D1D2 | D1 | D1D2 | D1I | D1D2I | D1D2 | D1D2 | D1I | I |
| Aichi (YT-19) | D1D2 | D2I | DI | D2I | D1I | I | D1I | D2 | D1D2 | D1D2 | D1D2 | D2I | D1 |
| Auraria (YT-2) | D1D2I | D2I | D | D2 | D1D2 | D1D2 | D1I | D1D2I | D1D2 | D1D2 | D1D2 | D2I |
| Meile (YT-20) | D1D2I | D2I | I | D2I | D1I | D1I | D1D2 | D1I | D1D2I | D2 | D1 | D2I | I |
| Qiulimeng (YT-21) | D1D2 | D2I | D | D2 | D1D2 | D1D2 | D2 | D1D2 | D1D2I | D2 | D1D2 | I | D1I |

-continued

| Construction results of InDel marker genotype database of *Malus* germplasm resources | | | | | | | | | | | | | |
|---|---|---|---|---|---|---|---|---|---|---|---|---|
| Aliusitan (YT-22) | D1I | D2I | D | D2 | D1 | D1 | D1D2 | D2 | D1D2I | D2 | D2I | I | I |
| Geaooza (YT-23) | D2 | D2I | D | D2 | D1D2 | D1D2 | D2I | D1 | D1D2I | D1D2 | D1 | D2I | I |
| Golden Spur (YT-24) | I | D2I | DI | I | I | I | D2I | D2I | D1D2I | D1D2I | D1I | I | I |
| Starking (YT-25) | D1D2 | D2I | I | D2I | D1 | D1I | D1I | D1D2 | D1D2I | D1D2 | D1 | D1D2 | I |
| Indo (YT-26) | D1I | D2I | D | D1D2 | D1I | I | D1D2 | D2 | D1D2I | D2 | D1 | D2I | I |
| Teser (YT-27) | D1I | D1D2I | NA | D2I | D1I | D1 | D2I | D2I | D1D2I | D2 | D1I | D2I | D1I |
| Xianhong (YT-28) | D1D2I | D1D2I | DI | D1D2 | D1I | D2I | D1I | D1I | D1D2 | D2I | D1D2 | D2I | D2I |
| Gala × Mato 8 (YT-29) | D1D2 | D2I | I | D2I | D1I | D1I | D1 | D1I | D2I | D1 | D1D2 | D2I | D2I |
| Very Early Fuji (YT-3) | D1D2I | D2I | I | D2I | D1I | D1I | D1D2 | D1I | D1D2I | D2 | D1 | D2I | I |
| Qiuhuapi (YT-30) | D1D2I | D2I | D | D2 | I | D1I | D2I | D1 | D1D2 | D2 | D1 | D2I | D2I |
| Piga 70 (YT-31) | D1I | D2I | I | I | I | I | D1I | D1I | D1D2I | D1I | D2I | D1D2 | I |
| Yanzhen 1 (YT-32) | D1I | D2I | D | D2I | D1 | D1D2 | D2I | D1D2 | D1D2 | D2 | D1D2 | D1I | I |
| Matail (YT-34) | D1I | D2I | DI | D2I | D1I | I | D1I | D1I | D2I | D1 | D2I | D2I | I |
| Jonathan-csan (YT-35) | D1D2 | D1D2I | D | D1D2 | D1D2 | D1 | D1I | D1D2 | D1D2I | D1D2 | D1D2 | D2I | D1I |
| Huashuai (YT-36) | D1D2 | D2I | DI | D2 | D1D2 | D1 | D1I | D1D2 | D1D2 | D2 | D1 | D2I | I |
| Wengao 1 (YT-38) | D1D2I | D2I | I | D2I | D1I | D1I | D1D2 | D1I | D1D2I | D2 | D1 | D2I | I |
| Wengao 2 (YT-39) | D1D2I | D2I | I | D2I | D1I | D1I | D1D2 | D1I | D1D2I | D2 | D1 | D2I | I |
| Elegia (YT-4) | D2 | D2I | DI | D2I | D1D2 | D1I | D1I | D2I | D1D2I | D1D2 | D1 | D2I | I |
| Wengao 3 (YT-40) | D1D2I | D2I | I | D2I | D1I | D1I | D1D2 | D1I | D1D2I | D2 | D1 | D2I | I |
| Hong Anka (YT-41) | D1D2I | D2I | D | D1I | D1D2 | D1I | D1I | D1I | D1D2I | D1 | D1I | D2I | I |
| Yanfu 2 (YT-42) | D1D2I | D2I | I | D2I | D1I | D1I | D1D2 | D1I | D1D2I | D2 | D1 | D2I | I |
| Belgolden (YT-43) | I | D2I | DI | I | I | I | D2I | D2I | D1D2I | D1D2I | D1I | I | I |
| Rubinola (YT-44) | D1I | D2I | DI | D2 | D1I | D1I | D2I | D1D2 | D1D2I | D2 | D1 | D2 | I |
| Wangqiuhong (YT-45) | D1D2 | D2I | NA | D1D2I | D1D2I | D1I | I | D2I | D1D2I | D2 | D1I | D1I | I |
| Pulanhong (YT-46) | D2 | D2I | D | D1D2 | D1 | D2I | D2 | D1D2 | D1D2 | D2 | D1 | D2I | D1D2 |
| Bosh (YT-47) | D1D2I | D2I | DI | D1D2 | D1 | D1D2 | D1D2I | D2I | D1D2I | D1D2 | D1D2 | D1I | D1I |
| Chengji 1 (YT-48) | D1D2I | D2I | I | D2I | D1I | D1I | D1D2 | D1I | D1D2I | D2 | D1 | D2I | I |
| Hongli (YT-49) | D1D2 | D2I | DI | D2 | I | D1I | D2 | D2 | D1D2I | D1D2 | D2I | I | D1D2 |
| Guoqinghong (YT-5) | I | D2I | D | D2I | D1I | D1I | D2I | I | D1D2I | D2 | D1I | D2I | I |
| Reandra (YT-50) | D1I | D2I | DI | I | I | I | D2I | D2I | D1D2I | D1D2 | D1 | D2I | D1I |
| Revbihola (YT-51) | D1 | D1D2I | D | D2I | D1I | D1I | D1I | D1I | D1D2 | D1D2 | D1I | D2I |  |
| Melrose (YT-52) | D1D2 | D1D2I | D | D2I | D1D2 | D1I | I | D2 | D1D2I | D2 | D1D2 | D1D2 | I |
| Rewena (YT-53) | D1I | D2I | DI | D2 | D1 | D2 | D1D2 | D1I | D1D2 | D2 | D1I | D1D2I |  |
| Mrxl(robusta × Liberte) (YT-54) | D1D2 | D2I | I | D2I | D1 | D1I | D1I | D1D2 | D1D2I | D1D2 | D1 | D1D2 | I |
| Mollies_Del_open (YT-55) | I | D2I | I | D2I | D1D2I | D1I | D2I | D2I | D1D2I | D2I | D1I | D2I |  |
| Renora (YT-56) | D1I | D2I | D | D2I | D1D2I | I | D1D2 | D2I | D1D2I | D1I | D1I | D2I | I |
| Rosmadzin (YT-57) | D1D2I | D2I | DI | D1D2 | D1 | D1D2 | D1D2I | D2 | D1D2I | D1D2 | D1D2 | D1I | D1I |
| Remo (YT-58) | D1D2I | D2I | D | D2I | D1D2I | D1I | D1 | D1 | D2I | D1 | D1D2 | D2I | I |
| Pilot (YT-59) | D1I | D2I | D | I | I | I | D1I | D1I | D1D2 | D2 | D1 | I | D1I |

-continued

Construction results of InDel marker genotype database of *Malus* germplasm resources

| | | | | | | | | | | | | |
|---|---|---|---|---|---|---|---|---|---|---|---|---|
| Yangbai Crab (YT-6) | D1D2 | D2I | D | D1D2 | D1D2 | D2 | D2 | D1D2 | D1D2I | D2 | D2 | I | D1 |
| Free Red Star (YT-60) | D1D2 | D2I | D | D2 | D1D2 | D1I | D1I | D1I | D1D2 | D2I | D1I | D2I | D1D2 |
| Idared (YT-61) | D1I | D1D2I | D | D2I | D1I | D1I | D1I | D2I | D1D2 | D2 | D1 | D1I | I |
| Mingyue (YT-62) | I | D1D2I | I | D2I | D1D2 | D1I | D1I | D1I | D2I | D1D2 | D1I | I | I |
| Piga 101 (YT-63) | I | D2I | D | D2I | D1I | D1I | D2I | D1I | D1D2I | D2I | D2I | D2I | I |
| Yanfu 5 (YT-64) | D1D2I | D2I | I | D2I | D1I | D1I | D1D2 | D1I | D1D2I | D2 | D1 | D2I | I |
| Early Jonagold (YT-65) | D1D2I | D2I | DI | D1I | D1I | D1I | D1D2I | D2I | D1D2I | D1D2I | D1I | I | I |
| Wengao 2 mutant (YT-66) | D1D2I | D2I | I | D2I | D1I | D1I | D1D2 | D1I | D1D2I | D2 | D1 | D2I | I |
| Fenhong Gala 44 (YT-67) | D1 | D2I | D | D2 | D1D2 | D1I | D1I | D1D2 | D1D2I | D1D2I | I | I | D2I |
| Yiyuanhong (YT-68) | D1D2I | D2I | I | D2I | D1I | D1I | D1D2 | D1I | D1D2I | D2 | D1 | D2I | I |
| Yanfu 4 (YT-69) | D1D2I | D2I | I | D2I | D1I | D1I | D1D2 | D1I | D1D2I | D2 | D1 | D2I | I |
| White Pearmain (YT-70) | D1D2I | D2I | DI | D1I | D1I | I | D1D2 | D1D2 | D1D2I | D2 | D1 | D1D2 | I |
| Jonathan-early (YT-73) | D1D2 | D1D2I | D | D1D2 | D1D2 | D1 | D1I | D1D2 | D1D2I | D1D2 | D1D2 | D2I | D1I |
| Jonathan-midle (YT-74) | D1D2 | D1D2I | D | D1D2 | D1D2 | D1 | D1I | D1D2 | D1D2I | D1D2 | D1D2 | D2I | D1I |
| Gornan (YT-75) | D1D2I | D2I | D | D2I | D1D2I | D1I | D1I | D2I | D1D2 | D1D2 | D1 | D1I | I |
| Regilndel (YT-76) | D1 | D1D2I | D | D2I | D1I | D1I | D1I | D1I | D1D2 | D2 | D1D2 | D1I | D2I |
| Golden Bell (YT-77) | D1D2I | D2I | D | I | D1I | D2I | D1I | D1I | D1D2I | D1D2 | D1I | D1I | D1I |
| Arkcharm (YT-78) | D1D2I | D2I | D | D1D2 | D1D2 | D1I | D2 | D1D2 | D1D2I | D2 | D1 | D2I | D2 |
| Redchif (YT-79) | D1D2I | D2I | D | D2 | D1 | D1D2 | D1I | D1 | D2I | D1 | D1D2 | D2I | I |
| Mouping Guanghua Fuji (YT-8) | D1D2I | D2I | I | D2I | D1I | D1I | D1D2 | D1I | D1D2I | D2 | D1 | D2I | I |
| Freedom (YT-80) | D1I | D2I | D | I | I | I | D1I | D1I | D1D2 | D2 | D1 | I | D1I |
| Martinike (YT-81) | D1I | D2I | D | D2 | D1D2 | D1I | D2I | D1D2 | D1D2 | D2 | D1D2 | D1D2 | I |
| Sweetle (YT-82) | D1I | D2I | I | D1I | D1I | D1I | D1I | D1I | D1D2I | D1D2 | D2 | D2 | I |
| Aleksanader (YT-83) | D1D2 | D1D2I | I | D2 | D1D2I | D1I | D2I | D1 | D1D2I | D1D2 | D1 | D2I | D2I |
| Yan 6 Fenhong 143 (YT-84) | I | D2I | D | D2I | D1D2I | I | I | D1D2 | D2I | D1 | D1D2 | I | D2I |
| Ruitina (YT-85) | D1 | D2I | D | D2I | D1I | D1I | D1I | D1I | D1D2 | D2I | D1I | D2I | D2I |
| Wengao 1 mutant (YT-86) | D1D2I | D2I | I | D2I | D1I | D1I | D1D2 | D1I | D1D2I | D2 | D1 | D2I | I |
| Wengao 3 mutant (YT-87) | D1D2I | D2I | I | D2I | D1I | D1I | D1D2 | D1I | D1D2I | D2 | D1 | D2I | D1I |
| Shajinyilamu (YT-88) | D2 | D1D2I | D | D2 | D1 | D1D2 | D2 | D2 | D1D2I | D2 | D2 | I | D1 |
| Qiuhong (YT-89) | D1D2 | D2I | I | D1D2 | D1D2I | D1D2 | D1I | D1D2 | D1D2 | D2 | D1 | D1D2 | D1I |
| Changyanghong (YT-9) | D1D2I | D2I | I | D2I | D1I | D1I | D1D2 | D1I | D1D2I | D2 | D1 | D2I | I |
| Yanfu 8 (YT-90) | D1D2I | D2I | I | D2I | D1I | D1I | D1D2 | D1I | D1D2I | D2 | D1 | D2I | I |
| Jinduhong Gala (YT-91) | D1I | D2I | DI | D2I | D1I | I | D1I | D1I | D2I | D1 | D2I | D2I | I |
| Nagafu 2 (YT-92) | D1D2I | D2I | I | D2I | D1I | D1I | D1D2 | D1I | D1D2I | D2 | D1 | D2I | I |
| Honglu seedling 65 (YT-93) | D2 | D2I | I | D1I | D1 | D2I | D1I | D1I | D1D2I | D2I | D1 | D2I | D2I |
| Tsugaru (YT-94) | D1D2I | D1D2I | D | D1I | D1D2I | D1I | D1I | D1I | D2I | D1 | D2I | I | I |
| Jinshuai mutant (YT-95) | D1I | D2I | DI | D2I | D1I | I | D2I | D2I | D1D2 | D2I | D1I | D1I | I |
| Taishan Crab (YT-96) | D1 | D2I | D | D1D2 | D1 | D1D2 | D1D2 | D1 | D1D2 | NA | D1D2 | D2I | D1 |

-continued

| Construction results of InDel marker genotype database of *Malus* germplasm resources | | | | | | | | | | | | |
|---|---|---|---|---|---|---|---|---|---|---|---|---|
| Luli (YT-98) | D1D2 | D2I | I | I | D1I | D2I | D1 | D1 | D2I | D1 | D1D2 | I | D2I |
| 10-182 (YX-10-182) | I | D2I | DI | D2 | D1I | D1D2 | D2 | D1I | D1D2I | D2 | D1 | D2I | D1I |
| 01-001 (YX-01-001) | I | D2I | D | D2I | D1I | D2I | D1D2 | D1 | D1D2I | D2 | D1 | D2I | D1I |
| 01-121 (YX-01-121) | I | D2I | DI | D2 | I | I | D2 | D1I | D1D2I | D2 | D1D2 | I | D1I |
| 02-009 (YX-02-009) | D2 | D2I | D | D2I | D1 | D2I | D2 | D1I | D1D2I | D2 | D1D2 | D2I | I |
| 03-010 (YX-03-010) | D1D2I | D2I | D | D2I | D1I | I | D1D2 | D1 | D1D2I | D2 | D1D2 | D2I | D1I |
| 03-111 (YX-03-111) | D2 | D2I | DI | D2 | D1I | D1D2 | D2 | D1I | D1D2I | D2 | D1D2 | I | D1I |
| 04-033 (YX-04-033) | D1D2I | D2I | D | D2 | D1 | D1D2 | D1D2 | D1 | D1D2I | D2 | D1D2 | D2I | D1I |
| 04-087 (YX-04-087) | D2 | D2I | DI | D2I | D1 | D2I | D1D2 | D1 | D1D2I | D2 | D1D2 | D2I | I |
| 06-056 (YX-06-056) | D1D2I | D2I | DI | D2 | I | D1I | D1D2 | D1 | D1D2I | D2 | D1 | D2I | I |
| 08-034 (YX-08-034) | I | D2I | DI | D2 | D1I | D1D2 | D1D2 | D1I | D1D2 | D2 | D1 | I | I |
| 09-037 (YX-09-037) | D1D2I | D2I | DI | D2I | D1I | D2I | D1D2 | D1 | D1D2I | D2 | D1 | I | D1I |
| 09-079 (YX-09-079) | D2 | D2I | D | D2I | D1 | D2I | D1D2 | D1 | D1D2I | D2 | D1 | D2I | I |
| 10-010 (YX-10-010) | I | D2I | DI | D2 | D1I | D1D2 | D2 | D1I | D1D2I | D2 | D1 | D2I | D1I |
| 11-037 (YX-11-037) | D1D2I | D2I | D | D2 | D1I | D1D2 | D2 | D1I | D1D2 | D2 | D1D2 | D2I | I |
| 11-206 (YX-11-206) | D2 | D2I | D | D2I | D1 | D2I | D2 | D1I | D1D2I | D2 | D1D2 | I | D1I |
| 12-206 (YX-12-206) | D1D2I | D2I | DI | D2 | I | D1I | D1D2 | D1 | D1D2I | D2 | D1 | D2I | D1I |
| 13-025 (YX-13-025) | D1D2I | D2I | DI | D2I | D1I | D1I | D1D2 | D1I | D1D2I | D2 | D1D2 | I | D1I |
| 16-155 (YX-16-155) | D1D2I | D2I | D | D2I | D1I | I | D1D2 | D1 | D1D2 | D2 | D1 | D2I | D1I |
| 16-157 (YX-16-157) | D1D2I | D2I | D | D2 | I | D1I | D2 | D1I | D1D2I | D2 | D1D2 | I | D1I |
| 17-023 (YX-17-023) | I | D2I | D | D2I | D1I | D2I | D2 | D1I | D1D2I | D2 | D1 | D2I | D1I |
| 17-199 (YX-17-199) | D2 | D2I | D | D2 | D1I | D1D2 | D1D2 | D1 | D1D2I | D2 | D1 | I | D1I |
| 21-005 (YX-21-005) | D1D2I | D2I | DI | D2I | D1I | D2I | D2I | D1I | D1D2I | D2I | D1D2 | I | D1I |
| 21-018 (YX-21-018) | D1D2I | D2I | D | D2I | D1I | D2I | D2 | D1D2 | D1D2I | D2I | D1D2 | I | D1I |
| 22-186 (YX-22-186) | D1D2I | D2I | D | D2I | I | I | D2 | D1D2 | D1D2 | D2I | D1I | I | D1I |
| 27-003 (YX-27-003) | D1D2I | D2I | D | D2I | I | I | D2I | D1I | D2I | D1D2 | D1 | I | I |
| 29-176 (YX-29-176) | I | D2I | DI | D2I | I | D2I | D2I | D1I | D1D2I | D2I | D1I | I | D1I |
| 30-001 (YX-30-001) | I | D2I | DI | D2I | D1I | D2I | D2I | D1I | D1D2I | D1D2 | D1 | I | D1I |
| 33-018 (YX-33-018) | I | D2I | D | D2 | D1 | D1D2 | D2 | D1I | D2I | D2 | D1D2 | D2I | D1I |
| 33-101 (YX-33-101) | I | D1D2I | D | D2 | I | D1I | D1D2 | D1 | D2I | D2 | D1D2 | I | D1I |
| 33-151 (YX-33-151) | I | D2I | DI | D2I | I | I | D2I | D1I | D1D2I | D1D2 | D2I | I | D1I |
| 51-007 (YX-51-007) | D1I | D2I | D | D2I | D1I | D1I | D2I | D2 | D1D2I | D1D2 | D1I | D2I | D1I |
| 51-031 (YX-51-031) | D1D2I | D2I | I | D2I | D1D2I | D1I | D1I | D2I | D1D2I | D2I | D1I | I | D1I |
| 51-077 (YX-51-077) | D1D2I | D2I | DI | D1I | D1I | D1I | D1I | D1I | D2I | D1 | D1 | I | D1I |
| 51-102 (YX-51-102) | D1D2I | I | DI | D1I | D2I | D1I | D1D2I | D2 | D2 | D2I | D1D2I | D2I | NA |
| 51-139 (YX-51-139) | D1I | D1D2I | D | D1I | D1D2I | D1I | I | D2I | D1D2 | D2I | D1 | I | D1I |
| 51-165 (YX-51-165) | D1I | D1D2I | I | D2I | D1I | D1I | D1I | D2I | D1D2I | D1D2 | D1 | I | I |
| 51-166 (YX-51-166) | D1I | D2I | D | D2I | D1I | D1I | I | D2I | D2I | D1 | D1I | I | I |
| 51-209 (YX-51-209) | D1D2I | D2I | DI | D2I | D1I | D1I | D1I | D1I | D1D2 | D2I | D1 | I | I |

-continued

| Construction results of InDel marker genotype database of *Malus* germplasm resources | | | | | | | | | | | | |
|---|---|---|---|---|---|---|---|---|---|---|---|---|
| 52-049 (YX-52-049) | D1I | D1D2I | D | D2I | D1D2I | D1I | D2I | D2 | D1D2I | D1I | D1 | I | D1I |
| 52-151 (YX-52-151) | D1I | D1D2I | D | D2I | D1D2I | D1I | D1I | D1I | D1D2I | D1D2 | D2I | D2I | D1I |
| 52-160 (YX-52-160) | D1D2I | D2I | DI | D2I | D1I | D1I | I | D2I | D1D2I | D1D2 | D1I | D2I | D1I |
| 53-040 (YX-53-040) | D1I | D1D2I | I | D2I | D1I | D1I | D1I | D2I | D1 | D2I | I | I |
| 53-205 (YX-53-205) | D1D2I | D2I | I | D2 | D1I | D1I | D1 | D1 | D1D2I | D2 | D1 | D2 | D1I |
| 54-001 (YX-54-001) | D1I | D1D2I | D | I | D1D2I | D1I | D2I | D2 | D2I | D1 | D1D2 | I | D1I |
| 54-188 (YX-54-188) | D1D2I | D1D2I | I | D1I | D1I | D1I | D2I | D2 | D2I | D1 | D1 | D2I | D1I |
| 55-006 (YX-55-006) | D1I | D1D2I | DI | D2I | D1I | D1I | I | D2I | D1D2I | D1I | D1D2 | I | I |
| 55-023 (YX-55-023) | D1I | D2I | DI | D2I | D1I | D1I | D1I | D1I | D1D2 | D2I | D1 | I | D1I |
| 55-042 (YX-55-042) | D1I | D1D2I | D | D2I | D1D2I | D1I | D1D2 | D1D2 | D1D2I | D1I | D1I | I | I |
| 56-081 (YX-56-081) | D1D2I | D1D2I | DI | D2I | D1D2I | D1I | D2I | D2 | D1D2 | D2I | D1 | I | I |
| 57-128 (YX-57-128) | D1I | D1D2I | D | D1I | D1D2I | D1I | I | D2I | D1D2 | D2I | D1 | I | D1I |
| 58-036 (YX-58-036) | D1I | D1D2I | D | D1D2I | D1I | D1I | D1I | D1I | D1D2 | D2I | D1 | I | D1I |
| 58-089 (YX-58-089) | D1D2I | D2I | I | D2I | D1I | D1I | I | D2I | D1D2 | D2I | D2I | D2I | I |
| 58-144 (YX-58-144) | D1D2I | D1D2I | I | D1I | D1I | D1I | D2I | D2 | D2I | D1 | D1 | D2I | D1 |
| 58-177 (YX-58-177) | D1I | D2 | NA | D2 | D1I | D1I | D2I | D2 | D2I | D1 | D1D2 | D2I | D1I |
| 58-211 (YX-58-211) | D1D2I | D1D2I | D | D2I | D1I | D1I | D1D2 | NA | D1D2 | D2I | D2I | I | D1I |
| 59-086 (YX-59-086) | D1D2I | D2I | I | D1D2I | D1D2I | D1I | D1I | D1I | D1D2I | D1I | D2I | D2I | D1I |
| 59-130 (YX-59-130) | D1I | D1D2I | I | D2I | D1D2I | D1I | D1D2 | D1D2 | D1D2 | D2I | D1D2 | I | D1I |
| Jersey Mac (Z-1) | D1D2I | D2I | D | D2 | I | I | D2 | D2 | D1D2 | D2 | D1I | D1I | D1D2 |
| Gale Gala (Z-10) | D1I | D2I | DI | D2I | D1I | I | D1I | D1I | D2I | NA | D2I | D2I | I |
| Li Gala (Z-11) | D1I | D2I | DI | D2I | D1I | I | D1I | D1I | D2I | D1 | D2I | D2I | I |
| Yanga 1 (Z-12) | D1I | D2I | DI | D2I | D1I | I | D1I | D1I | D2I | I | D2I | D2I | I |
| NAKT M9 clone (Z-13) | D2 | D2I | D | D2 | D1I | D1I | D1I | D1I | D1D2I | D2 | D1 | D2I | D1I |
| Royal Gala (Z-14) | D1I | D2I | DI | D1I | D1I | I | D1I | D1I | D2I | D1 | D2I | D2I | I |
| Huajia (Z-15) | D1D2 | D2I | DI | D2 | D1 | I | D1D2 | D1 | D1D2 | D2 | D1D2 | I | D2I |
| Dorsett Golden (Z-16) | D2 | D2I | D | D1I | D1I | I | D2I | D2I | D1D2I | D2 | D1I | D2I | D1D2 |
| 99-2-58 (Z-17) | D1D2I | I | D | D2I | D1I | D1I | D1D2 | D1I | D1D2 | D2 | D1D2 | D2I | D2I |
| Galaxy (Z-18) | D1I | D2I | DI | D2I | D1I | I | D1I | D1I | D2I | D1 | D2I | D2I | I |
| Royal New Gala (Z-19) | D1I | D2I | DI | D2I | D1I | I | D1I | D1I | D2I | D1 | D2I | D2I | I |
| 99-1-29 (Z-22) | D1D2I | D2I | DI | D1I | D1I | D2I | D1D2 | D2I | D1D2 | D2 | D1D2 | D1 | D1D2 |
| Seokwang (Z-23) | D1I | D1D2I | D | D2I | D2I | D1I | D2I | D1I | D1D2I | D1D2 | D1I | I | D1I |
| Fuhong Zaoga (Z-24) | D1I | D2I | DI | D2I | D1I | I | D1I | D1I | D2I | D1 | D2I | D2I | I |
| Maiyan (Z-25) | D1D2I | I | D | D2 | D1 | D1I | D2I | D1I | D1D2 | D2 | D1 | I | D2I |
| Shandong 1 (Z-26) | D1I | D2I | DI | D2I | D1I | I | D1I | D1I | D2I | D1 | D2I | D2I | I |
| Gala Queen (Z-27) | D1I | D2I | DI | D2I | D1I | I | D1I | D1I | D2I | D1 | D2I | D2I | I |
| 99-2-39 (Z-29) | D1D2I | I | D | D2I | D1I | D1I | D1I | D1I | D1D2I | I | D1D2 | I | D2 |
| Sweetle (Z-3) | D1I | D2I | I | D1I | D1I | D1I | D1I | D1I | D1D2I | D1D2 | D1D2 | D2 | I |

-continued

Construction results of InDel marker genotype database of *Malus* germplasm resources

| | | | | | | | | | | | | |
|---|---|---|---|---|---|---|---|---|---|---|---|---|
| Dalian Da Gala (Z-30) | D1I | D2I | DI | D2I | D1I | I | D1I | D1I | D2I | D1 | D2I | D2I | I |
| Huaxing (Z-31) | D1D2I | D2I | DI | D2I | D1 | D2I | D2I | D2I | D2I | D1 | D1D2 | I | D2I |
| Li Gala (Z-32) | D1I | D2I | DI | D2I | D1I | I | D1I | D1I | D2I | D1 | D2I | D2I | I |
| Fuhong Zaoga (Z-33) | D1I | D2I | I | D2I | D1I | D1I | D1D2 | D1D2 | D2I | D1 | D1D2 | I | D2I |
| Yanga (Z-34) | D1I | D2I | I | D2I | D1I | D1I | D1D2 | D1D2 | D2I | D1 | D1D2 | I | D2I |
| Royal Gala (Z-35) | D1I | D2I | DI | D2I | D1I | I | D1I | D1I | D2I | D1 | D2I | D2I | I |
| Shijiazhuang Gala (Z-37) | D1I | D2I | DI | D2I | D1I | I | D1I | D1I | D2I | D1 | D2I | D2I | I |
| Taihong Gala (Z-38) | D1I | D2I | DI | D2I | D1I | I | D1I | D1I | D2I | D1 | D2I | D2I | I |
| Anna (Z-39) | D2 | D1D2I | D | D2 | D1 | D2 | D2I | D1D2 | D1D2 | D2 | D1 | D2I | D1D2 |
| Hong Zhenzhu (Z-4) | D1I | D2I | I | D2I | D1 | D2I | D1D2 | D1D2 | D2I | D1 | D1I | D2I | D2I |
| Qiuhong Gala (Z-40) | D1D2I | D1D2I | D | D1I | D1D2I | D1I | D1I | D1I | D2I | D1 | D2I | I | I |
| Shandong 2 (Z-41) | D1I | D2I | DI | D2I | D1I | I | D1I | D1I | D2I | D1 | D2I | D2I | I |
| Shandong 6 (Z-42) | D1I | D2I | DI | D2I | D1I | I | D1I | D1I | D2I | D1 | D2I | D2I | I |
| Chenyang (Z-43) | D1I | D2I | D | I | D1I | I | D1I | I | D2I | D1 | I | I | I |
| Dongqie Gala (Z-44) | D1D2I | D2I | D | D2I | D1D2I | D1I | D1 | D1 | D2I | D1 | D1D2 | D2I | I |
| Royal Gala (Z-45) | D1I | D2I | DI | D2I | D1I | I | D1I | D1I | D2I | D1 | D2I | D2I | I |
| Taishan Gala (Z-47) | D1I | D2I | DI | D2I | D1I | I | D1I | D1I | D2I | D1 | D2I | D2I | I |
| Shandong 7 (Z-48) | D1I | D2I | DI | D2I | D1I | I | D1I | D1I | D2I | D1 | D2I | D2I | I |
| Regal gala (Z-49) | D1I | D2I | DI | D2I | D1I | I | D1I | D1I | D2I | D1 | D2I | D2I | I |
| NAKB clone (Z-5) | D2 | D2I | D | D2 | D1I | D1I | D1 | D1I | D1D2I | D2 | D1 | D2I | D1I |
| Royal gala (Z-50) | D1I | D2I | DI | D2I | D1I | I | D1I | D1I | D2I | D1 | D2I | D2I | I |
| Znoga (Z-51) | D1I | D2I | DI | D1D2 | D1I | D1D2 | D2 | D1D2I | D1D2I | D1D2I | D1D2 | D1D2I | I |
| Shandong 5 (Z-52) | D1I | D2I | DI | D2I | D1I | I | D1I | D1I | D2I | D1 | D2I | D2I | I |
| Rockit (Z-53) | D1I | D2I | I | D2I | D1I | D1I | D1 | D1 | D2I | D1 | D1I | I | I |
| Shandong 3 (Z-54) | D1I | D2I | DI | D2I | D1I | I | D1I | D1I | D2I | D1 | D2I | D2I | I |
| Mondel Gala (Z-55) | D1I | D2I | DI | D2I | D1I | I | D1I | D1I | D2I | D1 | D2I | D2I | I |
| Alvinagala (Z-56) | D1I | D2I | DI | D2I | D1I | I | D1I | D1I | D2I | D1 | D2I | D2I | I |
| M9 pajam2 (Z-6) | D2 | D2I | D | D2 | D1I | D1I | D1 | D1I | D1D2I | D2 | D1 | D2I | D1I |
| Jinshiji (Z-7) | D1I | D2I | DI | D2I | D1I | I | D1I | D1I | D2I | D1 | D2 | D2I | I |
| Huarui (Z-8) | D1D2 | D2I | I | D2I | D1 | D2 | D1D2 | D1D2 | D1D2I | D1D2 | D1D2 | D2I | D2 |
| Hongcuibao (Z-9) | D1D2 | D2I | DI | I | D1I | D2I | D2I | D2I | D2I | D1 | D1I | I | D2I |

| Accession name (Accession ID) | C04021 | C07048 | C08057 | C08058 | C09068 | C12086 | C05135 | C12090 | C05032 | C08056 | C13096 |
|---|---|---|---|---|---|---|---|---|---|---|---|
| Black Ben Davis (10--1) | DI2 | I1 | DI1I2 | DI2 | DI1I2 | DI2 | I1I2 | DI2I3 | D2I2 | D1 | D1D2D3I |
| Lysgolden (10--10) | DI1 | DI1 | DI1I2 | DI2 | DI1I2 | D | DI1I2 | I1I2I3 | DI2 | D1 | D1D2D3 |
| Dongchengguan 13 (10--11) | DI1 | DI1 | DI1I2 | DI2 | DI1I2 | D | DI1I2 | I1I2I3 | DI2 | D1 | D1D2D3 |
| Nagafu 1 (10--12) | DI1I2 | DI1 | DI1I2 | DI2 | DI1I2 | D | DI1I2 | I1I2I3 | DI2 | D1 | D1D2D3 |
| Shengli Hongguan (10--14) | I2 | D | DI1 | DI1 | DI1I2 | DI2 | DI1 | DI2I3 | D2 | D1I | D1D2D3I |
| Shizishan 1 (10--15) | I2 | D | DI1 | DI1 | DI1I2 | DI2 | DI1 | DI2I3 | D2 | D1I | D1D2D3I |

-continued

| Construction results of InDel marker genotype database of *Malus* germplasm resources | | | | | | | | | | | |
|---|---|---|---|---|---|---|---|---|---|---|---|
| Baoman (10--2) | I2 | D | DI1 | DI2 | DI1I2 | DI1 | I1I2 | DI2 | D1D2 | D1 | D1D2D3 |
| Melba (10--20) | I2 | I1I2 | DI1I2 | DI2 | DI1I2 | DI1 | I1I2 | DI2I3 | D1D2 | D1 | D1D3 |
| Kuliesa (10--21) | I2 | DI1 | DI1I2 | DI1I2 | DI1I2 | DI2 | DI1I2 | I2I3 | D2I2 | D1I | D1D2D3 |
| De 8 (10--22) | DI2 | I2 | DI1I2 | DI1I2 | DI1I2 | I1I2 | DI1I2 | I2 | D2 | D1I | D1D2D3 |
| Bo 5 (10--23) | I1I2 | D | DI1I2 | DI2 | DI1I2 | DI2 | DI1 | DI2I3 | D2I2 | D1 | D1D2D3 |
| Iran Pippin (10--4) | D | DI1 | DI1 | DI2 | DI1I2 | D | DI1I2 | DI2I3 | D2I2 | D1 | D1D2D3 |
| Sakatakei Tsugaru (10--5) | I1I2 | DI2 | DI1I2 | DI1I2 | DI1I2 | DI2 | DI1I2 | I2I3 | D2 | D1I | D1D2D3I |
| Khrushchev (10--6) | I1I2 | DI2 | DI1I2 | DI2 | DI1I2 | DI1I2 | DI1I2 | DI1I2I3 | D2I2 | D1 | D1D2D3 |
| Batul (10--7) | DI2 | D | DI1I2 | DI1I2 | DI1I2 | I1 | I1I2 | DI2I3 | D1D2 | D1 | D1D2D3 |
| Prime Gold (10--9) | DI2 | DI1 | DI1I2 | DI1I2 | DI1I2 | I1 | I1I2 | DI2I3 | D1D2 | D1 | D1D2D3 |
| Jie 1 (11--0) | I2 | D | DI1I2 | DI2 | DI1I2 | DI2 | DI1I2 | DI2I3 | D2 | D1 | D1D2D3I |
| Guldborg (1--11) | DI1 | DI1 | DI1I2 | DI2 | DI1I2 | D | DI1I2 | I1I2I3 | D1D2 | D1 | D1D2D3 |
| Shajin Yilamu (11--10) | DI2 | D | DI1I2 | DI2 | DI1I2 | DI1 | I1I2 | DI2 | D2 | D1 | D1D2D3 |
| Soviet (11--11) | DI2 | D | DI1I2 | DI2 | I1I2 | I1 | DI1I2 | I2I3 | D2 | D1 | D1D2D3 |
| Lobo (11--13) | I1I2 | D | DI1I2 | DI2 | DI1I2 | I1 | DI1I2 | DI2I3 | D2 | D1 | D1D3 |
| Allington Pippin (11--14) | I2 | DI1 | DI1I2 | DI1I2 | DI1I2 | DI2 | DI1I2 | DI1I2 | D1D2 | D1 | D1D2D3 |
| Malinova (11--15) | I1I2 | D | DI1I2 | DI2 | DI1I2 | DI1 | I1I2 | DI2I3 | D1D2 | D1 | D1D2D3 |
| Sweet McIntosh (11--16) | I1I2 | D | DI1I2 | DI2 | DI1I2 | DI1 | I1I2 | DI2I3 | D1D2 | D1 | D1D2D3 |
| McIntosh (11--18) | I2 | DI1 | DI1I2 | DI1I2 | DI1I2 | DI2 | I1I2 | DI1I2I3 | D2I2 | D1 | D1D2D3 |
| Spartan (11--2) | I2 | DI2 | DI1I2 | DI1I2 | DI1I2 | I1I2 | I1I2 | DI1I2I3 | D2I2 | D1 | D1D2D3 |
| Fushuai (1--12) | I1I2 | I1I2 | DI1I2 | DI2 | DI1I2 | DI2 | I1I2 | DI1I2 | D2I2 | D1 | D1D2D3I |
| Summer Pearmain (11--20) | DI1 | DI1 | DI1I2 | DI1 | DI1I2 | I1I2 | I1I2 | DI2I3 | D2 | D1 | D1D2D3 |
| Helm (11--21) | DI2 | DI2 | DI1 | DI1I2 | DI1I2 | D | I1I2 | I2I3 | D2 | D1 | D1D2D3 |
| Domenesti (11--3) | DI1I2 | DI1 | DI1I2 | DI2 | DI1I2 | DI2 | DI1I2 | DI1I2I3 | D2 | D1 | D1D2D3I |
| I2arly Harvest (1--13) | I1I2 | I1I2 | DI1I2 | DI2 | DI1I2 | DI2 | I1I2 | DI1I2 | D2I2 | D1 | D1D2D3I |
| Silver Spur Red Delicious (11--4) | DI2 | DI1 | DI1I2 | DI1I2 | DI1I2 | DI2 | I1I2 | DI1I2I3 | I2 | D1 | D1D2D3 |
| Dongxiangjiao (11--5) | DI2 | I1I2 | DI1I2 | DI1I2 | DI1I2 | D | DI1 | DI1I2I3 | D1D2 | D1 | D1D2D3I |
| Guoling (1--15) | I2 | D | DI1I2 | DI2 | DI1I2 | D | I1I2 | DI2I3 | D1D2 | D1I | D1D2D3I |
| Skyline Spureme (11--8) | DI2 | DI1 | DI1I2 | DI1I2 | DI1I2 | DI2 | I1I2 | DI1I2I3 | I2 | D1 | D1D2D3 |
| Chantecler (11--9) | I2 | I1 | DI1I2 | DI2 | DI1I2 | I1 | I1I2 | DI2I3 | D1D2 | D1 | D1D2D3I |
| Close (1--19) | DI2 | DI2 | DI1I2 | DI1I2 | DI1I2 | DI2 | DI1I2 | DI2 | D1D2 | D1 | D1D2D3I |
| Aizaohui (1--2) | I2 | DI1 | DI1I2 | DI2 | DI1I2 | DI2 | I1I2 | DI2I3 | D2I1 | D1I | D1D2D3I |
| Wuyue (12--1) | DI2 | DI1 | DI1I2 | DI1I2 | DI1I2 | DI1 | DI1I2 | DI2I3 | D1I1 | D1 | D1D2D3I |
| Bukowka (12--11) | D | DI1 | DI1I2 | DI1I2 | DI1I2 | I1 | I1I2 | DI1I2 | D1D2 | D1 | D1D2D3 |
| Jinyu (12--12) | I2 | D | DI1I2 | DI2 | DI1I2 | DI2 | DI1I2 | DI2I3 | D2 | D1 | D1D2D3I |
| Calville Rouge (12--14) | DI2 | DI1 | DI1I2 | DI2 | DI1I2 | DI2 | DI1I2 | DI1I2 | D2 | D1 | D1D2D3I |
| Doyle (12--15) | DI2 | DI1 | DI1I2 | DI2 | DI1I2 | I1I2 | I1I2 | DI2I3 | D2I2 | D1 | D1D2D3 |
| Melrose (12--16) | I2 | DI1 | DI1I2 | DI1I2 | DI1I2 | DI2 | DI1I2 | I2I3 | D2I2 | D1 | D1D2D3I |

-continued

| Construction results of InDel marker genotype database of *Malus* germplasm resources | | | | | | | | | | | |
|---|---|---|---|---|---|---|---|---|---|---|---|
| Menage (12--17) | I1I2 | DI1 | DI1I2 | DI2 | DI1I2 | DI1 | I1I2 | DI2 | D1D2 | D1 | D1D2D3I |
| Bo 26 (12--18) | DI2 | I1I2 | DI1 | DI1I2 | DI1I2 | D | I1I2 | DI2I3 | D1D2 | D1 | D1D2D3 |
| Duoyilu (12--19) | DI1 | I1I2 | DI1I2 | DI2 | DI1I2 | DI2 | DI1 | I2 | D2 | D1 | D1D2D3I |
| De 6 (12--20) | I1I2 | D | DI1I2 | DI1I2 | DI1I2 | D | DI1I2 | DI2I3 | D1I2 | D1 | D1D2D3 |
| Red June (12--21) | D | I1I2 | DI1I2 | DI1I2 | DI1I2 | I1I2 | DI1 | DI2 | D2 | D1 | D1D2D3 |
| Helasang (12--23) | I2 | DI2 | DI1I2 | DI2 | DI1I2 | DI1 | I1I2 | DI2I3 | D1I1 | D1 | D1D2D3 |
| Hesetiaowen (12--3) | DI2 | DI2 | DI1I2 | DI2 | DI1I2 | I1 | I1I2 | DI2I3 | D2 | D1 | D1D2D3 |
| James Grieve (1--23) | D | DI2 | DI1 | DI2 | I1I2 | D | I1I2 | DI2I3 | D2I1 | D1 | D1D2D3 |
| Bailuosi Malin (12--4) | DI1 | DI1 | DI1I2 | DI1I2 | DI1I2 | DI1 | I1I2 | DI2I3 | D2 | D1 | D1D2D3 |
| Jinnhong (12--5) | DI2 | D | DI1I2 | DI2 | DI1I2 | I2 | I1I2 | DI2I3 | D1D2 | D1 | D2D3I |
| Kay Sai William (12--6) | I2 | DI2 | DI1I2 | DI1I2 | DI1I2 | I1I2 | I1I2 | DI1I2I3 | I2 | D1 | D1D2D3 |
| Xingjiang Pingguo (12--7) | D | D | DI1I2 | DI2 | DI1I2 | DI1 | I1I2 | DI2 | D1D2 | D1 | D1D2D3 |
| Jie 15 (12--8) | DI2 | DI1 | DI1I2 | DI1I2 | DI1I2 | DI2 | I1I2 | DI1I2I3 | I2 | D1 | D1D2D3 |
| Mianpingguo (12--9) | I2 | D | DI1I2 | DI2 | DI1I2 | DI1 | I1I2 | DI2 | D1D2 | D1 | D1D2D3 |
| Lowver (1--3) | D | DI2 | DI1I2 | DI2 | DI1I2 | I1 | I1I2 | DI2I3 | D1D2 | D1D3 | D1D2D3 |
| Benoni (13--1) | I2 | DI1 | DI1I2 | DI1I2 | DI1I2 | D | DI1I2 | I2I3 | D2 | D1 | D1D3I |
| Fa 5 (13--11) | I2 | DI1 | DI1I2 | DI2 | DI1I2 | DI1I2 | DI1I2 | DI1I2 | D1D2 | D1 | D1D2D3I |
| Babskino (13--12) | DI2 | DI2 | DI1I2 | DI2 | DI1I2 | I1 | I1I2 | DI2I3 | D1 | D1 | D1D2D3 |
| Kuluona (13--13) | DI1 | DI1 | DI1I2 | DI1I2 | DI1I2 | DI2 | DI1I2 | DI1I2I3 | D1D2 | D1 | D1D2D3I |
| Shidonghaoji (13--16) | I2 | D | DI1 | DI1 | DI1I2 | DI2 | DI1 | DI2I3 | D2 | D1I | D1D2D3I |
| Oberkika (13--17) | D | I1 | DI1I2 | DI1I2 | DI1I2 | DI2 | DI1I2 | I1I2 | D1I2 | D1 | D1D2D3 |
| Budayi (13--19) | DI1 | DI1 | DI1I2 | DI2 | DI1I2 | D | DI1I2 | I1I2I3 | D1I2 | D1 | D1D2D3 |
| Red Canada (13--2) | I2 | DI1 | DI1I2 | DI2 | DI1I2 | DI1I2 | DI1I2 | DI1I2 | D1D2 | D1 | D1D2D3I |
| Laidi (13--20) | DI2 | D | DI1 | DI2 | DI1I2 | I1 | DI1I2 | DI2 | D1D2 | D1 | D1D2D3 |
| N2 (13--22) | DI2 | DI1 | DI1I2 | DI1I2 | DI1I2 | D | DI1I2 | DI2I3 | D2I2 | D1 | D1D2D3 |
| Norsan (13--5) | DI2 | DI1 | DI1I2 | DI1I2 | DI1I2 | DI2 | I1I2 | DI1I2I3 | I2 | D1 | D1D2D3 |
| Hebei Kangbing Golden Delicious (13--6) | I2 | I1 | DI1I2 | DI1I2 | DI1I2 | DI1 | DI1I2 | DI1I2I3 | I2 | D1 | D1D2D3 |
| Zhanxuan 14 (13--9) | DI1 | DI1 | DI1I2 | DI2 | DI1I2 | D | DI1I2 | I1I2I3 | D1I2 | D1 | D1D2D3 |
| Xiangguoguang (14--11) | DI2 | DI1 | DI1I2 | DI2 | DI1I2 | I1I2 | I1I2 | DI1I2I3 | D2I2 | D1 | D1D2D3I |
| Shengfang 1 (14--14) | DI2 | DI1 | DI1I2 | DI1I2 | DI1I2 | D | DI1I2 | DI2I3 | D2I2 | D1 | D1D2D3 |
| Yujing I1 (14--16) | DI2 | DI1 | DI1I2 | DI1I2 | DI1I2 | D | DI1I2 | DI2I3 | D2I2 | D1 | D1D2D3 |
| Cox's Orange Pippin (14--2) | I2 | D | DI1I2 | DI2 | DI1I2 | DI1 | DI1I2 | I2I3 | D1D2 | D1I | D1D2D3 |
| Nagafu 7 (14--20) | DI2 | DI1 | DI1I2 | DI1I2 | DI1I2 | D | DI1I2 | DI2I3 | D2I2 | D1 | D1D2D3 |
| Boiken (14--21) | I2 | DI2 | DI1 | DI2 | DI1I2 | DI1 | DI1I2 | DI2I3 | D1D2 | D1 | D1D2D3I |
| Qunfu 1 (14--23) | DI2 | DI1 | NA | DI1I2 | DI1I2 | D | DI1I2 | DI2I3 | D2I2 | D1 | D1D2D3 |
| Calville Blanche (14--3) | I2 | DI2 | DI1 | DI2 | DI1I2 | DI1 | DI1I2 | DI2I3 | D1D2 | D1 | D1D2D3I |
| Freybreg (14--4) | I1I2 | DI2 | DI1I2 | DI1I2 | I1I2 | DI1 | I1I2 | DI2I3 | D2I2 | D1I | D1D2D3 |
| Husveti Rosmaring (14--5) | DI1 | DI2 | DI1I2 | DI2 | DI1I2 | DI1 | DI1I2 | DI2I3 | D1D2 | D1 | D1D2D3I |

-continued

Construction results of InDel marker genotype database of *Malus* germplasm resources

| | | | | | | | | | | | |
|---|---|---|---|---|---|---|---|---|---|---|---|
| Sweet Jonathan (14--7) | I2 | D | DI1I2 | DI2 | DI1I2 | DI2 | DI1I2 | DI2I3 | D2 | D1 | D1D2D3I |
| King of Pippin (14--8) | I2 | D | DI1I2 | DI2 | DI1I2 | DI1 | DI1I2 | I2I3 | D1D2 | D1I | D1D2D3 |
| Duchess of Oldenburg (1--5) | DI2 | I1I2 | DI1I2 | DI1I2 | DI1I2 | D | I1I2 | DI2I3 | D1D2 | D1 | D2D3 |
| Kangbing Golden 5 (15--11) | I1I2 | I1I2 | DI1I2 | DI1I2 | DI1I2 | DI1 | I1I2 | DI1I2I3 | D2I2 | D1I | D1D2D3I |
| Pingzhi Ralls Janet (15--15) | I1I2 | DI1 | DI1I2 | DI2 | DI1I2 | D | DI1I2 | DI1I2I3 | D1D2 | D1 | D1D3I |
| Wase16 (15--16) | DI1 | I1I2 | DI1I2 | DI2 | DI1I2 | DI1 | I1I2 | DI2I3 | D1D2 | D1 | D1D2D3 |
| Kogetsu (15--17) | I1I2 | DI1 | DI1I2 | DI1I2 | DI1I2 | D | I1I2 | DI2I3 | D2I2 | D1 | D1D2D3 |
| Jonared (15--18) | I2 | D | DI1I2 | DI2 | DI1I2 | DI2 | DI1I2 | DI2I3 | D2 | D1 | D1D2D3I |
| Zhanxuan 4 (15--21) | DI1 | DI1 | DI1I2 | DI2 | DI1I2 | D | DI1I2 | I1I2I3 | D1I2 | D1 | D1D2D3 |
| Strawberry (15--23) | DI2 | DI2 | DI1I2 | DI1I2 | DI1I2 | DI1 | DI1 | DI1I2 | D1 | D1 | D1D2D3I |
| StarkSpur Ultra Red Delicious (15--3) | DI2 | DI1 | DI1I2 | DI1I2 | DI1I2 | DI2 | I1I2 | DI1I2I3 | I2 | D1 | D1D2D3 |
| Sharp Red Delicious (15--4) | DI2 | DI1 | DI1I2 | DI1I2 | DI1I2 | DI2 | I1I2 | DI1I2I3 | I2 | D1 | D1D2D3 |
| Mensi (15--5) | I2 | DI1 | DI1I2 | DI1I2 | DI1I2 | I2 | I1I2 | DI1I2I3 | D2 | D1 | D1D2D3I |
| Norand (15--6) | DI2 | DI1 | DI1I2 | DI2 | DI1I2 | DI1 | I1I2 | DI1I2 | D2I1 | D1 | D1D2D3 |
| Zhanxuan 18 (15--7) | DI2 | DI1 | DI1I2 | DI1I2 | DI1I2 | DI2 | I1I2 | DI1I2I3 | I2 | D1 | D1D2D3 |
| Xishan 1 (15--8) | DI2 | DI1 | DI1I2 | DI1I2 | DI1I2 | DI2 | I1I2 | DI1I2I3 | I2 | D1 | D1D2D3 |
| Hongrou Pingguo (15--9) | DI1 | D | DI1I2 | DI2 | DI1I2 | I1 | I1I2 | DI2 | D2 | D1 | D1D2D3 |
| Gravenstein (1--6) | DI1 | DI2 | DI1I2 | DI1 | DI1I2 | DI1 | I1I2 | DI2I3 | D1D2 | D1 | D1D2D3I |
| Xinhong (16--1) | D | D | DI1I2 | DI2 | DI1I2 | D | I1I2 | DI2I3 | D2I2 | D1D3 | D1D2D3 |
| Zhanxuan 6 (16--10) | I2 | D | DI1I2 | DI2 | DI1I2 | I1 | I1I2 | DI2 | D1 | D1 | D1D2D3 |
| Behene (16--11) | I2 | DI2 | DI1I2 | DI1I2 | DI1I2 | DI1 | DI1I2 | DI1I2I3 | D1D2 | D1 | D1D2D3 |
| Xindong (16--14) | D | DI1 | DI1I2 | DI2 | DI1I2 | DI1 | I1I2 | DI2I3 | D2 | D1 | D1D2D3 |
| Hardi Brite (16--16) | DI2 | DI1 | DI1I2 | DI1I2 | DI1I2 | DI2 | I1I2 | DI1I2I3 | I2 | D1 | D1D2D3 |
| Charden (16--17) | I1I2 | I1I2 | DI1I2 | DI1I2 | DI1I2 | DI1I2 | I1I2 | DI1I2I3 | D2I2 | D1I | D1D2D3I |
| Zhuoai 1 (16--2) | DI1 | DI1 | DI1I2 | DI2 | DI1I2 | D | DI1I2 | I1I2I3 | D1I2 | D1 | D1D2D3 |
| Jinse Luosuoshan (16--22) | D | D | DI1I2 | DI2 | DI1I2 | DI1 | DI1I2 | DI2I3 | D1D2 | D1 | D1D3 |
| Zhaiteng I1 (16--23) | DI2 | DI1 | DI1I2 | DI1I2 | DI1I2 | D | DI1I2 | DI2I3 | D2I2 | D1 | D1D2D3 |
| Zhanxuan 16 (16--6) | DI1 | DI1 | DI1I2 | DI2 | DI1I2 | D | DI1I2 | I1I2I3 | D1I2 | D1 | D1D2D3 |
| Fa 3 (16--8) | DI1I2 | DI1 | DI1I2 | DI2 | DI1I2 | DI2 | DI1I2 | DI1I2I3 | D2 | D1 | D1D2D3I |
| Jerseymac (1--7) | DI2 | I2 | DI1I2 | DI2 | DI1I2 | DI2 | I1I2 | DI2I3 | I1 | D1 | D1D2D3 |
| Mother (17--1) | DI2 | I1 | DI1I2 | DI2 | DI1I2 | DI2 | DI1I2 | DI1I2I3 | D2 | D1I | D1D2D3I |
| Northern Spy (17--10) | DI2 | DI2 | DI1I2 | DI1 | DI1I2 | DI1 | I1I2 | DI2I3 | D2I2 | D1 | D1D2D3 |
| Rome Beauty (17--11) | DI2 | DI1 | DI1I2 | DI2 | DI1I2 | I1I2 | I1I2 | DI2I3 | D2I2 | D1 | D1D2D3 |
| Black Ben David (17--12) | DI1 | DI1 | DI1 | DI2 | I1I2 | I1I2 | DI1I2 | DI2I3 | D2I2 | D1I | D1D2D3I |
| Atlas (17--13) | I1I2 | DI2 | DI1I2 | DI1I2 | DI2 | DI2 | DI1I2 | DI1I2I3 | D1 | D1 | D1D2D3 |
| Roxbury (17--14) | I2 | DI1 | I1I2 | DI1 | DI1I2 | DI2 | I1I2 | DI1I2I3 | D1D2 | D1 | D1D2D3I |
| Laxtons Superb (17--15) | I2 | D | DI1I2 | DI1I2 | DI1I2 | DI1 | DI1I2 | DI1I2 | D1I2 | D1 | D1D2D3I |

-continued

| Construction results of InDel marker genotype database of *Malus* germplasm resources | | | | | | | | | | | |
|---|---|---|---|---|---|---|---|---|---|---|---|
| Changhong (17--16) | I2 | D | DI1I2 | DI2 | DI1I2 | DI2 | I1I2 | DI2I3 | D1D2 | D1I | D2D3I |
| Cogswell Pearmain (17--17) | DI2 | DI1 | DI1I2 | DI2 | DI1I2 | DI2 | I1I2 | DI2I3 | D1D2 | D1I | D1D2D3I |
| Twenty Ounce (17--18) | DI2 | DI1 | DI1I2 | DI2 | DI1I2 | DI1 | I1I2 | DI2I3 | D2 | D1 | D1D2D3I |
| Lowtosh (17--19) | DI2 | I1 | DI1I2 | DI2 | DI1I2 | DI1 | DI1I2 | DI2I3 | D2I1 | D1 | D1D2D3 |
| Iwaki (17--21) | I2 | DI1 | DI1I2 | DI2 | DI1I2 | D | DI1I2 | DI2I3 | D2 | D1 | D2D3I |
| Qin'guan (17--22) | DI1 | DI2 | DI1I2 | DI1I2 | DI1I2 | D | DI1I2 | DI2I3 | D1I2 | D1I | D2D3I |
| Bancroft (17--23) | I2 | I2 | DI1I2 | DI2 | I1I2 | D | I1I2 | DI1I2I3 | D1 | D1 | D1D2D3I |
| Chenango Strawberry (17--4) | DI1 | D | I1I2 | DI2 | I1I2 | DI2 | I1I2 | DI1I2 | D2I2 | D1 | D1D3I |
| Newfane (17--7) | DI2 | DI1 | DI1I2 | DI1I2 | DI1I2 | DI2 | I1I2 | DI1I2I3 | D2I2 | D1 | D2D3 |
| Lord Lambourne (17--9) | DI2 | DI2 | DI1I2 | DI1 | DI1I2 | DI1 | I1I2 | DI2I3 | D2I2 | D1 | D2D3I |
| Rizhiwan (18--0) | I1I2 | DI1 | DI1I2 | DI2 | DI1I2 | I1I2 | I1I2 | DI1I2 | D2I2 | D1I | D2D3I |
| Campbell (18--11) | I2 | DI1 | I1I2 | DI1 | DI1I2 | DI2 | I1I2 | DI1I2I3 | D1D2 | D1 | D1D2D3I |
| Pigeon (18--13) | D | I1 | DI1I2 | DI2 | DI1I2 | D | I1I2 | I1I2 | D2 | D1 | D1D2D3 |
| Summer Champion (18--14) | I1 | DI1 | DI1I2 | DI2 | I1I2 | DI1 | I1I2 | DI1I2 | I2 | D1 | D2D3I |
| Nanpu 3 (18--15) | I1 | DI1 | DI1I2 | DI2 | DI1I2 | DI1 | DI1 | DI1I2I3 | D2I2 | D1 | D2D3I |
| Qiulimeng (18--16) | DI2 | DI2 | DI1I2 | DI2 | DI1I2 | I1I2 | I1I2 | DI2 | D1 | D1 | D1D2D3I |
| Rutosh (18--17) | I2 | I1I2 | DI1I2 | DI2 | DI1I2 | D | I1I2 | DI2I3 | D1D2 | D1 | D1D2D3 |
| Xinlimei (18--19) | DI2 | D | DI1 | DI2 | DI1I2 | I1 | DI1I2 | DI2 | D1D2 | D1 | D1D2D3 |
| Huanong 1 (18--2) | DI2 | DI1 | DI1I2 | DI2 | DI1I2 | DI2 | DI1 | DI2 | D2I2 | D1I | D1D2D3 |
| Lawfam (18--20) | I1I2 | DI2 | DI1I2 | DI2 | I1I2 | I1I2 | DI1I2 | DI1I2I3 | D2I2 | D1 | D1D2D3 |
| Akin's Red (18--21) | DI2 | D | DI1I2 | DI2 | DI1I2 | DI2 | DI1I2 | DI2I3 | D2I1 | D1 | D1D2D3I |
| Meltosh (18--22) | DI2 | DI1 | DI1I2 | DI2 | DI1I2 | D | DI1I2 | DI2I3 | D1D2 | D1I | D1D2D3 |
| Hubbardston (18--23) | I1I2 | DI2 | DI1I2 | DI1I2 | I1I2 | DI1 | I1I2 | DI2I3 | D2I2 | D1I | D1D2D3 |
| Fenghuangluan Crab (18--3) | DI2 | DI1 | DI1I2 | DI2 | DI1I2 | DI2 | DI1 | DI2 | D2I2 | D1I | D1D2D3 |
| Jie 9 (18--4) | DI2 | D | DI1I2 | DI2 | DI1I2 | I1I2 | I1I2 | DI2 | D2 | D1 | D1D2D3 |
| Bramley's Seedling (18--5) | DI2 | DI1 | DI1I2 | DI1I2 | DI1I2 | DI2 | DI1I2 | DI1I2I3 | D1I2 | D1 | D1D2D3I |
| Shuangyang 1 (18--7) | I1I2 | DI2 | DI1I2 | DI1I2 | I1I2 | DI1 | I1I2 | DI2I3 | D2I2 | D1I | D1D2D3 |
| Shengli (18--8) | I1I2 | DI2 | DI1I2 | DI1I2 | I1I2 | DI1 | I1I2 | DI2I3 | D2I2 | D1I | D1D2D3 |
| Qingguan (18--9) | DI2 | DI1 | DI1I2 | DI2 | DI1I2 | DI1 | I1I2 | DI2I3 | D2 | D1 | D1D2D3 |
| Weeping Ralls (19--0) | I1I2 | DI1 | DI1I2 | DI2 | DI1I2 | D | DI1I2 | DI1I2I3 | D1D2 | D1 | D1D3I |
| Giant Jeniton (19--1) | I1I2 | DI1 | DI1I2 | DI2 | DI1I2 | DI1 | I1I2 | DI2 | D1D2 | D1 | D1D2D3I |
| Baldwin (19--10) | I2 | DI1I2 | DI1I2 | DI1I2 | DI1I2 | I2 | DI1I2 | I2I3 | D2I2 | D1I | D1D2D3 |
| Lele Fuji (19--11) | DI2 | DI1 | DI1I2 | DI1I2 | DI1I2 | D | DI1I2 | DI2I3 | D2I2 | D1 | D1D2D3 |
| Shuahong (19--12) | D | DI2 | DI1I2 | DI1I2 | DI1I2 | D | DI1I2 | DI2I3 | D2I1 | D1 | D1D2D3 |
| Red Fuji TAO (19--14) | DI2 | DI1 | DI1I2 | DI1I2 | DI1I2 | D | DI1I2 | DI2I3 | D2I2 | D1 | D1D2D3 |
| Jizaohong (19--17) | I1I2 | DI2 | DI1I2 | DI1I2 | I1I2 | DI1 | I1I2 | DI2I3 | D2I2 | D1I | D1D2D3 |
| Karas Tor (19--19) | DI2 | DI1 | DI1I2 | DI2 | DI1I2 | D | I1I2 | DI2I3 | D2 | D1 | D1D2D3 |
| Ralls Janet (19--2) | I1I2 | DI1 | DI1I2 | DI2 | DI1I2 | D | DI1I2 | DI1I2I3 | D1D2 | D1 | D1D3I |

-continued

| | | | | | | | | | | | |
|---|---|---|---|---|---|---|---|---|---|---|---|
| Construction results of InDel marker genotype database of *Malus* germplasm resources | | | | | | | | | | | |
| Stonetosh (19--22) | DI2 | I1I2 | DI1I2 | DI2 | DI1I2 | I1 | I1I2 | DI2 | D1D2 | D1I | D1D2D3 |
| White Pearmain (19--23) | DI2 | I1 | DI1I2 | DI1I2 | DI1I2 | D | I1I2 | DI1I2 | D2I2 | D1 | D1D2D3 |
| Xiushui Guoguang (19--3) | I2 | DI1 | DI1I2 | DI1I2 | DI1I2 | D | DI1I2 | DI1I2I3 | D2I2 | D1 | D1D2D3 |
| Chimeric Ralls Janet (19--4) | I1I2 | DI1 | DI1I2 | DI2 | DI1I2 | D | DI1I2 | DI1I2I3 | D1D2 | D1 | D1D3I |
| Mutsu (19--7) | I1I2 | I1I2 | DI1I2 | DI1I2 | DI1I2 | DI1 | I1I2 | DI1I2I3 | D2I2 | D1I | D1D2D3I |
| Ben David (19--8) | DI1 | DI1 | DI1 | DI2 | I1I2 | I1I2 | DI1I2 | DI2I3 | D2I2 | D1I | D1D2D3I |
| Saint Lawrence (19--9) | DI2 | DI1 | DI1 | DI2 | DI1I2 | DI1 | I1I2 | DI2I3 | D1D2 | D1 | D1D2D3 |
| Newtosh (20--0) | D | D | DI1I2 | DI1I2 | DI1I2 | I1 | I1I2 | DI2 | NA | D2D3 | D1D3 |
| Geliekekukui (20--1) | DI1 | DI1 | DI1I2 | DI2 | DI1I2 | I1 | I1I2 | DI2 | D1D2 | D1I | D1D2D3 |
| Sweet Jonathan (20--10) | I2 | D | DI1I2 | DI2 | DI1I2 | DI2 | DI1I2 | DI2I3 | D2 | D1 | D1D2D3I |
| Apple of Commerce (20--11) | DI2 | DI1 | DI1I2 | DI2 | I1I2 | DI1 | I1I2 | I2I3 | D2I2 | D1I | D1D2D3I |
| 600 g Andong (20--12) | I2 | DI2 | DI1I2 | DI1I2 | DI1I2 | DI1 | DI1I2 | DI1I2I3 | D1D2 | D1 | D1D2D3 |
| Winter Banana (20--14) | I2 | DI1 | DI1 | DI2 | I1I2 | D | DI1I2 | DI2I3 | D2 | D1 | D1D2D3I |
| Rainier (20--15) | I1I2 | I1I2 | DI1I2 | DI2 | DI1I2 | D | I1I2 | DI1I2 | D1D2 | D1I | D1D2D3I |
| Winesap (20--16) | DI1 | DI2 | DI1I2 | DI2 | DI1I2 | I1 | I1I2 | DI2I3 | D1 | D1 | D1D2D3I |
| Drumbo (20--17) | DI2 | DI1 | DI1I2 | DI2 | DI1I2 | D | DI1I2 | DI2I3 | D1D2 | D1I | D1D2D3 |
| Blengstid Gaurd (20--2) | DI1I2 | DI1 | DI1I2 | DI2 | DI1I2 | DI2 | DI1I2 | DI1I2I3 | D2 | D1 | D1D2D3I |
| Jierjisi (20--21) | I2 | D | DI1I2 | DI2 | DI1I2 | I1I2 | I1I2 | DI2 | D1D2 | D1D2 | D1D2D3I |
| Radiant (20--23) | D | D | DI1I2 | DI1I2 | DI1I2 | I1 | I1I2 | DI2 | NA | D2D3 | D1D3 |
| King David (20--5) | I2 | DI1 | DI1I2 | DI2 | DI1I2 | I2 | I1I2 | I2I3 | D2I2 | D1I | D1D2D3I |
| Clapp's Seedling (20--6) | DI2 | DI1 | DI1I2 | DI2 | DI1I2 | DI1 | I1I2 | DI2I3 | D2 | D1 | D1D2D3 |
| Ingram (20--7) | DI2 | I1 | DI1I2 | DI2 | DI1I2 | DI2 | I1I2 | DI1I2 | D2 | D1 | D1D3I |
| Qiujin (20--8) | DI1 | DI1 | DI1I2 | DI2 | DI1I2 | D | DI1I2 | I1I2I3 | D1D2 | D1 | D1D2D3 |
| Sujsleppskoe (2--1) | DI1 | DI1 | DI1I2 | DI2 | DI1I2 | DI1 | I1I2 | DI1I2I3 | D1D2 | D1 | D1D2D3 |
| Qian 1 Ace (21--0) | DI2 | DI1 | DI1I2 | DI1I2 | DI1I2 | D | DI1I2 | DI2I3 | D2I2 | D1 | D1D2D3 |
| Toko (2--10) | I1I2 | I1I2 | DI1I2 | DI1I2 | DI1I2 | D | I1I2 | DI2I3 | D2I2 | D1 | D1D2D3 |
| Antalue (21--1) | I1I2 | I1I2 | DI1I2 | DI1I2 | DI1I2 | DI1 | DI1I2 | DI1I2I3 | I2 | D1I | D1D2D3I |
| Boskoopske Cervene (2--11) | DI1I2 | DI1 | DI1I2 | DI2 | DI1I2 | DI2 | DI1I2 | DI1I2I3 | D2 | D1 | D1D2D3I |
| Heoersitai (21--10) | I2 | DI1 | DI1I2 | DI1I2 | DI1I2 | D | DI1 | DI2 | D2I2 | D1 | D1D2D3 |
| Lanfengwang (21--11) | D | DI2 | DI1I2 | DI2 | DI1I2 | D | DI1I2 | DI2I3 | D1D2 | D1 | D1D2D3 |
| Aohong (21--14) | I2 | I1 | DI1I2 | DI2 | DI1I2 | DI2 | I1I2 | DI1I2 | D2I2 | D1 | D1D2D3 |
| Weiqinni (21--15) | DI2 | DI2 | DI1I2 | DI1I2 | DI1I2 | DI2 | DI1I2 | DI1I2I3 | D2 | D1D3 | D1D2D3 |
| Smoothee (21--17) | I1I2 | DI1 | DI1I2 | DI1I2 | DI1I2 | DI1 | I1I2 | DI1I2I3 | D2I2 | D1I | D1D2D3I |
| Hongzhiwu (21--18) | DI1 | I1I2 | DI1I2 | DI1 | DI1I2 | DI2 | DI1I2 | I2I3 | D2 | D1I | D1D2D3 |
| Jieba (21--2) | I2 | DI2 | DI1I2 | DI1I2 | DI1I2 | DI1I2 | DI1I2 | DI2I3 | D1D2 | D1 | D1D2D3 |
| Kizashi (21--20) | I2 | DI1 | DI1I2 | DI1I2 | DI1I2 | DI1 | DI1I2 | DI2I3 | D1I2 | D1 | D1D2D3I |
| Aifeng (21--21) | I2 | DI1 | DI1I2 | DI1I2 | DI1I2 | DI1 | DI1I2 | DI2I3 | D1I2 | D1 | D1D2D3I |
| Xingping (21--4) | I1I2 | DI1 | DI1I2 | DI2 | DI1I2 | D | DI1I2 | DI1I2I3 | D1D2 | D1 | D1D2D3I |

-continued

| Construction results of InDel marker genotype database of *Malus* germplasm resources | | | | | | | | | | | |
|---|---|---|---|---|---|---|---|---|---|---|---|
| I2sopus Spitzenburg (2--14) | I2 | DI2 | DI1I2 | DI2 | DI1I2 | D | DI1 | DI1I2I3 | D2 | D1I | D2D3I |
| Lvguang (21--6) | I2 | D | DI1I2 | DI2 | DI1I2 | I1 | I1I2 | DI2 | D1 | D1 | D1D2D3 |
| Nvyoujidui (2--16) | I2 | DI1 | DI1 | DI1I2 | DI1I2 | DI2 | DI1 | DI2I3 | D2I2 | D1 | D1D3I |
| Bell Poos (21--7) | I2 | DI1 | DI1I2 | DI1I2 | DI1I2 | DI1I2 | DI1I2 | I2I3 | D1D2 | D1I | D1D2D3I |
| Tian Andongnuo (2--17) | D | D | DI1I2 | DI1I2 | DI1I2 | I1 | I1I2 | DI2I3 | D1D2 | D1 | D1D2D3I |
| Pacific Rose (21--8) | I2 | I1 | DI1I2 | DI2 | DI1I2 | DI2 | I1I2 | DI1I2 | D2I2 | D1 | D1D2D3 |
| 500 g (21--9) | DI2 | DI2 | DI1I2 | DI1I2 | DI1I2 | DI1 | I1I2 | I2 | D1D2 | D1 | D1D2D3I |
| Nvyoujidui 2 (2--19) | DI1 | DI1 | DI1I2 | DI2 | DI1I2 | DI1 | I1I2 | DI2I3 | D1D2 | D1 | D1D2D3 |
| Tian Andongnuo 2 (2--2) | I2 | D | DI1I2 | DI2 | DI1I2 | DI1 | DI1I2 | DI2I3 | D2 | D1 | D1D3I |
| Spur Mutsu (22--1) | I1I2 | I1I2 | DI1I2 | DI1I2 | DI1I2 | DI1 | NA | DI1I2I3 | D2I2 | D1I | D1D2D3I |
| Red June Sweet (2--21) | D | DI1 | DI1I2 | DI1I2 | DI1I2 | I1 | I1I2 | DI1I2 | D1D2 | D1 | D1D2D3 |
| Chu Tsugaru (22--11) | I1I2 | DI2 | DI1I2 | DI1I2 | DI1I2 | DI2 | DI1I2 | I2I3 | D2 | D1I | D1D2D3I |
| Kermemen (22--13) | I2 | DI1 | DI1 | DI2 | DI1I2 | I2 | I1I2 | DI1I2I3 | D1I2 | D1 | D1D2 |
| Bedan (22--14) | I2 | D | DI1I2 | DI1I2 | DI1I2 | I2 | I1I2 | DI2I3 | D1D2 | D1 | D1D2D3 |
| Dabinette (22--15) | DI2 | DI1 | DI1I2 | DI1I2 | DI1I2 | D | DI1I2 | DI2I3 | D2I2 | D1 | D1D2D3 |
| Zaocuilv (22--16) | I1I2 | DI2 | DI1I2 | DI1I2 | I1I2 | DI1 | I1I2 | DI2I3 | D2I2 | D1I | D1D2D3 |
| Chanteline (22--17) | DI2 | I1 | DI1I2 | DI2 | DI1I2 | DI2 | DI1I2 | DI1I2 | D1I2 | D1D2 | D1D2D3I |
| Red Baron (22--2) | DI2 | D | DI1I2 | DI2 | DI1I2 | DI1 | I1I2 | DI2I3 | D1D2 | D1 | D1D2D3 |
| Hongjin Gala (22--4) | I1I2 | I1I2 | DI1I2 | DI1I2 | DI1I2 | D | DI1I2 | DI2I3 | D2I2 | D1I | D1D2D3 |
| Generos (22--7) | I2 | D | DI1I2 | DI2 | DI1I2 | DI2 | DI1I2 | DI2I3 | D2 | D1 | D1D2D3I |
| Alberta (2--3) | D | D | DI1I2 | DI1I2 | DI1I2 | I1 | I1I2 | DI2I3 | D2 | D1 | D1D2D3 |
| Hirosaki Fuji (23--1) | I1I2 | DI2 | DI1I2 | DI1I2 | DI1I2 | DI2 | DI1I2 | I2I3 | D2 | D1I | D1D2D3I |
| Miya Fuji (23--10) | DI2 | DI1 | DI1I2 | DI1I2 | DI1I2 | D | DI1I2 | DI2I3 | D2I2 | D1 | D1D2D3 |
| Yanshanhong (23--13) | DI2 | D | DI1I2 | DI1I2 | DI1I2 | DI2 | I1I2 | DI2I3 | D2I2 | D1 | D1D2D3I |
| Dailv (23--14) | DI2 | I1 | DI1I2 | DI1I2 | DI1I2 | D | DI1I2 | DI1I2 | D2 | D1I | D1D2D3 |
| Frequin Rouge (23--15) | D | DI1 | DI1I2 | DI2 | DI1I2 | I1I2 | DI1I2 | I1I2 | D1 | D1 | D1D2D3 |
| Jinguang (23--16) | I2 | DI2 | DI1I2 | DI1I2 | DI1I2 | DI1 | DI1I2 | DI1I2I3 | D1D2 | D1 | D1D2D3 |
| Avrolles (23--17) | DI2 | D | DI1I2 | DI1I2 | DI1I2 | DI2 | DI1I2 | DI1I2I3 | D2I2 | D1 | D1D2D3I |
| Marie Menard (23--18) | DI2 | DI1I2 | DI1 | DI2 | DI1I2 | DI1I2 | I1I2 | DI1I2I3 | D1D2 | D1 | D1D2D3I |
| Golden B (23--2) | I1I2 | I1I2 | DI1I2 | DI1I2 | DI1I2 | DI1 | I1I2 | DI1I2I3 | D2I2 | D1I | D1D2D3I |
| Jurella (23--20) | DI2 | DI2 | DI1I2 | DI1I2 | DI1I2 | DI2 | DI1I2 | I1I2 | D2I2 | D1I | D1D2D3 |
| GS58 (23--21) | DI2 | I1 | DI1I2 | DI1 | DI1I2 | D | I1I2 | DI1I2 | I2 | D1 | D1D2D3I |
| Lianji (23--22) | I1I2 | DI2 | DI1I2 | DI2 | DI1I2 | D | I1I2 | DI1I2I3 | D1I1 | D1I | D1D2D3I |
| Aomori Spur Fuji (23--4) | DI2 | DI1 | DI1I2 | DI1I2 | DI1I2 | D | DI1I2 | DI2I3 | D2I2 | D1 | D1D2D3 |
| Akifu 39 (23--9) | DI2 | DI1 | DI1I2 | DI1I2 | DI1I2 | D | DI1I2 | DI2I3 | D2I2 | D1 | D1D2D3 |
| Shalatuoni (2--4) | DI2 | DI1 | DI1I2 | DI1I2 | DI1I2 | DI1 | I1I2 | DI2I3 | D2 | D1 | D1D2D3 |
| Guoqing (24--13) | DI2 | DI1 | DI1I2 | DI1I2 | DI1I2 | D | DI1I2 | I2I3 | D2I1I2 | D1 | D1D2D3 |
| Ningguang (24--15) | I1 | I1 | DI1I2 | DI2 | DI1I2 | DI1 | I1I2 | DI1I2 | D2I2 | D1 | D1D2D3I |

-continued

| Construction results of InDel marker genotype database of *Malus* germplasm resources | | | | | | | | | | | |
|---|---|---|---|---|---|---|---|---|---|---|---|
| Hongqiaowang (24--17) | I1I2 | DI1I2 | DI1I2 | DI1I2 | DI1I2 | DI1 | I1I2 | DI1I2I3 | D2I2 | DI1 | D1D2D3I |
| Wemhong (24--18) | I2 | DI2 | DI1I2 | DI2 | DI1I2 | DI2 | I1I2 | DI2I3 | D1 | D1 | D1D3 |
| Wijcik McIntosh (24--19) | I2 | DI2 | DI1I2 | DI2 | DI1I2 | DI1 | I1I2 | I2I3 | D1 | D1 | D1D2D3 |
| Xinguoguang (24--21) | I1I2 | DI1 | DI1I2 | DI2 | DI1I2 | D | DI1I2 | DI1I2I3 | D1D2 | D1 | D1D3I |
| Fengcun Fuji (24--22) | DI2 | DI1 | DI1I2 | DI1I2 | DI1I2 | D | DI1I2 | DI2I3 | D2I2 | D1 | D1D2D3 |
| America 8 (24--23) | DI2 | DI1 | DI1I2 | DI1I2 | DI1I2 | D | DI1I2 | I2I3 | I1I2 | D1 | D1D2D3 |
| GS48 (24--3) | D | DI2 | DI1I2 | DI1I2 | DI1I2 | I1 | I1I2 | DI2 | D1 | D1D3 | D1D2D3 |
| Granny Smith (24--4) | I2 | I1 | DI1 | DI2 | DI1I2 | DI2 | I1I2 | I1I2I3 | D2I2 | D1 | D1D2D3 |
| Stark Spur (24--7) | I1I2 | I1I2 | DI1I2 | DI1I2 | DI1I2 | DI1 | I1I2 | DI1I2I3 | D2I2 | DI1 | D1D2D3I |
| Huangguniang (2--5) | DI2 | I1I2 | DI1I2 | DI2 | DI1I2 | DI1 | DI1I2 | DI2I3 | D2I1 | D1 | D1D2D3I |
| Judaine (25--11) | I1I2 | DI1 | DI1I2 | DI2 | DI1I2 | DI2 | I1I2 | DI1I2 | D1D2 | D1 | D2D3I |
| Judeline (25--12) | I1 | DI2 | DI1I2 | DI1I2 | DI1I2 | I1I2 | DI1I2 | DI1I2I3 | D2I2 | I | D1D2D3I |
| HoneyCrisp (25--14) | DI2 | I1 | DI1I2 | DI2 | DI1I2 | DI1 | I1I2 | DI1I2 | D2 | D1 | D1D2D3 |
| Korin (25--15) | DI2 | DI1 | DI1I2 | DI1I2 | DI1I2 | D | DI1I2 | DI2I3 | D2I2 | D1 | D1D2D3 |
| Hongao (25--18) | I1I2 | I2 | DI1I2 | DI1I2 | DI1I2 | DI1 | I1I2 | I2I3 | D1I2 | D1 | D1D2D3I |
| Ningguang (25--19) | I1I2 | I2 | DI1I2 | DI1I2 | DI1I2 | DI1 | I1I2 | I2I3 | D1I2 | D1 | D1D2D3I |
| Red Delicious (25--2) | DI2 | DI1 | DI1I2 | DI1I2 | DI1I2 | DI2 | I1I2 | DI1I2I3 | I2 | D1 | D1D2D3 |
| Youlixiang (25--21) | I1I2 | DI2 | DI1I2 | DI2 | DI1I2 | D | I1I2 | DI1I2I3 | D2I2 | DI1 | D1D2D3 |
| Fuqiu (25--3) | I2 | D | DI1I2 | DI2 | DI1I2 | DI1 | DI1I2 | DI2I3 | D1I2 | D1 | D1D2D3 |
| Chunxiang (25--4) | D | DI2 | DI1I2 | DI1I2 | DI1I2 | D | DI1I2 | DI2I3 | D2I1 | D1 | D1D2D3 |
| Fu Hong (25--5) | DI2 | D | DI1I2 | DI1I2 | DI1I2 | DI1 | DI1I2 | DI2I3 | D2I2 | D1 | D1D3 |
| Qingxiang (25--6) | DI2 | I1I2 | DI1I2 | DI1I2 | DI1I2 | D | I1I2 | DI1I2 | D2 | DI1 | D1D2D3 |
| Zhongxing (25--7) | I1I2 | DI2 | DI1I2 | DI1I2 | I1I2 | DI1 | DI1I2 | DI2I3 | D2 | D1 | D1D3I |
| Weixishengming (25--8) | I1I2 | I1I2 | DI1I2 | DI2 | DI1I2 | DI2 | DI1 | DI2I3 | D2 | D1 | D2D3I |
| Shichinohe 1 (25--9) | DI2 | DI1 | DI1I2 | DI1I2 | DI1 | D | DI1I2 | DI2I3 | D2I2 | D1 | D1D2D3 |
| Arkansas Black (2--6) | I2 | I1I2 | DI1I2 | DI1I2 | DI1I2 | I2 | DI1 | DI1I2I3 | D2I2 | I | D1D2D3 |
| Douce Coetligne (26--10) | DI2 | DI2 | DI1I2 | DI1I2 | DI1I2 | DI2 | I1I2 | DI1I2 | D1I2 | D1 | D1D2D3 |
| Golden Spur (26--14) | I1I2 | DI2 | DI1I2 | DI1I2 | DI1I2 | DI1 | I1I2 | DI1I2I3 | D2I2 | DI1 | D1D2D3I |
| Orei (26--15) | I2 | D | DI1I2 | DI2 | DI1I2 | DI1 | DI1I2 | I2I3 | D1D2 | DI1 | D1D2D3 |
| Sekaiichii (26--18) | I1I2 | I1I2 | DI1I2 | DI1I2 | DI1I2 | D | DI1I2 | DI2I3 | D2I2 | DI1 | D1D2D3 |
| Kokyu (26--19) | I1I2 | I1I2 | DI1I2 | DI2 | I1I2 | D | I1I2 | DI1I2I3 | D2I2 | DI1 | D1D2D3I |
| Douce Moen (26--2) | D | DI1 | DI1 | DI1 | DI1I2 | DI2 | I1I2 | DI2I3 | D2 | D1 | D1D2D3 |
| Yanfu 1 (26--22) | DI2 | DI1 | DI1I2 | DI1I2 | DI1I2 | D | DI1I2 | DI1I2 | D2I2 | D1 | D1D2D3 |
| Ningfeng (26--23) | DI2 | DI1 | DI1I2 | DI1I2 | DI1I2 | D | DI1I2 | I2I3 | D2I1I2 | D1 | D1D2D3 |
| Juliana (26--5) | DI2 | DI1 | DI1I2 | DI2 | DI1I2 | DI1 | I1I2 | DI1I2I3 | D2 | D1 | D1D2D3 |
| Judestar (26--9) | I1I2 | DI1 | DI1I2 | DI2 | DI1I2 | DI2 | I1I2 | DI2I3 | D2 | DI1 | D1D2D3 |
| Liaofu (2--7) | DI2 | DI1 | DI1I2 | DI1I2 | DI1I2 | DI2 | I1I2 | DI2I3 | D1D2 | D1 | D1D2D3 |
| Sinano Red (27--10) | DI2 | D | DI1I2 | DI1I2 | DI1I2 | DI2 | DI1I2 | DI2I3 | D1I2 | D1 | D1D2D3 |

-continued

Construction results of InDel marker genotype database of *Malus* germplasm resources

| | | | | | | | | | | |
|---|---|---|---|---|---|---|---|---|---|---|
| Jinyang (27--12) | DI2 | D | DI1I2 | DI2 | DI1I2 | DI2 | DI1I2 | DI2I3 | D1D2 | D1I | D2D3I |
| I2nqi (27--13) | I2 | I1 | DI1I2 | DI1I2 | DI1I2 | DI1 | DI1I2 | DI1I2I3 | I2 | D1 | D1D2D3 |
| Miki (27--14) | I1I2 | I1I2 | DI1I2 | DI2 | DI1I2 | DI2 | DI1 | DI2I3 | D2 | D1 | D2D3I |
| Hongbaoshi (27--15) | DI1 | DI1 | DI1I2 | DI1I2 | DI1I2 | D | I1I2 | DI1I2I3 | I2 | D1 | D1D2D3I |
| Nagafu 2 (27--16) | DI2 | DI1 | DI1I2 | DI1I2 | DI1I2 | D | DI1I2 | DI2I3 | D2I2 | D1 | D1D2D3 |
| Longguan (27--4) | I2 | DI1 | DI1I2 | DI2 | DI1I2 | D | DI1I2 | DI1I2I3 | D1D2 | D1 | D1D3I |
| K9 (27--5) | DI2 | D | DI1I2 | DI2 | DI1I2 | DI2 | DI1I2 | DI2I3 | D1D2 | D1I | D2D3I |
| Zaohongda Gala (27--6) | DI2 | D | DI1I2 | DI2 | DI1I2 | DI2 | DI1I2 | DI2I3 | D1D2 | D1I | D2D3I |
| Lvshuai (27--7) | I1 | DI2 | DI1I2 | DI1I2 | DI1I2 | DI1 | I1I2 | DI2I3 | D2I2 | D1I | D1D2D3 |
| Hongxia (27--8) | I2 | DI1 | DI1I2 | DI1I2 | DI1I2 | DI1 | DI1I2 | DI2I3 | D1I2 | D1 | D1D2D3I |
| Zaohongxia (27--9) | DI2 | DI1 | DI1I2 | DI1I2 | DI1I2 | D | DI1I2 | DI2I3 | D2I2 | D1 | D1D2D3 |
| I2arly Golden (2--8) | DI1 | I1I2 | DI1I2 | DI1I2 | DI1I2 | D | I1I2 | DI2I3 | D2I2 | D1D3 | D1D2D3I |
| Indo (28--0) | I2 | I1 | DI1I2 | DI1I2 | DI1I2 | D | DI1I2 | DI2I3 | D2I2 | D1 | D1D2D3I |
| Jie 1 (28--11) | I2 | D | DI1I2 | DI2 | DI1I2 | DI2 | DI1I2 | DI2I3 | D2 | D1 | D1D2D3I |
| Beauty of Bath (28--13) | DI2 | DI2 | DI1I2 | DI1 | DI1I2 | DI2 | I1I2 | DI2I3 | D2 | D1 | D1D2D3I |
| K10 (28--14) | I2 | D | DI1I2 | DI2 | DI1I2 | DI2 | I1I2 | DI2I3 | D2 | D1I | D2D3I |
| Beifang Xina (28--16) | DI2 | D | DI1I2 | DI2 | DI1I2 | DI1 | DI1I2 | DI2I3 | D1D2 | D1 | D1D2D3 |
| Yellow Fuji (28--18) | DI2 | DI2 | DI1I2 | DI2 | DI1I2 | I1I2 | DI1I2 | DI1I2 | D2I2 | D1I | D1D2D3I |
| Sinano Sweet (28--2) | I1I2 | DI2 | DI1I2 | DI2 | I1I2 | D | I1I2 | I2I3 | D2I1 | D1 | D1D2D3 |
| Miguo (28--3) | DI1 | DI1 | DI1I2 | DI2 | DI1I2 | D | DI1I2 | I1I2I3 | D1I2 | D1 | D1D2D3 |
| Ace (28--4) | DI2 | DI1 | DI1I2 | DI1I2 | DI1I2 | D | DI1I2 | DI2I3 | D2I2 | D1 | D1D2D3 |
| Tsugaru (28--5) | I1I2 | DI2 | DI1I2 | DI1I2 | DI1I2 | DI2 | DI1I2 | I2I3 | D2 | D1I | D1D2D3I |
| K12 (28--8) | DI1 | I2 | DI1I2 | DI1I2 | DI1I2 | DI2 | DI1I2 | DI2I3 | D2I1 | D1I | D1D2D3 |
| Jieernianke (28--9) | I2 | DI2 | DI1I2 | DI2 | DI1I2 | DI1 | DI1I2 | DI1I2 | D1D2 | D1 | D1D2D3I |
| Macoun (2--9) | DI2 | D | DI1I2 | DI2 | DI1I2 | DI1 | DI1I2 | DI2I3 | D1D2 | D1 | D1D2D3 |
| Qingping (29--1) | DI2 | I1 | DI1 | DI1I2 | DI1I2 | DI1 | I1I2 | DI2I3 | D2 | D1 | D1D2D3 |
| Polka (29--11) | I2 | DI1 | DI1I2 | DI2 | DI1I2 | I1 | I1I2 | I1I2I3 | D1I2 | D1I | D1D2D3 |
| Longfeng (29--13) | I2 | DI2 | DI1I2 | DI2 | DI1I2 | DI1 | I1 | DI1I2I3 | D2I1 | D1 | D1D2D3 |
| Very I2arly Fuji (29--14) | DI2 | DI1 | DI1I2 | DI1I2 | DI1I2 | D | DI1I2 | DI2I3 | D2I2 | D1 | D1D2D3 |
| Longhong (29--15) | DI2 | DI2 | DI1I2 | DI2 | DI1I2 | DI1 | I1I2 | DI1I2 | D2 | D1 | D1D2D3 |
| Pinova (29--16) | I2 | DI1 | DI1I2 | DI1I2 | DI1I2 | DI1 | DI1I2 | DI2I3 | D2I2 | D1 | D1D2D3 |
| Fuga (29--17) | I2 | DI1 | DI1I2 | DI1I2 | DI1I2 | DI1 | DI1I2 | DI2I3 | D1I2 | D1 | D1D2D3I |
| Qing n3 (29--2) | DI2 | DI1 | DI1I2 | DI1I2 | DI1I2 | DI2 | I1I2 | DI1I2I3 | I2 | D1 | D1D2D3 |
| Xinyuanshuai (29--3) | DI2 | DI1 | DI1I2 | DI1I2 | DI1I2 | DI2 | I1I2 | DI1I2I3 | I2 | D1 | D1D2D3 |
| Xinhua (29--5) | DI2 | DI1 | DI1I2 | DI2 | DI1I2 | DI1 | I1I2 | DI2I3 | D2 | D1D3 | D1D3 |
| Nanpu 2 (29--6) | I2 | DI1 | DI1I2 | DI1I2 | DI1I2 | DI2 | DI1 | DI2I3 | D2 | D1 | D1D2D3I |
| Liuyu mutant (29--7) | I2 | D | DI1I2 | DI2 | DI1I2 | D | I1I2 | DI2I3 | D2I1 | D1 | D1D2D3 |
| Shandao Fuji (30--1) | DI2 | DI1 | DI1I2 | DI1I2 | DI1I2 | D | DI1I2 | DI2I3 | D2I2 | D1 | D1D2D3 |
| Sinano Gold (30--2) | I1I2 | D | DI1I2 | DI1I2 | DI1I2 | D | DI1I2 | DI2I3 | D2I2 | D1 | D1D2D3I |

-continued

Construction results of InDel marker genotype database of *Malus* germplasm resources

| | | | | | | | | | | | |
|---|---|---|---|---|---|---|---|---|---|---|---|
| Whitney (3--1) | DI2 | DI2 | DI1I2 | DI2 | DI1I2 | D | DI1 | DI2I3 | D1D2 | D1D3 | D1D2D3I |
| Feixia (31--1) | I1I2 | I1I2 | DI1I2 | DI1I2 | DI1I2 | DI1 | DI1I2 | DI1I2I3 | I2 | D1I | D1D2D3I |
| Willams Faborite (3--11) | DI2 | DI2 | DI1I2 | DI2 | DI1I2 | D | I1I2 | I2I3 | D2 | D1 | D1D2D3 |
| Zhangye 2 (31--12) | I2 | DI2 | DI1I2 | DI1I2 | I1I2 | DI2 | I1I2 | DI2I3 | D2I2 | D1I | D1D2D3 |
| Youfangcun Ralls Janet (31--14) | DI1 | DI1 | DI1 | DI2 | I1I2 | I1I2 | DI1I2 | DI2I3 | D2I2 | D1I | D1D2D3I |
| Yueyanghong (31--15) | I2 | DI1 | DI1I2 | DI1I2 | DI1I2 | DI1 | DI1I2 | DI2I3 | D2 | D1 | D1D2D3 |
| Shuohong (31--17) | DI2 | D | DI1I2 | DI2 | DI1I2 | DI2 | DI1I2 | DI1I2I3 | D1I2 | D1 | D1D2D3 |
| Tianwang 1 (31--18) | DI2 | DI1 | DI1I2 | DI1I2 | DI1I2 | DI2 | I1I2 | DI1I2I3 | I2 | D1 | D1D2D3 |
| Huadan (31--2) | DI2 | DI1 | DI1I2 | DI1I2 | DI1I2 | D | DI1I2 | DI1I2I3 | D2I2 | D1 | D1D2D3 |
| Dalu 52 (3--12) | I2 | I2 | DI1I2 | DI2 | DI1I2 | DI1 | I1I2 | I2I3 | D2I2 | D1 | D1D2D3 |
| Cameo (31--3) | DI1 | DI1 | DI1I2 | DI1 | I1I2 | I1I2 | I1I2 | DI1I2I3 | I2 | D1 | D1D2D3I |
| Tianhuangkui (3--13) | DI1 | DI1 | DI1I2 | DI1I2 | DI1I2 | DI1 | I1I2 | DI2I3 | D2 | D1 | D1D2D3 |
| Qiulu (31--4) | I2 | D | DI1I2 | DI1I2 | DI1I2 | I1I2 | I1I2 | DI2I3 | D2 | D1 | D1D2D3 |
| Liehuangjiatena (3--15) | I2 | DI2 | DI1I2 | DI1I2 | I1I2 | DI1 | I1I2 | DI2I3 | D2I2 | D1I | D1D2D3 |
| Lubi (3--16) | I2 | D | DI1I2 | DI2 | DI1I2 | DI2 | I1I2 | DI1I2 | D1I2 | D1 | D1D2D3 |
| Huayu (31--8) | DI2 | DI1 | DI1I2 | DI1 | NA | I1I2 | DI1 | DI1I2I3 | I2 | D1 | D1D2D3 |
| Fameuse (3--18) | DI2 | DI1 | DI1I2 | DI2 | DI1I2 | I1 | I1I2 | DI2 | D1D2 | D1I | D1D2D3 |
| Zhanhanxiang (3--19) | I2 | DI1 | DI1I2 | DI1I2 | DI1I2 | D | I1I2 | DI2I3 | D2I2 | D1 | D1D2D3 |
| Siberian White Spot (3--2) | D | DI1 | DI1I2 | DI2 | DI1I2 | I1I2 | I1I2 | DI2I3 | D1 | D1D3 | D1D2D3 |
| Zhengding 2 (3--21) | DI2 | DI2 | DI1I2 | DI1I2 | I1I2 | DI1I2 | DI2 | D1D2 | D1 | D1D2D3 |
| Kuihua (3--22) | I2 | I1 | DI1I2 | DI2 | DI1I2 | DI2 | DI1 | I1I2I3 | D2 | D1 | D1D2D3I |
| I2arly Worcester (3--23) | I2 | DI1 | DI1I2 | DI2 | DI1I2 | D | I1I2 | I2I3 | D2 | D1 | D1D2D3 |
| Lowland Raspderry (3--3) | DI1I2 | I1 | DI1I2 | DI2 | DI1I2 | DI1I2 | DI1I2 | DI2I3 | D1D2 | D1 | D1D2D3I |
| Miqiulin Jinian (3--4) | DI2 | D | DI1 | DI1I2 | DI1I2 | I1I2 | DI1I2 | DI2 | D1 | D1 | D1D3I |
| Huangtianguo (3--5) | I2 | D | DI1I2 | DI2 | DI1I2 | I1 | I1I2 | DI2 | D1D2 | D1 | D1D2 |
| Huadao (3--7) | I2 | DI1 | DI1I2 | DI1I2 | DI1I2 | DI1I2 | DI1I2 | I2I3 | D1D2 | D1I | D1D2D3I |
| Red Astrachan (3--9) | DI2 | DI1I2 | DI1I2 | DI1 | DI1I2 | D | I1I2 | DI2I3 | D1D2 | D1 | D1D2D3 |
| Black Gilliflower (4--1) | D | I1I2 | DI1I2 | DI1I2 | DI1I2 | I1I2 | DI1 | DI2 | D2 | D1 | D1D2D3 |
| Nimaiyisuo (4--10) | D | DI1 | DI1 | DI1 | DI1I2 | DI1 | I1I2 | DI1I2I3 | D1D2 | D1 | D1D2D3I |
| Zaohong (4--11) | I1I2 | DI1 | DI1I2 | DI2 | DI1I2 | D | DI1I2 | DI1I2I3 | D1D2 | D1 | D1D3I |
| Xiangguo (4--12) | I2 | D | DI1I2 | DI2 | DI1I2 | DI1 | I1I2 | DI2 | D1D2I2 | D1 | D1D2 |
| Vista Bella (4--16) | DI2 | I2 | DI1 | DI2 | DI1I2 | DI2 | I1I2 | I2I3 | D1I1 | D1 | D1D2D3 |
| Saiwen (4--17) | I2 | I1I2 | DI1I2 | DI1I2 | DI1I2 | I2 | DI1 | I1I2I3 | D2I2 | I | D1D2D3 |
| Summerland (4--20) | I1I2 | I1I2 | DI1I2 | DI1I2 | DI1I2 | DI1 | I1I2 | DI1I2I3 | D2I2 | D1I | D1D2D3I |
| Qihe Golden Spur (4--22) | I1I2 | I1I2 | DI1I2 | DI1I2 | DI1I2 | DI1 | I1I2 | DI1I2I3 | D2I2 | D1I | D1D2D3I |
| Yellow Risharde (4--3) | DI2 | DI1 | DI1I2 | DI1I2 | DI1I2 | DI2 | I1I2 | DI1I2I3 | D2I2 | D1 | D1D2D3 |
| Patten (4--5) | DI2 | D | DI1I2 | DI2 | DI1I2 | DI1 | DI1I2 | I2I3 | D1I1 | D1 | D1D2D3I |
| I2arly Red Bird (4--6) | I2 | D | DI1I2 | DI2 | DI1I2 | D | I1I2 | DI2I3 | D2I1 | D1 | D1D2D3 |

-continued

| Construction results of InDel marker genotype database of *Malus* germplasm resources | | | | | | | | | | | |
|---|---|---|---|---|---|---|---|---|---|---|---|
| Fuhong (4--7) | I2 | DI1 | DI1I2 | DI1I2 | DI1I2 | D | I1I2 | DI2I3 | D1D2 | D1 | D1D2D3I |
| Bisimake (4--8) | DI1 | D | DI1I2 | DI2 | DI1I2 | D | DI1I2 | I2I3 | D1D2 | D1 | D1D2D3 |
| York Imperial (4--9) | D | DI2 | DI1I2 | DI1I2 | DI1I2 | D | I1I2 | I1I2I3 | D2I2 | D1I | D1D2D3I |
| Jonagold (5--1) | I1I2 | DI1I2 | DI1I2 | DI1I2 | DI1I2 | DI1 | I1I2 | DI1I2I3 | D2I2 | D1I | D1D2D3I |
| Ayiwaniya (5--10) | DI2 | D | DI1I2 | DI2 | DI1I2 | DI1 | I1I2 | DI2 | D1 | D1 | D1D2D3 |
| Fushan 5 (5--14) | DI2 | DI1 | DI1I2 | DI1I2 | DI1I2 | DI2 | I1I2 | I1I2I3 | I2 | D1 | D1D2D3 |
| Houjiadian Spur (5--18) | DI2 | DI1 | DI1I2 | DI1I2 | DI1I2 | DI2 | I1I2 | I1I2I3 | I2 | D1 | D1D2D3 |
| Guoshuai (5--19) | I2 | DI1 | DI1I2 | DI2 | DI1I2 | DI2 | I1I2 | I1I2I3 | D2I2 | D1 | D1D2D3I |
| Huashuai 1 (5--21) | DI2 | DI2 | DI1I2 | DI1I2 | DI1I2 | D | I1I2 | DI1I2I3 | D1I2 | D1 | D1D2D3I |
| Xiongyue 2 (5--22) | DI2 | DI1 | DI1I2 | DI1I2 | DI1I2 | DI2 | I1I2 | I1I2I3 | I2 | D1 | D1D2D3 |
| Honeygod (5--3) | I2 | I1I2 | DI1I2 | DI1I2 | DI1I2 | DI1 | DI1I2 | DI1I2 | D1D2I1I2 | D1I | D1D2D3I |
| Joyal (5--4) | I2 | I1I2 | DI1I2 | DI2 | DI1I2 | D | I1I2 | DI2I3 | D1D2 | D1 | D1D2D3 |
| Stark Spur Golden (5--5) | I1I2 | I1I2 | DI1I2 | DI1I2 | DI1I2 | DI1 | I1I2 | DI1I2I3 | D2I2 | D1I | D1D2D3I |
| I2nweier Golden (5--6) | I1I2 | I1I2 | DI1I2 | DI1I2 | DI1I2 | DI1 | I1I2 | DI1I2I3 | D2I2 | D1I | D1D2D3I |
| Stark Gold (5--8) | I1I2 | DI1 | DI1I2 | DI2 | DI1I2 | D | DI1I2 | I1I2I3 | D1D2 | D1 | D1D3I |
| Sishui Spur (6--10) | DI2 | DI1 | DI1I2 | DI1I2 | DI1I2 | DI2 | I1I2 | DI1I2I3 | I2 | D1 | D1D2D3 |
| Red Spur Delicious (6--12) | DI2 | DI1 | DI1I2 | DI1I2 | DI1I2 | DI2 | I1I2 | DI1I2I3 | I2 | D1 | D1D2D3 |
| Qingdao 1 (6--13) | DI2 | DI1 | DI1I2 | DI1I2 | DI1I2 | DI2 | I1I2 | DI1I2I3 | I2 | D1 | D2D3 |
| Bianqiangzi 1 (6--14) | DI2 | DI1 | DI1I2 | DI1I2 | DI1I2 | DI2 | I1I2 | DI1I2I3 | I2 | D1 | D1D2D3 |
| Zhangjiakou Spur (6--16) | DI2 | DI1 | DI1I2 | DI1I2 | DI1I2 | DI2 | I1I2 | DI1I2I3 | I2 | D1 | D1D2D3 |
| Richard Red Delicious (6--18) | DI2 | DI1 | DI1I2 | DI1I2 | DI1I2 | DI2 | I1I2 | DI1I2I3 | I2 | D1 | D1D2D3 |
| Well Spur Delicious (6--19) | DI2 | DI1 | DI1I2 | DI1I2 | DI1I2 | DI2 | I1I2 | DI1I2I3 | I2 | D1 | D1D2D3 |
| Bianqiangzi 2 (6--20) | DI2 | DI1 | DI1I2 | DI1I2 | DI1I2 | DI2 | I1I2 | DI1I2I3 | I2 | D1 | D1D2D3 |
| Hardi Spur Delicious (6--21) | DI2 | DI1 | DI1I2 | DI1I2 | DI1I2 | DI2 | I1I2 | I1I2I3 | I2 | D1 | D1D2D3 |
| Fushan 1 (6--3) | DI2 | DI1 | DI1I2 | DI1I2 | DI1I2 | DI2 | I1I2 | DI1I2I3 | I2 | D1 | D1D2D3 |
| Pinyin Spur (6--4) | DI2 | DI1 | DI1I2 | DI1I2 | DI1I2 | DI2 | I1I2 | DI1I2I3 | I2 | D1 | D1D2D3 |
| Nanshan 2 (6--8) | DI2 | DI1 | DI1I2 | DI1I2 | DI1I2 | DI2 | I1I2 | DI1I2I3 | I2 | D1 | D1D2D3 |
| Meiduan 1 (7--10) | DI1 | I1 | DI1I2 | DI2 | I1I2 | DI2 | I1I2 | DI1I2I3 | I2 | D1 | D1D2D3I |
| Shisanling Spur (7--11) | DI2 | DI1 | DI1I2 | DI1I2 | DI1I2 | DI2 | I1I2 | DI1I2I3 | I2 | D1 | D1D2D3 |
| Kelisike (7--13) | D | DI1 | DI1I2 | DI1I2 | DI1I2 | DI1 | I1I2 | DI2 | D2 | D1 | D1D2D3 |
| Jie 18 (7--16) | DI1 | DI1 | DI1I2 | DI2 | DI1I2 | I2 | I1I2 | DI2I3 | D1D2 | D1 | D1D2D3 |
| Bo 25 (7--17) | I1I2 | DI1 | DI1I2 | DI1I2 | DI1I2 | D | I1I2 | DI2I3 | D1 | D1 | D1D2D3 |
| Ruixiang (7--18) | I2 | DI2 | DI1I2 | DI2 | DI1I2 | DI2 | I1I2 | I2I3 | D2 | D1 | D1D2D3 |
| Wealthy (7--19) | DI2 | DI1 | DI1I2 | DI2 | DI1I2 | D | DI1I2 | DI2I3 | D2I1 | D1 | D1D2D3I |
| Nanshan 4 (7--2) | DI2 | I1 | DI1I2 | DI2 | DI1I2 | DI2 | I1I2 | DI2I3 | D2I2 | D1 | D1D2D3I |
| De 14 (7--20) | DI1 | DI1 | DI1I2 | DI2 | DI1I2 | I2 | I1I2 | DI2I3 | D1D2 | D1 | D1D2D3 |

-continued

Construction results of InDel marker genotype database of *Malus* germplasm resources

| | | | | | | | | | | | |
|---|---|---|---|---|---|---|---|---|---|---|---|
| Napoleon (7--22) | DI1 | DI1 | DI1I2 | DI2 | DI1I2 | D | DI1I2 | I1I2I3 | D1I2 | D1 | D1D2D3 |
| Youyi (7--23) | DI2 | D | DI1I2 | DI1I2 | DI1I2 | DI2 | DI1I2 | DI2I3 | D2 | D1 | D1D2D3 |
| Oregon Spur (7--3) | DI2 | I1 | DI1I2 | DI2 | DI1I2 | DI2 | I1I2 | DI2I3 | D2I2 | D1 | D1D2D3I |
| Kangtun Spur (7--6) | DI2 | DI1 | DI1I2 | DI1I2 | DI1I2 | DI2 | DI1I2 | DI1I2I3 | I2 | D1 | D1D2D3 |
| White Pippin (7--9) | DI2 | DI1 | DI1I2 | DI2 | DI1I2 | I1 | I1I2 | DI2 | D1D2 | D1I | D1D2D3 |
| Zach Lebel (8--1) | DI1I2 | DI1 | DI1I2 | DI1I2 | DI1I2 | DI1I2 | I1I2 | DI1I2I3 | D1D2 | D1 | D1D2D3 |
| Cortland (8--10) | DI2 | DI1 | DI1I2 | DI2 | DI1I2 | D | DI1I2 | DI2I3 | D2I1 | D1 | D1D2D3I |
| Raritan (8--12) | DI2 | DI1 | DI1I2 | DI1I2 | DI1I2 | D | DI1I2 | DI2I3 | D2I2 | D1 | D1D2D3 |
| Meilingxi Tsugaru (8--13) | I2 | DI1 | DI1I2 | DI2 | DI1I2 | D | DI1I2 | DI1I2I3 | D2I2 | D1I | D1D2D3I |
| Moscow Transparent (8--14) | DI2 | D | DI1I2 | DI2 | DI1I2 | DI1 | I1I2 | DI1I2I3 | D1D2I1 | D1 | D1D3 |
| Cooper's Market (8--15) | I2 | DI1 | DI1I2 | DI2 | DI1I2 | DI1 | DI1I2 | DI1I2I3 | D2 | D1 | D1D2D3I |
| Xite Shisheng (8--16) | I2 | DI2 | DI1I2 | DI2 | DI1I2 | DI1 | I1I2 | DI2I3 | D1I2 | D1 | D1D2D3I |
| Tian Yisaye (8--17) | DI2 | DI2 | DI1I2 | DI2 | DI1I2 | DI1 | DI1I2 | DI2I3 | D2 | D1 | D1D3 |
| Shennong 2 (8--19) | DI1 | DI1 | DI1I2 | DI1I2 | DI1I2 | DI1 | I1I2 | DI2I3 | D2 | D1D3 | D1D2D3I |
| Maigold (8--20) | I2 | I1I2 | DI1I2 | DI1 | DI1I2 | DI1 | DI1I2 | DI1I2 | D2 | D1 | D1D2D3I |
| Magu (8--21) | DI2 | DI1 | DI1I2 | DI2 | DI1I2 | DI2 | DI1I2 | DI2I3 | D2 | D1 | D1D2D3I |
| Cellini (8--23) | DI1 | D | DI1I2 | DI2 | DI1I2 | D | DI1I2 | DI2I3 | D1D2 | D1 | D1D2D3 |
| Simonffy Piros (8--3) | DI2 | DI1 | DI1I2 | DI1I2 | DI1I2 | DI1 | DI1I2 | DI1I2I3 | D1 | D1 | D1D2D3I |
| Luxiang (8--5) | I2 | D | DI1I2 | DI2 | DI1I2 | DI2 | I1I2 | DI1I2I3 | D2I2 | D1 | D1D2D3 |
| Zhongqiu (8--6) | DI2 | D | DI1I2 | DI1I2 | DI1I2 | D | DI1I2 | DI2I3 | D1D2 | D1 | D1D2D3 |
| De 2 (8--7) | I2 | I1I2 | DI1I2 | DI2 | DI1I2 | DI2 | DI1I2 | DI1I2I3 | D1D2 | D1I | D2D3I |
| Grimes Golden (8--8) | I2 | I2 | DI1I2 | DI1I2 | DI1I2 | DI1 | DI1I2 | DI1I2I3 | D2 | I | D1D2D3I |
| I2arly Straw Berry (8--9) | I1I2 | D | DI1I2 | DI2 | DI1I2 | DI2 | DI1I2 | I2I3 | D2I2 | D1 | D1D2D3 |
| Kelia (9--10) | I1I2 | DI2 | DI1I2 | DI2 | DI1I2 | DI1I2 | DI1I2 | DI1I2I3 | D2I2 | D1 | D1D2D3I |
| French Apple (9--11) | DI1 | D | DI1I2 | DI1I2 | DI1I2 | I2 | DI1I2 | DI2I3 | D1D2 | D1 | D1D2D3I |
| Todoroki Tsugaru (9--12) | I1I2 | DI2 | DI1I2 | DI1I2 | DI1I2 | DI2 | DI1I2 | I2I3 | D2 | D1I | D1D2D3I |
| Cuihong (9--13) | I1I2 | DI1 | DI1I2 | DI1I2 | DI1I2 | I1I2 | I1I2 | DI2I3 | D2 | D1 | D1D2D3 |
| De 4 (9--14) | DI1I2 | DI1 | DI1I2 | DI2 | DI1I2 | DI2 | DI1I2 | DI1I2I3 | D2 | D1 | D1D2D3I |
| I2arly McIntosh (9--18) | DI2 | DI2 | DI1I2 | DI2 | I1I2 | D | I1I2 | DI2I3 | D1D2 | D1 | D1D2D3 |
| Adam Mickewier (9--19) | I2 | DI1 | DI1I2 | DI2 | DI1I2 | I2 | I1I2 | DI2 | D2 | D1 | D1D2D3I |
| Norda (9--2) | D | DI2 | DI1I2 | DI1I2 | DI1I2 | I1 | I1I2 | DI2I3 | D1D2 | D1 | D1D3I |
| Cardinal (9--20) | I1I2 | DI2 | DI1I2 | DI1I2 | I1I2 | DI1 | I1I2 | DI2I3 | D2I2 | D1I | D1D2D3 |
| I2velyn (9--21) | DI2 | DI1 | DI1 | DI2 | DI1I2 | DI2 | DI1I2 | DI2I3 | D2I1 | D1 | D1D2D3I |
| Situonuowei (9--22) | DI1 | DI1 | DI1I2 | DI2 | DI1I2 | DI1 | I1I2 | DI2I3 | D1D2 | D1 | D1D2D3 |
| Yingqiu (9--23) | I1I2 | D | DI1I2 | DI1I2 | DI1I2 | I2 | DI1I2 | DI2I3 | D2 | D1 | D1D2D3I |
| Kelongxieer (9--3) | DI2 | D | DI1I2 | DI2 | DI1I2 | DI1 | I1I2 | DI1I2I3 | D1I1 | D1 | D1D3 |
| Cloden (9--5) | I2 | I1 | DI1I2 | DI1I2 | DI1I2 | I1I2 | DI1I2 | DI1I2I3 | D1I2 | D1 | D1D2D3I |
| Qiutianhong (9--6) | DI1 | DI1 | DI1I2 | DI2 | DI1I2 | DI1 | I1I2 | DI2I3 | D1D2 | D1 | D1D2D3 |
| Gaidebao (9--7) | I1I2 | D | DI1I2 | DI2 | DI1I2 | DI2 | I1I2 | I1I2I3 | D1D2 | D1 | NA |

-continued

Construction results of InDel marker genotype database of *Malus* germplasm resources

| | | | | | | | | | | | |
|---|---|---|---|---|---|---|---|---|---|---|---|
| Starkjam (9--9) | DI1 | DI1 | DI1I2 | DI2 | DI1I2 | D | DI1I2 | I1I2I3 | D1I2 | D1 | D1D2D3 |
| Wan Crab (B-1) | D | DI2 | DI1 | DI1I2 | DI1I2 | D | I1I2 | DI2I3 | D2 | D3I | D1D2D3I |
| Minjiandaguo Crab (B-10) | I1I2 | D | DI1 | DI2 | DI1I2 | DI1 | I1I2 | DI2 | D2I2 | D1I | D1D2D3 |
| Luanzhuang Crab (B1-11) | DI1 | D | DI1I2 | DI2 | DI1I2 | D | DI1 | DI2I3 | D2 | D1 | D1D2D3I |
| Sankuaishi Crab (B1-12) | I2 | D | DI1 | DI2 | DI1I2 | I1 | I1I2 | I2 | D2 | D1D3 | D1 |
| Xiongyue Crab 1 (B1-13) | D | DI2 | DI1I2 | DI1I2 | DI1I2 | DI1 | I1I2 | DI2I3 | D2I2 | D1I | D1D2D3I |
| Sankuaishi Crab 2 (B1-14) | I2 | DI2 | DI1I2 | DI2 | DI1I2 | D | I1I2 | DI2I3 | D2 | D1I | D1D2D3 |
| Dabaleng (B-12) | I2 | DI1 | DI1I2 | DI1I2 | DI1I2 | D | DI1I2 | DI2I3 | D2 | D1D3 | D1D2D3I |
| Sankuaishi Crab 2 (B-13) | DI2 | DI1 | DI1I2 | DI1I2 | DI1I2 | D | DI1I2 | DI2I3 | D2I2 | D1 | D1D2D3 |
| Changguo Crab (B-14) | I1 | DI2 | DI1I2 | DI1I2 | DI1I2 | DI1 | I1I2 | DI2I3 | D2 | D3I | D1D2D3I |
| Dagucheng Baleng (B1-5) | I2 | D | DI1I2 | DI1I2 | DI1I2 | D | I1 | DI2 | D2 | D1 | D1D2D3 |
| Zumi Crab 3x (B-15) | I1 | DI1 | DI1I2 | DI1 | DI1I2 | DI1 | I1I2 | DI2I3 | D2 | D2I | D1D2D3I |
| 26105 (B-16) | I2 | DI1 | DI1I2 | DI1I2 | DI1I2 | DI2 | DI1I2 | DI2 | D2 | D1 | D1D2D3 |
| Daguo Crab (B-17) | I1I2 | D | DI1 | DI2 | DI1I2 | DI1 | I1I2 | DI2 | D2I2 | D1I | D1D2D3 |
| Xiongyue Crab 2 (B1-8) | D | NA | DI1I2 | DI2 | I1I2 | DI1 | DI1I2 | DI2 | D1 | D1D2 | D1D2D3 |
| Watermelon Crab (B-18) | I2 | DI2 | DI1I2 | DI2 | DI1I2 | I1 | I1I2 | DI1I2 | D2 | D1I | D1D2D3 |
| Mudanjiang Crab (B1-9) | DI2 | D | DI1I2 | DI1I2 | DI1I2 | I1I2 | I1I2 | DI2 | D2I2 | D3 | D1D2D3 |
| Tianhong 1 (B-19) | DI2 | DI1 | DI1I2 | DI1I2 | DI1I2 | D | DI1I2 | DI2I3 | D2I2 | D1 | D1D2D3 |
| Jiping 1 (B-2) | I2 | DI1 | DI1I2 | DI1I2 | DI1I2 | DI1 | DI1 | DI2I3 | D1I2 | D1 | D1D2D3 |
| Caoyuan Crab (B2-1) | D | NA | NA | D | I1I2 | D | I1I2 | NA | NA | D1 | D1I |
| Zumi Crab 4x (B-21) | I1 | DI1 | DI1I2 | DI1 | DI1I2 | DI1 | I1I2 | DI2I3 | D2 | D2I | D1D2D3I |
| Luanzhuang Shaguo (B2-11) | I2 | D | DI1I2 | DI1I2 | DI1I2 | I1 | I1I2 | DI2I3 | D2 | D1D3 | D1D2D3 |
| Xiaofan Crab (B2-13) | I2 | D | DI1I2 | DI2 | DI1I2 | DI1 | I1I2 | DI2 | D1D2 | D1 | D1D2 |
| Hebing Pingding Crab (B2-14) | I2 | D | DI1I2 | DI1I2 | I1I2 | D | I1I2 | DI2 | D2 | D1 | D1D2D3 |
| Zumi Crab 3x 2 (B-22) | I1 | DI1 | DI1I2 | DI1 | DI1I2 | DI1 | I1I2 | DI2I3 | D2 | D2I | D1D2D3I |
| Baleng Crab (B2-3) | I2 | D | DI1I2 | DI1I2 | DI1I2 | D | I1I2 | DI2 | D2 | D1D3 | D1D2D3 |
| Baleng seedling 14 (B-25) | I1I2 | DI1 | DI1I2 | DI1I2 | DI1I2 | I1 | I1I2 | DI1I2 | D2I2 | D1D3 | D1D2D3I |
| Russian White apple (B2-6) | DI2 | D | DI1I2 | DI1I2 | DI1I2 | D | DI1I2 | DI2I3 | D1D2 | D1 | D1D2D3 |
| Nagafu 2 (B-26) | DI2 | DI1 | DI1I2 | DI1I2 | DI1I2 | D | DI1I2 | DI2I3 | D2I2 | D1 | D1D2D3 |
| Ambrosia (B-27) | I2 | DI1 | DI1I2 | DI1 | DI1I2 | I1I2 | I1I2 | DI1I2I3 | I2 | D1 | D1D2D3 |
| Aihonghua (B-2-8) | DI2 | DI1 | DI1I2 | DI1I2 | DI1I2 | D | I1I2 | I2I3 | D2 | D1 | D1D2D3I |
| Nanshennan (B-28) | DI2 | DI1 | DI1I2 | DI1I2 | DI1I2 | D | DI1I2 | DI2I3 | D2I2 | D1 | D1D2D3 |
| Zumi Crab W1 (B-29) | I1 | DI1 | DI1I2 | DI1 | DI1I2 | DI1 | I1I2 | DI3 | D2 | D2I | D1D2D3I |
| Hong 4G (B-3) | I2 | D | DI1I2 | DI1I2 | DI1I2 | I1I2 | DI1I2 | DI2I3 | D2I2 | D1 | D1D2D3 |
| Zumi Crab (B-30) | I1 | DI1 | DI1I2 | DI1 | DI1 | DI1 | I1I2 | DI2I3 | D2 | D2I | D1D2D3I |
| Zaobai Crab (B3-1) | I2 | D | DI1I2 | DI2 | DI1I2 | DI1 | I1I2 | DI2 | D1 | D1 | D1D2D3 |
| Mollie's Delicious (B-31) | DI2 | DI2 | DI1I2 | DI1I2 | DI1I2 | I1I2 | I1I2 | I1I2I3 | D2I2 | D1I | D2D3I |

-continued

| Construction results of InDel marker genotype database of *Malus* germplasm resources |||||||||||
| --- | --- | --- | --- | --- | --- | --- | --- | --- | --- | --- |
| Regunzi Spur (B3-10) | I2 | D | DI1I2 | DI1I2 | DI1I2 | DI2 | I1I2 | DI2 | D2 | D1D3 | D1D3 |
| Xiaofanshan Baleng (B3-11) | I1I2 | DI1 | DI1I2 | DI1I2 | DI1I2 | I1 | DI1I2 | DI2I3 | D2I1 | D1D3 | D1D2D3 |
| Huamei (B3-12) | I2 | I1 | DI1I2 | DI1I2 | DI1I2 | DI1 | DI1I2 | DI1I2I3 | I2 | D1 | D1D2D3I |
| Huashuo (B3-13) | DI1 | DI1 | DI1I2 | DI1I2 | DI1I2 | I1I2 | I1I2 | DI2I3 | D1D2 | D1 | D1D2D3 |
| Yuhong (B3-14) | DI2 | DI1 | DI1I2 | DI1I2 | DI1I2 | DI2 | I1I2 | DI1I2I3 | I2 | D1 | D1D2D3 |
| Huayue (B3-15) | I2 | DI1 | DI1I2 | DI2 | DI1I2 | DI1I2 | DI1I2 | DI1I2 | D1D2 | D1 | D1D2D3I |
| Jingbohu Shandingzi (B3-2) | D | D | DI1 | DI1 | I1I2 | NA | I1 | DI2 | D2 | D3 | D1D2 |
| I2luosi Daguo Shandingzi (B3-3) | D | DI2 | DI1I2 | DI1I2 | DI1I2 | I1 | I1I2 | DI2I3 | D2I2 | D1D3 | D1D3 |
| HY (B-33) | I2 | DI1 | DI1I2 | DI2 | DI1I2 | D | I1I2 | DI1I2 | D1 | D1 | D1D2D3 |
| Hong Crab (B3-6) | I2 | D | DI1I2 | DI1I2 | DI1I2 | D | I1I2 | DI2 | D2 | D1D3 | D1D3 |
| 23# (B-37) | I2 | DI1 | DI1I2 | DI2 | DI1I2 | DI1 | DI1 | DI1I2I3 | D1I2 | D1 | D1D2D3I |
| Russian apple (B3-8) | D | D | DI1 | DI2 | DI1I2 | DI1 | DI1 | DI2 | D2 | D1I | D1D2D3 |
| 147 (B-38) | I2 | DI1 | DI1 | DI2 | DI1I2 | DI1 | I1I2 | DI1I2 | D1I2 | D1 | D1D2D3 |
| Xiaofanshan Baleng 1 (B3-9) | I2 | D | DI1I2 | DI1I2 | DI1I2 | D | DI1I2 | DI2 | D2 | D1D3 | D1D2D3 |
| Lvshuai (B-4) | I1 | DI2 | DI1I2 | DI1I2 | DI1I2 | DI1 | I1I2 | DI2I3 | D2I2 | D1I | D1D2D3 |
| Dounan (B-40) | I2 | DI1 | DI1I2 | DI1I2 | DI1I2 | DI1 | I1I2 | DI2I3 | D2I2 | D1 | D1D2D3 |
| 11906 (B-41) | D | DI2 | DI1I2 | DI1I2 | DI1I2 | I2 | I1I2 | DI2 | D2 | D1I | D1D3I |
| Luli (B-5) | DI2 | DI1 | DI1I2 | DI2 | DI1I2 | DI1 | I1I2 | DI1I2I3 | D1I2 | D1 | D1D2D3I |
| Jinxiuhong (B-6) | I1I2 | I1I2 | DI1I2 | DI1I2 | DI1I2 | I1 | DI1I2 | DI1I2I3 | I2 | D1I | D1D2D3I |
| B68 (B-7) | DI2 | D | DI1 | DI1 | DI1I2 | DI1 | I1I2 | DI2 | D1 | D1I | D1D2D3 |
| Huaida (B-8) | DI2 | DI2 | DI1I2 | DI2 | DI1I2 | DI1 | I1I2 | I2I3 | D2 | D1I | D1D2D3I |
| Nanshennan mutant (B-9) | DI2 | DI1 | DI1I2 | DI1I2 | DI1I2 | D | DI1I2 | DI2I3 | D2I2 | D1 | D1D2D3 |
| Xiahong (BH-1) | I1I2 | DI2 | DI1I2 | DI2 | DI1I2 | D | I1I2 | DI1I2I3 | D1I1 | D1I | D1D2D3I |
| Wuming1 (BJ-1) | DI1 | I2 | DI1I2 | DI1 | DI1I2 | I1 | I1I2 | I1I2I3 | D2 | D1 | D1D2D3I |
| Canzy ? (BJ-10) | DI2 | DI1 | DI1 | DI1I2 | DI1I2 | DI1 | DI1 | DI1I2I3 | I2 | D1 | D1D2D3I |
| Xiangfu (BJ-11) | DI2 | DI1 | DI1I2 | DI1I2 | DI1I2 | D | DI1I2 | DI2I3 | D2I2 | D1 | D1D2D3 |
| I2nvy (BJ-12) | I2 | DI1 | DI1I2 | DI1I2 | DI1I2 | DI1 | I1I2 | DI1I2I3 | I2 | D1 | D1D2D3 |
| Fuji_KiKu (BJ-2) | DI2 | DI1 | DI1I2 | DI1I2 | DI1I2 | D | DI1I2 | DI2I3 | D2I2 | D1 | D1D2D3 |
| Banxiu Crab (BJ-4) | DI1 | D | DI1 | DI1I2 | DI1I2 | D | DI1I2 | I2 | D1 | D1D2 | D1D2D3I |
| Jazz (BJ-5) | I2 | DI1 | DI1 | DI1I2 | DI1 | DI1 | DI1 | DI1I2I3 | I2 | D1 | D1D2D3 |
| I2arly Red Bird 2 (BJ-7) | DI1 | DI1 | DI1I2 | DI1I2 | DI1I2 | DI1 | I1I2 | I1I2I3 | D1I2 | D1 | D1D2D3 |
| Qiuhong Gala (BJ-8) | DI2 | DI1 | DI1I2 | DI1I2 | DI1I2 | D | DI1I2 | DI2I3 | D2I2 | D1 | D1D2D3 |
| Hongxiangcui (BJ-9) | DI2 | DI1 | DI1I2 | DI1 | DI1I2 | D | DI1I2 | DI1I2I3 | D2I2 | D1 | D1D2D3I |
| 07-115 (BK-1) | D | DI1 | DI1I2 | DI1I2 | DI1I2 | DI1 | DI1I2 | DI2I3 | D1D2 | D1D2 | D1D2D3 |
| Nagafu 3 (BK-2) | DI2 | DI1 | DI1I2 | DI1I2 | DI1I2 | D | DI1I2 | DI2I3 | D2I2 | D1 | D1D2D3 |
| 28-253 (BK-28-253) | I2 | DI2 | DI1I2 | DI1 | DI1I2 | DI1 | I1I2 | DI2I3 | D2I2 | D1I | D1D2D3 |

-continued

| Construction results of InDel marker genotype database of *Malus* germplasm resources | | | | | | | | | | | |
|---|---|---|---|---|---|---|---|---|---|---|---|
| Nagafu 3-R (BK-3) | DI2 | DI1 | DI1I2 | DI1I2 | DI1I2 | D | DI1I2 | DI2I3 | D2I2 | D1 | D1D2D3 |
| 4354 (BK-4) | DI2 | DI1 | DI1 | DI1I2 | DI1I2 | D | I1I2 | DI1I2 | D2I2 | D1 | D1D2D3 |
| 4-23 (BK-4-23) | DI2 | I1 | DI1I2 | DI1I2 | DI1I2 | DI1 | DI1I2 | DI2I3 | D2I2 | D1 | D1D2D3 |
| 4354-R ? (BK-5) | DI2 | DI2 | DI1I2 | DI1 | DI1 | I1I2 | DI2I3 | D2I2 | D1 | D1D2D3I | |
| 77-34 (BK-77-34) | I2 | D | DI1I2 | DI2 | DI1I2 | DI1 | I1I2 | DI2 | D1I1 | D1D3 | D1D2D3I |
| Red Spur Delicious (BK-AH) | DI2 | DI1 | DI1I2 | DI1I2 | DI1I2 | DI2 | I1I2 | DI1I2I3 | I2 | D1 | D1D2D3 |
| Ozark Gold (BK-AJ) | DI2 | DI2 | DI1I2 | DI2 | DI1I2 | I1I2 | DI1I2 | DI1I2 | D2I2 | D1I | D1D2D3I |
| Michinoku (BK-AZ) | DI2 | D | DI1I2 | DI1I2 | DI1I2 | DI2 | DI1I2 | DI2I3 | D1I2 | D1 | D1D2D3 |
| Azwell (BK-Azwell) | DI2 | DI1 | DI1I2 | DI1I2 | DI1I2 | DI2 | I1I2 | I1I2I3 | D1I2 | D1 | D1D2D3 |
| Banbishan Crab (BK-BBSHT) | I2 | D | DI1I2 | DI1I2 | DI1I2 | D | I1I2 | DI2 | D1D2I2 | D1D3 | D1D3 |
| Hokudo (BK-BD) | DI2 | DI1I2 | DI1I2 | DI1I2 | DI1I2 | D | DI1I2 | DI2I3 | D2I2 | D1 | D1D2D3 |
| Baifugao (BK-BFG) | D | DI2 | DI1I2 | DI1I2 | DI1I2 | I1 | I1I2 | DI2I3 | D2I2 | D1I | D1D3 |
| White Crab (BK-BHT) | I1I2 | DI1 | DI1I2 | DI1I2 | DI1I2 | I1 | DI1I2 | DI2I3 | D2I1 | D1D3 | D1D2D3I |
| Buming Kangbing (BK-BMKB) | DI2 | DI1 | DI1I2 | DI2 | DI1I2 | I1 | I1I2 | DI2 | D1D2 | D1I | D1D2D3 |
| Batougou 1 (BK-BTG1H) | D | D | DI1I2 | DI1 | DI1I2 | NA | I1 | DI2 | D2 | D1D3 | D1D3 |
| Batougou 2 (BK-BTG2H) | I2 | D | DI1I2 | DI1 | DI1I2 | DI1 | I1 | DI2 | D2 | D1D3 | D1D3 |
| Batougou Aizhen (BK-BTGAZ) | D | D | DI1 | DI1I2 | I1I2 | DI1 | I1I2 | DI2 | D2 | D1D3 | D1D2D3 |
| Binzi (BK-BZ) | I2 | D | DI1I2 | DI2 | DI1I2 | DI1 | I1I2 | DI2 | D1D2 | D1 | D1D2D3 |
| Kitanosach (BK-BZX) | I1 | D | DI1I2 | DI1I2 | DI1I2 | DI2 | DI1I2 | DI2I3 | D2 | D1 | D1D2D3 |
| Binzi (SW) (BK-BZXN) | I2 | D | DI1I2 | DI2 | DI1I2 | DI1 | I1I2 | DI2 | D1D2 | D1 | D1D2D3 |
| Nagafu 2 (BK-CF2H) | DI2 | DI1 | DI1I2 | DI1I2 | DI1I2 | D | DI1I2 | DI2I3 | D2I2 | D1 | D1D2D3 |
| Nagafu 36 (BK-CF36) | DI2 | DI1 | DI1I2 | DI1I2 | DI1I2 | D | DI1I2 | DI2I3 | D2I2 | D1 | D1D2D3 |
| Nagafu 6 (BK-CF6H) | DI2 | DI1 | DI1I2 | DI1I2 | DI1I2 | D | DI1I2 | DI2I3 | D2I2 | D1 | D1D2D3 |
| CG24 (BK-CG24) | DI2 | DI1 | DI1I2 | DI1I2 | DI1I2 | DI2 | I1I2 | DI1I2I3 | I2 | D1 | D1D2D3 |
| CG3 (BK-CG3) | I2 | DI2 | DI1I2 | DI1 | DI1I2 | DI1 | I1I2 | DI2I3 | D2I2 | D1I | D1D2D3 |
| CG80 (BK-CG80) | DI2 | I1 | DI1I2 | DI2 | DI1I2 | D | DI1I2 | DI2 | D2 | D1 | D1D2D3 |
| Changhong (BK-CH) | DI2 | DI1 | DI1I2 | DI1I2 | DI1I2 | D | DI1I2 | DI2I3 | D2I2 | D1 | D1D2D3 |
| Chieftan (BK-chieftan) | DI2 | DI2 | DI1I2 | DI2 | DI1I2 | I1I2 | I1I2 | I2I3 | D1I2 | D1 | D1D3 |
| Cangjiang Crab (BK-CJHT) | D | NA | DI1I2 | DI1 | DI1I2 | DI1 | I1 | I2 | D1 | D2 | D1D3 |
| Chuanling Crab (BK-CLHT) | I2 | D | DI1I2 | DI1I2 | DI1I2 | DI1 | I1I2 | DI2I3 | D2I2 | D1D3 | D1D3 |
| Hatsuaki (BK-CQ) | I1I2 | DI2 | DI1I2 | DI2 | DI1I2 | DI1 | I1I2 | I1I2 | D1D2 | D1I | D1D2D3I |
| Crispin (BK-crispin) | I1I2 | DI1I2 | DI1I2 | DI1I2 | DI1I2 | DI1 | I1I2 | DI1I2I3 | D2I2 | D1I | D1D2D3 |
| Caozigang Yuanshuai (BK-CZGYS) | DI2 | DI1 | DI1I2 | DI1I2 | DI1I2 | DI2 | I1I2 | DI1I2I3 | I2 | D1 | D1D2D3 |
| Danxia (BK-DANXIA) | I1I2 | DI1 | DI1I2 | DI1I2 | DI1I2 | D | I1I2 | DI2I3 | I2 | D1 | D1D2D3 |
| Dolgo (BK-DDG) | D | DI2 | DI1I2 | DI1I2 | DI1I2 | I1 | I1I2 | DI2I3 | D2I2 | D1D3 | D1D3 |
| Darwin (BK-DI2W) | I2 | D | DI1I2 | DI2 | DI1I2 | DI1 | I1I2 | DI2 | D1 | D1 | D1D2D3 |
| Oriental Apple (BK-DFPG) | D | DI2 | DI1I2 | DI2 | DI1I2 | D | DI1I2 | DI2I3 | D1 | D1I | D1D2D3 |

-continued

| | | | | | | | | | | |
|---|---|---|---|---|---|---|---|---|---|---|
| Construction results of InDel marker genotype database of *Malus* germplasm resources | | | | | | | | | | |
| Big Crab (BK-DGHT) | I2 | D | DI1 | DI1I2 | DI1I2 | D | DI1I2 | DI2I3 | D1D2 | D1I | D1D2I |
| Daguo Jinhong (BK-DGJH) | DI2 | DI2 | DI1I2 | DI2 | DI1I2 | DI1 | I1I2 | I2I3 | D2 | D1I | D1D2D3I |
| Daihong (BK-DH) | DI2 | DI1 | DI1I2 | DI1I2 | DI1I2 | DI2 | I1I2 | DI1I2I3 | I2 | D1 | D1D2D3 |
| Daihao 261 (BK-DH261) | DI2 | DI2 | DI1I2 | DI1I2 | DI1I2 | I1I2 | I1I2 | DI2I3 | D2 | D1D3 | D1D2D3I |
| Spur Golden Delicious (BK-DJG) | I1I2 | I1I2 | DI1I2 | DI1I2 | DI1I2 | DI1 | I1I2 | DI1I2I3 | D2I2 | D1I | D1D2D3I |
| Daxianguo (BK-DXG) | I2 | D | DI1I2 | DI1I2 | DI1I2 | DI1 | I1I2 | DI2 | D2 | D1D3 | D1D3 |
| Daye Crab (BK-DYHT) | I2 | D | DI1 | DI2 | DI1I2 | D | I1I2 | DI2 | D2 | D3 | D1D2D3 |
| Spur Fuji (BK-DZFS) | DI2 | DI1 | DI1I2 | DI1I2 | DI1I2 | D | DI1I2 | DI2I3 | D2I2 | D1 | D1D2D3 |
| Huaguan Spur (BK-DZHG) | I1I2 | I1I2 | DI1I2 | DI1I2 | DI1I2 | DI1 | DI1I2 | DI1I2I3 | I2 | D1I | D1D2D3I |
| I2lite (BK-I2lite) | DI2 | DI1 | DI1I2 | DI1I2 | DI1I2 | DI2 | I1I2 | DI1I2I3 | I2 | D1 | D1D2D3 |
| Fa 8 (BK-F8) | I2 | DI1 | DI1I2 | DI2 | DI1I2 | DI1I2 | DI1I2 | DI1I2 | D1D2 | D1 | D1D2D3I |
| Fukushima Spur Fuji (BK-FDDZ) | DI2 | DI1 | DI1I2 | DI1I2 | DI1I2 | D | DI1I2 | DI2I3 | D2I2 | D1 | D1D2D3 |
| Fujin (BK-FJ) | DI2 | DI1 | DI1I2 | DI1I2 | DI1I2 | DI2 | DI1I2 | DI2I3 | D2I2 | D1 | D1D2D3 |
| Florina (BK-Florina) | I1I2 | D | DI1I2 | DI1I2 | DI1I2 | DI2 | DI1I2 | I2I3 | D2I2 | D1 | D1D2D3 |
| Fangming (BK-FM) | I1I2 | DI2 | DI1I2 | DI1I2 | DI1I2 | DI2 | DI1I2 | I2I3 | D2 | D1I | D1D2D3I |
| Fuji (BK-Fuji) | DI2 | DI1 | DI1I2 | DI1I2 | DI1I2 | D | DI1I2 | DI2I3 | D2I2 | D1 | D1D2D3 |
| Fengyan (BK-FY) | DI2 | I1I2 | DI1I2 | DI2 | DI1I2 | DI2 | DI1I2 | I2I3 | D2I1 | D1 | D1D3 |
| Yanfu 1 (BK-FY1) | DI2 | DI1 | DI1I2 | DI1I2 | DI1I2 | D | DI1I2 | DI2I3 | D2I2 | D1 | D1D2D3 |
| King of Tompkins County (BK-FZY) | I1I2 | DI2 | DI1I2 | DI2 | DI1I2 | D | DI1 | DI1I2I3 | D2 | D1I | D2D3I |
| G30 (BK-G30) | I2 | D | DI1I2 | DI1I2 | DI1I2 | I1 | I1I2 | DI2 | D1D2 | D1D3 | D1D2D3 |
| Gao #5 (BK-G-5) | DI2 | DI1 | DI1I2 | DI2 | DI1I2 | D | DI1I2 | DI2I3 | D1D2 | D1I | D1D2D3 |
| Gala (BK-gala) | I2 | I1 | DI1I2 | DI1I2 | DI1I2 | DI1 | DI1I2 | DI1I2I3 | I2 | D1 | D1D2D3I |
| Golden Delicious (BK-GD) | I1I2 | I1I2 | DI1I2 | DI1I2 | DI1I2 | DI1 | I1I2 | DI1I2I3 | D2I2 | D1I | D1D2D3I |
| Gloster69 (BK-Gloster69) | DI2 | DI1 | DI1I2 | DI2 | DI1I2 | DI2 | DI1I2 | DI1I2 | D1I2 | D1 | D1D2D3I |
| GM256 (BK-GM256) | I2 | D | DI1I2 | DI2 | DI1I2 | D | I1I2 | DI2 | D1D2 | D1 | D1D2D3I |
| GM310 (BK-GM310) | I2 | DI2 | DI1I2 | DI2 | DI1I2 | DI1 | I1I2 | I2I3 | D1D2 | D1I | D1D2D3I |
| Gaoqiu (BK-GQ) | DI1 | DI1 | DI1I2 | DI1I2 | I1I2 | D | I1I2 | DI2I3 | D2 | D1 | D1D2D3I |
| Miyazaki Spur Fuji (BK-GQDZ) | DI2 | DI1 | DI1I2 | DI1I2 | DI1I2 | D | DI1I2 | DI2I3 | D2I2 | D1 | D1D2D3 |
| HAC-9 (BK-HAC-9) | DI1I2 | DI1 | DI1I2 | DI1I2 | DI1I2 | DI1 | DI1I2 | DI2I3 | D2I2 | D1 | D1D2D3 |
| Huifeng Orin (BK-HFWL) | I2 | DI1 | DI1I2 | DI2 | DI1I2 | D | DI1 | I2I3 | D2 | D1 | D1D2D3I |
| Red Ralls Janet (BK-HGG) | I1I2 | DI1 | DI1I2 | DI2 | DI1I2 | D | DI1I2 | DI1I2I3 | D1D2 | D1 | D1D3I |
| Huaguan Crab (BK-HGHT) | I2 | D | DI1I2 | DI2 | DI1I2 | DI1 | I1I2 | DI2 | D1 | D1D3 | D1D2D3 |
| Harrold Red Delicious (BK-HH) | DI2 | DI1 | DI1I2 | DI1I2 | DI1I2 | DI2 | I1I2 | DI1I2I3 | I2 | D1 | D1D2D3 |
| Hong Crab 2 (BK-HHT2H) | I2 | D | DI1I2 | DI1I2 | DI1I2 | D | I1I2 | DI2 | D2 | D1D3 | D1D3 |
| Stark Redgold (BK-HJ) | I2 | I1 | DI1 | DI1I2 | DI1 | I1I2 | I2I3 | D2I2 | D1 | D1D2D3 | |
| HLWQ (BK-HLWQ) | DI2 | DI1 | DI1I2 | DI2 | DI1I2 | DI1 | DI1I2 | DI2I3 | D2 | D1 | D1D2D3I |
| Holly (BK-Holly) | DI2 | DI1 | DI1I2 | DI2 | DI1I2 | DI2 | DI1I2 | DI1I2I3 | D2I2 | D1 | D1D2D3I |

-continued

Construction results of InDel marker genotype database of *Malus* germplasm resources

| | | | | | | | | | | | |
|---|---|---|---|---|---|---|---|---|---|---|---|
| Red Jonagold (BK-HQNJ) | DI2 | DI1 | DI1I2 | DI1I2 | DI1I2 | I1 | DI1I2 | DI2I3 | D2 | D1 | D1D2D3 |
| Red Sekaiichii (BK-HSJY) | I1I2 | I1I2 | DI1I2 | DI2 | I1I2 | D | I1I2 | DI1I2I3 | D2I2 | D1I | D1D2D3I |
| Hongte (BK-HT) | DI2 | DI1 | DI1I2 | DI1I2 | DI1I2 | DI2 | I1I2 | DI1I2I3 | D2I2 | D1 | D1D2D3 |
| Haitangguo (BK-HTG) | I2 | DI2 | DI1 | DI1I2 | DI1I2 | D | I1I2 | DI2I3 | D2 | D1I | D1D2D3 |
| Haitanghua (BK-HTH) | DI2 | D | DI1I2 | DI2 | DI1I2 | DI1 | I1I2 | DI2 | D1D2 | D1D2 | D1D2D3 |
| Huangtaiping (BK-HTP) | I1I2 | DI1 | DI1I2 | DI1I2 | DI1I2 | I1 | DI1I2 | DI2I3 | D2I1 | D1D3 | D1D2D3 |
| Hongxue (BK-HX) | DI2 | DI1 | DI1I2 | DI2 | DI1I2 | I1 | I1I2 | DI2 | D1D2 | D1I | D1D2D3 |
| Jincui (BK-JC) | DI1 | DI1 | DI1I2 | DI1 | DI1I2 | I1I2 | I1I2 | DI1I2 | I2 | D1I | D1D2D3 |
| Juda Fuji (BK-JDFS) | DI2 | DI1 | DI1I2 | DI1I2 | DI1I2 | D | DI1I2 | DI2I3 | D2I2 | D1 | D1D2D3 |
| Jiguan (BK-JG) | DI2 | D | DI1I2 | DI2 | DI1I2 | DI2 | DI1I2 | DI2I3 | D1D2 | D1I | D2D3I |
| Jinhong (BK-JH) | DI2 | DI2 | DI1I2 | DI2 | DI1 | DI1 | I1I2 | I3 | D2 | D1I | D1D2D3I |
| Jonagored (BK-Jonagored) | I1I2 | DI1I2 | DI1I2 | DI1I2 | DI1I2 | DI1 | I1I2 | DI1I2I3 | D2I2 | D1I | D1D2D3 |
| Jonathan (BK-Jonathan) | I2 | D | DI1I2 | DI2 | DI1I2 | DI2 | DI1I2 | DI2I3 | D2 | D1 | D1D2D3I |
| Himekami (BK-JS) | I2 | DI1 | DI1I2 | DI2 | DI1I2 | D | DI1I2 | DI2I3 | D2I2 | D1 | D1D2D3I |
| Stark Blushing Golden (BK-JY) | I2 | DI1 | DI1I2 | DI2 | DI1I2 | DI2 | I1I2 | DI1I2I3 | D2I2 | D1I | D1D2D3I |
| Classic Red Delicious (BK-KAHONG) | DI2 | DI1 | DI1I2 | DI1I2 | DI1I2 | DI2 | I1I2 | DI1I2I3 | I2 | D1 | D1D2D3 |
| KLGDG Shandingzi (BK-KLGDGSDZ) | D | D | DI1 | DI1I2 | I1I2 | D | I1 | DI2 | D1 | D3 | D1D2 |
| KOSZTI2LQ (BK-KOSZTI2LQ) | DI1I2 | I1I2 | DI1 | DI1I2 | DI1I2 | D | I1I2 | DI2I3 | D1D2 | D1 | D1D2D3 |
| Sunflower (BK-KUIHUA) | I2 | DI2 | DI1I2 | DI1 | I1I2 | DI1 | I1I2 | DI1I2I3 | I2 | D1I | D1D2D3I |
| Lenghaitang (BK-LHT) | I2 | D | DI1I2 | DI1I2 | DI1I2 | D | I1I2 | DI2 | D1D2 | D1D3 | D1D3 |
| Liberty (BK-liberty) | DI2 | DI2 | DI1I2 | DI2 | DI1I2 | I1I2 | I1I2 | I2I3 | D1I2 | D1 | D1D3 |
| Lijiang Shandingzi (BK-LJSDZ) | I2 | D | DI1I2 | DI2 | DI1I2 | I1I2 | I1I2 | DI2 | D1D2 | D1D2 | D1D2D3I |
| Laoshan 4 (BK-LS4H) | I2 | D | DI1I2 | DI1I2 | DI1I2 | I1 | I1I2 | DI2 | D2 | D1D3 | D1D3 |
| Ryoka no Kisetsu (BK-LX) | DI2 | DI1 | DI1I2 | DI1I2 | DI1I2 | D | DI1I2 | DI2I3 | D2I2 | D1 | D1D2D3 |
| Lvxiangjiao (BK-LXJ) | I1I2 | I1I2 | DI1I2 | DI2 | DI1I2 | DI1 | I1I2 | DI2I3 | D2 | D1I | D1D2D3 |
| Liaozhen 1 (BK-LZ1H) | DI2 | D | DI1I2 | DI2 | DI1I2 | DI1 | I1I2 | I2 | D1D2 | D1D3 | D1D2D3 |
| M7 (BK-M7) | DI2 | D | DI1I2 | DI2 | DI1I2 | DI1 | I1I2 | DI2I3 | D2 | D1 | D1D2D3I |
| Meiguihong (BK-MGH) | DI2 | DI1 | DI1I2 | DI1I2 | DI1I2 | DI2 | I1I2 | DI1I2I3 | I2 | D1 | D1D2D3 |
| Meile (BK-ML) | I2 | I1I2 | DI1I2 | DI1I2 | DI1I2 | DI1 | DI1I2 | DI1I2I3 | D2 | I | D2D3I |
| MM106 (BK-MM106) | DI2 | I1 | DI1I2 | DI2 | DI1I2 | D | I1I2 | DI2 | D2 | D1 | D1D2D3 |
| Mengpaisi (BK-MPS) | DI1I2 | DI1 | DI1I2 | DI2 | DI1I2 | DI2 | DI1I2 | DI1I2I3 | D2 | D1 | D1D2D3I |
| Meixiang (BK-MX) | DI2 | DI1 | DI1I2 | DI1I2 | DI1I2 | D | DI1I2 | DI2I3 | D2I2 | D1 | D1D2D3 |
| Ningqiu (BK-NQ) | DI1 | D | DI1I2 | DI1I2 | DI1I2 | D | DI1I2 | DI2I3 | D2 | D1 | D1D2D3 |
| P16 (BK-P16) | I2 | D | DI1I2 | DI2 | DI1I2 | D | DI1 | DI2 | D2 | D1I | D1D2D3I |
| P22 (BK-P22) | I2 | D | DI1I2 | DI1I2 | DI1I2 | D | I1I2 | DI2 | D2 | D1D3 | D1D2D3 |
| Pingdinghaitang (BK-PDHT) | I2 | D | DI1I2 | DI1I2 | DI1I2 | I1 | I1I2 | DI2 | D2 | D1D3 | D1D3 |
| Bianguo Crab (BK-PGHT) | DI2 | DI2 | DI1I2 | DI1I2 | DI1I2 | DI2 | I1I2 | DI1I2I3 | D2 | D1D3 | D1D2D3 |

-continued

Construction results of InDel marker genotype database of *Malus* germplasm resources

| | | | | | | | | | | | |
|---|---|---|---|---|---|---|---|---|---|---|---|
| Pionier (BK-Pionier) | I1I2 | DI2 | DI1I2 | DI2 | DI1I2 | I2 | I1I2 | DI1I2I3 | D2 | D1 | D1D2D3 |
| Prima (BK-Prima) | I1I2 | I1I2 | DI1I2 | DI2 | DI1I2 | DI2 | I1I2 | DI2I3 | D2I1 | D1I | D1D2D3 |
| Pingyitiancha (BK-PYTC) | D | D | DI1 | DI1I2 | DI1I2 | D | I1I2 | DI2 | D2 | D1D2D3 | D1D2D3 |
| Qianxue (BK-QAINXUI2) | I2 | I1I2 | DI1I2 | DI1I2 | I1I2 | DI1 | I1I2 | DI1I2I3 | D2 | D1 | D1D2D3I |
| Akifu 1 (BK-QF1) | DI2 | DI1 | DI1I2 | DI1I2 | DI1I2 | D | DI1I2 | DI2I3 | D2I2 | D1 | D1D2D3 |
| Qingfu 13 (BK-QF13) | DI2 | DI1 | DI1I2 | DI1I2 | DI1I2 | D | DI1I2 | DI2I3 | D2I2 | D1 | D1D2D3 |
| Seimei (BK-QM) | I1I2 | I1I2 | DI1I2 | DI1I2 | DI1I2 | D | DI1I2 | DI2I3 | D2I2 | D1I | D1D2D3 |
| Senshu (BK-QQ) | I1I2 | I1 | DI1I2 | DI1I2 | I1I2 | D | DI1I2 | DI2I3 | D1D2I2 | D1 | D1D2D3I |
| Aomori I2arly (BK-QSZS) | I1I2 | I1I2 | DI1I2 | DI1I2 | DI1I2 | DI1 | DI1I2 | DI1I2I3 | D2I2 | D1I | D1D2D3 |
| Qiuxiang (BK-QX) | I1I2 | DI2 | DI1I2 | DI1I2 | DI1I2 | DI2 | DI1I2 | I2I3 | D2 | D1I | D1D2D3I |
| Qiuxing Crab (BK-QXHT) | I1I2 | DI1 | DI1I2 | DI2 | DI1I2 | I1 | DI1 | DI2 | D2 | D1D3 | D1D2D3I |
| Yanqing (BK-QY) | DI2 | I1 | DI1I2 | DI1I2 | DI1I2 | D | I1I2 | DI1I2 | D2I2 | D1 | D1D2D3 |
| Regunzi (BK-RGZ) | I2 | D | DI1I2 | DI1I2 | DI1I2 | DI2 | I1I2 | DI2 | D2 | D1D3 | D1D3 |
| Ruby (BK-Ruby) | DI2 | I1 | DI1I2 | DI2 | DI1I2 | DI2 | I1I2 | DI2I3 | D2I2 | D1 | D1D2D3I |
| Scarlet (BK-scarlet) | DI2 | DI1 | DI1I2 | DI1I2 | DI1I2 | DI2 | I1I2 | DI1I2I3 | I2 | D1 | D1D2D3 |
| Sdw1 (BK-Sdw1) | D | D | DI1 | DI1 | DI1I2 | NA | I1I2 | DI2 | D2 | D1D3 | D1D2D3 |
| Shandingzi 2 (BK-SDZ2H) | I2 | D | DI1 | DI1I2 | DI1I2 | D | I1 | DI2 | D2 | D1D3 | D1D2D3 |
| Su I2 Shandingzi (BK-SI2SDZ) | D | D | DI1I2 | DI1I2 | DI1I2 | NA | I1I2 | DI2 | D1D2 | D1D3 | D1D2D3 |
| Shengfang 2 (BK-SF2) | DI2 | DI1 | DI1I2 | DI1I2 | DI1I2 | D | DI1I2 | DI2I3 | D2I2 | D1 | D1D2D3 |
| SH6 (BK-SH6) | DI2 | D | DI1I2 | DI1I2 | DI1I2 | D | DI1I2 | DI2I3 | D2 | D1 | D1D2D3I |
| Sankuaishi Crab 1 (BK-SKSHT1H) | I2 | D | DI1I2 | DI1I2 | I1I2 | D | I1I2 | DI2 | D2 | D1D3 | D1D2D3 |
| Forest Apple (BK-SLPG) | DI1 | DI2 | DI1I2 | DI1I2 | DI1I2 | D | DI1I2 | DI2I3 | D1I2 | D1I | D2D3I |
| Sieversii (BK-SWS) | I2 | D | DI1I2 | DI2 | DI1I2 | I1I2 | I1I2 | DI2 | D1D2 | D1D2 | D1D2D3I |
| Sansa (BK-SX) | I2 | I1 | DI1I2 | DI1 | DI1I2 | DI1 | DI1I2 | DI1I2I3 | D2I2 | D1 | D2D3I |
| Szampion (BK-Szampion) | DI1 | DI1 | DI1I2 | DI1I2 | DI1 | DI1I2 | DI1I2I3 | D1D2 | D1 | D1D2D3I |
| T337 (BK-T337) | I2 | D | DI1I2 | DI2 | DI1I2 | DI1 | I1I2 | DI2 | D1D2 | D1 | D1D2D3I |
| Turkmen Apple (BK-TKMPG) | I2 | D | DI1I2 | DI2 | DI1I2 | I1I2 | I1I2 | DI2 | D1D2 | D1D2 | D1D2D3I |
| Mato 1 (BK-TMYH) | DI2 | D | DI1I2 | DI1I2 | DI1I2 | DI2 | DI1I2 | DI2I3 | D1I2 | D1 | D1D2D3 |
| Trajian (BK-Trajian) | DI2 | D | DI1I2 | DI2 | DI1I2 | DI1 | DI1I2 | DI2I3 | D1D2 | D1 | D1D2D3 |
| Weiai 3 (BK-WA3) | I2 | D | DI1I2 | DI1I2 | DI1I2 | D | I1I2 | DI2 | D2 | D1D3 | D1D2D3 |
| Wanbai Crab (BK-WBHT) | I1 | DI2 | DI1I2 | DI1I2 | DI1I2 | DI1 | I1I2 | DI2I3 | D2 | D3I | D1D2D3I |
| Wufengshan 1 (BK-WFS1H) | I2 | D | I1I2 | DI2 | DI1I2 | DI1 | I1I2 | DI2 | D1D2 | D1 | D1D2 |
| Wufengshan 4 (BK-WFS4H) | I1I2 | DI1 | DI1I2 | DI1I2 | DI1I2 | D | I1I2 | DI1I2 | D2 | D1 | D1D2D3 |
| Wufengshan Crab (BK-WFSHT) | I1I2 | DI1 | DI1 | DI2 | I1I2 | I1 | DI1 | DI2 | D2I2 | D1 | D1D2D3I |
| Wufengshan Crab 2 (BK-WFSHT2H) | I2 | DI1 | DI1I2 | DI1I2 | DI1I2 | DI2 | I1I2 | DI2I3 | D2I2 | D1 | D1D2D3 |
| Wufengshan Crab 6 (BK-WFSHT6H) | DI2 | D | DI2 | DI1I2 | DI1I2 | DI1 | I1 | DI2I3 | D2 | D1 | D1D3 |
| Wifos (BK-wifos) | DI2 | DI2 | DI1I2 | DI1I2 | DI1I2 | DI1I2 | DI1I2 | DI2I3 | D1 | D1 | D1D2D3I |
| Orei (BK-WL) | I2 | DI1 | DI1I2 | DI2 | DI1I2 | DI2 | I1I2 | DI1I2I3 | D2I2 | D1I | D1D2D3I |

-continued

Construction results of InDel marker genotype database of *Malus* germplasm resources

| | | | | | | | | | | | |
|---|---|---|---|---|---|---|---|---|---|---|---|
| Maypole (BK-WM) | I2 | D | DI1I2 | DI2 | I1I2 | I1 | I1I2 | DI2I3 | D2 | D1D2 | D1D2D3 |
| Waltz (BK-WZ) | I2 | DI1 | DI1I2 | DI2 | DI1I2 | I1 | I1I2 | I1I2I3 | D1D2 | D1I | D1D2D3 |
| Kotoku (BK-XD) | I1I2 | DI1 | DI1I2 | DI2 | DI1I2 | I1I2 | I1I2 | DI1I2 | D2I2 | D1I | D2D3I |
| Xiaofanshan Binzi (BK-XFSBZ) | I2 | D | DI1I2 | DI2 | DI1I2 | DI1 | I1I2 | DI2 | D1D2 | D1 | D1D2D3 |
| Xiaofanshan Crab 4 (BK-XFSHT4H) | I2 | D | DI1I2 | DI2 | DI1I2 | DI1 | I1I2 | DI2 | D1D2 | D1 | D1D2 |
| Xiaogoumen Naizi (BK-XGMNZ) | I2 | D | DI1I2 | DI2 | DI1I2 | DI1 | I1I2 | DI2 | D1D2 | D1 | D1D2D3 |
| XGM Suan Binzi (BK-XGMSBZ) | I2 | D | DI1I2 | DI2 | DI1I2 | DI1 | I1I2 | DI2 | D1D2 | D1 | D1D2D3 |
| XGM Tian Binzi (BK-XGMTBZ) | I2 | D | DI1I2 | DI2 | DI1I2 | DI1 | I1I2 | DI2 | D1D2 | D1 | D1D2D3 |
| Starkrimson (BK-XHX) | DI2 | DI1 | DI1I2 | DI1I2 | DI1I2 | DI2 | I1I2 | DI1I2I3 | I2 | D1 | D1D2D3 |
| Xinjiang 1 (BK-XJ1) | D | D | DI1I2 | DI2 | DI1I2 | I1 | I1I2 | DI2I3 | D1D2 | D1 | D1D2D3 |
| Xinjiang 11 (BK-XJ11) | DI1 | DI2 | DI1I2 | DI1 | DI1I2 | DI1 | I1I2 | DI2I3 | D1D2 | D1 | D1D2D3I |
| Xinjiang 14 (BK-XJ14) | DI1 | DI2 | DI1I2 | DI1 | DI1I2 | DI1 | I1I2 | DI2I3 | D1D2 | D1 | D1D2D3I |
| Xinjiang 15 (BK-XJ15) | DI1 | DI2 | DI1I2 | DI1 | DI1I2 | I1 | I1I2 | DI2I3 | D1D2 | D1D3 | D1D2D3I |
| Xinjiang 16 (BK-XJ16) | I2 | D | DI1 | DI2 | DI1I2 | D | DI1 | DI2 | D1D2 | D1 | D1D2D3 |
| Xinjiang 17 (BK-XJ17) | DI2 | I2 | DI1I2 | DI1I2 | DI1I2 | I1I2 | I1I2 | I2I3 | D1 | D1 | D1D2D3I |
| Xinjiang 18 (BK-XJ18) | DI2 | I2 | DI1I2 | DI1I2 | DI1I2 | I1I2 | I1I2 | I2I3 | D1 | D1 | D1D2D3I |
| Xinjiang 19 (BK-XJ19) | I1I2 | I1I2 | DI1I2 | DI2 | DI1I2 | D | I1I2 | DI1I2 | D1D2 | D1I | D1D3I |
| Xinjiang 21 (BK-XJ21) | D | DI1 | DI1I2 | DI2 | DI1I2 | DI1 | I1I2 | DI2I3 | D2 | D1 | D1D2D3 |
| Xinjiang 22 (BK-XJ22) | I2 | D | DI1I2 | DI2 | DI1I2 | I1 | I1I2 | DI2 | D1D2 | D1 | D1D3 |
| Xinjiang 24 (BK-XJ24) | DI2 | D | DI1I2 | DI2 | DI1I2 | I1 | I1I2 | DI2I3 | D1 | D1 | D1D3 |
| Xinjiang 26 (BK-XJ26) | DI1 | DI2 | DI1I2 | DI1 | DI1I2 | DI1 | I1I2 | DI2I3 | D1D2 | D1 | D1D2D3I |
| Xinjiang 28 (BK-XJ28) | I1I2 | I1I2 | DI1I2 | DI2 | DI1I2 | D | I1I2 | DI1I2 | D1D2 | D1I | D1D3I |
| Xinjiang 29 (BK-XJ29) | DI1 | DI2 | DI1I2 | DI2 | DI1I2 | DI1 | I1I2 | I1I2 | D2 | D1D3 | D1D2D3I |
| Xinjiang 31 (BK-XJ31) | DI2 | DI1 | DI1I2 | DI2 | DI1I2 | D | I1I2 | DI2I3 | D2I2 | D1D3 | D1D2D3 |
| Xinjiang 3 (BK-XJ3H) | DI2 | DI1 | DI1I2 | DI1I2 | DI1I2 | DI1 | DI1I2 | DI2I3 | D2I2 | D1 | D1D2D3 |
| Xinjiang 6 (BK-XJ6H) | I2 | I1I2 | DI1I2 | DI1I2 | DI1I2 | I1I2 | I1I2 | DI2I3 | D1D2 | D1D3 | D1D2D3I |
| Xinjiang 7 (BK-XJ7) | DI1 | DI2 | DI1I2 | DI1 | DI1I2 | DI1 | I1I2 | DI2I3 | D1 | D1 | D1D2D3 |
| Xinjiang 8 (BK-XJ8) | D | DI2 | DI1I2 | DI2 | DI1I2 | I1 | I1I2 | DI2 | D1D2 | D1 | D1D2D3 |
| Xinjiang 9 (BK-XJ9) | DI1 | DI2 | DI1I2 | DI2 | DI1I2 | DI1 | I1I2 | I1I2 | D2 | D1D3 | D1D2D3I |
| Xijin Crab (BK-XJHT) | D | D | DI1 | DI1I2 | DI1I2 | D | I1I2 | I2I3 | D2 | D1I | D1D2D3I |
| Xiaomian Crab (BK-XMHT) | I2 | D | DI1 | DI1 | DI1I2 | I1 | I1I2 | DI2 | D2 | D3 | D1D2D3 |
| New Jonagold (BK-XQNJ) | I1I2 | DI1I2 | DI1I2 | DI1I2 | DI1I2 | DI1 | I1I2 | DI1I2I3 | D2I2 | D1I | D1D2D3 |
| Xiaoshuai (BK-XS) | D | DI2 | DI1 | DI2 | DI1I2 | I1I2 | I1I2 | DI1I2 | D2I2 | D1 | D1D2D3 |
| Shinsekai (BK-XSJ) | I2 | DI2 | DI1I2 | DI1 | DI1I2 | DI1 | I1I2 | DI2I3 | D2I2 | D1I | D1D2D3 |
| Xiangyanghong (BK-XYH) | I2 | D | DI1I2 | DI1I2 | DI1I2 | DI2 | DI1I2 | DI1I2I3 | D2I2 | D1 | D1D2D3I |
| Italy I2arly Red (BK-YDLZH) | I2 | I1 | DI1I2 | DI1I2 | DI1I2 | DI1 | DI1I2 | DI1I2I3 | I2 | D1 | D1D2D3I |
| Yanfu 10 (BK-YF10) | DI2 | DI1 | DI1I2 | DI1I2 | DI1I2 | D | DI1I2 | DI2I3 | D2I2 | D1 | D1D2D3 |
| Yoko (BK-YG) | I1I2 | DI1 | DI1I2 | DI1I2 | DI1I2 | I1I2 | DI1I2 | DI1I2I3 | D2I2 | D1 | D1D2D3I |
| Yuanhong (BK-YH) | DI2 | D | DI1I2 | DI1I2 | I1I2 | DI1 | I1I2 | DI1I2I3 | D2I2 | D1D3 | D1D2D3 |

-continued

| Construction results of InDel marker genotype database of *Malus* germplasm resources | | | | | | | | | | |
|---|---|---|---|---|---|---|---|---|---|---|
| Tehong 2 (BK-YH2) | DI2 | DI1 | DI1I2 | DI1I2 | DI1I2 | D | DI1I2 | DI2I3 | D2I2 | D1 | D1D2D3 |
| Yanhongmi (BK-YHM) | I1I2 | D | DI1I2 | DI2 | DI1I2 | DI2 | I1I2 | DI2I3 | D2 | D1 | D1D2D3 |
| Youliang Spur (BK-YLDZ) | DI2 | DI1 | DI1I2 | DI1I2 | DI1I2 | D | DI1I2 | DI2I3 | D2I2 | D1 | D1D2D3 |
| Yuanye Crab (BK-YYHT) | I2 | D | DI1I2 | DI1I2 | DI1I2 | DI2 | I1I2 | DI2 | D2 | D1D3 | D1D3 |
| Stark Jumbo (BK-ZB) | I2 | DI1 | DI1I2 | DI2 | DI1I2 | D | I1I2 | DI1I2 | D1D2 | D1 | D1D2D3 |
| Jumbo Orin (BK-ZBWL) | I1I2 | I1I2 | DI1I2 | DI1I2 | DI1I2 | DI1 | I1I2 | DI1I2I3 | D2I2 | D1I | D1D2D3 |
| Zhuifeng 1 (BK-ZF1H) | I2 | DI2 | D | DI1I2 | DI1I2 | DI1 | I1 | DI2I3 | D2 | D3I | D1D2D3I |
| Zhuifeng 2 (BK-ZF2H) | I2 | D | DI1 | DI1I2 | DI1I2 | D | I1 | DI2 | D1D2 | D1D3 | D1D2D3 |
| I2arly Fuji (BK-ZFS) | DI2 | DI1 | DI1I2 | DI1I2 | DI1I2 | D | DI1I2 | DI2I3 | D2I2 | D1 | D1D2D3 |
| Xiaofanshan Crab (BK-ZFSHT) | I2 | D | DI1I2 | DI2 | DI1I2 | DI1 | I1I2 | DI2 | D1D2 | D1 | D1D2 |
| Zisai Pearl (BK-Zisai) | I2 | D | DI1I2 | DI2 | DI1I2 | DI1 | I1I2 | DI2 | D1D2 | D1 | D1D2 |
| Geneva I2arly (BK-ZJ) | DI2 | DI2 | DI1I2 | DI2 | DI1I2 | D | I1I2 | DI2I3 | D2I1 | D1 | D1D3 |
| 13-26W (CL-1) | I1I2 | DI2 | DI1I2 | DI1I2 | DI1I2 | D | I1I2 | DI2I3 | D2 | D1I | D1D2D3 |
| 23-127 (CL-2) | I1I2 | DI2 | DI1I2 | DI2 | DI1I2 | DI1 | I1I2 | I2I3 | D2I2 | D1I | D2D3I |
| 50-30 (CL-3) | DI2 | DI1 | DI1 | DI1I2 | I1I2 | DI2 | DI1I2 | I1I2I3 | D2I2 | D1 | D1D2D3 |
| 50-32 (CL-4) | DI1I2 | DI2 | DI1I2 | DI2 | DI1I2 | DI1 | I1I2 | DI2I3 | I2 | D1I | D1D2D3I |
| H5-101 (CL-5) | DI1 | DI1 | DI1I2 | DI1I2 | I1I2 | DI1 | DI1I2 | DI2I3 | D2 | D1 | D1D2D3 |
| Pingyan (CL-6) | I2 | D | DI1I2 | DI1I2 | I1I2 | DI2 | DI1 | DI2I3 | D2 | D1 | D1D2D3 |
| Deqin Crab (DQ) | D | D | DI1 | DI1 | DI1I2 | D | I1I2 | I2 | NA | D1 | D1D2D3 |
| Jin 18 (GY-1) | DI2 | DI1 | DI1I2 | DI1I2 | DI1I2 | D | DI1I2 | DI2I3 | D2I2 | D1 | D1D2D3 |
| Fengfeng Baleng (GY-2) | DI1 | D | DI1 | DI1I2 | DI1I2 | D | DI1I2 | I2 | D1D2 | D1D2 | D1D2D3I |
| Hanfu 6 (GY-3) | DI2 | DI1 | DI1I2 | DI1I2 | DI1I2 | D | DI1I2 | DI2I3 | D2I2 | D1 | D1D2D3 |
| Hanfu 3 (GY-4) | DI2 | D | DI1 | DI2 | DI1I2 | DI2 | DI1I2 | DI1I2I3 | I2 | D1 | D1D2D3 |
| 95/06 (GZ-1) | DI2 | DI1 | DI1I2 | DI1I2 | DI1I2 | D | DI1I2 | DI2 | D2 | D1 | D1D2D3 |
| 107/06 (GZ-2) | DI2 | DI1 | DI1 | DI1I2 | DI1I2 | DI2 | DI1I2 | DI2 | D2 | D1 | D1D2D3I |
| 117/06 (GZ-3) | DI2 | DI2 | DI1I2 | DI1I2 | DI1I2 | DI2 | I1I2 | DI2 | D2 | D1I | D1D3I |
| 119/06 (GZ-4) | D | DI2 | DI1I2 | DI1I2 | DI1I2 | I2 | I1I2 | DI2 | D2 | D1I | D1D3I |
| Jinxiu Crab (GZ-5) | D | D | DI1I2 | DI1I2 | DI1I2 | D | I1I2 | DI1I2I3 | I2 | D1D3 | D1D2D3 |
| Zhizun Fuji (HS-1) | DI2 | DI1 | DI1I2 | DI1I2 | DI1I2 | D | DI1I2 | DI2I3 | D2I2 | D1 | D1D2D3 |
| Fuji No. 1 (HS-10) | DI2 | DI1 | DI1I2 | DI1I2 | DI1I2 | D | DI1I2 | DI2I3 | D2I2 | D1 | D1D2D3 |
| Red Jonaprince (HS-12) | I1I2 | DI1I2 | DI1I2 | DI1I2 | DI1I2 | DI1 | I1I2 | DI1I2I3 | D2I2 | D1I | D1D2D3I |
| Nic29 (HS-13) | I2 | D | DI1I2 | DI2 | DI1I2 | DI1 | I1I2 | DI2 | D1D2 | D1 | D1D2D3I |
| Azhen Fuji (HS-14) | DI2 | DI1 | DI1I2 | DI1I2 | DI1I2 | D | DI1I2 | DI2I3 | D2I2 | D1 | D1D2D3 |
| I2nvy (HS-15) | I2 | DI1 | DI1I2 | DI1I2 | DI1I2 | DI1 | I1I2 | DI1I2I3 | I2 | D1 | D1D2D3 |
| Rosegrow (HS-16) | I2 | I1 | DI1I2 | DI2 | DI1I2 | DI2 | I1I2 | DI1I2 | D2I2 | D1 | D1D2D3 |
| Canzy (HS-17) | DI2 | DI1 | DI1 | DI1I2 | DI1I2 | DI1 | DI1 | DI1I2I3 | I2 | D1 | D1D2D3I |
| Fubrax (HS-2) | DI2 | DI1 | DI1I2 | DI1I2 | DI1I2 | D | DI1I2 | DI2I3 | D2I2 | D1 | D1D2D3 |
| Mitchgla (HS-3) | I2 | I1 | DI1I2 | DI1I2 | DI1I2 | DI1 | DI1I2 | DI1I2I3 | I2 | D1 | D1D2D3I |

-continued

| Construction results of InDel marker genotype database of *Malus* germplasm resources | | | | | | | | | | | |
|---|---|---|---|---|---|---|---|---|---|---|---|
| Fujiko (HS-4) | DI2 | DI1 | DI1I2 | DI1I2 | DI1I2 | D | DI1I2 | DI2I3 | D2I2 | D1 | D1D2D3 |
| Buckeye Gala (HS-5) | I2 | I1 | DI1I2 | DI1I2 | DI1I2 | DI1 | DI1I2 | DI1I2I3 | I2 | D1 | D1D2D3I |
| Fujion (HS-6) | DI1 | DI1 | DI1I2 | D | I1I2 | D | DI1 | NA | D2I2 | D1 | D1D2D3 |
| Modi (HS-7) | DI2 | DI1 | DI1I2 | DI2 | I1I2 | DI1 | I1I2 | I2I3 | D1I2 | D1 | D1D2D3I |
| Jiangxue (HS-8) | D | DI1 | DI1I2 | DI1I2 | DI1I2 | I2 | I1I2 | DI1I2 | D2I2 | D1 | D1D2D3 |
| September Wonder Fuji (HS-9) | DI2 | DI1 | DI1I2 | DI1I2 | DI1I2 | D | DI1I2 | DI2I3 | D2I2 | D1 | D1D2D3 |
| Linqin Crab (LQ) | I2 | D | DI1I2 | DI1I2 | DI1I2 | I1 | I1I2 | DI2 | D1 | D1D3 | D1D2D3 |
| Lushan Sanye (LSSY) | D | NA | I1 | DI1 | DI1I2 | D | I1 | DI2 | D2 | D1D2 | D1D2D3 |
| 83-2 (MDJ-1) | DI2 | I1I2 | DI1I2 | DI2 | DI1I2 | DI1 | DI1 | I2I3 | D2I2 | D1I | D1D2D3I |
| Tianfeng (MDJ-9) | D | D | DI1 | NA | DI1I2 | DI1 | DI1 | D | D2 | D1I | D1D2D3 |
| Oregon Spur I1-red (OR-1) | DI2 | DI1 | DI1I2 | DI1I2 | DI1I2 | DI2 | I1I2 | DI1I2I3 | I2 | D1 | D1D2D3 |
| Oregon Spur I1-green (OR-2) | DI2 | DI1 | DI1I2 | DI1I2 | DI1I2 | DI2 | I1I2 | DI1I2I3 | I2 | D1 | D1D2D3 |
| I23N2 (OR-3) | DI2 | DI1 | DI1I2 | DI1I2 | DI1I2 | DI2 | I1I2 | DI1I2I3 | I2 | D1 | D1D2D3 |
| I24N1 (OR-4) | DI2 | DI1 | DI1I2 | DI1I2 | DI1I2 | DI2 | I1I2 | DI1I2I3 | I2 | D1 | D1D2D3 |
| I24N2 (OR-5) | DI2 | DI1 | DI1I2 | DI1I2 | DI1I2 | DI2 | I1I2 | DI1I2I3 | I2 | D1 | D1D2D3 |
| W6N1 (OR-6) | DI2 | DI1 | DI1I2 | DI1I2 | DI1I2 | DI2 | I1I2 | DI1I2I3 | I2 | D1 | D1D2D3 |
| W6S5 (OR-7) | DI2 | DI1 | DI1I2 | DI1I2 | DI1I2 | DI2 | I1I2 | DI1I2I3 | I2 | D1 | D1D2D3 |
| W8S3 (OR-8) | DI2 | DI1 | DI1I2 | DI1I2 | DI1I2 | DI2 | I1I2 | DI1I2I3 | I2 | D1 | D1D2D3 |
| Daihong (QD-1) | I1I2 | DI1 | DI1I2 | DI2 | DI1I2 | D | I1I2 | DI2I3 | D2I2 | D1 | D1D2D3I |
| Tangmutian (QD-10) | DI2 | DI1 | DI1I2 | DI1I2 | DI1I2 | D | DI1I2 | DI2I3 | D2I2 | D1 | D1D2D3 |
| Shanjin Crab N1 (QD-11) | D | D | DI1 | DI1 | DI1I2 | D | I1 | DI2 | D2 | D1D2 | D1D2D3I |
| Shanjin Crab N2 (QD-12) | D | D | DI1 | DI1I2 | DI1I2 | D | I1 | DI2 | D2 | D1D2 | D1D2D3I |
| I2 zhen 1 (QD-13) | I2 | D | DI1I2 | DI2 | DI1I2 | D | I1I2 | DI2 | D1D2 | D1D2 | D1D3 |
| I2 zhen 2 (QD-14) | DI2 | D | DI1I2 | DI1I2 | DI1I2 | DI1 | I1I2 | DI2 | D1 | D1 | D1D2D3I |
| I2 zhen 3 (QD-15) | DI2 | D | DI1I2 | DI2 | DI1I2 | DI1 | DI1 | DI2 | D2 | D1D2 | D1D2D3 |
| I2 zhen 4 (QD-16) | I2 | D | DI1I2 | DI1I2 | DI1I2 | DI1 | I1I2 | I2 | D2 | D1 | D1D2D3I |
| I2 zhen 5 (QD-17) | I2 | D | DI1I2 | DI1I2 | DI1I2 | DI1 | I1I2 | I2 | D2 | D1 | D1D2D3I |
| Haihong (QD-19) | I2 | D | DI1I2 | DI1I2 | DI1I2 | DI1 | I1I2 | DI2 | D1D2 | D1D3 | D2 |
| Qingfu 2 (QD-2) | DI2 | DI1 | DI1I2 | DI1I2 | DI1I2 | D | DI1I2 | DI2I3 | D2I2 | D1 | D1D2D3 |
| Telamon (QD-20) | I2 | DI1 | DI1I2 | DI2 | DI1I2 | I1 | I1I2 | DI1I2I3 | D1I2 | D1D3 | D1D2D3 |
| Fuyan (QD-21) | DI2 | DI1 | DI1I2 | DI1I2 | DI1I2 | DI1 | I1I2 | DI2I3 | I2 | D1I | D1D2D3 |
| Hongxun 1 (QD-22) | D | D | DI1I2 | D | DI1I2 | I1 | I1I2 | D | D1 | D1D3 | D1D2 |
| Rushan Fuji (QD-23) | DI2 | DI1 | DI1I2 | DI1I2 | DI1I2 | D | DI1I2 | DI2I3 | D2I2 | D1 | D1D2D3 |
| Jiudian Spur (QD-24) | DI2 | DI1 | DI1I2 | DI1I2 | DI1I2 | D | DI1I2 | DI2I3 | D2I2 | D1 | D1D2D3 |
| Ruihong (QD-25) | I2 | DI1 | DI1I2 | DI1I2 | DI1I2 | DI1 | DI1I2 | DI1I2I3 | I2 | D1 | D1D2D3I |
| Zhongnvshi (QD-26) | D | DI2 | DI1I2 | DI1I2 | DI1I2 | I1 | I1I2 | DI2I3 | D2I2 | D1D3 | D1D2D3 |
| 2001 Spur (QD-27) | DI2 | DI1 | DI1I2 | DI1I2 | DI1I2 | D | DI1I2 | DI2I3 | D2I2 | D1 | D1D2D3 |

-continued

Construction results of InDel marker genotype database of *Malus* germplasm resources

| | | | | | | | | | | | |
|---|---|---|---|---|---|---|---|---|---|---|---|
| Fuli (QD-28) | DI2 | DI1 | DI1I2 | DI1I2 | DI1I2 | DI1 | DI1I2 | I2I3 | DI2 | D1 | D1D2D3 |
| Tuanwang semi-Spur (QD-29) | DI2 | DI1 | DI1I2 | DI1I2 | DI1I2 | D | DI1I2 | DI2I3 | D2I2 | D1 | D1D2D3 |
| Qingfu 3 (QD-3) | DI2 | DI1 | DI1I2 | DI1I2 | DI1I2 | D | DI1I2 | DI2I3 | D2I2 | D1 | D1D2D3 |
| Longfu (QD-30) | DI2 | DI1 | DI1I2 | DI1I2 | DI1I2 | D | DI1I2 | DI2I3 | D2I2 | D1 | D1D2D3 |
| Baotou Linqin (QD-31) | I2 | D | DI1I2 | DI1 | DI1I2 | NA | I1I2 | DI2I3 | I1 | D1D3 | D1D2 |
| Yanfu 6 (QD-32) | DI2 | DI1 | DI1I2 | DI1I2 | DI1I2 | D | DI1I2 | DI2I3 | D2I2 | D1 | D1D2D3 |
| SH40-2 seedling (QD-4) | D | DI1 | D | DI1 | DI1I2 | D | I1I2 | DI2 | D2 | D1D2 | D1D2D3 |
| Saijin (QD-5) | I2 | I1 | DI1I2 | DI1I2 | DI1I2 | I1 | I1I2 | DI1I2I3 | I2 | D1I | D1D2D3I |
| Nagafu 12 (QD-6) | DI2 | DI1 | DI1I2 | DI1I2 | DI1I2 | D | DI1I2 | DI2I3 | D2I2 | D1 | D1D2D3 |
| Caoyuan Crab (QD-7) | NA | D | I1 | D | I1I2 | D | I1I2 | NA | NA | D1 | D1I |
| Xiaojin Crab (QD-8) | DI2 | DI1 | DI1 | DI1I2 | DI1I2 | D | I1I2 | I2I3 | D2 | D1 | D1D2D3I |
| Shuangyanghong (QD-9) | I2 | DI1 | DI1I2 | DI1I2 | DI1I2 | DI1 | DI1I2 | DI1I2I3 | I2 | D1 | D1D2D3I |
| Qianxian Crab (QX-1) | DI1 | D | DI1 | DI1I2 | DI1I2 | D | DI1I2 | I2 | D1 | D1D2 | D1D2D3I |
| Ruixue (ruixue) | I1I2 | DI2 | DI1I2 | DI1I2 | DI1I2 | D | DI1I2 | DI2I3 | D1D2 | D1 | D1D2D3I |
| Ruiyang (RY) | I1I2 | DI2 | DI1I2 | DI1I2 | DI1I2 | D | DI1I2 | DI2I3 | D1D2 | D1 | D1D2D3I |
| Yanyuan 1 (SC-1) | I1I2 | I1I2 | DI1I2 | DI1I2 | DI1I2 | DI1 | DI1I2 | DI1I2I3 | D2I2 | D1I | D1D2D3I |
| Yanyuan 2 (SC-2) | I1I2 | DI2 | DI1I2 | DI1I2 | DI1I2 | DI2 | DI1I2 | I2I3 | D2 | D1I | D1D2D3I |
| Yanyuan 3 (SC-3) | DI2 | DI1 | DI1I2 | DI1I2 | DI1I2 | D | DI1I2 | DI2I3 | D2I2 | D1 | D1D2D3 |
| Yanyuan 4 (SC-4) | I1I2 | DI2 | DI1I2 | DI1I2 | DI1I2 | DI2 | DI1I2 | I2I3 | D2 | D1I | D1D2D3I |
| Yanyuan 5 (SC-5) | DI2 | DI1 | DI1I2 | DI2 | DI1I2 | D | I1I2 | I2I3 | D1D2 | D1 | D1D2D3 |
| Yanyuan 6 (SC-6) | DI1 | I1I2 | DI1I2 | DI1 | DI1I2 | DI2 | DI1I2 | I2I3 | D2 | D1I | D1D2D3 |
| Yanyuan 7 (SC-7) | I1I2 | DI1I2 | DI1I2 | DI1I2 | DI1I2 | DI1 | I1I2 | DI1I2I3 | D2I2 | D1I | D1D2D3I |
| Mitchgala (SX-10) | I2 | I1 | DI1I2 | DI1I2 | DI1I2 | DI1 | DI1I2 | DI1I2I3 | I2 | D1 | D1D2D3I |
| Zhongqiuwang Linyi (SX-11) | I2 | DI2 | DI1I2 | DI1I2 | DI1I2 | D | I1I2 | DI2I3 | I2 | D1I | D1D2D3 |
| Linyi Meiguo 5 (SX-12) | I2 | DI1 | DI1I2 | DI1I2 | DI1I2 | D | DI1I2 | I2I3 | I2 | NA | D1D2D3I |
| Liquan Spur Fuji (SX-13) | DI2 | DI1 | DI1I2 | DI1I2 | DI1I2 | D | DI1I2 | DI2I3 | D2I2 | D1 | D1D2D3 |
| Qiulimu (SX-14) | DI2 | DI2 | I1I2 | DI2 | DI1I2 | I1I2 | I1I2 | DI2 | D1 | D1 | D1D2D3I |
| Qincui (SX-15) | DI2 | DI1 | DI1I2 | DI2 | DI1I2 | DI1 | DI1I2 | DI1I2I3 | D2I2 | D1 | D1D2D3 |
| Taigu Shaguo Late (SX-17) | I2 | D | DI1I2 | DI2 | DI1I2 | DI1 | I1I2 | DI2 | D1D2 | D1 | D1D2 |
| Lingyige Hongrou (SX-18) | DI2 | DI1 | DI1 | DI1I2 | DI1I2 | DI2 | DI1I2 | DI2 | D2 | D1 | D1D2D3I |
| Shenai LS (SX-19) | DI2 | DI1 | DI1I2 | DI1I2 | DI1I2 | DI1 | I1I2 | DI1I2 | D2 | D1 | D1D2D3I |
| Linyi Meiguo 8 (SX-2) | I1I2 | DI1I2 | DI1I2 | DI1I2 | DI1I2 | D | DI1I2 | DI2I3 | D2I2 | D1I | D1D2D3 |
| Liga (SX-20) | I2 | I1 | DI1I2 | DI1I2 | DI1I2 | DI1 | DI1I2 | DI1I2I3 | I2 | D1 | D1D2D3I |
| Y-1 (SX-21) | NA | D | DI1 | DI1I2 | DI1I2 | D | I1 | DI2 | D2 | D1 | D1D2 |
| B009 (SX-22) | I2 | D | DI1I2 | DI1 | DI1I2 | D | I1I2 | DI2 | NA | D1 | D1D2 |
| Jinfu 1 (SX-23) | DI2 | DI1 | DI1I2 | DI1I2 | DI1I2 | D | DI1I2 | DI2I3 | D2I2 | D1 | D1D2D3 |
| Hongmantang (SX-24) | I2 | D | DI1I2 | DI1I2 | DI1I2 | DI1 | DI1I2 | DI2I3 | D2 | D2D3 | D1D3 |
| Y-2 (SX-25) | NA | D | DI1 | DI1 | DI1I2 | D | I1 | I2 | D2 | D1 | D1D2 |

-continued

Construction results of InDel marker genotype database of *Malus* germplasm resources

| | | | | | | | | | | | |
|---|---|---|---|---|---|---|---|---|---|---|---|
| Y-3 (SX-26) | NA | D | DI1 | DI1 | DI1I2 | D | I1 | I2 | D2 | D1 | D1D2 |
| Xinliangxiang (SX-27) | DI2 | DI1 | DI1I2 | DI1I2 | DI1I2 | D | DI1I2 | DI2I3 | D2I2 | D1 | D1D2D3 |
| I2nnike Gala (SX-28) | I2 | I1 | DI1I2 | DI1I2 | DI1I2 | DI1 | DI1I2 | DI1I2I3 | I2 | D1 | D1D2D3I |
| Linyi Meiguo 6 (SX-3) | DI1I2 | DI1 | DI1I2 | DI2 | DI1I2 | DI2 | DI1I2 | I1I2I3 | D2I2 | D1 | D1D2D3I |
| Linyi Meiguo 2 (SX-30) | DI2 | DI1 | DI1I2 | DI1I2 | DI1I2 | D | DI1I2 | DI2I3 | D2I2 | D1 | D1D2D3 |
| Donglimu (SX-33) | DI2 | DI2 | DI1I2 | DI2 | DI1I2 | I1I2 | I1I2 | DI2 | D1 | D1 | D1D2D3I |
| Linyi Meiguo 1 (SX-34) | I1I2 | DI1I2 | DI1I2 | DI1I2 | DI1I2 | D | DI1I2 | DI2I3 | D2I2 | D1I | D1D2D3 |
| Linyi Meiguo 4 (SX-4) | I1I2 | D | DI1I2 | DI1I2 | DI1I2 | D | DI1I2 | DI2I3 | D2I2 | D1 | D1D2D3I |
| Qinyang (SX-6) | I1I2 | I1 | DI1I2 | DI1I2 | DI1I2 | DI1 | DI1 | DI2I3 | D1I2 | D1 | D1D2D3I |
| Taiguo Shaguo I2arly (SX-7) | I2 | D | DI1I2 | DI2 | DI1I2 | DI1 | I1I2 | DI2 | D1D2 | D1 | D1D2 |
| Yuhua Zaofu (SX-8) | DI2 | DI1 | DI1I2 | DI1I2 | DI1I2 | D | DI1I2 | DI2I3 | D2I2 | D1 | D1D2D3 |
| 78-M18 (SY-1) | DI2 | DI2 | DI1I2 | DI2 | DI1I2 | I1 | I1I2 | DI1I2I3 | D2 | D1I | D1D2D3I |
| Jinping (SY-10) | DI2 | D | DI1 | DI2 | DI1 | DI1 | DI1 | DI2I3 | D2I2 | D1 | D1D2D3I |
| Longqiu (SY-11) | I2 | D | DI1I2 | DI2 | DI1I2 | I2 | I1I2 | DI2 | D2 | D1D3 | D2D3I |
| Longfeng (SY-12) | I2 | DI2 | DI1I2 | D | DI1I2 | DI1 | I1 | DI2 | D2I1 | D1 | D1D2D3 |
| Xiangjiaoguo (SY-14) | DI1 | DI1 | DI1I2 | DI1I2 | DI1I2 | DI1 | I1I2 | DI2I3 | D2 | D1D3 | D1D2D3I |
| Longguan (SY-15) | DI2 | DI2 | DI1I2 | DI1I2 | DI1I2 | DI1 | I1I2 | DI1I2 | D2 | D1 | D1D2D3 |
| Longshuai (SY-16) | DI2 | DI1I2 | D | D | DI1I2 | DI1 | DI1 | I2I3 | D2I2 | D1 | D1D2D3I |
| Zixiang (SY-17) | I2 | D | DI1I2 | DI2 | DI1I2 | I1 | I1I2 | DI2I3 | D2 | NA | D1D2D3 |
| Huahong (SY-19) | I2 | D | DI1I2 | DI2 | DI1I2 | DI1 | I1I2 | DI2 | D1D2 | D1 | D1D2 |
| Binlang (SY-2) | DI1 | DI1 | DI1I2 | DI1I2 | DI1I2 | DI1 | I1I2 | DI2I3 | D2 | D1D3 | D1D2D3I |
| Qiufengmi (SY-20) | I2 | D | DI1I2 | DI2 | DI1I2 | I1 | I1I2 | DI2 | D1D2 | D1 | D1D2D3 |
| Honglingdang (SY-21) | D | D | DI1 | DI2 | DI1I2 | DI1 | I1I2 | DI2 | D1D2 | D1D3 | D1D2D3 |
| Qiulu (SY-22) | I2 | D | DI1I2 | DI1I2 | DI1I2 | DI1 | I1I2 | DI1I2I3 | D1D2I2 | D1 | D1D2D3 |
| Longhong (SY-23) | DI2 | DI2 | DI1I2 | DI2 | DI1I2 | DI1 | I1I2 | DI1I2 | D2 | D1 | D1D2D3 |
| Milk (SY-3) | D | DI2 | DI1 | DI2 | DI1 | I1I2 | I1I2 | DI1I2 | D2I2 | D1 | D1D2D3 |
| Hanfu (SY-4) | DI2 | DI1 | DI1 | DI2 | DI1I2 | DI1 | DI1I2 | DI2I3 | D2I1I2 | D1 | D1D2D3 |
| Toko (SY-5) | D | DI1 | DI1 | D | DI1I2 | D | DI1 | I2 | D2I1 | D1 | D1D2D3 |
| Jinhong (SY-6) | DI2 | DI2 | DI1I2 | DI2 | DI1I2 | DI1 | I1I2 | I2I3 | D2 | D1I | D1D2D3I |
| K9 (SY-7) | D | D | DI1 | DI2 | DI1I2 | DI1 | I1I2 | DI2 | D1D2 | D1D3 | D1D2D3 |
| 03-06-04 (SY-8) | I2 | D | D | DI1I2 | DI1I2 | D | I1I2 | DI1I2 | D1D2 | D1D3 | D1D2D3 |
| Olga (SY-9) | I2 | D | DI1I2 | DI1I2 | DI1I2 | I1 | I1I2 | DI2I3 | D2I1 | D1 | D1D2D3 |
| Gala 4x (TA-1) | I2 | DI1 | DI1I2 | DI1I2 | DI1I2 | DI1 | DI1I2 | DI1I2I3 | I2 | D1 | D1D2D3 |
| Juda Fuji (TA-11) | DI2 | DI1 | DI1I2 | DI1I2 | DI1I2 | D | DI1I2 | DI2I3 | D2I2 | D1 | D1D2D3 |
| Luli (TA-12) | DI2 | DI1 | DI1I2 | DI2 | DI1I2 | DI1 | I1I2 | DI1I2I3 | D1I2 | D1 | D1D2D3I |
| Luping 1 (TA-13) | DI2 | DI1 | DI1I2 | DI1I2 | DI1I2 | D | DI1I2 | I2I3 | I2 | D1 | D1D2D3I |
| Luping 2 (TA-14) | I2 | DI1 | DI1I2 | DI1I2 | DI1I2 | DI1 | DI1I2 | DI1I2I3 | I2 | D1 | D1D2D3I |
| Luping 5 (TA-15) | I2 | DI1 | DI1I2 | DI2 | DI1I2 | DI1 | DI1I2 | DI2I3 | I2 | D1 | D1D2D3I |

-continued

Construction results of InDel marker genotype database of *Malus* germplasm resources

| | | | | | | | | | | | |
|---|---|---|---|---|---|---|---|---|---|---|---|
| Luyan (TA-16) | DI2 | DI1 | DI1I2 | DI1I2 | DI1I2 | D | DI1 | DI2I3 | D1I2 | D1 | D1D2D3I |
| Meinong (TA-17) | D | DI1 | DI1I2 | DI2 | DI1I2 | D | DI1I2 | DI2I3 | D2I2 | D1 | D1D2D3 |
| Akifu 19 (TA-18) | DI2 | DI1 | DI1I2 | DI1I2 | DI1I2 | D | DI1I2 | DI2I3 | D2I2 | D1 | D1D2D3 |
| Akifu 39 (TA-19) | DI2 | DI1 | DI1I2 | DI1I2 | DI1I2 | D | DI1I2 | DI2I3 | D2I2 | D1 | D1D2D3 |
| Hanfu 4x (TA-2) | DI1 | DI1I2 | DI1I2 | DI2 | DI1I2 | DI1 | I1I2 | DI2I3 | D2I2 | D1I | D1D2D3I |
| Qiufuhong (TA-20) | DI2 | DI1 | DI1I2 | DI1I2 | DI1I2 | D | DI1I2 | DI2I3 | D2I2 | D1 | D1D2D3 |
| Qunfu 1 (TA-21) | DI2 | DI1 | DI1I2 | DI1I2 | DI1I2 | D | DI1I2 | DI2I3 | D2I2 | D1 | D1D2D3 |
| Shengfang (TA-22) | DI2 | DI1 | DI1I2 | DI1I2 | DI1I2 | D | DI1I2 | DI2I3 | D2I2 | D1 | D1D2D3 |
| Alps Otome (TA-27) | DI2 | D | DI1I2 | DI1I2 | DI1I2 | DI2 | I1I2 | I2I3 | D2 | D1 | D1D2D3I |
| I2arly Fuji (TA-28) | DI2 | DI1 | DI1I2 | DI1I2 | DI1I2 | D | DI1I2 | DI2I3 | D2I2 | D1 | D1D2D3 |
| BP (TA-3) | I2 | D | NA | DI2 | DI1I2 | DI1 | DI1I2 | DI2 | D1D2 | D1 | D1D3 |
| Yishuihong (TA-32) | DI2 | DI1 | DI1I2 | DI1I2 | DI1I2 | D | DI1I2 | I2I3 | D2I2 | D1 | D1D2D3 |
| BP-176 (TA-4) | I2 | D | DI1I2 | DI2 | DI1I2 | DI1 | DI1I2 | DI2 | D1D2 | D1 | D1D3 |
| G41 (TA-5) | I2 | D | DI1 | DI2 | DI1I2 | D | I1I2 | DI2 | D1D2 | D1D3 | D1D2D3I |
| G935 (TA-6) | DI2 | D | DI1 | DI1I2 | DI1I2 | I1 | I1I2 | DI2 | D1D2 | D1D3 | D1D3 |
| P60 (TA-7) | DI2 | D | DI1I2 | DI2 | DI1I2 | DI1 | DI1I2 | DI2 | D1D2 | D1I | D1D2D3 |
| Fuji (TA-9) | DI2 | DI1 | DI1I2 | DI1I2 | DI1I2 | D | DI1I2 | DI2I3 | D2I2 | D1 | D1D2D3 |
| Tianfu 1 (TS-1) | DI2 | DI1 | DI1I2 | DI1I2 | DI1I2 | D | DI1I2 | DI2I3 | D2I2 | D1 | D1D2D3 |
| &28 (TS-13) | DI2 | DI1 | DI1I2 | DI1I2 | DI1I2 | D | DI1I2 | DI2I3 | D2I2 | D1 | D1D2D3 |
| Red Chief (TS-14) | DI2 | DI1 | DI1I2 | DI1I2 | DI1I2 | DI2 | I1I2 | DI1I2I3 | I2 | D1 | D1D2D3 |
| New Redchief (TS-2) | DI2 | DI1 | DI1I2 | D | DI1I2 | DI2 | I1I2 | NA | I2 | D1 | D1D2D3 |
| Chaohongxing (TS-3) | DI2 | DI1 | DI1I2 | DI1I2 | DI1I2 | DI2 | I1I2 | I1I2I3 | I2 | D1 | D1D2D3 |
| Aozhou 1 (TS-5) | DI2 | DI1 | DI1I2 | DI2 | DI1I2 | I1I2 | I1I2 | DI2I3 | D2 | D1 | D1D2D3I |
| Tianfu 2 (TS-6) | DI2 | DI1 | DI1I2 | DI1I2 | DI1I2 | D | DI1I2 | DI2I3 | D2I2 | D1 | D1D2D3 |
| Judeline (TS-7) | I1 | DI2 | DI1I2 | DI1I2 | DI1I2 | I1I2 | DI1I2 | DI1I2I3 | D2I2 | I | D1D2D3I |
| Judestar (TS-8) | I1I2 | DI2 | DI1I2 | DI1I2 | I1I2 | DI1 | I1I2 | DI2I3 | I2 | D1 | D1D2D3I |
| Judaine (TS-9) | I1 | DI2 | DI1I2 | DI1I2 | I1I2 | DI1I2 | DI1I2 | DI1I2I3 | D2I2 | I | D1D2D3I |
| WH-5 (WH-1) | DI2 | DI1 | DI1I2 | DI1I2 | DI1I2 | D | DI1I2 | DI2I3 | D2I2 | D1 | D1D2D3 |
| Italy Smothe (WH-10) | I1I2 | DI1I2 | DI1I2 | DI1I2 | DI1I2 | DI1 | I1I2 | DI1I2I3 | D2I2 | D1I | D1D2D3I |
| Bai Crab (WH-2) | I2 | D | DI1I2 | DI2 | DI1I2 | DI1 | I1I2 | DI2 | D1 | D1 | D1D2D3 |
| Hongguang (WH-4) | DI1 | DI1 | DI1 | DI1I2 | I1I2 | D | DI1I2 | DI1I2I3 | D2I2 | D1 | D1D2D3I |
| Huangcui (WH-5) | I1I2 | I1 | DI1I2 | DI1I2 | DI1I2 | DI1 | DI1I2 | DI2I3 | D2I2 | D1 | D1D2D3 |
| Qinglin (WH-6) | I1I2 | DI1I2 | DI1I2 | DI1 | DI1I2 | DI1 | I1I2 | DI1I2I3 | I2 | D1 | D1D2D3I |
| Harlikar (WH-8) | I1I2 | DI1 | DI1I2 | DI1 | DI1I2 | I1I2 | I1I2 | DI1I2I3 | I2 | D1 | D1D2D3 |
| Italy Gala (WH-9) | I2 | I1 | DI1I2 | DI1I2 | DI1I2 | DI1 | DI1I2 | DI1I2I3 | I2 | D1 | D1D2D3I |
| Wushan Bianye (WSBY) | D | D | DI1 | NA | DI1I2 | D | I1I2 | I2I3 | NA | D1 | D1D2 |
| Xin 1 (XC-1) | I2 | DI1 | DI1I2 | DI2 | I1I2 | I1 | DI1 | DI2I3 | I2 | D1 | D1D2D3 |
| Xin 5 (XC-2) | I2 | DI1 | DI1I2 | DI2 | DI1I2 | I1 | DI1 | I2I3 | I2 | D1 | D1D2D3 |
| Hanfu 3x (XC-3) | I2 | I1 | DI1 | DI2 | DI1I2 | D | I1I2 | DI2I3 | I2 | D1 | D1D2D3 |

-continued

Construction results of InDel marker genotype database of *Malus* germplasm resources

| | | | | | | | | | | | |
|---|---|---|---|---|---|---|---|---|---|---|---|
| Gala 4x (XC-4) | I2 | DI1 | DI1I2 | DI1I2 | DI1I2 | DI1 | DI1I2 | DI1I2I3 | I2 | D1 | D1D2D3I |
| Weizhimuben (XC-5) | I1I2 | DI1 | DI1I2 | DI1I2 | DI1I2 | I1 | DI1I2 | DI2I3 | D2I1 | D1D3 | D1D2D3I |
| Chaguo (XC-CG) | I2 | D | DI1I2 | DI1I2 | DI1I2 | I1 | I1I2 | DI2 | D1 | D1D3 | D1D2D3 |
| Donghongguo (XC-DHG) | D | DI1 | DI1 | DI2 | DI1I2 | DI1 | DI1 | DI2 | I2 | D1D3 | D1D2D3I |
| Fuxian Sanye (XC-FXXY) | D | D | DI1 | DI1 | DI1I2 | D | I1 | DI2 | D2 | D1D2D3 | D1D2D3 |
| Hongsanye (XC-HSY) | D | D | DI1 | DI1 | I1I2 | NA | I1 | DI2 | NA | D1D2D3 | D1D2D3 |
| Jilin Xiaohong Crab (XC-JILINXIAOHONG-HAITANG) | D | D | DI1I2 | DI1I2 | DI1I2 | I1 | I1I2 | DI2I3 | D2 | D1D3 | D1D2D3I |
| Jilin Xiaohuang Crab (XC-JILINXIAOHUANG-HAITANG) | I2 | D | DI1I2 | DI1I2 | DI1I2 | I1 | I1I2 | DI2I3 | D2I1 | D1D3 | D1D2D3I |
| Jilin Huang Crab (XC-JLHHT) | I2 | D | DI1I2 | DI1I2 | DI1I2 | I1 | I1I2 | DI2I3 | D2I1 | D1D3 | D1D2D3I |
| Shajin Crab (XC-JSHT) | D | NA | DI1 | D | DI1I2 | D | I1I2 | I2 | D2 | D1D2 | D1D2D3 |
| Longdong Crab (XC-LDHT) | D | NA | DI1 | DI1 | DI1I2 | D | I1I2 | NA | D2 | D1D2 | D1D2D3I |
| Lushi Crab (XC-LSHT) | D | NA | DI1 | D | DI1I2 | D | I1I2 | DI2 | D2 | D2 | D1D2D3 |
| Laiwunanyan (XC-LWNY) | I2 | D | DI1I2 | DI1I2 | DI1I2 | I1 | I1I2 | DI2 | D1 | D1D3 | D1D2D3 |
| Linzhi (XC-LZ) | D | D | DI1 | DI1 | DI1I2 | D | I1I2 | I2 | NA | D1 | D1D2 |
| Mao Shandingzi (XC-MSDZ) | I2 | D | DI1 | DI1 | I1I2 | D | I1I2 | DI2 | D2 | D3 | D1D2 |
| Pingyitiancha (XC-PYTC) | D | D | DI1 | DI1I2 | DI1I2 | D | I1I2 | DI2 | D2 | D1D2D3 | D1D2D3 |
| Qiuzi (XC-QZ) | DI2 | D | DI1I2 | DI2 | DI1I2 | D | I1I2 | DI2 | D2 | D1 | D1D3 |
| Sichuan Bianye (XC-SCBY) | D | D | DI1 | DI1 | DI1I2 | D | I1I2 | I2 | NA | D1 | D1D2 |
| Shandingzi (XC-SDZ) | D | D | DI1 | DI1 | I1I2 | D | I1 | DI2 | D2 | D3 | D1D2 |
| Weixi Sanye (XC-WXSY) | D | D | DI1I2 | DI1I2 | DI1I2 | D | DI1 | I2 | D1 | D1D2 | D1D2D3 |
| Xifu Crb (XC-XFHT) | I2 | D | DI1 | DI1 | DI1I2 | I1I2 | I1I2 | DI2 | D1D2 | D1D3 | D1D2D3 |
| Xiaojin Bianye (XC-XJBY) | D | D | DI1 | D | I1I2 | D | I1 | I2 | NA | D1 | D1D2 |
| Xinjiang Yepingguo (XC-XJYHT) | DI2 | D | DI1I2 | DI2 | DI1I2 | I1I2 | I1I2 | DI1I2 | D1D2 | D1D2 | D1D2D3I |
| Yajiang Bianye (XC-YJBY) | D | NA | DI1 | DI1 | I1I2 | D | I1I2 | NA | NA | D1 | D1D2 |
| Yingye Crab (XC-YYHT) | D | D | DI1 | DI1 | DI1I2 | D | I1 | DI2 | D2 | D1D2D3 | D1D2D3 |
| Zhaai (XC-ZA) | D | D | DI1 | DI1 | I1I2 | NA | I1 | DI2 | D2 | D3 | D1D2 |
| Zumi Crab (XC-ZMHT) | D | D | DI1I2 | DI1I2 | DI1I2 | I1 | I1I2 | DI2I3 | D2 | D3 | D1D2 |
| Pink Lady (XN-FHNS) | I2 | I1 | DI1I2 | DI2 | DI1I2 | DI2 | I1I2 | DI1I2 | D2I2 | D1 | D1D2D3 |
| Hongrou 1 (XN-HR1) | I2 | D | DI1I2 | DI2 | DI1I2 | I1 | I1I2 | DI1I2 | D1D2 | D1 | D1D2D3 |
| Hongrou 2 (XN-HR2) | D | DI2 | DI1I2 | DI2 | DI1I2 | I1 | I1I2 | DI2 | D1D2 | D1 | D1D2D3I |
| Hongrou 3 (XN-HR3) | D | D | DI1I2 | DI2 | DI1I2 | DI1 | I1I2 | DI2 | D1D2 | D1 | D1D2D3 |
| Hongrou 4 (XN-HR4) | D | D | DI1I2 | DI2 | DI1I2 | I1I2 | I1I2 | DI2 | D1D2 | D1 | D1D2D3I |
| Hongrou 5 (XN-HR5) | DI2 | DI1 | DI1I2 | DI2 | DI1I2 | I1 | I1I2 | DI2I3 | D1D2 | D1 | D1D2D3 |
| Hongrou 6 (XN-HR6) | I2 | D | DI1I2 | DI2 | DI1I2 | I1 | I1I2 | DI1I2 | D1D2 | D1 | D1D2D3 |
| Hongrou 7 (XN-HR7) | I2 | D | DI1I2 | DI1I2 | DI1I2 | DI1 | DI1I2 | DI2I3 | D1D2 | D1 | D1D2D3 |
| Ambrosia (XN-MW) | I2 | DI1 | DI1I2 | DI1 | DI1I2 | I1I2 | I1I2 | DI1I2I3 | I2 | D1 | D1D2D3 |

-continued

Construction results of InDel marker genotype database of *Malus* germplasm resources

| Xinjiang 10 (XN-XJ10) | DI2 | D | DI1I2 | DI1I2 | DI1I2 | I1 | I1I2 | DI2I3 | D1 | D1 | D1D2D3 |
|---|---|---|---|---|---|---|---|---|---|---|---|
| Xinjiang 11 (XN-XJ11) | I2 | D | DI1I2 | DI2 | DI1I2 | I1 | I1I2 | DI2 | D1D2 | D1 | D1D2D3 |
| Xinjiang 12 (XN-XJ12) | DI2 | D | DI1I2 | DI1I2 | DI1I2 | I1 | I1I2 | DI2I3 | D1 | D1 | D1D2D3 |
| Xinjiang 13 (XN-XJ13) | DI2 | DI2 | DI1 | DI1I2 | DI1I2 | DI1 | I1I2 | DI2I3 | D1D2 | D1D3 | D1D2D3 |
| Xinjiang 14 (XN-XJ14) | I2 | D | DI1I2 | DI2 | DI1I2 | I1 | I1I2 | DI2 | D1D2 | D1 | D1D2D3I |
| Xinjiang 15 (XN-XJ15) | DI2 | DI1 | DI1I2 | DI2 | DI1I2 | I1 | I1I2 | I2I3 | D2 | D1 | D1D2D3 |
| Xinjiang 16 (XN-XJ16) | DI2 | DI2 | DI1I2 | DI2 | DI1I2 | I1I2 | I1I2 | DI2 | D1 | D1 | D1D2D3I |
| Xinjiang 17 (XN-XJ17) | I2 | D | DI1I2 | DI2 | DI1I2 | I1 | I1I2 | DI2 | D1 | D1 | D1D2D3 |
| Xinjiang 18 (XN-XJ18) | D | D | DI1I2 | DI2 | DI1I2 | I1 | DI1I2 | DI2I3 | D1 | D1 | D1D2D3 |
| Xinjiang 19 (XN-XJ19) | DI2 | D | DI1I2 | DI2 | DI1I2 | DI1 | I1I2 | DI2I3 | D1 | D1 | D1D2D3 |
| Xinjiang 2 (XN-XJ2) | DI2 | D | DI1I2 | DI2 | DI1I2 | DI1 | I1I2 | DI2 | D2 | D1 | D1D2D3 |
| Xinjiang 20 (XN-XJ20) | DI2 | D | DI1I2 | DI2 | DI1I2 | D | I1I2 | DI2I3 | D1D2 | D1 | D1D2D3 |
| Xinjiang 21 (XN-XJ21) | DI2 | DI2 | DI1I2 | DI2 | DI1I2 | I1I2 | I1I2 | DI2I3 | D1 | D1 | D1D2D3I |
| Xinjiang 23 (XN-XJ23) | D | D | DI1I2 | DI2 | DI1I2 | D | DI1I2 | DI2 | D1D2 | D1I | D1D2D3 |
| Xinjiang 24 (XN-XJ24) | DI1 | DI1 | DI1I2 | DI1I2 | DI1I2 | DI1 | I1I2 | DI2I3 | D2 | D1 | D1D2D3 |
| Xinjiang 25 (XN-XJ25) | DI2 | D | DI1I2 | DI2 | DI1I2 | I1 | I1I2 | DI2 | D2 | D1 | D1D2D3 |
| Xinjiang 27 (XN-XJ27) | DI2 | DI1 | DI1I2 | DI2 | DI1I2 | I1 | I1I2 | I2I3 | D2 | D1 | D1D2D3 |
| Xinjiang 3 (XN-XJ3) | DI2 | D | DI1I2 | DI2 | DI1I2 | DI1 | I1I2 | DI2I3 | D1 | D1 | D1D3 |
| Xinjiang 4 (XN-XJ4) | I2 | D | DI1I2 | DI2 | DI1I2 | DI1 | DI1I2 | DI2I3 | D1D2 | D1 | D1D2D3 |
| Xinjiang 5 (XN-XJ5) | I2 | D | NA | D | D | D | NA | D | D1D2 | D1 | D1D2D3 |
| Xinjiang 7 (XN-XJ7) | D | D | DI1I2 | DI1I2 | DI1I2 | DI1 | I1I2 | DI2I3 | D1D2 | D1 | NA |
| Xinjiang 8 (XN-XJ8) | DI1 | DI1 | DI1I2 | DI1I2 | DI1I2 | DI1 | I1I2 | DI2I3 | D1D2 | D1 | D1D2D3 |
| Xinjiang 9 (XN-XJ9) | I2 | DI2 | DI1I2 | DI2 | DI1I2 | DI2 | I1I2 | DI2I3 | D1I2 | D1 | D1D3I |
| Yueguan (XY-10) | DI2 | I1 | DI1I2 | DI1I2 | DI1I2 | DI2 | DI1I2 | DI2I3 | D2I1 | D1 | D1D2D3 |
| Yuehua (XY-11) | I2 | D | DI1I2 | DI2 | DI1I2 | I2 | I1I2 | DI2 | D2 | D1D3 | D2D3I |
| Yueyan (XY-12) | DI2 | DI1 | DI1 | DI1I2 | DI1I2 | I1 | DI1 | DI1I2I3 | D2I1 | D1 | D1D2D3I |
| Bud Sport 5 (XY-13) | DI2 | DI1 | DI1I2 | DI1I2 | DI1I2 | D | DI1I2 | DI2I3 | D2I2 | D1 | D1D2D3 |
| Bud Sport 3 (XY-14) | DI2 | DI1 | DI1I2 | DI1I2 | DI1I2 | D | DI1I2 | DI2I3 | D2I2 | D1 | D1D2D3 |
| Longfu (XY-15) | DI2 | DI1 | DI1I2 | DI1I2 | DI1I2 | D | DI1I2 | DI2I3 | D2I2 | D1 | D1D2D3 |
| Yuemei (XY-18) | D | DI2 | DI1I2 | DI1 | DI1I2 | DI1 | DI1I2 | DI1I2I3 | D1D2 | D1 | D1D2D3I |
| Hanfu (XY-2) | DI2 | DI1 | DI1 | DI2 | DI1I2 | DI1 | DI1I2 | DI2I3 | D2I1I2 | D1 | D1D2D3 |
| Linyi Fuji (XY-20) | I2 | DI1 | DI1I2 | DI1I2 | DI1I2 | D | DI1I2 | DI1I2I3 | D2I2 | D1 | D1D2D3 |
| Yishui Fuji (XY-22) | DI2 | DI1 | DI1I2 | DI1I2 | DI1I2 | D | DI1I2 | DI2I3 | D2I2 | D1 | D1D2D3 |
| Hongjinfu (XY-25) | DI2 | DI1 | DI1I2 | DI1I2 | DI1I2 | D | DI1I2 | DI2I3 | D2I2 | D1 | D1D2D3 |
| Beni Oshu (XY-26) | DI2 | DI1 | DI1I2 | DI1I2 | DI1I2 | D | DI1I2 | DI2I3 | D2I2 | D1 | D1D2D3 |
| Chuizhi Fuji (XY-27) | DI2 | DI1 | DI1I2 | DI1I2 | DI1I2 | D | DI1I2 | DI2I3 | D2I2 | D1 | D1D2D3 |
| Yueshuai (XY-28) | I2 | DI1 | DI1I2 | DI1I2 | DI1I2 | DI2 | NA | DI1I2I3 | D2 | D1 | D1D2D3 |
| Shichinohe 2 (XY-29) | DI2 | DI1 | DI1I2 | DI1I2 | DI1I2 | D | DI1I2 | DI2I3 | D2I2 | D1 | D1D2D3 |
| 74-178 (XY-3) | DI1 | I1I2 | DI1I2 | DI2 | DI1I2 | DI1 | DI1I2 | DI2I3 | D2I1I2 | D1I | D1D3 |

-continued

Construction results of InDel marker genotype database of *Malus* germplasm resources

| Name | | | | | | | | | | | |
|---|---|---|---|---|---|---|---|---|---|---|---|
| KAKUFUJI (XY-30) | DI2 | DI1 | DI1I2 | DI1I2 | DI1I2 | D | DI1I2 | DI2I3 | D2I2 | D1 | D1D2D3 |
| Royal Fuji 21 (XY-35) | DI2 | DI1 | DI1I2 | DI1I2 | DI1I2 | D | DI1I2 | DI2I3 | D2I2 | D1 | D1D2D3 |
| Qiquan Spur (XY-36) | DI2 | DI1 | DI1I2 | DI1I2 | DI1I2 | D | DI1I2 | DI2I3 | D2I2 | D1 | D1D2D3 |
| Juda Fuji (XY-37) | DI1 | DI1 | DI1 | DI1I2 | I1I2 | D | DI1I2 | DI1I2I3 | D2I2 | D1 | D1D2D3I |
| 7-211 (XY-4) | DI2 | DI2 | DI1I2 | DI2 | DI1I2 | DI2 | I1I2 | DI1I2I3 | D1I2 | D1I | D1D2D3I |
| Yanfu 0 (XY-41) | DI2 | DI1 | DI1I2 | DI1I2 | DI1I2 | D | DI1I2 | DI2I3 | D2I2 | D1 | D1D2D3 |
| Spur Fuji (XY-42) | DI2 | DI1 | DI1I2 | DI1I2 | DI1I2 | D | DI1I2 | DI2I3 | D2I2 | D1 | D1D2D3 |
| Bayue fushiwang (XY-43) | DI2 | DI1 | DI1I2 | DI1I2 | DI1I2 | D | DI1I2 | DI2I3 | D2I2 | D1 | D1D2D3 |
| Huangfu 7 (XY-44) | DI2 | DI1 | DI1I2 | DI1I2 | DI1I2 | D | DI1I2 | DI2I3 | D2I2 | D1 | D1D2D3 |
| Aomori Spur Fuji (XY-46) | DI2 | DI1 | DI1I2 | DI1I2 | DI1I2 | D | DI1I2 | DI2I3 | D2I2 | D1 | D1D2D3 |
| Qiu Fuji (XY-47) | DI2 | DI1 | DI1I2 | DI1I2 | DI1I2 | D | DI1I2 | DI2I3 | D2I2 | D1 | D1D2D3 |
| Fuji Champion (XY-48) | DI2 | DI1 | DI1I2 | DI1I2 | DI1I2 | D | DI1I2 | DI2I3 | D2I2 | D1 | D1D2D3 |
| 26-34 (XY-5) | I1I2 | DI1 | DI1I2 | DI2 | DI1I2 | I1I2 | I1I2 | DI1I2I3 | D2I1I2 | D1 | D1D2D3I |
| Akifu 19 (XY-50) | DI2 | DI1 | DI1I2 | DI1I2 | DI1I2 | D | DI1I2 | DI2I3 | D2I2 | D1 | D1D2D3 |
| Fuji (XY-54) | DI2 | DI1 | DI1I2 | DI1I2 | DI1I2 | D | DI1I2 | DI2I3 | D2I2 | D1 | D1D2D3 |
| Qinfu 1 (XY-55) | DI2 | DI1 | DI1I2 | DI1I2 | DI1I2 | D | DI1I2 | DI2I3 | D2I2 | D1 | D1D2D3 |
| Feng Fuji (XY-56) | DI2 | DI1 | DI1I2 | DI1I2 | DI1I2 | D | DI1I2 | DI2I3 | D2I2 | D1 | D1D2D3 |
| Tianxing (XY-57) | DI2 | DI1 | DI1I2 | DI1I2 | DI1I2 | D | DI1I2 | DI2I3 | D2I2 | D1 | D1D2D3 |
| Taiyang Fuji (XY-58) | DI2 | DI1 | DI1I2 | DI1I2 | DI1I2 | D | DI1I2 | DI2I3 | D2I2 | D1 | D1D2D3 |
| Cherry Crab (XY-6) | I2 | D | DI1I2 | DI1I2 | DI1 | I1 | I1I2 | DI2I3 | D2 | D3 | D1D2D3 |
| Yueping (XY-60) | DI2 | DI1 | DI1 | DI2 | DI1I2 | DI1 | NA | DI1I2I3 | D2I2 | D1 | D1D2D3 |
| 23-63 (XY-61) | I2 | DI1 | DI1 | DI2 | DI1I2 | DI1 | DI1I2 | I2I3 | D2I1 | D1 | D1D2D3 |
| 23-42 (XY-62) | DI2 | DI1 | DI1I2 | DI1I2 | DI1I2 | D | NA | DI2I3 | D2I1I2 | D1 | D1D2D3 |
| 7-171 (XY-63) | DI2 | DI2 | DI1I2 | DI1 | DI1I2 | DI2 | I1I2 | I2I3 | D1D2 | D1 | D1D2D3I |
| Shengfang 3A (XY-65) | DI2 | DI1 | DI1I2 | DI1I2 | DI1I2 | D | DI1I2 | DI2I3 | D2I2 | D1 | D1D2D3 |
| Meinong Fuji (XY-67) | DI2 | DI1 | DI1I2 | DI1I2 | DI1I2 | D | DI1I2 | DI2I3 | D2I2 | D1 | D1D2D3 |
| 62-45 (XY-68) | DI2 | DI1 | DI1 | DI1I2 | DI1I2 | DI1 | DI1I2 | DI1I2I3 | D2I1 | D1 | D1D2D3 |
| Fengfeng Fuji (XY-70) | DI2 | DI1 | DI1I2 | DI1I2 | DI1I2 | D | DI1I2 | DI2I3 | D2I2 | D1 | D1D2D3 |
| GM256 (XY-71) | DI2 | DI1 | DI1I2 | DI1I2 | DI1I2 | D | NA | DI2I3 | D2I2 | D1 | D1D2D3 |
| Jinfu 2 (XY-73) | DI2 | DI1 | DI1I2 | DI1I2 | DI1I2 | D | DI1I2 | DI2I3 | D2I2 | D1 | D1D2D3 |
| Qiufu (XY-75) | DI2 | DI1 | DI1I2 | DI1I2 | DI1I2 | D | DI1I2 | DI2I3 | D2I2 | D1 | D1D2D3 |
| Shanfu 6 (XY-76) | DI2 | DI1 | DI1I2 | DI1I2 | DI1I2 | D | DI1I2 | DI2I3 | D2I2 | D1 | D1D2D3 |
| Nagafu 8 (XY-77) | DI2 | DI1 | DI1I2 | DI1I2 | DI1I2 | D | DI1I2 | DI2I3 | D2I2 | D1 | D1D2D3 |
| 58-34 (XY-78) | I2 | DI1 | DI1I2 | DI1I2 | DI1I2 | DI1 | DI1I2 | DI2I3 | D2I1 | D1 | D1D2D3 |
| 2001 Fuji (XY-79) | DI2 | DI1 | DI1I2 | DI1I2 | DI1I2 | D | DI1I2 | DI2I3 | D2I2 | D1 | D1D2D3 |
| 15-26 (XY-8) | D | DI1I2 | DI1I2 | DI1I2 | DI1I2 | I1I2 | I1I2 | DI1I2 | D1I2 | D1 | D1D2D3I |
| Wangshanhong (XY-80) | DI2 | DI1 | DI1I2 | DI1I2 | DI1I2 | D | DI1I2 | DI2I3 | D2I2 | D1 | D1D2D3 |
| Jinfu 1 (XY-81) | DI2 | DI1 | DI1I2 | DI1I2 | DI1I2 | D | DI1I2 | DI2I3 | D2I1 | D1 | D1D2D3 |

-continued

Construction results of InDel marker genotype database of *Malus* germplasm resources

| | | | | | | | | | | |
|---|---|---|---|---|---|---|---|---|---|---|
| Qingfu 1 (XY-84) | DI2 | DI1 | DI1I2 | DI1I2 | DI1I2 | D | DI1I2 | DI2I3 | D2I2 | D1 | D1D2D3 |
| Qiufu 39 (XY-85) | DI2 | DI1 | DI1I2 | DI1I2 | DI1I2 | D | DI1I2 | DI2I3 | D2I2 | D1 | D1D2D3 |
| Nagafu 1 (XY-86) | DI2 | DI1 | DI1I2 | DI1I2 | DI1I2 | D | DI1I2 | DI2I3 | D2I2 | D1 | D1D2D3 |
| Shou Fuji (XY-87) | DI2 | DI1 | DI1I2 | DI1I2 | DI1I2 | D | DI1I2 | DI2I3 | D2I2 | D1 | D1D2D3 |
| Yueli (XY-88) | DI2 | DI2 | DI1I2 | DI1 | DI1I2 | DI1 | I1I2 | DI2I3 | D1I2 | D1I | D1D2D3I |
| Shanfu 2 (XY-89) | DI2 | DI1 | DI1I2 | DI1I2 | DI1I2 | D | DI1I2 | DI2I3 | D2I2 | D1 | D1D2D3 |
| Chongban Crab (XY-9) | I2 | D | DI1 | DI1I2 | DI1I2 | DI1 | I1I2 | DI2 | D2 | D3 | D1D2D3 |
| Harica (XY-90) | I1I2 | DI1I2 | DI1I2 | DI1 | DI1I2 | DI1 | I1I2 | DI1I2I3 | I2 | D1 | D1D2D3I |
| Akifu 1 (XY-91) | DI2 | DI1 | DI1I2 | DI1I2 | DI1I2 | D | DI1I2 | DI2I3 | D2I2 | D1 | D1D2D3 |
| Wangfu (XY-92) | DI2 | DI1 | DI1I2 | DI1I2 | DI1I2 | D | DI1I2 | DI2I3 | D2I2 | D1 | D1D2D3 |
| Hong Manao (XYZ-1) | DI1 | D | DI1 | DI1I2 | DI1I2 | D | DI1I2 | I2 | D1 | D1D2 | D1D2D3I |
| Modi (XYZ-10) | DI2 | DI1 | DI1I2 | DI1I2 | I1I2 | DI1 | I1I2 | I2I3 | D1I2 | D1 | D1D2D3I |
| C37 (XYZ-11) | I2 | I1 | DI1I2 | DI1I2 | DI1I2 | DI1 | DI1I2 | DI2I3 | D2I2 | D1 | D2D3I |
| I2nvy ? (XYZ-12) | I2 | DI1 | DI1I2 | DI1I2 | DI1I2 | DI1 | I1I2 | DI1I2I3 | D2I2 | D1 | D1D2D3 |
| Xichang Yuanzhuiguo (XYZ-2) | DI1 | DI1 | DI1I2 | DI2 | DI1I2 | D | DI1I2 | DI2I3 | D2 | D1D3 | D1D3 |
| Ziye Zixiaoguo (XYZ-3) | D | D | DI1I2 | DI1I2 | DI1I2 | I1 | I1 | DI2 | D2 | D2D3 | D1D2D3 |
| Ziye Zidaguo (XYZ-4) | I2 | D | I1I2 | DI1I2 | DI1I2 | D | DI1I2 | I2I3 | D2 | D1D3 | D1D3 |
| Shoufenshu 6 (XYZ-5) | I2 | DI1 | DI1I2 | DI1I2 | DI1I2 | D | DI1 | DI1I2 | D1D2 | D1D3 | D1D2D3I |
| Changhua (XYZ-6) | I2 | I1 | DI1I2 | DI1I2 | DI1I2 | DI1 | DI1I2 | DI1I2I3 | I2 | D1 | D1D2D3I |
| Jinshiji (XYZ-7) | I2 | I1 | DI1I2 | DI1I2 | DI1I2 | DI1 | DI1I2 | DI1I2I3 | I2 | D1 | D1D2D3I |
| 19-147 (XYZ-9) | DI2 | DI1 | DI1I2 | DI1I2 | DI1I2 | D | I1I2 | DI1I2I3 | D2I2 | D1I | D1D2D3I |
| Malong Gala 1 (YN-1) | I2 | DI1 | DI1I2 | DI1I2 | DI1I2 | DI1 | DI1I2 | DI1I2I3 | I2 | D1 | D1D2D3I |
| Shouer hong (YN-11) | DI2 | DI1 | DI1I2 | DI1I2 | DI1I2 | D | DI1I2 | DI2I3 | D2I2 | D1 | D1D2D3 |
| Yun Hongrou (YN-12) | DI2 | DI1 | DI1I2 | DI1I2 | DI1I2 | I1I2 | I1I2 | I2I3 | D2I2 | D1 | D1D2D3 |
| Lixing Crab (YN-13) | I2 | D | DI1I2 | DI2 | DI1I2 | DI1 | I1I2 | DI2 | D1 | D1D3 | D1D2D3 |
| Siana (YN-15) | DI2 | I1 | DI1I2 | DI2 | DI1I2 | D | I1I2 | DI2 | D2 | D1 | D1D2D3 |
| Jonathan-M41 (YN-17) | I2 | D | DI1I2 | DI2 | DI1I2 | DI2 | DI1I2 | DI2I3 | D2 | D1 | D1D2D3 |
| Morlie's Delicious (YN-18) | DI2 | I2 | DI1I2 | DI1I2 | DI1I2 | I1I2 | I1I2 | I1I2I3 | D2I2 | D1I | D2D3I |
| Britegold (YN-19) | DI2 | DI1 | DI1I2 | DI1I2 | DI1I2 | D | DI1I2 | DI2I3 | D2I2 | D1 | D1D2D3 |
| Malong Gala 1 blush (YN-2) | I2 | I1 | DI1I2 | DI1I2 | DI1I2 | DI1 | DI1I2 | DI1I2I3 | I2 | D1 | D1D2D3I |
| Line 5 (YN-22) | DI2 | I1 | DI1I2 | DI2 | DI1I2 | D | I1I2 | DI2 | D2 | D1 | D1D2D3 |
| Line 6 (YN-23) | DI1 | DI1 | DI1 | DI1I2 | DI1I2 | D | I1I2 | DI2 | D2I2 | D1I | D1D2D3I |
| Line 13 (YN-24) | DI2 | DI2 | DI1I2 | DI1I2 | DI1I2 | I1 | I1I2 | DI2I3 | I2 | D1I | D1D2D3I |
| row 3 (YN-25) | DI2 | DI1 | DI1I2 | DI2 | DI1I2 | DI1 | I1I2 | DI1I2I3 | D1I2 | D1 | D1D2D3I |
| row 4 (YN-26) | DI2 | DI1 | DI1I2 | DI2 | DI1I2 | DI1 | I1I2 | DI1I2I3 | D1I2 | D1 | D1D2D3I |
| row 5 (YN-27) | DI2 | DI1 | DI1I2 | DI2 | DI1I2 | DI1 | I1I2 | DI1I2I3 | D1I2 | D1 | D1D2D3I |
| row 6 (YN-28) | DI2 | DI1 | DI1I2 | DI2 | DI1I2 | DI1 | I1I2 | DI1I2I3 | D1I2 | D1 | D1D2D3I |
| row 9 (YN-29) | I2 | DI1 | DI1 | DI1I2 | DI1I2 | DI1 | DI1 | DI1I2I3 | I2 | D1 | D1D2D3 |
| Malong xin Gala 1 (YN-3) | I2 | I1 | DI1I2 | DI1I2 | DI1I2 | DI1 | DI1I2 | DI1I2I3 | I2 | D1 | D1D2D3I |

-continued

| Construction results of InDel marker genotype database of *Malus* germplasm resources | | | | | | | | | | | |
|---|---|---|---|---|---|---|---|---|---|---|---|
| row 10 (YN-30) | I2 | I1 | DI1I2 | DI2 | DI1I2 | DI2 | I1I2 | I1I2 | D2I2 | D1 | D1D2D3 |
| row 11 (YN-31) | I2 | DI1 | DI1 | DI1I2 | DI1I2 | DI1 | DI1 | DI1I2I3 | I2 | D1 | D1D2D3 |
| row 12 (YN-32) | I2 | I1 | DI1I2 | DI1I2 | DI1I2 | DI1 | DI1I2 | DI1I2I3 | I2 | D1 | D1D2D3I |
| row 13 (YN-33) | DI2 | DI1 | DI1I2 | DI1I2 | DI1I2 | D | DI1 | DI2I3 | D1I2 | D1 | D1D2D3I |
| row 14 (YN-34) | DI2 | DI1 | DI1I2 | DI2 | DI1I2 | DI1 | I1I2 | DI1I2I3 | D1I2 | D1 | D1D2D3I |
| row 15 (YN-35) | DI2 | I1 | DI1I2 | DI1I2 | DI1I2 | D | DI1I2 | DI2I3 | I2 | D1 | D1D2D3I |
| row 16 (YN-36) | I1I2 | DI1I2 | DI1I2 | DI1I2 | DI1I2 | DI1 | I1I2 | DI1I2I3 | D2I2 | D1I | D1D2D3I |
| row 17 (YN-37) | DI2 | DI1 | DI1I2 | DI2 | DI1I2 | D | I1I2 | I2I3 | D1D2 | D1 | D1D2D3 |
| row 18 (YN-38) | DI1 | I1I2 | DI1I2 | DI1 | DI1I2 | DI2 | DI1I2 | I2I3 | D2 | D1I | D1D2D3 |
| row 19 (YN-39) | DI1 | DI1 | DI1I2 | DI1I2 | I1I2 | D | DI1I2 | DI2I3 | D2I1I2 | D1 | D1D2D3 |
| Malong xin Gala 1 strip (YN-4) | I2 | I1 | DI1I2 | DI1I2 | DI1I2 | DI1 | DI1I2 | DI1I2I3 | I2 | D1 | D1D2D3I |
| row 20 (YN-40) | I1I2 | DI2 | DI1I2 | DI1I2 | DI1I2 | DI2 | DI1I2 | I2I3 | D2 | D1I | D1D2D3I |
| row 21 (YN-41) | DI2 | DI1 | DI1I2 | DI1I2 | DI1I2 | D | DI1I2 | DI2I3 | D2I2 | D1 | D1D2D3 |
| row 22 (YN-42) | I1I2 | DI2 | DI1I2 | DI1I2 | DI1I2 | DI2 | DI1I2 | I2I3 | D2 | D1I | D1D2D3I |
| row 23 (YN-43) | I1I2 | DI2 | DI1I2 | DI1I2 | DI1I2 | DI2 | DI1I2 | I2I3 | D2 | D1I | D1D2D3I |
| row 24 (YN-44) | DI2 | DI1 | DI1I2 | DI1I2 | DI1I2 | D | DI1I2 | DI2I3 | D2I2 | D1 | D1D2D3 |
| row 25 (YN-45) | DI2 | DI1 | DI1I2 | DI1I2 | DI1I2 | D | DI1I2 | DI2I3 | D2I2 | D1 | D1D2D3 |
| Malong Gala2 (YN-5) | I2 | I1 | DI1I2 | DI1I2 | DI1I2 | DI1 | DI1I2 | DI1I2I3 | I2 | D1 | D1D2D3I |
| Malong Gala 2 blush (YN-6) | I2 | I1 | DI1I2 | DI1I2 | DI1I2 | DI1 | DI1I2 | DI1I2I3 | I2 | D1 | D1D2D3I |
| Longwei (YN-7) | DI2 | DI1 | DI1I2 | DI2 | DI1I2 | DI2 | DI1 | DI1I2I3 | I2 | D1 | D1D2D3 |
| Longwei I2arly Mutant (YN-8) | DI2 | DI1 | DI1I2 | DI2 | DI1I2 | DI2 | DI1 | DI1I2I3 | I2 | D1 | D1D2D3 |
| Cherry Gala (YN-9) | I2 | I1 | DI1I2 | DI1I2 | DI1I2 | DI1 | DI1I2 | DI1I2I3 | I2 | D1 | D1D2D3I |
| Siyana (YT-1) | I2 | DI1 | DI1 | DI2 | I1I2 | DI1I2 | I1I2 | DI1I2I3 | D2 | D1 | D1D2D3 |
| Yanfu 10 (YT-100) | DI2 | DI1 | DI1I2 | DI1I2 | DI1I2 | D | DI1I2 | DI2I3 | D2I2 | D1 | D1D2D3 |
| Chadel (YT-102) | I1 | DI1 | DI1I2 | DI1I2 | DI1I2 | DI1 | I1I2 | DI2I3 | D2I2 | D1 | D1D2D3 |
| Charden (YT-103) | I1I2 | DI1I2 | DI1I2 | DI1I2 | DI1I2 | DI1I2 | I1I2 | DI1I2I3 | D2I2 | D1I | D1D2D3I |
| Tuskan (YT-104) | I2 | DI2 | DI1I2 | DI1I2 | DI1I2 | D | DI1I2 | DI2I3 | D2I2 | D1I | D1D2D3 |
| Prima × Sekaiichii (YT-105) | I2 | D | DI1I2 | DI1I2 | DI1I2 | DI2 | DI1I2 | DI1I2I3 | I2 | D1 | D1D2D3 |
| Toppax_apple (YT-11) | DI1 | DI2 | DI1I2 | DI2 | I1I2 | DI1 | DI1I2 | DI2I3 | D1D2 | D1 | D1D2D3 |
| Xinjiang Hongrou Crab (YT-12) | D | DI2 | DI1 | DI1 | DI1I2 | I1 | I1 | DI2I3 | D2 | D1D3 | D1D2D3I |
| Melfree (YT-13) | DI1 | DI1I2 | DI1I2 | DI2 | I1I2 | DI1 | I1I2 | DI1I2I3 | D1D2 | D1 | D1D2D3 |
| Yanfu 3 (YT-14) | I2 | D | DI1I2 | DI1I2 | DI1I2 | DI2 | DI1I2 | DI2I3 | D2 | D1 | D1D2D3I |
| Gold milecnirum (YT-15) | I2 | D | DI1I2 | DI1I2 | DI1I2 | I1 | I1I2 | DI2I3 | D2I1I2 | D1 | D1D2D3I |
| Ganhong (YT-16) | I2 | I1I2 | DI1I2 | DI2 | DI1I2 | DI2 | I1I2 | DI2I3 | D2I1I2 | D1I | D1D2D3I |
| Cornoet (YT-17) | I2 | DI1I2 | DI1I2 | DI2 | DI1I2 | I1I2 | I1I2 | DI1I2 | D2 | D1 | D1D2D3 |
| Priw (YT-18) | I2 | D | DI1 | DI2 | DI1I2 | D | DI1I2 | DI2I3 | D1D2 | D1 | D1D2D3 |
| Aichi (YT-19) | DI2 | DI1I2 | DI1I2 | DI2 | DI1I2 | DI1I2 | I1I2 | DI2I3 | D1D2 | D1 | D1D2D3 |
| Auraria (YT-2) | I2 | D | DI1I2 | DI1I2 | DI1I2 | D | DI1I2 | DI2I3 | D1I2 | D1I | D1D2D3 |

-continued

Construction results of InDel marker genotype database of *Malus* germplasm resources

| | | | | | | | | | | | |
|---|---|---|---|---|---|---|---|---|---|---|---|
| Meile (YT-20) | DI2 | DI1 | DI1I2 | DI1I2 | DI1I2 | D | DI1I2 | DI2I3 | D2I2 | D1 | D1D2D3 |
| Qiulimeng (YT-21) | DI2 | DI2 | DI1I2 | DI2 | DI1I2 | I1I2 | I1I2 | DI2 | D1 | D1 | D1D2D3I |
| Aliusitan (YT-22) | DI2 | DI2 | DI1I2 | DI2 | DI1I2 | I1 | I1I2 | DI2I3 | D1 | D1 | D1D2D3 |
| Geaooza (YT-23) | DI2 | D | DI1 | DI2 | DI1I2 | I1I2 | DI1I2 | DI2 | D1D2 | D1 | D1D2D3I |
| Golden Spur (YT-24) | I1I2 | I1I2 | DI1I2 | DI1I2 | DI1I2 | DI1 | I1I2 | DI1I2I3 | D2I2 | D1I | D1D2D3I |
| Starking (YT-25) | DI2 | DI1 | DI1I2 | DI1I2 | DI1I2 | DI2 | I1I2 | DI1I2I3 | I2 | D1 | D1D2D3 |
| Indo (YT-26) | I2 | I1 | DI1I2 | DI1I2 | DI1I2 | D | DI1I2 | DI2I3 | D2I2 | D1 | D1D2D3I |
| Teser (YT-27) | I1I2 | DI1 | DI1I2 | DI1I2 | DI1I2 | I2 | DI1I2 | DI1I2I3 | D2I2 | D1 | D1D2D3I |
| Xianhong (YT-28) | I2 | D | DI1I2 | DI2 | DI1I2 | DI2 | I1I2 | DI2I3 | D2 | D1I | D2D3I |
| Gala × Mato 8 (YT-29) | DI2 | DI1 | DI1I2 | DI1I2 | DI1I2 | D | DI1 | DI2I3 | D1I2 | D1 | D1D2D3 |
| Very I2arly Fuji (YT-3) | DI2 | DI1 | DI1I2 | DI1I2 | DI1I2 | D | DI1I2 | DI2I3 | D2I2 | D1 | D1D2D3 |
| Qiuhuapi (YT-30) | DI1 | DI1 | DI1 | DI2 | I1I2 | I1I2 | DI1I2 | DI2I3 | D2I2 | D1I | D1D2D3I |
| Piga 70 (YT-31) | I2 | I1I2 | DI1I2 | DI2 | DI1I2 | DI1 | I1I2 | DI1I2I3 | D2I2 | D1 | D1D2D3 |
| Yanzhen 1 (YT-32) | DI1 | D | DI1I2 | DI1I2 | DI1I2 | D | DI1I2 | I2I3 | D1D2 | D1I | D1D2D3I |
| Matail (YT-34) | I2 | I1 | DI1I2 | DI1I2 | DI1I2 | DI1 | DI1I2 | DI1I2I3 | I2 | D1 | D1D2D3I |
| Jonathan-csan (YT-35) | I2 | D | DI1I2 | DI2 | DI1I2 | DI2 | DI1I2 | DI2I3 | D2 | D1 | D1D2D3I |
| Huashuai (YT-36) | DI1 | DI1 | DI1I2 | DI2 | DI1I2 | DI2 | I1I2 | DI1I2 | D1I2 | D1 | D1D2D3I |
| Wengao 1 (YT-38) | DI2 | DI1 | DI1I2 | DI1I2 | DI1I2 | D | DI1I2 | DI2I3 | D2I2 | D1 | D1D2D3 |
| Wengao 2 (YT-39) | DI2 | DI1 | DI1I2 | DI1I2 | DI1I2 | D | DI1I2 | DI2I3 | D2I2 | D1 | D1D2D3 |
| I2legia (YT-4) | I2 | DI1 | DI1I2 | DI2 | DI1I2 | D | I1I2 | DI2I3 | D1I2 | D1 | D1D2D3 |
| Wengao 3 (YT-40) | DI2 | DI1 | DI1I2 | DI1I2 | DI1I2 | D | DI1I2 | DI2I3 | D2I2 | D1 | D1D2D3 |
| Hong Anka (YT-41) | DI2 | D | DI1I2 | DI2 | DI1I2 | D | DI1I2 | DI2I3 | D2 | D1I | D1D2D3I |
| Yanfu 2 (YT-42) | DI2 | DI1 | DI1I2 | DI1I2 | DI1I2 | D | DI1I2 | DI2I3 | D2I2 | D1 | D1D2D3 |
| Belgolden (YT-43) | I1I2 | I1I2 | DI1I2 | DI1I2 | DI1I2 | DI1 | I1I2 | DI1I2I3 | D2I2 | D1I | D1D2D3I |
| Rubinola (YT-44) | DI2 | DI1 | DI1I2 | DI1I2 | DI1I2 | DI1 | DI1I2 | DI2I3 | I1I2 | D1 | D1D2D3 |
| Wangqiuhong (YT-45) | I2 | DI2 | DI1I2 | DI1I2 | I1I2 | DI1 | I1I2 | I2I3 | D2I2 | D1I | D1D2D3 |
| Pulanhong (YT-46) | I2 | I1I2 | DI1I2 | DI2 | DI1I2 | D | I1I2 | DI2I3 | D2 | D1 | D1D2D3 |
| Bosh (YT-47) | DI2 | DI1 | DI1I2 | DI2 | DI1I2 | DI2 | DI1I2 | DI2 | D1 | D1 | D1D2D3 |
| Chengji 1 (YT-48) | DI2 | DI1 | DI1I2 | DI1I2 | DI1I2 | D | DI1I2 | DI2I3 | D2I2 | D1 | D1D2D3 |
| Hongli (YT-49) | D | DI2 | DI1I2 | DI1I2 | DI1I2 | D | DI1I2 | DI2I3 | D2I1 | D1 | D1D2D3 |
| Guoqinghong (YT-5) | I2 | DI1 | DI1I2 | DI1I2 | DI1I2 | DI1 | I1I2 | DI2I3 | D2I2 | D1 | D1D2D3 |
| Reandra (YT-50) | I1I2 | I1I2 | DI1I2 | DI2 | DI1I2 | I1I2 | I1I2 | DI1I2I3 | D2I2 | D1I | D2D3I |
| Revbihola (YT-51) | I1I2 | DI1 | DI1I2 | DI1I2 | DI1I2 | DI2 | DI1I2 | DI2 | D2 | D1I | D1D3 |
| Melrose (YT-52) | I2 | DI1 | DI1I2 | DI1I2 | DI1I2 | DI2 | DI1I2 | I2I3 | D2I2 | D1 | D1D2D3I |
| Rewena (YT-53) | I1I2 | DI2 | DI1I2 | DI1I2 | DI1I2 | DI2 | I1I2 | DI2I3 | D1I2 | D1 | D1D2D3 |
| Mrxl(robusta × Liberte) (YT-54) | DI2 | DI1 | DI1I2 | DI1I2 | DI1I2 | DI2 | I1I2 | DI1I2I3 | I2 | D1 | D1D2D3 |
| Mollies_Del_open (YT-55) | I2 | DI2 | DI1I2 | DI1I2 | DI1I2 | DI1 | I1I2 | DI1I2I3 | D1I2 | D1 | D1D2D3I |
| Renora (YT-56) | DI2 | DI1I2 | DI1I2 | DI2 | DI1I2 | DI1 | DI1I2 | DI1I2 | D1I2 | D1 | D1D2D3 |
| Rosmadzin (YT-57) | DI2 | DI1 | DI1I2 | DI2 | DI1I2 | DI2 | DI1I2 | DI2 | D1 | D1 | D1D2D3 |

-continued

Construction results of InDel marker genotype database of *Malus* germplasm resources

| | | | | | | | | | | | |
|---|---|---|---|---|---|---|---|---|---|---|---|
| Remo (YT-58) | I2 | I1 | DI1I2 | DI1 | DI1I2 | DI1 | DI1I2 | DI1I2I3 | D2I2 | D1 | D2D3I |
| Pilot (YT-59) | I2 | DI1 | DI1I2 | DI2 | DI1I2 | I1 | I1I2 | DI2I3 | D2I2 | D1I | D1D2D3 |
| Yangbai Crab (YT-6) | I2 | D | DI1I2 | DI2 | DI1I2 | DI1 | I1I2 | DI2 | D1 | D1 | D1D2D3 |
| Free Red Star (YT-60) | I2 | I2 | DI1I2 | DI1I2 | DI1I2 | I2 | DI1I2 | DI1I2I3 | D2I1I2 | D1 | D1D2D3 |
| Idared (YT-61) | I1I2 | D | DI1I2 | DI2 | DI1I2 | DI2 | I1I2 | DI2I3 | D2 | D1 | D1D2D3 |
| Mingyue (YT-62) | DI1 | DI1 | DI1I2 | DI1 | DI1I2 | DI2 | I1I2 | DI2I3 | I2 | D1 | D1D2D3 |
| Piga 101 (YT-63) | DI2 | DI1 | DI1I2 | DI2 | DI1I2 | DI1 | DI1I2 | DI2I3 | D2 | D1 | D1D2D3I |
| Yanfu 5 (YT-64) | DI2 | DI1 | DI1I2 | DI1I2 | DI1I2 | D | DI1I2 | DI2I3 | D2I2 | D1 | D1D2D3 |
| I2arly Jonagold (YT-65) | I1I2 | DI1I2 | DI1I2 | DI1I2 | DI1I2 | DI1 | I1I2 | DI1I2I3 | D2I2 | D1I | D1D2D3I |
| Wengao 2 mutant (YT-66) | DI2 | DI1 | DI1I2 | DI1I2 | DI1I2 | D | DI1I2 | DI2I3 | D2I2 | D1 | D1D2D3 |
| Fenhong Gala 44 (YT-67) | I2 | DI1 | DI1I2 | DI1I2 | DI1I2 | I1I2 | DI1I2 | DI1I2 | D2I2 | D1 | D1D2D3I |
| Yiyuanhong (YT-68) | DI2 | DI1 | DI1I2 | DI1I2 | DI1I2 | D | DI1I2 | DI2I3 | D2I2 | D1 | D1D2D3 |
| Yanfu 4 (YT-69) | DI2 | DI1 | DI1I2 | DI1I2 | DI1I2 | D | DI1I2 | DI2I3 | D2I2 | D1 | D1D2D3 |
| White Pearmain (YT-70) | DI2 | DI1 | DI1I2 | DI1I2 | DI1I2 | D | I1I2 | DI1I2 | D2I2 | D1 | D1D2D3 |
| Jonathan-early (YT-73) | I2 | D | DI1I2 | DI2 | DI1I2 | DI2 | DI1I2 | DI2I3 | D2 | D1 | D1D2D3I |
| Jonathan-midle (YT-74) | I2 | D | DI1I2 | DI2 | DI1I2 | DI2 | DI1I2 | DI2I3 | D2 | D1 | D1D2D3I |
| Gornan (YT-75) | I2 | DI2 | DI1I2 | DI2 | DI1I2 | D | I1I2 | DI1I2I3 | D1D2 | D1 | D1D2D3I |
| RegiIndel (YT-76) | I1I2 | DI1 | DI1I2 | DI2 | DI1I2 | DI2 | DI1I2 | DI2 | D2 | D1I | D1D3 |
| Golden Bell (YT-77) | I2 | DI1I2 | DI1I2 | DI1I2 | DI1I2 | DI1 | I1I2 | DI2I3 | D1D2 | D1I | D1D2D3I |
| Arkcharm (YT-78) | DI2 | I2 | DI1 | DI2 | DI1I2 | DI2 | I1I2 | DI1I2I3 | D2I2 | D1I | D2D3I |
| Redchif (YT-79) | DI2 | D | DI1I2 | DI2 | DI1I2 | DI1 | DI1I2 | DI2 | D1 | D1I | D1D2D3I |
| Mouping Guanghua Fuji (YT-8) | DI2 | DI1 | DI1I2 | DI1I2 | DI1I2 | D | DI1I2 | DI2I3 | D2I2 | D1 | D1D2D3 |
| Freedom (YT-80) | I2 | DI1 | DI1I2 | DI2 | DI1I2 | I1 | I1I2 | DI2I3 | D2I2 | D1I | D1D2D3 |
| Martinike (YT-81) | DI2 | DI1 | DI1 | DI2 | DI1I2 | DI2 | DI1I2 | DI2I3 | D2 | D1 | D1D2D3 |
| Sweetle (YT-82) | DI2 | DI1 | DI1I2 | DI2 | DI1I2 | DI2 | DI1 | DI1I2I3 | I2 | D1 | D1D2D3 |
| Aleksanader (YT-83) | DI2 | DI2 | DI1 | DI2 | DI1I2 | DI2 | DI1I2 | DI2 | D1D2 | D1 | D1D2D3 |
| Yan 6 Fenhong 143 (YT-84) | I2 | DI1 | DI1I2 | DI2 | DI1I2 | DI1 | I1I2 | DI1I2 | D2I2 | D1 | D1D2D3I |
| Ruitina (YT-85) | DI1 | DI2 | DI1I2 | DI2 | DI1I2 | D | DI1I2 | DI2I3 | D2 | I | D1D2D3 |
| Wengao 1 mutant (YT-86) | DI2 | DI1 | DI1I2 | DI1I2 | DI1I2 | D | DI1I2 | DI2I3 | D2I2 | D1 | D1D2D3 |
| Wengao 3 mutant (YT-87) | DI2 | DI1 | DI1I2 | DI1I2 | DI1I2 | D | DI1I2 | DI2I3 | D2I2 | D1 | D1D2D3 |
| Shajinyilamu (YT-88) | DI2 | D | DI1I2 | DI2 | DI1I2 | DI1 | I1I2 | DI2 | D2 | D1 | D1D2D3 |
| Qiuhong (YT-89) | I2 | D | DI1I2 | DI1I2 | DI1I2 | I1I2 | I1I2 | DI2I3 | D2I2 | D1 | D1D2D3 |
| Changyanghong (YT-9) | DI2 | DI1 | DI1I2 | DI1I2 | DI1I2 | D | DI1I2 | DI2I3 | D2I2 | D1 | D1D2D3 |
| Yanfu 8 (YT-90) | DI2 | DI1 | DI1I2 | DI1I2 | DI1I2 | D | DI1I2 | DI2I3 | D2I2 | D1 | D1D2D3 |
| Jinduhong Gala (YT-91) | I2 | DI1 | DI1I2 | DI1I2 | DI1I2 | DI1 | DI1I2 | DI1I2I3 | I2 | D1 | D1D2D3I |
| Nagafu 2 (YT-92) | DI2 | DI1 | DI1I2 | DI1I2 | DI1I2 | D | DI1I2 | DI2I3 | D2I2 | D1 | D1D2D3 |
| Honglu seedling 65 (YT-93) | DI2 | DI1 | DI1I2 | DI1I2 | DI1I2 | D | DI1I2 | DI2I3 | D2I2 | D1 | D1D2D3I |
| Tsugaru (YT-94) | I1I2 | DI2 | DI1I2 | DI1I2 | DI1I2 | DI2 | DI1I2 | I2I3 | D2 | D1I | D1D2D3I |

-continued

| Construction results of InDel marker genotype database of *Malus* germplasm resources | | | | | | | | | | | |
|---|---|---|---|---|---|---|---|---|---|---|---|
| Jinshuai mutant (YT-95) | I1I2 | I1I2 | DI1I2 | DI2 | DI1I2 | DI1 | I1I2 | DI1I2I3 | D2I2 | DI1 | D1D2D3I |
| Taishan Crab (YT-96) | I2 | D | DI1I2 | DI1I2 | DI1I2 | D | DI1 | DI2I3 | D2 | D1D2 | D1D2D3I |
| Luli (YT-98) | DI2 | DI1 | DI1I2 | DI2 | DI1I2 | DI1 | I1I2 | DI1I2I3 | D1I2 | D1 | D1D2D3I |
| 10-182 (YX-10-182) | D | D | DI1I2 | DI2 | DI1 | I1I2 | DI1 | DI2I3 | D2I2 | D1D2 | D1D2D3 |
| 01-001 (YX-01-001) | I2 | DI1 | DI1 | DI2 | DI1I2 | DI1 | DI1 | DI2I3 | D2 | D1D3 | D1D2D3 |
| 01-121 (YX-01-121) | I2 | I1 | DI1I2 | DI1I2 | DI1I2 | DI1 | I1I2 | DI2I3 | I2 | D1D2 | D1D2D3 |
| 02-009 (YX-02-009) | DI2 | DI1 | DI1I2 | DI1I2 | I1I2 | DI1 | DI1 | DI2I3 | D2I2 | D1D3 | D1D2D3 |
| 03-010 (YX-03-010) | DI2 | I1 | DI1 | DI1I2 | DI1I2 | DI1 | DI1I2 | DI2I3 | D2 | DI1 | D1D2D3 |
| 03-111 (YX-03-111) | I2 | D | DI1I2 | DI2 | DI1I2 | DI1 | I1I2 | DI2I3 | D2 | D1D3 | D1D2D3 |
| 04-033 (YX-04-033) | D | D | DI1 | DI2 | I1I2 | DI1 | DI1 | DI2I3 | D2I2 | D1D3 | D1D2D3 |
| 04-087 (YX-04-087) | DI2 | DI1 | DI1 | DI2 | DI1I2 | DI1 | DI1I2 | DI2I3 | D2 | D1D3 | D1D2D3 |
| 06-056 (YX-06-056) | DI2 | DI1 | DI1 | DI1I2 | I1I2 | DI1 | DI1I2 | DI2I3 | D2 | DI1 | D1D2D3 |
| 08-034 (YX-08-034) | D | D | DI1I2 | DI2 | I1I2 | DI1 | DI1 | DI2I3 | D2I2 | D1D3 | D1D2D3 |
| 09-037 (YX-09-037) | I2 | DI1 | DI1 | DI2 | I1I2 | DI1 | DI1I2 | DI2I3 | D2I2 | D1D3 | D1D2D3 |
| 09-079 (YX-09-079) | D | DI1 | DI1 | DI1I2 | I1I2 | DI1 | DI1I2 | DI2I3 | I2 | D1D3 | D1D2D3I |
| 10-010 (YX-10-010) | D | D | DI1I2 | DI2 | DI1I2 | DI1 | I1I2 | DI2I3 | D2I2 | D1D2 | D1D2D3 |
| 11-037 (YX-11-037) | I2 | D | DI1I2 | DI2 | I1I2 | DI1 | DI1 | DI2I3 | D2 | DI1 | D1D2D3 |
| 11-206 (YX-11-206) | DI2 | DI1 | DI1I2 | DI2 | I1I2 | DI1 | DI1 | DI2I3 | D2 | D1D3 | D1D2D3I |
| 12-206 (YX-12-206) | DI2 | DI1 | DI1 | DI2 | DI1I2 | DI1 | I1I2 | DI2I3 | I2 | DI1 | D1D2D3 |
| 13-025 (YX-13-025) | DI2 | DI1 | DI1I2 | DI1I2 | DI1I2 | DI1 | DI1 | DI2I3 | D2I2 | DI1 | D1D2D3 |
| 16-155 (YX-16-155) | DI2 | I1 | DI1 | DI2 | I1I2 | DI1 | DI1 | DI2I3 | I2 | D1D3 | D1D2D3I |
| 16-157 (YX-16-157) | I2 | DI1 | DI1I2 | DI2 | DI1I2 | DI1 | DI1 | DI2I3 | D2 | DI1 | D1D2D3I |
| 17-023 (YX-17-023) | DI2 | DI1 | DI1I2 | DI1I2 | DI1 | DI1 | I1I2 | DI2I3 | D2I2 | D1D3 | D1D2D3I |
| 17-199 (YX-17-199) | DI2 | D | DI1 | DI1I2 | DI1I2 | DI1 | I1I2 | DI2I3 | D2I2 | D1D3 | D1D2D3I |
| 21-005 (YX-21-005) | DI1 | DI1 | DI1I2 | DI2 | DI1I2 | I1 | I1I2 | DI2I3 | D2I2 | D3I | D1D2D3 |
| 21-018 (YX-21-018) | DI2 | DI1 | DI1I2 | DI2 | I1I2 | DI1 | I1I2 | DI1I2 | D2I2 | D1D2 | D2D3I |
| 22-186 (YX-22-186) | I2 | I1 | DI1I2 | DI1I2 | I1I2 | DI1 | I1I2 | DI2I3 | D2I2 | I | D2D3I |
| 27-003 (YX-27-003) | DI1 | I1I2 | DI1I2 | DI1I2 | DI1I2 | I1 | DI1I2 | DI2I3 | D2I2 | DI1 | D1D2D3 |
| 29-176 (YX-29-176) | DI2 | DI1 | DI1I2 | DI1I2 | I1I2 | I1 | DI1I2 | DI2I3 | D2I2 | D3I | D2D3I |
| 30-001 (YX-30-001) | I2 | DI1 | DI1I2 | DI2 | DI1I2 | DI1 | I1I2 | DI1I2I3 | D2I2 | D1D3 | D1D2D3 |
| 33-018 (YX-33-018) | DI2 | D | DI1I2 | DI1I2 | I1I2 | DI1 | I1I2 | DI2I3 | D2I2 | D1D3 | D1D2D3 |
| 33-101 (YX-33-101) | I2 | D | DI1I2 | DI2 | I1I2 | I1I2 | DI1 | DI2I3 | D2 | D1D3 | D1D2D3I |
| 33-151 (YX-33-151) | I1I2 | I1 | DI1I2 | DI1I2 | I1I2 | I1 | I1I2 | DI2I3 | D2I2 | I | D2D3I |
| 51-007 (YX-51-007) | I2 | DI1 | DI1I2 | DI1I2 | DI1I2 | D | I1I2 | DI1I2I3 | D2 | D1 | D1D2D3I |
| 51-031 (YX-51-031) | I2 | DI1 | DI1I2 | DI1I2 | DI1I2 | DI1 | I1I2 | DI2I3 | D2 | D1 | D1D2D3I |
| 51-077 (YX-51-077) | I2 | DI1 | DI1I2 | DI2 | DI1I2 | DI1 | I1I2 | DI1I2I3 | D2I2 | D1 | D1D2D3I |
| 51-102 (YX-51-102) | I2 | DI1I2 | DI2 | D | DI1 | DI2 | DI1I2 | NA | D1D2I2 | D1 | D1D2D3I |
| 51-139 (YX-51-139) | I1I2 | DI2 | DI1I2 | DI1I2 | DI1I2 | I1I2 | I1I2 | DI2I3 | D2 | DI1 | D1D2D3I |

-continued

| Construction results of InDel marker genotype database of *Malus* germplasm resources | | | | | | | | | | |
|---|---|---|---|---|---|---|---|---|---|---|
| 51-165 (YX-51-165) | I2 | DI2 | DI1I2 | DI1I2 | DI1I2 | I1I2 | DI2I3 | D2I2 | D1I | D1D2D3 |
| 51-166 (YX-51-166) | I2 | DI1 | DI1I2 | DI2 | DI1I2 | DI1 | DI1I2 | DI2I3 | D2 | D1I | D2D3I |
| 51-209 (YX-51-209) | I2 | DI1 | DI1I2 | DI2 | DI1I2 | DI2 | DI1I2 | DI1I2I3 | D2I2 | D1 | D2D3I |
| 52-049 (YX-52-049) | I2 | DI1 | DI1I2 | DI2 | DI1I2 | DI2 | I1I2 | DI1I2I3 | D2 | D1 | D1D2D3 |
| 52-151 (YX-52-151) | I2 | DI2 | DI1I2 | DI2 | DI1I2 | DI2 | I1I2 | DI2I3 | D2 | D1 | D2D3I |
| 52-160 (YX-52-160) | I1I2 | DI2 | DI1I2 | DI1I2 | DI1I2 | DI1 | DI1I2 | DI2I3 | D2I2 | D1I | D1D2D3I |
| 53-040 (YX-53-040) | I1I2 | DI2 | DI1I2 | DI1I2 | DI1I2 | I1I2 | I1I2 | DI2I3 | D2I2 | D1I | D2D3I |
| 53-205 (YX-53-205) | DI2 | D | DI1I2 | DI1I2 | DI1I2 | D | DI1I2 | DI2I3 | D2I2 | D1 | D1D2D3I |
| 54-001 (YX-54-001) | I2 | DI1 | DI1I2 | DI1I2 | DI1I2 | I1I2 | I1I2 | DI2I3 | D2I2 | D1 | D1D2D3 |
| 54-188 (YX-54-188) | I2 | DI1 | DI1I2 | DI1I2 | DI1I2 | DI2 | I1I2 | I2I3 | D2I2 | D1 | D2D3I |
| 55-006 (YX-55-006) | I2 | DI2 | DI1I2 | DI2 | DI1I2 | DI2 | DI1I2 | DI2I3 | D2I2 | D1I | D2D3I |
| 55-023 (YX-55-023) | I2 | DI1 | DI1I2 | D | DI1I2 | DI1 | I1I2 | DI2I3 | D2I2 | D1 | D1D2D3I |
| 55-042 (YX-55-042) | I2 | DI1 | DI1I2 | DI2 | DI1I2 | DI2 | DI1I2 | DI1I2I3 | D2I2 | D1 | D1D2D3I |
| 56-081 (YX-56-081) | I2 | DI2 | DI1I2 | DI2 | DI1I2 | DI2 | I1I2 | DI1I2I3 | D2I2 | D1I | D2D3I |
| 57-128 (YX-57-128) | I1I2 | DI2 | DI1I2 | DI1I2 | DI1I2 | I1I2 | I1I2 | DI2I3 | D2 | D1I | D1D2D3I |
| 58-036 (YX-58-036) | I1I2 | DI2 | DI1I2 | DI2 | DI1I2 | DI1 | I1I2 | DI2I3 | D2 | D1I | D2D3I |
| 58-089 (YX-58-089) | I1I2 | DI2 | DI1I2 | DI2 | DI1I2 | DI1 | DI1I2 | DI2I3 | D2 | D1I | D1D2D3I |
| 58-144 (YX-58-144) | I2 | DI1 | DI1I2 | DI1I2 | DI1I2 | DI2 | I1I2 | DI2I3 | D2I2 | D1 | D2D3I |
| 58-177 (YX-58-177) | I1I2 | DI1 | DI1I2 | DI1I2 | DI1I2 | D | DI1I2 | DI1I2I3 | D2 | D1 | D2D3 |
| 58-211 (YX-58-211) | I2 | DI2 | DI1I2 | DI1I2 | DI1I2 | DI2 | I1I2 | DI1I2I3 | D2 | D1I | D1D2D3 |
| 59-086 (YX-59-086) | I2 | DI2 | DI1I2 | DI2 | DI1I2 | DI1 | I1I2 | DI2I3 | D2I2 | D1 | D2D3I |
| 59-130 (YX-59-130) | I2 | DI2 | DI1I2 | DI2 | DI1I2 | DI2 | I1I2 | DI1I2I3 | D2I2 | D1 | D2D3I |
| Jersey Mac (Z-1) | DI2 | I2 | DI1I2 | DI2 | DI1I2 | DI2 | I1I2 | DI2I3 | I1 | D1 | D1D2D3 |
| Gale Gala (Z-10) | I2 | DI1 | DI1I2 | DI1I2 | DI1I2 | DI1 | DI1I2 | DI1I2I3 | I2 | D1 | D1D2D3I |
| Li Gala (Z-11) | I2 | DI1 | DI1I2 | DI1I2 | DI1I2 | DI1 | DI1I2 | DI1I2I3 | I2 | D1 | D1D2D3I |
| Yanga 1 (Z-12) | I2 | I1 | DI1I2 | DI1I2 | DI1I2 | DI1 | DI1I2 | DI1I2I3 | I2 | D1 | D1D2D3I |
| NAKT M9 clone (Z-13) | I2 | D | DI1I2 | DI2 | DI1I2 | DI1 | I1I2 | DI2 | D1D2 | D1 | D1D2D3I |
| Royal Gala (Z-14) | I2 | I1 | DI1I2 | DI1I2 | DI1I2 | DI1 | DI1I2 | DI1I2I3 | I2 | D1 | D1D2D3I |
| Huajia (Z-15) | DI2 | DI1 | DI1 | DI1I2 | DI1I2 | DI1 | DI1I2 | DI1I2I3 | D2I1I2 | D1 | D1D2D3 |
| Dorsett Golden (Z-16) | DI2 | DI1I2 | DI1I2 | DI1I2 | DI1I2 | D | I1I2 | DI2 | D1 | D1I | D1D2D3I |
| 99-2-58 (Z-17) | DI2 | DI1 | DI1I2 | DI1I2 | DI1I2 | D | DI1I2 | DI1I2I3 | D2I1I2 | D1 | D1D2D3 |
| Galaxy (Z-18) | I2 | I1 | DI1I2 | DI1I2 | DI1I2 | DI1 | DI1I2 | DI1I2I3 | I2 | D1 | D1D2D3I |
| Royal New Gala (Z-19) | I2 | DI1 | DI1I2 | DI1I2 | DI1I2 | DI1 | DI1I2 | DI1I2I3 | I2 | D1 | D1D2D3I |
| 99-1-29 (Z-22) | DI1 | DI1 | DI1I2 | DI1I2 | DI1I2 | D | DI1I2 | DI2I3 | D2I1I2 | D1 | D1D2D3 |
| Seokwang (Z-23) | DI1 | DI2 | DI1I2 | DI1I2 | DI1I2 | DI2 | DI1I2 | I2I3 | D2I1 | D1I | D1D2D3 |
| Fuhong Zaoga (Z-24) | I2 | DI1 | DI1I2 | DI1I2 | DI1I2 | DI1 | DI1I2 | DI1I2I3 | I2 | D1 | D1D2D3I |
| Maiyan (Z-25) | DI2 | D | DI1I2 | DI2 | DI1I2 | DI1 | I1I2 | DI2I3 | D2I1 | D1 | D1D2D3 |
| Shandong 1 (Z-26) | I2 | DI1 | DI1I2 | DI1I2 | DI1I2 | DI1 | DI1I2 | DI1I2I3 | I2 | D1 | D1D2D3I |

-continued

Construction results of InDel marker genotype database of *Malus* germplasm resources

| | | | | | | | | | | | |
|---|---|---|---|---|---|---|---|---|---|---|---|
| Gala Queen (Z-27) | I2 | DI1 | DI1I2 | DI1I2 | DI1I2 | DI1 | DI1I2 | DI1I2I3 | I2 | D1 | D1D2D3I |
| 99-2-39 (Z-29) | DI1 | DI1 | DI1I2 | DI1I2 | DI1I2 | D | DI1I2 | DI1I2I3 | I1 | D1 | D1D2D3 |
| Sweetle (Z-3) | DI2 | DI1 | DI1I2 | DI2 | DI1I2 | DI2 | DI1 | DI1I2I3 | I2 | D1 | D1D2D3 |
| Dalian Da Gala (Z-30) | I2 | I1 | DI1I2 | DI1I2 | DI1I2 | DI1 | DI1I2 | DI1I2I3 | I2 | D1 | D1D2D3I |
| Huaxing (Z-31) | DI2 | DI1 | DI1I2 | DI1 | DI1I2 | DI2 | I1I2 | I1I2I3 | I2 | D1 | D1D2D3I |
| Li Gala (Z-32) | I2 | DI1 | DI1I2 | DI1I2 | DI1I2 | DI1 | DI1I2 | DI1I2I3 | I2 | D1 | D1D2D3I |
| Fuhong Zaoga (Z-33) | DI2 | DI1 | DI1I2 | DI1 | DI1I2 | I1I2 | DI1 | DI1I2I3 | I2 | D1 | D1D2D3 |
| Yanga (Z-34) | DI2 | DI1 | DI1I2 | DI1 | DI1I2 | I1I2 | DI1 | DI1I2I3 | I2 | D1 | D1D2D3 |
| Royal Gala (Z-35) | I2 | I1 | DI1I2 | DI1I2 | DI1I2 | DI1 | DI1I2 | DI1I2I3 | I2 | D1 | D1D2D3I |
| Shijiazhuang Gala (Z-37) | I2 | I1 | DI1I2 | DI1I2 | DI1I2 | DI1 | DI1I2 | DI1I2I3 | I2 | D1 | D1D2D3I |
| Taihong Gala (Z-38) | I2 | I1 | DI1I2 | DI1I2 | DI1I2 | DI1 | DI1I2 | DI1I2I3 | D2I2 | D1 | D1D2D3I |
| Anna (Z-39) | DI2 | DI2 | DI1I2 | DI1 | DI1I2 | DI1 | I1I2 | DI1I2 | D1I2 | D1 | D1D2D3 |
| Hong Zhenzhu (Z-4) | DI2 | DI1 | DI1I2 | DI1I2 | DI1I2 | DI2 | I1I2 | DI1I2I3 | I2 | D1 | D1D2D3 |
| Qiuhong Gala (Z-40) | I1I2 | DI2 | DI1I2 | DI1I2 | DI1I2 | DI2 | DI1I2 | I2I3 | D2 | D1I | D1D2D3I |
| Shandong 2 (Z-41) | I2 | I1 | DI1I2 | DI1I2 | DI1I2 | DI1 | DI1I2 | DI1I2I3 | I2 | D1 | D1D2D3I |
| Shandong 6 (Z-42) | I2 | I1 | DI1I2 | DI1I2 | DI1I2 | DI1 | DI1I2 | DI1I2I3 | I2 | D1 | D1D2D3I |
| Chenyang (Z-43) | DI1 | I2 | DI1I2 | DI1 | DI1I2 | I1 | I1 | I1I2I3 | D2 | D1 | D1D2D3I |
| Dongqie Gala (Z-44) | I2 | I1 | DI1I2 | DI1 | DI1I2 | DI1 | DI1I2 | DI1I2I3 | D2I2 | D1 | D2D3I |
| Royal Gala (Z-45) | I2 | I1 | DI1I2 | DI1I2 | DI1I2 | DI1 | DI1I2 | DI1I2I3 | I2 | D1 | D1D2D3I |
| Taishan Gala (Z-47) | I2 | I1 | DI1I2 | DI1I2 | DI1I2 | DI1 | DI1I2 | DI1I2I3 | I2 | D1 | D1D2D3I |
| Shandong 7 (Z-48) | I2 | I1 | DI1I2 | DI1I2 | DI1I2 | DI1 | DI1I2 | DI1I2I3 | I2 | D1 | D1D2D3I |
| Regal gala (Z-49) | I2 | I1 | DI1I2 | DI1I2 | DI1I2 | DI1 | DI1I2 | DI1I2I3 | I2 | D1 | D1D2D3I |
| NAKB clone (Z-5) | I2 | D | DI1I2 | DI2 | DI1I2 | DI1 | I1I2 | DI2 | D1D2 | D1 | D1D2D3I |
| Royal gala (Z-50) | I2 | I1 | DI1I2 | DI1I2 | DI1I2 | DI1 | DI1I2 | DI1I2I3 | I2 | D1 | D1D2D3I |
| Znoga (Z-51) | DI2 | D | DI1I2 | DI1I2 | DI1I2 | DI1I2 | DI1I2 | DI1I2I3 | D1D2I2 | D1 | D1D2D3I |
| Shandong 5 (Z-52) | I2 | I1 | DI1I2 | DI1I2 | DI1I2 | DI1 | DI1I2 | DI1I2I3 | I2 | D1 | D1D2D3I |
| Rockit (Z-53) | I2 | DI1 | DI1I2 | DI1I2 | DI1I2 | I1 | DI1I2 | DI1I2I3 | I2 | D1 | D1D2D3 |
| Shandong 3 (Z-54) | I2 | I1 | DI1I2 | DI1I2 | DI1I2 | DI1 | DI1I2 | DI1I2I3 | I2 | D1 | D1D2D3I |
| Mondel Gala (Z-55) | I2 | I1 | DI1I2 | DI1I2 | DI1I2 | DI1 | DI1I2 | DI1I2I3 | I2 | D1 | D1D2D3I |
| Alvinagala (Z-56) | I2 | I1 | DI1I2 | DI1I2 | DI1I2 | DI1 | DI1I2 | DI1I2I3 | I2 | D1 | D1D2D3I |
| M9 pajam2 (Z-6) | I2 | D | DI1I2 | DI2 | DI1I2 | DI1 | I1I2 | DI2 | D1D2 | D1 | D1D2D3I |
| Jinshiji (Z-7) | I2 | DI1 | DI1I2 | DI1I2 | DI1I2 | DI1 | DI1I2 | DI1I2I3 | I2 | D1 | D1D2D3I |
| Huarui (Z-8) | DI1 | DI1 | DI1I2 | DI1I2 | DI1I2 | DI1 | I1I2 | I1I2I3 | D1I2 | D1 | D1D2D3 |
| Hongcuibao (Z-9) | DI2 | DI1 | DI1I2 | DI2 | DI1I2 | DI1 | DI1 | DI1I2I3 | D1I2 | D1 | D1D2D3I |

Example 3

Identification of Germplasm Specificity in Database

AppleParentage1.0 software was used to analyze the specificity of all accessions in the database obtained in Example 2, the results showed that 942 of the 1251 accessions had unique genotype combination, that is, they had specificity, and their InDel genotype data were used to generate two-dimensional code molecular ID cards by online two-dimensional code generating software. There were 309 accessions with shared InDel marker genotype data, which were divided into 76 groups, as shown in Table 5; among them, there were 197 bud sports, including 107 (11 groups) bud sports of 'Fuji', 35 (3 groups) bud sports of 'Red Delicious', 33 (6 groups) bud sports of 'Gala', 4 (1 group) bud sports of 'Golden Delicious' and 7 (2 groups) bud sports of 'Jonathan', 5 (2 groups) bud sports of 'Rails Janet', 4 (1 group) bud sports of 'Tsugaru' and 2 (1 group) bud sports of 'Longwei' (Table 5).

Among them, Yanyuan 3 (SC-3), Yanyuan 2 (SC-2), row 22 (YN-42), row 25 (YN-45), row 24 (YN-44), row 12 (YN-32) and Jie 1 (11-0) were seven accessions with variety names unknown. The specificity analysis showed that Yanyuan 2 (SC-2) and row 22 (YN-42) might be 'Tsugaru' or bud sports of 'Tsugaru'; Yanyuan 3 (SC-3), row 25 (YN-45) and row 24 (YN-44) might be 'Fuji' or bud sports of 'Fuji'; row 12 (YN-32) might be 'Gala' or bud sports of 'Gala'; Jie 1 (11-0) might be 'Jonathan' or bud sports of 'Jonathan'.

According to the above analysis results, the InDel marker genotype database provided by the application can be used for the specific identification of Malus germplasm resources.

TABLE 5

Identification results of germplasm specificity

| Mutants | Group | Number | Accessions name (Accession ID) |
|---|---|---|---|
| Fuji mutants | 1 | 75 | Miyazaki Spur Fuji (BK-GQDZ), 2001 Fuji (XY-79), N2 (13--22), Fengcun Fuji (24--22), Lele Fuji (19--11), Bayue Fushiwang (XY-43), Nanshennan (B-28), Nanshennan mutant (B-9), Tianfu 1 (TS-1), Tianfu 2 (TS-6), Tianhong 1 (B-19), Tianhong 2 (B-13), Fuji No. 1 (HS-10), Fuji Champion (XY-48), Shandao Fuji (30--1), Yanfu 1 (BK-FY1), Yanfu 10 (BK-YF10), Fengfeng Fuji (XY-70), Miya Fuji (23--10), Juda Fuji (BK-JDFS), Raritan (8--12), Wengao 1 mutant (YT-86), Wengao 2 mutant (YT-66), Early Fuji (BK-ZFS), Early Fuji (TA-28), Korin (25--15), Changfong (BK-CH), Changyanghong (YT-9), Jinfa 1 (SX-23), Jinfa 2 (XY-73), Yiyuanhong (YT-68), Nagafu 2 (YT-92), Yanfu 0 (XY-41), Yanfu 1 (26-22), Yanfu 8 (YT-90), Yuhua Zaofu (SX-8), Royal Fuji 21 (XY-35), Shengfang 1(14--14), Spur Fuji (BK-DZFS), Spur Fuji (XY-42), Liquan Spur Fuji (SX-13), Akifu 1 (BK-QF1), Akifu 1 (XY-91), Akifu 19 (TA-18), Qiu Fuji (XY-47), Qiufuhong (TA-20), Qinfa 1 (XY-55), Red Fuji TAO (19-14), Beni Oshu (XY-26), Hongjinfu (XY-25), Meinong Fuji (XY-67), Meile (YT-20), Meixiang (BK-MX), Qunfu 1 (TA-21), Zhizun Fuji(HS-1), Yujing II (14--16), Bud Sport 3 (XY-14), Bud Sport 5 (XY-13), (21--0), Nagafu 1 (XY-86), Nagafu 12 (QD-6), Nagafu 2 (27--16), Nagafu 2 (BK-CF2H), Nagafu 2 (B-26), Nagafu 3 (BK-2), Nagafu 36 (BK-CF36), Nagafu 7 (14--20), Nagafu 8 (XY-77), Shanfu 6 (XY-76), Qingfu 13 (BK-QF13), Qingfu 1 (XY-84), Aomori Spur Fuji (23--4), Longfu (XY-15), Yanyuan 3(SC-3), row 25 (YN-45) |
| | 2 | 6 | 2001 Spur (QD-27), Youliang Spur (BK-YLDZ), Tuanwang semi-Spur (QD-29), Juda Fuji (TA-11), Wangfu (XY-92), Longfu (QD-30) |
| | 3 | 5 | Qingfu 2 (QD 2), Taiyang Fuji (XY-58), Very Early Fuji (YT-3), Shengfang (TA-22), row 24 (YN-44) |
| | 4 | 4 | Akifu 19 (XY-50), KAKUFUJI (XY-30), Feng Fuji (XY-56), Fuji (XY-54) |
| | 5 | 3 | Fubrax (HS-2), Qiufu (XY-75), Azhen Fuji (HS-14) |
| | 6 | 3 | Jiudian Spur (QD-24), Chengji 1 (YT-48), Yishui Fuji (XY-22) |
| | 7 | 3 | Shengfang 2 (BK-SF2), Tianxing (XY-57), Zhaiteng II (16--23) |
| | 8 | 2 | Dabinette (22--15), Mouping guanghua Fuji (YT-8) |
| | 9 | 2 | Fukushima Spur Fuji (BK-FDDZ), Qiquan Spur (XY-36) |
| | 10 | 2 | Fujiko (HS-4), Yanfu 5 (YT-64) |
| | 11 | 2 | Yanfu 6 (QD-32), &28 (TS-13) |
| Red Delicious mutants | 12 | 28 | Starkrimson (BK-XHX), Red Delicious (25--2), Shisanling Spur (7--11), Nanshan 2 (6--8), Classic Red Delicious (BK-KAHONG), Harrold Red Delicious (BK-HH), (16--16), Tianwang 1 (31--18), Daihong (BK-DH), Pingyin Spur (6--4), Kangtun Spur (7--6), Zhangjiakou Spur (6--16), Jie 15 (12--8), Sishui Spur (6--10), Meiguihong (BK-MGH), Well Spur Delicious (6--19), Red Spur Delicious (BK-AH), Red Spur Delicious (6--12), Fushan 1 (6--3), Zhanxuan 18 (15--7), Richard Red Delicious (6--18), Sharp Red Delicious (15--4), Yuyong(B3-14), StarkSpur Ultra Red Delicious (15--3), Xishan 1 (15--8), Norsan (13--5), Bianqiangzi 1 (6--14), Bianqiangzi 2 (6--20) |
| | 13 | 4 | Fushan 5 (5--14), Houjiadian Spur (5--18), Xiongyue 2 (5--22), HardiSpur Delicious (6--21) |
| | 14 | 3 | Ruby (BK-Ruby), Nanshan 4 (7--2), Oregon Spur (7--3) |
| Gala mutants | 15 | 20 | Alvina Gala (Z-56), Regal Gala (Z-49), Royal Gala (Z-50), Mondel Gala (Z-55), Liga (SX-20), Dalian Da Gala (Z-30), Shandong 2 (Z-41), Shandong 3 (Z-54), Shandong 5 (Z-52), Shandong 7 (Z-48), Ennike Gala (SX-28), Italy Gala (WH-9), Royal Gala (Z-45), Royal Gala (Z-14), Royal Gala (Z-35), Shijiazhuang Gala (Z-37), Malong Gala 1 blush (YN-2), Malong xin Gala 1 strip (YN-4), Malong Xin Gala 1 (YN-3), row 12(YN-32) |
| | 16 | 5 | Royal New Gala (Z-19), Li Gala (Z-11), Li Gala (Z-32), Gala Queen (Z-27), Fuhong Zaoga (Z-24) |
| | 17 | 2 | Shandong 1 (Z-26), Malong Gala 1 (YN-1) |
| | 18 | 2 | Galaxy (Z-18), Malong Gala 2 (YN-5) |
| | 19 | 2 | Matail (YT-34), Cherry Gala (YN-9) |
| | 20 | 2 | yanga(Z-34), Fuhong Zaoga (Z-33) |
| Jonathan mutants | 21 | 5 | Sweet Jonathan (20--10), Sweet Jonathan(14--7), Jinyu (12--12), Jie 1 (11--0), Jie 1 (28--11) |
| | 22 | 2 | Jonathan-early (YT-73), Jonathan-midle(YT-74) |
| Golden Delicious mutants | 23 | 4 | Golden B (23--2), Kangbing Golden 5 (15--11), (24--7), Spur Golden Delicious (BK-DJG) |
| Tsugaru mutants | 24 | 4 | Fangming(BK-FM), Yanyuan 2(SC-2), Qiuxiang(BK-QX), row 22(YN-42) |
| Ralls Janet mutants | 25 | 3 | Red Ralls Janet (BK-HGG), Pingzhi Ralls Janet (15--15), Xinguoguang (24--21) |
| | 26 | 2 | Ralls Janet (19--2), Weeping Ralls (19--0) |
| Longwei mutation | 27 | 2 | Longwei (YN-7), Longwei Early Mutant (YN-8) |
| | 28 | 8 | Starkjam (9--9), Dongchengguan 13 (10--11), Guldborg (1--11), Budayi (13--19), Napoleon (7--22), Qiujin (20--8), Zhanxuan 14 (13--9), Zhanxuan 16 (16--6) |
| | 29 | 4 | Freybreg (14--4), Shuangyang 1 (18--7), Hubbardston (18--23), Shengli (18--8) |
| | 30 | 4 | Ben David (19--8), Black Ben David (17--12), Youfangcun Ralls Janet (31--14), Qiuhuapi (YT-30) |
| | 31 | 4 | row 3 (YN-25), row 5 (YN-27), row 14 (YN-34), row 4 (YN-26) |
| | 32 | 3 | K9 (27--5), Jinyang (27--12), Jiguan (BK-JG) |
| | 33 | 3 | Yuanye Crab (BK-YYHT), Regunzi (BK-RGZ), Regunzi Spur (B3-10) |
| | 34 | 2 | Sweet McIntosh (11--16), Malinova (11--15) |
| | 35 | 2 | Boskoopske Cervene (2--11), Domenesti (11--3) |

TABLE 5-continued

Identification results of germplasm specificity

| Mutants | Group | Number | Accessions name (Accession ID) |
|---|---|---|---|
| | 36 | 2 | Giant Jeniton (19--1), Menage (12--17) |
| | 37 | 2 | Red Canada (13--2), Fa 5 (13--11) |
| | 38 | 2 | Xinlimei (18--19), Laidi (13--20) |
| | 39 | 2 | Calville Blanche (14--3), Boiken (14--21) |
| | 40 | 2 | Zhuoai 1 (16--2), Zhanxuan 4 (15--21) |
| | 41 | 2 | Gravenstein (1--6), Xinjiang 7 (BK-XJ7) |
| | 42 | 2 | Northern Spy (17--10), 4354-R ? (BK-5) |
| | 43 | 2 | Campbell (18--11), Roxbury (17--14) |
| | 44 | 2 | Newfane (17--7), Yellow Risharde (4--3) |
| | 45 | 2 | Kotoku (BK-XD), Rizhiwan (18--0) |
| | 46 | 2 | Zaocuilv (22--16), Jizaohong (19--17) |
| | 47 | 2 | Yanqing (BK-QY), White Pearmain (19--23) |
| | 48 | 2 | Radiant (20--23), Newtosh (20--0) |
| | 49 | 2 | Hongzhiwu (21--18), row 18 (YN-38) |
| | 50 | 2 | Judeline (25--12), Judeline (TS-7) |
| | 51 | 2 | Ningguang (25--19), Hongao(25--18) |
| | 52 | 2 | Red Sekaiichii (BK-HSJY), Kokyu (26--19) |
| | 53 | 2 | Fameuse (3--18), White Pippin (7--9) |
| | 54 | 2 | Daguo Crab (B-17), Minjian Daguo Crab (B-10) |
| | 55 | 2 | Ambrosia (B-27), Ambrosia (XN-MW) |
| | 56 | 2 | Luli (B-5), Luli (TA-12) |
| | 57 | 2 | Mato 1 (BK-TMYH), Michinoku (BK-AZ) |
| | 58 | 2 | CG80 (BK-CG80), MM106 (BK-MM106) |
| | 59 | 2 | Chieftan (BK-chieftan), Liberty (BK-liberty) |
| | 60 | 2 | Orei (BK-WL), Stark Blushing Golden (BK-JY) |
| | 61 | 2 | Laoshan 4 (BK-LS4H), Pingdinghaitang (BK-PDHT) |
| | 62 | 2 | Xinjiang 14 (BK-XJ14), Xinjiang 26 (BK-XJ26) |
| | 63 | 2 | Xinjiang 17 (BK-XJ17), Xinjiang 18 (BK-XJ18) |
| | 64 | 2 | Xinjiang 19 (BK-XJ19), Xinjiang 28 (BK-XJ28) |
| | 65 | 2 | Hanfu (SY-4), Hanfu (XY-2) |
| | 66 | 2 | Chaguo (XC-CG), Laiwunanyan (XC-LWNY) |
| | 67 | 2 | Jilin Huang Crab (XC-JLHHT), Jilin xiaohuang Crab (XC-JILINXIAOHUANGHAITANG) |
| | 68 | 2 | Xinjiang 10 (XN-XJ10), Xinjiang 12 (XN-XJ12) |
| | 69 | 2 | Xinjiang 15 (XN-XJ15), Xinjiang 27 (XN-XJ27) |
| | 70 | 2 | Xinjiang 16 (XN-XJ16), Qiulimeng (YT-21) |
| | 71 | 2 | row 20 (YN-40), row 23 (YN-43) |
| | 72 | 2 | Freedom (YT-80), Pilot (YT-59) |
| | 73 | 2 | 51-139 (YX-51-139), 57-128 (YX-57-128) |
| | 74 | 2 | Zumi Crab (B-30), Zumi Crab 4x (B-21) |
| | 75 | 2 | Gala 4x (XC-4), Ruihong(QD-25) |
| | 76 | 2 | Crispin (BK-crispin), New Jonagold (BK-XQNJ) |

Example 4

Paternity Testing of Partial Breeding Materials in Database

Eighty-two accessions with documented parents were selected from the above database, and the parents were searched in the database by using the AppleParentage1.0 software to check whether the proposed parents were consistent with the documented parents, thus verifying the feasibility of applying the database for paternity testing of *Malus* germplasm resources.

The documented parents of 27 materials were 'Jonathan'×'Golden Delicious'. After AppleParentage1.0 analysis, the search results of 26 materials were consistent with the documented parents, only 53-205 search results showed that they should be descendants of 'Jonathan' and 'Miyazaki Spur Fuji'. Among the 9 materials with documented parents as 'Zisai Pearl'×'Golden Delicious', the results of the proposed parents of two materials were inconsistent with the documented parents. The search results of 33-018 showed that their parents were 'Zisai Pearl' and 'Miyazaki Spur Fuji', while the search results of 33-101 only showed the descendants of 'Zisai Pearl', but the other parent could not be searched in the database. One of three materials whose documented parents were 'America 8' could only be retrieved from the other parent, but it could not be proved that they were descendants of 'America 8' in the database. The documented parent of 'H5-101' was 'Golden Delicious'×'Jonathan', but the analysis results showed that it should be the offspring of 'Golden Delicious' and 'Fuji'. Analysis showed that the parents of 23-63 and 23-42 were 'Fuji' and 'Lowtosh' instead of 'Fuji' and 'Toko'. For 'Yueshuai', 'Yueguan', 'Yuehua', '58-34', '13-26W' and '50-32', only one of the documented parents could be retrieved. The analysis results of the remaining 34 accessions were consistent with the documented parents (Table 6).

TABLE 6

Paternity testing results of partial breeding materials

| Accession ID | Accession name | Documented parents | | Proposed parents |
|---|---|---|---|---|
| YX-51-007 | 51-007 | Jonathan × Golden Delicious | Jonathan (BK-Jonathan) | Golden Delicious (BK-GD) |
| YX-51-031 | 51-031 | Jonathan × Golden Delicious | Jonathan (BK-Jonathan) | Golden Delicious (BK-GD) |
| YX-51-077 | 51-077 | Jonathan × Golden Delicious | Jonathan (BK-Jonathan) | Golden Delicious (BK-GD) |

TABLE 6-continued

Paternity testing results of partial breeding materials

| Accession ID | Accession name | Documented parents | | Proposed parents |
|---|---|---|---|---|
| YX-51-102 | 51-102 | Jonathan × Golden Delicious | Jonathan (BK-Jonathan) | Golden Delicious (BK-GD) |
| YX-51-139 | 51-139 | Jonathan × Golden Delicious | Jonathan (BK-Jonathan) | Golden Delicious (BK-GD) |
| YX-51-165 | 51-165 | Jonathan × Golden Delicious | Jonathan (BK-Jonathan) | Golden Delicious (BK-GD) |
| YX-51-166 | 51-166 | Jonathan × Golden Delicious | Jonathan (BK-Jonathan) | Golden Delicious (BK-GD) |
| YX-51-209 | 51-209 | Jonathan × Golden Delicious | Jonathan (BK-Jonathan) | Golden Delicious (BK-GD) |
| YX-52-049 | 52-049 | Jonathan × Golden Delicious | Jonathan (BK-Jonathan) | Golden Delicious (BK-GD) |
| YX-52-151 | 52-151 | Jonathan × Golden Delicious | Jonathan (BK-Jonathan) | Golden Delicious (BK-GD) |
| YX-52-160 | 52-160 | Jonathan × Golden Delicious | Jonathan (BK-Jonathan) | Golden Delicious (BK-GD) |
| YX-53-040 | 53-040 | Jonathan × Golden Delicious | Jonathan (BK-Jonathan) | Golden Delicious (BK-GD) |
| YX-53-205 | 53-205 | Jonathan × Golden Delicious | Jonathan (BK-Jonathan) | Miyazaki Spur Fuji (BK-GQDZ) |
| YX-54-001 | 54-001 | Jonathan × Golden Delicious | Jonathan (BK-Jonathan) | Golden Delicious (BK-GD) |
| YX-54-188 | 54-188 | Jonathan × Golden Delicious | Jonathan (BK-Jonathan) | Golden Delicious (BK-GD) |
| YX-55-006 | 55-006 | Jonathan × Golden Delicious | Jonathan (BK-Jonathan) | Golden Delicious (BK-GD) |
| YX-55-023 | 55-023 | Jonathan × Golden Delicious | Jonathan (BK-Jonathan) | Golden Delicious (BK-GD) |
| YX-55-042 | 55-042 | Jonathan × Golden Delicious | Jonathan (BK-Jonathan) | Golden Delicious (BK-GD) |
| YX-56-081 | 56-081 | Jonathan × Golden Delicious | Jonathan (BK-Jonathan) | Golden Delicious (BK-GD) |
| YX-58-036 | 58-036 | Jonathan × Golden Delicious | Jonathan (BK-Jonathan) | Golden Delicious (BK-GD) |
| YX-58-089 | 58-089 | Jonathan × Golden Delicious | Jonathan (BK-Jonathan) | Golden Delicious (BK-GD) |
| YX-58-144 | 58-144 | Jonathan × Golden Delicious | Jonathan (BK-Jonathan) | Golden Delicious (BK-GD) |
| YX-58-177 | 58-177 | Jonathan × Golden Delicious | Jonathan (BK-Jonathan) | Golden Delicious (BK-GD) |
| YX-58-211 | 58-211 | Jonathan × Golden Delicious | Jonathan (BK-Jonathan) | Golden Delicious (BK-GD) |
| YX-59-086 | 59-086 | Jonathan × Golden Delicious | Jonathan (BK-Jonathan) | Golden Delicious (BK-GD) |
| YX-59-130 | 59-130 | Jonathan × Golden Delicious | Jonathan (BK-Jonathan) | Golden Delicious (BK-GD) |
| YX-12-206 | 12-206 | Miyazaki Spur Fuji × Zisai Pearl | Zisai Pearl (BK-Zisai) | Miyazaki Spur Fuji (BK-GQDZ) |
| YX-13-025 | 13-025 | Miyazaki Spur Fuji × Zisai Pearl | Zisai Pearl (BK-Zisai) | Miyazaki Spur Fuji (BK-GQDZ) |
| YX-16-155 | 16-155 | Miyazaki Spur Fuji × Zisai Pearl | Zisai Pearl (BK-Zisai) | Miyazaki Spur Fuji (BK-GQDZ) |
| YX-16-157 | 16-157 | Miyazaki Spur Fuji × Zisai Pearl | Zisai Pearl (BK-Zisai) | Miyazaki Spur Fuji (BK-GQDZ) |
| YX-17-023 | 17-023 | Miyazaki Spur Fuji × Zisai Pearl | Zisai Pearl (BK-Zisai) | Miyazaki Spur Fuji (BK-GQDZ) |
| YX-17-199 | 17-199 | Miyazaki Spur Fuji × Zisai Pearl | Zisai Pearl (BK-Zisai) | Miyazaki Spur Fuji (BK-GQDZ) |
| YX-01-001 | 01-001 | Zisai Pearl × Miyazaki Spur Fuji | Zisai Pearl (BK-Zisai) | Miyazaki Spur Fuji (BK-GQDZ) |
| YX-01-121 | 01-121 | Zisai Pearl × Miyazaki Spur Fuji | Zisai Pearl (BK-Zisai) | Miyazaki Spur Fuji (BK-GQDZ) |
| YX-02-009 | 02-009 | Zisai Pearl × Miyazaki Spur Fuji | Zisai Pearl (BK-Zisai) | Miyazaki Spur Fuji (BK-GQDZ) |
| YX-03-010 | 03-010 | Zisai Pearl × Miyazaki Spur Fuji | Zisai Pearl (BK-Zisai) | Miyazaki Spur Fuji (BK-GQDZ) |
| YX-03-111 | 03-111 | Zisai Pearl × Miyazaki Spur Fuji | Zisai Pearl (BK-Zisai) | Miyazaki Spur Fuji (BK-GQDZ) |
| YX-04-033 | 04-033 | Zisai Pearl × Miyazaki Spur Fuji | Zisai Pearl (BK-Zisai) | Miyazaki Spur Fuji (BK-GQDZ) |
| YX-04-087 | 04-087 | Zisai Pearl × Miyazaki Spur Fuji | Zisai Pearl (BK-Zisai) | Miyazaki Spur Fuji (BK-GQDZ) |
| YX-06-056 | 06-056 | Zisai Pearl × Miyazaki Spur Fuji | Zisai Pearl (BK-Zisai) | Miyazaki Spur Fuji (BK-GQDZ) |
| YX-08-034 | 08-034 | Zisai Pearl × Miyazaki Spur Fuji | Zisai Pearl (BK-Zisai) | Miyazaki Spur Fuji (BK-GQDZ) |
| YX-09-037 | 09-037 | Zisai Pearl × Miyazaki Spur Fuji | Zisai Pearl (BK-Zisai) | Miyazaki Spur Fuji (BK-GQDZ) |
| YX-09-079 | 09-079 | Zisai Pearl × Miyazaki Spur Fuji | Zisai Pearl (BK-Zisai) | Miyazaki Spur Fuji (BK-GQDZ) |
| YX-10-010 | 10-010 | Zisai Pearl × Miyazaki Spur Fuji | Zisai Pearl (BK-Zisai) | Miyazaki Spur Fuji (BK-GQDZ) |
| YX-10-182 | 10-182 | Zisai Pearl × Miyazaki Spur Fuji | Zisai Pearl (BK-Zisai) | Miyazaki Spur Fuji (BK-GQDZ) |
| YX-11-037 | 11-037 | Zisai Pearl × Miyazaki Spur Fuji | Zisai Pearl (BK-Zisai) | Miyazaki Spur Fuji (BK-GQDZ) |
| YX-11-206 | 11-206 | Zisai Pearl × Miyazaki Spur Fuji | Zisai Pearl (BK-Zisai) | Miyazaki Spur Fuji (BK-GQDZ) |
| YX-21-005 | 21-005 | Zisai Pearl × Golden Delicious | Zisai Pearl (BK-Zisai) | Golden Delicious (BK-GD) |
| YX-21-018 | 21-018 | Zisai Pearl × Golden Delicious | Zisai Pearl (BK-Zisai) | Golden Delicious (BK-GD) |
| YX-22-186 | 22-186 | Zisai Pearl × Golden Delicious | Zisai Pearl (BK-Zisai) | Golden Delicious (BK-GD) |
| YX-27-003 | 27-003 | Zisai Pearl × Golden Delicious | Zisai Pearl (BK-Zisai) | Golden Delicious (BK-GD) |
| YX-29-176 | 29-176 | Zisai Pearl × Golden Delicious | Zisai Pearl (BK-Zisai) | Golden Delicious (BK-GD) |
| YX-30-001 | 30-001 | Zisai Pearl × Golden Delicious | Zisai Pearl (BK-Zisai) | Golden Delicious (BK-GD) |
| YX-33-018 | 33-018 | Zisai Pearl × Golden Delicious | Zisai Pearl (BK-Zisai) | Miyazaki Spur Fuji (BK-GQDZ) |
| YX-33-101 | 33-101 | Zisai Pearl × Golden Delicious | Zisai Pearl (BK-Zisai) | — |
| YX-33-151 | 33-151 | Zisai Pearl × Golden Delicious | Zisai Pearl (BK-Zisai) | Golden Delicious (BK-GD) |
| XY-28 | Yueshuai | Golden Delicious × Starking | Golden Delicious (BK-GD) | — |
| XY-3 | 74-178 | Hanfu × Huaguan | Hanfu (SY-4) | Huaguan Spur (BK-DZHG) |
| XY-5 | 26-34 | Hanfu × Huashuai | Hanfu (SY-4) | Huashuai (YT-36) |
| XY-12 | Yueyan | Hanfu × Shan Xia | Hanfu (SY-4) | Sansa (BK-SX) |
| XY-10 | Yueguan | Hanfu × Hua Shuai | Hanfu (SY-4) | — |
| XY-11 | Yuehua | Hanfu × Hua Shuai | Qingfu 2 (QD-2) or Longqiu (SY-11) | — |
| XY-60 | Yueping | Hanfu × Yueshuai | Hanfu (SY-4) | Yueshuai (XY-28) |
| XY-68 | 62-45 | Hanfu × Yueshuai | Fuji (BK-Fuji) | Yueshuai (XY-28) |
| XY-78 | 58-34 | Hanfu × Yueshuai | Hanfu (SY-4) or Yueshuai (XY-28) | — |
| XY-8 | 15-26 | Liaofu × Mollie's Delicious | Liaofu (2-7) | Mollie's Delicious (B-31) |
| XY-18 | Yuemei | Mato 1 × Mollie's Delicious | Mato 1 (BK-TMYH) | Mollie's Delicious (B-31) |
| XY-4 | 7-211 | Mato 1 × Mollie's Delicious | Mato 1 (BK-TMYH) | Mollie's Delicious (B-31) |
| XY-63 | 7-171 | Mato 1 × Mollie's Delicious | Mato 1 (BK-TMYH) | Mollie's Delicious (B-31) |
| XY-88 | Yueli | Mato 1 × Mollie's Delicious | Mato 1 (BK-TMYH) | Mollie's Delicious (B-31) |
| XY-61 | 23-63 | Toko × Fuji | Miyazaki Spur Fuji (BK-GQDZ) | Lowtosh (17--19) |
| XY-62 | 23-42 | Toko × Fuji | Miyazaki Spur Fuji (BK-GQDZ) | Lowtosh (17--19) |
| CL-5 | H5-101 | Golden Delicious × Jonathan | Golden B (23--2) (bud sport of Golden Delicious) | Fuji (BK-Fuji) |
| CL-2 | 23-127 | Jonathan × Golden Delicious | Jonathan (BK-Jonathan) | Golden B (23--2) (bud sport of Golden Delicious) |
| CL-1 | 13-26W | Miyazaki Spur Fuji × Red Tsugaru | Fangming (BK-FM) (bud sport of Tsugaru) | — |

TABLE 6-continued

Paternity testing results of partial breeding materials

| Accession ID | Accession name | Documented parents | | Proposed parents |
|---|---|---|---|---|
| CL-3 | 50-30 | Miyazaki Spur Fuji × Starkrimson | Miyazaki Spur Fuji (BK-GQDZ) | Starkrimson (BK-XHX) |
| CL-4 | 50-32 | Miyazaki Spur Fuji × Starkrimson | Miyazaki Spur Fuji (BK-GQDZ) | — |
| CL-6 | Pingyan | Yanfu10 × Red Tsugaru | Tsugaru (28--5) | Miyazaki Spur Fuji (BK-GQDZ) (sharing genotype with Yanfu10 (BK-YF10)) |
| Z-17 | 99-2-58 | America 8 × Maiyan | Maiyan (Z-25) | — |
| Z-22 | 99-1-29 | Geneva Early × America 8 | Geneva Early (BK-ZJ) | — |
| Z-29 | 99-2-39 | America 8 × Maiyan | Maiyan (Z-25) | — |
| B-5 | Luli | Mato 1 × Gala | Gala (BK-gala) | Mato 1 (BK-TMYH) |

The above described are only preferred embodiments of the present application, It should be understood by those skilled in the art that, without departing from the principle of the present application, any variations and modifications fall into the scope of the present application.

What is claimed is:

1. A method for constructing an InDel marker genotype database for *Malus*, comprising the following steps:
  genotyping InDel markers of genomic DNA samples of *Malus* germplasm resources by multiplex PCR;
  recording the results of the genotyping for each *Malus* germplasm resource;
  assembling the recorded results into an InDel marker genotype database;
  wherein the markers genotyped correspond to the loci represented by SEQ ID Nos. 1-102;
  wherein upstream primers used for PCR of the loci represented by SEQ ID Nos. 1-102 are SEQ ID Nos. 103-204, respectively;
  wherein downstream primers used for PCR of the loci represented by SEQ ID Nos. 1-102 are SEQ ID Nos. 205-306, respectively;
  wherein the multiplex PCR reactions are performed according to the following, wherein G1-G9 represent nine multiplex PCR reactions, each containing primers for amplifying the indicated combination of markers:

| Group number | Marker number | Fluorescent label | Marker combination |
| --- | --- | --- | --- |
| G1 | 24 | HEX | C06039, C08054, C11078, C15109, C15115, C16124 |
| | | PET | C03012, C04022, C04024, C07044, C09064, C13096 |
| | | NED | C03011, C05028, C08056, C08059, C10073 |
| | | FAM | C02009, C05026, C06037, C13101, C14104, C15110, C15114 |
| G2 | 15 | HEX | C01001, C04019, C09068, C15116, C16120 |
| | | PET | C01002, C03017, C07043, C17127 |
| | | NED | C01003, C06040, C11081, C17126 |
| | | FAM | C05030, C09063 |
| G3 | 9 | HEX | C05032, C07049, C12089 |
| | | PET | C17128 |
| | | NED | C13094 |
| | | FAM | C03018, C08052, C12086, C13093 |
| G4 | 11 | HEX | C01004, C07047, C10070, C12090, C13097 |

-continued

| Group number | Marker number | Fluorescent label | Marker combination |
|---|---|---|---|
| | | NED | C04020, C06038, C08058, C16122 |
| | | FAM | C05029, C15111 |
| G5 | 10 | HEX | C02008, C05031, C12092 |
| | | NED | C11082, C12088 |
| | | FAM | C06041, C07050, C12087, C13100, C13102 |
| G6 | 13 | HEX | C08051, C08057, C14108 |
| | | NED | C01005, C02006, C03014, C04023 |
| | | FAM | C09062, C11077, C11080, C13098, C15119, C16123 |
| G7 | 9 | HEX | C07045, C11079, C17129 |
| | | NED | C07048 |
| | | FAM | C04021, C08060, C12091, C14105, C16125 |
| G8 | 8 | HEX | C05135, C10136 |
| | | NED | C12132, C04133, C06137 |
| | | FAM | C09067, C04134, C07138 |
| G9 | 3 | HEX | C08055 |
| | | NED | C10071 |
| | | FAM | C10072. |

2. The database method according to claim 1, wherein the reaction procedure of the multiplex PCR is: pre-denaturation at 95° C. for 5 minutes; denaturation at 95° C. for 30 seconds, annealing at 55° C. for 90 seconds, extension at 72° C. for 90 seconds, 35 cycles; and extension at 60° C. for 30 minutes.

3. The method according to claim 1, further comprising using the genotype combination of all InDel markers of any Malus germplasm resources in the InDel marker genotype database of Malus as molecular identity information to identify the germplasm resources with the genotypes presented in the database.

4. The method according to claim 3, wherein the molecular identity information is presented, stored, identified and used in a two-dimensional code.

5. A method for identifying Malus germplasm resources by using the InDel marker genotype database of Malus constructed according to claim 1, comprising:

extracting genomic DNA of a sample to be tested, genotyping the genomic DNA by using primer pairs, obtaining InDel marker genotype data of the sample to be tested, and comparing the InDel marker genotype data of the sample to be tested with the data in the InDel marker genotype database of Malus;

when the InDel marker genotype combination of the sample to be tested is the same as the molecular identity information of any germplasm resource in the InDel marker genotype database of the Malus, it is judged that the sample to be tested has a genotype represented in the database;

when the InDel marker genotype combination of the sample to be tested is different from the molecular identity information of all germplasm resources in the InDel marker genotype database of the of Malus, and is different from the molecular identity information of other samples to be tested with known InDel marker genotype combinations, it is judged that the sample to be tested has a genotype not represented in the database.

6. A method for performing paternity test on Malus germplasm resources by using the InDel marker genotype database of Malus according to claim 1, comprising:

searching the parents and parents pair of the sample to be tested by using the InDel marker genotype database of Malus constructed according to claim 1, the search criteria are as follows:

testing the marker genotype of the sample, when the marker genotype of the sample is D, the genotype of parents is D or DI, and the genotype combination of parents pair is D×D, D×DI, DI×D or DI×DI;

when the marker genotype of the sample is I, the genotype of the parent is I or DI, and the genotype combination of the parents pair can be I×I, I×DI, DI×I or DI×DI;

when the marker genotype of the sample is DI, the genotype of parents is D, I or DI, and the genotype combination of parents pair is D×I, I×D, D×DI, I×DI, DI×D, DI×I or DI×DI;

wherein D is deletion homozygous genotype, I is insertion homozygous genotype and DI is insertion deletion heterozygous genotype.

7. The method according to claim 1, wherein the reaction procedure of the multiplex PCR is: pre-denaturation at 95° C. for 5 minutes; denaturation at 95° C. for 30 seconds, annealing at 55° C. for 90 seconds, extension at 72° C. for 90 second, 35 cycles; and extension at 60° C. for 30 minutes.

* * * * *